(12) United States Patent
Searle et al.

(10) Patent No.: US 8,691,865 B2
(45) Date of Patent: *Apr. 8, 2014

(54) SUBSTITUTED OCTAHYDROCYCLOPENTA[C]PYRROL-4-AMINES AS CALCIUM CHANNEL BLOCKERS

(75) Inventors: Xenia B. Searle, Grayslake, IL (US); Ming C. Yeung, Grayslake, IL (US); Stanley DiDomenico, Richmond, IL (US); Andrew O. Stewart, Libertyville, IL (US); Daria Darczak, Chicago, IL (US); Michael Schrimpf, Grayslake, IL (US); Michael J. Rozema, Kenosha, WI (US)

(73) Assignee: AbbVie Inc., North Chicago, IL (US)

( * ) Notice: Subject to any disclaimer, the term of this patent is extended or adjusted under 35 U.S.C. 154(b) by 350 days.

This patent is subject to a terminal disclaimer.

(21) Appl. No.: 13/114,829

(22) Filed: May 24, 2011

(65) Prior Publication Data

US 2011/0281870 A1 Nov. 17, 2011

Related U.S. Application Data

(63) Continuation-in-part of application No. 12/625,754, filed on Nov. 25, 2009, now Pat. No. 8,129,417.

(60) Provisional application No. 61/348,115, filed on May 25, 2010, provisional application No. 61/117,995, filed on Nov. 26, 2008.

(51) Int. Cl.
*A61K 31/40* (2006.01)
*C07D 209/00* (2006.01)
*C07D 209/44* (2006.01)

(52) U.S. Cl.
USPC ............................ 514/412; 548/452; 548/515

(58) Field of Classification Search
USPC ................................... 548/452, 515; 514/412
See application file for complete search history.

(56) References Cited

U.S. PATENT DOCUMENTS

| 7,838,547 | B2 | 11/2010 | Schwink et al. |
| 8,129,417 | B2 | 3/2012 | Stewart et al. |
| 2003/0232818 | A1 | 12/2003 | Anderson et al. |
| 2005/0148587 | A1 | 7/2005 | Fraser et al. |
| 2010/0093730 | A1 | 4/2010 | Bhatia et al. |
| 2010/0130558 | A1 | 5/2010 | Stewart et al. |
| 2010/0261773 | A1 | 10/2010 | Lindsley et al. |

FOREIGN PATENT DOCUMENTS

| EP | 0359172 A1 | 3/1990 |
| WO | 9510519 A1 | 4/1995 |
| WO | 0059882 A1 | 10/2000 |
| WO | 2005079496 A2 | 9/2005 |
| WO | 2006012396 A1 | 2/2006 |
| WO | 2006018280 A2 | 2/2006 |
| WO | WO2006/012396 | * 2/2006 | .................... 546/122 |
| WO | 2006113471 A2 | 10/2006 |
| WO | WO2010039947 A1 | 4/2010 |
| WO | 2010054398 A1 | 5/2010 |
| WO | WO2010062927 A2 | 6/2010 |
| WO | WO2010068851 A1 | 6/2010 |

OTHER PUBLICATIONS

Benington J.H., et al., "Cellular and Molecular Connections Between Sleep and Synaptic Plasticity," Progress in Neurobiology, 2003, vol. 69 (2), pp. 71-101.

Bennett G.J., et al., "A Peripheral Mononeuropathy in Rat that Produces Disorders of Pain Sensation like those Seen in Man," Pain, 1988, vol. 33 (1), pp. 87-107.

Bourinet E., et al., "Silencing of the Cav3.2 T-type Calcium Channel Gene in Sensory Neurons Demonstrates its Major Role in Nociception," The EMBO Journal, 2005, vol. 24 (2), pp. 315-324.

Chen C.C., et al., "Abnormal Coronary Function in Mice Deficient in Alpha1H T-type Ca2+ Channels," Science, 2003, vol. 302 (5649), pp. 1416-1418.

Choi S., et al., "Attenuated Pain Responses in Mice Lacking Ca(V)3.2 T-type Channels," Genes Brain and Behavior, 2007, vol. 6 (5), pp. 425-431.

Dixon W.J., "Efficient Analysis of Experimental Observations," Annual Review of Pharmacology and Toxicology, 1980, vol. 20, pp. 441-462.

Greene, T.W., et al., Protective Groups in Organic Synthesis, 3rd Edition, John Wiley and Sons, Inc., 1999, Table of Contents.

Jagodic M.M., et al., "Cell-Specific Alterations of T-type Calcium Current in Painful Diabetic Neuropathy Enhance Excitability of Sensory Neurons," Journal of Neuroscience, 2007, vol. 27 (12), pp. 3305-3316.

(Continued)

*Primary Examiner* — Andrew D Kosar
*Assistant Examiner* — Raymond Covington

(57) ABSTRACT

The present application relates to calcium channel inhibitors containing compounds of formula (I)

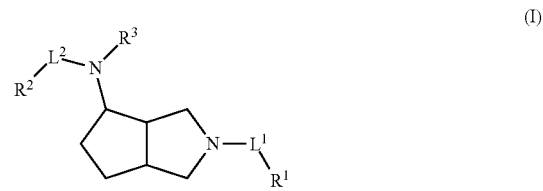

wherein $L^1$, $L^2$, $R^1$, $R^2$, and $R^3$ are as defined in the specification. The present application also relates to compositions comprising such compounds, and methods of treating conditions and disorders using such compounds and compositions.

23 Claims, No Drawings

(56) References Cited

OTHER PUBLICATIONS

Jagodic M.M., et al., "Upregulation of the T-Type Calcium Current in Small Rat Sensory Neurons after Chronic Constrictive Injury of the Sciatic Nerve," Journal of Neurophysiology, 2008, vol. 99 (6), pp. 3151-3156.
Nordskog B.K., et al., "Diurnal Gene Expression Patterns of T-type Calcium Channels and their Modulation by Ethanol," Neuroscience, 2006, vol. 141 (3), pp. 1365-1373.
Perez-Reyes E., et al., "Molecular Pharmacology of Human Cav3.2 T-type Ca2+ Channels: Block by Antihypertensives, Antiarrhythmics, and their Analogs," Journal of Pharmacology and Experimental Therapeutics, 2009, vol. 328 (2), pp. 621-627.
Prescott D.M., "Methods in Cell Biology", Academic Press, 1976, Table of Contents.
Santora V.J., et al., "A new family of H3 Receptor Antagonists Based on the Natural Product Conessine," Bioorganic & Medicinal Chemistry Letters, 2008, vol. 18 (4), pp. 1490-1494.
Talley E.M., et al., "Differential Distribution of Three Members of a Gene Family Encoding Low Voltage-activated (T-type) Calcium Channels," Journal of Neuroscience, 1999, vol. 19 (6), pp. 1895-1911.
Uslaner J.M., et al., "T-type Calcium Channel Antagonism Decreases Motivation for Nicotine and Blocks Nicotine- and Cue-induced Reinstatement for a Response Previously Reinforced with Nicotine," Biological Psychiatry, 2010, vol. 68 (8), pp. 712-718.
Uslaner J.M., et al., "T-type Calcium Channel Antagonism Produces Antipsychotic-like Effects and Reduces Stimulant-induced Glutamate Release in the Nucleus Accumbens of Rats," Neuropharmacology, 2010, pp. 1-9.
Angeli et al., "Calcium channel blockade to prevent stroke in hypertension: A meta-analysis of 13 studies with 103,793 subjects," Am J Hypertens. 2004, 17(9): 817-822.
Arulmozhi, et al., "Migraine: current concepts and emerging therapies," Vascul Pharmacol. 2005, 43(3): 176-187.
Bao et al., "Differences in Ca2+ channels governing generation of miniature and evoked excitatory synaptic currents in spinal laminae I and II," J Netupsci. 1998, 18(21): 8740-8750.
Barone et al., "SB 201823-A antagonizes calcium currents in central neurons and reduces the effects of focal ischemia in rats and mice," Stroke. 1995, 26(9): 1683-1690.
Bell et al., "Cell-specific alternative splicing increases calcium channel current density in the pain pathway," Neuron. 2004, 41(1): 127-138.
Berge et al., "Pharmaceutical Salts," J Pharm Sci. 1977, 66(1):1-19.
Beuckmann et al., "N-type calcium channel α1B subunit (CaV2.2) knock-out mice display hyperactivity and vigilance state differences," J Neurosci. 2003, 23(17):6793-6797.
Bhatia et al., "Fresh and globular amyloid β protein (1-42) induces rapid cellular degeneration: evidence for AβP channel-mediated cellular toxicity," FASEB J. 2000, 14(9): 1233-1243.
Bhattacharjee et al., "T-type calcium channels facilitate insulin secretion by enhancing general excitability in the insulin-secreting β-cell line, INS-1," Endocrinology. 1997, 138(9): 3735-3740.
Bilici et al., "Protective effect of T-type calcium channel blocker in histamine-induced paw inflammation in rat," Pharmacol Res. 2001, 44(6): 527-531.
Bowersox et al., "Selective N-type neuronal voltage-sensitive calcium channel blocker, SNX-111, produces spinal antinociception in rat models of acute, persistent and neuropathic pain," J Pharmacol Exp Ther. 1996, 279(3):1243-1249.
Castiglioni et al., "Alternative splicing in the C-terminus of CaV2.2 controls expression and gating of N-type calcium channels," J Physiol. 2006, 576(Pt 1):119-134.
Cavalli et al., "Multi-target-directed ligands to combat neurodegenerative diseases," J Med Chem. 2008, 51(3):347-372.
Chaplan et al., "Quantitative assessment of tactile allodynia in the rat paw," J Neurosci Methods. 1994, 53(1):55-63.

Chaplan et al., "Role of voltage-dependent calcium channel subtypes in experimental tactile allodynia," J Pharmacol Exp Ther. 1994, 269(3):1117-1123.
Cizkova et al., "Localization of N-type Ca2+ channels in the rat spinal cord following chronic constrictive nerve injury," Exp Brain Res. 2002, 147(4):456-463.
Colbourne et al., "Continuing postischemic neuronal death in CA1: influence of ischemia duration and cytoprotective doses of NBQX and SNX-111 in rats," Stroke. 1999, 30(3):662-668.
Croom et al., "Modified-release nifedipine: a review of the use of modified-release formulations in the treatment of hypertension and angina pectoris," Drugs. 2006, 66(4):497-528.
Darszon et al., "Ion channels in sperm physiology," Physiol Rev. 1999, 79(2):481-510.
Dolphin, A.C., "A short history of voltage-gated calcium channels," Br J Pharmacol. 2006, 147(Suppl. 1): S56-S62.
Eliel, E. L. and Wilen, S.H., Stereochemistry of Organic Compounds, John Wiley & Sons, Inc., New York, 1994 (Table of Contents only).
Evans et al., "Differential regulation of evoked peptide release by voltage-sensitive calcium channels in rat sensory neurons," Brain Res. 1996, 712(2):265-273.
Feng et al., "Determinants of inhibition of transiently expressed voltage-gated calcium channels by omega-conotoxins GVIA and MVIIA," J Biol Chem. 2003, 278(22):20171-20178.
Geldenhuys et al., "Structure-activity relationships of pentacycloundecylamines at the N-methyl-d-aspartate receptor," Bioorg Med Chem. 2007, 15(3):1525-1532.
Gitlin, M., "Treatment-resistant bipolar disorder," Mol Psychiatry. 2006, 11(3):227-240.
Gladstone et al., "Current and emerging treatment options for migraine and other primary headache disorders," Expert Rev Neurother. 2003, 3(6):845-872.
Gould et al., "Antischizophrenic drugs of the diphenylbutylpiperidine type act as calcium channel antagonists," Proc Natl Acad Sci USA. 1983, 80(16):5122-5125.
Gray et al., "Neuronal calcium channels: splicing for optimal performance," Cell Calcium. 2007, 42(4-5): 409-417.
Greene et al, Editors, Protective Groups in Organic Synthesis (3rd ed.), John Wiley & Sons, NY (1999) (52 pages).
Hatakeyama et al., "Differential nociceptive responses in mice lacking the α1B subunit of N-type Ca2+ channels," Neuroreport. 2001, 12(11):2423-2427.
Heinemann et al., "Extracellular free calcium and potassium during paroxsmal activity in the cerebral cortex of the cat," Exp Brain Res. 1977, 27(3-4):237-243.
Heinke et al., "Pre- and postsynaptic contributions of voltage-dependent Ca2+ channels to nociceptive transmission in rat spinal lamina I neurons," Eur J Neurosci. 2004, 19(1):103-111.
Ino et al., "Functional disorders of the sympathetic nervous system in mice lacking the α1B subunit (CaV 2.2) of N-type calcium channels," Proc Natl Acad Sci USA. 2001, 98(9):5323-5328.
International Search Report and Written Opinion mailed Jun. 1, 2010, and International Preliminary Report on Patentability mailed May 31, 2011, for Application No. PCT/US2009/065847.
International Search Report and Written Opinion mailed on Sep. 5, 2011, and International Preliminary Report on Patentability mailed Nov. 27, 2012, for Application No. PCT/US2011/037820.
IUPAC 1974 Recommendations for Section E, Fundamental Stereochemistry, Pure Appl Chem. 1976, 45: 13-30.
Kim et al., "Altered nociceptive response in mice deficient in the α1B subunit of the voltage-dependent calcium channel," Mol Cell Neurosci. 2001, 18(2):235-245.
Levy et al., "Calcium channel antagonists for the treatment of bipolar disorder," Bipolar Disord. 2000, 2(2):108-119.
Leza et al. Editors, Velasquez Basic and Clinical Pharmacology, 18th Ed. Editorial Medica Panamericana, S.A., 2008, pp. 80-81 (no English translation).
Little et al., "Calcium channel antagonists decrease the ethanol withdrawal syndrome," Life Sci. 1986, 39(22):2059-2065.
Liu et al., "In vivo analysis of voltage-dependent calcium channels," J Bioenerg Biomembr. 2003, 35(6):671-685.

(56) References Cited

OTHER PUBLICATIONS

Lorton, D., "β-Amyloid-induced IL-1β release from an activated human monocyte cell line is calcium- and G-protein-dependent," Mech Ageing Dev. 1997, 94(1-3):199-211.
Lubin et al., "A nonadherent cell-based HTS assay for N-type calcium channel using calcium 3 dye," Assay Drug Dev Technol. 2006, 4(6):689-694.
Luebke et al., "Multiple calcium channel types control glutamatergic synaptic transmission in the hippocampus," Neuron. 1993, 11(5):895-902.
Luo et al., "Upregulation of dorsal root ganglion α2δ calcium channel subunit and its correlation with allodynia in spinal nerve-injured rats," J Neurosci. 2001, 21(6):1868-1875.
Malmberg et al., "Voltage-sensitive calcium channels in spinal nociceptive processing: blockade of N- and P-type channels inhibits formalin-induced nociception," J. Neurosci. 1994, 14(8):4882-4890.
Mason et al., "Antioxidant and cytoprotective activities of the calcium channel blocker mibefradil," Biochem Pharmacol. 1998, 55(11):1843-1852.
Matthews et al., "Effects of spinally delivered N- and P-type voltage-dependent calcium channel antagonists on dorsal horn neuronal responses in a rat model of neuropathy," Pain. 2001, 92(1-2):235-246.
McGivern J.G., "Targeting N-type and T-type calcium channels for the treatment of pain," Drug Discov Today. 2006, 11(5-6):245-253.
Miljanich et al., "Antagonists of neuronal calcium channels: structure, function, and therapeutic implications," Annu Rev Pharmacol Toxicol. 1995, 35:707-734.
Neira et al., "NMDA glutamatergic receptor antagonists for the management of chronic pain," Rev Soc Esp Dolor. 2004, 11(4): 210-222. (with English Summary).
Newton et al., "Dorsal root ganglion neurons show increased expression of the calcium channel α2δ-1 subunit following partial sciatic nerve injury," Brain Res Mol Brain Res. 2001, 95(1-2):1-8.
Olivera et al., "Calcium channel diversity and neurotransmitter release: the omega-conotoxins and omega-agatoxins," Annu Rev Biochem. 1994, 63:823-867.
Otoom et al., "Nifedipine inhibits picrotoxin-induced seizure activity: further evidence on the involvement of L-type calcium channel blockers in epilepsy," Fundam Clin Pharmacol. 2006, 20(2):115-119.
Pietrobon, D., "Function and dysfunction of synaptic calcium channels: insights from mouse models," Curr Opin Neurobiol. 2005, 15(3):257-265.
Prescott et al., Editors, Methods in Cell Biology, vol. XIV, Academic Press, New York, N.Y. (1976), pp. 33-71 (Table of Contents only).
Raingo et al., "Alternative splicing controls G protein-dependent inhibition of N-type calcium channels in nociceptors," Nat Neurosci. 2007, 10(3):285-292.
Robles-Bayon et al., "The Action of Memantine on the Cognitive Disorders of Patients with Dementia: Reflections following Two Years' Experience in Spain," Revista Neurol., 2006, 42(5), p. 288 (with English Abstract).
Rodnitzky, R.L., "Can calcium antagonists provide a neuroprotective effect in Parkinson's disease?" Drugs. 1999, 57(6):845-849.
Saade et al., "The L-type calcium channel blocker nimodipine mitigates "learned helplessness" in rats," Pharmacol Biochem Behav. 2003, 74(2):269-278.
Saegusa et al., "Suppression of inflammatory and neuropathic pain symptoms in mice lacking the N-type Ca2+ channel," EMBO J. 2001, 20(10):2349-2356.
Scott et al., "Actions of intrathecal omega-conotoxins CVID, GVIA, MVIIA, and morphine in acute and neuropathic pain in the rat," Eur J Pharmacol. 2002, 451(3):279-286.
Shin et al., "T-type Ca2+ channels as therapeutic targets in the nervous system," Curr Opin Pharmacol. 2008, 8(1):33-41.
Smith et al., "The novel N-type calcium channel blocker, AM336, produces potent dose-dependent antinociception after intrathecal dosing in rats and inhibits substance P release in rat spinal cord slices," Pain. 2002, 96(1-2):119-127.
Takahashi et al., "Different types of calcium channels mediate central synaptic transmission," Nature. 1993, 366(6451):156-158.
Takei et al, "Increased sensitivity to halothane but decreased sensitivity to propofol in mice lacking the N-type Ca2+ channel," Neurosci Lett. 2003, 350(1):41-45.
Tort et al., "Atypical antipsychotic profile of flunarizine in animal models," Psychopharmacology (Berl). 2005, 177(3):344-348.
Urban et al., "Medullary N-type and P/Q-type calcium channels contribute to neuropathy-induced allodynia," Neuroreport. 2005, 16(6):563-566.
Vagnucci et al., "Alzheimer's disease and angiogenesis," Lancet. 2003, 361(9357):605-608.
Veng et al., "Age-related working memory impairment is correlated with increases in the L-type calcium channel protein α1D (Cav1.3) in area CA1 of the hippocampus and both are ameliorated by chronic nimodipine treatment," Brain Res Mol Brain Res. 2003, 110(2):193-202.
Vezzani et al., "Effect of various calcium channel blockers on three different models of limbic seizures in rats," Neuropharmacology. 1988, 27(5):451-458.
Wang et al., "Effects of intrathecal administration of ziconotide, a selective neuronal N-type calcium channel blocker, on mechanical allodynia and heat hyperalgesia in a rat model of postoperative pain," Pain. 2000, 84(2-3):151-158.
Westenbroek et al., "Localization of Ca2+ channel subtypes on rat spinal motor neurons, interneurons, and nerve terminals," J Neurosci. 1998, 18(16):6319-6330.
Wolff et al., Burger's Medicinal Chemistry and Drug Discovery, 1994, Wiley-Interscience, Fifth Edition, vol. I: Principles and Practice, pp. 975-977.
Yamamoto et al., "Differential effects of intrathecally administered N- and P-type voltage-sensitive calcium channel blockers upon two models of experimental mononeuropathy in the rat," Brain Res. 1998, 794(2):329-332.
Yokoyama et al., "Plastic change of N-type Ca channel expression after preconditioning is responsible for prostaglandin E2-induced long-lasting allodynia," Anesthesiology. 2003, 99(6):1364-1370.
Zanchetti et al., "Calcium antagonist lacidipine slows down progression of asymptomatic carotid atherosclerosis: principal results of the European Lacidipine Study on Atherosclerosis (ELSA), a randomized, double-blind, long-term trial," Circulation. 2002, 106(19):2422-2427.

\* cited by examiner

SUBSTITUTED OCTAHYDROCYCLOPENTA[C]PYRROL-4-AMINES AS CALCIUM CHANNEL BLOCKERS

CROSS-REFERENCE TO RELATED APPLICATIONS

The present application claims the benefit of priority from U.S. Provisional Patent Application Ser. No. 61/348,115 filed on May 25, 2010 and is a continuation-in-part of U.S. patent application Ser. No. 12/625,754 filed on Nov. 25, 2009 which claims priority to 61/117,995 filed on Nov. 26, 2008, all of which are incorporated herein by reference.

TECHNICAL FIELD

The present application relates to compounds that are calcium channel blockers, compositions comprising such compounds, and methods of treating conditions and disorders using such compounds and compositions.

BACKGROUND

Voltage-gated calcium channels (VGCC) play an integral role in the regulation of membrane ion conductance, neurotransmitter release, and cellular excitability. VGCC are composed of the pore-forming α1 subunit and auxiliary α2δ and β subunits that modulate channel expression and functional properties (Dolphin, A. C. British Journal of Pharmacology 2006, 147 (Suppl. 1), S56-S62.). These channels can be classified into low-voltage activated (LVA; T-type or $Ca_v3.x$) and high-voltage activated (HVA; L-type or $Ca_v1.x$ and N-, P/Q- and R-types or $Ca_v2.x$) channels. N-, P/Q and R channels typically activate at more positive membrane potentials (~-30 mV) and are involved in "presynaptic" neurotransmission (McGivern J. G. Drug Discovery Today 2006, 11, 245-253.). T-type channels are activated at relatively negative membrane potentials (~-60 mV) and are primarily involved in "postsynaptic" excitability (Shin, H.-S.; et al. Curr. Opin. in Pharmacology 2008, 8, 33-41.).

N-type channel $α_1$ subunits are encoded by a single gene ($α_1B$ or $Ca_v2.2$) in contrast to pharmacologically defined L- and T-type currents that are encoded by multiple $α_1$-subunit genes. A diversity of N-type channels arises due to extensive alternative splicing of the α subunit gene that generates variants with different expression patterns and GPCR-modulated biophysical properties (Gray, A. C.; et al. Cell Calcium, 2007, 42(4-5), 409-417.). The primary sequence for $Ca_v2.2$ is highly conserved across species (rat and human share 91% identity at the amino acid level).

N-type channels are widely expressed in the central nervous system (CNS) (cortex, hippocampus, striatum, thalamus, brain stem nuclei and spinal cord) and in the peripheral nervous system (PNS) (adult sympathetic nervous system and dorsal root ganglia) (Ino, M.; et al. Proc. Natl. Acad. Sci. USA 2001, 98(9), 5323-5328). In pain pathways, N-type channels are expressed in the rostral ventral medulla, an important site of descending pain modulation (Urban, M. O.; et al. Neuroreport 2005, 16(6), 563-566.) and are a major contributor to the synaptic neurotransmission that occurs between C/Aδ nociceptors and spinal lamina I neurons (Bao, J.; et al. J. Neurosci. 1998, 18(21), 8740-50. Heinke, B.; et al. Eur. J. Neurosci. 2004, 19(1), 103-111.). In contrast, P/Q type channels are expressed almost exclusively in laminae II-IV of the spinal cord and show little co-localization with Substance P and N-type channels (Westenbroek, R. E.; et al. J. Neurosci. 1998, 18(16), 6319-6330.).

Following nerve injury there is increased expression of $Ca_v2.2$ (Westenbroek, R. E.; et al. J. Neurosci. 1998, 18(16), 6319-6330. Cizkova, D.; et al. Exp. Brain Res. 2002, 147, 456-463. Yokoyama, K.; et al. Anesthesiology 2003, 99(6), 1364-1370.) and α2δ1 subunits (Luo, Z. D.; et al. J. Neurosci. 2001, 21(6), 1868-1875. Newton, R. A.; et al. Mol. Brain. Res. 2001, 95(1-2), 1-8.) in addition to increases in the superficial layers of the dorsal horn of the spinal cord supporting a role for N-type channels in neuropathic pain. Recently a nociceptor-specific $Ca_v2.2$ splice variant has been identified in the dorsal root ganglion (Bell, T. J.; et al. Neuron 2004, 41(1), 127-138.). These channels have distinct electrophysiological properties and current densities (Castiglioni, A. J.; et al. J. Physiol. 2006, 576(Pt 1), 119-134.) compared to wild-type $Ca_v2.2$ channels. While G-protein coupled receptor inhibition of wildtype N-type channels is typically mediated by Gβγ and is voltage-dependent, the nociceptor specific splice variant is inhibited by GPCR activation (e.g. opioids) in a voltage-independent fashion (Raingo, J.; et al. Nat. Neurosci. 2007, 10(3), 285-292.). This mechanism substantially increases the sensitivity of $Ca_v2.2$ channels to opiates and gamma-aminobutyric acid (GABA) suggesting that cell-specific alternative splicing of mRNA for $Ca_v2.2$ channels serves as a molecular switch that controls the sensitivity of N-type channels to neurotransmitters and drugs that modulate nociception. Collectively these data provide further support for the role of $Ca_v2.2$ channels in pain states.

The relative contributions of various HVA $Ca^{2+}$ channels in nociceptive signaling have been evaluated using knockout mice studies. $Ca_v2.2$ knockout mice are healthy, fertile, and do not display overt neurological deficits (Ino, M.; et al. Proc. Natl. Acad. Sci. USA 2001, 98(9), 5323-5328. Kim, C.; et al. Mol. Cell. Neurosci. 2001, 18(2), 235-245. Hatakeyama, S.; et al. Neuroreport 2001, 12(11), 2423-2427. Liu; L.; et al. J. Bioenerg. Biomembr. 2003, 35(6), 671-685.). This finding suggests that other types of $Ca_v$ channels are able to compensate for the lack of $Ca_v2.2$ channels at most synapses in these mice (Pietrobon, D. Curr. Opin. Neurobiol. 2005, 15(3), 257-265.). $Ca_v2.2$ deficient mice are resistant to the development of inflammatory and neuropathic pain (Kim, C.; et al. Mol. Cell. Neurosci. 2001, 18(2), 235-245. Hatakeyama, S.; et al. Neuroreport 2001, 12(11), 2423-2427. Saegusa, H.; et al. EMBO J. 2001, 20(10), 2349-2356.), have decreased sympathetic nervous system function (Ino, M.; et al. Proc. Natl. Acad. Sci. USA 2001, 98(9), 5323-5328.), and altered responses to both ethanol and anesthetics (Newton, R. A.; et al. Brain Res. Mol. Brain. Res. 2001, 95(1-2), 1-8. Takei, R. et al. Neurosci. Lett. 2003, 350(1), 41-45.). Additional behavioral studies indicate that $Ca_v2.2$ knockout mice are less anxious, are hyperactive, and show enhanced vigilance compared to wild-type littermates (Beuckmann, C. T.; et al. J. Neurosci. 2003, 23(17), 6793-6797.).

N- and P/Q-type channels are localized at neuronal synaptic junctions and contribute significantly to neurotransmitter release (Olivera, B. M.; et al. Annu. Rev. Biochem. 1994, 63, 823-867. Miljanich, G. P.; et al. Annu. Rev. Pharmacol. Toxicol. 1995, 35, 707-734.). N-type channels play a major role in the release of glutamate, acetylcholine, dopamine, norepinephrine, GABA, substance P and calcitonin gene-related protein (CGRP). P/Q-type channels may be involved in the release of glutamate, aspartate, 5HT, GABA and probably glycine (Pietrobon, D. Curr. Opin. Neurobiol. 2005, 15(3), 257-265.).

L, P/Q and N-type channels are blocked by channel specific antagonists i.e., dihydropyridines, ω-agatoxin IVA and ω-conotoxin MVIIA/ziconotide, respectively. Agatoxin IVa has been shown to block excitatory (Luebke, J. I.; et al.

Neuron 1993, 11(5), 895-902.) as well as inhibitory neurotransmission (Takahashi, T.; et al. Nature 1993, 366(6451), 156-158.). Intrathecal injection of selective N-type channel blockers (e.g. conotoxin-derived peptides such as GVIA, MVIIA (ziconotide), and CVID) significantly attenuates pain responses in animal models of neuropathic pain, formalin-induced pain, and post-operative pain (Chaplan, S. R.; et al. J. Pharmacol. Exp. Ther. 1994, 269(3), 1117-1123. Malmberg, A. B.; et al. J. Neurosci. 1994, 14(8), 4882-4890. Bowersox, S. S.; et al. J. Pharmacol. Exp. Ther. 1996, 279(3), 1243-1249. Wang, Y. X.; et al. Pain 2000, 84(2-3), 151-158. Scott, D. A.; et al. Eur. J. Pharmacol. 2002, 451(3), 279-286.). These peptide blockers bind to the pore region of the channel, do not show voltage- or frequency-dependent activity, and show irreversible channel block (Feng, Z. P.; et al. J. Biol. Chem. 2003, 278(22), 20171-20178.). Ziconotide potently blocks neurotransmitter release in the spinal cord dorsal horn (Matthews, E. A.; et al. Pain 2001, 92(1-2), 235-246. Smith, M. T.; et al. Pain 2002, 96(1-2), 119-127. Heinke, B.; et al. Eur. J. Neurosci. 2004, 19(1), 103-111.) and in dorsal root ganglion (DRG) neurons (Evans, A. R.; et al. Brain Res. 1996, 712(2), 265-273. Smith, M. T.; et al. Pain 2002, 96(1-2), 119-127.). It also potently and fully blocks depolarization-induced release of substance P from rat spinal cord slices. In contrast, intrathecal delivery of the selective P/Q type blocker ω-agatoxin IVA had no effects on mechanical allodynia in the spinal nerve ligation model (Chaplan, S. R.; et al. J. Pharmacol. Exp. Ther. 1994, 269(3), 1117-1123.) or thermal hyperalgesia in the chronic constriction injury model (Yamamoto, T.; et al. Brain Res. 1998, 794(2), 329-332.) of neuropathic pain.

T-Type or LVA calcium channels are composed of a single pore forming $\alpha_1$ subunit of which there are three subtypes: Cav3.1, Cav3.2 and Cav3.3 (Perez-Reyes, E.; et al. J Pharmacol Exp Ther. 2009, 328(2), 621-7). These channels are activated at relatively hyperpolarized cell membrane potentials and contribute to membrane depolarization following action potential generation. As a result, T-type calcium channel activation triggers secondary bursts of neuronal action potentials with increased action potential duration. Evidence supporting a role of T-type calcium channels in neuropathic pain comes from studies that have shown a concurrent increase in the expression of Cav3.2 channels after-depolarization potentials in medium diameter Aδ high threshold mechanoreceptor dorsal root ganglia (DRG) neurons in diabetic neuropathy (Jagodic, M. M.; et al. J Neurosci 2007, 27, 3305-3316.) and in small diameter neurons from the chronic constriction injury (CCI) neuropathic pain model (Jagodic, M. M.; et al. J Neurophysiol 2008, 99, 3151-3156.). Additional support comes from gene knockdown studies whereby intrathecal Cav3.2 antisense administration produces a significant knockdown (~80-90%) of T-type calcium currents in small and medium diameter DRG neurons, and produces robust anti-allodynic and antihyperalgesic effects in the CCI rat model of neuropathic pain (Bourinet, E.; et al. Embo J 2005, 24, 315-324). Moreover, Cav3.2 knockout mice show decreased pain responses compared to wild-type mice in acute mechanical, thermal, and chemical pain models (Choi, S.; et al. Genes Brain Behav 2007, 6, 425-431).

Recently, T-type calcium channel blockers have been proposed to have potential in treating schizophrenia and substance dependence. The T-type calcium channels are located in brain regions that have relevance to schizophrenia and substance dependence (Talley, E. M.; et al. J Neurosci 1999, 19, 1895-1911). More importantly, it has been demonstrated that selective T-type calcium channel blockers, such as TTA-A2, have antipsychotic-like effects in preclinical animal models of psychosis (Uslaner, J. M.; et al. Neuropharmacology 2010 (in press)) and were able to decrease nicotine seeking behavior in rats trained to self-administer nicotine (Uslaner, J. M.; et al. Biol Psychiatry 2010, 68, 712-718).

In addition to a role in nociception, T-type calcium channels have also been implicated to play roles in sleep disorders and absence epilepsy (Shin, H.-S.; et al. Curr Opin Pharmacol, 2008, 8, 33-41). Based on expression in the thalamus, T-type calcium channels may play a role in arousal from sleep (Benington, J. H.; et al. Prog Neurobiol 2003, 69, 71-101; Nordskog, B. K.; et al. Neuroscience 2006, 141, 1365-1373). Expression in the adrenal, pituitary and pineal glands suggests that these channels modulate hormone secretion. Notably, Cav3.2 knockout mice appear normal and healthy, although smaller than wild-type mice (Chen, C.-C.; et al. Science 2003, 302, 1416-1418; Choi, S.; et al. Genes Brain Behav 2007, 6, 425-431).

Pain is the most common symptom of disease and the most frequent complaint with which patients present to physicians. Inadequate pain management across the spectrum of pain etiologies remains a major public health problem. Going forward, the development of novel therapeutics with new mechanisms of action for the treatment of pain including calcium channel blockade will have a significant impact on the ongoing struggle to balance efficacy and safety for those patients most in need. The compounds of the present invention are novel calcium channel blockers that have utility in treating pain, amongst other conditions.

SUMMARY OF THE INVENTION

The invention is directed to compounds of formula (I)

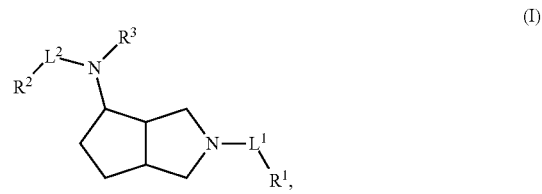

or a pharmaceutically acceptable salt, prodrug, salt of a prodrug, or a combination thereof, wherein $L^1$ is C(O), S(O)$_2$, SO$_2$N(R$^4$), C(O)O or —(CR$^a$R$^b$)$_m$—;

R$^1$ is alkyl, G$^1$, —CH(G$^1$)$_2$, —(CR$^a$R$^b$)$_m$-G$^1$, —(CR$^a$R$^b$)$_m$—CH(G$^1$)$_2$, —(CR$^e$R$^f$)$_n$—N(R$^5$)$_2$, —(CR$^e$R$^f$)$_n$—N(R$^5$)—C(O)O(alkyl), —(CR$^e$R$^f$)$_n$—N(R$^5$)—C(O)(alkyl), or —(CR$^e$R$^f$)$_n$—N(R$^5$)—SO$_2$R$^6$; or L$^1$-R$^1$ taken together are hydrogen, alkyl, hydroxyalkyl, G$^1$, or —CH(G$^1$)$_2$;

L$^2$ is —(CR$^c$R$^d$)$_p$—, C(O), C(O)N(R$^4$), S(O)$_2$, SO$_2$N(R$^5$), or C(O)O;

R$^2$ is alkyl, haloalkyl, hydroxyalkyl, G$^2$, -G$^2$-G$^3$, —C(R$^c$)(G$^2$)(G$^3$), —CH(OH)CF$_3$, —(CR$^c$R$^d$)$_p$—CH(OH)CF$_3$, —(CR$^c$R$^d$)$_p$-G$^2$, —(CR$^c$R$^d$)$_p$—CH(G$^2$)(G$^3$), —(CR$^g$R$^h$)$_q$—N(R$^5$)—C(O)O(alkyl), —(CR$^g$R$^h$)$_q$—N(R$^5$)—C(O)O-G$^2$, —(CR$^g$R$^h$)$_q$—N(R$^5$)—C(O)(alkyl), —(CR$^g$R$^h$)$_q$—N(R$^5$)—SO$_2$R$^6$, —(CR$^g$R$^h$)$_q$—N(R$^4$)(R$^5$), —(CR$^g$R$^h$)$_q$—N(R$^5$)—C(O)N(R$^5$)-(alkyl), —(CR$^g$R$^h$)$_q$—N(R$^5$)—C(O)N(R$^5$)-G$^2$, or —C(O)N(R$^4$)(R$^5$); or L$^2$-R$^2$ taken together are hydrogen, alkyl, G$^2$, or —C(R$^c$)(G$^2$)(G$^3$);

m and p, at each occurrence, are each independently 1, 2, 3, 4, 5, or 6;

n and q, at each occurrence, are each independently 1, 2, 3, 4, or 5;

$R^a$, $R^b$, $R^c$, and $R^d$, at each occurrence, are each independently hydrogen, alkyl, arylalkyl, halogen, haloalkyl or $OR^7$; or $R^a$ and $R^b$, or $R^c$ and $R^d$, together with the carbon atom to which they are attached, optionally form a $C_{3-6}$ cycloalkyl ring;

$R^e$, $R^f$, $R^g$, and $R^h$, at each occurrence, are each independently hydrogen, alkyl, halogen, haloalkyl, hydroxyalkyl, $OR^7$, cycloalkylalkyl, heteroaryl, arylalkyl, or heteroarylalkyl; wherein the aryl, cycloalkyl and heteroaryl groups of aryl, cycloalkyl and heteroaryl are each independently unsubstituted or substituted with 1, 2, 3, 4, or 5 substituents independently selected from the group consisting of alkyl and haloalkyl;

$G^1$, $G^2$, and $G^3$ at each occurrence, are each independently aryl, cycloalkyl, cycloalkenyl, heteroaryl, or heterocycle; wherein $G^1$, $G^2$, and $G^3$ at each occurrence are each independently unsubstituted or substituted with 1, 2, 3, 4, or 5 substituents selected from the group consisting of alkyl, alkenyl, alkynyl, cyano, haloalkyl, halogen, nitro, oxo, phenyl, $N(R^7)_2$, $N(R^7)C(O)R^7$, $OR^7$, $C(O)R^7$, $C(O)OR^7$, $C(O)N(R^7)_2$, $SR^7$, $SO_2R^8$, and $SO_2N(R^7)_2$; and wherein $G^1$ is other than quinoline, quinazolinedione, or pyridopyrimidinedione;

$R^3$ is hydrogen, alkyl, haloalkyl, cycloalkyl, or cycloalkylalkyl;

$R^4$, $R^5$, and $R^7$, at each occurrence, are each independently hydrogen, alkyl, aryl, arylalkyl, cycloalkyl, cycloalkylalkyl, or haloalkyl; wherein said aryl, the aryl of arylalkyl and cycloalkyl are independently unsubstituted or substituted with 1, 2 3, 4, or 5 substituents independently selected from the group consisting of alkyl, haloalkyl, and halogen;

$R^6$ is alkyl, aryl, cycloalkyl, cycloalkenyl, heteroaryl, or heterocycle; wherein said aryl, heteroaryl, and heterocycle are independently unsubstituted or substituted with 1, 2 3, 4, or 5 substituents independently selected from the group consisting of alkyl, haloalkyl, and halogen;

$R^8$ is alkyl or haloalkyl;

with the proviso that $L^1$-$R^1$ and $L^2$-$R^2$ are not both alkyl at the same time;

and with the proviso that when $L^2$-$R^2$ taken together are hydrogen and $R^3$ is hydrogen, then $L^1$-$R^1$ taken together is other than hydrogen, or $L^1$ is other than —$(CR^aR^b)_m$— and $R^1$ is other than $G^1$ wherein $G^1$ is aryl or heteroaryl;

and with the proviso that when $L^1$-$R^1$ is alkyl, $L^2$-$R^2$ is other than $C(O)N(R^4)$, wherein $R^4$ is alkyl;

and with the further proviso that the compound is other than:

N-(2-trityloctahydrocyclopenta[c]pyrrol-4-yl)acetamide;
N-(octahydrocyclopenta[c]pyrrol-4-yl)acetamide
N-methyl-N-(2-trityloctahydrocyclopenta[c]pyrrol-4-yl)acetamide;
N-methyl-N-(octahydrocyclopenta[c]pyrrol-4-yl)acetamide;
6-(2-(2-(3-fluoro-6-methoxy-1,5-naphthyridin-4-yl)ethyl)octahydrocyclopenta[c]pyrrol-4-ylamino)methyl-2H-pyrido[3,2-b][1,4]thiazin-3(4H)-one;
tert-butyl 2-(2-(3-fluoro-6-methoxy-1,5-naphthyridin-4-yl)ethyl)octahydrocyclopenta[c]pyrrol-4-ylcarbamate;
tert-butyl 2-benzyl octahydrocyclopenta[c]pyrrol-4-ylcarbamate; or
tert-butyl octahydrocyclopenta[c]pyrrol-4-ylcarbamate.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to calcium channels. More particularly, the method is useful for treating conditions related to a method of treating pain in a subject in need thereof. The method comprises administering to the subject a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof.

Another aspect of the invention provides a method of treating disorders of the central nervous system in a subject in need thereof. The method comprising the step of: administering a therapeutically suitable amount of a compound of formula (I), or a pharmaceutically acceptable salt thereof. The disorders of the central nervous system include stroke, epilepsy, absence epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; substance dependence and drug addiction withdrawal symptoms, including ethanol addiction withdrawal symptoms; skin disorders including pruritus and allergic dermatitis, inflammatory bowel disease; sleep disorders; cancer; diabetes; and infertility and sexual dysfunction, or combinations thereof.

The compounds, compositions comprising the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

Compounds of formula (I) are disclosed in this invention

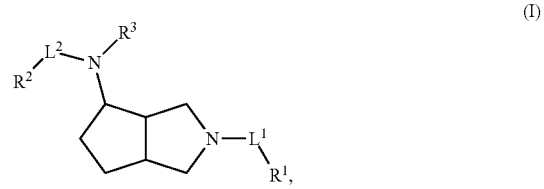

(I)

wherein $L^1$, $L^2$, $R^1$, $R^2$, and $R^3$ are as defined above in the Summary of the Invention. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double bond. Representative examples of alkylene include, but are not limited to, —CH=CH— and —CH$_2$CH=CH—.

The term "alkyl" as used herein, means a straight or branched, saturated hydrocarbon chain containing from 1 to 10 carbon atoms. The term "lower alkyl" or "C$_{1-6}$ alkyl" means a straight or branched chain hydrocarbon containing 1 to 6 carbon atoms. The term "C$_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "cyano" as used herein, means a —CN group.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl group appended to the parent molecular moiety through an alkyl group, as defined herein.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring can contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 3,4-dihydrobenzothienyl, 2,3-dihydroisoquinolinyl or indolinyl, 2,3-dihydroisoquinolinyl, 1,1-dioxidoisothiazolidinyl, azabicyclo[2.2.1]heptyl (including 2-azabicyclo[2.2.1]hept-2-yl), 2,3-dihydro-1H-indolyl, isoindolinyl, octahydro-1H-indolyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring can contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,2-oxazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, 2,1,3-benzothiadiazolyl, benzimidazolyl, benzoxadiazolyl, 6,7-dihydro-1,3-benzothiazolyl, furo[3,2-b]pyrrolyl, imidazo[1,2-a]pyridinyl, indazolyl, indolyl, isoindolyl, isoquinolinyl, naphthyridinyl, pyridoimidazolyl, pyrrolopyridinyl, quinolinyl, thiazolo[5,4-b]pyridin-2-yl, thiazolo[5,4-d]pyrimidin-2-yl, thienopyridinyl and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl," as used herein, means a heteroaryl group appended to the parent molecular moiety through an alkyl group, as defined herein.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "nitro" as used herein, means a —NO$_2$ group.

The term "oxo" as used herein, means a =O group.

b. Compounds

Compounds of the invention have the formula (I) as described above. Particular values of variable groups in compounds of formula (I) are as follows. Such values can be used where appropriate with any of the other values, definitions, claims or embodiments defined hereinbefore or hereinafter.

More particularly, compound of formula (I) can include, but are not limited to compounds wherein L$^1$-R$^1$ taken together are hydrogen, alkyl, hydroxyalkyl, G$^1$, or CH(G$^1$)$_2$.

In another embodiment, compound of formula (I) can include, but are not limited to compounds wherein L$^1$ is C(O), S(O)$_2$, SO$_2$N(R$^4$), C(O)O or —(CR$^a$R$^b$)$_m$—; wherein m is 1, 2, 3, 4, 5, or 6.

In a further embodiment, compound of formula (I) can include, but are not limited to compounds wherein L$^1$ is C(O), S(O)$_2$, or —(CR$^a$R$^b$)$_m$—.

In another embodiment, compound of formula (I) can include, but are not limited to compounds wherein R$^1$ is alkyl, G$^1$, CH(G$^1$)$_2$, —(CR$^a$R$^b$)$_m$-G$^1$, —(CR$^a$R$^b$)$_m$—CH(G$^1$)$_2$, —(CR$^e$R$^f$)$_n$—N(R$^5$)$_2$, —(CR$^e$R$^f$)$_n$—N(R$^5$)—C(O)O(alkyl), —(CR$^e$R$^f$)$_n$—N(R$^5$)—C(O)(alkyl), or —(CR$^e$R$^f$)$_n$—N(R$^5$)—SO$_2$R$^6$; wherein m is 1, 2, 3, 4, 5, or 6; and wherein n is 1, 2, 3, 4, or 5.

In a further embodiment, compound of formula (I) can include, but are not limited to compounds wherein R$^1$ is G$^1$, CH(G$^1$)$_2$, —(CR$^a$R$^b$)$_m$-G$^1$, or —(CR$^a$R$^b$)$_m$—CH(G$^1$)$_2$.

In one embodiment, compound of formula (I) can include, but are not limited to compounds wherein L$^2$-R$^2$ taken together are hydrogen, alkyl, G$^2$, or C(R$^c$)(G$^2$)(G$^3$).

In a further embodiment, compound of formula (I) can include, but are not limited to compounds wherein L$^2$-R$^2$ together are hydrogen, alkyl, aryl, cycloalkyl, heteroaryl or —C(R$^c$)(G$^2$)(G$^3$), wherein R$^c$ is hydrogen and G$^2$ and G$^3$ are each aryl or heteroaryl.

In another embodiment, compound of formula (I) can include, but are not limited to compounds wherein L$^2$ is —(CR$^e$R$^d$)$_p$—, C(O), C(O)N(R$^4$), S(O)$_2$, SO$_2$N(R$^5$), or C(O)O; wherein p is 1, 2, 3, 4, 5, or 6.

In a further embodiment, compound of formula (I) can include, but are not limited to compounds wherein $L^2$ is $-(CR^cR^d)_p-$, $C(O)$, $C(O)N(R^4)$, or $S(O)_2$, wherein p is 1.

In another embodiment, compound of formula (I) can include, but are not limited to compounds wherein $R^2$ is alkyl, haloalkyl, hydroxyalkyl, $G^2$, $-G^2-G^3$, $-C(R^c)(G^2)(G^3)$, $-CH(OH)CF_3$, $-(CR^cR^d)_p-CH(OH)CF_3$, $-(CR^cR^d)_p-G^2$, $-(CR^cR^d)_p-CH(G^2)(G^3)$, $-(CR^gR^h)_q-N(R^5)-C(O)O(alkyl)$, $-(CR^gR^h)_q-N(R^5)-C(O)O-G^2$, $-(CR^gR^h)_q-N(R^5)-C(O)(alkyl)$, $-(CR^gR^h)_q-N(R^5)-SO_2R^6$, $-(CR^gR^h)_q-N(R^4)(R^5)$, $-(CR^gR^h)_q-N(R^5)-C(O)N(R^5)-(alkyl)$, $-(CR^gR^h)_q-N(R^5)-C(O)N(R^5)-G^2$, or $-C(O)N(R^4)(R^5)$; wherein q is 1, 2, 3, 4, or 5; and wherein p is 1, 2, 3, 4, 5, or 6.

In another embodiment, compound of formula (I) can include, but are not limited to compounds wherein $R^a$ and $R^b$, at each occurrence, are each independently hydrogen, alkyl, arylalkyl, halogen, or haloalkyl or $OR^7$.

In a further embodiment, compound of formula (I) can include, but are not limited to compounds wherein $R^a$ and $R^b$, at each occurrence, are each independently hydrogen, alkyl, or arylalkyl.

In yet another embodiment, compound of formula (I) can include, but are not limited to compounds wherein $R^a$ and $R^b$, together with the carbon atom to which they are attached, optionally form a $C_{3-6}$ cycloalkyl ring.

In another embodiment, compound of formula (I) can include, but are not limited to compounds wherein $R^c$ and $R^d$, at each occurrence, are each independently hydrogen, alkyl, arylalkyl, halogen, or haloalkyl or $OR^7$.

In a further embodiment, compound of formula (I) can include, but are not limited to compounds wherein $R^c$ and $R^d$, at each occurrence, are each independently hydrogen, alkyl, arylalkyl, or $OR^7$, wherein $R^7$ is hydrogen.

In yet another embodiment, compound of formula (I) can include, but are not limited to compounds wherein $R^c$ and $R^d$, together with the carbon atom to which they are attached, optionally form a $C_{3-6}$ cycloalkyl ring.

In one embodiment, compound of formula (I) can include, but are not limited to compounds wherein $R^e$ and $R^f$, at each occurrence, are each independently hydrogen, alkyl, halogen, haloalkyl, $OR^7$, cycloalkylalkyl, heteroaryl, arylalkyl, or heteroarylalkyl; wherein the aryl, cycloalkyl and heteroaryl groups of aryl, cycloalkyl and heteroaryl are each independently unsubstituted or substituted with 1, 2, 3, 4, or 5 substituents independently selected from the group consisting of alkyl and haloalkyl.

In another embodiment, compound of formula (I) can include, but are not limited to compounds wherein $R^g$, and $R^h$, at each occurrence, are each independently hydrogen, alkyl, halogen, haloalkyl, hydroxyalkyl, $OR^7$, cycloalkylalkyl, heteroaryl, arylalkyl, or heteroarylalkyl; wherein the aryl, cycloalkyl and heteroaryl groups of aryl, cycloalkyl and heteroaryl are each independently unsubstituted or substituted with 1, 2, 3, 4, or 5 substituents independently selected from the group consisting of alkyl and haloalkyl.

In a further embodiment, compound of formula (I) can include, but are not limited to compounds wherein $R^g$, and $R^h$, at each occurrence, are each independently hydrogen, alkyl, arylalkyl, cycloalkyl, cycloalkylalkyl, or hydroxyalkyl.

In one embodiment, compound of formula (I) can include, but are not limited to compounds wherein $G^1$ at each occurrence, is independently aryl, cycloalkyl, cycloalkenyl, heteroaryl, or heterocycle; wherein $G^1$ at each occurrence is independently unsubstituted or substituted with 1, 2, 3, 4, or 5 substituents selected from the group consisting of alkyl, alkenyl, alkynyl, cyano, haloalkyl, halogen, nitro, oxo, phenyl, $N(R^7)_2$, $N(R^7)C(O)R^7$, $OR^7$, $C(O)R^7$, $C(O)OR^7$, $C(O)N(R^7)_2$, $SR^7$, $SO_2R^8$, and $SO_2N(R^7)_2$.

In another embodiment, compound of formula (I) can include, but are not limited to compounds wherein $G^1$ at each occurrence, is independently aryl, cycloalkyl, or heteroaryl; wherein $G^1$ at each occurrence is independently unsubstituted or substituted with 1, 2, or 3 substituents selected from the group consisting of alkyl, cyano, haloalkyl, halogen, $OR^7$, or $SR^7$.

In one embodiment, compound of formula (I) can include, but are not limited to compounds wherein $G^2$ at each occurrence, is independently aryl, cycloalkyl, cycloalkenyl, heteroaryl, or heterocycle; wherein $G^2$ at each occurrence is independently unsubstituted or substituted with 1, 2, 3, 4, or 5 substituents selected from the group consisting of alkyl, alkenyl, alkynyl, cyano, haloalkyl, halogen, nitro, oxo, phenyl, $N(R^7)_2$, $N(R^7)C(O)R^7$, $OR^7$, $C(O)R^7$, $C(O)OR^7$, $C(O)N(R^7)_2$, $SO_2R^8$, and $SO_2N(R^7)_2$.

In a further embodiment, compound of formula (I) can include, but are not limited to compounds wherein $G^2$ at each occurrence, is independently aryl, cycloalkyl, heteroaryl or heterocycle; wherein $G^2$ at each occurrence is independently unsubstituted or substituted with 1, 2, or 3 substituents selected from the group consisting of alkyl, cyano, haloalkyl, halogen, nitro, oxo, $OR^7$, $C(O)R^7$, $C(O)OR^7$ or $SO_2R^8$.

In one embodiment, compound of formula (I) can include, but are not limited to compounds wherein $G^3$ at each occurrence, is independently aryl, cycloalkyl, cycloalkenyl, heteroaryl, or heterocycle; wherein $G^3$ at each occurrence is independently unsubstituted or substituted with 1, 2, 3, 4, or 5 substituents selected from the group consisting of alkyl, alkenyl, alkynyl, cyano, haloalkyl, halogen, nitro, oxo, phenyl, $N(R^7)_2$, $N(R^7)C(O)R^7$, $OR^7$, $C(O)R^7$, $C(O)OR^7$, $C(O)N(R^7)_2$, $SO_2R^8$, and $SO_2N(R^7)_2$.

In a further embodiment, compound of formula (I) can include, but are not limited to compounds wherein $G^3$ at each occurrence, is independently aryl, cycloalkyl, heteroaryl or heterocycle; wherein $G^2$ at each occurrence is independently unsubstituted or substituted with 1, 2, or 3 substituents selected from the group consisting of alkyl, cyano, haloalkyl, halogen, nitro, oxo, $OR^7$, $C(O)R^7$, $C(O)OR^7$ or $SO_2R^8$, In one embodiment, compound of formula (I) can include, but are not limited to compounds wherein $R^3$ is hydrogen, alkyl, haloalkyl, cycloalkyl, or cycloalkylalkyl.

In a further embodiment, compound of formula (I) can include, but are not limited to compounds wherein $R^3$ is hydrogen, alkyl, or cycloalkyl.

In one embodiment, compound of formula (I) can include, but are not limited to compounds wherein $R^4$ and $R^5$, at each occurrence, are each independently hydrogen, alkyl, aryl, arylalkyl, cycloalkyl, cycloalkylalkyl, or haloalkyl; wherein said aryl, the aryl of arylalkyl and cycloalkyl are independently unsubstituted or substituted with 1, 2 3, 4, or 5 substituents independently selected from the group consisting of alkyl, haloalkyl, and halogen.

In a further embodiment, compound of formula (I) can include, but are not limited to compounds wherein $R^4$ and $R^5$, at each occurrence, are each independently hydrogen, alkyl, arylalkyl, cycloalkyl or cycloalkylalkyl.

In one embodiment; compound of formula (I) can include, but are not limited to compounds wherein $R^6$ is alkyl, aryl, cycloalkyl, cycloalkenyl, heteroaryl, or heterocycle; wherein said aryl, heteroaryl, and heterocycle are independently unsubstituted or substituted with 1, 2 3, 4, or 5 substituents independently selected from the group consisting of alkyl, haloalkyl, and halogen.

In another embodiment, compound of formula (I) can include, but are not limited to compounds wherein $R^6$ is alkyl or cycloalkyl.

In one embodiment, compound of formula (I) can include, but are not limited to compounds wherein $R^7$, at each occurrence, is independently hydrogen, alkyl, aryl, arylalkyl, cycloalkyl, cycloalkylalkyl, or haloalkyl; wherein said aryl, the aryl of arylalkyl and cycloalkyl are independently unsubstituted or substituted with 1, 2 3, 4, or 5 substituents independently selected from the group consisting of alkyl, haloalkyl, and halogen.

In a further embodiment, compound of formula (I) can include, but are not limited to compounds wherein $R^7$, at each occurrence, is independently hydrogen, alkyl, or haloalkyl.

In one embodiment, compound of formula (I) can include, but are not limited to compounds wherein $R^8$ is alkyl or haloalkyl.

In a further embodiment, compound of formula (I) can include, but are not limited to compounds wherein $R^8$ is alkyl.

In one embodiment, in a compound of formula (I), $L^1$ is $-(CR^aR^b)_m-$; $R^a$ and $R^b$ are each hydrogen; m is 1; $R^1$ is $G^1$, wherein $G^1$ is aryl; $L^2$ is C(O); $R^2$ is $-(CR^cR^d)_p-G^2$, wherein $G^2$ is aryl and p is 1; $R^c$ and $R^d$, together with the carbon atom to which they are attached form a $C_{3-6}$ cycloalkyl ring; and $R^3$ is hydrogen.

In another embodiment, in a compound of formula (I), $L^1$-$R^1$ together are alkyl; or $L^1$ is $-(CR^aR^b)_m-$ or C(O); and $R^1$ is $G^1$; wherein $G^1$ is aryl, cycloalkyl, or heteroaryl; $L^2$ is C(O); $R^2$ is $-(CR^cR^d)_p-G^2$; wherein $G^2$ is aryl and p is 1 or 2; $R^a$, $R^b$, $R^c$, and $R^d$, at each occurrence are independently hydrogen, alkyl or arylalkyl; and $R^3$ is hydrogen or alkyl.

In one embodiment, in a compound of formula (I), $L^1$ is $-(CR^aR^b)_m-$; m is 1 or 2; $R^a$ and $R^b$ are each hydrogen; $R^1$ is $G^1$, wherein $G^1$ is aryl; $L^2$ is C(O)N($R^4$), wherein $R^4$ is alkyl; $R^2$ is $G^2$, wherein $G^2$ is aryl; and $R^3$ is hydrogen.

In another embodiment, in a compound of formula (I), $L^1$ is $-(CR^aR^b)_m-$, C(O), or S(O)$_2$; $R^a$ and $R^b$ at each occurrence are each hydrogen; m is 1; $R^1$ is alkyl or $G^1$, wherein $G^1$ is aryl or cycloalkyl; $L^2$ is C(O); and $R^2$ is $-(CR^cR^d)_p-G^2$; wherein Rc and Rd at each occurrence are independently hydrogen, alkyl or $OR^7$; p is 1; $G^2$ is cycloalkyl or heterocycle; wherein said cycloalkyl or heterocycle is unsubstituted or substituted with 1, 2, 3, 4, or 5 substituents independently selected from the group consisting of alkyl, haloalkyl, halogen, oxo and C(O)$OR^7$; $R^7$ is hydrogen; and $R^3$ is hydrogen.

In one embodiment, in a compound of formula (I), $L^1$ is $-(CR^aR^b)_m-$; $R^a$ and $R^b$ are each hydrogen; m is 1; $R^1$ is $G^1$; wherein $G^1$ is aryl; $L^2$-$R^2$ together are cycloalkyl; and $R^3$ is hydrogen or cycloalkyl.

In another embodiment, in a compound of formula (I), $L^1$ is $-(CR^aR^b)_m-$; $R^a$ and $R^b$ are each hydrogen; m is 1; $R^1$ is $G^1$; wherein $G^1$ is aryl; $L^2$ is C(O); $R^2$ is $-C(R^c)(G^2)(G^3)$ or $-(CR^cR^d)_p-CH(G^2)(G^3)$; wherein $G^2$ is aryl and $G^3$ is aryl or cycloalkyl; $R^c$ and $R^d$, at each occurrence are independently hydrogen; p is 1, 2, 3, 4, or 5; and $R^3$ is hydrogen.

In a further embodiment, in a compound of formula (I), $L^1$-$R^1$ together are hydrogen or $-CH(G^1)_2$; wherein each $G^1$ is aryl or heteroaryl; or $L^1$ is $-(CR^aR^b)_m-$, C(O), or S(O)$_2$; and $R^1$ is $G^1$, $-CH(G^1)_2$, $-(CR^aR^b)_m-G^1$, $-(CR^aR^b)_m-CH(G^1)_2$, $-(CR^eR^f)_n-N(R^5)_2$, wherein each $G^1$ is aryl or heteroaryl; $R^a$ and $R^b$ at each occurrence, are each independently hydrogen; $R^e$ and $R^f$ at each occurrence are each independently hydrogen or alkyl; m is 1, 2, 3, 4, or 5; n is 1 or 2; $R^5$, at each occurrence, is independently hydrogen or alkyl; $L^2$ is C(O); $R^2$ is $-C(R^c)(G^2)(G^3)$; wherein $G^2$ and $G^3$ are each cycloalkyl; $R^c$ is hydrogen or $OR^7$, wherein $R^7$ is hydrogen; and $R^3$ is hydrogen.

In one embodiment, in a compound of formula (I), $L^1$ is $-(CR^aR^b)_m-$; $R^a$ and $R^b$ are each hydrogen; m is 1; $R^1$ is $G^1$, wherein $G^1$ is aryl; or $L^1$-$R^1$ taken together are $G^1$, wherein $G^1$ is aryl or heteroaryl; $L^2$ is C(O); $R^2$ is alkyl or $G^2$; wherein $G^2$ is cycloalkyl or heterocycle; and $R^3$ is hydrogen.

In another embodiment, in a compound of formula (I), $L^1$ is $-(CR^aR^b)_m-$, C(O) or S(O)$_2$, wherein $R^a$ and $R^b$ are each hydrogen and m is 1 or 2; $R^1$ is $G^1$, $-CH(G^1)_2$ or $-(CR^aR^b)_m-G^1$, wherein $G^1$, at each occurrence, is independently aryl or heteroaryl; $L^2$ is C(O); $R^2$ is $-(CR^gR^h)_q-N(R^5)-C(O)O(alkyl)$, $-(CR^gR^h)_q-N(R^5)-C(O)O-G^2$, $-(CR^gR^h)_q-N(R^5)-C(O)(alkyl)$, $-(CR^gR^h)_q-N(R^5)-SO_2R^6$, $-(CR^gR^h)_q-N(R^4)(R^5)$, $-(CR^gR^h)_q-N(R^5)-C(O)N(R^5)-(alkyl)$, or $-(CR^gR^h)_q-N(R^5)-C(O)N(R^5)-G^2$; q is 1 or 2; $R^g$ and $R^h$, at each occurrence, are each independently hydrogen, alkyl, arylalkyl or cycloalkylalkyl; $R^4$ and $R^5$ at each occurrence, are each independently hydrogen, alkyl, arylalkyl, cycloalkyl, or cycloalkylalkyl; $R^6$ is alkyl, aryl, or cycloalkyl; $G^2$ is aryl or cycloalkyl; and $R^3$ is hydrogen, alkyl, cycloalkyl or cycloalkylalkyl.

In one embodiment, in a compound of formula (I), $L^1$-$R^1$ together are hydrogen or hydroxyalkyl; or $L^1$ is $-(CR^aR^b)_m-$, C(O) or S(O)$_2$; $R^1$ is $G^1$, $-(CR^aR^b)_m-G^1$ or $-CH(G^1)_2$, wherein $G^1$ is aryl or heteroaryl, and wherein $R^a$ and $R^b$, at each occurrence, are each independently hydrogen or alkyl; m is 1, 2, 3, 4, or 5; $L^2$ is S(O)$_2$; $R^2$ is $G^2$, wherein $G^2$ is aryl or heteroaryl; and $R^3$ is hydrogen, alkyl or cycloalkyl.

In a further embodiment, in a compound of formula (I), $L^1$ is $-(CR^aR^b)_m-$; $R^a$ and $R^b$, at each occurrence, are each independently hydrogen; m is 1, 2, 3, 4, or 5; $R^1$ is $-CH(G^1)_2$, wherein each $G^1$ is aryl; $L^2$ is C(O); $R^2$ is $-(CR^cR^d)_p-G^2$; wherein $G^2$ is aryl; p is 1; $R^c$ and $R^d$, at each occurrence, are each independently hydrogen or alkyl; and $R^3$ is hydrogen.

In another embodiment, in a compound of formula (I), $L^1$ is C(O), S(O)$_2$ or $-(CR^aR^b)_m-$; $R^a$ and $R^b$, at each occurrence, are independently hydrogen or alkyl; m is 1; $R^1$ is $G^1$ or $-(CR^aR^b)_m-G^1$, wherein $G^1$ is aryl or heteroaryl; or $L^1$-$R^1$ taken together are $G^1$, wherein $G^1$ is aryl or heteroaryl; $L^2$ is $-(CR^cR^d)_p-$; $R^c$ and $R^d$ are each hydrogen or alkyl; p is 1; $R^2$ is $G^2$ or $-C(O)N(R^4)(R^5)$, wherein $G^2$ is aryl, cycloalkyl or heteroaryl and $R^4$ and $R^5$, are independently hydrogen or alkyl; or $L^2$-$R^2$ taken together are hydrogen, alkyl, $G^2$, or $-C(R^c)(G^2)(G^3)$, wherein $G^2$ and $G^3$ are each aryl or heteroaryl and $R^c$ is hydrogen; and $R^3$ is hydrogen or alkyl.

In a further embodiment, in a compound of formula (I), $L^1$ is C(O); $R^1$ is $-(CR^eR^f)_n-N(R^5)_2$; n is 1 or 2; $R^e$ and $R^f$ at each occurrence are each independently hydrogen or alkyl; $R^5$ at each occurrence is independently hydrogen or alkyl; $L^2$ is C(O) or S(O)$_2$; $R^2$ is $G^2$ or $-C(R^c)(G^2)(G^3)$, wherein $G^2$ and $G^3$ are each aryl or heteroaryl and $R^c$ is hydrogen; and $R^3$ is hydrogen, alkyl, or cycloalkyl. In an additional embodiment, in a compound of formula (I), $L^1$ is C(O); $R^1$ is $-(CR^eR^f)_n-N(R^5)_2$ or $-(CR^eR^f)_n-N(R^5)C(O)O(alkyl)$; n is 1 or 2; $R^e$ and $R^f$ at each occurrence are each independently hydrogen, alkyl, or arylalkyl; $R^5$ at each occurrence is independently hydrogen, alkyl or cycloalkyl; $L^2$ is C(O); $R^2$ is $-(CR^gR^h)_qN(R^4)(R^5)$ or $-(CR^gR^h)_q-N(R^5)C(O)O(alkyl)$; q is 1 or 2; $R^4$ is hydrogen or alkyl; $R^g$ and $R^h$ at each occurrence are each independently hydrogen or alkyl; and $R^3$ is hydrogen.

In another embodiment, in a compound of formula (I), $L^1$-$R^1$ taken together are hydrogen, $G^1$ or $CH(G^1)_2$, wherein $G^1$ is aryl or heteroaryl; $L^2$ is C(O); $R^2$ is haloalkyl, hydroxyalkyl, $-CH(OH)CF_3$, $-(CR^cR^d)_p-CH(OH)CF_3$, $-(CR^gR^h)_qN(R^4)(R^5)$ or $-(CR^gR^h)_q-N(R^5)C(O)O(alkyl)$; p is 1 or 2; q is 1 or 2; $R^4$ is hydrogen, alkyl, or cycloalkylalkyl; $R^5$ is hydrogen or alkyl; $R^c$ and $R^d$ at each occurrence are each independently hydrogen or alkyl; $R^g$ and $R^h$ at each occurrence are each independently hydrogen, alkyl, cycloalkylalkyl or hydroxyalkyl; and $R^3$ is hydrogen. In a further embodiment, in a compound of formula (I), $L^1$-$R^1$ taken together are $G^1$, wherein $G^1$ is aryl or heteroaryl; $L^2$ is C(O) or S(O)$_2$; $R^2$ is $G^2$ or $G^2$-$G^3$, wherein $G^2$ is aryl or heteroaryl and $G^3$ is cycloalkyl or heteroaryl; and $R^3$ is hydrogen or alkyl.

In another embodiment, in a compound of formula (I), $L^1$-$R^1$ taken together are $G^1$, wherein $G^1$ is aryl or heteroaryl; $L^2$ is —(CR$^c$R$^d$)$_p$—, wherein R$^c$ and R$^d$, at each occurrence, are each independently hydrogen or alkyl; p is 1, 2 or 3; $R^2$ is $G^2$ or -$G^2$-$G^3$, wherein $G^2$ is aryl or heteroaryl and $G^3$ is aryl or heteroaryl; and $R^3$ is hydrogen or alkyl.

In another embodiment, in a compound of formula (I), $L^1$-$R^1$ taken together are $G^1$, wherein $G^1$ is aryl or heteroaryl; $L^2$ is C(O)N(R$^4$), wherein R$^4$ is hydrogen; $R^2$ is alkyl or $G^2$ or -$G^2$-$G^3$, wherein $G^2$ is aryl or heteroaryl and $G^3$ is aryl or heteroaryl; and $R^3$ is hydrogen or alkyl.

In a further embodiment, in a compound of formula (I), $L^1$-$R^1$ taken together are $G^1$, wherein $G^1$ is aryl or heteroaryl; $L^2$ is C(O) or S(O)$_2$; $R^2$ is, —C(R$^c$)(G$^2$)(G$^3$), —(CR$^c$R$^d$)$_p$-G$^2$, or —(CR$^c$R$^d$)$_p$—CH(G$^2$)(G$^3$); Rc and Rd, at each occurrence, are each independently hydrogen or alkyl; p is 1, 2, or 3; $G^2$ and $G^3$ are independently aryl or heteroaryl; and $R^3$ is hydrogen or alkyl.

Specific embodiments of compounds contemplated as part of the invention include, but are not limited to:
N-[(3aS*,4S*,6aR*)-2-benzyloctahydrocyclopenta[c]pyrrol-4-yl]-1-phenylcyclopentanecarboxamide;
N-[(3aS*,4R*,6aR*)-2-benzyloctahydrocyclopenta[c]pyrrol-4-yl]-1-phenylcyclopentanecarboxamide;
N-[(3aR*,4R*,6aS*)-2-benzyloctahydrocyclopenta[c]pyrrol-4-yl]-2-cyclohexyl-2-phenylacetamide;
N-[(3aS*,4R*,6aR*)-2-benzyloctahydrocyclopenta[c]pyrrol-4-yl]-2-cyclohexyl-2-phenylacetamide;
N-[(3aR*,4R*,6aS*)-2-benzyloctahydrocyclopenta[c]pyrrol-4-yl]-3-methyl-2-phenylbutanamide;
N-[(3aR*,4S*,6aS*)-2-benzyloctahydrocyclopenta[c]pyrrol-4-yl]-3-methyl-2-phenylbutanamide;
N-[(3aS*,4S*,6aR*)-2-benzyloctahydrocyclopenta[c]pyrrol-4-yl]-2-cyclopentyl-2-phenylacetamide;
N-[(3aS*,4R*,6aR*)-2-benzyloctahydrocyclopenta[c]pyrrol-4-yl]-2-cyclopentyl-2-phenylacetamide;
N-[(3aS*,4S*,6aR*)-2-benzyloctahydrocyclopenta[c]pyrrol-4-yl]-1-phenylcyclohexanecarboxamide;
N-[(3aS*,4R*,6aR*)-2-benzyloctahydrocyclopenta[c]pyrrol-4-yl]-1-phenylcyclohexanecarboxamide;
N-[(3aS*,4S*,6aR*)-2-benzyloctahydrocyclopenta[c]pyrrol-4-yl]-2,2-dicyclohexylacetamide;
(2S)-2-(3-benzoylphenyl)-N-[(3aS*,4S*,6aR*)-2-benzyloctahydrocyclopenta[c]pyrrol-4-yl]propanamide;
(2S)-2-(3-benzoylphenyl)-N-[(3aS*,4R*,6aR*)-2-benzyloctahydrocyclopenta[c]pyrrol-4-yl]propanamide;
N-[(3aS,4S,6aR)-2-benzyloctahydrocyclopenta[c]pyrrol-4-yl]-3-methyl-2-phenylbutanamide;
N-[(3aS,4S,6aR)-2-benzyloctahydrocyclopenta[c]pyrrol-4-yl]-2,2-dicyclohexylacetamide;
(2S)-N-[(3aS,4R,6aR)-2-benzyloctahydrocyclopenta[c]pyrrol-4-yl]-2-phenylbutanamide;
N-[(3aS,4R,6aR)-2-benzyloctahydrocyclopenta[c]pyrrol-4-yl]-2-cyclopentyl-2-phenylacetamide;
N-[(3aS,4R,6aR)-2-benzyloctahydrocyclopenta[c]pyrrol-4-yl]-3-methyl-2-phenylbutanamide;
(2S)-N-[(3aS,4R,6aR)-2-benzyloctahydrocyclopenta[c]pyrrol-4-yl]-2-phenylpropanamide;
N-[(3aS,4R,6aR)-2-benzyloctahydrocyclopenta[c]pyrrol-4-yl]-2,2-dicyclohexylacetamide;
N-[(3aS,4R,6aR)-2-benzyloctahydrocyclopenta[c]pyrrol-4-yl]-2-propylpentanamide;
N-[(3aS,4R,6aR)-2-benzyloctahydrocyclopenta[c]pyrrol-4-yl]cycloheptanecarboxamide;
(2S)-N-[(3aS,4R,6aR)-2-benzyloctahydrocyclopenta[c]pyrrol-4-yl]-2-(4-isobutylphenyl)propanamide;
N-[(3aS,4R,6aR)-2-benzyloctahydrocyclopenta[c]pyrrol-4-yl]-1-phenylcyclohexanecarboxamide;
N-[(3aS,4R,6aR)-2-benzyloctahydrocyclopenta[c]pyrrol-4-yl]-2,3-diphenylpropanamide;
N-[(3aS,4R,6aR)-2-benzyloctahydrocyclopenta[c]pyrrol-4-yl]-2-methyl-3-phenylpropanamide;
N-[(3aS,4R,6aR)-2-benzyloctahydrocyclopenta[c]pyrrol-4-yl]-2-methyl-2-phenylpropanamide;
N-[(3aS,4R,6aR)-2-benzyloctahydrocyclopenta[c]pyrrol-4-yl]-1-phenylcyclopropanecarboxamide;
2-benzyl-N-[(3aS,4R,6aR)-2-benzyloctahydrocyclopenta[c]pyrrol-4-yl]-3,3-dimethylbutanamide;
N-[(3aS,4R,6aR)-2-benzyloctahydrocyclopenta[c]pyrrol-4-yl]-3,3-dimethyl-2-phenylbutanamide;
(2S)-N-[(3aS,4R,6aR)-2-benzyloctahydrocyclopenta[c]pyrrol-4-yl]-3,3-dimethyl-2-phenylbutanamide;
(2R)-N-[(3aS,4R,6aR)-2-benzyloctahydrocyclopenta[c]pyrrol-4-yl]-3,3-dimethyl-2-phenylbutanamide;
(2S)-N-[(3aS,4S,6aS)-2-benzyloctahydrocyclopenta[c]pyrrol-4-yl]-2-phenylbutanamide;
N-[(3aR,4S,6aS)-2-benzyloctahydrocyclopenta[c]pyrrol-4-yl]-2-cyclopentyl-2-phenylacetamide;
N-[(3aS,4S,6aS)-2-benzyloctahydrocyclopenta[c]pyrrol-4-yl]-3-methyl-2-phenylbutanamide;
(2R)-N-[(3aR,4S,6aS)-2-benzyloctahydrocyclopenta[c]pyrrol-4-yl]-2-phenylbutanamide;
(2R)-N-[(3aR,4S,6aS)-2-benzyloctahydrocyclopenta[c]pyrrol-4-yl]-2-phenylpropanamide;
(2S)-N-[(3aR,4S,6aS)-2-benzyloctahydrocyclopenta[c]pyrrol-4-yl]-2-phenylpropanamide;
(2S)-N-[(3aR,4S,6aS)-2-benzyloctahydrocyclopenta[c]pyrrol-4-yl]-2-(4-isobutylphenyl)propanamide;
N-[(3aR,4S,6aS)-2-benzyloctahydrocyclopenta[c]pyrrol-4-yl]-2,2-dicyclohexylacetamide;
N-[(3aR,4S,6aS)-2-benzyloctahydrocyclopenta[c]pyrrol-4-yl]-2-cyclopropyl-2-phenylacetamide;
N-[(3aR,4S,6aS)-2-benzyloctahydrocyclopenta[c]pyrrol-4-yl]-2-cyclobutyl-2-phenylacetamide;
N-[(3aR,4S,6aS)-2-benzyloctahydrocyclopenta[c]pyrrol-4-yl]-2-(4-chlorophenyl)-3-methylbutanamide;
N-[(3aR,4S,6aS)-2-benzyloctahydrocyclopenta[c]pyrrol-4-yl]-3-ethyl-2-phenylpentanamide;
N-[(3aR,4S,6aS)-2-benzyloctahydrocyclopenta[c]pyrrol-4-yl]-2-(4-hydroxyphenyl)-3-methylbutanamide;
N-[(3aR,4S,6aS)-2-benzyloctahydrocyclopenta[c]pyrrol-4-yl]-1-phenylcyclohexanecarboxamide;
N-[(3aR,4S,6aS)-2-benzyloctahydrocyclopenta[c]pyrrol-4-yl]-2-methyl-2-phenylpropanamide;
N-[(3aR,4S,6aS)-2-benzyloctahydrocyclopenta[c]pyrrol-4-yl]-1-phenylcyclopropanecarboxamide;
2-benzyl-N-[(3aR,4S,6aS)-2-benzyloctahydrocyclopenta[c]pyrrol-4-yl]-3,3-dimethylbutanamide;
N-[(3aR,4S,6aS)-2-benzyloctahydrocyclopenta[c]pyrrol-4-yl]-2,3-diphenylpropanamide;
N-[(3aR,4S,6aS)-2-benzyloctahydrocyclopenta[c]pyrrol-4-yl]-2-methyl-3-phenylpropanamide;
N-[(3aR,4S,6aS)-2-benzyloctahydrocyclopenta[c]pyrrol-4-yl]-3,3-dimethyl-2-phenylbutanamide;

2,2-dicyclohexyl-N-[(3aS,4S,6aR)-octahydrocyclopenta[c]pyrrol-4-yl]acetamide;
2,2-dicyclohexyl-N-{(3aS,4S,6aR)-2-[3-(trifluoromethyl)benzyl]octahydrocyclopenta[c]pyrrol-4-yl}acetamide;
2,2-dicyclohexyl-N-[(3aS,4S,6aR)-2-(2-fluorobenzyl)octahydrocyclopenta[c]pyrrol-4-yl]acetamide;
2,2-dicyclohexyl-N-[(3aS,4S,6aR)-2-(4-fluorobenzyl)octahydrocyclopenta[c]pyrrol-4-yl]acetamide;
2,2-dicyclohexyl-N-{(3aS,4S,6aR)-2-[4-fluoro-3-(trifluoromethyl)benzyl]octahydrocyclopenta[c]pyrrol-4-yl}acetamide;
2,2-dicyclohexyl-N-{(3aS,4S,6aR)-2-[3-fluoro-4-(trifluoromethyl)benzyl]octahydrocyclopenta[c]pyrrol-4-yl}acetamide;
N-{(3aS,4S,6aR)-2-[3,5-bis(trifluoromethyl)benzyl]octahydrocyclopenta[c]pyrrol-4-yl}-2,2-dicyclohexylacetamide;
2,2-dicyclohexyl-N-{(3aS,4S,6aR)-2-[2-(trifluoromethyl)benzyl]octahydrocyclopenta[c]pyrrol-4-yl}acetamide;
2,2-dicyclohexyl-N-[(3aS,4S,6aR)-2-(3-methylbenzyl)octahydrocyclopenta[c]pyrrol-4-yl]acetamide;
2,2-dicyclohexyl-N-[(3aS,4S,6aR)-2-(4-methylbenzyl)octahydrocyclopenta[c]pyrrol-4-yl]acetamide;
2,2-dicyclohexyl-N-{(3aS,4S,6aR)-2-[3-(trifluoromethoxy)benzyl]octahydrocyclopenta[c]pyrrol-4-yl}acetamide;
2,2-dicyclohexyl-N-[(3aS,4S,6aR)-2-(3-fluorobenzyl)octahydrocyclopenta[c]pyrrol-4-yl]acetamide;
N-{(3aS,4S,6aR)-2-[3,3-bis(4-fluorophenyl)propyl]octahydrocyclopenta[c]pyrrol-4-yl}-2,2-dicyclohexylacetamide;
N-{(3aS,4S,6aR)-2-[6,6-bis(4-fluorophenyl)hexyl]octahydrocyclopenta[c]pyrrol-4-yl}-2,2-dicyclohexylacetamide;
N-{(3aS,4S,6aR)-2-[3-(3-chlorophenyl)propyl]octahydrocyclopenta[c]pyrrol-4-yl}-2,2-dicyclohexylacetamide;
2,2-dicyclohexyl-N-{(3aS,4S,6aR)-2-[3-(3-fluorophenyl)propyl]octahydrocyclopenta[c]pyrrol-4-yl}acetamide;
2,2-dicyclohexyl-N-[(3aS,4S,6aR)-2-(3-phenylpropyl)octahydrocyclopenta[c]pyrrol-4-yl]acetamide;
2,2-dicyclohexyl-N-((3aS,4S,6aR)-2-{3-[4-(trifluoromethyl)phenyl]propyl}octahydrocyclopenta[c]pyrrol-4-yl)acetamide;
2,2-dicyclohexyl-N-{(3aS,4S,6aR)-2-[3-(4-fluorophenyl)propyl]octahydrocyclopenta[c]pyrrol-4-yl}acetamide;
2,2-dicyclohexyl-N-[(3aS,4S,6aR)-2-(pyridin-4-ylmethyl)octahydrocyclopenta[c]pyrrol-4-yl]acetamide;
2,2-dicyclohexyl-N-[(3aS,4S,6aR)-2-(pyridin-3-ylmethyl)octahydrocyclopenta[c]pyrrol-4-yl]acetamide;
2,2-dicyclohexyl-N-[(3aS,4R,6aR)-octahydrocyclopenta[c]pyrrol-4-yl]acetamide;
2,2-dicyclohexyl-N-{(3aS,4R,6aR)-2-[3-(trifluoromethyl)benzyl]octahydrocyclopenta[c]pyrrol-4-yl}acetamide;
2,2-dicyclohexyl-N-{(3aS,4R,6aR)-2-[3-fluoro-4-(trifluoromethyl)benzyl]octahydrocyclopenta[c]pyrrol-4-yl}acetamide;
N-{(3aS,4R,6aR)-2-[3,5-bis(trifluoromethyl)benzyl]octahydrocyclopenta[c]pyrrol-4-yl}-2,2-dicyclohexylacetamide;
N-{(3aS,4R,6aR)-2-[6,6-bis(4-fluorophenyl)hexyl]octahydrocyclopenta[c]pyrrol-4-yl}-2,2-dicyclohexylacetamide;
2,2-dicyclohexyl-N-[(3aS,4R,6aR)-2-(3,3-diphenylpropyl)octahydrocyclopenta[c]pyrrol-4-yl]acetamide;
N-{(3aS,4R,6aR)-2-[3,3-bis(4-fluorophenyl)propyl]octahydrocyclopenta[c]pyrrol-4-yl}-2,2-dicyclohexylacetamide;
N-{(3aS,4R,6aR)-2-[4,4-bis(4-fluorophenyl)butyl]octahydrocyclopenta[c]pyrrol-4-yl}-2,2-dicyclohexylacetamide;
3-methyl-2-phenyl-N-{(3aS,4R,6aR)-2-[3-(trifluoromethyl)benzyl]octahydrocyclopenta[c]pyrrol-4-yl}butanamide;
N-[(3aR,4S,6aS)-2-(cyclohexylmethyl)octahydrocyclopenta[c]pyrrol-4-yl]-3-methyl-2-phenylbutanamide;
3-methyl-N-[(3aR,4S,6aS)-2-methyloctahydrocyclopenta[c]pyrrol-4-yl]-2-phenylbutanamide;
N-[(3aR,4S,6aS)-2-(2-fluorobenzyl)octahydrocyclopenta[c]pyrrol-4-yl]-3-methyl-2-phenylbutanamide;
N-[(3aR,4S,6aS)-2-(3-chlorobenzyl)octahydrocyclopenta[c]pyrrol-4-yl]-3-methyl-2-phenylbutanamide;
N-[(3aR,4S,6aS)-2-(3-fluorobenzyl)octahydrocyclopenta[c]pyrrol-4-yl]-3-methyl-2-phenylbutanamide;
3-methyl-2-phenyl-N-{(3aR,4S,6aS)-2-[3-(trifluoromethyl)benzyl]octahydrocyclopenta[c]pyrrol-4-yl}butanamide;
N-[(3aR,4S,6aS)-2-(4-fluorobenzyl)octahydrocyclopenta[c]pyrrol-4-yl]-3-methyl-2-phenylbutanamide;
N-[(3aR,4S,6aS)-2-(3-methoxybenzyl)octahydrocyclopenta[c]pyrrol-4-yl]-3-methyl-2-phenylbutanamide;
3-methyl-N-[(3aR,4S,6aS)-2-(3-methylbenzyl)octahydrocyclopenta[c]pyrrol-4-yl]-2-phenylbutanamide;
3-methyl-N-[(3aR,4S,6aS)-2-(2-methylbenzyl)octahydrocyclopenta[c]pyrrol-4-yl]-2-phenylbutanamide;
N-[(3aR,4S,6aS)-2-(2,6-dimethylbenzyl)octahydrocyclopenta[c]pyrrol-4-yl]-3-methyl-2-phenylbutanamide;
N-[(3aR,4S,6aS)-2-(2-methoxybenzyl)octahydrocyclopenta[c]pyrrol-4-yl]-3-methyl-2-phenylbutanamide;
N-[(3aR,4S,6aS)-2-(4-tert-butylbenzyl)octahydrocyclopenta[c]pyrrol-4-yl]-3-methyl-2-phenylbutanamide;
N-[(3aR,4S,6aS)-2-(4-methoxybenzyl)octahydrocyclopenta[c]pyrrol-4-yl]-3-methyl-2-phenylbutanamide;
N-[(3aR,4S,6aS)-2-(3-cyanobenzyl)octahydrocyclopenta[c]pyrrol-4-yl]-3-methyl-2-phenylbutanamide;
3-methyl-2-phenyl-N-{(3aR,4S,6aS)-2-[4-(trifluoromethyl)benzyl]octahydrocyclopenta[c]pyrrol-4-yl}butanamide;
3-methyl-2-phenyl-N-{(3aR,4S,6aS)-2-[2-(trifluoromethyl)benzyl]octahydrocyclopenta[c]pyrrol-4-yl}butanamide;
N-{(3aR,4S,6aS)-2-[4-fluoro-3-(trifluoromethyl)benzyl]octahydrocyclopenta[c]pyrrol-4-yl}-3-methyl-2-phenylbutanamide;
N-{(3aR,4S,6aS)-2-[3-fluoro-4-(trifluoromethyl)benzyl]octahydrocyclopenta[c]pyrrol-4-yl}-3-methyl-2-phenylbutanamide;
3-methyl-2-phenyl-N-[(3aR,4S,6aS)-2-(thien-2-ylmethyl)octahydrocyclopenta[c]pyrrol-4-yl]butanamide;
3-methyl-2-phenyl-N-[(3aR,4S,6aS)-2-(pyridin-4-ylmethyl)octahydrocyclopenta[c]pyrrol-4-yl]butanamide;
3-methyl-2-phenyl-N-[(3aR,4S,6aS)-2-(2-phenylethyl)octahydrocyclopenta[c]pyrrol-4-yl]butanamide;
3-methyl-2-phenyl-N-[(3aR,4S,6aS)-2-(3-phenylpropyl)octahydrocyclopenta[c]pyrrol-4-yl]butanamide;
N-{(3aR,4S,6aS)-2-[3-(4-tert-butylphenyl)propyl]octahydrocyclopenta[c]pyrrol-4-yl}-3-methyl-2-phenylbutanamide;
N-{(3aR,4S,6aS)-2-[6,6-bis(4-fluorophenyl)hexyl]octahydrocyclopenta[c]pyrrol-4-yl}-3-methyl-2-phenylbutanamide;
3-methyl-N-{(3aR,4S,6aS)-2-[3-(2-methylphenyl)propyl]octahydrocyclopenta[c]pyrrol-4-yl}-2-phenylbutanamide;
N-{(3aR,4S,6aS)-2-[3-(3-chlorophenyl)propyl]octahydrocyclopenta[c]pyrrol-4-yl}-3-methyl-2-phenylbutanamide;
3-methyl-N-{(3aR,4S,6aS)-2-[3-(3-methylphenyl)propyl]octahydrocyclopenta[c]pyrrol-4-yl}-2-phenylbutanamide;
3-methyl-2-phenyl-N-((3aR,4S,6aS)-2-{3-[3-(trifluoromethyl)phenyl]propyl}octahydrocyclopenta[c]pyrrol-4-yl)butanamide;
N-{(3aR,4S,6aS)-2-[3-(3-fluorophenyl)propyl]octahydrocyclopenta[c]pyrrol-4-yl}-3-methyl-2-phenylbutanamide;

3-methyl-2-phenyl-N-[(3aR,4S,6aS)-2-(4-phenylbutyl)octahydrocyclopenta[c]pyrrol-4-yl]butanamide;

N-{(3aR,4S,6aS)-2-[3-(3-chloro-5-fluorophenyl)propyl]octahydrocyclopenta[c]pyrrol-4-yl}-3-methyl-2-phenylbutanamide;

3-methyl-2-phenyl-N-((3aR,4S,6aS)-2-{3-[4-(trifluoromethyl)phenyl]propyl}octahydrocyclopenta[c]pyrrol-4-yl)butanamide;

N-[(3aR,4S,6aS)-2-(3,3-diphenylpropyl)octahydrocyclopenta[c]pyrrol-4-yl]-3-methyl-2-phenylbutanamide;

N-{(3aR,4S,6aS)-2-[3,3-bis(4-fluorophenyl)propyl]octahydrocyclopenta[c]pyrrol-4-yl}-3-methyl-2-phenylbutanamide;

N-{(3aR,4S,6aS)-2-[4,4-bis(4-fluorophenyl)butyl]octahydrocyclopenta[c]pyrrol-4-yl}-3-methyl-2-phenylbutanamide;

N-{(3aR,4S,6aS)-2-[5,5-bis(4-fluorophenyl)pentyl]octahydrocyclopenta[c]pyrrol-4-yl}-3-methyl-2-phenylbutanamide;

N-[(3aS,4S,6aR)-2-benzhydryloctahydrocyclopenta[c]pyrrol-4-yl]-2,2-dicyclohexylacetamide;

N-[(3aS,4R,6aR)-2-benzhydryloctahydrocyclopenta[c]pyrrol-4-yl]-2,2-dicyclohexylacetamide;

3-methyl-2-phenyl-N-{(3aS*,4S*,6aR*)-2-[3-(trifluoromethyl)benzyl]octahydrocyclopenta[c]pyrrol-4-yl}butanamide;

3,3-dimethyl-2-phenyl-N-{(3aS*,4S*,6aR*)-2-[3-(trifluoromethyl)benzyl]octahydrocyclopenta[c]pyrrol-4-yl}butanamide;

2,2-dicyclohexyl-N-{(3aS*,4S*,6aR*)-2-[3-(trifluoromethyl)benzyl]octahydrocyclopenta[c]pyrrol-4-yl}acetamide;

2-ethyl-N-{(3aS*,4S*,6aR*)-2-[3-(trifluoromethyl)benzyl]octahydrocyclopenta[c]pyrrol-4-yl}butanamide;

2-propyl-N-{(3aS*,4S*,6aR*)-2-[3-(trifluoromethyl)benzyl]octahydrocyclopenta[c]pyrrol-4-yl}pentanamide;

N-{(3aS*,4S*,6aR*)-2-[3-(trifluoromethyl)benzyl]octahydrocyclopenta[c]pyrrol-4-yl}cyclohexanecarboxamide;

N-{(3aS*,4S*,6aR*)-2-[3-(trifluoromethyl)benzyl]octahydrocyclopenta[c]pyrrol-4-yl}cycloheptanecarboxamide;

N-{(3aS*,4S*,6aR*)-2-[3-(trifluoromethyl)benzyl]octahydrocyclopenta[c]pyrrol-4-yl}cyclopentanecarboxamide;

6,6-bis(4-fluorophenyl)-N-{(3aS*,4S*,6aR*)-2-[3-(trifluoromethyl)benzyl]octahydrocyclopenta[c]pyrrol-4-yl}hexanamide;

3,3-diphenyl-N-{(3aS*,4S*,6aR*)-2-[3-(trifluoromethyl)benzyl]octahydrocyclopenta[c]pyrrol-4-yl}propanamide;

5,5-bis(4-fluorophenyl)-N-{(3aS*,4S*,6aR*)-2-[3-(trifluoromethyl)benzyl]octahydrocyclopenta[c]pyrrol-4-yl}pentanamide;

3,3-bis(4-fluorophenyl)-N-{(3aS*,4S*,6aR*)-2-[3-(trifluoromethyl)benzyl]octahydrocyclopenta[c]pyrrol-4-yl}propanamide;

4,4-bis(4-fluorophenyl)-N-{(3aS*,4S*,6aR*)-2-[3-(trifluoromethyl)benzyl]octahydrocyclopenta[c]pyrrol-4-yl}butanamide;

2,2-diphenyl-N-{(3aS*,4S*,6aR*)-2-[3-(trifluoromethyl)benzyl]octahydrocyclopenta[c]pyrrol-4-yl}acetamide;

2,2-bis(4-fluorophenyl)-N-{(3aS*,4S*,6aR*)-2-[3-(trifluoromethyl)benzyl]octahydrocyclopenta[c]pyrrol-4-yl}acetamide;

$N^2$-(tert-butyloxycarbonyl)-$N^1$-{(3aR*,4R*,6aS*)-2-[3-(trifluoromethyl)benzyl]octahydrocyclopenta[c]pyrrol-4-yl}-L-leucinamide;

$N^2$-(tert-butyloxycarbonyl)-$N^1$-{(3aS*,4S*,6aR*)-2-[3-(trifluoromethyl)benzyl]octahydrocyclopenta[c]pyrrol-4-yl}-D-leucinamide;

$N^2$-(tert-butyloxycarbonyl)-$N^2$-methyl-$N^1$-{(3aS*,4S*,6aR*)-2-[3-(trifluoromethyl)benzyl]octahydrocyclopenta[c]pyrrol-4-yl}-D-leucinamide;

6,6-bis(4-fluorophenyl)-N-{(3aS*,4R*,6aR*)-2-[3-(trifluoromethyl)benzyl]octahydrocyclopenta[c]pyrrol-4-yl}hexanamide;

3,3-diphenyl-N-{(3aS*,4R*,6aR*)-2-[3-(trifluoromethyl)benzyl]octahydrocyclopenta[c]pyrrol-4-yl}propanamide;

5,5-bis(4-fluorophenyl)-N-{(3aS*,4R*,6aR*)-2-[3-(trifluoromethyl)benzyl]octahydrocyclopenta[c]pyrrol-4-yl}pentanamide;

3,3-bis(4-fluorophenyl)-N-{(3aS*,4R*,6aR*)-2-[3-(trifluoromethyl)benzyl]octahydrocyclopenta[c]pyrrol-4-yl}propanamide;

4,4-bis(4-fluorophenyl)-N-{(3aS*,4R*,6aR*)-2-[3-(trifluoromethyl)benzyl]octahydrocyclopenta[c]pyrrol-4-yl}butanamide;

2,2-diphenyl-N-{(3aS*,4R*,6aR*)-2-[3-(trifluoromethyl)benzyl]octahydrocyclopenta[c]pyrrol-4-yl}acetamide;

2,2-bis(4-fluorophenyl)-N-{(3aS*,4R*,6aR*)-2-[3-(trifluoromethyl)benzyl]octahydrocyclopenta[c]pyrrol-4-yl}acetamide;

3,3-dimethyl-2-phenyl-N-{(3aS*,4R*,6aR*)-2-[3-(trifluoromethyl)benzyl]octahydrocyclopenta[c]pyrrol-4-yl}butanamide;

$N^2$-(tert-butyloxycarbonyl)-$N^1$-{(3aS*,4R*,6aR*)-2-[3-(trifluoromethyl)benzyl]octahydrocyclopenta[c]pyrrol-4-yl}-L-leucinamide;

$N^2$-(tert-butyloxycarbonyl)-$N^1$-{(3aS*,4R*,6aR*)-2-[3-(trifluoromethyl)benzyl]octahydrocyclopenta[c]pyrrol-4-yl}-D-leucinamide;

$N^2$-(tert-butyloxycarbonyl)-$N^2$-methyl-$N^1$-{(3aS*,4R*,6aR*)-2-[3-(trifluoromethyl)benzyl]octahydrocyclopenta[c]pyrrol-4-yl}-D-leucinamide;

$N^1$-[(3aS,4R,6aR)-2-benzyloctahydrocyclopenta[c]pyrrol-4-yl]-$N^2$-(tert-butyloxycarbonyl)-$N^2$-methyl-L-leucinamide;

2,2-dicyclohexyl-2-hydroxy-N-{(3aS,4S,6aS)-2-[3-(trifluoromethyl)benzyl]octahydrocyclopenta[c]pyrrol-4-yl}acetamide;

$N^2$-(tert-butyloxycarbonyl)-$N^2$-methyl-$N^1$-{(3aS,4S,6aS)-2-[3-(trifluoromethyl)benzyl]octahydrocyclopenta[c]pyrrol-4-yl}-L-leucinamide;

2,2-dicyclohexyl-2-hydroxy-N-{(3aS,4R,6aR)-2-[3-(trifluoromethyl)benzyl]octahydrocyclopenta[c]pyrrol-4-yl}acetamide;

$N^2$-(tert-butyloxycarbonyl)-$N^2$-methyl-$N^1$-{(3aS,4R,6aR)-2-[3-(trifluoromethyl)benzyl]octahydrocyclopenta[c]pyrrol-4-yl}-L-leucinamide;

2,2-dicyclohexyl-N-{(3aR,4S,6aS)-2-[3-(trifluoromethyl)benzyl]octahydrocyclopenta[c]pyrrol-4-yl}acetamide;

2,2-dicyclohexyl-N-{(3aR,4R,6aS)-2-[3-(trifluoromethyl)benzyl]octahydrocyclopenta[c]pyrrol-4-yl}acetamide;

$N^1$-{(3aS*,4S*,6aR*)-2-[3-(trifluoromethyl)benzyl]octahydrocyclopenta[c]pyrrol-4-yl}-L-leucinamide;

$N^1$-{(3aR*,4R*,6aS*)-2-[3-(trifluoromethyl)benzyl]octahydrocyclopenta[c]pyrrol-4-yl}-D-leucinamide;

$N^2$-methyl-$N^1$-{(3aS*,4S*,6aR*)-2-[3-(trifluoromethyl)benzyl]octahydrocyclopenta[c]pyrrol-4-yl}-D-leucinamide;

$N^1$-{(3aS*,4R*,6aR*)-2-[3-(trifluoromethyl)benzyl]octahydrocyclopenta[c]pyrrol-4-yl}-L-leucinamide;

$N^1$-{(3aS*,4R*,6aR*)-2-[3-(trifluoromethyl)benzyl]octahydrocyclopenta[c]pyrrol-4-yl}-D-leucinamide;

$N^2$-methyl-$N^1$-{(3aS*,4R*,6aR*)-2-[3-(trifluoromethyl)benzyl]octahydrocyclopenta[c]pyrrol-4-yl}-D-leucinamide;

N²-methyl-N¹-{(3aS,4S,6aR)-2-[3-(trifluoromethyl)benzyl]octahydrocyclopenta[c]pyrrol-4-yl}-L-leucinamide;

N¹-[(3aS,4R,6aR)-2-benzyloctahydrocyclopenta[c]pyrrol-4-yl]-N²-methyl-L-leucinamide;

N²-methyl-N¹-{(3aS,4R,6aR)-2-[3-(trifluoromethyl)benzyl]octahydrocyclopenta[c]pyrrol-4-yl}-L-leucinamide;

N²-methyl-N²-(methylsulfonyl)-N¹-{(3aS,4S,6aR)-2-[3-(trifluoromethyl)benzyl]octahydrocyclopenta[c]pyrrol-4-yl}-L-leucinamide;

N¹-[(3aS,4R,6aR)-2-benzyloctahydrocyclopenta[c]pyrrol-4-yl]-N²-methyl-N²-(methylsulfonyl)-L-leucinamide;

N²-methyl-N²-(methylsulfonyl)-N¹-{(3aS,4R,6aR)-2-[3-(trifluoromethyl)benzyl]octahydrocyclopenta[c]pyrrol-4-yl}-L-leucinamide;

N²-(methylsulfonyl)-N¹-{(3aS,4R,6aR)-2-[3-(trifluoromethyl)benzyl]octahydrocyclopenta[c]pyrrol-4-yl}-L-leucinamide;

N²-(methylsulfonyl)-N¹-{(3aS,4R,6aR)-2-[3-(trifluoromethyl)benzyl]octahydrocyclopenta[c]pyrrol-4-yl}-D-leucinamide;

N²-(cyclopropylsulfonyl)-N¹-{(3aS,4R,6aR)-2-[3-(trifluoromethyl)benzyl]octahydrocyclopenta[c]pyrrol-4-yl}-L-leucinamide;

N²-(isobutylsulfonyl)-N¹-{(3aS,4R,6aR)-2-[3-(trifluoromethyl)benzyl]octahydrocyclopenta[c]pyrrol-4-yl}-L-leucinamide;

N²-(cyclopropylsulfonyl)-N¹-{(3aS,4S,6aR)-2-[3-(trifluoromethyl)benzyl]octahydrocyclopenta[c]pyrrol-4-yl}-L-leucinamide;

N²-acetyl-N²-methyl-N¹-{(3aS,4S,6aR)-2-[3-(trifluoromethyl)benzyl]octahydrocyclopenta[c]pyrrol-4-yl}-L-leucinamide;

N²-(2,2-dimethylpropanoyl)-N²-methyl-N¹-{(3aS,4R,6aR)-2-[3-(trifluoromethyl)benzyl]octahydrocyclopenta[c]pyrrol-4-yl}-L-leucinamide;

N²-(2,2-dimethylpropanoyl)-N¹-{(3aS,4R,6aR)-2-[3-(trifluoromethyl)benzyl]octahydrocyclopenta[c]pyrrol-4-yl}-L-leucinamide;

isobutyl (S)-4-methyl-1-oxo-1-((3aS,4R,6aR)-2-(3-(trifluoromethyl)benzyl)octahydrocyclopenta[c]pyrrol-4-ylamino)pentan-2-ylcarbamate;

cyclopentyl(S)-4-methyl-1-oxo-1-((3aS,4R,6aR)-2-(3-(trifluoromethyl)benzyl)octahydrocyclopenta[c]pyrrol-4-ylamino)pentan-2-ylcarbamate;

N²-[(tert-butylamino)carbonyl]-N¹-{(3aS,4R,6aR)-2-[3-(trifluoromethyl)benzyl]octahydrocyclopenta[c]pyrrol-4-yl}-L-leucinamide;

N²-[(cyclopentylamino)carbonyl]-N¹-{(3aS,4R,6aR)-2-[3-(trifluoromethyl)benzyl]octahydrocyclopenta[c]pyrrol-4-yl}-L-leucinamide;

N²-methyl-N¹-((3aS,4R,6aR)-2-{[3-(trifluoromethyl)phenyl]sulfonyl}octahydrocyclopenta[c]pyrrol-4-yl)-L-leucinamide;

N²-methyl-N¹-((3aS,4R,6aR)-2-{[4-(trifluoromethyl)phenyl]sulfonyl}octahydrocyclopenta[c]pyrrol-4-yl)-L-leucinamide;

N¹-((3aS,4R,6aR)-2-{[3-(trifluoromethyl)phenyl]sulfonyl}octahydrocyclopenta[c]pyrrol-4-yl)-L-leucinamide;

3-(trifluoromethyl)-N-{(3aS*,4S*,6aR*)-2-[3-(trifluoromethyl)benzyl]octahydrocyclopenta[c]pyrrol-4-yl}benzenesulfonamide;

3-(trifluoromethyl)-N-{(3aS*,4R*,6aR*)-2-[3-(trifluoromethyl)benzyl]octahydrocyclopenta[c]pyrrol-4-yl}benzenesulfonamide;

3-(trifluoromethyl)-N-{(3aS,4S,6aR)-2-[3-(trifluoromethyl)benzyl]octahydrocyclopenta[c]pyrrol-4-yl}benzenesulfonamide;

3-(trifluoromethyl)-N-{(3aR,4R,6aS)-2-[3-(trifluoromethyl)benzyl]octahydrocyclopenta[c]pyrrol-4-yl}benzenesulfonamide;

3-(trifluoromethyl)-N-{(3aS,4R,6aR)-2-[3-(trifluoromethyl)benzyl]octahydrocyclopenta[c]pyrrol-4-yl}benzenesulfonamide;

N-[(3aS,4R,6aR)-2-benzyloctahydrocyclopenta[c]pyrrol-4-yl]-3-(trifluoromethyl)benzenesulfonamide;

N-{(3aS,4R,6aR)-2-[6,6-bis(4-fluorophenyl)hexyl]octahydrocyclopenta[c]pyrrol-4-yl}-3-(trifluoromethyl)benzenesulfonamide;

N-{(3aS,4R,6aR)-2-[3,5-bis(trifluoromethyl)benzyl]octahydrocyclopenta[c]pyrrol-4-yl}-3-(trifluoromethyl)benzenesulfonamide;

N-{(3aS,4R,6aR)-2-[3,3-bis(4-fluorophenyl)propyl]octahydrocyclopenta[c]pyrrol-4-yl}-3-(trifluoromethyl)benzenesulfonamide;

N-{(3aS,4R,6aR)-2-[3-fluoro-4-(trifluoromethyl)benzyl]octahydrocyclopenta[c]pyrrol-4-yl}-3-(trifluoromethyl)benzenesulfonamide;

N-[(3aS,4S,6aR)-2-(4-hydroxybutyl)octahydrocyclopenta[c]pyrrol-4-yl]-3-(trifluoromethyl)benzenesulfonamide;

(3aS*,4S*,6aR*)-N,N-dicyclopropyl-2-[3-(trifluoromethyl)benzyl]octahydrocyclopenta[c]pyrrol-4-amine;

(3aS*,4R*,6aR*)-2-benzyl-N-cyclopropyloctahydrocyclopenta[c]pyrrol-4-amine;

(3aS*,4S*,6aR*)-2-benzyl-N-cyclopropyloctahydrocyclopenta[c]pyrrol-4-amine;

N-[(3aS*,4S*,6aR*)-2-benzyloctahydrocyclopenta[c]pyrrol-4-yl]-N-cyclopropyl-3-(trifluoromethyl)benzenesulfonamide;

N-[(3aS*,4R*,6aR*)-2-benzyloctahydrocyclopenta[c]pyrrol-4-yl]-N-cyclopropyl-3-(trifluoromethyl)benzenesulfonamide;

N-cyclopropyl-N-[(3aS*,4S*,6aR*)-octahydrocyclopenta[c]pyrrol-4-yl]-3-(trifluoromethyl)benzenesulfonamide;

N-{(3aS*,4S*,6aR*)-2-[6,6-bis(4-fluorophenyl)hexyl]octahydrocyclopenta[c]pyrrol-4-yl}-N-cyclopropyl-3-(trifluoromethyl)benzenesulfonamide;

N-{(3aS*,4S*,6aR*)-2-[3,3-bis(4-fluorophenyl)propyl]octahydrocyclopenta[c]pyrrol-4-yl}-N-cyclopropyl-3-(trifluoromethyl)benzenesulfonamide;

N-cyclopropyl-3-(trifluoromethyl)-N-{(3aS*,4S*,6aR*)-2-[3-(trifluoromethyl)benzyl]octahydrocyclopenta[c]pyrrol-4-yl}benzenesulfonamide;

2,2-dicyclohexyl-N-((3aS,4S,6aR)-2-{[3-(trifluoromethyl)phenyl]sulfonyl}octahydrocyclopenta[c]pyrrol-4-yl)acetamide;

2,2-dicyclohexyl-N-{(3aS,4S,6aR)-2-[(2-phenylethyl)sulfonyl]octahydrocyclopenta[c]pyrrol-4-yl}acetamide;

2,2-dicyclohexyl-N-((3aS,4S,6aR)-2-{[2-(1-naphthyl)ethyl]sulfonyl}octahydrocyclopenta[c]pyrrol-4-yl)acetamide;

2,2-dicyclohexyl-N-((3aS,4S,6aR)-2-{[3-(trifluoromethyl)benzyl]sulfonyl}octahydrocyclopenta[c]pyrrol-4-yl)acetamide;

2,2-dicyclohexyl-N-((3aS,4S,6aR)-2-{[2-(4-fluorophenyl)ethyl]sulfonyl}octahydrocyclopenta[c]pyrrol-4-yl)acetamide;

(2S)-2-phenyl-N-{(3aR,4R,6aS)-2-[(1S)-1-phenylethyl]octahydrocyclopenta[c]pyrrol-4-yl}butanamide;

(2S)-2-phenyl-N-{(3aS,4S,6aS)-2-[(1S)-1-phenylethyl]octahydrocyclopenta[c]pyrrol-4-yl}butanamide;

(2S)-2-phenyl-N-{(3aS,4S,6aR)-2-[(1S)-1-phenylethyl]octahydrocyclopenta[c]pyrrol-4-yl}butanamide;

(2S)-2-phenyl-N-{(3aS,4R,6aR)-2-[(1S)-1-phenylethyl]oc-tahydrocyclopenta[c]pyrrol-4-yl}butanamide;
N-[(3aR,4S,6aS)-2-benzyloctahydrocyclopenta[c]pyrrol-4-yl]-N,3-dimethyl-2-phenylbutanamide;
N-[(3aS*,4R*,6aR*)-2-benzyloctahydrocyclopenta[c]pyrrol-4-yl]-N,3-dimethyl-2-phenylbutanamide;
(3aR*,4S*,6aS*)-N-benzyl-2-(3-methyl-2-phenylbutanoyl)octahydrocyclopenta[c]pyrrol-4-amine;
2,2-dicyclohexyl-N-[(3aS,4R,6aR)-2-(N,N-dimethyl-D-leucyl)octahydrocyclopenta[c]pyrrol-4-yl]acetamide;
N-[(3aR,4S,6aS)-2-benzoyloctahydrocyclopenta[c]pyrrol-4-yl]-3-methyl-2-phenylbutanamide;
N'-[(3aS,4S,6aS)-2-benzyloctahydrocyclopenta[c]pyrrol-4-yl]-N-isopropyl-N-phenylurea;
(2S)-N-[(3aS,4R,6aR)-2-benzyloctahydrocyclopenta[c]pyrrol-4-yl]-2-(1,1-dioxidoisothiazolidin-2-yl)-4-methylpentanamide;
tert-butyl(S)-1-((3aR,4S,6aS)-2-benzyloctahydrocyclopenta[c]pyrrol-4-ylamino)-4-methyl-1-oxopentan-2-ylcarbamate;
tert-butyl(S)-1-((3aR,4S,6aS)-2-benzyloctahydrocyclopenta[c]pyrrol-4-ylamino)-4-methyl-1-oxopentan-2-yl(methyl)carbamate;
tert-butyl(S)-1-((3aR,4S,6aS)-2-benzyloctahydrocyclopenta[c]pyrrol-4-ylamino)-4-methyl-1-oxopentan-2-yl(ethyl)carbamate;
tert-butyl(2S,3S)-1-((3aR,4S,6aS)-2-benzyloctahydrocyclopenta[c]pyrrol-4-ylamino)-3-methyl-1-oxopentan-2-yl(methyl)carbamate;
tert-butyl(S)-1-((3aR,4S,6aS)-2-benzyloctahydrocyclopenta[c]pyrrol-4-ylamino)-3,3-dimethyl-1-oxobutan-2-ylcarbamate;
tert-butyl(S)-1-((3aR,4S,6aS)-2-benzyloctahydrocyclopenta[c]pyrrol-4-ylamino)-4,4-dimethyl-1-oxopentan-2-ylcarbamate;
tert-butyl(S)-1-((3aR,4S,6aS)-2-benzyloctahydrocyclopenta[c]pyrrol-4-ylamino)-1-oxohexan-2-yl(methyl)carbamate;
N-[(3aR,4S,6aS)-2-benzyloctahydrocyclopenta[c]pyrrol-4-yl]-2,2-bis(4-fluorophenyl)acetamide;
N-[(3aR,4S,6aS)-2-benzyloctahydrocyclopenta[c]pyrrol-4-yl]-2-isopropyl-3-methylbutanamide;
N-[(3aR,4S,6aS)-2-benzyloctahydrocyclopenta[c]pyrrol-4-yl]-3-methylbutanamide;
tert-butyl(2S)-2-({[(3aS,4R,6aR)-2-benzyloctahydrocyclopenta[c]pyrrol-4-yl]amino}carbonyl)piperidine-1-carboxylate;
tert-butyl(S)-1-((3aS,4R,6aR)-2-benzyloctahydrocyclopenta[c]pyrrol-4-ylamino)-3-methyl-1-oxobutan-2-yl(methyl)carbamate;
tert-butyl(S)-1-((3aS,4R,6aR)-2-benzyloctahydrocyclopenta[c]pyrrol-4-ylamino)-1-oxopentan-2-yl(methyl)carbamate;
tert-butyl(S)-1-((3aS,4R,6aR)-2-benzyloctahydrocyclopenta[c]pyrrol-4-ylamino)-3,3-dimethyl-1-oxobutan-2-ylcarbamate;
N-[(3aS,4R,6aR)-2-benzyloctahydrocyclopenta[c]pyrrol-4-yl]-2-isopropyl-3-methylbutanamide;
N-[(3aS,4R,6aR)-2-benzyloctahydrocyclopenta[c]pyrrol-4-yl]-3-methylbutanamide;
2-cyclohexyl-2-hydroxy-N-{(3aS,4S,6aR)-2-[3-(trifluoromethyl)benzyl]octahydrocyclopenta[c]pyrrol-4-yl}acetamide;
tert-butyl(S)-1-((3aS,4S,6aR)-2-benzyloctahydrocyclopenta[c]pyrrol-4-ylamino)-1-oxopentan-2-yl(methyl)carbamate;
tert-butyl(S)-1-((3aS,4S,6aR)-2-benzyloctahydrocyclopenta[c]pyrrol-4-ylamino)-4-methyl-1-oxopentan-2-yl(methyl)carbamate;
tert-butyl(S)-1-((3aR,4R,6aS)-2-benzyloctahydrocyclopenta[c]pyrrol-4-ylamino)-1-oxopentan-2-yl(methyl)carbamate;
tert-butyl(S)-1-((3aR,4R,6aS)-2-benzyloctahydrocyclopenta[c]pyrrol-4-ylamino)-4-methyl-1-oxopentan-2-yl(methyl)carbamate;
S-[(3aS,4S,6aS)-2-benzyloctahydrocyclopenta[c]pyrrol-4-yl]-N$^2$-(methylsulfonyl)-L-leucinamide;
N$^1$-[(3aS,4R,6aR)-2-benzyloctahydrocyclopenta[c]pyrrol-4-yl]-N$^2$-(methylsulfonyl)-L-leucinamide;
N$^1$-[(3aR,4S,6aS)-2-benzyloctahydrocyclopenta[c]pyrrol-4-yl]-N$^2$-neopentyl-L-leucinamide;
N$^1$-[(3aS,4R,6aR)-2-benzyloctahydrocyclopenta[c]pyrrol-4-yl]-N$^2$-neopentyl-L-leucinamide;
N$^1$-[(3aS,4R,6aR)-2-benzyloctahydrocyclopenta[c]pyrrol-4-yl]-N$^2$-neopentyl-L-norvalinamide;
tert-butyl(S)-1-((3aR,4S,6aS)-2-benzyloctahydrocyclopenta[c]pyrrol-4-ylamino)-4,4-dimethyl-1-oxopentan-2-yl(methyl)carbamate;
tert-butyl(S)-1-((3aS,4R,6aR)-2-benzyloctahydrocyclopenta[c]pyrrol-4-ylamino)-4,4-dimethyl-1-oxopentan-2-yl(methyl)carbamate;
(2S)-N-[(3aS,4R,6aR)-2-benzyloctahydrocyclopenta[c]pyrrol-4-yl]-4-methyl-2-morpholin-4-ylpentanamide;
(2S)-N-[(3aS,4R,6aR)-2-benzyloctahydrocyclopenta[c]pyrrol-4-yl]-4-methyl-2-pyrrolidin-1-ylpentanamide;
(2S)-N-[(3aS,4R,6aR)-2-benzyloctahydrocyclopenta[c]pyrrol-4-yl]-4-methyl-2-piperidin-1-ylpentanamide;
N$^2$-neopentyl-N$^1$-((3aR,4S,6aS)-2-{[3-(trifluoromethyl)phenyl]sulfonyl}octahydrocyclopenta[c]pyrrol-4-yl)-L-leucinamide;
N$^2$-neopentyl-N$^1$-((3aR,4S,6aS)-2-{[3-(trifluoromethyl)phenyl]sulfonyl}octahydrocyclopenta[c]pyrrol-4-yl)-L-norvalinamide;
N$^2$-neopentyl-N$^1$-((3aS,4R,6aR)-2-{[3-(trifluoromethyl)phenyl]sulfonyl}octahydrocyclopenta[c]pyrrol-4-yl)-L-leucinamide;
N$^2$-neopentyl-N$^1$-((3aR,4R,6aR)-2-{[3-(trifluoromethyl)phenyl]sulfonyl}octahydrocyclopenta[c]pyrrol-4-yl)-L-norvalinamide;
N$^2$-neopentyl-N$^1$-((3aR,4S,6aS)-2-{[4-(trifluoromethyl)phenyl]sulfonyl}octahydrocyclopenta[c]pyrrol-4-yl)-L-leucinamide;
N$^2$-neopentyl-N$^1$-((3aR,4S,6aS)-2-{[4-(trifluoromethyl)phenyl]sulfonyl}octahydrocyclopenta[c]pyrrol-4-yl)-L-norvalinamide;
N-(tert-butoxycarbonyl)-N-methyl-N-((3aR,4S,6aS)-2-{[4-(trifluoromethyl)phenyl]sulfonyl}octahydrocyclopenta[c]pyrrol-4-yl)-L-phenylalaninamide;
tert-butyl methyl((S)-1-oxo-1-((3aR,4S,6aS)-2-(4-(trifluoromethyl)phenylsulfonyl)octahydrocyclopenta[c]pyrrol-4-ylamino)pentan-2-yl)carbamate;
N$^2$-neopentyl-N$^1$-((3aS,4R,6aR)-2-{[4-(trifluoromethyl)phenyl]sulfonyl}octahydrocyclopenta[c]pyrrol-4-yl)-L-norvalinamide;
N$^1$-{(3aR,4S,6aS)-2-[(4-fluorophenyl)sulfonyl]octahydrocyclopenta[c]pyrrol-4-yl}-N$^2$-neopentyl-L-leucinamide;
tert-butyl(S)-4,4-dimethyl-1-oxo-1-((3aR,4S,6aS)-2-(5-(trifluoromethyl)pyridin-2-yl)octahydrocyclopenta[c]pyrrol-4-ylamino)pentan-2-ylcarbamate;
isopropyl(S)-1-oxo-1-((3aR,4S,6aS)-2-(5-(trifluoromethyl)pyridin-2-yl)octahydrocyclopenta[c]pyrrol-4-ylamino)pentan-2-ylcarbamate;

tert-butyl(S)-4,4-dimethyl-1-oxo-1-((3aR,4S,6aS)-2-(6-(trifluoromethyl)pyridin-2-yl)octahydrocyclopenta[c]pyrrol-4-ylamino)pentan-2-ylcarbamate;
tert-butyl(S)-4,4-dimethyl-1-((3aR,4S,6aS)-2-(2-(methylsulfonyl)pyrimidin-5-yl)octahydrocyclopenta[c]pyrrol-4-ylamino)-1-oxopentan-2-ylcarbamate;
(S)-tert-butyl 2-((3aS,4R,6aR)-2-(3-(trifluoromethyl)phenylsulfonyl)octahydrocyclopenta[c]pyrrol-4-ylcarbamoyl)pyrrolidine-1-carboxylate;
tert-butyl(1R)-1-isopropyl-3-oxo-3-[((3aS,4R,6aR)-2-{[3-(trifluoromethyl)phenyl]sulfonyl}octahydrocyclopenta[c]pyrrol-4-yl)amino]propylcarbamate;
tert-butyl(2S)-2-{[((3aS,4R,6aR)-2-{[3-(trifluoromethyl)phenyl]sulfonyl}octahydrocyclopenta[c]pyrrol-4-yl)amino]carbonyl}piperidine-1-carboxylate;
N-(tert-butoxycarbonyl)-N-((3aR,4S,6aS)-2-{[3-(trifluoromethyl)phenyl]sulfonyl}octahydrocyclopenta[c]pyrrol-4-yl)-L-phenylalaninamide;
N-(tert-butoxycarbonyl)-N-methyl-N-((3aR,4S,6aS)-2-{[3-(trifluoromethyl)phenyl]sulfonyl}octahydrocyclopenta[c]pyrrol-4-yl)-L-phenylalaninamide;
(S)-tert-butyl 2-((3aR,4S,6aS)-2-(3-(trifluoromethyl)phenylsulfonyl)octahydrocyclopenta[c]pyrrol-4-ylcarbamoyl)pyrrolidine-1-carboxylate;
tert-butyl(1R)-1-isopropyl-3-oxo-3-[((3aR,4S,6aS)-2-{[3-(trifluoromethyl)phenyl]sulfonyl}octahydrocyclopenta[c]pyrrol-4-yl)amino]propylcarbamate;
tert-butyl methyl((S)-3-methyl-1-oxo-1-((3aR,4S,6aS)-2-(3-(trifluoromethyl)phenylsulfonyl)octahydrocyclopenta[c]pyrrol-4-ylamino)butan-2-yl)carbamate;
tert-butyl(2S)-2-{[((3aR,4S,6aS)-2-{[3-(trifluoromethyl)phenyl]sulfonyl}octahydrocyclopenta[c]pyrrol-4-yl)amino]carbonyl}piperidine-1-carboxylate;
tert-butyl(3S)-3-{[((3aR,4S,6aS)-2-{[3-(trifluoromethyl)phenyl]sulfonyl}octahydrocyclopenta[c]pyrrol-4-yl)amino]carbonyl}-3,4-dihydroisoquinoline-2(1H)-carboxylate;
tert-butyl(S)-4,4-dimethyl-1-oxo-1-((3aR,4S,6aS)-2-(3-(trifluoromethyl)phenylsulfonyl)octahydrocyclopenta[c]pyrrol-4-ylamino)pentan-2-ylcarbamate;
tert-butyl methyl((S)-1-oxo-1-((3aR,4S,6aS)-2-(3-(trifluoromethyl)phenylsulfonyl)octahydrocyclopenta[c]pyrrol-4-ylamino)hexan-2-yl)carbamate;
tert-butyl methyl((S)-1-oxo-1-((3aR,4S,6aS)-2-(3-(trifluoromethyl)phenylsulfonyl)octahydrocyclopenta[c]pyrrol-4-ylamino)pentan-2-yl)carbamate;
isopropyl(S)-1-oxo-1-((3aR,4S,6aS)-2-(4-(trifluoromethyl)phenylsulfonyl)octahydrocyclopenta[c]pyrrol-4-ylamino)pentan-2-ylcarbamate;
isopropyl(S)-1-oxo-1-((3aR,4S,6aS)-2-(4-(trifluoromethyl)benzyl)octahydrocyclopenta[c]pyrrol-4-ylamino)pentan-2-ylcarbamate;
(3aS,4R,6aR)-N-neopentyl-2-{[3-(trifluoromethyl)phenyl]sulfonyl}octahydrocyclopenta[c]pyrrol-4-amine;
(3aR,4S,6aS)-N-neopentyl-2-{[3-(trifluoromethyl)phenyl]sulfonyl}octahydrocyclopenta[c]pyrrol-4-amine;
(3aR,4S,6aS)-N-isopropyl-2-{[4-(trifluoromethyl)phenyl]sulfonyl}octahydrocyclopenta[c]pyrrol-4-amine;
(3aR,4S,6aS)-2-{[2-chloro-4-(trifluoromethyl)phenyl]sulfonyl}-N-isopropyloctahydrocyclopenta[c]pyrrol-4-amine;
(3aS,4R,6aR)-N-(4-fluorobenzyl)-2-{[3-(trifluoromethyl)phenyl]sulfonyl}octahydrocyclopenta[c]pyrrol-4-amine;
(3aR,4S,6aS)-N-(4-fluorobenzyl)-2-{[3-(trifluoromethyl)phenyl]sulfonyl}octahydrocyclopenta[c]pyrrol-4-amine;
(3aR,4S,6aS)-N-(4-fluorobenzyl)-2-[3-(trifluoromethyl)benzyl]octahydrocyclopenta[c]pyrrol-4-amine;
(3aR,4S,6aS)-N-ethyl-2-{[4-(trifluoromethyl)phenyl]sulfonyl}octahydrocyclopenta[c]pyrrol-4-amine;
(3aR,4S,6aS)-N,N-diethyl-2-{[4-(trifluoromethyl)phenyl]sulfonyl}octahydrocyclopenta[c]pyrrol-4-amine;
(3aR,4S,6aS)-N-propyl-2-{[4-(trifluoromethyl)phenyl]sulfonyl}octahydrocyclopenta[c]pyrrol-4-amine;
(3aR,4S,6aS)-N,N-dipropyl-2-{[4-(trifluoromethyl)phenyl]sulfonyl}octahydrocyclopenta[c]pyrrol-4-amine;
(3aR,4S,6aS)-N-(cyclopropylmethyl)-2-{[4-(trifluoromethyl)phenyl]sulfonyl}octahydrocyclopenta[c]pyrrol-4-amine;
(3aR,4S,6aS)-2-{[2-chloro-4-(trifluoromethyl)phenyl]sulfonyl}-N-ethyloctahydrocyclopenta[c]pyrrol-4-amine;
(3aR,4S,6aS)-2-{[2-chloro-4-(trifluoromethyl)phenyl]sulfonyl}-N,N-diethyloctahydrocyclopenta[c]pyrrol-4-amine;
(3aR,4S,6aS)-2-{[2-chloro-4-(trifluoromethyl)phenyl]sulfonyl}-N-[5-(trifluoromethyl)pyridin-2-yl]octahydrocyclopenta[c]pyrrol-4-amine;
tert-butyl(S)-1-(ethyl((3aR,4S,6aS)-2-(4-(trifluoromethyl)phenylsulfonyl)octahydrocyclopenta[c]pyrrol-4-yl)amino)-4,4-dimethyl-1-oxopentan-2-yl(methyl)carbamate;
tert-butyl(S)-4,4-dimethyl-1-oxo-1-(propyl((3aR,4S,6aS)-2-(4-(trifluoromethyl)phenylsulfonyl)octahydrocyclopenta[c]pyrrol-4-yl)amino)pentan-2-yl(methyl)carbamate;
tert-butyl(S)-1-((cyclopropylmethyl)((3aR,4S,6aS)-2-(4-(trifluoromethyl)phenylsulfonyl)octahydrocyclopenta[c]pyrrol-4-yl)amino)-4,4-dimethyl-1-oxopentan-2-yl(methyl)carbamate;
2-nitro-N-((3aR,4S,6aS)-2-{[4-(trifluoromethyl)phenyl]sulfonyl}octahydrocyclopenta[c]pyrrol-4-yl)benzenesulfonamide;
N-methyl-2-nitro-N-((3aR,4S,6aS)-2-{[4-(trifluoromethyl)phenyl]sulfonyl}octahydrocyclopenta[c]pyrrol-4-yl)benzenesulfonamide;
(3aR,4S,6aS)-N-methyl-2-{[4-(trifluoromethyl)phenyl]sulfonyl}octahydrocyclopenta[c]pyrrol-4-amine;
tert-butyl(S)-4,4-dimethyl-1-(methyl((3aR,4S,6aS)-2-(4-(trifluoromethyl)phenylsulfonyl)octahydrocyclopenta[c]pyrrol-4-yl)amino)-1-oxopentan-2-yl(methyl)carbamate;
(2S)-2-(1,1-dioxidoisothiazolidin-2-yl)-4-methyl-N-{(3aS,4R,6aR)-2-[3-(trifluoromethyl)benzyl]octahydrocyclopenta[c]pyrrol-4-yl}pentanamide;
2-isopropyl-3-methyl-N-{(3aS,4R,6aR)-2-[3-(trifluoromethyl)benzyl]octahydrocyclopenta[c]pyrrol-4-yl}butanamide;
2-isopropyl-3-methyl-N-{(3aR,4S,6aS)-2-[3-(trifluoromethyl)benzyl]octahydrocyclopenta[c]pyrrol-4-yl}butanamide;
tert-butyl(S)-4-methyl-1-oxo-1-((3aR,4S,6aS)-2-(3-(trifluoromethyl)benzyl)octahydrocyclopenta[c]pyrrol-4-ylamino)pentan-2-ylcarbamate;
tert-butyl methyl((S)-4-methyl-1-oxo-1-((3aR,4S,6aS)-2-(3-(trifluoromethyl)benzyl)octahydrocyclopenta[c]pyrrol-4-ylamino)pentan-2-yl)carbamate;
tert-butyl methyl((S)-4-methyl-1-oxo-1-((3aR,4S,6aS)-2-(4-(trifluoromethyl)benzyl)octahydrocyclopenta[c]pyrrol-4-ylamino)pentan-2-yl)carbamate;
tert-butyl(S)-1-((3aR,4S,6aS)-2-(4-fluorobenzyl)octahydrocyclopenta[c]pyrrol-4-ylamino)-4-methyl-1-oxopentan-2-yl(methyl)carbamate;
tert-butyl ethyl((S)-4-methyl-1-oxo-1-((3aR,4S,6aS)-2-(3-(trifluoromethyl)benzyl)octahydrocyclopenta[c]pyrrol-4-ylamino)pentan-2-yl)carbamate;

tert-butyl(S)-1-((3aS,4R,6aR)-2-(3-fluoro-4-(trifluorom-
ethyl)benzyl)octahydrocyclopenta[c]pyrrol-4-ylamino)-
4-methyl-1-oxopentan-2-yl(methyl)carbamate;
tert-butyl(S)-1-((3aS,4R,6aR)-2-(4-fluoro-3-(trifluorom-
ethyl)benzyl)octahydrocyclopenta[c]pyrrol-4-ylamino)-
4-methyl-1-oxopentan-2-yl(methyl)carbamate;
tert-butyl methyl((S)-1-oxo-1-((3aR,4S,6aS)-2-(3-(trifluo-
romethyl)benzyl)octahydrocyclopenta[c]pyrrol-4-
ylamino)pentan-2-yl)carbamate;
tert-butyl methyl((S)-1-oxo-1-((3aR,4S,6aS)-2-(4-(trifluo-
romethyl)benzyl)octahydrocyclopenta[c]pyrrol-4-
ylamino)pentan-2-yl)carbamate;
tert-butyl(S)-1-((3aR,4S,6aS)-2-(4-fluorobenzyl)octahydro-
cyclopenta[c]pyrrol-4-ylamino)-1-oxopentan-2-yl(me-
thyl)carbamate;
tert-butyl methyl((S)-3-methyl-1-oxo-1-((3aS,4R,6aR)-2-
(3-(trifluoromethyl)benzyl)octahydrocyclopenta[c]pyr-
rol-4-ylamino)butan-2-yl)carbamate;
tert-butyl methyl((S)-1-oxo-1-((3aS,4R,6aR)-2-(4-(trifluo-
romethyl)benzyl)octahydrocyclopenta[c]pyrrol-4-
ylamino)pentan-2-yl)carbamate;
tert-butyl(S)-1-((3aS,4R,6aR)-2-(4-fluorobenzyl)octahydro-
cyclopenta[c]pyrrol-4-ylamino)-1-oxopentan-2-yl(me-
thyl)carbamate;
(2S)-4-methyl-2-morpholin-4-yl-N-((3aS,4R,6aR)-2-{[3-
(trifluoromethyl)phenyl]sulfonyl}octahydrocyclopenta[c]
pyrrol-4-yl)pentanamide;
(2S)-4-methyl-2-pyrrolidin-1-yl-N-((3aS,4R,6aR)-2-{[3-
(trifluoromethyl)phenyl]sulfonyl}octahydrocyclopenta[c]
pyrrol-4-yl)pentanamide;
(2S)-4-methyl-2-piperidin-1-yl-N-((3aS,4R,6aR)-2-{[3-(tri-
fluoromethyl)phenyl]sulfonyl}octahydrocyclopenta[c]
pyrrol-4-yl)pentanamide;
tert-butyl methyl((S)-4-methyl-1-oxo-1-((3aR,4S,6aS)-2-(3-
(trifluoromethyl)phenylsulfonyl)octahydrocyclopenta[c]
pyrrol-4-ylamino)pentan-2-yl)carbamate;
tert-butyl ethyl((S)-4-methyl-1-oxo-1-((3aR,4S,6aS)-2-(3-
(trifluoromethyl)phenylsulfonyl)octahydrocyclopenta[c]
pyrrol-4-ylamino)pentan-2-yl)carbamate;
tert-butyl methyl((S)-4-methyl-1-oxo-1-((3aS,4R,6aR)-2-
(4-(trifluoromethyl)phenylsulfonyl)octahydrocyclopenta
[c]pyrrol-4-ylamino)pentan-2-yl)carbamate;
tert-butyl methyl((S)-4-methyl-1-oxo-1-((3aS,4R,6aR)-2-
(3-(trifluoromethyl)phenylsulfonyl)octahydrocyclopenta
[c]pyrrol-4-ylamino)pentan-2-yl)carbamate;
tert-butyl(S)-1-((3aS,4R,6aR)-2-(4-fluorophenylsulfonyl)
octahydrocyclopenta[c]pyrrol-4-ylamino)-4-methyl-1-
oxopentan-2-yl(methyl)carbamate;
tert-butyl(S)-1-((3aS,4R,6aR)-2-(4-fluoro-3-(trifluorom-
ethyl)phenylsulfonyl)octahydrocyclopenta[c]pyrrol-4-
ylamino)-4-methyl-1-oxopentan-2-yl(methyl)carbamate;
tert-butyl methyl((S)-1-oxo-1-((3aR,4S,6aS)-2-(4-(trifluo-
romethyl)phenylsulfonyl)octahydrocyclopenta[c]pyrrol-
4-ylamino)pentan-2-yl)carbamate;
tert-butyl methyl((S)-4-methyl-1-oxo-1-((3aR,4R,6aS)-2-
(4-(trifluoromethyl)phenylsulfonyl)octahydrocyclopenta
[c]pyrrol-4-ylamino)pentan-2-yl)carbamate;
tert-butyl(S)-1-((3aS,4R,6aR)-2-(4-fluorophenylsulfonyl)
octahydrocyclopenta[c]pyrrol-4-ylamino)-1-oxopentan-
2-yl(methyl)carbamate;
tert-butyl methyl((S)-1-oxo-1-((3aS,4R,6aR)-2-(4-(trifluo-
romethyl)phenylsulfonyl)octahydrocyclopenta[c]pyrrol-
4-ylamino)pentan-2-yl)carbamate;
tert-butyl methyl((2S,3S)-3-methyl-1-oxo-1-((3aR,4S,6aS)-
2-(3-(trifluoromethyl)phenylsulfonyl)octahydrocyclo-
penta[c]pyrrol-4-ylamino)pentan-2-yl)carbamate;
tert-butyl methyl((2S,3S)-3-methyl-1-oxo-1-((3aR,4S,6aS)-
2-(4-(trifluoromethyl)phenylsulfonyl)octahydrocyclo-
penta[c]pyrrol-4-ylamino)pentan-2-yl)carbamate;
tert-butyl methyl((2S,3S)-3-methyl-1-oxo-1-((3aS,4R,6aR)-
2-(3-(trifluoromethyl)phenylsulfonyl)octahydrocyclo-
penta[c]pyrrol-4-ylamino)pentan-2-yl)carbamate;
tert-butyl methyl((2S,3S)-3-methyl-1-oxo-1-((3aS,4R,6aR)-
2-(4-(trifluoromethyl)phenylsulfonyl)octahydrocyclo-
penta[c]pyrrol-4-ylamino)pentan-2-yl)carbamate;
tert-butyl(S)-4,4-dimethyl-1-oxo-1-((3aR,4S,6aS)-2-(3-(tri-
fluoromethyl)phenylsulfonyl)octahydrocyclopenta[c]pyr-
rol-4-ylamino)pentan-2-yl(methyl)carbamate;
tert-butyl(S)-4,4-dimethyl-1-oxo-1-((3aR,4S,6aS)-2-(4-(tri-
fluoromethyl)phenylsulfonyl)octahydrocyclopenta[c]pyr-
rol-4-ylamino)pentan-2-yl(methyl)carbamate;
tert-butyl(S)-4,4-dimethyl-1-oxo-1-((3aS,4R,6aR)-2-(3-(tri-
fluoromethyl)phenylsulfonyl)octahydrocyclopenta[c]pyr-
rol-4-ylamino)pentan-2-yl(methyl)carbamate;
tert-butyl(S)-4,4-dimethyl-1-oxo-1-((3aS,4R,6aR)-2-(4-(tri-
fluoromethyl)phenylsulfonyl)octahydrocyclopenta[c]pyr-
rol-4-ylamino)pentan-2-yl(methyl)carbamate;
tert-butyl methyl((S)-3-methyl-1-oxo-1-((3aS,4R,6aR)-2-
(3-(trifluoromethyl)phenylsulfonyl)octahydrocyclopenta
[c]pyrrol-4-ylamino)butan-2-yl)carbamate;
tert-butyl(S)-3,3-dimethyl-1-oxo-1-((3aR,4S,6aS)-2-(4-(tri-
fluoromethyl)phenylsulfonyl)octahydrocyclopenta[c]pyr-
rol-4-ylamino)butan-2-ylcarbamate;
tert-butyl(S)-3,3-dimethyl-1-oxo-1-((3aS,4R,6aR)-2-(4-(tri-
fluoromethyl)phenylsulfonyl)octahydrocyclopenta[c]pyr-
rol-4-ylamino)butan-2-ylcarbamate;
tert-butyl methyl((S)-1-oxo-1-((3aR,4S,6aS)-2-(4-(trifluo-
romethyl)phenylsulfonyl)octahydrocyclopenta[c]pyrrol-
4-ylamino)hexan-2-yl)carbamate;
tert-butyl(S)-4,4-dimethyl-1-oxo-1-((3aS,4R,6aR)-2-(4-(tri-
fluoromethyl)phenylsulfonyl)octahydrocyclopenta[c]pyr-
rol-4-ylamino)pentan-2-ylcarbamate;
(2S)-4-methyl-2-pyrrolidin-1-yl-N-{(3aS,4R,6aR)-2-[3-(tri-
fluoromethyl)benzoyl]octahydrocyclopenta[c]pyrrol-4-
yl}pentanamide;
(2S)-4-methyl-N-[(3aS,4R,6aR)-2-(methylsulfonyl)octahy-
drocyclopenta[c]pyrrol-4-yl]-2-pyrrolidin-1-ylpentana-
mide;
(2S)-N-[(3aS,4R,6aR)-2-(cyclopropylsulfonyl)octahydrocy-
clopenta[c]pyrrol-4-yl]-4-methyl-2-pyrrolidin-1-ylpen-
tanamide;
$N^1$-[(3aR,4S,6aS)-2-benzyloctahydrocyclopenta[c]pyrrol-4-
yl]-$N^2$-methyl-L-leucinamide;
tert-butyl methyl((S)-4-methyl-1-((3aS,4R,6aR)-octahydro-
cyclopenta[c]pyrrol-4-ylamino)-1-oxopentan-2-yl)car-
bamate;
(2S)-N-[(3aS,4R,6aR)-2-benzyloctahydrocyclopenta[c]pyr-
rol-4-yl]piperidine-2-carboxamide;
$N^1$-[(3aS,4R,6aR)-2-benzyloctahydrocyclopenta[c]pyrrol-
4-yl]-$N^2$-methyl-L-valinamide;
$N^1$-[(3aS,4R,6aR)-2-benzyloctahydrocyclopenta[c]pyrrol-
4-yl]-$N^2$-methyl-L-norvalinamide;
$N^1$-[(3aR,4S,6aS)-2-benzyloctahydrocyclopenta[c]pyrrol-4-
yl]-$N^2$-methyl-L-isoleucinamide;
$N^1$-[(3aS,4R,6aR)-2-benzyloctahydrocyclopenta[c]pyrrol-
4-yl]-$N^2$-methyl-L-isoleucinamide;
$N^1$-[(3aR,4S,6aS)-2-benzyloctahydrocyclopenta[c]pyrrol-4-
yl]-$N^2$,4-dimethyl-L-leucinamide;
$N^1$-[(3aS,4R,6aR)-2-benzyloctahydrocyclopenta[c]pyrrol-
4-yl]-3-methyl-L-valinamide;
$N^1$-[(3aR,4S,6aS)-2-benzyloctahydrocyclopenta[c]pyrrol-4-
yl]-3-methyl-L-valinamide;

N$^1$-[(3aS,4R,6aR)-2-benzyloctahydrocyclopenta[c]pyrrol-4-yl]-N$^2$,4-dimethyl-L-leucinamide;
N$^1$-[(3aS,4S,6aR)-2-benzyloctahydrocyclopenta[c]pyrrol-4-yl]-N$^2$-methyl-L-norvalinamide;
N$^1$-[(3aS,4S,6aR)-2-benzyloctahydrocyclopenta[c]pyrrol-4-yl]-N$^2$-methyl-L-leucinamide;
N$^1$-[(3aR,4S,6aS)-2-benzyloctahydrocyclopenta[c]pyrrol-4-yl]-4-methyl-L-leucinamide;
N$^1$-[(3aR,4S,6aS)-2-benzyloctahydrocyclopenta[c]pyrrol-4-yl]-N$^2$-methyl-L-norleucinamide;
N$^1$-[(3aS,4R,6aR)-2-benzyloctahydrocyclopenta[c]pyrrol-4-yl]-N$^2$-methyl-L-norvalinamide;
N$^1$-[(3aS,4R,6aR)-2-benzyloctahydrocyclopenta[c]pyrrol-4-yl]-N$^2$-methyl-L-leucinamide;
N$^1$-[(3aR,4S,6aS)-2-benzyloctahydrocyclopenta[c]pyrrol-4-yl]-N$^2$-methyl-L-norvalinamide;
N$^2$-ethyl-N$^1$-{(3aR,4S,6aS)-2-[3-(trifluoromethyl)benzyl]octahydrocyclopenta[c]pyrrol-4-yl}-L-leucinamide;
N$^2$-methyl-N$^1$-{(3aR,4R,6aR)-2-[4-(trifluoromethyl)benzyl]octahydrocyclopenta[c]pyrrol-4-yl}-L-valinamide;
(2S)-N-[(3aS,4R,6aR)-2-(4-fluorobenzyl)octahydrocyclopenta[c]pyrrol-4-yl]piperidine-2-carboxamide;
N$^1$-[(3aS,4R,6aR)-2-(4-fluorobenzyl)octahydrocyclopenta[c]pyrrol-4-yl]-N$^2$-methyl-L-valinamide;
(2S)-N-{(3aS,4R,6aR)-2-[4-(trifluoromethyl)benzyl]octahydrocyclopenta[c]pyrrol-4-yl}piperidine-2-carboxamide;
N$^2$-methyl-N$^1$-{(3aS,4R,6aR)-2-[4-(trifluoromethyl)benzyl]octahydrocyclopenta[c]pyrrol-4-yl}-L-norvalinamide;
N$^1$-[(3aS,4R,6aR)-2-(4-fluorobenzyl)octahydrocyclopenta[c]pyrrol-4-yl]-N$^2$-methyl-L-norvalinamide;
N$^2$-methyl-N$^1$-{(3aS,4R,6aR)-2-[3-(trifluoromethyl)benzyl]octahydrocyclopenta[c]pyrrol-4-yl}-L-valinamide;
N$^1$-{(3aS,4R,6aR)-2-[3-fluoro-4-(trifluoromethyl)benzyl]octahydrocyclopenta[c]pyrrol-4-yl}-N$^2$-methyl-L-leucinamide;
N$^1$-{(3aS,4R,6aR)-2-[4-fluoro-3-(trifluoromethyl)benzyl]octahydrocyclopenta[c]pyrrol-4-yl}-N$^2$-methyl-L-leucinamide;
N$^2$-methyl-N$^1$-{(3aR,4S,6aS)-2-[3-(trifluoromethyl)benzyl]octahydrocyclopenta[c]pyrrol-4-yl}-L-norvalinamide;
N$^2$-methyl-N$^1$-{(3aR,4S,6aS)-2-[4-(trifluoromethyl)benzyl]octahydrocyclopenta[c]pyrrol-4-yl}-L-norvalinamide;
N$^1$-[(3aR,4S,6aS)-2-(4-fluorobenzyl)octahydrocyclopenta[c]pyrrol-4-yl]-N$^2$-methyl-L-norvalinamide;
N$^2$-methyl-N$^1$-{(3aR,4S,6aS)-2-[3-(trifluoromethyl)benzyl]octahydrocyclopenta[c]pyrrol-4-yl}-L-leucinamide;
N$^2$-methyl-N$^1$-{(3aR,4S,6aS)-2-[4-(trifluoromethyl)benzyl]octahydrocyclopenta[c]pyrrol-4-yl}-L-leucinamide;
N$^1$-[(3aR,4S,6aS)-2-(4-fluorobenzyl)octahydrocyclopenta[c]pyrrol-4-yl]-N$^2$-methyl-L-leucinamide;
N$^1$-{(3aR,4S,6aS)-2-[4-(trifluoromethyl)benzyl]octahydrocyclopenta[c]pyrrol-4-yl}-L-norvalinamide;
N$^2$-ethyl-N$^1$-((3aR,4S,6aS)-2-{[3-(trifluoromethyl)phenyl]sulfonyl}octahydrocyclopenta[c]pyrrol-4-yl)-L-leucinamide;
N$^2$-methyl-N$^1$-((3aR,4S,6aS)-2-{[3-(trifluoromethyl)phenyl]sulfonyl}octahydrocyclopenta[c]pyrrol-4-yl)-L-leucinamide;
N-((3aR,4S,6aS)-2-{[3-(trifluoromethyl)phenyl]sulfonyl}octahydrocyclopenta[c]pyrrol-4-yl)-L-phenylalaninamide;
N-methyl-N-((3aR,4S,6aS)-2-{[3-(trifluoromethyl)phenyl]sulfonyl}octahydrocyclopenta[c]pyrrol-4-yl)-L-phenylalaninamide;
N-((3aR,4S,6aS)-2-{[3-(trifluoromethyl)phenyl]sulfonyl}octahydrocyclopenta[c]pyrrol-4-yl)-L-prolinamide;
(3R)-3-amino-4-methyl-N-((3aR,4S,6aS)-2-{[3-(trifluoromethyl)phenyl]sulfonyl}octahydrocyclopenta[c]pyrrol-4-yl)pentanamide;
N$^2$-methyl-N$^1$-((3aR,4S,6aS)-2-{[3-(trifluoromethyl)phenyl]sulfonyl}octahydrocyclopenta[c]pyrrol-4-yl)-L-valinamide;
(2S)-N-((3aR,4S,6aS)-2-{[3-(trifluoromethyl)phenyl]sulfonyl}octahydrocyclopenta[c]pyrrol-4-yl)piperidine-2-carboxamide;
(3S)-N-((3aR,4S,6aS)-2-{[3-(trifluoromethyl)phenyl]sulfonyl}octahydrocyclopenta[c]pyrrol-4-yl)-1,2,3,4-tetrahydroisoquinoline-3-carboxamide;
4-methyl-N$^1$-((3aR,4S,6aS)-2-{[3-(trifluoromethyl)phenyl]sulfonyl}octahydrocyclopenta[c]pyrrol-4-yl)-L-leucinamide;
N$^2$-methyl-N$^1$-((3aR,4S,6aS)-2-{[3-(trifluoromethyl)phenyl]sulfonyl}octahydrocyclopenta[c]pyrrol-4-yl)-L-norleucinamide;
N$^2$-methyl-N$^1$-((3aR,4S,6aS)-2-{[3-(trifluoromethyl)phenyl]sulfonyl}octahydrocyclopenta[c]pyrrol-4-yl)-L-norvalinamide;
N$^2$-methyl-N$^1$-((3aR,4S,6aS)-2-{[4-(trifluoromethyl)phenyl]sulfonyl}octahydrocyclopenta[c]pyrrol-4-yl)-L-leucinamide;
N-((3aS,4R,6aR)-2-{[3-(trifluoromethyl)phenyl]sulfonyl}octahydrocyclopenta[c]pyrrol-4-yl)-L-prolinamide;
(3R)-3-amino-4-methyl-N-((3aS,4R,6aR)-2-{[3-(trifluoromethyl)phenyl]sulfonyl}octahydrocyclopenta[c]pyrrol-4-yl)pentanamide;
(2S)-N-((3aS,4R,6aR)-2-{[3-(trifluoromethyl)phenyl]sulfonyl}octahydrocyclopenta[c]pyrrol-4-yl)piperidine-2-carboxamide;
(2S)-N-{(3aS,4R,6aR)-2-[(4-fluorophenyl)sulfonyl]octahydrocyclopenta[c]pyrrol-4-yl}piperidine-2-carboxamide;
N$^1$-{(3aS,4R,6aR)-2-[(4-fluorophenyl)sulfonyl]octahydrocyclopenta[c]pyrrol-4-yl}-N$^2$-methyl-L-valinamide;
(2S)-N-((3aS,4R,6aR)-2-{[4-(trifluoromethyl)phenyl]sulfonyl}octahydrocyclopenta[c]pyrrol-4-yl)piperidine-2-carboxamide;
N$^2$-methyl-N$^1$-((3aS,4R,6aR)-2-{[4-(trifluoromethyl)phenyl]sulfonyl}octahydrocyclopenta[c]pyrrol-4-yl)-L-valinamide;
N$^1$-{(3aS,4R,6aR)-2-[(4-fluorophenyl)sulfonyl]octahydrocyclopenta[c]pyrrol-4-yl}-N$^2$-methyl-L-norvalinamide;
N$^2$-methyl-N$^1$-((3aS,4R,6aR)-2-{[4-(trifluoromethyl)phenyl]sulfonyl}octahydrocyclopenta[c]pyrrol-4-yl)-L-norvalinamide;
N$^2$-methyl-N$^1$-((3aR,4S,6aS)-2-{[4-(trifluoromethyl)phenyl]sulfonyl}octahydrocyclopenta[c]pyrrol-4-yl)-L-norvalinamide;
N$^2$-methyl-N$^1$-((3aS,4R,6aR)-2-{[3-(trifluoromethyl)phenyl]sulfonyl}octahydrocyclopenta[c]pyrrol-4-yl)-L-valinamide;
N$^1$-((3aS,4R,6aR)-2-{[4-fluoro-3-(trifluoromethyl)phenyl]sulfonyl}octahydrocyclopenta[c]pyrrol-4-yl)-N$^2$-methyl-L-leucinamide;
3-methyl-N$^1$-((3aS,4R,6aR)-2-{[4-(trifluoromethyl)phenyl]sulfonyl}octahydrocyclopenta[c]pyrrol-4-yl)-L-valinamide;
3-methyl-N$^1$-((3aS,4R,6aR)-2-{[4-(trifluoromethyl)phenyl]sulfonyl}octahydrocyclopenta[c]pyrrol-4-yl)-L-valinamide;

N²-methyl-N¹-((3aR,4S,6aS)-2-{[3-(trifluoromethyl)phenyl]sulfonyl}octahydrocyclopenta[c]pyrrol-4-yl)-L-isoleucinamide;

N²-methyl-N¹-((3aR,4S,6aS)-2-{[4-(trifluoromethyl)phenyl]sulfonyl}octahydrocyclopenta[c]pyrrol-4-yl)-L-isoleucinamide;

N²-methyl-N¹-((3aS,4R,6aR)-2-{[3-(trifluoromethyl)phenyl]sulfonyl}octahydrocyclopenta[c]pyrrol-4-yl)-L-isoleucinamide;

N²-methyl-N¹-((3aS,4R,6aR)-2-{[4-(trifluoromethyl)phenyl]sulfonyl}octahydrocyclopenta[c]pyrrol-4-yl)-L-isoleucinamide;

N²,4-dimethyl-N¹-((3aR,4S,6aS)-2-{[3-(trifluoromethyl)phenyl]sulfonyl}octahydrocyclopenta[c]pyrrol-4-yl)-L-leucinamide;

N²,4-dimethyl-N¹-((3aR,4S,6aS)-2-{[4-(trifluoromethyl)phenyl]sulfonyl}octahydrocyclopenta[c]pyrrol-4-yl)-L-leucinamide;

N²,4-dimethyl-N¹-((3aS,4R,6aR)-2-{[3-(trifluoromethyl)phenyl]sulfonyl}octahydrocyclopenta[c]pyrrol-4-yl)-L-leucinamide;

N²,4-dimethyl-N¹-((3aS,4R,6aR)-2-{[4-(trifluoromethyl)phenyl]sulfonyl}octahydrocyclopenta[c]pyrrol-4-yl)-L-leucinamide;

N²-methyl-N¹-((3aR,4S,6aS)-2-{[4-(trifluoromethyl)phenyl]sulfonyl}octahydrocyclopenta[c]pyrrol-4-yl)-L-norleucinamide;

4-methyl-N¹-((3aR,4S,6aS)-2-{[4-(trifluoromethyl)phenyl]sulfonyl}octahydrocyclopenta[c]pyrrol-4-yl)-L-leucinamide;

N²-methyl-N¹-((3aR,4R,6aS)-2-{[4-(trifluoromethyl)phenyl]sulfonyl}octahydrocyclopenta[c]pyrrol-4-yl)-L-norvalinamide;

N²-methyl-N¹-((3aR,4R,6aS)-2-{[4-(trifluoromethyl)phenyl]sulfonyl}octahydrocyclopenta[c]pyrrol-4-yl)-L-leucinamide;

N¹-((3aR,4S,6aS)-2-{[4-(trifluoromethyl)phenyl]sulfonyl}octahydrocyclopenta[c]pyrrol-4-yl)-L-norvalinamide;

N¹-((3aS,4R,6aR)-2-{[4-(trifluoromethyl)phenyl]sulfonyl}octahydrocyclopenta[c]pyrrol-4-yl)-L-norvalinamide;

N¹-((3aR,4S,6aS)-2-{[3-(trifluoromethyl)phenyl]sulfonyl}octahydrocyclopenta[c]pyrrol-4-yl)-L-norvalinamide;

N¹-((3aS,4R,6aR)-2-{[3-(trifluoromethyl)phenyl]sulfonyl}octahydrocyclopenta[c]pyrrol-4-yl)-L-norvalinamide;

3-cyclohexyl-N¹-((3aR,4S,6aS)-2-{[4-(trifluoromethyl)phenyl]sulfonyl}octahydrocyclopenta[c]pyrrol-4-yl)-L-alaninamide;

3-cyclohexyl-N²-methyl-N¹-((3aR,4S,6aS)-2-{[4-(trifluoromethyl)phenyl]sulfonyl}octahydrocyclopenta[c]pyrrol-4-yl)-L-alaninamide;

N¹-((3aR,4S,6aS)-2-{[2-chloro-5-(trifluoromethyl)phenyl]sulfonyl}octahydrocyclopenta[c]pyrrol-4-yl)-4-methyl-L-leucinamide;

N¹-((3aR,4S,6aS)-2-{[2-chloro-4-(trifluoromethyl)phenyl]sulfonyl}octahydrocyclopenta[c]pyrrol-4-yl)-4-methyl-L-leucinamide;

N-methyl-N-((3aR,4S,6aS)-2-{[4-(trifluoromethyl)phenyl]sulfonyl}octahydrocyclopenta[c]pyrrol-4-yl)-L-phenylalaninamide;

N¹-((3aR,4S,6aS)-2-{[2-chloro-4-(trifluoromethyl)phenyl]sulfonyl}octahydrocyclopenta[c]pyrrol-4-yl)-N²,4-dimethyl-L-leucinamide;

N-((3aR,4S,6aS)-2-{[2-chloro-4-(trifluoromethyl)phenyl]sulfonyl}octahydrocyclopenta[c]pyrrol-4-yl)-N-methyl-L-phenylalaninamide;

N¹-cyclopropyl-N²,4-dimethyl-N¹-((3aR,4S,6aS)-2-{[4-(trifluoromethyl)phenyl]sulfonyl}octahydrocyclopenta[c]pyrrol-4-yl)-L-leucinamide;

N¹-ethyl-N²,4-dimethyl-N¹-((3aR,4S,6aS)-2-{[4-(trifluoromethyl)phenyl]sulfonyl}octahydrocyclopenta[c]pyrrol-4-yl)-L-leucinamide;

N²,4-dimethyl-N¹-propyl-N¹-((3aR,4S,6aS)-2-{[4-(trifluoromethyl)phenyl]sulfonyl}octahydrocyclopenta[c]pyrrol-4-yl)-L-leucinamide;

N¹-(cyclopropylmethyl)-N²,4-dimethyl-N¹-((3aR,4S,6aS)-2-{[4-(trifluoromethyl)phenyl]sulfonyl}octahydrocyclopenta[c]pyrrol-4-yl)-L-leucinamide;

N¹,N²,4-trimethyl-N¹-((3aR,4S,6aS)-2-{[4-(trifluoromethyl)phenyl]sulfonyl}octahydrocyclopenta[c]pyrrol-4-yl)-L-leucinamide;

N¹,N²-dimethyl-N¹-((3aR,4S,6aS)-2-{[4-(trifluoromethyl)phenyl]sulfonyl}octahydrocyclopenta[c]pyrrol-4-yl)-L-norvalinamide;

N¹-((3aR,4S,6aS)-2-{[2-chloro-4-(trifluoromethyl)phenyl]sulfonyl}octahydrocyclopenta[c]pyrrol-4-yl)-N¹,N²,4-trimethyl-L-leucinamide;

4-methyl-N¹-{(3aR,4S,6aS)-2-[5-(trifluoromethyl)pyridin-2-yl]octahydrocyclopenta[c]pyrrol-4-yl}-L-leucinamide;

4-methyl-N¹-{(3aR,4S,6aS)-2-[6-(trifluoromethyl)pyridin-2-yl]octahydrocyclopenta[c]pyrrol-4-yl}-L-leucinamide;

4-methyl-N¹-{(3aR,4S,6aS)-2-[2-(methylsulfonyl)pyrimidin-5-yl]octahydrocyclopenta[c]pyrrol-4-yl}-L-leucinamide;

N¹-{(3aS,4R,6aR)-2-[(3-fluorophenyl)sulfonyl]octahydrocyclopenta[c]pyrrol-4-yl}-N²-methyl-L-leucinamide;

N¹-{(3aS,4R,6aR)-2-[(4-fluorophenyl)sulfonyl]octahydrocyclopenta[c]pyrrol-4-yl}-N²-methyl-L-leucinamide;

N¹-{(3aS,4R,6aR)-2-[(3,4-difluorophenyl)sulfonyl]octahydrocyclopenta[c]pyrrol-4-yl}-N²-methyl-L-leucinamide;

N¹-{(3aS,4R,6aR)-2-[(3,5-difluorophenyl)sulfonyl]octahydrocyclopenta[c]pyrrol-4-yl}-N²-methyl-L-leucinamide;

N¹-{(3aS,4R,6aR)-2-[(4-chlorophenyl)sulfonyl]octahydrocyclopenta[c]pyrrol-4-yl}-N²-methyl-L-leucinamide;

N²-methyl-N¹-[(3aS,4R,6aR)-2-(phenylsulfonyl)octahydrocyclopenta[c]pyrrol-4-yl]-L-leucinamide;

N²-methyl-N¹-{(3aS,4R,6aR)-2-[4-(trifluoromethyl)benzyl]octahydrocyclopenta[c]pyrrol-4-yl}-L-leucinamide;

N¹-[(3aS,4R,6aR)-2-(4-fluorobenzyl)octahydrocyclopenta[c]pyrrol-4-yl]-N²-methyl-L-leucinamide;

N²-methyl-N¹-((3aR,4S,6aS)-2-{[4-(trifluoromethyl)phenyl]sulfonyl}octahydrocyclopenta[c]pyrrol-4-yl)-L-valinamide;

N¹-{(3aR,4S,6aS)-2-[(4-fluorophenyl)sulfonyl]octahydrocyclopenta[c]pyrrol-4-yl}-N²-methyl-L-valinamide;

N¹-{(3aR,4S,6aS)-2-[(4-fluorophenyl)sulfonyl]octahydrocyclopenta[c]pyrrol-4-yl}-4-methyl-L-leucinamide;

N¹-{(3aR,4S,6aS)-2-[(4-fluorophenyl)sulfonyl]octahydrocyclopenta[c]pyrrol-4-yl}-N²-methyl-L-norleucinamide;

N¹-{(3aR,4S,6aS)-2-[(4-fluorophenyl)sulfonyl]octahydrocyclopenta[c]pyrrol-4-yl}-N²-methyl-L-leucinamide;

N²-methyl-N¹-((3aS,4S,6aR)-2-{[4-(trifluoromethyl)phenyl]sulfonyl}octahydrocyclopenta[c]pyrrol-4-yl)-L-norvalinamide;

N²-methyl-N¹-((3aS,4S,6aR)-2-{[4-(trifluoromethyl)phenyl]sulfonyl}octahydrocyclopenta[c]pyrrol-4-yl)-L-leucinamide;

$N^1$-{(3aR,4S,6aS)-2-[3,3-bis(4-fluorophenyl)propyl]octahydrocyclopenta[c]pyrrol-4-yl}-$N^2$-methyl-L-norvalinamide;

2,2-bis(4-fluorophenyl)-N-[(3aR,4S,6aS)-2-(N-methyl-L-leucyl)octahydrocyclopenta[c]pyrrol-4-yl]acetamide;

2,2-bis(4-fluorophenyl)-N-[(3aR,4S,6aS)-2-(N-methyl-L-norvalyl)octahydrocyclopenta[c]pyrrol-4-yl]acetamide;

N-[(3aR,4S,6aS)-2-(N,4-dimethyl-L-leucyl)octahydrocyclopenta[c]pyrrol-4-yl]-2,2-bis(4-fluorophenyl)acetamide;

2,2-bis(4-fluorophenyl)-N-[(3aR,4S,6aS)-2-(4-methyl-L-leucyl)octahydrocyclopenta[c]pyrrol-4-yl]acetamide;

tert-butyl(S)-1-((3aR,4S,6aS)-4-((S)-2-(tert-butoxycarbonylamino)-4,4-dimethylpentanamido)hexahydrocyclopenta[c]pyrrol-2(1H)-yl)-4,4-dimethyl-1-oxopentan-2-ylcarbamate;

4-methyl-$N^1$-[(3aR,4S,6aS)-2-(4-methyl-L-leucyl)octahydrocyclopenta[c]pyrrol-4-yl]-L-leucinamide;

4-methyl-$N^1$-[(3aR,4S,6aS)-2-L-phenylalanyloctahydrocyclopenta[c]pyrrol-4-yl]-L-leucinamide;

(3aR,4S,6aS)-N-benzhydryl-2-[3-(trifluoromethyl)benzyl]octahydrocyclopenta[c]pyrrol-4-amine;

(3aS,4R,6aR)-N-benzhydryl-2-{[3-(trifluoromethyl)phenyl]sulfonyl}octahydrocyclopenta[c]pyrrol-4-amine;

(3aR,4S,6aS)-N-benzhydryl-2-{[3-(trifluoromethyl)phenyl]sulfonyl}octahydrocyclopenta[c]pyrrol-4-amine;

$N^1$-[(3aS,4R,6aR)-2-benzhydryloctahydrocyclopenta[c]pyrrol-4-yl]-$N^2$-methyl-L-leucinamide;

4-methyl-$N^2$-propyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-(cyclopropylmethyl)-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-(cyclobutylmethyl)-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-isobutyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-(cyclopentylmethyl)-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-(cyclohexylmethyl)-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-butyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-ethyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-(cyclopropylmethyl)-4-methyl-$N^1$-{(3aR,4S,6aS)-2-[5-(trifluoromethyl)pyridin-2-yl]octahydrocyclopenta[c]pyrrol-4-yl}-L-leucinamide;

$N^2$-(cyclopropylmethyl)-4-methyl-$N^1$-{(3aR,4S,6aS)-2-[6-(trifluoromethyl)pyridin-2-yl]octahydrocyclopenta[c]pyrrol-4-yl}-L-leucinamide;

$N^2$-isopropyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-isopropyl-$N^1$-((3aR,4S,6aS)-2-{[4-(trifluoromethyl)phenyl]sulfonyl}octahydrocyclopenta[c]pyrrol-4-yl)-L-norvalinamide;

$N^2$-isopropyl-$N^1$-((3aS,4R,6aR)-2-{[4-(trifluoromethyl)phenyl]sulfonyl}octahydrocyclopenta[c]pyrrol-4-yl)-L-norvalinamide;

$N^2$-isopropyl-$N^1$-((3aR,4S,6aS)-2-{[3-(trifluoromethyl)phenyl]sulfonyl}octahydrocyclopenta[c]pyrrol-4-yl)-L-norvalinamide;

$N^2$-isopropyl-$N^1$-((3aS,4R,6aR)-2-{[3-(trifluoromethyl)phenyl]sulfonyl}octahydrocyclopenta[c]pyrrol-4-yl)-L-norvalinamide;

3-cyclohexyl-$N^2$-isopropyl-$N^1$-((3aR,4S,6aS)-2-{[4-(trifluoromethyl)phenyl]sulfonyl}octahydrocyclopenta[c]pyrrol-4-yl)-L-alaninamide;

$N^1$-((3aR,4S,6aS)-2-{[2-chloro-5-(trifluoromethyl)phenyl]sulfonyl}octahydrocyclopenta[c]pyrrol-4-yl)-$N^2$-isopropyl-4-methyl-L-leucinamide;

$N^1$-((3aR,4S,6aS)-2-{[2-chloro-4-(trifluoromethyl)phenyl]sulfonyl}octahydrocyclopenta[c]pyrrol-4-yl)-$N^2$-isopropyl-4-methyl-L-leucinamide;

$N^2$-isopropyl-$N^1$-[(3aR,4S,6aS)-2-(N-isopropyl-4-methyl-L-leucyl)octahydrocyclopenta[c]pyrrol-4-yl]-4-methyl-L-leucinamide;

$N^2$-isopropyl-$N^1$-[(3aR,4S,6aS)-2-(N-isopropyl-L-phenylalanyl)octahydrocyclopenta[c]pyrrol-4-yl]-4-methyl-L-leucinamide;

$N^2$-isopropyl-4-methyl-$N^1$-{(3aR,4S,6aS)-2-[5-(trifluoromethyl)pyridin-2-yl]octahydrocyclopenta[c]pyrrol-4-yl}-L-leucinamide;

$N^2$-isopropyl-4-methyl-$N^1$-{(3aR,4S,6aS)-2-[6-(trifluoromethyl)pyridin-2-yl]octahydrocyclopenta[c]pyrrol-4-yl}-L-leucinamide;

2,2-bis(4-fluorophenyl)-N-[(3aR,4S,6aS)-2-(N-isopropyl-4-methyl-L-leucyl)octahydrocyclopenta[c]pyrrol-4-yl]acetamide;

$N^2$-isopropyl-4-methyl-$N^1$-{(3aR,4S,6aS)-2-[2-(methylsulfonyl)pyrimidin-5-yl]octahydrocyclopenta[c]pyrrol-4-yl}-L-leucinamide;

$N^1$-[(3aR,4S,6aS)-2-benzyloctahydrocyclopenta[c]pyrrol-4-yl]-$N^2$-isopropyl-L-norvalinamide;

$N^1$-[(3aS,4R,6aR)-2-benzyloctahydrocyclopenta[c]pyrrol-4-yl]-$N^2$-isopropyl-L-norvalinamide;

$N^2$-isopropyl-$N^1$-((3aR,4S,6aS)-2-{[3-(trifluoromethyl)phenyl]sulfonyl}octahydrocyclopenta[c]pyrrol-4-yl)-L-leucinamide;

$N^2$,$N^2$-dimethyl-$N^1$-((3aR,4S,6aS)-2-{[3-(trifluoromethyl)phenyl]sulfonyl}octahydrocyclopenta[c]pyrrol-4-yl)-L-leucinamide;

(3R)-3-(dimethylamino)-4-methyl-N-((3aR,4S,6aS)-2-{[3-(trifluoromethyl)phenyl]sulfonyl}octahydrocyclopenta[c]pyrrol-4-yl)pentanamide;

$N^2$-cyclopropyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$,$N^2$-dicyclopropyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-cyclopentyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-cyclohexyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-(1-ethylpropyl)-4-methyl-$N^1$-((3aR,4S,6aS)-2-{[4-(trifluoromethyl)phenyl]sulfonyl}octahydrocyclopenta[c]pyrrol-4-yl)-L-leucinamide;

$N^2$-cyclobutyl-4-methyl-$N^1$-((3aR,4S,6aS)-2-{[4-(trifluoromethyl)phenyl]sulfonyl}octahydrocyclopenta[c]pyrrol-4-yl)-L-leucinamide;

4-methyl-$N^2$-neopentyl-$N^1$-((3aR,4S,6aS)-2-{[4-(trifluoromethyl)phenyl]sulfonyl}octahydrocyclopenta[c]pyrrol-4-yl)-L-leucinamide;

N²-cyclopentyl-N¹-((3aR,4S,6aS)-2-{[4-(trifluoromethyl)phenyl]sulfonyl}octahydrocyclopenta[c]pyrrol-4-yl)-L-norvalinamide;

N²-cyclohexyl-N¹-((3aR,4S,6aS)-2-{[4-(trifluoromethyl)phenyl]sulfonyl}octahydrocyclopenta[c]pyrrol-4-yl)-L-norvalinamide;

N²-cyclopentyl-N¹-[(3aR,4S,6aS)-2-(N-cyclopentyl-4-methyl-L-leucyl)octahydrocyclopenta[c]pyrrol-4-yl]-4-methyl-L-leucinamide;

N²,N²-dimethyl-N¹-{(3aS,4S,6aR)-2-[3-(trifluoromethyl)benzyl]octahydrocyclopenta[c]pyrrol-4-yl}-L-leucinamide;

N¹-[(3aS,4R,6aR)-2-benzyloctahydrocyclopenta[c]pyrrol-4-yl]-N²-methyl-N²-neopentyl-L-leucinamide;

N¹-[(3aS,4R,6aR)-2-benzyloctahydrocyclopenta[c]pyrrol-4-yl]-N²-(3,3-dimethylbutyl)-N²-methyl-L-leucinamide;

N²,N²-dimethyl-N¹-((3aS,4R,6aR)-2-{[3-(trifluoromethyl)phenyl]sulfonyl}octahydrocyclopenta[c]pyrrol-4-yl)-L-leucinamide;

N¹-[(3aS,4R,6aR)-2-benzyloctahydrocyclopenta[c]pyrrol-4-yl]-N²-(4-fluorobenzyl)-N²-methyl-L-leucinamide;

(2S)-N-[(3aS,4R,6aR)-2-benzyloctahydrocyclopenta[c]pyrrol-4-yl]-1-(methylsulfonyl)piperidine-2-carboxamide;

(3R)-4-methyl-3-[(methylsulfonyl)amino]-N-((3aR,4S,6aS)-2-{[3-(trifluoromethyl)phenyl]sulfonyl}octahydrocyclopenta[c]pyrrol-4-yl)pentanamide;

N²-(methylsulfonyl)-N¹-{(3aS,4S,6aS)-2-[3-(trifluoromethyl)benzyl]octahydrocyclopenta[c]pyrrol-4-yl}-L-leucinamide;

N²-(methylsulfonyl)-N¹-{(3aS,4S,6aS)-2-[3-(trifluoromethyl)benzyl]octahydrocyclopenta[c]pyrrol-4-yl}-D-leucinamide;

N²-ethyl-N²-(methylsulfonyl)-N¹-{(3aS,4S,6aS)-2-[3-(trifluoromethyl)benzyl]octahydrocyclopenta[c]pyrrol-4-yl}-L-leucinamide;

4-methyl-N²-(methylsulfonyl)-N¹-{(3aS,4S,6aS)-2-[4-(trifluoromethyl)benzyl]octahydrocyclopenta[c]pyrrol-4-yl}-L-leucinamide;

3-methyl-N²-(methylsulfonyl)-N¹-{(3aS,4S,6aS)-2-[4-(trifluoromethyl)benzyl]octahydrocyclopenta[c]pyrrol-4-yl}-L-valinamide;

N²-(methylsulfonyl)-N¹-{(3aS,4S,6aS)-2-[4-(trifluoromethyl)benzyl]octahydrocyclopenta[c]pyrrol-4-yl}-L-norvalinamide;

N²-(isopropylsulfonyl)-N¹-{(3aS,4R,6aR)-2-[3-(trifluoromethyl)benzyl]octahydrocyclopenta[c]pyrrol-4-yl}-L-leucinamide;

N²-(phenylsulfonyl)-N¹-{(3aS,4R,6aR)-2-[3-(trifluoromethyl)benzyl]octahydrocyclopenta[c]pyrrol-4-yl}-L-leucinamide;

N²-(cyclopentylsulfonyl)-N¹-{(3aS,4R,6aR)-2-[3-(trifluoromethyl)benzyl]octahydrocyclopenta[c]pyrrol-4-yl}-L-leucinamide;

isopropyl(S)-4,4-dimethyl-1-oxo-1-((3aR,4S,6aS)-2-(4-(trifluoromethyl)benzyl)octahydrocyclopenta[c]pyrrol-4-ylamino)pentan-2-ylcarbamate;

isopropyl(S)-3,3-dimethyl-1-oxo-1-((3aR,4S,6aS)-2-(4-(trifluoromethyl)benzyl)octahydrocyclopenta[c]pyrrol-4-ylamino)butan-2-ylcarbamate;

cyclopentyl(S)-1-oxo-1-((3aR,4S,6aS)-2-(4-(trifluoromethyl)benzyl)octahydrocyclopenta[c]pyrrol-4-ylamino)pentan-2-ylcarbamate;

N²-(2,2-dimethylpropanoyl)-N¹-{(3aR,4S,6aS)-2-[4-(trifluoromethyl)benzyl]octahydrocyclopenta[c]pyrrol-4-yl}-L-norvalinamide;

tert-butyl(S)-1-((3aR,4S,6aS)-2-(3-chloro-4-fluorophenylsulfonyl)octahydrocyclopenta[c]pyrrol-4-ylamino)-1-oxopentan-2-yl(methyl)carbamate;

tert-butyl methyl((S)-1-oxo-1-((3aR,4S,6aS)-2-(pyridin-3-ylsulfonyl)octahydrocyclopenta[c]pyrrol-4-ylamino)pentan-2-yl)carbamate;

tert-butyl methyl((S)-1-oxo-1-((3aR,4S,6aS)-2-(thiophen-2-ylsulfonyl)octahydrocyclopenta[c]pyrrol-4-ylamino)pentan-2-yl)carbamate;

N²-methyl-N¹-((3aR,4S,6aS)-2-{[4-(trifluoromethoxy)phenyl]sulfonyl}octahydrocyclopenta[c]pyrrol-4-yl)-L-norvalinamide;

N²-methyl-N¹-[(3aR,4S,6aS)-2-(thien-2-ylsulfonyl)octahydrocyclopenta[c]pyrrol-4-yl]-L-norvalinamide;

N¹-{(3aR,4S,6aS)-2-[(3-chloro-4-fluorophenyl)sulfonyl]octahydrocyclopenta[c]pyrrol-4-yl}-N²-methyl-L-norvalinamide;

N²-methyl-N¹-[(3aR,4S,6aS)-2-(pyridin-3-ylsulfonyl)octahydrocyclopenta[c]pyrrol-4-yl]-L-norvalinamide;

N¹-{(3aR,4S,6aS)-2-[(4-cyanophenyl)sulfonyl]octahydrocyclopenta[c]pyrrol-4-yl}-N²-methyl-L-norvalinamide;

N¹-{(3aR,4S,6aS)-2-[(4-methoxyphenyl)sulfonyl]octahydrocyclopenta[c]pyrrol-4-yl}-N²-methyl-L-norvalinamide;

N¹-((3aR,4S,6aS)-2-{[3,5-bis(trifluoromethyl)phenyl]sulfonyl}octahydrocyclopenta[c]pyrrol-4-yl)-N²-methyl-L-norvalinamide;

N¹-{(3aR,4S,6aS)-2-[(2-chloro-4-fluorophenyl)sulfonyl]octahydrocyclopenta[c]pyrrol-4-yl}-N²-methyl-L-norvalinamide;

N²-methyl-N¹-[(3aR,4S,6aS)-2-(1-naphthylsulfonyl)octahydrocyclopenta[c]pyrrol-4-yl]-L-norvalinamide;

N¹-((3aR,4S,6aS)-2-{[4-bromo-3-(trifluoromethyl)phenyl]sulfonyl}octahydrocyclopenta[c]pyrrol-4-yl)-N²-methyl-L-norvalinamide;

N¹-{(3aR,4S,6aS)-2-[(3,4-dichlorophenyl)sulfonyl]octahydrocyclopenta[c]pyrrol-4-yl}-N²-methyl-L-norvalinamide;

N¹-{(3aR,4S,6aS)-2-[(4-tert-butylphenyl)sulfonyl]octahydrocyclopenta[c]pyrrol-4-yl}-N²-methyl-L-norvalinamide;

N¹-[(3aR,4S,6aS)-2-(1,1'-biphenyl-4-ylsulfonyl)octahydrocyclopenta[c]pyrrol-4-yl]-N²-methyl-L-norvalinamide;

N¹-{(3aR,4S,6aS)-2-[(3,4-dimethoxyphenyl)sulfonyl]octahydrocyclopenta[c]pyrrol-4-yl}-N²-methyl-L-norvalinamide;

N¹-{(3aR,4S,6aS)-2-[(3-cyanophenyl)sulfonyl]octahydrocyclopenta[c]pyrrol-4-yl}-N²-methyl-L-norvalinamide;

N¹-[(3aR,4S,6aS)-2-(2-furylsulfonyl)octahydrocyclopenta[c]pyrrol-4-yl]-N²-methyl-L-norvalinamide;

N¹-{(3aR,4S,6aS)-2-[(2,3-dichlorophenyl)sulfonyl]octahydrocyclopenta[c]pyrrol-4-yl}-N²-methyl-L-norvalinamide;

N²-methyl-N¹-((3aR,4S,6aS)-2-{[4-(trifluoromethyl)benzyl]sulfonyl}octahydrocyclopenta[c]pyrrol-4-yl)-L-norvalinamide;

N²-methyl-N¹-((3aR,4S,6aS)-2-{[2-(trifluoromethyl)phenyl]sulfonyl}octahydrocyclopenta[c]pyrrol-4-yl)-L-norvalinamide;

N¹-{(3aR,4S,6aS)-2-[(3-bromophenyl)sulfonyl]octahydrocyclopenta[c]pyrrol-4-yl}-N²-methyl-L-norvalinamide;

N¹-((3aR,4S,6aS)-2-{[2-chloro-4-(trifluoromethyl)phenyl]sulfonyl}octahydrocyclopenta[c]pyrrol-4-yl)-N²-methyl-L-norvalinamide;

N¹-((3aR,4S,6aS)-2-{[2-chloro-5-(trifluoromethyl)phenyl]sulfonyl}octahydrocyclopenta[c]pyrrol-4-yl)-N²-methyl-L-norvalinamide;

N²-methyl-N¹-{(3aR,4S,6aS)-2-[3-(trifluoromethyl)benzoyl]octahydrocyclopenta[c]pyrrol-4-yl}-L-norvalinamide;
N-[(3aR,4S,6aS)-2-benzyloctahydrocyclopenta[c]pyrrol-4-yl]-N-isopropyl-3-(trifluoromethyl)benzenesulfonamide;
N-[(3aR,4S,6aS)-2-benzyloctahydrocyclopenta[c]pyrrol-4-yl]-3-(trifluoromethyl)benzenesulfonamide;
N-isopropyl-N-[(3aR,4S,6aS)-2-(N-methyl-L-leucyl)octahydrocyclopenta[c]pyrrol-4-yl]-3-(trifluoromethyl)benzenesulfonamide;
N-[(3aR,4S,6aS)-2-(N-methyl-L-leucyl)octahydrocyclopenta[c]pyrrol-4-yl]-3-(trifluoromethyl)benzenesulfonamide;
N-cyclopropyl-N-[(3aS*,4S*,6aR*)-[2-(N-methyl-L-leucyl)octahydrocyclopenta[c]pyrrol-4-yl]-3-(trifluoromethyl)benzenesulfonamide;
4-fluoro-N-{(3aR,4S,6aS)-2-[6-(trifluoromethyl)pyridin-2-yl]octahydrocyclopenta[c]pyrrol-4-yl}benzamide;
4-fluoro-N-{(3aR,4S,6aS)-2-[6-(trifluoromethyl)pyridin-2-yl]octahydrocyclopenta[c]pyrrol-4-yl}benzamide;
2-hydroxy-N-{(3aR,4S,6aS)-2-[6-(trifluoromethyl)pyridin-2-yl]octahydrocyclopenta[c]pyrrol-4-yl}benzamide;
2-fluoro-N-{(3aR,4S,6aS)-2-[6-(trifluoromethyl)pyridin-2-yl]octahydrocyclopenta[c]pyrrol-4-yl}benzamide;
3-fluoro-N-{(3aR,4S,6aS)-2-[6-(trifluoromethyl)pyridin-2-yl]octahydrocyclopenta[c]pyrrol-4-yl}benzamide;
3,4-difluoro-N-{(3aR,4S,6aS)-2-[6-(trifluoromethyl)pyridin-2-yl]octahydrocyclopenta[c]pyrrol-4-yl}benzamide;
3-chloro-4-fluoro-N-{(3aR,4S,6aS)-2-[6-(trifluoromethyl)pyridin-2-yl]octahydrocyclopenta[c]pyrrol-4-yl}benzamide;
(2S)-2-hydroxy-4-methyl-N-{(3aR,4S,6aS)-2-[6-(trifluoromethyl)pyridin-2-yl]octahydrocyclopenta[c]pyrrol-4-yl}pentanamide;
N-{(3aR,4S,6aS)-2-[5-(trifluoromethyl)pyridin-2-yl]octahydrocyclopenta[c]pyrrol-4-yl}-1H-indole-2-carboxamide;
N-{(3aR,4S,6aS)-2-[6-(trifluoromethyl)pyridin-2-yl]octahydrocyclopenta[c]pyrrol-4-yl}quinoline-2-carboxamide;
N-{(3aR,4S,6aS)-2-[6-(trifluoromethyl)pyridin-2-yl]octahydrocyclopenta[c]pyrrol-4-yl}-1H-indole-2-carboxamide;
5-(2-thienyl)-N-{(3aR,4S,6aS)-2-[6-(trifluoromethyl)pyridin-2-yl]octahydrocyclopenta[c]pyrrol-4-yl}-2-furamide;
4-methyl-N-{(3aR,4S,6aS)-2-[6-(trifluoromethyl)pyridin-2-yl]octahydrocyclopenta[c]pyrrol-4-yl}-1H-pyrrole-2-carboxamide;
1-hydroxy-N-{(3aR,4S,6aS)-2-[6-(trifluoromethyl)pyridin-2-yl]octahydrocyclopenta[c]pyrrol-4-yl}cyclopentanecarboxamide;
N-{(3aR,4S,6aS)-2-[6-(trifluoromethyl)pyridin-2-yl]octahydrocyclopenta[c]pyrrol-4-yl}-4H-furo[3,2-b]pyrrole-5-carboxamide;
4-chloro-N-{(3aR,4S,6aS)-2-[6-(trifluoromethyl)pyridin-2-yl]octahydrocyclopenta[c]pyrrol-4-yl}-1H-pyrrole-2-carboxamide;
5-methyl-N-{(3aR,4S,6aS)-2-[6-(trifluoromethyl)pyridin-2-yl]octahydrocyclopenta[c]pyrrol-4-yl}-2-furamide;
3-hydroxy-N-{(3aR,4S,6aS)-2-[6-(trifluoromethyl)pyridin-2-yl]octahydrocyclopenta[c]pyrrol-4-yl}benzamide;
(2R)-2-hydroxy-4-methyl-N-{(3aR,4S,6aS)-2-[6-(trifluoromethyl)pyridin-2-yl]octahydrocyclopenta[c]pyrrol-4-yl}pentanamide;
5-methyl-N-{(3aR,4S,6aS)-2-[6-(trifluoromethyl)pyridin-2-yl]octahydrocyclopenta[c]pyrrol-4-yl}pyrazine-2-carboxamide;
(2S)-2-hydroxy-3,3-dimethyl-N-{(3aR,4S,6aS)-2-[6-(trifluoromethyl)pyridin-2-yl]octahydrocyclopenta[c]pyrrol-4-yl}butanamide;
5-methyl-N-{(3aR,4S,6aS)-2-[6-(trifluoromethyl)pyridin-2-yl]octahydrocyclopenta[c]pyrrol-4-yl}-1,2-oxazole-4-carboxamide;
4,4,4-trifluoro-N-{(3aR,4S,6aS)-2-[6-(trifluoromethyl)pyridin-2-yl]octahydrocyclopenta[c]pyrrol-4-yl}butanamide;
3-cyclopropyl-N-{(3aR,4S,6aS)-2-[6-(trifluoromethyl)pyridin-2-yl]octahydrocyclopenta[c]pyrrol-4-yl}-1H-pyrazole-5-carboxamide;
cis-4-hydroxy-N-{(3aR,4S,6aS)-2-[6-(trifluoromethyl)pyridin-2-yl]octahydrocyclopenta[c]pyrrol-4-yl}cyclohexanecarboxamide;
(2S)-3,3,3-trifluoro-2-hydroxy-N-{(3aR,4S,6aS)-2-[6-(trifluoromethyl)pyridin-2-yl]octahydrocyclopenta[c]pyrrol-4-yl}propanamide;
4,4,4-trifluoro-3-hydroxy-N-{(3aR,4S,6aS)-2-[6-(trifluoromethyl)pyridin-2-yl]octahydrocyclopenta[c]pyrrol-4-yl}butanamide;
N²,4-dimethyl-N-{(3aR,4S,6aS)-2-[6-(trifluoromethyl)pyridin-2-yl]octahydrocyclopenta[c]pyrrol-4-yl}-L-leucinamide;
N²-methyl-N-{(3aR,4S,6aS)-2-[6-(trifluoromethyl)pyridin-2-yl]octahydrocyclopenta[c]pyrrol-4-yl}-L-norvalinamide;
N²-methyl-N-{(3aR,4S,6aS)-2-[6-(trifluoromethyl)pyridin-2-yl]octahydrocyclopenta[c]pyrrol-4-yl}-L-norleucinamide;
N²-methyl-N-{(3aR,4S,6aS)-2-[6-(trifluoromethyl)pyridin-2-yl]octahydrocyclopenta[c]pyrrol-4-yl}-L-leucinamide;
3-methyl-N-{(3aR,4S,6aS)-2-[6-(trifluoromethyl)pyridin-2-yl]octahydrocyclopenta[c]pyrrol-4-yl}-L-valinamide;
(4R)-4-fluoro-N-{(3aR,4S,6aS)-2-[6-(trifluoromethyl)pyridin-2-yl]octahydrocyclopenta[c]pyrrol-4-yl}-L-prolinamide;
(2S,3aS,7aS)-N-{(3aR,4S,6aS)-2-[6-(trifluoromethyl)pyridin-2-yl]octahydrocyclopenta[c]pyrrol-4-yl}octahydro-1H-indole-2-carboxamide;
1-amino-N-{(3aR,4S,6aS)-2-[6-(trifluoromethyl)pyridin-2-yl]octahydrocyclopenta[c]pyrrol-4-yl}cyclopentanecarboxamide;
4,4-difluoro-N-{(3aR,4S,6aS)-2-[6-(trifluoromethyl)pyridin-2-yl]octahydrocyclopenta[c]pyrrol-4-yl}-L-prolinamide;
(4S)-4-fluoro-N-{(3aR,4S,6aS)-2-[6-(trifluoromethyl)pyridin-2-yl]octahydrocyclopenta[c]pyrrol-4-yl}-L-prolinamide;
(2S)-N-{(3aR,4S,6aS)-2-[6-(trifluoromethyl)pyridin-2-yl]octahydrocyclopenta[c]pyrrol-4-yl}piperidine-2-carboxamide;
N-{(3aR,4S,6aS)-2-[6-(trifluoromethyl)pyridin-2-yl]octahydrocyclopenta[c]pyrrol-4-yl}-L-prolinamide;
N²-methyl-N-{(3aR,4S,6aS)-2-[5-(trifluoromethyl)pyridin-2-yl]octahydrocyclopenta[c]pyrrol-4-yl}-L-norvalinamide;
N²-methyl-N-{(3aR,4S,6aS)-2-[5-(trifluoromethyl)pyridin-2-yl]octahydrocyclopenta[c]pyrrol-4-yl}-L-leucinamide;
N²-methyl-N-{(3aR,4S,6aS)-2-[5-(trifluoromethyl)pyridin-2-yl]octahydrocyclopenta[c]pyrrol-4-yl}-L-norleucinamide;
N²,4-dimethyl-N-{(3aR,4S,6aS)-2-[5-(trifluoromethyl)pyridin-2-yl]octahydrocyclopenta[c]pyrrol-4-yl}-L-leucinamide;
(2S,3aS,7aS)-N-{(3aR,4S,6aS)-2-[5-(trifluoromethyl)pyridin-2-yl]octahydrocyclopenta[c]pyrrol-4-yl}octahydro-1H-indole-2-carboxamide;

(2S)-N-{(3aR,4S,6aS)-2-[5-(trifluoromethyl)pyridin-2-yl]octahydrocyclopenta[c]pyrrol-4-yl}indoline-2-carboxamide;

(3aR,4S,6aS)-2-[3-(trifluoromethyl)phenyl]octahydrocyclopenta[c]pyrrol-4-amine;

$N^2$-methyl-N-{(3aR,4S,6aS)-2-[3-(trifluoromethyl)phenyl]octahydrocyclopenta[c]pyrrol-4-yl}-L-leucinamide;

(3aR,4S,6aS)-2-[4-(trifluoromethyl)phenyl]octahydrocyclopenta[c]pyrrol-4-amine;

$N^2$-methyl-N-{(3aR,4S,6aS)-2-[4-(trifluoromethyl)phenyl]octahydrocyclopenta[c]pyrrol-4-yl}-L-leucinamide;

(3aR,4S,6aS)-N-isopropyl-2-[6-(trifluoromethyl)pyridin-2-yl]octahydrocyclopenta[c]pyrrol-4-amine;

(3aR,4S,6aS)-N-isobutyl-2-[6-(trifluoromethyl)pyridin-2-yl]octahydrocyclopenta[c]pyrrol-4-amine;

(3aR,4S,6aS)-N-(3,3-dimethylbutyl)-2-[6-(trifluoromethyl)pyridin-2-yl]octahydrocyclopenta[c]pyrrol-4-amine;

(3aR,4S,6aS)-N-(1H-indol-2-ylmethyl)-2-[6-(trifluoromethyl)pyridin-2-yl]octahydrocyclopenta[c]pyrrol-4-amine;

(3aR,4S,6aS)-N-[(5-fluoro-1H-indol-2-yl)methyl]-2-[6-(trifluoromethyl)pyridin-2-yl]octahydrocyclopenta[c]pyrrol-4-amine;

(3aR,4S,6aS)-N-[(5-fluoro-1H-indol-2-yl)methyl]-2-[5-(trifluoromethyl)pyridin-2-yl]octahydrocyclopenta[c]pyrrol-4-amine;

(3aR,4S,6aS)-N-[(5-fluoro-1H-indol-2-yl)methyl]-2-[4-(trifluoromethyl)phenyl]octahydrocyclopenta[c]pyrrol-4-amine;

(3aR,4S,6aS)-N-[(5-fluoro-1H-indol-2-yl)methyl]-2-[3-(trifluoromethyl)phenyl]octahydrocyclopenta[c]pyrrol-4-amine;

(4R)-4-fluoro-N-{(3aR,4S,6aS)-2-[3-(trifluoromethyl)phenyl]octahydrocyclopenta[c]pyrrol-4-yl}-L-prolinamide;

$N^2$-methyl-N-{(3aR,4S,6aS)-2-[2-(trifluoromethyl)phenyl]octahydrocyclopenta[c]pyrrol-4-yl}-L-leucinamide;

N-[(3aR,4S,6aS)-2-(2-fluorophenyl)octahydrocyclopenta[c]pyrrol-4-yl]-$N^2$-methyl-L-leucinamide;

N-[(3aR,4S,6aS)-2-(4-fluorophenyl)octahydrocyclopenta[c]pyrrol-4-yl]-$N^2$-methyl-L-leucinamide;

N-{(3aR,4S,6aS)-2-[4-fluoro-3-(trifluoromethyl)phenyl]octahydrocyclopenta[c]pyrrol-4-yl}-$N^2$-methyl-L-leucinamide;

(4R)-4-fluoro-N-{(3aR,4S,6aS)-2-[2-(trifluoromethyl)phenyl]octahydrocyclopenta[c]pyrrol-4-yl}-L-prolinamide;

(4R)-4-fluoro-N-{(3aR,4S,6aS)-2-[2-fluoro-3-(trifluoromethyl)phenyl]octahydrocyclopenta[c]pyrrol-4-yl}-L-prolinamide;

$N^2$-methyl-N-{(3aR,4S,6aS)-2-[4-(trifluoromethoxy)phenyl]octahydrocyclopenta[c]pyrrol-4-yl}-L-leucinamide;

$N^2$-methyl-N-{(3aR,4S,6aS)-2-[3-(trifluoromethoxy)phenyl]octahydrocyclopenta[c]pyrrol-4-yl}-L-leucinamide;

(4R)-4-fluoro-N-{(3aR,4S,6aS)-2-[4-fluoro-3-(trifluoromethyl)phenyl]octahydrocyclopenta[c]pyrrol-4-yl}-L-prolinamide;

(4R)-4-fluoro-N-{(3aR,4S,6aS)-2-[3-(trifluoromethoxy)phenyl]octahydrocyclopenta[c]pyrrol-4-yl}-L-prolinamide;

N-[(3aR,4S,6aS)-2-(3-chlorophenyl)octahydrocyclopenta[c]pyrrol-4-yl]-$N^2$-methyl-L-leucinamide;

N-[(3aR,4S,6aS)-2-(3-fluorophenyl)octahydrocyclopenta[c]pyrrol-4-yl]-$N^2$-methyl-L-leucinamide;

$N^2$-methyl-N-[(3aR,4S,6aS)-2-(2-methylphenyl)octahydrocyclopenta[c]pyrrol-4-yl]-L-leucinamide;

(4R)-4-fluoro-N-{(3aR,4S,6aS)-2-[4-(trifluoromethoxy)phenyl]octahydrocyclopenta[c]pyrrol-4-yl}-L-prolinamide;

(4R)-N-[(3aR,4S,6aS)-2-(3-cyanophenyl)octahydrocyclopenta[c]pyrrol-4-yl]-4-fluoro-L-prolinamide;

(4R)-N-[(3aR,4S,6aS)-2-(4-cyanophenyl)octahydrocyclopenta[c]pyrrol-4-yl]-4-fluoro-L-prolinamide;

N-[(3aR,4S,6aS)-2-(2-chlorophenyl)octahydrocyclopenta[c]pyrrol-4-yl]-$N^2$-methyl-L-leucinamide;

N-{(3aR,4S,6aS)-2-[2-fluoro-3-(trifluoromethyl)phenyl]octahydrocyclopenta[c]pyrrol-4-yl}-$N^2$-methyl-L-leucinamide;

$N^2$-methyl-N-[(3aR,4S,6aS)-2-(3-methylphenyl)octahydrocyclopenta[c]pyrrol-4-yl]-L-leucinamide;

(4R)-4-fluoro-N-{(3aR,4S,6aS)-2-[4-(trifluoromethyl)pyridin-2-yl]octahydrocyclopenta[c]pyrrol-4-yl}-L-prolinamide;

(4R)-4-fluoro-N-{(3aR,4S,6aS)-2-[2-(trifluoromethyl)pyridin-4-yl]octahydrocyclopenta[c]pyrrol-4-yl}-L-prolinamide;

N-[(3aR,4S,6aS)-2-(4-chlorophenyl)octahydrocyclopenta[c]pyrrol-4-yl]-$N^2$-methyl-L-leucinamide;

(4R)-4-fluoro-N-[(3aR,4S,6aS)-2-(3-fluorophenyl)octahydrocyclopenta[c]pyrrol-4-yl]-L-prolinamide;

(4R)-4-fluoro-N-[(3aR,4S,6aS)-2-(4-fluorophenyl)octahydrocyclopenta[c]pyrrol-4-yl]-L-prolinamide;

(4R)-4-fluoro-N-[(3aR,4S,6aS)-2-(3-methylphenyl)octahydrocyclopenta[c]pyrrol-4-yl]-L-prolinamide;

(4R)-N-[(3aR,4S,6aS)-2-(3-chlorophenyl)octahydrocyclopenta[c]pyrrol-4-yl]-4-fluoro-L-prolinamide;

(4R)-N-[(3aR,4S,6aS)-2-(4-chlorophenyl)octahydrocyclopenta[c]pyrrol-4-yl]-4-fluoro-L-prolinamide;

(4R)-4-fluoro-N-[(3aR,4S,6aS)-2-(3-methoxyphenyl)octahydrocyclopenta[c]pyrrol-4-yl]-L-prolinamide;

N-[(3aR,4S,6aS)-2-(3-cyanophenyl)octahydrocyclopenta[c]pyrrol-4-yl]-$N^2$-methyl-L-leucinamide;

N-[(3aR,4S,6aS)-2-(4-cyanophenyl)octahydrocyclopenta[c]pyrrol-4-yl]-$N^2$-methyl-L-leucinamide;

$N^2$-methyl-N-[(3aR,4S,6aS)-2-(4-methylphenyl)octahydrocyclopenta[c]pyrrol-4-yl]-L-leucinamide;

(3aR,4S,6aS)-N-(4-methylbenzyl)-2-[6-(trifluoromethyl)pyridin-2-yl]octahydrocyclopenta[c]pyrrol-4-amine;

(3aR,4S,6aS)-N-[(5-fluoro-1H-indol-2-yl)methyl]-2-{[3-(trifluoromethyl)phenyl]sulfonyl}octahydrocyclopenta[c]pyrrol-4-amine;

(4R)-N-[(3aR,4S,6aS)-2-(2-cyanophenyl)octahydrocyclopenta[c]pyrrol-4-yl]-4-fluoro-L-prolinamide;

(4R)-4-fluoro-N-[(3aR,4S,6aS)-2-(4-methylphenyl)octahydrocyclopenta[c]pyrrol-4-yl]-L-prolinamide;

(4R)-4-fluoro-N-[(3aR,4S,6aS)-2-(4-methoxyphenyl)octahydrocyclopenta[c]pyrrol-4-yl]-L-prolinamide;

(3aR,4S,6aS)-N-[(5-fluoro-1H-indol-2-yl)methyl]-2-{[4-(trifluoromethyl)phenyl]sulfonyl}octahydrocyclopenta[c]pyrrol-4-amine;

(4R)-N-{(3aR,4S,6aS)-2-[5-(difluoromethyl)-3-thienyl]octahydrocyclopenta[c]pyrrol-4-yl}-4-fluoro-L-prolinamide;

(4R)-4-fluoro-N-{(3aR,4S,6aS)-2-[2-(trifluoromethoxy)phenyl]octahydrocyclopenta[c]pyrrol-4-yl}-L-prolinamide;

N-{(3aR,4S,6aS)-2-[3-fluoro-4-(trifluoromethoxy)phenyl]octahydrocyclopenta[c]pyrrol-4-yl}-$N^2$-methyl-L-leucinamide;

(4R)-4-fluoro-N-[(3aR,4S,6aS)-2-(2-methylphenyl)octahydrocyclopenta[c]pyrrol-4-yl]-L-prolinamide;

(4R)-N-[(3aR,4S,6aS)-2-(2-chlorophenyl)octahydrocyclopenta[c]pyrrol-4-yl]-4-fluoro-L-prolinamide;

(4R)-4-fluoro-N-{(3aR,4S,6aS)-2-[3-(trifluoromethyl)pyridin-2-yl]octahydrocyclopenta[c]pyrrol-4-yl}-L-prolinamide;

(4R)-4-fluoro-N-[(3aR,4S,6aS)-2-(2-fluorophenyl)octahydrocyclopenta[c]pyrrol-4-yl]-L-prolinamide;
(4R)-4-fluoro-N-[(3aR,4S,6aS)-2-(2-methoxyphenyl)octahydrocyclopenta[c]pyrrol-4-yl]-L-prolinamide;
(3aR,4S,6aS)-N-(1H-pyrazol-5-ylmethyl)-2-[6-(trifluoromethyl)pyridin-2-yl]octahydrocyclopenta[c]pyrrol-4-amine;
(3aR,4S,6aS)-N-[(3-methyl-1H-indol-2-yl)methyl]-2-[6-(trifluoromethyl)pyridin-2-yl]octahydrocyclopenta[c]pyrrol-4-amine;
(3aR,4S,6aS)-N-[(5-chloro-1H-indol-2-yl)methyl]-2-[6-(trifluoromethyl)pyridin-2-yl]octahydrocyclopenta[c]pyrrol-4-amine;
(3aR,4S,6aS)-N-{[3-(4-chlorophenyl)-1H-pyrazol-4-yl]methyl}-2-[6-(trifluoromethyl)pyridin-2-yl]octahydrocyclopenta[c]pyrrol-4-amine;
(3aR,4S,6aS)-N-[(5-fluoro-3-methyl-1H-indol-2-yl)methyl]-2-[6-(trifluoromethyl)pyridin-2-yl]octahydrocyclopenta[c]pyrrol-4-amine;
(3aR,4S,6aS)-N-[(5-methoxy-3-methyl-1H-indol-2-yl)methyl]-2-[6-(trifluoromethyl)pyridin-2-yl]octahydrocyclopenta[c]pyrrol-4-amine;
(3aR,4S,6aS)-N-{[3-(2-thienyl)-1H-pyrazol-4-yl]methyl}-2-[6-(trifluoromethyl)pyridin-2-yl]octahydrocyclopenta[c]pyrrol-4-amine;
(3aR,4S,6aS)-N-[(4-methyl-1H-imidazol-2-yl)methyl]-2-[6-(trifluoromethyl)pyridin-2-yl]octahydrocyclopenta[c]pyrrol-4-amine;
(3aR,4S,6aS)-N-[(7-methyl-1H-indol-3-yl)methyl]-2-[6-(trifluoromethyl)pyridin-2-yl]octahydrocyclopenta[c]pyrrol-4-amine;
(3aR,4S,6aS)-N-{[3-(4-fluorophenyl)-1H-pyrazol-4-yl]methyl}-2-[6-(trifluoromethyl)pyridin-2-yl]octahydrocyclopenta[c]pyrrol-4-amine;
(3aR,4S,6aS)-N-{[3-(4-methylphenyl)-1H-pyrazol-4-yl]methyl}-2-[6-(trifluoromethyl)pyridin-2-yl]octahydrocyclopenta[c]pyrrol-4-amine;
(3aR,4S,6aS)-N-[(2-butyl-1H-imidazol-4-yl)methyl]-2-[6-(trifluoromethyl)pyridin-2-yl]octahydrocyclopenta[c]pyrrol-4-amine;
(3aR,4S,6aS)-N-(1H-imidazol-2-ylmethyl)-2-[6-(trifluoromethyl)pyridin-2-yl]octahydrocyclopenta[c]pyrrol-4-amine;
(3aR,4S,6aS)-N-[(2-methyl-1H-imidazol-4-yl)methyl]-2-[6-(trifluoromethyl)pyridin-2-yl]octahydrocyclopenta[c]pyrrol-4-amine;
(3aR,4S,6aS)-N-(1H-imidazol-4-ylmethyl)-2-[6-(trifluoromethyl)pyridin-2-yl]octahydrocyclopenta[c]pyrrol-4-amine;
(3aR,4S,6aS)-N-[(5-fluoro-1H-indol-3-yl)methyl]-2-[6-(trifluoromethyl)pyridin-2-yl]octahydrocyclopenta[c]pyrrol-4-amine;
(3aR,4S,6aS)-N-[(3-chloro-1H-indol-2-yl)methyl]-2-[6-(trifluoromethyl)pyridin-2-yl]octahydrocyclopenta[c]pyrrol-4-amine;
(3aR,4S,6aS)-N-[(5-chloro-1H-indol-3-yl)methyl]-2-[6-(trifluoromethyl)pyridin-2-yl]octahydrocyclopenta[c]pyrrol-4-amine;
(3aR,4S,6aS)-N-{[3-(4-methoxyphenyl)-1H-pyrazol-4-yl]methyl}-2-[6-(trifluoromethyl)pyridin-2-yl]octahydrocyclopenta[c]pyrrol-4-amine;
(3aR,4S,6aS)-N-[(3-phenyl-1H-pyrazol-4-yl)methyl]-2-[6-(trifluoromethyl)pyridin-2-yl]octahydrocyclopenta[c]pyrrol-4-amine;
(3aR,4S,6aS)-N-(1H-benzimidazol-2-ylmethyl)-2-[6-(trifluoromethyl)pyridin-2-yl]octahydrocyclopenta[c]pyrrol-4-amine;
(3aR,4S,6aS)-N-(1H-indol-3-ylmethyl)-2-[6-(trifluoromethyl)pyridin-2-yl]octahydrocyclopenta[c]pyrrol-4-amine;
(3aR,4S,6aS)-N-[(5-methoxy-1H-indol-3-yl)methyl]-2-[6-(trifluoromethyl)pyridin-2-yl]octahydrocyclopenta[c]pyrrol-4-amine;
(3aR,4S,6aS)-N-[(6-fluoro-1H-indol-3-yl)methyl]-2-[6-(trifluoromethyl)pyridin-2-yl]octahydrocyclopenta[c]pyrrol-4-amine;
(3aR,4S,6aS)-N-{[3-(3,5-difluorophenyl)-1H-pyrazol-4-yl]methyl}-2-[6-(trifluoromethyl)pyridin-2-yl]octahydrocyclopenta[c]pyrrol-4-amine;
(3aR,4S,6aS)-N-[(2-phenyl-1H-imidazol-4-yl)methyl]-2-[6-(trifluoromethyl)pyridin-2-yl]octahydrocyclopenta[c]pyrrol-4-amine;
(3aR,4S,6aS)-N-[(4-methoxy-1H-indol-3-yl)methyl]-2-[6-(trifluoromethyl)pyridin-2-yl]octahydrocyclopenta[c]pyrrol-4-amine;
(3aR,4S,6aS)-N-[(5-fluoro-1H-pyrrolo[2,3-b]pyridin-3-yl)methyl]-2-[6-(trifluoromethyl)pyridin-2-yl]octahydrocyclopenta[c]pyrrol-4-amine;
(3aR,4S,6aS)-N-[(6-fluoro-1H-benzimidazol-2-yl)methyl]-2-[6-(trifluoromethyl)pyridin-2-yl]octahydrocyclopenta[c]pyrrol-4-amine;
(3aR,4S,6aS)-N-[(4-chloro-1H-indol-3-yl)methyl]-2-[6-(trifluoromethyl)pyridin-2-yl]octahydrocyclopenta[c]pyrrol-4-amine;
(3aR,4S,6aS)-N-(1H-pyrrolo[2,3-b]pyridin-2-ylmethyl)-2-[6-(trifluoromethyl)pyridin-2-yl]octahydrocyclopenta[c]pyrrol-4-amine;
(3aR,4S,6aS)-N-(1H-1,2,3-triazol-4-ylmethyl)-2-[6-(trifluoromethyl)pyridin-2-yl]octahydrocyclopenta[c]pyrrol-4-amine;
(3aR,4S,6aS)-N-[(3-methyl-1H-pyrazol-4-yl)methyl]-2-[6-(trifluoromethyl)pyridin-2-yl]octahydrocyclopenta[c]pyrrol-4-amine;
(3aR,4S,6aS)-N-(1H-pyrazol-4-ylmethyl)-2-[6-(trifluoromethyl)pyridin-2-yl]octahydrocyclopenta[c]pyrrol-4-amine;
5-fluoro-N-{(3aR,4S,6aS)-2-[6-(trifluoromethyl)pyridin-2-yl]octahydrocyclopenta[c]pyrrol-4-yl}-1H-indole-2-carboxamide;
(4R)-4-fluoro-N-{(3aR,4S,6aS)-2-[4-fluoro-2-(trifluoromethyl)phenyl]octahydrocyclopenta[c]pyrrol-4-yl}-L-prolinamide;
$N^2$-methyl-N-{(3aR,4S,6aS)-2-[2-(trifluoromethoxy)phenyl]octahydrocyclopenta[c]pyrrol-4-yl}-L-leucinamide;
4-chloro-N-{(3aR,4S,6aS)-2-[6-(trifluoromethyl)pyridin-2-yl]octahydrocyclopenta[c]pyrrol-4-yl}benzenesulfonamide;
2-chloro-N-{(3aR,4S,6aS)-2-[6-(trifluoromethyl)pyridin-2-yl]octahydrocyclopenta[c]pyrrol-4-yl}benzenesulfonamide;
3-fluoro-N-{(3aR,4S,6aS)-2-[6-(trifluoromethyl)pyridin-2-yl]octahydrocyclopenta[c]pyrrol-4-yl}benzenesulfonamide;
2-fluoro-N-{(3aR,4S,6aS)-2-[6-(trifluoromethyl)pyridin-2-yl]octahydrocyclopenta[c]pyrrol-4-yl}benzenesulfonamide;
3-chloro-N-{(3aR,4S,6aS)-2-[6-(trifluoromethyl)pyridin-2-yl]octahydrocyclopenta[c]pyrrol-4-yl}benzenesulfonamide;
4-fluoro-N-{(3aR,4S,6aS)-2-[6-(trifluoromethyl)pyridin-2-yl]octahydrocyclopenta[c]pyrrol-4-yl}benzenesulfonamide;
$N^2$-{(3aR,4S,6aS)-2-[6-(trifluoromethyl)pyridin-2-yl]octahydrocyclopenta[c]pyrrol-4-yl}-L-leucinamide;

N²-methyl-N-[(3aR,4S,6aS)-2-{4-[(trifluoromethyl)thio] phenyl}octahydrocyclopenta[c]pyrrol-4-yl]-L-leucinamide;
N-{(3aR,4S,6aS)-2-[6-(trifluoromethyl)pyridin-2-yl]octahydrocyclopenta[c]pyrrol-4-yl}benzenesulfonamide;
1-(4-fluorophenyl)-3-{(3aR,4S,6aS)-2-[6-(trifluoromethyl) pyridin-2-yl]octahydrocyclopenta[c]pyrrol-4-yl}urea;
3-chloro-4-fluoro-N-{(3aR,4S,6aS)-2-[6-(trifluoromethyl) pyridin-2-yl]octahydrocyclopenta[c]pyrrol-4-yl}benzenesulfonamide;
1-tert-butyl-3-{(3aR,4S,6aS)-2-[6-(trifluoromethyl)pyridin-2-yl]octahydrocyclopenta[c]pyrrol-4-yl}urea;
N²-methyl-N-[(3aR,4S,6aS)-2-{3-[(trifluoromethyl)thio] phenyl}octahydrocyclopenta[c]pyrrol-4-yl]-L-leucinamide;
1-(4-chlorophenyl)-3-{(3aR,4S,6aS)-2-[6-(trifluoromethyl) pyridin-2-yl]octahydrocyclopenta[c]pyrrol-4-yl}urea;
1-(3-chloro-4-fluorophenyl)-3-{(3aR,4S,6aS)-2-[6-(trifluoromethyl)pyridin-2-yl]octahydrocyclopenta[c]pyrrol-4-yl}urea;
(3aR,4S,6aS)-N-[(5-fluoro-1H-indol-2-yl)methyl]-2-[3-(trifluoromethoxy)phenyl]octahydrocyclopenta[c]pyrrol-4-amine;
(3aR,4S,6aS)-N-[(5-fluoro-1H-indol-2-yl)methyl]-2-[4-(trifluoromethoxy)phenyl]octahydrocyclopenta[c]pyrrol-4-amine;
1-(4-chlorophenyl)-N-{(3aR,4S,6aS)-2-[6-(trifluoromethyl) pyridin-2-yl]octahydrocyclopenta[c]pyrrol-4-yl}methanesulfonamide;
N²-methyl-N-{(3aR,4S,6aS)-2-[3-(trifluoromethoxy)phenyl]octahydrocyclopenta[c]pyrrol-4-yl}-L-norvalinamide;
N²-methyl-N-{(3aR,4S,6aS)-2-[4-(trifluoromethoxy)phenyl]octahydrocyclopenta[c]pyrrol-4-yl}-L-norvalinamide;
(3aR,4S,6aS)-N-[(1-methyl-1H-indol-2-yl)methyl]-2-[6-(trifluoromethyl)pyridin-2-yl]octahydrocyclopenta[c]pyrrol-4-amine;
(3aR,4S,6aS)-N-(thieno[2,3-c]pyridin-2-ylmethyl)-2-[6-(trifluoromethyl)pyridin-2-yl]octahydrocyclopenta[c]pyrrol-4-amine;
N²-methyl-N-{(3aR,4S,6aS)-2-[4-(trifluoromethyl)pyrimidin-2-yl]octahydrocyclopenta[c]pyrrol-4-yl}-L-leucinamide;
N²-methyl-N-{(3aR,4S,6aS)-2-[2-(trifluoromethyl)pyrimidin-4-yl]octahydrocyclopenta[c]pyrrol-4-yl}-L-leucinamide;
N²-methyl-N-{(3aR,4S,6aS)-2-[6-(trifluoromethyl)pyridazin-3-yl]octahydrocyclopenta[c]pyrrol-4-yl}-L-leucinamide;
(3aR,4S,6aS)-N-[(1-methyl-1H-pyrazol-5-yl)methyl]-2-[6-(trifluoromethyl)pyridin-2-yl]octahydrocyclopenta[c]pyrrol-4-amine;
(3aR,4S,6aS)-N-[(5-chloro-2-phenyl-1H-imidazol-4-yl)methyl]-2-[6-(trifluoromethyl)pyridin-2-yl]octahydrocyclopenta[c]pyrrol-4-amine;
(3aR,4S,6aS)-N-(thieno[2,3-b]pyridin-2-ylmethyl)-2-[6-(trifluoromethyl)pyridin-2-yl]octahydrocyclopenta[c]pyrrol-4-amine;
(3aR,4S,6aS)-N-(2,1,3-benzothiadiazol-4-ylmethyl)-2-[6-(trifluoromethyl)pyridin-2-yl]octahydrocyclopenta[c]pyrrol-4-amine;
N-{(3aR,4S,6aS)-2-[3-(difluoromethyl)phenyl]octahydrocyclopenta[c]pyrrol-4-yl}-N²-methyl-L-leucinamide;
N-[(3aR,4S,6aS)-2-(2,3-difluorophenyl)octahydrocyclopenta[c]pyrrol-4-yl]-N²-methyl-L-leucinamide;
(3aR,4S,6aS)-N-[(1-methyl-1H-benzimidazol-2-yl)methyl]-2-[6-(trifluoromethyl)pyridin-2-yl]octahydrocyclopenta[c]pyrrol-4-amine;
(3aR,4S,6aS)-N-(2,1,3-benzothiadiazol-5-ylmethyl)-2-[6-(trifluoromethyl)pyridin-2-yl]octahydrocyclopenta[c]pyrrol-4-amine;
tert-butyl methyl{(2S)-3-methyl-1-[(3aR,4S,6aS)-octahydrocyclopenta[c]pyrrol-4-ylamino]-1-oxobutan-2-yl}carbamate;
N²-methyl-N-{(3aR,4S,6aS)-2-[5-(trifluoromethyl)-1,3,4-thiadiazol-2-yl]octahydrocyclopenta[c]pyrrol-4-yl}-L-leucinamide;
N²-methyl-N-{(3aR,4S,6aS)-2-[6-(trifluoromethyl)pyridin-3-yl]octahydrocyclopenta[c]pyrrol-4-yl}-L-leucinamide;
N²-methyl-N-{(3aR,4S,6aS)-2-[5-(trifluoromethyl)pyridin-3-yl]octahydrocyclopenta[c]pyrrol-4-yl}-L-leucinamide;
N-{(3aR,4S,6aS)-2-[4-fluoro-2-(trifluoromethyl)phenyl]octahydrocyclopenta[c]pyrrol-4-yl}-N²-methyl-L-leucinamide;
N²-methyl-N-{(3aS,4R,6aR)-2-[5-(trifluoromethyl)pyridin-2-yl]octahydrocyclopenta[c]pyrrol-4-yl}-L-leucinamide;
N²-methyl-N-{(3aS,4R,6aR)-2-[4-(trifluoromethoxy)phenyl]octahydrocyclopenta[c]pyrrol-4-yl}-L-leucinamide;
N²-methyl-N-{(3aS,4R,6aR)-2-[4-(trifluoromethyl)phenyl] octahydrocyclopenta[c]pyrrol-4-yl}-L-leucinamide;
(3aR,4S,6aS)-N-{[2-(4-chlorophenyl)-1,3-oxazol-4-yl]methyl}-2-[6-(trifluoromethyl)pyridin-2-yl]octahydrocyclopenta[c]pyrrol-4-amine;
(3aR,4S,6aS)-N-({2-[4-(trifluoromethyl)phenyl]-1H-imidazol-4-yl}methyl)-2-[6-(trifluoromethyl)pyridin-2-yl]octahydrocyclopenta[c]pyrrol-4-amine;
(3aR,4S,6aS)-N-{[2-(4-fluorophenyl)-1,3-oxazol-4-yl]methyl}-2-[6-(trifluoromethyl)pyridin-2-yl]octahydrocyclopenta[c]pyrrol-4-amine;
(3aR,4S,6aS)-N-{[4-(4-fluorophenyl)-1H-imidazol-2-yl] methyl}-2-[6-(trifluoromethyl)pyridin-2-yl]octahydrocyclopenta[c]pyrrol-4-amine;
(3aR,4S,6aS)-N-{[4-(4-chlorophenyl)-1H-imidazol-2-yl] methyl}-2-[6-(trifluoromethyl)pyridin-2-yl]octahydrocyclopenta[c]pyrrol-4-amine;
(3aR,4S,6aS)-N-[(4-phenyl-1H-imidazol-2-yl)methyl]-2-[6-(trifluoromethyl)pyridin-2-yl]octahydrocyclopenta[c] pyrrol-4-amine;
N²-methyl-N-{(3aR,4S,6aS)-2-[4-(trifluoromethyl)phenyl] octahydrocyclopenta[c]pyrrol-4-yl}-L-valinamide;
(3aR,4S,6aS)-N-[(5-fluoro-1-methyl-1H-indol-2-yl)methyl]-2-[6-(trifluoromethyl)pyridin-2-yl]octahydrocyclopenta[c]pyrrol-4-amine;
N²-methyl-N-{(3aR,4S,6aS)-2-[4-(trifluoromethyl)phenyl] octahydrocyclopenta[c]pyrrol-4-yl}-L-serinamide;
N²-methyl-N-{(3aR,4S,6aS)-2-[4-(trifluoromethyl)phenyl] octahydrocyclopenta[c]pyrrol-4-yl}-L-allothreoninamide;
N-{(3aR,4S,6aS)-2-[4-(trifluoromethyl)phenyl]octahydrocyclopenta[c]pyrrol-4-yl}glycinamide;
N²-methyl-N-{(3aR,4S,6aS)-2-[4-(trifluoromethyl)phenyl] octahydrocyclopenta[c]pyrrol-4-yl}glycinamide;
N²-methyl-N-{(3aR,4S,6aS)-2-[4-(trifluoromethyl)phenyl] octahydrocyclopenta[c]pyrrol-4-yl}-L-alaninamide;
N²,2-dimethyl-N-{(3aR,4S,6aS)-2-[4-(trifluoromethyl)phenyl]octahydrocyclopenta[c]pyrrol-4-yl}alaninamide;
(2S)-2-amino-N-{(3aR,4S,6aS)-2-[4-(trifluoromethyl)phenyl]octahydrocyclopenta[c]pyrrol-4-yl}butanamide;
N²-methyl-N-{(3aR,4S,6aS)-2-[4-(trifluoromethoxy)phenyl]octahydrocyclopenta[c]pyrrol-4-yl}-L-valinamide;
N²-methyl-N-{(3aR,4S,6aS)-2-[3-(trifluoromethyl)phenyl] octahydrocyclopenta[c]pyrrol-4-yl}-L-valinamide;

N²-methyl-N-{(3aR,4S,6aS)-2-[3-(trifluoromethoxy)phenyl]octahydrocyclopenta[c]pyrrol-4-yl}-L-valinamide;
N²-methyl-N-{(3aR,4S,6aS)-2-[4-(trifluoromethyl)phenyl]octahydrocyclopenta[c]pyrrol-4-yl}-L-norvalinamide;
N²-methyl-N-{(3aR,4S,6aS)-2-[4-(trifluoromethyl)phenyl]octahydrocyclopenta[c]pyrrol-4-yl}-D-leucinamide;
N²-isopropyl-N-{(3aR,4S,6aS)-2-[4-(trifluoromethyl)phenyl]octahydrocyclopenta[c]pyrrol-4-yl}glycinamide;
(2S)-2-(isopropylamino)-N-{(3aR,4S,6aS)-2-[4-(trifluoromethyl)phenyl]octahydrocyclopenta[c]pyrrol-4-yl}butanamide;
N²-methyl-N-{(3aR,4S,6aS)-2-[5-(trifluoromethyl)pyridin-2-yl]octahydrocyclopenta[c]pyrrol-4-yl}-L-valinamide;
N²-methyl-N-{(3aR,4S,6aS)-2-[6-(trifluoromethyl)pyridin-2-yl]octahydrocyclopenta[c]pyrrol-4-yl}-L-valinamide;
N²-methyl-N-{(3aR,4S,6aS)-2-[4-(trifluoromethyl)pyridin-3-yl]octahydrocyclopenta[c]pyrrol-4-yl}-L-leucinamide;
N-{(3aR,4S,6aS)-2-[3-bromo-5-(trifluoromethyl)pyridin-2-yl]octahydrocyclopenta[c]pyrrol-4-yl}-N²-methyl-L-leucinamide;
N²-methyl-N-{(3aR,4S,6aS)-2-[2-(trifluoromethyl)pyridin-3-yl]octahydrocyclopenta[c]pyrrol-4-yl}-L-leucinamide;
N²-methyl-N-{(3aS,4R,6aR)-2-[4-(trifluoromethyl)phenyl]octahydrocyclopenta[c]pyrrol-4-yl}-D-leucinamide;
N-{(3aR,4S,6aS)-2-[3-(difluoromethyl)-4-fluorophenyl]octahydrocyclopenta[c]pyrrol-4-yl}-N²-methyl-L-leucinamide;
N-{(3aR,4S,6aS)-2-[2-(difluoromethyl)-5-fluorophenyl]octahydrocyclopenta[c]pyrrol-4-yl}-N²-methyl-L-leucinamide;
N-{(3aR,4S,6aS)-2-[2-(difluoromethyl)phenyl]octahydrocyclopenta[c]pyrrol-4-yl}-N²-methyl-L-leucinamide;
N-{(3aR,4S,6aS)-2-{4-fluoro-3-(trifluoromethoxy)phenyl]octahydrocyclopenta[c]pyrrol-4-yl}-N²-methyl-L-leucinamide;
N-[(3aR,4S,6aS)-2-(3-chloro-4-fluorophenyl)octahydrocyclopenta[c]pyrrol-4-yl]-N²-methyl-L-leucinamide;
N-{(3aR,4S,6aS)-2-[2-fluoro-4-(trifluoromethoxy)phenyl]octahydrocyclopenta[c]pyrrol-4-yl}-N²-methyl-L-leucinamide;
3-cyclopropyl-N²-methyl-N-{(3aR,4S,6aS)-2-[4-(trifluoromethoxy)phenyl]octahydrocyclopenta[c]pyrrol-4-yl}-L-alaninamide;
3-cyclopropyl-N-{(3aR,4S,6aS)-2-[4-(trifluoromethoxy)phenyl]octahydrocyclopenta[c]pyrrol-4-yl}-L-alaninamide;
3-cyclopropyl-N²,N²-dimethyl-N-{(3aR,4S,6aS)-2-[4-(trifluoromethoxy)phenyl]octahydrocyclopenta[c]pyrrol-4-yl}-L-alaninamide;
1-tert-butyl-3-{(3aR,4S,6aS)-2-[4-(trifluoromethoxy)phenyl]octahydrocyclopenta[c]pyrrol-4-yl}urea;
1-tert-butyl-3-{(3aR,4S,6aS)-2-[3-(trifluoromethoxy)phenyl]octahydrocyclopenta[c]pyrrol-4-yl}urea;
(4R)-4-fluoro-N-{(3aR,4S,6aS)-2-[5-(trifluoromethyl)pyridin-2-yl]octahydrocyclopenta[c]pyrrol-4-yl}-L-prolinamide;
(4R)-4-fluoro-N-{(3aR,4S,6aS)-2-[4-(trifluoromethyl)phenyl]octahydrocyclopenta[c]pyrrol-4-yl}-L-prolinamide;
(4S)-4-fluoro-N-{(3aR,4S,6aS)-2-[4-(trifluoromethyl)phenyl]octahydrocyclopenta[c]pyrrol-4-yl}-L-prolinamide;
(4S)-4-fluoro-N-{(3aR,4S,6aS)-2-[5-(trifluoromethyl)-2-thienyl]octahydrocyclopenta[c]pyrrol-4-yl}-L-prolinamide;
(4S)-4-fluoro-N-{(3aR,4S,6aS)-2-[2-(trifluoromethyl)-3-thienyl]octahydrocyclopenta[c]pyrrol-4-yl}-L-prolinamide;
N-[(3aR,4S,6aS)-2-(2-methoxyphenyl)octahydrocyclopenta[c]pyrrol-4-yl]-N²-methyl-L-leucinamide;
N-[(3aR,4S,6aS)-2-(3-methoxyphenyl)octahydrocyclopenta[c]pyrrol-4-yl]-N²-methyl-L-leucinamide;
N-[(3aR,4S,6aS)-2-(4-methoxyphenyl)octahydrocyclopenta[c]pyrrol-4-yl]-N²-methyl-L-leucinamide;
N-[(3aR,4S,6aS)-2-(2-cyanophenyl)octahydrocyclopenta[c]pyrrol-4-yl]-N²-methyl-L-leucinamide;
N²-methyl-N-{(3aR,4S,6aS)-2-[5-(trifluoromethyl)-2-thienyl]octahydrocyclopenta[c]pyrrol-4-yl}-L-leucinamide;
N²-methyl-N-{(3aR,4S,6aS)-2-[2-(trifluoromethyl)-3-thienyl]octahydrocyclopenta[c]pyrrol-4-yl}-L-leucinamide; and
N-{(3aR,4S,6aS)-2-[5-(difluoromethyl)-3-thienyl]octahydrocyclopenta[c]pyrrol-4-yl}-N²-methyl-L-leucinamide.

Compounds of the present application can exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206. In a particular enantiomeric pair, the relative descriptors are reversed to indicate that this pair of enantiomers is of unknown absolute stereochemistry.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application can be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers can exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein can exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of this invention can exist in an isotopic form containing one or more atoms having an atomic mass or mass number different from the atomic mass or mass number most abundantly found in nature. Isotopes of atoms such as hydrogen, carbon, phosphorous, sulfur fluorine, chlorine, and iodine include, but are not limited to $^2H$, $^3H$, $^{11}C$, $^{14}C$, $^{32}P$, $^{35}S$, $^{18}F$, $^{36}Cl$, and $^{125}I$, respectively. Compounds that contain other isotopes of these and/or other atoms are within the scope of this invention. Compounds containing tritium ($^3H$) and $^{14}C$ radioisotopes are preferred in general for their ease in preparation and detectability for radiolabeled compounds. Isotopically labeled compounds of this invention can be prepared by the general methods well known to persons having ordinary skill in the art. Such Isotopically labeled compounds can be conveniently prepared by carrying out the procedures disclosed in the Examples and Schemes below by substituting a readily available isotopically labeled reagent for a non-isotopically labeled reagent.

c. Biological Data

Abbreviations which have been used in the descriptions of Biological Data that follow are: EDTA for ethylenediaminetetraacetic acid; FBS for fetal bovine serum; FLIPR for fluorometric imaging plate reader; HBSS for Hank's balanced salt solution; HEPES for 4-(2-hydroxyethyl)-1-piperazineethanesulfonic acid; i.p. for intraperitoneal; MEM for minimum essential medium; MEM NEAA for minimum essential medium non-essential amino acid; p.o. for per orem (by mouth).

(i) In Vitro Methods—Assessment of Calcium Channel Activity Using FLIPR:

IMR32 cells endogenously expressing human $Ca_v2.2$ were assayed for $Ca^{2+}$ influx using a no-wash calcium indicator dye (Calcium 4 dye: Molecular Probes) and FLIPR technology (Lubin, M. L.; Reitz, T. L.; Todd, M. J.; Flores, C. M.; Qin, N.; Xin, H. Assay and Drug Development Technologies 2006, 4(6), 689-694.). The IMR32 cells were maintained in MEM media containing 10% (v/v) FBS, 1% (v/v) antibiotic/antimitotic, 1% (v/v) sodium pyruvate and 1% (v/v) MEM NEAA. Following dissociation in 0.05% (v/v) trypsin/EDTA, cells were seeded into black 1×96-well plates (Corning Cellbind) at a density of $1-1.2\times10^5$ cells/well and incubated in the maintenance media above for 48 hours at 37° C. Immediately prior to performing the assay the media was removed and cells were loaded for 1.5 hours with 1× Calcium 4 dye prepared in HBSS (137 mM NaCl, 5.4 mM KCl, 0.25 mM $Na_2HPO_4$, 0.44 mM $KH_2PO_4$, 1.3 mM $CaCl_2$, 1 mM $MgSO_4$, 4.2 mM $NaHCO_3$) containing HEPES pH 7.4 at room temperature. After dye loading and a subsequent 3 minute or 60 minute pre-incubation with compounds (full log dilutions from 10 µM to 0.1 nM) in the presence of 1.3 mM $CaCl_2$ and 2 µM nifedipine to block endogenous L-type channels, the external $Ca^{2+}$ concentration was increased to 5 mM $CaCl_2$ and the cells concomitantly depolarized with 80 mM KCl to assay channel activity. To determine the $IC_{50}$ values, the percent inhibition of the compound at each concentration was determined relative to the activity in the absence of inhibitor, and data was fitted using non-linear regression sigmoidal dose response curve analysis with GraphPad Prism®.

| Example | $IC_{50}$ (µM) or percent inhibition (* indicates 3 minute incubation, otherwise 60 minute) |
|---|---|
| 1 | 1.93 |
|   | 3.5* |
| 2 | 4.2* |
| 3 | 1.06 |
| 4 | 3.5* |
| 5 | 1.46 |
|   | 3.8* |
| 6 | 2.20 |
|   | 2.2* |
| 7 | 0.92 |
|   | 1.8* |
| 8 | 1.07 |
| 9 | 1.04 |
|   | 1.8* |
| 10 | 1.3* |
| 11 | 4.67 |
| 12 | 1.22 |
| 13 | 23.62 |
| 14 | 3.79 |
| 15 | 16.46 |
| 16 | 9.75 |
| 17 | 1.57 |
| 18 | 2.68 |
| 19 | 25% @ 10 µM* |
| 20 | 1.80 |
| 21 | 10.1* |
| 22 | 14.7* |
| 23 | 2.5 |
| 24 | 2.9* |
| 25 | 3.7* |
| 26 | 17.3* |
| 27 | 9.7* |
| 28 | 13.9* |
| 29 | 5.6* |
| 30 | 1.81 |
| 31 | 1.65 |
| 32 | 1.42 |
| 33 | 7.41 |
| 34 | 1.51 |
| 35 | 3.26 |
| 36 | 44% @ 10 µM* |
| 37 | 15% @ 10 µM* |
| 38 | 27% @ 10 µM* |
| 39 | 92% @ 10 µM* |
| 40 | 3.6* |
| 41 | 56% @ 10 µM* |
| 43 | 1.49 |
| 44 | 1.7* |
| 46 | 3.1* |
| 47 | 15.6* |
| 48 | 10.5* |
| 49 | 4.6* |
| 50 | 5.0* |
| 51 | 15.2* |
| 52 | 3.36 |
| 53 | 8.54 |
| 54 | 0.46 |
| 55 | 1.12 |
| 56 | 0.74 |
| 57 | 0.29 |
| 58 | 1.35 |
| 59 | 0.51 |
| 60 | 2.43 |
| 61 | 0.86 |
| 62 | 1.64 |
| 63 | 0.51 |
| 64 | 0.99 |
| 65 | 4.50 |
| 66 | 0.90 |
| 67 | 1.32 |
| 68 | 0.82 |
| 69 | 1.69 |
| 70 | 1.93 |
| 71 | 1.20 |
| 72 | 3.23 |
| 73 | 3.26 |
| 74 | 11.2* |

| Example | IC$_{50}$ (μM) or percent inhibition (* indicates 3 minute incubation, otherwise 60 minute) |
|---|---|
| 75 | 0.45 |
| 76 | 5.67 |
| 77 | 9.36 |
| 78 | 1.34 |
| 79 | 0.94 |
| 80 | 1.67 |
| 81 | 1.13 |
| 82 | 1.48 |
| 83 | 2.6* |
| 84 | 5.8% @ 10 μM* |
| 85 | 3.59 |
| 86 | 1.63 |
| 87 | 3.14 |
| 88 | 1.18 |
| 89 | 2.01 |
| 90 | 83% @ 10 μM* |
| 91 | 1.78 |
| 92 | 2.04 |
| 93 | 3.26 |
| 94 | 2.33 |
| 95 | 1.04 |
| 96 | 2.4* |
| 97 | 5.3* |
| 98 | 4.9* |
| 99 | 4.8* |
| 100 | 4.2* |
| 101 | 4.7* |
| 102 | 2.77 |
| 103 | 31* |
| 104 | 79% @ 10 μM* |
| 105 | 1.21 |
| 106 | 5.8* |
| 107 | 1.14 |
| 108 | 11.3* |
| 109 | 9.0* |
| 110 | 2.0* |
| 111 | 2.2* |
| 112 | 2.8* |
| 113 | 0.59 |
| | 3.1* |
| 114 | 2.81 |
| | 2.8* |
| 115 | 1.20 |
| 116 | 1.17 |
| 117 | 0.88 |
| 118 | 1.04 |
| 119 | 1.12 |
| 120 | 3.44 |
| 121 | 14.31 |
| 122 | 0.36 |
| 123 | 0.57 |
| 124 | 1.07 |
| 125 | 2.07 |
| 126 | 0.95 |
| 127 | 1.26 |
| 128 | 0.56 |
| 129 | 2.31 |
| 130 | 0.79 |
| 131 | 0.66 |
| 132 | 1.13 |
| 133 | 0.69 |
| 134 | 1.15 |
| 135 | 0.67 |
| 136 | 0.64 |
| 137 | 0.65 |
| 138 | 0.82 |
| 139 | 1.01 |
| 140 | 0.62 |
| 141 | 0.60 |
| 142 | 0.86 |
| 143 | 0.61 |
| 144 | 1.04 |
| 145 | 1.14 |
| 146 | 0.79 |
| 147 | 0.51 |
| 148 | 0.83 |
| 149 | 0.62 |
| 150 | 0.51 |
| 151 | 0.71 |
| 152 | 0.51 |
| 153 | 0.40 |
| 154 | 1.33 |
| 155 | 0.69 |
| 156 | 0.76 |
| 157 | 2.10 |
| 158 | 3.51 |
| 159 | 5.55 |
| 160 | 3.78 |
| 161 | 3.89 |
| 162 | 3.94 |
| 163 | 4.59 |
| 164 | 1.64 |
| 165 | >30 |
| 166 | 2.72 |
| 167 | 1.21 |
| 168 | 12.93 |
| 169 | 0.92 |
| 170 | 4.55 |
| 171 | 6.16 |
| 172 | 2.03 |
| 173 | 1.81 |
| 174 | 1.04 |
| 175 | 1.50 |
| 176 | 0.86 |
| 177 | 2.64 |
| 178 | 1.00 |
| 179 | 0.89 |
| 180 | 1.83 |
| 181 | 0.94 |
| 182 | 1.45 |
| 183 | 1.41 |
| 184 | 1.45 |
| 185 | 0.91 |
| 186 | 0.64 |
| 187 | 1.24 |
| 188 | 0.85 |
| 189 | 1.01 |
| 190 | 1.30 |
| 191 | 0.51 |
| 192 | 2.27 |
| 193 | 0.57 |
| 194 | 1.37 |
| 195 | 22.11 |
| 196 | 3.18 |
| 197 | 69.70 |
| 198 | 40.46 |
| 199 | 2.21 |
| 200 | 1.00 |
| 201 | 5.20 |
| 202 | 0.83 |
| 203 | 1.54 |
| 204 | 1.27 |
| 205 | 3.40 |
| 206 | >100 |
| 207 | >100 |
| 208 | >100 |
| 209 | >100 |
| 210 | 76% @ 10 μM* |
| 211 | 3.82 |
| 212 | 4.13 |
| 213 | 60% @ 10 μM* |
| 215 | 1.99 |
| 216 | 85% @ 10 μM* |
| 217 | 1.28 |
| 218 | 56% @ 10 μM* |
| 219 | 63% @ 10 μM* |
| 220 | >9 |
| 221 | 3.93 |
| 222 | 2.05 |
| 223 | 2.06 |
| 224 | 4.64 |
| 225 | 9.36 |
| 226 | 4.06 |
| 227 | 3.17 |

| Example | IC$_{50}$ (μM) or percent inhibition (* indicates 3 minute incubation, otherwise 60 minute) |
|---|---|
| 228 | 2.09 |
| 229 | 13.42 |
| 230 | >30 |
| 231 | 6.13 |
| 232 | 3.60 |
| 233 | 2.80 |
| 234 | 7.40 |
| 235 | 10.99 |
| 236 | >30 |
| 237 | 1.46 |
| 238 | 5.73 |
| 239 | 3.32 |
| 240 | 2.67 |
| 241 | 2.08 |
| 242 | 7.92 |
| 243 | 8.58 |
| 244 | 9.11 |
| 245 | 8.08 |
| 246 | 8.38 |
| 247 | 3.62 |
| 248 | 1.67 |
| 249 | >30 |
| 250 | >30 |
| 252 | 0.64 |
| 253 | 0.36 |
| 254 | 0.72 |
| 255 | 0.55 |
| 256 | 1.38 |
| 257 | 0.70 |
| 258 | 0.85 |
| 259 | 1.14 |
| 260 | 1.11 |
| 261 | 1.25 |
| 262 | 1.80 |
| 263 | >30 |
| 264 | 0.28 |
| 265 | 2.62 |
| 266 | 0.87 |
| 267 | 14.10 |
| 268 | 0.73 |
| 269 | 1.90 |
| 270 | 0.77 |
| 271 | 3.41 |
| 272 | 5.14 |
| 273 | 0.18 |
| 274 | 1.38 |
| 275 | 0.92 |
| 276 | 0.38 |
| 277 | 0.72 |
| 278 | 0.34 |
| 279 | >16.43 |
| 280 | 5.04 |
| 281 | 4.18 |
| 282 | 5.24 |
| 283 | 8.69 |
| 284 | 3.70 |
| 285 | 0.48 |
| 286 | 0.38 |
| 287 | 3.09 |
| 288 | 10.36 |
| 289 | 9.75 |
| 290 | 7.80 |
| 291 | 4.40 |
| 292 | 3.91 |
| 293 | 4.82 |
| 294 | 7.80 |
| 295 | 2.98 |
| 296 | 2.14 |
| 297 | 7.88 |
| 298 | 8.99 |
| 299 | 3.68 |
| 300 | 1.54 |
| 301 | >9 |
| 302 | 1.14 |
| 303 | 3.11 |
| 304 | 3.78 |
| 305 | 1.63 |
| 306 | 0.50 |
| 307 | 1.54 |
| 308 | 1.93 |
| 309 | 1.74 |
| 310 | 0.68 |
| 311 | 2.05 |
| 312 | 1.59 |
| 313 | 2.10 |
| 314 | 2.15 |
| 315 | 5.36 |
| 316 | 2.02 |
| 317 | 0.90 |
| 318 | 1.07 |
| 319 | 1.21 |
| 320 | 0.70 |
| 321 | 0.44 |
| 322 | 0.70 |
| 323 | 0.20 |
| 324 | 0.69 |
| 325 | 0.25 |
| 326 | 1.46 |
| 327 | 1.83 |
| 328 | 1.39 |
| 329 | 2.60 |
| 330 | 1.11 |
| 331 | 0.75 |
| 332 | 0.48 |
| 333 | 0.57 |
| 334 | 0.69 |
| 335 | 0.83 |
| 336 | 0.48 |
| 337 | 0.78 |
| 338 | 0.23 |
| 339 | 1.11 |
| 340 | 1.03 |
| 341 | 2.01 |
| 342 | 2.17 |
| 343 | 1.01 |
| 344 | 0.99 |
| 345 | 4.32 |
| 346 | >30 |
| 347 | >5.2 |
| 348 | >30 |
| 349 | 17.60 |
| 350 | >30 |
| 351 | >30 |
| 352 | >30 |
| 353 | >30 |
| 354 | >30 |
| 355 | >30 |
| 356 | >30 |
| 357 | >30 |
| 358 | 9.00 |
| 359 | >30 |
| 360 | >30 |
| 361 | 24.70 |
| 362 | >30 |
| 363 | >30 |
| 364 | 8.12 |
| 365 | >30 |
| 366 | 5.28 |
| 367 | 7.00 |
| 368 | 12.40 |
| 369 | >16.43 |
| 370 | 6.02 |
| 371 | 8.88 |
| 372 | >9 |
| 373 | 7.58 |
| 374 | 5.36 |
| 375 | 8.22 |
| 376 | 10.60 |
| 377 | 13.35 |
| 378 | >30 |
| 379 | 8.60 |
| 380 | 9.71 |
| 381 | >30 |
| 382 | 14.40 |

| Example | IC$_{50}$ (μM) or percent inhibition (* indicates 3 minute incubation, otherwise 60 minute) |
|---|---|
| 383 | 0.80 |
| 384 | 1.14 |
| 385 | 1.85 |
| 386 | 1.62 |
| 387 | 5.87 |
| 388 | 4.53 |
| 389 | 1.48 |
| 390 | 2.46 |
| 391 | 1.45 |
| 392 | 0.95 |
| 393 | 1.08 |
| 394 | 0.98 |
| 395 | 2.12 |
| 396 | 3.55 |
| 397 | 1.46 |
| 398 | 3.25 |
| 399 | 15.30 |
| 400 | 6.86 |
| 401 | 2.95 |
| 402 | 2.06 |
| 403 | 8.65 |
| 404 | 1.02 |
| 405 | 3.83 |
| 406 | 3.69 |
| 407 | 5.43 |
| 408 | 5.11 |
| 409 | 5.02 |
| 410 | 1.80 |
| 411 | 2.31 |
| 412 | 4.72 |
| 413 | 0.78 |
| 414 | 0.90 |
| 415 | 1.31 |
| 416 | 1.33 |
| 417 | 1.16 |
| 418 | 0.82 |
| 419 | 0.80 |
| 420 | 5.70 |
| 421 | 2.56 |
| 422 | 7.83 |
| 423 | 6.46 |
| 424 | 3.11 |
| 425 | 3.21 |
| 426 | 1.79 |
| 427 | 6.45 |
| 428 | 2.31 |
| 429 | 0.96 |
| 430 | 1.75 |
| 431 | 0.58 |
| 432 | 1.66 |
| 433 | 1.26 |
| 434 | 2.70 |
| 435 | 2.32 |
| 436 | 1.77 |
| 437 | 2.43 |
| 438 | 5.70 |
| 439 | 1.42 |
| 440 | 3.19 |
| 441 | 0.37 |
| 442 | 7.18 |
| 443 | 7.68 |
| 444 | 2.11 |
| 445 | 7.96 |
| 446 | 4.96 |
| 447 | 2.71 |
| 448 | 12.39 |
| 449 | 4.06 |
| 450 | 9.26 |
| 451 | 0.80 |
| 452 | 9.12 |
| 453 | 4.23 |
| 454 | 2.03 |
| 455 | 3.03 |
| 456 | 5.33 |
| 457 | 3.07 |
| 458 | 3.08 |
| 459 | 1.62 |
| 460 | 2.69 |
| 461 | 1.46 |
| 462 | 2.96 |
| 463 | 2.03 |
| 464 | >30 |
| 465 | >30 |
| 466 | 2.33 |
| 467 | 3.50 |
| 468 | 2.26 |
| 469 | 2.24 |
| 470 | 1.03 |
| 471 | 0.65 |
| 472 | 1.27 |
| 473 | 2.66 |
| 474 | 1.74 |
| 475 | 1.84 |
| 476 | 1.31 |
| 477 | 1.88 |
| 478 | 0.46 |
| 479 | 0.26 |
| 480 | 1.31 |
| 481 | 2.28 |
| 482 | 1.97 |
| 483 | 0.49 |
| 484 | 0.97 |
| 485 | 1.49 |
| 486 | 1.21 |
| 487 | 0.56 |
| 488 | 7.43 |
| 489 | 15.67 |
| 490 | 3.12 |
| 491 | 0.26 |
| 492 | 2.00 |
| 493 | 5.08 |
| 494 | >30 |
| 495 | >30 |
| 496 | 0.53 |
| 497 | 0.57 |
| 498 | 1.59 |
| 499 | 2.70 |
| 500 | 1.69 |
| 501 | 0.82 |
| 502 | 0.97 |
| 503 | 0.89 |
| 504 | 0.91 |
| 505 | 2.23 |
| 506 | 1.71 |
| 507 | 0.87 |
| 508 | 8.60 |
| 509 | 4.55 |
| 510 | 1.68 |
| 511 | 2.12 |
| 512 | 0.47 |
| 513 | 2.15 |
| 514 | >22.50 |
| 515 | 3.17 |
| 516 | 2.99 |
| 517 | 4.45 |
| 518 | 0.80 |
| 519 | 5.14 |
| 520 | 12.84 |
| 521 | 9.60 |
| 522 | 2.90 |
| 523 | 4.44 |
| 524 | 2.07 |
| 525 | 1.39 |
| 526 | 2.77 |
| 527 | 2.29 |
| 528 | 7.23 |
| 529 | 0.96 |
| 530 | 7.63 |
| 531 | 3.49 |
| 532 | 3.16 |
| 533 | 9.68 |
| 534 | 6.38 |
| 535 | >30 |
| 536 | 8.37 |

| Example | IC$_{50}$ (μM) or percent inhibition (* indicates 3 minute incubation, otherwise 60 minute) |
|---|---|
| 537 | 11.31 |
| 538 | 3.75 |
| 539 | 4.39 |
| 540 | 1.67 |
| 541 | 2.57 |
| 542 | 2.36 |
| 543 | 3.20 |
| 544 | 2.15 |
| 545 | >30 |
| 546 | 6.32 |
| 547 | >30 |
| 548 | 1.05 |
| 549 | 2.73 |
| 550 | 2.57 |
| 551 | 2.49 |
| 552 | 0.78 |
| 553 | 1.94 |
| 554 | 10.30 |
| 555 | 2.51 |
| 556 | 2.58 |
| 557 | 1.14 |
| 558 | 4.88 |
| 559 | 1.68 |
| 561 | 1.45 |
| 562 | 1.69 |
| 563 | 1.32 |
| 564 | 0.34 |
| 565 | 0.81 |
| 566 | 0.81 |
| 567 | 0.40 |
| 568 | 2.10 |
| 569 | 0.98 |
| 570 | 0.61 |
| 571 | 1.11 |
| 572 | 1.01 |
| 573 | 1.68 |
| 574 | 1.38 |
| 575 | 0.70 |
| 576 | 1.08 |
| 577 | 2.06 |
| 578 | 1.00 |
| 579 | 2.63 |
| 580 | 1.88 |
| 581 | 2.99 |
| 582 | 0.96 |
| 583 | 1.12 |
| 584 | 2.06 |
| 585 | 1.52 |
| 586 | 2.56 |
| 587 | 0.39 |
| 588 | 1.02 |
| 589 | 0.32 |
| 590 | 0.45 |
| 591 | 0.50 |
| 592 | 4.50 |
| 593 | 0.52 |
| 594 | 1.45 |
| 595 | 2.18 |
| 596 | 4.47 |
| 597 | 1.30 |
| 598 | 2.57 |
| 599 | 4.43 |
| 600 | 2.86 |
| 601 | 2.11 |
| 602 | 1.88 |
| 603 | 2.22 |
| 604 | 2.78 |
| 605 | 4.33 |
| 606 | 1.19 |
| 607 | 6.40 |
| 608 | 1.65 |
| 609 | 1.45 |
| 610 | 2.01 |
| 611 | 0.50 |
| 612 | 2.24 |
| 613 | 0.91 |
| 614 | 3.33 |
| 615 | 13.74 |
| 616 | 4.22 |
| 617 | 2.57 |
| 618 | 0.63 |
| 619 | 2.84 |
| 620 | 5.31 |
| 621 | 0.99 |
| 622 | 1.69 |
| 623 | 1.32 |
| 624 | 4.91 |
| 625 | 1.42 |
| 626 | 4.52 |
| 627 | 2.71 |
| 628 | 3.53 |
| 629 | 4.22 |
| 630 | 3.34 |
| 631 | >30 |
| 632 | 18.92 |
| 633 | 26.24 |
| 634 | 2.39 |
| 635 | 0.92 |
| 636 | 3.73 |
| 637 | 20.53 |
| 638 | >30 |
| 639 | 7.77 |
| 640 | 14.40 |
| 641 | 26.21 |
| 642 | 15.63 |
| 643 | 3.57 |
| 644 | 8.50 |
| 645 | >30 |
| 646 | 2.16 |
| 647 | 3.77 |
| 648 | 3.55 |
| 649 | 0.41 |
| 650 | 0.59 |
| 651 | 14.94 |
| 652 | 21.20 |
| 653 | >30 |
| 654 | 0.82 |
| 655 | 19.55 |
| 656 | 2.16 |
| 657 | 1.80 |
| 658 | 6.37 |
| 659 | 6.85 |
| 660 | 7.03 |
| 661 | 14.70 |
| 662 | >30 |
| 663 | 1.89 |
| 664 | 1.69 |
| 665 | 2.99 |
| 666 | 1.37 |
| 667 | 1.49 |
| 668 | 1.55 |
| 669 | 0.80 |
| 670 | 1.17 |
| 671 | 1.53 |
| 672 | 1.65 |
| 673 | 0.74 |
| 674 | 0.53 |
| 675 | 2.22 |
| 676 | 4.20 |
| 677 | 3.35 |
| 678 | 0.69 |
| 679 | 1.62 |
| 680 | 1.66 |
| 681 | 0.98 |
| 682 | 0.87 |
| 683 | 0.71 |
| 684 | 1.05 |
| 685 | 1.10 |
| 686 | 0.88 |
| 687 | 1.27 |
| 688 | 1.03 |
| 689 | 0.82 |
| 690 | 0.75 |
| 691 | 0.61 |

-continued

| Example | IC$_{50}$ (µM) or percent inhibition (* indicates 3 minute incubation, otherwise 60 minute) |
|---|---|
| 692 | 0.99 |
| 693 | 1.42 |
| 694 | 4.00 |
| 695 | 2.55 |
| 696 | 3.52 |
| 697 | 2.24 |
| 698 | 1.52 |
| 699 | 0.65 |
| 700 | 4.96 |
| 701 | 4.50 |
| 702 | 2.55 |
| 703 | 3.17 |
| 704 | 4.63 |
| 705 | 3.82 |
| 706 | 1.12 |
| 707 | 7.26 |
| 708 | 3.35 |
| 709 | 6.18 |
| 710 | 5.56 |
| 711 | 1.38 |
| 712 | 1.01 |
| 713 | 2.99 |
| 714 | 2.80 |
| 715 | 2.78 |
| 716 | 8.15 |
| 717 | 3.54 |
| 718 | 1.30 |
| 719 | 10.61 |
| 720 | 1.44 |
| 721 | 0.87 |
| 722 | 2.53 |
| 723 | 11.88 |
| 724 | 22.34 |
| 725 | 0.94 |
| 726 | 2.16 |
| 727 | 0.58 |
| 728 | 0.48 |
| 729 | 1.08 |
| 730 | 1.26 |
| 731 | 0.94 |
| 732 | 0.56 |
| 734 | 26.40 |
| 735 | 3.62 |
| 736 | 3.34 |
| 737 | 0.36 |
| 738 | 2.98 |
| 739 | 2.85 |
| 740 | 2.00 |
| 741 | 1.16 |
| 742 | 1.30 |
| 743 | 1.00 |
| 744 | 1.21 |
| 745 | 3.51 |
| 746 | 1.71 |
| 747 | >9.5 |
| 748 | 0.81 |
| 749 | >3 |
| 750 | >3 |
| 751 | >3 |
| 752 | >9.5 |
| 753 | >9.5 |
| 754 | 6.78 |
| 755 | >3 |
| 756 | >9.5 |
| 757 | 1.13 |
| 758 | 1.42 |
| 759 | 12.95 |
| 760 | 2.32 |
| 761 | 3.59 |
| 762 | 5.11 |
| 763 | 12.34 |
| 764 | 0.95 |
| 765 | 2.59 |
| 766 | 0.63 |
| 767 | 6.93 |
| 768 | 2.36 |
| 769 | 1.13 |
| 770 | 0.75 |
| 771 | 2.90 |
| 772 | 1.08 |
| 773 | 1.79 |
| 774 | 1.15 |
| 775 | 2.77 |
| 776 | 2.53 |
| 777 | 2.16 |
| 778 | 4.27 |
| 779 | 1.86 |
| 780 | 14.0 |
| 781 | 8.26 |

(ii) In Vivo Data—Capsaicin Induced Secondary Mechanical Hyperalgesia Model:

Sprague Dawley rats were briefly restrained, and capsaicin was administered at 10 µg in 10 µL of vehicle by intraplantar injection into the center of the right hind paw. Secondary mechanical hyperalgesia (SMH) was measured at the heel away from the site of injection 180 minutes following capsaicin exposure. Compounds and gabapentin (positive control), were administered p.o. 60 minutes before testing (2 hours after capsaicin) or i.p. 30 minutes before testing (2.5 hours after capsaicin). SMH was measured using calibrated von Frey filaments (Stoelting, Woodale, Ill.). Following the 1 hour habituation in the testing room, rats were moved to individual plexiglass chambers that sit on top of a wire mesh to allow for access for stimulation of the plantar surface of the hind paws. Rats were allowed to acclimate to the new chambers for 15 minutes before the onset of testing. The paw withdrawal threshold was determined by increasing and decreasing stimulus intensity (force: g) and calculated using Dixon's up-down method (Chaplan, S. R.; Bach, F. W.; Pogrel, J. W.; Chung, J. M.; Yaksh, T. L.; J. Neuroscience Methods 1994, 53(1), 55-63.). The filaments (maximum force of 15.0 g) were held in place for 8 seconds or until there was a withdrawal response from the mechanical stimulation.

| Example | % inhibition @ 30 mg/kg p.o. |
|---|---|
| 54 | 38 |
| 75 | 85 |
| 156 | 67 |
| 157 | 57 |
| 165 | 92 |
| 170 | 57 |
| 172 | 85 |
| 183 | 78 |
| 220 | 76 |
| 280 | 38 |
| 405 | 32 |
| 415 | 52 |
| 461 | 43 |
| 478 | 57 |
| 479 | 40 |
| 480 | 64 |
| 488 | 55 |
| 489 | 47 |
| 560 | 42 |
| 573 | 57 |
| 587 | 16 |
| 592 | 54 |
| 593 | 76 |
| 597 | 54 |
| 598 | 54 |

-continued

| Example | % inhibition @ 30 mg/kg p.o. |
|---|---|
| 599 | 32 |
| 600 | 63 |

(iii) In Vivo Data—Determination of Analgesic Effect Against Neuropathic Pain—Bennett Model Animals were prepared for testing, by use of a surgical procedure that induces neuropathic pain in one paw. IACUC guidelines for rodent survival surgery are followed. All surgical procedures are conducted on a clean, uncluttered surgical station. The area is wiped with a 70% ethanol solution before and after use. All instruments are sterilized by either autoclave or chemical sterilant (such as 2% glutaraldehyde >10 hr). Surgeons wear sterile gloves (for the initial procedure), clean lab coat or scrubs, hairnet or cap, and a half-mask respirator (when not working under a hood). Surgeons thoroughly wash their hands prior to donning sterile gloves. Gloves are disinfected in-between animals by cleansing with povidone iodine, chlorhexidine or 70% alcohol for at least 30 seconds. If multiple surgeries are performed, the instruments are cleaned and sterilized between procedures with hot glass beads (>10 seconds). To prevent thermal or chemical burns, the instruments are cooled by rinsing in sterile saline before use.

Male, Sprague Dawley rats, 175-200 g are used for surgeries. To minimize post-operative dehydration/maintain blood volume during the surgery, warmed sterile saline or Lactate Ringers solution at 10-15 mL/kg is administered subcutaneously immediately before or after surgery. This facilitates better renal function and presumably anesthesia product excretion post surgery. For all surgical procedures, anesthesia is induced with 4-5% isoflurane. Anesthesia is be maintained during surgery with 1-3% isoflurane. Following induction, the surgical site is carefully shaved and the exposed area is aseptically prepared with povidone-iodine scrub solution and 70% ethanol 2-3 times.

Chronic constriction injury (CCI), a model of neuropathic pain, is produced by following the method of Bennett and Xie (Bennett, G., et al. Pain, 1988, 33, 87-107). After site sterilization and anesthetic procedures outline above are completed, a 1.5 cm incision is made at the mid-thigh level to expose the biceps femoris and gluteous superficialis (right side), which are then separated by blunt dissection. The common sciatic nerve is exposed, isolated, and loosely ligated by four 5-0 chromic gut ligatures with <1 mm spacing between each. The surgical site is closed in layers—muscle is closed with 6.0 absorbable sutures, and the skin closed with wound clips. Animals are allowed to recover on a warming plate and are returned to their home cages when fully ambulatory. Animals are not be used for testing until at least 10 days following surgery.

To measure mechanical sensitivity, tactile allodynia is measured using calibrated von Frey filaments (Stoelting, Wood Dale, Ill.) as described by Chaplan et al. (Chaplan S., et al. J of Neuroscience Methods 1994, 53, 55-63). Filament strengths used are: 0.4, 0.6, 1.0, 2, 4, 6, 8, and 15 g. Rats are be placed into inverted individual plastic containers (20× 12.5×20 cm) on top of a suspended wire mesh grid, and acclimated to the test chambers for at least 20 minutes. Filaments are applied perpendicular to the mid-plantar paw surface with enough force to cause slight buckling and held in place for 6-8 seconds. Positive responses include an abrupt withdrawal of the paw from the stimulus or flinching behavior immediately following removal of the stimulus. The maximum force applied will be 15 g. The 50% paw withdrawal threshold (PWT) is calculated in grams (g) using the up-down method of Dixon (Dixon W. Ann Rev Pharmacol Toxicol 1980, 20, 441-462). Only rats exhibiting increased mechanical sensitivity are used (threshold responses below 5 g). All compounds were orally administered in 10% dimethyl sulfoxide/polyethylene glycol at a volume of 2.0 mL/kg, and mechanical allodynia was determined 60 minutes following compound administration. Data are reported as log g values and the percentage of maximum possible effect (% MPE) is calculated using log g values with the formula:

% MPE=(log [observed PWT in grams]−log [mean PWT vehicle])/(log [15]−log [mean PWT vehicle])*100

All statistical procedures are run on log g values.

| Example | dose mg/kg | route | % MPE |
|---|---|---|---|
| 480 | 30 | po | 57 |
| 580 | 30 | po | 5 |
| 600 | 30 | po | 40 |
| 608 | 30 | po | 79 |
| 613 | 30 | po | 61 |
| 624 | 30 | po | 85 |
| 625 | 30 | po | 42 |
| 627 | 30 | po | 54 |
| 718 | 30 | po | 29 |
| 722 | 30 | po | 8 |
| 729 | 30 | po | 85 |
| 735 | 30 | po | 60 |
| 739 | 30 | po | 63 | d. Methods of Using the Compounds

One embodiment of the present invention provides a method of treating pain in a subject in need thereof. The method comprises administering to the subject, including a mammal, such as a human, a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof. Preferably, the method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more of the following: nonsteroidal anti-inflammatory drug (NSAID), opioid analgesic, barbiturate, benzodiazapine, histamine antagonist, sedative, skeletal muscle relaxant, transient receptor potential ion channel antagonist, α-adrenergic, tricyclic antidepressant, anticonvulsant, tachykinin antagonist, muscarinic antagonist, cyclooxygenase-2 selective inhibitor, neuroleptic, vanilloid receptor agonist, vanilloid receptor antagonist, β-adrenergic, local anesthetic, corticosteroid, 5-HT receptor agonist, 5-HT receptor antagonist, 5-HT$_{2A}$ receptor antagonist, cholinergic analgesic, α$_2$δ ligand such as gabapentin or pregabalin, cannabinoid receptor ligand, metabotropic glutamate subtype 1 receptor antagonist, serotonin reuptake inhibitor, norepinephrine reuptake inhibitor, dual serotonin-noradrenaline reuptake inhibitor, Rho kinase inhibitor, inducible nitric oxide synthase inhibitor, acetylcholinesterase inhibitor, prostaglandin $E_2$ subtype 4 antagonist, leukotriene B4 antagonist, 5-lipoxygenase inhibitor, sodium channel blocker, 5-HT3 antagonist, N-methyl-D-aspartic acid receptor antagonist, and phosphodiesterase V inhibitor.

Yet another embodiment of the present invention relates to a method for providing a method for treating disorders of the central nervous system including stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritus and allergic dermatitis, inflammatory bowel disease; cancer; diabetes; and infertility and sexual dysfunction in a mammal in need of such treatment. This method comprises administering to the mammal (including human) a therapeutically effective amount of a compound of the invention or a pharmaceutically acceptable salt thereof.

Calcium channel blockers have been associated with a slightly greater decreased risk of stroke compared to other types of antihypertensive agents (Angeli, F.; et al. American Journal of Hypertension 2004, 17(9), 817-822). The enhanced effect did not correlate with differences in systolic blood pressure and the mechanism of action remains unknown. However, calcium channel blockers have been associated with blockade of central neuronal calcium influx and subsequent ischemic injury in two rodent models (Barone, F. C.; et al. Stroke 1995, 26, 1683-1690.). In another model of global ischemia, a calcium channel blocker offered neuroprotection although not permanently (Colbourne, F.; et al. Stroke 1999, 30(3), 662-668.). Additionally, diminished progression of carotid atherosclerosis has been observed with calcium channel blocker use (Zanchetti, A.; et al. Circulation 2002, 106, r47-r52.).

An increase in intracellular calcium concentration has been correlated with seizure activity (Heinemann, U.; et al. Exp. Brain Res. 1977, 27, 237-243.). Several studies have indicated that calcium channel blockers produce anticonvulsant activity (Vezzani, A.; et al. Neuropharmacology 1988, 27(5), 451-458. Otoom, S.; et al. Fundamental & Clinical Pharmacology 2006, 20, 115-119.).

Calcium channel blockers have been evaluated in the treatment of bipolar disorders and manic depression for decades. There are suggestions that the calcium channel subtype has influence on efficacy of these disorders (Gitlin, M. Molecular Psychiatry 2006, 11, 227-240. Levy, N. A.; Janicak, P. G. Bipolar Disorders 2000, 2, 108-119.).

Calcium channel blockers have also been associated with the treatment of anxiety and depression (Saade, S.; et al. Pharmacology, Biochemistry and Behavior 2003, 74, 269-278.).

Antischizophrenic drugs have been found to be calcium channel antagonists (Gould, R. J.; et al. Proc. Natl. Acad. Sci. USA 1983, 80, 5122-5125.). Other calcium channel blockers have been suggested for the treatment of schizophrenia (Tort, A. B. L.; et al. Psychopharmacology 2005, 177, 344-348.). T-type calcium channels have been located in brain regions with relevance to schizophrenia and substance dependence (Talley, E. M.; et al. J Neurosci 1999, 19, 1895-1911).

Migraines are treated with calcium channel blockers (Arulmoshi, D. K.; et al. Vascular Pharmacology 2005, 43, 176-187. Gladstone, J. P.; et al. Expert Rev. Neurotherapeutics 2003, 3(6), 845-872.).

Disorders of the lower urinary tract including overactive bladder, prostatis, prostadynia, interstitial cystitis, and benign prostatic hyperplasia can be treated with calcium channel blockers (Fraser, M. O.; et al. US20050148587, 2005).

Ethanol withdrawal syndrome is decreased with calcium channel blockers (Little, H. J.; et al. Life Sciences 1986, 39, 2059-2065.).

Dependence on nicotine has been decreased upon treatment with T-type calcium channel blockers (Uslaner, J. M.; et al. Neuropharmacology 2010 (in press)).

Several cardiac disorders are treated with calcium channel blockers. Atherosclerosis can be reduced by a decrease in free radical-mediated damage as a result of influence on the biophysical properties of membranes (Mason, R. P.; et al. Biochemical Pharmacology 1998, 55, 1843-1852.). Hypertension and angina are both successfully treated with calcium channel blockers (Croom, K. F.; et al. Drugs 2006, 66(4), 497-528.).

There is data suggesting that calcium channel blockers inhibit the proliferation of cancer cells (Gray, L. S.; et al. International Publication No. WO200059882, 2000.).

Calcium channels have been suggested as a target for the treatment of diabetes (Bhattacharjee, A.; et al. Endocrinology 1997, 138(9), 3735-3740.).

Ion channels including calcium channels play an important role in sperm physiology and fertilization (Darszon, A.; et al. Physiological Reviews 1999, 79(2), 481-510).

Calcium channel blockers modulate inflammation (Bilici, D.; et al. Pharmacological Research 2001, 44(6), 527-531.).

Increased calcium levels in neurones has been implicated in Alzheimer's disease. Two suggested mechanisms of increased calcium influx are that β-amyloid can form calcium permeable channels (Bhatia, R.; et al. FASEB J. 2000, 14(9), 1233-1243.) or a G-protein-coupled receptor can be activated by β-amyloid (Lorton, D. Mech. Ageing Dev. 1997, 94(1-3), 199-211.).

Neurodegenerative diseases, including Parkinson's and Alzheimer's diseases can be modulated by calcium channel blockers (Rodnitzky, R. L. Drugs 1999, 57(6), 845-849. Vagnucci, A. H., Jr.; et al. The Lancet 2003, 361(9357), 605-608. Veng, L. M.; et al. Molecular Brain Research 2203, 110, 193-202. Geldenhuys, W. J.; et al. Bioorganic and Medicinal Chemistry 2007, 15, 1525-1532. Cavalli, A.; et al. J. Med. Chem. 2008, 51(3), 347-372.).

Sleep disorders and absence epilepsy have been associated with calcium channels (Shin, H.-S.; et al. Curr Opin Pharmacol, 2008, 8, 33-41).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level can depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It can be understood, however, that the total daily usage of the compounds and compositions of the invention can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions can contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that can be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drugs (NSAID), opioid analgesics, barbiturates, benzodiazepines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-$HT_{2A}$ receptor antagonists, cholinergic analgesics, $α_2δ$ ligands such as gabapentin or pregabalin, cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin $E_2$ subtype 4 antagonists, leukotriene B4 antagonists, 5-lipoxygenase inhibitors, sodium channel blockers, 5-HT3 antagonists, N-methyl-D-aspartic acid receptor antagonists, and phosphodiesterase V inhibitors.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type can also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They can optionally contain opacifying agents and can also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound can be mixed under sterile conditions with a pharmaceutically acceptable carrier and any needed preservatives, buffers or propellants which can be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention can be prepared by a variety of processes well known for the preparation of compounds of this class. For example, the compounds of the invention wherein the groups $L^1$, $L^2$, $R^1$, $R^2$, $R^3$, $R^4$, $R^5$, $R^6$, $R^e$, $R^f$, $R^g$, $R^h$, n, q, and $G^1$, have the meanings as set forth in the Summary of the Invention section unless otherwise noted, can be synthesized as shown in Schemes 1-23.

Abbreviations which have been used in the descriptions of the Schemes and the Examples that follow are: Ac for acetyl; AlMe$_3$ for trimethylaluminum; Boc for t-butoxy carbonyl; Boc$_2$O for di-tert-butyl dicarbonate; Bu for butyl; Et for ethyl, EtOH for ethanol; DMF or N,N-dimethylformamide; DMSO for dimethyl sulfoxide; LCMS for liquid chromatography/mass spec; MeOH for methanol; MsCl for methanesulfonyl chloride; NEt$_3$ for triethylamine; OAc for acetate; Ph for phenyl; PPh$_3$ for triphenylphosphine; PS-cyanoborohydride for polymer-supported cyanoborohydride; psi for pounds per square inch; tBu for tert-butyl; THF for tetrahydrofuran, and TLC for thin layer chromatography.

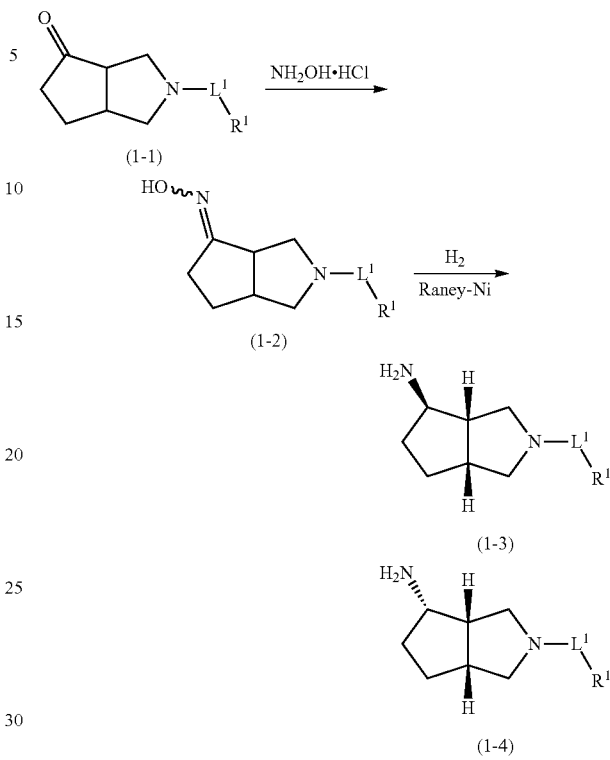

Compounds of formula (1-3) and (1-4), wherein $L^1$ and $R^1$ are as defined in the Summary of the Invention, can be prepared as illustrated in Scheme 1. Compounds of formula (1-1) can be treated with hydroxylamine hydrochloride in the presence of a base such as sodium carbonate, sodium bicarbonate, or sodium acetate in a solvent such as water or aqueous methanol and optionally heated to furnish oximes of formula (1-2). Oximes of formula (1-2) can then be reduced in the presence of hydrogen (30 psi) in the presence of Raney®-nickel in a solvent such as 20% ammonia in methanol at ambient temperature over 1 to 24 hours to provide a diastereomeric mixture of amines, compounds of formulas (1-3) and (1-4). The diastereomeric amines can be separated by techniques know to one skilled in the art such as chromatography.

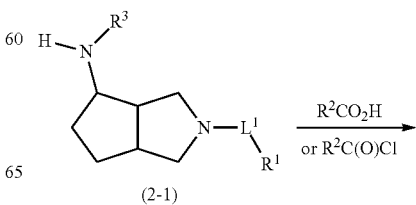

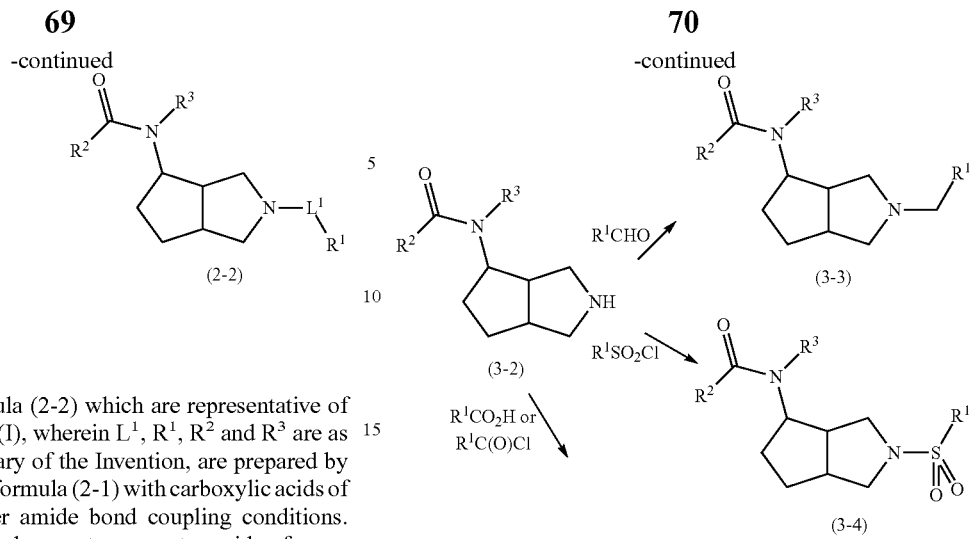

Compounds of formula (2-2) which are representative of compounds of formula (I), wherein $L^1$, $R^1$, $R^2$ and $R^3$ are as described in the Summary of the Invention, are prepared by reacting compounds of formula (2-1) with carboxylic acids of formula $R^2CO_2H$ under amide bond coupling conditions. Examples of conditions known to generate amides from a mixture of a carboxylic acid and an amine include but are not limited to adding a coupling reagent such as but not limited to N-(3-dimethylaminopropyl)-N-ethylcarbodiimide (EDC or EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents can be added as a solid, a solution or as the reagent bound to a solid support resin. In addition to the coupling reagents, auxiliary-coupling reagents can facilitate the coupling reaction. Auxiliary coupling reagents that are often used in the coupling reactions include but are not limited to (dimethylamino) pyridine (DMAP), 1-hydroxy-7-azabenzotriazole (HOAT) and 1-hydroxybenzotriazole (HOBT). The reaction can be carried out optionally in the presence of a base such as triethylamine or diisopropylethylamine. The coupling reaction can be carried out in solvents such as but not limited to tetrahydrofuran, N,N-dimethylformamide, dichloromethane, and ethyl acetate. The reaction can be conducted at ambient or elevated temperatures.

Alternatively, compounds of formula (2-2) can be prepared from compounds of formula (2-1) by reacting with an acid chloride of formula $R^2C(O)Cl$. Compounds of formula (2-1), can be treated $R_2C(O)Cl$ in a solvent such as dichloromethane in the presence of an amine such as triethylamine or diisopropylethylamine at room temperature over 1 to 24 hours to afford compounds of formula (2-2).

Scheme 3

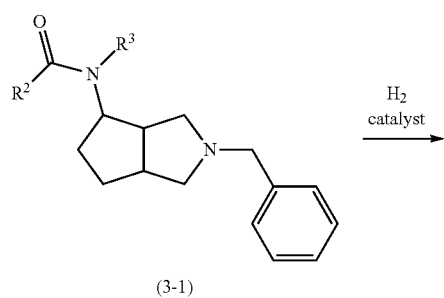

(3-1)

As illustrated in Scheme 3, compounds of formulas (3-3), (3-4), and (3-5) which are representative of compounds of formula (I), and wherein $R^1$, $R^2$ and $R^3$ are as defined in the Summary of the Invention, can be obtained from compounds of formula (3-1). Compounds of formula (3-1) can be converted to compounds of formula (3-2) by treatment with hydrogen (15-60 psi) in the presence of a catalyst such as palladium hydroxide on carbon or palladium on carbon in a solvent such as methanol or ethanol at ambient temperature over 3-36 hours. Compounds of formula (3-2) can then be reductively aminated with aldehydes of formula $R^1CHO$ in the presence of a reducing agent such as PS-cyanoborohydride, sodium cyanoborohydride, or sodium triacetoxyborohydride and acetic acid in a solvent such as methanol or dichloromethane at room temperature over 4-24 hours to supply compounds of formula (3-3). Alternatively, compounds of formula (3-2) can be reacted with a sulfonyl chloride of formula $R^1SO_2Cl$ in the presence of a base such as triethylamine or diisopropylamine optionally in the presence of (dimethylamino)pyridine in a solvent such as dichloromethane at ambient temperature over 4-24 hours to supply compounds of formula (3-4). Compounds of formula (3-5) can also be prepared from compounds of formula (3-2). Compounds of formula (3-2) can be treated with a carboxylic acid of formula $R^1CO_2H$ or and acid chloride of formula $R^1C(O)Cl$ under the amide bond forming conditions described in Scheme 2 to give compounds of formula (3-5).

Scheme 4

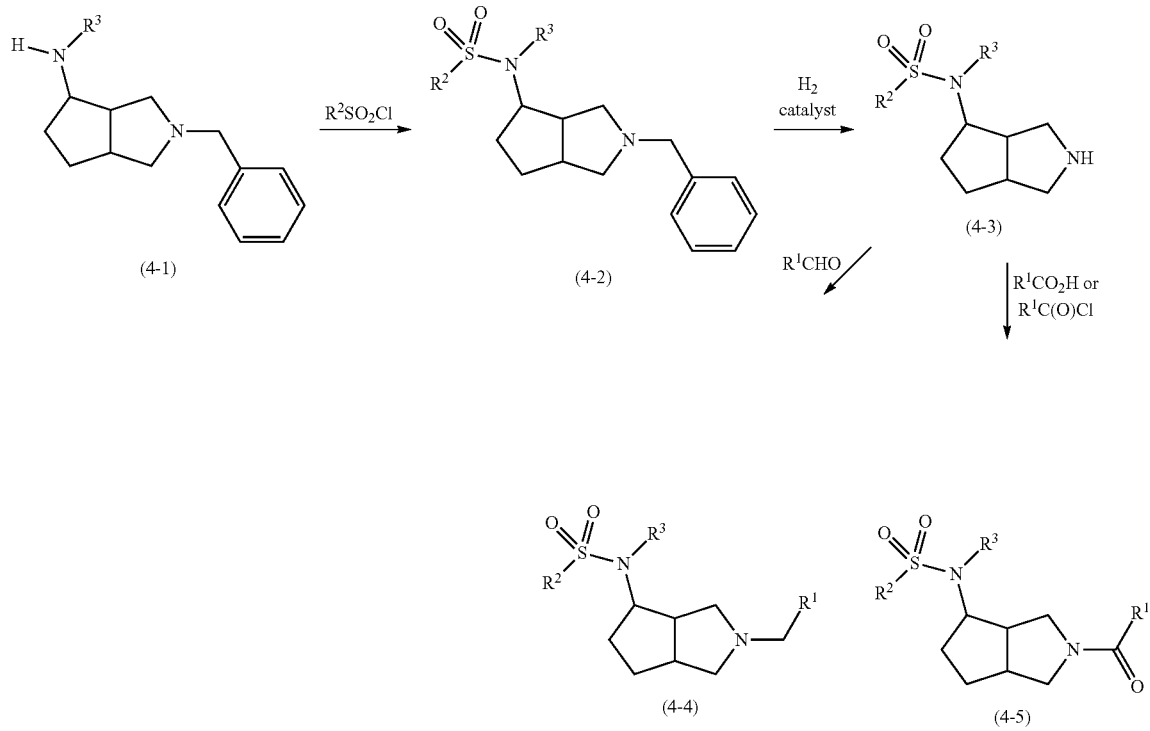

As illustrated in Scheme 4, compounds of formulas (4-2), (4-3), (4-4) and (4-5) which are representative of compounds of formula (I), wherein $R^1$, $R^2$ and $R^3$ are as defined in the Summary of the Invention, can be obtained from compounds of formula (4-1). Accordingly, compounds of formula (4-1) can be treated with sulfonyl chlorides of formula $R_2SO_2Cl$ using the conditions described in Scheme 3 to give compounds of formula (4-2). The benzyl group can be reductively cleaved with hydrogen and a palladium catalyst as described in Scheme 3 to deliver compounds of formula (4-3). Compounds of formula (4-3) can be reductively alkylated with aldehydes of formula $R^1CHO$ under the reaction conditions described in Scheme 3 to give compounds of formula (4-4). The secondary amine of compounds of formula (4-3) can be coupled with a carboxylic acid or acid chloride with the conditions described in Scheme 2 to give amides of formula (4-5).

Scheme 5

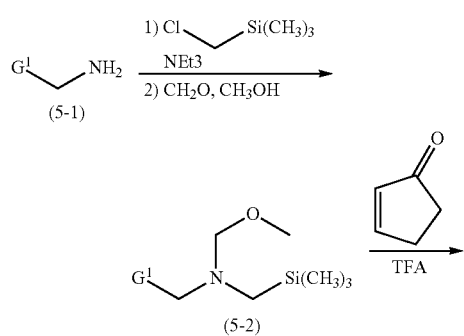

-continued

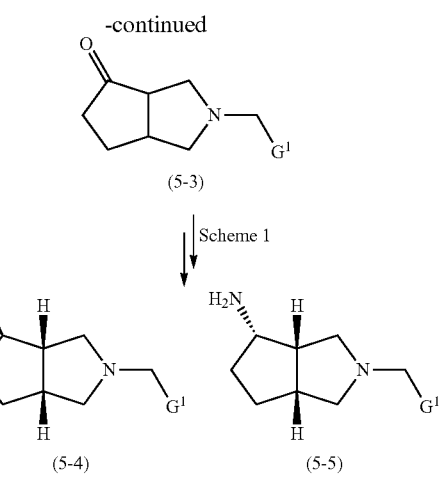

Compounds of formula (5-4) and (5-5), wherein $G^1$ is aryl or heteroaryl and unsubstituted or substituted as described in the Summary of the Invention, can be prepared from compounds of formula (5-1) as described in Scheme 5. Compounds of formula (5-1) can be combined with chloromethyltrimethylsilane and triethylamine and refluxed for 8-24 hours. The intermediate can then be reacted with formaldehyde in the presence of potassium carbonate and in methanol to give compounds of formula (5-2). Compounds of formula (5-2) can be reacted with cyclopent-2-enone at room temperature in the presence of trifluoroacetic acid in a solvent such as dichloromethane to give compounds of formula (5-3). Alternatively, compounds of formula (5-2) can be reacted with cyclopent-2-enone at room temperature in the presence in a solvent such as acetonitrile to give compounds of formula (5-3) (Santore, V. J.; et al. Bioorganic & Medicinal Chemistry Letters, 2008, 18, 1490-1494). Compounds of formula (5-3) can be transformed to compounds of formulas (5-4) and (5-5) upon treatment first with hydroxylamine hydrochloride and subsequently with hydrogen in the presence of Raney®-nickel as described in Scheme 1.

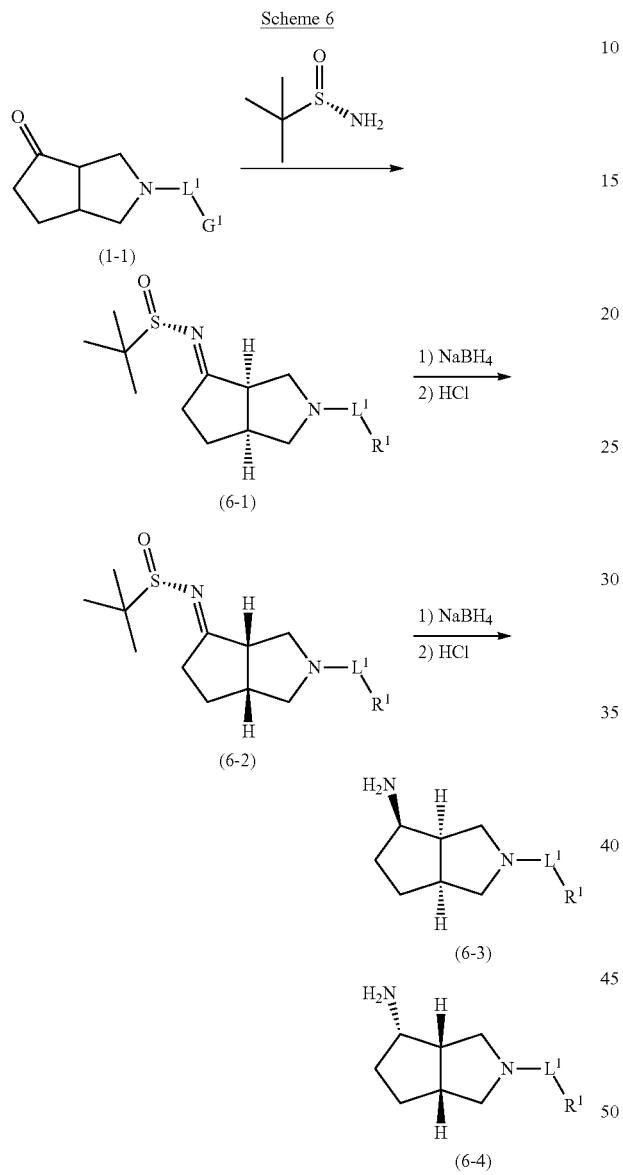

Chiral compounds of formulas (6-3) and (6-4), wherein $L^1$ and $R^1$ are as defined in the Summary of the Invention, can be synthesized as described in Scheme 6. To this end, compounds of formula (1-1) can be treated with a chiral sulfinamide such as (S)-2-methylpropane-2-sulfinamide in the presence of titanium tetraethoxide in a solvent such as tetrahydrofuran and heated to 30-65° C. for 4 to 24 hours to give the diastereomeric compounds (6-1) and (6-2). The chiral diastereomers can be chromatographically separated and then treated individually in the following sequence. Chiral compounds of formula (6-1) can be reduced with sodium borohydride in methanol at −78° C. with gradual warming to room temperature over 8 to 20 hours. Subsequent hydrolysis with hydrochloric acid in methanol delivers chiral compounds of formula (6-3). In similar fashion, chiral compounds of formula (6-2) can be converted to chiral compounds of formula (6-4).

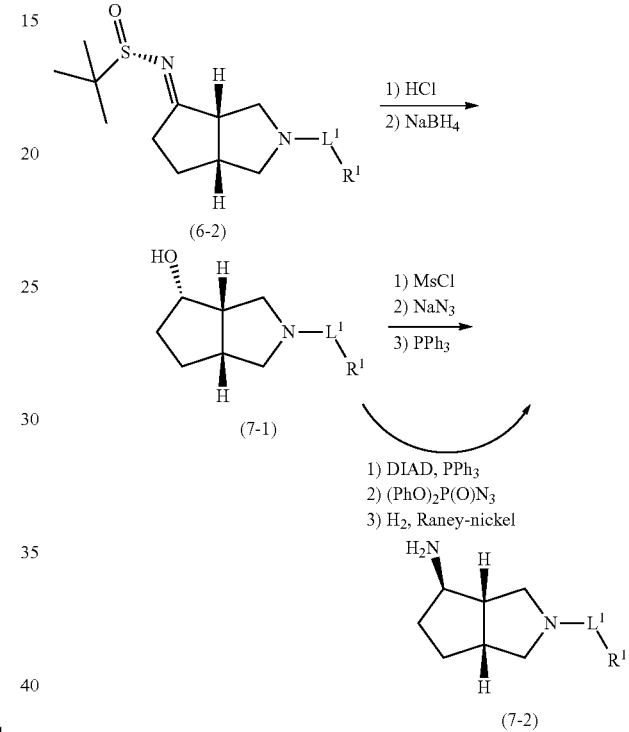

As illustrated in Scheme 7, chiral compounds of formulas (7-2), wherein $L^1$ and $R^1$ are as defined in the Summary of the Invention, can be obtained from chiral compounds of formula (6-2). Chiral compounds of formula (6-2) can be hydrolyzed with hydrochloric acid in tetrahydrofuran at room temperature over 1-8 hours. Subsequent reduction with sodium borohydride in methanol at −40° C. to room temperature over 8-24 hours supplies chiral alcohols (7-1). Alcohols (7-1) can be transformed to chiral amines (7-2) in a three-step process. Compounds of formula (7-1) can be treated with methanesulfonyl chloride in the presence of triethylamine in dichloromethane at ambient temperature for 10 minutes to 2 hours. The sulfonates can then be displaced with inversion with sodium azide in heated N,N-dimethylacetamide over 8-24 hours. The derived azides can finally be reduced with triphenylphosphine in a heated mixture of water and tetrahydrofuran to give chiral compounds of formula (7-2).

As an alternative procedure, compounds of formula (7-1) can be converted to compounds of formula (7-2) under Mitsunobu reaction conditions. Accordingly, treatment of compounds of formula (7-1) with an azodicarboxylate such as diisopropyl azodicarboxylate in the presence of triphenylphosphine followed by an azide source such as diphenyl phosphoryl azide produces an intermediate azide. This azide can be reduced with hydrogen in the presence of a catalyst such as Raney-Nickel® to give compound of formula (7-2).

As illustrated in Scheme 9, compounds of formula (9-1), wherein $R^2$ and $R^3$ are as defined in the Summary of the Invention, can be obtained from compounds of formula (3-2). Compounds of formula (3-2) can be reacted with (bromomethylene)dibenzene in the presence of potassium iodide, and sodium carbonate in methyl ethyl ketone heated to 90° C. for 6 to 24 hours to give compounds of formula (9-1) which are representative of compounds of formula (I).

Scheme 8

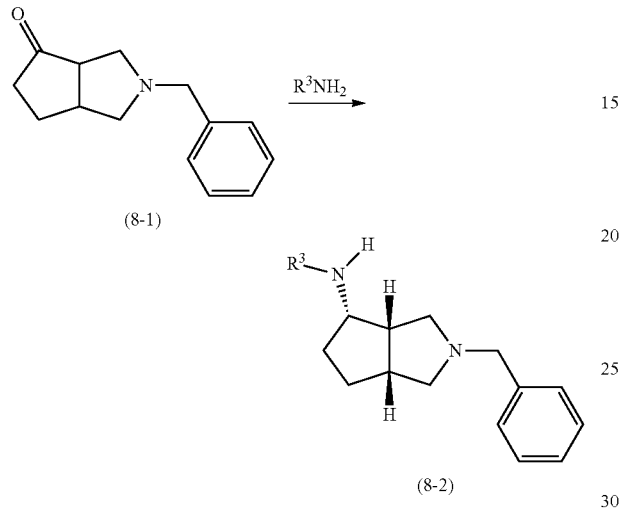

Scheme 10

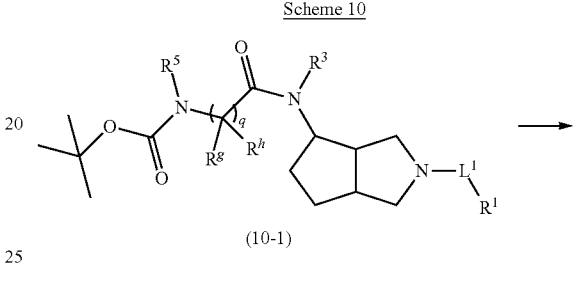

As described in Scheme 8, compounds of formula (8-1) can be converted to compounds of formula (8-2) wherein $R^3$ is alkyl, haloalkyl, cycloalkyl, or cycloalkylalkyl. Compounds of formula (8-1) can be treated with amines of formula $R^3NH_2$ in the presence of PS-cyanoborohydride, sodium cyanoborohydride, or triacetoxy borohydride and acetic acid in dichloromethane at ambient temperature for 1-6 hours to give compounds of formula (8-2). Compounds of formula (8-2) can be used in Scheme 4 in place of compounds of formula (4-1).

Scheme 9

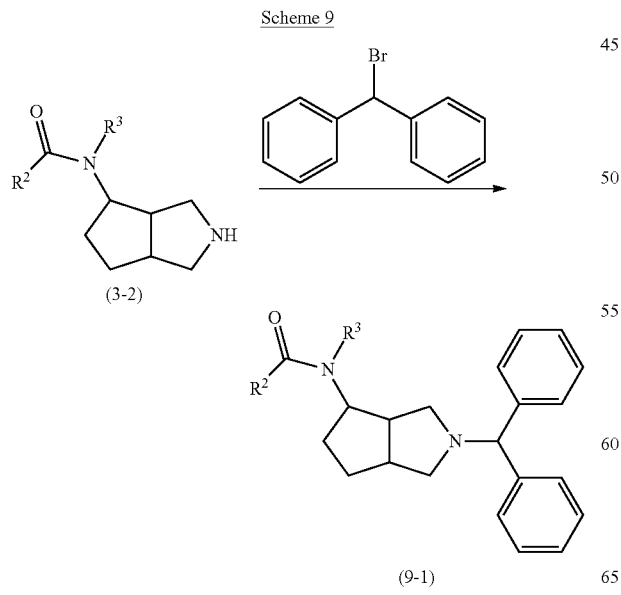

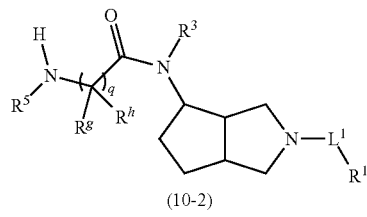

As illustrated in Scheme 10, compounds of formula (10-2) which are representative of compounds of formula (I) and wherein $L^1$, $R^1$, $R^3$, $R^5$, $R^g$, $R^h$, and q are as defined in the Summary of the Invention can be obtained from compounds of formula (10-1). Compounds of formula (10-1) can be treated with an acid such as hydrochloric acid or trifluoroacetic acid at room temperature in a solvent such as ether, dioxane, or dichloromethane for 2-24 hours to supply compounds of formula (10-2).

Scheme 11

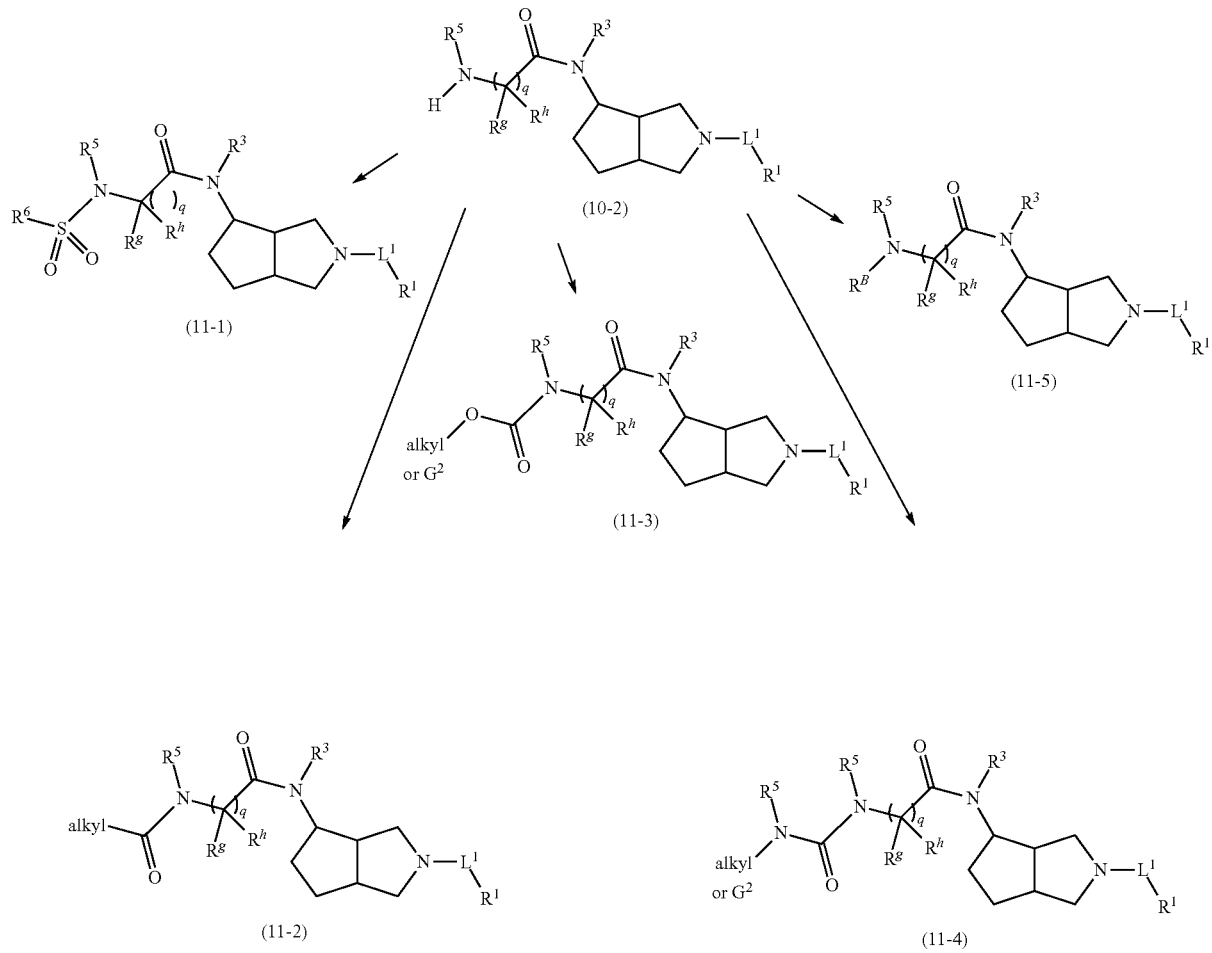

As illustrated in Scheme 11, compounds of formula (11-1), (11-2), (11-3), (11-4), and (11-5) which are representative of compounds of formula (I) and wherein $L^1$, $R^1$, $R^3$, $R^5$, $R^g$, $R^h$, q, and $G^2$ are as defined in the Summary of the Invention can be obtained from compounds of formula (10-2). Compounds of formula (10-2) can be treated with a sulfonyl chloride of formula $R^6SO_2Cl$ in dichloromethane in the presence of diisopropylethylamine at room temperature for 2-24 hours to provide compounds of formula (11-1). Similarly, compounds of formula (11-2) can be obtained upon treatment of compounds of formula (10-2) with an anhydride or acid chloride in dichloromethane at ambient temperature in the presence of diisopropylethylamine over 2-24 hours. Compounds of formula (11-3) are obtained from compounds of formula (10-2) upon treatment with a carbonochloridate in the presence of diisopropylethylamine in dichloromethane at room temperature over 2-24 hours. In like manner, compounds of formula (11-4) are made from compounds of formula (10-2) by reacting with an isocyanate in dichloromethane at room temperature over 2-24 hours. Compounds of formula (11-5), wherein $R^B$ is alkyl, arylalkyl, cycloalkyl, cycloalkylalkyl, or heteroarylalkyl can be prepared either by alkylation or reductive amination of compounds of formula (10-2) using methodology known to one skilled in the art.

Scheme 12

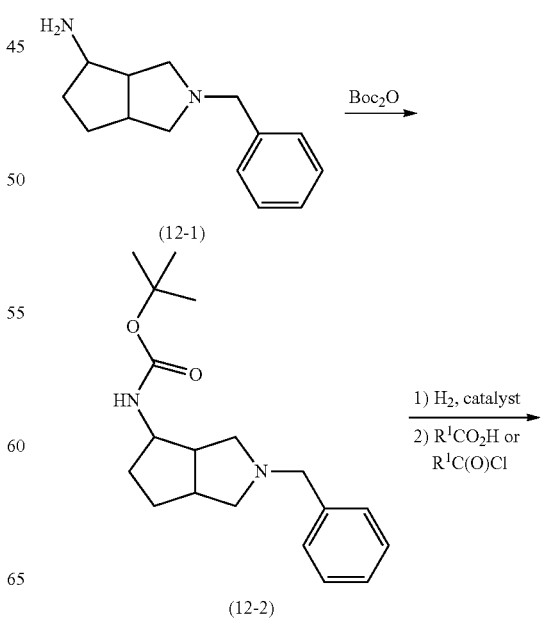

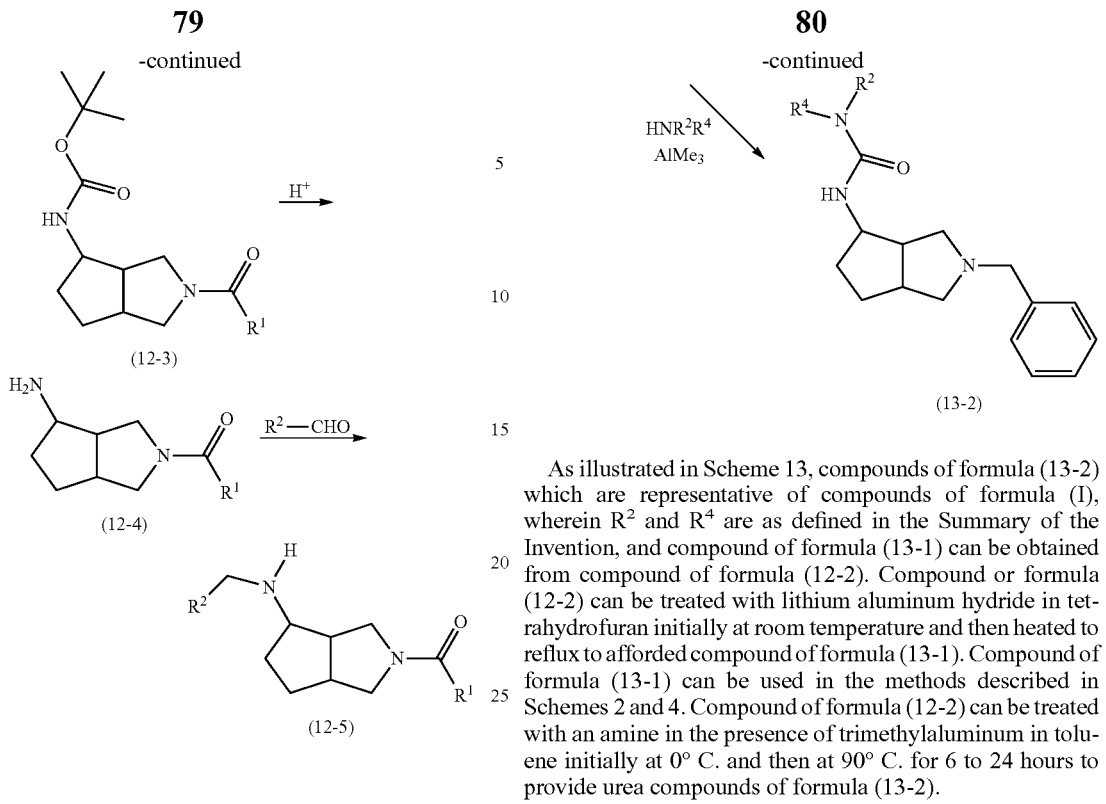

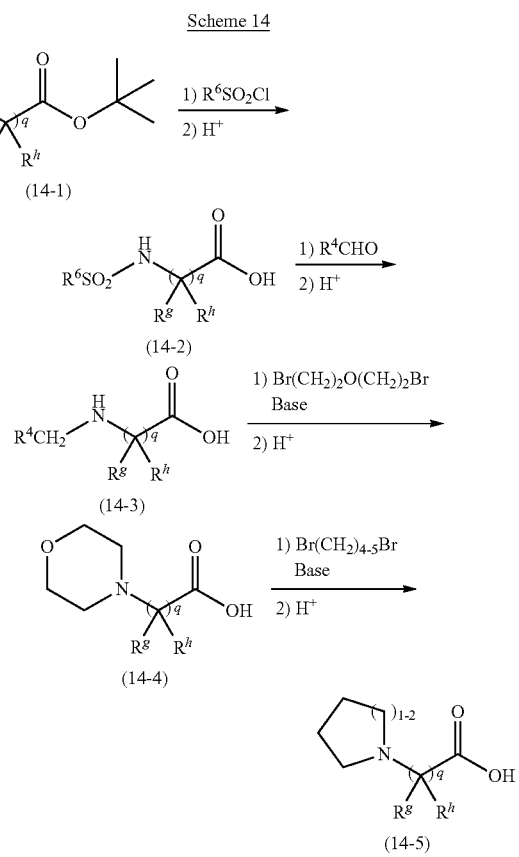

As illustrated in Scheme 13, compounds of formula (13-2) which are representative of compounds of formula (I), wherein $R^2$ and $R^4$ are as defined in the Summary of the Invention, and compound of formula (13-1) can be obtained from compound of formula (12-2). Compound or formula (12-2) can be treated with lithium aluminum hydride in tetrahydrofuran initially at room temperature and then heated to reflux to afforded compound of formula (13-1). Compound of formula (13-1) can be used in the methods described in Schemes 2 and 4. Compound of formula (12-2) can be treated with an amine in the presence of trimethylaluminum in toluene initially at 0° C. and then at 90° C. for 6 to 24 hours to provide urea compounds of formula (13-2).

As illustrated in Scheme 12, compounds of formula (12-5) which are representative of compounds of formula (I) and wherein $R^1$ and $R^2$ are as defined in the Summary of the Invention can be obtained from compound of formula (12-1). Compound (12-1) can reacted with di-tert-butyl dicarbonate in the presence of (dimethylamino)pyridine in a solvent such as dichloromethane or dioxane at room temperature for 20 minutes to 4 hours to provide compound of formula (12-2). The benzyl group of compound of formula (12-2) can be removed with hydrogen in the presence of a palladium catalyst as described in Scheme 3 and then coupled with a carboxylic acid or acid chloride as described in the methods of Scheme 3 to provide compounds of formula (12-3). Removal of the tert-butoxy carbonyl group from compounds of formula (12-3) with the acid conditions described in Scheme 10 supplies compounds of formula (12-4). Compounds of formula (12-4) can be reductively aminated with aldehydes of formula $R^2$—CHO using the conditions described in Scheme 3 to give compounds of formula (12-5).

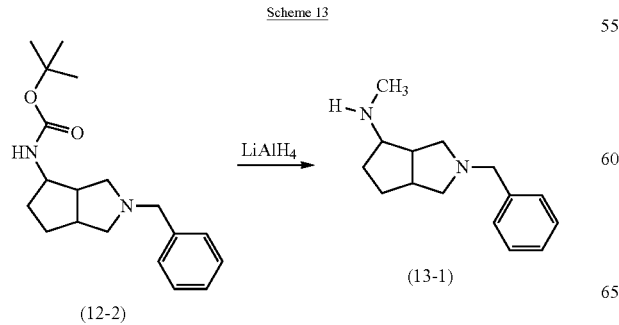

As shown in Scheme 14, compounds of formulas (14-2), (14-3), (14-4), and (14-5), wherein $R^4$, $R^6$, $R^g$, $R^h$, and q are as defined in the Summary of the Invention can be obtained from compounds of formula (14-1). Compounds of formula (14-1) can be treated with a sulfonyl chloride of formula $R^6SO_2Cl$ in the presence of a base such as triethylamine or diisopropylethylamine in a solvent such as dichloromethane. Subsequent removal of the t-butyl group under acidic conditions deliver compounds of formula (14-2). Compounds of formula (14-1) can also be reductively aminated with an aldehyde of formula $R^4CHO$ and a reductant such as sodium cyanoborohydride, polymer supported cyanoborohydride resin, or sodium triacetoxyborohydride optionally in the presence of an acid such as acetic acid in solvents such as dichloromethane or methanol. Acidic removal of the t-butyl group supplies compounds of formula (14-3). Compounds of formula (14-1) can also be dialkylated with dibromo compounds. Accordingly, alkylation of (14-1) with 1-bromo-2-(2-bromoethoxy)ethane in heated acetonitrile in the presence of a base followed by acid catalyzed t-butyl removal delivers compounds of formula (14-4). Alkylation with 1,4-dibromobutane or 1,5-dibromopentane under similar conditions followed by acid catalyzed t-butyl removal delivers compounds of formula (14-5). Compounds of formulas (14-2), (14-3), (14-4), and (14-5) can be used in Schemes 2, 3, 4 and 12.

Scheme 15

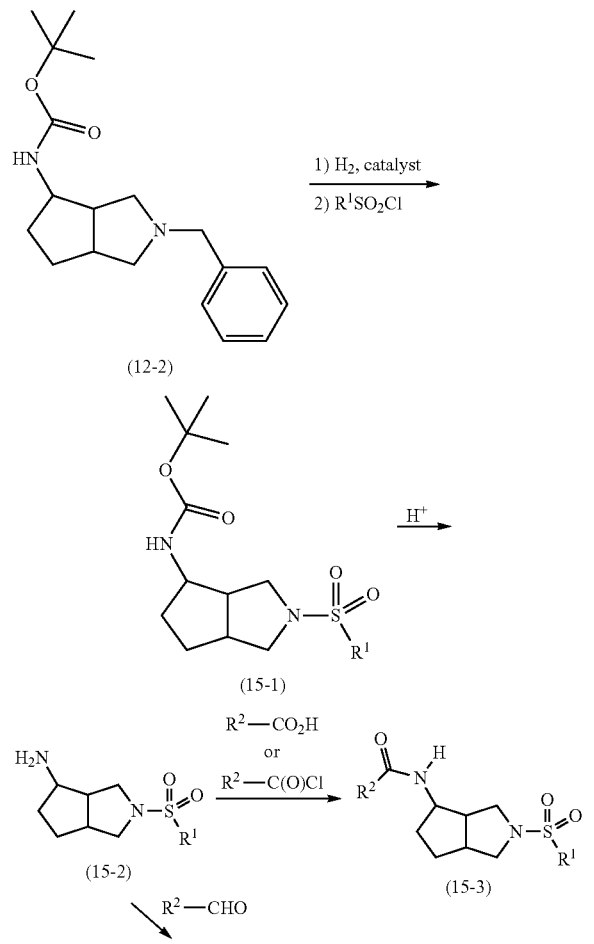

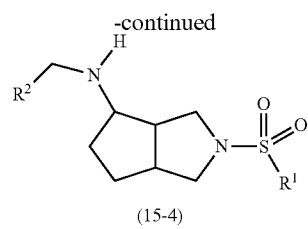

As illustrated in Scheme 15, compounds of formula (15-3) and compounds of formula (15-4) which are representative of compounds of formula (I) and wherein $R^1$ and $R^2$ are as defined in the Summary of the Invention can be obtained from compound of formula (12-2). The benzyl group of compound of formula (12-2) can be removed with hydrogen in the presence of a palladium catalyst as described in Scheme 3 and then coupled with a sulfonyl chloride of formula $R^1SO_2Cl$ as described in the methods of Scheme 3 to provide compounds of formula (15-1). Removal of the tert-butoxy carbonyl group from compounds of formula (15-1) with the acid conditions described in Scheme 10 supplies compounds of formula (15-2). Compounds of formula (15-2) can be coupled with carboxylic acids of formula $R^2$—$CO_2H$ or acid chlorides of formula $R^2$—C(O)Cl under the reaction conditions described in Scheme 2 to give compounds of formula (15-3). Compounds of (15-2) can also be converted to compounds of formula (15-4) Compounds of formula (15-2) can be reductively aminated with an aldehyde of formula $R^2$—CHO using conditions similar to those described in Scheme 3 to give compounds of formula of formula (15-4).

Scheme 16

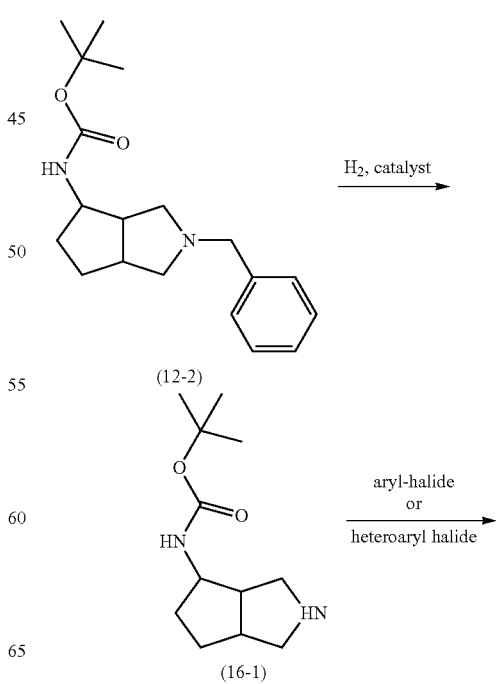

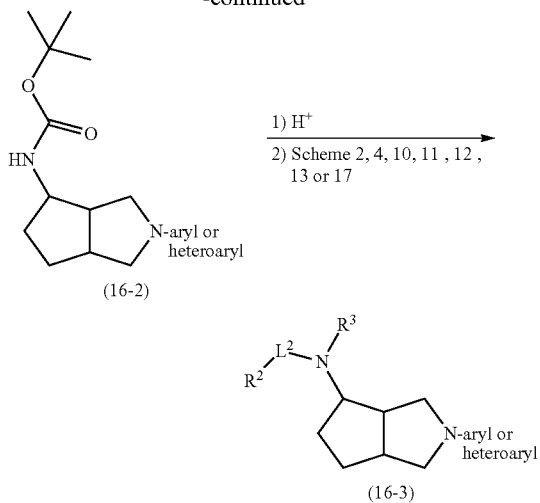

As illustrated in Scheme 16, compounds of formulas (16-3) which are representative of compounds of formula (I), wherein $L^2$, $R^1$, $R^2$ and $R^3$ are as defined in the Summary of the Invention, can be obtained from compounds of formula (12-2). Compounds of formula (12-2) can be converted to compounds of formula (16-1) by treatment with hydrogen (15-60 psi) in the presence of a catalyst such as palladium hydroxide on carbon or palladium on carbon in a solvent such as methanol or ethanol at ambient temperature over 3-36 hours. Compounds of formula (16-1) can then be reacted with an aryl halide or heteroaryl halide suitable for a nucleophilic aromatic substitution reaction to furnish compounds of formula (16-2). For example, a compound of formula (16-1) can be heated in a solvent such as ethanol in the presence of an optional base and heteroaryl bromide or heteroaryl fluoride to supply compounds of formula (16-2). Alternatively, compounds of formula (16-1) can then be reacted with an aryl halide or heteroaryl halide in a cross-coupling reaction to furnish compounds of formula (16-2). For example, a compound of formula (16-1) can be heated in a solvent such as toluene or t-amyl alcohol in the presence of a palladium catalyst, base, and suitable ligand to give compounds of formula (16-2). Compounds of formula (16-2) can then be deprotected under acidic conditions and further functionalized as described in but not limited to Schemes 2, 4, 10, 11, 12, 13 or 17 to give compounds of formula (16-3).

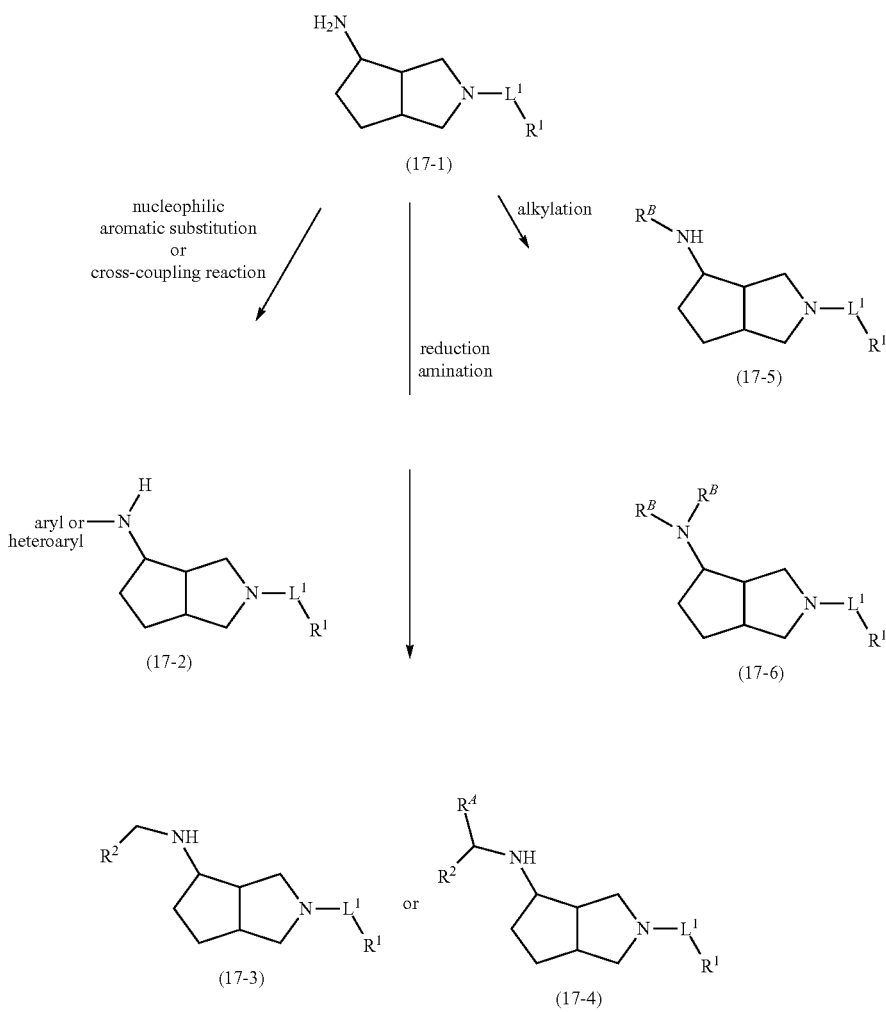

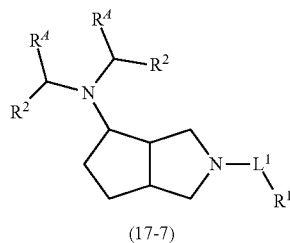

(17-7)

As illustrated in Scheme 17, compounds of formula (17-1) can be transformed into compounds of formulas (17-2), (17-3), (17-4), (17-5), and (17-6) which are representative of compounds of formula (I), wherein $L^1$, $R^1$, and $R^2$ are as defined in the Summary of the Invention. Compounds of formula (17-1) can be converted to compounds of formula (17-2) through either a nucleophilic aromatic substitution reaction under conditions described in Scheme 16 or under cross-coupling reaction conditions known to one skilled in the art. Compounds of formula (17-1) can also be reductively aminated with an aldehyde to give compounds of formula (17-3) or a ketone or ketone equivalent to give compounds of formula (17-4) and/or compounds of formula &17-7), wherein $R^A$ is alkyl, aryl, arylalkyl, cycloalkyl, cycloalkylalkyl, heteroaryl, or heteroarylalkyl. Alternatively, in compounds of formula (17-4), $R^A$ and $R^2$ together with the atom to which they are attached can be joined to form a cyclic group. Reductive amination conditions are described in but not limited to those in Schemes 3, 4, 8, 12, and 14. Compounds of formula (17-1) can be mono-alkylated to give compounds of formula (17-5) or di-alkylated to give compounds of formula (17-6). Compounds of formula (17-1) can be treated with an alkyl-, arylalkyl-, cycloalkyl-, cycloalkylalkyl-, or heteroarylalkyl-halide or sulfonate optionally in the presence of a base in an optionally heated solvent such as tetrahydrofuran or N,N-dimethylformamide to give compounds of formula (17-5), wherein $R^B$ is alkyl, arylalkyl, cycloalkyl, cycloalkylalkyl, or heteroarylalkyl. Excess alkylating agent leads to compounds of formula (17-6).

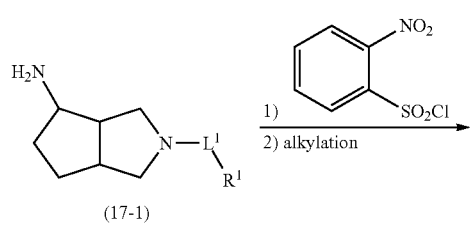

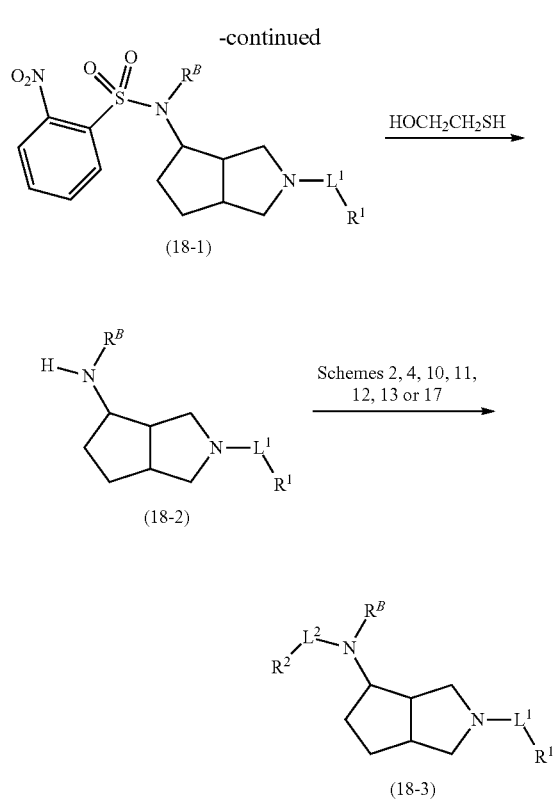

As illustrated in Scheme 18, compounds of formula (17-1) can be converted to compounds of formulas (18-1), (18-2), and (18-3) which are representative of compounds of formula (I), wherein, $L^1$, $L^2$, $R^1$, and $R^2$ are as defined in the Summary of the Invention and $R^B$ is alkyl, arylalkyl, cycloalkyl, cycloalkylalkyl, or heteroarylalkyl. Compounds of formula (17-1) can be reacted with 2-nitrobenzene-1-sulfonyl chloride in the presence of a base. The resultant sulfonamide can then be alkylated under conditions known to one skilled in the art to give compounds of formula (18-1). Treatment with 2-mercaptoethanol in the presence of a base in a solvent such as N,N-dimethylformamide gives compounds of formula (18-2). Compounds of formula (18-2) can be reacted as described in Schemes 2, 4, 10, 11, 12, 13, or 17 to give compounds of formula (18-3).

Scheme 19

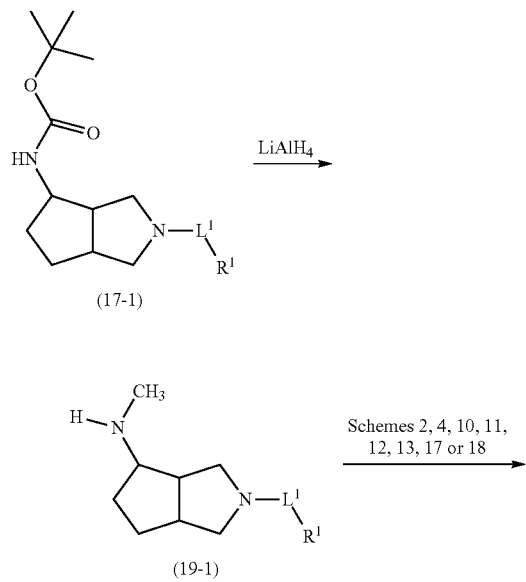

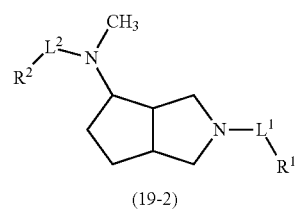

As illustrated in Scheme 19, compounds of formula (19-2) which are representative of compounds of formula (I), wherein $L^1$, $L^2$, $R^1$ and $R^2$ are as defined in the Summary of the Invention, can be obtained from compound of formula (17-1). Compound or formula (17-1) can be treated with lithium aluminum hydride in tetrahydrofuran initially at room temperature and then heated to reflux to afforded compound of formula (19-1). Compound of formula (19-1) can be used in the methods described in Schemes 2, 4, 10, 11, 12, 13, 17 or 18 to give compounds of formula (19-2).

Scheme 20

As illustrated in Scheme 20, compounds of formula (20-3), (20-4), (20-5), (20-6) and (20-7) which are representative of compounds of formula (I) and wherein $L^2$, $R^2$, $R^3$, $R^4$, $R^5$, $R^6$, $R^e$, $R^f$, and n are as defined in the Summary of the Invention can be obtained from compounds of formula (20-2). Compounds of formula (20-2) are obtained from compounds of formula (20-1) upon treatment with an acid such as trifluoroacetic acid in dichloromethane or hydrochloric acid in dioxane. Compounds of formula (20-2) can be treated with a sulfonyl chloride of formula $R^6SO_2Cl$ in dichloromethane in the presence of diisopropylethylamine at room temperature for 2-24 hours to provide compounds of formula (20-3). Similarly, compounds of formula (20-4) can be obtained upon treatment of compounds of formula (20-2) with an anhydride or acid chloride in dichloromethane at ambient temperature in the presence of diisopropylethylamine over 2-24 hours. Compounds of formula (20-5) are obtained from compounds of formula (20-2) upon treatment with a carbonochloridate in the presence of diisopropylethylamine in dichloromethane at room temperature over 2-24 hours. In like manner, compounds of formula (20-6) are made from compounds of formula (20-2) by reacting with an isocyanate in dichloromethane at room temperature over 2-24 hours. Compounds of formula (20-7), wherein $R^B$ is alkyl, arylalkyl, cycloalkyl, cycloalkylalkyl, or heteroarylalkyl can be prepared either by alkylation or reductive amination of compounds of formula (20-2) using methodology known to one skilled in the art.

Scheme 21

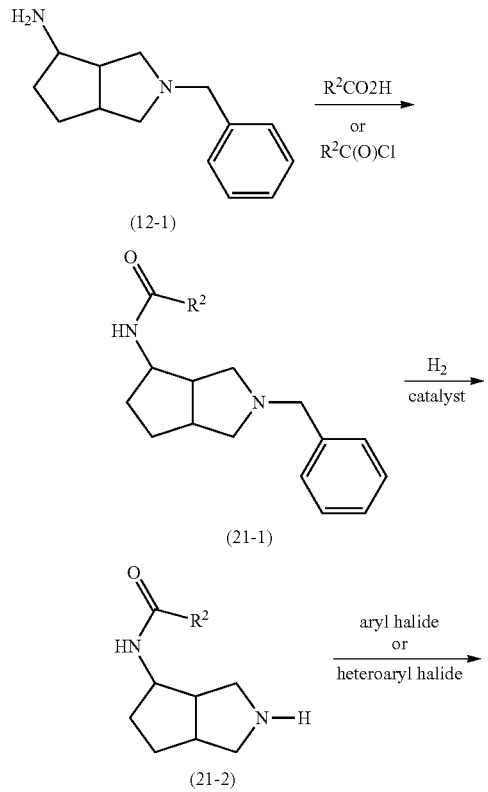

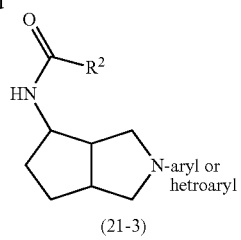

As illustrated in Scheme 21, compounds of formula (21-3) which are representative of compounds of formula (I) and wherein $R^2$ is as defined in the Summary of the Invention can be obtained from compounds of formula (12-1). Compounds of formula (12-1) can be coupled with compounds of formula $R^2CO_2H$ or $R^2C(O)Cl$ using the conditions described in Scheme 2 to give compounds of formula (21-1). The benzyl protecting group can then be removed reductively under a hydrogen environment in the presence of a palladium catalyst to give compounds of formula (21-2). Compounds of formula (21-2) are converted to compounds of formula (21-3) either under nucleophilic aromatic substitution reaction conditions or cross-coupling reaction conditions as described in Scheme 16 to give compounds of formula (21-3).

Scheme 22

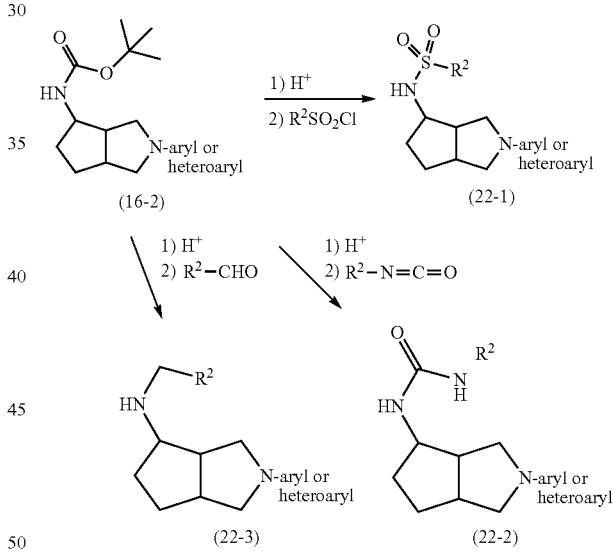

As illustrated in Scheme 22, compounds of formula (22-1), (22-2), and (22-3) which are representative of compounds of formula (I) and wherein $R^2$ is as defined in the Summary of the Invention can be obtained from compounds of formula (16-2). Compounds of formula (16-2) can be deprotected under acidic conditions and then sulfonylated with $R^2SO_2Cl$ under conditions similar to those described in Scheme 3 to give compounds of formula (22-1). Compounds of formula (16-2) can be deprotected under acidic conditions and reacted with an isocyanate of formula $R^2$—N=C=O to give compounds of formula (22-2). Compounds of formula (16-2) can also be deprotected under acidic conditions and then reductively aminated with aldehydes of formula $R^2$—CHO under conditions similar to those described in Scheme 3 to give compounds of formula (22-3).

Scheme 23

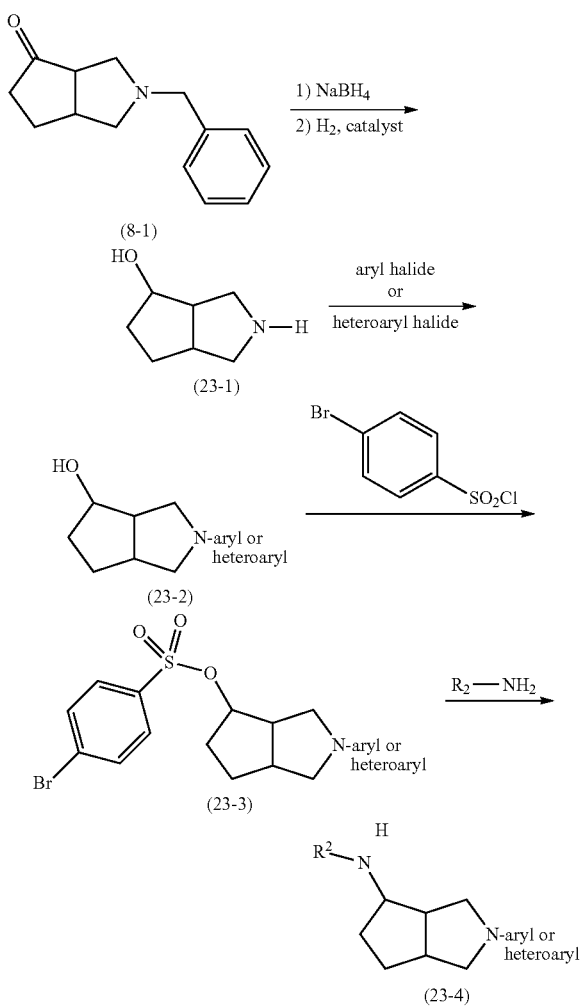

As illustrated in Scheme 23, compounds of formula (23-4) which are representative of compounds of formula (I) and wherein $R^2$ is as defined in the Summary of the Invention can be obtained from a compound of formula (8-1). A compound of formula (8-1) can be prepared as described in Santora, V. J. et. al. Bioorganic & Medicinal Chemistry Letters (2008), 18, 1490-1494. The ketone of a compound of formula (8-1) can be reduced with a reagent such as sodium borohydride. The benzyl group can be subsequently removed by catalytic hydrogenation to give a compound of formula (23-1). A compound or formula (23-1) can then be reacted with an aryl halide or heteroaryl halide under conditions described in Scheme 16 to convert compounds of formula (16-1) to compounds of formula (16-2) to give compounds of formula (23-2). Compounds of formula (23-2) can then be reacted with 4-bromobenzene-1-sulfonyl chloride and 1-methylimidazole in the presence of a base such as triethylamine in a solvent such as dichloromethane to give sulfonates of formula (23-3). Other sulfonates may be similarly prepared and used in the next step. Compounds of formula (23-3) can be reacted with an amine of formula $R^2$—$NH_2$ in an optionally heated solvent such as but not limited to acetonitrile to give compounds of formula (23-4).

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that can not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts, Protective Groups in Organic Synthesis ($3^{rd}$ ed.), John Wiley & Sons, NY (1999), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

g. Examples

Example 1 and Example 2

N-[(3aS*,4S*,6aR*)-2-benzyloctahydrocyclopenta [c]pyrrol-4-yl]-1-phenylcyclopentanecarboxamide (Example 1) and N-[(3aS*,4R*,6aR*)-2-benzyloctahydrocyclopenta [c]pyrrol-4-yl]-1-phenylcyclopentanecarboxamide (Example 2)

1-Hydroxybenzotriazole (33 mg, 0.24 mmol) and N-(3-dimethylaminopropyl)-N'-ethylcarbodiimide (43 µL, 0.24 mmol) were added to a solution of 1-phenylcyclopentanecarboxylic acid (46 mg, 0.24 mmol) in dichloromethane (2 mL). The reaction was stirred at room temperature for 10 minutes, then (3aS*,6aR*)-2-benzyloctahydrocyclopenta[c]pyrrol-4-amine (52 mg, 0.24 mmol) was added and the reaction stirred at room temperature overnight. The reaction mixture was quenched with water, and extracted with dichloromethane, then purified by silica gel chromatography using 1-10% methanol (2 N ammonia)/chloroform as eluent to give the title compounds.

Example 1: $^1$H NMR (500 MHz, pyridine-$d_5$) δ ppm 7.52-7.28 (m, 9H), 7.25 (d, J=7.7, 1H), 4.43-4.34 (m, 1H), 3.56 (d, J=12.9, 1H), 3.17 (d, J=12.9, 1H), 2.83-2.67 (m, 2H), 2.59-2.50 (m, 1H), 2.50-2.44 (m, 1H), 2.35-2.29 (m, 2H), 2.04-1.87 (m, 4H), 1.84-1.54 (m, 6H), 1.43-1.26 (m, 1H), 1.04-0.94 (m, 1H); MS (ESI+) m/z 389 (M+H)$^+$.

Example 2: $^1$H NMR (500 MHz, pyridine-$d_5$) δ ppm 7.52-7.47 (m, 2H), 7.41 (d, J=7.4, 2H), 7.38-7.29 (m, 4H), 7.25 (q, J=7.3, 2H), 4.36 (m, 1H), 3.57 (d, J=13.2, 1H), 3.40 (d, J=13.2, 1H), 2.78 (m, 3H), 2.33 (m, 3H), 2.27 (d, J=8.7, 1H), 2.21-2.13 (m, 1H), 1.99 (dt, J=5.8, 11.7, 3H), 1.87-1.75 (m, 2H), 1.71-1.60 (m, 3H), 1.44 (ddd, J=7.7, 12.1, 14.5, 1H), 1.31 (m, 1H); MS (ESI+) m/z 389 (M+H)$^+$.

Example 3 and Example 4

N-[(3aR*,4R*,6aS*)-2-benzyloctahydrocyclopenta[c]pyrrol-4-yl]-2-cyclohexyl-2-phenylacetamide (Example 3) and N-[(3aS*,4R*,6aR*)-2-benzyloctahydrocyclopenta[c]pyrrol-4-yl]-2-cyclohexyl-2-phenylacetamide (Example 4)

The title compounds were prepared by substituting 2-cyclohexyl-2-phenylacetic acid for 1-phenylcyclopentanecarboxylic acid in the procedure that describes the preparation of Examples 1 and 2.

Example 3: $^1$H NMR (500 MHz, pyridine-$d_5$) δ ppm 8.10 (s, 1H), 7.67 (d, J=7.2, 1H), 7.44 (dd, J=5.7, 12.3, 3H), 7.40-7.35 (m, 3H), 7.33 (t, J=7.4, 1H), 7.27 (dd, J=7.6, 16.2, 1H), 4.43-4.37 (m, 0.5H), 4.36-4.29 (m, 0.5H), 3.56 (d, J=12.6, 0.5H), 3.42 (t, J=11.7, 1H), 3.26 (dd, J=6.6, 11.7, 1H), 3.14 (d, J=10.5, 0.5H), 2.80 (d, J=8.3, 1H), 2.63 (d, J=6.9, 0.5H), 2.24-2.13 (m, 1.5H), 2.02 (d, J=12.5, 0.5H), 1.91 (d, J=7.0, 1H), 1.74-1.59 (m, 2.5H), 1.58-1.34 (m, 4H), 1.33-1.19 (m, 1.5H), 1.18-0.99 (m, 3H), 0.87 (d, J=14.3, 0.5H), 0.81-0.68 (m, 1H); MS (ESI+) m/z 417 (M+H)$^+$.

Example 4: $^1$H NMR (500 MHz, pyridine-$d_5$) δ ppm 8.65-8.56 (m, 1H), 7.66 (dd, J=3.1, 7.3, 2H), 7.43 (d, J=7.4, 1H), 7.39-7.30 (m, 5H), 7.27 (dd, J=5.0, 7.6, 2H), 4.35 (s, 1H), 3.59 (d, J=13.1, 0.5H), 3.52 (d, J=13.2, 0.5H), 3.44 (d, J=13.1, 0.5H), 3.33 (dd, J=8.2, 11.7, 1.5H), 2.89 (dd, J=3.1, 9.1, 0.5H), 2.63-2.54 (m, 1H), 2.53-2.45 (m, 1H), 2.36 (m, 2H), 2.28 (t, J=8.0, 1H), 2.22 (t, J=7.0, 2H), 2.16 (dd, J=6.0, 12.2, 1H), 1.92 (dd, J=6.1, 12.2, 0.5H), 1.84 (dd, J=7.5, 12.6, 0.5H), 1.71 (d, J=6.2, 12.8, 2H), 1.44 (dd, J=20.6, 55.0, 4H), 1.29 (m, 1.5H), 1.18 (m, 1H), 1.06 (m, 2H), 0.70 (m, 1H); MS (ESI+) m/z 389 (M+H)$^+$.

Example 5 and Example 6

N-[(3aR*,4R*,6aS*)-2-benzyloctahydrocyclopenta[c]pyrrol-4-yl]-3-methyl-2-phenylbutanamide (Example 5) and N-[(3aR*,4S*,6aS*)-2-benzyloctahydrocyclopenta[c]pyrrol-4-yl]-3-methyl-2-phenylbutanamide (Example 6)

The title compounds were prepared by substituting 3-methyl-2-phenylbutanoic acid for 1-phenylcyclopentanecarboxylic acid in the procedure that describes the preparation of Examples 1 and 2.

Example 5: $^1$H NMR (500 MHz, pyridine-$d_5$) δ ppm 8.13-8.03 (m, 1H), 7.65 (d, J=7.2, 1H), 7.55 (d, J=7.3, 1H), 7.44 (d, J=4.3, 2H), 7.41 (d, J=7.0, 1H), 7.36 (t, J=6.9, 3H), 7.28 (ddd, J=7.3, 14.7, 17.5, 2H), 4.40 (dd, J=6.7, 13.3, 0.5H), 4.35-4.27 (m, 0.5H), 3.55 (d, J=12.7, 0.5H), 3.40 (dd, J=4.5, 12.8, 1H), 3.26 (d, J=12.9, 0.5H), 3.16 (d, J=10.5, 0.5H), 3.05 (d, J=10.5, 0.5H), 2.78 (dd, J=8.1, 15.8, 1H), 2.69-2.54 (m, 1.5H), 2.43-2.26 (m, 3H), 2.23-2.13 (m, 1H), 1.94-1.82 (m, 1H), 1.73-1.57 (m, 1.5H), 1.50 (dt, J=7.1, 15.0, 0.5H), 1.38 (td, J=6.4, 12.2, 0.5H), 1.27 (m, 0.5H), 1.19 (d, J=6.4, 1.5H), 1.11 (dd, J=5.7, 12.0, 0.5H), 1.03 (d, J=13.2, 0.5H), 1.45 (d, J=6.5, 1.5H), 0.73 (dd, J=6.7, 10.7, 3H); MS (ESI+) m/z 377 (M+H)$^+$.

Example 6: $^1$H NMR (500 MHz, pyridine-$d_5$) δ ppm 8.56 (d, J=12.9, 1H), 7.67-7.61 (m, 2H), 7.43 (d, J=7.1, 1H), 7.39-7.31 (m, 5H), 7.29-7.24 (m, 2H), 4.40-4.28 (m, 1H), 3.60 (d, J=13.1, 0.5H), 3.52 (d, J=13.1, 0.5H), 3.44 (d, J=13.2, 0.5H), 3.33 (d, J=13.2, 0.5H), 3.22 (d, J=10.4, 1H), 2.89 (dd, J=3.0, 9.1, 0.5H), 2.64 (m, 1H), 2.55 (m, 1H), 2.51-2.44 (m, 1H), 2.36 (s, 1H), 2.28 (t, J=8.3, 1H), 2.24-2.10 (m, 2H), 1.95-1.87 (m, 0.5H), 1.81 (d, J=8.1, 0.5H), 1.77-1.62 (m, 1H), 1.36 (m, 1.5H), 1.20 (dt, J=5.3, 10.6, 3H), 0.70 (dd, J=1.6, 6.7, 3H); MS (ESI+) m/z 377 (M+H)$^+$.

Example 7 and Example 8

N-[(3aS*,4S*,6aR*)-2-benzyloctahydrocyclopenta[c]pyrrol-4-yl]-2-cyclopentyl-2-phenylacetamide (Example 7) and N-[(3aS*,4R*,6aR*)-2-benzyloctahydrocyclopenta[c]pyrrol-4-yl]-2-cyclopentyl-2-phenylacetamide (Example 8)

The title compounds were prepared by substituting 2-cyclopentyl-2-phenylacetic acid for 1-phenylcyclopentanecarboxylic acid in the procedure that describes the preparation of Examples 1 and 2.

Example 7: $^1$H NMR (500 MHz, pyridine-$d_5$) δ ppm 8.06 (dd, J=6.8, 23.5, 1H), 7.67 (d, J=7.2, 1H), 7.46-7.39 (m, 3H), 7.40-7.29 (m, 4H), 7.29-7.22 (m, 1H), 4.45-4.37 (m, 0.5H), 4.35-4.27 (m, 0.5H), 3.54 (d, J=12.7, 0.5H), 3.42 (dd, J=4.0, 12.8, 1H), 3.34-3.19 (m, 1.5H), 2.97-2.77 (m, 2.5H), 2.63 (d, J=7.2, 0.5H), 2.46-2.27 (m, 3H), 2.26-2.05 (m, 1.5H), 2.03-1.84 (m, 1.5H), 1.71 (dt, J=7.0, 14.1, 0.5H), 1.65-1.36 (m, 8H), 1.33-1.22 (m, 0.5H), 1.20-0.98 (m, 2H); MS (ESI+) m/z 403 (M+H)$^+$.

Example 8: $^1$H NMR (500 MHz, pyridine-$d_5$) δ ppm 8.60-8.49 (m, 1H), 7.67 (dd, J=2.3, 7.6, 2H), 7.44 (d, J=7.2, 1H), 7.36 (dt, J=5.0, 7.6, 5H), 7.26 (t, J=6.9, 2H), 4.36 (m, 1H), 3.61 (d, J=13.1, 0.5H), 3.52 (d, J=13.1, 0.5H), 3.45 (d, J=13.2, 0.5H), 3.36 (d, J=12.0, 16.0, 1.5H), 2.95-2.83 (m, 1.5H), 2.63-2.55 (m, 1H), 2.53-2.46 (m, 1H), 2.38 (s, 1H), 2.29 (dd, J=7.0, 12.8, 1.5H), 2.22 (dd, J=6.1, 12.3, 1H), 2.18-2.504 (m, 1.5H), 1.94 (dd, J=6.1, 12.2, 0.5H), 1.84 (dd, J=7.5, 12.7, 0.5H), 1.79-1.66 (m, 1H), 1.65-1.24 (m, 8.5H), 1.09-0.92 (m, 1H); MS (ESI+) m/z 403 (M+H)+.

Example 9 and Example 10

N-[(3aS*,4S*,6aR*)-2-benzyloctahydrocyclopenta[c]pyrrol-4-yl]-1-phenylcyclohexanecarboxamide (Example 9) and N-[(3aS*,4R*,6aR*)-2-benzyloctahydrocyclopenta[c]pyrrol-4-yl]-1-phenylcyclohexanecarboxamide (Example 10)

The title compounds were prepared by substituting 1-phenylcyclohexanecarboxylic acid for 1-phenylcyclopentanecarboxylic acid in the procedure that describes the preparation of Examples 1 and 2.

Example 9: $^1$H NMR (500 MHz, pyridine-$d_5$) δ ppm 7.57-7.54 (m, 2H), 7.45 (t, J=7.3, 2H), 7.37 (dd, J=7.6, 15.3, 5H), 7.29 (d, J=6.9, 1H), 7.25 (t, J=7.3, 1H), 4.41 (m, 1H), 3.59 (d, J=12.9, 1H), 3.18 (d, J=12.9, 1H), 2.52 (dd, J=8.9, 17.6, 4H), 2.34 (dd, J=8.5, 15.2, 2H), 2.01-1.92 (m, 2H), 1.91-1.80 (m, 2H), 1.79-1.68 (m, 3H), 1.61 (d, J=25.2, 4H), 1.43-1.33 (m, 1H), 1.27 (d, J=8.7, 1H), 1.04-0.93 (m, 1H); MS (ESI+) m/z 403 (M+H)+.

Example 10: $^1$H NMR (400 MHz, pyridine-$d_5$) δ ppm 7.60 (s, 1H), 7.42 (d, J=7.2, 2H), 7.36 (t, J=6.7, 4H), 7.27 (d, J=7.5, 2H), 4.42 (m, 1H), 3.58 (d, J=13.2, 1H), 3.40 (d, J=13.1, 1H), 2.81 (d, J=8.1, 1H), 2.68 (m, 2H), 1.41-2.24 (m, 4H), 2.18 (m, 1H), 2.00 (m, 1H), 1.80 (m, 4H), 1.73-1.54 (m, 4H), 1.52-1.39 (m, 1H), 1.36-1.18 (m, 2H); MS (ESI+) m/z 403 (M+H)+.

Example 11

N-[(3aS*,4S*,6aR*)-2-benzyloctahydrocyclopenta[c]pyrrol-4-yl]-2,2-dicyclohexylacetamide (3aS*,6aR*)-2-Benzyloctahydrocyclopenta[c]pyrrol-4-amine (500 mg, 2.311 mmol), 2,2-dicyclohexylacetic acid (570 mg, 2.54 mmol), and 1-hydroxybenzotriazole (389 mg, 2.54 mmol) were combined in dichloromethane (20 mL). The reaction was stirred at room temperature for 10 minutes, then N-(3-dimethylaminopropyl)-N-ethylcarbodiimide (0.449 mL, 2.54 mmol) was added dropwise. The reaction was stirred at room temperature for 20 hours, and then the reaction was quenched with 10 mL of water. The reaction mixture was extracted with 2×20 mL of dichloromethane, the solvent was removed in vacuo, and the crude material was chromatographed over a silica gel cartridge (Analogix®, Burlington, Wis., RS-40) eluting with 30-50% ethyl acetate/hexanes to give the title compound as the first eluting diastereomer: $^1$H NMR (500 MHz, pyridine-$d_5$) δ ppm 7.60 (d, J=5.1, 1H), 7.45-7.38 (m, 4H), 7.35 (m, 1H), 4.49-4.41 (m, 1H), 3.57 (d, J=12.6, 1H), 3.37 (d, J=12.5, 1H), 2.76 (d, J=9.6, 1H), 2.69 (dd, J=7.9, 15.7, 1H), 2.50 (d, J=9.1, 1H), 2.48-2.41 (m, 2H), 2.28 (t, J=8.2, 1H), 2.15-2.08 (m, 1H), 1.99-1.06 (m, 26H), 1.04-0.92 (m, 1H); MS (ESI+) m/z 423 (M+H)+.

Example 12 and Example 13

(2S)-2-(3-benzoylphenyl)-N-[(3aS*,4S*,6aR*)-2-benzyloctahydrocyclopenta[c]pyrrol-4-yl]propanamide (Example 12) and (2S)-2-(3-benzoylphenyl)-N-[(3aS*,4R*,6aR*)-2-benzyloctahydrocyclopenta[c]pyrrol-4-yl]propanamide (Example 13)

The title compounds were prepared by substituting (S)-2-(3-benzoylphenyl)propanoic acid for 1-phenylcyclopentanecarboxylic acid in the procedure that describes the preparation of Examples 1 and 2.

Example 12: $^1$H NMR (400 MHz, pyridine-$d_5$) δ ppm 8.28 (d, J=6.9, 0.5H), 8.21 (d, J=7.1, 0.5H), 8.13 (d, J=15.9, 1H), 7.92-7.82 (m, 2H), 7.75 (t, J=9.1, 2H), 7.56-7.52 (m, 1H), 7.50-7.25 (m, 8H), 4.49-4.32 (m, 1H), 3.90 (q, J=7.1, 0.5H), 3.81 (t, J=7.0, 0.5H), 3.45 (q, J=12.8, 1.5H), 3.25 (d, J=13.0, 0.5H), 2.75 (d, J=9.2, 1.5H), 2.49 (dd, J=2.9, 9.5, 0.5H), 2.44-2.31 (m, 1.5H), 2.24 (dt, J=7.7, 16.5, 1.5H), 2.14 (d, J=9.6, 0.5H), 2.09-2.01 (m, 0.5H), 1.90-1.71 (m, 1H), 1.66-1.44 (m, 5H), 1.20 (dd, J=5.4, 28.1, 1H); MS (ESI+) m/z 453 (M+H)+.

Example 13: $^1$H NMR (500 MHz, pyridine-$d_5$) δ ppm 8.67 (d, J=7.1, 1H), 8.10 (s, 1H), 7.91-7.86 (m, 2H), 7.83 (d, J=7.7, 1H), 7.74 (d, J=7.6, 1H), 7.56-7.51 (m, 1H), 7.47-7.32 (m, 7H), 7.30-7.24 (m, 1H), 4.47-4.29 (m, 1H), 3.93 (q, J=6.9, 1H), 3.56 (t, J=12.3, 1H), 3.44 (d, J=13.1, 0.5H), 3.37 (d, J=13.1, 0.5H), 2.81 (dd, J=3.0, 9.1, 0.5H), 2.72 (d, J=7.0, 0.5H), 2.53 (m, 0.5H), 2.49-2.39 (m, 2H), 2.37-2.32 (m, 0.5H), 2.31-2.18 (m, 2H), 2.12 (dd, J=6.0, 12.1, 0.5H), 2.03 (dd, J=6.0, 12.2, 0.5H), 1.86-1.71 (m, 1H), 1.63 (t, J=9.9, 3H), 1.57-1.47 (m, 1H), 1.40-1.27 (m, 1H); MS (ESI+) m/z 453 (M+H)+.

Example 14

N-[(3aS,4S,6aR)-2-benzyloctahydrocyclopenta[c]pyrrol-4-yl]-3-methyl-2-phenylbutanamide Step A: 2-Benzylhexahydrocyclopenta[c]pyrrol-4(5H)-one (16.28 g, 76 mmol), titanium tetraethoxide (28.5 mL, 137 mmol), and (S)-2-methylpropane-2-sulfinamide (10.452 g, 86 mmol) were combined in tetrahydrofuran (200 mL). The reaction was heated at 60° C. overnight. The reaction was then reduced in volume to about half and poured into 150 mL of saturated aqueous ammonium chloride. The precipitate was collected by filtration and washed with ethyl acetate. The filtrate was poured into a separatory funnel and the organic layer was removed. The aqueous layer was extracted with ethyl acetate (3×100 mL). The organic washes were combined and washed with brine, dried ($Na_2SO_4$) and concentrated. The crude material was chromatographed using silica gel cartridge (Analogix®, Burlington, Wis., RS65-400) eluting with 5-100% ethyl acetate/hexanes to give (S,E)-N-((3aR,6aS)-2-benzylhexahydrocyclopenta[c]pyrrol-4(5H)-ylidene)-2-methylpropane-2-sulfinamide and (S,E)-N-((3aS,6aR)-2-benzylhexahydrocyclopenta[c]pyrrol-4(5H)-ylidene)-2-methylpropane-2-sulfinamide.

Step B: A mixture of (S,E)-N-((3aS,6aR)-2-benzylhexahydrocyclopenta[c]pyrrol-4(5H)-ylidene)-2-methylpropane-2-sulfinamide (0.940 g, 2.95 mmol) from Step A in methanol (20 mL) was cooled to −78° C. in a dry ice/acetone bath. Sodium borohydride (0.335 g, 8.85 mmol) was added, and the reaction was allowed to warm to room temperature overnight. The reaction was quenched with saturated aqueous ammonium chloride, and the mixture was diluted with water, and extracted with 3×100 mL of ethyl acetate. The extracts were dried (Na$_2$SO$_4$) and filtered. The solvent was removed in vacuo, and the crude material was chromatographed using a silica gel cartridge (Analogix®, Burlington, Wis., RS-40) with 5-50% acetone/hexanes to give (S)-N-((3aS,4S,6aR)-2-benzyloctahydrocyclopenta[c]pyrrol-4-yl)-2-methylpropane-2-sulfinamide: $^1$H NMR (300 MHz, CDCl$_3$) δ ppm 7.37-7.11 (m, 5H), 4.85 (d, J=7.0, 1H), 3.90-3.71 (m, 2H), 3.28 (d, J=13.0, 1H), 3.09 (d, J=9.8, 1H), 2.72-2.50 (m, 2H), 2.46 (d, J=9.6, 1H), 2.32-2.12 (m, 2H), 1.82 (td, J=5.5, 12.7, 1H), 1.68-1.60 (m, J=10.6, 2H), 1.35-1.24 (m, 1H), 1.20 (s, J=5.5, 9H).

Step C: (S)-N-((3aS,4S,6aR)-2-Benzyloctahydrocyclopenta[c]pyrrol-4-yl)-2-methylpropane-2-sulfinamide (855 mg, 2.67 mmol) from Step B and 2 N HCl (10 mL, 40.0 mmol) were combined in methanol (10 mL). After 30 minutes, the solvent was removed and the crude material was purified on a silica gel cartridge (Analogix®, Burlington, Wis., RS-25) loading with 10% methanol (2 N ammonia)/dichloromethane solution and eluting with 2-10% methanol (2 N ammonia)/dichloromethane to give (3aS,4S,6aR)-2-benzyloctahydrocyclopenta[c]pyrrol-4-amine: $^1$H NMR (500 MHz, pyridine-d$_5$) δ ppm 7.44 (d, J=7.4, 2H), 7.36 (t, J=7.5, 2H), 7.28 (t, J=7.3, 1H), 3.52 (q, J=13.0, 2H), 3.29 (q, J=7.3, 1H), 2.84 (dd, J=3.7, 9.3, 1H), 2.55-2.43 (m, 3H), 2.37-2.30 (m, 1H), 2.24 (d, J=5.3, 1H), 1.74-1.64 (m, 2H), 1.62-1.53 (m, 1H), 1.34 (dd, J=5.0, 10.1, 1H).

Step D: 3-Methyl-2-phenylbutanoic acid (1.049 mmol), 1-hydroxybenzotriazole hydrate (1.049 mmol), and N-(3-dimethylaminopropyl)-N'-ethylcarbodiimide (185 μL, 1.049 mmol) were combined in dichloromethane (4 mL). The mixture was stirred at room temperature for 10 minutes, then (3aS,4S,6aR)-2-benzyloctahydrocyclopenta[c]pyrrol-4-amine (1.049 mmol) from Step C was added in 2 mL of dichloromethane. The reaction was stirred at room temperature for 3.5 hours, and then quenched with 0.5 mL of water. The organic layer was separated and chromatographed using a silica gel cartridge (Analogix®, Burlington, Wis., RS-12) eluting with 1-10% methanol(ammonia)/dichloromethane to give the title compound: $^1$H NMR (500 MHz, pyridine-d$_5$) δ ppm 8.08 (dd, J=7.2, 14.4, 1H), 7.64 (dd, J=7.5, 14.5, 1H), 7.56-7.52 (m, 1H), 7.43 (d, J=4.4, 2H), 7.42-7.40 (m, 1H), 7.38-7.22 (m, 5H), 4.40 (dt, J=7.2, 14.3, 0.5H), 4.35-4.28 (m, 0.5H), 3.55 (d, J=12.7, 0.5H), 3.40 (dd, J=4.5, 12.8, 1H), 3.26 (d, J=12.9, 0.5H), 3.15 (d, J=10.5, 0.5H), 3.05 (d, J=10.5, 0.5H), 2.83-2.74 (m, 1H), 2.70-2.55 (m, 1.5H), 2.43-2.26 (m, 3H), 2.23-2.13 (m, 1H), 1.94-1.83 (m, 1H), 1.74-1.57 (m, 1.5H), 1.50 (dt, J=7.1, 15.3, 0.5H), 1.37 (td, J=6.5, 12.1, 0.5H), 1.31-1.23 (m, 0.5H), 1.18 (d, J=6.5, 1.5H), 1.10 (dt, J=6.5, 11.5, 0.5H), 1.03 (d, J=6.5, 1.5H), 0.73 (dd, J=6.7, 10.7, 3H); MS (ESI+) m/z 377 (M+H)$^+$.

Example 15

N-[(3aS,4S,6aR)-2-benzyloctahydrocyclopenta[c]pyrrol-4-yl]-2,2-dicyclohexylacetamide The title compound was prepared by substituting 2,2-dicyclohexylacetic acid for 3-methyl-2-phenylbutanoic acid in the procedure used to prepare Example 14: $^1$H NMR (500 MHz, pyridine-d$_5$) δ ppm 7.44-7.38 (m, 4H), 7.37-7.32 (m, 1H), 4.49-4.38 (m, 1H), 3.57 (d, J=12.6, 1H), 3.37 (d, J=12.5, 1H), 2.77 (dd, J=1.7, 9.6, 1H), 2.68 (td, J=2.0, 9.3, 1H), 2.51 (dd, J=1.9, 9.0, 1H), 2.45 (dd, J=7.1, 15.9, 1H), 2.30-2.25 (m, 1H), 2.11 (dd, J=7.1, 9.6, 1H), 1.98-1.83 (m, 3H), 1.83-1.58 (m, 12H), 1.57-1.51 (m, 1H), 1.48 (d, J=13.0, 1H), 1.44-1.37 (m, 1H), 1.36-1.09 (m, 9H), 1.04-0.94 (m, 1H); MS (ESI+) m/z 423 (M+H)$^+$.

Example 16

(2S)-N-[(3aS,4R,6aR)-2-benzyloctahydrocyclopenta[c]pyrrol-4-yl]-2-phenylbutanamide Step A: (S,E)-N-((3aS,6aR)-2-Benzylhexahydrocyclopenta[c]pyrrol-4(5H)-ylidene)-2-methylpropane-2-sulfinamide (2.67 g, 8.38 mmol) from Example 14 Step A and 2.0 N aqueous HCl (18.86 mL, 37.7 mmol) were combined in tetrahydrofuran (25 mL). The reaction was stirred at room temperature for 2 hours and the tetrahydrofuran was removed in vacuo and the remaining aqueous portion was made slightly basic with aqueous sodium bicarbonate solution. The aqueous layer was extracted with 3×200 mL of dichloromethane. The combined organic layers were separated, and the solvent was removed in vacuo. The crude material was purified on a silica gel cartridge (Analogix®, Burlington, Wis., RS25-25) eluting with 5-50% ethyl acetate/hexanes to give (3aS,6aR)-2-benzylhexahydrocyclopenta[c]pyrrol-4(5H)-one: $^1$H NMR (300 MHz, CDCl$_3$) δ ppm 7.35-7.16 (m, 5H), 3.61 (d, J=13.1, 1H), 3.48 (d, J=13.1, 1H), 3.02 (dd, J=1.8, 9.1, 1H), 2.96-2.82 (m, 1H), 2.71-2.56 (m, 2H), 2.43 (dt, J=8.2, 17.4, 3H), 2.34-2.21 (m, 1H), 2.12 (ddd, J=8.3, 13.0, 16.9, 1H), 1.79 (dddd, J=4.2, 6.4, 9.2, 13.2, 1H).

Step B: A mixture of (3aS,6aR)-2-benzylhexahydrocyclopenta[c]pyrrol-4(5H)-one (1.462 g, 6.79 mmol) from Step A in methanol (20 mL) was cooled in an dry ice/acetone bath to −40° C. Sodium borohydride (0.514 g, 13.58 mmol) was added in portions over 5 minutes. The reaction allowed to warm to room temperature overnight, then it was quenched with saturated aqueous ammonium chloride, diluted with water, and extracted with 3×150 mL of ethyl acetate. The combined extracts were dried (Na$_2$SO$_4$) and the solvent was removed in vacuo to give (3aS,4S,6aR)-2-benzyloctahydrocyclopenta[c]pyrrol-4-ol: $^1$H NMR (300 MHz, CDCl$_3$) δ ppm 7.38-7.16 (m, 5H), 4.21-4.04 (m, 1H), 3.66 (d, J=12.8, 1H), 3.51 (d, J=12.8, 1H), 3.07 (d, J=9.3, 1H), 2.65-2.53 (m, J=11.8, 2H), 2.52-2.43 (m, 1H), 2.18-2.07 (m, J=7.5, 16.3, 2H), 2.05-1.94 (m, J=8.7, 12.6, 1H), 1.84-1.74 (m, J=6.2, 1H), 1.49-1.34 (m, 3H).

Step C: (3aS,4S,6aR)-2-Benzyloctahydrocyclopenta[c]pyrrol-4-ol (1.476 g, 6.79 mmol) from Step B and triethylamine (1.420 mL, 10.19 mmol) were combined in dichloromethane (30 mL). Methanesulfonyl chloride (0.635 mL, 8.15 mmol) was added as a solution in 20 mL of dichloromethane dropwise via addition funnel. The reaction was stirred at room temperature for 30 minutes and concentrated. The crude material was absorbed onto silica gel and chromatographed on a silica gel cartridge (Analogix®, Burlington, Wis., RS25-25) eluting with 20-100% ethyl acetate/hexanes to give (3aS,4S,6aR)-2-benzyloctahydrocyclopenta[c]pyrrol-4-yl methanesulfonate: $^1$H NMR (300 MHz, CDCl$_3$) δ ppm 7.35-7.27 (m, 4H), 7.27-7.20 (m, 1H), 4.96 (ddd, J=6.1, 7.6, 9.1, 1H), 3.71-3.44 (m, 1H), 2.94 (s, J=13.5, 3H), 2.85 (ddd, J=4.9, 8.1, 16.0, 1H), 2.75-2.68 (m, 2H), 2.67-2.55 (m, 1H), 2.54-2.44 (m, 1H), 2.31 (dd, J=4.1, 8.7, 1H), 2.20-2.04 (m, 1H), 1.97 (dtd, J=3.4, 6.2, 9.6, 1H), 1.79-1.63 (m, 1H), 1.61-1.49 (m, 2H).

Step D: (3aS,4S,6aR)-2-Benzyloctahydrocyclopenta[c]pyrrol-4-yl methanesulfonate (1.686 g, 5.71 mmol) from Step C and sodium azide (0.557 g, 8.56 mmol) were combined in N,N-dimethylacetamide (10 mL). The reaction was heated at 90° C. for 15 hours. The reaction was cooled and diluted with 200 mL of ethyl acetate and then quenched with 30 mL water. The organic layer was removed and washed with 2×20 mL of water, then 20 mL of brine. The solvent was removed in vacuo to give (3aS,4R,6aR)-4-azido-2-benzyloctahydrocyclopenta[c]pyrrole: $^1$H NMR (300 MHz, CDCl$_3$) δ ppm 7.36-7.27 (m, 4H), 7.22 (dd, J=2.9, 5.8, 1H), 3.72-3.61 (m, 1H), 3.54 (s, 2H), 2.76-2.60 (m, 1H), 2.55-2.40 (m, 4H), 2.35 (dd, J=3.5, 9.1, 1H), 2.07-1.86 (m, 2H), 1.72-1.60 (m, 1H), 1.49-1.38 (m, 1H).

Step E: Triphenylphosphine (4.49 g, 17.13 mmol) and water (1.234 mL, 68.5 mmol) were added successively to a mixture of (3aS,4R,6aR)-4-azido-2-benzyloctahydrocyclopenta[c]pyrrole (1.384 g, 5.71 mmol) in tetrahydrofuran (30 mL). The reaction was refluxed at 80° C. for 2 hours. The crude material was adsorbed onto silica gel and applied to a silica gel cartridge (Analogix®, Burlington, Wis., RS-40) and eluted with 1-10% methanol (2 N ammonia)/chloroform to give (3aS,4R,6aR)-2-benzyloctahydrocyclopenta[c]pyrrol-4-amine: $^1$H NMR (500 MHz, pyridine-d$_5$) δ ppm 7.45 (d, J=7.4, 2H), 7.38 (t, J=7.5, 2H), 7.29 (t, J=7.3, 1H), 3.52 (s, 2H), 3.14 (dd, J=5.7, 10.7, 1H), 2.62-2.55 (m, 1H), 2.52 (dd, J=3.2, 9.0, 1H), 2.38-2.29 (m, 3H), 2.20-2.13 (m, 1H), 2.01-1.84 (m, 2H), 1.40-1.29 (m, 2H).

Step F: (S)-2-Phenylbutanoic acid (41.7 mg, 0.254 mmol), 1-hydroxybenzotriazole (38.9 mg, 0.254 mmol), and N-(3-dimethylaminopropyl)-N'-ethylcarbodiimide (0.045 mL, 0.254 mmol) were combined in dichloromethane (1 mL). The reaction was stirred at room temperature for 10 minutes, and then (3aS,4R,6aR)-2-benzyloctahydrocyclopenta[c]pyrrol-4-amine (50 mg, 0.231 mmol) from Step E was added in 0.5 mL of dichloromethane. The reaction was stirred at room temperature for 20 hours, and then quenched with 0.5 mL of water. The organic layer was separated. The crude material was chromatographed using a silica gel cartridge (Analogix®, Burlington, Wis., RS-4) eluting with 1-10% methanol(ammonia)/dichloromethane to give the title compound: $^1$H NMR (400 MHz, pyridine-d$_5$) δ ppm 8.47 (d, J=7.0, 1H), 7.59 (m, 2H), 7.42 (d, J=7.1, 2H), 7.34 (dd, J=7.6, 16.5, 4H), 7.25 (dt, J=5.0, 10.1, 2H), 4.45-4.29 (m, 1H), 3.62-3.51 (m, 2H), 3.44 (d, J=13.2, 1H), 2.85 (dd, J=2.7, 9.0, 1H), 2.58-2.50 (m, 1H), 2.50-2.42 (m, 2H), 2.40-2.31 (m, 1H), 2.31-2.22 (m, 2H), 1.97 (dq, J=6.1, 12.1, 1H), 1.85 (td, J=6.9, 13.6, 1H), 1.74 (dt, J=6.4, 14.3, 1H), 1.46 (dt, J=7.1, 19.2, 1H), 1.31 (dt, J=6.2, 20.5, 1H), 0.96 (dd, J=5.5, 9.1, 3H); MS (ESI+) m/z 363 (M+H)$^+$.

Example 17

N-[(3aS,4R,6aR)-2-benzyloctahydrocyclopenta[c]pyrrol-4-yl]-2-cyclopentyl-2-phenylacetamide The title compound was prepared by substituting 2-cyclopentyl-2-phenylacetic acid for (S)-2-phenylbutanoic acid in Step F of the procedure used to prepare Example 16: $^1$H NMR (500 MHz, pyridine-d$_5$) δ ppm 8.61 (dd, J=7.4, 10.6, 1H), 7.69 (dd, J=1.5, 8.1, 2H), 7.44 (d, J=7.3, 1H), 7.36 (dt, J=7.2, 15.3, 5H), 7.30-7.25 (m, 2H), 4.42-4.29 (m, 1H), 3.61 (d, J=13.1, 0.5H), 3.52 (d, J=13.2, 0.5H), 3.43 (dd, J=12.0, 18.8, 1.5H), 3.34 (d, J=13.2, 0.5H), 2.96-2.83 (m, 1.5H), 2.55 (dt, J=15.9, 16.3, 2H), 2.41 (t, J=18.3, 1H), 2.31 (d, J=9.0, 0.5H), 2.28 (d, J=6.3, 1H), 2.23 (d, J=5.0, 1H), 2.20-2.04 (m, 1.5H), 1.94 (dt, J=7.1, 12.1, 0.5H), 1.89-1.81 (m, 0.5H), 1.80-1.67 (m, 1H), 1.65-1.26 (m, 7H), 1.05-0.94 (m, 1H); MS (ESI+) m/z 403 (M+H)$^+$.

Example 18

N-[(3aS,4R,6aR)-2-benzyloctahydrocyclopenta[c]pyrrol-4-yl]-3-methyl-2-phenylbutanamide The title compound was prepared by substituting 3-methyl-2-phenylbutanoic acid for (S)-2-phenylbutanoic acid in Step F of the procedure used to prepare Example 16: $^1$H NMR (500 MHz, pyridine-d$_5$) δ ppm 8.64 (dd, J=7.3, 11.3, 1H), 7.66 (dd, J=2.4, 7.5, 2H), 7.43 (d, J=7.5, 1H), 7.40-7.30 (m, 5H), 7.29-7.23 (m, 2H), 4.40-4.28 (m, 1H), 3.60 (d, J=13.2, 0.5H), 3.52 (d, J=13.1, 0.5H), 3.44 (d, J=13.1, 0.5H), 3.33 (d, J=13.1, 0.5H), 3.25 (d, J=10.5, 1H), 2.88 (dd, J=3.1, 9.1, 0.5H), 2.66 (s, 1H), 2.60-2.56 (m, 0.5H), 2.55-2.46 (m, 1.5H), 2.39 (t, J=18.7, 1H), 2.28 (t, J=8.0, 1.5H), 2.22 (d, J=5.1, 1H), 2.18-2.09 (m, 0.5H), 1.91 (dd, J=6.0, 12.0, 0.5H), 1.84 (dd, J=7.1, 13.4, 0.5H), 1.72 (ddd, J=6.5, 12.3, 25.1, 1H), 1.49-1.40 (m, 0.5H), 1.33 (ddd, J=13.3, 19.9, 32.3, 1H), 1.20 (dd, J=5.0, 6.4, 3H), 0.70 (dd, J=1.7, 6.7, 3H); MS (ESI+) m/z 377 (M+H)$^+$.

Example 19

(2S)-N-[(3aS,4R,6aR)-2-benzyloctahydrocyclopenta[c]pyrrol-4-yl]-2-phenylpropanamide The title compound was prepared by substituting (S)-2-phenylpropanoic acid for (S)-2-phenylbutanoic acid in Step F of the procedure used to prepare Example 16: $^1$H NMR (500 MHz, pyridine-d$_5$) δ ppm 8.41 (d, J=6.8, 1H), 7.54 (d, J=7.0, 2H), 7.41 (t, J=9.7, 2H), 7.38-7.30 (m, 4H), 7.26 (dd, J=5.3, 16.7, 2H), 4.43-4.32 (m, 1H), 3.84 (q, J=7.0, 1H), 3.56 (t, J=12.3, 1H), 3.40 (dd, J=13.1, 33.2, 1H), 2.81 (dd, J=2.9, 9.0, 1H), 2.51 (m, 1H), 2.48-2.36 (m, 2H), 2.33-2.17 (m, 2H), 2.14 (s, 3H, OAc), 2.00 (dq, J=6.1, 12.1, 1H), 1.73 (dt, J=6.3, 14.2, 1H), 1.60 (d, J=7.0, 3H), 1.47 (dt, J=7.1, 14.8, 1H), 1.39-1.24 (m, 1H); MS (ESI+) m/z 349 (M+H)$^+$.

Example 20

N-[(3aS,4R,6aR)-2-benzyloctahydrocyclopenta[c]pyrrol-4-yl]-2,2-dicyclohexylacetamide The title compound was prepared by substituting 2,2-dicyclohexylacetic acid for (S)-2-phenylbutanoic acid in Step F of the procedure used to prepare Example 16: $^1$H NMR (500 MHz, pyridine-d$_5$) δ ppm 8.12 (d, J=7.2, 1H), 7.45 (d, J=7.4, 2H), 7.36 (t, J=7.5, 2H), 7.27 (t, J=7.3, 1H), 4.52-4.43 (m, 1H), 3.63 (d, J=13.1, 1H), 3.48 (d, J=13.1, 1H), 2.89 (dd, J=2.7, 8.9, 1H), 2.65-2.50 (m, 3H), 2.35 (d, J=4.5, 2H), 2.18-2.10 (m, 1H), 2.03 (t, J=7.4, 1H), 1.96 (d, J=13.0, 2H), 1.87 (dt, J=7.4, 13.9, 3H), 1.80 (d, J=12.6, 2H), 1.76-1.64 (m, 5H), 1.60 (d, J=10.7, 2H), 1.51-1.38 (m, 3H), 1.30-1.05 (m, 8H); MS (ESI+) m/z 423 (M+H)$^+$.

Example 21

N-[(3aS,4R,6aR)-2-benzyloctahydrocyclopenta[c]pyrrol-4-yl]-2-propylpentanamide

The title compound was prepared by substituting 2-propylpentanoic acid for (S)-2-phenylbutanoic acid in the procedure used to prepare Example 16: $^1$H NMR (500 MHz, pyridine-d$_5$) δ ppm 8.36 (d, J=7.2, 1H), 7.43 (d, J=7.4, 2H), 7.36 (t, J=7.5, 2H), 7.27 (t, J=7.3, 1H), 4.56-4.38 (m, 1H), 3.60 (d, J=11.8, 1H), 3.45 (d, J=13.1, 1H), 2.85 (dd, J=2.8, 9.0, 1H), 2.61-2.50 (m, 2H), 2.50-2.45 (m, 1H), 2.39-2.25 (m, 3H), 2.20-2.09 (m, 1H), 1.93-1.79 (m, 3H), 1.66 (dd, J=7.7, 12.2, 1H), 1.53-1.29 (m, 7H), 0.87 (td, J=3.1, 7.2, 6H); MS (ESI+) m/z 343 (M+H)+.

Example 22

N-[(3aS,4R,6aR)-2-benzyloctahydrocyclopenta[c]pyrrol-4-yl]cycloheptanecarboxamide The title compound was prepared by substituting cycloheptanecarboxylic acid for (S)-2-phenylbutanoic acid in Step F of the procedure used to prepare Example 16: $^1$H NMR (500 MHz, pyridine-$d_5$) δ ppm 8.08 (d, J=7.2, 1H), 7.44 (d, J=7.4, 2H), 7.36 (t, J=7.6, 2H), 7.27 (t, J=7.3, 1H), 4.50-4.34 (m, 1H), 3.60 (d, J=13.7, 1H), 3.44 (d, J=13.1, 1H), 2.83 (d, J=9.0, 1H), 2.54 (s, 2H), 2.49-2.41 (m, 2H), 2.33 (d, J=6.8, 1H), 2.30-2.25 (m, 1H), 2.19-2.10 (m, 1H), 2.01-1.81 (m, 5H), 1.74-1.58 (m, 3H), 1.47-1.37 (m, 5H), 1.31 (s, 2H); MS (ESI+) m/z 341 (M+H)+.

Example 23

(2S)-N-[(3aS,4R,6aR)-2-benzyloctahydrocyclopenta[c]pyrrol-4-yl]-2-(4-isobutylphenyl)propanamide The title compound was prepared by substituting (S)-2-(3-isobutylphenyl)propanoic acid for (S)-2-phenylbutanoic acid in Step F of the procedure used to prepare Example 16: $^1$H NMR (500 MHz, pyridine-$d_5$) δ ppm 8.37 (d, J=7.2, 1H), 7.49 (d, J=8.0, 2H), 7.42 (d, J=7.5, 2H), 7.36 (t, J=7.5, 2H), 7.27 (t, J=7.3, 1H), 7.14 (d, J=8.0, 2H), 4.43-4.31 (m, 1H), 3.84 (q, J=7.0, 1H), 3.58 (d, J=13.1, 1H), 3.44 (d, J=13.1, 1H), 2.82 (dd, J=2.8, 9.1, 1H), 2.55-2.48 (m, 1H), 2.48-2.42 (m, 2H), 2.39 (d, J=7.2, 2H), 2.31-2.21 (m, 2H), 2.00 (dt, J=6.0, 12.1, 1H), 1.83-1.69 (m, 2H), 1.63 (d, J=7.0, 3H), 1.48 (dt, J=7.0, 19.1, 1H), 1.36-1.25 (m, 1H), 0.86-0.77 (m, 6H); MS (ESI+) m/z 405 (M+H)+.

Example 24

N-[(3aS,4R,6aR)-2-benzyloctahydrocyclopenta[c]pyrrol-4-yl]-1-phenylcyclohexanecarboxamide The title compound was prepared by substituting 1-phenylcyclohexanecarboxylic acid for (S)-2-phenylbutanoic acid in Step F of the procedure used to prepare Example 16: $^1$H NMR (500 MHz, pyridine-$d_5$) δ ppm 7.73 (d, J=7.8, 1H), 7.63-7.59 (m, 1H), 7.41 (d, J=7.3, 2H), 7.39-7.31 (m, 4H), 7.29-7.23 (m, 3H), 4.45-4.35 (m, 1H), 3.58 (d, J=13.2, 1H), 3.40 (d, J=13.2, 1H), 2.80 (d, J=7.7, 1H), 2.69-2.59 (m, 2H), 2.41-2.31 (m, 3H), 2.28 (d, J=8.6, 1H), 2.20-2.13 (m, 1H), 2.00 (td, J=5.7, 11.7, 1H), 1.87-1.75 (m, 4H), 1.74-1.54 (m, J=9.1, 18.8, 38.4, 4H), 1.46 (dt, J=7.8, 14.8, 1H), 1.36-1.19 (m, 2H); MS (ESI+) m/z 403 (M+H)+.

Example 25

N-[(3aS,4R,6aR)-2-benzyloctahydrocyclopenta[c]pyrrol-4-yl]-2,3-diphenylpropanamide The title compound was prepared by substituting 2,3-diphenylpropanoic acid for (S)-2-phenylbutanoic acid in Step F of the procedure used to prepare Example 16: $^1$H NMR (400 MHz, pyridine-$d_5$) δ ppm 8.52 (dd, J=7.3, 13.3, 1H), 7.65 (d, J=7.4, 2H), 7.44 (d, J=7.1, 1H), 7.41-7.29 (m, 8H), 7.26 (dt, J=4.8, 10.9, 4H), 4.35-4.22 (m, 1H), 3.96 (dt, J=5.0, 10.0, 1H), 3.77 (ddd, J=3.7, 10.1, 13.5, 1H), 3.52 (dt, J=13.2, 18.8, 1.5H), 3.33 (d, J=13.1, 0.5H), 3.05 (dt, J=4.7, 13.0, 1H), 2.77 (d, J=8.9, 0.5H), 2.56 (d, J=6.2, 0.5H), 2.38-2.23 (m, 3H), 2.23-2.17 (m, J=8.7, 1H), 1.94 (ddd, J=5.7, 11.8, 23.8, 1H), 1.72-1.57 (m, J=6.0, 1H), 1.51-1.19 (m, 3H); MS (ESI+) m/z 425 (M+H)+.

Example 26

N-[(3aS,4R,6aR)-2-benzyloctahydrocyclopenta[c]pyrrol-4-yl]-2-methyl-3-phenylpropanamide The title compound was prepared by substituting 2-methyl-3-phenylpropanoic acid for (S)-2-phenylbutanoic acid in Step F of the procedure used to prepare Example 16: $^1$H NMR (400 MHz, pyridine-$d_5$) δ ppm 8.12 (dd, J=7.0, 21.5, 1H), 7.47-7.22 (m, 10H), 4.43-4.29 (m, 1H), 3.58 (dd, J=6.6, 13.2, 1H), 3.45 (dd, J=13.2, 21.2, 1H), 3.20 (ddd, J=4.6, 10.8, 15.0, 1H), 2.81-2.66 (m, 3H), 2.48-2.19 (m, 5H), 2.04 (ddt, J=6.0, 12.1, 24.4, 1H), 1.82-1.63 (m, 1H), 1.47 (ddd, J=7.1, 15.9, 18.8, 1H), 1.39-1.30 (m, 1H), 1.28 (d, J=6.3, 3H); MS (ESI+) m/z 363 (M+H)+.

Example 27

N-[(3aS,4R,6aR)-2-benzyloctahydrocyclopenta[c]pyrrol-4-yl]-2-methyl-2-phenylpropanamide The title compound was prepared by substituting 2-methyl-2-phenylpropanoic acid for (S)-2-phenylbutanoic acid in Step F of the procedure used to prepare Example 16: $^1$H NMR (400 MHz, pyridine-$d_5$) δ ppm 7.44 (dd, J=7.9, 16.1, 4H), 7.31 (ddd, J=7.7, 14.5, 22.6, 6H), 7.12-7.03 (m, 1H), 4.46-4.36 (m, 1H), 3.58 (d, J=13.2, 1H), 3.43 (d, J=13.2, 1H), 2.84 (d, J=6.5, 1H), 2.39-2.26 (m, J=6.9, 20.1, 4H), 2.23-2.14 (m, J=6.7, 1H), 2.04 (dd, J=5.8, 11.8, 1H), 1.67 (s, 7H), 1.54-1.40 (m, 1H), 1.38-1.24 (m, 1H); MS (ESI+) m/z 363 (M+H)+.

Example 28

N-[(3aS,4R,6aR)-2-benzyloctahydrocyclopenta[c]pyrrol-4-yl]-1-phenylcyclopropanecarboxamide The title compound was prepared by substituting 1-phenylcyclopropanecarboxylic acid for (S)-2-phenylbutanoic acid in Step F of the procedure used to prepare Example 16: $^1$H NMR (500 MHz, pyridine-$d_5$) δ ppm 7.42 (dd, J=7.2, 16.3, 4H), 7.33 (dt, J=7.6, 17.1, 4H), 7.25 (dd, J=5.8, 13.1, 2H), 6.27 (d, J=7.5, 1H), 4.41-4.24 (m, J=5.8, 1H), 3.56 (d, J=13.2, 1H), 3.40 (d, J=13.2, 1H), 2.87-2.74 (m, 1H), 2.37-2.19 (m, 4H), 2.12 (t, J=8.0, 1H), 2.03-1.94 (m, 1H), 1.75 (dd, J=3.5, 6.6, 2H), 1.68-1.58 (m, J=8.7, 16.8, 1H), 1.37-1.23 (m, 2H), 1.01 (dd, J=3.5, 6.6, 2H); MS (ESI+) m/z 361 (M+H)+.

Example 29

2-benzyl-N-[(3aS,4R,6aR)-2-benzyloctahydrocyclopenta[c]pyrrol-4-yl]-3,3-dimethylbutanamide The title compound was prepared by substituting 2-benzyl-3,3-dimethylbutanoic acid for (S)-2-phenylbutanoic acid in Step F of the procedure used to prepare Example 16: $^1$H NMR (500 MHz, pyridine-$d_5$) δ ppm 8.08 (dd, J=7.4, 13.5, 1H), 7.46 (d, J=7.3, 1H), 7.44-7.32 (m, 5H), 7.32-7.23 (m, 4H), 4.33 (s, 1H), 3.58 (d, J=13.2, 16.9, 1H), 3.50 (d, J=13.1, 0.5H), 3.40 (d, J=13.1, 0.5H), 3.25 (q, J=11.9, 1H), 2.80-2.66 (m, 2H), 2.45 (d, J=6.9, 1H), 2.41-2.23 (m, 3.5H), 2.20 (t, J=8.3, 0.5H), 2.16-2.09 (m, 0.5H), 2.06 (dd, J=5.8, 11.6, 0.5H), 1.89 (dd, J=5.8, 11.8, 0.5H), 1.75 (s, 0.5H), 1.61 (s, 0.5H), 1.47 (s, 0.5H), 1.38-1.20 (m, 2H), 1.16 (s, 9H); MS (ESI+) m/z 405 (M+H)+.

Example 30

N-[(3aS,4R,6aR)-2-benzyloctahydrocyclopenta[c]pyrrol-4-yl]-3,3-dimethyl-2-phenylbutanamide The title compound was prepared by substituting 3,3-dimethyl-2-phenylbutanoic acid for (S)-2-phenylbutanoic acid in Step F of the procedure used to prepare Example 16: $^1$H NMR (500 MHz, pyridine-$d_5$) δ ppm 8.57-8.49 (m, 1H), 7.73 (dd, J=3.3, 5.3, 2H), 7.44 (d, J=7.1, 1H), 7.41-7.24 (m, 7H), 4.41-4.29 (m, J=6.9, 13.0, 1H), 3.62 (d, J=13.2, 0.5H), 3.53 (d, J=13.1, 0.5H), 3.43 (s, 0.5H), 3.35 (d, J=13.1, 0.5H), 2.90 (dd, J=3.1, 8.9, 1H), 2.63-2.46 (m, 2H), 2.44-2.37 (m, 0.5H), 2.36-2.30 (m, J=8.3, 1H), 2.28 (d, J=5.3, 1H), 2.23 (d, J=5.5, 1H), 2.15 (dt, J=6.2, 12.5, 0.5H), 1.91 (dt, J=6.1, 12.2, 0.5H), 1.88-1.79 (m, 0.5H), 1.77-1.66 (m, 1H), 1.46-1.35 (m, 1H), 1.34-1.23 (m, 1H), 1.15 (s, 4.5H), 1.14 (s, 4.5H); MS (ESI+) m/z 391 (M+H)+.

Example 31 and Example 32

(2S)-N-[(3aS,4R,6aR)-2-benzyloctahydrocyclopenta[c]pyrrol-4-yl]-3,3-dimethyl-2-phenylbutanamide (Example 31) and (2R)-N-[(3aS,4R,6aR)-2-benzyloctahydrocyclopenta[c]pyrrol-4-yl]-3,3-dimethyl-2-phenylbutanamide (Example 32)

The material from example 30 was subjected to separation by chiral supercritical fluid chromatography on a ChiralCel® OD-H column (21×250 mm, 5 μm, Chiral Technologies, Inc.), 5-50% methanol:$CO_2$ (100 bar), at 40 mL/minute over 10 minutes to give the title compounds.

Example 31: $^1$H NMR (500 MHz, pyridine-$d_5$) δ ppm 8.50 (d, J=7.1, 1H), 7.74-7.70 (m, 1H), 7.44 (d, J=7.2, 2H), 7.40-7.24 (m, J=8.0, 15.4, 18.2, 7H), 4.43-4.31 (m, 1H), 3.63 (d, J=13.1, 1H), 3.49-3.41 (m, J=6.6, 2H), 2.91 (dd, J=3.0, 8.9, 1H), 2.63-2.43 (m, 3H), 2.28 (d, J=5.3, 2H), 1.92 (dq, J=6.1, 12.1, 1H), 1.78-1.68 (m, 1H), 1.41 (dt, J=7.0, 18.9, 1H), 1.30 (dt, J=6.4, 14.5, 1H), 1.14 (s, 9H); MS (ESI+) m/z 391 (M+H)+.

Example 32: $^1$H NMR (500 MHz, pyridine-$d_5$) δ ppm 8.52 (d, J=7.0, 1H), 7.72 (d, J=7.0, 2H), 7.41-7.24 (m, J=7.2, 21.5, 29.9, 8H), 4.41-4.25 (m, 1H), 3.53 (d, J=13.1, 1H), 3.45 (s, 1H), 3.35 (d, J=13.1, 1H), 2.57 (d, J=5.7, 1H), 2.45-2.36 (m, 1H), 2.31 (dd, J=5.1, 10.5, 2H), 2.25-2.20 (m, 2H), 2.15 (td, J=6.4, 12.4, 1H), 1.83 (td, J=6.8, 14.8, 1H), 1.69 (td, J=6.7, 13.4, 1H), 1.38 (td, J=6.7, 12.4, 1H), 1.14 (s, 9H); MS (ESI+) m/z 391 (M+H)+.

Example 33

(2S)-N-[(3aR,4S,6aS)-2-benzyloctahydrocyclopenta[c]pyrrol-4-yl]-2-phenylbutanamide Step A: (3aR,4S,6aS)-2-Benzyloctahydrocyclopenta[c]pyrrol-4-amine was prepared according to the procedure described in Example 16 Steps A-E substituting (S,E)-N-((3aR,6aS)-2-benzylhexahydrocyclopenta[c]pyrrol-4(5H)-ylidene)-2-methylpropane-2-sulfinamide from Step A in Example 14 for (S,E)-N-((3aS,6aR)-2-benzylhexahydrocyclopenta[c]pyrrol-4(5H)-ylidene)-2-methylpropane-2-sulfinamide in Step A of Example 16 to give (3aR,4S,6aS)-2-benzyloctahydrocyclopenta[c]pyrrol-4-amine: $^1$H NMR (300 MHz, $CDCl_3$) δ ppm 7.34-7.28 (m, 4H), 7.25-7.18 (m, 1H), 3.54 (s, 2H), 3.09 (dd, J=4.8, 10.9, 1H), 2.75-2.58 (m, 1H), 2.48 (dd, J=8.6, 16.5, 2H), 2.40 (dd, J=3.9, 9.3, 1H), 2.30 (dd, J=3.9, 9.0, 1H), 2.21-2.09 (m, 1H), 2.01-1.84 (m, J=6.9, 12.0, 2H), 1.47-1.25 (m, 4H).

Step B: The title compound was prepared by substituting (3aR,4S,6aS)-2-benzyloctahydrocyclopenta[c]pyrrol-4-amine from Step A for (3aS,4R,6aR)-2-benzyloctahydrocyclopenta[c]pyrrol-4-amine in Step F of the procedure used to prepare Example 16: $^1$H NMR (500 MHz, pyridine-$d_5$) δ ppm 8.55 (d, J=4.5, 1H), 7.59 (s, J=5.1, 1H), 7.39 (d, J=7.2, 2H), 7.34 (dd, J=7.7, 16.5, 4H), 7.25 (dd, J=7.6, 16.2, 3H), 4.43-4.33 (m, 1H), 3.59-3.50 (m, 2H), 3.36 (d, J=13.1, 1H), 2.69-2.61 (m, 1H), 2.43-2.28 (m, 4H), 2.28-2.23 (m, 1H), 2.22-2.18 (m, 1H), 2.13 (dq, J=6.3, 12.3, 1H), 1.89-1.77 (m, 2H), 1.65 (td, J=7.0, 14.2, 1H), 1.40-1.32 (m, 1H), 0.97 (t, J=7.3, 3H); MS (ESI+) m/z 363 (M+H)+.

Alternative Preparation For Example 33, Step A as a Salt (3aR,4S,6aS)-2-benzyloctahydrocyclopenta[c]pyrrol-4-amine Step 1: (3aR,4R,6aS)-2-Benzyloctahydrocyclopenta[c]pyrrol-4-ol (3.00 g, 13.81 mmol, Example 706, Step 1) and triphenylphosphine (4.35 g, 16.57 mmol) were combined in toluene (69 mL). Diisopropyl azodicarboxylate (3.49 g, 17.26 mmol) was added dropwise via addition funnel to the reaction solution at 5° C. Diphenylphosphoryl azide (4.56 g, 16.57 mmol) was then added to the reaction solution. The reaction was allowed to proceed at room temperature for 16 hours and then quenched with saturated aqueous sodium bicarbonate (100 mL). The resulting layers were separated and the product containing phase was extracted with 1.2 M hydrochloric acid (2×40 mL). The acid layer was extracted with ethyl acetate (50 mL) and then basified with 1.9 M potassium hydroxide (68 mL). The aqueous solution was extracted with methyl tert-butyl ether (2×50 mL). The methyl tert-butyl ether was removed under reduced pressure by co-distillation with ethanol and then filtered to provide (3aR,4S,6aS)-4-azido-2-benzyloctahydrocyclopenta-[c]pyrrole in ethanol.

Step 2: (3aR,4S,6aS)-4-Azido-2-benzyloctahydrocyclopenta[c]pyrrole (1.70 g, 7.02 mmol), Raney®-nickel (0.46 g, 20% wt), and ethanol (47 mL) were combined in a Parr stirrer reactor. The reactor was pressured with hydrogen gas to 30 psi and the reaction mixture was agitated for 24 hours. The slurry was filtered to provide (3aR,4S,6aS)-2-benzyloctahydrocyclopenta[c]pyrrol-4-amine in ethanol.

Step 3: (3aR,4S,6aS)-2-Benzyloctahydrocyclopenta[c]pyrrol-4-amine (1.26 g, 5.82 mmol) from Step 2 and ethanol (12 mL) were combined. L-Tartaric acid in ethanol (4.7 mL) was added to the reaction solution over 2 hours. The resulting slurry was further diluted with ethanol (10 mL). The slurry was filtered and the cake was rinsed with ethanol (10 mL) to provide (3aR,4S,6aS)-2-benzyloctahydrocyclopenta-[c]pyrrol-4-amine(2R,3R)-2,3-dihydroxysuccinate: $^1$H NMR (400 MHz, dimethyl sulfoxide-$d_6$) δ ppm 7.37-7.30 (m, 4H), 7.29-7.24 (m, 1H) 3.91 (s, 2H), 3.56 (q, J=13.2, 2H), 3.19 (dt, J=5.4, 7.4, 1H), 2.71-2.61 (m, 2H), 2.50-2.41 (m, 2H), 2.36-2.28 (m, 2H), 2.05-1.95 (m, 2H), 1.65-1.55 (m, 1H), 1.43-1.33 (m, 1H).

Example 34

N-[(3aR,4S,6aS)-2-benzyloctahydrocyclopenta[c]pyrrol-4-yl]-2-cyclopentyl-2-phenylacetamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 2-cyclopentyl-2-phenylacetic acid for (S)-2-phenylbutanoic acid in Step F of the procedure used to prepare Example 16: $^1$H NMR (500 MHz, pyridine-d$_5$) δ ppm 8.54 (d, J=14.7, 1H), 7.66 (dd, J=2.5, 7.5, 2H), 7.43 (d, J=7.4, 1H), 7.40-7.31 (m, 5H), 7.26 (t, J=6.9, 2H), 4.41-4.30 (m, 1H), 3.61 (d, J=13.1, 0.5H), 3.52 (d, J=13.1, 0.5H), 3.45 (d, J=13.2, 0.5H), 3.36 (app. t, J=12.7, 1.5H), 2.89 (d, J=9.0, 1H), 2.61-2.55 (m, 1H), 2.53-2.46 (m, 1H), 2.44-2.33 (m, 1H), 2.29 (dd, J=7.3, 12.8, 1.5H), 2.22 (t, J=4.9, 1H), 2.19-2.04 (m, 1.5H), 1.98-1.89 (m, 0.5H), 1.88-1.80 (m, 0.5H), 1.79-1.65 (m, 1H), 1.65-1.25 (m, 8H), 1.05-0.95 (m, 1H); MS (ESI+) m/z 403 (M+H)$^+$.

Example 35

N-[(3aR,4S,6aS)-2-benzyloctahydrocyclopenta[c]pyrrol-4-yl]-3-methyl-2-phenylbutanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 3-methyl-2-phenylbutanoic acid for (S)-2-phenylbutanoic acid in Step F of the procedure used to prepare Example 16: $^1$H NMR (500 MHz, pyridine-d$_5$) δ ppm 8.64-8.49 (m, J=20.1, 1H), 7.67-7.61 (m, 2H), 7.43 (d, J=7.0, 1H), 7.39-7.30 (m, 5H), 7.29-7.24 (m, 2H), 4.41-4.27 (m, 1H), 3.60 (d, J=13.1, 0.5H), 3.52 (d, J=13.1, 0.5H), 3.44 (d, J=13.2, 0.5H), 3.33 (d, J=13.2, 0.5H), 3.23 (d, J=10.5, 1H), 2.89 (dd, J=3.0, 9.1, 0.5H), 2.69-2.60 (m, J=10.0, 1H), 2.59-2.53 (m, J=3.0, 9.0, 1H), 2.52-2.44 (m, 1H), 2.44-2.33 (m, 1H), 2.30-2.25 (m, J=6.4, 10.0, 1.5H), 2.25-2.20 (m, 1H), 2.14 (dd, J=5.9, 12.3, 0.5H), 1.91 (dd, J=6.1, 12.1, 0.5H), 1.86-1.79 (m, J=4.7, 0.5H), 1.78-1.64 (m, 1H), 1.47-1.24 (m, J=30.2, 37.0, 1.5H), 1.20 (dd, J=4.9, 6.4, 3H), 0.70 (dd, J=1.6, 6.7, 3H); MS (ESI+) m/z 377 (M+H)$^+$.

Example 36

(2R)-N-[(3aR,4S,6aS)-2-benzyloctahydrocyclopenta[c]pyrrol-4-yl]-2-phenylbutanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting (R)-2-phenylbutanoic acid for (S)-2-phenylbutanoic acid in Step F of the procedure used to prepare Example 16: $^1$H NMR (500 MHz, CDCl$_3$) δ ppm 7.38-7.21 (m, 10H), 5.29 (d, J=6.9, 1H), 4.04-3.90 (m, 1H), 3.65 (d, J=12.9, 1H), 3.52 (d, J=12.9, 1H), 3.15 (t, J=7.6, 1H), 2.68 (t, J=8.6, 1H), 2.64-2.48 (m, J=8.5, 3H), 2.30-2.22 (m, J=3.7, 8.3, 1.5H), 2.14 (ddd, J=7.4, 13.9, 19.9, 1.5H), 1.93 (dt, J=6.2, 12.5, 1H), 1.84-1.62 (m, J=7.6, 14.5, 20.6, 2H), 1.45-1.27 (m, 2H), 0.95-0.80 (m, 4H); MS (ESI+) m/z 363 (M+H)$^+$.

Example 37

(2R)-N-[(3aR,4S,6aS)-2-benzyloctahydrocyclopenta[c]pyrrol-4-yl]-2-phenylpropanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting (R)-2-phenylpropanoic acid for (S)-2-phenylbutanoic acid in Step F of the procedure used to prepare Example 16: $^1$H NMR (500 MHz, CDCl$_3$) δ ppm 7.37-7.26 (m, J=5.5, 7.5, 8H), 7.25-7.18 (m, 2H), 5.19 (d, J=5.9, 1H), 4.06-3.89 (m, 1H), 3.59 (d, J=13.0, 1H), 3.48 (ddd, J=7.6, 13.7, 21.0, 2H), 2.60-2.46 (m, 3H), 2.43-2.33 (m, J=7.0, 14.4, 1H), 2.26 (dd, J=3.8, 9.0, 1H), 2.20-2.07 (m, J=34.2, 1H), 2.03-1.93 (m, 1H), 1.49 (d, J=7.2, 3H), 1.44-1.22 (m, 3H); MS (ESI+) m/z 349 (M+H)$^+$.

Example 38

(2S)-N-[(3aR,4S,6aS)-2-benzyloctahydrocyclopenta[c]pyrrol-4-yl]-2-phenylpropanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting (S)-2-phenylpropanoic acid for (S)-2-phenylbutanoic acid in Step F of the procedure used to prepare Example 16: $^1$H NMR (500 MHz, CDCl$_3$) δ ppm 7.38-7.26 (m, 8H), 7.25-7.20 (m, 2H), 5.20 (d, J=6.7, 1H), 4.03-3.91 (m, 1H), 3.60 (d, J=13.0, 1H), 3.52-3.43 (m, 2H), 2.54 (dd, J=5.7, 13.8, 2H), 2.43 (dd, J=7.1, 16.0, 1H), 2.29-2.23 (m, 1H), 2.22-2.08 (m, 2H), 1.98 (ddd, J=5.8, 11.9, 15.7, 1H), 1.74-1.60 (m, 1H), 1.50 (t, J=6.4, 3H), 1.44-1.30 (m, 2H); MS (ESI+) m/z 349 (M+H)$^+$.

Example 39

(2S)-N-[(3aR,4S,6aS)-2-benzyloctahydrocyclopenta[c]pyrrol-4-yl]-2-(4-isobutylphenyl)propanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting (S)-2-(4-isobutylphenyl)propanoic acid for (S)-2-phenylbutanoic acid in Step F of the procedure used to prepare Example 16: $^1$H NMR (400 MHz, CDCl$_3$) δ ppm 7.28 (d, J=4.4, 3H), 7.25-7.18 (m, 1H), 7.15 (dd, J=2.3, 8.2, 2H), 7.09 (dd, J=1.8, 8.2, 2H), 5.17 (d, J=7.2, 1H), 4.03-3.89 (m, 1H), 3.58 (d, J=13.0, 1H), 3.51-3.41 (m, 2H), 2.55-2.48 (m, 3H), 2.45 (d, J=7.2, 2H), 2.39 (dd, J=7.3, 9.0, 1H), 2.27-2.20 (m, 1H), 2.19-2.06 (m, 1H), 2.05-1.91 (m, 1H), 1.85 (dt, J=6.8, 13.5, 1H), 1.72-1.61 (m, 2H), 1.48 (d, J=7.2, 3H), 1.44-1.28 (m, 2H), 0.89 (d, J=6.6, 6H); MS (ESI+) m/z 405 (M+H)$^+$.

Example 40

N-[(3aR,4S,6aS)-2-benzyloctahydrocyclopenta[c]pyrrol-4-yl]-2,2-dicyclohexylacetamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 2,2-dicyclohexylacetic acid for (S)-2-phenylbutanoic acid in Step F of the procedure used to prepare Example 16: $^1$H NMR (400 MHz, CDCl$_3$) δ ppm 7.32-7.27 (m, J=6.3, 4H), 7.24-7.18 (m, 1H), 5.22 (d, J=6.9, 1H), 4.11-3.99 (m, 1H), 3.62 (d, J=13.0, 1H), 3.46 (d, J=13.0, 1H), 2.67-2.58 (m, 2H), 2.54 (dd, J=4.2, 9.4, 1H), 2.51-2.43 (m, 1H), 2.31 (dt, J=4.0, 7.6, 1H), 2.25 (dd, J=4.2, 9.0, 1H), 2.08-1.99 (m, 1H), 1.87-1.76 (m, 1H), 1.67 (dd, J=15.7, 26.7, 10H), 1.55 (s, 3H), 1.50-1.38 (m, 2H), 1.31-1.02 (m, 8H), 1.00-0.85 (m, 2H); MS (ESI+) m/z 423 (M+H)$^+$.

Example 41

N-[(3aR,4S,6aS)-2-benzyloctahydrocyclopenta[c]pyrrol-4-yl]-2-cyclopropyl-2-phenylacetamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 2-cyclopropyl-2-phenylacetic acid for (S)-2-phenylbutanoic acid in Step F of the procedure used to prepare Example 16: $^1$H NMR (500 MHz, CDCl$_3$) δ ppm 7.36-7.26 (m, 8H), 7.25-7.18 (m, 2H), 5.57-5.40 (m, 1H), 4.08-3.97 (m, 1H), 3.60 (dd, J=5.8, 13.0, 1H), 3.46 (dd, J=3.0, 13.0, 1H), 2.65 (d, J=9.5, 1H), 2.62-2.50 (m, 2H), 2.46-2.38 (m, 1H), 2.30-2.18 (m, 2H), 2.03 (ddd, J=6.0, 12.1, 18.9, 1H), 1.80-1.69 (m, 1H), 1.49-1.30 (m, 4H), 0.71 (ddd, J=5.7, 9.1, 10.4, 1H), 0.60-0.51 (m, 1H), 0.38 (td, J=4.7, 9.0, 1H), 0.19 (dq, J=4.7, 9.4, 1H); MS (ESI+) m/z 375 (M+H)$^+$.

Example 42

N-[(3aR,4S,6aS)-2-benzyloctahydrocyclopenta[c]pyrrol-4-yl]-2-cyclobutyl-2-phenylacetamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 2-cyclobutyl-2-phenylacetic acid for (S)-2-phenylbutanoic acid in Step F of the procedure used to prepare Example 16: $^1$H NMR (500 MHz, pyridine-d$_5$) δ ppm 8.51 (t, J=6.2, 1H), 7.61 (d, J=7.7, 2H), 7.43 (dd, J=7.3, 16.6, 2H), 7.38-7.30 (m, 4H), 7.30-7.23 (m, 2H), 4.42-4.31 (m, 1H), 3.67 (d, J=10.7, 1H), 3.59 (dd, J=13.1, 28.6, 1H), 3.43 (dd, J=13.0, 35.2, 1H), 3.34-3.23 (m, 1H), 2.85 (d, J=7.5, 0.5H), 2.67 (d, J=7.1, 0.5H), 2.61-2.47 (m, J=9.6, 29.9, 1.5H), 2.46-2.33 (m, 1.5H), 2.28 (d, J=17.6, 3H), 2.12 (dt, J=4.5, 12.2, 0.5H), 2.03-1.91 (m, 1.5H), 1.87-1.55 (m, J=7.8, 17.0, 28.7, 5H), 1.47 (dt, J=7.8, 14.5, 0.5H), 1.42-1.26 (m, J=16.4, 37.6, 1.5H); MS (ESI+) m/z 389 (M+H)$^+$.

Example 43

N-[(3aR,4S,6aS)-2-benzyloctahydrocyclopenta[c]pyrrol-4-yl]-2-(4-chlorophenyl)-3-methylbutanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 2-(4-chlorophenyl)-3-methylbutanoic acid for (S)-2-phenylbutanoic acid in Step F of the procedure used to prepare Example 16: $^1$H NMR (500 MHz, pyridine-d$_5$) δ ppm 8.69 (s, 1H), 7.54 (dd, J=2.9, 8.4, 2H), 7.47 (d, J=7.5, 1H), 7.42 (d, J=7.3, 1H), 7.38-7.31 (m, 4H), 7.28 (t, J=7.5, 1H), 4.36 (s, 1H), 3.66 (d, J=13.1, 0.5H), 3.58 (d, J=13.1, 0.5H), 3.51 (d, J=13.1, 0.5H), 3.42 (d, J=13.1, 0.5H), 3.19 (d, J=10.4, 1H), 2.94 (d, J=5.0, 0.5H), 2.66 (d, J=5.0, 0.5H), 2.62-2.49 (m, 2.5H), 2.40 (m, 1.5H), 2.34 (m, 1H), 2.31-2.25 (m, 1H), 2.14 (dt, J=6.2, 12.3, 0.5H), 2.01-1.91 (m, J=4.7, 13.4, 0.5H), 1.87-1.62 (m, 1.5H), 1.52-1.43 (m, 0.5H), 1.42-1.33 (m, J=10.3, 30.3, 1H), 1.17 (t, J=5.9, 3H), 0.67 (dd, J=2.2, 6.7, 3H); MS (ESI+) m/z 411 (M+H)$^+$.

Example 44

N-[(3aR,4S,6aS)-2-benzyloctahydrocyclopenta[c]pyrrol-4-yl]-3-ethyl-2-phenylpentanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and substituting 3-ethyl-2-phenylpentanoic acid for (S)-2-phenylbutanoic acid in Step F of the procedure used to prepare Example 16: $^1$H NMR (500 MHz, pyridine-d$_5$) δ ppm 8.69-8.62 (m, 1H), 7.65 (s, 2H), 7.45 (s, 1H), 7.41 (d, J=7.8, 1H), 7.38-7.31 (m, 4H), 7.27 (d, J=7.0, 2H), 4.34 (dd, J=5.5, 10.8, 1H), 3.68-3.62 (m, 0.5H), 3.60-3.47 (m, 2H), 3.45-3.32 (m, 0.5H), 2.97-2.86 (m, 0.5H), 2.67-2.21 (m, 5H), 2.19-2.08 (m, 0.5H), 1.94-1.55 (m, 4H), 1.48-1.38 (m, 2H), 1.12-1.00 (m, 1H), 0.97 (q, J=7.5, 3H), 0.93-0.84 (m, 1.5H), 0.83-0.74 (m, 0.5H), 0.61 (t, J=6.6, 3H); MS (ESI+) m/z 405 (M+H)$^+$.

Example 45

N-[(3aR,4S,6aS)-2-benzyloctahydrocyclopenta[c]pyrrol-4-yl]-2-(4-hydroxyphenyl)-3-methylbutanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 2-(4-hydroxyphenyl)-3-methylbutanoic acid for (S)-2-phenylbutanoic acid in Step F of the procedure used to prepare Example 16: $^1$H NMR (500 MHz, pyridine-d$_5$) δ ppm 8.53-8.46 (m, 1H), 7.56 (d, J=2.8, 1H), 7.43 (d, J=7.2, 1H), 7.36 (dt, J=7.5, 18.2, 4H), 7.26 (q, J=7.1, 1H), 7.16 (dd, J=3.0, 8.6, 2H), 4.44-4.32 (m, 1H), 3.60 (d, J=13.1, 0.5H), 3.53 (d, J=13.1, 0.5H), 3.44 (d, J=13.2, 0.5H), 3.33 (d, J=13.1, 0.5H), 3.18 (d, J=10.4, 1H), 2.90 (dd, J=3.0, 9.1, 0.5H), 2.66 (s, 1H), 2.58 (d, J=8.8, 1H), 2.49 (t, J=10.5, 1H), 2.44-2.35 (m, J=10.0, 1H), 2.33-2.11 (m, 2H), 1.99-1.89 (m, 0.5H), 1.88-1.63 (m, 1.5H), 1.53-1.42 (m, 0.5H), 1.41-1.24 (m, 2H), 1.22 (dd, J=4.4, 6.3, 3H), 0.97-0.82 (m, J=21.9, 35.1, 1H), 0.79 (d, J=6.7, 3H); MS (ESI+) m/z 393 (M+H)$^+$.

Example 46

N-[(3aR,4S,6aS)-2-benzyloctahydrocyclopenta[c]pyrrol-4-yl]-1-phenylcyclohexanecarboxamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 1-phenylcyclohexanecarboxylic acid for (S)-2-phenylbutanoic acid in Step F of the procedure used to prepare Example 16: $^1$H NMR (500 MHz, pyridine-d$_5$) δ ppm 7.73 (d, J=8.2, 1H), 7.59 (s, 1H), 7.41 (d, J=7.4, 2H), 7.36 (td, J=2.7, 7.6, 4H), 7.26 (dd, J=6.0, 8.7, 2H), 4.45-4.33 (m, 1H), 3.58 (d, J=13.2, 1H), 3.40 (d, J=13.2, 1H), 2.81 (d, J=7.3, 1H), 2.68-2.59 (m, J=10.2, 2H), 2.41-2.31 (m, J=6.2, 14.8, 3H), 2.28 (d, J=8.8, 1H), 2.20-2.13 (m, 1H), 1.99 (dt, J=7.4, 14.8, 1H), 1.88-1.75 (m, J=9.0, 4H), 1.74-1.53 (m, J=8.8, 36.2, 4H), 1.50-1.40 (m, 1H), 1.36-1.20 (m, 2H); MS (ESI+) m/z 403 (M+H)$^+$.

Example 47

N-[(3aR,4S,6aS)-2-benzyloctahydrocyclopenta[c]pyrrol-4-yl]-2-methyl-2-phenylpropanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 2-methyl-2-phenylpropanoic acid for (S)-2-phenylbutanoic acid in Step F of the procedure used to prepare Example 16: $^1$H NMR (400 MHz, pyridine-$d_5$) δ ppm 7.49-7.38 (m, 4H), 7.31 (ddd, J=7.3, 14.4, 22.5, 5H), 7.08 (d, J=7.3, 1H), 4.46-4.35 (m, 1H), 3.58 (d, J=13.2, 1H), 3.43 (d, J=13.2, 1H), 2.84 (d, J=6.7, 1H), 2.36 (d, J=4.8, 3H), 2.31 (d, J=9.6, 1H), 2.21-2.13 (m, 1H), 2.04 (td, J=5.9, 11.7, 1H), 1.70 (dd, J=6.7, 12.3, 1H), 1.67 (s, 6H), 1.53-1.41 (m, 1H), 1.38-1.26 (m, 1H); MS (ESI+) m/z 363 (M+H)$^+$.

Example 48

N-[(3aR,4S,6aS)-2-benzyloctahydrocyclopenta[c]pyrrol-4-yl]-1-phenylcyclopropanecarboxamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 1-phenylcyclopropanecarboxylic acid for (S)-2-phenylbutanoic acid in Step F of the procedure used to prepare Example 16: $^1$H NMR (400 MHz, pyridine-$d_5$) δ ppm 7.46-7.37 (m, 4H), 7.33 (dt, J=7.5, 11.5, 4H), 7.28-7.22 (m, 2H), 6.22 (d, J=7.3, 1H), 4.31 (dd, J=6.7, 12.7, 1H), 3.56 (d, J=13.2, 1H), 3.40 (d, J=13.2, 1H), 2.81 (dd, J=2.1, 8.9, 1H), 2.39-2.18 (m, J=7.3, 12.5, 18.1, 4H), 2.13 (dd, J=7.3, 8.9, 1H), 1.99 (dt, J=5.6, 11.0, 1H), 1.75 (q, J=3.6, 2H), 1.67-1.58 (m, J=8.3, 16.6, 1H), 1.38-1.22 (m, 2H), 1.01 (q, J=3.6, 2H); MS (ESI+) m/z 361 (M+H)$^+$.

Example 49

2-benzyl-N-[(3aR,4S,6aS)-2-benzyloctahydrocyclopenta[c]pyrrol-4-yl]-3,3-dimethylbutanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 2-benzyl-3,3-dimethylbutanoic acid for (S)-2-phenylbutanoic acid in Step F of the procedure used to prepare Example 16: $^1$H NMR (500 MHz, pyridine-$d_5$) δ ppm 8.08 (dd, J=7.4, 13.6, 1H), 7.46 (d, J=7.3, 1H), 7.44-7.40 (m, 1H), 7.38 (dd, J=7.6, 15.7, 2H), 7.34 (d, J=4.3, 2H), 7.31-7.23 (m, 4H), 4.36-4.29 (m, 1H), 3.59 (d, J=13.1, 0.5H), 3.53 (dd, J=13.2, 32.6, 1H), 3.40 (d, J=13.1, 0.5H), 3.25 (q, J=12.0, 1H), 2.79-2.67 (m, 2H), 2.48-2.42 (m, J=7.0, 1H), 2.41-2.23 (m, 3.5H), 2.20 (t, J=8.3, 0.5H), 2.12 (d, J=6.7, 0.5H), 2.06 (dd, J=5.9, 11.7, 0.5H), 1.88 (dd, J=5.8, 11.7, 0.5H), 1.74 (dd, J=9.4, 16.4, 0.5H), 1.60 (dd, J=7.0, 13.2, 0.5H), 1.51-1.42 (m, 0.5H), 1.37-1.21 (m, 2H), 1.15 (s, 9H); MS (ESI+) m/z 405 (M+H)$^+$.

Example 50

N-[(3aR,4S,6aS)-2-benzyloctahydrocyclopenta[c]pyrrol-4-yl]-2,3-diphenylpropanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 2,3-diphenylpropanoic acid for (S)-2-phenylbutanoic acid in Step F of the procedure used to prepare Example 16: $^1$H NMR (400 MHz, pyridine-$d_5$) δ ppm 8.53 (dd, J=7.3, 13.7, 1H), 7.66 (d, J=7.4, 2H), 7.44 (d, J=7.1, 1H), 7.41-7.22 (m, 12H), 4.36-4.23 (m, J=7.5, 14.9, 1H), 3.97 (dt, J=4.9, 9.9, 1H), 3.77 (ddd, J=3.7, 10.1, 13.5, 1H), 3.52 (dt, J=13.1, 18.6, 1H), 3.33 (d, J=13.1, 0.5H), 3.05 (dt, J=4.7, 13.0, 1H), 2.77 (dd, J=2.6, 9.0, 0.5H), 2.55 (d, J=6.3, 0.5H), 2.38-2.24 (m, 3H), 2.21 (d, J=9.2, 1.5H), 2.03-1.86 (m, 1.5H), 1.72-1.56 (m, 1H), 1.52-1.20 (m, 2.5H); MS (ESI+) m/z 425 (M+H)$^+$.

Example 51

N-[(3aR,4S,6aS)-2-benzyloctahydrocyclopenta[c]pyrrol-4-yl]-2-methyl-3-phenylpropanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 2-methyl-3-phenylpropanoic acid for (S)-2-phenylbutanoic acid in Step F of the procedure used to prepare Example 16: $^1$H NMR (400 MHz, pyridine-$d_5$) δ ppm 8.13 (dd, J=7.0, 21.3, 1H), 7.40 (ddd, J=7.5, 15.5, 25.3, 4H), 7.31-7.22 (m, 6H), 4.42-4.27 (m, 1H), 3.58 (dd, J=6.6, 13.1, 1H), 3.45 (dd, J=13.1, 21.0, 1H), 3.25-3.15 (m, 1H), 2.81-2.67 (m, 3H), 2.49-2.19 (m, 5H), 2.04 (ddd, J=6.0, 12.1, 24.6, 1H), 1.82-1.64 (m, 1H), 1.57-1.40 (m, 1H), 1.40-1.30 (m, 1H), 1.28 (d, J=6.4, 3H); MS (ESI+) m/z 363 (M+H)$^+$.

Example 52

N-[(3aR,4S,6aS)-2-benzyloctahydrocyclopenta[c]pyrrol-4-yl]-3,3-dimethyl-2-phenylbutanamide The title compound was prepared by substituting (3aR,4S,6aS)-2-benzyloctahydrocyclopenta[c]pyrrol-4-amine from Step A of Example 33 for (3aS,4R,6aR)-2-benzyloctahydrocyclopenta[c]pyrrol-4-amine and 3,3-dimethyl-2-phenylbutanoic acid for (S)-2-phenylbutanoic acid in Step F of the procedure used to prepare Example 16: $^1$H NMR (500 MHz, pyridine-$d_5$) δ ppm 8.53 (dd, J=7.4, 10.9, 1H), 7.73 (dd, J=3.3, 5.3, 2H), 7.44 (d, J=7.0, 1H), 7.41-7.24 (m, 7H), 4.41-4.30 (m, 1H), 3.62 (d, J=13.1, 0.5H), 3.53 (d, J=13.1, 0.5H), 3.45 (d, J=15.0, 0.5H), 3.35 (d, J=13.1, 0.5H), 2.90 (dd, J=3.1, 8.9, 0.5H), 2.63-2.45 (m, 2.5H), 2.44-2.36 (m, 0.5H), 2.31 (d, J=6.5, 1H), 2.28 (d, J=5.3, 1H), 2.23 (d, J=5.8, 1H), 2.15 (dd, J=5.9, 12.3, 0.5H), 1.92 (dd, J=6.1, 12.2, 0.5H), 1.84 (dd, J=8.1, 12.6, 0.5H), 1.72 (ddd, J=6.5, 12.5, 18.9, 1H), 1.46-1.25 (m, 2H), 1.14 (d, J=1.8, 9H); MS (ESI+) m/z 391 (M+H)$^+$.

Example 53

2,2-dicyclohexyl-N-[(3aS,4S,6aR)-octahydrocyclopenta[c]pyrrol-4-yl]acetamide N-[(3aS,4S,6aR)-2-benzyloctahydrocyclopenta[c]pyrrol-4-yl]-2,2-dicyclohexylacetamide (2.65 g, 6.27 mmol) from Example 15 and methanol (60 mL) were added to 20% palladium hydroxide on carbon (wet, 0.530 g, 3.77 mmol) in a 250 mL pressure bottle. The reaction was stirred for 16 hours under hydrogen (30 psi) at room temperature. The mixture was filtered through a nylon membrane and the solvent removed in vacuo. The crude material was chromatographed on a silica gel cartridge (Analogix®, Burlington, Wis., RS25-25) eluting with 1-10% methanol (2 N ammonia)/dichloromethane to give the title compound: $^1$H NMR (500 MHz, pyridine-$d_5$) δ ppm 7.97 (d, J=7.1, 1H), 4.57 (dt, J=7.0, 13.8, 1H), 3.03 (dd, J=3.2, 10.1, 1H), 2.89 (dd, J=7.8, 9.7, 1H), 2.78 (dd, J=7.4, 10.1, 1H), 2.71 (ddd, J=3.2, 7.5, 16.7, 1H), 2.58 (dd, J=3.2, 9.8, 1H), 2.50-2.39 (m, J=8.3, 1H), 1.98-1.89 (m, 3H), 1.89-1.80 (m, 3H), 1.79-1.67 (m, J=6.4, 14.9, 7H), 1.66-1.56 (m, 3H), 1.49-1.36 (m, 2H), 1.36-1.28 (m, 1H), 1.28-1.02 (m, 8H); MS (ESI+) m/z 333 (M+H)$^+$.

Example 54

2,2-dicyclohexyl-N-{(3aS,4S,6aR)-2-[3-(trifluoromethyl)benzyl]octahydrocyclopenta[c]pyrrol-4-yl}acetamide 2,2-Dicyclohexyl-N-[(3aS,4S,6aR)-octahydrocyclopenta[c]pyrrol-4-yl]acetamide (154 mg, 0.463 mmol) from Example 53 and 3-(trifluoromethyl)benzaldehyde (0.062 mL, 0.463 mmol) were combined in dichloromethane (5 mL), and then 2 mL of acetic acid was added. The reaction was stirred at room temperature for 20 minutes, and then PS-cyanoborohydride (396 mg, 0.926 mmol) was added. The reaction was stirred at room temperature overnight, then filtered and the resin was washed with dichloromethane. The solvent was removed in vacuo, and the crude material was purified using a silica gel cartridge (Analogix®, Burlington, Wis., RS-25) eluting with 1-10% methanol (2 N ammonia)/dichloromethane to give the title compound: $^1$H NMR (500 MHz, pyridine-$d_5$) δ ppm 7.73 (s, 1H), 7.66 (d, J=7.7, 1H), 7.56 (s, 1H), 7.50 (t, J=7.7, 1H), 4.51-4.43 (m, 1H), 3.55 (d, J=12.9, 1H), 3.46 (d, J=12.9, 1H), 2.75 (d, J=8.6, 2H), 2.52-2.41 (m, J=8.5, 19.1, 2H), 2.34-2.29 (m, 1H), 2.20 (dd, J=7.7, 9.8, 1H), 2.14 (s, 3H, OAc), 1.96-1.54 (m, 15H), 1.49-1.05 (m, 12H), 1.03-0.93 (m, J=11.7, 21.1, 1H); MS (ESI+) m/z 491 (M+H)$^+$.

Example 55

2,2-dicyclohexyl-N-[(3aS,4S,6aR)-2-(2-fluorobenzyl)octahydrocyclopenta[c]pyrrol-4-yl]acetamide The title compound was prepared by substituting 2-fluorobenzaldehyde for 3-(trifluoromethyl)benzaldehyde in Example 54: $^1$H NMR (500 MHz, pyridine-$d_5$) δ ppm 7.55 (s, 1H), 7.36 (dt, J=6.6, 24.8, 2H), 7.20-7.15 (m, 2H), 4.44 (s, 1H), 3.68 (d, J=12.6, 1H), 3.44 (d, J=12.6, 1H), 2.77 (d, J=9.6, 1H), 2.64 (dd, J=7.5, 15.0, 1H), 2.53 (d, J=9.0, 1H), 2.49-2.40 (m, 1H), 2.29 (t, J=8.3, 1H), 2.16-2.09 (m, 1H), 1.98-1.64 (m, 12H), 1.61 (d, J=11.4, 2H), 1.55-1.37 (m, J=13.8, 20.5, 31.3, 3H), 1.34-1.08 (m, 9H), 1.00 (dd, J=13.4, 22.1, 1H); MS (ESI+) m/z 441 (M+H)$^+$.

Example 56

2,2-dicyclohexyl-N-[(3aS,4S,6aR)-2-(4-fluorobenzyl)octahydrocyclopenta[c]pyrrol-4-yl]acetamide The title compound was prepared by substituting 4-fluorobenzaldehyde for 3-(trifluoromethyl)benzaldehyde in Example 54: $^1$H NMR (500 MHz, pyridine-$d_5$) δ ppm 7.54 (d, J=6.0, 1H), 7.40-7.29 (m, 2H), 7.18 (d, J=8.7, 2H), 4.53-4.38 (m, 1H), 3.55 (d, J=12.5, 1H), 3.29 (d, J=12.6, 1H), 2.72 (dd, J=8.6, 17.7, 2H), 2.56-2.39 (m, 2H), 2.29 (t, J=8.3, 1H), 2.10 (t, J=8.1, 1H), 1.98-1.07 (m, 26H), 0.99 (dd, J=10.2, 22.0, 1H); MS (ESI+) m/z 441 (M+H)$^+$.

Example 57

2,2-dicyclohexyl-N-{(3aS,4S,6aR)-2-[4-fluoro-3-(trifluoromethyl)benzyl]octahydrocyclopenta[c]pyrrol-4-yl}acetamide The title compound was prepared by substituting 4-fluoro-3-(trifluoromethyl)benzaldehyde for 3-(trifluoromethyl)benzaldehyde in Example 54: $^1$H NMR (500 MHz, pyridine-$d_5$) δ ppm 7.69 (d, J=6.9, 1H), 7.56-7.54 (m, 1H), 7.36-7.28 (m, 1H), 4.52-4.42 (m, 1H), 3.53 (d, J=12.9, 1H), 3.39 (d, J=12.9, 1H), 2.85-2.68 (m, 2H), 2.53-2.41 (m, 2H), 2.34 (t, J=8.3, 1H), 2.24-2.16 (m, 1H), 1.96-1.56 (m, 16H), 1.49 (d, J=12.4, 1H), 1.44-1.05 (m, 10H), 1.05-0.94 (m, 1H); MS (ESI+) m/z 509 (M+H)$^+$.

Example 58

2,2-dicyclohexyl-N-{(3aS,4S,6aR)-2-[3-fluoro-4-(trifluoromethyl)benzyl]octahydrocyclopenta[c]pyrrol-4-yl}acetamide The title compound was prepared by substituting 3-fluoro-4-(trifluoromethyl)benzaldehyde for 3-(trifluoromethyl)benzaldehyde in Example 54: $^1$H NMR (400 MHz, pyridine-$d_5$) δ ppm 7.62 (d, J=7.5, 2H), 7.32 (d, J=11.8, 1H), 7.25 (d, J=8.0, 1H), 4.51-4.40 (m, 1H), 3.54 (d, J=13.5, 1H), 3.42 (d, J=13.5, 1H), 2.84 (dd, J=7.5, 16.5, 1H), 2.76 (dd, J=2.6, 9.5, 1H), 2.56-2.47 (m, 1H), 2.44 (dd, J=2.6, 8.8, 1H), 2.40-2.34 (m, 1H), 2.23 (dd, J=7.7, 9.3, 1H), 1.97-1.52 (m, 16H), 1.45-0.97 (m, J=14.9, 40.1, 72.1, 11H); MS (ESI+) m/z 509 (M+H)$^+$.

Example 59

N-{(3aS,4S,6aR)-2-[3,5-bis(trifluoromethyl)benzyl]octahydrocyclopenta[c]pyrrol-4-yl}-2,2-dicyclohexylacetamide The title compound was prepared by substituting 3,5-bis(trifluoromethyl)benzaldehyde for 3-(trifluoromethyl)benzaldehyde in Example 54: $^1$H NMR (500 MHz, pyridine-$d_5$) δ ppm 8.10 (s, 1H), 7.97 (s, 2H), 4.53-4.44 (m, 1H), 3.64-3.55 (m, 2H), 2.85-2.75 (m, 2H), 2.55-2.46 (m, 1H), 2.45-2.35 (m, 2H), 2.31 (t, J=8.3, 1H), 1.95-1.55 (m, 15H), 1.48 (d, J=12.6, 1H), 1.44-0.92 (m, 12H); MS (ESI+) m/z 559 (M+H)$^+$.

Example 60

2,2-dicyclohexyl-N-{(3aS,4S,6aR)-2-[2-(trifluoromethyl)benzyl]octahydrocyclopenta[c]pyrrol-4-yl}acetamide The title compound was prepared by substituting 2-(trifluoromethyl)benzaldehyde for 3-(trifluoromethyl)benzaldehyde in Example 54: $^1$H NMR (500 MHz, pyridine-$d_5$) δ ppm 7.74 (d, J=7.8, 1H), 7.64 (d, J=7.7, 1H), 7.55 (d, J=7.6, 1H), 7.43 (dd, J=7.0, 13.9, 2H), 4.51-4.43 (m, 1H), 3.82 (d, J=13.7, 1H), 3.54 (d, J=13.7, 1H), 2.81-2.70 (m, 2H), 2.53-2.43 (m, 2H), 2.35 (t, J=8.1, 1H), 2.23-2.17 (m, 1H), 1.95-1.68 (m, 10H), 1.67-1.52 (m, 5H), 1.46-1.04 (m, 11H), 0.97-0.86 (m, 1H); MS (ESI+) m/z 491 (M+H)$^+$.

Example 61

2,2-dicyclohexyl-N-[(3aS,4S,6aR)-2-(3-methylbenzyl)octahydrocyclopenta[c]pyrrol-4-yl]acetamide The title compound was prepared by substituting 3-methylbenzaldehyde for 3-(trifluoromethyl)benzaldehyde in Example 54: $^1$H NMR (500 MHz, pyridine-$d_5$) δ ppm 7.53 (d, J=5.8, 1H), 7.32 (t, J=7.5, 1H), 7.24-7.22 (m, 1H), 7.20-7.14 (m, 2H), 4.50-4.42 (m, 1H), 3.57 (d, J=12.4, 1H), 3.34 (d, J=12.3, 1H), 2.78 (d, J=9.4, 1H), 2.66 (dd, J=7.5, 15.1, 1H), 2.55 (d, J=8.8, 1H), 2.50-2.42 (m, 1H), 2.33 (s, 3H), 2.31-2.24 (m, 1H), 2.14-2.07 (m, 1H), 1.98-1.57 (m, 13H), 1.53 (ddd, J=6.4, 11.9, 18.4, 1H), 1.42 (t, J=10.0, 2H), 1.38-1.08 (m, 10H), 1.02-0.92 (m, 1H); MS (ESI+) m/z 437 (M+H)$^+$.

Example 62

2,2-dicyclohexyl-N-[(3aS,4S,6aR)-2-(4-methylbenzyl)octahydrocyclopenta[c]pyrrol-4-yl]acetamide The title compound was prepared by substituting 4-methylbenzaldehyde for 3-(trifluoromethyl)benzaldehyde in Example 54: $^1$H NMR (500 MHz, pyridine-$d_5$) δ ppm 7.54 (d, J=7.8, 1H), 7.30 (d, J=7.7, 2H), 7.21-7.18 (m, 2H), 4.49-4.42 (m, 1H), 3.58 (d, J=12.3, 1H), 3.31 (d, J=12.4, 1H), 2.77 (d, J=9.5, 1H), 2.66 (dd, J=8.3, 15.9, 1H), 2.54 (d, J=8.8, 1H), 2.50-2.41 (m, 1H), 2.32 (s, 3H), 2.30-2.23 (m, 2H), 2.11-2.03 (m, 1H), 1.99-1.58 (m, 13H), 1.57-1.08 (m, 12H), 1.03-0.90 (m, 1H); MS (ESI+) m/z 437 (M+H)$^+$.

Example 63

2,2-dicyclohexyl-N-{(3aS,4S,6aR)-2-[3-(trifluoromethoxy)benzyl]octahydrocyclopenta[c]pyrrol-4-yl}acetamide The title compound was prepared by substituting 3-(trifluoromethoxy)benzaldehyde for 3-(trifluoromethyl)benzaldehyde in Example 54: $^1$H NMR (500 MHz, pyridine-$d_5$) δ ppm 7.60 (d, J=7.3, 1H), 7.42 (t, J=7.9, 1H), 7.37 (s, 1H), 7.30 (dd, J=7.9, 16.8, 2H), 4.51-4.44 (m, 1H), 3.50 (d, J=13.0, 1H), 3.45 (d, J=13.0, 1H), 2.80-2.72 (m, J=4.8, 16.2, 2H), 2.51-2.42 (m, J=8.7, 2H), 2.29 (t, J=8.3, 1H), 2.20 (dd, J=7.2, 9.2, 1H), 1.96-1.89 (m, 2H), 1.89-1.78 (m, 4H), 1.77-1.65 (m, 5H), 1.64-1.51 (m, 4H), 1.42 (dd, J=9.4, 23.0, 1H), 1.36-1.09 (m, 10H), 1.08-0.98 (m, 1H); MS (ESI+) m/z 507 (M+H)$^+$.

Example 64

2,2-dicyclohexyl-N-[(3aS,4S,6aR)-2-(3-fluorobenzyl)octahydrocyclopenta[c]pyrrol-4-yl]acetamide The title compound was prepared by substituting 3-fluorobenzaldehyde for 3-(trifluoromethyl)benzaldehyde in Example 54: $^1$H NMR (500 MHz, pyridine-$d_5$) δ ppm 7.36 (dd, J=7.8, 13.9, 1H), 7.19-7.11 (m, 3H), 4.49-4.42 (m, 1H), 3.55 (d, J=12.8, 1H), 3.34 (d, J=12.8, 1H), 2.78-2.69 (m, J=8.0, 15.6, 2H), 2.51-2.43 (m, J=10.6, 2H), 2.29 (t, J=8.4, 1H), 2.13 (dd, J=7.2, 9.5, 1H), 1.97-1.77 (m, 7H), 1.77-1.64 (m, 5H), 1.63-1.47 (m, 4H), 1.42 (ddd, J=3.0, 12.2, 23.0, 1H), 1.33 (dd, J=9.7, 23.2, 1H), 1.29-1.08 (m, 8H), 1.02 (dd, J=11.8, 22.6, 1H); MS (ESI+) m/z 441 (M+H)$^+$.

Example 65

N-{(3aS,4S,6aR)-2-[3,3-bis(4-fluorophenyl)propyl]octahydrocyclopenta[c]pyrrol-4-yl}-2,2-dicyclohexylacetamide The title compound was prepared by substituting 3,3-bis(4-fluorophenyl)propanal for 3-(trifluoromethyl)benzaldehyde in Example 54: $^1$H NMR (500 MHz, pyridine-$d_5$) δ ppm 7.77 (d, J=7.3, 1H), 7.39-7.31 (m, 4H), 7.20-7.13 (m, 4H), 4.58-4.50 (m, 1H), 4.13 (d, J=7.5, 1H), 2.85 (dd, J=2.2, 9.4, 1H), 2.74 (dd, J=7.2, 14.4, 1H), 2.47 (d, J=7.4, 2H), 2.38-2.26 (m, 4H), 2.22 (t, J=8.6, 1H), 2.12 (dd, J=7.4, 9.3, 1H), 1.98-1.90 (m, 4H), 1.90-1.82 (m, 2H), 1.82-1.76 (m, J=8.6, 2H), 1.76-1.66 (m, 5H), 1.65-1.57 (m, 3H), 1.47-1.33 (m, 3H), 1.30-1.18 (m, 4H), 1.18-1.03 (m, 4H); MS (ESI+) m/z 563 (M+H)$^+$.

Example 66

N-{(3aS,4S,6aR)-2-[6,6-bis(4-fluorophenyl)hexyl]octahydrocyclopenta[c]pyrrol-4-yl}-2,2-dicyclohexylacetamide The title compound was prepared by substituting 6,6-bis(4-fluorophenyl)hexanal for 3-(trifluoromethyl)benzaldehyde in Example 54: $^1$H NMR (500 MHz, pyridine-$d_5$) δ ppm 7.80 (d, J=6.7, 1H), 7.35 (ddd, J=2.1, 5.4, 7.9, 4H), 7.16 (td, J=3.1, 8.8, 4H), 4.56-4.47 (m, 1H), 3.99 (t, J=7.8, 1H), 2.82 (d, J=9.3, 1H), 2.65 (d, J=7.7, 1H), 2.49 (dd, J=8.5, 19.2, 2H), 2.30 (d, J=31.9, 2H), 2.16-2.01 (m, 4H), 1.99-1.68 (m, 11H), 1.67-1.57 (m, 2H), 1.57-1.04 (m, 14H); MS (ESI+) m/z 605 (M+H)$^+$.

Example 67

N-{(3aS,4S,6aR)-2-[3-(3-chlorophenyl)propyl]octahydrocyclopenta[c]pyrrol-4-yl}-2,2-dicyclohexylacetamide The title compound was prepared by substituting 3-(3-chlorophenyl)propanal for 3-(trifluoromethyl)benzaldehyde in Example 54: $^1$H NMR (500 MHz, pyridine-$d_5$) δ ppm 7.87 (s, 1H), 7.31 (d, J=13.4, 2H), 7.27 (t, J=7.6, 1H), 7.13 (d, J=7.3, 1H), 4.57-4.49 (m, 1H), 2.86 (d, J=8.6, 1H), 2.74 (dd, J=7.3, 14.6, 1H), 2.62 (dd, J=7.0, 15.3, 2H), 2.53-2.45 (m, J=6.7, 2H), 2.39-2.32 (m, J=6.1, 2H), 2.23 (t, J=8.0, 1H), 2.01-1.68 (m, 16H), 1.65-1.56 (m, 3H), 1.48-1.33 (m, 3H), 1.32-1.18 (m, 4H), 1.17-1.04 (m, J=12.5, 25.1, 4H); MS (ESI+) m/z 485 (M+H)$^+$.

Example 68

2,2-dicyclohexyl-N-{(3aS,4S,6aR)-2-[3-(3-fluorophenyl)propyl]octahydrocyclopenta[c]pyrrol-4-yl}acetamide The title compound was prepared by substituting 3-(3-fluorophenyl)propanal for 3-(trifluoromethyl)benzaldehyde in Example 54: $^1$H NMR (500 MHz, pyridine-$d_5$) δ ppm 7.81 (d, J=3.1, 1H), 7.31 (dd, J=7.3, 14.5, 1H), 7.10-7.02 (m, J=11.5, 3H), 4.60-4.46 (m, 1H), 2.85 (d, J=8.2, 1H), 2.76-2.59 (m, 3H), 2.55-2.43 (m, 2H), 2.41-2.28 (m, 2H), 2.25-2.16 (m, 1H), 2.15-2.06 (m, 1H), 2.00-1.90 (m, 4H), 1.89-1.67 (m, J=37.4, 11H), 1.67-1.54 (m, 3H), 1.49-1.33 (m, 3H), 1.30-1.18 (m, J=10.6, 4H), 1.17-1.05 (m, 4H); MS (ESI+) m/z 469 (M+H)$^+$.

Example 69

2,2-dicyclohexyl-N-[(3aS,4S,6aR)-2-(3-phenylpropyl)octahydrocyclopenta[c]pyrrol-4-yl]acetamide The title compound was prepared by substituting 3-phenylpropanal for 3-(trifluoromethyl)benzaldehyde in Example 54: $^1$H NMR (500 MHz, pyridine-$d_5$) δ ppm 7.83 (d, J=5.1, 1H), 7.38 (t, J=7.6, 2H), 7.28 (d, J=7.4, 3H), 4.57-4.48 (m, 1H), 2.85 (d, J=8.7, 1H), 2.75-2.61 (m, 3H), 2.48 (dd, J=8.7, 19.0, 2H), 2.35 (dd, J=7.0, 17.3, 2H), 2.17 (t, J=7.8, 1H), 2.12-2.07 (m, 1H), 1.93 (dd, J=8.6, 14.2, 4H), 1.89-1.75 (m, 7H), 1.71 (d, J=10.9, 4H), 1.65-1.53 (m, J=6.0, 14.1, 3H), 1.49-1.32 (m, 3H), 1.30-1.18 (m, 4H), 1.17-1.04 (m, J=9.5, 21.4, 4H); MS (ESI+) m/z 451 (M+H)$^+$.

Example 70

2,2-dicyclohexyl-N-((3aS,4S,6aR)-2-{3-[4-(trifluoromethyl)phenyl]propyl}octahydrocyclopenta[c]pyrrol-4-yl)acetamide The title compound was prepared by substituting 3-(4-(trifluoromethyl)phenyl)propanal for 3-(trifluoromethyl)benzaldehyde in Example 54: $^1$H NMR (500 MHz, pyridine-$d_5$) δ ppm 7.82 (d, J=7.1, 1H), 7.67 (d, J=8.1, 2H), 7.36 (d, J=8.1, 2H), 4.57-4.50 (m, 1H), 2.85 (d, J=9.5, 1H), 2.70 (tt, J=7.0, 14.1, 3H), 2.49 (d, J=7.5, 2H), 2.35 (t, J=6.4, 2H), 2.22 (t, J=8.5, 1H), 2.16-2.09 (m, 1H), 1.98-1.89 (m, 4H), 1.89-1.74 (m, 7H), 1.70 (d, J=8.5, 4H), 1.60 (dd, J=4.9, 12.1, 3H), 1.41 (dt, J=9.0, 20.3, 3H), 1.30-1.17 (m, 4H), 1.10 (dt, J=10.4, 12.0, 4H); MS (ESI+) m/z 519 (M+H)$^+$.

Example 71

2,2-dicyclohexyl-N-{(3aS,4S,6aR)-2-[3-(4-fluorophenyl)propyl]octahydrocyclopenta[c]pyrrol-4-yl}acetamide The title compound was prepared by substituting 3-(4-fluorophenyl)propanal for 3-(trifluoromethyl)benzaldehyde in Example 54: $^1$H NMR (500 MHz, pyridine-$d_5$) δ ppm 7.94-7.77 (m, 1H), 7.25-7.20 (m, 2H), 7.14 (t, J=8.7, 2H), 4.61-4.47 (m, 1H), 2.93-2.80 (m, 1H), 2.79-2.69 (m, 1H), 2.62 (dd, J=7.6, 15.5, 2H), 2.55-2.44 (m, 2H), 2.43-2.29 (m, 2H), 2.27-2.08 (m, 2H), 2.02-1.90 (m, 4H), 1.89-1.75 (m, 7H), 1.70 (d, J=11.2, 4H), 1.60 (d, J=6.9, 3H), 1.49-1.32 (m, 3H), 1.30-1.17 (m, 4H), 1.12 (dd, J=12.0, 24.1, 4H); MS (ESI+) m/z 469 (M+H)$^+$.

Example 72

2,2-dicyclohexyl-N-[(3aS,4S,6aR)-2-(pyridin-4-ylmethyl)octahydrocyclopenta[c]pyrrol-4-yl]acetamide The title compound was prepared by substituting isonicotinaldehyde for 3-(trifluoromethyl)benzaldehyde in Example 54: $^1$H NMR (500 MHz, pyridine-$d_5$) δ ppm 8.76 (d, J=5.7, 2H), 7.75-7.69 (m, 1H), 7.31 (d, J=5.5, 2H), 4.48 (dd, J=6.9, 13.1, 1H), 3.47 (d, J=13.5, 1H), 3.39 (d, J=13.5, 1H), 2.87-2.75 (m, J=9.2, 21.0, 2H), 2.53-2.45 (m, 1H), 2.43 (d, J=9.0, 1H), 2.34 (t, J=8.3, 1H), 2.26-2.20 (m, 1H), 1.97-1.87 (m, 4H), 1.87-1.76 (m, 4H), 1.75-1.64 (m, J=6.5, 12.2, 17.6, 5H), 1.63-1.56 (m, J=13.2, 3H), 1.43 (d, J=10.1, 22.9, 1H), 1.35 (dd, J=5.6, 12.1, 1H), 1.30-1.18 (m, J=12.4, 24.4, 4H), 1.17-1.08 (m, J=10.1, 19.2, 4H), 1.09-0.99 (m, 1H); MS (ESI+) m/z 424 (M+H)$^+$.

Example 73

2,2-dicyclohexyl-N-[(3aS,4S,6aR)-2-(pyridin-3-ylmethyl)octahydrocyclopenta[c]pyrrol-4-yl]acetamide The title compound was prepared by substituting nicotinaldehyde for 3-(trifluoromethyl)benzaldehyde in Example 54: $^1$H NMR (500 MHz, pyridine-$d_5$) δ ppm 8.80 (d, J=1.7, 1H), 7.64 (d, J=6.4, 2H), 7.30 (dd, J=4.8, 7.7, 1H), 4.49-4.41 (m, 1H), 3.54 (d, J=12.9, 1H), 3.35 (d, J=12.8, 1H), 2.80-2.71 (m, J=7.7, 2H), 2.51-2.42 (m, J=8.7, 2H), 2.31 (t, J=8.3, 1H), 2.16 (t, J=8.8, 1H), 1.91 (dd, J=6.4, 11.9, 2H), 1.86-1.64 (m, 10H), 1.57 (dd, J=11.4, 24.2, 4H), 1.42 (d, J=12.8, 1H), 1.35-1.08 (m, 10H), 1.03 (d, J=14.0, 1H); MS (ESI+) m/z 424 (M+H)$^+$.

Example 74

2,2-dicyclohexyl-N-[(3aS,4R,6aR)-octahydrocyclopenta[c]pyrrol-4-yl]acetamide

The title compound was prepared by substituting N-[(3aS,4R,6aR)-2-benzyloctahydrocyclopenta[c]pyrrol-4-yl]-2,2-dicyclohexylacetamide from Example 20 for N-[(3aS,4S,6aR)-2-benzyloctahydrocyclopenta[c]pyrrol-4-yl]-2,2-dicyclohexylacetamide in Example 53: $^1$H NMR (300 MHz, CDCl$_3$) δ ppm 5.31 (d, J=7.5, 1H), 3.97-3.82 (m, 1H), 3.09-2.85 (m, 3H), 2.66 (dd, J=3.7, 12.5, 2H), 2.40-2.26 (m, 1H), 2.10-1.80 (m, 6H), 1.79-1.53 (m, 11H), 1.52-1.30 (m, J=21.5, 31.0, 2H), 1.29-1.03 (m, 7H), 0.93 (dd, J=11.9, 23.1, 2H); MS (ESI+) m/z 333 (M+H)$^+$.

Example 75

2,2-dicyclohexyl-N-{(3aS,4R,6aR)-2-[3-(trifluoromethyl)benzyl]octahydrocyclopenta[c]pyrrol-4-yl}acetamide The title compound was prepared by substituting 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (400 MHz, pyridine-$d_5$) δ ppm 8.07 (d, J=7.2, 1H), 7.75 (s, 1H), 7.63-7.54 (m, 2H), 7.43 (t, J=7.8, 1H), 4.51-4.42 (m, 1H), 3.61 (d, J=13.6, 1H), 3.46 (d, J=13.5, 1H), 2.87 (dd, J=2.4, 8.9, 1H), 2.64-2.52 (m, 2H), 2.52-2.46 (m, 1H), 2.30 (s, 2H), 2.18-2.08 (m, 1H), 2.03 (t, J=7.3, 1H), 1.99-1.76 (m, 7H), 1.75-1.55 (m, 7H), 1.51-1.35 (m, 3H), 1.31-1.03 (m, 8H); MS (ESI+) m/z 491 (M+H)$^+$.

Example 76

2,2-dicyclohexyl-N-{(3aS,4R,6aR)-2-[3-fluoro-4-(trifluoromethyl)benzyl]octahydrocyclopenta[c]pyrrol-4-yl}acetamide The title compound was prepared by substituting 3-fluoro-4-(trifluoromethyl)benzaldehyde for 3-(trifluoromethyl)benzaldehyde and 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.16 (d, J=7.3, 1H), 7.59 (d, J=10.3, 1H), 7.33 (d, J=11.7, 1H), 7.28 (d, J=8.0, 1H), 4.52-4.44 (m, 1H), 3.56 (d, J=14.2, 1H), 3.45 (d, J=14.2, 1H), 2.92 (dd, J=1.8, 8.9, 1H), 2.63-2.52 (m, J=11.3, 2H), 2.43 (dd, J=6.9, 8.8, 1H), 2.34 (dd, J=2.0, 9.0, 1H), 2.29-2.23 (m, 1H), 2.13 (dq, J=5.9, 11.8, 1H), 2.04 (t, J=7.4, 1H), 2.00-1.84 (m, 5H), 1.80 (d, J=12.4, 2H), 1.76-1.56 (m, 7H), 1.46 (dd, J=10.4, 23.5, 3H), 1.30-1.18 (m, 4H), 1.17-1.05 (m, 4H); MS (ESI+) m/z 509 (M+H)$^+$.

Example 77

N-{(3aS,4R,6aR)-2-[3,5-bis(trifluoromethyl)benzyl]octahydrocyclopenta[c]pyrrol-4-yl}-2,2-dicyclohexylacetamide The title compound was prepared by substituting 3,5-bis(trifluoromethyl)benzaldehyde for 3-(trifluoromethyl)benzaldehyde and 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.16 (d, J=7.1, 1H), 7.99 (s, 3H), 4.50-4.42 (m, 1H), 3.69 (d, J=13.9, 1H), 3.54 (d, J=13.9, 1H), 2.92 (dd, J=2.7, 9.0, 1H), 2.65-2.56 (m, J=10.2, 15.6, 2H), 2.55-2.50 (m, 1H), 2.31 (d, J=4.2, 2H), 2.10 (dq, J=5.9, 11.8, 1H), 2.03 (t, J=7.4, 1H), 1.99-1.83 (m, 5H), 1.80 (d, J=12.4, 2H), 1.75-1.64 (m, J=12.4, 18.4, 5H), 1.63-1.56 (m, J=8.7, 2H), 1.44 (td, J=7.6, 21.0, 3H), 1.31-1.16 (m, 4H), 1.16-1.04 (m, 4H); MS (ESI+) m/z 559 (M+H)$^+$.

Example 78

N-{(3aS,4R,6aR)-2-[6,6-bis(4-fluorophenyl)hexyl]octahydrocyclopenta[c]pyrrol-4-yl}-2,2-dicyclohexylacetamide The title compound was prepared by substituting 6,6-bis(4-fluorophenyl)hexanal for 3-(trifluoromethyl)benzaldehyde and 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.14 (d, J=7.3, 1H), 7.33 (dd, J=5.6, 8.5, 4H), 7.14 (t, J=8.7, 4H), 4.52-4.44 (m, 1H), 3.96 (t, J=7.8, 1H), 2.94 (d, J=8.8, 1H), 2.58 (s, 2H), 2.42 (d, J=8.1, 2H), 2.31 (d, J=22.9, 3H), 2.17-2.09 (m, 1H), 2.08-1.85 (m, 8H), 1.85-1.77 (m, 2H), 1.76-1.64 (m, 5H), 1.61 (d, J=12.0, 2H), 1.52-1.42 (m, 5H), 1.41-1.34 (m, 2H), 1.31-1.19 (m, 5H), 1.18-1.07 (m, 5H); MS (ESI+) m/z 605 (M+H)$^+$.

Example 79

2,2-dicyclohexyl-N-[(3aS,4R,6aR)-2-(3,3-diphenylpropyl)octahydrocyclopenta[c]pyrrol-4-yl]acetamide The title compound was prepared by substituting 3,3-diphenylpropanol for 3-(trifluoromethyl)benzaldehyde and 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.10 (d, J=7.7, 1H), 7.45 (d, J=7.3, 2H), 7.42 (d, J=7.1, 3H), 7.38-7.30 (m, 5H), 4.56-4.48 (m, 1H), 4.27 (t, J=7.5, 1H), 2.92-2.86 (m, 1H), 2.59-2.48 (m, J=6.7, 14.0, 2H), 2.38-2.26 (m, 5H), 2.21-2.12 (m, 2H), 2.05 (t, J=7.4, 1H), 1.97 (dd, J=8.3, 17.0, 2H), 1.94-1.85 (m, 4H), 1.81 (d, J=11.8, 2H), 1.72 (d, J=13.2, 4H), 1.66 (dd, J=7.4, 11.8, 1H), 1.61 (d, J=12.6, 2H), 1.48 (ddd, J=3.4, 12.8, 15.5, 3H), 1.30-1.19 (m, 4H), 1.19-1.06 (m, 4H); MS (ESI+) m/z 527 (M+H)$^+$.

Example 80

N-{(3aS,4R,6aR)-2-[3,3-bis(4-fluorophenyl)propyl]octahydrocyclopenta[c]pyrrol-4-yl}-2,2-dicyclohexylacetamide The title compound was prepared by substituting 3,3-bis(4-fluorophenyl)propanal for 3-(trifluoromethyl)benzaldehyde and 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.13 (s, 1H), 7.41 (dd, J=5.5, 8.7, 2H), 7.35 (dd, J=5.1, 13.8, 3H), 7.14 (dt, J=8.8, 14.7, 4H), 4.60-4.51 (m, J=21.3, 1H), 4.30 (t, J=7.7, 1H), 2.95 (d, J=8.9, 1H), 2.57-2.51 (m, 2H), 2.40 (d, J=8.7, 1H), 2.30 (d, J=7.0, 3H), 2.26-2.12 (m, 4H), 2.05 (t, J=7.4, 1H), 2.02-1.94 (m, J=12.5, 2H), 1.94-1.85 (m, J=6.7, 18.0, 2H), 1.82 (d, J=11.7, 2H), 1.72 (d, J=11.8, 4H), 1.67-1.57 (m, J=10.6, 16.3, 3H), 1.48 (qd, J=3.3, 12.7, 3H), 1.25 (dd, J=15.5, 28.8, 4H), 1.13 (t, J=18.3, 4H); MS (ESI+) m/z 563 (M+H)$^+$.

Example 81

N-{(3aS,4R,6aR)-2-[4,4-bis(4-fluorophenyl)butyl]octahydrocyclopenta[c]pyrrol-4-yl}-2,2-dicyclohexylacetamide The title compound was prepared by substituting 4,4-bis(4-fluorophenyl)butanal for 3-(trifluoromethyl)benzaldehyde and 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.12 (d, J=7.5, 1H), 7.36 (ddd, J=5.5, 8.6, 16.2, 4H), 7.17 (t, J=8.8, 2H), 7.11 (t, J=8.8, 2H), 4.52-4.45 (m, 1H), 3.99 (t, J=7.9, 1H), 2.91 (d, J=9.1, 1H), 2.59-2.50 (m, 2H), 2.36 (t, J=7.1, 3H), 2.24-2.16 (m, J=6.6, 13.0, 2H), 2.14-2.02 (m, J=9.6, 17.5, 3H), 2.02-1.86 (m, J=9.2, 27.4, 5H), 1.81 (t, J=10.7, 2H), 1.73 (d, J=9.6, 4H), 1.68-1.57 (m, J=13.6, 3H), 1.53-1.37 (m, 6H), 1.31-1.19 (m, J=11.2, 23.8, 4H), 1.18-1.07 (m, J=10.5, 22.1, 4H); MS (ESI+) m/z 577 (M+H)$^+$.

Example 82

3-methyl-2-phenyl-N-{(3aS,4R,6aR)-2-[3-(trifluoromethyl)benzyl]octahydrocyclopenta[c]pyrrol-4-yl}butanamide Step A: 3-Methyl-N-[(3aS,4R,6aR)-octahydrocyclopenta[c]pyrrol-4-yl]-2-phenylbutanamide was prepared by substituting N-[(3aS,4R,6aR)-2-benzyloctahydrocyclopenta[c]pyrrol-4-yl]-3-methyl-2-phenylbutanamide from Example 18 for N-[(3aS,4S,6aR)-2-benzyloctahydrocyclopenta[c]pyrrol-4-yl]-2,2-dicyclohexylacetamide in the procedure described for Example 53: $^1$H NMR (300 MHz, CDCl$_3$) δ ppm 7.31 (dd, J=1.5, 6.6, 2H), 5.50-5.38 (m, J=3.8, 9.7, 1H), 3.84 (dd, J=4.1, 13.5, 1H), 2.92 (ddd, J=10.1, 15.8, 20.7, 3H), 2.76 (dt, J=3.7, 11.5, 2H), 2.65-2.53 (m, J=7.9, 12.1, 3H), 2.47-2.25 (m, J=9.8, 17.7, 31.5, 2H), 2.20-2.07 (m, J=9.3, 17.5, 1H), 2.05-1.80 (m, 2H), 1.53-1.39 (m, 1H), 1.27 (s, 2H), 1.03 (dd, J=3.4, 6.5, 3H), 0.70 (d, J=6.7, 3H); MS (ESI+) m/z 287 (M+H)+.

Step B: The title compound was prepared by substituting 3-methyl-N-[(3aS,4R,6aR)-octahydrocyclopenta[c]pyrrol-4-yl]-2-phenylbutanamide from Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.60 (t, J=7.9, 1H), 7.73 (d, J=26.6, 1H), 7.63 (dd, J=2.0, 7.5, 1H), 7.57-7.52 (m, 2H), 7.43 (dd, J=7.7, 17.9, 1H), 7.33 (td, J=4.1, 7.5, 2H), 7.26 (dt, J=3.6, 7.2, 1H), 4.38-4.28 (m, 1H), 3.60 (d, J=13.6, 0.5H), 3.52 (d, J=13.5, 0.5H), 3.46 (d, J=13.6, 0.5H), 3.35 (d, J=13.5, 0.5H), 3.22 (dd, J=1.4, 10.4, 1H), 2.90 (dd, J=3.0, 9.1, 0.5H), 2.70-2.60 (m, J=5.3, 11.8, 1H), 2.59-2.53 (m, 1H), 2.52-2.46 (m, 1H), 2.44-2.32 (m, 1H), 2.28 (d, J=9.1, 0.5H), 2.25 (d, J=5.1, 1H), 2.20 (dd, J=2.4, 4.7, 1H), 2.13-2.07 (m, 1.5H), 1.92-1.80 (m, 1H), 1.75 (dt, J=6.3, 18.8, 0.5H), 1.71-1.64 (m, 0.5H), 1.47-1.39 (m, 0.5H), 1.39-1.32 (m, 0.5H), 1.32-1.24 (m, J=4.2, 16.6, 0.5H), 1.20 (dd, J=4.3, 6.4, 3H), 0.70 (d, J=6.7, 3H); MS (ESI+) m/z 445 (M+H)+.

Example 83

N-[(3aR,4S,6aS)-2-(cyclohexylmethyl)octahydrocyclopenta[c]pyrrol-4-yl]-3-methyl-2-phenylbutanamide Step A: 3-Methyl-N-[(3aR,4S,6aS)-octahydrocyclopenta[c]pyrrol-4-yl]-2-phenylbutanamide was prepared by substituting N-[(3aR,4S,6aS)-2-benzyloctahydrocyclopenta[c]pyrrol-4-yl]-3-methyl-2-phenylbutanamide from Example 35 for N-[(3aS,4S,6aR)-2-benzyloctahydrocyclopenta[c]pyrrol-4-yl]-2,2-dicyclohexylacetamide in Example 53: $^1$H NMR (500 MHz, pyridine-$d_5$) δ ppm 8.61 (d, J=6.9, 1H), 7.65 (dd, J=4.6, 6.9, 2H), 7.34 (t, J=7.5, 2H), 7.26 (t, J=7.3, 1H), 4.24 (tt, J=6.2, 12.6, 1H), 3.23 (d, J=10.4, 1H), 3.19 (dd, J=2.7, 10.8, 0.5H), 2.99 (dd, J=7.2, 10.9, 0.5H), 2.84-2.72 (m, 2H), 2.70-2.61 (m, 1H), 2.58 (dd, J=2.8, 10.7, 0.5H), 2.53 (dd, J=3.3, 10.5, 1H), 2.49-2.44 (m, 0.5H), 2.43-2.35 (m, J=10.5, 0.5H), 2.35-2.28 (m, J=12.5, 0.5H), 2.06 (dq, J=6.1, 12.2, 0.5H), 1.91-1.72 (m, 1.5H), 1.66 (dt, J=7.2, 19.4, 0.5H), 1.42 (dd, J=7.9, 19.3, 0.5H), 1.30-1.13 (m, 4H), 0.71 (d, J=6.7, 3H); MS (ESI+) m/z 287 (M+H)+.

Step B: The title compound was prepared by substituting cyclohexanecarbaldehyde for 3-(trifluoromethyl)benzaldehyde and 3-methyl-N-[(3aR,4S,6aS)-octahydrocyclopenta[c]pyrrol-4-yl]-2-phenylbutanamide from Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (dd, J=7.0, 10.9, 1H), 7.64 (dd, J=4.9, 7.0, 2H), 7.34 (t, J=7.6, 2H), 7.25 (t, J=7.4, 1H), 4.37-4.28 (m, 1H), 3.23 (d, J=10.4, 1H), 2.85 (dd, J=2.8, 9.0, 0.5H), 2.70-2.60 (m, 1H), 2.59-2.53 (m, J=4.6, 11.8, 0.5H), 2.51 (dd, J=3.1, 9.1, 1H), 2.44-2.38 (m, 1H), 2.37-2.32 (m, 0.5H), 2.31-2.28 (m, 0.5H), 2.27-2.08 (m, 3.5H), 2.08-1.99 (m, 1H), 1.93-1.73 (m, 3.5H), 1.73-1.54 (m, 3.5H), 1.47-1.27 (m, 2.5H), 1.22 (dd, J=6.5, 10.5, 3H), 1.19-1.06 (m, 3H), 0.90-0.75 (m, 2H), 0.71 (dd, J=2.2, 6.7, 3H); MS (ESI+) m/z 383 (M+H)+.

Example 84

3-methyl-N-[(3aR,4S,6aS)-2-methyloctahydrocyclopenta[c]pyrrol-4-yl]-2-phenylbutanamide The title compound was prepared by substituting formaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.55 (t, J=5.4, 1H), 7.65 (t, J=6.5, 2H), 7.34 (ddd, J=3.7, 7.6, 10.9, 2H), 7.29-7.25 (m, 1H), 4.42-4.28 (m, 1H), 3.22 (d, J=10.5, 1H), 2.91 (dd, J=2.2, 9.0, 0.5H), 2.65 (dt, J=6.7, 17.3, 1H), 2.53 (dd, J=2.5, 9.2, 1H), 2.46 (dd, J=4.4, 10.2, 0.5H), 2.42-2.35 (m, 0.5H), 2.30 (d, J=8.8, 1.5H), 2.25 (dd, J=2.8, 9.0, 0.5H), 2.19 (s, 1.5H), 2.16-2.05 (m, 3.5H), 1.85 (td, J=6.2, 12.0, 1H), 1.75 (dd, J=6.6, 13.8, 0.5H), 1.63 (dt, J=7.0, 15.3, 0.5H), 1.39 (dd, J=8.1, 14.4, 1H), 1.31 (dt, J=2.9, 9.4, 0.5H), 1.22 (dd, J=6.5, 11.7, 3H), 0.71 (dd, J=2.9, 6.7, 3H); MS (ESI+) m/z 301 (M+H)+.

Example 85

N-[(3aR,4S,6aS)-2-(2-fluorobenzyl)octahydrocyclopenta[c]pyrrol-4-yl]-3-methyl-2-phenylbutanamide The title compound was prepared by substituting 2-fluorobenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.66-8.58 (m, 1H), 7.63 (dd, J=3.1, 7.4, 2H), 7.53 (t, J=7.4, 1H), 7.33 (td, J=2.2, 7.6, 2H), 7.28-7.22 (m, J=7.4, 9.9, 2H), 7.17-7.06 (m, J=8.2, 14.8, 26.9, 2H), 4.34 (dd, J=6.0, 11.5, 1H), 3.75 (d, J=13.6, 0.5H), 3.71-3.62 (m, 1H), 3.57 (d, J=13.6, 0.5H), 3.22 (dd, J=2.2, 10.4, 1H), 3.00 (d, J=6.7, 0.5H), 2.69-2.48 (m, J=23.7, 34.8, 3H), 2.47-2.28 (m, 3.5H), 2.17-2.07 (m, 0.5H), 1.93-1.78 (m, J=6.7, 12.4, 20.1, 1H), 1.78-1.62 (m, 1H), 1.49-1.27 (m, J=10.3, 19.5, 26.3, 1.5H), 1.20 (dd, J=2.9, 6.4, 3H), 0.70 (dd, J=1.4, 6.6, 3H); MS (ESI+) m/z 395 (M+H)+.

Example 86

N-[(3aR,4S,6aS)-2-(3-chlorobenzyl)octahydrocyclopenta[c]pyrrol-4-yl]-3-methyl-2-phenylbutanamide The title compound was prepared by substituting 3-chlorobenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.62 (t, J=6.5, 1H), 7.64 (dd, J=4.3, 7.0, 2H), 7.51 (s, 0.5H), 7.46 (s, 0.5H), 7.33 (td, J=2.5, 7.5, 3H), 7.30-7.28 (m, 1H), 7.28-7.23 (m, 2H), 4.37-4.28 (m, 1H), 3.60 (d, J=13.4, 0.5H), 3.51 (d, J=13.4, 0.5H), 3.45 (d, J=13.4, 0.5H), 3.33 (d, J=13.4, 0.5H), 3.22 (dd, J=2.2, 10.4, 1H), 2.93 (d, J=6.3, 0.5H), 2.69-2.48 (m, 3H), 2.31 (dddd, J=8.9, 13.2, 14.5, 20.2, 3H), 2.16-2.05 (m, 1H), 1.92-1.79 (m, 1H), 1.78-1.62 (m, 1H), 1.49-1.40 (m, 0.5H), 1.37 (dd, J=5.8, 12.6, 0.5H), 1.30 (dd, J=7.2, 13.5, 0.5H), 1.20 (dd, J=3.0, 6.5, 3H), 0.70 (dd, J=1.5, 6.7, 3H); MS (ESI+) m/z 411 (M+H)+.

Example 87

N-[(3aR,4S,6aS)-2-(3-fluorobenzyl)octahydrocyclopenta[c]pyrrol-4-yl]-3-methyl-2-phenylbutanamide The title compound was prepared by substituting 3-fluorobenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.61 (t, J=8.0, 1H), 7.64 (dd, J=4.1, 7.0, 2H), 7.37-7.16 (m, 5H), 7.13 (d, J=7.6, 1H), 7.04 (s, 1H), 4.33 (dd, J=5.7, 12.4, 1H), 3.57 (d, J=13.5, 0.5H), 3.48 (d, J=13.4, 0.5H), 3.42 (d, J=13.5, 0.5H), 3.30 (d, J=13.5, 0.5H), 3.23 (d, J=10.5, 1H), 2.90 (dd, J=2.9, 9.1, 0.5H), 2.70-2.61 (m, 1H), 2.59-2.53 (m, 1H), 2.53-2.45 (m, 1H), 2.44-2.31 (m, J=18.5, 1H), 2.27 (t, J=7.7, 1H), 2.19 (dd, J=6.3, 13.0, 1H), 2.12 (dd, J=6.0, 12.3, 0.5H), 1.93-1.80 (m, J=6.9, 12.4, 20.6, 1H), 1.79-1.64 (m, 1H), 1.47-1.24 (m, 2H), 1.20 (dd, J=3.1, 6.4, 3H), 0.70 (d, J=6.7, 3H); MS (ESI+) m/z 395 (M+H)$^+$.

Example 88

3-methyl-2-phenyl-N-{(3aR,4S,6aS)-2-[3-(trifluoromethyl)benzyl]octahydrocyclopenta[c]pyrrol-4-yl}butanamide The title compound was prepared by substituting 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.60 (t, J=7.6, 1H), 7.76 (s, 0.5H), 7.71 (s, 0.5H), 7.64 (d, J=7.8, 2H), 7.57-7.53 (m, J=7.1, 2H), 7.43 (dd, J=7.8, 17.8, 1H), 7.36-7.30 (m, 2H), 7.28-7.23 (m, 1H), 4.33 (dd, J=5.8, 12.3, 1H), 3.61 (d, J=13.6, 0.5H), 3.53 (d, J=13.5, 0.5H), 3.47 (d, J=13.5, 0.5H), 3.36 (d, J=13.5, 0.5H), 3.22 (dd, J=1.5, 10.4, 1H), 2.91 (dd, J=3.0, 9.0, 0.5H), 2.69-2.59 (m, 1H), 2.55 (dd, J=3.0, 9.0, 1H), 2.52-2.47 (m, 1H), 2.44-2.32 (m, J=10.5, 32.1, 1H), 2.29 (d, J=8.9, 0.5H), 2.26 (d, J=5.2, 1H), 2.22-2.18 (m, 1H), 2.16-2.06 (m, 0.5H), 1.92-1.79 (m, 1H), 1.79-1.63 (m, 1H), 1.48-1.25 (m, 1.5H), 1.20 (dd, J=4.5, 6.4, 3H), 0.70 (d, J=5.8, 3H); MS (ESI+) m/z 445 (M+H)$^+$.

Example 89

N-[(3aR,4S,6aS)-2-(4-fluorobenzyl)octahydrocyclopenta[c]pyrrol-4-yl]-3-methyl-2-phenylbutanamide The title compound was prepared by substituting 4-fluorobenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.61 (t, J=7.2, 1H), 7.64 (dd, J=2.4, 7.5, 2H), 7.39 (dd, J=5.8, 8.2, 1H), 7.33 (dt, J=5.8, 11.6, 3H), 7.28-7.23 (m, 1H), 7.11 (dd, J=8.8, 19.1, 2H), 4.34 (dd, J=5.8, 12.6, 1H), 3.56 (d, J=13.3, 0.5H), 3.45 (dd, J=13.3, 16.8, 1H), 3.31 (d, J=13.1, 0.5H), 3.22 (dd, J=2.3, 10.5, 1H), 2.92 (d, J=6.5, 0.5H), 2.69-2.60 (m, 1H), 2.57 (d, J=6.6, 1H), 2.51 (d, J=8.4, 1H), 2.46-2.33 (m, 1H), 2.29 (d, J=4.4, 1H), 2.22 (d, J=6.5, 1H), 2.14 (dq, J=6.2, 12.2, 0.5H), 1.95-1.80 (m, J=7.1, 12.4, 20.7, 1H), 1.79-1.72 (m, 0.5H), 1.71-1.64 (m, 1H), 1.48-1.23 (m, 1.5H), 1.20 (t, J=6.1, 3H), 0.70 (dd, J=2.1, 6.7, 3H); MS (ESI+) m/z 395 (M+H)$^+$.

Example 90

N-[(3aR,4S,6aS)-2-(3-methoxybenzyl)octahydrocyclopenta[c]pyrrol-4-yl]-3-methyl-2-phenylbutanamide The title compound was prepared by substituting 3-methoxybenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.61-8.54 (m, 1H), 7.63 (d, J=7.6, 2H), 7.36-7.24 (m, J=5.6, 12.0, 20.6, 4H), 7.17 (s, 0.5H), 7.11 (s, 0.5H), 7.06 (d, J=7.8, 0.5H), 7.00 (d, J=7.5, 0.5H), 6.95-6.88 (m, 1H), 4.42-4.29 (m, 1H), 3.72 (s, 1.5H), 3.70 (s, 1.5H), 3.60 (d, J=13.3, 0.5H), 3.52 (d, J=13.2, 0.5H), 3.48 (d, J=13.3, 0.5H), 3.36 (d, J=13.2, 0.5H), 3.23-3.19 (m, 1H), 2.93 (dd, J=2.7, 9.0, 0.5H), 2.68-2.61 (m, 1H), 2.58 (dd, J=3.0, 8.9, 1H), 2.52-2.46 (m, 1H), 2.45-2.20 (m, 3H), 2.18-2.11 (m, 1H), 1.91 (dd, J=6.0, 12.0, 0.5H), 1.87-1.80 (m, 0.5H), 1.78-1.64 (m, 1H), 1.48-1.26 (m, J=28.4, 35.4, 1.5H), 1.20 (t, J=6.7, 3H), 0.70 (dd, J=2.8, 6.7, 3H); MS (ESI+) m/z 407 (M+H)$^+$.

Example 91

3-methyl-N-[(3aR,4S,6aS)-2-(3-methylbenzyl)octahydrocyclopenta[c]pyrrol-4-yl]-2-phenylbutanamide The title compound was prepared by substituting 3-methylbenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.62-8.50 (m, 1H), 7.64 (d, J=7.5, 2H), 7.33 (td, J=3.7, 7.5, 2H), 7.29-7.23 (m, J=5.5, 11.0, 3H), 7.18 (s, 1H), 7.07 (d, J=7.0, 1H), 4.42-4.29 (m, 1H), 3.60 (d, J=13.1, 0.5H), 3.51 (d, J=13.0, 0.5H), 3.45 (d, J=13.1, 0.5H), 3.33 (d, J=13.0, 0.5H), 3.22 (d, J=10.4, 1H), 2.90 (dd, J=2.9, 8.9, 0.5H), 2.64 (tt, J=6.8, 13.6, 1H), 2.59-2.46 (m, J=5.3, 12.0, 23.8, 2H), 2.44-2.34 (m, 1H), 2.30 (d, J=5.3, 1H), 2.28-2.23 (m, J=8.0, 4H), 2.13 (dt, J=6.3, 12.4, 1H), 1.94-1.78 (m, 1H), 1.78-1.64 (m, 1H), 1.48-1.25 (m, 1.5H), 1.20 (t, J=6.1, 3H), 0.70 (dd, J=1.9, 6.7, 3H); MS (ESI+) m/z 391 (M+H)$^+$.

Example 92

3-methyl-N-[(3aR,4S,6aS)-2-(2-methylbenzyl)octahydrocyclopenta[c]pyrrol-4-yl]-2-phenylbutanamide The title compound was prepared by substituting 2-methylbenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57-8.51 (m, 1H), 7.63 (dd, J=3.5, 7.1, 2H), 7.43-7.36 (m, 1H), 7.36-7.30 (m, 3H), 7.25 (dd, J=6.9, 9.6, 2H), 7.20-7.13 (m, J=10.0, 2H), 4.31 (dd, J=5.5, 11.3, 1H), 3.57 (d, J=13.1, 0.5H), 3.48 (d, J=13.0, 0.5H), 3.39 (d, J=13.0, 0.5H), 3.29 (d, J=13.0, 0.5H), 3.21 (d, J=10.3, 1H), 2.92 (dd, J=2.8, 9.0, 0.5H), 2.68-2.60 (m, 1H), 2.60-2.53 (m, 1H), 2.51-2.45 (m, 1H), 2.35 (s, 1.5H), 2.30 (s, 1.5H), 2.28-2.17 (m, 2H), 2.15-2.06 (m, 1H), 1.84 (ddd, J=6.8, 12.4, 20.0, 1H), 1.76-1.62 (m, 1H), 1.42 (dt, J=7.2, 19.2, 0.5H), 1.33 (dt, J=7.0, 12.5, 0.5H), 1.29-1.22 (m, 0.5H), 1.20 (d, J=6.5, 3H), 0.70 (d, J=6.7, 3H); MS (ESI+) m/z 391 (M+H)$^+$.

Example 93

N-[(3aR,4S,6aS)-2-(2,6-dimethylbenzyl)octahydrocyclopenta[c]pyrrol-4-yl]-3-methyl-2-phenylbutanamide The title compound was prepared by substituting 2,6-dimethylbenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.54-8.50 (m, J=6.7, 1H), 7.65-7.60 (m, 2H), 7.32 (t, J=7.1, 2H), 7.28-7.23 (m, 1H), 7.11 (dd, J=6.2, 14.3, 1H), 7.04 (t, J=8.3, 2H), 4.27-4.19 (m, 1H), 3.57 (d, J=12.5, 0.5H), 3.44 (dd, J=12.5, 15.5, 1H), 3.34 (d, J=12.5, 0.5H), 3.20 (d, J=10.4, 1H), 2.92 (d, J=5.9, 0.5H), 2.68-2.58 (m, J=10.2, 18.3, 1H), 2.55-2.51 (m, J=4.5, 1H), 2.48-2.42 (m, 0.5H), 2.39 (s, 3H), 2.34 (s, 3H), 2.32-2.18 (m, 3H), 2.07 (td, J=6.6, 12.6, 0.5H), 1.87-1.73 (m, 1H), 1.72-1.62 (m, 1H), 1.33 (dd, J=19.1, 78.6, 2.5H), 1.19 (dd, J=4.9, 6.3, 3H), 0.69 (d, J=6.6, 3H); MS (ESI+) m/z 405 (M+H)$^+$.

Example 94

N-[(3aR,4S,6aS)-2-(2-methoxybenzyl)octahydrocyclopenta[c]pyrrol-4-yl]-3-methyl-2-phenylbutanamide The title compound was prepared by substituting 2-methoxybenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (400 MHz, pyridine-$d_5$) δ ppm 8.50 (t, J=7.3, 1H), 7.62 (d, J=7.3, 2H), 7.55 (d, J=7.8, 1H), 7.32 (dq, J=3.8, 11.6, 2H), 7.25 (dd, J=3.6, 7.5, 2H), 7.04 (dt, J=7.4, 11.4, 1H), 6.89 (t, J=8.3, 1H), 4.43-4.31 (m, 1H), 3.80-3.57 (m, 5H), 3.21 (d, J=10.4, 1H), 2.99 (d, J=6.2, 0.5H), 2.61 (ddd, J=4.5, 12.6, 15.9, 2.5H), 2.52-2.45 (m, 0.5H), 2.45-2.31 (m, 3.5H), 2.19-2.09 (m, 0.5H), 2.00-1.80 (m, 1H), 1.72 (ddd, J=6.5, 12.3, 19.3, 1H), 1.47-1.25 (m, 2.5H), 1.20 (dd, J=3.0, 6.4, 3H), 0.70 (d, J=6.7, 3H); MS (ESI+) m/z 407 (M+H)$^+$.

Example 95

N-[(3aR,4S,6aS)-2-(4-tert-butylbenzyl)octahydrocyclopenta[c]pyrrol-4-yl]-3-methyl-2-phenylbutanamide The title compound was prepared by substituting 4-tert-butylbenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (dd, J=6.7, 11.0, 1H), 7.63 (dd, J=3.4, 7.1, 2H), 7.44-7.30 (m, 6H), 7.25 (t, J=7.4, 1H), 4.36 (tt, J=6.3, 12.6, 1H), 3.63 (d, J=13.1, 0.5H), 3.55 (d, J=13.0, 0.5H), 3.46 (d, J=13.0, 0.5H), 3.35 (d, J=13.0, 0.5H), 3.21 (d, J=10.4, 1H), 2.90 (dd, J=2.7, 8.7, 0.5H), 2.65 (dt, J=6.6, 16.9, 1H), 2.58-2.44 (m, 2H), 2.44-2.34 (m, 1H), 2.32 (d, J=8.6, 0.5H), 2.30 (d, J=5.2, 1H), 2.24 (d, J=5.0, 1H), 2.19-2.12 (m, 1H), 1.92 (dq, J=6.1, 12.1, 0.5H), 1.82 (td, J=7.3, 14.3, 0.5H), 1.70 (dq, J=8.1, 14.7, 1H), 1.48-1.30 (m, J=22.3, 41.1, 1H), 1.27 (s, J=1.6, 9H), 1.20 (dd, J=3.5, 6.4, 3H), 0.70 (d, J=6.4, 3H); MS (ESI+) m/z 433 (M+H)$^+$.

Example 96

N-[(3aR,4S,6aS)-2-(4-methoxybenzyl)octahydrocyclopenta[c]pyrrol-4-yl]-3-methyl-2-phenylbutanamide The title compound was prepared by substituting 4-methoxybenzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (dd, J=8.3, 10.9, 1H), 7.63 (dd, J=2.8, 7.4, 2H), 7.39-7.28 (m, 4H), 7.28-7.23 (m, 1H), 6.98 (dd, J=8.7, 10.2, 2H), 4.41-4.30 (m, 1H), 3.68 (s, 3H), 3.57 (d, J=12.9, 0.5H), 3.48 (d, J=12.9, 0.5H), 3.42 (d, J=12.9, 0.5H), 3.31 (d, J=12.8, 0.5H), 3.21 (d, J=10.4, 1H), 2.90 (dd, J=2.8, 8.9, 0.5H), 2.69-2.59 (m, 1H), 2.56 (dd, J=2.9, 9.0, 1H), 2.53-2.46 (m, 1H), 2.45-2.33 (m, 1H), 2.32-2.26 (m, J=10.0, 1H), 2.24 (t, J=5.2, 1H), 2.15 (dt, J=6.3, 12.3, 0.5H), 1.96-1.88 (m, 0.5H), 1.88-1.79 (m, 0.5H), 1.79-1.65 (m, 1H), 1.48-1.24 (m, J=19.9, 48.8, 3H), 1.20 (dd, J=4.3, 6.4, 3H), 0.70 (dd, J=2.0, 6.7, 2H); MS (ESI+) m/z 407 (M+H)$^+$.

Example 97

N-[(3aR,4S,6aS)-2-(3-cyanobenzyl)octahydrocyclopenta[c]pyrrol-4-yl]-3-methyl-2-phenylbutanamide The title compound was prepared by substituting 3-formylbenzonitrile for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.60 (t, J=7.1, 1H), 7.63 (d, J=5.9, 2H), 7.56-7.50 (m, 2H), 7.39-7.30 (m, 3H), 7.29-7.23 (m, J=8.9, 13.2, 2H), 4.32 (dd, J=5.7, 11.2, 1H), 3.53 (d, J=13.6, 0.5H), 3.44 (d, J=13.5, 0.5H), 3.40 (d, J=13.6, 0.5H), 3.28 (d, J=13.6, 0.5H), 3.21 (dd, J=1.3, 10.4, 1H), 2.90 (dd, J=2.8, 9.1, 0.5H), 2.64 (qd, J=6.6, 13.2, 1H), 2.59-2.47 (m, 1H), 2.46-2.37 (m, 1H), 2.37-2.30 (m, 0.5H), 2.26-2.20 (m, 1H), 2.19-2.13 (m, 1H), 2.10 (dt, J=6.2, 12.3, 0.5H), 1.89-1.79 (m, 1H), 1.75 (dt, J=6.1, 20.0, 0.5H), 1.66 (dt, J=7.0, 19.3, 0.5H), 1.47-1.38 (m, 0.5H), 1.38-1.23 (m, 2H), 1.20 (dd, J=3.6, 6.4, 3H), 0.70 (d, J=6.7, 3H); MS (ESI+) m/z 402 (M+H)$^+$.

Example 98

3-methyl-2-phenyl-N-{(3aR,4S,6aS)-2-[4-(trifluoromethyl)benzyl]octahydrocyclopenta[c]pyrrol-4-yl}butanamide The title compound was prepared by substituting 4-(trifluoromethyl)benzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.62 (t, J=7.8, 1H), 7.64 (dd, J=7.0, 11.8, 4H), 7.51 (d, J=8.0, 1H), 7.46 (d, J=7.9, 1H), 7.33 (dd, J=7.4, 12.1, 2H), 7.29-7.24 (m, 1H), 4.40-4.30 (m, 1H), 3.58 (d, J=13.7, 0.5H), 3.48 (t, J=13.8, 1H), 3.35 (d, J=13.7, 0.5H), 3.23 (dd, J=1.4, 10.4, 1H), 2.92 (dd, J=2.7, 9.0, 0.5H), 2.69-2.60 (m, 1H), 2.57 (dd, J=2.7, 9.1, 1H), 2.54-2.47 (m, 0.5H), 2.47-2.39 (m, 1H), 2.39-2.32 (m, 0.5H), 2.31-2.20 (m, 2H), 2.19-2.11 (m, 1H), 1.95-1.82 (m, J=6.4, 37.0, 1H), 1.77 (dt, J=6.4, 13.8, 0.5H), 1.69 (dt, J=6.9, 19.1, 0.5H), 1.50-1.25 (m, J=34.6, 62.0, 1.5H), 1.21 (t, J=6.4, 3H), 0.70 (d, J=5.1, 3H); MS (ESI+) m/z 445 (M+H)$^+$.

Example 99

3-methyl-2-phenyl-N-{(3aR,4S,6aS)-2-[2-(trifluoromethyl)benzyl]octahydrocyclopenta[c]pyrrol-4-yl}butanamide The title compound was prepared by substituting 2-(trifluoromethyl)benzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.61 (d, J=6.0, 1H), 7.93 (d, J=7.6, 0.5H), 7.85 (d, J=7.8, 0.5H), 7.63 (t, J=5.8, 3H), 7.53 (dd, J=7.9, 16.0, 1H), 7.38-7.23 (m, 5H), 4.36 (dd, J=5.7, 13.2, 1H), 3.76 (q, J=14.5, 1H), 3.66 (q, J=15.0, 1H), 3.23 (dd, J=2.2, 10.5, 1H), 3.03 (dd, J=2.2, 9.0, 0.5H), 2.69-2.60 (m, J=5.6, 17.6, 1H), 2.59-2.47 (m, 1H), 2.47-2.40 (m, J=10.2, 17.4, 1H), 2.39-2.12 (m, 3H), 1.96-1.82 (m, 1H), 1.78 (dt, J=6.2, 20.1, 0.5H), 1.68 (dt, J=7.2, 13.8, 0.5H), 1.48-1.24 (m, 1.5H), 1.20 (t, J=6.7, 3H), 0.70 (dd, J=1.7, 6.7, 3H); MS (ESI+) m/z 445 (M+H)$^+$.

Example 100

N-{(3aR,4S,6aS)-2-[4-fluoro-3-(trifluoromethyl)benzyl]octahydrocyclopenta[c]pyrrol-4-yl}-3-methyl-2-phenylbutanamide The title compound was prepared by substituting 4-fluoro-3-(trifluoromethyl)benzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.63 (t, J=7.0, 1H), 7.69 (d, J=6.3, 1H), 7.64 (d, J=7.6, 2H), 7.55-7.49 (m, 1H), 7.33 (dd, J=7.2, 13.6, 2H), 7.25 (dd, J=7.6, 15.5, 2H), 4.33 (dd, J=5.7, 11.4, 1H), 3.54 (d, J=13.5, 0.5H), 3.44 (t, J=14.0, 1H), 3.31 (d, J=13.4, 0.5H), 3.22 (d, J=10.4, 1H), 2.91 (dd, J=2.6, 9.0, 0.5H), 2.69-2.60 (m, J=7.5, 13.7, 1H), 2.55 (dd, J=3.1, 9.1, 1H), 2.53-2.39 (m, 2H), 2.38-2.32 (m, J=8.0, 0.5H), 2.29-2.21 (m, 1H), 2.19 (d, J=4.0, 1H), 2.12 (dd, J=6.1, 12.1, 0.5H), 1.91-1.81 (m, J=10.9, 16.7, 1H), 1.77 (dt, J=6.3, 19.8, 0.5H), 1.68 (td, J=7.0, 14.0, 0.5H), 1.44 (dt, J=7.6, 14.7, 0.5H), 1.40-1.25 (m, 1H), 1.20 (t, J=5.7, 3H), 0.70 (d, J=6.4, 3H); MS (ESI+) m/z 463 (M+H)$^+$.

Example 101

N-{(3aR,4S,6aS)-2-[3-fluoro-4-(trifluoromethyl)benzyl]octahydrocyclopenta[c]pyrrol-4-yl}-3-methyl-2-phenylbutanamide The title compound was prepared by substituting 3-fluoro-4-(trifluoromethyl)benzaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.63 (t, J=6.6, 1H), 7.64 (dd, J=3.0, 7.5, 2H), 7.37-7.30 (m, 3H), 7.30-7.23 (m, 3H), 4.38-4.30 (m, 1H), 3.56 (d, J=14.1, 0.5H), 3.46 (t, J=13.4, 1H), 3.33 (d, J=14.1, 0.5H), 3.23 (d, J=10.4, 1H), 2.94 (dd, J=2.5, 9.0, 0.5H), 2.65 (dt, J=6.2, 10.9, 1H), 2.58 (dd, J=2.8, 9.2, 1H), 2.54-2.48 (m, 0.5H), 2.47-2.39 (m, 1H), 2.39-2.32 (m, 0.5H), 2.28 (dd, J=2.7, 8.9, 0.5H), 2.26-2.20 (m, 1H), 2.19-2.09 (m, 1H), 1.87 (ddd, J=6.4, 12.3, 18.7, 1H), 1.78 (dt, J=6.2, 19.6, 0.5H), 1.68 (dt, J=7.5, 14.6, 0.5H), 1.49-1.24 (m, 2H), 1.21 (dd, J=4.3, 6.2, 3H), 0.70 (d, J=6.7, 3H); MS (ESI+) m/z 463 (M+H)$^+$.

Example 102

3-methyl-2-phenyl-N-[(3aR,4S,6aS)-2-(thien-2-ylmethyl)octahydrocyclopenta[c]pyrrol-4-yl]butanamide The title compound was prepared by substituting thiophene-2-carbaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.62-8.53 (m, 1H), 7.63 (dd, J=4.4, 7.0, 2H), 7.33 (t, J=7.6, 3H), 7.28-7.23 (m, 1H), 6.98 (dd, J=4.8, 9.3, 1H), 6.94 (d, J=3.0, 1H), 4.33 (dd, J=7.7, 13.5, 1H), 3.77 (d, J=13.7, 0.5H), 3.68 (dd, J=4.6, 13.7, 1H), 3.57 (d, J=13.7, 0.5H), 3.21 (d, J=10.4, 1H), 2.94 (d, J=8.5, 0.5H), 2.69-2.44 (m, 3H), 2.44-2.28 (m, 3H), 2.28-2.22 (m, 0.5H), 2.18-2.09 (m, 0.5H), 1.90 (td, J=6.1, 12.1, 0.5H), 1.86-1.79 (m, 0.5H), 1.78-1.63 (m, 1H), 1.47-1.35 (m, 1H), 1.32 (dd, J=7.1, 13.2, 0.5H), 1.20 (dd, J=2.0, 6.4, 3H), 0.70 (d, J=6.7, 3H); MS (ESI+) m/z 383 (M+H)$^+$.

Example 103

3-methyl-2-phenyl-N-[(3aR,4S,6aS)-2-(pyridin-4-ylmethyl)octahydrocyclopenta[c]pyrrol-4-yl]butanamide The title compound was prepared by substituting isonicotinaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.70 (d, J=5.9, 2H), 8.62 (s, 1H), 7.64 (dd, J=3.0, 7.5, 2H), 7.36-7.30 (m, 2H), 7.25 (dd, J=7.0, 12.4, 3H), 4.39-4.30 (m, 1H), 3.51 (d, J=14.2, 0.5H), 3.41 (dd, J=11.5, 14.2, 1H), 3.28 (d, J=14.3, 0.5H), 3.23 (dd, J=1.8, 10.5, 1H), 2.94 (dd, J=2.6, 9.2, 0.5H), 2.69-2.60 (m, 1H), 2.57 (dd, J=2.9, 9.2, 1H), 2.52-2.46 (m, 0.5H), 2.42 (dd, J=7.2, 8.8, 1H), 2.38-2.31 (m, 0.5H), 2.28 (dd, J=2.7, 9.0, 0.5H), 2.24-2.18 (m, 1H), 2.17-2.11 (m, 1H), 1.95-1.82 (m, 1H), 1.77 (dt, J=5.8, 12.3, 0.5H), 1.73-1.64 (m, 0.5H), 1.49-1.25 (m, 2H), 1.23-1.17 (m, 3H), 0.70 (d, J=6.5, 3H); MS (ESI+) m/z 378 (M+H)$^+$.

Example 104

3-methyl-2-phenyl-N-[(3aR,4S,6aS)-2-(2-phenylethyl)octahydrocyclopenta[c]pyrrol-4-yl]butanamide The title compound was prepared by substituting 2-phenylacetaldehyde for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (dd, J=5.2, 12.0, 1H), 7.65 (t, J=7.1, 2H), 7.38-7.23 (m, 8H), 4.40-4.29 (m, 1H), 3.23 (d, J=10.5, 1H), 3.00 (dd, J=2.6, 9.0, 0.5H), 2.80 (t, J=7.8, 1H), 2.75-2.70 (m, 1H), 2.70-2.61 (m, 1H), 2.61-2.52 (m, 1H), 2.52-2.46 (m, 1H), 2.43 (dd, J=7.6, 8.7, 0.5H), 2.38 (dd, J=2.7, 8.8, 1H), 2.34 (dd, J=2.7, 8.5, 1H), 2.26 (d, J=8.3, 0.5H), 2.24-2.18 (m, 1H), 2.12 (td, J=6.4, 12.4, 0.5H), 1.91-1.82 (m, 1H), 1.76 (dt, J=6.2, 18.7, 0.5H), 1.70-1.61 (m, 0.5H), 1.46-1.26 (m, 2H), 1.23 (dd, J=6.5, 13.5, 3H), 0.97-0.83 (m, 1H), 0.71 (dd, J=2.7, 6.7, 3H); MS (ESI+) m/z 391 (M+H)$^+$.

Example 105

3-methyl-2-phenyl-N-[(3aR,4S,6aS)-2-(3-phenylpropyl)octahydrocyclopenta[c]pyrrol-4-yl]butanamide The title compound was prepared by substituting 3-phenylpropanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.60 (t, J=6.8, 1H), 7.69-7.63 (m, 2H), 7.39-7.22 (m, 8H), 4.41-4.31 (m, 1H), 3.25 (d, J=10.4, 1H), 2.95 (dd, J=2.5, 8.9, 0.5H), 2.68 (td, J=2.7, 7.2, 2H), 2.65-2.60 (m, 1H), 2.58 (dd, J=2.8, 9.2, 0.5H), 2.56-2.52 (m, 0.5H), 2.51-2.46 (m, 0.5H), 2.44-2.38 (m, 0.5H), 2.37-2.26 (m, 3H), 2.23 (t, J=7.2, 1H), 2.18 (d, J=7.3, 0.5H), 2.13 (t, J=8.8, 1.5H), 1.88 (dd, J=6.1, 12.1, 1H), 1.79 (dd, J=7.2, 14.5, 1.5H), 1.74-1.64 (m, 1.5H), 1.48-1.37 (m, 1H), 1.37-1.28 (m, 0.5H), 1.23 (dd, J=6.5, 12.2, 3H), 0.71 (dd, J=3.0, 6.7, 3H); MS (ESI+) m/z 405 (M+H)$^+$.

Example 106

N-{(3aR,4S,6aS)-2-[3-(4-tert-butylphenyl)propyl]octahydrocyclopenta[c]pyrrol-4-yl}-3-methyl-2-phenylbutanamide The title compound was prepared by substituting 3-(4-tert-butylphenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (t, J=8.5, 1H), 7.65 (t, J=6.6, 2H), 7.40 (dd, J=5.4, 8.0, 2H), 7.34 (t, J=7.4, 2H), 7.30-7.23 (m, 3H), 4.37 (dt, J=6.1, 11.1, 1H), 3.23 (d, J=10.4, 1H), 2.96 (dd, J=1.9, 8.9, 0.5H), 2.67 (ddd, J=6.7, 11.6, 23.3, 2H), 2.59 (dd, J=2.6, 9.3, 0.5H), 2.57-2.51 (m, 0.5H), 2.50-2.44 (m, 0.5H), 2.43-2.38 (m, 0.5H), 2.35 (t, J=8.1, 2H), 2.29 (dd, J=2.6, 8.8, 0.5H), 2.25 (t, J=7.1, 1H), 2.19 (d, J=7.2, 0.5H), 2.17-2.11 (m, 1H), 1.92-1.85 (m, 1H), 1.81 (dd, J=7.7, 15.5, 1H), 1.74 (dt, J=7.9, 15.9, 1H), 1.69-1.63 (m, 0.5H), 1.46-1.31 (m, 2H), 1.28 (s, 9H), 1.23 (dd, J=6.5, 13.4, 3H), 0.94-0.84 (m, 2H), 0.71 (dd, J=3.2, 6.6, 3H); MS (ESI+) m/z 461 (M+H)$^+$.

Example 107

N-{(3aR,4S,6aS)-2-[6,6-bis(4-fluorophenyl)hexyl]octahydrocyclopenta[c]pyrrol-4-yl}-3-methyl-2-phenylbutanamide The title compound was prepared by substituting 6,6-bis(4-fluorophenyl)hexanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.59 (t, J=6.4, 1H), 7.65 (dd, J=4.9, 6.9, 2H), 7.33 (dd, J=6.8, 11.6, 6H), 7.25 (dd, J=6.5, 8.2, 1H), 7.14 (dd, J=1.4, 8.7, 4H), 4.40-4.30 (m, 1H), 3.97 (q, J=7.7, 1H), 3.23 (d, J=10.4, 1H), 2.96 (d, J=6.8, 0.5H), 2.71-2.61 (m, 1H), 2.59 (dd, J=2.5, 9.0, 0.5H), 2.56-2.46 (m, 1H), 2.40 (dd, J=8.4, 16.1, 1H), 2.37-2.33 (m, 1H), 2.30 (dd, J=4.4, 8.1, 1H), 2.20 (t, J=6.2, 2H), 2.17-2.10 (m, 1H), 2.01 (ddd, J=7.8, 11.6, 15.5, 2H), 1.88 (dq, J=6.0, 11.8, 1H), 1.78 (dt, J=6.3, 20.2, 0.5H), 1.67 (td, J=7.1, 14.5, 0.5H), 1.49-1.30 (m, 6H), 1.29-1.25 (m, 2H), 1.22 (dd, J=6.5, 11.0, 3H), 0.71 (dd, J=3.2, 6.7, 3H); MS (ESI+) m/z 559 (M+H)$^+$.

Example 108

3-methyl-N-{(3aR,4S,6aS)-2-[3-(2-methylphenyl)propyl]octahydrocyclopenta[c]pyrrol-4-yl}-2-phenylbutanamide The title compound was prepared by substituting 3-o-tolylpropanol for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (dd, J=7.2, 14.2, 1H), 7.68-7.62 (m, 2H), 7.34 (t, J=7.5, 2H), 7.29-7.23 (m, 2H), 7.23-7.22 (m, 1H), 7.17 (dd, J=2.6, 3.9, 2H), 4.42-4.31 (m, 1H), 3.23 (d, J=10.4, 1H), 2.98 (dd, J=2.3, 8.8, 0.5H), 2.69-2.64 (m, 2H), 2.64-2.59 (m, 2H), 2.58-2.51 (m, 0.5H), 2.51-2.45 (m, 0.5H), 2.45-2.39 (m, 0.5H), 2.39-2.34 (m, 2H), 2.32 (dd, J=2.7, 8.9, 1H), 2.28 (s, 1.5H), 2.25 (s, 1.5H), 2.19 (d, J=8.1, 0.5H), 2.17-2.11 (m, 1.5H), 1.93-1.85 (m, 1H), 1.84-1.77 (m, 0.5H), 1.73 (dd, J=7.6, 15.1, 1H), 1.66 (dt, J=7.4, 9.4, 1.5H), 1.43 (dt, J=7.5, 13.8, 1H), 1.38-1.30 (m, 1H), 1.23 (dd, J=6.5, 12.1, 3H), 0.71 (dd, J=2.8, 6.7, 3H); MS (ESI+) m/z 419 (M+H)$^+$.

Example 109

N-{(3aR,4S,6aS)-2-[3-(3-chlorophenyl)propyl]octahydrocyclopenta[c]pyrrol-4-yl}-3-methyl-2-phenylbutanamide The title compound was prepared by substituting 3-(3-chlorophenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.60 (d, J=4.6, 1H), 7.66 (dd, J=4.3, 7.0, 2H), 7.35 (dd, J=10.9, 18.3, 3H), 7.29-7.23 (m, 3H), 7.16 (d, J=6.8, 0.5H), 7.12 (d, J=7.0, 0.5H), 4.41-4.31 (m, 1H), 3.24 (d, J=10.4, 1H), 2.98 (d, J=8.9, 0.5H), 2.72-2.62 (m, 2H), 2.62-2.55 (m, 2H), 2.55-2.51 (m, 0.5H), 2.50-2.45 (m, 0.5H), 2.43-2.37 (m, 0.5H), 2.31 (ddd, J=2.6, 7.2, 12.1, 3H), 2.23-2.16 (m, 1H), 2.15-2.09 (m, 1H), 1.91-1.84 (m, 1H), 1.80 (td, J=6.3, 12.5, 1H), 1.72 (dd, J=7.5, 14.5, 1H), 1.69-1.61 (m, 1H), 1.46-1.37 (m, 1H), 1.37-1.28 (m, 1H), 1.23 (dd, J=6.5, 13.3, 3H), 0.71 (dd, J=3.9, 6.7, 3H); MS (ESI+) m/z 439 (M+H)$^+$.

Example 110

3-methyl-N-{(3aR,4S,6aS)-2-[3-(3-methylphenyl)propyl]octahydrocyclopenta[c]pyrrol-4-yl}-2-phenylbutanamide The title compound was prepared by substituting 3-m-tolylpropanol for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.57 (dd, J=7.1, 13.5, 1H), 7.65 (dd, J=4.8, 7.0, 2H), 7.34 (t, J=7.5, 2H), 7.29-7.22 (m, 2H), 7.12 (d, J=5.9, 1H), 7.09 (d, J=7.1, 1H), 7.06-7.02 (m, 1H), 4.42-4.31 (m, 1H), 3.24 (d, J=10.4, 1H), 2.97 (d, J=6.8, 0.5H), 2.71-2.58 (m, 4H), 2.56-2.44 (m, 1H), 2.43-2.38 (m, 0.5H), 2.35 (t, J=6.6, 3H), 2.29 (s, 1.5H), 2.27 (s, 1.5H), 2.27-2.23 (m, 1H), 2.17-2.11 (m, 1.5H), 1.89 (dt, J=6.1, 11.8, 1H), 1.79 (dd, J=7.4, 14.7, 1.5H), 1.72 (dt, J=7.6, 15.1, 1H), 1.66 (dd, J=5.9, 13.1, 0.5H), 1.42 (dt, J=7.5, 12.0, 1H), 1.37-1.30 (m, 0.5H), 1.23 (dd, J=6.5, 11.7, 3H), 0.71 (dd, J=3.0, 6.6, 3H); MS (ESI+) m/z 419 (M+H)$^+$.

Example 111

3-methyl-2-phenyl-N-((3aR,4S,6aS)-2-{3-[3-(trifluoromethyl)phenyl]propyl}octahydrocyclopenta[c]pyrrol-4-yl)butanamide The title compound was prepared by substituting 3-(3-(trifluoromethyl)phenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.61 (d, J=6.4, 1H), 7.69-7.62 (m, 3H), 7.53 (d, J=6.5, 1H), 7.46 (t, J=7.8, 1H), 7.42 (d, J=5.5, 1H), 7.34 (t, J=7.5, 2H), 7.26 (t, J=7.3, 1H), 4.37 (tt, J=6.4, 12.7, 1H), 3.24 (d, J=10.5, 1H), 3.00 (dd, J=1.9, 8.9, 0.5H), 2.78-2.63 (m, 3H), 2.61 (dd, J=2.3, 9.1, 0.5H), 2.57-2.45 (m, 1H), 2.40 (dd, J=7.1, 14.3, 0.5H), 2.37-2.26 (m, 3H), 2.24-2.07 (m, 3H), 1.93-1.83 (m, 1H), 1.83-1.71 (m, 2H), 1.71-1.63 (m, 1H), 1.48-1.37 (m, 1H), 1.37-1.30 (m, 0.5H), 1.23 (dd, J=6.5, 13.6, 3H), 0.72 (dd, J=4.4, 6.6, 3H); MS (ESI+) m/z 473 (M+H)$^+$.

Example 112

N-{(3aR,4S,6aS)-2-[3-(3-fluorophenyl)propyl]octahydrocyclopenta[c]pyrrol-4-yl}-3-methyl-2-phenylbutanamide The title compound was prepared by substituting 3-(3-fluorophenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (400 MHz, pyridine-$d_5$) δ ppm 8.52 (s, 1H), 7.69-7.61 (m, 2H), 7.33 (t, J=7.5, 2H), 7.27 (ddd, J=3.5, 7.6, 10.6, 2H), 7.14-6.95 (m, 3H), 4.43-4.29 (m, 1H), 3.23 (d, J=10.4, 1H), 2.97 (dd, J=2.2, 8.8, 0.5H), 2.72-2.58 (m, 3H), 2.57-2.44 (m, 1H), 2.44-2.38 (m, 0.5H), 2.36-2.26 (m, 3H), 2.25-2.16 (m, 1H), 2.16-2.09 (m, 1H), 1.93-1.83 (m, 1H), 1.77 (dt, J=7.2, 14.6, 1.5H), 1.72-1.63 (m, 1.5H), 1.47-1.27 (m, 2H), 1.22 (dd, J=6.5, 10.4, 3H), 0.94-0.83 (m, 1H), 0.71 (dd, J=2.7, 6.7, 3H); MS (ESI+) m/z 423 (M+H)$^+$.

Example 113

3-methyl-2-phenyl-N-[(3aR,4S,6aS)-2-(4-phenylbutyl)octahydrocyclopenta[c]pyrrol-4-yl]butanamide The title compound was prepared by substituting 4-phenylbutanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.58 (dd, J=9.0, 16.5, 1H), 7.66 (t, J=6.4, 2H), 7.34 (t, J=5.6, 4H), 7.29-7.22 (m, 4H), 4.39-4.29 (m, 1H), 3.24 (d, J=10.4, 1H), 2.91 (dd, J=2.4, 9.0, 0.5H), 2.66 (ddd, J=6.5, 10.6, 13.1, 1H), 2.57 (ddd, J=5.3, 12.3, 17.7, 3H), 2.51-2.45 (m, 1H), 2.43-2.29 (m, 3H), 2.26 (dd, J=3.0, 8.8, 0.5H), 2.24-2.08 (m, 2H), 1.91-1.83 (m, 1H), 1.81-1.72 (m, 1H), 1.71-1.58 (m, 2H), 1.49 (dt, J=7.8, 15.9, 1H), 1.41 (dt, J=6.9, 17.2, 2H), 1.31 (ddd, J=6.7, 13.2, 20.5, 1H), 1.23 (dd, J=6.5, 13.0, 3H), 0.71 (dd, J=2.6, 6.6, 3H); MS (ESI+) m/z 419 (M+H)$^+$.

Example 114

N-{(3aR,4S,6aS)-2-[3-(3-chloro-5-fluorophenyl)propyl]octahydrocyclopenta[c]pyrrol-4-yl}-3-methyl-2-phenylbutanamide The title compound was prepared by substituting 3-(3-chloro-5-fluorophenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 8.61 (d, J=7.4, 1H), 7.66 (dd, J=3.2, 7.5, 2H), 7.35 (dd, J=7.5, 15.0, 2H), 7.25 (dd, J=6.1, 13.7, 2H), 7.12 (d, J=7.5, 1H), 7.06-6.95 (m, 1H), 4.43-4.31 (m, 1H), 3.24 (d, J=10.4, 1H), 3.01 (dd, J=1.3, 8.7, 0.5H), 2.73-2.64 (m, 1H), 2.62 (dd, J=6.0, 9.0, 1H), 2.59-2.54 (m, 1H), 2.53-2.45 (m, 1H), 2.43-2.38 (m, 0.5H), 2.37-2.25 (m, 3H), 2.24-2.06 (m, 3H), 1.93-1.76 (m, 2H), 1.75-1.58 (m, 2H), 1.47-1.28 (m, 2H), 1.23 (dd, J=6.5, 14.4, 3H), 0.72 (dd, J=5.0, 6.2, 3H); MS (ESI+) m/z 457 (M+H)$^+$.

Example 115

3-methyl-2-phenyl-N-((3aR,4S,6aS)-2-{3-[4-(trifluoromethyl)phenyl]propyl}octahydrocyclopenta[c]pyrrol-4-yl)butanamide The title compound was prepared by substituting 3-(4-(trifluoromethyl)phenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 7.69-7.62 (m, 4H), 7.39 (d, J=8.0, 1H), 7.37-7.32 (m, 3H), 7.26 (t, J=7.3, 1H), 4.41-4.33 (m, 1H), 3.25 (d, J=10.5, 1H), 3.00 (dd, J=2.2, 9.0, 0.5H), 2.76-2.59 (m, 3H), 2.56-2.46 (m, 1H), 2.44-2.39 (m, 0.5H), 2.37 (dd, J=2.1, 8.9, 0.5H), 2.31 (dt, J=5.8, 14.1, 2H), 2.23-2.07 (m, 3H), 1.94-1.71 (m, 2.5H), 1.67 (ddd, J=5.6, 7.9, 11.8, 1H), 1.47-1.28 (m, 2H), 1.23 (dd, J=6.5, 13.1, 3H), 0.89 (dt, J=7.2, 24.8, 1H), 0.72 (dd, J=3.7, 6.7, 3H); MS (ESI+) m/z 473 (M+H)$^+$.

Example 116

N-[(3aR,4S,6aS)-2-(3,3-diphenylpropyl)octahydrocyclopenta[c]pyrrol-4-yl]-3-methyl-2-phenylbutanamide The title compound was prepared by substituting 3,3-diphenylpropanol for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.59 (dd, J=2.9, 7.0, 1H), 7.65 (d, J=8.1, 2H), 7.46 (d, J=7.2, 1H), 7.44-7.37 (m, 4H), 7.33 (tt, J=3.7, 7.7, 6H), 7.28-7.24 (m, 1H), 7.23-7.18 (m, 1H), 4.44-4.34 (m, 1H), 4.28 (d, J=7.2, 1H), 4.20 (dd, J=5.4, 9.1, 1H), 3.24 (d, J=10.4, 1H), 2.93 (dd, J=2.4, 9.0, 0.5H), 2.71-2.61 (m, 1H), 2.56 (dd, J=2.7, 9.2, 0.5H), 2.54-2.50 (m, 0.5H), 2.50-2.43 (m, 0.5H), 2.43-2.36 (m, 0.5H), 2.35-2.28 (m, 3H), 2.24 (tt, J=5.1, 10.0, 2H), 2.18-2.07 (m, 2H), 1.94-1.83 (m, 1H), 1.82-1.74 (m, 0.5H), 1.68 (td, J=7.0, 14.3, 0.5H), 1.47-1.37 (m, 1H), 1.37-1.29 (m, 0.5H), 1.22 (dd, J=4.6, 6.4, 3H), 0.71 (dd, J=1.7, 6.7, 3H); MS (ESI+) m/z 481 (M+H)$^+$.

Example 117

N-{(3aR,4S,6aS)-2-[3,3-bis(4-fluorophenyl)propyl]octahydrocyclopenta[c]pyrrol-4-yl}-3-methyl-2-phenylbutanamide The title compound was prepared by substituting 3,3-bis(4-fluorophenyl)propanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.62 (d, J=5.3, 1H), 7.65 (d, J=7.3, 2H), 7.42 (dd, J=5.6, 8.6, 1H), 7.39-7.29 (m, 5H), 7.26 (td, J=5.3, 7.2, 1H), 7.19-7.09 (m, 4H), 4.47-4.37 (m, 1H), 4.29 (t, J=7.7, 0.5H), 4.21 (t, J=7.6, 0.5H), 3.24 (d, J=10.4, 1H), 3.02 (dd, J=1.2, 8.9, 0.5H), 2.71-2.60 (m, 1H), 2.57-2.46 (m, 1H), 2.44-2.30 (m, 3H), 2.27-2.20 (m, 2H), 2.19-2.09 (m, 4H), 1.90 (dq, J=6.0, 17.7, 1H), 1.81 (dq, J=6.2, 18.7, 0.5H), 1.67 (ddd, J=7.6, 12.3, 14.8, 0.5H), 1.48-1.38 (m, 1H), 1.38-1.30 (m, 0.5H), 1.22 (dd, J=2.5, 6.5, 3H), 0.71 (dd, J=1.4, 6.7, 3H); MS (ESI+) m/z 517 (M+H)$^+$.

Example 118

N-{(3aR,4S,6aS)-2-[4,4-bis(4-fluorophenyl)butyl]octahydrocyclopenta[c]pyrrol-4-yl}-3-methyl-2-phenylbutanamide The title compound was prepared by substituting 4,4-bis(4-fluorophenyl)butanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.61 (d, J=7.0, 1H), 7.66 (dd, J=5.3, 7.0, 2H), 7.44-7.31 (m, 6H), 7.26 (t, J=7.4, 1H), 7.19-7.08 (m, 4H), 4.41-4.30 (m, 1H), 4.03-3.92 (m, 1H), 3.24 (d, J=10.4, 1H), 2.95 (dd, J=2.3, 8.9, 0.5H), 2.67 (ddd, J=6.6, 13.3, 17.1, 1H), 2.56 (dd, J=2.8, 9.1, 0.5H), 2.54-2.43 (m, 1H), 2.42-2.30 (m, 2H), 2.29-2.20 (m, 2.5H), 2.19-2.02 (m, 4H), 1.90-1.72 (m, 1.5H), 1.65 (dt, J=7.1, 19.2, 0.5H), 1.52-1.34 (m, 3H), 1.34-1.26 (m, 0.5H), 1.23 (dd, J=6.5, 15.3, 3H), 0.71 (dd, J=5.0, 6.5, 3H); MS (ESI+) m/z 531 (M+H)$^+$.

Example 119

N-{(3aR,4S,6aS)-2-[5,5-bis(4-fluorophenyl)pentyl]octahydrocyclopenta[c]pyrrol-4-yl}-3-methyl-2-phenylbutanamide The title compound was prepared by substituting 5,5-bis(4-fluorophenyl)pentanal for 3-(trifluoromethyl)benzaldehyde and 3-methyl-N-[(3aR,4S,6aS)-octahydrocyclopenta[c]pyrrol-4-yl]-2-phenylbutanamide from Example 83 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-d$_5$) δ ppm 8.61 (s, 1H), 7.66 (dd, J=4.3, 7.3, 2H), 7.37-7.30 (m, 5H), 7.25 (dd, J=5.6, 13.1, 2H), 7.19-7.11 (m, 4H), 4.38-4.29 (m, 1H), 3.96 (dd, J=7.9, 18.0, 1H), 3.25 (d, J=10.5, 1H), 2.96 (d, J=10.4, 0.5H), 2.72-2.62 (m, 1H), 2.62-2.57 (m, 0.50H), 2.56-2.51 (m, 0.5H), 2.50-2.45 (m, 0.5H), 2.43-2.36 (m, 1H), 2.36-2.31 (m, 1H), 2.30-2.26 (m, 1H), 2.23-2.06 (m, 3H), 2.07-1.96 (m, 2H), 1.86 (d, J=6.0, 12.2, 1H), 1.81-1.72 (m, 1H), 1.66 (dt, J=7.0, 19.1, 1H), 1.56-1.49 (m, 1H), 1.48-1.40 (m, 1H), 1.38-1.26 (m, 3H), 1.23 (dd, J=6.5, 9.7, 3H), 0.71 (dd, J=2.5, 6.7, 3H); MS (ESI+) m/z 545 (M+H)$^+$.

Example 120

N-[(3aS,4S,6aR)-2-benzhydryloctahydrocyclopenta[c]pyrrol-4-yl]-2,2-dicyclohexylacetamide Potassium iodide (12.48 mg, 0.075 mmol) and sodium carbonate (80 mg, 0.752 mmol) were combined with methyl ethyl ketone (5 mL) and then 2,2-dicyclohexyl-N-[(3aS,4S,6aR)-octahydrocyclopenta[c]pyrrol-4-yl]acetamide (200 mg, 0.601 mmol) from Example 53 was added followed by the addition of (bromomethylene)dibenzene (124 mg, 0.501 mmol). The reaction was heated overnight at 90° C. The reaction mixture was concentrated with a stream of nitrogen and then purified by silica gel chromatography eluting with 2-10% methanol (2 N ammonia)/dichloromethane to give the title compound: $^1$H NMR (500 MHz, pyridine-d$_5$) δ ppm 7.74 (dd, J=6.7, 15.4, 1H), 7.61 (t, J=6.7, 3H), 7.35 (t, J=7.6, 4H), 7.28-7.23 (m, 3H), 4.42 (dt, J=7.4, 14.4, 1H), 4.16 (s, 1H), 2.96 (qd, J=4.2, 8.0, 1H), 2.63 (dd, J=4.1, 9.8, 1H), 2.57-2.48 (m, 1H), 2.42 (dt, J=9.4, 14.6, 2H), 2.33 (dd, J=3.7, 9.3, 1H), 2.09-1.90 (m, 3H), 1.90-1.80 (m, 3H), 1.79-1.70 (m, 4H), 1.69-1.55 (m, 6H), 1.46 (d, J=14.7, 1H), 1.39 (s, 1H), 1.33-1.00 (m, 8H), 1.00-0.89 (m, 1H); MS (ESI+) m/z 499 (M+H)$^+$.

Example 121

N-[(3aS,4R,6aR)-2-benzhydryloctahydrocyclopenta[c]pyrrol-4-yl]-2,2-dicyclohexylacetamide The title compound was prepared by substituting 2,2-dicyclohexyl-N-[(3aS,4R,6aR)-octahydrocyclopenta[c]pyrrol-4-yl]acetamide from Example 74 for 2,2-dicyclohexyl-N-[(3aS,4S,6aR)-octahydrocyclopenta[c]pyrrol-4-yl]acetamide in the procedure described for Example 120: $^1$H NMR (500 MHz, pyridine-d$_5$) δ ppm 8.11 (d, J=7.2, 1H), 7.64 (d, J=7.1, 2H), 7.32 (t, J=7.6, 4H), 7.20-7.15 (m, 4H), 4.55-4.48 (m, 1H), 4.21 (s, 1H), 2.81 (dd, J=2.9, 9.4, 1H), 2.63-2.57 (m, 1H), 2.57-2.51 (m, 1H), 2.41 (dd, J=7.0, 9.2, 1H), 2.36-2.24 (m, 3H), 2.01 (t, J=7.4, 1H), 1.99-1.90 (m, 3H), 1.86 (ddd, J=3.3, 8.1, 15.4, 2H), 1.82-1.76 (m, 2H), 1.70 (ddd, J=8.9, 13.9, 15.3, 5H), 1.63-1.55 (m, 2H), 1.51-1.37 (m, 3H), 1.28-1.01 (m, 8H); MS (ESI+) m/z 499 (M+H)$^+$.

Example 122

3-methyl-2-phenyl-N-{(3aS*,4S*,6aR*)-2-[3-(trifluoromethyl)benzyl]octahydrocyclopenta[c]pyrrol-4-yl}butanamide Step A: (3-(Trifluoromethyl)phenyl)methanamine (25 g, 143 mmol), (chloromethyl)trimethylsilane (19.92 mL, 143 mmol), and triethylamine (23.87 mL, 171 mmol) were combined neat and the resultant mixture was refluxed overnight. The reaction was cooled to room temperature and 150 mL of heptane was added. The HCl salts were removed by filtration and washed with heptane. The solvent was removed by placing under house vacuum and then high vacuum. N-(3-(Trifluoromethyl)benzyl)-1-(trimethylsilyl)methanamine was isolated by vacuum distillation (bp 70-90° C./3.2 torr): $^1$H NMR (300 MHz, CDCl$_3$) δ ppm 7.59 (s, 1H), 7.53-7.38 (m, 3H), 3.86 (s, 2H), 2.04 (s, 2H), 1.34 (s, 1H), 0.06 (s, 9H).

Step B: Formaldehyde (4.08 g, 50.2 mmol) and methanol (2.032 mL, 50.2 mmol) were combined, and the mixture was cooled to 0° C. (ice bath). N-(3-(trifluoromethyl)benzyl)-1-(trimethylsilyl)methanamine (10.94 g, 41.9 mmol) was added dropwise via addition funnel over 30 minutes. Potassium carbonate (4.63 g, 33.5 mmol) was added, and the reaction stirred at 0° C. for 2 additional hours. The reaction product was decanted from the potassium carbonate, treated with more potassium carbonate, and decanted again. The potassium carbonate solids were washed several times with ether, and these washes were added to the product solution. The solvent was removed in vacuo to give 1-methoxy-N-(3-(trifluoromethyl)benzyl)-N-((trimethylsilyl)methyl)methanamine which was used directly in the next step.

Step C: Cyclopent-2-enone (3.31 g, 40.4 mmol) and trifluoroacetic acid (0.031 mL, 0.404 mmol) were combined in dichloromethane (40 mL). 1-Methoxy-N-(3-(trifluoromethyl)benzyl)-N-((trimethylsilyl)methyl)methanamine (12.33 g, 40.4 mmol) from Step B was added as a solution in 10 mL of dichloromethane dropwise via addition funnel over 45 minutes at room temperature under nitrogen. The reaction was quenched with aqueous sodium bicarbonate and extracted with 2×100 mL of dichloromethane. The organic washes were combined and washed with brine. The solvent was removed in vacuo to give 2-(3-(trifluoromethyl)benzyl)hexahydrocyclopenta[c]pyrrol-4(5H)-one: $^1$H NMR (300 MHz, CDCl$_3$) δ ppm 7.54-7.34 (m, 4H), 3.66 (d, J=13.4, 1H), 3.52 (d, J=13.4, 1H), 3.04 (dd, J=1.8, 8.9, 1H), 2.91 (ddd, J=2.8, 7.4, 11.7, 1H), 2.72-2.65 (m, 1H), 2.62 (d, J=8.9, 1H), 2.52-2.23 (m, 4H), 2.15 (ddd, J=8.1, 12.9, 17.1, 1H), 1.85-1.70 (m, 1H).

Step D: Hydroxylamine hydrochloride (3.47 g, 50.0 mmol) and sodium acetate (4.27 g, 52.0 mmol) were dissolved in 15 mL of water and added to a solution of 2-(3-(trifluoromethyl)benzyl)hexahydrocyclopenta[c]pyrrol-4(5H)-one (11.33 g, 40 mmol) from Step C in ethanol (80 mL). The reaction was brought to reflux for 5 minutes and allowed to cool to 70° C. After 1 hour, the reaction mixture was cooled, and the solvent was removed in vacuo to give (E)-2-(3-(trifluoromethyl)benzyl)hexahydrocyclopenta[c]pyrrol-4(5H)-one oxime which was used without additional purification in the next step.

Step E: (E)-2-(3-(Trifluoromethyl)benzyl)hexahydrocyclopenta[c]pyrrol-4(5H)-one oxime (11.9 g, 39.9 mmol) from Step D in 20% ammonia-methanol (115 mL) was added to methanol-washed Raney®-nickel, (water-wet, 38.52 g, 295 mmol) in a 500 mL pressure bottle. The vessel was pressurized with hydrogen (30 psi), and the mixture was shaken for 16 hours at ambient temperature. The mixture was filtered through a nylon membrane, the solvent was removed in vacuo, and the crude material was adsorbed onto silica gel. Silica gel chromatography using a cartridge (Analogix®, Burlington, Wis., SF65-400) eluting with 1-10% methanol (2 N ammonia)/dichloromethane gave the following diastereomers. (3aS*,4R*,6aR*)-2-(3-(trifluoromethyl)benzyl)octahydrocyclopenta[c]pyrrol-4-amine: $^1$H NMR (300 MHz, pyridine-d$_5$) δ ppm 7.58 (s, 1H), 7.50 (t, J=6.7, 2H), 7.45-7.37 (m, 1H), 3.59 (s, 2H), 3.26 (dt, J=6.3, 12.6, 1H), 2.67-2.50 (m, 4H), 2.38 (dd, J=6.6, 8.4, 1H), 2.31-2.20 (m, 1H), 1.79-1.62 (m, 2H), 1.60-1.33 (m, 4H); and (3aS*,4S*,6aR*)-2-(3-(trifluoromethyl)benzyl)octahydrocyclopenta[c]pyrrol-4-amine: $^1$H NMR (300 MHz, pyridine-d$_5$) δ ppm 7.58 (s, 1H), 7.50 (t, J=7.2, 2H), 7.45-7.37 (m, 1H), 3.59 (s, 2H), 3.09 (dd, J=4.9, 11.4, 1H), 2.77-2.57 (m, J=3.9, 1H), 2.52-2.38 (m, 3H), 2.34 (dd, J=3.7, 9.0, 1H), 2.22-2.09 (m, 1H), 2.03-1.85 (m, J=4.7, 7.0, 10.8, 2H), 1.42-1.21 (m, 4H).

Step F: The title compound was prepared by substituting 3-methyl-2-phenylbutanoic acid for 1-phenylcyclopentanecarboxylic acid and (3aS*,4S*,6aR*)-2-(3-(trifluoromethyl)benzyl)octahydrocyclopenta[c]pyrrol-4-amine from Step E for (3aS*,6aR*)-2-benzyloctahydrocyclopenta[c]pyrrol-4-amine in Example 1: $^1$H NMR (500 MHz, pyridine-d$_5$) δ ppm 8.23 (d, J=6.9, 0.5H), 8.13 (d, J=7.1, 0.5H), 7.73 (s, 0.5H), 7.67 (s, 0.5H), 7.63 (dd, J=6.7, 8.0, 2H), 7.56-7.53 (m, 1H), 7.50 (t, J=8.5, 2H), 7.38-7.22 (m, 3H), 4.45-4.38 (m, 0.5H), 4.33-4.26 (m, 0.5H), 3.50 (s, 1H), 3.44 (d, J=13.4, 0.5H), 3.21 (d, J=13.4, 0.5H), 3.17 (d, J=10.5, 0.5H), 3.10 (d, J=10.5, 0.5H), 2.91 (qd, J=3.4, 7.9, 0.5H), 2.79 (dd, J=3.4, 9.5, 0.5H), 2.74-2.56 (m, 1.5H), 2.47-2.31 (m, 2.5H), 2.27 (dd, J=3.1, 8.9, 0.5H), 2.21 (d, J=2.7, 0.5H), 1.98-1.93 (m, 0.5H), 1.89-1.79 (m, 0.5H), 1.74-1.56 (m, 1.5H), 1.53-1.46 (m, 0.5H), 1.46-1.39 (m, 0.5H), 1.30-1.23 (m, 1H), 1.19 (d, J=6.5, 1.5H), 1.17-1.11 (m, 0.5H), 1.08 (d, J=6.5, 1.5H), 0.72 (dd, J=6.7, 9.6, 3H); MS (ESI+) m/z 445 (M+H)$^+$.

Example 123

3,3-dimethyl-2-phenyl-N-{(3aS*,4S*,6aR*)-2-[3-(trifluoromethyl)benzyl]octahydrocyclopenta[c]pyrrol-4-yl}butanamide The title compound was prepared by substituting 3,3-dimethyl-2-phenylbutanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-d$_5$) δ ppm 8.32 (d, J=6.7, 0.5H), 8.13 (d, J=7.1, 0.5H), 7.74-7.70 (m, 1H), 7.69-7.66 (m, 1H), 7.61 (t, J=8.6, 3H), 7.48-7.43 (m, 1H), 7.37-7.24 (m, 3H), 4.48-4.39 (m, 0.5H), 4.36-4.28 (m, 0.5H), 3.51 (q, J=13.1, 0.5H), 3.41 (d, J=17.1, 1H), 3.35 (d, J=13.3, 0.5H), 3.13 (d, J=13.4, 0.5H), 2.98 (qd, J=4.0, 8.2, 0.5H), 2.81 (dd, J=3.9, 9.5, 0.5H), 2.74 (ddd, J=3.4, 7.8, 16.6, 0.5H), 2.49-2.37 (m, 2H), 2.31 (dd, J=3.4, 9.6, 0.5H), 2.24-2.15 (m, 2H), 2.01-1.94 (m, 0.5H), 1.84 (ddd, J=8.1, 11.7, 14.5, 0.5H), 1.73-1.65 (m, 1H), 1.64-1.56 (m, 0.5H), 1.52-1.38 (m, 1H), 1.27 (dt, J=5.6, 12.2, 1H), 1.16 (s, 4.5H), 1.11 (s, 4.5H); MS (ESI+) m/z 459 (M+H)+.

Example 124

2,2-dicyclohexyl-N-{(3aS*,4S*,6aR*)-2-[3-(trifluoromethyl)benzyl]octahydrocyclopenta[c]pyrrol-4-yl}acetamide The title compound was prepared by substituting 2,2-dicyclohexylacetic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^{1}$H NMR (400 MHz, pyridine-$d_5$) δ ppm 7.73 (s, 1H), 7.65 (d, J=7.6, 1H), 7.57-7.44 (m, 3H), 4.46 (dt, J=6.4, 12.6, 1H), 3.55 (d, J=12.9, 1H), 3.47 (d, J=12.8, 1H), 2.75 (d, J=8.1, 2H), 2.53-2.39 (m, 2H), 2.32 (t, J=8.2, 1H), 2.21 (t, J=8.3, 1H), 1.97-1.53 (m, 15H), 1.50-1.04 (m, 11H), 0.98 (dd, J=11.3, 23.1, 1H); MS (ESI+) m/z 491 (M+H)+.

Example 125

2-ethyl-N-{(3aS*,4S*,6aR*)-2-[3-(trifluoromethyl)benzyl]octahydrocyclopenta[c]pyrrol-4-yl}butanamide The title compound was prepared by substituting 2-ethylbutanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^{1}$H NMR (500 MHz, pyridine-$d_5$) δ ppm 7.90 (d, J=6.7, 1H), 7.71 (s, 1H), 7.61 (d, J=7.7, 1H), 7.54 (d, J=7.7, 1H), 7.46 (t, J=7.7, 1H), 4.51-4.43 (m, 1H), 3.49 (s, 2H), 2.83 (ddd, J=2.9, 7.8, 16.8, 1H), 2.75 (dd, J=2.9, 9.5, 1H), 2.52-2.43 (m, 1H), 2.37 (dd, J=2.9, 9.1, 1H), 2.35-2.30 (m, 1H), 2.25 (dd, J=7.6, 9.4, 1H), 2.01 (tt, J=4.8, 9.5, 1H), 1.89 (dt, J=7.3, 11.6, 1H), 1.77 (ddt, J=7.5, 9.3, 15.2, 2H), 1.70-1.60 (m, 2H), 1.51-1.37 (m, 2H), 1.34-1.26 (m, 1H), 0.95 (t, J=7.4, 3H), 0.83 (t, J=7.4, 3H); MS (ESI+) m/z 383 (M+H)+.

Example 126

2-propyl-N-{(3aS*,4S*,6aR*)-2-[3-(trifluoromethyl)benzyl]octahydrocyclopenta[c]pyrrol-4-yl}pentanamide The title compound was prepared by substituting 2-propylpentanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^{1}$H NMR (500 MHz, pyridine-$d_5$) δ ppm 7.94 (d, J=6.9, 1H), 7.72 (s, 1H), 7.62 (d, J=7.7, 1H), 7.56 (d, J=7.7, 1H), 7.47 (t, J=7.7, 1H), 4.48 (dt, J=7.3, 14.6, 1H), 3.52 (d, J=13.0, 1H), 3.48 (d, J=13.0, 1H), 2.84 (ddd, J=3.0, 7.7, 16.7, 1H), 2.74 (dd, J=3.1, 9.5, 1H), 2.52-2.45 (m, 1H), 2.38-2.34 (m, 2H), 2.27 (dd, J=7.6, 9.5, 1H), 2.22 (td, J=4.6, 9.5, 1H), 1.90 (dt, J=7.3, 11.5, 1H), 1.84-1.75 (m, 1H), 1.73-1.61 (m, 2H), 1.48-1.27 (m, 6H), 1.20-1.08 (m, 1H), 0.88 (t, J=7.0, 3H), 0.83 (t, J=7.1, 3H); MS (ESI+) m/z 411 (M+H)+.

Example 127

N-{(3aS*,4S*,6aR*)-2-[3-(trifluoromethyl)benzyl]octahydrocyclopenta[c]pyrrol-4-yl}cyclohexanecarboxamide The title compound was prepared by substituting cyclohexanecarboxylic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^{1}$H NMR (500 MHz, pyridine-$d_5$) δ ppm 7.74 (d, J=6.1, 1H), 7.71 (s, 1H), 7.62 (d, J=7.7, 1H), 7.57 (d, J=9.2, 1H), 7.47 (t, J=7.7, 1H), 4.48-4.41 (m, 1H), 3.53 (d, J=13.2, 1H), 3.47 (d, J=13.2, 1H), 2.84 (ddd, J=2.8, 7.9, 10.3, 1H), 2.75 (dd, J=2.8, 9.5, 1H), 2.51-2.43 (m, 1H), 2.37 (dd, J=2.8, 9.1, 1H), 2.34-2.29 (m, 1H), 2.27-2.19 (m, 2H), 1.94-1.83 (m, 2H), 1.80 (d, J=12.9, 1H), 1.73-1.60 (m, 6H), 1.57-1.51 (m, 1H), 1.35-1.27 (m, 1H), 1.22-1.10 (m, 3H); MS (ESI+) m/z 395 (M+H)+.

Example 128

N-{(3aS*,4S*,6aR*)-2-[3-(trifluoromethyl)benzyl]octahydrocyclopenta[c]pyrrol-4-yl}cycloheptanecarboxamide The title compound was prepared by substituting cycloheptanecarboxylic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^{1}$H NMR (500 MHz, pyridine-$d_5$) δ ppm 7.79 (d, J=6.9, 1H), 7.71 (s, 1H), 7.62 (d, J=7.7, 1H), 7.56 (s, 1H), 7.47 (t, J=7.7, 1H), 4.48-4.40 (m, 1H), 3.54 (d, J=13.2, 1H), 3.46 (d, J=13.2, 1H), 2.86 (ddd, J=3.0, 7.8, 16.6, 1H), 2.76 (dd, J=3.0, 9.5, 1H), 2.51-2.39 (m, 2H), 2.37-2.30 (m, 2H), 2.26 (dd, J=7.5, 9.4, 1H), 2.00-1.80 (m, 5H), 1.75-1.60 (m, 4H), 1.49-1.41 (m, 4H), 1.33 (ddt, J=7.2, 8.9, 12.1, 3H); MS (ESI+) m/z 409 (M+H)+.

Example 129

N-{(3aS*,4S*,6aR*)-2-[3-(trifluoromethyl)benzyl]octahydrocyclopenta[c]pyrrol-4-yl}cyclopentanecarboxamide The title compound was prepared by substituting cyclopentanecarboxylic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^{1}$H NMR (500 MHz, pyridine-$d_5$) δ ppm 7.82 (d, J=6.9, 1H), 7.71 (s, 1H), 7.61 (d, J=7.7, 1H), 7.55 (d, J=7.7, 1H), 7.46 (t, J=7.7, 1H), 4.48-4.41 (m, 1H), 4.07 (q, J=7.1, 1H), 2.82 (ddd, J=2.9, 7.8, 16.7, 1H), 2.72 (dd, J=2.9, 9.5, 1H), 2.66 (p, J=7.9, 1H), 2.50-2.42 (m, 1H), 2.37 (dd, J=2.9, 9.0, 1H), 2.34-2.29 (m, 1H), 2.21 (dd, J=7.5, 9.4, 1H), 2.03 (dt, J=7.0, 15.3, 1H), 1.86 (dddd, J=7.4, 12.3, 20.5, 23.4, 3H), 1.75-1.60 (m, 5H), 1.53-1.41 (m, 2H), 1.30 (td, J=4.7, 11.1, 1H), 1.11 (t, J=7.1, 1H); MS (ESI+) m/z 381 (M+H)+.

Example 130

6,6-bis(4-fluorophenyl)-N-{(3aS*,4S*,6aR*)-2-[3-(trifluoromethyl)benzyl]octahydrocyclopenta[c]pyrrol-4-yl}hexanamide The title compound was prepared by substituting 6,6-bis(4-fluorophenyl)hexanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 7.99 (d, J=7.1, 1H), 7.69 (s, 1H), 7.58 (s, 1H), 7.54 (d, J=7.6, 1H), 7.42 (dd, J=6.9, 14.5, 1H), 7.26 (dd, J=5.5, 8.6, 4H), 7.14-7.08 (m, 4H), 4.51-4.41 (m, 1H), 3.91 (t, J=7.8, 1H), 3.47 (d, J=2.3, 2H), 2.84 (qd, J=3.0, 8.0, 1H), 2.69 (dd, J=3.1, 9.5, 1H), 2.53-2.43 (m, 1H), 2.38-2.20 (m, 5H), 1.99 (dd, J=7.8, 15.6, 2H), 1.89-1.78 (m, 3H), 1.70-1.59 (m, 2H), 1.37-1.25 (m, 3H); MS (ESI+) m/z 571 (M+H)$^+$.

Example 131

3,3-diphenyl-N-{(3aS*,4S*,6aR*)-2-[3-(trifluoromethyl)benzyl]octahydrocyclopenta[c]pyrrol-4-yl}propanamide The title compound was prepared by substituting 3,3-diphenylpropanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 8.10 (d, J=7.0, 1H), 7.72 (s, 1H), 7.62 (d, J=7.8, 1H), 7.48 (t, J=7.7, 1H), 7.39 (dd, J=2.6, 7.5, 5H), 7.26 (dt, J=7.6, 15.1, 5H), 7.17 (dd, J=6.2, 13.5, 2H), 4.38-4.27 (m, 1H), 3.54 (d, J=13.4, 1H), 3.38 (d, J=13.4, 1H), 3.15-3.09 (m, 2H), 2.75 (qd, J=3.6, 7.9, 1H), 2.44-2.35 (m, 2H), 2.32 (t, J=8.3, 1H), 2.20 (dd, J=3.3, 8.9, 1H), 2.08 (dd, J=7.8, 9.5, 1H), 1.70 (t, J=7.9, 1H), 1.58-1.46 (m, 2H), 1.18-1.10 (m, 1H); MS (ESI+) m/z 493 (M+H)$^+$.

Example 132

5,5-bis(4-fluorophenyl)-N-{(3aS*,4S*,6aR*)-2-[3-(trifluoromethyl)benzyl]octahydrocyclopenta[c]pyrrol-4-yl}pentanamide The title compound was prepared by substituting 5,5-bis(4-fluorophenyl)pentanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 8.06 (d, J=7.0, 1H), 7.70 (s, 1H), 7.60 (d, J=8.0, 1H), 7.54 (d, J=7.7, 1H), 7.44 (t, J=7.7, 1H), 7.26 (dd, J=5.6, 8.4, 4H), 7.08 (td, J=1.2, 8.8, 4H), 4.51-4.42 (m, 1H), 3.96 (t, J=7.8, 1H), 2.86 (qd, J=3.2, 7.9, 1H), 2.69 (dd, J=3.2, 9.5, 1H), 2.52-2.43 (m, 1H), 2.43-2.29 (m, 5H), 2.24 (dd, J=7.7, 9.4, 1H), 2.15-2.06 (m, 3H), 1.85 (dt, J=9.9, 17.8, 1H), 1.76 (dt, J=7.3, 15.3, 2H), 1.70-1.59 (m, 2H), 1.33-1.26 (m, 1H); MS (ESI+) m/z 557 (M+H)$^+$.

Example 133

3,3-bis(4-fluorophenyl)-N-{(3aS*,4S*,6aR*)-2-[3-(trifluoromethyl)benzyl]octahydrocyclopenta[c]pyrrol-4-yl}propanamide The title compound was prepared by substituting 3,3-bis(4-fluorophenyl)propanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 8.13 (d, J=7.0, 1H), 7.71 (s, 1H), 7.61 (d, J=7.7, 1H), 7.56 (s, 1H), 7.47 (t, J=7.7, 1H), 7.32 (ddd, J=3.7, 5.4, 8.8, 4H), 7.11-7.02 (m, 4H), 4.94 (d, J=8.0, 1H), 4.39-4.25 (m, 1H), 3.52 (d, J=13.4, 1H), 3.41 (d, J=13.4, 1H), 3.06 (d, J=7.9, 2H), 2.76 (qd, J=3.4, 7.9, 1H), 2.43 (dd, J=3.3, 9.5, 2H), 2.31 (t, J=8.3, 1H), 2.23 (dd, J=3.1, 9.0, 1H), 2.10 (dd, J=7.8, 9.4, 1H), 1.76-1.67 (m, 1H), 1.59-1.49 (m, 2H), 1.22-1.11 (m, 1H); MS (ESI+) m/z 529 (M+H)$^+$.

Example 134

4,4-bis(4-fluorophenyl)-N-{(3aS*,4S*,6aR*)-2-[3-(trifluoromethyl)benzyl]octahydrocyclopenta[c]pyrrol-4-yl}butanamide The title compound was prepared by substituting 4,4-bis(4-fluorophenyl)butanoic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 8.16 (d, J=6.9, 1H), 7.66 (s, 1H), 7.58 (s, 1H), 7.50 (d, J=7.7, 1H), 7.38 (t, J=7.7, 1H), 7.28 (dd, J=5.5, 7.3, 4H), 7.10-7.02 (m, 4H), 4.49 (dt, J=7.6, 14.7, 1H), 4.10 (t, J=7.9, 1H), 3.50 (d, J=13.4, 1H), 3.42 (d, J=13.4, 1H), 2.92 (qd, J=3.6, 7.9, 1H), 2.67 (dd, J=3.5, 9.5, 1H), 2.55 (dd, J=7.2, 15.0, 2H), 2.52-2.46 (m, 1H), 2.40 (t, J=8.3, 1H), 2.36-2.24 (m, 4H), 1.91-1.82 (m, 1H), 1.71 (td, J=5.8, 11.3, 1H), 1.67-1.60 (m, 1H), 1.35-1.27 (m, 1H); MS (ESI+) m/z 543 (M+H)$^+$.

Example 135

2,2-diphenyl-N-{(3aS*,4S*,6aR*)-2-[3-(trifluoromethyl)benzyl]octahydrocyclopenta[c]pyrrol-4-yl}acetamide The title compound was prepared by substituting 2,2-diphenylacetic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 8.50 (s, 1H), 7.71 (d, J=7.5, 2H), 7.63 (d, J=7.2, 2H), 7.45 (d, J=7.4, 2H), 7.39-7.28 (m, 5H), 7.25 (dd, J=5.8, 8.9, 3H), 4.51-4.42 (m, 1H), 3.44 (d, J=13.3, 1H), 3.25 (d, J=13.3, 1H), 2.85 (qd, J=3.2, 7.9, 1H), 2.59 (dd, J=3.4, 9.5, 1H), 2.47-2.37 (m, 1H), 2.26 (t, J=8.3, 1H), 2.21-2.13 (m, 2H), 1.85-1.76 (m, 1H), 1.67-1.52 (m, 3H), 1.27-1.18 (m, 1H); MS (ESI+) m/z 479 (M+H)$^+$.

Example 136

2,2-bis(4-fluorophenyl)-N-{(3aS*,4S*,6aR*)-2-[3-(trifluoromethyl)benzyl]octahydrocyclopenta[c]pyrrol-4-yl}acetamide The title compound was prepared by substituting 2,2-bis(4-fluorophenyl)acetic acid for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-$d_5$) δ ppm 8.68 (d, J=7.0, 1H), 7.64 (s, 1H), 7.60 (t, J=6.4, 1H), 7.57-7.54 (m, 2H), 7.52-7.43 (m, 4H), 7.17-7.07 (m, 4H), 4.48-4.41 (m, 1H), 3.46 (d, J=13.3, 1H), 3.30 (d, J=13.3, 1H), 2.90 (qd, J=3.5, 8.0, 1H), 2.59 (dd, J=3.5, 9.5, 1H), 2.50-2.42 (m, 1H), 2.32 (t, J=8.3, 1H), 2.25-2.19 (m, 3H), 1.87-1.77 (m, 1H), 1.66 (td, J=5.7, 11.4, 1H), 1.62-1.54 (m, 1H), 1.29-1.20 (m, 1H); MS (ESI+) m/z 515 (M+H)$^+$.

Example 137

N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide The title compound was prepared by substituting N-(tert-butoxycarbonyl)-L-leucine for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in Example the procedure described for Example 1: $^1$H NMR (500 MHz, pyridine-d$_5$) δ ppm 8.50 (d, J=7.1, 0.5H), 8.46 (d, J=6.8, 0.5H), 8.03 (dd, J=8.2, 17.0, 1H), 7.74 (s, 1H), 7.71 (d, J=7.7, 0.5H), 7.61 (d, J=6.5, 0.5H), 7.47 (t, J=7.7, 1H), 4.67 (dd, J=8.2, 14.1, 0.5H), 4.61 (dd, J=8.1, 14.7, 0.5H), 4.53-4.39 (m, 1H), 3.81 (d, J=13.1, 0.5H), 3.70 (d, J=13.3, 0.5H), 3.44 (d, J=13.3, 0.5H), 3.29 (d, J=13.2, 0.5H), 2.93-2.86 (m, 1H), 2.85-2.74 (m, 1H), 2.46 (d, J=4.1, 1H), 2.39-2.21 (m, 3H), 1.96-1.76 (m, 5H), 1.73-1.55 (m, 2H), 1.50 (s, 4.5H), 1.50 (s, 4.5H), 1.34-1.23 (m, 1H), 0.91-0.82 (m, 6H); MS (ESI+) m/z 498 (M+H)$^+$.

Example 138

N$^2$-(tert-butyloxycarbonyl)-N$^1$-{(3aS*,4S*,6aR*)-2-[3-(trifluoromethyl)benzyl]octahydrocyclopenta[c]pyrrol-4-yl}-D-leucinamide The title compound was prepared by substituting N-(tert-butoxycarbonyl)-D-leucine for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (500 MHz, pyridine-d$_5$) δ ppm 8.50 (d, J=7.0, 0.5H), 8.46 (d, J=6.8, 0.5H), 8.03 (dd, J=8.1, 17.2, 1H), 7.74 (s, 1H), 7.71 (d, J=7.7, 1H), 7.61 (d, J=5.8, 1H), 7.48 (t, J=7.7, 1H), 4.67 (dd, J=8.3, 14.3, 0.5H), 4.61 (dd, J=7.9, 14.5, 0.5H), 4.47 (ddd, J=7.0, 13.9, 17.8, 1H), 3.81 (d, J=13.1, 0.5H), 3.70 (d, J=13.1, 0.5H), 3.44 (d, J=13.3, 0.5H), 3.29 (d, J=13.2, 0.5H), 2.89 (t, J=13.2, 1H), 2.85-2.75 (m, 1H), 2.51-2.42 (m, 1H), 2.39-2.30 (m, 1H), 2.28 (dd, J=6.1, 15.3, 2H), 1.97-1.77 (m, 4H), 1.73-1.55 (m, 2H), 1.50 (s, 4.5H), 1.50 (s, 4.5H), 1.34-1.22 (m, 1H), 0.91-0.81 (m, 6H); MS (ESI+) m/z 498 (M+H)$^+$.

Example 139

N$^2$-(tert-butyloxycarbonyl)-N$^2$-methyl-N$^1$-{(3aS*,4S*,6aR*)-2-[3-(trifluoromethyl)benzyl]octahydrocyclopenta[c]pyrrol-4-yl}-D-leucinamide The title compound was prepared by substituting N-(tert-butoxycarbonyl)-N-methyl-D-leucine for 1-phenylcyclopentanecarboxylic acid and (3aS*,4S*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 1: $^1$H NMR (300 MHz, pyridine-d$_5$) δ ppm 7.76 (d, J=15.9, 2H), 7.57 (s, 3H), 7.54-7.43 (m, 1H), 7.42-7.36 (m, 0.5H), 7.34-7.21 (m, 1H), 4.86 (t, J=9.6, 0.5H), 4.48-4.35 (m, 0.5H), 3.71 (d, J=13.3, 0.5H), 3.52 (d, J=13.4, 0.5H), 3.40 (d, J=13.2, 0.5H), 2.98 (s, 1.5H), 2.97 (s, 1.5H), 2.77 (ddd, J=2.0, 7.2, 9.8, 2H), 2.57-2.46 (m, 1H), 2.43 (dd, J=2.9, 9.2, 0.5H), 2.36 (dd, J=2.3, 6.4, 0.5H), 2.34-2.22 (m, 2H), 1.93 (dddd, J=2.0, 6.2, 8.1, 14.3, 1H), 1.85-1.59 (m, 4H), 1.52 (s, 4.5H), 1.50 (s, 4.5H), 1.39-1.28 (m, 1H), 0.96-0.89 (m, 6H); MS (ESI+) m/z 512 (M+H)$^+$.

Example 140

6,6-bis(4-fluorophenyl)-N-{(3aS*,4R*,6aR*)-2-[3-(trifluoromethyl)benzyl]octahydrocyclopenta[c]pyrrol-4-yl}hexanamide The title compound was prepared by substituting 6,6-bis(4-fluorophenyl)hexanoic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-d$_5$) δ ppm 8.31 (d, J=7.3, 1H), 7.77 (s, 1H), 7.61 (t, J=7.4, 1H), 7.57 (d, J=7.2, 1H), 7.45 (t, J=7.7, 1H), 7.25 (dd, J=5.6, 8.2, 4H), 7.10 (t, J=8.7, 4H), 4.46-4.37 (m, 1H), 3.90 (t, J=7.8, 1H), 3.61 (d, J=13.5, 1H), 3.47 (d, J=13.5, 1H), 2.85-2.79 (m, 1H), 2.49 (d, J=16.3, 2H), 2.47-2.41 (m, 1H), 2.30 (ddd, J=8.1, 15.0, 20.0, 4H), 2.15-2.06 (m, 1H), 1.98 (dd, J=7.8, 15.5, 2H), 1.90-1.79 (m, 3H), 1.60 (dt, J=7.4, 19.3, 1H), 1.44-1.36 (m, 1H), 1.32 (dq, J=7.8, 15.3, 2H); MS (ESI+) m/z 571 (M+H)$^+$.

Example 141

3,3-diphenyl-N-{(3aS*,4R*,6aR*)-2-[3-(trifluoromethyl)benzyl]octahydrocyclopenta[c]pyrrol-4-yl}propanamide The title compound was prepared by substituting 3,3-diphenylpropanoic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-d$_5$) δ ppm 8.28 (d, J=7.4, 1H), 7.74 (s, 1H), 7.45 (t, J=7.7, 1H), 7.33 (dd, J=1.8, 7.4, 4H), 7.28 (dt, J=7.6, 9.4, 4H), 7.20-7.17 (m, 4H), 5.00 (t, J=7.8, 1H), 4.34-4.26 (m, 1H), 3.56 (d, J=13.5, 1H), 3.43 (d, J=13.5, 1H), 3.14 (d, J=7.9, 2H), 2.65 (dd, J=2.1, 8.3, 1H), 2.45-2.36 (m, 1H), 2.36-2.28 (m, 2H), 2.26-2.19 (m, 2H), 1.98-1.89 (m, 1H), 1.72 (ddd, J=6.3, 12.5, 14.5, 1H), 1.43 (dt, J=7.4, 14.1, 1H), 1.34-1.25 (m, 1H); MS (ESI+) m/z 493 (M+H)$^+$.

Example 142

5,5-bis(4-fluorophenyl)-N-{(3aS*,4R*,6aR*)-2-[3-(trifluoromethyl)benzyl]octahydrocyclopenta[c]pyrrol-4-yl}pentanamide The title compound was prepared by substituting 5,5-bis(4-fluorophenyl)pentanoic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-d$_5$) δ ppm 8.36 (d, J=7.2, 1H), 7.75 (s, 1H), 7.62-7.54 (m, 2H), 7.44 (t, J=7.7, 1H), 7.24 (dt, J=5.7, 11.3, 4H), 7.07 (t, J=8.7, 4H), 4.47-4.39 (m, 1H), 3.96 (t, J=7.8, 1H), 3.59 (d, J=13.5, 1H), 3.46 (d, J=13.5, 1H), 2.84 (d, J=9.0, 1H), 2.51 (s, 2H), 2.42 (dd, J=7.0, 14.2, 3H), 2.30 (d, J=7.1, 1H), 2.27-2.22 (m, 1H), 2.15-2.06 (m, 3H), 1.85 (dd, J=6.2, 13.9, 1H), 1.78 (dt, J=7.4, 15.1, 2H), 1.60 (dt, J=7.6, 14.6, 1H), 1.43-1.34 (m, 1H); MS (ESI+) m/z 557 (M+H)$^+$.

Example 143

3,3-bis(4-fluorophenyl)-N-{(3aS*,4R*,6aR*)-2-[3-(trifluoromethyl)benzyl]octahydrocyclopenta[c]pyrrol-4-yl}propanamide The title compound was prepared by substituting 3,3-bis(4-fluorophenyl)propanoic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-$d_5$) δ ppm 8.36 (d, J=7.4, 1H), 7.74 (s, 1H), 7.62-7.56 (m, 2H), 7.45 (t, J=7.7, 1H), 7.32 (ddd, J=2.0, 5.4, 7.8, 4H), 7.07 (dt, J=8.7, 11.2, 4H), 4.36-4.26 (m, 1H), 3.56 (d, J=13.5, 1H), 3.45 (d, J=13.5, 1H), 3.09 (d, J=7.9, 2H), 2.70-2.63 (m, 1H), 2.47-2.37 (m, 1H), 2.33 (t, J=6.7, 3H), 2.26 (dd, J=3.0, 9.0, 1H), 2.24-2.18 (m, 1H), 1.96 (tt, J=6.0, 11.8, 1H), 1.79-1.70 (m, 1H), 1.44 (dt, J=7.6, 14.4, 1H), 1.35-1.26 (m, 1H); MS (ESI+) m/z 529 (M+H)$^+$.

Example 144

4,4-bis(4-fluorophenyl)-N-{(3aS*,4R*,6aR*)-2-[3-(trifluoromethyl)benzyl]octahydrocyclopenta[c]pyrrol-4-yl}butanamide The title compound was prepared by substituting 4,4-bis(4-fluorophenyl)butanoic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-$d_5$) δ ppm 8.39 (d, J=7.2, 1H), 7.77 (s, 1H), 7.62 (d, J=7.9, 2H), 7.45 (t, J=7.7, 1H), 7.25 (dd, J=5.5, 7.3, 4H), 7.05 (t, J=8.7, 4H), 4.50-4.40 (m, 1H), 4.08 (t, J=7.9, 1H), 3.61 (d, J=13.5, 1H), 3.49 (d, J=13.5, 1H), 2.87 (dd, J=1.4, 8.8, 1H), 2.56 (dd, J=7.7, 15.3, 4H), 2.48 (d, J=8.8, 1H), 2.31 (dd, J=8.0, 15.4, 4H), 2.13 (dq, J=6.0, 12.0, 1H), 1.87 (td, J=6.3, 12.5, 1H), 1.62 (dt, J=7.4, 14.3, 1H), 1.41 (dd, J=11.7, 20.8, 1H); MS (ESI+) m/z 543 (M+H)$^+$.

Example 145

2,2-diphenyl-N-{(3aS*,4R*,6aR*)-2-[3-(trifluoromethyl)benzyl]octahydrocyclopenta[c]pyrrol-4-yl}acetamide The title compound was prepared by substituting 2,2-diphenylacetic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-$d_5$) δ ppm 8.94 (d, J=6.8, 1H), 7.74 (s, 2H), 7.64 (d, J=7.8, 4H), 7.47-7.40 (m, 1H), 7.38-7.29 (m, 5H), 7.28-7.23 (m, 3H), 4.45-4.37 (m, 1H), 3.57 (d, J=13.5, 1H), 3.42 (d, J=13.5, 1H), 2.76 (dd, J=3.0, 9.1, 1H), 2.54-2.47 (m, 1H), 2.47-2.42 (m, 1H), 2.39 (dd, J=7.3, 9.0, 1H), 2.23 (d, J=3.0, 2H), 2.06 (dq, J=6.2, 12.2, 1H), 1.83-1.74 (m, 1H), 1.59 (dt, J=6.9, 14.5, 1H), 1.33 (dt, J=6.3, 19.6, 1H); MS (ESI+) m/z 479 (M+H)$^+$.

Example 146

2,2-bis(4-fluorophenyl)-N-{(3aS*,4R*,6aR*)-2-[3-(trifluoromethyl)benzyl]octahydrocyclopenta[c]pyrrol-4-yl}acetamide The title compound was prepared by substituting 2,2-bis(4-fluorophenyl)acetic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-$d_5$) δ ppm 9.07 (d, J=7.1, 1H), 7.74 (s, 1H), 7.59 (s, 1H), 7.56 (d, J=5.3, 5H), 7.44 (t, J=7.7, 1H), 7.12 (q, J=8.6, 4H), 5.23 (s, 1H), 4.45-4.36 (m, 1H), 3.57 (d, J=13.5, 1H), 3.44 (d, J=13.5, 1H), 2.78 (dd, J=2.9, 9.1, 1H), 2.56-2.49 (m, 1H), 2.49-2.44 (m, 1H), 2.41 (dd, J=7.3, 8.9, 1H), 2.27-2.22 (m, 2H), 2.07 (dq, J=6.1, 12.1, 1H), 1.86-1.76 (m, 1H), 1.60 (td, J=7.2, 14.6, 1H), 1.35 (td, J=6.3, 12.6, 1H); MS (ESI+) m/z 515 (M+H)$^+$.

Example 147

3,3-dimethyl-2-phenyl-N-{(3aS*,4R*,6aR*)-2-[3-(trifluoromethyl)benzyl]octahydrocyclopenta[c]pyrrol-4-yl}butanamide The title compound was prepared by substituting 3,3-dimethyl-2-phenylbutanoic acid for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (400 MHz) δ ppm 8.47 (t, J=6.7, 1H), 7.77 (s, 0.5H), 7.71 (d, J=7.3, 2H), 7.60 (d, J=7.7, 0.5H), 7.54 (s, 1H), 7.43 (dd, J=8.1, 16.6, 1H), 7.35-7.24 (m, 4H), 4.39-4.29 (m, 1H), 3.62 (d, J=13.6, 0.5H), 3.53 (d, J=13.5, 0.5H), 3.47 (d, J=13.6, 0.5H), 3.44 (s, 1H), 3.38 (d, J=13.5, 0.5H), 2.92 (dd, J=2.9, 9.0, 0.5H), 2.62-2.54 (m, 1H), 2.54-2.46 (m, 1H), 2.46-2.36 (m, 0.5H), 2.32 (dd, J=9.1, 12.0, 1H), 2.27 (d, J=5.2, 1H), 2.21 (d, J=5.6, 1H), 2.17-2.07 (m, 0.5H), 1.86 (ddd, J=6.4, 13.3, 21.3, 1H), 1.71 (tdd, J=6.4, 13.0, 19.3, 1H), 1.36 (ddt, J=8.2, 14.4, 20.6, 1.5H), 1.14 (d, J=1.3, 9H); MS (ESI+) m/z 459 (M+H)$^+$.

Example 148

N$^2$-(tert-butyloxycarbonyl)-N$^1$-{(3aS*,4R*,6aR*)-2-[3-(trifluoromethyl)benzyl]octahydrocyclopenta[c]pyrrol-4-yl}-L-leucinamide The title compound was prepared by substituting N-(tert-butoxycarbonyl)-L-leucine for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-$d_5$) δ ppm 8.66 (dd, J=7.6, 11.3, 1H), 7.98 (d, J=6.0, 1H), 7.74 (d, J=7.5, 1H), 7.58 (d, J=21.6, 2H), 7.44 (t, J=7.8, 1H), 4.74-4.66 (m, 1H), 4.45-4.36 (m, 1H), 3.58 (t, J=13.6, 1H), 3.43 (dd, J=13.6, 20.1, 1H), 2.81 (s, 0.5H), 2.73 (s, 0.5H), 2.57 (s, 0.5H), 2.47 (d, J=9.1, 2H), 2.34 (s, 0.5H), 2.26 (d, J=6.7, 1H), 2.24-2.20 (m, 0.5H), 2.11 (s, 1H), 2.07-1.99 (m, 0.5H), 1.87 (s, 4H), 1.71-1.62 (m, 0.5H), 1.61-1.55 (m, 0.5H), 1.50 (d, J=2.8, 9H), 1.40 (s, 1H), 0.87 (d, J=5.8, 3H), 0.84 (d, J=5.5, 3H); MS (ESI+) m/z 498 (M+H)$^+$.

Example 149

$N^2$-(tert-butyloxycarbonyl)-$N^1$-{(3aS*,4R*,6aR*)-2-[3-(trifluoromethyl)benzyl]octahydrocyclopenta[c]pyrrol-4-yl}-D-leucinamide The title compound was prepared by substituting N-(tert-butoxycarbonyl)-D-leucine for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-d$_5$) δ ppm 8.66 (dd, J=7.4, 11.1, 1H), 7.97 (d, J=6.0, 1H), 7.74 (d, J=7.6, 1H), 7.57 (d, J=10.9, 2H), 7.44 (dd, J=5.9, 13.6, 1H), 4.74-4.66 (m, 1H), 4.41 (dd, J=6.2, 11.5, 1H), 3.58 (t, J=13.4, 1H), 3.43 (dd, J=13.6, 19.7, 1H), 2.82 (dd, J=2.4, 9.0, 0.5H), 2.74 (d, J=8.7, 0.5H), 2.62-2.54 (m, 0.5H), 2.54-2.43 (m, 2H), 2.37-2.32 (m, 0.5H), 2.27 (d, J=6.7, 1H), 2.24-2.19 (m, 0.5H), 2.16-2.08 (m, 0.5H), 2.06-1.99 (m, 0.5H), 1.94-1.78 (m, 4.5H), 1.66 (dt, J=7.2, 19.6, 0.5H), 1.62-1.56 (m, 0.5H), 1.50 (d, J=2.9, 9H), 1.43-1.31 (m, 1H), 0.86 (dd, J=5.7, 13.5, 6H); MS (ESI+) m/z 498 (M+H)$^+$.

Example 150

$N^2$-(tert-butyloxycarbonyl)-$N^2$-methyl-$N^1$-{(3aS*,4R*,6aR*)-2-[3-(trifluoromethyl)benzyl]octahydrocyclopenta[c]pyrrol-4-yl}-D-leucinamide The title compound was prepared by substituting N-(tert-butoxycarbonyl)-N-methyl-D-leucine for 1-phenylcyclopentanecarboxylic acid and (3aS*,4R*,6aR*)-2-(3-(trifluoromethyl)benzyl)octahydrocyclopenta[c]pyrrol-4-amine from Example 122 Step E for (3aS*,6aR*)-2-benzyloctahydrocyclopenta[c]pyrrol-4-amine in the procedure described for Example 2: $^1$H NMR (500 MHz, pyridine-d$_5$) δ ppm 8.31 (s, 1H), 7.75 (s, 1H), 7.57 (d, J=11.6, 2H), 7.44 (t, J=7.7, 1H), 5.18-5.09 (m, 0.5H), 4.84-4.73 (m, 0.5H), 4.44-4.32 (m, 1H), 3.59 (d, J=13.5, 1H), 3.47 (d, J=13.6, 1H), 3.07 (d, J=25.1, 2.5H), 2.83 (d, J=8.5, 0.5H), 2.79-2.72 (m, 0.5H), 2.55-2.44 (m, 2H), 2.44-2.39 (m, 1H), 2.37-2.33 (m, 0.5H), 2.29 (d, J=7.4, 1H), 2.23 (dd, J=7.9, 15.2, 1H), 2.08 (dt, J=5.2, 11.8, 1H), 1.88-1.78 (m, 3H), 1.64-1.51 (m, 2H), 1.46 (s, 9H), 1.41-1.33 (m, 1H), 0.88 (d, J=6.4, 3H), 0.84 (d, J=6.5, 3H); MS (ESI+) m/z 512 (M+H)$^+$.

Example 151

$N^1$-[(3aS,4R,6aR)-2-benzyloctahydrocyclopenta[c]pyrrol-4-yl]-$N^2$-(tert-butyloxycarbonyl)-$N^2$-methyl-L-leucinamide The title compound was prepared by substituting N-(tert-butoxycarbonyl)-N-methyl-L-leucine for 1-phenylcyclopentanecarboxylic acid in the procedure described for Example 2: $^1$H NMR (500 MHz, pyridine-d$_5$) δ ppm 8.28 (d, J=6.6, 1H), 7.41 (s, 2H), 7.38-7.34 (m, 2H), 7.27 (t, J=7.3, 1H), 5.16-5.11 (m, 0.5H), 4.82-4.74 (m, 0.5H), 4.44-4.33 (m, 1H), 3.57 (s, 1H), 3.46-3.38 (m, 1H), 3.07 (d, J=26.9, 3H), 2.89- 2.82 (m, 0.5H), 2.80-2.73 (m, 1H), 2.50-2.43 (m, 2H), 2.40-2.29 (m, 2H), 2.24-2.19 (m, 1H), 2.10 (dq, J=5.8, 11.6, 1H), 1.92-1.87 (m, 0.5H), 1.83 (dd, J=5.2, 9.3, 2H), 1.64-1.51 (m, 2H), 1.46 (s, 9H), 1.42-1.35 (m, 1H), 0.88 (d, J=6.3, 3H), 0.84 (d, J=6.6, 3H); MS (ESI+) m/z 444 (M+H)$^+$.

Example 152

2,2-dicyclohexyl-2-hydroxy-N-{(3aS,4S,6aR)-2-[3-(trifluoromethyl)benzyl]octahydrocyclopenta[c]pyrrol-4-yl}acetamide Step A: (3aS,4S,6aR)-2-(3-(Trifluoromethyl)benzyl)octahydrocyclopenta[c]pyrrol-4-amine was prepared according to the procedure described in Example 14 Step A-C. Substituting 2-(3-(trifluoromethyl)benzyl)hexahydrocyclopenta[c]pyrrol-4(5H)-one from Steps A-C in Example 122 for 2-benzylhexahydrocyclopenta[c]pyrrol-4(5H)-one in Step A of Example 14 gave (S,E)-2-methyl-N-((3aR,6aS)-2-(3-(trifluoromethyl)benzyl)hexahydrocyclopenta[c]pyrrol-4(5H)-ylidene)propane-2-sulfinamide and (S,E)-2-methyl-N-((3aS,6aR)-2-(3-(trifluoromethyl)benzyl)hexahydrocyclopenta[c]pyrrol-4(5H)-ylidene)propane-2-sulfinamide. (S,E)-2-Methyl-N-((3aS,6aR)-2-(3-(trifluoromethyl)benzyl)hexahydrocyclopenta[c]pyrrol-4(5H)-ylidene)propane-2-sulfinamide was used as described in Example 14 Steps B-C to give (3aS,4S,6aR)-2-(3-(trifluoromethyl)benzyl)octahydrocyclopenta[c]pyrrol-4-amine: $^1$H NMR (500 MHz, pyridine-d$_5$) δ ppm 7.72 (s, 1H), 7.59 (d, J=12.2, 1H), 7.54 (d, J=7.7, 1H), 7.39 (t, J=7.7, 1H), 3.71-3.66 (m, 1H), 3.64 (d, J=13.3, 1H), 3.49 (d, J=13.3, 1H), 3.22 (dd, J=3.7, 9.9, 1H), 2.77 (qd, J=3.8, 7.9, 1H), 2.49 (dd, J=8.9, 16.7, 2H), 2.39 (t, J=8.3, 1H), 2.29 (dd, J=3.4, 9.0, 1H), 2.10 (ddd, J=6.1, 9.7, 15.6, 1H), 1.90 (td, J=5.9, 12.0, 1H), 1.69-1.60 (m, 1H), 1.42 (dt, J=5.6, 12.2, 1H); MS (ESI+) m/z 284 (M+H)$^+$.

Step B: The title compound was prepared by substituting 2,2-dicyclohexyl-2-hydroxyacetic acid for 3-methyl-2-phenylbutanoic acid and (3aS,4S,6aR)-2-(3-(trifluoromethyl)benzyl)octahydrocyclopenta[c]pyrrol-4-amine from Step A for (3aS,4S,6aR)-2-benzyloctahydrocyclopenta[c]pyrrol-4-amine in the procedure described in Step D of Example 14: $^1$H NMR (500 MHz, pyridine-d$_5$) δ ppm 8.45 (br s, 1H), 7.85 (s, 1H), 7.75 (d, J=7.4, 1H), 7.54 (d, J=7.6, 1H), 7.36 (dd, J=5.4, 13.2, 1H), 5.93 (br s, 1H), 4.64-4.57 (m, 1H), 3.85 (d, J=13.2, 1H), 3.29 (d, J=13.2, 1H), 2.92 (d, J=9.5, 1H), 2.66 (dd, J=7.4, 15.2, 1H), 2.49-2.41 (m, 1H), 2.39 (d, J=9.1, 1H), 2.24-2.01 (m, 5H), 1.96-1.83 (m, 4H), 1.83-1.70 (m, 6H), 1.63 (t, J=13.2, 2H), 1.58-1.49 (m, 1H), 1.45-1.08 (m, 10H); MS (ESI+) m/z 507 (M+H)$^+$.

Example 153

$N^2$-(tert-butyloxycarbonyl)-$N^2$-methyl-$N^1$-{(3aS,4S,6aR)-2-[3-(trifluoromethyl)benzyl]octahydrocyclopenta[c]pyrrol-4-yl}-L-leucinamide The title compound was prepared by substituting N-(tert-butoxycarbonyl)-N-methyl-L-leucine for 3-methyl-2-phenylbutanoic acid and (3aS,4S,6aR)-2-(3-(trifluoromethyl)benzyl)octahydrocyclopenta[c]pyrrol-4-amine from 152 Step A for (3aS,4S,6aR)-2-benzyloctahydrocyclopenta[c]pyrrol-4-amine in the procedure described in Step D of Example 14: $^1$H NMR (500 MHz, pyridine-d$_5$) δ ppm 8.01 (s, 1H), 7.83 (s, 1H), 7.76 (s, 1H), 7.64 (d, J=7.7, 2H), 5.12-5.04 (m, 1H), 4.42 (s, 1H), 3.61 (s, 1H), 3.52 (s, 1H), 3.12-2.97 (m, 3H), 2.78 (s, 1H), 2.72 (d, J=9.5, 1H), 2.50-2.41 (m, 1H), 2.37 (d, J=7.3, 1H), 2.32-2.16 (m, 2H), 1.98-1.72 (m, 3H), 1.64 (dt, J=6.8, 14.9, 1H), 1.60-1.53 (m, 2H), 1.50 (s, 9H), 1.33-1.20 (m, 1H), 0.89 (d, J=6.5, 6H); MS (ESI+) m/z 512 (M+H)+.

Example 154

2,2-dicyclohexyl-2-hydroxy-N-{(3aS,4R,6aR)-2-[3-(trifluoromethyl)benzyl]octahydrocyclopenta[c]pyrrol-4-yl}acetamide Step A: (3aS,4R,6aR)-2-(3-(Trifluoromethyl)benzyl)octahydrocyclopenta[c]pyrrol-4-amine was prepared according to the procedure described in Example 16 Steps A-E substituting (S,E)-2-methyl-N-((3aS,6aR)-2-(3-(trifluoromethyl)benzyl)hexahydrocyclopenta[c]pyrrol-4(5H)-ylidene)propane-2-sulfinamide from Step A in Example 152 for (S,E)-N-((3aS,6aR)-2-benzylhexahydrocyclopenta[c]pyrrol-4(5H)-ylidene)-2-methylpropane-2-sulfinamide in Step A-E of Example 16 to give (3aS,4R,6aR)-2-(3-(trifluoromethyl)benzyl)octahydrocyclopenta[c]pyrrol-4-amine: $^1$H NMR (500 MHz, pyridine-$d_5$) δ ppm 7.78 (s, 1H), 7.59 (d, J=6.0, 2H), 7.45 (t, J=7.7, 1H), 4.94 (br s, 2H), 3.53 (s, 2H), 3.13 (dd, J=5.1, 11.6, 1H), 2.63-2.54 (m, 1H), 2.49 (dd, J=3.3, 9.0, 1H), 2.35 (dd, J=7.5, 9.0, 1H), 2.32 (d, J=5.9, 2H), 2.21-2.13 (m, 1H), 1.96 (dt, J=6.0, 8.7, 1H), 1.88 (td, J=3.9, 9.7, 1H), 1.38-1.29 (m, 2H); MS (ESI+) m/z 284 (M+H)+.

Step B: The title compound was prepared by substituting (3aS,4R,6aR)-2-(3-(trifluoromethyl)benzyl)octahydrocyclopenta[c]pyrrol-4-amine from Step A for (3aS,4R,6aR)-2-benzyloctahydrocyclopenta[c]pyrrol-4-amine and 2,2-dicyclohexyl-2-hydroxyacetic acid for (S)-2-phenylbutanoic acid in the procedure described in Step F of Example 16: $^1$H NMR (500 MHz, pyridine-$d_5$) δ ppm 7.75 (s, 1H), 7.70 (d, J=7.8, 1H), 7.63-7.54 (m, 1H), 7.44 (t, J=7.7, 1H), 6.25-6.09 (m, 1H), 4.45-4.37 (m, 1H), 3.61 (d, J=13.5, 1H), 3.44 (d, J=13.5, 1H), 2.91 (dd, J=2.1, 9.0, 1H), 2.58-2.46 (m, 1H), 2.40 (dd, J=7.1, 8.8, 1H), 2.33 (dd, J=2.3, 8.9, 1H), 2.22 (dd, J=7.0, 8.7, 1H), 2.19-2.04 (m, 5H), 1.94-1.82 (m, 4H), 1.82-1.71 (m, 4H), 1.63 (s, 3H), 1.58-1.46 (m, 1H), 1.37 (s, 4H), 1.25 (s, 7H); MS (ESI+) m/z 507 (M+H)+.

Example 155

N$^2$-(tert-butyloxycarbonyl)-N$^2$-methyl-N$^1$-{(3aS,4R,6aR)-2-[3-(trifluoromethyl)benzyl]octahydrocyclopenta[c]pyrrol-4-yl}-L-leucinamide The title compound was prepared by substituting (3aS,4R,6aR)-2-(3-(trifluoromethyl)benzyl)octahydrocyclopenta[c]pyrrol-4-amine from Example 154 Step A for (3aS,4R,6aR)-2-benzyloctahydrocyclopenta[c]pyrrol-4-amine and N-(tert-butoxycarbonyl)-N-methyl-L-leucine for (S)-2-phenylbutanoic acid in the procedure described in Step F of Example 16: $^1$H NMR (500 MHz, pyridine-$d_5$) δ ppm 8.30 (s, 1H), 7.74 (s, 1H), 7.57 (d, J=9.4, 2H), 7.44 (t, J=7.7, 1H), 5.21-5.04 (m, 1H), 4.37 (s, 1H), 3.58 (d, J=12.2, 1H), 3.44 (d, J=13.8, 1H), 3.07 (d, J=25.6, 3H), 2.77 (d, J=8.6, 1H), 2.47 (s, 2H), 2.41-2.32 (m, 1H), 2.29 (d, J=7.2, 1H), 2.25-2.18 (m, 1H), 2.08 (dq, J=5.8, 11.7, 1H), 1.83 (dd, J=5.4, 9.0, 3H), 1.64-1.52 (m, 1H), 1.46 (s, 9H), 1.41-1.32 (m, 1H), 0.88 (d, J=6.3, 3H), 0.84 (d, J=6.5, 3H); MS (ESI+) m/z 512 (M+H)+.

Example 156

2,2-dicyclohexyl-N-{(3aR,4S,6aS)-2-[3-(trifluoromethyl)benzyl]octahydrocyclopenta[c]pyrrol-4-yl}acetamide Step A: (3aR,4S,6aS)-2-(3-(Trifluoromethyl)benzyl)octahydrocyclopenta[c]pyrrol-4-amine was prepared according to the procedure described in Example 16 Step A-E substituting (S,E)-2-methyl-N-((3aR,6aS)-2-(3-(trifluoromethyl)benzyl)hexahydrocyclopenta[c]pyrrol-4(5H)-ylidene)propane-2-sulfinamide from Example 152 Step A for (S,E)-N-((3aS,6aR)-2-benzylhexahydrocyclopenta[c]pyrrol-4(5H)-ylidene)-2-methylpropane-2-sulfinamide prepared in Step A of Example 14 to give (3aR,4S,6aS)-2-(3-(trifluoromethyl)benzyl)octahydrocyclopenta[c]pyrrol-4-amine: $^1$H NMR (500 MHz, pyridine-$d_5$) δ ppm 7.78 (s, 1H), 7.59 (d, J=11.1, 2H), 7.45 (t, J=7.7, 1H), 4.94 (br s, 2H), 3.14 (dd, J=5.2, 11.5, 1H), 2.58 (tt, J=5.1, 10.1, 1H), 2.49 (dd, J=3.3, 9.0, 1H), 2.35 (dd, J=7.5, 9.0, 1H), 2.31 (d, J=5.8, 2H), 2.21-2.14 (m, 1H), 2.01-1.91 (m, 1H), 1.88 (td, J=4.2, 9.9, 1H), 1.38-1.29 (m, 2H).

Step B: The title compound was prepared by substituting (3aR,4S,6aS)-2-(3-(trifluoromethyl)benzyl)octahydrocyclopenta[c]pyrrol-4-amine from Step A for (3aS,4R,6aR)-2-benzyloctahydrocyclopenta[c]pyrrol-4-amine and 2,2-dicyclohexylacetic acid for (S)-2-phenylbutanoic acid in the procedure described for Example 16 Step F: $^1$H NMR (500 MHz, pyridine-$d_5$) δ ppm 8.13 (d, J=7.2, 1H), 7.76 (s, 1H), 7.63-7.53 (m, 2H), 7.44 (t, J=7.9, 1H), 4.51-4.43 (m, 1H), 3.61 (d, J=13.5, 1H), 3.46 (d, J=13.5, 1H), 2.88 (dd, J=2.8, 9.0, 1H), 2.63-2.52 (m, 2H), 2.49 (dd, J=7.1, 8.9, 1H), 2.32-2.27 (m, 2H), 2.13 (dq, J=6.1, 11.9, 1H), 2.03 (t, J=7.4, 1H), 1.96 (d, J=13.0, 2H), 1.92-1.83 (m, 3H), 1.80 (d, J=12.2, 2H), 1.75-1.68 (m, 4H), 1.67-1.63 (m, 1H), 1.63-1.57 (m, 2H), 1.50-1.37 (m, 3H), 1.30-1.18 (m, 4H), 1.12 (dtd, J=2.7, 12.5, 24.6, 4H); MS (ESI+) m/z 491 (M+H)+.

Example 157

2,2-dicyclohexyl-N-{(3aR,4R,6aS)-2-[3-(trifluoromethyl)benzyl]octahydrocyclopenta[c]pyrrol-4-yl}acetamide Step A: (3aR,4R,6aS)-2-(3-(Trifluoromethyl)benzyl)octahydrocyclopenta[c]pyrrol-4-amine was prepared according to the procedure described in Example 14 Steps B-C substituting (S,E)-2-methyl-N-((3aR,6aS)-2-(3-(trifluoromethyl)benzyl)hexahydrocyclopenta[c]pyrrol-4(5H)-ylidene)propane-2-sulfinamide from Example 152 Step A for (S,E)-N-((3aS,6aR)-2-benzylhexahydrocyclopenta[c]pyrrol-4(5H)-ylidene)-2-methylpropane-2-sulfinamide prepared in Step A of Example 14 to give (3aR,4R,6aS)-2-(3-(trifluoromethyl)benzyl)octahydrocyclopenta[c]pyrrol-4-amine: $^1$H NMR (500 MHz, pyridine-$d_5$) δ ppm 7.78 (s, 1H), 7.59 (d, J=11.1, 2H), 7.45 (t, J=7.7, 1H), 4.94 (br s, 2H), 3.14 (dd, J=5.2, 11.5, 1H), 2.58 (tt, J=5.1, 10.1, 1H), 2.49 (dd, J=3.3, 9.0, 1H), 2.35 (dd, J=7.5, 9.0, 1H), 2.31 (d, J=5.8, 2H), 2.21-2.14 (m, 1H), 2.00-1.92 (m, 1H), 1.88 (td, J=4.2, 9.9, 1H), 1.39-1.29 (m, 2H); MS (ESI+) m/z 284 (M+H)+.

Step B: The title compound was prepared by substituting 2,2-dicyclohexylacetic acid for 3-methyl-2-phenylbutanoic acid in and (3aR,4R,6aS)-2-(3-(trifluoromethyl)benzyl)octahydrocyclopenta[c]pyrrol-4-amine from Step A for (3aS,4S,6aR)-2-benzyloctahydrocyclopenta[c]pyrrol-4-amine in the procedure described in Step D of Example 14: $^1$H NMR (500 MHz, pyridine-$d_5$) δ ppm 7.73 (s, 1H), 7.66 (d, J=7.7, 1H), 7.55 (d, J=7.3, 2H), 7.50 (t, J=7.7, 1H), 4.50-4.43 (m, 1H), 3.54 (d, J=12.9, 1H), 3.46 (d, J=12.9, 1H), 2.74 (td, J=2.6, 10.5, 2H), 2.51-2.42 (m, 2H), 2.31 (t, J=8.3, 1H), 2.20 (dd, J=7.8, 9.8, 1H), 1.94-1.54 (m, 15H), 1.46 (d, J=13.0, 1H), 1.40 (d, J=14.4, 1H), 1.35-1.07 (m, 9H), 0.98 (qd, J=3.0, 12.3, 1H); MS (ESI+) m/z 491 (M+H)+.

Example 158

N$^1$-{(3aS*,4S*,6aR*)-2-[3-(trifluoromethyl)benzyl]octahydrocyclopenta[c]pyrrol-4-yl}-L-leucinamide N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide (140 mg, 0.281 mmol) from Example 137 and 2 N HCl (2.5 mL, 5.00 mmol) were combined in ether (0.5 mL), and the reaction was stirred at room temperature overnight. The solids were collected and dried to give the title compound as the hydrochloride salt: $^1$H NMR (500 MHz, pyridine-d$_5$) δ ppm 8.59 (s, 0.5H), 8.48 (s, 0.5H), 7.89 (s, 0.5H), 7.83 (s, 0.5H), 7.69 (t, J=6.8, 1H), 7.60 (d, J=7.8, 1H), 7.50-7.44 (m, 1H), 4.96 (br s, 2H), 4.57-4.48 (m, 1H), 3.73 (d, J=13.2, 0.5H), 3.67 (s, 1H), 3.64 (d, J=13.2, 1H), 3.39 (d, J=13.1, 0.5H), 3.35 (d, J=13.2, 0.5H), 2.81-2.70 (m, 2H), 2.45 (dd, J=7.5, 15.3, 1H), 2.39-2.31 (m, 1H), 2.27-2.14 (m, 2H), 1.95-1.79 (m, 2.5H), 1.72-1.56 (m, 2H), 1.53-1.46 (m, 0.5H), 1.33-1.23 (m, 1.5H), 0.90 (dt, J=6.2, 14.1, 6H); MS (ESI+) m/z 398 (M+H)$^+$.

Example 159

N$^1$-{(3aR*,4R*,6aS*)-2-[3-(trifluoromethyl)benzyl]octahydrocyclopenta[c]pyrrol-4-yl}-D-leucinamide The title compound was prepared as the hydrochloride salt by substituting N$^2$-(tert-butyloxycarbonyl)-N$^1$-{(3aS*,4S*,6aR*)-2-[3-(trifluoromethyl)benzyl]octahydrocyclopenta[c]pyrrol-4-yl}-D-leucinamide from Example 138 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.67 (d, J=7.4, 0.5H), 8.57 (d, J=7.6, 0.5H), 7.88 (s, 0.5H), 7.81 (s, 0.5H), 7.68 (d, J=7.3, 1H), 7.61 (s, 1H), 7.48 (dd, J=7.3, 14.5, 1H), 4.56-4.47 (m, 1H), 3.79-3.70 (m, 1H), 3.65 (d, J=13.2, 0.5H), 3.38 (t, J=13.5, 1H), 2.82-2.71 (m, 2H), 2.50-2.42 (m, 1H), 2.38-2.31 (m, 1H), 2.27-2.16 (m, 2H), 2.08 (dt, J=6.8, 19.9, 0.5H), 1.96-1.88 (m, 1.5H), 1.88-1.80 (m, 1H), 1.70-1.59 (m, 2H), 1.58-1.52 (m, 0.5H), 1.42-1.20 (m, 4H), 0.90 (dt, J=6.1, 13.2, 6H); MS (ESI+) m/z 398 (M+H)$^+$.

Example 160

N$^2$-methyl-N$^1$-{(3aS*,4S*,6aR*)-2-[3-(trifluoromethyl)benzyl]octahydrocyclopenta[c]pyrrol-4-yl}-D-leucinamide The title compound was prepared as the hydrochloride salt by substituting N$^2$-(tert-butyloxycarbonyl)-N$^2$-methyl-N$^1$-{(3aS*,4S*,6aR*)-2-[3-(trifluoromethyl)benzyl]octahydrocyclopenta[c]pyrrol-4-yl}-D-leucinamide from Example 139 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.52 (s, 0.5H), 8.29 (s, 0.5H), 7.92 (s, 0.5H), 7.79 (s, 0.5H), 7.69 (dd, J=7.6, 18.7, 1H), 7.62 (d, J=7.6, 1H), 7.48 (dd, J=7.8, 18.2, 1H), 4.59-4.48 (m, 1H), 3.82 (d, J=13.2, 0.5H), 3.63 (d, J=13.1, 0.5H), 3.42 (d, J=13.1, 0.5H), 3.31-3.18 (m, 1H), 2.81 (dd, J=1.9, 9.4, 0.5H), 2.74 (dd, J=8.5, 18.2, 1H), 2.50-2.43 (m, 1H), 2.41 (s, 1.5H), 2.40 (s, 1.5H), 2.33 (dd, J=1.9, 9.0, 0.5H), 2.25 (dd, J=7.3, 9.4, 0.5H), 2.21-2.03 (m, 1.5H), 1.92-1.81 (m, 2H), 1.80-1.48 (m, 4H), 1.42-1.21 (m, 3.5H), 0.94 (d, J=6.6, 1.5H), 0.93 (d, J=6.6, 1.5H), 0.90 (d, J=6.6, 1.5H), 0.87 (d, J=6.6, 1.5H); MS (ESI+) m/z 412 (M+H)$^+$.

Example 161

N$^1$-{(3aS*,4R*,6aR*)-2-[3-(trifluoromethyl)benzyl]octahydrocyclopenta[c]pyrrol-4-yl}-L-leucinamide The title compound was prepared as the hydrochloride salt by substituting N$^2$-(tert-butyloxycarbonyl)-N$^1$-{(3aS*,4R*,6aR*)-2-[3-(trifluoromethyl)benzyl]octahydrocyclopenta[c]pyrrol-4-yl}-L-leucinamide from Example 148 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 9.33 (s, 1H), 7.76 (s, 1H), 7.63-7.58 (m, 2H), 7.45 (d, J=4.3, 1H), 4.40 (dd, J=6.5, 12.5, 1H), 3.63-3.53 (m, 1H), 3.46 (dd, J=6.1, 13.6, 1H), 2.82-2.73 (m, 1H), 2.69-2.51 (m, 2H), 2.48-2.38 (m, 1H), 2.33 (dd, J=8.8, 16.3, 1H), 2.24 (dd, J=7.6, 16.5, 1H), 2.16-1.88 (m, 5H), 1.85 (dt, J=7.8, 15.2, 0.5H), 1.76-1.62 (m, 1H), 1.39 (qd, J=6.6, 14.9, 1.5H), 1.31-1.20 (m, 2H), 0.95 (d, J=6.0, 3H), 0.91 (dd, J=3.2, 5.6, 3H); MS (ESI+) m/z 398 (M+H)$^+$.

Example 162

N$^1$-{(3aS*,4R*,6aR*)-2-[3-(trifluoromethyl)benzyl]octahydrocyclopenta[c]pyrrol-4-yl}-D-leucinamide The title compound was prepared as the hydrochloride salt by substituting N$^2$-(tert-butyloxycarbonyl)-N$^1$-{(3aS*,4R*,6aR*)-2-[3-(trifluoromethyl)benzyl]octahydrocyclopenta[c]pyrrol-4-yl}-D-leucinamide from Example 149 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.31 (s, 1H), 7.75 (s, 1H), 7.62-7.53 (m, 2H), 7.44 (dd, J=7.4, 15.0, 1H), 4.44-4.35 (m, 1H), 3.60 (d, J=13.5, 2H), 3.46 (dd, J=5.5, 13.5, 1H), 2.87-2.79 (m, 1H), 2.57-2.43 (m, 2H), 2.42-2.37 (m, 1H), 2.32 (dt, J=3.0, 8.8, 1H), 2.27-2.20 (m, 1H), 2.08 (td, J=6.0, 12.2, 1H), 1.96-1.80 (m, 3H), 1.61-1.50 (m, 2H), 1.44-1.35 (m, 1H), 1.30-1.19 (m, 2H), 0.90 (d, J=6.2, 3H), 0.85 (d, J=6.2, 3H); MS (ESI+) m/z 398 (M+H)$^+$.

Example 163

N$^2$-methyl-N$^1$-{(3aS*,4R*,6aR*)-2-[3-(trifluoromethyl)benzyl]octahydrocyclopenta[c]pyrrol-4-yl}-D-leucinamide The title compound was prepared as the hydrochloride salt by substituting N$^2$-(tert-butyloxycarbonyl)-N$^2$-methyl-N$^1$-{(3aS*,4R*,6aR*)-2-[3-(trifluoromethyl)benzyl]octahydrocyclopenta[c]pyrrol-4-yl}-D-leucinamide from Example 150 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.32 (d, J=6.0, 1H), 7.76 (s, 1H), 7.61 (d, J=7.6, 1H), 7.55 (d, J=14.8, 1H), 7.45 (t, J=7.7, 1H), 4.47-4.40 (m, 1H), 3.61 (d, J=13.5, 1H), 3.47 (dd, J=3.1, 13.6, 1H), 3.30 (t, J=6.7, 1H), 2.86 (d, J=8.9, 1H), 2.59-2.51 (m, 1H), 2.46 (d, J=2.5, 3H), 2.42 (dd, J=8.5, 15.4, 1H), 2.35-2.30 (m, 1H), 2.28-2.23 (m, 1H), 2.14-2.05 (m, 1H), 1.93-1.82 (m, 2H), 1.74 (ddd, J=4.0, 9.7, 13.7, 1H), 1.62 (dt, J=7.4, 15.4, 1H), 1.40 (dt, J=14.2, 15.7, 1H), 1.3-1.22 (m, 3H), 0.91 (dt, J=3.0, 6.0, 3H), 0.85 (d, J=6.7, 3H); MS (ESI+) m/z 412 (M+H)$^+$.

Example 164

N$^2$-methyl-N$^1$-{(3aS,4S,6aR)-2-[3-(trifluoromethyl)benzyl]octahydrocyclopenta[c]pyrrol-4-yl}-L-leucinamide The title compound was prepared as the hydrochloride salt by substituting N$^2$-(tert-butyloxycarbonyl)-N$^2$-methyl-N$^1$-{(3aS,4S,6aR)-2-[3-(trifluoromethyl)benzyl]octahydrocyclopenta[c]pyrrol-4-yl}-L-leucinamide from Example 153 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.56 (d, J=7.4, 1H), 7.91 (s, 1H), 7.67 (d, J=7.6, 1H), 7.61 (d, J=7.8, 1H), 7.47 (t, J=7.7, 1H), 4.54 (dt, J=6.6, 13.2, 1H), 3.81 (d, J=13.2, 1H), 3.32 (dd, J=6.0, 7.9, 1H), 3.28 (d, J=13.2, 1H), 2.81 (d, J=9.5, 1H), 2.78-2.71 (m, 1H), 2.48-2.44 (m, 1H), 2.42 (s, 3H), 2.33 (d, J=9.1, 1H), 2.26 (dd, J=7.4, 9.3, 1H), 2.16-2.11 (m, 1H), 1.91-1.83 (m, 2H), 1.82-1.75 (m, 1H), 1.65 (ddq, J=6.3, 12.1, 18.8, 3H), 1.26 (td, J=6.2, 12.7, 1H), 0.95 (d, J=6.5, 3H), 0.90 (d, J=6.6, 3H); MS (ESI+) m/z 412 (M+H)$^+$.

Example 165

N$^1$-[(3aS,4R,6aR)-2-benzyloctahydrocyclopenta[c]pyrrol-4-yl]-N$^2$-methyl-L-leucinamide The title compound was prepared as the hydrochloride salt by substituting N$^1$-[(3aS,4R,6aR)-2-benzyloctahydrocyclopenta[c]pyrrol-4-yl]-N$^2$-(tert-butyloxycarbonyl)-N$^2$-methyl-L-leucinamide from Example 151 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.35 (d, J=6.9, 1H), 7.44 (d, J=7.4, 2H), 7.37 (t, J=7.6, 2H), 7.27 (t, J=7.3, 1H), 4.50-4.42 (m, 1H), 3.61 (d, J=13.1, 1H), 3.45 (d, J=13.2, 1H), 3.33 (t, J=7.0, 1H), 2.87 (d, J=8.7, 1H), 2.56-2.50 (m, 1H), 2.47 (s, 3H), 2.43 (dd, J=5.5, 14.6, 1H), 2.37 (d, J=8.7, 1H), 2.29-2.23 (m, 1H), 2.17-2.04 (m, 1H), 1.94-1.82 (m, 2H), 1.79-1.73 (m, 1H), 1.68-1.57 (m, 1H), 1.41 (dd, J=7.2, 13.5, 1H), 1.27 (s, 2H), 0.92 (d, J=6.6, 3H), 0.85 (d, J=6.6, 3H); MS (ESI+) m/z 344 (M+H)$^+$.

Example 166

N$^2$-methyl-N$^1$-{(3aS,4R,6aR)-2-[3-(trifluoromethyl)benzyl]octahydrocyclopenta[c]pyrrol-4-yl}-L-leucinamide The title compound was prepared as the hydrochloride salt by substituting N$^2$-(tert-butyloxycarbonyl)-N$^2$-methyl-N$^1$-{(3aS,4R,6aR)-2-[3-(trifluoromethyl)benzyl]octahydrocyclopenta[c]pyrrol-4-yl}-L-leucinamide from Example 155 for N$^2$-(tert-butyloxycarbonyl)-N$^1$-{(3aR*,4R*,6aS*)-2-[3-(trifluoromethyl)benzyl]octahydrocyclopenta[c]pyrrol-4-yl}-L-leucinamide in the procedure described for Example 158: $^1$H NMR (500 MHz, pyridine-d$_5$) δ ppm 8.09-7.97 (m, 1H), 7.76 (s, 1H), 7.63-7.61 (m, 1H), 7.45 (d, J=7.6, 1H), 7.42 (d, J=7.6, 1H), 4.49-4.40 (m, 1H), 3.60 (d, J=12.4, 1H), 3.47 (d, J=13.6, 1H), 2.87 (d, J=7.6, 1H), 2.59 (d, J=9.4, 4H), 2.43 (dt, J=7.2, 9.1, 1H), 2.34 (dd, J=1.7, 8.9, 1H), 2.28-2.23 (m, 1H), 2.16-2.03 (m, 2H), 1.98-1.77 (m, 3H), 1.70-1.61 (m, 1H), 1.46-1.33 (m, 1H), 1.32-1.21 (m, 2H), 0.93 (d, J=6.4, 3H), 0.86 (d, J=6.4, 3H); MS (ESI+) m/z 412 (M+H)$^+$.

Example 167

N$^2$-methyl-N$^2$-(methylsulfonyl)-N$^1$-{(3aS,4S,6aR)-2-[3-(trifluoromethyl)benzyl]octahydrocyclopenta[c]pyrrol-4-yl}-L-leucinamide To N$^2$-methyl-N$^1$-{(3aS,4S,6aR)-2-[3-(trifluoromethyl)benzyl]octahydrocyclopenta[c]pyrrol-4-yl}-L-leucinamide from Example 164 (122 mg, 0.296 mmol) in dichloromethane (0.5 mL) was added N,N-diisopropylethylamine (78 μL, 0.445 mmol) followed by methanesulfonyl chloride (25.4 μL, 0.326 mmol), and the reaction mixture was stirred at room temperature overnight. The reaction was reduced in volume and loaded onto a silica gel cartridge (Analogix®, Burlington, Wis., RS-12). The title compound was eluted with a gradient of 0% to 5% methanol (2 N ammonia)/dichloromethane over 20 minutes: $^1$H NMR (500 MHz, pyridine-d$_5$) δ ppm 8.59 (d, J=6.7, 1H), 7.73 (s, 1H), 7.66 (d, J=7.6, 1H), 7.62 (d, J=7.8, 1H), 7.51 (t, J=7.7, 1H), 4.78 (dd, J=6.2, 9.5, 1H), 4.41-4.33 (m, 1H), 3.67 (d, J=13.3, 1H), 3.16 (s, 3H), 3.15 (s, 3H), 2.90 (qd, J=3.3, 7.9, 1H), 2.75 (dd, J=3.3, 9.6, 1H), 2.53-2.44 (m, 1H), 2.38-2.29 (m, 3H), 1.89-1.70 (m, 4H), 1.70-1.58 (m, 3H), 1.36-1.26 (m, 1H), 0.83 (d, J=6.6, 3H), 0.81 (d, J=6.5, 3H); MS (ESI+) m/z 490 (M+H)$^+$.

Example 168

N$^1$-[(3aS,4R,6aR)-2-benzyloctahydrocyclopenta[c]pyrrol-4-yl]-N$^2$-methyl-N$^2$-(methylsulfonyl)-L-leucinamide The title compound was prepared by substituting N$^1$-[(3aS,4R,6aR)-2-benzyloctahydrocyclopenta[c]pyrrol-4-yl]-N$^2$-methyl-L-leucinamide from Example 165 for N$^2$-methyl-N$^1$-{(3aS,4S,6aR)-2-[3-(trifluoromethyl)benzyl]octahydrocyclopenta[c]pyrrol-4-yl}-L-leucinamide in the procedure described in Example 167: $^1$H NMR (500 MHz, pyridine-d$_5$) δ ppm 8.97 (d, J=7.0, 1H), 7.43 (d, J=7.3, 2H), 7.37 (d, J=7.3, 2H), 7.30-7.25 (m, 1H), 4.78 (dd, J=5.1, 10.2, 1H), 4.42-4.35 (m, 1H), 3.58 (d, J=13.1, 1H), 3.46 (d, J=13.2, 1H), 3.21 (s, 3H), 3.12 (s, 3H), 2.83 (d, J=8.7, 1H), 2.55-2.47 (m, 2H), 2.36 (dd, J=8.1, 14.7, 2H), 2.26-2.22 (m, 1H), 2.13 (dt, J=5.9, 11.7, 1H), 1.93-1.82 (m, 2H), 1.70-1.61 (m, 2H), 1.44-1.36 (m, 1H), 0.82 (d, J=6.2, 3H), 0.73 (d, J=5.9, 3H); MS (ESI+) m/z 422 (M+H)$^+$.

Example 169

N$^2$-methyl-N$^2$-(methylsulfonyl)-N$^1$-{(3aS,4R,6aR)-2-[3-(trifluoromethyl)benzyl]octahydrocyclopenta[c]pyrrol-4-yl}-L-leucinamide The title compound was prepared by substituting N$^2$-methyl-N$^1$-{(3aS,4R,6aR)-2-[3-(trifluoromethyl)benzyl]octahydrocyclopenta[c]pyrrol-4-yl}-L-leucinamide from Example 166 for N$^2$-methyl-N$^1$-{(3aS,4S,6aR)-2-[3-(trifluoromethyl)benzyl]octahydrocyclopenta[c]pyrrol-4-yl}-L-leucinamide in the procedure described in Example 167: $^1$H NMR (500 MHz, pyridine-d$_5$) δ ppm 8.98 (d, J=7.4, 1H), 7.77 (s, 1H), 7.62-7.58 (m, 2H), 7.45 (t, J=7.7, 1H), 4.78 (dd, J=5.0, 10.2, 1H), 4.41-4.33 (m, 1H), 3.59 (d, J=13.5, 1H), 3.48 (d, J=13.6, 1H), 3.21 (s, 3H), 3.12 (s, 3H), 2.84 (d, J=7.4, 1H), 2.51 (t, J=5.4, 2H), 2.37 (dd, J=6.9, 8.9, 1H), 2.32 (d, J=7.1, 1H), 2.23 (dd, J=6.8, 8.9, 1H), 2.11 (dd, J=5.8, 11.8, 1H), 1.93-1.82 (m, 2H), 1.70-1.61 (m, 3H), 1.44-1.35 (m, 1H), 0.82 (d, J=6.2, 3H), 0.73 (d, J=6.0, 3H); MS (ESI+) m/z 490 (M+H)$^+$.

Example 170

$N^2$-(methylsulfonyl)-$N^1$-{(3aS,4R,6aR)-2-[3-(trifluoromethyl)benzyl]octahydrocyclopenta[c]pyrrol-4-yl}-L-leucinamide Step A: N-(tert-Butoxycarbonyl)-L-leucine (180 mg, 0.778 mmol), hydroxybenzotriazole (119 mg, 0.778 mmol), and (3aS,4R,6aR)-2-(3-(trifluoromethyl)benzyl)octahydrocyclopenta[c]pyrrol-4-amine (201 mg, 0.707 mmol) from Example 154 Step A were combined in dichloromethane (1 mL). After 20 minutes, N-(3-dimethylaminopropyl)-N'-ethylcarbodiimide (0.138 mL, 0.778 mmol) was added and the reaction stirred at room temperature for 24 hours. The reaction was quenched with water, and the layers were separated. The aqueous layer extracted with 1 mL of dichloromethane. The combined organic layers were applied to a silica gel cartridge (Analogix®, Burlington, Wis., RS15-24) and eluted with 1-10% methanol (2 N ammonia)/dichloromethane to give $N^2$-(tert-butyloxycarbonyl)-$N^1$-{(3aS,4R,6aR)-2-[3-(trifluoromethyl)benzyl]octahydrocyclopenta[c]pyrrol-4-yl}-L-leucinamide: $^1$H NMR (500 MHz, pyridine-d$_5$) δ ppm 8.66 (d, J=7.1, 1H), 7.97 (d, J=8.5, 1H), 7.73 (s, 1H), 7.56 (s, 2H), 7.44 (t, J=7.7, 1H), 4.70 (dd, J=5.9, 11.0, 1H), 4.40 (br s, 1H), 3.56 (d, J=13.5, 1H), 3.41 (d, J=13.5, 1H), 2.74 (d, J=8.9, 1H), 2.48 (s, 2H), 2.37-2.31 (m, 1H), 2.27 (d, J=8.4, 1H), 2.24-2.19 (m, 1H), 2.12 (dq, J=6.0, 12.0, 1H), 1.91-1.81 (m, 4H), 1.66 (td, J=7.4, 14.7, 1H), 1.50 (s, 9H), 1.43-1.35 (m, 1H), 0.87 (d, J=5.9, 3H), 0.84 (d, J=5.6, 3H); MS (ESI+) m/z 498 (M+H)$^+$.

Step B: $N^2$-(tert-Butyloxycarbonyl)-$N^1$-{(3aS,4R,6aR)-2-[3-(trifluoromethyl)benzyl]octahydrocyclopenta[c]pyrrol-4-yl}-L-leucinamide from Step A (0.731 g, 1.469 mmol) in ethanol (5 mL) was treated with HCl (4 N in dioxane, 10.0 mL, 40.0 mmol). The reaction was stirred at room temperature for 2 hours and the solvent removed in vacuo. The reaction was quenched with saturated aqueous sodium bicarbonate and extracted with 3×50 mL of dichloromethane. The solvent was removed in vacuo to give $N^1$-{(3aS,4R,6aR)-2-[3-(trifluoromethyl)benzyl]octahydrocyclopenta[c]pyrrol-4-yl}-L-leucinamide: $^1$H NMR (500 MHz, pyridine-d$_5$) δ ppm 8.27 (d, J=7.6, 1H), 7.75 (s, 1H), 7.63-7.54 (m, 2H), 7.44 (dd, J=6.9, 14.6, 1H), 4.44-4.33 (m, 1H), 3.62-3.53 (m, 2H), 3.45 (d, J=13.5, 1H), 2.84 (dd, J=2.5, 8.9, 1H), 2.52 (dd, J=7.2, 14.0, 1H), 2.50-2.43 (m, 1H), 2.42-2.37 (m, 1H), 2.32 (dd, J=2.8, 9.0, 1H), 2.23 (dd, J=7.2, 8.8, 1H), 2.09 (td, J=6.0, 12.0, 2H), 1.94-1.81 (m, 4H), 1.61-1.50 (m, 2H), 1.39 (ddt, J=6.3, 8.7, 12.6, 1H), 0.90 (d, J=6.4, 3H), 0.84 (d, J=6.3, 3H); MS (ESI+) m/z 398 (M+H)$^+$.

Step C: The title compound was prepared by substituting $N^1$-{(3aS,4R,6aR)-2-[3-(trifluoromethyl)benzyl]octahydrocyclopenta[c]pyrrol-4-yl}-L-leucinamide from Step B for $N^2$-methyl-$N^1$-{(3aS,4S,6aR)-2-[3-(trifluoromethyl)benzyl]octahydrocyclopenta[c]pyrrol-4-yl}-L-leucinamide in the procedure described in Example 167: $^1$H NMR (500 MHz, pyridine-d$_5$) δ ppm 9.41 (d, J=9.4, 1H), 9.22 (d, J=7.3, 1H), 7.76 (s, 1H), 7.59 (d, J=14.0, 2H), 7.43 (dd, J=6.2, 13.9, 1H), 4.47 (tt, J=6.3, 12.5, 2H), 3.59 (d, J=13.5, 1H), 3.48 (d, J=13.6, 1H), 3.17 (s, 3H), 2.87 (dd, J=2.3, 9.1, 1H), 2.59-2.50 (m, 2H), 2.38 (dd, J=7.0, 9.0, 1H), 2.34 (dd, J=2.3, 9.0, 1H), 2.24 (dd, J=6.9, 8.8, 1H), 2.20-2.12 (m, 1H), 1.99 (dq, J=6.7, 20.2, 1H), 1.89 (ddd, J=6.0, 10.8, 15.0, 2H), 1.80-1.66 (m, 2H), 1.43 (ddd, J=6.3, 10.7, 12.2, 1H), 0.82 (d, J=6.7, 3H), 0.79 (d, J=6.6, 3H); MS (ESI+) m/z 476 (M+H)$^+$.

Example 171

$N^2$-(methylsulfonyl)-$N^1$-{(3aS,4R,6aR)-2-[3-(trifluoromethyl)benzyl]octahydrocyclopenta[c]pyrrol-4-yl}-D-leucinamide The title compound was prepared by substituting N-(tert-butoxycarbonyl)-D-leucine for N-(tert-butoxycarbonyl)-L-leucine in the procedure described in Step A of Example 170 and then following the procedures described in Steps B and C of Example 170: $^1$H NMR (500 MHz, pyridine-d$_5$) δ ppm 9.42 (d, J=9.3, 1H), 9.22 (d, J=7.3, 1H), 7.78 (s, 1H), 7.61 (d, J=7.7, 2H), 7.44 (dd, J=8.7, 16.4, 1H), 4.51-4.41 (m, 2H), 3.62 (d, J=13.5, 1H), 3.49 (d, J=13.6, 1H), 3.19 (s, 3H), 2.87 (dd, J=2.8, 9.1, 1H), 2.66-2.60 (m, 1H), 2.55 (dd, J=9.0, 15.6, 1H), 2.49 (dd, J=7.3, 9.0, 1H), 2.33 (dd, J=3.0, 9.0, 1H), 2.30-2.25 (m, 1H), 2.12 (dq, J=5.8, 11.9, 1H), 1.98 (td, J=6.7, 13.5, 1H), 1.93-1.83 (m, 2H), 1.77 (ddd, J=5.6, 8.5, 13.8, 1H), 1.63 (dt, J=7.5, 19.4, 1H), 1.45-1.36 (m, 1H), 0.82 (d, J=6.7, 3H), 0.78 (d, J=6.5, 3H); MS (ESI+) m/z 476 (M+H)$^+$.

Example 172

$N^2$-(cyclopropylsulfonyl)-$N^1$-{(3aS,4R,6aR)-2-[3-(trifluoromethyl)benzyl]octahydrocyclopenta[c]pyrrol-4-yl}-L-leucinamide The title compound was prepared by substituting cyclopropanesulfonyl chloride for methanesulfonyl chloride and $N^1$-{(3aS,4R,6aR)-2-[3-(trifluoromethyl)benzyl]octahydrocyclopenta[c]pyrrol-4-yl}-L-leucinamide from Example 170 Step B for $N^2$-methyl-$N^1$-{(3aS,4S,6aR)-2-[3-(trifluoromethyl)benzyl]octahydrocyclopenta[c]pyrrol-4-yl}-L-leucinamide in the procedure described in Example 167: $^1$H NMR (500 MHz, pyridine-d$_5$) δ ppm 9.34 (d, J=9.4, 1H), 9.03 (d, J=7.2, 1H), 7.76 (s, 1H), 7.60 (d, J=10.5, 2H), 7.44 (dd, J=6.1, 13.8, 1H), 4.45 (dd, J=6.4, 11.7, 2H), 3.57 (d, J=13.5, 1H), 3.49 (d, J=13.5, 1H), 2.84 (dd, J=2.4, 9.1, 1H), 2.80-2.73 (m, 1H), 2.61-2.50 (m, 2H), 2.38 (dd, J=7.0, 8.9, 1H), 2.34 (dd, J=2.5, 9.0, 1H), 2.28-2.23 (m, 1H), 2.18 (td, J=5.8, 11.9, 1H), 2.04 (dt, J=6.9, 20.3, 1H), 1.91 (ddd, J=4.1, 7.2, 14.3, 2H), 1.77 (ddd, J=5.3, 8.7, 13.8, 1H), 1.73-1.65 (m, 1H), 1.44 (ddd, J=6.1, 12.3, 18.6, 1H), 1.33 (td, J=4.7, 11.0, 1H), 1.22-1.16 (m, 1H), 0.91 (ddd, J=4.5, 8.5, 11.2, 1H), 0.88-0.85 (m, 1H), 0.84 (d, J=6.7, 3H), 0.82 (d, J=6.6, 3H); MS (ESI+) m/z 502 (M+H)$^+$.

Example 173

$N^2$-(isobutylsulfonyl)-$N^1$-{(3aS,4R,6aR)-2-[3-(trifluoromethyl)benzyl]octahydrocyclopenta[c]pyrrol-4-yl}-L-leucinamide The title compound was prepared by substituting 2-methylpropane-1-sulfonyl chloride for methanesulfonyl chloride and $N^1$-{(3aS,4R,6aR)-2-[3-(trifluoromethyl)benzyl]octahydrocyclopenta[c]pyrrol-4-yl}-L-leucinamide from Example 170 Step B for $N^2$-methyl-$N^1$-{(3aS,4S,6aR)-2-[3-(trifluoromethyl)benzyl]octahydrocyclopenta[c]pyrrol-4-yl}-L-leucinamide in the procedure described in Example 167: $^1$H NMR (500 MHz, pyridine-d$_5$) δ ppm 9.34 (d, J=9.3, 1H), 9.20 (d, J=7.4, 1H), 7.77 (s, 1H), 7.62 (d, J=7.6, 1H), 7.60-7.55 (m, 1H), 7.45 (t, J=7.7, 1H), 4.52-4.43 (m, 2H), 3.61 (d, J=13.5, 1H), 3.52 (d, J=13.6, 1H), 3.19-3.16 (m, 2H), 2.91 (dd, J=2.0, 9.0, 1H), 2.63-2.46 (m, 3H), 2.42 (dd, J=6.8, 8.9, 1H), 2.37 (dd, J=2.1, 9.0, 1H), 2.27 (dd, J=6.9, 8.8, 1H), 2.18 (td, J=5.8, 11.7, 1H), 2.01 (tt, J=6.7, 13.4, 1H), 1.96-1.85 (m, 2H), 1.73 (tdd, J=6.3, 10.3, 14.9, 2H), 1.45 (ddt, J=6.2, 9.0, 12.2, 1H), 1.08 (d, J=6.7, 3H), 1.04 (d, J=6.7, 3H), 0.81 (app t, J=7.0, 6H); MS (ESI+) m/z 518 (M+H)$^+$.

Example 174

N$^2$-(cyclopropylsulfonyl)-N$^1$-{(3aS,4S,6aR)-2-[3-(trifluoromethyl)benzyl]octahydrocyclopenta[c]pyrrol-4-yl}-L-leucinamide Step A: N$^1$-{(3aS,4S,6aR)-2-[3-(trifluoromethyl)benzyl]octahydrocyclopenta[c]pyrrol-4-yl}-L-leucinamide was prepared as described in the procedures in Example 170 Steps A-B by substituting (3aS,4S,6aR)-2-(3-(trifluoromethyl)benzyl)octahydrocyclopenta[c]pyrrol-4-amine from 152 Step A for (3aS,4R,6aR)-2-(3-(trifluoromethyl)benzyl)octahydrocyclopenta[c]pyrrol-4-amine: $^1$H NMR (500 MHz, pyridine-d$_5$) δ ppm 8.57-8.51 (m, 1H), 7.90 (bs, 1H), 7.71-7.65 (m, 1H), 7.47 (t, J=7.7, 1H), 4.57-4.49 (m, 1H), 3.73 (d, J=13.1, 1H), 3.66-3.59 (m, 1H), 3.35 (d, J=13.1, 1H), 2.80 (dd, J=2.6, 9.4, 1H), 2.78-2.69 (m, 1H), 2.49-2.40 (m, 1H), 2.35 (dd, J=2.5, 9.0, 1H), 2.24-1.79 (m, 7H), 1.73-1.50 (m, 3H), 1.47-1.21 (m, 2H), 0.95-0.85 (m, 6H).

Step B: To N$^1$-{(3aS,4S,6aR)-2-[3-(trifluoromethyl)benzyl]octahydrocyclopenta[c]pyrrol-4-yl}-L-leucinamide from Step A (80 mg, 0.184 mmol) in dichloromethane (0.5 mL) was added triethylamine (0.064 mL, 0.461 mmol) followed by cyclopropanesulfonyl chloride (38.9 mg, 0.277 mmol) in a solution of 300 μL dichloromethane and the reaction mixture was stirred at room temperature overnight. The reaction was reduced in volume and loaded onto a silica gel cartridge (Analogix®, Burlington, Wis., RS-12). The title compound was eluted with a gradient of 20% to 100% ethyl acetate/hexanes over 20 minutes to give N$^2$-(cyclopropylsulfonyl)-N$^1$-{(3aS,4S,6aR)-2-[3-(trifluoromethyl)benzyl]octahydrocyclopenta[c]pyrrol-4-yl}-L-leucinamide: $^1$H NMR (500 MHz, pyridine-d$_5$) δ ppm 9.34 (d, J=9.0, 1H), 8.84 (d, J=6.8, 1H), 7.73 (s, 1H), 7.64 (d, J=7.5, 1H), 7.59 (d, J=12.3, 1H), 7.43 (dd, J=6.6, 14.3, 1H), 4.53-4.42 (m, 2H), 3.76 (d, J=13.2, 1H), 3.41 (d, J=13.2, 1H), 2.99 (qd, J=4.2, 8.0, 1H), 2.90 (dd, J=3.6, 9.5, 1H), 2.82-2.74 (m, 1H), 2.57-2.48 (m, 1H), 2.40 (dd, J=8.5, 19.8, 2H), 2.30 (dd, J=3.4, 9.2, 1H), 2.02 (td, J=6.5, 13.7, 1H), 1.94-1.85 (m, 2H), 1.85-1.78 (m, 1H), 1.71 (td, J=6.2, 11.6, 1H), 1.67-1.58 (m, 1H), 1.40-1.28 (m, 2H), 1.22 (dt, J=4.7, 10.8, 1H), 0.93 (ddd, J=6.6, 12.3, 14.0, 2H), 0.87 (d, J=6.5, 3H), 0.84 (d, J=6.7, 3H); MS (ESI+) m/z 502 (M+H)$^+$.

Example 175

N$^2$-acetyl-N$^2$-methyl-N$^1$-{(3aS,4S,6aR)-2-[3-(trifluoromethyl)benzyl]octahydrocyclopenta[c]pyrrol-4-yl}-L-leucinamide To N$^2$-methyl-N$^1$-{(3aS,4S,6aR)-2-[3-(trifluoromethyl)benzyl]octahydrocyclopenta[c]pyrrol-4-yl}-L-leucinamide (123 mg, 0.299 mmol) from Example 164 in dichloromethane (0.5 mL) was added N,N-diisopropylethylamine (78 μL, 0.448 mmol) followed by acetic anhydride (33.9 μL, 0.359 mmol), and the reaction mixture was stirred at room temperature overnight. The reaction was reduced in volume and loaded onto a silica gel cartridge (Analogix®, Burlington, Wis., RS-12), and the product was eluted with a gradient of 0% to 5% methanol (2 N ammonia)/dichloromethane over 20 minutes. The solvent was removed in vacuo to supply the title compound: $^1$H NMR (500 MHz, pyridine-d$_5$) δ ppm 8.10 (d, J=7.1, 1H), 7.81 (d, J=7.5, 1H), 7.76 (s, 1H), 7.63 (d, J=7.8, 1H), 7.56 (d, J=7.7, 1H), 5.54 (dd, J=6.5, 9.2, 1H), 4.41 (dt, J=7.3, 14.5, 1H), 3.62 (d, J=13.2, 1H), 3.49 (d, J=13.2, 1H), 3.01 (s, 3H), 2.84-2.77 (m, 1H), 2.73 (dd, J=2.8, 9.5, 1H), 2.48-2.41 (m, 1H), 2.34 (dd, J=2.8, 9.0, 1H), 2.25 (dt, J=7.7, 17.0, 2H), 2.09 (s, 3H), 1.85 (ddd, J=5.6, 9.9, 13.2, 1H), 1.81-1.70 (m, 2H), 1.66-1.46 (m, 3H), 1.30-1.23 (m, 1H), 0.87 (d, J=2.7, 3H), 0.85 (d, J=2.6, 3H); MS (ESI+) m/z 454 (M+H)$^+$.

Example 176

N$^2$-(2,2-dimethylpropanoyl)-N$^2$-methyl-N$^1$-{(3aS,4R,6aR)-2-[3-(trifluoromethyl)benzyl]octahydrocyclopenta[c]pyrrol-4-yl}-L-leucinamide To N$^2$-methyl-N$^1$-{(3aS,4R,6aR)-2-[3-(trifluoromethyl)benzyl]octahydrocyclopenta[c]pyrrol-4-yl}-L-leucinamide (38.9 mg, 0.095 mmol) from Example 166 in dichloromethane (0.5 mL) was added N,N-diisopropylethylamine (24.77 μL, 0.142 mmol) followed by pivaloyl chloride (12.79 μL, 0.104 mmol), and the resultant reaction mixture was stirred at room temperature overnight. The reaction was reduced in volume and loaded onto a silica gel cartridge (Analogix®, Burlington, Wis., RS-4). The title compound was eluted with a gradient of 0% to 100% ethyl acetate/hexanes over 15 minutes: $^1$H NMR (500 MHz, pyridine-d$_5$) δ ppm 7.81 (d, J=7.4, 1H), 7.74 (s, 1H), 7.60-7.55 (m, 2H), 7.43 (dd, J=6.6, 14.3, 1H), 5.45 (dd, J=7.0, 8.7, 1H), 4.35-4.29 (m, 1H), 3.57 (d, J=13.5, 1H), 3.44 (d, J=13.5, 1H), 3.13 (s, 3H), 2.73 (dd, J=2.6, 8.9, 1H), 2.53-2.45 (m, 1H), 2.41 (ddd, J=2.7, 8.3, 12.0, 1H), 2.37-2.32 (m, 1H), 2.29 (dd, J=3.0, 9.0, 1H), 2.26-2.21 (m, 1H), 2.05 (dq, J=6.0, 12.0, 1H), 1.86-1.80 (m, 3H), 1.55 (ddd, J=6.9, 12.8, 19.6, 2H), 1.41-1.31 (m, 1H), 1.30 (s, 9H), 0.88 (d, J=6.7, 3H), 0.82 (d, J=6.6, 3H); MS (ESI+) m/z 496 (M+H)$^+$.

Example 177

N$^2$-(2,2-dimethylpropanoyl)-N$^1$-{(3aS,4R,6aR)-2-[3-(trifluoromethyl)benzyl]octahydrocyclopenta[c]pyrrol-4-yl}-L-leucinamide The title compound was prepared as described in Example 176 substituting N$^1$-{(3aS,4R,6aR)-2-[3-(trifluoromethyl)benzyl]octahydrocyclopenta[c]pyrrol-4-yl}-L-leucinamide from Example 170 Step B for N$^2$-methyl-N$^1$-{(3aS,4R,6aR)-2-[3-(trifluoromethyl)benzyl]octahydrocyclopenta[c]pyrrol-4-yl}-L-leucinamide: $^1$H NMR (500 MHz, pyridine-d$_5$) δ ppm 8.77 (d, J=7.3, 1H), 7.86 (d, J=8.4, 1H), 7.73 (s, 1H), 7.60-7.55 (m, J=10.6, 2H), 7.45 (t, J=7.7, 1H), 4.42-4.35 (m, 1H), 3.55 (d, J=13.5, 1H), 3.41 (d, J=13.5, 1H), 2.71 (d, J=9.0, 1H), 2.50 (s, 2H), 2.34 (dd, J=6.9, 8.9, 1H), 2.29-2.20 (m, 2H), 2.12 (dq, J=6.1, 12.3, 1H), 1.94-1.74 (m, 5H), 1.66 (dt, J=7.1, 19.3, 1H), 1.39 (d, J=6.9, 1H), 1.33 (s, 9H), 0.84 (d, J=6.1, 3H), 0.82 (d, J=6.1, 3H); MS (ESI+) m/z 482 (M+H)$^+$.

Example 178 isobutyl (S)-4-methyl-1-oxo-1-((3aS,4R,6aR)-2-(3-(trifluoromethyl)benzyl)octahydrocyclopenta[c]pyrrol-4-ylamino)pentan-2-ylcarbamate The title compound was prepared by substituting isobutyl carbonochloridate for methanesulfonyl chloride and N$^1$-{

(3aS,4R,6aR)-2-[3-(trifluoromethyl)benzyl]octahydrocyclopenta[c]pyrrol-4-yl}-L-leucinamide from Example 170 Step B for N²-methyl-N¹-{(3aS,4S,6aR)-2-[3-(trifluoromethyl)benzyl]octahydrocyclopenta[c]pyrrol-4-yl}-L-leucinamide in the procedure described in Example 167: ¹H NMR (500 MHz, pyridine-d₅) δ ppm 8.83 (d, J=6.8, 1H), 8.42 (d, J=8.5, 1H), 7.73 (s, 1H), 7.65-7.53 (m, 2H), 7.46-7.40 (m, 1H), 4.77 (dd, J=7.5, 15.2, 1H), 4.48-4.39 (m, 1H), 4.01 (dd, J=6.7, 10.3, 1H), 3.92 (dd, J=6.7, 10.4, 1H), 3.56 (d, J=13.4, 1H), 3.40 (d, J=13.5, 1H), 2.77 (d, J=7.0, 1H), 2.57-2.45 (m, 2H), 2.38-2.32 (m, 1H), 2.30-2.24 (m, 1H), 2.23-2.19 (m, 1H), 2.14 (td, J=5.9, 11.9, 1H), 1.95-1.79 (m, 5H), 1.73-1.63 (m, 1H), 1.45-1.34 (m, 1H), 0.87 (d, J=5.9, 3H), 0.84 (d, J=5.8, 3H), 0.82 (d, J=4.3, 3H), 0.80 (d, J=4.3, 3H); MS (ESI+) m/z 498 (M+H)⁺.

Example 179 cyclopentyl(S)-4-methyl-1-oxo-1-((3aS,4R,6aR)-2-(3-(trifluoromethyl)benzyl)octahydrocyclopenta[c]pyrrol-4-ylamino)pentan-2-ylcarbamate The title compound was prepared by substituting cyclopentyl carbonochloridate for methanesulfonyl chloride and N¹-{(3aS,4R,6aR)-2-[3-(trifluoromethyl)benzyl]octahydrocyclopenta[c]pyrrol-4-yl}-L-leucinamide from Example 170 Step B for N²-methyl-N¹-{(3aS,4S,6aR)-2-[3-(trifluoromethyl)benzyl]octahydrocyclopenta[c]pyrrol-4-yl}-L-leucinamide in the procedure describe in Example 167: ¹H NMR (500 MHz, pyridine-d₅) δ ppm 8.82 (d, J=7.0, 1H), 8.26 (d, J=8.6, 1H), 7.73 (s, 1H), 7.62-7.53 (m, 2H), 7.43 (t, J=7.8, 1H), 5.32-5.24 (m, 1H), 4.77 (dd, J=7.0, 15.0, 1H), 4.47-4.36 (m, 1H), 3.56 (d, J=13.4, 1H), 3.40 (d, J=13.6, 1H), 2.76 (d, J=9.0, 1H), 2.55-2.46 (m, 2H), 2.38-2.31 (m, 1H), 2.27 (d, J=7.2, 1H), 2.21 (t, J=7.9, 1H), 2.13 (dq, J=6.2, 12.5, 1H), 1.94-1.83 (m, 4H), 1.77 (dd, J=6.9, 12.4, 2H), 1.73-1.64 (m, 3H), 1.58 (dt, J=8.0, 14.7, 2H), 1.39 (td, J=9.0, 14.1, 3H), 0.87 (d, J=5.9, 3H), 0.84 (d, J=5.3, 3H); MS (ESI+) m/z 510 (M+H)⁺.

Example 180

N²-[(tert-butylamino)carbonyl]-N¹-{(3aS,4R,6aR)-2-[3-(trifluoromethyl)benzyl]octahydrocyclopenta[c]pyrrol-4-yl}-L-leucinamide To N¹-{(3aS,4R,6aR)-2-[3-(trifluoromethyl)benzyl]octahydrocyclopenta[c]pyrrol-4-yl}-L-leucinamide (113 mg, 0.284 mmol) from Example 170 Step B in dichloromethane (0.5 mL) was added 2-isocyanato-2-methylpropane (35.1 μL, 0.313 mmol) and the reaction mixture was stirred at room temperature overnight. The reaction was reduced in volume and loaded onto a silica gel cartridge (Analogix®, Burlington, Wis., RS-12). The title compound was eluted with a gradient of 0% to 10% methanol (2 N ammonia)/dichloromethane over 20 minutes: ¹H NMR (500 MHz, pyridine-d₅) δ ppm 8.74 (d, J=8.3, 1H), 7.73 (s, 1H), 7.57 (d, J=9.5, 2H), 7.44 (t, J=7.7, 1H), 6.56 (d, J=8.6, 1H), 6.33 (s, 1H), 4.88 (td, J=5.6, 8.9, 1H), 4.41-4.33 (m, 1H), 3.56 (d, J=13.5, 1H), 3.41 (d, J=13.6, 1H), 2.71 (dd, J=1.7, 9.2, 1H), 2.55-2.45 (m, 2H), 2.35 (dd, J=6.9, 8.9, 1H), 2.29-2.20 (m, 2H), 2.11 (dq, J=6.1, 12.1, 1H), 1.92-1.77 (m, 3H), 1.73-1.64 (m, 2H), 1.44 (s, 9H), 1.43-1.35 (m, 1H), 0.85 (d, J=3.3, 3H), 0.84 (d, J=3.2, 3H); MS (ESI+) m/z 497 (M+H)⁺.

Example 181

N²-[(cyclopentylamino)carbonyl]-N¹-{(3aS,4R,6aR)-2-[3-(trifluoromethyl)benzyl]octahydrocyclopenta[c]pyrrol-4-yl}-L-leucinamide The title compound was prepared by substituting isocyanatocyclopentane for 2-isocyanato-2-methylpropane as described in the procedure in Example 180: ¹H NMR (500 MHz, pyridine-d₅) δ ppm 8.84 (d, J=7.2, 1H), 7.73 (s, 1H), 7.64-7.53 (m, 2H), 7.44 (t, J=9.1, 2H), 6.60 (d, J=7.4, 1H), 6.57 (d, J=8.8, 1H), 4.42-4.36 (m, 2H), 3.56 (d, J=13.7, 1H), 3.40 (d, J=13.6, 1H), 2.73 (dd, J=1.9, 9.3, 1H), 2.53-2.49 (m, 2H), 2.34 (dd, J=7.0, 9.0, 1H), 2.26 (dd, J=1.8, 8.9, 1H), 2.24-2.20 (m, 1H), 2.16-2.09 (m, 1H), 1.90 (tdd, J=5.7, 12.5, 18.4, 4H), 1.80 (ddd, J=5.7, 7.9, 13.6, 1H), 1.76-1.65 (m, 2H), 1.51 (dt, J=6.3, 14.9, 3H), 1.41 (tt, J=7.2, 11.8, 4H), 0.85 (d, J=6.5, 6H); MS (ESI+) m/z 509 (M+H)⁺.

Example 182

N²-methyl-N¹-((3aS,4R,6aR)-2-{[3-(trifluoromethyl)phenyl]sulfonyl}octahydrocyclopenta[c]pyrrol-4-yl)-L-leucinamide Step A: N¹-[(3aS,4R,6aR)-Octahydrocyclopenta[c]pyrrol-4-yl]-N²-(tert-butyloxycarbonyl)-N²-methyl-L-leucinamide was prepared by substituting N¹-[(3aS,4R,6aR)-2-benzyloctahydrocyclopenta[c]pyrrol-4-yl]-N²-(tert-butyloxycarbonyl)-N²-methyl-L-leucinamide from Example 151 for N-[(3aS,4S,6aR)-2-benzyloctahydrocyclopenta[c]pyrrol-4-yl]-2,2-dicyclohexylacetamide in Example 53.

Step B: To N¹-[(3aS,4R,6aR)-Octahydrocyclopenta[c]pyrrol-4-yl]-N²-(tert-butyloxycarbonyl)-N²-methyl-L-leucinamide from Step A (220 mg, 0.622 mmol) in dichloromethane (5.0 mL) was added triethylamine (0.130 mL, 0.934 mmol) followed by 3-(trifluoromethyl)benzene-1-sulfonyl chloride (0.110 mL, 0.685 mmol) and the reaction mixture was stirred at room temperature overnight. The reaction was reduced in volume and loaded onto a silica gel cartridge (Analogix®, Burlington, Wis., RS-24). The title compound was eluted with a gradient of 0% to 10% methanol (2 N ammonia)/dichloromethane over 20 minutes to give N²-(tert-butyloxycarbonyl)-N²-methyl-N¹-((3aS,4R,6aR)-2-{[3-(trifluoromethyl)phenyl]sulfonyl}octahydrocyclopenta[c]pyrrol-4-yl)-L-leucinamide: ¹H NMR (500 MHz, pyridine-d₅) δ ppm 8.32 (bs, 1H), 8.18-8.13 (m, 1H), 8.02-7.95 (m, 1H), 7.90-7.84 (m, 1H), 7.68 (t, J=7.9, 1H), 4.17-4.09 (m, 1H), 3.77-3.69 (m, 1H), 3.20-3.11 (m, 2H), 3.05-2.97 (m, 4H), 2.53-2.47 (m, 2H), 1.98-1.88 (m, 1H), 1.87-1.71 (m, 3H), 1.62-1.48 (m, 3H), 1.46 (s, 9H), 1.32-1.22 (m, 1H), 0.87 (dd, J=6.6, 15.5, 6H).

Step C: The title compound was prepared by substituting N²-(tert-butyloxycarbonyl)-N²-methyl-N¹-((3aS,4R,6aR)-2-{[3-(trifluoromethyl)phenyl]sulfonyl}octahydrocyclopenta[c]pyrrol-4-yl)-L-leucinamide for N²-(tert-butyloxycarbonyl)-N¹-{(3aR*,4R*,6aS*)-2-[3-(trifluoromethyl)benzyl]octahydrocyclopenta[c]pyrrol-4-yl}-L-leucinamide in the procedure described in Example 158: ¹H NMR (500 MHz, pyridine-d₅) δ ppm 8.38 (s, 1H), 8.30 (d, J=6.8, 1H), 8.20 (d, J=7.8, 1H), 7.91 (d, J=8.0, 1H), 7.72 (t, J=7.8, 1H), 4.31-4.24 (m, 1H), 3.87 (dd, J=2.2, 10.0, 1H), 3.21-3.17 (m, 2H), 3.15 (dd, J=7.4, 9.9, 1H), 2.95 (dd, J=7.2, 9.6, 1H), 2.60-2.49 (m, 2H), 2.38 (s, 3H), 2.00-1.92 (m, 2H), 1.91-1.80 (m, 2H), 1.68 (ddd, J=5.8, 7.9, 13.6, 1H), 1.60-1.52 (m, 2H), 1.29 (ddd, J=6.4, 12.8, 16.2, 1H), 0.89 (d, J=6.6, 3H), 0.84 (d, J=6.6, 3H); MS (ESI+) m/z 462 (M+H)+.

Example 183

$N^2$-methyl-$N^1$-((3aS,4R,6aR)-2-{[4-(trifluoromethyl)phenyl]sulfonyl}octahydrocyclopenta[c]pyrrol-4-yl)-L-leucinamide The title compound was prepared as described in Example 182 substituting 4-(trifluoromethyl)benzene-1-sulfonyl chloride for 3-(trifluoromethyl)benzene-1-sulfonyl chloride in Step B: $^1$H NMR (500 MHz, pyridine-$d_5$) δ ppm 8.30 (d, J=7.1, 1H), 8.14 (d, J=8.2, 2H), 7.90 (d, J=8.3, 2H), 4.30-4.23 (m, 1H), 3.86 (dd, J=2.6, 10.0, 1H), 3.22-3.13 (m, 3H), 2.97 (dd, J=7.3, 9.6, 1H), 2.61-2.50 (m, 2H), 2.39 (s, 3H), 2.00-1.92 (m, 2H), 1.91-1.80 (m, 2H), 1.68 (ddd, J=5.9, 7.9, 13.7, 1H), 1.61-1.52 (m, 2H), 1.30 (ddt, J=6.7, 9.9, 13.4, 1H), 0.90 (d, J=6.6, 3H), 0.84 (d, J=6.6, 3H); MS (ESI+) m/z 462 (M+H)+.

Example 184

$N^1$-((3aS,4R,6aR)-2-{[3-(trifluoromethyl)phenyl]sulfonyl}octahydrocyclopenta[c]pyrrol-4-yl)-L-leucinamide Step A: $N^1$-[(3aS,4R,6aR)-2-Benzyloctahydrocyclopenta[c]pyrrol-4-yl]-$N^2$-(tert-butyloxycarbonyl)-L-leucinamide was prepared by substituting N-(tert-butoxycarbonyl)-L-leucine for (S)-2-phenylbutanoic acid in the procedure described in Example 16 Step F: $^1$H NMR (500 MHz, pyridine-$d_5$) δ ppm 8.64 (d, J=7.1, 1H), 7.97 (d, J=8.5, 1H), 7.41 (d, J=7.3, 2H), 7.36 (t, J=7.5, 2H), 7.27 (t, J=7.3, 1H), 4.71 (s, 1H), 4.41 (s, 1H), 3.56 (d, J=13.1, 1H), 3.39 (d, J=13.1, 1H), 2.74 (d, J=8.9, 1H), 2.48 (s, 2H), 2.39-2.19 (m, 3H), 2.14 (td, J=6.3, 12.4, 1H), 2.00-1.78 (m, 4H), 1.73-1.55 (m, 1H), 1.50 (s, 9H), 1.39 (d, J=7.0, 1H), 0.86 (dd, J=5.8, 13.4, 6H).

Step B: The title compound was prepared as described with the procedures in Example 182 Steps A-C substituting $N^1$-[(3aS,4R,6aR)-2-benzyloctahydrocyclopenta[c]pyrrol-4-yl]-$N^2$-(tert-butyloxycarbonyl)-L-leucinamide from Step A for $N^1$-[(3aS,4R,6aR)-2-benzyloctahydrocyclopenta[c]pyrrol-4-yl]-$N^2$-(tert-butyloxycarbonyl)-$N^2$-methyl-L-leucinamide: $^1$H NMR (500 MHz, pyridine-$d_5$) δ ppm 8.37 (s, 1H), 8.33 (d, J=6.9, 1H), 8.18 (d, J=7.9, 1H), 7.91 (d, J=7.8, 1H), 7.72 (t, J=7.9, 1H), 4.27-4.19 (m, 1H), 3.84 (dd, J=2.5, 9.9, 1H), 3.55 (dd, J=4.4, 9.3, 1H), 3.17 (dd, J=2.7, 9.7, 1H), 3.07 (dd, J=7.6, 9.8, 1H), 2.91 (dd, J=7.3, 9.6, 1H), 2.55-2.45 (m, 2H), 2.09 (s, 1H), 1.97-1.78 (m, 5H), 1.52 (ddd, J=4.5, 9.5, 18.5, 2H), 1.27 (ddt, J=6.7, 9.6, 13.2, 1H), 0.89 (d, J=6.4, 3H), 0.83 (d, J=6.3, 3H); MS (ESI+) m/z 448 (M+H)+.

Example 185 and Example 186

3-(trifluoromethyl)-N-{(3aS*,4S*,6aR*)-2-[3-(trifluoromethyl)benzyl]octahydrocyclopenta[c]pyrrol-4-yl}benzenesulfonamide (Example 185) and 3-(trifluoromethyl)-N-{(3aS*,4S*,6aR*)-2-[3-(trifluoromethyl)benzyl]octahydrocyclopenta[c]pyrrol-4-yl}benzenesulfonamide (Example 186)

To (3aS*,6aR*)-2-(3-(trifluoromethyl)benzyl)octahydrocyclopenta[c]pyrrol-4-amine from Example 122 Step E (200 mg, 0.703 mmol) in dichloromethane (2 mL) was added triethylamine (0.147 mL, 1.055 mmol) followed by 3-(trifluoromethyl)benzene-1-sulfonyl chloride (0.124 mL, 0.774 mmol), and the reaction mixture was stirred at room temperature overnight. The reaction was quenched with water and extracted with dichloromethane. The organics were reduced in volume and loaded onto a silica gel cartridge (Analogix®, Burlington, Wis., RS-24). The title compounds were eluted with a gradient of 0% to 10% methanol (2 N ammonia)/dichloromethane over 20 minutes.

Example 185: $^1$H NMR (500 MHz, pyridine-$d_5$) δ ppm 8.42 (s, 1H), 8.27 (d, J=7.9, 1H), 7.82 (d, J=7.8, 1H), 7.64 (s, 1H), 7.61 (d, J=7.8, 1H), 7.57 (d, J=8.2, 2H), 7.50 (d, J=7.7, 1H), 7.40 (t, J=7.7, 1H), 3.91-3.84 (m, 1H), 3.47 (d, J=13.4, 1H), 3.37 (d, J=13.4, 1H), 2.78 (dd, J=4.3, 9.6, 1H), 2.69 (dd, J=4.4, 7.7, 1H), 2.47-2.39 (m, 2H), 2.22 (dt, J=8.0, 12.6, 2H), 1.89 (qd, J=7.1, 11.0, 1H), 1.65 (dtd, J=2.9, 6.2, 8.9, 1H), 1.57-1.47 (m, 1H), 1.34-1.26 (m, 1H); MS (ESI+) m/z 493 (M+H)+.

Example 186: $^1$H NMR (500 MHz, pyridine-$d_5$) δ ppm 9.51 (d, J=7.3, 1H), 8.43 (s, 1H), 8.30 (d, J=7.9, 1H), 7.81 (d, J=7.7, 1H), 7.72 (s, 1H), 7.60 (dd, J=3.2, 7.9, 2H), 7.55 (d, J=7.7, 1H), 7.46 (t, J=7.7, 1H), 3.82-3.74 (m, 1H), 3.54-3.44 (m, 2H), 2.61 (dd, J=1.9, 9.2, 1H), 2.57-2.44 (m, 2H), 2.33 (dd, J=2.0, 9.0, 1H), 2.18 (ddd, J=6.8, 9.0, 12.7, 2H), 1.96 (td, J=5.9, 11.8, 1H), 1.89-1.79 (m, 1H), 1.64-1.54 (m, 1H), 1.29 (ddt, J=6.4, 10.0, 12.6, 1H); MS (ESI+) m/z 493 (M+H)+.

Example 187

3-(trifluoromethyl)-N-{(3aS,4S,6aR)-2-[3-(trifluoromethyl)benzyl]octahydrocyclopenta[c]pyrrol-4-yl}benzenesulfonamide The title compound was prepared by substituting (3aS,4S,6aR)-2-(3-(trifluoromethyl)benzyl)octahydrocyclopenta[c]pyrrol-4-amine from Example 152 Step A for (3aS*,6aR*)-2-(3-(trifluoromethyl)benzyl)octahydrocyclopenta[c]pyrrol-4-amine in the procedure described in Example 185: $^1$H NMR (500 MHz, pyridine-$d_5$) δ ppm 9.26 (s, 1H), 8.41 (s, 1H), 8.27 (d, J=7.9, 1H), 7.82 (d, J=7.8, 1H), 7.62 (d, J=7.9, 1H), 7.57 (d, J=9.8, 2H), 7.50 (d, J=7.7, 1H), 7.40 (t, J=7.7, 1H), 3.87 (dd, J=7.1, 16.1, 1H), 3.48 (d, J=13.4, 1H), 3.38 (d, J=13.4, 1H), 2.77 (dd, J=4.3, 9.6, 1H), 2.73-2.65 (m, 1H), 2.47-2.41 (m, 2H), 2.26-2.19 (m, 2H), 1.89 (qd, J=7.1, 10.9, 1H), 1.65 (dtd, J=2.9, 6.2, 8.9, 1H), 1.52 (dq, J=8.3, 12.8, 1H), 1.34-1.26 (m, 1H); MS (ESI+) m/z 493 (M+H)+.

Example 188

3-(trifluoromethyl)-N-{(3aR,4R,6aS)-2-[3-(trifluoromethyl)benzyl]octahydrocyclopenta[c]pyrrol-4-yl}benzenesulfonamide The title compound was prepared by substituting (3aR,4R,6aS)-2-(3-(trifluoromethyl)benzyl)octahydrocyclopenta[c]pyrrol-4-amine from Example 157 Step A for (3aS*,6aR*)-2-(3-(trifluoromethyl)benzyl)octahydrocyclopenta[c]pyrrol-4-amine in the procedure described in Example 185: $^1$H NMR (500 MHz, pyridine-$d_5$) δ ppm 9.27 (s, 1H), 8.42 (s, 1H), 8.27 (d, J=7.9, 1H), 7.82 (d, J=7.8, 1H), 7.64 (s, 1H), 7.62 (d, J=7.9, 1H), 7.57 (d, J=9.2, 1H), 7.50 (d, J=7.6, 1H), 7.40 (t, J=7.7, 1H), 3.87 (dd, J=7.1, 16.2, 1H), 3.47 (d, J=13.4, 1H), 3.37 (d, J=13.4, 1H), 2.77 (dd, J=4.3, 9.6, 1H), 2.73-2.66 (m, 1H), 2.47-2.41 (m, 2H), 2.26-2.19 (m, 2H), 1.89 (qd, J=7.1, 11.0, 1H), 1.65 (dtd, J=2.9, 6.2, 8.9, 1H), 1.52 (dq, J=8.4, 12.9, 1H), 1.33-1.26 (m, 1H); MS (ESI+) m/z 493 (M+H)+.

Example 189

3-(trifluoromethyl)-N-{(3aS,4R,6aR)-2-[3-(trifluoromethyl)benzyl]octahydrocyclopenta[c]pyrrol-4-yl}benzenesulfonamide

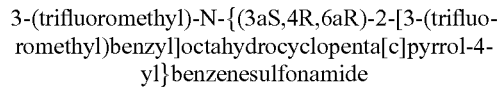

The title compound was prepared by substituting (3aS,4R,6aR)-2-(3-(trifluoromethyl)benzyl)octahydrocyclopenta[c]pyrrol-4-amine from Example 154 Step A for (3aS*,6aR*)-2-(3-(trifluoromethyl)benzyl)octahydrocyclopenta[c]pyrrol-4-amine in the procedure described in Example 185: $^1$H NMR (500 MHz, pyridine-$d_5$) δ ppm 9.51 (d, J=6.7, 1H), 8.43 (s, 1H), 8.30 (d, J=7.8, 1H), 7.81 (d, J=7.9, 1H), 7.72 (s, 1H), 7.62-7.52 (m, 3H), 7.45 (t, J=7.6, 1H), 3.82-3.74 (m, 1H), 3.54-3.44 (m, 2H), 2.61 (d, J=9.4, 1H), 2.57-2.44 (m, 2H), 2.33 (dd, J=1.9, 9.0, 1H), 2.18 (ddd, J=6.9, 9.0, 13.4, 2H), 1.96 (ddd, J=5.1, 11.0, 16.3, 1H), 1.84 (dt, J=7.5, 12.3, 1H), 1.58 (dt, J=9.3, 12.1, 1H), 1.35-1.25 (m, 1H); MS (ESI+) m/z 493 (M+H)$^+$.

Example 190

N-[(3aS,4R,6aR)-2-benzyloctahydrocyclopenta[c]pyrrol-4-l]-3-(trifluoromethyl)benzenesulfonamide

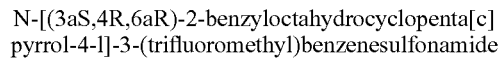

The title compound was prepared by substituting (3aS,4R,6aR)-2-benzyloctahydrocyclopenta[c]pyrrol-4-amine from Example 16 Step E for (3aS*,6aR*)-2-(3-(trifluoromethyl)benzyl)octahydrocyclopenta[c]pyrrol-4-amine in the procedure described in Example 185: $^1$H NMR (500 MHz, pyridine-$d_5$) δ ppm 9.49 (d, J=7.0, 1H), 8.43 (s, 1H), 8.29 (d, J=7.9, 1H), 7.81 (d, J=7.8, 1H), 7.60 (d, J=8.0, 1H), 7.38 (d, J=4.7, 4H), 7.33-7.27 (m, 1H), 3.84-3.75 (m, 1H), 3.47 (q, J=13.1, 2H), 2.61 (dd, J=2.0, 9.2, 1H), 2.56-2.43 (m, 2H), 2.35 (dd, J=2.0, 9.0, 1H), 2.21-2.12 (m, 2H), 1.99 (td, J=5.9, 11.7, 1H), 1.87-1.77 (m, 1H), 1.64-1.53 (m, 1H), 1.29 (ddt, J=6.4, 10.0, 12.6, 1H); MS (ESI+) m/z 425 (M+H)$^+$.

Example 191

N-{(3aS,4R,6aR)-2-[6,6-bis(4-fluorophenyl)hexyl]octahydrocyclopenta[c]pyrrol-4-yl}-3-(trifluoromethyl)benzenesulfonamide

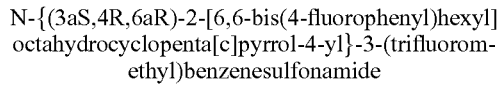

Step A: N$^1$-((3aS,4R,6aR)-Octahydrocyclopenta[c]pyrrol-4-l) -3-(trifluoromethyl)benzenesulfonamide was prepared by substituting N-[(3aS,4R,6aR)-2-benzyloctahydrocyclopenta[c]pyrrol-4-yl]-3-(trifluoromethyl)benzenesulfonamide from Example 190 for N-[(3aS,4S,6aR)-2-benzyloctahydrocyclopenta[c]pyrrol-4-yl]-2,2-dicyclohexylacetamide in the procedure described in Example 53.

Step B: The title compound was prepared by substituting 6,6-bis(4-fluorophenyl)hexanal for 3-(trifluoromethyl)benzaldehyde and N-((3aS,4R,6aR)-octahydrocyclopenta[c]pyrrol-4-yl)-3-(trifluoromethyl)benzenesulfonamide from Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 9.53 (d, J=6.8, 1H), 8.46 (s, 1H), 8.33 (d, J=7.9, 1H), 7.82 (d, J=7.8, 1H), 7.63 (t, J=7.8, 1H), 7.36-7.31 (m, 4H), 7.15 (t, J=8.7, 4H), 3.97 (t, J=7.8, 1H), 3.83-3.74 (m, 1H), 2.66 (d, J=9.4, 1H), 2.56-2.43 (m, 2H), 2.39 (d, J=8.5, 1H), 2.24 (dt, J=5.8, 12.0, 2H), 2.10-2.04 (m, 2H), 2.04-1.99 (m, 2H), 1.99-1.91 (m, 1H), 1.87 (dt, J=6.8, 11.4, 1H), 1.62-1.52 (m, 1H), 1.34 (ddd, J=6.9, 17.6, 29.2, 7H); MS (ESI+) m/z 607 (M+H)$^+$.

Example 192

N-{(3aS,4R,6aR)-2-[3,5-bis(trifluoromethyl)benzyl]octahydrocyclopenta[c]pyrrol-4-yl}-3-(trifluoromethyl)benzenesulfonamide

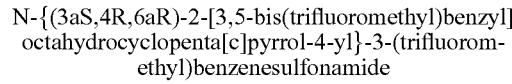

The title compound was prepared by substituting 3,5-bis(trifluoromethyl)benzaldehyde for 3-(trifluoromethyl)benzaldehyde and N-((3aS,4R,6aR)-octahydrocyclopenta[c]pyrrol-4-yl)-3-(trifluoromethyl)benzenesulfonamide from Example 191 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 9.53 (d, J=7.4, 1H), 8.42 (s, 1H), 8.30 (d, J=7.9, 1H), 8.03 (s, 1H), 7.96 (s, 2H), 7.81 (d, J=7.8, 1H), 7.60 (t, J=7.9, 1H), 3.82-3.74 (m, 1H), 3.59 (s, 2H), 2.68-2.64 (m, 1H), 2.59-2.49 (m, 2H), 2.38-2.33 (m, 1H), 2.23 (dt, J=5.9, 8.9, 2H), 1.97-1.81 (m, 2H), 1.59 (ddd, J=8.2, 11.8, 13.0, 1H), 1.35-1.24 (m, 1H); MS (ESI+) m/z 561 (M+H)$^+$.

Example 193

N-{(3aS,4R,6aR)-2-[3,3-bis(4-fluorophenyl)propyl]octahydrocyclopenta[c]pyrrol-4-yl}-3-(trifluoromethyl)benzenesulfonamide

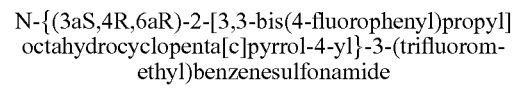

The title compound was prepared by substituting 3,3-bis(4-fluorophenyl)propanal for 3-(trifluoromethyl)benzaldehyde and N-((3aS,4R,6aR)-octahydrocyclopenta[c]pyrrol-4-yl)-3-(trifluoromethyl)benzenesulfonamide from Example 191 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 9.56 (d, J=7.4, 1H), 8.46 (s, 1H), 8.35 (d, J=7.9, 1H), 7.80 (d, J=7.8, 1H), 7.61 (d, J=7.8, 1H), 7.37 (dd, J=5.6, 8.4, 2H), 7.34-7.30 (m, 2H), 7.16 (dt, J=8.7, 12.8, 4H), 4.19 (t, J=7.7, 1H), 3.87-3.78 (m, 1H), 2.69 (d, J=9.1, 1H), 2.55-2.44 (m, 2H), 2.39 (d, J=8.7, 1H), 2.28-2.24 (m, 2H), 2.17 (dd, J=7.8, 15.3, 2H), 2.06 (dd, J=9.2, 16.3, 2H), 1.98 (dt, J=5.7, 16.5, 1H), 1.89 (dd, J=12.0, 19.0, 1H), 1.64-1.53 (m, 1H), 1.38-1.23 (m, 1H); MS (ESI+) m/z 565 (M+H)$^+$.

Example 194

N-{(3aS,4R,6aR)-2-[3-fluoro-4-(trifluoromethyl)benzyl]octahydrocyclopenta[c]pyrrol-4-yl}-3-(trifluoromethyl)benzenesulfonamide

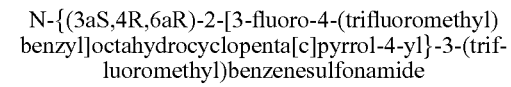

The title compound was prepared by substituting 3-fluoro-4-(trifluoromethyl)benzaldehyde for 3-(trifluoromethyl)benzaldehyde and N-((3aS,4R,6aR)-octahydrocyclopenta[c]pyrrol-4-yl)-3-(trifluoromethyl)benzenesulfonamide from Example 191 Step A for 2,2-dicyclohexyl-N-[(3aS,4S,6aR)-octahydrocyclopenta[c]pyrrol-4-yl]acetamide in the procedure described for Example 54: $^1$H NMR (500 MHz, pyridine-$d_5$) δ ppm 9.56 (d, J=6.8, 1H), 8.44 (s, 1H), 8.33 (d, J=7.9, 1H), 7.82 (d, J=7.6, 1H), 7.65-7.59 (m, 2H), 7.29 (d, J=11.8, 1H), 7.21 (s, 1H), 3.81-3.74 (m, 1H), 3.46 (s, 2H), 2.64 (d, J=9.3, 1H), 2.55 (ddd, J=8.5, 13.8, 27.5, 2H), 2.35 (d, J=8.7, 1H), 2.17 (dd, J=7.9, 15.7, 2H), 1.99 (dt, J=5.9, 16.5, 1H), 1.87 (dt, J=7.3, 12.1, 1H), 1.60 (dt, J=8.3, 10.0, 1H), 1.35-1.26 (m, 1H); MS (ESI+) m/z 510 (M+H)$^+$.

Example 195

N-[(3aS,4S,6aR)-2-(4-hydroxybutyl)octahydrocyclopenta[c]pyrrol-4-yl]-3-(trifluoromethyl)benzenesulfonamide

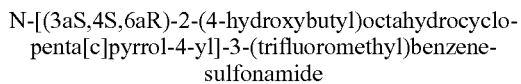

Step A: N-((3aS,4S,6aR)-2-Benzyloctahydrocyclopenta[c]pyrrol-4-yl)-3-(trifluoromethyl)benzenesulfonamide was prepared by substituting (3aS,4S,6aR)-2-benzyloctahydrocyclopenta[c]pyrrol-4-amine from Example 14 Step C for (3aS*,6aR*)-2-(3-(trifluoromethyl)benzyl)octahydrocyclopenta[c]pyrrol-4-amine in the procedure described in Example 185.

Step B: N-((3aS,4S,6aR)-2-Benzyloctahydrocyclopenta[c]pyrrol-4-yl)-3-(trifluoromethyl)benzenesulfonamide (0.4237 g, 0.998 mmol) from Step A in tetrahydrofuran (10 mL) was added to 20% palladium hydroxide on carbon (wet, 0.085 g, 0.603 mmol) in a 50 mL pressure bottle under nitrogen. The reaction mixture was then placed under a hydrogen atmosphere (30 psi) and shaken at 50° C. for 18 hours. The mixture was filtered through a nylon membrane and the solvent was removed in vacuo. The crude material was purified by silica gel chromatography using 1-10% methanol (2 N ammonia)/dichloromethane supplied the title compound: $^1$H NMR (500 MHz, pyridine-$d_5$) δ ppm 8.50 (s, 1H), 8.38 (d, J=7.9, 1H), 7.85 (d, J=7.8, 1H), 7.68 (t, J=7.8, 1H), 3.89 (dd, J=8.4, 14.2, 1H), 3.82 (t, J=6.2, 2H), 2.82 (dd, J=3.3, 9.7, 1H), 2.62 (qd, J=3.4, 7.9, 1H), 2.42-2.36 (m, 1H), 2.32 (d, J=4.5, 2H), 2.26 (dd, J=6.8, 11.7, 2H), 2.10 (t, J=8.7, 1H), 1.91-1.82 (m, 1H), 1.74-1.67 (m, 2H), 1.64-1.49 (m, 5H), 1.32 (dd, J=6.1, 9.6, 1H); MS (ESI+) m/z 407 (M+H)$^+$.

Example 196

(3aS*,4S*,6aR*)-N,N-dicyclopropyl-2-[3-(trifluoromethyl)benzyl]octahydrocyclopenta[c]pyrrol-4-amine (3aS*,4S*,6aR*)-2-(3-(Trifluoromethyl)benzyl)octahydrocyclopenta[c]pyrrol-4-amine (228 mg, 0.802 mmol) from Example 122 Step E and (1-ethoxycyclopropoxy)trimethylsilane (140 mg, 0.802 mmol) were combined in dichloromethane (1.5 mL) and 5 mL of acetic acid was added. The reaction was stirred at room temperature for 20 minutes, and then PS-cyanoborohydride (343 mg, 0.802 mmol) was added. The reaction was heated to 40° C. overnight. Silica gel chromatography eluting with 1-10% methanol (2 N ammonia)/dichloromethane to gave the title compound: $^1$H NMR (300 MHz, CDCl$_3$) δ ppm 7.58 (s, 1H), 7.48 (d, J=7.6, 2H), 7.42 (d, J=7.6, 1H), 3.64 (d, J=13.6, 1H), 3.51 (d, J=13.6, 1H), 2.94-2.82 (m, 3H), 2.80-2.71 (m, 2H), 2.55 (dd, J=5.4, 9.4, 3H), 2.41 (t, J=8.3, 1H), 2.16 (dd, J=4.7, 8.7, 1H), 1.97-1.70 (m, 7H), 1.70-1.59 (m, 3H), 1.40 (dd, J=6.7, 12.6, 1H); MS (ESI+) m/z 365 (M+H)$^+$.

Example 197 and Example 198

(3aS*,4R*,6aR*)-2-benzyl-N-cyclopropyloctahydrocyclopenta[c]pyrrol-4-amine (Example 197) and (3aS*,4S*,6aR*)-2-benzyl-N-cyclopropyloctahydrocyclopenta[c]pyrrol-4-amine (Example 198)

2-Benzylhexahydrocyclopenta[c]pyrrol-4(5H)-one (0.578 g, 2.68 mmol), cyclopropylamine (0.189 mL, 2.68 mmol), and acetic acid (10 mL) were combined in dichloromethane (20 mL). PS-Cyanoborohydride (1.147 g, 2.68 mmol) was added. The reaction was stirred at room temperature for 2 hours, then filtered and the resin was washed with dichloromethane. The solvent was removed in vacuo, and the crude material was applied to a silica gel column and was eluted with 1-10% methanol (2 N ammonia)/dichloromethane to give the title compounds.

(3aS*,4R*,6aR*)-2-benzyl-N-cyclopropyloctahydrocyclopenta[c]pyrrol-4-amine (Example 197): $^1$H NMR (300 MHz, CDCl$_3$) δ ppm 7.34-7.29 (m, 2H), 7.28-7.20 (m, 2H), 3.56 (s, 2H), 3.14 (ddd, J=5.7, 7.3, 10.5, 1H), 2.84 (t, J=8.4, 1H), 2.77-2.55 (m, 3H), 2.41 (dd, J=6.2, 9.4, 1H), 2.14-2.02 (m, 2H), 1.83-1.72 (m, 2H), 1.63-1.47 (m, 3H), 1.46-1.35 (m, 1H), 0.40 (tdd, J=1.3, 3.0, 4.7, 2H), 0.31 (ddd, J=2.8, 4.3, 6.2, 2H); MS (ESI+) m/z 256 (M+H)$^+$.

(3aS*,4S*,6aR*)-2-benzyl-N-cyclopropyloctahydrocyclopenta[c]pyrrol-4-amine (Example 198): $^1$H NMR (300 MHz, CDCl$_3$) δ ppm 7.34-7.29 (m, 4H), 7.29-7.20 (m, 1H), 3.66-3.50 (m, 2H), 3.04-2.92 (m, 1H), 2.63 (s, 1H), 2.54-2.50 (m, 2H), 2.48-2.40 (m, 1H), 2.34 (dd, J=3.8, 9.0, 1H), 2.26 (dt, J=5.0, 16.3, 1H), 2.13-2.04 (m, 2H), 2.03-1.82 (m, 2H), 1.46-1.35 (m, 2H), 0.46-0.38 (m, 2H), 0.36-0.30 (m, 2H); MS (ESI+) m/z 256 (M+H)$^+$.

Example 199

N-[(3aS*,4S*,6aR*)-2-benzyloctahydrocyclopenta[c]pyrrol-4-yl]-N-cyclopropyl-3-(trifluoromethyl)benzenesulfonamide (3aS*,4S*,6aR*)-2-Benzyl-N-cyclopropyloctahydrocyclopenta[c]pyrrol-4-amine (382 mg, 1.490 mmol) from Example 198, triethylamine (312 μL, 2.235 mmol), and 3-(trifluoromethyl)benzene-1-sulfonyl chloride (262 μL, 1.639 mmol) were combined in tetrahydrofuran (7 mL). A catalytic amount of (dimethylamino)pyridine was added, and the reaction mixture was stirred at room temperature overnight. The solvent was reduced in volume, and the crude material applied to silica gel and eluted with 20% to 100% ethyl acetate/hexanes to give the title compound: $^1$H NMR (500 MHz, pyridine-$d_5$) δ ppm 8.46 (s, 1H), 8.31 (d, J=7.9, 1H), 7.93 (d, J=7.8, 1H), 7.74 (t, J=7.9, 1H), 7.41 (d, J=7.2, 2H), 7.36 (t, J=7.4, 2H), 7.29 (t, J=7.2, 1H), 3.97 (ddd, J=6.1, 7.7, 13.5, 1H), 3.54-3.45 (m, 2H), 3.17 (dt, J=5.9, 11.8, 1H), 2.82 (dd, J=3.6, 9.7, 1H), 2.55 (t, J=8.2, 1H), 2.51-2.43 (m, 2H), 2.36-2.22 (m, 2H), 1.88-1.82 (m, 1H), 1.57 (dt, J=5.9, 11.6, 1H), 1.43-1.32 (m, 3H), 1.05-0.98 (m, 1H), 0.80 (ddd, J=6.9, 9.8, 12.4, 1H), 0.73-0.65 (m, 1H); MS (ESI+) m/z 465 (M+H)$^+$.

Example 200

N-[(3aS*,4R*,6aR*)-2-benzyloctahydrocyclopenta[c]pyrrol-4-yl]-N-cyclopropyl-3-(trifluoromethyl)benzenesulfonamide The title compound was prepared by substituting (3aS*,4R*,6aR*)-2-benzyl-N-cyclopropyloctahydrocyclopenta[c]pyrrol-4-amine from Example 197 for (3aS*,4S*,6aR*)-2-benzyl-N-cyclopropyloctahydrocyclopenta[c]pyrrol-4-amine in the procedure described in Example 199: $^1$H NMR (500 MHz, pyridine-$d_5$) δ ppm 8.45 (s, 1H), 8.29 (d, J=7.8, 1H), 7.92 (d, J=7.8, 1H), 7.69 (t, J=7.9, 1H), 7.49 (d, J=7.4, 2H), 7.41 (t, J=7.6, 2H), 7.31 (t, J=7.3, 1H), 4.41 (dd, J=7.7, 17.3, 1H), 3.63 (d, J=13.2, 1H), 3.53 (d, J=13.2, 1H), 2.87 (d, J=8.9, 1H), 2.70 (dd, J=8.2, 15.9, 1H), 2.49 (d, J=8.9, 1H), 2.46-2.37 (m, 1H), 2.16-2.07 (m, 2H), 1.99-1.94 (m, 1H), 1.84-1.77 (m, 1H), 1.73-1.65 (m, 1H), 1.65-1.57 (m, 1H), 1.35-1.25 (m, 1H), 1.18 (ddd, J=5.1, 6.9, 10.5, 1H), 0.99 (dq, J=4.7, 6.7, 1H), 0.81-0.74 (m, 1H), 0.69 (ddd, J=6.9, 10.8, 11.8, 1H); MS (ESI+) m/z 465 (M+H)$^+$.

Example 201

N-cyclopropyl-N-[(3aS*,4S*,6aR*)-octahydrocyclopenta[c]pyrrol-4-yl]-3-(trifluoromethyl)benzenesulfonamide (3aS*,4S*,6aR*)-2-benzyl-N-cyclopropyloctahydrocyclopenta[c]pyrrol-4-amine (0.308 g, 0.663 mmol) from Example 199 and methanol (2 mL) were added to 20% palladium hydroxide on carbon (wet, 4 mg) in a 50 mL pressure bottle. The reaction was stirred for 16 hours under hydrogen (30 psi) at room temperature. The mixture was filtered through a nylon membrane and the solvent removed in vacuo. The crude material was chromatographed on a silica gel cartridge (Analogix®, Burlington, Wis., RS15-24) eluting with 1-10% methanol (2 N ammonia)/dichloromethane to give the title compound: $^1$H NMR (300 MHz, CDCl$_3$) δ ppm 8.14 (s, 1H), 8.07 (d, J=7.9, 1H), 7.87 (d, J=7.9, 1H), 7.70 (t, J=7.8, 1H), 3.80-3.69 (m, 1H), 3.25 (dd, J=7.8, 10.7, 1H), 3.06-2.88 (m, 2H), 2.79-2.71 (m, 1H), 2.63-2.51 (m, 1H), 2.46 (dd, J=5.9, 10.8, 1H), 2.05 (qd, J=7.0, 12.1, 1H), 1.79 (ddd, J=3.9, 6.8, 10.7, 1H), 1.72-1.63 (m, 2H), 1.56 (dd, J=4.8, 6.1, 1H), 1.48 (td, J=6.9, 12.8, 1H), 1.31 (ddd, J=2.7, 5.5, 8.8, 1H), 0.92-0.70 (m, 3H); MS (ESI+) m/z 375 (M+H)$^+$.

Example 202

N-{(3aS*,4S*,6aR*)-2-[6,6-bis(4-fluorophenyl)hexyl]octahydrocyclopenta[c]pyrrol-4-yl}-N-cyclopropyl-3-(trifluoromethyl)benzenesulfonamide N-Cyclopropyl-N-[(3aS*,4S*,6aR*)-octahydrocyclopenta[c]pyrrol-4-yl]-3-(trifluoromethyl)benzenesulfonamide from Example 201 (140 mg, 0.374 mmol) and 6,6-bis(4-fluorophenyl)hexanal (108 mg, 0.374 mmol) were combined in dichloromethane (2 mL) and then acetic acid (1 mL) was added. The reaction was stirred at room temperature for 20 minutes, then PS-cyanoborohydride (306 mg, 0.748 mmol) was added. The reaction mixture was stirred at room temperature overnight, then filtered and the resin washed with dichloromethane. The solvent was removed in vacuo and the crude material purified using a silica gel cartridge (Analogix®, Burlington, Wis., RS-12) eluting with 1-10% methanol (2 N ammonia)/dichloromethane to give the title compound: $^1$H NMR (500 MHz, pyridine-d$_5$) δ ppm 8.50 (s, 1H), 8.36 (d, J=7.9, 1H), 7.95 (d, J=7.9, 1H), 7.76 (dd, J=6.4, 14.2, 1H), 7.33 (dd, J=5.6, 8.3, 4H), 7.18-7.11 (m, 4H), 3.96 (dd, J=8.0, 16.3, 2H), 3.18-3.10 (m, 1H), 2.82 (dd, J=3.5, 9.5, 1H), 2.50-2.44 (m, 2H), 2.39 (t, J=8.0, 1H), 2.31-2.21 (m, 4H), 2.03 (dd, J=7.8, 15.3, 2H), 1.91 (dt, J=3.5, 10.4, 1H), 1.59 (dt, J=5.6, 11.5, 1H), 1.51 (dd, J=10.6, 16.2, 1H), 1.46-1.33 (m, 6H), 1.28 (dd, J=7.4, 15.1, 2H), 1.08 (td, J=5.0, 10.5, 1H), 0.84 (dt, J=6.9, 12.6, 1H), 0.75-0.66 (m, 1H); MS (ESI+) m/z 647 (M+H)$^+$.

Example 203

N-{(3aS*,4S*,6aR*)-2-[3,3-bis(4-fluorophenyl)propyl]octahydrocyclopenta[c]pyrrol-4-yl}-N-cyclopropyl-3-(trifluoromethyl)benzenesulfonamide The title compound was prepared by substituting 3,3-bis(4-fluorophenyl)propanal for 6,6-bis(4-fluorophenyl)hexanal in the procedure described for Example 202: $^1$H NMR (500 MHz, pyridine-d$_5$) δ ppm 8.49 (s, 1H), 8.35 (d, J=7.9, 1H), 7.94 (d, J=7.8, 1H), 7.77 (t, J=7.9, 1H), 7.34 (ddd, J=2.1, 5.5, 8.4, 4H), 7.14 (td, J=2.2, 8.8, 4H), 4.16 (t, J=7.3, 1H), 3.97-3.90 (m, 1H), 3.24-3.15 (m, 1H), 2.77 (dd, J=4.1, 9.1, 1H), 2.54 (t, J=8.1, 1H), 2.47 (dd, J=7.1, 15.3, 2H), 2.32-2.20 (m, 6H), 1.91 (dt, J=3.5, 10.5, 1H), 1.63 (dt, J=5.8, 11.6, 1H), 1.52-1.36 (m, 3H), 1.03 (dt, J=4.5, 10.6, 1H), 0.83 (dt, J=6.8, 12.6, 1H), 0.78-0.70 (m, 1H); MS (ESI+) m/z 605 (M+H)$^+$.

Example 204

N-cyclopropyl-3-(trifluoromethyl)-N-{(3aS*,4S*,6aR*)-2-[3-(trifluoromethyl)benzyl]octahydrocyclopenta[c]pyrrol-4-yl}benzenesulfonamide The title compound was prepared by substituting 3-(trifluoromethyl)benzaldehyde for 6,6-bis(4-fluorophenyl)hexanal in the procedure described for Example 202: $^1$H NMR (500 MHz, pyridine-d$_5$) δ ppm 8.46 (s, 1H), 8.32 (d, J=7.9, 1H), 7.93 (d, J=7.8, 1H), 7.76-7.72 (m, 2H), 7.52 (d, J=7.7, 1H), 7.44 (t, J=7.7, 1H), 4.00-3.93 (m, 1H), 3.50 (d, J=13.2, 1H), 3.43 (d, J=13.2, 1H), 3.15 (qd, J=3.8, 7.8, 1H), 2.78 (dd, J=3.8, 9.7, 1H), 2.52-2.43 (m, 2H), 2.39 (dd, J=8.0, 9.5, 1H), 2.32-2.22 (m, 2H), 1.90-1.82 (m, 1H), 1.59 (dt, J=5.9, 11.5, 1H), 1.48-1.32 (m, 4H), 0.99-0.93 (m, 1H), 0.81 (ddd, J=6.9, 9.8, 12.4, 1H), 0.75-0.67 (m, 1H); MS (ESI+) m/z 533 (M+H)$^+$.

Example 205

2,2-dicyclohexyl-N-((3aS,4S,6aR)-2-{[3-(trifluoromethyl)phenyl]sulfonyl}octahydrocyclopenta[c]pyrrol-4-yl)acetamide 2,2-Dicyclohexyl-N-((3aS,4S,6aR)-octahydrocyclopenta[c]pyrrol-4-yl)acetamide from Example 53 (101 mg, 0.304 mmol), triethylamine (0.042 mL, 0.304 mmol), and 3-(trifluoromethyl)benzene-1-sulfonyl chloride (0.049 mL, 0.304 mmol) were combined in dichloromethane (2 mL). A catalytic amount of N,N-dimethylaminopyridine was added. The reaction was stirred at room temperature for 1 hour, LCMS showed product, and TLC showed no more starting material. The reaction was quenched with aqueous sodium bicarbonate and the aqueous layer was separated. The organic layers was concentrated to give a precipitate. The precipitate was washed with water and ether and dried under a stream of nitrogen to give the title compound: $^1$H NMR (500 MHz, pyridine-d$_5$) δ ppm 8.49 (d, J=6.3, 1H), 8.34 (s, 1H), 8.19 (d, J=7.9, 1H), 7.93 (d, J=7.8, 1H), 7.73 (t, J=7.8, 1H), 4.46-4.38 (m, 1H), 3.73 (dd, J=3.4, 9.3, 1H), 3.17 (dd, J=2.8, 9.7, 1H), 3.07 (ddd, J=6.4, 12.0, 23.6, 3H), 2.49 (dd, J=8.0, 15.9, 1H), 2.12 (t, J=7.2, 1H), 2.02-1.77 (m, 8H), 1.73 (dd, J=5.3, 9.0, 4H), 1.68-1.58 (m, 3H), 1.52 (ddd, J=3.2, 12.5, 14.7, 1H), 1.43 (ddd, J=3.1, 12.6, 15.0, 1H), 1.37-1.03 (m, 9H); MS (ESI+) m/z 541 (M+H)$^+$.

Example 206

2,2-dicyclohexyl-N-{(3aS,4S,6aR)-2-[(2-phenylethyl)sulfonyl]octahydrocyclopenta[c]pyrrol-4-yl}acetamide The title compound was prepared by substituting 2-phenylethanesulfonyl chloride for 3-(trifluoromethyl)benzene-1-sulfonyl chloride in the procedure described in Example 205: $^1$H NMR (500 MHz, pyridine-d$_5$) δ ppm 8.35 (d, J=7.0, 1H), 7.33-7.25 (m, 4H), 4.60-4.51 (m, 1H), 3.79 (dd, J=4.8, 10.2, 1H), 3.56-3.39 (m, 4H), 3.27 (t, J=8.3, 2H), 3.24-3.16 (m, 2H), 2.66-2.57 (m, 1H), 2.09 (t, J=7.4, 1H), 2.00-1.76 (m, 9H), 1.72 (d, J=12.9, 4H), 1.67-1.64 (m, 1H), 1.59 (t, J=13.7, 2H), 1.54-1.36 (m, 3H), 1.30-1.18 (m, 4H), 1.18-1.06 (m, 4H); MS (ESI+) m/z 501 (M+H)$^+$.

Example 207

2,2-dicyclohexyl-N-((3aS,4S,6aR)-2-{[2-(1-naphthyl)ethyl]sulfonyl}octahydrocyclopenta[c]pyrrol-4-yl)acetamide The title compound was prepared by substituting 2-(naphthalen-1-yl)ethanesulfonyl chloride for 3-(trifluoromethyl)benzene-1-sulfonyl chloride in the procedure described in Example 205: $^1$H NMR (500 MHz, pyridine-d$_5$) δ ppm 8.37 (d, J=6.8, 1H), 8.13 (d, J=9.0, 1H), 7.97-7.94 (m, 1H), 7.85 (d, J=8.2, 1H), 7.53 (p, J=6.9, 2H), 7.46-7.40 (m, 1H), 7.36 (t, J=7.9, 1H), 4.60-4.49 (m, 1H), 3.81 (dd, J=4.8, 10.2, 1H), 3.75 (t, J=8.3, 2H), 3.57-3.46 (m, 4H), 3.27-3.16 (m, 2H), 2.67-2.59 (m, 1H), 2.09 (t, J=7.3, 1H), 1.95 (t, J=13.3, 2H), 1.89-1.76 (m, 5H), 1.72 (d, J=12.2, 4H), 1.66 (dd, J=5.1, 7.2, 1H), 1.60 (t, J=10.5, 2H), 1.46 (dt, J=10.8, 20.4, 3H), 1.29-1.18 (m, 4H), 1.18-1.03 (m, 5H); MS (ESI+) m/z 551 (M+H)$^+$.

Example 208

2,2-dicyclohexyl-N-((3aS,4S,6aR)-2-{[3-(trifluoromethyl)benzyl]sulfonyl}octahydrocyclopenta[c]pyrrol-4-yl)acetamide The title compound was prepared by substituting (3-(trifluoromethyl)phenyl)methanesulfonyl chloride for 3-(trifluoromethyl)benzene-1-sulfonyl chloride in the procedure described in Example 205: $^1$H NMR (500 MHz, pyridine-d$_5$) δ ppm 8.32 (d, J=6.7, 1H), 7.96 (s, 1H), 7.81 (d, J=7.7, 1H), 7.64 (d, J=7.7, 1H), 7.46 (t, J=7.7, 1H), 4.69 (q, J=13.5, 2H), 4.58-4.49 (m, 1H), 3.81 (dd, J=4.9, 10.4, 1H), 3.52 (dd, J=5.8, 13.7, 2H), 3.26 (dd, J=3.1, 9.9, 1H), 3.23-3.15 (m, 1H), 2.65-2.58 (m, 1H), 2.06 (t, J=7.3, 1H), 1.93 (d, J=13.8, 2H), 1.82 (dt, J=9.9, 14.4, 6H), 1.71 (t, J=10.2, 4H), 1.67 (dd, J=7.0, 11.0, 1H), 1.60 (d, J=9.5, 2H), 1.51-1.35 (m, 3H), 1.29-1.02 (m, 8H); MS (ESI+) m/z 555 (M+H)$^+$.

Example 209

2,2-dicyclohexyl-N-((3aS,4S,6aR)-2-{[2-(4-fluorophenyl)ethyl]sulfonyl}octahydrocyclopenta[c]pyrrol-4-yl)acetamide The title compound was prepared by substituting 2-(4-fluorophenyl)ethanesulfonyl chloride for 3-(trifluoromethyl)benzene-1-sulfonyl chloride in the procedure described in Example 205: $^1$H NMR (500 MHz, pyridine-d$_5$) δ ppm 8.37 (d, J=6.8, 1H), 7.18 (dd, J=5.6, 8.5, 2H), 7.09 (t, J=8.7, 2H), 4.60-4.49 (m, 1H), 3.80 (dd, J=4.9, 10.3, 1H), 3.57-3.39 (m, 4H), 3.27-3.16 (m, 4H), 2.67-2.59 (m, 1H), 2.09 (t, J=7.3, 1H), 1.99-1.77 (m, 8H), 1.72 (d, J=12.4, 4H), 1.66 (dd, J=3.0, 8.1, 1H), 1.59 (t, J=14.2, 2H), 1.46 (ddd, J=7.9, 16.4, 33.2, 3H), 1.24 (ddd, J=3.2, 12.7, 25.7, 4H), 1.18-1.03 (m, 4H); MS (ESI+) m/z 519 (M+H)$^+$.

Examples 210 and Example 211

(2S)-2-phenyl-N-{(3aR,4R,6aS)-2-[(1S)-1-phenylethyl]octahydrocyclopenta[c]pyrrol-4-yl}butanamide (Example 210) and (2S)-2-phenyl-N-{(3aR,4S,6aS)-2-[(1S)-1-phenylethyl]octahydrocyclopenta[c]pyrrol-4-yl}butanamide (Example 211)

Step A: (3aR,6aS)-2-((S)-1-Phenylethyl)hexahydrocyclopenta[c]pyrrol-4(5H)-one and (3aS,6aR)-2-((S)-1-phenylethyl)hexahydrocyclopenta[c]pyrrol-4(5H)-one were prepared as described in the procedure described in Example 122 Step C substituting S(−)-N-methoxymethyl-N-(trifluorosilyl)methyl-1-phenylethyl amine for 1-methoxy-N-(3-(trifluoromethyl)benzyl)-N-((trimethylsilyl)methyl)methanamine.

(3aR,6aS)-2-((S)-1-phenylethyl)hexahydrocyclopenta[c]pyrrol-4(5H)-one: $^1$H NMR (300 MHz, CDCl$_3$) δ ppm 7.34-7.16 (m, 5H), 3.23 (d, J=8.9, 1H), 3.12 (q, J=6.6, 1H), 2.80 (dt, J=7.5, 14.9, 1H), 2.60 (t, J=8.6, 1H), 2.48 (dd, J=2.0, 9.5, 1H), 2.44-2.20 (m, 5H), 2.08 (ddd, J=8.2, 13.0, 17.0, 1H), 1.72 (ddd, J=6.7, 10.1, 17.4, 1H), 1.31 (d, J=6.6, 3H); MS (ESI+) m/z 230 (M+H)$^+$.

(3aS,6aR)-2-((S)-1-phenylethyl)hexahydrocyclopenta[c]pyrrol-4(5H)-one: $^1$H NMR (300 MHz, CDCl$_3$) δ ppm 7.39-7.13 (m, 5H), 3.15 (dd, J=6.5, 13.1, 1H), 2.88 (dd, J=7.1, 13.7, 1H), 2.76 (t, J=9.0, 3H), 2.54 (dd, J=9.9, 18.1, 2H), 2.45-2.35 (m, 2H), 2.34-2.26 (m, 1H), 2.13 (ddd, J=6.5, 10.8, 17.2, 1H), 1.91-1.77 (m, 1H), 1.33 (d, J=6.2, 3H); MS (ESI+) m/z 230 (M+H)$^+$.

Step B: (3aR,6aS)-2-((S)-1-Phenylethyl)octahydrocyclopenta[c]pyrrol-4-amine was prepared as described in Example 122 Step D-E substituting (3aR,6aS)-2-((S)-1-phenylethyl)hexahydrocyclopenta[c]pyrrol-4(5H)-one from Step A for 2-(3-(trifluoromethyl)benzyl)hexahydrocyclopenta[c]pyrrol-4(5H)-one: $^1$H NMR (300 MHz, CDCl$_3$) δ ppm 7.47-7.09 (m, 5H), 3.12 (dd, J=6.1, 12.5, 1H), 2.75 (br s, 2H), 2.48 (d, J=6.5, 3H), 2.33-2.20 (m, 1H), 2.11-1.95 (m, 1H), 1.94-1.73 (m, 2H), 1.73-1.54 (m, 2H), 1.43 (s, 3H), 1.35 (d, J=6.3, 3H); MS (ESI+) m/z 231 (M+H)$^+$.

Step C: The title compounds were prepared by substituting (S)-2-phenylbutanoic acid for 1-phenylcyclopentanecarboxylic acid and (3aR,6aS)-2-((S)-1-phenylethyl)octahydrocyclopenta[c]pyrrol-4-amine for (3aS*,6aR*)-2-benzyloctahydrocyclopenta[c]pyrrol-4-amine in the procedure described in Examples 1 and 2.

Example 210: $^1$H NMR (500 MHz, pyridine-d$_5$) δ ppm 11.04 (d, J=6.9, 1H), 10.39 (d, J=7.2, 2H), 10.16 (q, J=8.0, 4H), 10.13-10.04 (m, 4H), 7.19 (dt, J=7.1, 14.1, 1H), 6.36 (dd, J=6.3, 8.7, 1H), 5.82 (q, J=6.5, 1H), 5.69 (dd, J=2.5, 9.4, 1H), 5.56 (qd, J=2.7, 7.7, 1H), 5.22-5.07 (m, 2H), 4.99-4.92 (m, 2H), 4.90 (dd, J=2.7, 9.2, 1H), 4.65 (td, J=6.8, 13.6, 1H), 4.55 (dt, J=7.1, 11.8, 1H), 4.32-4.20 (m, 2H), 4.11 (d, J=6.5, 3H), 3.86-3.80 (m, 1H), 3.75 (t, J=7.3, 3H); MS (ESI+) m/z 377 (M+H)$^+$.

Example 211: $^1$H NMR (500 MHz, pyridine-d$_5$) δ ppm 11.35 (d, J=7.1, 1H), 10.40 (d, J=7.1, 2H), 10.13 (dt, J=7.6, 15.2, 6H), 10.04 (dt, J=4.6, 14.8, 2H), 7.22-7.14 (m, 1H), 6.36 (dd, J=6.3, 8.8, 1H), 5.78 (q, J=6.5, 1H), 5.55 (d, J=8.8, 1H), 5.22-5.09 (m, 3H), 5.04-4.98 (m, 1H), 4.92 (dd, J=8.9, 15.9, 3H), 4.70-4.60 (m, 1H), 4.59-4.52 (m, 1H), 4.42 (dt, J=6.9, 19.0, 1H), 4.10 (dd, J=6.6, 18.3, 1H), 4.01 (d, J=6.5, 3H), 3.75 (t, J=7.3, 3H); MS (ESI+) m/z 377 (M+H)$^+$.

Example 212 and Example 213

(2S)-2-phenyl-N-{(3aS,4S,6aR)-2-[(1S)-1-phenylethyl]octahydrocyclopenta[c]pyrrol-4-yl}butanamide (Example 212) and (2S)-2-phenyl-N-{(3aS,4R,6aR)-2-[(1S)-1-phenylethyl]octahydrocyclopenta[c]pyrrol-4-yl}butanamide (Example 213)

Step A: (3aS,6aR)-2-((S)-1-phenylethyl)octahydrocyclopenta[c]pyrrol-4-amine was prepared as described in Example 122 Steps D-E substituting (3aS,6aR)-2-((S)-1-phenylethyl)hexahydrocyclopenta[c]pyrrol-4(5H)-one from Example 210 Step A for 2-(3-(trifluoromethyl)benzyl)hexahydrocyclopenta[c]pyrrol-4(5H)-one: $^1$H NMR (300 MHz, CDCl$_3$) δ ppm 7.47-7.09 (m, 5H), 3.12 (dd, J=6.1, 12.5, 1H), 2.75 (br s, 2H), 2.48 (d, J=6.5, 3H), 2.33-2.20 (m, 1H), 2.11-1.95 (m, 1H), 1.94-1.73 (m, 2H), 1.73-1.54 (m, 2H), 1.43 (br s, 2H), 1.35 (d, J=6.3, 3H); MS (ESI+) m/z 231 (M+H)$^+$.

Step B: The title compounds were prepared by substituting (S)-2-phenylbutanoic acid for 1-phenylcyclopentanecarboxylic acid and (3aS,6aR)-2-((S)-1-phenylethyl)octahydrocyclopenta[c]pyrrol-4-amine for (3aS*,6aR*)-2-benzyloctahydrocyclopenta[c]pyrrol-4-amine in the procedure described in Examples 1 and 2.

Example 212: $^1$H NMR (500 MHz, pyridine-d$_5$) δ ppm 10.86 (d, J=6.3, 1H), 10.31 (d, J=7.3, 2H), 10.18-10.07 (m, 7H), 10.04 (t, J=7.3, 1H), 7.12 (dt, J=7.2, 14.6, 1H), 6.31 (dd, J=6.4, 8.6, 1H), 5.77 (q, J=6.6, 1H), 5.61-5.53 (m, 1H), 5.21-5.08 (m, 3H), 4.99 (dd, J=4.6, 9.8, 1H), 4.94 (dd, J=8.3, 16.1, 2H), 4.70-4.60 (m, 2H), 4.46 (dt, J=5.8, 16.8, 1H), 4.41-4.33 (m, 1H), 4.13-4.06 (m, 1H), 4.01 (d, J=6.6, 3H), 3.75 (t, J=7.3, 3H); MS (ESI+) m/z 377 (M+H)$^+$.

Example 213: $^1$H NMR (500 MHz, pyridine-d$_5$) δ ppm 8.50 (d, J=7.1, 1H), 7.56 (s, 1H), 7.45 (d, J=7.3, 2H), 7.34 (dt, J=7.6, 16.7, 4H), 7.25 (dd, J=7.3, 13.4, 3H), 4.37-4.30 (m, 1H), 3.52 (dd, J=6.2, 8.8, 1H), 3.11 (q, J=6.5, 1H), 2.60 (dd, J=2.3, 8.1, 1H), 2.56-2.44 (m, 3H), 2.37-2.27 (m, 3H), 2.04-1.96 (m, 1H), 1.85-1.74 (m, 2H), 1.49 (dq, J=6.8, 13.3, 1H), 1.38-1.32 (m, 1H), 1.29 (d, J=6.6, 3H), 0.92 (t, J=7.3, 3H); MS (ESI+) m/z 377 (M+H)$^+$.

Example 214

N-[(3aR,4S,6aS)-2-benzyloctahydrocyclopenta[c]pyrrol-4-yl]-N,3-dimethyl-2-phenylbutanamide Step A: Di-tert-butyl dicarbonate (0.429 mL, 1.849 mmol), (3aR,4S,6aS)-2-benzyloctahydrocyclopenta[c]pyrrol-4-amine (200 mg, 0.925 mmol) from Example 33 Step A, and (dimethylamino)pyridine (22.59 mg, 0.185 mmol) were combined in dichloromethane (5 mL). The reaction mixture was stirred at room temperature for 30 minutes. The crude material was purified on a silica gel cartridge (Analogix®, Burlington, Wis., RS-4) eluting with ethyl acetate/hexanes to give tert-butyl(3aR,4S,6aS)-2-benzyloctahydrocyclopenta[c]pyrrol-4-ylcarbamate: $^1$H NMR (400 MHz, CDCl$_3$) δ ppm 7.39-7.12 (m, 5H), 4.47 (s, 1H), 3.74 (s, 1H), 3.61 (s, 1H), 3.52 (s, 1H), 2.55 (t, J=31.6, 4H), 2.31 (s, 2H), 2.03 (d, J=6.1, 1H), 1.83 (d, J=8.0, 1H), 1.58 (s, 1H), 1.43 (s, 9H), 0.98-0.79 (m, 1H); MS (ESI+) m/z 317 (M+H)$^+$.

Step B: tert-Butyl(3aR,4S,6aS)-2-benzyloctahydrocyclopenta[c]pyrrol-4-ylcarbamate (59 mg, 0.187 mmol) from Step A was treated with lithium aluminum hydride (0.374 mmol) in tetrahydrofuran (0.5 mL). The reaction was stirred at room temperature for 1 hour and then heated to reflux for 2 hours. The reaction was cooled to room temperature and quenched with dropwise addition of saturated aqueous sodium sulfate (50 μL) to give a precipitate. The precipitate was washed with tetrahydrofuran, and then the solvent was removed to give (3aR,4S,6aS)-2-benzyl-N-methyloctahydrocyclopenta[c]pyrrol-4-amine: $^1$H NMR (500 MHz, pyridine-d$_5$) δ ppm 7.34-7.28 (m, 4H), 7.25-7.19 (m, 1H), 3.60-3.51 (m, 2H), 2.76 (q, J=5.6, 1H), 2.64 (d, J=15.7, 1H), 2.58-2.53 (m, 1H), 2.51-2.46 (m, 1H), 2.40-2.35 (m, 4H), 2.31-2.22 (m, 2H), 1.98-1.85 (m, 2H), 1.39 (dt, J=5.7, 10.6, 3H); MS (ESI+) m/z 231 (M+H)$^+$.

Step C: The title compound was prepared by substituting 3-methyl-2-phenylbutanoic acid for 1-phenylcyclopentanecarboxylic acid and (3aR,4S,6aS)-2-benzyl-N-methyloctahydrocyclopenta[c]pyrrol-4-amine from Step B for (3aS*,6aR*)-2-benzyloctahydrocyclopenta[c]pyrrol-4-amine in the procedure described in Example 2: $^1$H NMR (300 MHz, CDCl$_3$) δ ppm 7.59-7.41 (m, 5H), 7.39-7.16 (m, 5H), 3.64 (d, J=13.2, 1H), 3.50 (d, J=9.5, 1H), 2.69-2.52 (m, 2H), 2.50-2.33 (m, 3H), 2.25-2.15 (m, 1H), 2.05 (dd, J=6.3, 9.2, 1H), 1.88-1.67 (m, 2H), 1.34 (dd, J=13.4, 19.6, 3H), 1.08 (d, J=6.4, 3H), 1.03-0.95 (m, 1H), 0.79-0.66 (m, 6H); MS (ESI+) m/z 391 (M+H)$^+$.

Example 215

N-[(3aS*,4R*,6aR*)-2-benzyloctahydrocyclopenta[c]pyrrol-4-yl]-N,3-dimethyl-2-phenylbutanamide The title compound was prepared as described in Example 214 substituting (3aR*,4S*,6aS*)-2-benzyloctahydrocyclopenta[c]pyrrol-4-amine (International Publication No. WO2006/012396) for (3aR,4S,6aS)-2-benzyloctahydrocyclopenta[c]pyrrol-4-amine in Example 214 Step A: $^1$H NMR (300 MHz, CDCl$_3$) δ ppm 7.61-7.41 (m, 5H), 7.26 (dd, J=15.4, 37.9, 5H), 3.65 (d, J=13.2, 1H), 3.54 (dd, J=7.6, 19.9, 2H), 2.70-2.53 (m, 2H), 2.50-2.36 (m, 2H), 2.25-2.15 (m, 1H), 2.07 (s, 1H), 1.87-1.66 (m, 2H), 1.43-1.26 (m, 3H), 1.19 (d, J=6.4, 2H), 1.08 (d, J=6.5, 2H), 1.01 (d, J=6.4, 1H), 0.79-0.63 (m, 5H); MS (ESI+) m/z 391 (M+H)$^+$.

Example 216

(3aR*,4S*,6aS*)-N-benzyl-2-(3-methyl-2-phenylbutanoyl)octahydrocyclopenta[c]pyrrol-4-amine Step A: tert-Butyl(3aR,4S,6aS)-2-benzyloctahydrocyclopenta[c]pyrrol-4-ylcarbamate was prepared as described in Example 214 Step A substituting (3aR*,4S*,6aS*)-2-benzyloctahydrocyclopenta[c]pyrrol-4-amine (International Publication No. WO2006/012396) for (3aR,4S,6aS)-2-benzyloctahydrocyclopenta[c]pyrrol-4-amine: MS (ESI+) m/z 317 (M+H)$^+$.

Step B: tert-Butyl(3aR,4S,6aS)-2-benzyloctahydrocyclopenta[c]pyrrol-4-ylcarbamate (100 mg, 0.316 mmol) from Step A and ammonium formate (100 mg, 1.580 mmol) were combined in ethanol. The reaction was deoxygenated at low temperature, and palladium on carbon (3.36 mg, 0.032 mmol) was added. The reaction was heated to reflux under nitrogen. After 3 hours, TLC and LCMS showed mostly starting material. Degussa's catalyst and 5 equivalents more ammonium formate were added and the reaction mixture was refluxed under nitrogen overnight. More ammonium formate and Degussa's catalyst were added and the reaction heated to 90° C. After 2 hours, TLC and LCMS showed no remaining starting material. The reaction was filtered through diatomaceous earth containing carbonate functionalized silica gel (Silicycle, Quebec, Canada) with methanol. Solvent removal in vacuo gave tert-butyl(3aR,4S,6aS)-octahydrocyclopenta[c]pyrrol-4-ylcarbamate: MS (ESI+) m/z 226 (M+H)$^+$.

Step C: 3-Methyl-2-phenylbutanoic acid (63 mg, 0.353 mmol), 1-hydroxybenzotriazole (54.1 mg, 0.353 mmol), and N-(3-dimethylaminopropyl)-N-ethylcarbodiimide (0.063 mL, 0.353 mmol) were combined in dichloromethane (5 mL). The reaction was stirred at room temperature for 20 minutes, and then tert-butyl(3aR,4S,6aS)-octahydrocyclopenta[c]pyrrol-4-ylcarbamate (80 mg, 0.353 mmol) from Step B was added.

After 30 minutes, the reaction was quenched with water and extracted with dichloromethane. The combined extracts were concentrated, and the crude material purified using 10-100% ethyl acetate/hexanes to give tert-butyl(3aR,4S,6aS)-2-(3-methyl-2-phenylbutanoyl)octahydrocyclopenta[c]pyrrol-4-ylcarbamate: MS (ESI+) m/z 387 (M+H)⁺.

Step D: tert-Butyl(3aR,4S,6aS)-2-(3-methyl-2-phenylbutanoyl)octahydrocyclopenta[c]pyrrol-4-ylcarbamate (39 mg, 0.101 mmol) from Step C was combined with 4 M HCl in dioxane (5 mL, 20.00 mmol) in ether (5 mL). After about 2 hours, the solvent was removed in vacuo to give 1-((3aR,4S,6aS)-4-aminohexahydrocyclopenta[c]pyrrol-2(1H)-yl)-3-methyl-2-phenylbutan-1-one hydrochloric acid salt which was used in the next step without additional purification: MS (ESI+) m/z 287 (M+H)⁺.

Step E: 1-((3aR,4S,6aS)-4-aminohexahydrocyclopenta[c]pyrrol-2(1H)-yl)-3-methyl-2-phenylbutan-1-one hydrochloric acid salt (49 mg, 0.152 mmol) and benzaldehyde (0.023 mL, 0.228 mmol) were combined in dichloromethane (1.5 mL). Acetic acid (1.5 mL) was added. The reaction was stirred at room temperature for 30 minutes, then PS-cyanoborohydride (64.9 mg, 0.152 mmol) was added. After 72 hours, LCMS of the reaction showed no more starting material. The reaction mixture was filtered, and the solvent was removed under a stream of nitrogen. The crude material was purified using a silica gel cartridge (Analogix®, Burlington, Wis., RS-4) eluting with 1-10% methanol (2 N ammonia)/dichloromethane to give the title compound: ¹H NMR (500 MHz, pyridine-d₅) δ ppm 7.69-7.60 (m, 2H), 7.54-7.44 (m, 2H), 7.44-7.34 (m, 5H), 7.29 (tdd, J=4.8, 7.8, 13.0, 2H), 3.90-3.36 (m, 4H), 3.29 (dd, J=3.8, 10.6, 0.5H), 2.99 (dd, J=5.7, 11.4, 0.5H), 2.93 (dd, J=6.0, 11.3, 0.5H), 2.75-2.63 (m, 1H), 2.59-2.48 (m, 1H), 2.46-2.31 (m, 1H), 2.25 (dt, J=4.1, 8.7, 0.5H), 1.97 (dt, J=9.3, 11.6, 1H), 1.93-1.85 (m, 0.5H), 1.84-1.74 (m, 1H), 1.65-1.55 (m, 0.5H), 1.51-1.35 (m, 1H), 1.33-1.21 (m, 1H), 1.18-1.10 (m, 3H), 1.01 (td, J=7.7, 13.1, 0.5H), 0.87 (dt, J=6.6, 12.9, 0.5H), 0.75 (t, J=7.2, 3H); MS (ESI+) m/z 377 (M+H)⁺.

Example 217

2,2-dicyclohexyl-N-[(3aS,4R,6aR)-2-(N,N-dimethyl-D-leucyl)octahydrocyclopenta[c]pyrrol-4-yl]acetamide Step A: N-(tert-Butoxycarbonyl)-D-leucine (72.7 mg, 0.314 mmol), 2,2-dicyclohexyl-N-[(3aS,4R,6aR)-octahydrocyclopenta[c]pyrrol-4-yl]acetamide (95 mg, 0.286 mmol) from Example 74, and hydroxybenzotriazole (48.1 mg, 0.314 mmol) were combined in dichloromethane (10 mL). After 20 minutes, N-(3-dimethylaminopropyl)-N-ethylcarbodiimide (0.056 mL, 0.314 mmol) was added, and the reaction mixture was stirred at room temperature for 18 hours. The reaction was quenched with water. The separated organic layer was reduced in volume, and the crude material was applied to a silica gel cartridge (Analogix®, Burlington, Wis., RS-12) and eluted first with 10% to 100% ethyl acetate/hexanes and then with 1-10% methanol (2 N ammonia)/dichloromethane to give tert-butyl(R)-1-((3aS,4R,6aR)-4-(2,2-dicyclohexylacetamido)hexahydrocyclopenta[c]pyrrol-2(1H)-yl)-4-methyl-1-oxopentan-2-ylcarbamate: ¹H NMR (500 MHz, pyridine-d₅) δ ppm 8.26 (dd, J=7.2, 24.0, 1H), 7.91 (d, J=8.6, 1H), 4.48-4.36 (m, 1H), 4.12-3.96 (m, 1H), 3.87 (dd, J=7.4, 10.3, 1H), 3.70 (ddd, J=8.0, 14.4, 23.7, 1H), 3.40 (dd, J=5.7, 12.3, 1H), 2.77 (s, 1H), 2.58 (d, J=6.1, 1H), 2.08 (s, 1H), 2.01 (dd, J=5.6, 10.4, 2H), 1.96-1.55 (m, 17H), 1.54-1.50 (m, 9H), 1.49-1.37 (m, 2H), 1.19 (qdd, J=12.3, 22.3, 24.7, 11H), 1.00 (t, J=6.6, 3H), 0.88 (d, J=6.6, 1H).

Step B: tert-Butyl(R)-1-((3aS,4R,6aR)-4-(2,2-dicyclohexylacetamido)hexahydrocyclopenta[c]pyrrol-2(1H)-yl)-4-methyl-1-oxopentan-2-ylcarbamate (185 mg, 0.339 mmol) from Step A, and 2 N HCl in ether (2.5 mL, 5.00 mmol) were combined in ether (1 mL). The reaction mixture was stirred at room temperature overnight. The solids were collected and dried to give N-((3aS,4R,6aR)-2-((R)-2-amino-4-methylpentanoyl)octahydrocyclopenta[c]pyrrol-4-yl)-2,2-dicyclohexylacetamide: ¹H NMR (500 MHz, pyridine-d₅) δ ppm 8.34-8.24 (m, 1H), 4.92 (br s, 2H), 4.46-4.31 (m, 1H), 4.07 (d, J=9.2, 0.5H), 3.91-3.81 (m, 1.5H), 3.77 (dd, J=8.8, 12.1, 1H), 3.72-3.64 (m, 0.5H), 3.59-3.53 (m, 0.5H), 3.45 (dd, J=5.2, 12.2, 0.5H), 3.32 (d, J=6.5, 0.5H), 2.82-2.69 (m, 1H), 2.63 (dd, J=8.4, 14.5, 0.5H), 2.54 (dd, J=8.0, 16.4, 0.5H), 2.21-2.06 (m, 2H), 2.02 (q, J=7.6, 1H), 1.99-1.55 (m, 15H), 1.50-1.38 (m, 3H), 1.37-1.12 (m, 9H), 1.09 (d, J=6.5, 3H), 1.01 (d, J=6.6, 2H), 0.96 (d, J=6.4, 1H), 0.91 (d, J=6.6, 1H). MS (ESI+) m/z 466 (M+H)⁺.

Step C: To N-((3aS,4R,6aR)-2-((R)-2-amino-4-methylpentanoyl)octahydrocyclopenta[c]pyrrol-4-yl)-2,2-dicyclohexylacetamide (0.133 g, 0.298 mmol) from Step B was added formaldehyde (0.228 mL, 2.98 mmol) in dichloromethane (0.5 mL). Acetic acid (0.5 mL) was added. The reaction was stirred at room temperature for 30 minutes, PS-cyanoborohydride (0.255 g, 0.597 mmol) was then added, and the reaction mixture was stirred at room temperature overnight. The reaction was filtered, and the solvent was removed in vacuo. The crude material was purified on silica gel chromatography on a silica gel cartridge (Analogix®, Burlington, Wis., RS-12) eluting with 1-10% methanol (2 N ammonia)/dichloromethane to give
the title compound: ¹H NMR (500 MHz, pyridine-d₅) δ ppm 8.29 (dd, J=7.1, 15.9, 1H), 4.46-4.35 (m, 1H), 4.09-3.99 (m, 1H), 3.92-3.80 (m, 1H), 3.70 (dd, J=8.6, 12.4, 1H), 3.66-3.58 (m, 2H), 3.45 (dd, J=4.8, 9.1, 0.5H), 2.78-2.64 (m, 1H), 2.63-2.53 (m, 1H), 2.42 (s, 3H), 2.38 (s, 3H), 2.23-2.14 (m, 0.5H), 2.13-1.99 (m, 2H), 1.99-1.82 (m, 5H), 1.82-1.63 (m, 8H), 1.60 (d, J=14.0, 1H), 1.57-1.51 (m, 1H), 1.45 (ddd, J=8.6, 18.8, 29.3, 3H), 1.36-1.05 (m, 9H), 1.01 (d, J=6.6, 3H), 0.91 (dd, J=6.6, 19.9, 3H); MS (ESI+) m/z 474 (M+H)⁺.

Example 218

N-[(3aR,4S,6aS)-2-benzoyloctahydrocyclopenta[c]pyrrol-4-yl]-3-methyl-2-phenylbutanamide 3-Methyl-N-[(3aR,4S,6aS)-octahydrocyclopenta[c]pyrrol-4-yl]-2-phenylbutanamide from Example 83 Step A (25 mg, 0.087 mmol), triethylamine (0.018 mL, 0.131 mmol), and benzoyl chloride (10.12 µL, 0.087 mmol) were combined in dichloromethane (5 mL). After 5 minutes, TLC shows no more starting material. The crude reaction mixture was concentrated and applied to a silica gel cartridge (Analogix®, Burlington, Wis., RS-4) eluting with 1-10% methanol (2 N ammonia)/dichloromethane to give the title compound: ¹H NMR (300 MHz, CDCl₃) δ ppm 7.49-7.42 (m, 2H), 7.41-7.35 (m, 3H), 7.33-7.27 (m, 3H), 5.43 (d, J=6.7, 1H), 3.97 (m, 1H), 3.74 (m, 2H), 3.56 (m, 2H), 3.39 (m, 1H), 2.74 (m, 2H), 2.48 (m, 1H), 2.38 (m, 2H), 2.07 (dd, J=4.6, 10.8, 1H), 1.94 (m, 1H), 1.52-1.31 (m, 2H), 1.01 (d, J=6.3, 3H), 0.68 (d, J=6.6, 3H); MS (ESI+) m/z 391 (M+H)⁺.

Example 219

N'-[(3aR,4S,6aS)-2-benzyloctahydrocyclopenta[c]pyrrol-4-yl]-N-isopropyl-N-phenylurea 2 M Trimethylaluminum in toluene (0.198 mL, 0.395 mmol) was added dropwise to N-isopropylaniline (0.068 mL, 0.474 mmol) in toluene (2 mL) at 0° C. The reaction was warmed to room temperature and stirred for 1 hour. The aluminum amide solution was then added dropwise to a solution of tert-butyl(3aR,4S,6aS)-2-benzyloctahydrocyclopenta[c]pyrrol-4-ylcarbamate from Example 214 Step A (50 mg, 0.158 mmol) in 1 mL of toluene at 0° C. The reaction was heated at 90° C. overnight, and then the reaction was quenched with 1 mL of 5% aqueous sodium hydroxide. The separated toluene layer was applied directly to a silica gel cartridge (Analogix®, Burlington, Wis., RS-4) eluting with 1-10% methanol (2 N ammonia)/dichloromethane to give the title compound: $^1$H NMR (300 MHz, CDCl$_3$) δ ppm 7.40 (ddd, J=1.8, 3.2, 5.7, 3H), 7.29 (d, J=4.4, 4H), 7.24-7.18 (m, 1H), 7.14 (t, J=2.0, 1H), 7.13-7.10 (m, 1H), 4.87 (dt, J=6.8, 13.6, 1H), 3.94-3.84 (m, 1H), 3.74 (d, J=7.1, 1H), 3.60 (d, J=13.0, 1H), 3.44 (d, J=13.0, 1H), 2.53 (t, J=5.5, 2H), 2.48-2.40 (m, 1H), 2.40-2.33 (m, 1H), 2.22 (dd, J=3.7, 8.8, 1H), 2.07 (ddd, J=5.1, 9.2, 11.7, 1H), 1.95 (td, J=6.0, 12.0, 1H), 1.63-1.52 (m, 1H), 1.40-1.30 (m, 1H), 1.29-1.17 (m, 1H), 1.05 (d, J=3.2, 3H), 1.02 (d, J=3.2, 3H); MS (ESI+) m/z 378 (M+H)$^+$.

Example 220

(2S)-N-[(3aS,4R,6aR)-2-benzyloctahydrocyclopenta[c]pyrrol-4-yl]-2-(1,1-dioxidoisothiazolidin-2-yl)-4-methylpentanamide Step A: (S)-tert-Butyl 2-amino-4-methylpentanoate hydrochloride (0.516 g, 2.306 mmol) were dissolved in dichloromethane (15 mL) and triethylamine (1.061 mL, 7.61 mmol) was added. 3-Chloropropane-1-sulfonyl chloride (0.337 mL, 2.77 mmol) was added dropwise, and the reaction mixture was stirred at room temperature overnight. The solvent was removed in vacuo, and the crude material was taken up in ether, filtered, and concentrated to give (S)-tert-butyl 2-(3-chloropropylsulfonamido)-4-methylpentanoate: $^1$H NMR (300 MHz, CDCl$_3$) δ ppm 4.70 (d, J=9.7, 1H), 4.02-3.91 (m, 1H), 3.77-3.60 (m, 2H), 3.25-2.96 (m, 3H), 2.31 (tdd, J=2.2, 6.6, 9.2, 2H), 1.83 (dq, J=6.5, 13.0, 1H), 1.58-1.53 (m, 8H), 1.38 (t, J=7.3, 1H), 0.96 (dd, J=2.1, 6.6, 6H); MS (ESI+) m/z 345 (M+NH$_4$)$^+$.

Step B: (S)-tert-Butyl 2-(3-chloropropylsulfonamido)-4-methylpentanoate (0.756 g, 2.306 mmol) from Step A was dissolved in tetrahydrofuran and potassium tert-butoxide (0.517 g, 4.61 mmol) was added. The reaction was stirred at room temperature overnight. The solvent was removed in vacuo, and the crude material was partitioned between ether and water. The ether layer was separated, washed with brine, dried (Na$_2$SO$_4$), and concentrated in vacuo to supply tert-butyl(2S)-2-(1,1-dioxidoisothiazolidin-2-yl)-4-methylpentanoate: $^1$H NMR (300 MHz, CDCl$_3$) δ ppm 4.17-4.05 (m, 1H), 3.68 (dd, J=7.9, 16.6, 1H), 3.40-3.28 (m, 1H), 3.21-3.09 (m, 2H), 2.39 (td, J=5.3, 13.6, 2H), 1.68 (m, 3H), 1.47 (s, 9H), 0.97 (dd, J=3.2, 6.2, 6H).

Step C: tert-butyl(2S)-2-(1,1-dioxidoisothiazolidin-2-yl)-4-methylpentanoate (0.656 g, 2.251 mmol) from Step B was combined with HCl (4 N in dioxane, 5 mL, 20.00 mmol). The reaction mixture was stirred at room temperature for 24 hours, then the solvent removed in vacuo to furnish (2S)-2-(1,1-dioxidoisothiazolidin-2-yl)-4-methylpentanoic acid: MS (DCI+) m/z 253 (M+NH$_4$)$^+$.

Step D: (2S)-2-(1,1-Dioxidoisothiazolidin-2-yl)-4-methylpentanoic acid (359 mg, 1.526 mmol) was combined with triethylamine (0.387 mL, 2.77 mmol) in dichloromethane (10 mL). 1-Hydroxybenzotriazole (234 mg, 1.526 mmol) and N-(3-dimethylaminopropyl)-N'-ethylcarbodiimide (0.270 mL, 1.526 mmol) were added, and the reaction mixture was stirred for 15 minutes. Then (3aS,4R,6aR)-2-benzyloctahydrocyclopenta[c]pyrrol-4-amine (300 mg, 1.387 mmol) from Example 16 Step E was added, and the reaction mixture was stirred at room temperature for 24 hours. The reaction was quenched with 10 mL of aqueous sodium bicarbonate and extracted with 3×20 mL of dichloromethane. The solvent was removed in vacuo. The crude material was applied to a silica gel cartridge (Analogix®, Burlington, Wis., RS15-24) and eluted with 1-10% methanol (2 N ammonia)/dichloromethane to give the title compound: $^1$H NMR (500 MHz, pyridine-d$_5$) δ ppm 8.76 (d, J=6.9, 1H), 7.46-7.39 (m, 2H), 7.40-7.33 (m, 2H), 7.26 (dd, J=9.9, 17.2, 1H), 4.52 (t, J=7.7, 1H), 4.44-4.34 (m, 1H), 3.93 (dt, J=7.0, 14.5, 1H), 3.57 (dd, J=5.4, 13.1, 1H), 3.49-3.36 (m, 2H), 3.30-3.20 (m, 2H), 2.83-2.74 (m, 1H), 2.62-2.45 (m, 2H), 2.44-2.37 (m, 1H), 2.33-2.17 (m, 4H), 2.11 (qd, J=6.5, 12.5, 1H), 1.92-1.78 (m, 3H), 1.77-1.59 (m, 2H), 1.45-1.32 (m, 1H), 0.88 (d, J=6.6, 3H), 0.83 (dd, J=2.5, 6.5, 3H); MS (ESI+) m/z 434 (M+H)$^+$.

Example 221 tert-butyl(S)-1-((3aR,4S,6aS)-2-benzyloctahydrocyclopenta[c]pyrrol-4-ylamino)-4-methyl-1-oxopentan-2-ylcarbamate N-(tert-Butoxycarbonyl)-L-leucine (0.374 g, 1.617 mmol), 1-hydroxybenzotriazole hydrate (0.248 g, 1.617 mmol), and (3aR,4S,6aS)-2-benzyloctahydrocyclopenta[c]pyrrol-4-amine from Step A of Example 33 (0.318 g, 1.470 mmol) were combined in dichloromethane (3.0 mL). After 20 minutes, N$^1$-((ethylimino)methylene)-N$^3$,N$^3$-dimethylpropane-1,3-diamine (0.286 mL, 1.617 mmol) was added, and the reaction was stirred at room temperature overnight. The reaction was quenched with water and extracted with dichloromethane (2×2 mL), and the extracts were applied directly to a 25 g silica gel cartridge and purified with a gradient of 5-40% acetone/hexanes over 30 minutes to give the title compound: $^1$H NMR (500 MHz, pyridine-d$_5$) δ ppm 8.61-8.64 (m, 1H), 7.96-7.99 (m, 1H), 7.42-7.44 (m, 2H), 7.36 (t, J=7.4 Hz, 2H), 7.28 (d, J=7.3 Hz, 1H), 4.65-4.73 (m, 1H), 4.37-4.45 (m, 1H), 3.59 (d, J=13.1 Hz, 1H), 3.43 (d, J=13.1 Hz, 1H), 2.81-2.84 (m, 1H), 2.55-2.58 (m, 1H), 2.44-2.54 (m, 2H), 2.24-2.36 (m, 2H), 2.02-2.13 (m, 1H), 1.78-1.94 (m, 4H), 1.53-1.66 (m, 1H), 1.50 (s, 9H), 1.26-1.43 (m, 1H), 0.87 (d, J=5.5 Hz, 3H), 0.83-0.85 (m, 3H); MS (ESI+) m/z 430 (M+H)$^+$.

Example 222 tert-butyl(S)-1-((3aR,4S,6aS)-2-benzyloctahydrocyclopenta[c]pyrrol-4-ylamino)-4-methyl-1-oxopentan-2-yl(methyl)carbamate The title compound was prepared by substituting N-(tert-butoxycarbonyl)-N-methyl-L-leucine for N-(tert-butoxycarbonyl)-L-leucine in the procedure described in Example 221: $^1$H NMR (500 MHz, pyridine-d$_5$) δ ppm 8.23-8.32 (m, 1H), 7.42-7.44 (m, 2H), 7.36 (t, J=7.5 Hz, 2H), 7.27 (t, J=7.4 Hz, 1H), 5.02 (m, 0.7H), 4.69 (m, 0.3H), 4.37-4.43 (m, 1H), 3.58 (d, J=13.1 Hz, 1H), 3.45 (d, J=13.1 Hz, 1H), 3.04-3.11 (m, 3H), 2.82-2.91 (m, 1H), 2.40-2.52 (m, 3H), 2.31-2.34 (m, 1H), 2.21-2.25 (m, 1H), 1.99-2.14 (m, 1H), 1.77-1.94 (m, 3H), 1.51-1.62 (m, 2H), 1.47 (s, 9H), 1.34-1.37 (m, 1H), 0.88 (d, J=6.4 Hz, 3H), 0.85 (d, J=6.4 Hz, 3H); MS (ESI+) m/z 444 (M+H)$^+$.

Example 223 tert-butyl(S)-1-((3aR,4S,6aS)-2-benzyloctahydrocyclopenta[c]pyrrol-4-ylamino)-4-methyl-1-oxopentan-2-yl(ethyl)carbamate The title compound was prepared by substituting N-(tert-butoxycarbonyl)-N-ethyl-L-leucine for N-(tert-butoxycarbonyl)-L-leucine in the procedure described in Example 221: $^1$H NMR (500 MHz, pyridine-$d_5$) δ ppm 8.11-8.14 (m, 1H), 7.42-7.44 (m, 2H), 7.36 (t, J=7.4 Hz, 2H), 7.27 (t, J=7.3 Hz, 1H), 4.36-4.41 (m, 1H), 3.59 (d, J=13.1 Hz, 1H), 3.43-3.47 (m, 3H), 2.80-2.85 (m, 1H), 2.47-2.51 (m, 2H), 2.39-2.43 (m, 1H), 2.33-2.35 (m, 1H), 2.22-2.25 (m, 1H), 2.05-2.13 (m, 1H), 1.94-2.04 (m, 1H), 1.81-1.84 (m, 1H), 1.72-1.78 (m, 1H), 1.52-1.61 (m, 1H), 1.46-1.49 (m, 9H), 1.34-1.41 (m, 2H), 1.17-1.33 (m, 3H), 0.89-0.91 (m, 6H); MS (ESI+) m/z 458 (M+H)$^+$.

Example 224 tert-butyl(2S,3S)-1-((3aR,4S,6aS)-2-benzyloctahydrocyclopenta[c]pyrrol-4-ylamino)-3-methyl-1-oxopentan-2-yl(methyl)carbamate The title compound was prepared by substituting N-(tert-butoxycarbonyl)-N-methyl-L-isoleucine for N-(tert-butoxycarbonyl)-L-leucine in the procedure described in Example 221: $^1$H NMR (500 MHz, pyridine-$d_5$) δ ppm 8.43 (d, J=8.7 Hz, 1H), 7.43 (s, 1H), 7.37 (t, J=7.4 Hz, 2H), 7.25-7.30 (m, 1H), 4.68-4.72 (m, 1H), 4.34-4.44 (m, 1H), 3.61 (d, J=13.1 Hz, 1H), 3.46 (d, J=13.1 Hz, 1H), 3.22-3.26 (m, 1H), 3.13-3.14 (m, 2H), 2.87-2.90 (m, 1H), 2.46-2.54 (m, 3H), 2.25-2.35 (m, 3H), 2.00-2.12 (m, 1H), 1.82 (dq, J=12.7, 6.3 Hz, 1H), 1.52-1.63 (m, 1H), 1.48-1.50 (m, 9H), 1.32-1.43 (m, 3H), 0.96-1.10 (m, 4H), 0.78-0.86 (m, 3H); MS (ESI+) m/z 444 (M+H)$^+$.

Example 225 tert-butyl(S)-1-((3aR,4S,6aS)-2-benzyloctahydrocyclopenta[c]pyrrol-4-ylamino)-3,3-dimethyl-1-oxobutan-2-ylcarbamate The title compound was prepared by substituting N-(tert-butoxycarbonyl)-N-methyl-L-tert-leucine for N-(tert-butoxycarbonyl)-L-leucine in the procedure described in Example 221: $^1$H NMR (500 MHz, pyridine-$d_5$) δ ppm 8.71 (m, 1H), 7.70 (d, J=9.6 Hz, 1H), 7.43-7.45 (m, 2H), 7.37 (t, J=7.5 Hz, 2H), 7.26-7.30 (m, 1H), 4.61 (d, J=9.7 Hz, 1H), 4.39-4.45 (m, 1H), 3.63 (d, J=13.1 Hz, 1H), 3.44 (d, J=13.1 Hz, 1H), 2.86 (dd, J=9.0, 2.9 Hz, 1H), 2.57-2.63 (m, 1H), 2.45-2.55 (m, 2H), 2.26-2.33 (m, 2H), 2.00 (dd, J=12.1, 6.1 Hz, 1H), 1.77-1.84 (m, 1H), 1.48-1.56 (m, 1H), 1.48 (s, 9H), 1.25-1.38 (m, 1H), 1.18 (s, 9H); MS (ESI+) m/z 430 (M+H)$^+$.

Example 226 tert-butyl(S)-1-((3aR,4S,6aS)-2-benzyloctahydrocyclopenta[c]pyrrol-4-ylamino)-4,4-dimethyl-1-oxopentan-2-ylcarbamate The title compound was prepared by substituting N-(tert-butoxycarbonyl)-L-neopentylglycine for N-(tert-butoxycarbonyl)-L-leucine in the procedure described in Example 221: $^1$H NMR (500 MHz, pyridine-$d_5$) δ ppm 8.54-8.57 (m, 1H), 8.10-8.13 (m, 1H), 7.41-7.45 (m, 2H), 7.36 (t, J=7.4 Hz, 2H), 7.25-7.29 (m, 1H), 4.72-4.76 (m, 1H), 4.38-4.42 (m, 1H), 3.59 (d, J=13.1 Hz, 1H), 3.43 (d, J=13.1 Hz, 1H), 2.84 (dd, J=9.0, 2.9 Hz, 1H), 2.53-2.60 (m, 1H), 2.46-2.53 (m, 1H), 2.42-2.46 (m, 1H), 2.29-2.32 (m, 1H), 2.22-2.27 (m, 1H), 2.16 (dd, J=14.1, 4.8 Hz, 1H), 2.01-2.07 (m, 1H), 1.77-1.87 (m, 2H), 1.54-1.62 (m, 1H), 1.50 (s, 9H), 1.31-1.41 (m, 1H), 0.98 (s, 9H); MS (ESI+) m/z 444 (M+H)$^+$.

Example 227 tert-butyl(S)-1-((3aR,4S,6aS)-2-benzyloctahydrocyclopenta[c]pyrrol-4-ylamino)-1-oxohexan-2-ylm-ethyl)carbamate The title compound was prepared by substituting N-(tert-butoxycarbonyl)-N-methyl-L-norleucine for N-(tert-butoxycarbonyl)-L-leucine in the procedure described in Example 221: $^1$H NMR (500 MHz, pyridine-$d_5$) δ ppm 8.21-8.24 (m, 1H), 7.42-7.44 (m, 2H), 7.36 (t, J=7.4 Hz, 2H), 7.24-7.31 (m, 1H), 5.02 (m, 0.7H), 4.66 (m, 0.3H), 4.34-4.47 (m, 1H), 3.59 (d, J=13.1 Hz, 1H), 3.45 (d, J=13.1 Hz, 1H), 3.05-3.10 (m, 3H), 2.82-2.85 (m, 1H), 2.45-2.50 (m, 2H), 2.37-2.45 (m, 1H), 2.31-2.37 (m, 1H), 2.24 (t, J=7.5 Hz, 1H), 2.05-2.12 (m, 2H), 1.79-1.84 (m, 2H), 1.53-1.62 (m, 1H), 1.47 (s, 9H), 1.34-1.38 (m, 1H), 1.21-1.29 (m, 4H), 0.75-0.81 (m, 3H); MS (ESI+) m/z 444 (M+H)$^+$.

Example 228

N-[(3aR,4S,6aS)-2-benzyloctahydrocyclopenta[c]pyrrol-4-yl]-2,2-bis(4-fluorophenyl)acetamide The title compound was prepared by substituting 2,2-bis(4-fluorophenyl)acetic acid for N-(tert-butoxycarbonyl)-L-leucine in the procedure described in Example 221: $^1$H NMR (500 MHz, pyridine-$d_5$) δ ppm 9.04 (d, J=7.0, 1H), 7.57-7.52 (m, 4H), 7.42 (d, J=7.1, 2H), 7.36 (t, J=7.5, 2H), 7.27 (t, J=7.3, 1H), 7.12 (dt, J=15.8, 8.0, 4H), 5.23 (s, 1H), 4.45-4.37 (m, 1H), 3.57 (d, J=13.1, 1H), 3.43 (d, J=13.1, 1H), 2.78 (dd, J=9.1, 2.9, 1H), 2.54-2.47 (m, 1H), 2.47-2.43 (m, 1H), 2.40 (dd, J=8.9, 7.3, 1H), 2.29 (dd, J=9.0, 3.0, 1H), 2.27-2.21 (m, 1H), 2.10 (dq, J=12.2, 6.2, 1H), 1.84-1.75 (m, 1H), 1.60 (td, J=14.6, 7.3, 1H), 1.41-1.31 (m, 1H); MS (ESI+) m/z 447 (M+H)$^+$.

Example 229

N-[(3aR,4S,6aS)-2-benzyloctahydrocyclopenta[c]pyrrol-4-yl]-2-isopropyl-3-methylbutanamide The title compound was prepared by substituting 2-isopropyl-3-methylbutanoic acid for N-(tert-butoxycarbonyl)-L-leucine in the procedure described in Example 221: $^1$H NMR (500 MHz, pyridine-$d_5$) δ ppm 8.18 (d, J=7.5, 1H), 7.44 (d, J=7.5, 2H), 7.37 (t, J=7.6, 2H), 7.27 (t, J=7.3, 1H), 4.52-4.37 (m, 1H), 3.62 (d, J=13.2, 1H), 3.44 (d, J=13.1, 1H), 2.83 (dd, J=9.0, 2.8, 1H), 2.62-2.51 (m, 2H), 2.48 (dd, J=8.8, 7.1, 1H), 2.34-2.26 (m, 2H), 2.17-2.05 (m, 3H), 1.92-1.81 (m, 2H), 1.64 (dt, J=19.2, 7.1, 1H), 1.44-1.34 (m, 1H), 1.13 (dd, J=6.6, 3.9, 6H), 0.98 (d, J=6.8, 6H); MS (ESI+) m/z 343 (M+H)$^+$.

Example 230

N-[(3aR,4S,6aS)-2-benzyloctahydrocyclopenta[c]pyrrol-4-yl]-3-methylbutanamide

The title compound was prepared by substituting 3-methylbutanoic acid for N-(tert-butoxycarbonyl)-L-leucine in the procedure described in Example 221: $^1$H NMR (500 MHz, pyridine-d$_5$) δ ppm 8.36 (d, J=7.8, 1H), 7.44 (d, J=7.6, 2H), 7.37 (t, J=7.5, 2H), 7.28 (t, J=7.2, 1H), 4.48-4.40 (m, 1H), 3.60 (d, J=13.1, 1H), 3.45 (d, J=13.2, 1H), 2.82 (dd, J=9.0, 2.2, 1H), 2.59-2.50 (m, 2H), 2.50-2.43 (m, 1H), 2.31 (tt, J=19.8, 7.9, 3H), 2.23 (d, J=7.3, 2H), 2.17-2.08 (m, 1H), 1.87 (dd, J=13.1, 6.7, 1H), 1.68-1.58 (m, 1H), 1.46-1.34 (m, 1H), 0.95 (d, J=6.6, 5H); MS (ESI+) m/z 343 (M+H)$^+$.

Example 231 tert-butyl(2S)-2-({[(3aS,4R,6aR)-2-benzyloctahydrocyclopenta[c]pyrrol-4-yl]amino}carbonyl)piperidine-1-carboxylate The title compound was prepared by substituting (S)-1-(tert-butoxycarbonyl)piperidine-2-carboxylic acid for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$, temperature 90° C.) δ ppm 7.35-7.39 (m, 2H), 7.30 (t, J=7.5 Hz, 2H), 7.21 (t, J=7.2 Hz, 2H), 4.86-4.88 (m, 1H), 4.25-4.30 (m, 1H), 4.08-4.12 (m, 1H), 3.58 (d, J=13.2 Hz, 1H), 3.47 (d, J=13.1 Hz, 1H), 3.29 (td, J=12.8, 3.1 Hz, 1H), 2.80 (d, J=6.1 Hz, 1H), 2.49-2.56 (m, 1H), 2.42-2.47 (m, 2H), 2.36 (dd, J=9.0, 3.2 Hz, 1H), 2.32 (d, J=7.7 Hz, 1H), 2.22-2.26 (m, 1H), 2.03-2.11 (m, 1H), 1.79-1.93 (m, 1H), 1.49-1.68 (m, 5H), 1.48 (s, 9H), 1.32-1.44 (m, 2H); MS (ESI+) m/z 428 (M+H)$^+$.

Example 232 tert-butyl(S)-1-((3aS,4R,6aR)-2-benzyloctahydrocyclopenta[c]pyrrol-4-ylamino)-3-methyl-1-oxobutan-2-yl(methyl)carbamate The title compound was prepared by substituting N-(tert-butoxycarbonyl)-N-methyl-L-valine for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (501 MHz, pyridine-d$_5$, temperature 90° C.) δ ppm 7.35-7.39 (m, 3H), 7.29 (t, J=7.5 Hz, 2H), 7.21 (t, J=7.3 Hz, 1H), 4.30-4.38 (m, 1H), 4.20-4.29 (m, 1H), 3.56 (d, J=13.0 Hz, 1H), 3.47 (d, J=13.2 Hz, 1H), 3.00-3.02 (m, 3H), 2.76 (d, J=6.5 Hz, 1H), 2.48-2.55 (m, 1H), 2.33-2.47 (m, 4H), 2.28-2.32 (m, 1H), 2.04-2.12 (m, 1H), 1.81-1.88 (m, 1H), 1.49-1.59 (m, 1H), 1.46 (s, 9H), 1.36-1.45 (m, 1H), 1.00 (d, J=6.5 Hz, 3H), 0.87 (d, J=6.7 Hz, 3H); MS (ESI+) m/z 430 (M+H)$^+$.

Example 233 tert-butyl(S)-1-((3aS,4R,6aR)-2-benzyloctahydrocyclopenta[c]pyrrol-4-ylamino)-1-oxopentan-2-yl(methyl)carbamate The title compound was prepared by substituting N-(tert-butoxycarbonyl)-N-methyl-L-norvaline for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$, temperature 90° C.) δ ppm 7.36-7.38 (m, 2H), 7.28-7.31 (m, 3H), 7.21 (t, J=7.2 Hz, 1H), 4.70-4.79 (m, 1H), 4.23-4.29 (m, 1H), 3.57 (d, J=13.2 Hz, 1H), 3.47 (d, J=13.2 Hz, 1H), 2.95 (s, 3H), 2.77-2.81 (m, 1H), 2.48-2.52 (m, 1H), 2.39-2.46 (m, 2H), 2.36 (dd, J=9.0, 2.9 Hz, 1H), 2.30 (t, J=8.0 Hz, 1H), 2.07 (dq, J=12.1, 6.1 Hz, 1H), 1.92-2.03 (m, 1H), 1.72-1.86 (m, 2H), 1.50-1.59 (m, 1H), 1.47 (s, 9H), 1.36-1.44 (m, 1H), 1.25-1.35 (m, 2H), 0.86 (t, J=7.3 Hz, 3H); MS (ESI+) m/z 430 (M+H)$^+$.

Example 234 tert-butyl(S)-1-((3aS,4R,6aR)-2-benzyloctahydrocyclopenta[c]pyrrol-4-ylamino)-3,3-dimethyl-1-oxobutan-2-ylcarbamate The title compound was prepared by substituting N-(tert-butoxycarbonyl)-L-tert-leucine for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$) δ ppm 8.71 (m, 1H), 7.69 (d, J=9.6 Hz, 1H), 7.39-7.42 (m, 2H), 7.36 (t, J=7.5 Hz, 2H), 7.25-7.29 (m, 1H), 4.61 (d, J=9.7 Hz, 1H), 4.32-4.42 (m, 1H), 3.53-3.56 (m, 1H), 3.37-3.40 (m, 1H), 2.63-2.66 (m, 1H), 2.41-2.51 (m, 2H), 2.27-2.33 (m, 2H), 2.20-2.25 (m, 1H), 2.11-2.19 (m, 1H), 1.80-1.91 (m, 1H), 1.61-1.73 (m, 1H), 1.48 (s, 9H), 1.35-1.44 (m, 1H), 1.18 (s, 9H); MS (ESI+) m/z 430 (M+H)$^+$.

Example 235

N-[(3aS,4R,6aR)-2-benzyloctahydrocyclopenta[c]pyrrol-4-yl]-2-isopropyl-3-methylbutanamide The title compound was prepared by substituting 2-isopropyl-3-methylbutanoic acid for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$) δ ppm 8.18 (d, J=7.1, 1H), 7.44 (d, J=7.3, 2H), 7.36 (t, J=7.6, 2H), 7.27 (t, J=7.3, 1H), 4.51-4.37 (m, 1H), 3.61 (d, J=13.1, 1H), 3.44 (d, J=13.2, 1H), 2.83 (dd, J=9.0, 2.8, 1H), 2.61-2.51 (m, 2H), 2.48 (dd, J=8.8, 7.2, 1H), 2.35-2.24 (m, 2H), 2.16-2.06 (m, 3H), 1.93-1.81 (m, 2H), 1.64 (dt, J=14.6, 7.1, 1H), 1.44-1.35 (m, 1H), 1.13 (dd, J=6.6, 3.9, 6H), 0.98 (d, J=6.7, 6H); MS (ESI+) m/z 343 (M+H)$^+$.

Example 236

N-[(3aS,4R,6aR)-2-benzyloctahydrocyclopenta[c]pyrrol-4-yl]-3-methylbutanamide

The title compound was prepared by substituting 3-methylbutanoic acid for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$) δ ppm 8.30-8.17 (m, 1H), 7.43 (dd, J=11.2, 4.2, 2H), 7.37 (t, J=7.5, 2H), 7.27 (t, J=7.3, 1H), 4.49-4.39 (m, 1H), 3.60 (d, J=13.1, 1H), 3.45 (d, J=13.1, 1H), 2.89-2.78 (m, 1H), 2.55-2.49 (m, 2H), 2.45 (dd, J=10.4, 5.3, 1H), 2.36-2.24 (m, 3H), 2.21 (d, J=7.1, 2H), 2.17-2.08 (m, 1H), 1.90-1.79 (m, 1H), 1.62 (ddd, J=15.1, 12.3, 7.2, 1H), 1.40 (dtd, J=9.2, 8.2, 6.1, 1H), 0.95 (d, J=6.6, 6H); MS (ESI+) m/z 301 (M+H)$^+$.

Example 237

2-cyclohexyl-2-hydroxy-N-{(3aS,4S,6aR)-2-[3-(trifluoromethyl)benzyl]octahydrocyclopenta[c]pyrrol-4-yl}acetamide The title compound was prepared by substituting 2-cyclohexyl-2-hydroxyacetic acid for N-(tert-butoxycarbonyl)-L-leucine and (3aS,4S,6aR)-2-(3-trifluoromethyl)benzyloctahydrocyclopenta[c]pyrrol-4-amine from Step A of Example 152 for (3aR,4S,6aS)-2-benzyloctahydrocyclopenta[c]pyrrol-4-amine in the procedure described in Example 221: $^1$H NMR (500 MHz, pyridine-$d_5$) δ ppm 8.59 (d, J=7.9, 0.5H), 8.40-8.33 (m, 0.5H), 7.97 (s, 0.5H), 7.77 (dd, J=42.9, 9.6, 1.5H), 7.48-7.39 (m, 1.5H), 7.29 (d, J=5.3, 0.5H), 4.67-4.57 (m, 1H), 4.37 (t, J=3.8, 1H), 3.80 (dd, J=21.0, 13.1, 1H), 3.27 (dd, J=64.7, 13.0, 1H), 2.86 (dd, J=13.0, 4.7, 1H), 2.73-2.61 (m, 1H), 2.50-2.40 (m, 1H), 2.36 (d, J=9.1, 1H), 2.28-2.08 (m, 3H), 2.03 (dd, J=14.3, 6.2, 0.5H), 2.00-1.93 (m, 0.5H), 1.92-1.88 (m, 0.5H), 1.86-1.45 (m, 9.5H), 1.35-1.06 (m, 4H); MS (ESI+) m/z 425 (M+H)$^+$.

Example 238 tert-butyl(S)-1-((3aS,4S,6aR)-2-benzyloctahydrocyclopenta[c]pyrrol-4-ylamino)-1-oxopentan-2-yl(methyl)carbamate The title compound was prepared by substituting N-(tert-butoxycarbonyl)-N-methyl-L-norvaline for N-(tert-butoxycarbonyl)-L-leucine and (3aS,4S,6aR)-2-benzyloctahydrocyclopenta[c]pyrrol-4-amine from Step C of Example 14 for (3aR,4S,6aS)-2-benzyloctahydrocyclopenta[c]pyrrol-4-amine in the procedure described in Example 221: $^1$H NMR (501 MHz, pyridine-$d_5$, temperature 90° C.) δ ppm 7.44-7.45 (bs, 2H), 7.35-7.40 (m, 2H), 7.30-7.37 (m, 1H), 7.25-7.29 (m, 1H), 4.70-4.75 (bs, 1H), 4.37-4.43 (m, 1H), 3.56 (d, J=12.9 Hz, 1H), 3.52 (d, J=12.8 Hz, 1H), 2.95 (s, 3H), 2.71 (d, J=8.9 Hz, 1H), 2.62-2.68 (m, 1H), 2.44-2.48 (m, 2H), 2.25 (t, J=8.5 Hz, 1H), 2.14 (t, J=8.3 Hz, 1H), 1.91-1.99 (m, 1H), 1.66-1.80 (m, 3H), 1.56-1.63 (m, 1H), 1.50 (s, 9H), 1.26-1.38 (m, 3H), 0.88 (t, J=7.4 Hz, 3H); MS (ESI+) m/z 430 (M+H)$^+$.

Example 239 tert-butyl(S)-1-((3aS,4S,6aR)-2-benzyloctahydrocyclopenta[c]pyrrol-4-ylamino)-4-methyl-1-oxopentan-2-yl(methyl)carbamate The title compound was prepared by substituting N-(tert-butoxycarbonyl)-N-methyl-L-leucine for N-(tert-butoxycarbonyl)-L-leucine and (3aS,4S,6aR)-2-benzyloctahydrocyclopenta[c]pyrrol-4-amine from Step C of Example 14 for (3aR,4S,6aS)-2-benzyloctahydrocyclopenta[c]pyrrol-4-amine in the procedure described in Example 221: $^1$H NMR (501 MHz, pyridine-$d_5$, temperature 90° C.) δ ppm 7.44-7.49 (m, 2H), 7.36-7.40 (m, 2H), 7.32-7.39 (m, 1H), 7.27 (t, J=7.4 Hz, 1H), 4.82-4.89 (m, 1H), 4.37-4.43 (m, 1H), 3.63 (d, J=13.2 Hz, 1H), 3.50 (d, J=13.0 Hz, 1H), 2.94 (s, 3H), 2.73 (dd, J=9.7, 1.8 Hz, 1H), 2.64-2.70 (m, 1H), 2.44-2.47 (m, 2H), 2.22-2.28 (m, 1H), 2.15-2.19 (m, 1H), 1.88 (ddd, J=14.1, 8.2, 6.0 Hz, 1H), 1.64-1.81 (m, 3H), 1.55-1.65 (m, 2H), 1.50 (s, 9H), 1.28-1.38 (m, 1H), 0.90-0.93 (m, 6H); MS (ESI+) m/z 444 (M+H)$^+$.

Example 240 tert-butyl(S)-1-((3aR,4R,6aS)-2-benzyloctahydrocyclopenta[c]pyrrol-4-ylamino)-1-oxopentan-2-yl(methyl)carbamate Step A: (3aR,4R,6aS)-2-Benzyloctahydrocyclopenta[c]pyrrol-4-amine was prepared according to the procedure described in Example 14 Steps B-C substituting (S,E)-N-((3aR,6aS)-2-benzylhexahydrocyclopenta[c]pyrrol-4(5H)-ylidene)-2-methylpropane-2-sulfinamide from Example 14 Step A for (S,E)-N-((3aS,6aS)-2-benzylhexahydrocyclopenta[c]pyrrol-4(5H)-ylidene)-2-methylpropane-2-sulfinamide prepared in Step A of Example 14 to give (3aR,4R,6aS)-2-benzyloctahydrocyclopenta[c]pyrrol-4-amine: $^1$H NMR (500 MHz, pyridine-$d_5$) δ ppm 7.44 (d, J=7.4, 2H), 7.36 (t, J=7.5, 2H), 7.28 (t, J=7.3, 1H), 3.52 (q, J=13.0, 2H), 3.29 (q, J=7.3, 1H), 2.84 (dd, J=3.7, 9.3, 1H), 2.55-2.43 (m, 3H), 2.37-2.30 (m, 1H), 2.24 (d, J=5.3, 1H), 1.74-1.64 (m, 2H), 1.62-1.53 (m, 1H), 1.34 (dd, J=5.0, 10.1, 1H).

Step B: The title compound was prepared by substituting N-(tert-butoxycarbonyl)-N-methyl-L-norvaline for N-(tert-butoxycarbonyl)-L-leucine and (3aR,4R,6aS)-2-benzyloctahydrocyclopenta[c]pyrrol-4-amine from Step A for (3aR,4S,6aS)-2-benzyloctahydrocyclopenta[c]pyrrol-4-amine in the procedure described in Example 221: 1H NMR (400 MHz, pyridine-$d_5$) δ ppm 7.40 (d, J=7.4, 2H), 7.34 (t, J=7.5, 2H), 7.25 (t, J=7.3, 1H), 4.79-4.68 (m, 1H), 4.44-4.32 (m, 1H), 3.82 (d, J=13.2, 1H), 3.36 (d, J=13.0, 1H), 2.94 (s, 3H), 2.80-2.65 (m, 2H), 2.46 (s, 1H), 2.35 (dd, J=9.2, 2.7, 1H), 2.31-2.25 (m, 2H), 1.99 (dt, J=14.0, 7.0, 1H), 1.83-1.72 (m, 2H), 1.70-1.56 (m, 2H), 1.49 (d, J=4.5, 1H), 1.48 (s, 9H), 1.41-1.23 (m, 3H), 0.89 (t, J=7.4, 3H); MS (ESI+) m/z 430 (M+H)$^+$.

Example 241 tert-butyl(S)-1-((3aR,4R,6aS)-2-benzyloctahydrocyclopenta[c]pyrrol-4-ylamino)-4-methyl-1-oxopentan-2-ylmethyl)carbamate The title compound was prepared by substituting N-(tert-butoxycarbonyl)-N-methyl-L-leucine for N-(tert-butoxycarbonyl)-L-leucine and (3aR,4R,6aS)-2-benzyloctahydrocyclopenta[c]pyrrol-4-amine from Step A of Example 240 for (3aR,4S,6aS)-2-benzyloctahydrocyclopenta[c]pyrrol-4-amine in the procedure described in Example 221: $^1$H NMR (400 MHz, pyridine-$d_5$, temperature 90° C.) δ ppm 7.40-7.43 (m, 2H), 7.31-7.37 (m, 3H), 7.23-7.30 (m, 1H), 4.82-4.89 (m, 1H), 4.35-4.42 (m, 1H), 3.35 (d, J=12.9 Hz, 1H), 2.95 (s, 3H), 2.68-2.78 (m, 2H), 2.42-2.50 (m, 1H), 2.26-2.36 (m, 3H), 1.89 (ddd, J=14.1, 8.2, 5.9 Hz, 1H), 1.71-1.82 (m, 2H), 1.60-1.70 (m, 3H), 1.48-1.51 (m, 1H), 1.48 (s, 9H), 1.22-1.35 (m, 1H), 0.88-0.98 (m, 6H); MS (ESI+) m/z 444 (M+H)$^+$.

Example 242

N$^1$-[(3aR,4S,6aS)-2-benzyloctahydrocyclopenta[c]pyrrol-4-yl]-N$^2$-(methylsulfonyl)-L-leucinamide Step A: (S)-tert-Butyl 2-amino-4-methylpentanoate hydrochloride (1.53 g, 6.84 mmol) was dissolved in dichloromethane and triethylamine (3.15 mL, 22.57 mmol). Methanesulfonyl chloride (0.638 mL, 8.21 mmol) was added dropwise, and the reaction stirred at room temperature for 1 hour. The reaction was quenched with saturated aqueous NaHCO$_3$ and extracted with dichloromethane (3×50 mL). The solvent was removed in vacuo to give (S)-tert-butyl 4-methyl-2-(methylsulfonamido)pentanoate: $^1$H NMR (300 MHz, CDCl$_3$) δ ppm 4.71 (d, J=9.7, 1H), 3.98 (td, J=9.5, 5.5, 1H), 2.92 (s, 3H), 1.84 (dt, J=13.1, 6.6, 1H), 1.54 (s, 9H), 1.44-1.48 br s, 1H), 0.96 (dd, J=6.6, 2.4, 6H); MS (ESI−) m/z 264 (M−H)$^−$. (S)-tert-Butyl 4-methyl-2-(methylsulfonamido)pentanoate was dissolved in 10 mL of 4 N HCl in dioxane and stirred at room temperature overnight. The solvent was removed under a stream of nitrogen and under high vacuum to give (S)-4-methyl-2-(methylsulfonamido)pentanoic acid: $^1$H NMR (300 MHz, CDCl$_3$) δ ppm 4.86 (d, J=9.6, 1H), 4.17 (td, J=9.6, 4.8, 1H), 3.18-3.07 (m, 1H), 2.99 (s, 3H), 1.96-1.80 (m, 1H), 1.64 (dddd, J=23.4, 13.9, 9.1, 5.0, 2H), 1.40 (t, J=7.3, 1H), 0.98 (dd, J=6.6, 3.3, 6H).

Step B: The title compound was prepared by substituting (S)-4-methyl-2-(methylsulfonamido)pentanoic acid from Step A for N-(tert-butoxycarbonyl)-L-leucine in the procedure described in Example 221: $^1$H NMR (500 MHz, pyridine-d$_5$) δ ppm 9.41 (d, J=9.4, 1H), 9.21 (d, J=7.3, 1H), 7.45 (d, J=7.2, 2H), 7.37 (t, J=7.5, 2H), 7.29 (t, J=7.3, 1H), 4.53-4.42 (m, 2H), 3.62 (d, J=13.1, 1H), 3.47 (d, J=13.1, 1H), 3.19 (s, 3H), 2.87 (dd, J=9.1, 2.9, 1H), 2.66-2.58 (m, 1H), 2.57-2.45 (m, 2H), 2.35 (dd, J=9.0, 3.0, 1H), 2.31-2.25 (m, 1H), 2.14 (dq, J=12.0, 6.0, 1H), 1.99 (dq, J=13.2, 6.5, 1H), 1.93-1.82 (m, 1H), 1.77 (ddd, J=13.8, 8.5, 5.6, 1H), 1.63 (dt, J=19.3, 7.2, 1H), 1.46-1.35 (m, 1H), 0.82 (d, J=6.7, 3H), 0.79 (d, J=6.5, 3H); MS (ESI+) m/z 408 (M+H)$^+$.

Example 243

N$^1$-[(3aS,4R,6aR)-2-benzyloctahydrocyclopenta[c]pyrrol-4-yl]-N$^2$-(methylsulfonyl)-L-leucinamide The title compound was prepared by substituting (S)-4-methyl-2-(methylsulfonamido)pentanoic acid from Step A of Example 242 for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$) δ ppm 9.40 (d, J=9.4, 1H), 9.21 (d, J=7.2, 1H), 7.43 (d, J=7.5, 2H), 7.36 (t, J=7.6, 2H), 7.27 (t, J=7.3, 1H), 4.52-4.38 (m, 2H), 3.57 (d, J=13.1, 1H), 3.47 (d, J=13.1, 1H), 3.17 (s, 3H), 2.85 (dd, J=9.1, 2.2, 1H), 2.59-2.48 (m, 2H), 2.37 (dd, J=9.0, 6.8, 2H), 2.25 (dd, J=8.7, 7.1, 1H), 2.19 (dq, J=11.9, 5.9, 1H), 1.99 (dq, J=13.1, 6.5, 1H), 1.94-1.84 (m, 2H), 1.80-1.66 (m, 2H), 1.44 (ddd, J=18.9, 12.5, 6.2, 1H), 0.82 (d, J=6.7, 3H), 0.79 (d, J=6.5, 3H); MS (ESI+) m/z 408 (M+H)$^+$.

Example 244

N$^1$-[(3aR,4S,6aS)-2-benzyloctahydrocyclopenta[c]pyrrol-4-yl]-N$^2$-neopentyl-L-leucinamide Step A: (S)-tert-Butyl 2-amino-4-methylpentanoate hydrochloride (1.022 g, 4.57 mmol) and pivalaldehyde (0.502 mL, 4.57 mmol) were combined in dichloromethane (25 mL). Acetic acid (1.0 mL) was added. The reaction was stirred at room temperature for 5 minutes, then PS-cyanoborohydride (3.90 g, 9.14 mmol) was added. The reaction was stirred at room temperature overnight, then filtered and the solvent was removed in vacuo. The crude material was diluted with dichloromethane and basified using saturated aqueous sodium bicarbonate to give (S)-tert-butyl 4-methyl-2-(neopentylamino)pentanoate: $^1$H NMR (300 MHz, CDCl$_3$) δ ppm 3.04 (t, J=7.4, 1H), 2.40 (d, J=11.1, 1H), 2.09 (d, J=11.1, 1H), 1.86-1.70 (m, 1H), 1.46 (s, 10H), 1.40 (t, J=7.2, 3H), 0.95-0.89 (m, 6H), 0.89 (s, 9H). (S)-tert-butyl 4-methyl-2-(neopentylamino)pentanoate was dissolved in 10 mL of 4 N HCl in dioxane and stirred at room temperature overnight. The solvent was removed under a stream of nitrogen and under high vacuum to give (S)-4-methyl-2-(neopentylamino)pentanoic acid: $^1$H NMR (300 MHz, DMSO-d$_6$) δ ppm 8.89-8.37 (m, 1H), 8.34-8.03 (m, 1H), 3.82 (t, J=6.5, 1H), 2.88 (d, J=12.3, 1H), 2.62 (d, J=12.2, 1H), 1.83-1.67 (m, 2H), 1.67-1.56 (m, 1H), 1.00 (s, 9H), 0.97-0.88 (m, 6H).

Step B: The title compound was prepared by substituting (S)-4-methyl-2-(neopentylamino)pentanoic acid from Step A for N-(tert-butoxycarbonyl)-L-leucine in the procedure described in Example 221: $^1$H NMR (500 MHz, pyridine-d$_5$) δ ppm 8.06-8.08 (m, 1H), 7.43-7.46 (m, 2H), 7.37 (t, J=7.5 Hz, 2H), 7.28 (t, J=7.3 Hz, 1H), 4.39-4.46 (m, 1H), 3.61 (d, J=13.1 Hz, 1H), 3.46 (d, J=13.1 Hz, 1H), 3.27 (dd, J=8.5, 5.6 Hz, 1H), 2.84 (dd, J=8.7, 2.5 Hz, 1H), 2.49-2.61 (m, 2H), 2.43-2.49 (m, 2H), 2.36 (dd, J=9.1, 2.9 Hz, 1H), 2.32-2.36 (m, 1H), 2.30 (dd, J=8.8, 7.0 Hz, 1H), 2.15 (dq, J=12.1, 6.1 Hz, 1H), 1.80-1.96 (m, 2H), 1.55-1.76 (m, 4H), 1.39-1.46 (m, 1H), 0.94 (s, 9H), 0.93 (d, J=6.8 Hz, 3H), 0.87 (d, J=6.5 Hz, 3H); MS (ESI+) m/z 400 (M+H)$^+$.

Example 245

N$^1$-[(3aS,4R,6aR)-2-benzyloctahydrocyclopenta[c]pyrrol-4-yl]-N$^2$-neopentyl-L-leucinamide The title compound was prepared by substituting (S)-4-methyl-2-(neopentylamino)pentanoic acid from Step A of Example 244 for N-(tert-butoxycarbonyl)-L-leucine and (3aS,4R,6aR)-2-benzyloctahydrocyclopenta[c]pyrrol-4-amine of Step E from Example 16 for (3aR,4S,6aS)-2-benzyloctahydrocyclopenta[c]pyrrol-4-amine in the procedure described in Example 221: $^1$H NMR (500 MHz, pyridine-d$_5$) δ ppm 8.07-8.09 (m, 1H), 7.43-7.45 (m, 2H), 7.37 (t, J=7.5 Hz, 2H), 7.28 (t, J=7.3 Hz, 1H), 4.43 (p, J=6.2 Hz, 1H), 3.60 (d, J=13.1 Hz, 1H), 3.45 (d, J=13.1 Hz, 1H), 3.26 (dd, J=8.6, 5.6 Hz, 1H), 2.86 (dd, J=8.9, 2.6 Hz, 1H), 2.47-2.60 (m, 2H), 2.42-2.47 (m, 2H), 2.36 (dd, J=9.1, 3.0 Hz, 1H), 2.29-2.35 (m, 1H), 2.29 (dd, J=8.7, 7.3 Hz, 1H), 2.14 (dq, J=12.1, 6.0 Hz, 1H), 1.81-1.95 (m, 2H), 1.52-1.76 (m, 4H), 1.44 (dq, J=13.2, 6.6 Hz, 1H), 0.94 (s, 9H), 0.93 (d, J=6.6 Hz, 3H), 0.87 (d, J=6.5 Hz, 3H); MS (ESI+) m/z 400 (M+H)$^+$.

Example 246

N$^1$-[(3aS,4R,6aR)-2-benzyloctahydrocyclopenta[c]pyrrol-4-yl]-N$^2$-neopentyl-L-norvalinamide Step A: (S)-2-(Neopentylamino)pentanoic acid hydrochloride was prepared by substituting (S)-tert-butyl 2-amino pentanoate for (S)-tert-butyl 2-amino-4-methylpentanoate in the procedure described in Step A of Example 244: $^1$H NMR (300 MHz, DMSO-d$_6$) δ ppm 8.49 (ddd, J=34.9, 23.2, 14.1, 2H), 3.84 (dd, J=8.0, 5.2, 1H), 2.86 (d, J=12.3, 1H), 2.66 (d, J=12.3, 1H), 1.99-1.73 (m, 2H), 1.58-1.42 (m, 1H), 1.41-1.26 (m, 1H), 1.00 (s, 9H), 0.92 (t, J=7.3, 3H); MS (ESI+) m/z 188 (M+H)$^+$.

Step B: The title compound was prepared by substituting (S)-2-(neopentylamino)pentanoic acid from Step A for N-(tert-butoxycarbonyl)-L-leucine and (3aR,4S,6aS)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: $^1$H NMR (500 MHz, pyridine-d$_5$) δ ppm 8.00-8.03 (m, 1H), 7.43-7.45 (m, 2H), 7.37 (t, J=7.5 Hz, 2H), 7.28 (t, J=7.3

Hz, 1H), 4.40-4.45 (m, 1H), 3.60 (d, J=13.1 Hz, 1H), 3.45 (d, J=13.1 Hz, 1H), 3.20 (t, J=6.5 Hz, 1H), 2.85 (dd, J=8.8, 2.6 Hz, 1H), 2.52-2.60 (m, 1H), 2.46-2.52 (m, 1H), 2.38-2.46 (m, 2H), 2.31-2.38 (m, 2H), 2.28 (dd, J=8.8, 7.3 Hz, 1H), 2.13 (dq, J=12.1, 6.0 Hz, 1H), 1.79-1.92 (m, 2H), 1.71-1.80 (m, 1H), 1.65-1.73 (m, 1H), 1.57-1.65 (m, 1H), 1.39-1.57 (m, 3H), 0.93 (s, 9H), 0.86 (t, J=7.3 Hz, 3H); MS (ESI−) m/z 384 (M−H)⁻.

Example 247 tert-butyl(S)-1-((3aR,4S,6aS)-2-benzyloctahydrocyclopenta[c]pyrrol-4-ylamino)-4,4-dimethyl-1-oxopentan-2-yl(methyl)carbamate Step A: (S)-2-(tert-Butoxycarbonylamino)-4,4-dimethylpentanoic acid (50 mg, 0.204 mmol) and iodomethane (0.102 mL, 1.631 mmol) were dissolved in tetrahydrofuran (2 mL) at 0° C. and sodium hydride (24.46 mg, 0.611 mmol) was added. The reaction was stirred at 0° C. for a half hour and at room temperature overnight. The reaction was cooled to 0° C. and ethyl acetate (1 mL) was added followed by dropwise quenching with water (2 mL). The solvent was removed in vacuo and the crude material was partitioned between ether and water. The ether layer was separated. The aqueous layer was acidified to pH~5 using 1 N citric acid and extracted with ethyl acetate. The organic layer was washed with 1 N sodium thiosulfate and brine, dried (Na₂SO₄) and concentrated in vacuo. The compound was purified using a 4 g silica gel cartridge with a gradient of 0-3% methanol/dichloromethane over 20 minutes to give (S)-2-(tert-butoxycarbonyl(methyl)amino)-4,4-dimethylpentanoic acid: ¹H NMR (300 MHz, DMSO-d₆) δ ppm 12.63 (s, 1H), 4.57 (ddd, J=74.4, 9.5, 3.1, 1H), 2.69 (s, 3H), 1.83-1.53 (m, 2H), 1.39 (s, 9H), 0.89 (s, 9H); MS (DSI+) m/z 260 (M+H)⁺.

Step B: The title compound was prepared by substituting (S)-2-(tert-butoxycarbonyl(methyl)amino)-4,4-dimethylpentanoic acid from Step A for N-(tert-butoxycarbonyl)-L-leucine in the procedure described in Example 221: ¹H NMR (400 MHz, pyridine-d₅, temperature 90° C.) δ ppm 7.35-7.38 (m, 2H), 7.29 (t, J=7.5 Hz, 2H), 7.20 (t, J=7.3 Hz, 1H), 6.98-7.02 (m, 1H), 4.85-4.90 (m, 1H), 4.20-4.26 (m, 1H), 3.56 (d, J=13.2 Hz, 1H), 3.48 (d, J=13.2 Hz, 1H), 2.92 (s, 3H), 2.79 (d, J=6.5 Hz, 1H), 2.51-2.55 (m, 1H), 2.39-2.47 (m, 2H), 2.37 (dd, J=9.0, 3.1 Hz, 1H), 2.32 (dd, J=8.9, 7.2 Hz, 1H), 2.19 (dd, J=14.3, 5.6 Hz, 1H), 2.00-2.08 (m, 1H), 1.77-1.86 (m, 1H), 1.62 (dd, J=14.3, 6.9 Hz, 1H), 1.50-1.56 (m, 1H), 1.48 (s, 9H), 1.35-1.47 (m, 1H), 0.95 (s, 9H); MS (DSI+) m/z 458 (M+H)⁺.

Example 248 tert-butyl(S)-1-((3aS,4R,6aR)-2-benzyloctahydrocyclopenta[c]pyrrol-4-ylamino)-4,4-dimethyl-1-oxopentan-2-yl(methyl)carbamate The title compound was prepared by substituting (S)-2-(tert-butoxycarbonyl(methyl)amino)-4,4-dimethylpentanoic acid from Step A of Example 247 for N-(tert-butoxycarbonyl)-L-leucine and (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in the procedure described in Example 221: ¹H NMR (500 MHz, pyridine-d₅) δ ppm 7.41-7.43 (m, 2H), 7.36 (t, J=7.5 Hz, 2H), 7.25-7.29 (m, 1H), 5.14 (m, 0.7H), 4.79 (m, 0.2H), 4.35 (dd, J=5.6, 2.9 Hz, 1H), 3.56-3.60 (m, 1H), 3.40-3.44 (m, 1H), 3.02-3.09 (m, 3H), 2.76-2.84 (m, 1H), 2.42-2.51 (m, 2H), 2.31-2.40 (m, 2H), 2.17-2.24 (m, 2H), 2.06-2.15 (m, 1H), 1.79-1.83 (m, 1H), 1.62-1.70 (m, 1H), 1.51-1.63 (m, 2H), 1.47 (s, 9H), 1.32-1.42 (m, 1H), 0.94 (s, 9H); MS (ESI+) m/z 458 (M+H)⁺.

Example 249

(2S)-N-[(3aS,4R,6aR)-2-benzyloctahydrocyclopenta[c]pyrrol-4-yl]-4-methyl-2-morpholin-4-ylpentanamide Step A: (S)-tert-Butyl 2-amino-4-methylpentanoate (1.0042 g, 5.36 mmol), potassium carbonate (2.446 g, 17.69 mmol), and 1-bromo-2-(2-bromoethoxy)ethane (1.368 g, 5.90 mmol) were combined in acetonitrile (30 mL). The reaction was heated at 80° C. overnight. The reaction was cooled and filtered and the solvent removed in vacuo. The crude material was purified by silica gel chromatography using 5-50% ethyl acetate/hexanes to give (S)-tert-butyl 4-methyl-2-morpholinopentanoate: ¹H NMR (300 MHz, CDCl₃) δ ppm 3.76-3.58 (m, 4H), 3.11 (dd, J=6.9, 8.1, 1H), 2.74-2.53 (m, 4H), 1.71-1.55 (m, 2H), 1.51-1.34 (m, 10H), 0.92 (dd, J=6.6, 7.3, 6H). (S)-tert-Butyl 4-methyl-2-morpholinopentanoate (0.637 g, 2.475 mmol) and 4 N hydrochloric acid in dioxane (5 mL) were combined. The reaction mixture was stirred at ambient temperature for 24 hours, then the solvent removed in vacuo to give (S)-4-methyl-2-morpholinopentanoic acid hydrochloride: MS (DCI+) m/z 202 (M+H)⁺.

Step B: (S)-4-Methyl-2-morpholinopentanoic acid hydrochloride (363 mg, 1.526 mmol) and triethylamine (0.387 mL, 2.77 mmol) were combined in dichloromethane (10 mL). 1-Hydroxybenzotriazole hydrate (234 mg, 1.526 mmol) and N¹-((ethylimino)methylene)-N³,N³-dimethylpropane-1,3-diamine (0.270 mL, 1.526 mmol) were added, and the reaction was stirred for 15 minutes. Then (3aS,4R,6aR)-2-benzyloctahydrocyclopenta[c]pyrrol-4-amine (300 mg, 1.387 mmol) from Example 16 Step E was added, and the reaction mixture was stirred at ambient temperature for 24 hours. The reaction was quenched with aqueous sodium bicarbonate and extracted with dichloromethane. The solvent was removed in vacuo and the crude material was purified by silica gel chromatography using 1-10% methanol (2 N ammonia)/dichloromethane to give the title compound: ¹H NMR (500 MHz, pyridine-d₅) δ ppm 8.27 (d, J=7.3, 1H), 7.44 (d, J=7.4, 2H), 7.37 (t, J=7.5, 2H), 7.27 (dd, J=9.8, 17.3, 1H), 4.51-4.39 (m, 1H), 3.74 (t, J=4.5, 4H), 3.62 (d, J=13.1, 1H), 3.45 (d, J=13.1, 1H), 3.29-3.21 (m, 1H), 2.87 (dd, J=2.4, 9.0, 1H), 2.79 (dt, J=4.5, 9.3, 2H), 2.75-2.68 (m, 2H), 2.55 (d, J=14.8, 2H), 2.49-2.43 (m, 1H), 2.35 (dd, J=2.6, 8.9, 1H), 2.32-2.26 (m, 1H), 2.11 (dq, J=6.1, 12.1, 1H), 1.86 (dd, J=6.6, 12.2, 3H), 1.67-1.55 (m, 2H), 1.41 (dt, J=6.2, 20.1, 1H), 0.94 (dd, J=6.2, 11.1, 6H); MS (ESI+) m/z 400 (M+H)⁺.

Example 250

(2S)-N-[(3aS,4R,6aR)-2-benzyloctahydrocyclopenta[c]pyrrol-4-yl]-4-methyl-2-pyrrolidin-1-ylpentanamide The title compound was prepared by substituting 1,4-dibromobutane for 1-bromo-2-(2-bromoethoxy)ethane in Step A of Example 249: ¹H NMR (500 MHz, pyridine-d₅) δ ppm 7.98-7.93 (m, 1H), 7.47-7.41 (m, 2H), 7.36 (t, J=7.4, 2H), 7.31-7.24 (m, 1H), 4.45 (t, J=5.2, 1H), 3.61 (d, J=13.1, 1H), 3.45 (d, J=13.1, 1H), 3.16 (dd, J=5.1, 9.3, 1H), 2.87 (d, J=7.9, 1H), 2.73-2.65 (m, 2H), 2.66-2.52 (m, 4H), 2.44 (dd, J=6.2, 8.9, 1H), 2.36 (dd, J=2.1, 9.0, 1H), 2.30-2.23 (m, 1H), 2.12 (dq, J=6.0, 11.9, 1H), 1.95-1.78 (m, 3H), 1.66-1.54 (m, 6H), 1.47-1.36 (m, 1H), 1.00 (d, J=6.4, 3H), 0.91 (d, J=6.4, 3H); MS (ESI+) m/z 384 (M+H)$^+$.

Example 251

(2S)-N-[(3aS,4R,6aR)-2-benzyloctahydrocyclopenta[c]pyrrol-4-yl]-4-methyl-2-piperidin-1-ylpentanamide The title compound was prepared by substituting 1,5-dibromopentane for 1-bromo-2-(2-bromoethoxy)ethane in Step A of Example 249: $^1$H NMR (500 MHz, pyridine-d$_5$) δ ppm 8.09 (d, J=7.5, 1H), 7.44 (d, J=7.3, 2H), 7.36 (d, J=7.7, 2H), 7.28 (t, J=7.3, 1H), 4.46-4.36 (m, 1H), 3.61 (d, J=13.1, 1H), 3.45 (d, J=13.1, 1H), 3.21 (dd, J=8.1, 5.4, 1H), 2.85 (d, J=8.8, 1H), 2.70-2.50 (m, 6H), 2.49-2.44 (m, 1H), 2.32 (dt, J=27.0, 7.9, 2H), 2.11 (dq, J=12.1, 6.1, 1H), 1.95-1.79 (m, 3H), 1.63-1.47 (m, 6H), 1.45-1.32 (m, 3H), 0.94 (d, J=5.8, 6H); MS (ESI+) m/z 398 (M+H)$^+$.

Example 252

N$^2$-neopentyl-N$^1$-((3aR,4S,6aS)-2-{[3-(trifluoromethyl)phenyl]sulfonyl}octahydrocyclopenta[c]pyrrol-4-yl)-L-leucinamide Step A: (3aR,4S,6aS)-2-Benzyloctahydrocyclopenta[c]pyrrol-4-amine (0.83 g, 3.84 mmol) from Step A of Example 33 was dissolved in anhydrous dichloromethane (5 mL) under nitrogen and triethylamine (0.588 mL, 4.22 mmol) was added followed by di-tert-butyl dicarbonate (1.010 mL, 4.22 mmol). The reaction was stirred at 25° C. for 1 hour. Thin-layer chromatography (SiO$_2$, 5% methanol/dichloromethane) showed complete reaction. The volatiles were removed in vacuo, and the crude material was purified using a 24 g silica gel cartridge eluting with a gradient of 1-5% methanol (2 N ammonia)/dichloromethane over 20 minutes to give tert-butyl(3aR,4S,6aS)-2-benzyloctahydrocyclopenta[c]pyrrol-4-ylcarbamate: $^1$H NMR (500 MHz, pyridine-d$_5$) δ ppm 7.54 (d, J=6.3, 1H), 7.43 (d, J=7.3, 2H), 7.36 (t, J=7.4, 2H), 7.27 (t, J=7.2, 1H), 4.12 (q, J=12.1, 1H), 3.59 (d, J=12.9, 1H), 3.43 (d, J=13.0, 1H), 2.78 (s, 1H), 2.59-2.49 (m, 2H), 2.49-2.41 (m, 1H), 2.37-2.25 (m, 2H), 2.16-2.05 (m, 1H), 1.88 (td, J=13.1, 6.1, 1H), 1.65 (td, J=14.8, 7.3, 1H), 1.52 (s, 9H), 1.43-1.35 (m, 1H); MS (ESI+) m/z 317 (M+H)$^+$.

Step B: tert-Butyl(3aR,4S,6aS)-2-benzyloctahydrocyclopenta[c]pyrrol-4-ylcarbamate (1.06 g, 3.35 mmol) from Step A and ethanol (20 mL) were added to 20% Pd(OH)$_2$ on carbon, wet (212.0 mg, 1.51 mmol) in a 250 mL stainless steel pressure bottle. The reaction mixture was stirred for 16 hours under 30 psi hydrogen at room temperature. The mixture was filtered through a nylon membrane and the solvent was removed in vacuo to give tert-butyl(3aR,4S,6aS)-octahydrocyclopenta[c]pyrrol-4-ylcarbamate: $^1$H NMR (500 MHz, pyridine-d$_5$) δ ppm 4.02-3.99 (m, 1H), 3.03 (d, J=10.4, 1H), 2.98-2.89 (m, 1H), 2.84 (dd, J=10.1, 6.4, 1H), 2.61-2.50 (m, 3H), 2.06-1.98 (m, 1H), 1.91 (td, J=12.9, 6.7, 1H), 1.63 (dt, J=19.5, 7.6, 1H), 1.53 (s, 9H), 1.29-1.23 (m, 1H); MS (ESI+) m/z 227 (M+H)$^+$.

Step C: tert-Butyl(3aR,4S,6aS)-octahydrocyclopenta[c]pyrrol-4-ylcarbamate (0.71 g, 3.14 mmol) from Step B, triethylamine (0.656 mL, 4.71 mmol), and 3-(trifluoromethyl)benzene-1-sulfonyl chloride (0.552 mL, 3.45 mmol) were combined in dichloromethane (10.0 mL). The reaction was stirred at room temperature for 16 hours and quenched with saturated aqueous NaHCO$_3$. The organic layer was separated and concentrated in vacuo. The resultant crude material was applied to a SF-25-60 g cartridge (Analogix®, Burlington, Wis.) and purified with a gradient of 0-2% methanol/dichloromethane over 20 minutes to give tert-butyl(3aR,4S,6aS)-2-(3-(trifluoromethyl)phenylsulfonyl)octahydrocyclopenta[c]pyrrol-4-ylcarbamate: $^1$H NMR (500 MHz, pyridine-d$_5$) δ ppm 8.30 (s, 1H), 8.14 (d, J=7.8, 1H), 7.84 (d, J=7.8, 1H), 7.65 (t, J=7.8, 1H), 6.83-6.71 (m, 1H), 3.88-3.76 (m, 1H), 3.61 (dd, J=10.1, 3.3, 1H), 3.24 (dd, J=9.8, 8.1, 1H), 3.12 (d, J=5.6, 2H), 2.64-2.44 (m, 2H), 1.99-1.78 (m, 2H), 1.55 (tt, J=12.4, 7.7, 1H), 1.48 (s, 9H), 1.38-1.20 (m, 1H); MS (ESI−) m/z 433 (M−H)$^−$.

Step D: tert-Butyl(3aR,4S,6aS)-2-(3-(trifluoromethyl)phenylsulfonyl)octahydrocyclopenta[c]pyrrol-4-ylcarbamate (0.814 g, 1.874 mmol) from Step C and HCl (26.2 mL, 52.5 mmol, 2 M in ether) in ethanol (3 mL) were combined. The reaction was stirred at room temperature overnight and then the volatiles were removed. The compound was purified using a 24 g silica gel cartridge with a gradient of 1-10% methanol (2 N ammonia)/dichloromethane over 20 minutes to give (3aR,4S,6aS)-2-(3-(trifluoromethyl)phenylsulfonyl)octahydrocyclopenta[c]pyrrol-4-amine: $^1$H NMR (500 MHz, pyridine-d$_5$) δ ppm 8.37 (s, 1H), 8.21 (d, J=7.9, 1H), 7.93 (d, J=7.9, 1H), 7.75 (t, J=7.9, 1H), 3.41 (dd, J=9.8, 2.8, 1H), 3.13 (dd, J=9.7, 3.1, 1H), 3.03-2.98 (m, 1H), 2.97-2.89 (m, 2H), 2.56-2.45 (m, 1H), 2.14 (tdd, J=8.7, 5.9, 2.9, 1H), 1.5-2.0 (m, 2H) 1.95-1.85 (m, 1H), 1.79-1.69 (m, 1H), 1.32-1.15 (m, 2H); MS (ESI+) m/z 335 (M+H)$^+$.

Step E: The title compound was prepared by substituting (S)-4-methyl-2-(neopentylamino)pentanoic acid from Step A of Example 244 for N-(tert-butoxycarbonyl)-L-leucine and (3aR,4S,6aS)-2-(3-(trifluoromethyl)phenylsulfonyl)octahydrocyclopenta[c]pyrrol-4-amine from Step D for (3aR,4S,6aS)-2-benzyloctahydrocyclopenta[c]pyrrol-4-amine in the procedure described in Example 221: $^1$H NMR (400 MHz, pyridine-d$_5$) δ ppm 8.38 (s, 1H), 8.19-8.22 (m, 2H), 7.90-7.93 (m, 1H), 7.72 (t, J=7.8 Hz, 1H), 4.21-4.29 (m, 1H), 3.87 (dd, J=9.9, 2.6 Hz, 1H), 3.25 (dd, J=8.6, 5.6 Hz, 1H), 3.15-3.21 (m, 2H), 2.97 (dd, J=9.6, 7.0 Hz, 1H), 2.43-2.60 (m, 3H), 2.28-2.32 (m, 1H), 1.79-2.01 (m, 3H), 1.67-1.78 (m, 1H), 1.69 (ddd, J=13.6, 7.9, 5.7 Hz, 1H), 1.51-1.60 (m, 2H), 1.32 (ddt, J=9.3, 12.8, 6.4 Hz, 1H), 0.93 (d, J=6.6 Hz, 3H), 0.93 (s, 9H), 0.86 (d, J=6.5 Hz, 3H); MS (ESI+) m/z 518 (M+H)$^+$.

Example 253

N$^2$-neopentyl-N$^1$-((3aR,4S,6aS)-2-{[3-(trifluoromethyl)phenyl]sulfonyl}octahydrocyclopenta[c]pyrrol-4-yl)-L-norvalinamide The title compound was prepared by substituting (S)-2-(Neopentylamino)pentanoic acid from Step A of Example 246 for N-(tert-butoxycarbonyl)-L-leucine and (3aR,4S,6aS)-2-(3-(trifluoromethyl)phenylsulfonyl)octahydrocyclopenta[c]pyrrol-4-amine from Step D of Example 252 for (3aR,4S,6aS)-2-benzyloctahydrocyclopenta[c]pyrrol-4-amine in the procedure described in Example 221: $^1$H NMR (500 MHz, pyridine-d$_5$) δ ppm 8.38-8.39 (bs, 1H), 8.19-8.21 (m, 1H), 8.13-8.16 (m, 1H), 7.90-7.93 (m, 1H), 7.72 (t, J=7.8 Hz, 1H), 4.21-4.28 (m, 1H), 3.87 (dd, J=9.9, 2.8 Hz, 1H), 3.15-3.21 (m, 3H), 2.97 (dd, J=9.6, 7.3 Hz, 1H), 2.45-2.59 (m, 2H), 2.40 (d, J=11.2 Hz, 1H), 2.31 (d, J=11.2 Hz, 1H), 1.93-2.00 (m, 1H), 1.76-1.89 (m, 2H), 1.61-1.93 (m, 1H), 1.61-

1.70 (m, 1H), 1.41-1.58 (m, 3H), 1.31 (ddt, J=9.4, 13.0, 6.5 Hz, 1H), 0.92 (s, 9H), 0.86 (t, J=7.3 Hz, 3H); MS (ESI+) m/z 504 (M+H)$^+$.

Example 254

$N^2$-neopentyl-$N^1$-((3aS,4R,6aR)-2-{[3-(trifluoromethyl)phenyl]sulfonyl}octahydrocyclopenta[c]pyrrol-4-yl)-L-leucinamide Step A: (3aS,4R,6aR)-2-(3-(Trifluoromethyl)phenylsulfonyl)octahydrocyclopenta[c]pyrrol-4-amine was prepared by substituting (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in Step A of Example 252 and following steps B-D in Example 252: $^1$H NMR (500 MHz, pyridine-$d_5$) δ ppm 8.37 (s, 1H), 8.20 (d, J=7.9, 1H), 7.93 (d, J=7.8, 1H), 7.74 (t, J=7.8, 1H), 3.40 (dd, J=9.8, 2.8, 1H), 3.13 (dd, J=9.7, 3.1, 1H), 3.00 (dd, J=12.9, 5.7, 1H), 2.93 (ddd, J=12.0, 9.7, 7.9, 2H), 2.52 (qd, J=8.6, 4.3, 1H), 2.17-2.09 (m, 1H), 1.94-1.84 (m, 1H), 1.78-1.69 (m, 1H), 1.67-1.33 (m, 2H), 1.30-1.15 (m, 2H); MS (ESI+) m/z 335 (M+H)$^+$.

Step B: The title compound was prepared by substituting (S)-4-methyl-2-(neopentylamino)pentanoic acid from Step A of Example 244 for N-(tert-butoxycarbonyl)-L-leucine and (3aS,4R,6aR)-2-(3-(trifluoromethyl)phenylsulfonyl)octahydrocyclopenta[c]pyrrol-4-amine from Step A for (3aR,4S,6aS)-2-benzyloctahydrocyclopenta[c]pyrrol-4-amine in the procedure described in Example 221: $^1$H NMR (500 MHz, pyridine-$d_5$) δ ppm 8.37-8.38 (bs, 1H), 8.15-8.19 (m, 2H), 7.90-7.92 (m, 1H), 7.71 (t, J=7.8 Hz, 1H), 4.22-4.28 (m, 1H), 3.88 (dd, J=9.9, 2.8 Hz, 1H), 3.23 (dd, J=8.5, 5.7 Hz, 1H), 3.19 (dd, J=9.7, 2.8 Hz, 1H), 3.15 (dd, J=9.9, 7.6 Hz, 1H), 2.96 (dd, J=9.6, 7.2 Hz, 1H), 2.50-2.59 (m, 2H), 2.41-2.44 (m, 1H), 2.32 (d, J=11.2 Hz, 1H), 1.92-2.01 (m, 1H), 1.82-1.92 (m, 2H), 1.60-1.78 (m, 1H), 1.69 (ddd, J=13.5, 7.8, 5.7 Hz, 1H), 1.50-1.59 (m, 2H), 1.32 (ddt, J=9.4, 13.0, 6.5 Hz, 1H), 0.92 (s, 9H), 0.92 (d, J=6.6 Hz, 3H), 0.86 (d, J=6.5 Hz, 3H); MS (ESI+) m/z 518 (M+H)$^+$.

Example 255

$N^2$-neopentyl-$N^1$-((3aS,4R,6aR)-2-{[3-(trifluoromethyl)phenyl]sulfonyl}octahydrocyclopenta[c]pyrrol-4-yl)-L-norvalinamide The title compound was prepared by substituting (S)-2-(neopentylamino)pentanoic acid from Step A of Example 246 for N-(tert-butoxycarbonyl)-L-leucine and (3aS,4R,6aR)-2-(3-(trifluoromethyl)phenylsulfonyl)octahydrocyclopenta[c]pyrrol-4-amine from Step A of Example 254 for (3aR,4S,6aS)-2-benzyloctahydrocyclopenta[c]pyrrol-4-amine in the procedure described in Example 221: $^1$H NMR (500 MHz, pyridine-$d_5$) δ ppm 8.37-8.38 (bs, 1H), 8.18 (d, J=7.9 Hz, 1H), 8.09-8.11 (m, 1H), 7.90-7.92 (m, 1H), 7.71 (t, J=7.8 Hz, 1H), 4.20-4.27 (m, 1H), 3.88 (dd, J=9.9, 2.8 Hz, 1H), 3.20 (dd, J=6.6, 3.1 Hz, 1H), 3.16-3.20 (m, 3H), 3.14 (dd, J=9.9, 7.8 Hz, 1H), 2.96 (dd, J=9.6, 7.3 Hz, 1H), 2.46-2.61 (m, 2H), 2.38 (d, J=11.3 Hz, 1H), 2.33 (d, J=11.3 Hz, 1H), 1.92-1.99 (m, 1H), 1.83-1.90 (m, 1H), 1.76-1.83 (m, 1H), 1.66-1.87 (m, 1H), 1.61-1.70 (m, 1H), 1.38-1.58 (m, 3H), 1.26-1.37 (m, 1H), 0.92 (s, 9H), 0.85 (t, J=7.3 Hz, 3H); MS (ESI+) m/z 504 (M+H)$^+$.

Example 256

$N^2$-neopentyl-$N^1$-((3aR,4S,6aS)-2-{[4-(trifluoromethyl)phenyl]sulfonyl}octahydrocyclopenta[c]pyrrol-4-yl)-L-leucinamide Step A: (3aR,4S,6aS)-2-(4-(Trifluoromethyl)phenylsulfonyl)octahydrocyclopenta[c]pyrrol-4-amine was prepared by substituting 4-(trifluoromethyl)benzene-1-sulfonyl chloride for 3-(trifluoromethyl)benzene-1-sulfonyl chloride in Step C of Example 252 and following the procedure of Step D in Example 252: $^1$H NMR (500 MHz, pyridine-$d_5$) δ ppm 8.15 (d, J=8.2, 2H), 7.92 (d, J=8.3, 2H), 3.40 (dd, J=9.8, 2.9, 1H), 3.13 (dd, J=9.7, 3.2, 1H), 3.06-2.93 (m, 3H), 2.54 (s, 1H), 2.21-2.12 (m, 1H), 1.93-1.85 (m, 1H), 1.78-1.69 (m, 1H), 1.67-1.33 (m, 2H), 1.33-1.15 (m, 2H); MS (ESI+) m/z 335 (M+H)$^+$.

Step B: The title compound was prepared by substituting (S)-4-methyl-2-(neopentylamino)pentanoic acid from Step A of Example 244 for N-(tert-butoxycarbonyl)-L-leucine and (3aR,4S,6aS)-2-(4-(trifluoromethyl)phenylsulfonyl)octahydrocyclopenta[c]pyrrol-4-amine from Step A for (3aR,4S,6aS)-2-benzyloctahydrocyclopenta[c]pyrrol-4-amine in the procedure described in Example 221: $^1$H NMR (400 MHz, pyridine-$d_5$) δ ppm 8.20-8.23 (m, 1H), 8.13-8.16 (m, 2H), 7.89-7.92 (m, 2H), 4.21-4.29 (m, 1H), 3.86 (dd, J=9.9, 2.8 Hz, 1H), 3.22-3.28 (m, 1H), 3.15-3.22 (m, 2H), 2.99 (dd, J=9.6, 7.0 Hz, 1H), 2.50-2.62 (m, 2H), 2.43-2.47 (m, 1H), 2.28-2.32 (m, 1H), 1.92-2.02 (m, 1H), 1.80-1.92 (m, 2H), 1.64-1.76 (m, 1H), 1.69 (ddd, J=13.5, 7.7, 5.8 Hz, 1H), 1.50-1.61 (m, 2H), 1.25-1.40 (m, 1H), 0.93 (d, J=6.8 Hz, 3H), 0.93 (s, 9H), 0.86 (d, J=6.5 Hz, 3H); MS (ESI+) m/z 518 (M+H)$^+$.

Example 257

$N^2$-neopentyl-$N^1$-((3aR,4S,6aS)-2-{[4-(trifluoromethyl)phenyl]sulfonyl}octahydrocyclopenta[c]pyrrol-4-yl)-L-norvalinamide The title compound was prepared by substituting (S)-2-(neopentylamino)pentanoic acid from Step A of Example 246 for N-(tert-butoxycarbonyl)-L-leucine and (3aR,4S,6aS)-2-(4-(trifluoromethyl)phenylsulfonyl)octahydrocyclopenta[c]pyrrol-4-amine from Step A of Example 256 for (3aR,4S,6aS)-2-benzyloctahydrocyclopenta[c]pyrrol-4-amine in the procedure described in Example 221: $^1$H NMR (500 MHz, pyridine-$d_5$) δ ppm 8.37-8.38 (bs, 1H), 8.13-8.18 (m, 3H), 7.89-7.91 (m, 2H), 4.21-4.28 (m, 1H), 3.86 (dd, J=9.9, 2.9 Hz, 1H), 3.16-3.22 (m, 3H), 2.98 (dd, J=9.6, 7.3 Hz, 1H), 2.47-2.61 (m, 2H), 2.41 (d, J=11.2 Hz, 1H), 2.32 (d, J=11.2 Hz, 1H), 1.93-2.00 (m, 1H), 1.78-1.88 (m, 2H), 1.63-1.70 (m, 1H), 1.41-1.58 (m, 3H), 1.28-1.36 (m, 1H), 0.93 (s, 9H), 0.86 (t, J=7.3 Hz, 3H); MS (ESI+) m/z 504 (M+H)$^+$.

Example 258

N-(tert-butoxycarbonyl)-N-methyl-N-((3aR,4S,6aS)-2-{[4-(trifluoromethyl)phenyl]sulfonyl}octahydrocyclopenta[c]pyrrol-4-yl)-L-phenylalaninamide The title compound was prepared by substituting N-(tert-butoxycarbonyl)-N-methyl-L-phenylalanine for N-(tert-butoxycarbonyl)-L-leucine and (3aR,4S,6aS)-2-(4-(trifluoromethyl)phenylsulfonyl)octahydrocyclopenta[c]pyrrol-4-amine from Step A of Example 256 for (3aR,4S,6aS)-2-benzyloctahydrocyclopenta[c]pyrrol-4-amine in the procedure described in Example 221: ¹H NMR (400 MHz, pyridine-d₅, temperature 90° C.) δ ppm 8.09-8.12 (m, 2H), 7.83-7.86 (m, 2H), 7.52-7.59 (bs, 1H), 7.28-7.32 (m, 2H), 7.23-7.28 (m, 2H), 7.15-7.21 (m, 1H), 4.95-5.12 (m, 1H), 4.09 (p, J=6.9 Hz, 1H), 3.62 (dd, J=10.4, 3.4 Hz, 1H), 3.48 (dd, J=14.0, 7.0 Hz, 1H), 3.26 (dd, J=10.1, 7.9 Hz, 1H), 3.10-3.18 (m, 1H), 3.04-3.13 (m, 1H), 2.97 (s, 3H), 2.46-2.57 (m, 1H), 2.36-2.46 (m, 1H), 1.86-1.96 (m, 1H), 1.74-1.83 (m, 1H), 1.44-1.55 (m, 1H), 1.42-1.46 (m, 1H), 1.38 (s, 9H), 1.21-1.32 (m, 1H); MS (ESI+) m/z 596 (M+H)⁺.

Example 259 tert-butyl methyl((S)-1-oxo-1-((3aR,4S,6aS)-2-(4-(trifluoromethyl)phenylsulfonyl)octahydrocyclopenta[c]pyrrol-4-ylamino)pentan-2-yl)carbamate The title compound was prepared by substituting N-(tert-butoxycarbonyl)-N-methyl-L-norvaline for N-(tert-butoxycarbonyl)-L-leucine and (3aR,4S,6aS)-2-(4-(trifluoromethyl)phenylsulfonyl)octahydrocyclopenta[c]pyrrol-4-amine from Step A of Example 256 for (3aR,4S,6aS)-2-benzyloctahydrocyclopenta[c]pyrrol-4-amine in the procedure described in Example 221: ¹H NMR (400 MHz, pyridine-d₅, temperature 90° C.) δ ppm 8.06-8.09 (m, 2H), 7.79-7.82 (m, 2H), 7.40 (d, J=3.1 Hz, 1H), 4.66-4.76 (m, 1H), 4.07 (p, J=6.8 Hz, 1H), 3.65 (dd, J=10.2, 3.4 Hz, 1H), 3.28 (dd, J=10.2, 7.7 Hz, 1H), 3.06-3.17 (m, 2H), 2.93 (s, 3H), 2.53-2.62 (m, 1H), 2.45-2.53 (m, 1H), 1.93-2.02 (m, 1H), 1.86-1.95 (m, 1H), 1.70-1.85 (m, 2H), 1.47-1.57 (m, 1H), 1.45 (s, 9H), 1.27-1.37 (m, 2H), 1.22-1.32 (m, 1H), 0.86 (t, J=7.4 Hz, 3H); MS (ESI+) m/z 548 (M+H)⁺.

Example 260

N²-neopentyl-N¹-((3aS,4R,6aR)-2-{[4-(trifluoromethyl)phenyl]sulfonyl}octahydrocyclopenta[c]pyrrol-4-yl)-L-norvalinamide Step A: (3aS,4R,6aR)-2-(4-(Trifluoromethyl)phenylsulfonyl)octahydrocyclopenta[c]pyrrol-4-amine was prepared by following the procedures described in Example 252 Steps A-D substituting (3aS,4R,6aR)-2-benzyloctahydrocyclopenta[c]pyrrol-4-amine from Step E of Example 16 for (3aR,4S,6aS)-2-benzyloctahydrocyclopenta[c]pyrrol-4-amine in Step A of Example 252 and 4-(trifluoromethyl)benzene-1-sulfonyl chloride for 3-(trifluoromethyl)benzene-1-sulfonyl chloride in the procedure described in Step C of Example 252: ¹H NMR (500 MHz, pyridine-d₅) δ ppm 8.15 (d, J=8.2, 2H), 7.92 (d, J=8.3, 2H), 3.40 (dd, J=9.8, 2.9, 1H), 3.13 (dd, J=9.7, 3.2, 1H), 3.06-2.93 (m, 3H), 2.54 (s, 1H), 2.21-2.12 (m, 1H), 1.93-1.85 (m, 1H), 1.78-1.69 (m, 1H), 1.67-1.33 (m, 2H), 1.33-1.15 (m, 2H); MS (ESI+) m/z 335 (M+H)⁺.

Step B: The title compound was prepared by substituting (S)-2-(neopentylamino)pentanoic acid from Step A of Example 246 for N-(tert-butoxycarbonyl)-L-leucine and (3aS,4R,6aR)-2-(4-(trifluoromethyl)phenylsulfonyl)octahydrocyclopenta[c]pyrrol-4-amine from Step A for (3aR,4S,6aS)-2-benzyloctahydrocyclopenta[c]pyrrol-4-amine in the procedure described in Example 221: ¹H NMR (500 MHz, pyridine-d₅) δ ppm 8.09-8.14 (m, 3H), 7.88-7.91 (m, 2H), 4.20-4.26 (m, 1H), 3.88 (dd, J=9.9, 2.9 Hz, 1H), 3.13-3.21 (m, 3H), 2.98 (dd, J=9.6, 7.4 Hz, 1H), 2.49-2.64 (m, 2H), 2.38 (d, J=11.2 Hz, 1H), 2.33 (d, J=11.2 Hz, 1H), 1.91-1.99 (m, 1H), 1.76-1.90 (m, 2H), 1.66-1.95 (m, 1H), 1.62-1.71 (m, 1H), 1.41-1.58 (m, 3H), 1.33 (ddt, J=9.5, 13.0, 6.5 Hz, 1H), 0.92 (s, 9H), 0.86 (t, J=7.3 Hz, 3H); MS (ESI+) m/z 504 (M+H)⁺.

Example 261

N¹-{(3aR,4S,6aS)-2-[(4-fluorophenyl)sulfonyl]octahydrocyclopenta[c]pyrrol-4-yl}-N²-neopentyl-L-leucinamide Step A: (3aR,4S,6aS)-2-(4-Fluorophenylsulfonyl)octahydrocyclopenta[c]pyrrol-4-amine was prepared by substituting 4-fluorobenzene-1-sulfonyl chloride for 3-(trifluoromethyl)benzene-1-sulfonyl chloride in Step C of Example 252 and following Step D in Example 252: ¹H NMR (500 MHz, pyridine-d₅) δ ppm 8.05-7.96 (m, 2H), 7.38-7.31 (m, 2H), 3.34 (dd, J=9.8, 3.0, 1H), 3.08 (dd, J=9.7, 3.3, 1H), 3.05-2.98 (m, 1H), 2.97-2.89 (m, 2H), 2.59-2.49 (m, 1H), 2.20-2.10 (m, 1H), 1.95-1.85 (m, 1H), 1.79-1.69 (m, 1H), 1.67-1.33 (m, 2H) 1.31-1.15 (m, 2H); MS (ESI+) m/z 285 (M+H)⁺.

Step B: The title compound was prepared by substituting (S)-4-methyl-2-(neopentylamino)pentanoic acid from Step A of Example 244 for N-(tert-butoxycarbonyl)-L-leucine and (3aR,4S,6aS)-2-(4-fluorophenylsulfonyl)octahydrocyclopenta[c]pyrrol-4-amine from Step A for (3aR,4S,6aS)-2-benzyloctahydrocyclopenta[c]pyrrol-4-amine in the procedure described in Example 221: ¹H NMR (500 MHz, pyridine-d₅) δ ppm 8.21-8.23 (m, 1H), 7.99-8.02 (m, 2H), 7.32 (t, J=8.5 Hz, 2H), 4.23-4.29 (m, 1H), 3.78 (dd, J=9.9, 2.9 Hz, 1H), 3.26 (dd, J=8.5, 5.7 Hz, 1H), 3.12-3.18 (m, 2H), 2.96 (dd, J=9.6, 7.1 Hz, 1H), 2.51-2.60 (m, 2H), 2.44-2.47 (m, 1H), 2.29-2.32 (m, 1H), 1.93-2.01 (m, 1H), 1.81-1.93 (m, 2H), 1.67-1.79 (m, 1H), 1.70 (ddd, J=13.5, 7.8, 5.7 Hz, 1H), 1.53-1.60 (m, 2H), 1.23-1.36 (m, 1H), 0.93 (d, J=6.7 Hz, 3H), 0.93 (s, 9H), 0.87 (d, J=6.5 Hz, 3H); MS (ESI+) m/z 468 (M+H)⁺.

Example 262 tert-butyl(S)-4,4-dimethyl-1-oxo-1-((3aR,4S,6aS)-2-(5-(trifluoromethyl)pyridin-2-yl)octahydrocyclopenta[c]pyrrol-4-ylamino)pentan-2-ylcarbamate Step A: tert-Butyl(3aR,4S,6aS)-octahydrocyclopenta[c]pyrrol-4-ylcarbamate from Step B of Example 252 (250 mg, 1.105 mmol), 2-bromo-5-(trifluoromethyl)pyridine (250 mg, 1.105 mmol), and triethylamine (0.462 mL, 3.31 mmol) were combined in ethanol (0.6 mL). The reaction was heated at 81° C. for 16 hours. To the reaction mixture was added 50% water/ethanol (5 mL), and the precipitate was collected by filtration. This crude material was purified using a 12 g silica gel cartridge with a gradient of 0-1.5% methanol (2 N ammonia)/dichloromethane over 20 minutes to give tert-butyl(3aR,4S,6aS)-2-(5-(trifluoromethyl)pyridin-2-yl)octahydrocyclopenta[c]pyrrol-4-ylcarbamate: ¹H NMR (500 MHz, pyridine-d₅) δ ppm 8.62 (s, 1H), 7.76 (d, J=6.4, 1H), 7.68 (d, J=8.6, 1H), 6.38 (d, J=8.8, 1H), 4.10 (s, 1H), 3.73 (d, J=10.4, 1H), 3.65 (s, 1H), 3.61-3.53 (m, 1H), 3.32 (d, J=10.1, 1H), 2.82-2.71 (m, 2H), 2.15 (td, J=12.6, 6.8, 1H), 1.97 (dt, J=13.1, 6.4, 1H), 1.74 (dq, J=15.6, 7.9, 1H), 1.54 (s, 9H), 1.45-1.34 (m, 1H); MS (DCI+) m/z 372 (M+H)⁺.

Step B: tert-butyl(3aR,4S,6aS)-2-(5-(trifluoromethyl)pyridin-2-yl)octahydrocyclopenta[c]pyrrol-4-ylcarbamate (282 mg, 0.759 mmol) from Step A was combined with 4 N HCl in 1,4-dioxane (2.5 mL, 9.87 mmol). The reaction was stirred at room temperature overnight and then the volatiles were removed in vacuo. The compound was purified using a 12 g silica gel cartridge eluting with a gradient of 0-7.5% methanol (2 N ammonia)/dichloromethane over 20 minutes to give (3aR,4S,6aS)-2-(5-(trifluoromethyl)pyridin-2-yl)octahydrocyclopenta[c]pyrrol-4-amine: ¹H NMR (500 MHz, pyridine-d₅) δ ppm 8.64 (s, 1H), 7.69 (dd, J=8.9, 2.5, 1H), 6.38 (d, J=8.9, 1H), 4.95 (s, 2H), 3.56 (dd, J=23.7, 14.1, 3H), 3.25 (d, J=6.2, 1H), 3.11 (q, J=6.0, 1H), 2.83-2.68 (m, 1H), 2.35 (ddd, J=13.1, 7.9, 5.3, 1H), 2.02 (dtd, J=13.5, 8.3, 5.5, 1H), 1.92 (ddd, J=18.3, 7.4, 5.6, 1H), 1.46-1.30 (m, 2H); MS (ESI+) m/z 272 (M+H)⁺.

Step C: The title compound was prepared by substituting N-(tert-butoxycarbonyl)-L-neopentylglycine for N-(tert-butoxycarbonyl)-L-leucine and (3aR,4S,6aS)-2-(5-(trifluoromethyl)pyridin-2-yl)octahydrocyclopenta[c]pyrrol-4-amine from Step B for (3aR,4S,6aS)-2-benzyloctahydrocyclopenta[c]pyrrol-4-amine in the procedure described in Example 221: ¹H NMR (400 MHz, pyridine-d₅) δ ppm 8.52 (s, 1H), 7.81 (d, J=5.8, 1H), 7.60 (dd, J=8.9, 2.5, 1H), 7.07 (d, J=7.0, 1H), 6.35 (d, J=8.9, 1H), 4.53 (td, J=8.3, 4.7, 1H), 4.30-4.18 (m, 1H), 3.72 (dd, J=11.3, 3.5, 1H), 3.65 (dd, J=11.3, 7.6, 1H), 3.57 (dd, J=11.1, 7.8, 1H), 3.31 (dd, J=11.2, 3.9, 1H), 2.80-2.67 (m, 2H), 2.10 (ddd, J=19.9, 13.5, 5.8, 2H), 1.93 (td, J=13.1, 7.7, 1H), 1.74 (dd, J=14.3, 8.0, 1H), 1.64 (dq, J=12.9, 7.8, 1H), 1.50 (s, 9H), 1.44-1.33 (m, 1H), 1.00 (s, 9H); MS (ESI+) m/z 499 (M+H)⁺.

Example 263 isopropyl(S)-1-oxo-1-((3aR,4S,6aS)-2-(5-(trifluoromethyl)pyridin-2-yl)octahydrocyclopenta[c]pyrrol-4-ylamino)pentan-2-ylcarbamate Step A: (S)-2-Aminopentanoic acid (1.874 g, 16 mmol) was dissolved in dioxane (16 mL) and 16 mL of 1 N NaOH at 0° C. 1 M Isopropyl carbonochloridate in toluene (16.00 mL, 16.00 mmol) was added simultaneously with 16 mL of 1 N NaOH dropwise using addition funnels. The reaction was stirred at 0° C. for 3 hours and allowed to warm to room temperature overnight to give a biphasic solution pH 8-9. The solvent was reduced in volume. The aqueous layer was washed with ether, acidified with 1 M KHSO₄, and extracted with ethyl acetate to give (S)-2-(isopropoxycarbonylamino)pentanoic acid: ¹H NMR (300 MHz, DMSO-d₆) δ ppm 12.43 (s, 1H), 7.25 (d, J=8.0, 1H), 4.73 (hept, J=6.3, 1H), 3.89 (td, J=8.6, 5.2, 1H), 1.68-1.46 (m, 2H), 1.41-1.22 (m, 2H), 1.16 (d, J=6.2, 6H), 0.85 (t, J=7.3, 3H); MS (DCI+) m/z 204 (M+H)⁺

Step B: The title compound was prepared by substituting (S)-2-(isopropoxycarbonylamino)pentanoic acid from Step A for N-(tert-butoxycarbonyl)-L-leucine and (3aR,4S,6aS)-2-(5-(trifluoromethyl)pyridin-2-yl)octahydrocyclopenta[c]pyrrol-4-amine from Step B of Example 262 for (3aR,4S,6aS)-2-benzyloctahydrocyclopenta[c]pyrrol-4-amine in the procedure described in Example 221: ¹H NMR (400 MHz, pyridine-d₅) δ ppm 8.52 (d, J=1.0, 1H), 7.94 (dd, J=4.3, 2.4, 1H), 7.60 (dd, J=8.9, 2.5, 1H), 7.07 (d, J=7.0, 1H), 6.35 (d, J=8.9, 1H), 5.03 (dt, J=12.5, 6.2, 1H), 4.49 (dd, J=13.9, 8.0, 1H), 4.35-4.19 (m, 1H), 3.73 (dd, J=11.3, 3.6, 1H), 3.66 (dd, J=11.3, 7.6, 1H), 3.57 (dd, J=11.0, 8.0, 1H), 3.32 (dd, J=11.2, 3.9, 1H), 2.81-2.66 (m, 2H), 2.10 (dt, J=12.4, 7.0, 1H), 2.04-1.88 (m, 2H), 1.86-1.75 (m, 1H), 1.72-1.60 (m, 1H), 1.57-1.46 (m, 2H), 1.45-1.33 (m, 1H), 1.21 (d, J=6.2, 3H), 1.18 (d, J=6.2, 3H), 0.87 (t, J=7.4, 3H); MS (ESI+) m/z 457 (M+H)⁺.

Example 264 tert-butyl(S)-4,4-dimethyl-1-oxo-1-((3aR,4S,6aS)-2-(6-(trifluoromethyl)pyridin-2-yl)octahydrocyclopenta[c]pyrrol-4-ylamino)pentan-2-ylcarbamate Step A: (3aR,4S,6aS)-2-(6-(Trifluoromethyl)pyridin-2-yl)octahydrocyclopenta[c]pyrrol-4-amine was prepared as described for Example 262 Steps A-B substituting 2-bromo-6-(trifluoromethyl)pyridine for 2-bromo-5-(trifluoromethyl)pyridine in Step A of Example 262: ¹H NMR (500 MHz, pyridine-d₅) δ ppm 7.53 (t, J=7.9, 1H), 6.98 (d, J=7.2, 1H), 6.51 (d, J=8.6, 1H), 3.49 (dd, J=20.2, 8.4, 3H), 3.19 (dd, J=10.7, 4.8, 1H), 3.08 (q, J=6.0, 1H), 2.78-2.69 (m, 1H), 2.32 (td, J=12.2, 5.8, 1H), 2.04-1.95 (m, 1H), 1.89 (dt, J=12.7, 5.7, 1H), 1.80-1.49 (m, 2H), 1.44-1.36 (m, 1H), 1.35-1.27 (m, 1H); MS (ESI+) m/z 272 (M+H)⁺.

Step B: The title compound was prepared by substituting N-(tert-butoxycarbonyl)-L-neopentylglycine for N-(tert-butoxycarbonyl)-L-leucine and (3aR,4S,6aS)-2-(6-(trifluoromethyl)pyridin-2-yl)octahydrocyclopenta[c]pyrrol-4-amine from Step A for (3aR,4S,6aS)-2-benzyloctahydrocyclopenta[c]pyrrol-4-amine in the procedure described in Example 221: ¹H NMR (400 MHz, pyridine-d₅) δ ppm 7.78 (s, 1H), 7.45 (s, 1H), 7.05 (s, 1H), 6.91 (d, J=7.3, 1H), 6.47 (d, J=8.6, 1H), 4.53 (td, J=8.3, 4.7, 1H), 4.28-4.19 (m, 1H), 3.67-3.56 (m, 2H), 3.52 (dd, J=10.9, 7.9, 1H), 3.27 (dd, J=11.0, 3.7, 1H), 2.76-2.66 (m, 2H), 2.13 (dd, J=14.3, 4.6, 1H), 2.06 (dt, J=12.8, 6.4, 1H), 1.91 (td, J=13.3, 7.9, 1H), 1.73 (dd, J=14.3, 8.0, 1H), 1.62 (dq, J=15.1, 7.7, 1H), 1.50 (s, 9H), 1.37 (qd, J=7.9, 4.9, 1H), 1.00 (s, 9H); MS (ESI+) m/z 499 (M+H)⁺.

Example 265 tert-butyl(S)-4,4-dimethyl-1-((3aR,4S,6aS)-2-(2-(methylsulfonyl)pyrimidin-5-yl)octahydrocyclopenta[c]pyrrol-4-ylamino)-1-oxopentan-2-ylcarbamate Step A: (3aR,4S,6aS)-2-(2-(Methylsulfonyl)pyrimidin-5-yl)octahydrocyclopenta[c]pyrrol-4-amine was prepared as described in Example 262 Steps A-B substituting 5-bromo-2-(methylsulfonyl)pyrimidine for 2-bromo-5-(trifluoromethyl)pyridine in Step A of Example 262: ¹H NMR (500 MHz, pyridine-d₅) δ ppm 8.48 (s, 2H), 4.96 (s, 3H), 3.71 (dd, J=11.6, 8.6, 1H), 3.66 (d, J=6.1, 2H), 3.41 (dd, J=11.7, 4.9, 1H), 3.11 (q, J=6.0, 1H), 2.80-2.71 (m, 1H), 2.37-2.30 (m, 1H), 2.00 (ddd, J=21.4, 10.5, 6.5, 1H), 1.90 (td, J=12.5, 5.6, 1H), 1.82-1.51 (m, 2H), 1.44-1.29 (m, 2H); MS (ESI+) m/z 283 (M+H)⁺.

Step B: The title compound was prepared by substituting N-(tert-butoxycarbonyl)-L-neopentylglycine for N-(tert-butoxycarbonyl)-L-leucine and (3aR,4S,6aS)-2-(2-(methylsulfonyl)pyrimidin-5-yl)octahydrocyclopenta[c]pyrrol-4-amine from Step A for (3aR,4S,6aS)-2-benzyloctahydrocyclopenta[c]pyrrol-4-amine in the procedure described in Example 221: ¹H NMR (400 MHz, pyridine-d₅) δ ppm 8.34 (s, 2H), 7.79 (ddd, J=3.5, 1.7, 0.7, 1H), 7.10-6.93 (m, 1H), 4.52 (td, J=8.2, 4.7, 1H), 4.27 (qd, J=7.1, 5.4, 1H), 3.90 (d, J=11.1, 3H), 3.85 (dd, J=8.1, 3.9, 1H), 3.77 (dd, J=12.1, 7.6, 1H), 3.67 (dd, J=11.8, 7.9, 1H), 3.42 (dd, J=11.8, 4.1, 1H), 2.79-2.63 (m, 2H), 2.16-2.02 (m, 2H), 1.97-1.83 (m, 1H), 1.72 (dd, J=14.3, 8.0, 1H), 1.68-1.56 (m, 1H), 1.49 (s, 9H), 1.44-1.30 (m, 1H), 0.99 (s, 9H); MS (ESI+) m/z 510 (M+H)⁺.

Example 266

(S)-tert-butyl 2-((3aS,4R,6aR)-2-(3-(trifluoromethyl)phenylsulfonyl)octahydrocyclopenta[c]pyrrol-4-ylcarbamoyl)pyrrolidine-1-carboxylate (S)-1-(tert-Butoxycarbonyl)pyrrolidine-2-carboxylic acid (53.1 mg, 0.247 mmol), and 2-(3H-[1,2,3]triazolo[4,5-b]pyridin-3-yl)-1,1,3,3-tetramethylisouronium hexafluorophosphate(V) (94 mg, 0.247 mmol) were combined in dichloromethane (2 mL). After 10 minutes, (3aS,4R,6aR)-2-(3-(trifluoromethyl)phenylsulfonyl)octahydrocyclopenta[c]pyrrol-4-amine (75 mg, 0.224 mmol) from Step A of Example 254 was added. After stirring for 10 more minutes, N-ethyl-N-isopropylpropan-2-amine (0.098 mL, 0.561 mmol) was added and the reaction mixture was stirred at room temperature overnight. The reaction was quenched with saturated NaHCO$_3$ solution, extracted with 2 mL of dichloromethane, washed with 0.1 N HCl, and concentrated in vacuo. The crude material was purified using a 12 g silica gel cartridge with a gradient of 1-5% methanol (2 N ammonia)/dichloromethane over 20 minutes to give the title compound: $^1$H NMR (501 MHz, pyridine-d$_5$, temperature 90° C.) δ ppm 8.29-8.30 (bs, 1H), 8.13 (d, J=7.9 Hz, 1H), 7.83 (d, J=7.8 Hz, 1H), 7.66-7.72 (m, 1H), 7.64 (t, J=7.9 Hz, 1H), 4.29-4.32 (m, 1H), 4.06-4.10 (m, 1H), 3.68-3.71 (m, 1H), 3.46-3.51 (m, 1H), 3.34-3.42 (m, 1H), 3.26 (dd, J=9.9, 7.4 Hz, 1H), 3.06-3.17 (m, 2H), 2.55-2.57 (m, 2H), 2.09 (d, J=3.0 Hz, 1H), 1.88-1.98 (m, 3H), 1.80-1.88 (m, 1H), 1.59-1.68 (m, 1H), 1.55 (dd, J=13.2, 8.7 Hz, 1H), 1.50 (s, 9H), 1.25-1.37 (m, 1H); MS (ESI+) m/z 532 (M+H)$^+$.

Example 267 tert-butyl(1R)-1-isopropyl-3-oxo-3-[((3aS,4R,6aR)-2-{[3-(trifluoromethyl)phenyl]sulfonyl}octahydrocyclopenta[c]pyrrol-4-yl)amino]propylcarbamate The title compound was prepared by substituting (R)-3-(tert-butoxycarbonylamino)-4-methylpentanoic acid for (S)-1-(tert-butoxycarbonyl)pyrrolidine-2-carboxylic acid in the procedure described in Example 266: $^1$H NMR (501 MHz, pyridine-d$_5$, temperature 90° C.) δ ppm 8.29-8.31 (bs, 1H), 8.14 (d, J=7.8 Hz, 1H), 7.83 (d, J=7.8 Hz, 1H), 7.76-7.80 (bs, 1H), 7.65 (t, J=7.9 Hz, 1H), 6.53-6.62 (m, 1H), 4.08-4.15 (m, 1H), 4.02-4.08 (m, 1H), 3.67 (dd, J=10.1, 3.2 Hz, 1H), 3.28 (dd, J=9.9, 7.9 Hz, 1H), 3.08-3.16 (m, 2H), 2.46-2.59 (m, 4H), 1.87-1.98 (m, 2H), 1.79-1.87 (m, 1H), 1.50-1.62 (m, 1H), 1.48 (s, 9H), 1.24-1.36 (m, 1H), 0.89-0.93 (m, 6H); MS (ESI+) m/z 548 (M+H)$^+$.

Example 268 tert-butyl(2S)-2-{[((3aS,4R,6aR)-2-{[3-(trifluoromethyl)phenyl]sulfonyl}octahydrocyclopenta[c]pyrrol-4-yl)amino]carbonyl}piperidine-1-carboxylate The title compound was prepared by substituting (S)-1-(tert-butoxy carbonyl)piperidine-2-carboxylic acid for (S)-1-(tert-butoxycarbonyl)pyrrolidine-2-carboxylic acid in the procedure described in Example 266: $^1$H NMR (501 MHz, pyridine-d$_5$, temperature 90° C.) δ ppm 8.29-8.30 (bs, 1H), 8.14 (d, J=7.8 Hz, 1H), 7.83 (d, J=7.9 Hz, 1H), 7.64 (t, J=7.9 Hz, 1H), 7.39-7.43 (bs, 1H), 4.82-4.84 (m, 1H), 4.04-4.12 (m, 2H), 3.68 (dd, J=10.1, 3.3 Hz, 1H), 3.28-3.32 (m, 1H), 3.23-3.28 (m, 1H), 3.08-3.16 (m, 2H), 2.48-2.58 (m, 2H), 2.16-2.21 (m, 1H), 1.89-1.96 (m, 1H), 1.78-1.85 (m, 1H), 1.49-1.63 (m, 5H), 1.47 (s, 9H), 1.32-1.39 (m, 1H), 1.23-1.32 (m, 1H); MS (ESI+) m/z 544 (M+H)$^+$.

Example 269

N-(tert-butoxycarbonyl)-N-((3aR,4S,6aS)-2-{[3-(trifluoromethyl)phenyl]sulfonyl}octahydrocyclopenta[c]pyrrol-4-yl)-L-phenylalaninamide The title compound was prepared by substituting N-(tert-butoxycarbonyl)-L-phenylalanine for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$, temperature 90° C.) δ ppm 8.28-8.32 (m, 1H), 8.11-8.17 (m, 1H), 7.82-7.93 (m, 2H), 7.63-7.69 (m, 1H), 7.21-7.29 (m, 4H), 7.16-7.21 (m, 1H), 7.07-7.15 (m, 1H), 4.65-4.70 (m, 1H), 4.0 (m, 1H), 3.52-3.62 (m, 1H), 3.26-3.31 (m, 1H), 3.12-3.21 (m, 2H), 3.03-3.11 (m, 2H), 2.42-2.48 (m, 1H), 2.31-2.36 (m, 1H), 1.81-1.88 (m, 1H), 1.69-1.77 (m, 1H), 1.37-1.48 (m, 1H), 1.42 (s, 9H), 1.16-1.26 (m, 1H); MS (ESI+) m/z 599 (M+H)$^+$.

Example 270

N-(tert-butoxycarbonyl)-N-methyl-N-((3aR,4S,6aS)-2-{[3-(trifluoromethyl)phenyl]sulfonyl}octahydrocyclopenta[c]pyrrol-4-yl)-L-phenylalaninamide The title compound was prepared by substituting N-(tert-butoxycarbonyl)-N-methyl-L-phenylalanine for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$) δ ppm 8.65-8.52 (m, 1H), 8.38 (s, 1H), 8.22 (d, J=7.8, 1H), 7.93 (d, J=7.8, 1H), 7.75 (t, J=7.8, 1H), 7.39-7.23 (m, 5H), 5.40-5.29 (m, 1H), 4.30-4.14 (m, 1H), 3.84-3.72 (m, 1H), 3.65-3.45 (m, 1H), 3.13 (d, J=5.4, 2H), 3.06 (s, 3H), 3.03 (dd, J=9.7, 7.6, 1H), 2.89 (dd, J=9.5, 7.5, 1H), 2.41 (dd, J=13.4, 6.1, 1H), 2.39-2.30 (m, 1H), 1.95-1.80 (m, 1H), 1.74 (s, 1H), 1.55-1.40 (m, 1H), 1.36 (s, 5H), 1.25 (s, 4H), 1.22-1.15 (m, 1H); MS (ESI+) m/z 596 (M+H)$^+$.

Example 271

(S)-tert-butyl 2-((3aR,4S,6aS)-2-(3-(trifluoromethyl)phenylsulfonyl)octahydrocyclopenta[c]pyrrol-4-ylcarbamoyl)pyrrolidine-1-carboxylate The title compound was prepared by substituting (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$) δ ppm 8.42-8.59 (m, 1H), 8.36-8.38 (bs, 1H), 8.16-8.22 (m, 1H), 7.92 (d, J=7.3 Hz, 1H), 7.74 (t, J=7.5 Hz, 1H), 4.31-4.55 (m, 1H), 4.09-4.31 (m, 1H), 3.73-3.90 (m, 1H), 3.48-3.68 (m, 1H), 3.27-3.48 (m, 1H), 3.06-3.25 (m, 2H), 2.85-3.03 (m, 1H), 2.42-2.65 (m, 2H), 1.72-2.22 (m, 5H), 1.60-1.72 (m, 1H), 1.53-1.57 (bs, 5H), 1.49-1.54 (bs, 4H), 1.4 (m, 1H), 1.13-1.26 (m, 1H); MS (ESI+) m/z 532 (M+H)$^+$, 549 (M+NH$_4$)$^+$.

Example 272 tert-butyl(1R)-1-isopropyl-3-oxo-3-[((3aR,4S,6aS)-2-{[3-(trifluoromethyl)phenyl]sulfonyl}octahydrocyclopenta[c]pyrrol-4-yl)amino]propylcarbamate The title compound was prepared by substituting (R)-3-(tert-butoxycarbonylamino)-4-methylpentanoic acid for (S)-

1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$, temperature 90° C.) δ ppm 8.30-8.31 (bs, 1H), 8.14 (d, J=7.8 Hz, 1H), 7.84 (d, J=7.6 Hz, 1H), 7.76-7.85 (bs, 1H), 7.66 (t, J=7.8 Hz, 1H), 6.50-6.69 (bs, 1H), 4.08-4.16 (m, 1H), 3.64-3.72 (m, 1H), 3.24-3.33 (m, 1H), 3.12 (d, J=5.2 Hz, 2H), 2.42-2.63 (m, 4H), 1.89-2.00 (m, 2H), 1.79-1.89 (m, 1H), 1.49-1.63 (m, 1H), 1.48 (s, 9H), 1.23-1.33 (m, 2H), 0.88-0.95 (m, 6H); MS (ESI+) m/z 570 (M+Na)$^+$.

Example 273 tert-butyl methyl((S)-3-methyl-1-oxo-1-((3aR,4S,6aS)-2-(3-(trifluoromethyl)phenylsulfonyl)octahydrocyclopenta[c]pyrrol-4-ylamino)butan-2-yl)carbamate The title compound was prepared by substituting N-(tert-butoxycarbonyl)-N-methyl-L-valine for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$, temperature 90° C.) δ ppm 8.30-8.32 (bs, 1H), 8.14 (d, J=7.8 Hz, 1H), 7.84 (d, J=7.8 Hz, 1H), 7.64 (t, J=7.8 Hz, 1H), 7.58-7.69 (bs, 1H), 4.32 (d, J=9.5 Hz, 1H), 4.03-4.12 (m, 1H), 3.68 (dd, J=10.2, 3.3 Hz, 1H), 3.27-3.31 (m, 1H), 3.08-3.16 (m, 2H), 3.00 (s, 3H), 2.53-2.61 (m, 1H), 2.46-2.53 (m, 1H), 2.33-2.43 (m, 1H), 1.85-1.93 (m, 1H), 1.77-1.85 (m, 1H), 1.47-1.54 (m, 1H), 1.45 (s, 9H), 1.21-1.30 (m, 1H), 0.97 (d, J=6.5 Hz, 3H), 0.86 (d, J=6.7 Hz, 3H); MS (ESI+) m/z 570 (M+Na)$^+$.

Example 274 tert-butyl(2S)-2-{[((3aR,4S,6aS)-2-{[3-(trifluoromethyl)phenyl]sulfonyl}octahydrocyclopenta[c]pyrrol-4-yl)amino]carbonyl}piperidine-1-carboxylate The title compound was prepared by substituting (S)-1-(tert-butoxycarbonyl)piperidine-2-carboxylic acid for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252D for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$) δ ppm 8.37-8.38 (bs, 1H), 8.32 (d, J=5.2 Hz, 1H), 8.19 (d, J=7.9 Hz, 1H), 7.91 (d, J=7.9 Hz, 1H), 7.71 (t, J=7.8 Hz, 1H), 4.07-4.23 (m, 2H), 3.84 (dd, J=9.9, 2.2 Hz, 1H), 3.46 (td, J=12.9, 2.8 Hz, 1H), 3.16 (d, J=9.2 Hz, 1H), 3.12 (dd, J=9.5, 7.6 Hz, 1H), 2.90-2.94 (m, 1H), 2.41-2.57 (bs, 2H), 2.24-2.29 (m, 1H), 1.75-1.97 (m, 2H), 1.53-1.65 (m, 3H), 1.49-1.55 (m, 2H), 1.48 (s, 9H), 1.42-1.51 (m, 1H), 1.29-1.39 (m, 1H), 1.17-1.29 (m, 1H); MS (ESI+) m/z 563 (M+H)$^+$.

Example 275 tert-butyl(3S)-3-{[((3aR,4S,6aS)-2-{[3-(trifluoromethyl)phenyl]sulfonyl}octahydrocyclopenta[c]pyrrol-4-yl)amino]carbonyl}-3,4-dihydroisoquinoline-2(1H)-carboxylate The title compound was prepared by substituting (S)-2-(tert-butoxycarbonyl)-1,2,3,4-tetrahydroisoquinoline-3-carboxylic acid for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)ethyl)phenylsulfonyl)octahydrocyclopenta[c]pyrrol-4-amine in the procedure described in Example 266: $^1$H NMR (500 MHz, pyridine-d$_5$, temperature 90° C.) δ ppm 8.26-8.27 (bs, 1H), 8.08-8.10 (m, 1H), 7.81-7.84 (m, 1H), 7.62 (t, J=7.8 Hz, 1H), 7.29-7.36 (m, 1H), 7.12-7.14 (m, 2H), 7.08-7.11 (m, 2H), 4.83-5.02 (m, 1H), 4.78 (d, J=15.6 Hz, 1H), 4.67 (d, J=15.6 Hz, 1H), 3.90-3.97 (m, 1H), 3.52 (dd, J=10.1, 3.3 Hz, 1H), 3.30 (dd, J=15.3, 4.8 Hz, 1H), 3.14 (dd, J=9.9, 7.8 Hz, 1H), 3.11 (dd, J=15.4, 6.3 Hz, 1H), 3.04-3.08 (m, 2H), 2.45-2.53 (m, 1H), 2.38-2.45 (m, 1H), 1.64-1.75 (m, 2H), 1.50 (s, 9H), 1.35-1.46 (m, 1H), 1.15-1.25 (m, 1H); MS (ESI+) m/z 594 (M+H)$^+$, 611 (M+NH$_4$)$^+$.

Example 276 tert-butyl(S)-4,4-dimethyl-1-oxo-1-((3aR,4S,6aS)-2-(3-(trifluoromethyl)phenylsulfonyl)octahydrocyclopenta[c]pyrrol-4-ylamino)pentan-2-ylcarbamate The title compound was prepared by substituting N-(tert-butoxycarbonyl)-L-neopentylglycine for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252D for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$, temperature 90° C.) δ ppm 8.29-8.30 (bs, 1H), 8.14 (d, J=7.9 Hz, 1H), 7.83 (d, J=7.9 Hz, 1H), 7.79-7.87 (bs, 1H), 7.64 (t, J=7.8 Hz, 1H), 7.05-7.18 (bs, 1H), 4.46-4.51 (m, 1H), 4.06-4.14 (m, 1H), 3.67 (dd, J=10.2, 2.8 Hz, 1H), 3.27 (dd, J=10.1, 7.6 Hz, 1H), 3.07-3.15 (m, 2H), 2.50-2.59 (m, 2H), 2.08 (dd, J=14.2, 4.6 Hz, 1H), 1.85-1.92 (m, 1H), 1.77-1.85 (m, 1H), 1.70 (dd, J=14.2, 8.0 Hz, 1H), 1.48-1.54 (m, 1H), 1.47 (s, 9H), 1.21-1.30 (m, 1H), 0.96 (s, 9H); MS (ESI+) m/z 562 (M+H)$^+$.

Example 277 tert-butyl methyl((S)-1-oxo-1-((3aR,4S,6aS)-2-(3-(trifluoromethyl)phenylsulfonyl)octahydrocyclopenta[c]pyrrol-4-ylamino)hexan-2-yl)carbamate The title compound was prepared by substituting N-(tert-butoxycarbonyl)-N-methyl-L-norleucine for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-d$_5$) δ ppm 8.44 (d, J=6.9 Hz, 1H), 8.36-8.38 (bs, 1H), 8.19 (d, J=7.9 Hz, 1H), 7.91 (d, J=7.6 Hz, 1H), 7.72 (t, J=7.8 Hz, 1H), 5.0 (m, 0.7H), 4.6 (m, 0.3H), 4.18-4.24 (m, 1H), 3.83-3.86 (m, 1H), 3.13-3.19 (m, 1H), 3.08-3.13 (m, 1H), 2.97-3.10 (bs, 3H), 2.91 (dd, J=9.4, 7.4 Hz, 1H), 2.44-2.59 (m, 2H), 1.98-2.19 (m, 1H), 1.84-1.98 (m, 1H), 1.72-1.85 (m, 2H), 1.47-1.60 (m, 1H), 1.44-1.46 (m, 9H), 1.22-1.34 (m, 1H), 1.15-1.34 (m, 4H), 0.76-0.81 (m, 3H); MS (ESI+) m/z 562 (M+H)$^+$, 579 (M+NH$_4$)$^+$.

Example 278 tert-butyl methyl((S)-1-oxo-1-((3aR,4S,6aS)-2-(3-(trifluoromethyl)phenylsulfonyl)octahydrocyclopenta[c]pyrrol-4-ylamino)pentan-2-yl)carbamate The title compound was prepared by substituting N-(tert-butoxycarbonyl)-N-methyl-L-norvaline for (S)-1-(tert-butoxycarbonyl)pyrrolidine-2-carboxylic acid and (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-$d_5$, temperature 90° C.) δ ppm 8.30-8.31 (bs, 1H), 8.14 (d, J=7.9 Hz, 1H), 7.84 (d, J=7.8 Hz, 1H), 7.64 (t, J=7.8 Hz, 1H), 7.49 (d, J=5.6 Hz, 1H), 4.72-4.73 (m, 1H), 4.04-4.11 (m, 1H), 3.67 (dd, J=10.1, 3.3 Hz, 1H), 3.26 (dd, J=10.1, 7.7 Hz, 1H), 3.10-3.13 (m, 2H), 2.93 (s, 3H), 2.46-2.59 (m, 2H), 1.86-2.01 (m, 2H), 1.71-1.84 (m, 2H), 1.46-1.58 (m, 1H), 1.45 (s, 9H), 1.29-1.36 (m, 2H), 1.22-1.30 (m, 1H), 0.86 (t, J=7.3 Hz, 3H); MS (ESI+) m/z 548 (M+H)$^+$.

Example 279 isopropyl(S)-1-oxo-1-((3aR,4S,6aS)-2-(4-(trifluoromethyl)phenylsulfonyl)octahydrocyclopenta[c]pyrrol-4-ylamino)pentan-2-ylcarbamate The title compound was prepared by substituting (S)-2-(isopropoxycarbonylamino)pentanoic acid from Step A of Example 263 for (S)-1-(tert-butoxycarbonyl)pyrrolidine-2-carboxylic acid and (3aR,4S,6aS)-2-(4-(trifluoromethyl)phenylsulfonyl)octahydrocyclopenta[c]pyrrol-4-amine from Step A of Example 256 for (3aS,4R,6aR)-2-(3-(trifluoromethyl)phenylsulfonyl)octahydrocyclopenta[c]pyrrol-4-amine in the procedure described in Example 266: $^1$H NMR (501 MHz, pyridine-$d_5$) δ ppm 8.08 (d, J=8.2, 2H), 7.96 (d, J=4.8, 1H), 7.82 (d, J=8.3, 2H), 7.18 (d, J=4.5, 2H), 5.01 (hept, J=6.2, 1H), 4.45 (dd, J=14.0, 7.7, 1H), 4.11 (dt, J=13.0, 6.7, 1H), 3.67 (dd, J=10.2, 3.0, 1H), 3.30 (dd, J=10.2, 7.6, 1H), 3.16-3.07 (m, 2H), 2.57 (h, J=9.3, 2H), 1.99-1.85 (m, 2H), 1.86-1.72 (m, 2H), 1.58-1.50 (m, 1H), 1.45 (ddd, J=20.8, 11.7, 7.2, 2H), 1.26 (ddd, J=13.1, 10.9, 6.6, 1H), 1.19 (d, J=6.2, 3H), 1.16 (d, J=6.2, 3H), 0.84 (t, J=7.4, 3H); MS (ESI+) m/z 520 (M+H)$^+$.

Example 280 isopropyl(S)-1-oxo-1-((3aR,4S,6aS)-2-(4-(trifluoromethyl)benzyl)octahydrocyclopenta[c]pyrrol-4-ylamino)pentan-2-ylcarbamate The title compound was prepared by substituting N$^1$-{(3aR,4S,6aS)-2-[4-(trifluoromethyl)benzyl]octahydrocyclopenta[c]pyrrol-4-yl}-L-norvalinamide from Example 382 for (S)-tert-butyl 2-amino-4-methylpentanoate and isopropyl carbonochloridate for methanesulfonyl chloride in the procedure described in Example 242: $^1$H NMR (500 MHz, pyridine-$d_5$) δ ppm 8.22-8.15 (m, 1H), 7.65 (d, J=8.0, 2H), 7.51 (d, J=7.9, 2H), 7.39-7.34 (m, 1H), 5.11-5.02 (m, 1H), 4.74-4.64 (m, 1H), 4.48-4.40 (m, 1H), 3.57 (d, J=13.7, 1H), 3.46 (d, J=13.6, 1H), 2.90-2.82 (m, 1H), 2.62-2.49 (m, 2H), 2.44-2.38 (m, 1H), 2.34-2.28 (m, 1H), 2.24 (dd, J=9.7, 6.3, 1H), 2.10-2.00 (m, 2H), 1.92-1.81 (m, 2H), 1.65-1.57 (m, 1H), 1.55-1.45 (m, 2H), 1.42-1.33 (m, 1H), 1.22 (d, J=6.2, 3H), 1.15 (d, J=6.2, 3H), 0.81 (t, J=7.4, 3H); MS (ESI+) m/z 470 (M+H)$^+$.

Example 281

(3aS,4R,6aR)-N-neopentyl-2-{[3-(trifluoromethyl)phenyl]sulfonyl}octahydrocyclopenta[c]pyrrol-4-amine (3aS,4R,6aR)-2-(3-(Trifluoromethyl)phenylsulfonyl)octahydrocyclopenta[c]pyrrol-4-amine (100 mg, 0.299 mmol) from Step A of Example 254 and pivalaldehyde (0.043 mL, 0.389 mmol) were combined in dichloromethane (1 mL). Acetic acid (0.3 mL) was added. The reaction was stirred at room temperature for 20 minutes, then PS-cyanoborohydride (147 mg, 0.359 mmol) was added. The reaction was stirred at room temperature for 72 hours, then filtered. The reaction mixture was washed with 1 N NaHCO$_3$ and concentrate in vacuo. The crude material was purified using a 12 g silica gel cartridge with a gradient of 0-4% methanol (2 N ammonia)/dichloromethane to give the title compound: $^1$H NMR (500 MHz, pyridine-$d_5$) δ ppm 8.40-8.41 (bs, 1H), 8.22-8.25 (m, 1H), 7.92-7.95 (m, 1H), 7.75 (t, J=7.8 Hz, 1H), 3.42 (dd, J=9.8, 3.1 Hz, 1H), 3.17 (dd, J=9.6, 3.1 Hz, 1H), 3.06-3.10 (m, 1H), 2.96 (dd, J=9.6, 7.7 Hz, 1H), 2.74-2.77 (m, 1H), 2.48-2.53 (m, 1H), 2.30 (d, J=11.3 Hz, 1H), 2.22-2.27 (m, 1H), 2.22 (d, J=7.9 Hz, 1H), 1.78-1.92 (m, 2H), 1.18-1.31 (m, 3H), 0.90 (s, 9H); MS (ESI+) m/z 405 (M+H)$^+$.

Example 282

(3aR,4S,6aS)-N-neopentyl-2-{[3-(trifluoromethyl)phenyl]sulfonyl}octahydrocyclopenta[c]pyrrol-4-amine The title compound was prepared by substituting (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine in the procedure described in Example 281: $^1$H NMR (500 MHz, pyridine-$d_5$) δ ppm 8.40-8.41 (bs, 1H), 8.22-8.25 (m, 1H), 7.92-7.95 (m, 1H), 7.75 (t, J=7.9 Hz, 1H), 3.42 (dd, J=9.8, 3.1 Hz, 1H), 3.17 (dd, J=9.6, 3.0 Hz, 1H), 3.05-3.09 (m, 1H), 2.96 (dd, J=9.6, 7.7 Hz, 1H), 2.73-2.77 (m, 1H), 2.48-2.53 (m, 1H), 2.30 (d, J=11.3 Hz, 1H), 2.22-2.27 (m, 1H), 2.21 (d, J=11.0 Hz, 1H), 1.78-1.93 (m, 2H), 1.18-1.32 (m, 3H), 0.90 (s, 9H); MS (ESI+) m/z 405 (M+H)$^+$.

Example 283

(3aR,4S,6aS)-N-isopropyl-2-{[4-(trifluoromethyl)phenyl]sulfonyl}octahydrocyclopenta[c]pyrrol-4-amine The title compound was prepared by substituting (3aR,4S,6aS)-2-(4-(trifluoromethyl)phenylsulfonyl)octahydrocyclopenta[c]pyrrol-4-amine from Step A of Example 256 for (3aS,4R,6aR)-2-(3-(trifluoromethyl)phenylsulfonyl)octahydrocyclopenta[c]pyrrol-4-amine and acetone for pivaldehyde in the procedure described in Example 281: $^1$H NMR (400 MHz, pyridine-$d_5$) δ ppm 8.14-8.22 (m, 2H), 7.91-7.98 (m, 2H), 3.40 (dd, J=9.7, 3.0 Hz, 1H), 3.16 (dd, J=9.6, 3.3 Hz, 1H), 3.06 (dd, J=9.7, 7.8 Hz, 1H), 2.99 (dd, J=9.6, 7.7 Hz, 1H), 2.85-2.90 (m, 1H), 2.74 (hept, J=6.2 Hz, 1H), 2.46-2.53 (m, 1H), 2.14-2.25 (m, 1H), 1.80-1.91 (m, 2H), 1.07-1.43 (m, 3H), 1.00 (d, J=6.2 Hz, 3H), 0.96 (d, J=6.1 Hz, 3H); MS (ESI+) m/z 377 (M+H)$^+$.

Example 284

(3aR,4S,6aS)-2-{[2-chloro-4-(trifluoromethyl)phenyl]sulfonyl}-N-isopropyloctahydrocyclopenta[c]pyrrol-4-amine Step A: tert-Butyl(3aR,4S,6aS)-2-(2-chloro-4-(trifluoromethyl)phenylsulfonyl)octahydrocyclopenta[c]pyrrol-4-ylcarbamate was prepared by substituting 2-chloro-4-(trifluoromethyl)benzene-1-sulfonyl chloride for 3-(trifluoromethyl)benzene-1-sulfonyl chloride in Step C of Example 252: $^1$H NMR (500 MHz, pyridine-$d_5$) δ 8.33 (d, J=8.0, 1H), 8.00 (s, 1H), 7.77-7.68 (m, 2H), 4.04-3.96 (m, 1H), 3.83 (d, J=9.5, 1H), 3.48 (dd, J=10.2, 7.5, 1H), 3.41-3.29 (m, 2H), 2.72-2.59 (m, 2H), 2.02 (td, J=12.0, 6.4, 1H), 1.90 (qd, J=7.1, 4.5, 1H), 1.64 (ddd, J=16.1, 12.4, 8.8, 1H), 1.50 (s, 9H), 1.41-1.32 (m, 1H); MS (ESI+) m/z 486 (M+NH$_4$)$^+$.

Step B: (3aR,4S,6aS)-2-{[2-Chloro-4-(trifluoromethyl)phenyl]sulfonyl}octahydrocyclopenta[c]pyrrol-4-amine was prepared by substituting tert-butyl(3aR,4S,6aS)-2-(2-chloro-4-(trifluoromethyl)phenylsulfonyl)octahydrocyclopenta[c]pyrrol-4-ylcarbamate from Step A for tert-butyl(3aR,4S,6aS)-2-(3-(trifluoromethyl)phenylsulfonyl)octahydrocyclopenta[c]pyrrol-4-ylcarbamate in the procedure described in Step D of Example 252: $^1$H NMR (500 MHz, pyridine-$d_5$) δ 8.34 (d, J=8.2, 1H), 8.01 (s, 1H), 7.75 (d, J=8.3, 1H), 3.55 (dd, J=10.1, 3.1, 1H), 3.38-3.31 (m, 2H), 3.28 (dd, J=9.9, 3.7, 1H), 3.10 (q, J=6.1, 1H), 2.70-2.60 (m, 1H), 2.31-2.22 (m, 1H), 1.93 (ddd, J=11.1, 8.2, 5.7, 1H), 1.87-1.76 (m, 1H), 1.74-1.49 (m, 2H), 1.37-1.24 (m, 2H); MS (ESI+) m/z 369 (M+H)$^+$.

Step C: The title compound was prepared by substituting (3aR,4S,6aS)-2-{[2-chloro-4-(trifluoromethyl)phenyl]sulfonyl}octahydrocyclopenta[c]pyrrol-4-amine from Step A for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.37 (d, J=8.2 Hz, 1H), 8.03 (d, J=1.7 Hz, 1H), 7.77 (d, J=9.0 Hz, 1H), 3.56 (dd, J=10.0, 3.1 Hz, 1H), 3.41 (dd, J=10.1, 7.8 Hz, 1H), 3.31-3.38 (m, 2H), 2.97 (q, J=6.3 Hz, 1H), 2.78 (hept, J=6.2 Hz, 1H), 2.58-2.63 (m, 1H), 2.30-2.35 (m, 1H), 1.87-1.96 (m, 2H), 1.05-1.67 (m, 1H), 1.21-1.37 (m, 2H), 1.01 (d, J=6.2 Hz, 3H), 0.98 (d, J=6.1 Hz, 3H); MS (ESI+) m/z 411 (M+H)$^+$.

Example 285

(3aS,4R,6aR)-N-(4-fluorobenzyl)-2-{[3-(trifluoromethyl)phenyl]sulfonyl}octahydrocyclopenta[c]pyrrol-4-amine The title compound was prepared by substituting 4-fluorobenzaldehyde for pivalaldehyde in the procedure described in Example 281: $^1$H NMR (500 MHz, pyridine-$d_5$) δ ppm 8.39-8.40 (bs, 1H), 8.23 (d, J=7.9 Hz, 1H), 7.94 (d, J=7.9 Hz, 1H), 7.76 (t, J=7.8 Hz, 1H), 7.41 (dd, J=8.3, 5.5 Hz, 2H), 7.11-7.15 (m, 2H), 3.71 (d, J=13.2 Hz, 1H), 3.67 (d, J=13.2 Hz, 1H), 3.39 (dd, J=9.8, 3.1 Hz, 1H), 3.16 (dd, J=9.6, 3.0 Hz, 1H), 3.06 (dd, J=9.8, 8.0 Hz, 1H), 2.96 (dd, J=9.6, 7.6 Hz, 1H), 2.83-2.88 (m, 1H), 2.47-2.56 (m, 1H), 2.30-2.36 (m, 1H), 1.92-2.09 (m, 1H), 1.87-1.94 (m, 1H), 1.80-1.88 (m, 1H), 1.29-1.37 (m, 1H), 1.20-1.29 (m, 1H); MS (ESI+) m/z 443 (M+H)$^+$.

Example 286

(3aR,4S,6aS)-N-(4-fluorobenzyl)-2-{[3-(trifluoromethyl)phenyl]sulfonyl}octahydrocyclopenta[c]pyrrol-4-amine The title compound was prepared by substituting (3aR,4S,6aS)-2-(3-(trifluoromethyl)phenylsulfonyl)octahydrocyclopenta[c]pyrrol-4-amine from Step D of Example 252 for (3aS,4R,6aR)-2-(3-(trifluoromethyl)phenylsulfonyl)octahydrocyclopenta[c]pyrrol-4-amine and 4-fluorobenzaldehyde for pivalaldehyde in the procedure described in Example 281: $^1$H NMR (500 MHz, pyridine-$d_5$) δ ppm 8.39-8.40 (bs, 1H), 8.22-8.24 (m, 1H), 7.93-7.95 (m, 1H), 7.75 (t, J=7.8 Hz, 1H), 7.41 (dd, J=8.3, 5.5 Hz, 2H), 7.13 (t, J=8.7 Hz, 2H), 3.71 (d, J=13.3 Hz, 1H), 3.67 (d, J=13.2 Hz, 1H), 3.39 (dd, J=9.8, 3.1 Hz, 1H), 3.16 (dd, J=9.6, 3.0 Hz, 1H), 3.06 (dd, J=9.8, 8.0 Hz, 1H), 2.96 (dd, J=9.6, 7.6 Hz, 1H), 2.85 (q, J=6.1 Hz, 1H), 2.47-2.56 (m, 1H), 2.30-2.35 (m, 1H), 1.93-2.07 (m, 1H), 1.87-1.94 (m, 1H), 1.79-1.87 (m, 1H), 1.29-1.38 (m, 1H), 1.20-1.29 (m, 1H); MS (ESI+) m/z 443 (M+H)$^+$.

Example 287

(3aR,4S,6aS)-N-(4-fluorobenzyl)-2-[3-(trifluoromethyl)benzyl]octahydrocyclopenta[c]pyrrol-4-amine The title compound was prepared by substituting (3aR,4S,6aS)-2-benzyloctahydrocyclopenta[c]pyrrol-4-amine (0.83 g, 3.84 mmol) from Step A of Example 33 for (3aS,4R,6aR)-2-(3-(trifluoromethyl)phenylsulfonyl)octahydrocyclopenta[c]pyrrol-4-amine and 4-fluorobenzaldehyde for pivalaldehyde in the procedure described in Example 281: $^1$H NMR (500 MHz, pyridine-$d_5$) δ ppm 7.79-7.80 (bs, 1H), 7.58-7.61 (m, 1H), 7.60 (s, 1H), 7.44-7.49 (m, 1H), 7.39-7.44 (m, 2H), 7.12 (t, J=8.6 Hz, 2H), 3.71-3.79 (m, 2H), 3.55-3.56 (bs, 2H), 2.96 (q, J=5.1 Hz, 1H), 2.57-2.63 (m, 1H), 2.51 (dd, J=8.8, 3.2 Hz, 1H), 2.39-2.43 (m, 1H), 2.31-2.39 (m, 3H), 1.91-1.98 (m, 2H), 1.72-1.93 (m, 1H), 1.34-1.48 (m, 2H); MS (ESI+) m/z 393 (M+H)$^+$.

Example 288

(3aR,4S,6aS)-N-ethyl-2-{[4-(trifluoromethyl)phenyl]sulfonyl}octahydrocyclopenta[c]pyrrol-4-amine (3aR,4S,6aS)-2-(4-(Trifluoromethyl)phenylsulfonyl)octahydrocyclopenta[c]pyrrol-4-amine (120 mg, 0.359 mmol) from Step A of Example 256, iodoethane (0.287 mL, 3.59 mmol), and triethylamine (0.750 mL, 5.38 mmol) were in tetrahydrofuran (1 mL). The reaction was stirred at 65° C. for 3 days, and then the solvent was removed in vacuo. The residue was diluted with dichloromethane (5 mL), and addition of saturated aqueous sodium bicarbonate gave the products as a solid. This material was purified using a 12 g silica gel cartridge with a gradient of 0-5% methanol (2 N ammonia)/dichloromethane over 20 minutes to give two products. The second product was further purified on 4×0.25 mm preparative thin-layer chromatography plate eluting with 6% methanol (2 N ammonia)/dichloromethane to give the title compound: $^1$H NMR (500 MHz, pyridine-$d_5$) δ ppm 8.17-8.19 (m, 2H), 7.93-7.95 (m, 2H), 3.38 (dd, J=9.8, 3.1 Hz, 1H), 3.15 (dd, J=9.6, 3.2 Hz, 1H), 3.06 (dd, J=9.8, 8.0 Hz, 1H), 2.96 (dd, J=9.6, 7.7 Hz, 1H), 2.78 (q, J=6.1 Hz, 1H), 2.44-2.58 (m, 4H), 2.25-2.33 (m, 1H), 1.85-1.92 (m, 1H), 1.75-1.85 (m, 1H), 1.16-1.34 (m, 2H), 1.05 (t, J=7.1 Hz, 3H); MS (ESI+) m/z 363 (M+H)$^+$.

Example 289

(3aR,4S,6aS)-N,N-diethyl-2-{[4-(trifluoromethyl)phenyl]sulfonyl}octahydrocyclopenta[c]pyrrol-4-amine The first product from Example 288 was purified on a 2×0.25 mm preparative thin-layer chromatography plate eluting with acetone to give the title compound: $^1$H NMR (500 MHz, pyridine-$d_5$) δ ppm 8.18-8.20 (m, 2H), 7.94-7.97 (m, 2H), 3.43 (dd, J=9.6, 2.6 Hz, 1H), 3.22 (dd, J=9.5, 2.6 Hz, 1H), 2.98 (dd, J=9.6, 7.8 Hz, 1H), 2.88 (dd, J=9.5, 7.4 Hz, 1H), 2.70-2.75 (m, 1H), 2.30-2.50 (m, 5H), 2.22-2.29 (m, 1H), 1.75-1.81 (m, 1H), 1.62-1.68 (m, 1H), 1.25-1.34 (m, 1H), 1.16-1.25 (m, 1H), 0.92 (t, J=7.0 Hz, 6H); MS (ESI+) m/z 391 (M+H)$^+$.

Example 290

(3aR,4S,6aS)-N-propyl-2-{[4-(trifluoromethyl)phenyl]sulfonyl}octahydrocyclopenta[c]pyrrol-4-amine The title compound was prepared by substituting 1-iodopropane for iodoethane in the procedure described in Example 288: $^1$H NMR (500 MHz, pyridine-d$_5$) δ ppm 8.17-8.19 (m, 2H), 7.93-7.95 (m, 2H), 3.39 (dd, J=9.8, 3.1 Hz, 1H), 3.16 (dd, J=9.6, 3.2 Hz, 1H), 3.07 (dd, J=9.8, 8.0 Hz, 1H), 2.98 (dd, J=9.6, 7.7 Hz, 1H), 2.77 (q, J=5.9 Hz, 1H), 2.50-2.58 (m, 1H), 2.39-2.51 (m, 2H), 2.24-2.30 (m, 1H), 1.77-1.92 (m, 2H), 1.36-1.50 (m, 2H), 1.16-1.57 (m, 1H), 1.19-1.34 (m, 2H), 0.88 (t, J=7.4 Hz, 3H); MS (ESI+) m/z 377 (M+H)$^+$.

Example 291

(3aR,4S,6aS)-N,N-dipropyl-2-{[4-(trifluoromethyl)phenyl]sulfonyl}octahydrocyclopenta[c]pyrrol-4-amine The title compound was prepared as described in Example 290 following the procedures described in Examples 288 and 289: $^1$H NMR (500 MHz, pyridine-d$_5$) δ ppm 8.18-8.20 (m, 2H), 7.93-7.95 (m, 2H), 3.48 (dd, J=9.5, 2.3 Hz, 1H), 3.23 (dd, J=9.5, 2.8 Hz, 1H), 2.99 (dd, J=9.4, 7.7 Hz, 1H), 2.92 (dd, J=9.3, 7.8 Hz, 1H), 2.74-2.80 (m, 1H), 2.37-2.48 (m, 1H), 2.19-2.35 (m, 5H), 1.78-1.84 (m, 1H), 1.61-1.66 (m, 1H), 1.16-1.39 (m, 6H), 0.84 (t, J=7.3 Hz, 6H); MS (ESI+) m/z 419 (M+H)$^+$.

Example 292

(3aR,4S,6aS)-N-(cyclopropylmethyl)-2-{[4-(trifluoromethyl)phenyl]sulfonyl}octahydrocyclopenta[c]pyrrol-4-amine The title compound was prepared by substituting (bromomethyl)cyclopropane for iodoethane in the procedure described in Example 288: $^1$H NMR (500 MHz, pyridine-d$_5$) δ ppm 8.17-8.19 (m, 2H), 7.93-7.95 (m, 2H), 3.38 (dd, J=9.8, 3.2 Hz, 1H), 3.16 (dd, J=9.6, 3.2 Hz, 1H), 3.07 (dd, J=9.8, 8.0 Hz, 1H), 2.98 (dd, J=9.6, 7.6 Hz, 1H), 2.79-2.84 (m, 1H), 2.51-2.58 (m, 1H), 2.36-2.50 (m, 2H), 2.26-2.32 (m, 1H), 1.85-1.93 (m, 1H), 1.78-1.85 (m, 1H), 1.35-1.78 (m, 1H), 1.22-1.33 (m, 2H), 0.89-0.98 (m, 1H), 0.36-0.44 (m, 2H), 0.11-0.13 (m, 2H); MS (ESI+) m/z 389 (M+H)$^+$.

Example 293

(3aR,4S,6aS)-2-{[2-chloro-4-(trifluoromethyl)phenyl]sulfonyl}-N-ethyloctahydrocyclopenta[c]pyrrol-4-amine The title compound was prepared by substituting (3aR,4S,6aS)-2-{[2-chloro-4-(trifluoromethyl)phenyl]sulfonyl}octahydrocyclopenta[c]pyrrol-4-amine from Step B of Example 284 for (3aR,4S,6aS)-2-(4-(trifluoromethyl)phenylsulfonyl)octahydrocyclopenta[c]pyrrol-4-amine in the procedure described in Example 288: $^1$H NMR (500 MHz, pyridine-d$_5$) δ ppm 8.37 (d, J=8.2 Hz, 1H), 8.03 (s, 1H), 7.78 (dd, J=8.3, 1.7 Hz, 1H), 3.54 (dd, J=10.0, 3.5 Hz, 1H), 3.43 (dd, J=10.0, 8.0 Hz, 1H), 3.27-3.36 (m, 2H), 2.86 (q, J=5.9 Hz, 1H), 2.59-2.65 (m, 1H), 2.47-2.58 (m, 2H), 2.35-2.41 (m, 1H), 1.82-1.95 (m, 2H), 1.04-1.73 (m, 1H), 1.25-1.40 (m, 2H), 1.05 (t, J=7.1 Hz, 3H); MS (ESI+) m/z 397 (M+H)$^+$.

Example 294

(3aR,4S,6aS)-2-{[2-chloro-4-(trifluoromethyl)phenyl]sulfonyl}-N,N-diethyloctahydrocyclopenta[c]pyrrol-4-amine The title compound was prepared as described in Example 293 following the procedures described in Examples 288 and 289: $^1$H NMR (500 MHz, pyridine-d$_5$) δ ppm 8.38 (d, J=8.2 Hz, 1H), 8.04 (d, J=1.7 Hz, 1H), 7.77-7.79 (m, 1H), 3.57 (dd, J=9.9, 2.7 Hz, 1H), 3.34-3.41 (m, 2H), 3.29 (dd, J=9.9, 7.3 Hz, 1H), 2.81-2.87 (m, 1H), 2.33-2.57 (m, 6H), 1.80-1.86 (m, 1H), 1.68-1.74 (m, 1H), 1.22-1.43 (m, 2H), 0.94 (t, J=7.1 Hz, 6H); MS (ESI+) m/z 442 (M+NH$_4$)$^+$.

Example 295

(3aR,4S,6aS)-2-{[2-chloro-4-(trifluoromethyl)phenyl]sulfonyl}-N-[5-(trifluoromethyl)pyridin-2-yl]octahydrocyclopenta[c]pyrrol-4-amine (3aR,4S,6aS)-2-{[2-Chloro-4-(trifluoromethyl)phenyl]sulfonyl}octahydrocyclopenta[c]pyrrol-4-amine (70 mg, 0.190 mmol) from Step B of Example 284, 2-bromo-5-(trifluoromethyl)pyridine (42.9 mg, 0.190 mmol), and triethylamine (0.079 mL, 0.569 mmol) were combined in ethanol (0.6 mL). The reaction was heated at 86° C. for 5 days and the solvent was evaporated in vacuo. The resultant material was purified using a 12 g silica gel cartridge with a gradient of 0-0.8% methanol (2 N ammonia)/dichloromethane over 20 minutes to give crude product. It was further purified by loading it onto 2×0.25 mm preparative thin-layer chromatography plate and eluted with 30% acetone/hexanes to give the title compound: $^1$H NMR (500 MHz, pyridine-d$_5$) δ ppm 8.50-8.52 (bs, 1H), 8.40 (d, J=8.2 Hz, 1H), 8.03 (s, 1H), 7.96-7.98 (m, 1H), 7.75-7.78 (m, 1H), 7.54-7.59 (m, 1H), 6.59 (d, J=8.8 Hz, 1H), 4.30-4.42 (m, 1H), 3.89 (dd, J=10.2, 2.7 Hz, 1H), 3.57 (dd, J=10.2, 7.0 Hz, 1H), 3.43 (dd, J=9.9, 6.7 Hz, 1H), 3.39 (dd, J=10.0, 2.9 Hz, 1H), 2.68 (d, J=3.5 Hz, 2H), 2.13-2.20 (m, 1H), 1.90-1.97 (m, 1H), 1.59-1.66 (m, 1H), 1.40-1.48 (m, 1H); MS (ESI+) m/z 514 (M+H)$^+$.

Example 296 tert-butyl(S)-1-(ethyl((3aR,4S,6aS)-2-(4-(trifluoromethyl)phenylsulfonyl)octahydrocyclopenta[c]pyrrol-4-yl)amino)-4,4-dimethyl-1-oxopentan-2-yl(methyl)carbamate The title compound was prepared by substituting (S)-2-(tert-butoxycarbonyl(methyl)amino)-4,4-dimethylpentanoic acid from Step A of Example 247 for (S)-1-(tert-butoxycarbonyl)pyrrolidine-2-carboxylic acid and (3aR,4S,6aS)-N-ethyl-2-(4-(trifluoromethyl)phenylsulfonyl)octahydrocyclopenta[c]pyrrol-4-amine from Example 288 for (3aS,4R,6aR)-2-(3-(trifluoromethyl)phenylsulfonyl)octahydrocyclopenta[c]pyrrol-4-amine in the procedure described in Example 266: $^1$H NMR (400 MHz, pyridine-d$_5$) δ ppm 8.11 (d, J=8.3, 2H), 7.83 (d, J=8.4, 2H), 5.44-4.96 (m, 2H), 4.20-3.97 (m, 1H), 3.57-3.39 (m, 2H), 3.38-3.23 (m, 2H), 3.19 (d, J=4.1, 2H), 2.89 (s, 3H), 2.85-2.73 (m, 1H), 2.72-2.59 (m, 1H), 2.25-2.08 (m, 1H), 1.97-1.73 (m, 3H), 1.52 (s, 9H), 1.35-1.21 (m, 1H), 1.17 (t, J=7.0, 3H), 0.97 (s, 9H); MS (ESI+) m/z 604 (M+H)$^+$.

Example 297 tert-butyl(S)-4,4-dimethyl-1-oxo-1-(propyl((3aR,4S,6aS)-2-(4-(trifluoromethyl)phenylsulfonyl)octahydrocyclopenta[c]pyrrol-4-yl)amino)pentan-2-yl(methyl)carbamate The title compound was prepared by substituting (S)-2-(tert-butoxycarbonyl(methyl)amino)-4,4-dimethylpentanoic acid from Step A of Example 247 for (S)-1-(tert-butoxycarbonyl)pyrrolidine-2-carboxylic acid and (3aR,4S,6aS)-N-propyl-2-{[4-(trifluoromethyl)phenyl]sulfonyl}octahydrocyclopenta[c]pyrrol-4-amine from Example 290 for (3aS,4R,6aR)-2-(3-(trifluoromethyl)phenylsulfonyl)octahydrocyclopenta[c]pyrrol-4-amine in the procedure described in Example 266: $^1$H NMR (400 MHz, pyridine-d$_5$) δ ppm 8.11 (d, J=8.2, 2H), 7.83 (d, J=8.4, 2H), 5.37-5.09 (m, 1H), 4.15-3.99 (m, 1H), 3.54 (dd, J=10.1, 3.2, 1H), 3.48-3.35 (m, 1H), 3.29 (dt, J=9.1, 8.7, 1H), 3.18 (dd, J=9.1, 4.5, 3H), 2.90 (s, 3H), 2.86-2.77 (m, 1H), 2.74-2.64 (m, 1H), 2.24-2.09 (m, 1H), 1.96-1.86 (m, 2H), 1.85-1.75 (m, 1H), 1.59 (dt, J=15.2, 7.5, 3H), 1.52 (s, 9H), 1.34-1.22 (m, 1H), 0.98 (s, 9H), 0.90 (t, J=7.3, 3H); MS (ESI+) m/z 618 (M+H)$^+$.

Example 298 tert-butyl(S)-1-((cyclopropylmethyl)((3aR,4S,6aS)-2-(4-(trifluoromethyl)phenylsulfonyl)octahydrocyclopenta[c]pyrrol-4-yl)amino)-4,4-dimethyl-1-oxopentan-2-ylmethyl)carbamate The title compound was prepared by substituting (S)-2-(tert-butoxycarbonyl(methyl)amino)-4,4-dimethylpentanoic acid from Step A of Example 247 for (S)-1-(tert-butoxycarbonyl)pyrrolidine-2-carboxylic acid and (3aR,4S,6aS)-N-(cyclopropylmethyl)-2-{[4-(trifluoromethyl)phenyl]sulfonyl}octahydrocyclopenta[c]pyrrol-4-amine from Example 292 for (3aS,4R,6aR)-2-(3-(trifluoromethyl)phenylsulfonyl)octahydrocyclopenta[c]pyrrol-4-amine in the procedure described in Example 266: $^1$H NMR (400 MHz, pyridine-d$_5$) δ ppm 8.11 (d, J=8.2, 2H), 7.83 (d, J=8.3, 2H), 5.39-5.07 (m, 1H), 4.12-3.95 (m, 1H), 3.58 (dd, J=9.9, 3.4, 1H), 3.44-3.24 (m, 3H), 3.20 (d, J=4.7, 2H), 3.11-2.96 (m, 1H), 2.88 (s, 3H), 2.80-2.65 (m, 1H), 2.32-2.16 (m, 1H), 2.13-2.00 (m, 1H), 1.99-1.90 (m, 1H), 1.90-1.80 (m, 1H), 1.51 (m, 10H), 1.31 (ddd, J=20.7, 12.5, 7.9, 1H), 1.03-0.92 (m, 10H), 0.55 (tt, J=14.1, 7.5, 2H), 0.47-0.36 (m, 1H), 0.32-0.22 (m, 1H); MS (ESI+) m/z 630 (M+H)$^+$.

Example 299

2-nitro-N-((3aR,4S,6aS)-2-{[4-(trifluoromethyl)phenyl]sulfonyl}octahydrocyclopenta[c]pyrrol-4-yl)benzenesulfonamide (3aR,4S,6aS)-2-(4-(Trifluoromethyl)phenylsulfonyl)octahydrocyclopenta[c]pyrrol-4-amine (300 mg, 0.897 mmol) from Step A of Example 256 and triethylamine (0.313 mL, 2.243 mmol) were combined in dichloromethane (20 mL). 2-Nitrobenzene-1-sulfonyl chloride (258 mg, 1.166 mmol) in dichloromethane (5 mL) was added dropwise. The reaction mixture was stirred at room temperature for 16 hours. The reaction was quenched with water, and the organic layer was separated and concentrated. The resulted crude material was triturated with 50% diethyl ether/hexane, collected by filtration, washed with water then hexane to yield a solid. The crude solid was purified using a 12 g silica gel cartridge with a gradient of 10-100% ethyl acetate/hexane over 20 minutes to give the title compound: $^1$H NMR (500 MHz, pyridine-d$_5$) δ ppm 9.69 (s, 1H), 8.31 (dd, J=6.0, 3.3, 1H), 8.12 (d, J=8.2, 2H), 7.92 (dd, J=8.6, 2.1, 3H), 7.67 (dd, J=5.9, 3.3, 2H), 4.94 (s, 2H), 3.84 (dd, J=15.0, 6.2, 1H), 3.58 (dd, J=10.0, 2.4, 1H), 3.17 (dd, J=9.7, 2.7, 1H), 2.94 (dd, J=10.0, 7.7, 1H), 2.87 (dd, J=9.6, 7.7, 1H), 2.71 (td, J=9.3, 2.4, 1H), 2.60-2.50 (m, 1H), 1.94-1.80 (m, 2H), 1.71-1.58 (m, 1H), 1.23 (tt, J=10.5, 6.5, 1H); MS (ESI+) m/z 518 (M+H)$^+$.

Example 300

N-methyl-2-nitro-N-((3aR,4S,6aS)-2-{[4-(trifluoromethyl)phenyl]sulfonyl}octahydrocyclopenta[c]pyrrol-4-yl)benzenesulfonamide 2-Nitro-N-((3aR,4S,6aS)-2-(4-(trifluoromethyl)phenylsulfonyl)octahydrocyclopenta[c]pyrrol-4-yl)benzenesulfonamide (250 mg, 0.481 mmol) from Example 299 and dimethyl sulfate (0.138 mL, 1.444 mmol) were combined in N,N-dimethylformamide (3 mL) at 0° C. and 1,8-diazabicyclo[5.4.0]undec-7-ene (0.145 mL, 0.962 mmol) was added dropwise. The reaction mixture was stirred for 0.5 hours, water was added, and the precipitate was collected by filtration. The resultant crude material was purified using a 12 g silica gel cartridge eluting with a gradient of 0-60% ethyl acetate/hexane over 20 minutes to give the title compound: $^1$H NMR (500 MHz, pyridine-d$_5$) δ ppm 8.15 (dd, J=12.1, 4.7, 3H), 7.94 (d, J=8.3, 2H), 7.88 (dd, J=7.7, 1.3, 1H), 7.68 (dtd, J=19.1, 7.5, 1.3, 2H), 4.29 (dt, J=10.8, 7.0, 1H), 3.63 (dd, J=9.9, 1.5, 1H), 3.21 (dd, J=9.7, 2.3, 1H), 2.90 (s, 3H), 2.89-2.81 (m, 2H), 2.58-2.39 (m, 2H), 1.83-1.72 (m, 1H), 1.68-1.58 (m, 1H), 1.50 (qd, J=11.8, 7.3, 1H), 1.21 (ddd, J=19.4, 12.4, 7.1, 1H); MS (ESI+) m/z 551 (M+NH$_4$)$^+$.

Example 301

(3aR,4S,6aS)-N-methyl-2-{[4-(trifluoromethyl)phenyl]sulfonyl}octahydrocyclopenta[c]pyrrol-4-amine 2-Mercaptoethanol (0.056 mL, 0.793 mmol) was added dropwise to a mixture of N-methyl-2-nitro-N-((3aR,4S,6aS)-2-(4-(trifluoromethyl)phenylsulfonyl)octahydrocyclopenta[c]pyrrol-4-yl)benzenesulfonamide (235 mg, 0.440 mmol) from Example 300 and 1,8-diazabicyclo[5.4.0]undec-7-ene (0.166 mL, 1.101 mmol) in N,N-dimethylformamide (1 mL) at room temperature. The reaction mixture was stirred for 30 minutes, and 1 N NaHCO$_3$ solution was added, The mixture was extracted with dichloromethane, and the separated the organic layer was concentrated. The resultant crude material was purified using a SF15-12 g cartridge (Analogix®, Burlington, Wis.) with a gradient of 0-5.5% methanol (2 N NH$_3$)/dichloromethane over 20 minutes to give the title compound: $^1$H NMR (500 MHz, pyridine-d$_5$) δ ppm 8.17 (d, J=8.1, 2H), 7.94 (d, J=8.2, 2H), 4.93-4.86 (m, 1H), 3.34 (dd, J=9.8, 3.3, 1H), 3.14 (dd, J=9.7, 3.2, 1H), 3.06 (dd, J=9.7, 8.2, 1H), 2.65 (q, J=5.7, 1H), 2.57-2.46 (m, 1H), 2.29 (s, 3H), 2.25 (ddd, J=8.6, 5.0, 2.5, 1H), 1.86 (ddd, J=12.0, 8.6, 6.1, 1H), 1.80-1.72 (m, 1H), 1.61-1.32 (m, 1H), 1.32-1.19 (m, 2H); MS (ESI+) m/z 349 (M+H)$^+$.

Example 302 tert-butyl(S)-4,4-dimethyl-1-(methyl((3aR,4S,6aS)-2-(4-(trifluoromethyl)phenylsulfonyl)octahydrocyclopenta[c]pyrrol-4-yl)amino)-1-oxopentan-2-ylmethyl)carbamate The title compound was prepared by substituting (S)-2-(tert-butoxycarbonyl(methyl)amino)-4,4-dimethylpentanoic acid from Step A of Example 247 for (S)-1-(tert-butoxycarbonyl)pyrrolidine-2-carboxylic acid and (3aR,4S,6aS)-N-methyl-2-{[4-(trifluoromethyl)phenyl]sulfonyl}octahydrocyclopenta[c]pyrrol-4-amine from Example 301 for (3aS,4R,6aR)-2-(3-(trifluoromethyl)phenylsulfonyl)octahydrocyclopenta[c]pyrrol-4-amine in the procedure described in Example 266: $^1$H NMR (400 MHz, pyridine-$d_5$) δ ppm 8.11 (d, J=8.2, 2H), 7.83 (d, J=8.3, 2H), 5.37-5.10 (m, 1H), 4.73-4.53 (m, 1H), 3.57 (d, J=9.1, 1H), 3.24 (dd, J=16.5, 7.2, 2H), 3.16 (dd, J=9.9, 3.4, 1H), 2.94 (s, 3H), 2.88 (s, 3H), 2.64-2.51 (m, 2H), 2.25-2.09 (m, 1H), 1.89-1.78 (m, 1H), 1.77-1.54 (m, 3H), 1.52 (s, 9H), 1.26 (dt, J=17.5, 7.1, 1H), 0.96 (s, 9H); MS (ESI+) m/z 590 (M+H)$^+$.

Example 303

(2S)-2-(1,1-dioxidoisothiazolidin-2-yl)-4-methyl-N-{(3aS,4R,6aR)-2-[3-(trifluoromethyl)benzyl]octahydrocyclopenta[c]pyrrol-4-yl}pentanamide Step A: (2S)-N-[(3aS,4R,6aR)-2-Benzyloctahydrocyclopenta[c]pyrrol-4-yl]-2-(1,1-dioxidoisothiazolidin-2-yl)-4-methylpentanamide (265 mg, 0.611 mmol) from Example 220 Step D and ethanol (20 mL) were added to 20% Pd(OH)$_2$ on carbon, wet (53.0 mg, 0.377 mmol) in a 50 mL pressure bottle and stirred for 48 hours under 30 psi hydrogen at 50° C. The mixture was filtered through a nylon membrane and the solvent removed in vacuo to give (2S)-2-(1,1-dioxidoisothiazolidin-2-yl)-4-methyl-N-[(3aS,4R,6aR)-octahydrocyclopenta[c]pyrrol-4-yl]pentanamide: $^1$H NMR (500 MHz, pyridine-$d_5$) δ ppm 8.89 (dd, J=6.6, 18.9, 1H), 4.55-4.50 (m, 1H), 4.42-4.31 (m, 1H), 3.99-3.91 (m, 1H), 3.44-3.39 (m, 1H), 3.34 (dd, J=2.8, 11.4, 0.5H), 3.29-3.25 (m, 2H), 3.21 (dd, J=5.4, 13.2, 1H), 3.13 (dd, J=7.7, 11.2, 0.5H), 2.99 (td, J=7.5, 10.8, 1H), 2.79 (dd, J=3.3, 10.9, 0.5H), 2.73 (dd, J=3.3, 10.9, 0.5H), 2.69-2.55 (m, 2H), 2.31-2.16 (m, 2H), 2.12-2.00 (m, 1H), 1.94-1.78 (m, 4H), 1.69 (dddd, J=5.2, 11.0, 16.7, 19.8, 2H), 1.49-1.29 (m, 1H), 0.88 (t, J=6.5, 3H), 0.83 (t, J=6.4, 3H); MS (ESI+) m/z 344 (M+H)$^+$ Step B: (2S)-2-(1,1-Dioxidoisothiazolidin-2-yl)-4-methyl-N-[(3aS,4R,6aR)-octahydrocyclopenta[c]pyrrol-4-yl]pentanamide (204 mg, 0.594 mmol) and 3-(trifluoromethyl)benzaldehyde (0.158 mL, 1.188 mmol) were dissolved in dichloromethane (3 mL). Acetic acid (1 mL) was added. The reaction was stirred at ambient temperature for 20 min, then PS-cyanoborohydride (487 mg, 1.188 mmol) was added. The reaction was stirred at room temperature overnight, then filtered, and the solvent was removed in vacuo. The crude material was purified by silica gel chromatography using 1-10% methanol (2 N ammonia)/dichloromethane to the title compound: $^1$H NMR (500 MHz, pyridine-$d_5$) δ ppm 8.79 (d, J=7.0, 1H), 7.75 (d, J=10.3, 1H), 7.61-7.54 (m, 2H), 7.44 (t, J=7.7, 1H), 4.52 (dd, J=6.6, 8.9, 1H), 4.38 (dq, J=6.4, 12.6, 1H), 3.94 (dd, J=7.3, 16.2, 1H), 3.57 (dd, J=9.1, 13.5, 1H), 3.50-3.37 (m, 2H), 3.31-3.19 (m, 2H), 2.79 (ddd, J=3.0, 9.1, 19.0, 1H), 2.62-2.54 (m, 2H), 2.54-2.45 (m, 1H), 2.43-2.36 (m, 1H), 2.31-2.16 (m, 4H), 2.13-2.03 (m, 1H), 1.94-1.78 (m, 3H), 1.77-1.59 (m, 2H), 1.39 (dt, J=6.5, 19.8, 1H), 0.88 (d, J=6.6, 3H), 0.82 (dd, J=2.3, 6.5, 3H); MS (ESI+) m/z 502 (M+H)$^+$.

Example 304

2-isopropyl-3-methyl-N-{(3aS,4R,6aR)-2-[3-(trifluoromethyl)benzyl]octahydrocyclopenta[c]pyrrol-4-yl}butanamide The title compound was prepared by substituting N-[(3aS,4R,6aR)-2-benzyloctahydrocyclopenta[c]pyrrol-4-yl]-2-isopropyl-3-methylbutanamide from Example 235 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (500 MHz, pyridine-$d_5$) δ ppm 8.12-8.14 (m, 1H), 7.75-7.76 (bs, 1H), 7.55-7.63 (m, 2H), 7.44 (t, J=7.8 Hz, 1H), 4.42-4.48 (m, 1H), 3.62 (d, J=13.5 Hz, 1H), 3.46 (d, J=13.5 Hz, 1H), 2.86 (dd, J=9.0, 2.4 Hz, 1H), 2.50-2.57 (m, 2H), 2.44-2.49 (m, 1H), 2.25-2.31 (m, 2H), 2.06-2.15 (m, 3H), 1.83-1.90 (m, 2H), 1.58-1.65 (m, 1H), 1.35-1.42 (m, 1H), 1.14 (d, J=6.7 Hz, 3H), 1.13 (d, J=6.6 Hz, 3H), 0.98 (d, J=6.8 Hz, 6H); MS (ESI+) m/z 411 (M+H)$^+$.

Example 305

2-isopropyl-3-methyl-N-{(3aR,4S,6aS)-2-[3-(trifluoromethyl)benzyl]octahydrocyclopenta[c]pyrrol-4-yl}butanamide The title compound was prepared by substituting N-[(3aR,4S,6aS)-2-benzyloctahydrocyclopenta[c]pyrrol-4-yl]-2-isopropyl-3-methylbutanamide from Example 229 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (500 MHz, pyridine-$d_5$) δ ppm 8.12-8.14 (m, 1H), 7.75-7.77 (bs, 1H), 7.58-7.63 (m, 1H), 7.42-7.47 (m, 1H), 4.42-4.48 (m, 1H), 3.62 (d, J=13.5 Hz, 1H), 3.46 (d, J=13.5 Hz, 1H), 2.85 (dd, J=8.9, 2.5 Hz, 1H), 2.50-2.58 (m, 2H), 2.45-2.49 (m, 1H), 2.28 (d, J=6.6 Hz, 2H), 2.06-2.16 (m, 4H), 1.84-1.90 (m, 2H), 1.58-1.66 (m, 1H), 1.35-1.42 (m, 1H), 1.14 (d, J=6.6 Hz, 3H), 1.13 (d, J=6.6 Hz, 3H), 0.98 (d, J=6.8 Hz, 6H); MS (ESI−) m/z 409 (M−H)−.

Example 306 tert-butyl(S)-4-methyl-1-oxo-1-((3aR,4S,6aS)-2-(3-(trifluoromethyl)benzyl)octahydrocyclopenta[c]pyrrol-4-ylamino)pentan-2-ylcarbamate The title compound was prepared by substituting tert-butyl (S)-1-((3aR,4S,6aS)-2-benzyloctahydrocyclopenta[c]pyrrol-4-ylamino)-4-methyl-1-oxopentan-2-ylcarbamate from Example 221 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (400 MHz, pyridine-$d_5$) δ ppm 8.64 (d, J=7.2 Hz, 1H), 7.96-7.99 (m, 1H), 7.72-7.77 (m, 1H), 7.55-7.63 (m, 2H), 7.44 (t, J=7.7 Hz, 1H), 4.66-4.75 (m, 1H), 4.35-4.44 (m, 1H), 3.59 (d, J=13.5 Hz, 1H), 3.46 (d, J=13.6 Hz, 1H), 2.81-2.84 (m, 1H), 2.44-2.59 (m, 3H), 2.22-2.31 (m, 2H), 2.14 (s, 3H, OAc), 1.96-2.07 (m, 1H), 1.79-1.91 (m, 4H), 1.55-1.70 (m, 1H), 1.50 (s, 9H), 1.27-1.41 (m, 1H), 0.82-0.89 (m, 6H); MS (ESI+) m/z 498 (M+H)$^+$.

Example 307 tert-butyl methyl((S)-4-methyl-1-oxo-1-((3aR,4S, 6aS)-2-(3-(trifluoromethyl)benzyl)octahydrocyclopenta[c]pyrrol-4-ylamino)pentan-2-yl)carbamate The title compound was prepared by substituting tert-butyl (S)-1-((3aR,4S,6aS)-2-benzyloctahydrocyclopenta[c]pyrrol-4-ylamino)-4-methyl-1-oxopentan-2-yl(methyl)carbamate from Example 222 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (500 MHz, pyridine-$d_5$) δ ppm 8.27-8.34 (m, 1H), 7.75-7.76 (bs, 1H), 7.52-7.63 (m, 2H), 7.42-7.47 (m, 1H), 5.1 (m, 0.7H), 4.7 (0.3H), 4.35-4.41 (m, 1H), 3.59 (d, J=13.5 Hz, 1H), 3.45-3.49 (m, 1H), 3.04-3.13 (m, 3H), 2.82-2.85 (m, 1H), 2.42-2.54 (m, 3H), 2.22-2.31 (m, 2H), 1.98-2.11 (m, 1H), 1.80-2.11 (m, 1H), 1.79-1.87 (m, 2H), 1.53-1.62 (m, 2H), 1.46-1.48 (m, 9H), 1.33-1.38 (m, 1H), 0.88 (d, J=6.4 Hz, 3H), 0.85 (d, J=6.6 Hz, 3H); MS (ESI+) m/z 512 (M+H)$^+$.

Example 308 tert-butyl methyl((S)-4-methyl-1-oxo-1-((3aR,4S, 6aS)-2-(4-(trifluoromethyl)benzyl)octahydrocyclopenta[c]pyrrol-4-ylamino)pentan-2-yl)carbamate The title compound was prepared by substituting tert-butyl (S)-1-((3aR,4S,6aS)-2-benzyloctahydrocyclopenta[c]pyrrol-4-ylamino)-4-methyl-1-oxopentan-2-yl(methyl)carbamate from Example 222 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedures described in Example 303: $^1$H NMR (500 MHz, pyridine-$d_5$) δ ppm 8.31-8.36 (bs, 1H), 7.64-7.66 (m, 2H), 7.50-7.53 (m, 2H), 5.1 (m, 0.7H) 4.7 (0.3H), 4.38-4.43 (m, 1H), 3.57 (d, J=13.7 Hz, 1H), 3.45-3.49 (m, 1H), 3.04-3.12 (m, 3H), 2.84-2.87 (m, 1H), 2.51-2.56 (m, 2H), 2.35-2.42 (m, 1H), 2.30-2.35 (m, 1H), 2.20-2.24 (m, 1H), 2.05-2.10 (m, 1H), 1.81-1.93 (m, 3H), 1.55-1.61 (m, 2H), 1.46-1.48 (m, 9H), 1.35-1.40 (m, 1H), 0.88 (d, J=6.3 Hz, 3H), 0.85 (d, J=6.6 Hz, 3H); MS (ESI+) m/z 512 (M+H)$^+$.

Example 309 tert-butyl(S)-1-((3aR,4S,6aS)-2-(4-fluorobenzyl) octahydrocyclopenta[c]pyrrol-4-ylamino)-4-methyl-1-oxopentan-2-yl(methyl)carbamate The title compound was prepared by substituting tert-butyl (S)-1-((3aR,4S,6aS)-2-benzyloctahydrocyclopenta[c]pyrrol-4-ylamino)-4-methyl-1-oxopentan-2-yl(methyl)carbamate from Example 222 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluorobenzaldehyde for 3-(trifluoromethyl)benzaldehyde in the procedures described in Example 303: $^1$H NMR (500 MHz, pyridine-$d_5$) δ ppm 8.30-8.32 (m, 1H), 7.35-7.38 (m, 2H), 7.12 (t, J=8.6 Hz, 2H), 5.1 (m, 0.7H) 4.7 (0.3H), 4.37-4.41 (m, 1H), 3.50 (d, J=13.1 Hz, 1H), 3.40 (d, J=13.1 Hz, 1H), 3.04-3.11 (m, 3H), 2.81-2.84 (m, 1H), 2.47-2.53 (m, 2H), 2.29-2.39 (m, 1H), 2.19-2.23 (m, 1H), 2.02-2.11 (m, 1H), 1.79-1.94 (m, 3H), 1.53-1.62 (m, 2H), 1.46-1.48 (m, 9H), 1.34-1.39 (m, 1H), 0.89 (d, J=6.4 Hz, 3H), 0.85 (d, J=6.6 Hz, 3H); MS (ESI+) m/z 462 (M+H)$^+$.

Example 310 tert-butyl ethyl((S)-4-methyl-1-oxo-1-((3aR,4S,6aS)-2-(3-(trifluoromethyl)benzyl)octahydrocyclopenta[c]pyrrol-4-ylamino)pentan-2-yl)carbamate The title compound was prepared by substituting tert-butyl (S)-1-((3aR,4S,6aS)-2-benzyloctahydrocyclopenta[c]pyrrol-4-ylamino)-4-methyl-1-oxopentan-2-yl(ethyl)carbamate from Example 223 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (500 MHz, pyridine-$d_5$) δ ppm 8.14-8.17 (m, 1H), 7.74-7.77 (m, 1H), 7.55-7.61 (m, 2H), 7.41-7.46 (m, 1H), 5.1 (m, 0.7H) 4.7 (0.3H), 4.32-4.42 (m, 1H), 3.59 (d, J=13.4 Hz, 1H), 3.38-3.53 (m, 3H), 2.78-2.87 (m, 1H), 2.44-2.54 (m, 2H), 2.36-2.44 (m, 1H), 2.28-2.35 (m, 1H), 2.20-2.27 (m, 1H), 2.01-2.13 (m, 1H), 1.91-2.01 (m, 1H), 1.79-1.88 (m, 1H), 1.71-1.79 (m, 1H), 1.62-1.71 (m, 1H), 1.53-1.62 (m, 1H), 1.48 (s, 9H), 1.33-1.42 (m, 1H), 1.17-1.33 (m, 3H), 0.83-0.97 (m, 6H); MS (ESI+) m/z 526 (M+H)$^+$.

Example 311 tert-butyl(S)-1-((3aS,4R,6aR)-2-(3-fluoro-4-(trifluoromethyl)benzyl)octahydrocyclopenta[c]pyrrol-4-ylamino)-4-methyl-1-oxopentan-2-ylmethyl)carbamate The title compound was prepared by substituting $N^1$-[(3aS, 4R,6aR)-2-benzyloctahydrocyclopenta[c]pyrrol-4-yl]-$N^2$-(tert-butyloxycarbonyl)-$N^2$-methyl-L-leucinamide from Example 151 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 3-fluoro-4-(trifluoromethyl) benzaldehyde for 3-(trifluoromethyl)benzaldehyde in the procedures described in Example 303: $^1$H NMR (500 MHz, pyridine-$d_5$) δ ppm 8.33-8.42 (m, 1H), 7.31-7.35 (m, 1H), 7.24-7.29 (m, 1H), 5.1 (m, 0.7H) 4.7 (0.3H), 4.35-4.42 (m, 1H), 3.51-3.56 (m, 1H), 3.41-3.45 (m, 1H), 3.04-3.12 (m, 3H), 2.77-2.97 (m, 1H), 2.47-2.52 (m, 2H), 2.29-2.35 (m, 2H), 2.19-2.22 (m, 1H), 2.06-2.15 (m, 1H), 1.83-1.89 (m, 3H), 1.53-1.66 (m, 2H), 1.47 (s, 9H), 1.32-1.41 (m, 2H), 0.88-0.90 (m, 3H), 0.85 (d, J=6.6 Hz, 3H); MS (ESI+) m/z 530 (M+H)$^+$.

Example 312 tert-butyl(S)-1-((3aS,4R,6aR)-2-(4-fluoro-3-(trifluoromethyl)benzyl)octahydrocyclopenta[c]pyrrol-4-ylamino)-4-methyl-1-oxopentan-2-ylmethyl)carbamate The title compound was prepared by substituting $N^1$-[(3aS, 4R,6aR)-2-benzyloctahydrocyclopenta[c]pyrrol-4-yl]-$N^2$-(tert-butyloxycarbonyl)-$N^2$-methyl-L-leucinamide from Example 151 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluoro-3-(trifluoromethyl) benzaldehyde for 3-(trifluoromethyl)benzaldehyde in the procedures described in Example 303: $^1$H NMR (500 MHz, pyridine-$d_5$) δ ppm 8.32-8.39 (m, 1H), 7.62-7.75 (m, 1H), 7.20-7.27 (m, 2H), 5.1 (m, 0.7H) 4.7 (0.3H), 4.29-4.47 (m, 1H), 3.49-3.54 (m, 1H), 3.38-3.43 (m, 1H), 3.04-3.12 (m, 3H), 2.74-2.89 (m, 1H), 2.47-2.51 (m, 2H), 2.19-2.38 (m, 3H), 2.05-2.15 (m, 1H), 1.84 (dd, J=9.0, 5.2 Hz, 3H), 1.54-1.65 (m, 2H), 1.46 (s, 9H), 1.26-1.42 (m, 1H), 0.89 (d, J=6.4 Hz, 3H), 0.85 (d, J=6.6 Hz, 3H); MS (ESI+) m/z 530 (M+H)$^+$.

Example 313 tert-butyl methyl((S)-1-oxo-1-((3aR,4S,6aS)-2-(3-(trifluoromethyl)benzyl)octahydrocyclopenta[c]pyrrol-4-ylamino)pentan-2-yl)carbamate Step A: tert-Butyl methyl((S)-1-oxo-1-((3aR,4S,6aS)-2-benzyloctahydrocyclopenta[c]pyrrol-4-ylamino)pentan-2-yl)carbamate was prepared by substituting N-(tert-butoxycarbonyl)-N-methyl-L-norvaline for N-(tert-butoxycarbonyl)-L-leucine in the procedure described in Example 221: $^1$H NMR (500 MHz, pyridine-d$_5$) δ ppm 8.26-8.15 (m, 1H), 7.43 (d, J=7.4, 2H), 7.36 (t, J=7.5, 2H), 7.27 (t, J=7.3, 1H), 5.07-5.00 (m, 1H), 4.72-4.58 (m, 1H), 4.46-4.31 (m, 1H), 3.59 (d, J=13.1, 1H), 3.44 (d, J=13.1, 1H), 3.12-2.99 (m, 3H), 2.83 (d, J=8.9, 1H), 2.53-2.44 (m, 2H), 2.44-2.37 (m, 1H), 2.33 (d, J=7.9, 1H), 2.26-2.19 (m, 1H), 2.14-1.95 (m, 2H), 1.79 (ddt, J=7.1, 5.2, 4.2, 2H), 1.62-1.51 (m, 1H), 1.46 (s, 9H), 1.40-1.24 (m, 2H), 0.83 (t, J=6.7, 3H); MS (ESI+) m/z 430 (M+H)$^+$.

Step B: The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Step A for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (500 MHz, pyridine-d$_5$) δ ppm 8.24-8.26 (m, 1H), 7.75-7.76 (bs, 1H), 7.54-7.62 (m, 2H), 7.44 (t, J=7.7 Hz, 1H), 5.1 (m, 0.7H), 4.7 (0.3H), 4.33-4.44 (m, 1H), 3.59 (d, J=13.5 Hz, 1H), 3.45-3.48 (m, 1H), 3.02-3.10 (m, 3H), 2.82-2.85 (m, 1H), 2.46-2.54 (m, 2H), 2.40-2.43 (m, 1H), 2.28-2.32 (m, 1H), 2.21-2.25 (m, 1H), 1.99-2.04 (m, 2H), 1.76-1.86 (m, 2H), 1.48-1.63 (m, 1H), 1.46 (s, 9H), 1.20-1.41 (m, 3H), 0.80-0.86 (m, 3H); MS (ESI+) m/z 498 (M+H)$^+$.

Example 314 tert-butyl methyl((S)-1-oxo-1-((3aR,4S,6aS)-2-(4-(trifluoromethyl)benzyl)octahydrocyclopenta[c]pyrrol-4-ylamino)pentan-2-yl)carbamate The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Step A of Example 313 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedures described in Example 303: $^1$H NMR (500 MHz, pyridine-d$_5$) δ ppm 8.25-8.29 (bs, 1H), 7.64-7.66 (m, 2H), 7.50-7.52 (m, 2H), 5.1 (m, 0.7H), 4.7 (0.3H), 4.37-4.43 (m, 1H), 3.55-3.59 (m, 1H), 3.45-3.48 (m, 1H), 3.02-3.11 (m, 3H), 2.84-2.87 (m, 1H), 2.45-2.54 (m, 2H), 2.30-2.39 (m, 2H), 2.20-2.23 (m, 1H), 2.02-2.15 (m, 2H), 1.77-1.87 (m, 2H), 1.52-1.59 (m, 1H), 1.46-1.47 (m, 9H), 1.28-1.39 (m, 3H), 0.81-0.85 (m, 3H); MS (ESI+) m/z 498 (M+H)$^+$.

Example 315 tert-butyl(S)-1-((3aR,4S,6aS)-2-(4-fluorobenzyl)octahydrocyclopenta[c]pyrrol-4-ylamino)-1-oxopentan-2-ylmethyl)carbamate The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Step A of Example 313 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluorobenzaldehyde for 3-(trifluoromethyl)benzaldehyde in the procedures described in Example 303: $^1$H NMR (500 MHz, pyridine-d$_5$) δ ppm 8.23-8.27 (m, 1H), 7.34-7.38 (m, 2H), 7.12 (t, J=8.5 Hz, 2H), 5.1 (m, 0.7H), 4.7 (0.3H), 4.33-4.45 (m, 1H), 3.50 (d, J=13.1 Hz, 1H), 3.38-3.41 (m, 1H), 3.02-3.11 (m, 3H), 2.81-2.84 (m, 1H), 2.44-2.53 (m, 2H), 2.29-2.39 (m, 2H), 2.19-2.23 (m, 1H), 2.02-2.04 (m, 2H), 1.81-1.84 (m, 2H), 1.55-1.59 (m, 1H), 1.46-1.47 (m, 9H), 1.28-1.38 (m, 3H), 0.81-0.85 (m, 3H); MS (ESI+) m/z 448 (M+H)$^+$.

Example 316 tert-butyl methyl((S)-3-methyl-1-oxo-1-((3aS,4R,6aR)-2-(3-(trifluoromethyl)benzyl)octahydrocyclopenta[c]pyrrol-4-ylamino)butan-2-yl)carbamate The title compound was prepared by substituting tert-butyl (S)-1-((3aS,4R,6aR)-2-benzyloctahydrocyclopenta[c]pyrrol-4-ylamino)-3-methyl-1-oxobutan-2-yl(methyl)carbamate from Example 232 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedures described in Example 303: $^1$H NMR (400 MHz, pyridine-d$_5$, temperature 90° C.) δ ppm 7.69-7.70 (bs, 1H), 7.49-7.57 (m, 2H), 7.32-7.41 (m, 2H), 4.31-4.35 (m, 1H), 4.19-4.29 (m, 1H), 3.57 (d, J=13.5 Hz, 1H), 3.50 (d, J=13.6 Hz, 1H), 3.00 (s, 3H), 2.76 (d, J=6.4 Hz, 1H), 2.50-2.56 (m, 1H), 2.38-2.46 (m, 3H), 2.28-2.37 (m, 2H), 2.06 (dq, J=12.2, 6.1 Hz, 1H), 1.82-1.90 (m, 1H), 1.52-1.62 (m, 1H), 1.46 (s, 9H), 1.35-1.44 (m, 1H), 1.00 (d, J=6.5 Hz, 3H), 0.87 (d, J=6.7 Hz, 3H); MS (ESI+) m/z 498 (M+H)$^+$.

Example 317 tert-butyl methyl((S)-1-oxo-1-((3aS,4R,6aR)-2-(4-(trifluoromethyl)benzyl)octahydrocyclopenta[c]pyrrol-4-ylamino)pentan-2-yl)carbamate The title compound was prepared by substituting tert-butyl (S)-1-((3aS,4R,6aR)-2-benzyloctahydrocyclopenta[c]pyrrol-4-ylamino)-1-oxopentan-2-yl(methyl)carbamate from Example 233 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedures described in Example 303: $^1$H NMR (400 MHz, pyridine-d$_5$, temperature 90° C.) δ ppm 7.58-7.61 (m, 2H), 7.45-7.48 (m, 2H), 7.18-7.28 (m, 1H), 4.70-4.75 (m, 1H), 4.22-4.30 (m, 1H), 3.48-3.59 (m, 2H), 2.94 (s, 3H), 2.78-2.81 (m, 1H), 2.52-2.57 (m, 1H), 2.34-2.47 (m, 3H), 2.27-2.32 (m, 1H), 2.04-2.12 (m, 1H), 1.93-2.03 (m, 1H), 1.82-1.91 (m, 1H), 1.71-1.81 (m, 1H), 1.49-1.67 (m, 1H), 1.46-1.47 (m, 9H), 1.37-1.46 (m, 1H), 1.26-1.36 (m, 2H), 0.87 (t, J=7.4 Hz, 3H); MS (ESI+) m/z 498 (M+H)+.

Example 318 tert-butyl(S)-1-((3aS,4R,6aR)-2-(4-fluorobenzyl) octahydrocyclopenta[c]pyrrol-4-ylamino)-1-oxopentan-2-ylmethyl)carbamate The title compound was prepared by substituting tert-butyl (S)-1-((3aS,4R,6aR)-2-benzyloctahydrocyclopenta[c]pyrrol-4-ylamino)-1-oxopentan-2-yl(methyl)carbamate from Example 233 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluorobenzaldehyde for 3-(trifluoromethyl)benzaldehyde in the procedures described in Example 303: ¹H NMR (400 MHz, pyridine-d₅, temperature 90° C.) δ ppm 7.28-7.32 (m, 2H), 7.16-7.21 (m, 1H), 7.02 (t, J=8.6 Hz, 2H), 4.69-4.77 (m, 1H), 4.21-4.28 (m, 1H), 3.49 (d, J=13.2 Hz, 1H), 3.43 (d, J=13.2 Hz, 1H), 2.94 (s, 3H), 2.76-2.78 (m, 1H), 2.48-2.55 (m, 1H), 2.33-2.46 (m, 3H), 2.25-2.32 (m, 1H), 2.04-2.14 (m, 1H), 1.94-2.03 (m, 1H), 1.82-1.91 (m, 1H), 1.70-1.81 (m, 1H), 1.49-1.58 (m, 1H), 1.46-1.48 (m, 9H), 1.37-1.44 (m, 1H), 1.28-1.36 (m, 2H), 0.87 (t, J=7.4 Hz, 3H); MS (ESI+) m/z 448 (M+H)+.

Example 319

(2S)-4-methyl-2-morpholin-4-yl-N-((3aS,4R,6aR)-2-{[3-(trifluoromethyl)phenyl]sulfonyl}octahydrocyclopenta[c]pyrrol-4-yl)pentanamide Step A: (S)-N-((3aS,4R,6aR)-2-Benzyloctahydrocyclopenta[c]pyrrol-4-yl)-4-methyl-2-morpholinopentanamide (0.400 g, 1.001 mmol) from Step B of Example 249 and ethanol (40 mL) were added to 20% Pd(OH)₂ on carbon, wet (0.080 g, 0.570 mmol) in a 250 mL stainless steel pressure bottle and stirred for 16 hours under 30 psi hydrogen at 55° C. The mixture was filtered through a nylon membrane and the solvent removed in vacuo to give (S)-4-methyl-2-morpholino-N-((3aS,4R,6aR)-octahydrocyclopenta[c]pyrrol-4-yl)pentanamide: ¹H NMR (500 MHz, pyridine-d₅) δ ppm 8.46 (d, J=6.9, 1H), 4.46-4.38 (m, 1H), 3.74 (s, 4H), 3.45 (dd, J=2.0, 11.3, 1H), 3.31-3.21 (m, 2H), 3.10 (dd, J=7.0, 11.0, 1H), 2.89 (dd, J=2.3, 11.0, 1H), 2.83-2.77 (m, 2H), 2.76-2.67 (m, 4H), 2.09 (td, J=6.0, 11.8, 1H), 1.95-1.87 (m, 1H), 1.84 (dq, J=6.0, 9.7, 2H), 1.71-1.57 (m, 2H), 1.49 (ddt, J=6.3, 9.1, 12.5, 1H), 0.94 (dd, J=6.3, 11.2, 6H); MS (ESI+) m/z 310 (M+H)+

Step B: (S)-4-Methyl-2-morpholino-N-((3aS,4R,6aR)-octahydrocyclopenta[c]pyrrol-4-yl)pentanamide (191 mg, 0.617 mmol), triethylamine (0.129 mL, 0.926 mmol), and 3-(trifluoromethyl)benzene-1-sulfonyl chloride (0.109 mL, 0.679 mmol) were combined in dichloromethane (0.5 mL). The reaction was stirred at room temperature for 3 hours. The crude material was purified by silica gel chromatography using 1-10% methanol (2 N ammonia)/dichloromethane to give the title compound: ¹H NMR (500 MHz, pyridine-d₅) δ ppm 8.44 (d, J=6.2, 1H), 8.38 (s, 1H), 8.19 (d, J=7.9, 1H), 7.92 (d, J=7.8, 1H), 7.72 (t, J=7.9, 1H), 4.27-4.20 (m, 1H), 3.90 (dd, J=2.3, 10.0, 1H), 3.76-3.67 (m, 4H), 3.20 (ddd, J=3.9, 9.4, 10.9, 3H), 2.97 (dd, J=7.1, 9.6, 1H), 2.78-2.72 (m, 2H), 2.72-2.67 (m, 2H), 2.62-2.53 (m, 2H), 1.94 (dt, J=6.2, 12.1, 1H), 1.89-1.77 (m, 3H), 1.64-1.54 (m, 2H), 1.30 (ddt, J=6.5, 9.3, 12.8, 1H), 0.92 (d, J=4.4, 3H), 0.91 (d, J=4.4, 3H); MS (ESI+) m/z 518(M+H)+.

Example 320

(2S)-4-methyl-2-pyrrolidin-1-yl-N-((3aS,4R,6aR)-2-{[3-(trifluoromethyl)phenyl]sulfonyl}octahydrocyclopenta[c]pyrrol-4-yl)pentanamide The title compound was prepared by substituting (2S)-N-[(3aS,4R,6aR)-2-benzyloctahydrocyclopenta[c]pyrrol-4-yl]-4-methyl-2-pyrrolidin-1-ylpentanamide from Example 250 for (S)-N-((3aS,4R,6aR)-2-benzyloctahydrocyclopenta[c]pyrrol-4-yl)-4-methyl-2-morpholinopentanamide in the procedures described in Example 319: ¹H NMR (500 MHz, pyridine-d₅) δ ppm 8.37-8.39 (m, 1H), 8.17-8.20 (m, 1H), 8.12-8.15 (m, 1H), 7.89-7.92 (m, 1H), 7.71 (t, J=7.8 Hz, 1H), 4.23-4.29 (m, 1H), 3.86 (dd, J=9.9, 2.4 Hz, 1H), 3.16-3.20 (m, 2H), 3.13-3.15 (m, 1H), 2.97 (dd, J=9.6, 6.8 Hz, 1H), 2.65-2.69 (m, 2H), 2.55-2.61 (m, 4H), 1.90-2.00 (m, 1H), 1.76-1.90 (m, 3H), 1.54-1.62 (m, 6H), 1.25-1.34 (m, 1H), 0.98 (d, J=6.3 Hz, 3H), 0.91 (d, J=6.3 Hz, 3H); MS (ESI+) m/z 502 (M+H)+.

Example 321

(2S)-4-methyl-2-piperidin-1-yl-N-((3aS,4R,6aR)-2-{[3-(trifluoromethyl)phenyl]sulfonyl}octahydrocyclopenta[c]pyrrol-4-yl)pentanamide The title compound was prepared by substituting (2S)-N-[(3aS,4R,6aR)-2-benzyloctahydrocyclopenta[c]pyrrol-4-yl]-4-methyl-2-piperidin-1-ylpentanamide from Example 251 for (S)-N-((3aS,4R,6aR)-2-benzyloctahydrocyclopenta[c]pyrrol-4-yl)-4-methyl-2-morpholinopentanamide in the procedures described in Example 319: ¹H NMR (500 MHz, pyridine-d₅) δ ppm 8.38-8.39 (bs, 1H), 8.18-8.20 (m, 2H), 7.90-7.92 (m, 1H), 7.71 (t, J=7.8 Hz, 1H), 4.20-4.26 (m, 1H), 3.87 (dd, J=9.9, 2.1 Hz, 1H), 3.16-3.20 (m, 3H), 2.97 (dd, J=9.5, 6.3 Hz, 1H), 2.56-2.64 (m, 6H), 1.80-1.97 (m, 4H), 1.46-1.59 (m, 6H), 1.23-1.37 (m, 3H), 0.93 (d, J=6.6 Hz, 3H), 0.92 (d, J=6.7 Hz, 3H); MS (ESI+) m/z 516 (M+H)+.

Example 322 tert-butyl methyl((S)-4-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate The title compound was prepared by substituting tert-butyl (S)-1-((3aR,4S,6aS)-2-benzyloctahydrocyclopenta[c]pyrrol-4-ylamino)-4-methyl-1-oxopentan-2-yl(methyl)carbamate from Example 222 for (S)-N-((3aS,4R,6aR)-2-benzyloctahydrocyclopenta[c]pyrrol-4-yl)-4-methyl-2-morpholinopentanamide in the procedures described in Example 319: ¹H NMR (500 MHz, pyridine-d₅) δ ppm 8.48-8.50 (m, 1H), 8.36-8.37 (bs, 1H), 8.19 (d, J=7.9 Hz, 1H), 7.91 (d, J=7.9 Hz, 1H), 7.72 (t, J=7.8 Hz, 1H), 5.13 (m, 0.7H), 4.78 (m, 0.3H), 4.15-4.29 (m, 1H), 3.84 (dd, J=9.9, 2.1 Hz, 1H), 3.13-3.16 (m, 1H), 3.02-3.12 (m, 4H), 2.91 (dd, J=9.6, 6.9 Hz, 1H), 2.48-2.52 (m, 2H), 1.74-1.90 (m, 4H), 1.49-1.67 (m, 2H), 1.44-1.46 (m, 9H), 1.16-1.29 (m, 1H), 0.89 (d, J=6.4 Hz, 3H), 0.84 (d, J=6.4 Hz, 3H); MS (ESI+) m/z 562 (M+H)+.

Example 323 tert-butyl ethyl((S)-4-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate The title compound was prepared by substituting tert-butyl (S)-1-((3aR,4S,6aS)-2-benzyloctahydrocyclopenta[c]pyrrol-4-ylamino)-4-methyl-1-oxopentan-2-yl(ethyl)carbamate from Example 223 for (S)-N-((3aS,4R,6aR)-2-benzyloctahydrocyclopenta[c]pyrrol-4-yl)-4-methyl-2-morpholinopentanamide in the procedures described in Example 319: $^1$H NMR (500 MHz, pyridine-$d_5$) δ ppm 8.37-8.40 (m, 2H), 8.19 (d, J=7.9 Hz, 1H), 7.91 (d, J=7.9 Hz, 1H), 7.72 (t, J=7.9 Hz, 1H), 5.0 (m, 0.7H), 4.7 (m, 0.3H), 4.16-4.27 (m, 1H), 3.83-3.86 (m, 1H), 3.43-3.49 (m, 2H), 3.09-3.18 (m, 2H), 2.90-2.94 (m, 1H), 2.43-2.58 (m, 2H), 1.90-2.02 (m, 2H), 1.71-1.84 (m, 2H), 1.62-1.67 (m, 1H), 1.34-1.59 (m, 10H), 1.21-1.31 (m, 4H), 0.88-0.91 (m, 6H); MS (ESI+) m/z 576 (M+H)+.

Example 324 tert-butyl methyl((S)-4-methyl-1-oxo-1-((3aS,4R,6aR)-2-(4-(trifluoromethyl)phenylsulfonyl)octahydrocyclopenta[c]pyrrol-4-ylamino)pentan-2-yl)carbamate The title compound was prepared by substituting $N^1$-[(3aS,4R,6aR)-2-benzyloctahydrocyclopenta[c]pyrrol-4-yl]-$N^2$-(tert-butyloxycarbonyl)-$N^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (501 MHz, pyridine-$d_5$, temperature 60° C.) δ ppm 8.08-8.11 (m, 2H), 7.99-8.03 (bs, 1H), 7.84-7.87 (m, 2H), 4.95 (m, 0.7H), 4.4 (m, 0.3H), 4.11-4.17 (m, 1H), 3.70-3.74 (m, 1H), 3.15-3.21 (m, 1H), 3.13 (dd, J=9.8, 2.8 Hz, 1H), 3.03 (dd, J=9.7, 7.3 Hz, 1H), 3.00 (s, 3H), 2.50-2.54 (m, 2H), 1.89-1.97 (m, 1H), 1.72-1.89 (m, 3H), 1.50-1.61 (m, 2H), 1.45 (s, 9H), 1.28 (ddt, J=9.5, 12.9, 6.5 Hz, 1H), 0.89 (d, J=6.8 Hz, 3H), 0.85 (d, J=6.5 Hz, 3H); MS (DCI+) m/z 562 (M+H)+, 579 (M+NH$_4$)+.

Example 325 tert-butyl methyl((S)-4-methyl-1-oxo-1-((3aS,4R,6aR)-2-(3-(trifluoromethyl)phenylsulfonyl)octahydrocyclopenta[c]pyrrol-4-ylamino)pentan-2-yl)carbamate The title compound was prepared by substituting $N^1$-[(3aS,4R,6aR)-2-benzyloctahydrocyclopenta[c]pyrrol-4-yl]-$N^2$-(tert-butyloxycarbonyl)-$N^2$-methyl-L-leucinamide from Example 151 for (S)-N-((3aS,4R,6aR)-2-benzyloctahydrocyclopenta[c]pyrrol-4-yl)-4-methyl-2-morpholinopentanamide in the procedures described in Example 319: $^1$H NMR (501 MHz, pyridine-$d_5$, temperature 60° C.) δ ppm 8.32-8.33 (bs, 1H), 8.15 (d, J=8.1 Hz, 1H), 7.97-8.01 (m, 1H), 7.87 (d, J=7.7 Hz, 1H), 7.68 (t, J=7.9 Hz, 1H), 4.95 (m, 0.7H), 4.4 (m, 0.3H), 4.11-4.15 (m, 1H), 3.71-3.75 (m, 1H), 3.12-3.18 (m, 2H), 3.00-3.04 (m, 1H), 2.99 (s, 3H), 2.48-2.52 (m, 2H), 1.90-1.96 (m, 1H), 1.73-1.86 (m, 3H), 1.50-1.60 (m, 2H), 1.46 (s, 9H), 1.24-1.30 (m, 1H), 0.88 (d, J=6.6 Hz, 3H), 0.85 (d, J=6.5 Hz, 3H); MS (ESI+) m/z 579 (M+NH$_4$)+.

Example 326 tert-butyl(S)-1-((3aS,4R,6aR)-2-(4-fluorophenylsulfonyl)octahydrocyclopenta[c]pyrrol-4-ylamino)-4-methyl-1-oxopentan-2-ylmethyl)carbamate The title compound was prepared by substituting $N^1$-[(3aS,4R,6aR)-2-benzyloctahydrocyclopenta[c]pyrrol-4-yl]-$N^2$-(tert-butyloxycarbonyl)-$N^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 4-fluorobenzene-1-sulfonyl chloride for 3-(trifluoromethyl)benzene-1-sulfonyl chloride in the procedures described in Example 319: $^1$H NMR (500 MHz, pyridine-$d_5$) δ ppm 8.51-8.58 (m, 1H), 7.97-7.99 (m, 2H), 7.29-7.35 (m, 2H), 5.13 (m, 0.7H), 4.8 (m, 0.3H), 4.20-4.23 (m, 1H), 3.70-3.81 (m, 1H), 3.00-3.11 (m, 5H), 2.86-2.91 (m, 1H), 2.42-2.53 (m, 2H), 1.75-1.96 (m, 4H), 1.49-1.62 (m, 2H), 1.41-1.50 (bs, 9H), 1.23-1.39 (m, 1H), 0.81-0.88 (m, 6H); MS (ESI+) m/z 512 (M+H)+.

Example 327 tert-butyl(S)-1-((3aS,4R,6aR)-2-(4-fluoro-3-(trifluoromethyl)phenylsulfonyl)octahydrocyclopenta[c]pyrrol-4-ylamino)-4-methyl-1-oxopentan-2-yl(methyl)carbamate The title compound was prepared by substituting $N^1$-[(3aS,4R,6aR)-2-benzyloctahydrocyclopenta[c]pyrrol-4-yl]-$N^2$-(tert-butyloxycarbonyl)-$N^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 4-fluoro-3-(trifluoromethyl)benzene-1-sulfonyl chloride for 3-(trifluoromethyl)benzene-1-sulfonyl chloride in the procedures described in Example 319: $^1$H NMR (501 MHz, pyridine-$d_5$, temperature 90° C.) δ ppm 8.28 (dd, J=6.6, 2.3 Hz, 1H), 8.16-8.20 (m, 1H), 7.54-7.59 (m, 1H), 7.44 (t, J=9.4 Hz, 1H), 4.79-4.84 (m, 1H), 4.08 (p, J=6.9 Hz, 1H), 3.67 (dd, J=10.1, 3.3 Hz, 1H), 3.25 (dd, J=10.1, 7.7 Hz, 1H), 3.09-3.17 (m, 2H), 2.94 (s, 3H), 2.53-2.61 (m, 1H), 2.46-2.53 (m, 1H), 1.91-1.98 (m, 1H), 1.79-1.87 (m, 2H), 1.73 (ddd, J=14.1, 9.1, 5.1 Hz, 1H), 1.56-1.64 (m, 1H), 1.48-1.56 (m, 1H), 1.46 (s, 9H), 1.26-1.33 (m, 1H), 0.89 (d, J=6.6 Hz, 3H), 0.87 (d, J=6.6 Hz, 3H); MS (ESI+) m/z 580 (M+H)+.

Example 328 tert-butyl methyl((S)-1-oxo-1-((3aR,4R,6aS)-2-(4-(trifluoromethyl)phenylsulfonyl)octahydrocyclopenta[c]pyrrol-4-ylamino)pentan-2-yl)carbamate The title compound was prepared by substituting tert-butyl (S)-1-((3aR,4R,6aS)-2-benzyloctahydrocyclopenta[c]pyrrol-4-ylamino)-1-oxopentan-2-yl(methyl)carbamate from Example 240 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 8.04-8.07 (m, 2H), 7.80-7.83 (m, 2H), 7.54-7.57 (m, 1H), 4.79 (dd, J=9.4, 6.0 Hz, 1H), 4.29 (dq, J=9.8, 7.0 Hz, 1H), 3.49 (dd, J=10.3, 4.7 Hz, 1H), 3.21 (dd, J=9.9, 7.8 Hz, 1H), 3.07-3.13 (m, 2H), 3.01 (s, 3H), 2.92-3.01 (m, 1H), 2.46-2.54 (m, 1H), 1.95-2.07 (m, 1H), 1.75-1.85 (m, 1H), 1.68-1.77 (m, 1H), 1.55-1.66 (m, 2H), 1.54 (s, 9H), 1.25-1.39 (m, 3H), 0.87 (t, J=7.3 Hz, 3H); MS (ESI+) m/z 548 (M+H)+.

Example 329 tert-butyl methyl((S)-4-methyl-1-oxo-1-((3aR,4R,6aS)-2-(4-(trifluoromethyl)phenylsulfonyl)octahydrocyclopenta[c]pyrrol-4-ylamino)pentan-2-yl)carbamate The title compound was prepared by substituting tert-butyl (S)-1-((3aR,4R,6aS)-2-benzyloctahydrocyclopenta[c]pyrrol-4-ylamino)-4-methyl-1-oxopentan-2-yl(methyl)carbamate from Example 241 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 8.04-8.07 (m, 2H), 7.80-7.83 (m, 2H), 7.54-7.61 (m, 1H), 4.90 (dd, J=9.2, 6.0 Hz, 1H), 4.26-4.34 (m, 1H), 3.49 (dd, J=10.3, 4.7 Hz, 1H), 3.21 (dd, J=9.9, 7.8 Hz, 1H), 3.06-3.14 (m, 2H), 3.02 (s, 3H), 2.94-3.01 (m, 1H), 2.47-2.55 (m, 1H), 1.87 (ddd, J=14.2, 8.5, 5.6 Hz, 1H), 1.69-1.83 (m, 2H), 1.57-1.67 (m, 3H), 1.54 (s, 9H), 1.27-1.39 (m, 1H), 0.90 (d, J=6.9 Hz, 3H), 0.89 (d, J=6.9 Hz, 3H); MS (ESI+) m/z 562 (M+H)+.

Example 330 tert-butyl(S)-1-((3aS,4R,6aR)-2-(4-fluorophenylsulfonyl)octahydrocyclopenta[c]pyrrol-4-ylamino)-1-oxopentan-2-ylmethyl)carbamate The title compound was prepared by substituting tert-butyl (S)-1-((3aS,4R,6aR)-2-benzyloctahydrocyclopenta[c]pyrrol-4-ylamino)-1-oxopentan-2-yl(methyl)carbamate from Example 233 for (S)-N-((3aS,4R,6aR)-2-benzyloctahydrocyclopenta[c]pyrrol-4-yl)-4-methyl-2-morpholinopentanamide and 4-fluorobenzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 7.90-7.97 (m, 2H), 7.38-7.48 (bs, 1H), 7.18-7.24 (m, 2H), 7.18-7.23 (m, 1H), 4.65-4.75 (m, 1H), 4.03-4.13 (m, 1H), 3.58 (dd, J=10.1, 3.4 Hz, 1H), 3.22 (dd, J=10.1, 7.8 Hz, 1H), 3.03-3.13 (m, 2H), 2.94 (s, 3H), 2.51-2.60 (m, 1H), 2.43-2.51 (m, 1H), 1.89-2.01 (m, 2H), 1.80-1.86 (m, 1H), 1.69-1.81 (m, 1H), 1.47-1.62 (m, 1H), 1.45 (s, 9H), 1.23-1.38 (m, 3H), 0.86 (t, J=7.3 Hz, 2H); MS (ESI+) m/z 498 (M+H)+.

Example 331 tert-butyl methyl((S)-1-oxo-1-((3aS,4R,6aR)-2-(4-(trifluoromethyl)phenylsulfonyl)octahydrocyclopenta[c]pyrrol-4-ylamino)pentan-2-yl)carbamate The title compound was prepared by substituting tert-butyl (S)-1-((3aS,4R,6aR)-2-benzyloctahydrocyclopenta[c]pyrrol-4-ylamino)-1-oxopentan-2-yl(methyl)carbamate from Example 233 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 8.05-8.08 (m, 2H), 7.79-7.83 (m, 2H), 7.43-7.48 (bs, 1H), 4.68-4.72 (m, 1H), 4.01-4.11 (m, 1H), 3.65 (dd, J=10.2, 3.3 Hz, 1H), 3.26 (dd, J=10.1, 7.7 Hz, 1H), 3.07-3.18 (m, 2H), 2.94 (s, 3H), 2.45-2.58 (m, 2H), 1.89-2.00 (m, 2H), 1.70-1.86 (m, 2H), 1.46-1.57 (m, 1H), 1.45 (s, 9H), 1.31 (dt, J=15.2, 7.6 Hz, 2H), 1.23-1.37 (m, 1H), 0.85 (t, J=7.3 Hz, 3H); MS (ESI+) m/z 565 (M+NH$_4$)+.

Example 332 tert-butyl methyl((2S,3S)-3-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate The title compound was prepared by substituting tert-butyl (2S,3S)-1-((3aR,4S,6aS)-2-benzyloctahydrocyclopenta[c]pyrrol-4-ylamino)-3-methyl-1-oxopentan-2-yl(methyl)carbamate from Example 224 for (S)-N-((3aS,4R,6aR)-2-benzyloctahydrocyclopenta[c]pyrrol-4-yl)-4-methyl-2-morpholinopentanamide in the procedures described in Example 319: $^1$H NMR (500 MHz, pyridine-$d_5$) δ ppm 8.66 (d, J=6.0 Hz, 1H), 8.39-8.40 (m, 1H), 8.21 (d, J=7.9 Hz, 1H), 7.92 (d, J=7.6 Hz, 1H), 7.72 (t, J=7.9 Hz, 1H), 4.67 (d, J=11.1 Hz, 1H), 4.15-4.25 (m, 1H), 4.15-4.23 (m, 1H), 3.89 (d, J=9.9 Hz, 1H), 3.09-3.26 (m, 5H), 2.88-3.08 (m, 1H), 2.46-2.55 (m, 2H), 2.17-2.31 (m, 1H), 1.74-1.94 (m, 2H), 1.42-1.55 (m, 1H), 1.48 (s, 9H), 1.18-1.30 (m, 1H), 1.00-1.12 (m, 1H), 0.94 (d, J=6.3 Hz, 3H), 0.80 (t, J=7.0 Hz, 3H); MS (ESI+) m/z 562 (M+H)+.

Example 333 tert-butyl methyl((2S,3S)-3-methyl-1-oxo-1-((3aR,4S,6aS)-2-(4-(trifluoromethyl)phenylsulfonyl)octahydrocyclopenta[c]pyrrol-4-ylamino)pentan-2-yl)carbamate The title compound was prepared by substituting tert-butyl (2S,3S)-1-((3aR,4S,6aS)-2-benzyloctahydrocyclopenta[c]pyrrol-4-ylamino)-3-methyl-1-oxopentan-2-yl(methyl)carbamate from Example 224 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (500 MHz, pyridine-$d_5$) δ ppm 8.68 (d, J=6.3 Hz, 1H), 8.12-8.17 (m, 2H), 7.87-7.95 (m, 2H), 4.68 (d, J=11.0 Hz, 1H), 4.16-4.24 (m, 1H), 3.87 (d, J=9.8 Hz, 1H), 3.09-3.24 (m, 5H), 2.89-3.08 (m, 1H), 2.50-2.58 (m, 2H), 2.22-2.27 (m, 1H), 1.77-1.85 (m, 2H), 1.51-1.66 (m, 1H), 1.48 (s, 9H), 1.34-1.49 (m, 1H), 1.19-1.31 (m, 1H), 0.98-1.13 (m, 1H), 0.95 (d, J=6.1 Hz, 3H), 0.80 (t, J=6.9 Hz, 3H); MS (ESI+) m/z 562 (M+H)+.

Example 334 tert-butyl methyl((2S,3S)-3-methyl-1-oxo-1-((3aS,4R,6aR)-2-(3-(trifluoromethyl)phenylsulfonyl)octahydrocyclopenta[c]pyrrol-4-ylamino)pentan-2-yl)carbamate Step A: tert-butyl(2S,3S)-1-((3aS,4R,6aR)-2-benzyloctahydrocyclopenta[c]pyrrol-4-ylamino)-3-methyl-1-oxopentan-2-yl(methyl)carbamate was prepared by substituting N-(tert-butoxycarbonyl)-N-methyl-L-isoleucine for N-(tert-butoxycarbonyl)-L-leucine and (3aS,4R,6aR)-2-benzyloctahydrocyclopenta[c]pyrrol-4-amine from Example 16 Step E for (3aR,4S,6aS)-2-benzyloctahydrocyclopenta[c]pyrrol-4-amine in the procedure described in Example 221: $^1$H NMR (500 MHz, pyridine-$d_5$) δ ppm 8.43 (d, J=6.4, 1H), 7.41 (d, J=7.2, 2H), 7.36 (t, J=7.5, 2H), 7.27 (t, J=7.2, 1H), 4.70 (d, J=11.1, 1H), 4.36 (d, J=4.4, 2H), 3.56 (d, J=13.0, 1H), 3.40 (d, J=13.1, 1H), 3.24 (s, 1H), 3.13 (s, 3H), 2.72 (d, J=8.6, 1H), 2.47 (s, 2H), 2.37-2.18 (m, 4H), 2.13 (dd, J=11.7, 5.6, 1H), 1.91-1.76 (m, 1H), 1.65 (dd, J=11.4, 6.8, 1H), 1.48 (s, 9H), 1.11-0.95 (m, 4H), 0.80 (t, J=7.1, 3H); MS (ESI+) m/z 444 (M+H)$^+$.

Step B: The title compound was prepared by substituting tert-butyl(2S,3S)-1-((3aS,4R,6aR)-2-benzyloctahydrocyclopenta[c]pyrrol-4-ylamino)-3-methyl-1-oxopentan-2-yl(methyl)carbamate from Step A for (S)-N-((3aS,4R,6aR)-2-benzyloctahydrocyclopenta[c]pyrrol-4-yl)-4-methyl-2-morpholinopentanamide in the procedures described in Example 319: $^1$H NMR (400 MHz, pyridine-$d_5$) δ ppm 8.68 (d, J=7.2 Hz, 1H), 8.35-8.40 (m, 1H), 8.15 (d, J=7.8 Hz, 1H), 7.91 (d, J=7.6 Hz, 1H), 7.72 (t, J=7.8 Hz, 1H), 4.68 (d, J=11.3 Hz, 1H), 4.13-4.25 (m, 1H), 3.74-3.88 (m, 1H), 3.15-3.25 (m, 1H), 3.11-3.16 (bs, 3H), 2.95-3.05 (m, 1H), 2.83-2.94 (m, 1H), 2.38-2.61 (m, 2H), 2.17-2.32 (m, 1H), 1.88-2.03 (m, 1H), 1.76-1.88 (m, 1H), 1.52-1.66 (m, 1H), 1.44-1.53 (bs, 9H), 1.33-1.46 (m, 1H), 1.21-1.33 (m, 1H), 0.96-1.12 (m, 1H), 0.94 (d, J=6.4 Hz, 3H), 0.79 (t, J=7.2 Hz, 3H); MS (ESI+) m/z 562 (M+H)$^+$.

Example 335 tert-butyl methyl((2S,3S)-3-methyl-1-oxo-1-((3aS,4R,6aR)-2-(4-(trifluoromethyl)phenylsulfonyl)octahydrocyclopenta[c]pyrrol-4-ylamino)pentan-2-yl)carbamate The title compound was prepared by substituting tert-butyl (2S,3S)-1-((3aS,4R,6aR)-2-benzyloctahydrocyclopenta[c]pyrrol-4-ylamino)-3-methyl-1-oxopentan-2-yl(methyl)carbamate from Step A of Example 334 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$) δ ppm 8.66-8.72 (m, 1H), 8.05-8.13 (m, 2H), 7.88-7.91 (m, 2H), 4.69 (d, J=11.3 Hz, 1H), 4.15-4.22 (m, 1H), 3.73-3.87 (m, 1H), 3.16-3.23 (m, 1H), 3.11-3.18 (bs, 3H), 3.00 (t, J=8.3 Hz, 1H), 2.90 (t, J=8.4 Hz, 1H), 2.42-2.56 (m, 2H), 2.21-2.28 (m, 1H), 1.88-2.03 (m, 1H), 1.73-1.88 (m, 1H), 1.52-1.66 (m, 1H), 1.48 (s, 9H), 1.34-1.46 (m, 1H), 1.21-1.34 (m, 1H), 0.98-1.13 (m, 1H), 0.94 (d, J=6.3 Hz, 3H), 0.76-0.81 (m, 3H); MS (ESI+) m/z 562 (M+H)$^+$.

Example 336 tert-butyl(S)-4,4-dimethyl-1-oxo-1-((3aR,4S,6aS)-2-(3-(trifluoromethyl)phenylsulfonyl)octahydrocyclopenta[c]pyrrol-4-ylamino)pentan-2-yl(methyl)carbamate The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-yl(methyl)carbamate from Example 247 for (S)-N-((3aS,4R,6aR)-2-benzyloctahydrocyclopenta[c]pyrrol-4-yl)-4-methyl-2-morpholinopentanamide in the procedures described in Example 319: $^1$H NMR (500 MHz, pyridine-$d_5$) δ ppm 8.36-8.38 (bs, 1H), 8.30-8.37 (m, 1H), 8.19 (d, J=7.8 Hz, 1H), 7.91 (d, J=7.8 Hz, 1H), 7.72 (t, J=7.8 Hz, 1H), 5.4 (m, 0.7H), 4.7 (m, 0.3H), 4.16-4.20 (m, 1H), 3.86 (d, J=9.8 Hz, 1H), 3.13-3.18 (m, 1H), 3.08-3.13 (m, 1H), 2.96-3.08 (bs, 3H), 2.90-2.93 (m, 1H), 2.41-2.56 (m, 2H), 2.13-2.37 (m, 1H), 1.81-1.92 (m, 1H), 1.72-1.81 (m, 1H), 1.60-1.72 (m, 1H), 1.47-1.60 (m, 1H), 1.41-1.50 (bs, 9H), 1.19-1.33 (m, 1H), 0.87-0.99 (bs, 9H); MS (ESI+) m/z 576 (M+H)$^+$, 593 (M+NH$_4$)$^+$.

Example 337 tert-butyl(S)-4,4-dimethyl-1-oxo-1-((3aR,4S,6aS)-2-(4-(trifluoromethyl)phenylsulfonyl)octahydrocyclopenta[c]pyrrol-4-ylamino)pentan-2-yl(methyl)carbamate The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-yl(methyl)carbamate from Example 247 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (500 MHz, pyridine-$d_5$) δ ppm 8.35-8.38 (m, 1H), 8.12-8.15 (m, 2H), 7.89-7.91 (m, 2H), 5.11-5.19 (m, 1H), 4.15-4.19 (m, 1H), 3.83-3.86 (m, 1H), 3.13-3.17 (m, 1H), 3.09-3.14 (m, 1H), 2.97-3.09 (bs, 3H), 2.92-2.96 (m, 1H), 2.43-2.57 (m, 2H), 2.15-2.38 (m, 1H), 1.81-1.91 (m, 1H), 1.72-1.81 (m, 1H), 1.61-1.72 (m, 1H), 1.48-1.60 (m, 1H), 1.40-1.51 (bs, 9H), 1.20-1.36 (m, 1H), 0.89-0.99 (bs, 9H); MS (ESI+) m/z 576 (M+H)$^+$.

Example 338 tert-butyl(S)-4,4-dimethyl-1-oxo-1-((3aS,4R,6aR)-2-(3-(trifluoromethyl)phenylsulfonyl)octahydrocyclopenta[c]pyrrol-4-ylamino)pentan-2-yl(methyl)carbamate The title compound was prepared by substituting tert-butyl (S)-1-((3aS,4R,6aR)-2-benzyloctahydrocyclopenta[c]pyrrol-4-ylamino)-4,4-dimethyl-1-oxopentan-2-yl(methyl)carbamate from Example 248 for (S)-N-((3aS,4R,6aR)-2-benzyloctahydrocyclopenta[c]pyrrol-4-yl)-4-methyl-2-morpholinopentanamide in the procedures described in Example 319: $^1$H NMR (400 MHz, pyridine-$d_5$, temperature 90° C.) δ ppm 8.29-8.30 (bs, 1H), 8.13 (d, J=7.9 Hz, 1H), 7.83 (d, J=8.6 Hz, 1H), 7.64 (t, J=7.8 Hz, 1H), 7.29 (d, J=3.9 Hz, 1H), 4.82-4.87 (bs, 1H), 4.05 (p, J=6.7 Hz, 1H), 3.63 (dd, J=10.2, 3.3 Hz, 1H), 3.25 (dd, J=10.1, 7.8 Hz, 1H), 3.07-3.17 (m, 2H), 2.91 (s, 3H), 2.51-2.59 (m, 1H), 2.43-2.50 (m, 1H), 2.15 (dd, J=14.3, 5.6 Hz, 1H), 1.92 (dq, J=12.2, 6.1 Hz, 1H), 1.77-1.85 (m, 1H), 1.61 (dd, J=14.3, 7.2 Hz, 1H), 1.47-1.55 (m, 1H), 1.46 (s, 9H), 1.23-1.36 (m, 1H), 0.93 (s, 9H); MS (ESI+) m/z 576 (M+H)$^+$.

Example 339 tert-butyl(S)-4,4-dimethyl-1-oxo-1-((3aS,4R,6aR)-2-(4-(trifluoromethyl)phenylsulfonyl)octahydrocyclopenta[c]pyrrol-4-ylamino)pentan-2-yl(methyl)carbamate The title compound was prepared by substituting tert-butyl (S)-1-((3aS,4R,6aR)-2-benzyloctahydrocyclopenta[c]pyrrol-4-ylamino)-4,4-dimethyl-1-oxopentan-2-yl(methyl)carbamate from Example 248 for (S)-N-((3aS,4R,6aR)-2- benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 8.05-8.08 (m, 2H), 7.79-7.82 (m, 2H), 7.28-7.32 (m, 1H), 4.79-4.91 (m, 1H), 4.05 (p, J=6.7 Hz, 1H), 3.62 (dd, J=10.2, 3.4 Hz, 1H), 3.26 (dd, J=10.2, 7.8 Hz, 1H), 3.09-3.17 (m, 2H), 2.92 (s, 3H), 2.51-2.62 (m, 1H), 2.43-2.51 (m, 1H), 2.15 (dd, J=14.3, 5.6 Hz, 1H), 1.88-1.98 (m, 1H), 1.76-1.86 (m, 1H), 1.62 (dd, J=14.3, 7.0 Hz, 1H), 1.47-1.56 (m, 1H), 1.46 (s, 9H), 1.29 (ddt, J=9.0, 13.0, 6.5 Hz, 1H), 0.94 (s, 9H); MS (ESI+) m/z 576 (M+H)$^+$.

Example 340 tert-butyl methyl((S)-3-methyl-1-oxo-1-((3aS,4R,6aR)-2-(3-(trifluoromethyl)phenylsulfonyl)octahydrocyclopenta[c]pyrrol-4-ylamino)butan-2-yl)carbamate The title compound was prepared by substituting tert-butyl (S)-1-((3aS,4R,6aR)-2-benzyloctahydrocyclopenta[c]pyrrol-4-ylamino)-3-methyl-1-oxobutan-2-yl(methyl)carbamate from Example 232 for (S)-N-((3aS,4R,6aR)-2-benzyloctahydrocyclopenta[c]pyrrol-4-yl)-4-methyl-2-morpholinopentanamide in the procedures described in Example 319: $^1$H NMR (501 MHz, pyridine-$d_5$, temperature 90° C.) δ ppm 8.29-8.30 (bs, 1H), 8.13 (d, J=7.8 Hz, 1H), 7.83 (d, J=7.7 Hz, 1H), 7.64 (t, J=7.8 Hz, 1H), 7.59-7.68 (m, 1H), 4.32 (d, J=10.4 Hz, 1H), 4.07 (p, J=6.6 Hz, 1H), 3.64 (dd, J=10.2, 3.3 Hz, 1H), 3.23 (t, J=9.0 Hz, 1H), 3.07-3.15 (m, 2H), 3.00 (s, 3H), 2.49-2.59 (m, 1H), 2.42-2.49 (m, 1H), 2.31-2.42 (m, 1H), 1.90-1.97 (m, 1H), 1.79-1.86 (m, 1H), 1.47-1.59 (m, 1H), 1.45 (s, 9H), 1.24-1.33 (m, 1H), 0.97 (d, J=6.5 Hz, 3H), 0.86 (d, J=6.7 Hz, 3H); MS (ESI+) m/z 548 (M+H)$^+$.

Example 341 tert-butyl(S)-3,3-dimethyl-1-oxo-1-((3aR,4S,6aS)-2-(4-(trifluoromethyl)phenylsulfonyl)octahydrocyclopenta[c]pyrrol-4-ylamino)butan-2-ylcarbamate The title compound was prepared by substituting tert-butyl (S)-1-((3aR,4S,6aS)-2-benzyloctahydrocyclopenta[c]pyrrol-4-ylamino)-3,3-dimethyl-1-oxobutan-2-ylcarbamate from Example 225 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (500 MHz, pyridine-$d_5$) δ ppm 8.86 (d, J=6.7 Hz, 1H), 8.11-8.18 (m, 2H), 7.89-7.92 (m, 2H), 7.71 (d, J=9.5 Hz, 1H), 4.56 (d, J=9.8 Hz, 1H), 4.20 (p, J=6.4 Hz, 1H), 3.79 (dd, J=10.0, 3.0 Hz, 1H), 3.24 (dd, J=9.9, 7.7 Hz, 1H), 3.14 (d, J=3.2 Hz, 1H), 3.02 (dd, J=9.7, 7.3 Hz, 1H), 2.55-2.65 (m, 2H), 1.76-1.84 (m, 2H), 1.44-1.56 (m, 1H), 1.48 (s, 9H), 1.19-1.27 (m, 1H), 1.16 (s, 9H); MS (ESI+) m/z 548 (M+H)$^+$, 565 (M+NH$_4$)$^+$.

Example 342 tert-butyl(S)-3,3-dimethyl-1-oxo-1-((3aS,4R,6aR)-2-(4-(trifluoromethyl)phenylsulfonyl)octahydrocyclopenta[c]pyrrol-4-ylamino)butan-2-ylcarbamate The title compound was prepared by substituting tert-butyl (S)-1-((3aS,4R,6aR)-2-benzyloctahydrocyclopenta[c]pyrrol-4-ylamino)-3,3-dimethyl-1-oxobutan-2-ylcarbamate from Example 234 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (500 MHz, pyridine-$d_5$) δ ppm 8.89 (d, J=7.4, 1H), 8.10 (d, J=8.1, 2H), 7.90 (d, J=8.3, 2H), 7.73 (s, 1H), 4.55 (d, J=9.8, 1H), 4.27-4.16 (m, 1H), 3.70 (dd, J=9.8, 2.2, 1H), 3.14 (dd, J=9.8, 2.5, 1H), 2.98-2.92 (m, 1H), 2.91-2.85 (m, 1H), 2.53-2.39 (m, 2H), 1.99 (td, J=11.5, 5.7, 1H), 1.83 (td, J=12.4, 7.2, 1H), 1.60 (dt, J=12.3, 8.2, 1H), 1.48 (s, 9H), 1.34-1.25 (m, 1H), 1.15 (s, 9H); MS (ESI+) m/z 548 (M+H)$^+$, 565 (M+NH$_4$)$^+$.

Example 343 tert-butyl methyl((S)-1-oxo-1-((3aR,4S,6aS)-2-(4-(trifluoromethyl)phenylsulfonyl)octahydrocyclopenta[c]pyrrol-4-ylamino)hexan-2-yl)carbamate The title compound was prepared by substituting tert-butyl (S)-1-((3aR,4S,6aS)-2-benzyloctahydrocyclopenta[c]pyrrol-4-ylamino)-1-oxohexan-2-yl(methyl)carbamate from Example 227 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 8.06-8.09 (m, 2H), 7.79-7.82 (m, 2H), 7.40 (d, J=5.6 Hz, 1H), 4.68-4.72 (m, 1H), 4.07 (p, J=6.8 Hz, 1H), 3.65 (dd, J=10.2, 3.4 Hz, 1H), 3.28 (dd, J=10.2, 7.7 Hz, 1H), 3.09-3.17 (m, 2H), 2.94 (s, 3H), 2.54-2.59 (m, 1H), 2.47-2.53 (m, 1H), 1.97-2.07 (m, 1H), 1.87-1.96 (m, 1H), 1.72-1.86 (m, 2H), 1.47-1.56 (m, 1H), 1.46 (s, 9H), 1.23-1.35 (m, 1H), 1.27-1.30 (m, 4H), 0.80-0.84 (m, 3H); MS (ESI+) m/z 562 (M+H)$^+$, 579 (M+NH$_4$)$^+$, 620 (M+CH$_3$CN+NH$_4$)$^+$.

Example 344 tert-butyl(S)-4,4-dimethyl-1-oxo-1-((3aR,4S,6aS)-2-(4-(trifluoromethyl)phenylsulfonyl)octahydrocyclopenta[c]pyrrol-4-ylamino)pentan-2-ylcarbamate The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-ylcarbamate from Example 226 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedures described in Example 319: $^1$H NMR (400 MHz, pyridine-$d_5$, temperature 90° C.) δ ppm 8.06-8.08 (m, 1H), 8.06 (d, J=−0.9 Hz, 1H), 7.79-7.82 (m, 2H), 7.73-7.77 (m, 1H), 7.00-7.05 (m, 1H), 4.47 (td, J=8.2, 4.7 Hz, 1H), 4.04-4.11 (m, 1H), 3.65 (dd, J=10.2, 3.0 Hz, 1H), 3.29 (dd, J=10.2, 7.3 Hz, 1H), 3.15 (dd, J=10.0, 6.9 Hz, 1H), 3.11 (dd, J=9.9, 3.4 Hz, 1H), 2.51-2.59 (m, 2H), 2.08 (dd, J=14.2, 4.6 Hz, 1H), 1.84-1.93 (m, 1H), 1.75-1.83 (m, 1H), 1.69 (dd, J=14.2, 8.0 Hz, 1H), 1.48-1.56 (m, 1H), 1.47 (s, 9H), 1.22-1.33 (m, 1H), 0.96 (s, 9H); MS (ESI+) m/z 562 (M+H)$^+$.

Example 345

(2S)-4-methyl-2-pyrrolidin-1-yl-N-{(3aS,4R,6aR)-2-[3-(trifluoromethyl)benzoyl]octahydrocyclopenta[c]pyrrol-4-yl}pentanamide The title compound was prepared by substituting (2S)-N-[(3aS,4R,6aR)-2-benzyloctahydrocyclopenta[c]pyrrol-4- yl]-4-methyl-2-pyrrolidin-1-ylpentanamide from Example 250 for (S)-N-((3aS,4R,6aR)-2-benzyloctahydrocyclopenta[c]pyrrol-4-yl)-4-methyl-2-morpholinopentanamide and 3-(trifluoromethyl)benzoyl chloride for 3-(trifluoromethyl)benzene-1-sulfonyl chloride in the procedures described in Example 319: $^1$H NMR (500 MHz, pyridine-$d_5$) δ ppm 8.41-8.17 (m, 1H), 8.14-8.05 (m, 1H), 8.01-7.78 (m, 1H), 7.76-7.66 (m, 1H), 7.53 (t, J=7.6, 1H), 4.51-4.29 (m, 1H), 4.20-4.00 (m, 1H), 3.89 (ddd, J=12.0, 6.6, 1.5, 1H), 3.74 (tdd, J=8.3, 5.2, 2.8, 1H), 3.67-3.45 (m, 1H), 3.32-3.13 (m, 2H), 2.87-2.57 (m, 6H), 2.23-2.02 (m, 1H), 1.96-1.78 (m, 2H), 1.73-1.55 (m, 6H), 1.47-1.24 (m, 1H), 1.04-0.79 (m, 6H); MS (ESI+) m/z 466 (M+H)$^+$.

Example 346

(2S)-4-methyl-N-[(3aS,4R,6aR)-2-(methylsulfonyl)octahydrocyclopenta[c]pyrrol-4-yl]-2-pyrrolidin-1-ylpentanamide The title compound was prepared by substituting (2S)-N-[(3aS,4R,6aR)-2-benzyloctahydrocyclopenta[c]pyrrol-4-yl]-4-methyl-2-pyrrolidin-1-ylpentanamide from Example 250 for (S)-N-((3aS,4R,6aR)-2-benzyloctahydrocyclopenta[c]pyrrol-4-yl)-4-methyl-2-morpholinopentanamide and methanesulfonyl chloride for 3-(trifluoromethyl)benzene-1-sulfonyl chloride in the procedures described in Example 319: $^1$H NMR (500 MHz, pyridine-$d_5$) δ ppm 8.24-8.26 (m, 1H), 4.35 (p, J=6.8 Hz, 1H), 3.79 (dd, J=9.9, 2.6 Hz, 1H), 3.50 (dd, J=9.9, 7.0 Hz, 1H), 3.35 (dd, J=9.6, 7.0 Hz, 1H), 3.17-3.21 (m, 2H), 3.04 (s, 3H), 2.67-2.75 (m, 4H), 2.60-2.63 (m, 2H), 1.99-2.07 (m, 1H), 1.78-1.95 (m, 3H), 1.58-1.68 (m, 6H), 1.32-1.39 (m, 1H), 0.99 (d, J=6.2 Hz, 3H), 0.92 (d, J=6.3 Hz, 3H); MS (ESI+) m/z 372 (M+H)$^+$.

Example 347

(2S)-N-[(3aS,4R,6aR)-2-(cyclopropylsulfonyl)octahydrocyclopenta[c]pyrrol-4-yl]-4-methyl-2-pyrrolidin-1-ylpentanamide The title compound was prepared by substituting (2S)-N-[(3aS,4R,6aR)-2-benzyloctahydrocyclopenta[c]pyrrol-4-yl]-4-methyl-2-pyrrolidin-1-ylpentanamide from Example 250 for (S)-N-((3aS,4R,6aR)-2-benzyloctahydrocyclopenta[c]pyrrol-4-yl)-4-methyl-2-morpholinopentanamide and cyclopropanesulfonyl chloride for 3-(trifluoromethyl)benzene-1-sulfonyl chloride in the procedures described in Example 319: $^1$H NMR (500 MHz, pyridine-$d_5$) δ ppm 8.14 (d, J=7.3 Hz, 1H), 4.33-4.40 (m, 1H), 3.82 (dd, J=9.9, 2.6 Hz, 1H), 3.57 (dd, J=9.9, 7.0 Hz, 1H), 3.41 (dd, J=9.6, 7.0 Hz, 1H), 3.22 (dd, J=9.6, 3.2 Hz, 1H), 3.16 (dd, J=9.2, 5.1 Hz, 1H), 2.60-2.70 (m, 7H), 2.04 (dq, J=11.9, 5.9 Hz, 1H), 1.79-1.97 (m, 3H), 1.56-1.67 (m, 6H), 1.33-1.40 (m, 1H), 1.16-1.23 (m, 2H), 0.99 (d, J=6.3 Hz, 3H), 0.92 (d, J=6.4 Hz, 3H), 0.86-0.92 (m, 2H); MS (ESI+) m/z 398 (M+H)$^+$.

Example 348

N$^1$-[(3aR,4S,6aS)-2-benzyloctahydrocyclopenta[c]pyrrol-4-yl]-N$^2$-methyl-L-leucinamide tert-Butyl(S)-1-((3aR,4S,6aS)-2-benzyloctahydrocyclopenta[c]pyrrol-4-ylamino)-4-methyl-1-oxopentan-2-yl(methyl)carbamate (60 mg, 0.135 mmol) from Example 222 was combined with 4 N hydrogen chloride in 1,4-dioxane (0.698 mL, 2.79 mmol). The reaction was stirred at room temperature for 16 hours and then concentrated. The material was purified using a 12 g silica gel cartridge with a gradient of 1-10% methanol (2 N ammonia)/dichloromethane over 20 minutes to give the title compound: $^1$H NMR (500 MHz, pyridine-$d_5$) δ ppm 8.16-8.19 (m, 1H), 7.44-7.46 (m, 2H), 7.37 (t, J=7.5 Hz, 2H), 7.28 (t, J=7.3 Hz, 1H), 4.42-4.48 (m, 1H), 3.61 (d, J=13.1 Hz, 1H), 3.46 (d, J=13.1 Hz, 1H), 3.22 (dd, J=8.2, 5.8 Hz, 1H), 2.87 (d, J=10.3 Hz, 1H), 2.51-2.61 (m, 2H), 2.44 (dd, J=8.8, 7.1 Hz, 1H), 2.43 (s, 3H), 2.37 (dd, J=9.0, 2.0 Hz, 1H), 2.25-2.29 (m, 1H), 2.09-2.17 (m, 1H), 1.95-2.07 (m, 1H), 1.82-1.95 (m, 2H), 1.72 (ddd, J=13.5, 7.8, 5.8 Hz, 1H), 1.55-1.64 (m, 2H), 1.38-1.45 (m, 1H), 0.92 (d, J=6.6 Hz, 3H), 0.86 (d, J=6.6 Hz, 3H); MS (ESI+) m/z 344 (M+H)$^+$.

Example 349 tert-butyl methyl((S)-4-methyl-1-((3aS,4R,6aR)-octahydrocyclopenta[c]pyrrol-4-ylamino)-1-oxopentan-2-yl)carbamate The title compound was prepared by substituting N$^1$-[(3aS,4R,6aR)-2-benzyloctahydrocyclopenta[c]pyrrol-4-yl]-N$^2$-(tert-butyloxycarbonyl)-N$^2$-methyl-L-leucinamide from Example 151 for (S)-N-((3aS,4R,6aR)-2-benzyloctahydrocyclopenta[c]pyrrol-4-yl)-4-methyl-2-morpholinopentanamide in the procedure described in Example 319 Step A: $^1$H NMR (500 MHz, pyridine-$d_5$) δ 8.47-8.30 (m, 1H), 5.15 (dd, J=6.4, 5.1, 1H), 4.82-4.77 (m, 1H), 4.40-4.21 (m, 1H), 3.25-3.04 (m, 4H), 3.03-2.92 (m, 1H), 2.88 (dd, J=10.8, 7.1, 1H), 2.69 (d, J=10.2, 1H), 2.56-2.44 (m, 2H), 2.04 (td, J=11.6, 5.8, 1H), 1.93-1.78 (m, 3H), 1.64-1.53 (m, 2H), 1.47 (s, 9H), 1.34 (ddt, J=11.0, 7.1, 5.5, 1H), 0.89 (d, J=6.3 Hz, 3H), 0.85 (d, J=6.5, 3H); MS (ESI+) m/z 354 (M+H)$^+$.

Example 350

(2S)-N-[(3aS,4R,6aR)-2-benzyloctahydrocyclopenta[c]pyrrol-4-yl]piperidine-2-carboxamide The title compound was prepared by substituting tert-butyl (2S)-2-({[(3aS,4R,6aR)-2-benzyloctahydrocyclopenta[c]pyrrol-4-yl]amino}carbonyl)piperidine-1-carboxylate from Example 231 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 7.67-7.70 (m, 1H), 7.42-7.44 (m, 2H), 7.36 (t, J=7.5 Hz, 2H), 7.27 (t, J=7.3 Hz, 1H), 4.34-4.40 (m, 1H), 3.59 (d, J=13.1 Hz, 1H), 3.41 (d, J=13.1 Hz, 1H), 3.32 (dd, J=10.3, 3.2 Hz, 1H), 2.99-3.02 (m, 1H), 2.83 (dd, J=8.9, 2.5 Hz, 1H), 2.54-2.61 (m, 1H), 2.46-2.54 (m, 1H), 2.40-2.58 (m, 1H), 2.39-2.47 (m, 1H), 2.33-2.39 (m, 2H), 2.21 (dd, J=8.9, 7.2 Hz, 1H), 2.02-2.10 (m, 2H), 1.77-1.84 (m, 1H), 1.64-1.74 (m, 1H), 1.47-1.64 (m, 2H), 1.34-1.45 (m, 2H), 1.25-1.34 (m, 2H); MS (ESI+) m/z 328 (M+H)$^+$.

Example 351

N$^1$-[(3aS,4R,6aR)-2-benzyloctahydrocyclopenta[c]pyrrol-4-yl]-N$^2$-methyl-L-valinamide The title compound was prepared by substituting tert-butyl (S)-1-((3aS,4R,6aR)-2-benzyloctahydrocyclopenta[c]pyrrol-4-ylamino)-3-methyl-1-oxobutan-2-yl(methyl)carbamate from Example 232 for tert-butyl(S)-1-((3aR,4S,6aS)-2-benzyloctahydrocyclopenta[c]pyrrol-4-ylamino)-4-methyl- 1-oxopentan-2-yl(methyl)carbamate in the procedure described in Example 348: ¹H NMR (500 MHz, pyridine-d₅) δ ppm 8.10-8.12 (m, 1H), 7.43-7.45 (m, 2H), 7.37 (t, J=7.5 Hz, 2H), 7.28 (t, J=7.3 Hz, 1H), 4.44-4.50 (m, 1H), 3.62 (d, J=13.1 Hz, 1H), 3.44 (d, J=13.1 Hz, 1H), 2.85-2.90 (m, 2H), 2.47-2.57 (m, 2H), 2.43 (dd, J=8.8, 7.0 Hz, 1H), 2.40 (s, 3H), 2.36 (dd, J=8.9, 2.7 Hz, 1H), 2.26 (dd, J=8.9, 6.8 Hz, 1H), 2.07-2.16 (m, 2H), 1.91-2.06 (m, 1H), 1.81-1.89 (m, 1H), 1.59 (dq, J=12.1, 7.6 Hz, 1H), 1.38-1.45 (m, 1H), 1.06 (d, J=6.9 Hz, 3H), 1.05 (d, J=6.9 Hz, 3H); MS (ESI+) m/z 330 (M+H)⁺.

Example 352

N¹-[(3aS,4R,6aR)-2-benzyloctahydrocyclopenta[c]pyrrol-4-yl]-N²-methyl-L-norvalinamide The title compound was prepared by substituting tert-butyl (S)-1-((3aS,4R,6aR)-2-benzyloctahydrocyclopenta[c]pyrrol-4-ylamino)-1-oxopentan-2-yl(methyl)carbamate from Example 233 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.11-8.14 (m, 1H), 7.43-7.45 (m, 2H), 7.37 (t, J=7.5 Hz, 2H), 7.28 (t, J=7.3 Hz, 1H), 4.42-4.48 (m, 1H), 3.61 (d, J=13.1 Hz, 1H), 3.44 (d, J=13.1 Hz, 1H), 3.16 (t, J=6.5 Hz, 1H), 2.86 (dd, J=8.9, 2.6 Hz, 1H), 2.47-2.57 (m, 2H), 2.42 (dd, J=8.9, 7.2 Hz, 1H), 2.40 (s, 3H), 2.36 (dd, J=8.9, 2.7 Hz, 1H), 2.26 (dd, J=8.9, 7.0 Hz, 1H), 2.12 (dq, J=11.9, 6.0 Hz, 2H), 1.77-1.89 (m, 2H), 1.65-1.73 (m, 1H), 1.54-1.64 (m, 1H), 1.37-1.54 (m, 3H), 0.84 (t, J=7.3 Hz, 3H); MS (ESI+) m/z 330 (M+H)⁺.

Example 353

N¹-[(3aR,4S,6aS)-2-benzyloctahydrocyclopenta[c]pyrrol-4-yl]-N²-methyl-L-isoleucinamide The title compound was prepared by substituting tert-butyl (2S,3S)-1-((3aR,4S,6aS)-2-benzyloctahydrocyclopenta[c]pyrrol-4-ylamino)-3-methyl-1-oxopentan-2-yl(methyl)carbamate from Example 224 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (400 MHz, pyridine-d₅) δ ppm 8.10-8.14 (m, 1H), 7.44-7.46 (m, 2H), 7.37 (t, J=7.5 Hz, 2H), 7.26-7.30 (m, 1H), 4.42-4.50 (m, 1H), 3.61 (d, J=13.1 Hz, 1H), 3.46 (d, J=13.1 Hz, 1H), 2.97 (d, J=6.0 Hz, 1H), 2.87 (d, J=10.2 Hz, 1H), 2.50-2.57 (m, 2H), 2.41-2.45 (m, 1H), 2.41 (s, 3H), 2.35-2.39 (m, 1H), 2.24-2.29 (m, 1H), 2.07-2.16 (m, 1H), 1.89-2.09 (m, 1H), 1.73-1.92 (m, 3H), 1.55-1.68 (m, 1H), 1.26-1.46 (m, 2H), 1.03 (d, J=6.7 Hz, 3H), 0.86 (t, J=7.4 Hz, 3H); MS (ESI+) m/z 344 (M+H)⁺.

Example 354

N¹-[(3aS,4R,6aR)-2-benzyloctahydrocyclopenta[c]pyrrol-4-yl]-N²-methyl-L-isoleucinamide The title compound was prepared by substituting tert-butyl (2S,3S)-1-((3aS,4R,6aR)-2-benzyloctahydrocyclopenta[c]pyrrol-4-ylamino)-3-methyl-1-oxopentan-2-yl(methyl)carbamate from Step A of Example 334 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (400 MHz, pyridine-d₅) δ ppm 8.11-8.14 (m, 1H), 7.43-7.46 (m, 2H), 7.37 (t, J=7.5 Hz, 2H), 7.25-7.30 (m, 1H), 4.44-4.51 (m, 1H), 3.62 (d, J=13.1 Hz, 1H), 3.44 (d, J=13.1 Hz, 1H), 2.96 (d, J=6.0 Hz, 1H), 2.87 (dd, J=8.9, 2.1 Hz, 1H), 2.47-2.61 (m, 2H), 2.43 (dd, J=8.8, 7.0 Hz, 1H), 2.40 (s, 3H), 2.36 (dd, J=8.9, 2.4 Hz, 1H), 2.26 (dd, J=8.9, 6.6 Hz, 1H), 2.07-2.16 (m, 1H), 1.88-2.02 (m, 1H), 1.73-1.91 (m, 3H), 1.60 (dq, J=12.1, 7.5 Hz, 1H), 1.25-1.46 (m, 2H), 1.03 (d, J=6.8 Hz, 3H), 0.86 (t, J=7.4 Hz, 3H); MS (ESI+) m/z 344 (M+H)⁺.

Example 355

N¹-[(3aR,4S,6aS)-2-benzyloctahydrocyclopenta[c]pyrrol-4-yl]-N²,4-dimethyl-L-leucinamide The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-yl(methyl)carbamate from Example 247 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (400 MHz, pyridine-d₅) δ ppm 8.21-8.24 (m, 1H), 7.43-7.46 (m, 2H), 7.37 (t, J=7.4 Hz, 2H), 7.24-7.30 (m, 1H), 4.42-4.47 (m, 1H), 3.61 (d, J=13.0 Hz, 1H), 3.46 (d, J=13.1 Hz, 1H), 3.19-3.22 (m, 1H), 2.88 (d, J=10.0 Hz, 1H), 2.52 (d, J=4.7 Hz, 2H), 2.40-2.46 (m, 1H), 2.41 (s, 3H), 2.37 (dd, J=9.0, 2.4 Hz, 1H), 2.26 (dd, J=8.7, 6.2 Hz, 1H), 2.07-2.18 (m, 1H), 1.93 (dd, J=14.1, 5.1 Hz, 1H), 1.80-1.89 (m, 1H), 1.58-1.82 (m, 1H), 1.55-1.65 (m, 1H), 1.51 (dd, J=14.0, 6.6 Hz, 1H), 1.34-1.46 (m, 1H), 0.98 (s, 9H); MS (ESI+) m/z 358 (M+H)⁺.

Example 356

N¹-[(3aR,4R,6aR)-2-benzyloctahydrocyclopenta[c]pyrrol-4-yl]-3-methyl-L-valinamide The title compound was prepared by substituting tert-butyl (S)-1-((3aS,4R,6aR)-2-benzyloctahydrocyclopenta[c]pyrrol-4-ylamino)-3,3-dimethyl-1-oxobutan-2-ylcarbamate from Example 234 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.09-8.12 (m, 1H), 7.42-7.44 (m, 2H), 7.37 (t, J=7.3 Hz, 2H), 7.25-7.32 (m, 1H), 4.38-4.44 (m, 1H), 3.58 (d, J=13.0 Hz, 1H), 3.44 (d, J=13.1 Hz, 1H), 3.26 (s, 1H), 2.78 (dd, J=8.9, 2.5 Hz, 1H), 2.44-2.52 (m, 2H), 2.38-2.42 (m, 1H), 2.33 (dd, J=9.0, 2.7 Hz, 1H), 2.23-2.27 (m, 1H), 2.07-2.16 (m, 2H), 1.91-2.26 (m, 1H), 1.80-1.88 (m, 1H), 1.55-1.62 (m, 1H), 1.36-1.43 (m, 1H), 1.14 (s, 9H); MS (ESI+) m/z 330 (M+H)⁺.

Example 357

N¹-[(3aR,4S,6aS)-2-benzyloctahydrocyclopenta[c]pyrrol-4-yl]-3-methyl-L-valinamide The title compound was prepared by substituting tert-butyl (S)-1-((3aR,4S,6aS)-2-benzyloctahydrocyclopenta[c]pyrrol-4-ylamino)-3,3-dimethyl-1-oxobutan-2-ylcarbamate from Example 225 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.07-8.10 (m, 1H), 7.43-7.45 (m, 2H), 7.37 (t, J=7.4 Hz, 2H), 7.25-7.31 (m, 1H), 4.42 (t, J=5.0 Hz, 1H), 3.61 (d, J=13.1 Hz, 1H), 3.44 (d, J=13.1 Hz, 1H), 3.26 (s, 1H), 2.84-

2.87 (m, 1H), 2.44-2.55 (m, 2H), 2.41-2.44 (m, 1H), 2.33-2.36 (m, 1H), 2.24-2.27 (m, 1H), 1.96-2.20 (m, 1H), 2.03-2.12 (m, 2H), 1.79-1.86 (m, 1H), 1.51-1.59 (m, 1H), 1.35-1.41 (m, 1H), 1.14 (s, 9H); MS (ESI+) m/z 330 (M+H)$^+$.

Example 358

$N^1$-[(3aS,4R,6aR)-2-benzyloctahydrocyclopenta[c]pyrrol-4-yl]-$N^2$,4-dimethyl-L-leucinamide The title compound was prepared by substituting tert-butyl (S)-1-((3aS,4R,6aR)-2-benzyloctahydrocyclopenta[c]pyrrol-4-ylamino)-4,4-dimethyl-1-oxopentan-2-yl(methyl)carbamate from Example 248 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.21-8.24 (m, 1H), 7.43-7.45 (m, 2H), 7.37 (t, J=7.4 Hz, 2H), 7.27 (t, J=7.3 Hz, 1H), 4.42-4.48 (m, 1H), 3.61 (d, J=13.1 Hz, 1H), 3.45 (d, J=13.1 Hz, 1H), 3.19 (t, J=5.8 Hz, 1H), 2.88 (d, J=10.3 Hz, 1H), 2.50-2.55 (m, 1H), 2.42 (dd, J=9.0, 7.1 Hz, 1H), 2.40 (s, 3H), 2.36 (dd, J=8.6, 2.6 Hz, 1H), 2.23-2.27 (m, 1H), 2.12 (dq, J=11.9, 5.9 Hz, 1H), 1.93 (dd, J=14.0, 5.2 Hz, 1H), 1.80-1.90 (m, 2H), 1.68-1.93 (m, 1H), 1.55-1.64 (m, 1H), 1.51 (dd, J=14.0, 6.6 Hz, 1H), 1.36-1.45 (m, 1H), 0.98 (s, 9H); MS (ESI+) m/z 358 (M+H)$^+$.

Example 359

$N^1$-[(3aS,4S,6aR)-2-benzyloctahydrocyclopenta[c]pyrrol-4-yl]-$N^2$-methyl-L-norvalinamide The title compound was prepared by substituting tert-butyl (S)-1-((3aS,4S,6aR)-2-benzyloctahydrocyclopenta[c]pyrrol-4-ylamino)-1-oxopentan-2-yl(methyl)carbamate from Example 238 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.37-8.42 (m, 1H), 7.51-7.53 (m, 2H), 7.36-7.41 (m, 2H), 7.31 (t, J=7.4 Hz, 1H), 4.52-4.57 (m, 1H), 3.73 (d, J=12.7 Hz, 1H), 3.30 (d, J=12.8 Hz, 1H), 3.19 (t, J=6.2 Hz, 1H), 2.77-2.82 (m, 1H), 2.67-2.73 (m, 1H), 2.39-2.47 (m, 3H), 2.40 (s, 3H), 2.18 (dd, J=9.5, 7.1 Hz, 1H), 2.07-2.15 (m, 1H), 1.85-1.91 (m, 1H), 1.79-1.83 (m, 1H), 1.63-1.78 (m, 2H), 1.54-1.62 (m, 1H), 1.42-1.52 (m, 2H), 1.23-1.31 (m, 1H), 0.86 (t, J=7.3 Hz, 3H); MS (ESI+) m/z 330 (M+H)$^+$.

Example 360

$N^1$-[(3aS,4S,6aR)-2-benzyloctahydrocyclopenta[c]pyrrol-4-yl]-$N^2$-methyl-L-leucinamide The title compound was prepared by substituting tert-butyl (S)-1-((3aS,4S,6aR)-2-benzyloctahydrocyclopenta[c]pyrrol-4-ylamino)-4-methyl-1-oxopentan-2-yl(methyl)carbamate from Example 239 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.47 (d, J=7.3 Hz, 1H), 7.51-7.53 (m, 2H), 7.39 (t, J=7.5 Hz, 2H), 7.31 (t, J=7.3 Hz, 1H), 4.52-4.58 (m, 1H), 3.77 (d, J=12.8 Hz, 1H), 3.29 (d, J=12.8 Hz, 1H), 3.27 (dd, J=8.2, 5.7 Hz, 1H), 2.82 (dd, J=9.5, 2.3 Hz, 1H), 2.71-2.76 (m, 1H), 2.42-2.49 (m, 1H), 2.41 (s, 3H), 2.37-2.42 (m, 1H), 2.22 (dd, J=9.4, 7.2 Hz, 1H), 2.15 (t, J=8.3 Hz, 1H), 1.83-1.96 (m, 2H), 1.72-1.80 (m, 1H), 1.54-1.72 (m, 3H), 1.28 (dq, J=12.9, 6.4 Hz, 1H), 0.92 (d, J=6.6 Hz, 3H), 0.90 (d, J=6.6 Hz, 3H); MS (ESI+) m/z 344 (M+H)$^+$.

Example 361

$N^1$-[(3aR,4S,6aS)-2-benzyloctahydrocyclopenta[c]pyrrol-4-yl]-4-methyl-L-leucinamide The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-ylcarbamate from Example 226 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.27-8.30 (m, 1H), 7.43-7.45 (m, 2H), 7.37 (t, J=7.4 Hz, 2H), 7.25-7.29 (m, 1H), 4.36-4.42 (m, 1H), 3.58-3.61 (m, 2H), 3.45 (d, J=13.1 Hz, 1H), 2.86 (dd, J=9.0, 2.4 Hz, 1H), 2.45-2.54 (m, 2H), 2.39 (dd, J=9.0, 7.2 Hz, 1H), 2.36 (dd, J=9.1, 2.5 Hz, 1H), 2.24 (dd, J=8.8, 6.9 Hz, 1H), 2.18 (dd, J=14.0, 4.3 Hz, 1H), 2.01-2.23 (m, 2H), 2.07-2.14 (m, 1H), 1.79-1.87 (m, 1H), 1.56 (dq, J=12.0, 7.7 Hz, 1H), 1.44 (dd, J=14.0, 7.5 Hz, 1H), 1.35-1.44 (m, 1H), 0.98 (s, 9H); MS (ESI+) m/z 344 (M+H)$^+$.

Example 362

$N^1$-[(3aR,4S,6aS)-2-benzyloctahydrocyclopenta[c]pyrrol-4-yl]-$N^2$-methyl-L-norleucinamide The title compound was prepared by substituting tert-butyl (S)-1-((3aR,4S,6aS)-2-benzyloctahydrocyclopenta[c]pyrrol-4-ylamino)-1-oxohexan-2-yl(methyl)carbamate from Example 227 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.07-8.10 (m, 1H), 7.43-7.46 (m, 2H), 7.37 (t, J=7.5 Hz, 2H), 7.28 (t, J=7.4 Hz, 1H), 4.42-4.47 (m, 1H), 3.61 (d, J=13.1 Hz, 1H), 3.46 (d, J=13.1 Hz, 1H), 3.15 (t, J=6.5 Hz, 1H), 2.87 (dd, J=9.0, 2.5 Hz, 1H), 2.47-2.58 (m, 2H), 2.40-2.44 (m, 1H), 2.41 (s, 3H), 2.37 (dd, J=8.9, 2.6 Hz, 1H), 2.26 (dd, J=8.9, 6.8 Hz, 1H), 2.08-2.17 (m, 1H), 1.93-2.16 (m, 1H), 1.80-1.89 (m, 2H), 1.67-1.75 (m, 1H), 1.59 (dq, J=12.0, 7.6 Hz, 1H), 1.38-1.50 (m, 3H), 1.20-1.28 (m, 2H), 0.81 (t, J=7.3 Hz, 3H); MS (ESI+) m/z 344 (M+H)$^+$.

Example 363

$N^1$-[(3aR,4R,6aS)-2-benzyloctahydrocyclopenta[c]pyrrol-4-yl]-$N^2$-methyl-L-norvalinamide The title compound was prepared by substituting tert-butyl (S)-1-((3aR,4R,6aS)-2-benzyloctahydrocyclopenta[c]pyrrol-4-ylamino)-1-oxopentan-2-yl(methyl)carbamate from Example 240 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.26 (d, J=7.8 Hz, 1H), 7.50-7.52 (m, 2H), 7.39 (t, J=7.5 Hz, 2H), 7.32 (t, J=7.3 Hz, 2H), 4.51-4.57 (m, 1H), 3.57 (d, J=12.7 Hz, 1H), 3.42 (d, J=12.7 Hz, 1H), 3.13-3.16 (m, 1H), 2.75-2.78 (m, 1H), 2.63-2.70 (m, 1H), 2.45-2.49 (m, 1H), 2.39-2.47 (m, 1H), 2.39 (s, 3H), 2.14 (dd, J=8.9, 7.6 Hz, 1H), 2.09 (dd, J=9.5, 7.2 Hz, 1H), 1.82-2.27 (m, 1H), 1.83-1.91 (m, 1H), 1.63-1.81 (m, 3H), 1.54-1.63 (m, 1H), 1.39-1.54 (m, 2H), 1.25-1.33 (m, 1H), 0.86 (t, J=7.3 Hz, 3H); MS (ESI+) m/z 330 (M+H)$^+$.

Example 364

N$^1$-[(3aR,4R,6aS)-2-benzyloctahydrocyclopenta[c]pyrrol-4-yl]-N$^2$-methyl-L-leucinamide The title compound was prepared by substituting tert-butyl (S)-1-((3aR,4R,6aS)-2-benzyloctahydrocyclopenta[c]pyrrol-4-ylamino)-4-methyl-1-oxopentan-2-yl(methyl)carbamate from Example 241 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.24-8.27 (m, 1H), 7.50-7.52 (m, 2H), 7.40 (t, J=7.5 Hz, 2H), 7.32 (t, J=7.4 Hz, 1H), 4.50-4.56 (m, 1H), 3.54 (d, J=12.7 Hz, 1H), 3.45 (d, J=12.7 Hz, 1H), 3.20 (dd, J=8.2, 5.7 Hz, 1H), 2.76-2.78 (m, 1H), 2.64-2.71 (m, 1H), 2.46-2.49 (m, 1H), 2.41-2.47 (m, 1H), 2.39 (s, 3H), 2.16 (t, J=8.2 Hz, 1H), 2.06-2.12 (m, 1H), 1.78-2.09 (m, 1H), 1.82-1.93 (m, 2H), 1.63-1.76 (m, 2H), 1.55-1.63 (m, 1H), 1.48-1.56 (m, 1H), 1.25-1.35 (m, 1H), 0.93 (d, J=6.5 Hz, 3H), 0.88 (d, J=6.6 Hz, 3H); MS (ESI+) m/z 344 (M+H)$^+$.

Example 365

N$^1$-[(3aR,4S,6aS)-2-benzyloctahydrocyclopenta[c]pyrrol-4-yl]-N$^2$-methyl-L-norvalinamide The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Step A of Example 313 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.08-8.10 (m, 1H), 7.43-7.46 (m, 2H), 7.37 (t, J=7.4 Hz, 2H), 7.28 (t, J=7.3 Hz, 1H), 4.41-4.46 (m, 1H), 3.61 (d, J=13.1 Hz, 1H), 3.45 (d, J=13.1 Hz, 1H), 3.15 (t, J=6.5 Hz, 1H), 2.86 (dd, J=9.0, 2.5 Hz, 1H), 2.47-2.57 (m, 2H), 2.40-2.44 (m, 1H), 2.40 (s, 3H), 2.37 (dd, J=9.0, 2.3 Hz, 1H), 2.24-2.27 (m, 1H), 2.07-2.16 (m, 1H), 1.90-2.10 (m, 1H), 1.77-1.88 (m, 2H), 1.63-1.73 (m, 1H), 1.54-1.63 (m, 1H), 1.36-1.53 (m, 3H), 0.84 (t, J=7.3 Hz, 3H); MS (ESI+) m/z 330 (M+H)$^+$.

Example 366

N$^2$-ethyl-N$^1$-{(3aR,4S,6aS)-2-[3-(trifluoromethyl)benzyl]octahydrocyclopenta[c]pyrrol-4-yl}-L-leucinamide The title compound was prepared by substituting tert-butyl ethyl((S)-4-methyl-1-oxo-1-((3aR,4S,6aS)-2-(3-(trifluoromethyl)benzyl)octahydrocyclopenta[c]pyrrol-4-ylamino)pentan-2-yl)carbamate from Example 310 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.23-8.26 (m, 1H), 7.76-7.77 (bs, 1H), 7.55-7.63 (m, 2H), 7.45 (t, J=7.7 Hz, 1H), 4.41-4.45 (m, 1H), 3.61 (d, J=13.5 Hz, 1H), 3.48 (d, J=13.5 Hz, 1H), 3.33 (dd, J=8.2, 5.8 Hz, 1H), 2.86 (dd, J=9.0, 2.3 Hz, 1H), 2.70-2.78 (m, 1H), 2.60-2.64 (m, 1H), 2.53-2.55 (m, 2H), 2.43-2.47 (m, 1H), 2.33 (dd, J=9.0, 2.4 Hz, 1H), 2.28 (dd, J=8.8, 6.3 Hz, 1H), 2.08-2.12 (m, 1H), 1.80-2.05 (m, 1H), 1.82-1.95 (m, 2H), 1.72 (ddd, J=13.5, 7.8, 5.8 Hz, 1H), 1.56-1.63 (m, 2H), 1.39-1.45 (m, 1H), 1.08 (t, J=7.1 Hz, 3H), 0.92 (d, J=6.6 Hz, 3H), 0.86 (d, J=6.5 Hz, 3H); MS (ESI+) m/z 462 (M+H)$^+$.

Example 367

N$^2$-methyl-N$^1$-{(3aS,4R,6aR)-2-[4-(trifluoromethyl)benzyl]octahydrocyclopenta[c]pyrrol-4-yl}-L-valinamide Step A: tert-Butyl methyl((S)-3-methyl-1-oxo-1-((3aS,4R,6aR)-2-(4-(trifluoromethyl)benzyl)octahydrocyclopenta[c]pyrrol-4-ylamino)butan-2-yl)carbamate was prepared by substituting tert-butyl(S)-1-((3aS,4R,6aR)-2-benzyloctahydrocyclopenta[c]pyrrol-4-ylamino)-3-methyl-1-oxobutan-2-yl(methyl)carbamate from Example 232 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedures described in Example 303: $^1$H NMR (500 MHz, pyridine-d$_5$) δ ppm 7.59 (d, J=8.0, 2H), 7.46 (d, J=7.9, 2H), 4.35 (d, J=9.6, 1H), 4.30-4.23 (m, 1H), 3.55 (d, J=13.7, 1H), 3.48 (d, J=13.7, 1H), 3.01 (s, 3H), 2.77 (dd, J=8.9, 2.1, 1H), 2.57-2.48 (m, 1H), 2.42 (ddd, J=10.7, 9.3, 6.0, 2H), 2.36 (dd, J=14.0, 5.7, 2H), 2.30-2.25 (m, 1H), 2.12-2.03 (m, 2H), 1.87 (td, J=12.9, 6.3, 1H), 1.57 (dt, J=14.8, 7.9, 1H), 1.45 (s, 9H), 1.43-1.35 (m, 1H), 1.01 (d, J=6.5, 3H), 0.87 (d, J=6.7, 3H); MS (ESI+) m/z 498 (M+H)$^+$.

Step B: The title compound was prepared by substituting tert-butyl methyl((S)-3-methyl-1-oxo-1-((3aS,4R,6aR)-2-(4-(trifluoromethyl)benzyl)octahydrocyclopenta[c]pyrrol-4-ylamino)butan-2-yl)carbamate from Step A for tert-butyl(S)-1-((3aS,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.13-8.16 (m, 1H), 7.65-7.67 (m, 2H), 7.51-7.54 (m, 2H), 4.45-4.51 (m, 1H), 3.60 (d, J=13.7 Hz, 1H), 3.47 (d, J=13.7 Hz, 1H), 2.90 (d, J=13.1 Hz, 1H), 2.88-2.90 (m, 1H), 2.48-2.59 (m, 2H), 2.40 (s, 3H), 2.33-2.40 (m, 2H), 2.24 (dd, J=8.9, 7.0 Hz, 1H), 2.08-2.16 (m, 2H), 1.94-2.10 (m, 1H), 1.85-1.93 (m, 1H), 1.60 (dq, J=12.0, 7.7 Hz, 1H), 1.43 (ddt, J=8.9, 12.4, 6.2 Hz, 1H), 1.06 (t, J=6.9 Hz, 6H); MS (ESI+) m/z 398 (M+H)$^+$.

Example 368

(2S)-N-[(3aS,4R,6aR)-2-(4-fluorobenzyl)octahydrocyclopenta[c]pyrrol-4-yl]piperidine-2-carboxamide Step A: tert-butyl(2S)-2-({[(3aS,4R,6aR)-2-(4-fluorobenzyl)octahydrocyclopenta[c]pyrrol-4-yl]amino}carbonyl)piperidine-1-carboxylate was prepared by substituting tert-butyl(2S)-2-({[(3aS,4R,6aR)-2-benzyloctahydrocyclopenta[c]pyrrol-4-yl]amino}carbonyl)piperidine-1-carboxylate from Example 231 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluorobenzaldehyde for 3-(trifluoromethyl)benzaldehyde in the procedures described in Example 303: $^1$H NMR (500 MHz, pyridine-d$_5$) δ ppm 7.37 (d, J=7.2, 2H), 7.30 (t, J=7.5, 2H), 7.21 (t, J=7.3, 2H), 4.87 (d, J=3.9, 1H), 4.32-4.23 (m, 1H), 4.10 (d, J=12.8, 1H), 3.58 (d, J=13.2, 1H), 3.47 (d, J=13.2, 1H), 3.29 (td, J=12.8, 2.9, 1H), 2.83-2.76 (m, 1H), 2.52 (td, J=8.1, 3.4, 1H), 2.48-2.41 (m, 2H), 2.36 (dd, J=9.0, 3.1, 1H), 2.33-2.28 (m, 1H), 2.24 (dd, J=11.7, 1.6, 1H), 2.07 (dq, J=12.2, 6.1, 1H), 1.87-

1.78 (m, 1H), 1.69-1.59 (m, 1H), 1.59-1.49 (m, 3H), 1.48 (s, 9H), 1.45-1.29 (m, 3H); MS (ESI+) m/z 428 (M+H)+.

Step B: The title compound was prepared by substituting tert-butyl(2S)-2-({[(3aS,4R,6aR)-2-(4-fluorobenzyl)octahydrocyclopenta[c]pyrrol-4-yl]amino}carbonyl)piperidine-1-carboxylate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 7.68-7.70 (m, 1H), 7.35 (dd, J=8.3, 5.6 Hz, 2H), 7.10-7.14 (m, 2H), 4.34-4.40 (m, 1H), 3.51 (d, J=13.1 Hz, 1H), 3.36 (d, J=13.1 Hz, 1H), 3.32 (dd, J=10.4, 3.2 Hz, 1H), 2.98-3.02 (m, 1H), 2.82 (dd, J=9.0, 2.6 Hz, 1H), 2.54-2.61 (m, 1H), 2.48-2.54 (m, 1H), 2.39-2.46 (m, 1H), 2.33-2.45 (m, 1H), 2.29-2.35 (m, 2H), 2.16-2.22 (m, 1H), 2.01-2.10 (m, 2H), 1.78-1.87 (m, 1H), 1.65-1.74 (m, 1H), 1.56-1.64 (m, 1H), 1.47-1.56 (m, 1H), 1.34-1.44 (m, 2H), 1.26-1.34 (m, 2H); MS (ESI+) m/z 346 (M+H)+.

Example 369

N$^1$-[(3aS,4R,6aR)-2-(4-fluorobenzyl)octahydrocyclopenta[c]pyrrol-4-yl]-N$^2$-methyl-L-valinamide Step A: tert-Butyl methyl((S)-3-methyl-1-oxo-1-((3aS,4R,6aR)-2-(4-fluorobenzyl)octahydrocyclopenta[c]pyrrol-4-ylamino)butan-2-yl)carbamate was prepared by substituting tert-butyl(S)-1-((3aS,4R,6aR)-2-benzyloctahydrocyclopenta[c]pyrrol-4-ylamino)-3-methyl-1-oxobutan-2-yl(methyl)carbamate from Example 232 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluorobenzaldehyde for 3-(trifluoromethyl)benzaldehyde in the procedures described in Example 303: $^1$H NMR (500 MHz, pyridine-$d_5$) δ ppm 7.43 (s, 1H), 7.30 (dd, J=8.3, 5.7, 2H), 7.03 (t, J=8.8, 2H), 4.35 (d, J=9.5, 1H), 4.25 (s, 1H), 3.49 (d, J=13.2, 1H), 3.41 (d, J=13.2, 1H), 3.01 (s, 3H), 2.75 (dd, J=8.9, 2.3, 1H), 2.57-2.48 (m, 1H), 2.45-2.31 (m, 4H), 2.27 (dd, J=8.8, 7.4, 1H), 2.11-2.03 (m, 1H), 1.85 (dt, J=20.7, 6.5, 1H), 1.56 (dt, J=15.2, 7.3, 1H), 1.46 (s, 9H), 1.43-1.35 (m, 1H), 1.01 (d, J=6.5, 3H), 0.87 (d, J=6.7, 3H); MS (ESI+) m/z 448 (M+H)+.

Step B: The title compound was prepared by substituting tert-butyl methyl((S)-3-methyl-1-oxo-1-((3aS,4R,6aR)-2-(4-fluorobenzyl)octahydrocyclopenta[c]pyrrol-4-ylamino)butan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.11-8.14 (m, 1H), 7.37 (dd, J=8.3, 5.6 Hz, 2H), 7.11-7.15 (m, 2H), 4.43-4.49 (m, 1H), 3.54 (d, J=13.1 Hz, 1H), 3.39 (d, J=13.1 Hz, 1H), 2.90 (d, J=5.8 Hz, 1H), 2.86 (dd, J=9.0, 2.6 Hz, 1H), 2.47-2.56 (m, 2H), 2.40 (s, 3H), 2.38 (dd, J=9.0, 7.0 Hz, 1H), 2.34 (dd, J=9.0, 2.6 Hz, 1H), 2.23 (dd, J=8.9, 7.0 Hz, 1H), 2.07-2.16 (m, 2H), 1.93-2.04 (m, 1H), 1.83-1.92 (m, 1H), 1.59 (dq, J=12.1, 7.7 Hz, 1H), 1.41 (ddt, J=8.9, 12.4, 6.2 Hz, 1H), 1.06 (t, J=6.8 Hz, 6H); MS (ESI+) m/z 348 (M+H)+.

Example 370

(2S)-N-{(3aS,4R,6aR)-2-[4-(trifluoromethyl)benzyl]octahydrocyclopenta[c]pyrrol-4-yl}piperidine-2-carboxamide Step A: tert-butyl(2S)-2-({[(3aS,4R,6aR)-2-(4-(trifluoromethyl)benzyl)octahydrocyclopenta[c]pyrrol-4-yl]amino}carbonyl)piperidine-1-carboxylate was prepared by substituting tert-butyl(2S)-2-({[(3aS,4R,6aR)-2-benzyloctahydrocyclopenta[c]pyrrol-4-yl]amino}carbonyl)piperidine-1-carboxylate from Example 231 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedures described in Example 303: $^1$H NMR (500 MHz, pyridine-$d_5$) δ ppm 7.59 (d, J=8.1, 2H), 7.47 (d, J=8.0, 2H), 7.27-7.20 (m, 1H), 4.87 (d, J=3.7, 1H), 4.32-4.23 (m, 1H), 3.57 (d, J=13.7, 1H), 3.49 (d, J=13.8, 1H), 3.29 (td, J=12.8, 3.0, 1H), 2.81 (dd, J=8.7, 2.0, 1H), 2.59-2.50 (m, 1H), 2.46 (ddd, J=12.1, 7.0, 2.8, 1H), 2.43-2.38 (m, 1H), 2.36 (dd, J=9.0, 2.9, 1H), 2.32-2.27 (m, 1H), 2.27-2.20 (m, 1H), 2.11-2.03 (m, 2H), 1.86 (ddd, J=12.7, 8.1, 6.3, 1H), 1.70-1.60 (m, 1H), 1.59-1.49 (m, 4H), 1.47 (s, 9H), 1.45-1.29 (m, 2H); MS (ESI+) m/z 496 (M+H)+.

Step B: The title compound was prepared by substituting tert-butyl(2S)-2-({[(3aS,4R,6aR)-2-(4-(trifluoromethyl)benzyl)octahydrocyclopenta[c]pyrrol-4-yl]amino}carbonyl)piperidine-1-carboxylate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 7.71 (d, J=7.5 Hz, 1H), 7.64-7.66 (m, 2H), 7.49-7.52 (m, 2H), 4.36-4.41 (m, 1H), 3.57 (d, J=13.7 Hz, 1H), 3.43 (d, J=13.7 Hz, 1H), 3.33 (dd, J=10.3, 3.2 Hz, 1H), 2.98-3.03 (m, 1H), 2.85 (dd, J=9.0, 2.5 Hz, 1H), 2.50-2.60 (m, 2H), 2.36-2.58 (m, 1H), 2.41-2.46 (m, 1H), 2.34 (d, J=7.6 Hz, 1H), 2.31-2.33 (m, 1H), 2.20 (dd, J=8.9, 7.2 Hz, 1H), 2.02-2.10 (m, 2H), 1.81-1.88 (m, 1H), 1.66-1.71 (m, 1H), 1.50-1.63 (m, 2H), 1.35-1.42 (m, 2H), 1.24-1.34 (m, 2H); MS (ESI+) m/z 396 (M+H)+.

Example 371

N$^2$-methyl-N$^1$-{(3aS,4R,6aR)-2-[4-(trifluoromethyl)benzyl]octahydrocyclopenta[c]pyrrol-4-yl}-L-norvalinamide The title compound was prepared by substituting tert-butyl methyl((S)-1-oxo-1-((3aS,4R,6aR)-2-(4-(trifluoromethyl)benzyl)octahydrocyclopenta[c]pyrrol-4-ylamino)pentan-2-yl)carbamate from Example 317 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.14-8.17 (m, 1H), 7.64-7.67 (m, 2H), 7.51-7.54 (m, 2H), 4.43-4.49 (m, 1H), 3.59 (d, J=13.7 Hz, 1H), 3.47 (d, J=13.7 Hz, 1H), 3.16 (t, J=6.5 Hz, 1H), 2.88 (dd, J=9.0, 2.6 Hz, 1H), 2.44-2.58 (m, 2H), 2.40 (s, 3H), 2.34-2.39 (m, 2H), 2.24 (t, J=8.0 Hz, 1H), 2.12 (dq, J=11.8, 5.9 Hz, 1H), 1.95-2.18 (m, 1H), 1.85-1.93 (m, 1H), 1.76-1.85 (m, 1H), 1.66-1.73 (m, 1H), 1.56-1.64 (m, 1H), 1.39-1.53 (m, 3H), 0.84 (t, J=7.3 Hz, 3H); MS (ESI+) m/z 398 (M+H)+.

Example 372

N$^1$-[(3aS,4R,6aR)-2-(4-fluorobenzyl)octahydrocyclopenta[c]pyrrol-4-yl]-N$^2$-methyl-L-norvalinamide The title compound was prepared by substituting tert-butyl (S)-1-((3aS,4R,6aR)-2-(4-fluorobenzyl)octahydrocyclopenta[c]pyrrol-4-ylamino)-1-oxopentan-2-yl(methyl)carbamate from Example 318 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.12-8.15 (m, 1H), 7.35-7.39 (m, 2H), 7.11-7.15 (m, 2H), 4.41-4.47 (m, 1H), 3.53 (d, J=13.1 Hz, 1H), 3.39 (d, J=13.1 Hz, 1H), 3.16 (t, J=6.5 Hz, 1H), 2.85 (dd, J=9.0, 2.6 Hz, 1H), 2.46-2.59 (m, 2H), 2.40 (s, 3H), 2.38 (dd, J=8.9, 6.8 Hz, 1H), 2.34 (dd, J=8.9, 2.8 Hz, 1H), 2.23 (dd, J=8.9, 7.1 Hz, 1H), 2.07-2.16 (m, 1H), 1.91-2.12 (m, 1H), 1.84-1.91 (m, 1H), 1.76-1.83 (m, 1H), 1.66-1.73 (m, 1H), 1.54-1.63 (m, 1H), 1.36-1.54 (m, 3H), 0.84 (t, J=7.3 Hz, 3H); MS (ESI+) m/z 348 (M+H)$^+$.

Example 373

N$^2$-methyl-N$^1$-{(3aS,4R,6aR)-2-[3-(trifluoromethyl)benzyl]octahydrocyclopenta[c]pyrrol-4-yl}-L-valinamide The title compound was prepared by substituting tert-butyl methyl((S)-3-methyl-1-oxo-1-((3aS,4R,6aR)-2-(3-(trifluoromethyl)benzyl)octahydrocyclopenta[c]pyrrol-4-ylamino)butan-2-yl)carbamate from Example 316 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.13 (d, J=7.6, 1H), 7.76 (s, 1H), 7.61 (d, J=7.6, 1H), 7.56 (s, 1H), 7.45 (t, J=7.7, 1H), 4.52-4.36 (m, 1H), 3.62 (d, J=13.6, 1H), 3.46 (d, J=13.6, 1H), 2.92-2.79 (m, 2H), 2.59-2.46 (m, 2H), 2.43 (d, J=8.8, 1H), 2.40 (s, 3H), 2.33 (dd, J=9.0, 2.5, 1H), 2.28-2.22 (m, 1H), 2.15-2.05 (m, 2H), 2.04-1.93 (m, 1H), 1.86 (td, J=12.9, 6.4, 1H), 1.59 (dt, J=14.9, 7.7, 1H), 1.44-1.36 (m, 1H), 1.05 (t, J=7.0, 6H); MS (ESI+) m/z 398 (M+H)$^+$.

Example 374

N$^1$-{(3aS,4R,6aR)-2-[3-fluoro-4-(trifluoromethyl)benzyl]octahydrocyclopenta[c]pyrrol-4-yl}-N$^2$-methyl-L-leucinamide The title compound was prepared by substituting tert-butyl (S)-1-((3aS,4R,6aR)-2-(3-fluoro-4-(trifluoromethyl)benzyl)octahydrocyclopenta[c]pyrrol-4-ylamino)-4-methyl-1-oxopentan-2-yl(methyl)carbamate from Example 311 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.20-8.22 (m, 1H), 7.58-7.61 (m, 1H), 7.32-7.36 (m, 1H), 7.27-7.29 (m, 1H), 4.43-4.48 (m, 1H), 3.55-3.62 (m, 1H), 3.45 (d, J=14.1 Hz, 1H), 3.22 (dd, J=8.2, 5.8 Hz, 1H), 2.91 (dd, J=9.0, 2.5 Hz, 1H), 2.48-2.60 (m, 2H), 2.42 (s, 3H), 2.35-2.39 (m, 2H), 2.23 (dd, J=8.9, 7.1 Hz, 1H), 2.07-2.16 (m, 1H), 1.91-2.11 (m, 1H), 1.84-1.95 (m, 2H), 1.71 (ddd, J=13.5, 7.8, 5.8 Hz, 1H), 1.56-1.65 (m, 2H), 1.39-1.46 (m, 1H), 0.91 (d, J=6.6 Hz, 3H), 0.85 (d, J=6.5 Hz, 3H); MS (ESI+) m/z 430 (M+H)$^+$.

Example 375

N$^1$-{(3aS,4R,6aR)-2-[4-fluoro-3-(trifluoromethyl)benzyl]octahydrocyclopenta[c]pyrrol-4-yl}-N$^2$-methyl-L-leucinamide The title compound was prepared by substituting tert-butyl (S)-1-((3aS,4R,6aR)-2-(4-fluoro-3-(trifluoromethyl)benzyl)octahydrocyclopenta[c]pyrrol-4-ylamino)-4-methyl-1-oxopentan-2-yl(methyl)carbamate from Example 312 for tert-butyl(S)-1-((3aS,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.18-8.21 (m, 1H), 7.68-7.71 (m, 1H), 7.57-7.60 (m, 1H), 7.22-7.28 (m, 1H), 4.42-4.46 (m, 1H), 3.55 (d, J=13.5 Hz, 1H), 3.43 (d, J=13.4 Hz, 1H), 3.21 (dd, J=8.2, 5.8 Hz, 1H), 2.88 (dd, J=9.0, 2.6 Hz, 1H), 2.48-2.60 (m, 2H), 2.42 (s, 3H), 2.37-2.42 (m, 1H), 2.34 (dd, J=8.8, 2.4 Hz, 1H), 2.21-2.28 (m, 1H), 2.06-2.14 (m, 1H), 1.90-2.08 (m, 1H), 1.83-1.94 (m, 2H), 1.71 (ddd, J=13.5, 7.8, 5.8 Hz, 1H), 1.55-1.64 (m, 2H), 1.38-1.45 (m, 1H), 0.91 (d, J=6.5 Hz, 3H), 0.85 (d, J=6.5 Hz, 3H); MS (ESI+) m/z 430 (M+H)$^+$.

Example 376

N$^2$-methyl-N$^1$-{(3aR,4S,6aS)-2-[3-(trifluoromethyl)benzyl]octahydrocyclopenta[c]pyrrol-4-yl}-L-norvalinamide The title compound was prepared by substituting tert-butyl methyl((S)-1-oxo-1-((3aR,4S,6aS)-2-(3-(trifluoromethyl)benzyl)octahydrocyclopenta[c]pyrrol-4-ylamino)pentan-2-yl)carbamate from Example 313 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.09-8.12 (m, 1H), 7.76-7.77 (bs, 1H), 7.60-7.63 (m, 1H), 7.55-7.58 (m, 1H), 7.45 (t, J=7.7 Hz, 1H), 4.40-4.44 (m, 1H), 3.61 (d, J=13.5 Hz, 1H), 3.47 (d, J=13.5 Hz, 1H), 3.15 (t, J=6.5 Hz, 1H), 2.87 (dd, J=9.0, 2.6 Hz, 1H), 2.47-2.57 (m, 2H), 2.40-2.44 (m, 1H), 2.40 (s, 3H), 2.33 (dd, J=9.0, 2.7 Hz, 1H), 2.23-2.27 (m, 1H), 2.05-2.12 (m, 1H), 1.93-2.10 (m, 1H), 1.83-1.90 (m, 1H), 1.76-1.83 (m, 1H), 1.64-1.73 (m, 1H), 1.54-1.63 (m, 1H), 1.36-1.53 (m, 3H), 0.84 (t, J=7.3 Hz, 3H); MS (ESI+) m/z 398 (M+H)$^+$.

Example 377

N$^2$-methyl-N$^1$-{(3aR,4S,6aS)-2-[4-(trifluoromethyl)benzyl]octahydrocyclopenta[c]pyrrol-4-yl}-L-norvalinamide The title compound was prepared by substituting tert-butyl methyl((S)-1-oxo-1-((3aR,4S,6aS)-2-(4-(trifluoromethyl)benzyl)octahydrocyclopenta[c]pyrrol-4-ylamino)pentan-2-yl)carbamate from Example 314 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.12-8.15 (m, 1H), 7.64-7.67 (m, 2H), 7.51-7.54 (m, 2H), 4.42-4.47 (m, 1H), 3.57-3.61 (m, 1H), 3.48 (d, J=13.7 Hz, 1H), 3.16 (t, J=6.5 Hz, 1H), 2.89 (dd, J=9.0, 2.5 Hz, 1H), 2.48-2.58 (m, 2H), 2.41 (s, 3H), 2.34-2.41 (m, 2H), 2.24 (dd, J=8.9, 7.0 Hz, 1H), 2.03-2.18 (m, 1H), 1.94-2.26 (m, 1H), 1.77-1.95 (m, 2H), 1.66-1.73 (m, 1H), 1.55-1.64 (m, 1H), 1.38-1.55 (m, 3H), 0.84 (t, J=7.3 Hz, 3H); MS (ESI+) m/z 398 (M+H)$^+$.

Example 378

N$^1$-[(3aR,4S,6aS)-2-(4-fluorobenzyl)octahydrocyclopenta[c]pyrrol-4-yl]-N$^2$-methyl-L-norvalinamide The title compound was prepared by substituting tert-butyl (S)-1-((3aR,4S,6aS)-2-(4-fluorobenzyl)octahydrocyclopenta[c]pyrrol-4-ylamino)-1-oxopentan-2-yl(methyl)carbamate from Example 315 for tert-butyl(S)-1-((3aR,4S,6aS)-

2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.12-8.15 (m, 1H), 7.64-7.67 (m, 2H), 7.51-7.54 (m, 2H), 4.42-4.47 (m, 1H), 3.57-3.61 (m, 1H), 3.48 (d, J=13.7 Hz, 1H), 3.16 (t, J=6.5 Hz, 1H), 2.89 (dd, J=9.0, 2.5 Hz, 1H), 2.48-2.58 (m, 2H), 2.41 (s, 3H), 2.34-2.41 (m, 2H), 2.24 (dd, J=8.9, 7.0 Hz, 1H), 2.03-2.18 (m, 1H), 1.94-2.26 (m, 1H), 1.77-1.95 (m, 2H), 1.66-1.73 (m, 1H), 1.55-1.64 (m, 1H), 1.38-1.55 (m, 3H), 0.84 (t, J=7.3 Hz, 3H); MS (ESI+) m/z 398 (M+H)$^+$.

Example 379

N$^2$-methyl-N$^1$-{(3aR,4S,6aS)-2-[3-(trifluoromethyl) benzyl]octahydrocyclopenta[c]pyrrol-4-yl}-L-leucinamide The title compound was prepared by substituting tert-butyl methyl((S)-4-methyl-1-oxo-1-((3aR,4S,6aS)-2-(3-(trifluoromethyl)benzyl)octahydrocyclopenta[c]pyrrol-4-ylamino) pentan-2-yl)carbamate from Example 307 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.18-8.20 (m, 1H), 7.76-7.77 (bs, 1H), 7.60-7.64 (m, 1H), 7.54-7.59 (m, 1H), 7.45 (t, J=7.7 Hz, 1H), 4.40-4.47 (m, 1H), 3.61 (d, J=13.5 Hz, 1H), 3.47 (d, J=13.5 Hz, 1H), 3.22 (dd, J=8.2, 5.8 Hz, 1H), 2.87 (d, J=10.4 Hz, 1H), 2.49-2.57 (m, 2H), 2.40-2.46 (m, 1H), 2.42 (s, 3H), 2.33 (dd, J=8.9, 2.5 Hz, 1H), 2.26 (dd, J=8.9, 6.5 Hz, 1H), 2.01-2.16 (m, 1H), 1.92-2.12 (m, 1H), 1.83-1.97 (m, 2H), 1.71 (ddd, J=13.5, 7.7, 5.8 Hz, 1H), 1.55-1.64 (m, 2H), 1.37-1.44 (m, 1H), 0.91 (d, J=6.6 Hz, 3H), 0.85 (d, J=6.5 Hz, 3H); MS (ESI+) m/z 412 (M+H)$^+$.

Example 380

N$^2$-methyl-N$^1$-{(3aR,4S,6aS)-2-[4-(trifluoromethyl) benzyl]octahydrocyclopenta[c]pyrrol-4-yl}-L-leucinamide The title compound was prepared by substituting tert-butyl methyl((S)-4-methyl-1-oxo-1-((3aR,4S,6aS)-2-(4-(trifluoromethyl)benzyl)octahydrocyclopenta[c]pyrrol-4-ylamino) pentan-2-yl)carbamate from Example 308 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.19-8.22 (m, 1H), 7.64-7.67 (m, 2H), 7.51-7.54 (m, 2H), 4.43-4.48 (m, 1H), 3.59 (d, J=13.7 Hz, 1H), 3.48 (d, J=13.7 Hz, 1H), 3.23 (dd, J=8.2, 5.8 Hz, 1H), 2.90 (dd, J=9.0, 2.4 Hz, 1H), 2.49-2.58 (m, 2H), 2.43 (s, 3H), 2.38-2.42 (m, 1H), 2.37 (dd, J=19.2, 2.5 Hz, 1H), 2.24 (dd, J=8.9, 6.8 Hz, 1H), 2.09-2.17 (m, 1H), 1.95-2.13 (m, 1H), 1.83-1.97 (m, 2H), 1.72 (ddd, J=13.5, 7.8, 5.8 Hz, 1H), 1.56-1.65 (m, 2H), 1.39-1.46 (m, 1H), 0.91 (d, J=6.6 Hz, 3H), 0.85 (d, J=6.5 Hz, 3H); MS (ESI+) m/z 412 (M+H)$^+$.

Example 381

N$^1$-[(3aR,4S,6aS)-2-(4-fluorobenzyl)octahydrocyclopenta[c]pyrrol-4-yl]-N$^2$-methyl-L-leucinamide The title compound was prepared by substituting tert-butyl (S)-1-((3aR,4S,6aS)-2-(4-fluorobenzyl)octahydrocyclopenta[c]pyrrol-4-ylamino)-4-methyl-1-oxopentan-2-yl(methyl)carbamate from Example 309 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.17-8.20 (m, 1H), 7.37 (dd, J=8.2, 5.6 Hz, 2H), 7.11-7.15 (m, 2H), 4.41-4.47 (m, 1H), 3.52 (d, J=13.1 Hz, 1H), 3.40 (d, J=13.1 Hz, 1H), 3.22 (dd, J=8.2, 5.8 Hz, 1H), 2.86 (dd, J=9.0, 2.4 Hz, 1H), 2.46-2.57 (m, 2H), 2.42 (s, 3H), 2.34-2.41 (m, 2H), 2.24 (dd, J=8.9, 6.7 Hz, 1H), 2.05-2.18 (m, 1H), 1.98-2.11 (m, 1H), 1.83-1.97 (m, 2H), 1.71 (ddd, J=13.5, 7.8, 5.8 Hz, 1H), 1.55-1.64 (m, 2H), 1.41 (ddt, J=8.9, 12.3, 6.2 Hz, 1H), 0.91 (d, J=6.6 Hz, 3H), 0.85 (d, J=6.6 Hz, 3H); MS (ESI+) m/z 362 (M+H)$^+$.

Example 382

N$^1$-{(3aR,4S,6aS)-2-[4-(trifluoromethyl)benzyl] octahydrocyclopenta[c]pyrrol-4-yl}-L-norvalinamide Step A: tert-Butyl((S)-1-oxo-1-((3aR,4S,6aS)-2-benzyloctahydrocyclopenta[c]pyrrol-4-ylamino)pentan-2-yl)carbamate was prepared by substituting N-(tert-butoxycarbonyl)-L-norvaline for N-(tert-butoxycarbonyl)-L-leucine in the procedure described in Example 221: $^1$H NMR (400 MHz, pyridine-d$_5$) δ ppm 8.61-8.53 (m, 1H), 7.92 (d, J=8.2, 1H), 7.43 (d, J=7.4, 2H), 7.35 (d, J=7.6, 2H), 7.27 (t, J=7.2, 1H), 4.64 (dd, J=14.4, 7.8, 1H), 4.47-4.35 (m, 1H), 3.59 (d, J=13.1, 1H), 3.43 (d, J=13.2, 1H), 2.83 (dd, J=4.7, 4.1, 1H), 2.60-2.48 (m, 2H), 2.47-2.40 (m, 1H), 2.32 (dd, J=5.0, 3.9, 1H), 2.27-2.20 (m, 1H), 2.11-1.97 (m, 2H), 1.91-1.76 (m, 2H), 1.63-1.42 (m, 12H), 1.40-1.29 (m, 1H), 0.81 (t, J=7.3, 3H); MS (ESI+) m/z 416 (M+H)$^+$.

Step B: tert-Butyl-((S)-1-oxo-1-((3aR,4S,6aS)-2-(4-(trifluoromethyl)benzyl)octahydrocyclopenta[c]pyrrol-4-ylamino)pentan-2-yl)carbamate was prepared by substituting tert-butyl((S)-1-oxo-1-((3aR,4S,6aS)-2-benzyloctahydrocyclopenta[c]pyrrol-4-ylamino)pentan-2-yl)carbamate from Step A for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedures described in Example 303: $^1$H NMR (500 MHz, pyridine-d$_5$) δ ppm 8.60 (d, J=7.0, 1H), 7.93 (d, J=8.3, 1H), 7.65 (d, J=8.1, 2H), 7.51 (d, J=7.9, 2H), 4.64 (dd, J=13.0, 6.5, 1H), 4.47-4.37 (m, 1H), 3.57 (d, J=13.7, 1H), 3.45 (d, J=13.7, 1H), 2.86 (d, J=8.3, 1H), 2.55 (dd, J=14.1, 9.2, 2H), 2.43-2.36 (m, 1H), 2.31 (d, J=7.8, 1H), 2.26-2.20 (m, 1H), 2.14 (s, 1H), 2.04 (dd, J=12.1, 6.0, 2H), 1.90-1.80 (m, 2H), 1.59 (s, 1H), 1.49 (d, J=11.3, 10H), 1.37 (s, 1H), 0.81 (t, J=7.3, 3H); MS (ESI+) m/z 484 (M+H)$^+$.

Step C: The title compound was prepared by substituting tert-Butyl-45)-1-oxo-1-((3aR,4S,6aS)-2-(4-(trifluoromethyl)benzyl)octahydrocyclopenta[c]pyrrol-4-ylamino)pentan-2-yl)carbamate from Step B for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.19-8.22 (m, 1H), 7.64-7.67 (m, 2H), 7.50-7.53 (m, 2H), 4.37-4.43 (m, 1H), 3.53-3.58 (m, 2H), 3.46 (d, J=13.7 Hz, 1H), 2.86 (dd, J=9.0, 2.6 Hz, 1H), 2.49-2.57 (m, 1H), 2.43-2.49 (m, 1H), 2.33-2.36 (m, 2H), 2.19-2.25 (m, 1H), 2.11-2.20 (m, 2H), 2.06-2.14 (m, 1H), 1.91-2.01 (m, 1H), 1.82-1.90 (m, 2H), 1.62-1.69 (m, 1H), 1.38-1.58 (m, 4H), 0.84 (t, J=7.3 Hz, 3H); MS (ESI+) m/z 384 (M+H)$^+$.

Example 383

N²-ethyl-N¹-((3aR,4S,6aS)-2-{[3-(trifluoromethyl)phenyl]sulfonyl}octahydrocyclopenta[c]pyrrol-4-yl)-L-leucinamide The title compound was prepared by substituting tert-butyl ethyl((S)-4-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate from Example 323 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.37-8.39 (m, 1H), 8.32-8.37 (m, 1H), 8.19-8.21 (m, 1H), 7.90-7.93 (m, 1H), 7.73 (t, J=7.9 Hz, 1H), 4.23-4.29 (m, 1H), 3.86 (d, J=11.2 Hz, 1H), 3.31 (t, J=6.9 Hz, 1H), 3.18 (dd, J=9.7, 2.1 Hz, 1H), 3.16 (dd, J=9.9, 7.5 Hz, 1H), 2.96 (dd, J=9.5, 6.5 Hz, 1H), 2.68-2.75 (m, 1H), 2.51-2.63 (m, 3H), 1.90-2.12 (m, 1H), 1.91-1.99 (m, 1H), 1.80-1.91 (m, 2H), 1.66-1.72 (m, 1H), 1.52-1.60 (m, 2H), 1.26-1.34 (m, 1H), 1.06 (t, J=7.1 Hz, 3H), 0.92 (d, J=6.6 Hz, 3H), 0.85 (d, J=6.5 Hz, 3H); MS (ESI+) m/z 476 (M+H)⁺.

Example 384

N²-methyl-N¹-((3aR,4S,6aS)-2-{[3-(trifluoromethyl)phenyl]sulfonyl}octahydrocyclopenta[c]pyrrol-4-yl)-L-leucinamide The title compound was prepared by substituting tert-butyl methyl((S)-4-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate from Example 322 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.38-8.39 (bs, 1H), 8.29-8.31 (m, 1H), 8.19-8.21 (m, 1H), 7.91-7.93 (m, 1H), 7.73 (t, J=7.8 Hz, 1H), 4.24-4.29 (m, 1H), 3.87 (dd, J=9.9, 2.2 Hz, 1H), 3.17-3.22 (m, 2H), 3.15 (dd, J=9.8, 7.4 Hz, 1H), 2.95 (dd, J=9.6, 6.7 Hz, 1H), 2.49-2.60 (m, 2H), 2.39 (s, 3H), 1.93-2.10 (m, 1H), 1.91-1.99 (m, 1H), 1.80-1.91 (m, 2H), 1.68 (ddd, J=13.5, 7.8, 5.8 Hz, 1H), 1.53-1.59 (m, 2H), 1.25-1.33 (m, 1H), 0.91 (d, J=6.6 Hz, 3H), 0.85 (d, J=6.6 Hz, 3H); MS (ESI+) m/z 462 (M+H)⁺.

Example 385

N-((3aR,4S,6aS)-2-{[3-(trifluoromethyl)phenyl]sulfonyl}octahydrocyclopenta[c]pyrrol-4-yl)-L-phenylalaninamide The title compound was prepared by substituting N-(tert-butoxycarbonyl)-N-((3aR,4S,6aS)-2-{[3-(trifluoromethyl)phenyl]sulfonyl}octahydrocyclopenta[c]pyrrol-4-yl)-L-phenylalaninamide from Example 269 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.38-8.39 (bs, 1H), 8.19-8.22 (m, 2H), 7.91-7.94 (m, 1H), 7.74 (t, J=7.8 Hz, 1H), 7.29-7.35 (m, 4H), 7.24-7.29 (m, 1H), 4.92-4.95 (m, 1H), 4.16-4.23 (m, 1H), 3.80 (dd, J=7.6, 5.7 Hz, 1H), 3.77 (dd, J=9.8, 2.7 Hz, 1H), 3.32 (dd, J=13.2, 5.7 Hz, 1H), 3.15 (dd, J=9.6, 2.9 Hz, 1H), 2.99-3.03 (m, 2H), 2.89 (dd, J=9.6, 7.6 Hz, 1H), 2.41-2.47 (m, 1H), 2.32-2.37 (m, 1H), 1.98-2.15 (m, 1H), 1.83-1.89 (m, 1H), 1.71-1.77 (m, 1H), 1.35-1.43 (m, 1H), 1.17-1.26 (m, 1H); MS (ESI+) m/z 482 (M+H)⁺.

Example 386

N-methyl-N-((3aR,4S,6aS)-2-{[3-(trifluoromethyl)phenyl]sulfonyl}octahydrocyclopenta[c]pyrrol-4-yl)-L-phenylalaninamide The title compound was prepared by substituting N-(tert-butoxycarbonyl)-N-methyl-N-((3aR,4S,6aS)-2-{[3-(trifluoromethyl)phenyl]sulfonyl}octahydrocyclopenta[c]pyrrol-4-yl)-L-phenylalaninamide from Example 270 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.39-8.40 (bs, 1H), 8.25 (d, J=5.1 Hz, 1H), 7.94-7.96 (m, 1H), 7.79 (t, J=7.8 Hz, 1H), 7.31-7.33 (m, 4H), 7.24-7.28 (m, 1H), 4.17-4.24 (m, 1H), 3.73 (dd, J=9.9, 2.8 Hz, 1H), 3.45 (t, J=6.8 Hz, 1H), 3.13-3.20 (m, 2H), 3.01-3.10 (m, 2H), 2.91 (dd, J=9.6, 7.6 Hz, 1H), 2.39-2.50 (m, 1H), 2.36 (s, 3H), 2.28-2.37 (m, 1H), 2.0 (m, 1H), 1.89-2.26 (m, 1H), 1.84-1.92 (m, 1H), 1.72-1.79 (m, 1H), 1.40-1.48 (m, 1H), 1.18-1.26 (m, 1H); MS (ESI+) m/z 496 (M+H)⁺.

Example 387

N-((3aR,4S,6aS)-2-{[3-(trifluoromethyl)phenyl]sulfonyl}octahydrocyclopenta[c]pyrrol-4-yl)-L-prolinamide The title compound was prepared by substituting (S)-tert-butyl 2-((3aR,4S,6aS)-2-(3-(trifluoromethyl)phenylsulfonyl)octahydrocyclopenta[c]pyrrol-4-ylcarbamoyl)pyrrolidine-1-carboxylate from Example 271 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.35-8.38 (m, 1H), 8.17-8.19 (m, 2H), 7.90-7.92 (m, 1H), 7.72 (t, J=7.9 Hz, 1H), 4.13-4.19 (m, 1H), 3.86 (dd, J=8.6, 5.8 Hz, 1H), 3.79 (dd, J=9.9, 2.6 Hz, 1H), 3.16 (dd, J=9.6, 2.9 Hz, 1H), 3.02 (dd, J=9.9, 7.8 Hz, 1H), 2.66-3.18 (m, 1H), 2.79-2.91 (m, 3H), 2.48-2.55 (m, 1H), 2.40-2.45 (m, 1H), 1.99-2.10 (m, 2H), 1.76-1.92 (m, 2H), 1.55-1.65 (m, 1H), 1.48-1.56 (m, 1H), 1.39-1.48 (m, 1H), 1.21-1.29 (m, 1H); MS (ESI+) m/z 432 (M+H)⁺.

Example 388

(3R)-3-amino-4-methyl-N-((3aR,4S,6aS)-2-{[3-(trifluoromethyl)phenyl]sulfonyl}octahydrocyclopenta[c]pyrrol-4-yl)pentanamide The title compound was prepared by substituting tert-butyl (1R)-1-isopropyl-3-oxo-3-[((3R,4S,6aS)-2-{[3-(trifluoromethyl)phenyl]sulfonyl}octahydrocyclopenta[c]pyrrol-4-yl)amino]propylcarbamate from Example 272 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.74-8.76 (bs, 2H), 8.37-8.38 (bs, 1H), 8.19 (d, J=7.9 Hz, 1H), 7.91 (d, J=7.9 Hz, 1H), 7.72 (t, J=7.8 Hz, 1H), 4.23-4.28 (m, 1H), 3.85 (dd, J=9.9, 2.4 Hz, 1H), 3.14-3.19 (m, 2H), 3.12 (dd, J=9.9, 7.6 Hz, 1H), 2.94 (dd, J=9.6, 6.8 Hz, 1H), 2.50-2.55 (m, 2H), 2.43 (dd, J=14.4, 3.2 Hz, 1H), 2.27 (dd, J=14.4, 9.9 Hz, 1H), 1.92-1.99 (m, 1H), 1.80-1.88 (m, 1H), 1.65-1.90 (m, 1H), 1.50-1.61 (m, 2H), 1.25-1.32 (m, 1H), 0.85 (d, J=6.9 Hz, 3H), 0.83 (d, J=6.9 Hz, 3H); MS (ESI−) m/z 446 (M−H)⁻.

Example 389

N²-methyl-N¹-((3aR,4S,6aS)-2-{[3-(trifluoromethyl)phenyl]sulfonyl}octahydrocyclopenta[c]pyrrol-4-yl)-L-valinamide The title compound was prepared by substituting tert-butyl methyl((S)-3-methyl-1-oxo-1-((3aR,4S,6aS)-2-(3-(trifluoromethyl)phenylsulfonyl)octahydrocyclopenta[c]pyrrol-4-ylamino)butan-2-yl)carbamate from Example 273 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.39-8.40 (bs, 1H), 8.24 (d, J=6.9 Hz, 1H), 8.21 (d, J=7.8 Hz, 1H), 7.91-7.93 (m, 1H), 7.73 (t, J=7.8 Hz, 1H), 4.24-4.28 (m, 1H), 3.86 (dd, J=9.9, 2.4 Hz, 1H), 3.18 (dd, J=9.7, 2.4 Hz, 1H), 3.15 (dd, J=9.9, 7.5 Hz, 1H), 2.96 (dd, J=9.6, 6.9 Hz, 1H), 2.88 (d, J=5.9 Hz, 1H), 2.51-2.56 (m, 2H), 2.38 (s, 3H), 2.04-2.14 (m, 1H), 1.88-2.12 (m, 1H), 1.90-1.98 (m, 1H), 1.80-1.88 (m, 1H), 1.51-1.58 (m, 1H), 1.29 (ddt, J=9.6, 12.8, 6.4 Hz, 1H), 1.04 (d, J=6.9 Hz, 3H), 1.01-1.05 (m, 6H), 1.02 (d, J=6.9 Hz, 3H); MS (ESI+) m/z 448 (M+H)⁺.

Example 390

(2S)-N-((3aR,4S,6aS)-2-{[3-(trifluoromethyl)phenyl]sulfonyl}octahydrocyclopenta[c]pyrrol-4-yl)piperidine-2-carboxamide The title compound was prepared by substituting tert-butyl (2S)-2-{[((3aR,4S,6aS)-2-{[3-(trifluoromethyl)phenyl]sulfonyl}octahydrocyclopenta[c]pyrrol-4-yl)amino]carbonyl}piperidine-1-carboxylate from Example 274 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.35-8.36 (bs, 1H), 8.17-8.19 (m, 1H), 7.90-7.92 (m, 1H), 7.78-7.80 (m, 1H), 7.73 (t, J=7.8 Hz, 1H), 4.16-4.23 (m, 1H), 3.79 (dd, J=9.8, 2.6 Hz, 1H), 3.32 (dd, J=10.3, 3.2 Hz, 1H), 3.15 (dd, J=9.6, 2.9 Hz, 1H), 3.02 (dd, J=9.8, 7.7 Hz, 1H), 2.96-3.00 (m, 1H), 2.89 (dd, J=9.6, 7.4 Hz, 1H), 2.49-2.59 (m, 2H), 2.42-2.49 (m, 1H), 2.18-2.71 (m, 1H), 2.01-2.05 (m, 1H), 1.87-1.95 (m, 1H), 1.75-1.83 (m, 1H), 1.65-1.71 (m, 1H), 1.54-1.61 (m, 1H), 1.44-1.52 (m, 1H), 1.35-1.43 (m, 1H), 1.19-1.35 (m, 3H); MS (ESI+) m/z 446 (M+H)⁺.

Example 391

(3S)-N-((3aR,4S,6aS)-2-{[3-(trifluoromethyl)phenyl]sulfonyl}octahydrocyclopenta[c]pyrrol-4-yl)-1,2,3,4-tetrahydroisoquinoline-3-carboxamide The title compound was prepared by substituting tert-butyl (3S)-3-{[((3aR,4S,6aS)-2-{[3-(trifluoromethyl)phenyl]sulfonyl}octahydrocyclopenta[c]pyrrol-4-yl)amino]carbonyl}-3,4-dihydroisoquinoline-2(1H)-carboxylate from Example 275 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (501 MHz, pyridine-d₅, temperature 90° C.) δ ppm 8.30-8.31 (bs, 1H), 8.13-8.16 (m, 1H), 7.83-7.85 (m, 1H), 7.68-7.71 (m, 1H), 7.65 (t, J=7.9 Hz, 1H), 7.08-7.12 (m, 3H), 6.97-7.00 (m, 1H), 4.05-4.15 (m, 2H), 3.94-3.98 (m, 1H), 3.66 (dd, J=10.3, 3.4 Hz, 1H), 3.63 (dd, J=9.8, 5.2 Hz, 1H), 3.21-3.26 (m, 1H), 3.11-3.18 (m, 3H), 2.99-3.06 (m, 1H), 2.54-2.58 (m, 1H), 2.47-2.52 (m, 1H), 1.96 (m, 1H), 1.87-1.94 (m, 1H), 1.78-1.85 (m, 1H), 1.45-1.54 (m, 1H), 1.23-1.31 (m, 1H); MS (ESI−) m/z 492 (M−H)⁻.

Example 392

4-methyl-N¹-((3aR,4S,6aS)-2-{[3-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-((3aR,4S,6aS)-2-(3-(trifluoromethyl)phenylsulfonyl)octahydrocyclopenta[c]pyrrol-4-ylamino)pentan-2-ylcarbamate from Example 276 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (501 MHz, pyridine-d₅, temperature 90° C.) δ ppm 8.30-8.31 (bs, 1H), 8.13-8.16 (m, 1H), 7.82-7.85 (m, 2H), 7.65 (t, J=7.9 Hz, 1H), 4.03-4.10 (m, 1H), 3.69 (dd, J=10.1, 3.4 Hz, 1H), 3.48 (dd, J=7.5, 4.0 Hz, 1H), 3.23-3.27 (m, 1H), 3.11-3.13 (m, 2H), 2.54-2.59 (m, 1H), 2.46-2.51 (m, 1H), 2.07 (dd, J=14.1, 4.0 Hz, 1H), 2.0 (m, 1H), 1.89-1.96 (m, 1H), 1.78-1.87 (m, 1H), 1.65-1.92 (m, 1H), 1.46-1.55 (m, 1H), 1.34 (dd, J=14.1, 7.6 Hz, 1H), 1.23-1.32 (m, 1H), 0.96 (s, 9H); MS (ESI+) m/z 462 (M+H)⁺.

Example 393

N²-methyl-N¹-((3aR,4S,6aS)-2-{[3-(trifluoromethyl)phenyl]sulfonyl}octahydrocyclopenta[c]pyrrol-4-yl)-L-norleucinamide The title compound was prepared by substituting tert-butyl methyl((S)-1-oxo-1-((3aR,4S,6aS)-2-(3-(trifluoromethyl)phenylsulfonyl)octahydrocyclopenta[c]pyrrol-4-ylamino)hexan-2-yl)carbamate from Example 277 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.38-8.39 (bs, 1H), 8.19-8.23 (m, 2H), 7.91-7.93 (m, 1H), 7.73 (t, J=7.8 Hz, 1H), 4.24-4.29 (m, 1H), 3.87 (dd, J=9.9, 2.3 Hz, 1H), 3.18 (dd, J=9.8, 2.3 Hz, 1H), 3.11-3.16 (m, 2H), 2.94 (dd, J=9.6, 6.8 Hz, 1H), 2.53-2.66 (m, 2H), 2.39 (s, 3H), 1.98-2.19 (m, 1H), 1.91-1.99 (m, 1H), 1.78-1.88 (m, 2H), 1.65-1.73 (m, 1H), 1.50-1.59 (m, 1H), 1.35-1.48 (m, 2H), 1.20-1.33 (m, 3H), 0.81 (t, J=7.3 Hz, 3H); MS (ESI+) m/z 462 (M+H)⁺.

Example 394

N²-methyl-N¹-((3aR,4S,6aS)-2-{[3-(trifluoromethyl)phenyl]sulfonyl}octahydrocyclopenta[c]pyrrol-4-yl)-L-norvalinamide The title compound was prepared by substituting tert-butyl methyl((S)-1-oxo-1-((3aR,4S,6aS)-2-(3-(trifluoromethyl)phenylsulfonyl)octahydrocyclopenta[c]pyrrol-4-ylamino)pentan-2-yl)carbamate from Example 278 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500

MHz, pyridine-d$_5$) δ ppm 8.38-8.39 (bs, 1H), 8.19-8.21 (m, 2H), 7.90-7.93 (m, 1H), 7.72 (t, J=7.9 Hz, 1H), 4.22-4.29 (m, 1H), 3.87 (dd, J=9.9, 2.5 Hz, 1H), 3.18 (dd, J=9.6, 2.4 Hz, 1H), 3.10-3.15 (m, 2H), 2.94 (dd, J=9.6, 7.0 Hz, 1H), 2.49-2.57 (m, 2H), 2.37 (s, 3H), 1.92-2.22 (m, 1H), 1.89-1.99 (m, 1H), 1.74-1.87 (m, 2H), 1.62-1.70 (m, 1H), 1.40-1.58 (m, 3H), 1.25-1.32 (m, 1H), 0.84 (t, J=7.3 Hz, 3H); MS (ESI+) m/z 448 (M+H)$^+$.

Example 395

N$^2$-methyl-N$^1$-((3aR,4S,6aS)-2-{[4-(trifluoromethyl)phenyl]sulfonyl}octahydrocyclopenta[c]pyrrol-4-yl)-L-leucinamide Step A: tert-Butyl methyl((S)-4-methyl-1-oxo-1-((3aR,4S,6aS)-2-(4-(trifluoromethyl)phenylsulfonyl)octahydrocyclopenta[c]pyrrol-4-ylamino)pentan-2-yl)carbamate was prepared by substituting tert-butyl(S)-1-((3aR,4S,6aS)-2-benzyloctahydrocyclopenta[c]pyrrol-4-ylamino)-4-methyl-1-oxopentan-2-yl(methyl)carbamate from Example 222 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: $^1$H NMR (500 MHz, pyridine-d$_5$) δ ppm 8.08 (d, J=8.2, 2H), 7.82 (d, J=8.2, 2H), 7.51 (d, J=2.1, 1H), 4.83 (s, 1H), 4.12-4.04 (m, 1H), 3.67 (dd, J=10.2, 3.4, 1H), 3.27 (dd, J=10.2, 7.8, 1H), 3.14-3.09 (m, 2H), 2.94 (s, 3H), 2.63-2.46 (m, 2H), 1.95-1.68 (m, 4H), 1.60 (td, J=13.4, 6.8, 1H), 1.54-1.47 (m, 1H), 1.46 (s, 9H), 1.27 (ddt, J=13.3, 9.3, 6.7, 1H), 0.89 (dd, J=10.7, 6.6, 6H); MS (ESI+) m/z 562 (M+H)$^+$.

Step B: The title compound was prepared by substituting tert-butyl methyl((S)-4-methyl-1-oxo-1-((3aR,4S,6aS)-2-(4-(trifluoromethyl)phenylsulfonyl)octahydrocyclopenta[c]pyrrol-4-ylamino)pentan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.32-8.34 (m, 1H), 8.13-8.16 (m, 2H), 7.90-7.92 (m, 2H), 4.23-4.30 (m, 1H), 3.86 (dd, J=9.9, 2.4 Hz, 1H), 3.22 (dd, J=8.2, 5.9 Hz, 1H), 3.18 (dd, J=9.8, 2.4 Hz, 1H), 3.15 (dd, J=10.0, 7.6 Hz, 1H), 2.97 (dd, J=9.6, 6.8 Hz, 1H), 2.53-2.60 (m, 2H), 2.41 (s, 3H), 2.0 (m, 1H), 1.91-1.99 (m, 1H), 1.80-1.91 (m, 2H), 1.69 (ddd, J=13.5, 7.7, 5.9 Hz, 1H), 1.52-1.60 (m, 2H), 1.26-1.35 (m, 1H), 0.91 (d, J=6.6 Hz, 3H), 0.85 (d, J=6.5 Hz, 3H); MS (ESI+) m/z 462 (M+H)$^+$.

Example 396

N-((3aS,4R,6aR)-2-{[3-(trifluoromethyl)phenyl]sulfonyl}octahydrocyclopenta[c]pyrrol-4-yl)-L-prolinamide The title compound was prepared by substituting (S)-tert-butyl 2-((3aS,4R,6aR)-2-(3-(trifluoromethyl)phenylsulfonyl)octahydrocyclopenta[c]pyrrol-4-ylcarbamoyl)pyrrolidine-1-carboxylate from Example 266 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.36-8.37 (bs, 1H), 8.17-8.19 (m, 2H), 7.90-7.92 (m, 1H), 7.72 (t, J=7.8 Hz, 1H), 4.13-4.19 (m, 1H), 3.81-3.85 (m, 2H), 3.17 (dd, J=9.6, 2.9 Hz, 1H), 3.05 (dd, J=9.9, 7.8 Hz, 1H), 2.80-2.91 (m, 3H), 2.50-2.55 (m, 1H), 2.39-2.45 (m, 1H), 1.97-2.09 (m, 2H), 1.96 (m, 1H), 1.84-1.91 (m, 1H), 1.76-1.82 (m, 1H), 1.56-1.65 (m, 1H), 1.48-1.56 (m, 1H), 1.40-1.48 (m, 1H), 1.21-1.29 (m, 1H); MS (ESI+) m/z 432 (M+H)$^+$.

Example 397

(3R)-3-amino-4-methyl-N-((3aS,4R,6aR)-2-{[3-(trifluoromethyl)phenyl]sulfonyl}octahydrocyclopenta[c]pyrrol-4-yl)pentanamide The title compound was prepared by substituting tert-butyl (1R)-1-isopropyl-3-oxo-3-[((3aS,4R,6aR)-2-{[3-(trifluoromethyl)phenyl]sulfonyl}octahydrocyclopenta[c]pyrrol-4-yl)amino]propylcarbamate from Example 267 for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.37-8.38 (bs, 1H), 8.20 (d, J=7.9 Hz, 1H), 7.90-7.92 (m, 1H), 7.72 (t, J=7.8 Hz, 1H), 4.22-4.27 (m, 1H), 3.86 (dd, J=9.9, 2.4 Hz, 1H), 3.12-3.18 (m, 3H), 2.95 (dd, J=9.6, 6.8 Hz, 1H), 2.51-2.56 (m, 2H), 2.45 (dd, J=14.4, 3.2 Hz, 1H), 2.27 (dd, J=14.4, 9.9 Hz, 1H), 1.90-1.98 (m, 1H), 1.79-1.88 (m, 1H), 1.63-1.83 (m, 3H), 1.49-1.62 (m, 2H), 1.24-1.32 (m, 1H), 0.80-0.95 (m, 6H); MS (ESI+) m/z 448 (M+H)$^+$.

Example 398

(2S)-N-((3aS,4R,6aR)-2-{[3-(trifluoromethyl)phenyl]sulfonyl}octahydrocyclopenta[c]pyrrol-4-yl)piperidine-2-carboxamide The title compound was prepared by substituting tert-butyl (2S)-2-{[((3aS,4R,6aR)-2-{[3-(trifluoromethyl)phenyl]sulfonyl}octahydrocyclopenta[c]pyrrol-4-yl)amino]carbonyl}piperidine-1-carboxylate from Example 268 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.35-8.36 (bs, 1H), 8.17 (d, J=7.9 Hz, 1H), 7.90-7.92 (m, 1H), 7.78-7.80 (m, 1H), 7.72 (t, J=7.8 Hz, 1H), 4.16-4.23 (m, 1H), 3.83 (dd, J=9.9, 2.7 Hz, 1H), 3.30 (dd, J=10.3, 3.2 Hz, 1H), 3.16 (dd, J=9.6, 2.8 Hz, 1H), 3.04 (dd, J=9.8, 7.8 Hz, 1H), 2.95-3.00 (m, 1H), 2.89 (dd, J=9.6, 7.4 Hz, 1H), 2.49-2.59 (m, 2H), 2.41-2.49 (m, 1H), 2.29-2.51 (m, 1H), 1.96-2.04 (m, 1H), 1.86-1.92 (m, 1H), 1.77-1.83 (m, 1H), 1.64-1.70 (m, 1H), 1.52-1.61 (m, 1H), 1.43-1.53 (m, 1H), 1.34-1.43 (m, 1H), 1.20-1.34 (m, 3H); MS (ESI+) m/z 446 (M+H)$^+$.

Example 399

(2S)-N-{(3aS,4R,6aR)-2-[(4-fluorophenyl)sulfonyl]octahydrocyclopenta[c]pyrrol-4-yl}piperidine-2-carboxamide Step A: tert-butyl(2S)-2-{[((3aS,4R,6aR)-2-{[4-fluorophenyl]sulfonyl}octahydrocyclopenta[c]pyrrol-4-yl)amino]carbonyl}piperidine-1-carboxylate was prepared by substituting tert-butyl(2S)-2-({[((3aS,4R,6aR)-2-benzyloctahydrocyclopenta[c]pyrrol-4-yl]amino}carbonyl)piperidine-1-carboxylate from Example 231 for (S)-N-((3aS,4R,6aR)-2-benzyloctahydrocyclopenta[c]pyrrol-4-yl)-4-methyl-2-morpholinopentanamide and 4-fluorobenzene-1-sulfonyl chloride for 3-(trifluoromethyl)benzene-1-sulfonyl chloride in the procedure described in Example 319: ¹H NMR (500 MHz, pyridine-$d_5$) δ ppm 7.98-7.91 (m, 2H), 7.47-7.40 (m, 1H), 7.22 (dd, J=12.0, 5.3, 2H), 4.88-4.80 (m, 1H), 4.13-4.05 (m, 2H), 3.61 (dd, J=10.1, 3.3, 1H), 3.30 (td, J=12.8, 3.2, 1H), 3.23 (dd, J=10.0, 7.8, 1H), 3.07 (dd, J=8.6, 5.3, 2H), 2.60-2.46 (m, 2H), 2.19 (dd, J=12.5, 1.1, 1H), 1.97-1.89 (m, 1H), 1.85-1.77 (m, 1H), 1.66-1.49 (m, 5H), 1.47 (s, 9H), 1.31 (dtdd, J=13.3, 6.8, 6.0, 3.1, 2H); MS (ESI+) m/z 513 (M+NH$_4$)$^+$.

Step B: The title compound was prepared by substituting tert-butyl(2S)-2-{[((3aS,4R,6aR)-2-{[4-fluorophenyl]sulfonyl}octahydrocyclopenta[c]pyrrol-4-yl)amino]carbonyl}piperidine-1-carboxylate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-$d_5$) δ ppm 7.96-7.99 (m, 2H), 7.78 (d, J=7.0 Hz, 1H), 7.30-7.34 (m, 2H), 4.20 (p, J=7.0 Hz, 1H), 3.75 (dd, J=9.9, 2.9 Hz, 1H), 3.30 (dd, J=10.3, 3.2 Hz, 1H), 3.11 (dd, J=9.6, 2.9 Hz, 1H), 2.96-3.03 (m, 2H), 2.87 (dd, J=9.6, 7.4 Hz, 1H), 2.48-2.60 (m, 2H), 2.42-2.49 (m, 1H), 2.28-2.46 (m, 1H), 2.00-2.05 (m, 1H), 1.86-1.92 (m, 1H), 1.76-1.83 (m, 1H), 1.66-1.71 (m, 1H), 1.44-1.62 (m, 2H), 1.24-1.41 (m, 4H); MS (ESI+) m/z 396 (M+H)$^+$.

Example 400

N¹-{(3aS,4R,6aR)-2-[(4-fluorophenyl)sulfonyl]octahydrocyclopenta[c]pyrrol-4-yl}-N²-methyl-L-valinamide Step A: tert-Butyl methyl((S)-3-methyl-1-oxo-1-((3aS,4R,6aR)-2-(4-fluorophenylsulfonyl)octahydrocyclopenta[c]pyrrol-4-ylamino)butan-2-yl)carbamate was prepared by substituting tert-butyl(S)-1-((3aS,4R,6aR)-2-benzyloctahydrocyclopenta[c]pyrrol-4-ylamino)-3-methyl-1-oxobutan-2-yl(methyl)carbamate from Example 232 for (S)-N-((3aS,4R,6aR)-2-benzyloctahydrocyclopenta[c]pyrrol-4-yl)-4-methyl-2-morpholinopentanamide and 4-fluorobenzene-1-sulfonyl chloride for 3-(trifluoromethyl)benzene-1-sulfonyl chloride in the procedure described in Example 319: ¹H NMR (500 MHz, pyridine-$d_5$) δ ppm 7.97-7.89 (m, 2H), 7.74-7.63 (m, 1H), 7.25-7.18 (m, 2H), 4.34 (d, J=10.1, 1H), 4.08 (dt, J=13.5, 6.7, 1H), 3.57 (dd, J=10.1, 3.3, 1H), 3.22-3.16 (m, 1H), 3.07 (d, J=5.5, 2H), 3.01 (s, 3H), 2.57-2.50 (m, 1H), 2.50-2.43 (m, 1H), 2.38 (qd, J=13.2, 6.6, 1H), 1.94 (td, J=12.2, 6.5, 1H), 1.86-1.77 (m, 1H), 1.54 (ddd, J=16.4, 12.6, 7.7, 1H), 1.45 (s, 9H), 1.34-1.24 (m, 1H), 0.98 (d, J=6.5, 3H), 0.86 (d, J=6.7, 3H); MS (ESI+) m/z 498 (M+H)$^+$.

Step B: The title compound was prepared by substituting tert-butyl methyl((S)-3-methyl-1-oxo-1-((3aS,4R,6aR)-2-(4-fluorophenylsulfonyl)octahydrocyclopenta[c]pyrrol-4-ylamino)butan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-$d_5$) δ ppm 8.13-8.31 (m, 1H), 7.99-8.02 (m, 2H), 7.30-7.34 (m, 2H), 4.24-4.29 (m, 1H), 3.78 (dd, J=9.9, 2.5 Hz, 1H), 3.11-3.14 (m, 2H), 2.94 (dd, J=9.6, 6.9 Hz, 1H), 2.87 (d, J=5.8 Hz, 1H), 2.47-2.58 (m, 2H), 2.37 (s, 3H), 2.05-2.14 (m, 1H), 1.92-2.08 (m, 1H), 1.91-1.98 (m, 1H), 1.80-1.87 (m, 1H), 1.51-1.59 (m, 1H), 1.25-1.35 (m, 1H), 0.98-1.08 (m, 6H); MS (ESI+) m/z 398 (M+H)$^+$.

Example 401

(2S)-N-((3aS,4R,6aR)-2-{[4-(trifluoromethyl)phenyl]sulfonyl}octahydrocyclopenta[c]pyrrol-4-yl)piperidine-2-carboxamide Step A: tert-butyl(2S)-2-{[((3aS,4R,6aR)-2-{[4-(trifluoromethyl)phenyl]sulfonyl}octahydrocyclopenta[c]pyrrol-4-yl)amino]carbonyl}piperidine-1-carboxylate was prepared by substituting tert-butyl(2S)-2-({[(3aS,4R,6aR)-2-benzyloctahydrocyclopenta[c]pyrrol-4-yl]amino}carbonyl)piperidine-1-carboxylate from Example 231 for (S)-N-((3aS,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: ¹H NMR (500 MHz, pyridine-$d_5$) δ ppm 8.08 (d, J=8.1, 2H), 7.82 (d, J=8.2, 2H), 7.46 (d, J=5.2, 1H), 4.84 (d, J=3.3, 1H), 4.09 (dt, J=13.3, 6.6, 2H), 3.68 (dd, J=10.2, 3.3, 1H), 3.34-3.24 (m, 2H), 3.12 (d, J=5.5, 2H), 2.61-2.48 (m, 2H), 2.22-2.15 (m, 1H), 1.93 (dt, J=11.8, 6.6, 1H), 1.81 (dtd, J=12.7, 7.6, 4.8, 1H), 1.65-1.49 (m, 5H), 1.47 (s, 9H), 1.40-1.24 (m, 2H); MS (ESI+) m/z 563 (M+NH$_4$)$^+$.

Step B: The title compound was prepared by substituting tert-butyl(2S)-2-{[((3aS,4R,6aR)-2-{[4-(trifluoromethyl)phenyl]sulfonyl}octahydrocyclopenta[c]pyrrol-4-yl)amino]carbonyl}piperidine-1-carboxylate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-$d_5$) δ ppm 8.10-8.13 (m, 2H), 7.89-7.92 (m, 2H), 7.79 (d, J=7.0 Hz, 1H), 4.17-4.22 (m, 1H), 3.82 (dd, J=9.9, 2.8 Hz, 1H), 3.30 (dd, J=10.3, 3.2 Hz, 1H), 3.16 (dd, J=9.6, 2.9 Hz, 1H), 3.03-3.07 (m, 1H), 2.96-2.99 (m, 1H), 2.92 (dd, J=9.6, 7.4 Hz, 1H), 2.50-2.59 (m, 2H), 2.43-2.50 (m, 1H), 2.27-2.53 (m, 1H), 2.00-2.04 (m, 1H), 1.86-1.92 (m, 1H), 1.76-1.83 (m, 1H), 1.64-1.70 (m, 1H), 1.53-1.63 (m, 1H), 1.43-1.53 (m, 1H), 1.35-1.43 (m, 1H), 1.20-1.35 (m, 3H); MS (ESI+) m/z 446 (M+H)$^+$.

Example 402

N²-methyl-N¹-((3aS,4R,6aR)-2-{[4-(trifluoromethyl)phenyl]sulfonyl}octahydrocyclopenta[c]pyrrol-4-yl)-L-valinamide Step A: tert-Butyl methyl((S)-3-methyl-1-oxo-1-((3aS,4R,6aR)-2-(4-(trifluoromethyl)phenylsulfonyl)octahydrocyclopenta[c]pyrrol-4-ylamino)butan-2-yl)carbamate was prepared by substituting tert-butyl(S)-1-((3aS,4R,6aR)-2-benzyloctahydrocyclopenta[c]pyrrol-4-ylamino)-3-methyl-1-oxobutan-2-yl(methyl)carbamate from Example 232 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: ¹H NMR (500 MHz, pyridine-$d_5$) δ ppm 8.07 (d, J=8.2, 2H), 7.82 (d, J=8.2, 2H), 7.72 (s, 1H), 4.34 (d, J=10.4, 1H), 4.09 (dd, J=13.6, 6.7, 1H), 3.64 (dd, J=10.2, 3.3, 1H), 3.26-3.19 (m, 1H), 3.15-3.07 (m, 2H), 3.01 (s, 3H), 2.58-2.51 (m, 1H), 2.50-2.44 (m, 1H), 2.38 (qd, J=13.2, 6.6, 1H), 1.93 (td, J=12.1, 6.5, 1H), 1.82 (td, J=12.7, 7.5, 1H), 1.53 (ddd, J=15.6, 12.6, 8.3, 1H), 1.45 (s, 9H), 1.29 (ddd, J=15.9, 13.2, 6.7, 1H), 0.97 (d, J=6.5, 3H), 0.86 (d, J=6.7, 3H); MS (ESI+) m/z 548 (M+H)$^+$.

Step B: The title compound was prepared by substituting tert-butyl methyl((S)-3-methyl-1-oxo-1-((3aS,4R,6aR)-2-

(4-(trifluoromethyl)phenylsulfonyl)octahydrocyclopenta[c]pyrrol-4-ylamino)butan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.22-8.25 (m, 1H), 8.13-8.15 (m, 2H), 7.89-7.92 (m, 2H), 4.23-4.29 (m, 1H), 3.86 (dd, J=9.9, 2.6 Hz, 1H), 3.13-3.20 (m, 2H), 2.98 (dd, J=9.6, 7.0 Hz, 1H), 2.87 (d, J=5.8 Hz, 1H), 2.50-2.59 (m, 2H), 2.37 (s, 3H), 2.05-2.13 (m, 1H), 1.93-2.11 (m, 1H), 1.90-1.98 (m, 1H), 1.80-1.87 (m, 1H), 1.51-1.58 (m, 1H), 1.26-1.34 (m, 1H), 1.04 (d, J=6.9 Hz, 3H), 1.02 (d, J=6.9 Hz, 3H); MS (ESI+) m/z 448 (M+H)$^+$.

Example 403

N$^1$-{(3aS,4R,6aR)-2-[(4-fluorophenyl)sulfonyl]octahydrocyclopenta[c]pyrrol-4-yl}-N$^2$-methyl-L-norvalinamide The title compound was prepared by substituting tert-butyl (S)-1-((3aS,4R,6aR)-2-(4-fluorophenylsulfonyl)octahydrocyclopenta[c]pyrrol-4-ylamino)-1-oxopentan-2-yl(methyl)carbamate from Example 330 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.23 (d, J=7.2 Hz, 1H), 7.98-8.01 (m, 2H), 7.30-7.34 (m, 2H), 4.26 (p, J=6.8 Hz, 1H), 3.77 (dd, J=9.9, 2.7 Hz, 1H), 3.09-3.15 (m, 3H), 2.93 (dd, J=9.6, 7.1 Hz, 1H), 2.47-2.58 (m, 2H), 2.38 (s, 3H), 1.92-2.21 (m, 1H), 1.91-1.99 (m, 1H), 1.75-1.87 (m, 2H), 1.64-1.71 (m, 1H), 1.51-1.60 (m, 1H), 1.38-1.51 (m, 2H), 1.25-1.35 (m, 1H), 0.84 (t, J=7.3 Hz, 3H); MS (ESI+) m/z 398 (M+H)$^+$.

Example 404

N$^2$-methyl-N$^1$-((3aS,4R,6aR)-2-{[4-(trifluoromethyl)phenyl]sulfonyl}octahydrocyclopenta[c]pyrrol-4-yl)-L-norvalinamide The title compound was prepared by substituting tert-butyl methyl((S)-1-oxo-1-((3aS,4R,6aR)-2-(4-(trifluoromethyl)phenylsulfonyl)octahydrocyclopenta[c]pyrrol-4-ylamino)pentan-2-yl)carbamate from Example 331 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.24-8.26 (m, 1H), 8.12-8.15 (m, 2H), 7.89-7.92 (m, 2H), 4.26 (p, J=6.9 Hz, 1H), 3.85 (dd, J=9.9, 2.7 Hz, 1H), 3.18 (dd, J=9.6, 2.7 Hz, 1H), 3.15 (dd, J=7.7, 3.9 Hz, 1H), 3.13 (d, J=7.0 Hz, 1H), 2.97 (dd, J=9.6, 7.2 Hz, 1H), 2.51-2.61 (m, 2H), 2.38 (s, 3H), 1.95-2.31 (m, 1H), 1.92-1.98 (m, 1H), 1.75-1.87 (m, 2H), 1.64-1.72 (m, 1H), 1.51-1.59 (m, 1H), 1.39-1.52 (m, 2H), 1.30 (ddt, J=9.7, 13.0, 6.5 Hz, 1H), 0.84 (t, J=7.3 Hz, 3H); MS (ESI+) m/z 448 (M+H)$^+$.

Example 405

N$^2$-methyl-N$^1$-((3aR,4S,6aS)-2-{[4-(trifluoromethyl)phenyl]sulfonyl}octahydrocyclopenta[c]pyrrol-4-yl)-L-norvalinamide The title compound was prepared by substituting tert-butyl methyl((S)-1-oxo-1-((3aR,4S,6aS)-2-(4-(trifluoromethyl)phenylsulfonyl)octahydrocyclopenta[c]pyrrol-4-ylamino)pentan-2-yl)carbamate from Example 259 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.20-8.23 (m, 1H), 8.13-8.15 (m, 2H), 7.89-7.92 (m, 2H), 4.22-4.29 (m, 1H), 3.85 (dd, J=9.9, 2.7 Hz, 1H), 3.18 (dd, J=9.7, 2.7 Hz, 1H), 3.11-3.16 (m, 2H), 2.96 (dd, J=9.6, 7.1 Hz, 1H), 2.50-2.61 (m, 2H), 2.38 (s, 3H), 1.98-2.07 (m, 1H), 1.90-1.98 (m, 1H), 1.75-1.87 (m, 2H), 1.63-1.70 (m, 1H), 1.41-1.58 (m, 3H), 1.26-1.33 (m, 1H), 0.84 (t, J=7.3 Hz, 3H); MS (ESI+) m/z 448 (M+H)$^+$.

Example 406

N$^2$-methyl-N$^1$-((3aS,4R,6aR)-2-{[3-(trifluoromethyl)phenyl]sulfonyl}octahydrocyclopenta[c]pyrrol-4-yl)-L-valinamide The title compound was prepared by substituting tert-butyl methyl((S)-3-methyl-1-oxo-1-((3aS,4R,6aR)-2-(3-(trifluoromethyl)phenylsulfonyl)octahydrocyclopenta[c]pyrrol-4-ylamino)butan-2-yl)carbamate from Example 340 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.39-8.40 (bs, 1H), 8.24 (d, J=7.2 Hz, 1H), 8.18-8.22 (m, 1H), 7.90-7.92 (m, 1H), 7.72 (t, J=7.8 Hz, 1H), 4.24-4.30 (m, 1H), 3.86 (dd, J=9.9, 2.3 Hz, 1H), 3.14-3.20 (m, 2H), 2.96 (dd, J=9.7, 7.1 Hz, 1H), 2.86 (d, J=5.8 Hz, 1H), 2.50-2.57 (m, 2H), 2.37 (s, 3H), 2.04-2.13 (m, 1H), 1.88-2.08 (m, 1H), 1.89-1.98 (m, 1H), 1.80-1.89 (m, 1H), 1.50-1.59 (m, 1H), 1.25-1.34 (m, 1H), 1.03 (d, J=6.9 Hz, 3H), 1.01 (d, J=7.0 Hz, 3H); MS (ESI+) m/z 448 (M+H)$^+$.

Example 407

N$^1$-((3aS,4R,6aR)-2-{[4-fluoro-3-(trifluoromethyl)phenyl]sulfonyl}octahydrocyclopenta[c]pyrrol-4-yl)-N$^2$-methyl-L-leucinamide The title compound was prepared by substituting tert-butyl (S)-1-((3aS,4R,6aR)-2-(4-fluoro-3-(trifluoromethyl)phenylsulfonyl)octahydrocyclopenta[c]pyrrol-4-ylamino)-4-methyl-1-oxopentan-2-yl(methyl)carbamate from Example 327 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.35 (dd, J=6.5, 1.9 Hz, 1H), 8.31 (d, J=7.3 Hz, 1H), 8.26 (ddd, J=8.5, 4.7, 2.4 Hz, 1H), 7.53-7.58 (m, 1H), 4.24-4.30 (m, 1H), 3.88 (dd, J=9.9, 2.5 Hz, 1H), 3.16-3.20 (m, 3H), 3.00 (dd, J=9.6, 7.2 Hz, 1H), 2.53-2.62 (m, 2H), 2.38 (s, 3H), 1.82-2.01 (m, 4H), 1.67 (ddd, J=13.5, 7.8, 5.7 Hz, 1H), 1.53-1.59 (m, 2H), 1.32 (ddt, J=9.7, 12.9, 6.5 Hz, 1H), 0.89 (d, J=6.6 Hz, 3H), 0.84 (d, J=6.5 Hz, 3H); MS (ESI+) m/z 480 (M+H)$^+$.

Example 408

3-methyl-N$^1$-((3aR,4S,6aS)-2-{[4-(trifluoromethyl)phenyl]sulfonyl}octahydrocyclopenta[c]pyrrol-4-yl)-L-valinamide The title compound was prepared by substituting tert-butyl (S)-3,3-dimethyl-1-oxo-1-((3aR,4S,6aS)-2-(4-(trifluoromethyl)phenylsulfonyl)octahydrocyclopenta[c]pyrrol-4-ylamino)butan-2-ylcarbamate from Example 341 for tert-butyl(S)-1-((3aR,4S,6aS)-2-benzyloctahydrocyclopenta[c]

pyrrol-4-ylamino)-4-methyl-1-oxopentan-2-yl(methyl) carbamate in the procedure described in Example 348: $^1$H NMR (500 MHz, pyridine-$d_5$) δ ppm 8.25 (d, J=6.7 Hz, 1H), 8.12-8.16 (m, 2H), 7.90-7.92 (m, 2H), 4.18-4.24 (m, 1H), 3.82 (dd, J=10.0, 2.3 Hz, 1H), 3.24 (s, 1H), 3.13-3.18 (m, 2H), 2.98 (dd, J=9.5, 6.5 Hz, 1H), 2.49-2.60 (m, 2H), 1.93-2.29 (m, 2H), 1.85-1.95 (m, 1H), 1.77-1.85 (m, 1H), 1.47-1.55 (m, 1H), 1.22-1.31 (m, 1H), 1.12 (s, 9H); MS (ESI−) m/z 446 (M−H)$^-$.

Example 409

3-methyl-$N^1$-((3aS,4R,6aR)-2-{[4-(trifluoromethyl) phenyl]sulfonyl}octahydrocyclopenta[c]pyrrol-4-yl)-L-valinamide The title compound was prepared by substituting tert-butyl (S)-3,3-dimethyl-1-oxo-1-((3aS,4R,6aR)-2-(4-(trifluoromethyl)phenylsulfonyl)octahydrocyclopenta[c]pyrrol-4-ylamino)butan-2-ylcarbamate from Example 342 for tert-butyl(S)-1-((3aR,4S,6aS)-2-benzyloctahydrocyclopenta[c]pyrrol-4-ylamino)-4-methyl-1-oxopentan-2-yl(methyl) carbamate in the procedure described in Example 348: $^1$H NMR (500 MHz, pyridine-$d_5$) δ ppm 8.23 (d, J=6.7 Hz, 1H), 8.12-8.14 (m, 2H), 7.89-7.91 (m, 2H), 4.18-4.25 (m, 1H), 3.80 (dd, J=9.9, 2.7 Hz, 1H), 3.24 (s, 1H), 3.16 (dd, J=9.7, 2.8 Hz, 1H), 3.10 (dd, J=9.9, 7.5 Hz, 1H), 2.95 (dd, J=9.6, 7.2 Hz, 1H), 2.45-2.55 (m, 2H), 1.96-2.22 (m, 2H), 1.88-1.96 (m, 1H), 1.78-1.85 (m, 1H), 1.49-1.57 (m, 1H), 1.20-1.32 (m, 1H), 1.11 (s, 9H).

Example 410

$N^2$-methyl-$N^1$-((3aR,4S,6aS)-2-{[3-(trifluoromethyl) phenyl]sulfonyl}octahydrocyclopenta[c]pyrrol-4-yl)-L-isoleucinamide The title compound was prepared by substituting tert-butyl methyl((2S,3S)-3-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate from Example 332 for tert-butyl(S)-1-((3aR,4S,6aS)-2-benzyloctahydrocyclopenta[c]pyrrol-4-ylamino)-4-methyl-1-oxopentan-2-yl(methyl) carbamate in the procedure described in Example 348: $^1$H NMR (500 MHz, pyridine-$d_5$) δ ppm 8.39-8.40 (bs, 1H), 8.24 (d, J=7.2 Hz, 1H), 8.19-8.22 (m, 1H), 7.91-7.93 (m, 1H), 7.73 (d, J=7.9 Hz, 1H), 4.24-4.30 (m, 1H), 3.87 (dd, J=9.9, 2.3 Hz, 1H), 3.13-3.20 (m, 2H), 2.95 (d, J=6.3 Hz, 2H), 2.50-2.58 (m, 2H), 2.38 (s, 3H), 1.89-2.02 (m, 1H), 1.90-1.98 (m, 1H), 1.79-1.89 (m, 2H), 1.72-1.82 (m, 1H), 1.51-1.59 (m, 1H), 1.23-1.40 (m, 2H), 1.00 (d, J=6.8 Hz, 3H), 0.86 (t, J=7.4 Hz, 3H); MS (ESI+) m/z 462 (M+H)$^+$.

Example 411

$N^2$-methyl-$N^1$-((3aR,4S,6aS)-2-{[4-(trifluoromethyl) phenyl]sulfonyl}octahydrocyclopenta[c]pyrrol-4-yl)-L-isoleucinamide The title compound was prepared by substituting tert-butyl methyl((2S,3S)-3-methyl-1-oxo-1-((3aR,4S,6aS)-2-(4-(trifluoromethyl)phenylsulfonyl)octahydrocyclopenta[c]pyrrol-4-ylamino)pentan-2-yl)carbamate from Example 333 for tert-butyl(S)-1-((3aR,4S,6aS)-2-benzyloctahydrocyclopenta[c]pyrrol-4-ylamino)-4-methyl-1-oxopentan-2-yl(methyl) carbamate in the procedure described in Example 348: $^1$H NMR (500 MHz, pyridine-$d_5$) δ ppm 8.24-8.26 (m, 1H), 8.13-8.16 (m, 2H), 7.90-7.92 (m, 2H), 4.23-4.30 (m, 1H), 3.86 (dd, J=9.9, 2.5 Hz, 1H), 3.19 (dd, J=9.6, 2.4 Hz, 1H), 3.15 (dd, J=9.8, 7.6 Hz, 1H), 2.97 (dd, J=9.4, 6.9 Hz, 1H), 2.95 (d, J=6.0 Hz, 1H), 2.52-2.60 (m, 2H), 2.39 (s, 3H), 1.92-2.04 (m, 1H), 1.91-1.97 (m, 1H), 1.80-1.88 (m, 2H), 1.72-1.80 (m, 1H), 1.51-1.60 (m, 1H), 1.25-1.36 (m, 2H), 1.01 (d, J=6.9 Hz, 3H), 0.86 (t, J=7.4 Hz, 3H); MS (ESI+) m/z 462 (M+H)$^+$.

Example 412

$N^2$-methyl-$N^1$-((3aS,4R,6aR)-2-{[3-(trifluoromethyl)phenyl]sulfonyl}octahydrocyclopenta[c]pyrrol-4-yl)-L-isoleucinamide The title compound was prepared by substituting tert-butyl methyl((2S,3S)-3-methyl-1-oxo-1-((3aS,4R,6aR)-2-(3-(trifluoromethyl)phenylsulfonyl)octahydrocyclopenta[c]pyrrol-4-ylamino)pentan-2-yl)carbamate from Example 334 for tert-butyl(S)-1-((3aR,4S,6aS)-2-benzyloctahydrocyclopenta[c]pyrrol-4-ylamino)-4-methyl-1-oxopentan-2-yl(methyl) carbamate in the procedure described in Example 348: $^1$H NMR (500 MHz, pyridine-$d_5$) δ ppm 8.23-8.26 (m, 1H), 8.12-8.16 (m, 2H), 7.89-7.91 (m, 2H), 4.24-4.29 (m, 1H), 3.86 (dd, J=9.9, 2.5 Hz, 1H), 3.15-3.20 (m, 2H), 2.98 (dd, J=9.6, 6.9 Hz, 1H), 2.94 (d, J=6.1 Hz, 1H), 2.50-2.62 (m, 2H), 2.38 (s, 3H), 1.91-2.04 (m, 1H), 1.91-1.98 (m, 1H), 1.80-1.88 (m, 2H), 1.72-1.80 (m, 1H), 1.51-1.59 (m, 1H), 1.24-1.35 (m, 2H), 1.00 (d, J=6.8 Hz, 3H), 0.85 (t, J=7.4 Hz, 3H); MS (ESI+) m/z 462 (M+H)$^+$.

Example 413

$N^2$-methyl-$N^1$-((3aS,4R,6aR)-2-{[4-(trifluoromethyl)phenyl]sulfonyl}octahydrocyclopenta[c]pyrrol-4-yl)-L-isoleucinamide The title compound was prepared by substituting tert-butyl methyl((2S,3S)-3-methyl-1-oxo-1-((3aS,4R,6aR)-2-(4-(trifluoromethyl)phenylsulfonyl)octahydrocyclopenta[c]pyrrol-4-ylamino)pentan-2-yl)carbamate from Example 335 for tert-butyl(S)-1-((3aR,4S,6aS)-2-benzyloctahydrocyclopenta[c]pyrrol-4-ylamino)-4-methyl-1-oxopentan-2-yl(methyl) carbamate in the procedure described in Example 348: $^1$H NMR (500 MHz, pyridine-$d_5$) δ ppm 8.38-8.39 (bs, 1H), 8.24 (d, J=7.0 Hz, 1H), 8.19-8.22 (m, 1H), 7.90-7.92 (m, 1H), 7.72 (t, J=7.8 Hz, 1H), 4.23-4.30 (m, 1H), 3.86 (dd, J=9.9, 2.2 Hz, 1H), 3.14-3.20 (m, 2H), 2.97 (dd, J=9.6, 6.6 Hz, 1H), 2.93 (d, J=6.1 Hz, 1H), 2.55 (t, J=4.5 Hz, 2H), 2.37 (s, 3H), 1.92-2.10 (m, 1H), 1.91-1.99 (m, 1H), 1.80-1.89 (m, 2H), 1.71-1.81 (m, 1H), 1.51-1.59 (m, 1H), 1.24-1.40 (m, 2H), 0.99 (d, J=6.8 Hz, 3H), 0.84 (t, J=7.4 Hz, 3H); MS (ESI+) m/z 462 (M+H)$^+$.

Example 414

$N^2$,4-dimethyl-$N^1$-((3aR,4S,6aS)-2-{[3-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-((3aR,4S,6aS)-2-(3-(trifluoromethyl)phenylsulfonyl)octahydrocyclopenta[c]pyrrol-4-ylamino)pentan-2-yl(methyl)carbamate from Example 336 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.38-8.40 (m, 1H), 8.34 (d, J=6.9 Hz, 1H), 8.20-8.22 (m, 1H), 7.90-7.93 (m, 1H), 7.73 (d, J=7.9 Hz, 1H), 4.23-4.28 (m, 1H), 3.89 (dd, J=9.9, 2.1 Hz, 1H), 3.16-3.21 (m, 2H), 3.15 (dd, J=9.8, 7.4 Hz, 1H), 2.93-2.97 (m, 1H), 2.50-2.58 (m, 2H), 2.38 (s, 3H), 2.00-2.06 (m, 1H), 1.90-1.99 (m, 1H), 1.90 (dd, J=14.1, 5.1 Hz, 1H), 1.79-1.87 (m, 1H), 1.51-1.60 (m, 1H), 1.48 (dd, J=14.0, 6.5 Hz, 1H), 1.25-1.32 (m, 1H), 0.97 (s, 9H); MS (ESI+) m/z 476 (M+H)+.

Example 415

$N^2$,4-dimethyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-((3aR,4S,6aS)-2-(4-(trifluoromethyl)phenylsulfonyl)octahydrocyclopenta[c]pyrrol-4-ylamino)pentan-2-yl(methyl)carbamate from Example 337 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.37-8.40 (m, 1H), 8.14-8.16 (m, 2H), 7.90-7.92 (m, 2H), 4.23-4.27 (m, 1H), 3.87 (dd, J=9.9, 2.2 Hz, 1H), 3.22 (t, J=5.9 Hz, 1H), 3.18 (dd, J=9.7, 2.1 Hz, 1H), 3.15 (dd, J=9.9, 7.5 Hz, 1H), 2.95-2.99 (m, 1H), 2.55-2.58 (m, 2H), 2.40 (s, 3H), 1.91-1.98 (m, 1H), 1.92 (dd, J=14.0, 5.1 Hz, 2H), 1.80-1.86 (m, 1H), 1.52-1.61 (m, 1H), 1.50 (dd, J=14.0, 6.4 Hz, 1H), 1.25-1.34 (m, 1H), 0.97 (s, 9H); MS (ESI+) m/z 476 (M+H)+.

Example 416

$N^2$,4-dimethyl-$N^1$-((3aS,4R,6aR)-2-{[3-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-((3aS,4R,6aR)-2-(3-(trifluoromethyl)phenylsulfonyl)octahydrocyclopenta[c]pyrrol-4-ylamino)pentan-2-yl(methyl)carbamate from Example 338 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.37-8.39 (bs, 1H), 8.33-8.36 (m, 1H), 8.18-8.21 (m, 1H), 7.91 (d, J=7.0 Hz, 1H), 7.72 (t, J=7.8 Hz, 1H), 4.23-4.29 (m, 1H), 3.88 (dd, J=9.9, 2.1 Hz, 1H), 3.12-3.20 (m, 3H), 2.94 (dd, J=9.6, 6.6 Hz, 1H), 2.54 (t, J=4.6 Hz, 2H), 2.37 (s, 3H), 1.92-2.00 (m, 1H), 1.75-2.14 (m, 1H), 1.90 (dd, J=14.0, 5.2 Hz, 1H), 1.80-1.87 (m, 1H), 1.51-1.59 (m, 1H), 1.49 (dd, J=14.0, 6.6 Hz, 1H), 1.24-1.33 (m, 1H), 0.96 (s, 9H); MS (ESI+) m/z 476 (M+H)+.

Example 417

$N^2$,4-dimethyl-$N^1$-((3aS,4R,6aR)-2-{[4-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-((3aS,4R,6aR)-2-(4-(trifluoromethyl)phenylsulfonyl)octahydrocyclopenta[c]pyrrol-4-ylamino)pentan-2-yl(methyl)carbamate from Example 339 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.36-8.38 (m, 1H), 8.13-8.15 (m, 2H), 7.89-7.91 (m, 2H), 4.22-4.29 (m, 1H), 3.87 (d, J=10.4 Hz, 1H), 3.16-3.20 (m, 2H), 3.14 (dd, J=9.9, 7.5 Hz, 1H), 2.96 (dd, J=9.6, 6.8 Hz, 1H), 2.54-2.59 (m, 2H), 2.38 (s, 3H), 1.91-1.99 (m, 1H), 1.95 (m, 1H), 1.91 (dd, J=14.0, 5.2 Hz, 1H), 1.79-1.87 (m, 1H), 1.52-1.60 (m, 1H), 1.50 (dd, J=14.0, 6.6 Hz, 1H), 1.26-1.33 (m, 1H), 0.96 (s, 9H); MS (ESI+) m/z 476 (M+H)+.

Example 418

$N^2$-methyl-$N^1$-((3aR,4S,6aS)-2-{[4-(trifluoromethyl)phenyl]sulfonyl}octahydrocyclopenta[c]pyrrol-4-yl)-L-norleucinamide The title compound was prepared by substituting tert-butyl methyl((S)-1-oxo-1-((3aR,4S,6aS)-2-(4-(trifluoromethyl)phenylsulfonyl)octahydrocyclopenta[c]pyrrol-4-ylamino)hexan-2-yl)carbamate from Example 343 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.21-8.24 (m, 1H), 8.13-8.15 (m, 2H), 7.90-7.92 (m, 2H), 4.23-4.30 (m, 1H), 3.86 (dd, J=9.9, 2.5 Hz, 1H), 3.18 (dd, J=9.6, 2.6 Hz, 1H), 3.12-3.16 (m, 2H), 2.96 (dd, J=9.6, 7.0 Hz, 1H), 2.54-2.61 (m, 2H), 2.40 (s, 3H), 1.94-2.28 (m, 1H), 1.91-1.98 (m, 1H), 1.78-1.87 (m, 2H), 1.65-1.73 (m, 1H), 1.51-1.59 (m, 1H), 1.36-1.50 (m, 2H), 1.27-1.34 (m, 1H), 1.24 (h, J=7.4 Hz, 2H), 0.81 (t, J=7.3 Hz, 3H); MS (ESI+) m/z 462 (M+H)+.

Example 419

4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-((3aR,4S,6aS)-2-(4-(trifluoromethyl)phenylsulfonyl)octahydrocyclopenta[c]pyrrol-4-ylamino)pentan-2-ylcarbamate from Example 344 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.39-8.41 (m, 1H), 8.13-8.15 (m, 2H), 7.90-7.92 (m, 2H), 4.18-4.24 (m, 1H), 3.85 (dd, J=9.9, 2.6 Hz, 1H), 3.59 (dd, J=7.4, 4.3 Hz, 1H), 3.16 (dd, J=9.6, 2.8 Hz, 1H), 3.10 (dd, J=9.9, 7.4 Hz, 1H), 2.95 (dd, J=9.6, 7.1 Hz, 1H), 2.48-2.58 (m, 2H), 2.16 (dd, J=14.0, 4.3 Hz, 1H), 2.06-2.22 (m, 1H), 1.88-1.95 (m, 1H), 1.78-1.83 (m, 1H), 1.47-1.55 (m, 1H), 1.43 (dd, J=13.9, 7.4 Hz, 1H), 1.23-1.31 (m, 1H), 0.98 (s, 9H); MS (ESI+) m/z 462 (M+H)+.

Example 420

$N^2$-methyl-$N^1$-((3aR,4R,6aS)-2-{[4-(trifluoromethyl)phenyl]sulfonyl}octahydrocyclopenta[c]pyrrol-4-yl)-L-norvalinamide The title compound was prepared by substituting tert-butyl methyl((S)-1-oxo-1-((3aR,4R,6aS)-2-(4-(trifluoromethyl)phenylsulfonyl)octahydrocyclopenta[c]pyrrol-4-ylamino)pentan-2-yl)carbamate from Example 328 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.52 (d, J=7.9 Hz, 1H), 8.10-8.15

(m, 2H), 7.88-7.91 (m, 2H), 4.44-4.50 (m, 1H), 3.63 (dd, J=9.5, 2.8 Hz, 1H), 3.23-3.26 (m, 1H), 3.14-3.19 (m, 1H), 2.98 (dd, J=25.4, 9.3 Hz, 3H), 2.49-2.56 (m, 1H), 2.48 (s, 3H), 1.86-1.92 (m, 1H), 1.90 (m, 1H), 1.75-1.83 (m, 1H), 1.69-1.75 (m, 2H), 1.59-1.68 (m, 1H), 1.44-1.59 (m, 2H), 1.33-1.39 (m, 1H), 0.88 (t, J=7.3 Hz, 3H); MS (ESI+) m/z 448 (M+H)$^+$.

Example 421

N$^2$-methyl-N$^1$-((3aR,4R,6aS)-2-{[4-(trifluoromethyl)phenyl]sulfonyl}octahydrocyclopenta[c]pyrrol-4-yl)-L-leucinamide The title compound was prepared by substituting tert-butyl methyl((S)-4-methyl-1-oxo-1-((3aR,4R,6aS)-2-(4-(trifluoromethyl)phenylsulfonyl)octahydrocyclopenta[c]pyrrol-4-ylamino)pentan-2-yl)carbamate from Example 329 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.60-8.65 (m, 1H), 8.12-8.14 (m, 2H), 7.88-7.91 (m, 2H), 4.45-4.50 (m, 1H), 3.63-3.66 (m, 1H), 3.33-3.37 (m, 1H), 3.15 (dd, J=9.6, 3.0 Hz, 1H), 2.95-3.05 (m, 3H), 2.51 (s, 3H), 2.46-2.52 (m, 1H), 1.91-1.97 (m, 2H), 1.78-1.83 (m, 1H), 1.72-1.75 (m, 3H), 1.63 (dq, J=13.0, 8.2 Hz, 1H), 1.34-1.39 (m, 1H), 0.94 (d, J=6.5 Hz, 3H), 0.88 (d, J=6.5 Hz, 3H); MS (ESI+) m/z 462 (M+H)$^+$.

Example 422

N$^1$-((3aR,4S,6aS)-2-{[4-(trifluoromethyl)phenyl]sulfonyl}octahydrocyclopenta[c]pyrrol-4-yl)-L-norvalinamide Step A: tert-Butyl-((S)-1-oxo-1-((3aR,4S,6aS)-2-(4-(trifluoromethyl)phenylsulfonyl)octahydrocyclopenta[c]pyrrol-4-ylamino)pentan-2-yl)carbamate was prepared by substituting tert-butyl((S)-1-oxo-1-((3aR,4S,6aS)-2-benzyloctahydrocyclopenta[c]pyrrol-4-ylamino)pentan-2-yl)carbamate from Example 382 Step A for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: $^1$H NMR (500 MHz, pyridine-d$_5$) δ ppm 8.13 (d, J=8.1, 2H), 7.96 (d, J=8.0, 1H), 7.90 (d, J=8.3, 2H), 4.60 (dd, J=14.5, 8.2, 1H), 4.27-4.18 (m, 1H), 3.81 (dd, J=9.8, 1.5, 1H), 3.21-3.10 (m, 2H), 2.99-2.92 (m, 1H), 2.61-2.50 (m, 2H), 2.00 (dd, J=14.3, 5.4, 1H), 1.84 (ddd, J=13.4, 11.2, 6.8, 3H), 1.55-1.44 (m, 13H), 1.25 (d, J=8.9, 1H), 0.81 (t, J=7.3 Hz); MS (ESI+) m/z 551 (M+NH$_4$)$^+$.

Step B: The title compound was prepared by substituting tert-butyl-((S)-1-oxo-1-((3aR,4S,6aS)-2-(4-(trifluoromethyl)phenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.28 (d, J=7.0 Hz, 1H), 8.11-8.15 (m, 2H), 7.89-7.92 (m, 2H), 4.17-4.24 (m, 1H), 3.82 (d, J=9.5, 2.8 Hz, 1H), 3.52 (dd, J=7.9, 4.9 Hz, 1H), 3.16 (dd, J=9.6, 2.9 Hz, 1H), 3.09 (dd, J=9.9, 7.7 Hz, 1H), 2.94 (dd, J=9.6, 7.3 Hz, 1H), 2.46-2.57 (m, 2H), 2.07-2.18 (m, 2H), 1.88-1.96 (m, 2H), 1.77-1.84 (m, 1H), 1.63 (dddd, J=13.1, 8.0, 10.1, 5.1 Hz, 1H), 1.40-1.53 (m, 3H), 1.23-1.32 (m, 1H), 0.85 (t, J=7.3 Hz, 3H); MS (ESI+) m/z 434 (M+H)$^+$.

Example 423

N$^1$-((3aS,4R,6aR)-2-{[4-(trifluoromethyl)phenyl]sulfonyl}octahydrocyclopenta[c]pyrrol-4-yl)-L-norvalinamide Step A: tert-Butyl(S)-1-((3aS,4R,6aR)-2-benzyloctahydrocyclopenta[c]pyrrol-4-ylamino)-1-oxopentan-2-yl carbamate was prepared by substituting N-(tert-butoxycarbonyl)L-norvaline for N-(tert-butoxycarbonyl)-L-leucine and (3aS,4R,6aR)-2-benzyloctahydrocyclopenta[c]pyrrol-4-amine from Example 16 Step E for (3aS,4S,6aS)-2-benzyloctahydrocyclopenta[c]pyrrol-4-amine in the procedure described in Example 221: $^1$H NMR (400 MHz, pyridine-d$_5$) δ ppm 8.58 (d, J=7.2, 1H), 7.91 (d, J=8.3, 1H), 7.42 (d, J=7.3, 2H), 7.36 (t, J=7.4, 2H), 7.27 (t, J=7.2, 1H), 4.64 (dd, J=14.4, 7.7, 1H), 4.45-4.35 (m, 1H), 3.56 (d, J=13.1, 1H), 3.40 (d, J=13.2, 1H), 2.74 (d, J=8.9, 1H), 2.52-2.43 (m, 2H), 2.39-2.27 (m, 2H), 2.26-2.19 (m, 1H), 2.14 (dq, J=12.0, 6.0, 1H), 2.02 (dt, J=13.9, 6.7, 1H), 1.85 (td, J=13.8, 8.2, 2H), 1.65 (td, J=14.3, 7.3, 1H), 1.49 (d, J=8.5, 11H), 1.44-1.32 (m, 1H), 0.86-0.76 (m, 3H); MS (ESI+) m/z 416 (M+H)$^+$.

Step B: tert-Butyl-45)-1-oxo-1-((3aS,4R,6aR)-2-(4-(trifluoromethyl)phenylsulfonyl)octahydrocyclopenta[c]pyrrol-4-ylamino)pentan-2-yl)carbamate was prepared by substituting tert-butyl(S)-1-((3aS,4R,6aR)-2-benzyloctahydrocyclopenta[c]pyrrol-4-ylamino)-1-oxopentan-2-yl carbamate from Step A for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: $^1$H NMR (500 MHz, pyridine-d$_5$) δ ppm 8.79 (d, J=6.8, 1H), 8.11 (d, J=8.1, 2H), 7.98 (d, J=8.1, 1H), 7.90 (d, J=8.3, 2H), 4.59 (dd, J=14.4, 7.8, 1H), 4.28-4.20 (m, 1H), 3.78 (d, J=9.7, 1H), 3.14 (d, J=9.6, 1H), 3.05-2.98 (m, 1H), 2.93-2.86 (m, 1H), 2.50 (d, J=2.3, 2H), 2.02-1.92 (m, 2H), 1.88-1.77 (m, 2H), 1.63-1.53 (m, 1H), 1.53-1.38 (m, 11H), 1.33-1.22 (m, 1H), 0.79 (t, J=7.4, 3H); MS (ESI+) m/z 551 (M+NH$_4$)$^+$.

Step C: The title compound was prepared by substituting tert-butyl-((S)-1-oxo-1-((3aS,4R,6aR)-2-(4-(trifluoromethyl)phenylsulfonyl)octahydrocyclopenta[c]pyrrol-4-ylamino)pentan-2-yl)carbamate from Step B for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.27 (d, J=7.2 Hz, 1H), 8.10-8.14 (m, 2H), 7.89-7.91 (m, 2H), 4.18-4.24 (m, 1H), 3.83 (dd, J=9.9, 2.9 Hz, 1H), 3.51 (dd, J=7.9, 4.9 Hz, 1H), 3.16 (dd, J=9.6, 2.9 Hz, 1H), 3.08 (dd, J=9.9, 7.7 Hz, 1H), 2.93 (dd, J=9.6, 7.4 Hz, 1H), 2.45-2.56 (m, 2H), 2.03-2.23 (m, 2H), 1.88-1.95 (m, 2H), 1.77-1.84 (m, 1H), 1.64 (dddd, J=13.1, 8.1, 10.1, 5.1 Hz, 1H), 1.38-1.54 (m, 3H), 1.24-1.32 (m, 1H), 0.84 (t, J=7.3 Hz, 3H); MS (ESI−) m/z 432 (M−H)$^−$.

Example 424

N$^1$-((3aR,4S,6aS)-2-{[3-(trifluoromethyl)phenyl]sulfonyl}octahydrocyclopenta[c]pyrrol-4-yl)-L-norvalinamide Step A: tert-Butyl-45)-1-oxo-1-((3aR,4S,6aS)-2-(3-(trifluoromethyl)phenylsulfonyl)octahydrocyclopenta[c]pyrrol-4-ylamino)pentan-2-yl)carbamate was prepared by substituting tert-butyl((S)-1-oxo-1-((3aR,4S,6aS)-2-benzyloctahydrocyclopenta[c]pyrrol-4-ylamino)pentan-2-yl)carbamate from Example 382 Step A for (S)-N-((3aS,4R,6aR)-2-benzyloctahydrocyclopenta[c]pyrrol-4-yl)-4-methyl-2-morpholinopentanamide in the procedure described in Example 319: $^1$H NMR (500 MHz, pyridine-$d_5$) δ ppm 8.70 (d, J=6.9, 1H), 8.37 (s, 1H), 8.18 (d, J=7.8, 1H), 7.95 (d, J=8.0, 1H), 7.91 (d, J=7.8, 1H), 7.72 (t, J=7.9, 1H), 4.59 (dd, J=14.1, 7.8, 1H), 4.23 (dt, J=13.0, 6.5, 1H), 3.82 (dd, J=9.7, 1.4, 1H), 3.18-3.07 (m, 2H), 2.98-2.90 (m, 1H), 2.62-2.48 (m, 2H), 2.00 (ddd, J=15.3, 11.0, 6.5, 1H), 1.91-1.74 (m, 3H), 1.57-1.39 (m, 12H), 1.23 (ddd, J=16.9, 12.6, 6.1, 1H), 0.81 (t, J=7.3, 3H); MS (ESI+) m/z 551 (M+NH$_4$)$^+$.

Step B: The title compound was prepared by substituting tert-butyl-((S)-1-oxo-1-((3aR,4S,6aS)-2-(3-(trifluoromethyl)phenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.36-8.37 (bs, 1H), 8.26 (d, J=6.9 Hz, 1H), 8.17-8.20 (m, 1H), 7.90-7.92 (m, 1H), 7.70-7.74 (m, 1H), 4.18-4.24 (m, 1H), 3.83 (dd, J=9.8, 2.7 Hz, 1H), 3.52 (dd, J=7.9, 4.9 Hz, 1H), 3.16 (dd, J=9.6, 2.8 Hz, 1H), 3.07 (dd, J=9.9, 7.5 Hz, 1H), 2.91 (dd, J=9.6, 7.3 Hz, 1H), 2.44-2.54 (m, 2H), 1.95-2.28 (m, 2H), 1.86-1.99 (m, 2H), 1.77-1.84 (m, 1H), 1.59-1.66 (m, 1H), 1.39-1.54 (m, 3H), 1.22-1.32 (m, 1H), 0.84 (t, J=7.3 Hz, 3H); MS (ESI+) m/z 434 (M+H)$^+$.

Example 425

N$^1$-((3aS,4R,6aR)-2-{[3-(trifluoromethyl)phenyl]sulfonyl}octahydrocyclopenta[c]pyrrol-4-yl)-L-norvalinamide Step A: tert-Butyl-((S)-1-oxo-1-((3aR,4S,6aR)-2-(3-(trifluoromethyl)phenylsulfonyl)octahydrocyclopenta[c]pyrrol-4-ylamino)pentan-2-yl)carbamate was prepared by substituting tert-butyl(S)-1-((3aR,4R,6aR)-2-benzyloctahydrocyclopenta[c]pyrrol-4-ylamino)-1-oxopentan-2-yl carbamate from Example 423 Step A for (S)-N-((3aS,4R,6aR)-2-benzyloctahydrocyclopenta[c]pyrrol-4-yl)-4-methyl-2-morpholinopentanamide in the procedure described in Example 319: $^1$H NMR (500 MHz, pyridine-$d_5$) δ ppm 8.77 (d, J=6.9, 1H), 8.35 (s, 1H), 8.16 (d, J=7.7, 1H), 7.96 (d, J=8.2, 1H), 7.90 (d, J=8.0, 1H), 7.72 (t, J=7.9, 1H), 4.58 (dd, J=14.4, 8.0, 1H), 4.30-4.20 (m, 1H), 3.84-3.75 (m, 1H), 3.15 (d, J=9.4, 1H), 3.04-2.95 (m, 1H), 2.91-2.79 (m, 1H), 2.47 (dd, J=2.3, 1.2, 2H), 2.03-1.91 (m, 2H), 1.88-1.76 (m, 2H), 1.64-1.53 (m, 1H), 1.53-1.40 (m, 11H), 1.33-1.19 (m, 1H), 0.79 (t, J=7.3, 3H); MS (ESI+) m/z 551 (M+NH$_4$)$^+$.

Step B: The title compound was prepared by substituting tert-butyl-((S)-1-oxo-1-((3aS,4R,6aR)-2-(3-(trifluoromethyl)phenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.35-8.37 (m, 1H), 8.27 (d, J=7.0 Hz, 1H), 8.17-8.19 (m, 1H), 7.90-7.92 (m, 1H), 7.72 (t, J=7.8 Hz, 1H), 4.18-4.25 (m, 1H), 3.84 (dd, J=9.9, 2.7 Hz, 1H), 3.51 (dd, J=7.9, 4.9 Hz, 1H), 3.17 (dd, J=9.6, 2.8 Hz, 1H), 3.07 (dd, J=9.9, 7.6 Hz, 1H), 2.91 (dd, J=9.6, 7.3 Hz, 1H), 2.43-2.54 (m, 2H), 1.96-2.32 (m, 2H), 1.87-1.95 (m, 2H), 1.78-1.84 (m, 1H), 1.59-1.67 (m, 1H), 1.37-1.53 (m, 3H), 1.23-1.32 (m, 1H), 0.83 (t, J=7.3 Hz, 3H); MS (ESI−) m/z 432 (M−H)$^−$.

Example 426

3-cyclohexyl-N$^1$-((3aR,4S,6aS)-2-{[4-(trifluoromethyl)phenyl]sulfonyl}octahydrocyclopenta[c]pyrrol-4-yl)-L-alaninamide Step A: tert-Butyl(S)-3-cyclohexyl-1-oxo-1-((3aR,4S,6aS)-2-(4-(trifluoromethyl)phenylsulfonyl)octahydrocyclopenta[c]pyrrol-4-ylamino)propan-2-ylcarbamate was prepared by substituting (S)-2-(tert-butoxycarbonylamino)-3-cyclohexylpropanoic acid for (S)-1-(tert-butoxycarbonyl)pyrrolidine-2-carboxylic acid and (3aR,4S,6aS)-2-(4-(trifluoromethyl)phenylsulfonyl)octahydrocyclopenta[c]pyrrol-4-amine from Example 256 Step A for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-$d_5$) δ ppm 8.76 (s, 1H), 8.13 (d, J=8.1, 2H), 8.01 (d, J=8.3, 1H), 7.90 (d, J=8.3, 2H), 4.74-4.65 (m, 1H), 4.31-4.19 (m, 1H), 3.85-3.78 (m, 1H), 3.21-3.10 (m, 2H), 3.01-2.93 (m, 1H), 2.64-2.51 (m, 2H), 1.96-1.74 (m, 6H), 1.69-1.60 (m, 1H), 1.60-1.45 (m, 13H), 1.32-1.18 (m, 1H), 1.16-0.96 (m, 3H), 0.94-0.81 (m, 1H), 0.79-0.67 (m, 1H); MS (ESI+) m/z 605 (M+NH$_4$)$^+$.

Step B: The title compound was prepared by substituting tert-butyl(S)-3-cyclohexyl-1-oxo-1-((3aR,4S,6aS)-2-(4-(trifluoromethyl)phenylsulfonyl)octahydrocyclopenta[c]pyrrol-4-ylamino)propan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.35 (d, J=7.0 Hz, 1H), 8.12-8.15 (m, 2H), 7.90-7.92 (m, 2H), 4.20-4.26 (m, 1H), 3.83 (dd, J=9.9, 2.7 Hz, 1H), 3.63 (dd, J=9.2, 4.7 Hz, 1H), 3.17 (dd, J=9.7, 2.8 Hz, 1H), 3.10 (dd, J=9.8, 7.6 Hz, 1H), 2.96 (dd, J=9.6, 7.2 Hz, 1H), 2.46-2.61 (m, 2H), 1.97-2.47 (m, 2H), 1.86-1.96 (m, 2H), 1.78-1.86 (m, 1H), 1.72-1.78 (m, 1H), 1.65-1.71 (m, 1H), 1.47-1.62 (m, 6H), 1.22-1.33 (m, 1H), 0.99-1.23 (m, 3H), 0.91 (qd, J=12.5, 3.4 Hz, 1H), 0.79 (qd, J=12.0, 3.4 Hz, 1H); MS (ESI+) m/z 488 (M+H)$^+$.

Example 427

3-cyclohexyl-N$^2$-methyl-N$^1$-((3aR,4S,6aS)-2-{[4-(trifluoromethyl)phenyl]sulfonyl}octahydrocyclopenta[c]pyrrol-4-yl)-L-alaninamide Step A: tert-Butyl(S)-3-cyclohexyl-1-oxo-1-((3aR,4S,6aS)-2-(4-(trifluoromethyl)phenylsulfonyl)octahydrocyclopenta[c]pyrrol-4-ylamino)propan-2-yl(methyl)carbamate was prepared by substituting (S)-2-(tert-butoxycarbonyl(methyl)amino)-3-cyclohexylpropanoic acid for (S)-1-(tert-butoxycarbonyl)pyrrolidine-2-carboxylic acid and (3aR,4S,6aS)-2-(4-(trifluoromethyl)phenylsulfonyl)octahydrocyclopenta[c]pyrrol-4-amine from Example 256 Step A for (3aS,4R,6aR)-2-(3-(trifluoromethyl)phenylsulfonyl)octahydrocyclopenta[c]pyrrol-4-amine in the procedure described in Example 266: $^1$H NMR (500 MHz, pyridine-$d_5$) δ ppm 8.51 (d, J=6.9, 1H), 8.13 (d, J=8.2, 2H), 7.90 (d, J=8.3, 2H), 5.23-5.14 (m, 0.4H), 4.89-4.79 (m, 0.6H), 4.28-4.15 (m, 1H), 3.83 (d, J=10.6, 1H), 3.17-3.01 (m, 5H), 2.94 (dd, J=9.4, 7.2, 1H), 2.57-2.48 (m, 2H), 1.99-1.74 (m, 5H), 1.67 (d, J=13.1, 1H), 1.62-1.48 (m, 4H), 1.45 (s, 9H), 1.34-1.20 (m, 2H), 1.18-1.00 (m, 3H), 0.98-0.85 (m, 1H), 0.81-0.66 (m, 1H); MS (ESI+) m/z 602 (M+H)⁺.

Step B: The title compound was prepared by substituting tert-butyl(S)-3-cyclohexyl-1-oxo-1-((3aR,4S,6aS)-2-(4-(trifluoromethyl)phenylsulfonyl)octahydrocyclopenta[c]pyrrol-4-ylamino)propan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.30 (d, J=7.2 Hz, 1H), 8.13-8.16 (m, 2H), 7.89-7.93 (m, 2H), 4.24-4.32 (m, 1H), 3.86 (dd, J=9.9, 2.3 Hz, 1H), 3.25 (dd, J=7.8, 5.6 Hz, 1H), 3.13-3.21 (m, 2H), 2.98 (dd, J=9.5, 6.8 Hz, 1H), 2.47-2.63 (m, 2H), 2.41 (s, 3H), 1.95-2.23 (m, 1H), 1.91-1.99 (m, 1H), 1.79-1.90 (m, 1H), 1.66-1.78 (m, 3H), 1.51-1.62 (m, 6H), 1.26-1.35 (m, 1H), 1.00-1.23 (m, 3H), 0.76-0.93 (m, 2H); MS (ESI+) m/z 502 (M+H)⁺.

Example 428

N¹-((3aR,4S,6aS)-2-{[2-chloro-5-(trifluoromethyl)phenyl]sulfonyl}octahydrocyclopenta[c]pyrrol-4-yl)-4-methyl-L-leucinamide Step A: tert-Butyl(S)-4,4-dimethyl-1-oxo-1-((3aR,4S,6aS)-2-(2-chloro-5-(trifluoromethyl)phenylsulfonyl)octahydrocyclopenta[c]pyrrol-4-ylamino)pentan-2-ylcarbamate was prepared by substituting tert-butyl(S)-1-((3aR,4S,6aS)-2-benzyloctahydrocyclopenta[c]pyrrol-4-ylamino)-4,4-dimethyl-1-oxopentan-2-ylcarbamate from Example 226 for (S)-N-((3aS,4R,6aR)-2-benzyloctahydrocyclopenta[c]pyrrol-4-yl)-4-methyl-2-morpholinopentanamide and 2-chloro-5-(trifluoromethyl)benzene-1-sulfonyl chloride for 3-(trifluoromethyl)benzene-1-sulfonyl chloride in the procedure described in Example 319: ¹H NMR (500 MHz, pyridine-d₅) δ ppm 8.56 (d, J=1.9, 1H), 8.14 (d, J=8.7, 1H), 7.80 (dd, J=8.3, 1.9, 1H), 7.73 (d, J=8.3, 1H), 4.92 (s, 1H), 4.70 (td, J=8.3, 5.1, 1H), 4.34-4.25 (m, 1H), 3.91 (dd, J=10.1, 2.9, 1H), 3.54 (dd, J=10.2, 7.7, 1H), 3.36 (dd, J=9.9, 7.5, 1H), 3.27 (dd, J=10.0, 3.3, 1H), 2.72-2.57 (m, 2H), 2.13 (dd, J=14.1, 4.8, 1H), 1.94 (qd, J=6.4, 1.2, 1H), 1.86-1.77 (m, 2H), 1.60-1.52 (m, 1H), 1.49 (s, 9H), 1.35-1.25 (m, 1H), 0.96 (s, 9H); MS (ESI+) m/z 596 (M+H)⁺.

Step B: The title compound was prepared by substituting tert-butyl(S)-4,4-dimethyl-1-oxo-1-((3aR,4S,6aS)-2-(2-chloro-5-(trifluoromethyl)phenylsulfonyl)octahydrocyclopenta[c]pyrrol-4-ylamino)pentan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.56 (d, J=2.2 Hz, 1H), 8.41 (d, J=7.0 Hz, 1H), 7.80 (dd, J=8.3, 2.2 Hz, 1H), 7.74 (d, J=8.3 Hz, 1H), 4.25-4.32 (m, 1H), 3.94 (dd, J=10.2, 2.6 Hz, 1H), 3.58 (dd, J=7.4, 4.3 Hz, 1H), 3.49 (dd, J=10.1, 7.2 Hz, 1H), 3.34 (dd, J=9.9, 7.0 Hz, 1H), 3.30 (dd, J=9.9, 3.1 Hz, 1H), 2.58-2.66 (m, 2H), 1.87-2.45 (m, 2H), 2.14 (dd, J=14.0, 4.4 Hz, 1H), 1.96-2.04 (m, 1H), 1.82-1.88 (m, 1H), 1.52-1.60 (m, 1H), 1.41 (dd, J=13.9, 7.5 Hz, 1H), 1.30-1.38 (m, 1H), 0.97 (s, 9H); MS (ESI−) m/z 494 (M−H)⁻.

Example 429

N¹-((3aR,4S,6aS)-2-{[2-chloro-4-(trifluoromethyl)phenyl]sulfonyl}octahydrocyclopenta[c]pyrrol-4-yl)-4-methyl-L-leucinamide Step A: tert-Butyl(S)-4,4-dimethyl-1-oxo-1-((3aR,4S,6aS)-2-(2-chloro-4-(trifluoromethyl)phenylsulfonyl)octahydrocyclopenta[c]pyrrol-4-ylamino)pentan-2-ylcarbamate was prepared by substituting tert-butyl(S)-1-((3aR,4S,6aS)-2-benzyloctahydrocyclopenta[c]pyrrol-4-ylamino)-4,4-dimethyl-1-oxopentan-2-ylcarbamate from Example 226 for (S)-N-((3aS,4R,6aR)-2-benzyloctahydrocyclopenta[c]pyrrol-4-yl)-4-methyl-2-morpholinopentanamide and 2-chloro-4-(trifluoromethyl)benzene-1-sulfonyl chloride for 3-(trifluoromethyl)benzene-1-sulfonyl chloride in the procedure described in Example 319: ¹H NMR (500 MHz, pyridine-d₅) δ ppm 8.33 (d, J=8.2, 1H), 8.14 (d, J=8.7, 1H), 7.99 (s, 1H), 7.75-7.71 (m, 1H), 4.95 (s, 1H), 4.71 (td, J=8.3, 4.9, 1H), 4.33-4.25 (m, 1H), 3.92 (dd, J=10.2, 2.9, 1H), 3.53 (dd, J=10.2, 7.7, 1H), 3.38 (dd, J=9.9, 7.4, 1H), 3.30 (dd, J=10.0, 3.3, 1H), 2.72-2.58 (m, 2H), 2.14 (dd, J=14.1, 4.7, 1H), 1.93 (dt, J=18.2, 6.2, 1H), 1.86-1.77 (m, 2H), 1.57 (ddd, J=16.4, 12.5, 8.6, 1H), 1.50 (s, 9H), 1.31 (ddd, J=16.0, 13.2, 6.7, 1H), 0.97 (s, 9H); MS (ESI+) m/z 596 (M+H)⁺.

Step B: The title compound was prepared by substituting tert-butyl(S)-4,4-dimethyl-1-oxo-1-((3aR,4S,6aS)-2-(2-chloro-4-(trifluoromethyl)phenylsulfonyl)octahydrocyclopenta[c]pyrrol-4-ylamino)pentan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.44 (d, J=7.0 Hz, 1H), 8.35 (d, J=8.2 Hz, 1H), 7.99 (d, J=1.7 Hz, 1H), 7.74 (dd, J=8.2, 1.7 Hz, 1H), 4.25-4.32 (m, 1H), 3.94 (dd, J=10.1, 2.8 Hz, 1H), 3.59 (dd, J=7.4, 4.4 Hz, 1H), 3.49 (dd, J=10.2, 7.3 Hz, 1H), 3.31-3.39 (m, 2H), 2.58-2.67 (m, 2H), 1.86-2.48 (m, 2H), 2.15 (dd, J=14.0, 4.4 Hz, 1H), 1.97-2.05 (m, 1H), 1.82-1.88 (m, 1H), 1.53-1.61 (m, 1H), 1.42 (dd, J=14.0, 7.4 Hz, 1H), 1.31-1.39 (m, 1H), 0.98 (s, 9H); MS (ESI−) m/z 494 (M−H)⁻.

Example 430

N-methyl-N-((3aR,4S,6aS)-2-{[4-(trifluoromethyl)phenyl]sulfonyl}octahydrocyclopenta[c]pyrrol-4-yl)-L-phenylalaninamide The title compound was prepared by substituting N-(tert-butoxycarbonyl)-N-methyl-N-((3aR,4S,6aS)-2-{[4-(trifluoromethyl)phenyl]sulfonyl}octahydrocyclopenta[c]pyrrol-4-yl)-L-phenylalaninamide from Example 258 for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.15-8.20 (m, 3H), 7.92-7.96 (m, 2H), 7.29-7.34 (m, 4H), 7.24-7.28 (m, 1H), 3.75 (dd, J=9.9, 2.9 Hz, 1H), 3.43 (t, J=6.8 Hz, 1H), 3.13-3.20 (m, 3H), 3.04-3.10 (m, 3H), 2.95 (dd, J=9.6, 7.6 Hz, 1H), 2.43-2.52 (m, 1H), 2.34 (s, 3H), 1.75-2.16 (m, 1H), 1.84-1.91 (m, 1H), 1.70-1.79 (m, 1H), 1.37-1.47 (m, 1H), 1.19-1.28 (m, 1H); MS (ESI+) m/z 496 (M+H)⁺, 554 (M+CH₃CN+NH₄)'.

Example 431

N¹-((3aR,4S,6aS)-2-{[2-chloro-4-(trifluoromethyl)phenyl]sulfonyl}octahydrocyclopenta[c]pyrrol-4-yl)-N²,4-dimethyl-L-leucinamide Step A: tert-Butyl(S)-4,4-dimethyl-1-oxo-1-((3aR,4S,6aS)-2-(2-chloro-4-(trifluoromethyl)phenylsulfonyl)octahydrocyclopenta[c]pyrrol-4-ylamino)pentan-2-yl(methyl)carbamate was prepared by substituting tert-butyl(S)-1-((3aR,4S,6aS)-2-benzyloctahydrocyclopenta[c]pyrrol-4-ylamino)-4,4-dimethyl-1-oxopentan-2-yl(methyl)carbamate from Example 247 for (S)-N-((3aS,4R,6aR)-2-benzyloctahydrocyclopenta[c]pyrrol-4-yl)-4-methyl-2-morpholinopentanamide and 2-chloro-4-(trifluoromethyl)benzene-1-sulfonyl chloride for 3-(trifluoromethyl)benzene-1-sulfonyl chloride in the procedure described in Example 319: $^1$H NMR (400 MHz, pyridine-$d_5$) δ ppm 8.40 (d, J=6.9, 1H), 8.34 (d, J=8.1, 1H), 7.99 (d, J=1.1, 1H), 7.76-7.67 (m, 1H), 5.19-5.10 (m, 1H), 4.31-4.20 (m, 1H), 3.93 (dd, J=10.2, 2.0, 1H), 3.53-3.44 (m, 1H), 3.39-3.28 (m, 2H), 3.01 (s, 3H), 2.67-2.53 (m, 2H), 2.22-2.11 (m, 1H), 2.00-1.88 (m, 1H), 1.85-1.74 (m, 1H), 1.70-1.60 (m, 1H), 1.60-1.49 (m, 1H), 1.44 (d, J=11.0, 9H), 1.37-1.25 (m, 1H), 0.91 (d, J=8.9, 9H); MS (ESI+) m/z 610 (M+H)$^+$.

Step B: The title compound was prepared by substituting tert-butyl(S)-4,4-dimethyl-1-oxo-1-((3aR,4S,6aS)-2-(2-chloro-4-(trifluoromethyl)phenylsulfonyl)octahydrocyclopenta[c]pyrrol-4-ylamino)pentan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-$d_5$) δ ppm 8.34-8.37 (m, 2H), 7.99 (d, J=1.7 Hz, 1H), 7.72-7.75 (m, 1H), 4.30-4.35 (m, 1H), 3.96 (dd, J=10.2, 2.3 Hz, 1H), 3.53 (dd, J=10.1, 7.2 Hz, 1H), 3.39 (dd, J=10.0, 7.1 Hz, 1H), 3.35 (dd, J=9.9, 2.9 Hz, 1H), 3.17 (dd, J=6.5, 5.1 Hz, 1H), 2.64-2.70 (m, 2H), 2.38 (s, 3H), 2.03 (dtd, J=12.5, 6.3, 4.2 Hz, 1H), 1.89 (dd, J=14.0, 5.2 Hz, 1H), 1.83-1.92 (m, 1H), 1.67-2.06 (m, 1H), 1.56-1.66 (m, 1H), 1.47 (dd, J=14.0, 6.6 Hz, 1H), 1.32-1.43 (m, 1H), 0.96 (s, 9H); MS (ESI+) m/z 510 (M+H)$^+$.

Example 432

N-((3aR,4S,6aS)-2-{[2-chloro-4-(trifluoromethyl)phenyl]sulfonyl}octahydrocyclopenta[c]pyrrol-4-yl)-N-methyl-L-phenylalaninamide Step A: N-(tert-Butoxycarbonyl)-N-methyl-N-((3aR,4S,6aS)-2-{[2-chloro-4-(trifluoromethyl)phenyl]sulfonyl}octahydrocyclopenta[c]pyrrol-4-yl)-L-phenylalaninamide was prepared by substituting N-(tert-butoxycarbonyl)-N-methyl-L-phenylalanine for N-(tert-butoxycarbonyl)-L-leucine and (3aR,4S,6aS)-2-{[2-chloro-4-(trifluoromethyl)phenyl]sulfonyl}octahydrocyclopenta[c]pyrrol-4-amine from Example 284 Step B for (3aR,4S,6aS)-2-benzyloctahydrocyclopenta[c]pyrrol-4-amine in the procedure described in Example 221: $^1$H NMR (400 MHz, pyridine-$d_5$) δ ppm 8.69-8.55 (m, 1H), 8.37 (d, J=8.2, 1H), 8.01 (d, J=1.1, 1H), 7.76 (dd, J=8.3, 1.0, 1H), 7.28 (d, J=15.4, 4H), 7.23 (d, J=1.3, 1H), 5.38-5.26 (m, 1H), 4.38-4.20 (m, 1H), 3.95-3.80 (m, 1H), 3.65-3.48 (m, 1H), 3.48-3.40 (m, 1H), 3.37-3.25 (m, 2H), 3.15-3.07 (m, 1H), 3.05 (s, 3H), 2.59-2.48 (m, 1H), 2.48-2.39 (m, 1H), 2.06-1.86 (m, 1H), 1.83-1.70 (m, 1H), 1.61-1.43 (m, 1H), 1.39-1.20 (m, 10H); MS (ESI+) m/z 630 (M+H)$^+$.

Step B: The title compound was prepared by substituting N-(tert-butoxycarbonyl)-N-methyl-N-((3aR,4S,6aS)-2-{[2-chloro-4-(trifluoromethyl)phenyl]sulfonyl}octahydrocyclopenta[c]pyrrol-4-yl)-L-phenylalaninamide from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-$d_5$) δ ppm 8.37 (d, J=8.2, 1H), 8.20 (d, J=7.3, 1H), 8.01 (d, J=1.2, 1H), 7.76 (dd, J=8.3, 1.1, 1H), 7.35-7.23 (m, 5H), 4.34-4.24 (m, 1H), 3.85 (dd, J=10.2, 3.0, 1H), 3.49-3.27 (m, 4H), 3.17 (dd, J=13.3, 6.8, 1H), 3.05 (s, 3H), 2.61-2.50 (m, 1H), 2.49-2.39 (m, 1H), 2.34 (s, 3H), 2.10-2.01 (m, 1H), 1.96 (dtd, J=10.8, 6.5, 4.4, 1H), 1.83-1.72 (m, 1H), 1.53-1.41 (m, 1H), 1.31 (ddt, J=13.2, 9.6, 6.7, 1H); MS (ESI+) m/z 530 (M+H)$^+$.

Example 433

N$^1$-cyclopropyl-N$^2$,4-dimethyl-N$^1$-((3aR,4S,6aS)-2-{[4-(trifluoromethyl)phenyl]sulfonyl}octahydrocyclopenta[c]pyrrol-4-yl)-L-leucinamide Step A: (3aR,4S,6aS)-N-Cyclopropyl-2-(4-(trifluoromethyl)phenylsulfonyl)octahydrocyclopenta[c]pyrrol-4-amine was prepared by substituting (3aR,4S,6aS)-2-(4-(trifluoromethyl)phenylsulfonyl)octahydrocyclopenta[c]pyrrol-4-amine from Example 256 Step A for (3aS,4R,6aR)-2-(3-(trifluoromethyl)phenylsulfonyl)octahydrocyclopenta[c]pyrrol-4-amine and (1-ethoxycyclopropoxy)trimethylsilane for pivalaldehyde in the procedure described in Example 281: $^1$H NMR (500 MHz, pyridine-$d_5$) δ ppm 8.19 (d, J=8.1, 2H), 7.94 (d, J=8.3, 2H), 3.44 (dd, J=9.8, 2.9, 1H), 3.17 (dd, J=9.6, 3.2, 1H), 3.06 (dd, J=9.8, 7.9, 1H), 2.96 (dd, J=9.6, 7.7, 1H), 2.88 (dd, J=13.2, 5.8, 1H), 2.56-2.46 (m, 1H), 2.28 (ddd, J=12.1, 9.0, 2.9, 1H), 2.20-2.07 (m, 1H), 1.99 (dq, J=6.3, 4.0, 1H), 1.89-1.79 (m, 2H), 1.37-1.18 (m, 2H), 0.42-0.25 (m, 4H); MS (ESI+) m/z 375 (M+H)$^+$.

Step B: tert-Butyl(S)-1-(cyclopropyl((3aR,4S,6aS)-2-(4-(trifluoromethyl)phenylsulfonyl)octahydrocyclopenta[c]pyrrol-4-yl)amino)-4,4-dimethyl-1-oxopentan-2-yl(methyl)carbamate was prepared by substituting (S)-2-(tert-butoxycarbonyl(methyl)amino)-4,4-dimethylpentanoic acid for (S)-1-(tert-butoxycarbonyl)pyrrolidine-2-carboxylic acid and (3aR,4S,6aS)-N-cyclopropyl-2-(4-(trifluoromethyl)phenylsulfonyl)octahydrocyclopenta[c]pyrrol-4-amine from Step A for (3aS,4R,6aR)-2-(3-(trifluoromethyl)phenylsulfonyl)octahydrocyclopenta[c]pyrrol-4-amine in the procedure described in Example 266: $^1$H NMR (400 MHz, pyridine-$d_5$) δ ppm 8.12-8.07 (m, 2H), 7.86-7.80 (m, 2H), 5.85-5.57 (m, 1H), 3.93 (s, 1H), 3.56 (dd, J=10.0, 3.2, 1H), 3.19 (dd, J=10.0, 3.4, 2H), 3.13 (dd, J=16.7, 9.1, 1H), 2.98-2.88 (m, 4H), 2.76 (ddd, J=11.0, 7.1, 4.2, 1H), 2.72-2.64 (m, 1H), 2.15 (ddd, J=18.3, 11.1, 7.7, 1H), 2.05-1.97 (m, 1H), 1.97-1.88 (m, 1H), 1.80-1.71 (m, 1H), 1.68-1.56 (m, 1H), 1.49 (s, 9H), 1.35-1.20 (m, 1H), 1.05 (dtd, J=10.0, 6.8, 5.0, 1H), 0.99 (s, 9H), 0.88 (dddd, J=9.6, 8.1, 6.7, 3.3, 2H), 0.79-0.70 (m, 1H); MS (ESI+) m/z 616 (M+H)$^+$.

Step C: The title compound was prepared by substituting tert-butyl(S)-1-(cyclopropyl((3aR,4S,6aS)-2-(4-(trifluoromethyl)phenylsulfonyl)octahydrocyclopenta[c]pyrrol-4-yl)amino)-4,4-dimethyl-1-oxopentan-2-yl(methyl)carbamate from Step B for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-$d_5$, temperature 90° C.) δ ppm 8.08-8.11 (m, 2H), 7.81-7.85 (m, 2H), 4.00 (dd, J=8.3, 4.1 Hz, 1H), 3.91-3.97 (m, 2H), 3.51 (dd, J=9.6, 2.8 Hz, 1H), 3.08-3.24 (m, 4H), 2.66-2.77 (m, 1H), 2.60-2.66 (m, 1H), 2.30 (s, 3H), 2.11 (qd, J=11.1, 7.6 Hz, 1H), 1.89-2.02 (m, 1H), 1.79-1.86 (m, 1H), 1.59 (dd, J=14.1, 4.0 Hz, 1H), 1.45 (dd, J=14.2, 8.1 Hz, 1H), 1.27 (tt, J=11.9, 7.5 Hz, 1H), 1.02 (s, 9H), 0.73-0.97 (m, 4H); MS (ESI+) m/z 516 (M+H)$^+$.

Example 434

N$^1$-ethyl-N$^2$,4-dimethyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting tert-butyl (S)-1-(ethyl((3aR,4S,6aS)-2-(4-(trifluoromethyl)phenylsulfonyl)octahydrocyclopenta[c]pyrrol-4-yl)amino)-4,4-dimethyl-1-oxopentan-2-yl(methyl)carbamate from Example 296 for tert-butyl(S)-1-((3aR,4S,6aS)-2-benzyloctahydrocyclopenta[c]pyrrol-4-ylamino)-4-methyl-1-oxopentan-2-yl (methyl)carbamate in the procedure described in Example 348: $^1$H NMR (400 MHz, pyridine-d$_5$, temperature 90° C.) δ ppm 8.08-8.11 (m, 2H), 7.82-7.85 (m, 2H), 4.18-4.25 (m, 1H), 3.66 (d, J=9.9 Hz, 1H), 3.17-3.54 (m, 4H), 2.84-3.15 (m, 2H), 2.52-2.82 (m, 2H), 2.22-2.50 (m, 3H), 1.87-2.19 (m, 2H), 1.67-1.85 (m, 2H), 1.61 (dd, J=14.2, 3.8 Hz, 1H), 1.48 (dd, J=14.2, 8.2 Hz, 1H), 1.27-1.40 (m, 1H), 1.17 (t, J=7.0 Hz, 3H), 1.04 (s, 9H); MS (ESI+) m/z 505 (M+H)$^+$.

Example 435

N$^2$,4-dimethyl-N$^1$-propyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting tert-butyl (S)-4,4-dimethyl-1-oxo-1-(propyl((3aR,4S,6aS)-2-(4-(trifluoromethyl)phenylsulfonyl)octahydrocyclopenta[c]pyrrol-4-yl)amino)pentan-2-yl(methyl)carbamate from Example 297 for tert-butyl(S)-1-((3aR,4S,6aS)-2-benzyloctahydrocyclopenta[c]pyrrol-4-ylamino)-4-methyl-1-oxopentan-2-yl (methyl)carbamate in the procedure described in Example 348: $^1$H NMR (400 MHz, pyridine-d$_5$, temperature 90° C.) δ ppm 8.08-8.11 (m, 2H), 7.82-7.85 (m, 2H), 4.18-4.30 (m, 1H), 3.64-3.75 (m, 2H), 2.97-3.36 (m, 5H), 2.18-2.88 (m, 5H), 1.72-2.14 (m, 4H), 1.55-1.71 (m, 3H), 1.48 (dd, J=14.3, 8.3 Hz, 1H), 1.28-1.34 (m, 1H), 1.04-1.06 (m, 9H), 0.87 (t, J=7.4 Hz, 3H); MS (ESI+) m/z 518 (M+H)$^+$.

Example 436

N$^1$-(cyclopropylmethyl)-N$^2$,4-dimethyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting tert-butyl (S)-1-((cyclopropylmethyl)((3aR,4S,6aS)-2-(4-(trifluoromethyl)phenylsulfonyl)octahydrocyclopenta[c]pyrrol-4-yl) amino)-4,4-dimethyl-1-oxopentan-2-yl(methyl)carbamate from Example 298 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-d$_5$, temperature 90° C.) δ ppm 8.08-8.11 (m, 2H), 7.82-7.85 (m, 2H), 4.13-4.26 (m, 1H), 3.51-3.78 (m, 2H), 3.20-3.35 (m, 3H), 2.82-3.18 (m, 2H), 2.52-2.81 (m, 2H), 2.29-2.50 (m, 3H), 1.77-2.10 (m, 3H), 1.70-2.15 (m, 1H), 1.65 (dd, J=14.2, 3.8 Hz, 1H), 1.48 (dd, J=14.3, 8.2 Hz, 1H), 1.27-1.40 (m, 1H), 1.05 (s, 10H), 0.43-0.72 (m, 2H), 0.31-0.35 (m, 2H); MS (ESI+) m/z 530 (M+H)$^+$.

Example 437

N$^1$,N$^2$,4-trimethyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting tert-butyl (S)-4,4-dimethyl-1-(methyl((3aR,4S,6aS)-2-(4-(trifluoromethyl)phenylsulfonyl)octahydrocyclopenta[c]pyrrol-4-yl) amino)-1-oxopentan-2-yl(methyl)carbamate from Example 302 for tert-butyl(S)-1-((3aR,4S,6aS)-2-benzyloctahydrocyclopenta[c]pyrrol-4-ylamino)-4-methyl-1-oxopentan-2-yl (methyl)carbamate in the procedure described in Example 348: $^1$H NMR (400 MHz, pyridine-d$_5$, temperature 90° C.) δ ppm 8.08-8.11 (m, 2H), 7.82-7.85 (m, 2H), 4.14-4.96 (m, 1H), 3.62 (dd, J=9.9, 1.8 Hz, 2H), 3.00-3.30 (m, 3H), 2.89 (s, 3H), 2.49-2.65 (m, 2H), 2.25-2.47 (m, 3H), 1.59-2.10 (m, 5H), 1.46 (dd, J=14.2, 7.6 Hz, 1H), 1.22-1.41 (m, 1H), 1.01-1.03 (m, 9H); MS (ESI+) m/z 5490 (M+H)$^+$.

Example 438

N$^1$,N$^2$-dimethyl-N$^1$-((3aR,4S,6aS)-2-{[4-(trifluoromethyl)phenyl]sulfonyl}octahydrocyclopenta[c]pyrrol-4-yl)-L-norvalinamide Step A: tert-Butyl methyl((S)-1-(methyl((3aR,4S,6aS)-2-(4-(trifluoromethyl)phenylsulfonyl)octahydrocyclopenta[c]pyrrol-4-yl)amino)-1-oxopentan-2-yl)carbamate was prepared by substituting (S)-2-(tert-butoxycarbonyl(methyl) amino)pentanoic acid for (S)-1-(tert-butoxycarbonyl) pyrrolidine-2-carboxylic acid and (3aR,4S,6aS)-N-methyl-2-(4-(trifluoromethyl)phenylsulfonyl)octahydrocyclopenta [c]pyrrol-4-amine from Example 301 for (3aS,4R,6aR)-2-(3-(trifluoromethyl)phenylsulfonyl)octahydrocyclopenta[c] pyrrol-4-amine in the procedure described in Example 266: $^1$H NMR (400 MHz, pyridine-d$_5$) δ ppm 8.11 (d, J=8.3, 2H), 7.83 (d, J=8.3, 2H), 4.69-4.57 (m, 1H), 3.59 (dd, J=9.9, 1.2, 1H), 3.29-3.18 (m, 2H), 3.16 (dd, J=9.8, 3.3, 1H), 2.88 (s, 3H), 2.86 (s, 3H), 2.61-2.50 (m, 2H), 1.91-1.56 (m, 6H), 1.51 (s, 10H), 1.40-1.21 (m, 3H), 0.91 (t, J=7.4, 3H); MS (ESI+) m/z 562 (M+H)$^+$.

Step B: The title compound was prepared by substituting tert-butyl methyl((S)-1-(methyl((3aR,4S,6aS)-2-(4-(trifluoromethyl)phenylsulfonyl)octahydrocyclopenta[c]pyrrol-4-yl)amino)-1-oxopentan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl) carbamate in the procedure described in Example 348: $^1$H NMR (400 MHz, pyridine-d$_5$, temperature 90° C.) δ ppm 8.08-8.11 (m, 2H), 7.82-7.85 (m, 2H), 4.48-4.67 (bs, 1H), 3.61 (dd, J=10.0, 2.0 Hz, 1H), 3.41-3.56 (m, 1H), 2.93-3.34 (m, 4H), 2.86 (s, 3H), 2.50-2.62 (m, 2H), 2.22-2.49 (m, 3H), 1.80-1.95 (m, 1H), 1.39-1.79 (m, 6H), 1.23-1.38 (m, 1H), 0.89 (t, J=7.2 Hz, 3H); MS (ESI+) m/z 462 (M+H)$^+$.

Example 439

N$^1$-((3aR,4S,6aS)-2-{[2-chloro-4-(trifluoromethyl) phenyl]sulfonyl}octahydrocyclopenta[c]pyrrol-4-yl)-N$^1$,N$^2$,4-trimethyl-L-leucinamide Step A: tert-Butyl(3aR,4S,6aS)-2-(2-chloro-4-(trifluoromethyl)phenylsulfonyl)octahydrocyclopenta[c]pyrrol-4-ylcarbamate (62 mg, 0.132 mmol) from Example 284 Step A was dissolved in 1,2-dimethoxyethane (1.0 mL) and lithium aluminum hydride (10.04 mg, 0.264 mmol) was added portionwise. The reaction was stirred at 70° C. overnight, then it was quenched with wet sodium sulfate. The crude material was applied to a 4 g silica gel cartridge and purified with a gradient of 1-10% methanol (2 N ammonia)/dichloromethane over 20 minutes to give (3aR,4S,6aS)-2-(2-chloro-4-(trifluoromethyl)phenylsulfonyl)-N-methyloctahydrocyclopenta[c] pyrrol-4-amine: $^1$H NMR (500 MHz, pyridine-d$_5$) δ ppm 8.46 (s, 1H), 8.34 (d, J=8.2, 1H), 7.99 (s, 1H), 4.92 (s, 3H), 4.32 (dt, J=13.7, 7.0, 1H), 3.89 (dd, J=10.2, 3.0, 1H), 3.49 (dd, J=10.2, 7.5, 1H), 3.41-3.30 (m, 2H), 2.70-2.59 (m, 2H), 2.48 (dt, J=4.4, 2.2, 1H), 2.01 (td, J=11.8, 6.6, 1H), 1.95-1.83 (m, 1H), 1.59 (ddd, J=16.1, 10.8, 7.7, 1H), 1.37 (dt, J=22.2, 6.5, 1H); MS (APCI+) m/z 383 (M+H)+.

Step B: tert-Butyl(S)-1-(((3aR,4S,6aS)-2-(2-chloro-4-(trifluoromethyl)phenylsulfonyl)octahydrocyclopenta[c]pyrrol-4-yl)(methyl)amino)-4,4-dimethyl-1-oxopentan-2-yl(methyl)carbamate was prepared by substituting (S)-2-(tert-butoxycarbonyl(methyl)amino)-4,4-dimethylpentanoic acid for N-(tert-butoxycarbonyl)-L-leucine and (3aR,4S,6aS)-2-(2-chloro-4-(trifluoromethyl)phenylsulfonyl)-N-methyloctahydrocyclopenta[c]pyrrol-4-amine from Step A for (3aR, 4S,6aS)-2-benzyloctahydrocyclopenta[c]pyrrol-4-amine in the procedure described in Example 221: MS (ESI+) m/z 625 (M+H)+.

Step C: The title compound was prepared by substituting tert-butyl(S)-1-(((3aR,4S,6aS)-2-(2-chloro-4-(trifluoromethyl)phenylsulfonyl)octahydrocyclopenta[c]pyrrol-4-yl)(methyl)amino)-4,4-dimethyl-1-oxopentan-2-yl(methyl)carbamate from Step B for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-$d_5$) δ ppm 8.30 (d, J=8.2, 1H), 7.90 (s, 1H), 7.69 (d, J=8.1, 1H), 3.80-3.72 (m, J=7.3, 1H), 3.68 (d, J=9.8, 1H), 3.50-3.27 (m, 3H), 2.94 (s, 3H), 2.74-2.58 (m, J=5.3, 11.8, 2H), 2.38 (s, 3H), 1.99-1.87 (m, J=8.2, 18.8, 1H), 1.85-1.64 (m, 4H), 1.53 (dd, J=7.0, 14.1, 1H), 1.47-1.33 (m, 1H), 0.99 (s, 9H); MS (ESI+) m/z 525 (M+H)+.

Example 440

4-methyl-N$^1$-{(3aR,4S,6aS)-2-[5-(trifluoromethyl)pyridin-2-yl]octahydrocyclopenta[c]pyrrol-4-yl}-L-leucinamide The title compound was prepared by substituting tert-butyl (S)-4,4-dimethyl-1-oxo-1-((3aR,4S,6aS)-2-(5-(trifluoromethyl)pyridin-2-yl)octahydrocyclopenta[c]pyrrol-4-ylamino)pentan-2-ylcarbamate from Example 262 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.62 (d, J=2.4 Hz, 1H), 8.48-8.50 (m, 1H), 7.67 (dd, J=8.9, 2.5 Hz, 1H), 6.38 (d, J=8.9 Hz, 1H), 4.35-4.41 (m, 1H), 3.80-3.83 (m, 1H), 3.65 (dd, J=7.5, 4.4 Hz, 1H), 3.60-3.66 (m, 1H), 3.54-3.60 (m, 1H), 3.30-3.34 (m, 1H), 2.68-2.79 (m, 2H), 2.20 (dd, J=14.0, 4.4 Hz, 1H), 1.73-2.56 (m, 2H), 2.10-2.17 (m, 1H), 1.89-1.97 (m, 1H), 1.68 (dq, J=12.7, 8.1 Hz, 1H), 1.47 (dd, J=14.0, 7.5 Hz, 1H), 1.35-1.42 (m, 1H), 1.01 (s, 9H); MS (ESI+) m/z 399 (M+H)+.

Example 441

4-methyl-N$^1$-{(3aR,4S,6aS)-2-[6-(trifluoromethyl)pyridin-2-yl]octahydrocyclopenta[c]pyrrol-4-yl}-L-leucinamide The title compound was prepared by substituting tert-butyl (S)-4,4-dimethyl-1-oxo-1-((3aR,4S,6aS)-2-(6-(trifluoromethyl)pyridin-2-yl)octahydrocyclopenta[c]pyrrol-4-ylamino)pentan-2-ylcarbamate from Example 264 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.43-8.46 (m, 1H), 7.51 (t, J=7.9 Hz, 1H), 6.98 (d, J=7.2 Hz, 1H), 6.50 (d, J=8.5 Hz, 1H), 4.32-4.38 (m, 1H), 3.71 (dd, J=10.9, 2.9 Hz, 1H), 3.64 (dd, J=7.5, 4.3 Hz, 1H), 3.46-3.60 (m, 2H), 3.27 (dd, J=10.9, 3.5 Hz, 1H), 2.65-2.74 (m, 2H), 2.19 (dd, J=13.9, 4.3 Hz, 1H), 1.71-2.58 (m, 2H), 2.06-2.15 (m, 1H), 1.87-1.97 (m, 1H), 1.65 (dq, J=12.7, 8.0 Hz, 1H), 1.46 (dd, J=14.0, 7.5 Hz, 1H), 1.32-1.39 (m, 1H), 1.01 (s, 9H); MS (ESI+) m/z 399 (M+H)+.

Example 442

4-methyl-N$^1$-{(3aR,4S,6aS)-2-[2-(methylsulfonyl)pyrimidin-5-yl]octahydrocyclopenta[c]pyrrol-4-yl}-L-leucinamide The title compound was prepared by substituting tert-butyl (S)-4,4-dimethyl-1-((3aR,4S,6aS)-2-(2-(methylsulfonyl)pyrimidin-5-yl)octahydrocyclopenta[c]pyrrol-4-ylamino)-1-oxopentan-2-ylcarbamate from Example 265 for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.45 (s, 2H), 8.43 (d, J=7.3 Hz, 1H), 4.95 (s, 3H), 4.39 (p, J=7.0 Hz, 1H), 3.97 (dd, J=11.9, 3.3 Hz, 1H), 3.76 (dd, J=12.0, 7.7 Hz, 1H), 3.70 (dd, J=11.6, 8.1 Hz, 1H), 3.62 (dd, J=7.5, 4.2 Hz, 1H), 3.44 (dd, J=11.7, 4.5 Hz, 1H), 2.65-2.75 (m, 2H), 2.18 (dd, J=14.0, 4.3 Hz, 1H), 2.09-2.16 (m, 1H), 2.02-2.19 (m, 2H), 1.86-1.94 (m, 1H), 1.65 (dq, J=12.7, 8.2 Hz, 1H), 1.45 (dd, J=14.0, 7.5 Hz, 1H), 1.33-1.42 (m, 1H), 1.00 (s, 9H); MS (ESI+) m/z 411 (M+H)+.

Example 443

N$^1$-{(3aS,4R,6aR)-2-[(3-fluorophenyl)sulfonyl]octahydrocyclopenta[c]pyrrol-4-yl}-N$^2$-methyl-L-leucinamide Step A: tert-Butyl methyl((S)-4-methyl-1-oxo-1-((3aS,4R,6aR)-2-(3-fluorophenylsulfonyl)octahydrocyclopenta[c]pyrrol-4-ylamino)pentan-2-yl)carbamate was prepared by substituting N$^1$-[(3aR,4R,6aR)-2-benzyloctahydrocyclopenta[c]pyrrol-4-yl]-N$^2$-(tert-butyloxycarbonyl)-N$^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 3-fluorobenzene-1-sulfonyl chloride for 3-(trifluoromethyl)benzene-1-sulfonyl chloride in the procedure described in Example 319: MS (APCI+) m/z 512 (M+H)+.

Step B: The title compound was prepared by substituting tert-butyl methyl((S)-4-methyl-1-oxo-1-((3aS,4R,6aR)-2-(3-fluorophenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.38 (d, J=6.6 Hz, 1H), 7.84 (dt, J=8.2, 2.0 Hz, 1H), 7.77 (d, J=7.8 Hz, 1H), 7.53 (td, J=8.0, 5.5 Hz, 1H), 7.38 (td, J=8.4, 2.4 Hz, 1H), 4.23-4.29 (m, 1H), 3.81 (dd, J=9.9, 2.3 Hz, 1H), 3.25 (dd, J=8.1, 5.9 Hz, 1H), 3.11-3.16 (m, 2H), 2.94 (dd, J=9.6, 6.7 Hz, 1H), 2.53-2.56 (m, 2H), 2.42 (s, 3H), 1.92-2.00 (m, 1H), 1.79-1.92 (m, 2H), 1.9 (m, 1H), 1.68-1.74 (m, 1H), 1.52-1.62 (m, 2H), 1.24-1.36 (m, 1H), 0.90 (d, J=6.6 Hz, 3H), 0.85 (d, J=6.5 Hz, 3H); MS (ESI-) m/z 410 (M-H)-.

Example 444

N$^1$-{(3aS,4R,6aR)-2-[(4-fluorophenyl)sulfonyl]octahydrocyclopenta[c]pyrrol-4-yl}-N$^2$-methyl-L-leucinamide Step A: tert-Butyl methyl((S)-4-methyl-1-oxo-1-((3aS,4R, 6aR)-2-(4-fluorophenylsulfonyl)octahydrocyclopenta[c]

pyrrol-4-ylamino)pentan-2-yl)carbamate was prepared by substituting N$^1$-[(3aS,4R,6aR)-2-benzyloctahydrocyclopenta[c]pyrrol-4-yl]-N$^2$-(tert-butyloxycarbonyl)-N$^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 4-fluorobenzene-1-sulfonyl chloride for 3-(trifluoromethyl)benzene-1-sulfonyl chloride in the procedure described in Example 319: MS (APCI+) m/z 512 (M+H)$^+$.

Step B: The title compound was prepared by substituting tert-butyl methyl((S)-4-methyl-1-oxo-1-((3aS,4R,6aR)-2-(4-fluorophenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.30 (d, J=7.2 Hz, 1H), 7.98-8.01 (m, 2H), 7.30-7.35 (m, 2H), 4.25-4.29 (m, 1H), 3.79 (dd, J=9.9, 2.6 Hz, 1H), 3.19 (dd, J=8.2, 5.8 Hz, 1H), 3.14 (d, J=2.9 Hz, 1H), 3.10-3.12 (m, 1H), 2.93 (dd, J=9.6, 6.9 Hz, 1H), 2.52-2.58 (m, 2H), 2.39 (s, 3H), 1.92-2.00 (m, 1H), 1.78-2.08 (m, 1H), 1.80-1.92 (m, 2H), 1.68 (ddd, J=13.5, 7.7, 5.8 Hz, 1H), 1.58 (dd, J=8.1, 6.4 Hz, 1H), 1.52-1.58 (m, 1H), 1.26-1.35 (m, 1H), 0.90 (d, J=6.6 Hz, 3H), 0.84 (d, J=6.6 Hz, 3H); MS (ESI+) m/z 412 (M+H)$^+$.

Example 445

N$^1$-{(3aS,4R,6aR)-2-[(3,4-difluorophenyl)sulfonyl]octahydrocyclopenta[c]pyrrol-4-yl}-N$^2$-methyl-L-leucinamide Step A: tert-Butyl methyl((S)-4-methyl-1-oxo-1-((3aS,4R,6aR)-2-(3,4-difluorophenylsulfonyl)octahydrocyclopenta[c]pyrrol-4-ylamino)pentan-2-yl)carbamate was prepared by substituting N$^1$-[(3aS,4R,6aR)-2-benzyloctahydrocyclopenta[c]pyrrol-4-yl]-N$^2$-(tert-butyloxycarbonyl)-N$^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 3,4-difluorobenzene-1-sulfonyl chloride for 3-(trifluoromethyl)benzene-1-sulfonyl chloride in the procedure described in Example 319: MS (APCI+) m/z 530 (M+H)$^+$.

Step B: The title compound was prepared by substituting tert-butyl methyl((S)-4-methyl-1-oxo-1-((3aS,4R,6aR)-2-(3,4-difluorophenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.30 (d, J=7.3 Hz, 1H), 8.00 (ddd, J=9.6, 7.3, 2.2 Hz, 1H), 7.76-7.79 (m, 1H), 7.35-7.49 (m, 1H), 4.24-4.30 (m, 1H), 3.82 (dd, J=9.9, 2.6 Hz, 1H), 3.19 (dd, J=7.5, 5.0 Hz, 1H), 3.13-3.17 (m, 2H), 2.98 (dd, J=9.6, 7.1 Hz, 1H), 2.52-2.62 (m, 2H), 2.39 (s, 3H), 1.86-2.18 (m, 1H), 1.94-2.02 (m, 1H), 1.79-1.92 (m, 2H), 1.63-1.74 (m, 1H), 1.53-1.62 (m, 2H), 1.28-1.40 (m, 1H), 0.90 (d, J=6.7 Hz, 3H), 0.84 (d, J=6.6 Hz, 3H); MS (ESI+) m/z 430 (M+H)$^+$.

Example 446

N$^1$-{(3aS,4R,6aR)-2-[(3,5-difluorophenyl)sulfonyl]octahydrocyclopenta[c]pyrrol-4-yl}-N$^2$-methyl-L-leucinamide Step A: tert-Butyl methyl((S)-4-methyl-1-oxo-1-((3aS,4R,6aR)-2-(3,5-difluorophenylsulfonyl)octahydrocyclopenta[c]pyrrol-4-ylamino)pentan-2-yl)carbamate was prepared by substituting N$^1$-[(3aS,4R,6aR)-2-benzyloctahydrocyclopenta[c]pyrrol-4-yl]-N$^2$-(tert-butyloxycarbonyl)-N$^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 3,5-difluorobenzene-1-sulfonyl chloride for 3-(trifluoromethyl)benzene-1-sulfonyl chloride in the procedure described in Example 319: MS (APCI+) m/z 530 (M+H)$^+$.

Step B: The title compound was prepared by substituting tert-butyl methyl((S)-4-methyl-1-oxo-1-((3aS,4R,6aR)-2-(3,5-difluorophenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.32 (d, J=7.2 Hz, 1H), 7.66-7.69 (m, 2H), 7.33-7.42 (m, 1H), 4.24-4.30 (m, 1H), 3.84 (dd, J=9.9, 2.5 Hz, 1H), 3.16-3.21 (m, 3H), 3.00 (dd, J=9.7, 7.0 Hz, 1H), 2.48-2.60 (m, 2H), 2.39 (s, 3H), 1.89-2.25 (m, 1H), 1.93-2.01 (m, 1H), 1.81-1.92 (m, 2H), 1.68 (ddd, J=13.6, 7.8, 5.8 Hz, 1H), 1.52-1.63 (m, 2H), 1.31 (ddt, J=9.7, 12.9, 6.4 Hz, 1H), 0.90 (d, J=6.6 Hz, 3H), 0.84 (d, J=6.6 Hz, 3H); MS (ESI+) m/z 430 (M+H)$^+$.

Example 447

N$^1$-{(3aS,4R,6aR)-2-[(4-chlorophenyl)sulfonyl]octahydrocyclopenta[c]pyrrol-4-yl}-N$^2$-methyl-L-leucinamide Step A: tert-Butyl methyl((S)-4-methyl-1-oxo-1-((3aS,4R,6aR)-2-(4-chlorophenylsulfonyl)octahydrocyclopenta[c]pyrrol-4-ylamino)pentan-2-yl)carbamate was prepared by substituting N$^1$-[(3aS,4R,6aR)-2-benzyloctahydrocyclopenta[c]pyrrol-4-yl]-N$^2$-(tert-butyloxycarbonyl)-N$^2$-methyl-L-leucinamide from Example 151 for (S)-N-((3aS,4R,6aR)-2-benzyloctahydrocyclopenta[c]pyrrol-4-yl)-4-methyl-2-morpholinopentanamide and 4-chlorobenzene-1-sulfonyl chloride for 3-(trifluoromethyl)benzene-1-sulfonyl chloride in the procedure described in Example 319: MS (APCI+) m/z 530 (M+H)$^+$.

Step B: The title compound was prepared by substituting tert-butyl methyl((S)-4-methyl-1-oxo-1-((3aS,4R,6aR)-2-(4-chlorophenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.29-8.31 (m, 1H), 7.91-7.93 (m, 2H), 7.57-7.59 (m, 2H), 4.24-4.31 (m, 1H), 3.80 (dd, J=9.9, 2.5 Hz, 1H), 3.19 (dd, J=8.2, 5.8 Hz, 1H), 3.13 (dd, J=9.4, 2.7 Hz, 1H), 3.11 (dd, J=9.5, 7.2 Hz, 1H), 2.92 (dd, J=9.6, 7.0 Hz, 1H), 2.52-2.59 (m, 2H), 2.39 (s, 3H), 1.90-2.16 (m, 1H), 1.92-2.00 (m, 1H), 1.80-1.91 (m, 2H), 1.68 (ddd, J=13.5, 7.8, 5.8 Hz, 1H), 1.52-1.62 (m, 2H), 1.27-1.34 (m, 1H), 0.90 (d, J=6.6 Hz, 3H), 0.85 (d, J=6.5 Hz, 3H); MS (ESI−) m/z 426 (M−H)$^−$.

Example 448

N$^2$-methyl-N$^1$-[(3aS,4R,6aR)-2-(phenylsulfonyl)octahydrocyclopenta[c]pyrrol-4-yl]-L-leucinamide Step A: tert-Butyl methyl((S)-4-methyl-1-oxo-1-((3aS,4R,6aR)-2-(phenylsulfonyl)octahydrocyclopenta[c]pyrrol-4-ylamino)pentan-2-yl)carbamate was prepared by substituting M-[(3aS,4R,6aR)-2-benzyloctahydrocyclopenta[c]pyrrol-4-yl]-N²-(tert-butyloxycarbonyl)-N²-methyl-L-leucinamide from Example 151 for (S)-N-((3aS,4R,6aR)-2-benzyloctahydrocyclopenta[c]pyrrol-4-yl)-4-methyl-2-morpholinopentanamide and benzenesulfonyl chloride for 3-(trifluoromethyl)benzene-1-sulfonyl chloride in the procedure described in Example 319: MS (APCI+) m/z 494 (M+H)⁺.

Step B: The title compound was prepared by substituting tert-butyl methyl((S)-4-methyl-1-oxo-1-((3aS,4R,6aR)-2-(4-chlorophenylsulfonyl)octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (400 MHz, pyridine-d₅) δ ppm 8.28 (d, J=7.0 Hz, 1H), 7.97-8.00 (m, 2H), 7.52-7.58 (m, 3H), 4.24-4.31 (m, 1H), 3.79 (dd, J=9.9, 2.4 Hz, 1H), 3.19 (dd, J=8.2, 5.8 Hz, 1H), 3.08-3.15 (m, 2H), 2.91 (dd, J=9.6, 6.7 Hz, 1H), 2.48-2.52 (m, 2H), 2.39 (s, 3H), 1.77-2.03 (m, 4H), 1.68 (ddd, J=13.5, 7.8, 5.8 Hz, 1H), 1.49-1.60 (m, 2H), 1.24-1.33 (m, 1H), 0.90 (d, J=6.6 Hz, 3H), 0.84 (d, J=6.5 Hz, 3H); MS (ESI−) m/z 392 (M−H)⁻.

Example 449

N²-methyl-N¹-{(3aS,4R,6aR)-2-[4-(trifluoromethyl)benzyl]octahydrocyclopenta[c]pyrrol-4-yl}-L-leucinamide Step A: tert-Butyl(S)-1-((3aS,4R,6aR)-2-(4-(trifluoromethyl)benzyl)octahydrocyclopenta[c]pyrrol-4-ylamino)-4-methyl-1-oxopentan-2-yl(methyl)carbamate was prepared by substituting N¹-[(3aS,4R,6aR)-2-benzyloctahydrocyclopenta[c]pyrrol-4-yl]-N²-(tert-butyloxycarbonyl)-N²-methyl-L-leucinamide from Example 151 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-(trifluoromethyl)benzaldehyde for 3-(trifluoromethyl)benzaldehyde in the procedure described in Example 303: ¹H NMR (500 MHz, pyridine-d₅) δ ppm 8.36-8.27 (m, 1H), 7.65 (d, J=8.1, 2H), 7.50 (d, J=7.6, 2H), 5.14 (m, 0.4H), 4.78 (m, 0.6H), 4.45-4.31 (m, 1H), 3.62-3.51 (m, 1H), 3.45 (ddd, J=7.5, 5.3, 3.5, 1H), 3.05 (s, 3H), 2.90-2.73 (m, 1H), 2.55-2.41 (m, 2H), 2.31 (d, J=5.7, 2H), 2.23-2.17 (m, 2H), 2.10 (dt, J=11.5, 5.8, 1H), 1.94-1.75 (m, 3H), 1.65-1.51 (m, 2H), 1.46 (s, 9H), 1.42-1.34 (m, 1H), 0.88 (d, J=6.3, 3H), 0.84 (d, J=6.6, 3H); MS (ESI+) m/z 512 (M+H)⁺.

Step B: The title compound was prepared by substituting tert-butyl(S)-1-((3aS,4R,6aR)-2-(4-(trifluoromethyl)benzyl)octahydrocyclopenta[c]pyrrol-4-ylamino)-4-methyl-1-oxopentan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.19-8.21 (m, 1H), 7.64-7.67 (m, 2H), 7.51-7.53 (m, 2H), 4.44-4.50 (m, 1H), 3.57-3.61 (m, 1H), 3.47 (d, J=13.6 Hz, 1H), 3.22 (dd, J=8.2, 5.8 Hz, 1H), 2.89 (dd, J=9.0, 2.6 Hz, 1H), 2.48-2.58 (m, 2H), 2.42 (s, 3H), 2.34-2.40 (m, 2H), 2.24 (dd, J=8.9, 7.0 Hz, 1H), 2.09-2.17 (m, 1H), 1.92-2.08 (m, 1H), 1.84-1.94 (m, 2H), 1.71 (ddd, J=13.5, 7.8, 5.8 Hz, 1H), 1.56-1.65 (m, 2H), 1.39-1.47 (m, 1H), 0.91 (d, J=6.5 Hz, 3H), 0.85 (d, J=6.5 Hz, 3H); MS (ESI+) m/z 412 (M+H)⁺.

Example 450

N¹-[(3aS,4R,6aR)-2-(4-fluorobenzyl)octahydrocyclopenta[c]pyrrol-4-yl]-N²-methyl-L-leucinamide Step A: tert-Butyl(S)-1-((3aS,4R,6aR)-2-(4-fluorobenzyl)octahydrocyclopenta[c]pyrrol-4-ylamino)-4-methyl-1-oxopentan-2-yl(methyl)carbamate was prepared by substituting N¹-[(3aS,4R,6aR)-2-benzyloctahydrocyclopenta[c]pyrrol-4-yl]-N²-(tert-butyloxycarbonyl)-N²-methyl-L-leucinamide from Example 151 for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 4-fluorobenzaldehyde for 3-(trifluoromethyl)benzaldehyde in the procedure described in Example 303: ¹H NMR (500 MHz, pyridine-d₅) δ ppm 8.30 (d, J=6.2, 1H), 7.39-7.32 (m, 2H), 7.12 (t, J=8.8, 2H), 5.18-5.11 (m, 1H), 4.44-4.33 (m, 1H), 3.54-3.46 (m, 1H), 3.38 (t, J=13.8, 1H), 3.05 (s, 3H), 2.87-2.71 (m, 1H), 2.53-2.41 (m, 2H), 2.31 (d, J=6.3, 2H), 2.23-2.17 (m, 1H), 2.13-2.06 (m, 1H), 1.83 (dd, J=9.0, 5.2, 3H), 1.64-1.52 (m, 2H), 1.46 (s, 9H), 1.42-1.33 (m, 1H), 0.88 (d, J=6.4, 3H), 0.84 (d, J=6.5, 3H); MS (ESI+) m/z 462 (M+H)⁺.

Step B: The title compound was prepared by substituting tert-butyl(S)-1-((3aS,4R,6aR)-2-(4-fluorobenzyl)octahydrocyclopenta[c]pyrrol-4-ylamino)-4-methyl-1-oxopentan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.23-8.25 (m, 1H), 7.37 (dd, J=8.3, 5.4 Hz, 2H), 7.13 (t, J=8.6 Hz, 2H), 4.43-4.48 (m, 1H), 3.53 (d, J=13.1 Hz, 1H), 3.40 (d, J=13.1 Hz, 1H), 3.24 (dd, J=8.1, 5.9 Hz, 1H), 2.85 (dd, J=9.1, 2.6 Hz, 1H), 2.48-2.56 (m, 2H), 2.42 (s, 3H), 2.39 (dd, J=8.8, 7.1 Hz, 1H), 2.34 (dd, J=9.0, 2.3 Hz, 1H), 2.24 (dd, J=8.9, 6.9 Hz, 1H), 2.13 (dq, J=11.9, 6.0 Hz, 1H), 1.62-2.52 (m, 1H), 1.85-1.94 (m, 2H), 1.72 (ddd, J=13.5, 7.7, 5.8 Hz, 1H), 1.56-1.65 (m, 2H), 1.38-1.45 (m, 1H), 0.91 (d, J=6.6 Hz, 3H), 0.86 (d, J=6.5 Hz, 3H); MS (ESI+) m/z 362 (M+H)⁺.

Example 451

N²-methyl-N¹-((3aR,4S,6aS)-2-{[4-(trifluoromethyl)phenyl]sulfonyl}octahydrocyclopenta[c]pyrrol-4-yl)-L-valinamide Step A: tert-Butyl methyl((S)-3-methyl-1-oxo-1-((3aR,4S,6aS)-2-(4-(trifluoromethyl)phenylsulfonyl)octahydrocyclopenta[c]pyrrol-4-ylamino)butan-2-yl)carbamate was prepared by substituting (S)-2-(tert-butoxycarbonyl(methyl)amino)-3-methylbutanoic acid for N-(tert-butoxycarbonyl)-L-leucine and (3aR,4S,6aS)-2-(4-(trifluoromethyl)phenylsulfonyl)octahydrocyclopenta[c]pyrrol-4-amine from Example 256 Step A for (3aR,4S,6aS)-2-benzyloctahydrocyclopenta[c]pyrrol-4-amine in the procedure described in Example 221: ¹H NMR (400 MHz, pyridine-d₅) δ ppm 8.08 (d, J=8.1, 2H), 7.81 (d, J=8.3, 2H), 7.58-7.53 (m, 1H), 4.31 (d, J=10.6, 1H), 4.11-4.02 (m, 1H), 3.66 (dd, J=10.2, 3.3, 1H), 3.31 (dd, J=10.2, 7.8, 1H), 3.19-3.09 (m, 2H), 3.00 (s, 3H), 2.63-2.47 (m, 2H), 2.43-2.33 (m, 1H), 1.94-1.75 (m, 2H), 1.55-1.47 (m, 1H), 1.45 (s, 9H), 1.28 (ddd, J=13.0, 8.9, 6.2, 1H), 0.98 (d, J=6.5, 3H), 0.86 (d, J=6.7, 3H).

Step B: The title compound was prepared by substituting tert-butyl methyl((S)-3-methyl-1-oxo-1-((3aR,4S,6aS)-2-(4-(trifluoromethyl)phenylsulfonyl)octahydrocyclopenta[c]pyrrol-4-ylamino)butan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-d₅) δ ppm 8.25-8.27 (m, 1H), 8.13-8.16 (m, 2H), 7.90-7.92 (m, 2H), 4.23-4.30 (m, 1H), 3.85 (dd, J=9.9, 2.6 Hz, 1H), 3.13-3.20 (m, 2H), 2.97 (dd, J=9.6, 7.0 Hz, 1H), 2.88 (d, J=5.9 Hz, 1H), 2.48-2.62 (m, 2H), 2.39 (s, 3H), 2.05-2.13 (m, 1H), 1.94-2.09 (m, 1H), 1.90-1.97

(m, 1H), 1.80-1.87 (m, 1H), 1.51-1.59 (m, 1H), 1.30 (ddt, J=9.7, 12.9, 6.4 Hz, 1H), 1.02-1.05 (m, 6H); MS (ESI+) m/z 448 (M+H)$^+$.

Example 452

N$^1$-{(3aR,4S,6aS)-2-[(4-fluorophenyl)sulfonyl]octahydrocyclopenta[c]pyrrol-4-yl}-N$^2$-methyl-L-valinamide Step A: tert-Butyl(S)-1-((3aR,4S,6aS)-2-(4-fluorophenylsulfonyl)octahydrocyclopenta[c]pyrrol-4-ylamino)-3-methyl-1-oxobutan-2-yl(methyl)carbamate was prepared by substituting (S)-2-(tert-butoxycarbonyl(methyl)amino)-3-methylbutanoic acid for N-(tert-butoxycarbonyl)-L-leucine and (3aR,4S,6aS)-2-(4-fluorophenylsulfonyl)octahydrocyclopenta[c]pyrrol-4-amine from Example 261 Step A for (3aR,4S,6aS)-2-benzyloctahydrocyclopenta[c]pyrrol-4-amine in the procedure described in Example 221: $^1$H NMR (400 MHz, pyridine-d$_5$) δ ppm 7.94 (dd, J=8.6, 5.3, 2H), 7.20 (t, J=8.7, 2H), 4.31 (d, J=11.2, 1H), 4.07 (dt, J=13.3, 6.8, 1H), 3.59 (dd, J=9.9, 3.7, 1H), 3.27 (dd, J=10.1, 7.8, 1H), 3.15-3.03 (m, 2H), 2.99 (s, 3H), 2.61-2.46 (m, 2H), 2.38 (dq, J=17.5, 6.8, 1H), 1.94-1.75 (m, 2H), 1.51 (dd, J=14.6, 6.6, 1H), 1.45 (s, 9H), 1.33-1.21 (m, 1H), 0.98 (d, J=6.5, 3H), 0.86 (d, J=6.7, 3H); MS (ESI+) m/z 498 (M+H)$^+$.

Step B: The title compound was prepared by substituting tert-butyl(S)-1-((3aR,4S,6aS)-2-(4-fluorophenylsulfonyl)octahydrocyclopenta[c]pyrrol-4-ylamino)-3-methyl-1-oxobutan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.26 (d, J=6.7 Hz, 1H), 7.99-8.02 (m, 2H), 7.31-7.35 (m, 2H), 4.24-4.31 (m, 1H), 3.78 (dd, J=9.9, 2.5 Hz, 1H), 3.09-3.14 (m, 2H), 2.93 (dd, J=9.6, 6.8 Hz, 1H), 2.89 (d, J=5.9 Hz, 1H), 2.48-2.58 (m, 2H), 2.39 (s, 3H), 2.05-2.13 (m, 1H), 1.92-2.12 (m, 1H), 1.90-1.98 (m, 1H), 1.80-1.87 (m, 1H), 1.52-1.59 (m, 1H), 1.24-1.34 (m, 1H), 1.04 (d, J=7.2 Hz, 3H), 1.03 (d, J=7.2 Hz, 3H); MS (ESI–) m/z 396 (M–H)$^−$.

Example 453

N$^1$-{(3aR,4S,6aS)-2-[(4-fluorophenyl)sulfonyl]octahydrocyclopenta[c]pyrrol-4-yl}-4-methyl-L-leucinamide Step A: tert-Butyl(S)-1-((3aR,4S,6aS)-2-(4-fluorophenylsulfonyl)octahydrocyclopenta[c]pyrrol-4-ylamino)-4,4-dimethyl-1-oxopentan-2-ylcarbamate was prepared by substituting (S)-2-(tert-butoxycarbonylamino)-4,4-dimethylpentanoic acid for N-(tert-butoxycarbonyl)-L-leucine and (3aR,4S,6aS)-2-(4-fluorophenylsulfonyl)octahydrocyclopenta[c]pyrrol-4-amine from Example 261 Step A for (3aR,4S,6aS)-2-benzyloctahydrocyclopenta[c]pyrrol-4-amine in the procedure described in Example 221: $^1$H NMR (500 MHz, pyridine-d$_5$) δ ppm 8.70 (d, J=7.0, 1H), 8.14 (d, J=8.7, 1H), 7.99 (dd, J=8.6, 5.2, 2H), 7.32 (t, J=8.6, 2H), 4.75-4.65 (m, 1H), 4.27-4.18 (m, 1H), 3.74 (dd, J=9.9, 2.7, 1H), 3.10 (ddd, J=13.9, 9.6, 5.4, 2H), 2.92 (dd, J=9.4, 7.7, 1H), 2.61-2.47 (m, 2H), 2.15 (dd, J=14.2, 4.7, 1H), 1.89-1.73 (m, 3H), 1.56-1.45 (m, 10H), 1.28-1.18 (m, 1H), 0.98 (s, 9H); MS (ESI+) m/z 512 (M+H)$^+$.

Step B: The title compound was prepared by substituting tert-butyl(S)-1-((3aR,4S,6aS)-2-(4-fluorophenylsulfonyl)octahydrocyclopenta[c]pyrrol-4-ylamino)-4,4-dimethyl-1-oxopentan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.38-8.40 (m, 1H), 7.98-8.01 (m, 2H), 7.31-7.38 (m, 2H), 4.20-4.23 (m, 1H), 3.77 (dd, J=9.8, 2.6 Hz, 1H), 3.59 (dd, J=7.4, 4.3 Hz, 1H), 3.11 (dd, J=9.6, 2.7 Hz, 1H), 3.06 (dd, J=9.9, 7.3 Hz, 1H), 2.91 (dd, J=9.6, 7.0 Hz, 1H), 2.46-2.58 (m, 2H), 2.16 (dd, J=14.0, 4.3 Hz, 1H), 1.98-2.31 (m, 2H), 1.88-1.96 (m, 1H), 1.77-1.85 (m, 1H), 1.47-1.57 (m, 1H), 1.43 (dd, J=14.0, 7.6 Hz, 1H), 1.23-1.32 (m, 1H), 0.99 (s, 9H); MS (ESI–) m/z 410 (M–H)$^−$.

Example 454

N$^1$-{(3aR,4S,6aS)-2-[(4-fluorophenyl)sulfonyl]octahydrocyclopenta[c]pyrrol-4-yl}-N$^2$-methyl-L-norleucinamide Step A: tert-Butyl(S)-1-((3aR,4S,6aS)-2-(4-fluorophenylsulfonyl)octahydrocyclopenta[c]pyrrol-4-ylamino)-1-oxohexan-2-yl(methyl)carbamate was prepared by substituting (S)-2-(tert-butoxycarbonyl(methyl)amino)hexanoic acid for N-(tert-butoxycarbonyl)-L-leucine and (3aR,4S,6aS)-2-(4-fluorophenylsulfonyl)octahydrocyclopenta[c]pyrrol-4-amine from Example 261 Step A for (3aR,4S,6aS)-2-benzyloctahydrocyclopenta[c]pyrrol-4-amine in the procedure described in Example 221: $^1$H NMR (500 MHz, pyridine-d$_5$) δ ppm 8.45 (d, J=6.8, 1H), 7.99 (dd, J=8.7, 5.2, 2H), 7.32 (t, J=8.7, 2H), 4.94 (s, 3H), 4.28-4.15 (m, 1H), 3.75 (d, J=10.4, 1H), 3.07 (dd, J=20.0, 10.4, 4H), 2.89 (dd, J=9.5, 7.2, 1H), 2.57-2.46 (m, 2H), 2.13-1.98 (m, 1H), 1.93-1.68 (m, 3H), 1.45 (s, 9H), 1.26 (d, J=6.0, 5H), 0.78 (s, 3H); MS (ESI+) m/z 512 (M+H)$^+$.

Step B: The title compound was prepared by substituting tert-butyl(S)-1-((3aR,4S,6aS)-2-(4-fluorophenylsulfonyl)octahydrocyclopenta[c]pyrrol-4-ylamino)-1-oxohexan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.20-8.22 (m, 1H), 7.99-8.02 (m, 2H), 7.31-7.38 (m, 2H), 4.24-4.30 (m, 1H), 3.78 (dd, J=9.9, 2.5 Hz, 1H), 3.08-3.16 (m, 3H), 2.88-2.94 (m, 1H), 2.52-2.59 (m, 2H), 2.40 (s, 3H), 1.92-1.98 (m, 1H), 1.60-2.28 (m, 1H), 1.78-1.87 (m, 2H), 1.65-1.73 (m, 1H), 1.52-1.59 (m, 1H), 1.36-1.50 (m, 2H), 1.27-1.35 (m, 1H), 1.24 (h, J=7.4 Hz, 2H), 0.81 (t, J=7.3 Hz, 3H); MS (ESI–) m/z 410 (M–H)$^−$.

Example 455

N$^1$-{(3aR,4S,6aS)-2-[(4-fluorophenyl)sulfonyl]octahydrocyclopenta[c]pyrrol-4-yl}-N$^2$-methyl-L-leucinamide Step A: tert-Butyl(S)-1-((3aR,4S,6aS)-2-(4-fluorophenylsulfonyl)octahydrocyclopenta[c]pyrrol-4-ylamino)-4-methyl-1-oxopentan-2-yl(methyl)carbamate was prepared by substituting (S)-2-(tert-butoxycarbonyl(methyl)amino)-4-methylpentanoic acid for N-(tert-butoxycarbonyl)-L-leucine and (3aR,4S,6aS)-2-(4-fluorophenylsulfonyl)octahydrocyclopenta[c]pyrrol-4-amine from Example 261 Step A for (3aR,4S,6aS)-2-benzyloctahydrocyclopenta[c]pyrrol-4-amine in the procedure described in Example 221: $^1$H NMR (400 MHz, pyridine-d$_5$) δ ppm 7.94 (dd, J=8.1, 5.2, 2H), 7.44-7.37 (m, 1H), 7.20 (t, J=8.5, 2H), 4.85-4.77 (m, 1H), 4.12-4.03 (m, 1H), 3.61-3.55 (m, 1H), 3.27-3.21 (m, 1H), 3.13-3.02 (m, 2H), 2.93 (s, 3H), 2.59-2.44 (m, 2H), 1.83 (ddd, J=37.1, 15.2, 5.0, 4H), 1.50 (d, J=0.6, 2H), 1.46 (d, J=0.8, 9H), 1.33-1.22 (m, 1H), 0.89 (t, J=7.2, 6H); MS (ESI+) m/z 512 (M+H)$^+$.

Step B: The title compound was prepared by substituting tert-butyl(S)-1-((3aR,4S,6aS)-2-(4-fluorophenylsulfonyl)octahydrocyclopenta[c]pyrrol-4-ylamino)-4-methyl-1-oxopentan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.29-8.31 (m, 1H), 7.99-8.02 (m, 2H), 7.31-7.35 (m, 2H), 4.24-4.30 (m, 1H), 3.79 (dd, J=9.9, 2.4 Hz, 1H), 3.21 (dd, J=8.2, 5.9 Hz, 1H), 3.09-3.14 (m, 2H), 2.93 (dd, J=9.6, 6.7 Hz, 1H), 2.53-2.59 (m, 2H), 2.40 (s, 3H), 1.89-2.27 (m, 1H), 1.91-1.99 (m, 1H), 1.79-1.91 (m, 2H), 1.69 (ddd, J=13.5, 7.7, 5.8 Hz, 1H), 1.53-1.59 (m, 2H), 1.25-1.35 (m, 1H), 0.91 (d, J=6.6 Hz, 3H), 0.85 (d, J=6.6 Hz, 3H); MS (ESI–) m/z 410 (M–H)$^-$.

Example 456

N$^2$-methyl-N$^1$-((3aS,4S,6aR)-2-{[4-(trifluoromethyl)phenyl]sulfonyl}octahydrocyclopenta[c]pyrrol-4-yl)-L-norvalinamide Step A: tert-Butyl methyl((S)-1-oxo-1-((3aS,4S,6aR)-2-(4-(trifluoromethyl)phenylsulfonyl)octahydrocyclopenta[c]pyrrol-4-ylamino)pentan-2-yl)carbamate was prepared by substituting tert-butyl(S)-1-((3aS,4S,6aR)-2-benzyloctahydrocyclopenta[c]pyrrol-4-ylamino)-1-oxopentan-2-yl(methyl)carbamate from Example 238 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: MS (ESI+) m/z 548 (M+H)$^+$.

Step B: The title compound was prepared by substituting tert-butyl methyl((S)-1-oxo-1-((3aS,4S,6aR)-2-(4-(trifluoromethyl)phenylsulfonyl)octahydrocyclopenta[c]pyrrol-4-ylamino)pentan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.52 (d, J=6.8 Hz, 1H), 8.12-8.14 (m, 2H), 7.90-7.92 (m, 2H), 4.47 (p, J=7.6 Hz, 1H), 3.64 (dd, J=9.5, 2.9 Hz, 1H), 3.24 (dd, J=7.3, 5.4 Hz, 1H), 3.16 (dd, J=9.7, 3.1 Hz, 1H), 2.96-3.05 (m, 3H), 2.51 (s, 3H), 2.45-2.54 (m, 1H), 1.79-2.31 (m, 1H), 1.86-1.94 (m, 1H), 1.69-1.75 (m, 3H), 1.47-1.65 (m, 3H), 1.34-1.40 (m, 1H), 0.90 (t, J=7.3 Hz, 3H); MS (ESI+) m/z 448 (M+H)$^+$.

Example 457

N$^2$-methyl-N$^1$-((3aS,4S,6aR)-2-{[4-(trifluoromethyl)phenyl]sulfonyl}octahydrocyclopenta[c]pyrrol-4-yl)-L-leucinamide Step A: tert-Butyl methyl((S)-4-methyl-1-oxo-1-((3aS,4S,6aR)-2-(4-(trifluoromethyl)phenylsulfonyl)octahydrocyclopenta[c]pyrrol-4-ylamino)pentan-2-yl)carbamate was prepared by substituting tert-butyl(S)-1-((3aS,4S,6aR)-2-benzyloctahydrocyclopenta[c]pyrrol-4-ylamino)-4-methyl-1-oxopentan-2-yl(methyl)carbamate from Example 239 for (S)-N-((3aS,4R,6aR)-2-benzyloctahydrocyclopenta[c]pyrrol-4-yl)-4-methyl-2-morpholinopentanamide and 4-(trifluoromethyl)benzene-1-sulfonyl chloride for 3-(trifluoromethyl)benzene-1-sulfonyl chloride in the procedure described in Example 319: $^1$H NMR (500 MHz, pyridine-d$_5$) δ ppm 8.99-8.92 (m, 1H), 8.12 (d, J=8.0, 2H), 7.91 (d, J=8.2, 2H), 5.33-5.24 (m, 1H), 4.44-4.28 (m, 1H), 3.65 (dd, J=10.0, 2.8, 1H), 3.19-3.09 (m, 4H), 3.03-2.81 (m, 3H), 2.50-2.42 (m, 1H), 2.05-1.92 (m, 2H), 1.73-1.55 (m, 4H), 1.50 (s, 9H), 1.35-1.25 (m, 1H), 0.97 (d, J=6.6, 3H), 0.89-0.79 (m, 3H); MS (ESI+) m/z 562 (M+H)$^+$.

Step B: The title compound was prepared by substituting tert-butyl methyl((S)-4-methyl-1-oxo-1-((3aS,4S,6aR)-2-(4-(trifluoromethyl)phenylsulfonyl)octahydrocyclopenta[c]pyrrol-4-ylamino)pentan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.61 (d, J=6.9 Hz, 1H), 8.12-8.14 (m, 2H), 7.90-7.92 (m, 2H), 4.48 (s, 1H), 3.65 (dd, J=9.6, 3.1 Hz, 1H), 3.29-3.33 (m, 1H), 3.16 (dd, J=9.6, 3.1 Hz, 1H), 3.01-3.06 (m, 1H), 2.98-3.03 (m, 1H), 2.94-2.98 (m, 1H), 2.52 (s, 3H), 2.46-2.52 (m, 1H), 1.90-1.99 (m, 1H), 1.77-1.84 (m, 1H), 1.28-2.16 (m, 1H), 1.67-1.76 (m, 2H), 1.57-1.66 (m, 2H), 1.34-1.40 (m, 1H), 0.97 (d, J=6.6 Hz, 3H), 0.90 (d, J=6.6 Hz, 3H); MS (ESI+) m/z 462 (M+H)$^+$.

Example 458

N$^1$-{(3aR,4S,6aS)-2-[3,3-bis(4-fluorophenyl)propyl]octahydrocyclopenta[c]pyrrol-4-yl}-N$^2$-methyl-L-norvalinamide Step A: tert-Butyl(S)-1-((3aR,4S,6aS)-2-(3,3-bis(4-fluorophenyl)propyl)octahydrocyclopenta[c]pyrrol-4-ylamino)-1-oxopentan-2-yl(methyl)carbamate was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (2S)-N-[(3aS,4R,6aR)-2-benzyloctahydrocyclopenta[c]pyrrol-4-yl]-2-(1,1-dioxidoisothiazolidin-2-yl)-4-methylpentanamide and 3,3-bis(4-fluorophenyl)propanal for 3-(trifluoromethyl)benzaldehyde in the procedure described in Example 303: $^1$H NMR (500 MHz, pyridine-d$_5$) δ ppm 8.35-8.19 (m, 1H), 7.42-7.31 (m, 4H), 7.18-7.06 (m, 4H), 4.92-4.88 (m, 1H), 4.52-4.42 (m, 1H), 4.28 (dd, J=10.0, 5.3, 1H), 3.15-3.02 (m, 3H), 2.92 (dd, J=4.9, 4.1, 1H), 2.48 (dd, J=7.1, 5.7, 2H), 2.41-2.35 (m, 1H), 2.33-2.27 (m, 2H), 2.26-2.17 (m, 3H), 2.15-2.08 (m, 2H), 2.08-1.99 (m, 2H), 1.93-1.75 (m, 2H), 1.62-1.50 (m, 1H), 1.48 (d, J=7.3, 9H), 1.37-1.28 (m, 2H), 0.88-0.80 (m, 3H); MS (ESI+) m/z 570 (M+H)$^+$.

Step B: The title compound was prepared by substituting tert-butyl(S)-1-((3aR,4S,6aS)-2-(3,3-bis(4-fluorophenyl)propyl)octahydrocyclopenta[c]pyrrol-4-ylamino)-1-oxopentan-2-yl(methyl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.12-8.15 (m, 1H), 7.34-7.42 (m, 4H), 7.11-7.17 (m, 4H), 4.48-4.54 (m, 1H), 4.28 (t, J=7.6 Hz, 1H), 3.18 (t, J=6.5 Hz, 1H), 2.93 (dd, J=9.0, 2.2 Hz, 1H), 2.49-2.57 (m, 1H), 2.43-2.49 (m, 1H), 2.42 (s, 3H), 2.28-2.33 (m, 2H), 2.18-2.28 (m, 3H), 2.08-2.28 (m, 3H), 1.95-2.15 (m, 1H), 1.89-2.00 (m, 1H), 1.79-1.87 (m, 1H), 1.67-1.75 (m, 1H), 1.43-1.61 (m, 4H), 0.85 (t, J=7.3 Hz, 3H); MS (ESI+) m/z 470 (M+H)$^+$.

Example 459

2,2-bis(4-fluorophenyl)-N-[(3aR,4S,6aS)-2-(N-methyl-L-leucyl)octahydrocyclopenta[c]pyrrol-4-yl]acetamide Step A: N-((3aR,4S,6aS)-2-benzyloctahydrocyclopenta[c]pyrrol-4-yl)-2,2-bis(4-fluorophenyl)acetamide (150 mg, 0.336 mmol) from Example 228 and ethanol (20 mL) were added to 20% Pd(OH)$_2$ on carbon, wet (30.0 mg, 0.214 mmol) in a 50 mL pressure bottle and stirred for 2 hours under 30 psi hydrogen at 50° C. The mixture was filtered and the solvent was removed in vacuo to give 2,2-bis(4-fluorophenyl)-N-[(3aR,4S,6aS)-octahydrocyclopenta[c]pyrrol-4-yl]acetamide: $^1$H NMR (500 MHz, pyridine-d$_5$) δ ppm 9.09 (d, J=7.1, 1H), 7.60-7.55 (m, 4H), 7.13 (q, J=8.2, 4H), 5.26 (s, 1H), 4.36-4.27 (m, 1H), 3.06 (dd, J=10.9, 2.7, 1H), 2.92 (dd, J=10.9, 7.0, 1H), 2.81 (dd, J=10.7, 7.0, 1H), 2.59 (dd, J=10.8, 2.8, 1H), 2.52-2.41 (m, 2H), 2.33-2.25 (m, 1H), 2.06-1.96 (m, 1H), 1.83 (td, J=12.7, 6.9, 1H), 1.65-1.52 (m, 1H), 1.26 (ddt, J=12.3, 8.7, 6.1, 1H); MS (ESI+) m/z 357 (M+H)$^+$.

Step B: 2,2-Bis(4-fluorophenyl)-N-[(3aR,4S,6aS)-octahydrocyclopenta[c]pyrrol-4-yl]acetamide (30 mg, 0.084 mmol) and (S)-2-(tert-butoxycarbonyl(methyl)amino)-4-methylpentanoic acid (22.71 mg, 0.093 mmol) were dissolved in dichloromethane (0.5 mL) and then treated with 1-hydroxybenzotriazole hydrate (14.18 mg, 0.093 mmol). After 10 minutes, N$^1$-((ethylimino)methylene)-N$^3$,N$^3$-dimethylpropane-1,3-diamine (0.016 mL, 0.093 mmol) was added, and the reaction mixture was stirred at ambient temperature overnight followed by quenching with water. The material in the organic layer was purified with a 4 g silica gel cartridge eluting with 1-10% methanol (2 N ammonia)/dichloromethane to give tert-butyl(S)-1-((3aR,4S,6aS)-4-(2,2-bis(4-fluorophenyl)acetamido)hexahydrocyclopenta[c]pyrrol-2(1H)-yl)-4-methyl-1-oxopentan-2-yl(methyl)carbamate: $^1$H NMR (400 MHz, pyridine-d$_5$) δ ppm 8.25 (s, 1H), 7.46 (td, J=8.5, 5.5, 4H), 7.08-6.96 (m, 4H), 5.08 (s, 2H), 4.29-4.18 (m, 1H), 3.80 (s, 2H), 3.69 (s, 1H), 3.43 (dd, J=11.7, 3.5, 1H), 2.93 (s, 3H), 2.63 (s, 2H), 2.10 (td, J=12.9, 6.9, 1H), 1.91-1.69 (m, 3H), 1.63 (dt, J=13.2, 6.5, 2H), 1.51 (s, 9H), 1.40-1.26 (m, 1H), 0.97 (d, J=6.5, 3H), 0.92 (d, J=6.6, 3H); MS (ESI+) m/z 584 (M+H)$^+$.

Step C: The title compound was prepared by substituting tert-butyl(S)-1-((3aR,4S,6aS)-4-(2,2-bis(4-fluorophenyl)acetamido)hexahydrocyclopenta[c]pyrrol-2(1H)-yl)-4-methyl-1-oxopentan-2-yl(methyl)carbamate from Step B for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-d$_5$) δ ppm 8.36-8.22 (m, 1H), 7.46 (td, J=8.4, 5.5, 4H), 7.03 (td, J=8.7, 3.4, 4H), 5.10 (s, 1H), 4.34-4.23 (m, 1H), 3.77-3.66 (m, 2H), 3.63-3.52 (m, 2H), 3.47-3.37 (m, 2H), 2.67-2.56 (m, 2H), 2.38 (s, 3H), 2.14-2.02 (m, 1H), 1.99-1.82 (m, 2H), 1.70-1.57 (m, 1H), 1.49 (t, J=6.7, 2H), 1.36 (dt, J=15.6, 6.5, 1H), 0.91 (dd, J=8.7, 6.8, 6H); MS (ESI+) m/z 484 (M+H)$^+$.

Example 460

2,2-bis(4-fluorophenyl)-N-[(3aR,4S,6aS)-2-(N-methyl-L-norvalyl)octahydrocyclopenta[c]pyrrol-4-yl]acetamide The title compound was prepared by substituting (S)-2-(tert-butoxycarbonyl(methyl)amino)pentanoic acid for (S)-2-(tert-butoxycarbonyl(methyl)amino)-4-methylpentanoic acid in the procedure described in Example 459: $^1$H NMR (400 MHz, pyridine-d$_5$) δ ppm 8.35-8.24 (m, 1H), 7.50-7.40 (m, 4H), 7.07-6.98 (m, 4H), 5.10 (s, 1H), 4.31-4.21 (m, 1H), 3.75-3.64 (m, 2H), 3.61-3.51 (m, 2H), 3.41-3.31 (m, 1H), 2.66-2.54 (m, 2H), 2.37 (s, 3H), 2.14-2.02 (m, 1H), 1.92-1.83 (m, 1H), 1.71-1.40 (m, 6H), 1.33 (dd, J=12.9, 8.1, 1H), 0.87 (t, J=7.2, 3H); MS (ESI+) m/z 470 (M+H)$^+$.

Example 461

N-[(3aR,4S,6aS)-2-(N,4-dimethyl-L-leucyl)octahydrocyclopenta[c]pyrrol-4-yl]-2,2-bis(4-fluorophenyl)acetamide The title compound was prepared by substituting (S)-2-(tert-butoxycarbonyl(methyl)amino)-4,4-dimethylpentanoic acid for (S)-2-(tert-butoxycarbonyl(methyl)amino)-4-methylpentanoic acid in the procedure described in Example 459: $^1$H NMR (400 MHz, pyridine-d$_5$) δ ppm 8.36-8.25 (m, 1H), 7.49-7.40 (m, 4H), 7.03 (ddd, J=8.8, 6.3, 3.9, 4H), 5.10 (s, 1H), 4.35-4.20 (m, 1H), 3.77-3.66 (m, 2H), 3.63-3.51 (m, 2H), 3.49-3.38 (m, 1H), 2.68-2.54 (m, 2H), 2.36 (s, 3H), 2.16-2.00 (m, 1H), 1.95-1.78 (m, 2H), 1.71 (dd, J=14.1, 4.9, 1H), 1.66-1.56 (m, 1H), 1.53-1.43 (m, 1H), 1.41-1.27 (m, 1H), 0.99 (s, 9H); MS (ESI+) m/z 498 (M+H)$^+$.

Example 462

2,2-bis(4-fluorophenyl)-N-[(3aR,4S,6aS)-2-(4-methyl-L-leucyl)octahydrocyclopenta[c]pyrrol-4-yl]acetamide The title compound was prepared by substituting (S)-2-(tert-butoxycarbonylamino)-4,4-dimethylpentanoic acid for (S)-2-(tert-butoxycarbonyl(methyl)amino)-4-methylpentanoic acid in the procedure described in Example 459: $^1$H NMR (400 MHz, pyridine-d$_5$) δ ppm 8.37-8.15 (m, 1H), 7.46 (td, J=8.6, 5.6, 4H), 7.09-6.96 (m, 4H), 5.09 (s, 1H), 4.32-4.18 (m, 1H), 3.76-3.63 (m, 4H), 3.62-3.51 (m, 2H), 3.51-3.32 (m, 1H), 2.68-2.52 (m, 2H), 2.12-1.99 (m, 1H), 1.93-1.77 (m, 2H), 1.62 (td, J=15.7, 7.8, 1H), 1.44 (dd, J=14.1, 7.5, 1H), 1.39-1.23 (m, 1H), 0.99 (s, 9H); MS (ESI+) m/z 498 (M+H)$^+$.

Example 463 tert-butyl(S)-1-((3aR,4S,6aS)-4-((S)-2-(tert-butoxycarbonylamino)-4,4-dimethylpentanamido)hexahydrocyclopenta[c]pyrrol-2(1H)-yl)-4,4-dimethyl-1-oxopentan-2-ylcarbamate The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-ylcarbamate from Example 226 for N-((3aR,4S,6aS)-2-benzyloctahydrocyclopenta[c]pyrrol-4-yl)-2,2-bis(4-fluorophenyl)acetamide and (S)-2-(tert-butoxycarbonylamino)-4,4-dimethylpentanoic acid for (S)-2-(tert-butoxycarbonyl(methyl)amino)-4-methylpentanoic acid in the procedure described in Example 459 Steps A and B: $^1$H NMR (400 MHz, pyridine-d$_5$) δ ppm 7.76 (d, J=5.2, 1H), 7.02 (d, J=4.7, 1H), 6.97-6.86 (m, 1H), 4.78 (td, J=8.7, 4.5, 1H), 4.49 (td, J=8.2, 4.6, 1H), 4.25-4.14 (m, 1H), 3.84-3.76 (m, 2H), 3.54-3.35 (m, 1H), 2.73-2.59 (m, 2H), 2.07 (ddd, J=20.0, 13.7, 5.6, 2H), 1.94-1.81 (m, 2H), 1.69 (ddd, J=11.1, 7.4, 3.2, 2H), 1.64-1.55 (m, 1H), 1.48 (s, 9H), 1.48 (s, 9H), 1.38-1.27 (m, 1H), 1.02 (s, 9H), 0.97 (s, 9H); MS (ESI+) m/z 581 (M+H)$^+$.

Example 464

4-methyl-N$^1$-[(3aR,4S,6aS)-2-(4-methyl-L-leucyl) octahydrocyclopenta[c]pyrrol-4-yl]-L-leucinamide The title compound was prepared by substituting tert-butyl (S)-1-((3aR,4S,6aS)-4-((S)-2-(tert-butoxycarbonylamino)-4,4-dimethylpentanamido)hexahydrocyclopenta[c]pyrrol-2 (1H)-yl)-4,4-dimethyl-1-oxopentan-2-ylcarbamate from Example 463 for tert-butyl(S)-1-((3aR,4S,6aS)-4-(2,2-bis(4-fluorophenyl)acetamido)hexahydrocyclopenta[c]pyrrol-2 (1H)-yl)-4-methyl-1-oxopentan-2-yl(methyl)carbamate in the procedure described in Example 459 Step C: $^1$H NMR (400 MHz, pyridine-d$_5$) δ ppm 7.88-7.76 (m, 1H), 4.22-4.14 (m, 1H), 3.78-3.66 (m, 6H), 3.61 (dddd, J=9.1, 4.5, 2.1, 0.7, 2H), 3.50 (dd, J=7.5, 4.1, 2H), 2.70-2.60 (m, 1H), 2.60-2.51 (m, 1H), 2.11-2.00 (m, 2H), 1.96-1.83 (m, 2H), 1.66-1.53 (m, 1H), 1.45 (dd, J=14.1, 7.4, 1H), 1.36 (dd, J=14.1, 7.5, 2H), 1.00 (s, 9H), 0.97 (s, 9H); MS (ESI+) m/z 381 (M+H)$^+$.

Example 465

4-methyl-N$^1$-[(3aR,4S,6aS)-2-L-phenylalanyloctahydrocyclopenta[c]pyrrol-4-yl]-L-leucinamide The title compound was prepared by substituting tert-butyl (S)-1-((3aR,4S,6aS)-2-benzyloctahydrocyclopenta[c]pyrrol-4-ylamino)-4,4-dimethyl-1-oxopentan-2-ylcarbamate from Example 226 for N-((3aR,4S,6aS)-2-benzyloctahydrocyclopenta[c]pyrrol-4-yl)-2,2-bis(4-fluorophenyl)acetamide and (S)-2-(tert-butoxycarbonylamino)-3-phenylpropanoic acid for (S)-2-(tert-butoxycarbonyl(methyl)amino)-4-methylpentanoic acid in the procedure described in Example 459: $^1$H NMR (400 MHz, pyridine-d$_5$) δ ppm 7.84-7.68 (m, 1H), 7.34-7.24 (m, 3H), 7.18 (t, J=6.8, 2H), 4.08 (dt, J=14.3, 7.0, 1H), 3.81-3.67 (m, 6H), 3.53-3.46 (m, 4H), 3.10 (dd, J=13.2, 7.0, 1H), 2.88 (dd, J=13.2, 6.8, 1H), 2.53 (td, J=14.0, 7.9, 1H), 2.41 (dt, J=14.4, 7.0, 1H), 2.10-2.04 (m, 1H), 1.98 (ddd, J=19.6, 7.2, 5.1, 1H), 1.80 (dt, J=13.0, 7.8, 1H), 1.53 (dq, J=12.8, 8.1, 1H), 1.35 (dd, J=14.1, 7.6, 1H), 1.25-1.05 (m, 1H), 0.97 (s, 9H); MS (ESI+) m/z 401 (M+H)$^+$.

Example 466

(3aR,4S,6aS)-N-benzhydryl-2-[3-(trifluoromethyl) benzyl]octahydrocyclopenta[c]pyrrol-4-amine (3aR,4S,6aS)-2-(3-(Trifluoromethyl)benzyl)octahydrocyclopenta[c]pyrrol-4-amine (60 mg, 0.211 mmol), from Example 156 Step A was combined with (bromomethylene)dibenzene (62.6 mg, 0.253 mmol) and potassium carbonate (87 mg, 0.633 mmol) in N,N-dimethylformamide (1 mL). The reaction was stirred at room temperature for 72 hours. The reaction was quenched with water and extracted with diethyl ether. The ether extracts were washed with water (3×1 mL) and the solvent removed. The crude material was purified using a 12 g silica gel cartridge eluting with a gradient of 0-3% methanol (2 N ammonia)/dichloromethane to give (3aR,4S,6aS)-N-benzhydryl-2-(3-(trifluoromethyl)benzyl) octahydrocyclopenta[c]pyrrol-4-amine: $^1$H NMR (500 MHz, pyridine-d$_5$) δ ppm 7.71 (s, 1H), 7.64-7.59 (m, 4H), 7.52 (d, J=7.7, 1H), 7.44 (t, J=7.7, 1H), 7.33 (td, J=7.6, 4.7, 4H), 7.25-7.21 (m, 4H), 5.09 (s, 1H), 3.51 (q, J=13.5, 2H), 3.02 (dd, J=12.9, 5.5, 1H), 2.63-2.54 (m, 1H), 2.51 (dd, J=8.8, 2.8, 1H), 2.47-2.41 (m, 1H), 2.37 (t, J=8.0, 1H), 2.32-2.25 (m, 2H), 1.98 (td, J=11.4, 5.6, 1H), 1.89 (ddd, J=12.7, 10.4, 5.8, 1H), 1.45 (ddd, J=14.7, 11.9, 8.1, 1H), 1.32-1.23 (m, 1H); MS (ESI+) m/z 451 (M+H)$^+$.

Example 467

(3aS,4R,6aR)-N-benzhydryl-2-{[3-(trifluoromethyl) phenyl]sulfonyl}octahydrocyclopenta[c]pyrrol-4-amine The title compound was prepared by substituting (3aS,4R, 6aR)-2-{[3-(trifluoromethyl)phenyl] sulfonyl}octahydrocyclopenta[c]pyrrol-4-amine from Example 254 Step A for (3aR,4S,6aS)-2-(3-(trifluoromethyl) benzyl)octahydrocyclopenta[c]pyrrol-4-amine in the procedure described in Example 466: $^1$H NMR (500 MHz, pyridine-d$_5$) δ ppm 8.35-8.36 (bs, 1H), 8.17-8.19 (m, 1H), 7.92-7.95 (m, 1H), 7.75 (t, J=7.8 Hz, 1H), 7.61-7.64 (m, 2H), 7.57-7.60 (m, 2H), 7.32-7.38 (m, 4H), 7.22-7.26 (m, 2H), 5.02 (s, 1H), 3.33 (dd, J=9.7, 3.1 Hz, 1H), 3.07 (dd, J=9.6, 3.0 Hz, 1H), 3.03 (dd, J=9.8, 7.9 Hz, 1H), 2.90-2.95 (m, 2H), 2.48-2.57 (m, 1H), 2.39-2.45 (m, 1H), 2.17-2.48 (m, 1H), 1.80-1.88 (m, 2H), 1.31-1.39 (m, 1H), 1.04-1.12 (m, 1H); MS (ESI+) m/z 501 (M+H)$^+$.

Example 468

(3aR,4S,6aS)-N-benzhydryl-2-{[3-(trifluoromethyl) phenyl]sulfonyl}octahydrocyclopenta[c]pyrrol-4-amine The title compound was prepared by substituting (3aR,4S, 6aS)-2-(3-(trifluoromethyl)phenylsulfonyl)octahydrocyclopenta[c]pyrrol-4-amine from Example 252 Step D for (3aR, 4S,6aS)-2-(3-(trifluoromethyl)benzyl)octahydrocyclopenta [c]pyrrol-4-amine in the procedure described in Example 466: $^1$H NMR (500 MHz, pyridine-d$_5$) δ ppm 8.35-8.36 (bs, 1H), 8.17-8.19 (m, 1H), 7.92-7.95 (m, 1H), 7.74 (t, J=7.8 Hz, 1H), 7.61-7.64 (m, 2H), 7.57-7.60 (m, 2H), 7.31-7.39 (m, 4H), 7.22-7.27 (m, 2H), 5.01-5.06 (m, 1H), 3.33 (dd, J=9.8, 3.1 Hz, 1H), 3.07 (dd, J=9.6, 2.9 Hz, 1H), 3.03 (dd, J=9.5, 8.2 Hz, 1H), 2.90-2.94 (m, 2H), 2.49-2.55 (m, 1H), 2.38-2.45 (m, 1H), 2.28-2.38 (m, 1H), 1.80-1.88 (m, 2H), 1.31-1.39 (m, 1H), 1.04-1.12 (m, 1H); MS (ESI+) m/z 501 (M+H)$^+$.

Example 469

N$^1$-[(3aS,4R,6aR)-2-benzhydryloctahydrocyclopenta [c]pyrrol-4-yl]-N$^2$-methyl-L-leucinamide Step A: tert-Butyl(S)-1-((3aS,4R,6aR)-2-benzhydryloctahydrocyclopenta[c]pyrrol-4-ylamino)-4-methyl-1-oxopentan-2-yl(methyl)carbamate was prepared by substituting tert-butyl methyl((S)-4-methyl-1-((3aS,4R,6aR)-octahydrocyclopenta[c]pyrrol-4-ylamino)-1-oxopentan-2-yl)carbamate from Example 349 for (3aR,4S,6aS)-2-(3-(trifluoromethyl)benzyl)octahydrocyclopenta[c]pyrrol-4-amine in the procedure described in Example 466: MS (APCI+) m/z 520 (M+H)$^+$.

Step B: The title compound was prepared by substituting tert-butyl(S)-1-((3aS,4R,6aR)-2-benzhydryloctahydrocyclopenta[c]pyrrol-4-ylamino)-4-methyl-1-oxopentan-2-yl(methyl)carbamate from Step A for tert-butyl(S)-1-((3aR,4S, 6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-d$_5$) δ ppm 8.16-8.18 (m, 1H), 7.63-7.65 (m, 2H), 7.56-7.62 (m, 2H), 7.27-7.37 (m, 4H), 7.13-7.20 (m, 2H), 4.47-4.54 (m, 1H), 4.21 (s, 1H), 3.20 (dd, J=8.2, 5.9 Hz, 1H), 2.78-2.85 (m, 1H), 2.48-2.59 (m, 2H), 2.39 (s, 3H), 2.34-2.38 (m, 2H), 2.20-2.28 (m, 2H), 1.87-2.07 (m, 1H), 1.81-1.94 (m, 2H), 1.60-1.71 (m, 2H), 1.52-1.59 (m, 1H), 1.44-1.52 (m, 1H), 0.89 (d, J=6.6 Hz, 3H), 0.83 (d, J=6.5 Hz, 3H); MS (ESI+) m/z 420 (M+H)$^+$.

Example 470

4-methyl-N$^2$-propyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine and 1-iodopropane for iodoethane in the procedure described in Example 288: $^1$H NMR (500 MHz, pyridine-d$_5$) δ ppm 8.31-8.34 (m, 1H), 8.14-8.16 (m, 2H), 7.90-7.92 (m, 2H), 4.22-4.27 (m, 1H), 3.86 (d, J=11.3 Hz, 1H), 3.28 (t, J=5.7 Hz, 1H), 3.15-3.20 (m, 2H), 2.98 (dd, J=9.5, 6.5 Hz, 1H), 2.52-2.62 (m, 4H), 1.92-2.00 (m, 1H), 1.89 (dd, J=14.1, 4.8 Hz, 1H), 1.81-1.88 (m, 1H), 1.65-1.86 (m, 1H), 1.53-1.62 (m, 1H), 1.40-1.54 (m, 3H), 1.27-1.38 (m, 1H), 0.99 (s, 9H), 0.89 (t, J=7.4 Hz, 3H); MS (ESI+) m/z 504 (M+H)$^+$.

Example 471

N$^2$-(cyclopropylmethyl)-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine and (bromomethyl)cyclopropane for iodoethane in the procedure described in Example 288: $^1$H NMR (500 MHz, pyridine-d$_5$) δ ppm 8.29-8.31 (m, 1H), 8.13-8.15 (m, 2H), 7.89-7.91 (m, 2H), 4.21-4.26 (m, 1H), 3.87 (dd, J=9.9, 2.3 Hz, 1H), 3.31 (dd, J=7.0, 4.5 Hz, 1H), 3.18 (dd, J=9.8, 2.1 Hz, 1H), 3.16 (dd, J=9.8, 7.5 Hz, 1H), 2.97 (dd, J=9.6, 6.7 Hz, 1H), 2.49-2.59 (m, 4H), 1.90-2.04 (m, 1H), 1.92-1.98 (m, 1H), 1.90 (dd, J=14.1, 4.5 Hz, 1H), 1.80-1.87 (m, 1H), 1.53-1.61 (m, 1H), 1.50 (dd, J=14.1, 7.1 Hz, 1H), 1.26-1.34 (m, 1H), 0.99 (s, 9H), 0.92-1.03 (m, 1H), 0.39-0.47 (m, 2H), 0.13-0.19 (m, 2H); MS (ESI+) m/z 516 (M+H)$^+$.

Example 472

N$^2$-(cyclobutylmethyl)-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine and (bromomethyl)cyclobutane for iodoethane in the procedure described in Example 288: $^1$H NMR (500 MHz, pyridine-d$_5$) δ ppm 8.28-8.30 (m, 1H), 8.14-8.16 (m, 2H), 7.89-7.92 (m, 2H), 4.23-4.27 (m, 1H), 3.88 (dd, J=9.9, 2.2 Hz, 1H), 3.27 (dd, J=7.0, 4.6 Hz, 1H), 3.16-3.20 (m, 2H), 2.98 (dd, J=9.5, 6.5 Hz, 1H), 2.58-2.69 (m, 4H), 2.36-2.47 (m, 1H), 1.94-2.03 (m, 3H), 1.88 (dd, J=14.0, 4.6 Hz, 1H), 1.74-1.88 (m, 3H), 1.62-1.73 (m, 2H), 1.53-1.62 (m, 1H), 1.48 (dd, J=14.1, 7.1 Hz, 1H), 1.32 (ddt, J=9.6, 12.8, 6.4 Hz, 1H), 0.99 (s, 9H); MS (ESI+) m/z 530 (M+H)$^+$.

Example 473

N$^2$-isobutyl-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine and 1-iodo-2-methylpropane for iodoethane in the procedure described in Example 288: $^1$H NMR (500 MHz, pyridine-d$_5$) δ ppm 8.26-8.28 (m, 1H), 8.14-8.16 (m, 2H), 7.89-7.92 (m, 2H), 4.22-4.28 (m, 1H), 3.86 (dd, J=10.0, 2.4 Hz, 1H), 3.25 (dd, J=7.1, 4.6 Hz, 1H), 3.16-3.21 (m, 2H), 2.99 (dd, J=9.6, 6.8 Hz, 1H), 2.54-2.60 (m, 2H), 2.38-2.46 (m, 2H), 1.96 (dq, J=11.8, 5.9 Hz, 1H), 1.87 (dd, J=14.1, 4.7 Hz, 1H), 1.80-1.88 (m, 1H), 1.63-1.77 (m, 1H), 1.62-1.70 (m, 1H), 1.53-1.61 (m, 1H), 1.50 (dd, J=14.0, 7.2 Hz, 1H), 1.28-1.35 (m, 1H), 0.99 (s, 9H), 0.92 (d, J=6.7 Hz, 3H), 0.90 (d, J=6.7 Hz, 3H); MS (ESI+) m/z 518 (M+H)$^+$.

Example 474

N$^2$-(cyclopentylmethyl)-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine and (iodomethyl)cyclopentane for iodoethane in the procedure described in Example 288: $^1$H NMR (400 MHz, pyridine-d$_5$) δ ppm 8.30-8.32 (m, 1H), 8.13-8.16 (m, 2H), 7.89-7.92 (m, 2H), 4.22-4.27 (m, 1H), 3.87 (dd, J=9.9, 2.2 Hz, 1H), 3.28 (dd, J=7.1, 4.5 Hz, 1H), 3.15-3.22 (m, 2H), 2.96-3.01 (m, 1H), 2.46-2.60 (m, 4H), 1.82-2.01 (m, 4H), 1.20-2.29 (m, 1H), 1.67-1.79 (m, 2H), 1.42-1.63 (m, 6H), 1.13-1.36 (m, 3H), 1.00 (s, 9H); MS (ESI+) m/z 544 (M+H)$^+$.

Example 475

N$^2$-(cyclohexylmethyl)-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-

(trifluoromethyl)phenylsulfonyl)octahydrocyclopenta[c]pyrrol-4-amine and (bromomethyl)cyclohexane for iodoethane in the procedure described in Example 288: $^1$H NMR (500 MHz, pyridine-$d_5$) δ ppm 8.27-8.29 (m, 1H), 8.14-8.16 (m, 2H), 7.89-7.92 (m, 2H), 4.23-4.28 (m, 1H), 3.88 (dd, J=9.9, 2.2 Hz, 1H), 3.25 (dd, J=7.1, 4.5 Hz, 1H), 3.16-3.21 (m, 2H), 2.99 (dd, J=9.6, 6.5 Hz, 1H), 2.59-2.61 (m, 2H), 2.47 (dd, J=11.1, 6.7 Hz, 1H), 2.43 (dd, J=11.2, 6.2 Hz, 1H), 1.98 (dq, J=11.8, 5.9 Hz, 1H), 1.89 (dd, J=14.2, 4.4 Hz, 1H), 1.82-1.89 (m, 1H), 1.71-1.82 (m, 2H), 1.58-1.79 (m, 1H), 1.56-1.67 (m, 4H), 1.52 (dd, J=14.0, 7.2 Hz, 1H), 1.28-1.41 (m, 2H), 1.05-1.22 (m, 3H), 1.00 (s, 9H), 0.86-0.98 (m, 2H); MS (ESI+) m/z 558 (M+H)$^+$.

Example 476

$N^2$-butyl-4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-$N^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine and 1-iodobutane for iodoethane in the procedure described in Example 288: $^1$H NMR (500 MHz, pyridine-$d_5$) δ ppm 8.32-8.34 (m, 1H), 8.14-8.16 (m, 2H), 7.90-7.92 (m, 2H), 4.24-4.29 (m, 1H), 3.87 (dd, J=9.9, 2.1 Hz, 1H), 3.29 (dd, J=6.8, 4.8 Hz, 1H), 3.15-3.21 (m, 2H), 2.99 (dd, J=9.5, 6.4 Hz, 1H), 2.55-2.66 (m, 4H), 1.94-2.01 (m, 1H), 1.90 (dd, J=14.0, 4.9 Hz, 1H), 1.82-1.89 (m, 1H), 1.64-1.88 (m, 1H), 1.54-1.63 (m, 1H), 1.51 (dd, J=14.0, 6.9 Hz, 1H), 1.39-1.47 (m, 2H), 1.26-1.38 (m, 3H), 0.99 (s, 9H), 0.84 (t, J=7.3 Hz, 3H); MS (ESI−) m/z 516 (M−H)$^-$.

Example 477

$N^2$-ethyl-4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-$N^1$-((3aR,4S,6aS)-2-{[4-(trifluoromethyl)phenyl]sulfonyl}octahydrocyclopenta[c]pyrrol-4-yl)-L-leucinamide from Example 419 for (3aR,4S,6aS)-2-(4-(trifluoromethyl)phenylsulfonyl)octahydrocyclopenta[c]pyrrol-4-amine in the procedure described in Example 288: $^1$H NMR (500 MHz, pyridine-$d_5$) δ ppm 8.35-8.38 (m, 1H), 8.14-8.16 (m, 2H), 7.90-7.92 (m, 2H), 4.22-4.27 (m, 1H), 3.86 (dd, J=10.0, 2.2 Hz, 1H), 3.30 (t, J=5.8 Hz, 1H), 3.14-3.20 (m, 2H), 2.98 (dd, J=9.5, 6.4 Hz, 1H), 2.65-2.72 (m, 1H), 2.57-2.63 (m, 1H), 2.56-2.60 (m, 2H), 1.92-1.99 (m, 1H), 1.90 (dd, J=14.0, 5.0 Hz, 1H), 1.79-1.88 (m, 1H), 1.62-1.94 (m, 1H), 1.52-1.63 (m, 1H), 1.50 (dd, J=14.0, 6.6 Hz, 1H), 1.26-1.40 (m, 1H), 1.06 (t, J=7.1 Hz, 3H), 0.98 (s, 9H); MS (ESI+) m/z 490 (M+H)$^+$.

Example 478

$N^2$-(cyclopropylmethyl)-4-methyl-$N^1$-{(3aR,4S,6aS)-2-[5-(trifluoromethyl)pyridin-2-yl]octahydrocyclopenta[c]pyrrol-4-yl}-L-leucinamide The title compound was prepared by substituting 4-methyl-$N^1$-{(3aR,4S,6aS)-2-[5-(trifluoromethyl)pyridin-2-yl]octahydrocyclopenta[c]pyrrol-4-yl}-L-leucinamide from Example 440 for (3aR,4S,6aS)-2-(4-(trifluoromethyl)phenylsulfonyl)octahydrocyclopenta[c]pyrrol-4-amine and (bromomethyl)cyclopropane for iodoethane in the procedure described in Example 288: $^1$H NMR (500 MHz, pyridine-$d_5$) δ ppm 8.62-8.63 (bs, 1H), 8.38-8.41 (m, 1H), 7.68 (dd, J=8.9, 2.5 Hz, 1H), 6.40 (d, J=8.9 Hz, 1H), 4.38-4.44 (m, 1H), 3.82-3.86 (m, 1H), 3.66-3.70 (m, 1H), 3.56-3.61 (m, 1H), 3.29-3.41 (m, 2H), 2.75-2.78 (m, 2H), 2.57 (dd, J=6.7, 2.1 Hz, 2H), 2.12-2.21 (m, 1H), 1.92-2.00 (m, 1H), 1.95 (dd, J=14.0, 4.5 Hz, 1H), 1.71 (dq, J=12.7, 8.1 Hz, 1H), 1.54 (dd, J=14.1, 7.0 Hz, 1H), 1.38-1.48 (m, 1H), 1.02 (s, 9H), 0.96-1.05 (m, 1H), 0.45-0.48 (m, 2H), 0.16-0.24 (m, 2H); MS (ESI+) m/z 453 (M+H)$^+$.

Example 479

$N^2$-(cyclopropylmethyl)-4-methyl-$N^1$-{(3aR,4S,6aS)-2-[6-(trifluoromethyl)pyridin-2-yl]octahydrocyclopenta[c]pyrrol-4-yl}-L-leucinamide The title compound was prepared by substituting 4-methyl-$N^1$-{(3aR,4S,6aS)-2-[6-(trifluoromethyl)pyridin-2-yl]octahydrocyclopenta[c]pyrrol-4-yl}-L-leucinamide from Example 441 for (3aR,4S,6aS)-2-(4-(trifluoromethyl)phenylsulfonyl)octahydrocyclopenta[c]pyrrol-4-amine and (bromomethyl)cyclopropane for iodoethane in the procedure described in Example 288: $^1$H NMR (500 MHz, pyridine-$d_5$) δ ppm 8.34-8.36 (m, 1H), 7.51 (t, J=7.9 Hz, 1H), 6.98 (d, J=7.2 Hz, 1H), 6.52 (d, J=8.5 Hz, 1H), 4.35-4.41 (m, 1H), 3.73 (dd, J=10.9, 2.9 Hz, 1H), 3.60-3.65 (m, 1H), 3.52 (dd, J=10.7, 7.3 Hz, 1H), 3.36 (dd, J=7.1, 4.5 Hz, 1H), 3.29 (dd, J=10.9, 3.6 Hz, 1H), 2.69-2.77 (m, 2H), 2.55 (dd, J=6.7, 2.8 Hz, 2H), 2.10-2.16 (m, 1H), 1.94 (dd, J=14.1, 4.5 Hz, 1H), 1.89-1.96 (m, 1H), 1.74-2.09 (m, 1H), 1.69 (dq, J=12.7, 7.9 Hz, 1H), 1.53 (dd, J=14.1, 7.0 Hz, 1H), 1.31-1.42 (m, 1H), 1.02 (s, 9H), 0.95-1.05 (m, 1H), 0.42-0.51 (m, 2H), 0.15-0.25 (m, 2H); MS (ESI+) m/z 453 (M+H)$^+$.

Example 480

$N^2$-isopropyl-4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-$N^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.26-8.29 (m, 1H), 8.13-8.16 (m, 2H), 7.89-7.91 (m, 2H), 4.21-4.26 (m, 1H), 3.85 (dd, J=9.9, 2.3 Hz, 1H), 3.36 (dd, J=7.5, 4.1 Hz, 1H), 3.15-3.20 (m, 2H), 2.98 (dd, J=9.6, 6.7 Hz, 1H), 2.83 (hept, J=6.2 Hz, 1H), 2.51-2.62 (m, 2H), 1.91-1.97 (m, 1H), 1.79-1.88 (m, 2H), 1.63-1.81 (m, 1H), 1.51-1.59 (m, 1H), 1.47 (dd, J=14.1, 7.5 Hz, 1H), 1.31 (ddt, J=9.6, 12.8, 6.4 Hz, 1H), 1.03 (dd, J=6.2, 2.7 Hz, 6H), 0.98 (s, 9H); MS (ESI+) m/z 504 (M+H)$^+$.

Example 481

$N^2$-isopropyl-$N^1$-((3aR,4S,6aS)-2-{[4-(trifluoromethyl)phenyl]sulfonyl}octahydrocyclopenta[c]pyrrol-4-yl)-L-norvalinamide The title compound was prepared by substituting $N^1$-((3aR,4S,6aS)-2-{[4-(trifluoromethyl)phenyl]

sulfonyl}octahydrocyclopenta[c]pyrrol-4-yl)-L-norvalinamide from Example 422 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.31-8.34 (m, 1H), 8.13-8.15 (m, 2H), 7.89-7.91 (m, 2H), 4.21-4.27 (m, 1H), 3.84 (dd, J=9.9, 2.7 Hz, 1H), 3.31-3.34 (m, 1H), 3.18 (dd, J=9.8, 2.8 Hz, 1H), 3.16 (dd, J=10.2, 7.9 Hz, 1H), 2.98 (dd, J=9.6, 7.0 Hz, 1H), 2.83 (hept, J=6.1 Hz, 1H), 2.46-2.60 (m, 2H), 1.94 (dq, J=11.8, 5.9 Hz, 1H), 1.77-1.87 (m, 2H), 1.59-1.69 (m, 1H), 1.37-1.59 (m, 4H), 1.27-1.35 (m, 1H), 1.05 (d, J=6.3 Hz, 3H), 1.03 (d, J=6.3 Hz, 3H), 0.85 (t, J=7.4 Hz, 3H); MS (ESI+) m/z 476 (M+H)$^+$.

Example 482

$N^2$-isopropyl-$N^1$-((3aS,4R,6aR)-2-{[4-(trifluoromethyl)phenyl]sulfonyl}octahydrocyclopenta[c]pyrrol-4-yl)-L-norvalinamide The title compound was prepared by substituting $N^1$-((3aS,4R,6aR)-2-{[4-(trifluoromethyl)phenyl]sulfonyl}octahydrocyclopenta[c]pyrrol-4-yl)-L-norvalinamide from Example 423 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.26-8.28 (m, 1H), 8.11-8.14 (m, 2H), 7.88-7.91 (m, 2H), 4.23 (p, J=6.9 Hz, 1H), 3.85 (dd, J=9.9, 2.9 Hz, 1H), 3.30 (dd, J=7.5, 5.5 Hz, 1H), 3.18 (dd, J=9.7, 3.0 Hz, 1H), 3.14 (dd, J=9.9, 7.7 Hz, 1H), 2.97 (dd, J=9.6, 7.3 Hz, 1H), 2.81 (p, J=6.2 Hz, 1H), 2.49-2.61 (m, 2H), 1.90-1.99 (m, 1H), 1.81-1.92 (m, 1H), 1.81-1.88 (m, 1H), 1.74-1.81 (m, 1H), 1.59-1.68 (m, 1H), 1.37-1.58 (m, 3H), 1.27-1.36 (m, 1H), 1.02 (dd, J=6.2, 1.5 Hz, 6H), 0.85 (t, J=7.3 Hz, 3H); MS (ESI+) m/z 476 (M+H)$^+$.

Example 483

$N^2$-isopropyl-$N^1$-((3aR,4S,6aS)-2-{[3-(trifluoromethyl)phenyl]sulfonyl}octahydrocyclopenta[c]pyrrol-4-yl)-L-norvalinamide The title compound was prepared by substituting $N^1$-((3aR,4S,6aS)-2-{[3-(trifluoromethyl)phenyl]sulfonyl}octahydrocyclopenta[c]pyrrol-4-yl)-L-norvalinamide from Example 424 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.38-8.39 (bs, 1H), 8.26-8.28 (m, 1H), 8.20 (d, J=7.9 Hz, 1H), 7.90-7.92 (m, 1H), 7.72 (t, J=7.8 Hz, 1H), 4.20-4.27 (m, 1H), 3.85 (dd, J=9.9, 2.5 Hz, 1H), 3.29 (dd, J=7.6, 5.5 Hz, 1H), 3.18 (dd, J=20.2, 2.5 Hz, 1H), 3.14-3.18 (m, 1H), 2.96 (dd, J=9.6, 7.0 Hz, 1H), 2.77-2.83 (m, 1H), 2.51-2.57 (m, 2H), 1.89-1.99 (m, 1H), 1.82-1.93 (m, 1H), 1.80-1.88 (m, 1H), 1.73-1.81 (m, 1H), 1.56-1.67 (m, 1H), 1.36-1.56 (m, 3H), 1.25-1.35 (m, 1H), 1.02 (dd, J=9.4, 6.2 Hz, 6H), 0.85 (t, J=7.3 Hz, 3H); MS (ESI+) m/z 476 (M+H)$^+$.

Example 484

$N^2$-isopropyl-$N^1$-((3aS,4R,6aR)-2-{[3-(trifluoromethyl)phenyl]sulfonyl}octahydrocyclopenta[c]pyrrol-4-yl)-L-norvalinamide The title compound was prepared by substituting $N^1$-((3aS,4R,6aR)-2-{[3-(trifluoromethyl)phenyl]sulfonyl}octahydrocyclopenta[c]pyrrol-4-yl)-L-norvalinamide from Example 425 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.37-8.38 (bs, 1H), 8.26-8.28 (m, 1H), 8.17-8.20 (m, 1H), 7.90-7.92 (m, 1H), 7.71 (t, J=7.8 Hz, 1H), 4.21-4.27 (m, 1H), 3.86 (dd, J=9.9, 2.7 Hz, 1H), 3.29 (dd, J=7.5, 5.5 Hz, 1H), 3.18 (dd, J=9.6, 2.8 Hz, 1H), 3.14 (dd, J=9.9, 7.5 Hz, 1H), 2.95 (dd, J=9.6, 7.2 Hz, 1H), 2.76-2.84 (m, 1H), 2.47-2.58 (m, 2H), 1.91-1.98 (m, 1H), 1.82-1.93 (m, 1H), 1.81-1.89 (m, 1H), 1.73-1.81 (m, 1H), 1.57-1.66 (m, 1H), 1.36-1.57 (m, 3H), 1.25-1.35 (m, 1H), 1.02 (dd, J=6.2, 2.0 Hz, 6H), 0.84 (t, J=7.3 Hz, 3H).

Example 485

3-cyclohexyl-$N^2$-isopropyl-$N^1$-((3aR,4S,6aS)-2-{[4-(trifluoromethyl)phenyl]sulfonyl}octahydrocyclopenta[c]pyrrol-4-yl)-L-alaninamide The title compound was prepared by substituting 3-cyclohexyl-$N^1$-((3aR,4S,6aS)-2-{[4-(trifluoromethyl)phenyl]sulfonyl}octahydrocyclopenta[c]pyrrol-4-yl)-L-alaninamide from Example 426 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (400 MHz, pyridine-$d_5$) δ ppm 8.32 (d, J=7.2 Hz, 1H), 8.13-8.16 (m, 2H), 7.89-7.95 (m, 2H), 4.22-4.30 (m, 1H), 3.85 (dd, J=10.0, 2.3 Hz, 1H), 3.41 (dd, J=8.5, 5.2 Hz, 1H), 3.15-3.21 (m, 2H), 2.99 (dd, J=9.6, 6.7 Hz, 1H), 2.85 (p, J=6.2 Hz, 1H), 2.56-2.61 (m, 2H), 1.83-2.11 (m, 1H), 1.90-2.00 (m, 1H), 1.79-1.89 (m, 1H), 1.66-1.78 (m, 3H), 1.46-1.65 (m, 6H), 1.25-1.37 (m, 1H), 1.08-1.25 (m, 3H), 1.06 (d, J=6.3 Hz, 3H), 1.04 (d, J=6.3 Hz, 3H), 0.75-1.00 (m, 2H); MS (ESI+) m/z 530 (M+H)$^+$.

Example 486

$N^1$-((3aR,4S,6aS)-2-{[2-chloro-5-(trifluoromethyl)phenyl]sulfonyl}octahydrocyclopenta[c]pyrrol-4-yl)-$N^2$-isopropyl-4-methyl-L-leucinamide The title compound was prepared by substituting $N^1$-((3aR,4S,6aS)-2-{[2-chloro-5-(trifluoromethyl)phenyl]sulfonyl}octahydrocyclopenta[c]pyrrol-4-yl)-4-methyl-L-leucinamide from Example 428 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.57 (d, J=2.2 Hz, 1H), 8.32-8.35 (m, 1H), 7.81 (dd, J=8.3, 2.2 Hz, 1H), 7.75 (d, J=8.3 Hz, 1H), 4.29-4.35 (m, 1H), 3.93 (dd, J=10.2, 2.2 Hz, 1H), 3.56 (dd, J=10.1, 6.6 Hz, 1H), 3.35-3.41 (m, 2H), 3.32 (dd, J=10.0, 2.6 Hz, 1H), 2.83 (hept, J=6.2 Hz, 1H), 2.66-2.68 (m, 2H), 2.01-2.08 (m, 1H), 1.86-1.93 (m, 1H), 1.84 (dd, J=14.2, 4.3 Hz, 1H), 1.66-1.81 (m, 1H), 1.56-1.66 (m, 1H), 1.46 (dd, J=14.1, 7.4 Hz, 1H), 1.35-1.42 (m, 1H), 1.03 (d, J=6.1 Hz, 3H), 1.02 (d, J=6.1 Hz, 3H), 0.98 (s, 9H); MS (ESI+) m/z 538 (M+H)$^+$.

Example 487

$N^1$-((3aR,4S,6aS)-2-{[2-chloro-4-(trifluoromethyl)phenyl]sulfonyl}octahydrocyclopenta[c]pyrrol-4-yl)-$N^2$-isopropyl-4-methyl-L-leucinamide The title compound was prepared by substituting $N^1$-((3aR,4S,6aS)-2-{[2-chloro-4-(trifluoromethyl)phenyl]

sulfonyl}octahydrocyclopenta[c]pyrrol-4-yl)-4-methyl-L-leucinamide from Example 429 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (501 MHz, pyridine-$d_5$) δ ppm 8.35 (d, J=8.2 Hz, 1H), 8.29-8.32 (m, 1H), 7.99 (s, 1H), 7.73 (d, J=9.1 Hz, 1H), 4.29-4.35 (m, 1H), 3.95 (dd, J=10.2, 2.4 Hz, 1H), 3.54 (dd, J=10.1, 6.9 Hz, 1H), 3.40 (dd, J=10.0, 6.5 Hz, 1H), 3.33-3.36 (m, 2H), 2.82 (dq, J=12.4, 6.2 Hz, 1H), 2.65-2.68 (m, 2H), 2.00-2.07 (m, 1H), 1.85-1.92 (m, 1H), 1.84 (dd, J=14.1, 4.2 Hz, 1H), 1.65-1.82 (m, 1H), 1.55-1.65 (m, 1H), 1.46 (dd, J=14.1, 7.6 Hz, 1H), 1.34-1.43 (m, 1H), 1.03 (d, J=6.1 Hz, 3H), 1.02 (d, J=6.3 Hz, 3H), 0.98 (s, 9H); MS (ESI+) m/z 538 (M+H)$^+$.

Example 488

$N^2$-isopropyl-$N^1$-[(3aR,4S,6aS)-2-(N-isopropyl-4-methyl-L-leucyl)octahydrocyclopenta[c]pyrrol-4-yl]-4-methyl-L-leucinamide The title compound was prepared by substituting 4-methyl-$N^1$-[(3aR,4S,6aS)-2-(4-methyl-L-leucyl)octahydrocyclopenta[c]pyrrol-4-yl]-L-leucinamide from Example 464 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (400 MHz, pyridine-$d_5$) δ ppm 7.77-7.66 (m, 1H), 4.30-4.18 (m, 1H), 3.80-3.72 (m, 3H), 3.72-3.61 (m, 3H), 3.60-3.45 (m, 1H), 3.32 (dd, J=7.3, 4.2, 1H), 2.87-2.77 (m, 2H), 2.76-2.68 (m, 1H), 2.68-2.60 (m, 1H), 2.17-2.05 (m, 1H), 2.02-1.90 (m, 1H), 1.82 (dd, J=14.2, 4.2, 1H), 1.64 (dd, J=14.2, 4.2, 2H), 1.46 (ddd, J=27.5, 14.2, 7.7, 3H), 1.12-0.92 (m, 30H); MS (ESI+) m/z 465 (M+H)$^+$.

Example 489

$N^2$-isopropyl-$N^1$-[(3aR,4S,6aS)-2-(N-isopropyl-L-phenylalanyl)octahydrocyclopenta[c]pyrrol-4-yl]-4-methyl-L-leucinamide The title compound was prepared by substituting 4-methyl-$N^1$-[(3aR,4S,6aS)-2-L-phenylalanyloctahydrocyclopenta[c]pyrrol-4-yl]-L-leucinamide from Example 465 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (400 MHz, pyridine-$d_5$) δ ppm 7.74-7.61 (m, 1H), 7.36-7.23 (m, 4H), 7.22-7.15 (m, 2H), 4.19-4.02 (m, 2H), 3.77 (dd, J=11.9, 3.7, 5H), 3.56-3.48 (m, 1H), 3.32 (dd, J=7.3, 4.3, 1H), 3.05-2.94 (m, 2H), 2.92-2.76 (m, 2H), 2.66-2.50 (m, 1H), 2.48-2.35 (m, 1H), 2.06-1.92 (m, 1H), 1.83 (dd, J=14.2, 4.3, 2H), 1.55 (dq, J=12.8, 8.0, 1H), 1.42 (dd, J=14.2, 7.3, 1H), 1.08-1.00 (m, 12H), 0.99 (s, 9H); MS (ESI+) m/z 485 (M+H)$^+$.

Example 490

$N^2$-isopropyl-4-methyl-$N^1$-{(3aR,4S,6aS)-2-[5-(trifluoromethyl)pyridin-2-yl]octahydrocyclopenta[c]pyrrol-4-yl}-L-leucinamide The title compound was prepared by substituting 4-methyl-$N^1$-{(3aR,4S,6aS)-2-[5-(trifluoromethyl)pyridin-2-yl]octahydrocyclopenta[c]pyrrol-4-yl}-L-leucinamide from Example 440 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.62-8.63 (bs, 1H), 8.34-8.36 (m, 1H), 7.68 (dd, J=8.9, 2.5 Hz, 1H), 6.40 (d, J=8.9 Hz, 1H), 4.39-4.44 (m, 1H), 3.82-3.85 (m, 1H), 3.67-3.71 (m, 1H), 3.57-3.61 (m, 1H), 3.29-3.44 (m, 2H), 2.88 (hept, J=6.2 Hz, 1H), 2.74-2.76 (m, 2H), 2.13-2.20 (m, 1H), 1.64-2.00 (m, 4H), 1.51 (dd, J=14.1, 7.6 Hz, 1H), 1.39-1.46 (m, 1H), 1.08 (d, J=6.3 Hz, 3H), 1.07 (d, J=6.3 Hz, 3H), 1.01 (s, 9H); MS (ESI+) m/z 441 (M+H)$^+$.

Example 491

$N^2$-isopropyl-4-methyl-$N^1$-{(3aR,4S,6aS)-2-[6-(trifluoromethyl)pyridin-2-yl]octahydrocyclopenta[c]pyrrol-4-yl}-L-leucinamide The title compound was prepared by substituting 4-methyl-$N^1$-{(3aR,4S,6aS)-2-[6-(trifluoromethyl)pyridin-2-yl]octahydrocyclopenta[c]pyrrol-4-yl}-L-leucinamide from Example 441 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.31-8.34 (m, 1H), 7.51 (t, J=7.9 Hz, 1H), 6.98 (d, J=7.2 Hz, 1H), 6.52 (d, J=8.6 Hz, 1H), 4.36-4.41 (m, 1H), 3.73 (dd, J=10.9, 3.0 Hz, 1H), 3.63 (dd, J=10.9, 7.0 Hz, 1H), 3.53 (dd, J=10.8, 7.4 Hz, 1H), 3.40 (dd, J=7.5, 4.0 Hz, 1H), 3.29 (dd, J=10.9, 3.6 Hz, 1H), 2.88 (p, J=6.2 Hz, 1H), 2.74 (dd, J=5.6, 2.8 Hz, 2H), 2.09-2.16 (m, 1H), 1.89-1.98 (m, 1H), 1.90 (dd, J=14.1, 4.0 Hz, 1H), 1.69-1.85 (m, 1H), 1.63-1.73 (m, 1H), 1.50 (dd, J=14.1, 7.6 Hz, 1H), 1.36-1.43 (m, 1H), 1.07 (d, J=6.3 Hz, 3H), 1.07 (d, J=6.1 Hz, 3H), 1.01 (s, 9H); MS (ESI+) m/z 441 (M+H)$^+$.

Example 492

2,2-bis(4-fluorophenyl)-N-[(3aR,4S,6aS)-2-(N-isopropyl-4-methyl-L-leucyl)octahydrocyclopenta[c]pyrrol-4-yl]acetamide The title compound was prepared by substituting 2,2-bis(4-fluorophenyl)-N-[(3aR,4S,6aS)-2-(4-methyl-L-leucyl)octahydrocyclopenta[c]pyrrol-4-yl]acetamide from Example 462 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (400 MHz, pyridine-$d_5$) δ ppm 8.35-8.23 (m, 1H), 7.49-7.41 (m, 4H), 7.07-6.99 (m, 4H), 5.10 (s, 1H), 4.37-4.19 (m, 1H), 3.78-3.70 (m, 2H), 3.66-3.41 (m 4H), 2.84-2.71 (m, 1H), 2.69-2.54 (m, 2H), 2.14-2.00 (m, 1H), 1.95-1.80 (m, 1H), 1.63 (ddd, J=12.4, 9.1, 6.0, 2H), 1.48 (dd, J=14.2, 8.0, 1H), 1.42-1.29 (m, 1H), 1.08-0.95 (m, 15H); MS (ESI+) m/z 526 (M+H)$^+$.

Example 493

$N^2$-isopropyl-4-methyl-$N^1$-{(3aR,4S,6aS)-2-[2-(methylsulfonyl)pyrimidin-5-yl]octahydrocyclopenta[c]pyrrol-4-yl}-L-leucinamide The title compound was prepared by substituting 4-methyl-$N^1$-{(3aR,4S,6aS)-2-[2-(methylsulfonyl)pyrimidin-5-yl]octahydrocyclopenta[c]pyrrol-4-yl}-L-leucinamide from Example 442 for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.45

(s, 2H), 8.31-8.33 (m, 1H), 4.95 (s, 3H), 4.40-4.46 (m, 1H), 3.97 (dd, J=11.8, 2.8 Hz, 1H), 3.80 (dd, J=11.9, 7.6 Hz, 1H), 3.73 (dd, J=11.6, 8.1 Hz, 1H), 3.45 (dd, J=11.7, 4.1 Hz, 1H), 3.40 (dd, J=7.5, 4.0 Hz, 1H), 2.86 (hept, J=6.2 Hz, 1H), 2.70-2.78 (m, 2H), 2.13-2.19 (m, 1H), 1.89-1.98 (m, 1H), 1.89 (dd, J=14.2, 4.1 Hz, 1H), 1.65-1.81 (m, 1H), 1.63-1.72 (m, 1H), 1.49 (dd, J=14.1, 7.6 Hz, 1H), 1.38-1.45 (m, 1H), 1.06 (d, J=6.1 Hz, 3H), 1.05 (d, J=6.1 Hz, 3H), 1.00 (s, 9H); MS (ESI+) m/z 450 (M+H)+.

Example 494

$N^1$-[(3aR,4S,6aS)-2-benzyloctahydrocyclopenta[c]pyrrol-4-yl]-$N^2$-isopropyl-L-norvalinamide Step A: $N^1$-{(3aR,4S,6aS)-2-Benzyloctahydrocyclopenta[c]pyrrol-4-yl}-L-norvalinamide was prepared by substituting tert-butyl((S)-1-oxo-1-((3aR,4S,6aS)-2-benzyloctahydrocyclopenta[c]pyrrol-4-ylamino)pentan-2-yl)carbamate from Example 382 Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.17 (d, J=7.3, 1H), 7.43 (d, J=7.4, 2H), 7.36 (t, J=7.6, 2H), 7.27 (t, J=7.3, 1H), 4.42-4.35 (m, 1H), 3.59 (d, J=13.2, 1H), 3.53 (dd, J=7.9, 4.9, 1H), 3.44 (d, J=13.1, 1H), 2.84 (dd, J=8.9, 2.4, 1H), 2.54-2.42 (m, 2H), 2.41-2.33 (m, 2H), 2.23 (dd, J=8.7, 7.3, 1H), 2.10 (dt, J=17.7, 5.8, 3H), 1.98-1.90 (m, 1H), 1.82 (dt, J=20.2, 6.2, 1H), 1.69-1.61 (m, 1H), 1.58-1.34 (m, 4H), 0.84 (t, J=7.3, 3H); MS (ESI+) m/z 316 (M+H)+.

Step B: The title compound was prepared by substituting $N^1$-{(3aR,4S,6aS)-2-benzyloctahydrocyclopenta[c]pyrrol-4-yl}-L-norvalinamide from Step A for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.17-8.19 (m, 1H), 7.43-7.46 (m, 2H), 7.37 (t, J=7.5 Hz, 2H), 7.28 (t, J=7.3 Hz, 1H), 4.39-4.44 (m, 1H), 3.61 (d, J=13.1 Hz, 1H), 3.46 (d, J=13.1 Hz, 1H), 3.32 (dd, J=7.6, 5.5 Hz, 1H), 2.81-2.86 (m, 2H), 2.48-2.59 (m, 2H), 2.45 (dd, J=8.7, 7.2 Hz, 1H), 2.36 (dd, J=9.0, 2.7 Hz, 1H), 2.28 (dd, J=8.9, 6.8 Hz, 1H), 2.12 (dq, J=12.0, 6.0 Hz, 1H), 1.84-1.99 (m, 1H), 1.77-1.89 (m, 2H), 1.40-1.67 (m, 5H), 1.05 (d, J=6.1 Hz, 3H), 1.04 (d, J=6.0 Hz, 3H), 0.85 (t, J=7.3 Hz, 3H); MS (ESI+) m/z 358 (M+H)+.

Example 495

$N^1$-[(3aS,4R,6aR)-2-benzyloctahydrocyclopenta[c]pyrrol-4-yl]-$N^2$-isopropyl-L-norvalinamide Step A: tert-Butyl((S)-1-oxo-1-((3aS,4R,6aR)-2-benzyloctahydrocyclopenta[c]pyrrol-4-ylamino)pentan-2-yl)carbamate was prepared by substituting N-(tert-butoxycarbonyl)-L-norvaline for N-(tert-butoxycarbonyl)-L-leucine and (3aS,4R,6aR)-2-benzyloctahydrocyclopenta[c]pyrrol-4-amine from Example 16 Step D for (3aR,4S,6aS)-2-benzyloctahydrocyclopenta[c]pyrrol-4-amine in the procedure described in Example 221: $^1$H NMR (400 MHz, pyridine-$d_5$) δ ppm 8.58 (d, J=7.2, 1H), 7.91 (d, J=8.3, 1H), 7.42 (d, J=7.3, 2H), 7.36 (t, J=7.4, 2H), 7.27 (t, J=7.2, 1H), 4.64 (dd, J=14.4, 7.7, 1H), 4.45-4.34 (m, 1H), 3.56 (d, J=13.1, 1H), 3.40 (d, J=13.2, 1H), 2.74 (d, J=8.9, 1H), 2.48 (d, J=0.7, 2H), 2.39-2.27 (m, 2H), 2.26-2.19 (m, 1H), 2.14 (dq, J=12.0, 6.0, 1H), 2.07-1.96 (m, 1H), 1.85 (td, J=13.8, 8.2, 2H), 1.65 (td, J=14.3, 7.3, 1H), 1.49 (d, J=8.5, 11H), 1.45-1.33 (m, 1H), 0.81 (t, J=7.3, 3H); MS (ESI+) m/z 416 (M+H)+.

Step B: $N^1$-{(3aS,4R,6aR)-2-Benzyloctahydrocyclopenta[c]pyrrol-4-yl}-L-norvalinamide was prepared by substituting tert-butyl-((S)-1-oxo-1-((3aS,4R,6aR)-2-benzyloctahydrocyclopenta[c]pyrrol-4-ylamino)pentan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.19 (d, J=7.4, 1H), 7.43 (d, J=7.3, 2H), 7.36 (t, J=7.6, 2H), 7.27 (t, J=7.3, 1H), 4.43-4.35 (m, 1H), 3.59 (d, J=13.1, 1H), 3.53 (dd, J=7.9, 5.0, 1H), 3.43 (d, J=13.2, 1H), 2.83 (dd, J=8.9, 2.4, 1H), 2.55-2.48 (m, 1H), 2.44 (ddd, J=9.2, 6.0, 3.6, 1H), 2.41-2.33 (m, 2H), 2.23 (dd, J=8.8, 7.3, 1H), 2.10 (td, J=11.8, 5.9, 3H), 1.98-1.89 (m, 1H), 1.83 (dt, J=20.4, 6.2, 1H), 1.70-1.60 (m, 1H), 1.58-1.33 (m, 4H), 0.84 (t, J=7.3, 3H); MS (ESI+) m/z 316 (M+H)+.

Step C: The title compound was prepared by substituting $N^1$-{(3aS,4R,6aR)-2-benzyloctahydrocyclopenta[c]pyrrol-4-yl}-L-norvalinamide from Step B for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 8.18-8.20 (m, 1H), 7.43-7.45 (m, 2H), 7.37 (t, J=7.5 Hz, 2H), 7.28 (t, J=7.3 Hz, 1H), 4.40-4.46 (m, 1H), 3.60 (d, J=13.1 Hz, 1H), 3.44 (d, J=13.1 Hz, 1H), 3.32 (dd, J=7.5, 5.5 Hz, 1H), 2.80-2.86 (m, 2H), 2.46-2.59 (m, 2H), 2.43 (dd, J=8.8, 7.2 Hz, 1H), 2.35 (dd, J=8.9, 2.9 Hz, 1H), 2.27 (dd, J=8.9, 7.1 Hz, 1H), 2.12 (dq, J=12.0, 6.0 Hz, 1H), 1.86-2.04 (m, 1H), 1.77-1.90 (m, 2H), 1.55-1.70 (m, 2H), 1.38-1.55 (m, 3H), 1.05 (d, J=6.9 Hz, 3H), 1.04 (d, J=6.6 Hz, 3H), 0.85 (t, J=7.3 Hz, 3H); MS (ESI+) m/z 358 (M+H)+.

Example 496

$N^2$-isopropyl-$N^1$-((3aR,4S,6aS)-2-{[3-(trifluoromethyl)phenyl]sulfonyl}octahydrocyclopenta[c]pyrrol-4-yl)-L-leucinamide Step A: tert-Butyl-((S)-4-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate was prepared by substituting (3aR,4S,6aS)-2-(3-(trifluoromethyl)phenylsulfonyl)octahydrocyclopenta[c]pyrrol-4-amine from 252 Step D for (3aR,4S,6aS)-2-benzyloctahydrocyclopenta[c]pyrrol-4-amine in the procedure described in Example 221: $^1$H NMR (400 MHz, pyridine-$d_5$) δ ppm 8.75 (d, J=13.1, 1H), 8.37 (s, 1H), 8.18 (d, J=7.7, 1H), 8.00 (d, J=8.4, 1H), 7.91 (d, J=7.9, 1H), 7.71 (t, J=7.9, 1H), 4.70-4.59 (m, 1H), 4.29-4.18 (m, 1H), 3.82 (dd, J=10.1, 2.4, 1H), 3.15 (dd, J=9.9, 7.6, 2H), 2.99-2.89 (m, 1H), 2.62-2.44 (m, 2H), 1.93-1.70 (m, 5H), 1.55-1.44 (m, 10H), 1.30-1.16 (m, 1H), 0.86 (d, J=5.9, 3H), 0.83 (d, J=5.9, 3H); MS (ESI−) m/z 545 (M−H)−.

Step B: $N^1$-((3aR,4S,6aS)-2-{[3-(Trifluoromethyl)phenyl]sulfonyl}octahydrocyclopenta[c]pyrrol-4-yl)-L-leucinamide was prepared by substituting tert-butyl-((S)-4-methyl-1-oxo-1-((3aR,4S,6aS)-2-(3-(trifluoromethyl)phenylsulfonyl)octahydrocyclopenta[c]pyrrol-4-ylamino)pentan-2-yl)carbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (400 MHz, pyridine-$d_5$) δ ppm 8.44-8.32 (m, 2H), 8.19 (d, J=7.9, 1H), 7.91 (d, J=7.9, 1H), 7.79-7.66 (m, 1H), 4.72-4.38 (m, 3H), 4.29-4.15 (m, 1H), 3.84 (d, J=9.9, 2.4, 1H), 3.60 (dd, J=9.3, 4.5, 1H), 3.06 (dt, J=21.7, 10.8, 1H), 2.92 (dd, J=9.6, 7.2, 1H), 2.57-2.45 (m, 2H), 1.98-1.76 (m, 4H), 1.61-1.43 (m, 2H), 1.26 (ddt, J=13.2, 9.9, 6.5, 1H), 0.90 (d, J=6.4, 3H), 0.84 (d, J=6.3, 3H); MS (ESI−) m/z 448 (M−H)−.

Step C: The title compound was prepared by substituting $N^1$-((3aR,4S,6aS)-2-{[3-(trifluoromethyl)phenyl]sulfonyl}octahydrocyclopenta[c]pyrrol-4-yl)-L-leucinamide from Step B for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (400 MHz, pyridine-$d_5$) δ ppm 8.38 (s, 1H), 8.30-8.33 (m, 1H), 8.20 (d, J=7.9 Hz, 1H), 7.90-7.93 (m, 1H), 7.72 (t, J=7.8 Hz, 1H), 4.20-4.26 (m, 1H), 3.86 (dd, J=9.9, 2.3 Hz, 1H), 3.35 (dd, J=8.9, 5.1 Hz, 1H), 3.14-3.20 (m, 2H), 2.97 (dd, J=9.6, 6.8 Hz, 1H), 2.83 (hept, J=6.2 Hz, 1H), 2.52-2.56 (m, 2H), 2.07-2.81 (m, 1H), 1.78-2.01 (m, 3H), 1.64 (ddd, J=13.6, 8.4, 5.2 Hz, 1H), 1.47-1.59 (m, 2H), 1.25-1.36 (m, 1H), 1.04 (d, J=6.3 Hz, 3H), 1.02 (d, J=6.1 Hz, 3H), 0.91 (d, J=6.7 Hz, 3H), 0.85 (d, J=6.6 Hz, 3H); MS (ESI−) m/z 488 (M−H)−.

Example 497

$N^2,N^2$-dimethyl-$N^1$-((3aR,4S,6aS)-2-{[3-(trifluoromethyl)phenyl]sulfonyl}octahydrocyclopenta[c]pyrrol-4-yl)-L-leucinamide The title compound was prepared by substituting $N^2$-methyl-$N^1$-((3aR,4S,6aS)-2-{[3-(trifluoromethyl)phenyl]sulfonyl}octahydrocyclopenta[c]pyrrol-4-yl)-L-leucinamide from Example 384 for (3aS,4R,6aR)-2-(3-(trifluoromethyl)phenylsulfonyl)octahydrocyclopenta[c]pyrrol-4-amine and formaldehyde for pivalaldehyde in the procedure described in Example 281: $^1$H NMR (500 MHz, pyridine-$d_5$) δ ppm 8.37 (s, 1H), 8.26 (d, J=7.0, 1H), 8.19 (d, J=7.9, 1H), 7.91 (d, J=7.9, 1H), 7.72 (t, J=7.9, 1H), 4.24 (dt, J=13.3, 6.5, 1H), 3.85 (dd, J=10.0, 2.0, 1H), 3.20-3.11 (m, 3H), 2.94 (dd, J=9.6, 7.1, 1H), 2.59-2.48 (m, 2H), 2.33 (s, 6H), 1.96 (dt, J=12.3, 6.3, 1H), 1.81 (tdd, J=14.4, 11.4, 6.9, 3H), 1.56 (ddt, J=18.7, 13.2, 8.6, 2H), 1.28 (ddt, J=13.0, 9.8, 6.4, 1H), 0.93 (d, J=6.5 Hz, 3H), 0.90 (d, J=6.4, 3H); MS (ESI+) m/z 476 (M+H)+.

Example 498

(3R)-3-(dimethylamino)-4-methyl-N-((3aR,4S,6aS)-2-{[3-(trifluoromethyl)phenyl]sulfonyl}octahydrocyclopenta[c]pyrrol-4-yl)pentanamide The title compound was prepared by substituting (3R)-3-amino-4-methyl-N-((3aR,4S,6aS)-2-{[3-(trifluoromethyl)phenyl]sulfonyl}octahydrocyclopenta[c]pyrrol-4-yl)pentanamide from Example 388 for (3aS,4R,6aR)-2-(3-(trifluoromethyl)phenylsulfonyl)octahydrocyclopenta[c]pyrrol-4-amine and formaldehyde for pivalaldehyde in the procedure described in Example 281: $^1$H NMR (500 MHz, pyridine-$d_5$) δ ppm 8.47-8.49 (m, 1H), 8.37-8.38 (bs, 1H), 8.20 (d, J=7.9 Hz, 1H), 7.91 (d, J=7.9 Hz, 1H), 7.71 (t, J=7.8 Hz, 1H), 4.24 (p, J=6.4 Hz, 1H), 3.85 (dd, J=9.9, 2.4 Hz, 1H), 3.13-3.18 (m, 2H), 2.95-3.01 (m, 2H), 2.48-2.55 (m, 3H), 2.23 (s, 6H), 2.20 (dd, J=15.1, 5.8 Hz, 1H), 1.95 (dq, J=11.8, 5.9 Hz, 1H), 1.80-1.88 (m, 1H), 1.63-1.73 (m, 1H), 1.51-1.59 (m, 1H), 1.29 (ddt, J=9.4, 12.7, 6.4 Hz, 1H), 0.98 (d, J=6.6 Hz, 3H), 0.92 (d, J=6.6 Hz, 3H); MS (ESI+) m/z 476 (M+H)+.

Example 499

$N^2$-cyclopropyl-4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-$N^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and (1-ethoxycyclopropoxy)trimethylsilane for pivalaldehyde in the procedure described in Example 281: $^1$H NMR (500 MHz, pyridine-$d_5$) δ ppm 8.54-8.56 (m, 1H), 8.14-8.16 (m, 2H), 7.89-7.92 (m, 2H), 4.27-4.31 (m, 1H), 3.89 (dd, J=9.9, 2.6 Hz, 1H), 3.44 (t, J=6.0 Hz, 1H), 3.15-3.21 (m, 2H), 2.99 (dd, J=9.6, 6.9 Hz, 1H), 2.53-2.66 (m, 2H), 2.24-2.28 (m, 1H), 1.94-2.00 (m, 1H), 1.81-1.90 (m, 3H), 1.56-1.64 (m, 1H), 1.51 (dd, J=13.9, 6.6 Hz, 1H), 1.31 (ddt, J=9.7, 12.8, 6.4 Hz, 1H), 0.96 (s, 9H), 0.46-0.51 (m, 1H), 0.30-0.45 (m, 3H); MS (ESI+) m/z 502 (M+H)+.

Example 500

$N^2,N^2$-dicyclopropyl-4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-$N^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and (1-ethoxycyclopropoxy)trimethylsilane for pivalaldehyde in the procedure described in Example 281: $^1$H NMR (500 MHz, pyridine-$d_5$) δ ppm 8.13-8.15 (m, 2H), 7.88-7.90 (m, 2H), 7.83-7.85 (m, 1H), 4.21 (dq, J=9.1, 6.2 Hz, 1H), 3.89 (dd, J=9.9, 2.2 Hz, 1H), 3.53 (dd, J=9.1, 1.8 Hz, 1H), 3.16 (dd, J=9.9, 7.4 Hz, 2H), 2.96 (dd, J=9.6, 6.7 Hz, 1H), 2.62 (dd, J=13.6, 9.3 Hz, 1H), 2.46-2.57 (m, 2H), 2.23-2.28 (m, 2H), 1.88-1.94 (m, 1H), 1.76-1.82 (m, 1H), 1.65 (dd, J=13.6, 1.9 Hz, 1H), 1.48-1.58 (m, 1H), 1.23-1.32 (m, 1H), 1.00 (s, 9H), 0.44-0.56 (m, 8H); MS (ESI+) m/z 542 (M+H)+.

Example 501

$N^2$-cyclopentyl-4-methyl-$N^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-$N^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and cyclopentanone for pivalaldehyde in the procedure described in Example 281: $^1$H NMR (500 MHz, pyridine-$d_5$) δ ppm 8.34-8.36 (m, 1H), 8.13-8.16 (m, 2H), 7.89-7.91 (m, 2H), 4.23-4.29 (m, 1H), 3.88 (dd, J=10.0, 2.1 Hz, 1H), 3.34 (dd, J=7.4, 4.3 Hz, 1H), 3.10-3.22 (m, 3H), 2.96-3.00 (m, 1H), 2.56-2.58 (m, 2H), 1.90-2.02 (m, 1H), 1.81-1.89 (m, 2H), 1.70-1.84 (m, 1H), 1.55-1.75 (m, 5H), 1.36-1.54 (m, 5H), 1.24-1.35 (m, 1H), 0.99 (s, 9H); MS (ESI+) m/z 530 (M+H)+.

Example 502

N$^2$-cyclohexyl-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and cyclohexanone for pivalaldehyde in the procedure described in Example 281: $^1$H NMR (500 MHz, pyridine-d$_5$) δ ppm 8.25-8.27 (m, 1H), 8.13-8.16 (m, 2H), 7.89-7.91 (m, 2H), 4.22-4.28 (m, 1H), 3.86 (dd, J=9.9, 2.1 Hz, 1H), 3.42 (dd, J=7.6, 3.8 Hz, 1H), 3.12-3.22 (m, 2H), 2.99 (dd, J=9.6, 6.4 Hz, 1H), 2.55-2.65 (m, 2H), 2.47-2.53 (m, 1H), 1.91-2.01 (m, 1H), 1.78-1.91 (m, 4H), 1.65-1.76 (m, 1H), 1.60-1.67 (m, 2H), 1.54-1.60 (m, 1H), 1.45-1.52 (m, 2H), 1.28-1.37 (m, 1H), 1.03-1.25 (m, 5H), 1.00 (s, 9H); MS (ESI+) m/z 544 (M+H)+.

Example 503

N$^2$-(1-ethylpropyl)-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and pentan-3-one for pivalaldehyde in the procedure described in Example 281: $^1$H NMR (400 MHz, pyridine-d$_5$) δ ppm 8.25-8.27 (m, 1H), 8.13-8.16 (m, 2H), 7.89-7.92 (m, 2H), 4.21-4.27 (m, 1H), 3.85 (d, J=11.2 Hz, 1H), 3.40 (dd, J=7.0, 4.7 Hz, 1H), 3.18 (dd, J=10.2, 2.7 Hz, 2H), 2.97-3.02 (m, 1H), 2.55-2.59 (m, 2H), 2.45 (p, J=5.7 Hz, 1H), 1.96 (dt, J=11.8, 5.9 Hz, 1H), 1.86 (dd, J=14.1, 4.5 Hz, 1H), 1.78-1.89 (m, 1H), 1.53-1.81 (m, 1H), 1.26-1.63 (m, 7H), 1.00 (s, 9H), 0.92 (t, J=7.4 Hz, 3H), 0.84 (t, J=7.4 Hz, 3H); MS (ESI+) m/z 532 (M+H)+.

Example 504

N$^2$-cyclobutyl-4-methyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine and cyclobutanone for pivalaldehyde in the procedure described in Example 281: $^1$H NMR (501 MHz, pyridine-d$_5$) δ ppm 8.30-8.33 (m, 1H), 8.13-8.16 (m, 2H), 7.89-7.91 (m, 2H), 4.21-4.27 (m, 1H), 3.88 (dd, J=10.0, 2.0 Hz, 1H), 3.31 (t, J=6.5 Hz, 2H), 3.15-3.20 (m, 2H), 2.96-2.99 (m, 1H), 2.56-2.59 (m, 2H), 2.08-2.21 (m, 2H), 2.01-2.16 (m, 1H), 1.92-1.99 (m, 1H), 1.88 (dd, J=14.1, 5.3 Hz, 1H), 1.82-1.86 (m, 2H), 1.70-1.78 (m, 1H), 1.48-1.64 (m, 4H), 1.27-1.34 (m, 1H), 0.98 (s, 9H); MS (ESI+) m/z 516 (M+H)+.

Example 505

4-methyl-N$^2$-neopentyl-N$^1$-((3aR,4S,6aS)-2-{[4-(trifluoromethyl)phenyl]sulfonyl}octahydrocyclopenta[c]pyrrol-4-yl)-L-leucinamide The title compound was prepared by substituting 4-methyl-N$^1$-((3aR,4S,6aS)-2-{[4-(trifluoromethyl)phenyl]sulfonyl}octahydrocyclopenta[c]pyrrol-4-yl)-L-leucinamide from Example 419 for (3aS,4R,6aR)-2-(3-(trifluoromethyl)phenylsulfonyl)octahydrocyclopenta[c]pyrrol-4-amine in the procedure described in Example 281: $^1$H NMR (500 MHz, pyridine-d$_5$) δ ppm 8.20-8.22 (m, 1H), 8.14-8.16 (m, 2H), 7.89-7.92 (m, 2H), 4.21-4.28 (m, 1H), 3.86 (dd, J=10.0, 2.8 Hz, 1H), 3.23 (dd, J=7.9, 4.0 Hz, 1H), 3.17-3.21 (m, 2H), 3.00 (dd, J=9.7, 7.2 Hz, 1H), 2.52-2.58 (m, 2H), 2.39 (d, J=11.1 Hz, 1H), 2.31 (d, J=11.1 Hz, 1H), 1.94-2.01 (m, 1H), 1.87 (dd, J=14.1, 4.2 Hz, 1H), 1.83-1.89 (m, 2H), 1.52-1.61 (m, 1H), 1.50 (dd, J=14.0, 7.8 Hz, 1H), 1.29-1.36 (m, 1H), 0.99 (s, 9H), 0.92 (s, 9H); MS (ESI+) m/z 532 (M+H)+.

Example 506

N$^2$-cyclopentyl-N$^1$-((3aR,4S,6aS)-2-{[4-(trifluoromethyl)phenyl]sulfonyl}octahydrocyclopenta[c]pyrrol-4-yl)-L-norvalinamide The title compound was prepared by substituting N$^1$-((3aR,4S,6aS)-2-{[4-(trifluoromethyl)phenyl]sulfonyl}octahydrocyclopenta[c]pyrrol-4-yl)-L-norvalinamide from Example 422 for (3aS,4R,6aR)-2-(3-(trifluoromethyl)phenylsulfonyl)octahydrocyclopenta[c]pyrrol-4-amine and cyclopentanone for pivalaldehyde in the procedure described in Example 281: $^1$H NMR (400 MHz, pyridine-d$_5$) δ ppm 8.30-8.33 (m, 1H), 8.12-8.15 (m, 2H), 7.88-7.91 (m, 2H), 4.21-4.29 (m, 1H), 3.86 (d, J=11.3 Hz, 1H), 3.27 (t, J=6.5 Hz, 1H), 3.12-3.21 (m, 3H), 2.96-3.01 (m, 1H), 2.50-2.64 (m, 2H), 1.89-2.18 (m, 2H), 1.24-1.90 (m, 15H), 0.86 (t, J=7.3 Hz, 3H); MS (ESI+) m/z 502 (M+H)+.

Example 507

N$^2$-cyclohexyl-N$^1$-((3aR,4S,6aS)-2-{[4-(trifluoromethyl)phenyl]sulfonyl}octahydrocyclopenta[c]pyrrol-4-yl)-L-norvalinamide The title compound was prepared by substituting N$^1$-((3aR,4S,6aS)-2-{[4-(trifluoromethyl)phenyl]sulfonyl}octahydrocyclopenta[c]pyrrol-4-yl)-L-norvalinamide from Example 422 for (3aS,4R,6aR)-2-(3-(trifluoromethyl)phenylsulfonyl)octahydrocyclopenta[c]pyrrol-4-amine and cyclohexanone for pivalaldehyde in the procedure described in Example 281: $^1$H NMR (400 MHz, pyridine-d$_5$) δ ppm 8.25-8.27 (m, 1H), 8.12-8.15 (m, 2H), 7.89-7.92 (m, 2H), 4.20-4.28 (m, 1H), 3.84 (dd, J=10.0, 2.4 Hz, 1H), 3.35 (dd, J=7.6, 5.4 Hz, 1H), 3.14-3.21 (m, 2H), 2.96-3.01 (m, 1H), 2.51-2.65 (m, 2H), 2.40-2.51 (m, 1H), 1.75-2.01 (m, 6H), 1.44-1.67 (m, 7H), 1.26-1.38 (m, 1H), 1.04-1.24 (m, 5H), 0.87 (t, J=7.3 Hz, 3H); MS (ESI+) m/z 516 (M+H)+.

Example 508

N²-cyclopentyl-N¹-[(3aR,4S,6aS)-2-(N-cyclopentyl-4-methyl-L-leucyl)octahydrocyclopenta[c]pyrrol-4-yl]-4-methyl-L-leucinamide The title compound was prepared by substituting 4-methyl-N¹-[(3aR,4S,6aS)-2-(4-methyl-L-leucyl)octahydrocyclopenta[c]pyrrol-4-yl]-L-leucinamide from Example 464 for (3aS,4R,6aR)-2-(3-(trifluoromethyl)phenylsulfonyl)octahydrocyclopenta[c]pyrrol-4-amine and cyclopentanone for pivalaldehyde in the procedure described in Example 281: ¹H NMR (400 MHz, pyridine-$d_5$) δ ppm 7.73 (d, J=5.6, 1H), 4.31-4.20 (m, 1H), 3.83-3.71 (m, 2H), 3.72-3.49 (m, 3H), 3.31 (dd, J=7.2, 4.4, 1H), 3.19-3.07 (m, 2H), 2.78-2.63 (m, 2H), 2.12 (dt, J=12.6, 6.4, 1H), 1.96 (tt, J=5.7, 5.0, 1H), 1.86-1.59 (m, 12H), 1.57-1.33 (m, 12H), 1.04 (s, 9H), 0.99 (s, 9H); MS (ESI+) m/z 517 (M+H)⁺.

Example 509

N²,N²-dimethyl-N¹-{(3aS,4S,6aR)-2-[3-(trifluoromethyl)benzyl]octahydrocyclopenta[c]pyrrol-4-yl}-L-leucinamide The title compound was prepared by substituting N²-methyl-N¹-{(3aS,4S,6aR)-2-[3-(trifluoromethyl)benzyl]octahydrocyclopenta[c]pyrrol-4-yl}-L-leucinamide from Example 164 for (3aS,4R,6aR)-2-(3-(trifluoromethyl)phenylsulfonyl)octahydrocyclopenta[c]pyrrol-4-amine and formaldehyde for pivalaldehyde in the procedure described in Example 281: ¹H NMR (500 MHz, pyridine-$d_5$) δ ppm 8.17-8.20 (m, 1H), 7.76-7.77 (bs, 1H), 7.63-7.65 (m, 2H), 7.50 (t, J=7.7 Hz, 1H), 4.48-4.54 (m, 1H), 3.74 (d, J=13.1 Hz, 1H), 3.30 (d, J=13.1 Hz, 1H), 3.05 (dd, J=9.0, 5.0 Hz, 1H), 2.74-2.78 (m, 1H), 2.68-2.74 (m, 1H), 2.42-2.47 (m, 1H), 2.33 (s, 7H), 2.21 (dd, J=9.4, 7.2 Hz, 1H), 2.14 (dd, J=9.0, 7.5 Hz, 1H), 1.76-1.89 (m, 3H), 1.67-1.74 (m, 1H), 1.53-1.61 (m, 2H), 1.21-1.28 (m, 1H), 0.96 (d, J=6.6 Hz, 3H), 0.94 (d, J=6.7 Hz, 3H); MS (ESI−) m/z 424 (M−H)⁻.

Example 510

N¹-[(3aS,4R,6aR)-2-benzyloctahydrocyclopenta[c]pyrrol-4-yl]-N²-methyl-N²-neopentyl-L-leucinamide The title compound was prepared by substituting N¹-{(3aS,4R,6aR)-2-benzyloctahydrocyclopenta[c]pyrrol-4-yl}-N²-methyl-L-leucinamide from Example 165 for (3aS,4R,6aR)-2-(3-(trifluoromethyl)phenylsulfonyl)octahydrocyclopenta[c]pyrrol-4-amine in the procedure described in Example 281: ¹H NMR (500 MHz, pyridine-$d_5$) δ ppm 8.15-8.17 (m, 1H), 7.43-7.46 (m, 2H), 7.37 (t, J=7.5 Hz, 2H), 7.28 (t, J=7.3 Hz, 1H), 4.39-4.45 (m, 1H), 3.61 (d, J=13.1 Hz, 1H), 3.46 (d, J=13.1 Hz, 1H), 3.27 (dd, J=7.9, 6.0 Hz, 1H), 2.85 (dd, J=8.9, 2.0 Hz, 1H), 2.52-2.58 (m, 2H), 2.46-2.52 (m, 2H), 2.45 (s, 3H), 2.43 (d, J=13.8 Hz, 1H), 2.29-2.36 (m, 2H), 2.12 (dq, J=12.2, 6.1 Hz, 1H), 1.82-2.02 (m, 3H), 1.53-1.63 (m, 2H), 1.37-1.47 (m, 1H), 0.95 (d, J=6.6 Hz, 3H), 0.94 (d, J=6.6 Hz, 3H), 0.90 (s, 9H); MS (ESI+) m/z 414 (M+H)⁺.

Example 511

N¹-[(3aS,4R,6aR)-2-benzyloctahydrocyclopenta[c]pyrrol-4-yl]-N²-(3,3-dimethylbutyl)-N²-methyl-L-leucinamide The title compound was prepared by substituting N¹-{(3aS,4R,6aR)-2-benzyloctahydrocyclopenta[c]pyrrol-4-yl}-N²-methyl-L-leucinamide from Example 165 for (3aS,4R,6aR)-2-(3-(trifluoromethyl)phenylsulfonyl)octahydrocyclopenta[c]pyrrol-4-amine and 3,3-dimethylbutanal for pivalaldehyde in the procedure described in Example 281: ¹H NMR (500 MHz, pyridine-$d_5$) δ ppm 8.04-8.06 (m, 1H), 7.43-7.46 (m, 2H), 7.37 (t, J=7.5 Hz, 2H), 7.28 (t, J=7.4 Hz, 1H), 4.42-4.48 (m, 1H), 3.63 (d, J=13.1 Hz, 1H), 3.46 (d, J=13.1 Hz, 1H), 3.33 (dd, J=8.2, 5.3 Hz, 1H), 2.89-2.92 (m, 1H), 2.55-2.66 (m, 4H), 2.44-2.48 (m, 1H), 2.39 (s, 3H), 2.36-2.39 (m, 1H), 2.27 (dd, J=8.8, 6.1 Hz, 1H), 2.12 (dq, J=11.9, 6.0 Hz, 1H), 1.83-1.99 (m, 3H), 1.56-1.63 (m, 2H), 1.40-1.48 (m, 3H), 0.95 (d, J=6.3 Hz, 6H), 0.89 (s, 9H); MS (ESI+) m/z 428 (M+H)⁺.

Example 512

N²,N²-dimethyl-N¹-((3aS,4R,6aR)-2-{[3-(trifluoromethyl)phenyl]sulfonyl}octahydrocyclopenta[c]pyrrol-4-yl)-L-leucinamide The title compound was prepared by substituting N¹-((3aS,4R,6aR)-2-{[3-(trifluoromethyl)phenyl]sulfonyl}octahydrocyclopenta[c]pyrrol-4-yl)-L-leucinamide from Example 184 for (3aS,4R,6aR)-2-(3-(trifluoromethyl)phenylsulfonyl)octahydrocyclopenta[c]pyrrol-4-amine and formaldehyde for pivalaldehyde in the procedure described in Example 281: ¹H NMR (500 MHz, pyridine-$d_5$) δ ppm 8.38-8.39 (bs, 1H), 8.18-8.25 (m, 2H), 7.90-7.92 (m, 1H), 7.72 (t, J=7.8 Hz, 1H), 4.20-4.25 (m, 1H), 3.88 (d, J=10.8 Hz, 1H), 3.18 (dd, J=9.8, 2.5 Hz, 1H), 3.11-3.18 (m, 2H), 2.95-2.98 (m, 1H), 2.51-2.60 (m, 2H), 2.32 (s, 6H), 1.90-1.97 (m, 1H), 1.75-1.86 (m, 3H), 1.49-1.60 (m, 2H), 1.24-1.32 (m, 1H), 0.90 (d, J=6.4 Hz, 3H), 0.90 (d, J=6.4 Hz, 3H); MS (ESI+) m/z 476 (M+H)⁺.

Example 513

N¹-[(3aS,4R,6aR)-2-benzyloctahydrocyclopenta[c]pyrrol-4-yl]-N²-(4-fluorobenzyl)-N²-methyl-L-leucinamide The title compound was prepared by substituting N¹-{(3aS,4R,6aR)-2-benzyloctahydrocyclopenta[c]pyrrol-4-yl}-N²-methyl-L-leucinamide from Example 165 for (3aS,4R,6aR)-2-(3-(trifluoromethyl)phenylsulfonyl)octahydrocyclopenta[c]pyrrol-4-amine and 4-fluorobenzaldehyde for pivalaldehyde in the procedure described in Example 281: ¹H NMR (500 MHz, pyridine-$d_5$) δ ppm 8.25-8.27 (m, 1H), 7.36-7.46 (m, 6H), 7.28 (t, J=7.3 Hz, 1H), 7.13-7.17 (m, 2H), 4.45-4.50 (m, 1H), 3.86 (d, J=13.7 Hz, 1H), 3.76 (d, J=13.7 Hz, 1H), 3.63 (d, J=13.1 Hz, 1H), 3.47 (d, J=13.1 Hz, 1H), 3.41 (dd, J=7.7, 6.2 Hz, 1H), 2.91 (dd, J=9.0, 2.7 Hz, 1H), 2.53-2.64 (m, 2H), 2.49 (dd, J=8.8, 7.0 Hz, 1H), 2.34-2.39 (m, 1H), 2.36 (s, 3H), 2.30 (dd, J=8.9, 6.9 Hz, 1H), 2.10-2.22 (m, 1H), 1.84-1.94 (m, 3H), 1.67-1.76 (m, 1H), 1.59-1.67 (m, 1H), 1.39-1.46 (m, 1H), 0.93 (d, J=6.8 Hz, 3H), 0.91 (d, J=6.6 Hz, 3H); MS (ESI+) m/z 452 (M+H)⁺.

Example 514

(2S)-N-[(3aS,4R,6aR)-2-benzyloctahydrocyclopenta[c]pyrrol-4-yl]-1-(methylsulfonyl)piperidine-2-carboxamide The title compound was prepared by substituting (2S)-N-[(3aS,4R,6aR)-2-benzyloctahydrocyclopenta[c]pyrrol-4-yl]piperidine-2-carboxamide from Example 350 for (S)-tert-butyl 2-amino-4-methylpentanoate in the procedure described in Example 242 Step A: $^1$H NMR (400 MHz, pyridine-$d_5$) δ ppm 8.54 (d, J=7.2, 1H), 7.43 (d, J=7.2, 2H), 7.37 (dd, J=10.2, 4.7, 2H), 7.28 (t, J=7.2, 1H), 4.89 (d, J=3.1, 1H), 4.40-4.31 (m, 1H), 3.90-3.77 (m, 2H), 3.57 (d, J=13.1, 1H), 3.45 (d, J=13.1, 1H), 3.15 (s, 3H), 2.79 (dd, J=9.0, 2.1, 1H), 2.54-2.41 (m, 2H), 2.40-2.31 (m, 2H), 2.24 (dd, J=8.8, 6.9, 1H), 2.20-2.14 (m, 1H), 2.09 (dq, J=12.0, 6.0, 1H), 1.88-1.78 (m, 1H), 1.67-1.53 (m, 4H), 1.51-1.34 (m, 3H); MS (ESI+) m/z 406 (M+H)$^+$.

Example 515

(3R)-4-methyl-3-[(methylsulfonyl)amino]-N-((3aR,4S,6aS)-2-{[3-(trifluoromethyl)phenyl]sulfonyl}octahydrocyclopenta[c]pyrrol-4-yl)pentanamide The title compound was prepared by substituting (3R)-3-amino-4-methyl-N-((3aR,4S,6aS)-2-{[3-(trifluoromethyl)phenyl]sulfonyl}octahydrocyclopenta[c]pyrrol-4-yl)pentanamide from Example 388 for (S)-tert-butyl 2-amino-4-methylpentanoate in the procedure described in Example 242 Step A: $^1$H NMR (500 MHz, pyridine-$d_5$) δ ppm 8.77 (d, J=6.6, 1H), 8.42-8.34 (m, 2H), 8.20 (d, J=7.8, 1H), 7.91 (d, J=7.8, 1H), 7.72 (t, J=7.9, 1H), 4.21 (dq, J=13.4, 6.1, 2H), 3.85 (dd, J=9.9, 1.7, 1H), 3.23 (s, 3H), 3.17 (dd, J=9.6, 1.9, 1H), 3.11 (dd, J=9.8, 7.3, 1H), 2.93 (dd, J=9.5, 7.1, 1H), 2.76-2.65 (m, 2H), 2.56-2.45 (m, 2H), 2.11 (dq, J=13.5, 6.8, 1H), 1.95 (td, J=12.2, 6.3, 1H), 1.83 (dt, J=12.5, 6.4, 1H), 1.55 (ddd, J=15.9, 12.3, 9.1, 1H), 1.28 (ddd, J=12.8, 9.4, 6.3, 1H), 1.02 (d, J=6.8, 3H), 0.97 (d, J=6.8, 3H); MS (ESI+) m/z 524 (M+H)$^+$.

Example 516

N$^2$-(methylsulfonyl)-N$^1$-{(3aR,4S,6aS)-2-[3-(trifluoromethyl)benzyl]octahydrocyclopenta[c]pyrrol-4-yl}-L-leucinamide Step A: tert-Butyl(S)-4-methyl-1-oxo-1-((3aR,4S,6aS)-2-(3-(trifluoromethyl)benzyl)octahydrocyclopenta[c]pyrrol-4-ylamino)pentan-2-ylcarbamate was prepared by substituting (3aR,4S,6aS)-2-(3-(trifluoromethyl)benzyl)octahydrocyclopenta[c]pyrrol-4-amine from Example 156 Step A for (3aR,4S,6aS)-2-benzyloctahydrocyclopenta[c]pyrrol-4-amine in the procedure described in Example 221: $^1$H NMR (500 MHz, pyridine-$d_5$) δ ppm 8.67 (d, J=7.2, 1H), 7.96 (d, J=8.4, 1H), 7.75 (s, 1H), 7.61 (s, 1H), 7.56 (s, 1H), 7.45 (dd, J=14.3, 6.7, 1H), 4.75-4.66 (m, 1H), 4.45-4.36 (m, 1H), 3.59 (d, J=13.5, 1H), 3.46 (d, J=13.6, 1H), 2.81 (dd, J=9.1, 2.3, 1H), 2.62-2.56 (m, 1H), 2.56-2.49 (m, 1H), 2.49-2.43 (m, 1H), 2.27 (d, J=5.3, 2H), 2.03 (td, J=11.6, 5.7, 1H), 1.94-1.78 (m, 4H), 1.65-1.56 (m, 1H), 1.50 (s, 9H), 1.35 (dt, J=13.6, 5.7, 1H), 0.86 (dd, J=11.2, 5.7, 6H); MS (ESI+) m/z 498 (M+H)$^+$.
Step B: N$^1$-{(3aR,4S,6aS)-2-[3-(Trifluoromethyl)benzyl]octahydrocyclopenta[c]pyrrol-4-yl}-L-leucinamide was prepared by substituting tert-butyl(S)-4-methyl-1-oxo-1-((3aR,4S,6aS)-2-(3-(trifluoromethyl)benzyl)octahydrocyclopenta[c]pyrrol-4-ylamino)pentan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.31 (d, J=7.5, 1H), 7.76 (s, 1H), 7.62 (d, J=7.9, 1H), 7.56 (s, 1H), 7.46 (t, J=7.7, 1H), 4.44-4.33 (m, 1H), 3.63-3.56 (m, 2H), 3.47 (d, J=13.5, 1H), 2.83 (dd, J=9.0, 2.3, 1H), 2.58-2.46 (m, 2H), 2.44-2.39 (m, 1H), 2.32 (dd, J=9.0, 2.6, 1H), 2.28-2.23 (m, 1H), 2.08 (td, J=11.9, 5.9, 2H), 1.95-1.81 (m, 4H), 1.62-1.51 (m, 2H), 1.43-1.34 (m, 1H), 0.90 (d, J=6.3, 3H), 0.85 (d, J=6.2, 3H); MS (ESI+) m/z 398 (M+H)$^+$.
Step C: The title compound was prepared by substituting N$^1$-{(3aR,4S,6aS)-2-[3-(trifluoromethyl)benzyl]octahydrocyclopenta[c]pyrrol-4-yl}-L-leucinamide from Step B for (S)-tert-butyl 2-amino-4-methylpentanoate in the procedure described in Example 242 Step A: $^1$H NMR (500 MHz, pyridine-$d_5$) δ ppm 9.36 (d, J=8.9, 1H), 9.24 (d, J=7.3, 1H), 7.78 (s, 1H), 7.62 (d, J=8.2, 2H), 7.46 (t, J=7.7, 1H), 4.48 (qd, J=13.1, 7.5, 2H), 3.62 (d, J=13.5, 1H), 3.50 (d, J=13.5, 1H), 3.20 (s, 3H), 2.86 (dd, J=9.1, 2.9, 1H), 2.64 (dt, J=8.4, 6.1, 1H), 2.60-2.53 (m, 1H), 2.49 (dd, J=8.8, 7.5, 1H), 2.34-2.27 (m, 2H), 2.15-2.09 (m, 1H), 2.04-1.95 (m, 1H), 1.90 (ddd, J=14.5, 9.2, 4.2, 2H), 1.78 (ddd, J=13.9, 8.5, 5.7, 1H), 1.65 (dt, J=19.1, 7.2, 1H), 1.41 (dq, J=13.9, 6.1, 1H), 0.83 (d, J=6.7, 3H), 0.81 (d, J=6.6, 3H); MS (ESI+) m/z 476 (M+H)$^+$.

Example 517

N$^2$-(methylsulfonyl)-N$^1$-{(3aR,4S,6aS)-2-[3-(trifluoromethyl)benzyl]octahydrocyclopenta[c]pyrrol-4-yl}-D-leucinamide Step A: tert-Butyl(R)-4-methyl-1-oxo-1-((3aR,4S,6aS)-2-(3-(trifluoromethyl)benzyl)octahydrocyclopenta[c]pyrrol-4-ylamino)pentan-2-ylcarbamate was prepared by substituting (3aR,4S,6aS)-2-(3-(trifluoromethyl)benzyl)octahydrocyclopenta[c]pyrrol-4-amine from Example 156 Step A for (3aR,4S,6aS)-2-benzyloctahydrocyclopenta[c]pyrrol-4-amine and N-(tert-butoxycarbonyl)-D-leucine for N-(tert-butoxycarbonyl)-L-leucine in the procedure described in Example 221: $^1$H NMR (500 MHz, pyridine-$d_5$) δ ppm 8.70 (d, J=7.4, 1H), 7.95 (d, J=8.4, 1H), 7.73 (s, 1H), 7.59 (s, 1H), 7.56 (s, 1H), 7.45 (t, J=7.7, 1H), 4.72 (br s, 1H), 4.40 (br s, 1H), 3.57 (d, J=13.4, 1H), 3.42 (d, J=13.6, 1H), 2.73 (d, J=9.0, 1H), 2.50 (s, 2H), 2.39-2.32 (m, 1H), 2.25 (dd, J=12.9, 7.0, 2H), 2.11 (dq, J=12.3, 6.2, 1H), 1.94-1.78 (m, 4H), 1.66 (dq, J=21.9, 7.3, 1H), 1.50 (s, 9H), 1.39 (d, J=7.0, 1H), 0.86 (dd, J=10.2, 5.6, 6H); MS (ESI+) m/z 498 (M+H)$^+$.
Step B: N$^1$-{(3aR,4S,6aS)-2-[3-(Trifluoromethyl)benzyl]octahydrocyclopenta[c]pyrrol-4-yl}-D-leucinamide was prepared by substituting tert-butyl(R)-4-methyl-1-oxo-1-((3aR,4S,6aS)-2-(3-(trifluoromethyl)benzyl)octahydrocyclopenta[c]pyrrol-4-ylamino)pentan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 8.33 (d, J=7.6, 1H), 7.75 (s, 1H), 7.62 (s, 1H), 7.56 (s, 1H), 7.46 (t, J=7.7, 1H), 4.43-4.34 (m, 1H), 3.64-3.56 (m, 2H), 3.46 (d, J=13.5, 1H), 2.82 (dd, J=9.0, 2.5, 1H), 2.59-2.45 (m, 2H), 2.44-2.39 (m, 1H), 2.31 (dd, J=9.0, 2.8, 1H), 2.25 (dd, J=8.8, 7.1, 1H), 2.09 (td, J=11.9, 5.9, 2H), 1.88 (tdd, J=13.5, 8.9, 6.0, 4H), 1.57 (tt, J=18.0, 6.6, 2H), 1.44-1.34 (m, 1H), 0.90 (d, J=6.4, 3H), 0.85 (d, J=6.3, 3H); MS (ESI+) m/z 398 (M+H)$^+$.
Step C: The title compound was prepared by substituting N$^1$-{(3aR,4S,6aS)-2-[3-(trifluoromethyl)benzyl]octahydrocyclopenta[c]pyrrol-4-yl}-L-leucinamide from Step B for (S)-tert-butyl 2-amino-4-methylpentanoate in the procedure described in Example 242 Step A: $^1$H NMR (500 MHz, pyridine-$d_5$) δ ppm 9.35 (d, J=8.5, 1H), 9.24 (d, J=7.2, 1H), 7.76 (s, 1H), 7.63-7.56 (m, 2H), 7.45 (dd, J=14.6, 7.0, 1H), 4.47 (dt, J=13.0, 8.2, 2H), 3.59 (d, J=13.6, 1H), 3.48 (d, J=13.5, 1H), 3.18 (s, 3H), 2.85 (dd, J=9.1, 2.5, 1H), 2.63-2.49 (m, 2H), 2.39 (dd, J=9.0, 7.1, 1H), 2.33 (dd, J=9.0, 2.6, 1H), 2.29-2.22 (m, 1H), 2.15 (dt, J=12.2, 6.1, 1H), 2.04-1.95 (m, 1H), 1.94-1.84 (m, 2H), 1.81-1.66 (m, 2H), 1.43 (dt, J=21.0, 6.4, 1H), 0.85-0.79 (m, 6H); MS (ESI+) m/z 476 (M+H)+.

Example 518

N²-ethyl-N²-(methylsulfonyl)-N¹-{(3aR,4S,6aS)-2-[3-(trifluoromethyl)benzyl]octahydrocyclopenta[c]pyrrol-4-yl}-L-leucinamide The title compound was prepared by substituting N²-ethyl-N¹-{(3aR,4S,6aS)-2-[3-(trifluoromethyl)benzyl]octahydrocyclopenta[c]pyrrol-4-yl}-L-leucinamide from Example 366 for (S)-tert-butyl 2-amino-4-methylpentanoate in the procedure described in Example 242 Step A: ¹H NMR (500 MHz, pyridine-$d_5$) δ ppm 8.83 (d, J=7.3, 1H), 7.77 (s, 1H), 7.63-7.55 (m, 2H), 7.45 (t, J=7.7, 1H), 4.71 (t, J=6.9, 1H), 4.43-4.34 (m, 1H), 3.93 (td, J=13.9, 6.8, 1H), 3.63-3.45 (m, 3H), 3.15 (d, J=5.3, 3H), 2.89-2.81 (m, 1H), 2.54 (ddd, J=29.4, 12.7, 9.2, 2H), 2.46-2.42 (m, 1H), 2.39-2.30 (m, 1H), 2.24 (dd, J=17.4, 8.7, 1H), 2.08 (ddt, J=17.6, 11.7, 5.8, 1H), 1.90-1.75 (m, 4H), 1.68-1.53 (m, 1H), 1.40 (dd, J=12.7, 6.4, 1H), 1.36-1.30 (m, 3H), 0.85 (d, J=5.4, 3H), 0.82 (t, J=5.3, 3H); MS (ESI+) m/z 502 (M+H)+.

Example 519

4-methyl-N²-(methylsulfonyl)-N¹-{(3aR,4S,6aS)-2-[4-(trifluoromethyl)benzyl]octahydrocyclopenta[c]pyrrol-4-yl}-L-leucinamide Step A: tert-Butyl(S)-1-((3aR,4S,6aS)-2-[4-trifluoromethyl)benzyl]octahydrocyclopenta[c]pyrrol-4-ylamino)-4,4-dimethyl-1-oxopentan-2-ylcarbamate was prepared by substituting tert-butyl(S)-1-((3aR,4S,6aS)-2-benzyloctahydrocyclopenta[c]pyrrol-4-ylamino)-4,4-dimethyl-1-oxopentan-2-ylcarbamate from Example 226 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedure described in Example 303: ¹H NMR (500 MHz, pyridine-$d_5$) δ ppm 8.60 (d, J=7.5, 1H), 8.12 (d, J=8.9, 1H), 7.65 (d, J=8.0, 2H), 7.51 (d, J=8.0, 2H), 4.75 (td, J=8.4, 5.1, 1H), 4.45-4.37 (m, 1H), 3.56 (d, J=13.8, 1H), 3.46 (d, J=13.7, 1H), 2.86 (dd, J=9.0, 2.2, 1H), 2.62-2.46 (m, 2H), 2.42-2.36 (m, 1H), 2.30 (dd, J=8.7, 2.2, 1H), 2.26-2.20 (m, 1H), 2.19-2.12 (m, 1H), 2.04 (td, J=11.7, 5.7, 1H), 1.89-1.80 (m, 2H), 1.64-1.53 (m, 1H), 1.51 (s, 9H), 1.36 (dt, J=21.2, 7.3, 1H), 0.98 (s, 9H); MS (ESI+) m/z 512 (M+H)+.

Step B: 4-Methyl-N¹-{(3aR,4S,6aS)-2-[4-(trifluoromethyl)benzyl]octahydrocyclopenta[c]pyrrol-4-yl}-L-leucinamide was prepared by substituting tert-butyl(S)-1-((3aR,4S,6aS)-2-[4-trifluoromethyl)benzyl]octahydrocyclopenta[c]pyrrol-4-ylamino)-4,4-dimethyl-1-oxopentan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (400 MHz, pyridine-$d_5$) δ ppm 8.31 (d, J=7.7, 1H), 7.65 (d, J=8.0, 2H), 7.52 (d, J=7.9, 2H), 4.45-4.31 (m, 1H), 3.62-3.53 (m, 2H), 3.47 (d, J=13.9, 1H), 2.89 (d, J=8.4, 1H), 2.58-2.43 (m, 2H), 2.35 (t, J=7.6, 2H), 2.25-2.15 (m, 3H), 2.10 (dt, J=11.7, 6.7, 2H), 1.87 (td, J=13.1, 6.6, 1H), 1.57 (dt, J=14.8, 7.7, 1H), 1.48-1.36 (m, 2H), 0.98 (s, 9H); MS (ESI+) m/z 412 (M+H)+.

Step C: The title compound was prepared by substituting 4-methyl-N¹-{(3aR,4S,6aS)-2-[4-(trifluoromethyl)benzyl]octahydrocyclopenta[c]pyrrol-4-yl}-L-leucinamide from Step B for (S)-tert-butyl 2-amino-4-methylpentanoate in the procedure described in Example 242 Step A: ¹H NMR (500 MHz, pyridine-$d_5$) δ ppm 9.55 (d, J=9.7, 1H), 9.30 (d, J=7.3, 1H), 7.66 (d, J=8.1, 2H), 7.54 (d, J=8.0, 2H), 4.57-4.51 (m, 1H), 4.51-4.44 (m, 1H), 3.60 (d, J=13.8, 1H), 3.50 (d, J=13.8, 1H), 3.18 (s, 3H), 2.92 (dd, J=9.0, 2.5, 1H), 2.67-2.61 (m, 1H), 2.58-2.50 (m, 1H), 2.43 (dd, J=8.9, 7.3, 1H), 2.36 (dd, J=9.0, 2.6, 1H), 2.25 (dd, J=8.7, 7.5, 1H), 2.17-2.10 (m, 1H), 2.03 (dd, J=14.1, 5.4, 1H), 1.95-1.85 (m, 2H), 1.64 (dtd, J=12.2, 8.1, 5.8, 1H), 1.46-1.37 (m, 1H), 0.96 (s, 9H); MS (ESI+) m/z 490 (M+H)+.

Example 520

3-methyl-N²-(methylsulfonyl)-N¹-{(3aR,4S,6aS)-2-[4-(trifluoromethyl)benzyl]octahydrocyclopenta[c]pyrrol-4-yl}-L-valinamide Step A: tert-Butyl(S)-1-((3aR,4S,6aS)-2-[4-(trifluoromethyl)benzyl]octahydrocyclopenta[c]pyrrol-4-ylamino)-3,3-dimethyl-1-oxobutan-2-ylcarbamate was prepared by substituting tert-butyl(S)-1-((3aR,4S,6aS)-2-benzyloctahydrocyclopenta[c]pyrrol-4-ylamino)-3,3-dimethyl-1-oxobutan-2-ylcarbamate from Example 225 for (2S)-N-[(3aS,4R,6aR)-2-benzyloctahydrocyclopenta[c]pyrrol-4-yl]-2-(1,1-dioxidoisothiazolidin-2-yl)-4-methylpentanamide in the procedure described in Example 303: ¹H NMR (500 MHz, pyridine-$d_5$) δ ppm 7.72 (d, J=9.7, 1H), 7.66 (d, J=8.1, 2H), 7.52 (d, J=8.0, 2H), 7.37 (d, J=3.1, 1H), 4.61 (d, J=9.8, 1H), 4.46-4.39 (m, 1H), 3.60 (d, J=13.7, 1H), 3.46 (d, J=13.7, 1H), 2.89 (dd, J=9.1, 2.5, 1H), 2.63-2.57 (m, 1H), 2.57-2.50 (m, 1H), 2.46-2.41 (m, 1H), 2.35-2.29 (m, 1H), 2.28-2.22 (m, 1H), 1.99 (dq, J=11.8, 5.7, 1H), 1.84 (td, J=12.7, 6.2, 1H), 1.57-1.49 (m, 1H), 1.48 (s, 9H), 1.40-1.31 (m, 1H), 1.18 (s, 9H); MS (ESI+) m/z 498 (M+H)+.

Step B: 3-Methyl-N¹-{(3aR,4S,6aS)-2-[4-(trifluoromethyl)benzyl]octahydrocyclopenta[c]pyrrol-4-yl}-L-valinamide was prepared by substituting tert-butyl(S)-1-((3aR,4S,6aS)-2-[4-(trifluoromethyl)benzyl]octahydrocyclopenta[c]pyrrol-4-ylamino)-3,3-dimethyl-1-oxobutan-2-ylcarbamate from Step A for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: ¹H NMR (500 MHz, pyridine-$d_5$) δ ppm 8.15-8.06 (m, 1H), 7.66 (d, J=8.1, 2H), 7.52 (d, J=8.0, 2H), 4.47-4.40 (m, 1H), 3.59 (d, J=13.6, 1H), 3.46 (d, J=13.8, 1H), 3.27 (s, 1H), 2.89-2.85 (m, 1H), 2.56-2.50 (m, 2H), 2.41-2.36 (m, 1H), 2.35-2.32 (m, 1H), 2.26-2.21 (m, 1H), 2.19-2.12 (m, 2H), 2.11-2.02 (m, 1H), 1.90-1.82 (m, 1H), 1.60-1.52 (m, 1H), 1.43-1.35 (m, 1H), 1.14 (s, 9H); MS (ESI+) m/z 398 (M+H)+.

Step C: The title compound was prepared by substituting 3-methyl-N¹-{(3aR,4S,6aS)-2-[4-(trifluoromethyl)benzyl]octahydrocyclopenta[c]pyrrol-4-yl}-L-valinamide from Step B for (S)-tert-butyl 2-amino-4-methylpentanoate in the procedure described in Example 242 Step A: ¹H NMR (500 MHz, pyridine-$d_5$) δ ppm 9.28 (d, J=10.4, 1H), 9.13 (d, J=7.4, 1H), 7.67 (d, J=8.1, 2H), 7.55 (d, J=8.1, 2H), 4.54-4.46 (m, 1H), 4.19 (d, J=10.4, 1H), 3.64 (d, J=13.7, 1H), 3.50 (d, J=13.7, 1H), 3.13 (s, 3H), 2.92 (dd, J=9.0, 2.4, 1H), 2.67-2.52 (m, 2H), 2.46 (dd, J=8.8, 7.1, 1H), 2.37 (dd, J=9.0, 2.5, 1H), 2.30-2.23 (m, 1H), 2.09 (dq, J=11.7, 5.8, 1H), 1.94-1.83 (m, 1H), 1.62-1.53 (m, 1H), 1.45-1.37 (m, 1H), 1.18 (s, 9H); MS (ESI+) m/z 476 (M+H)+.

Example 521

N²-(methylsulfonyl)-N¹-{(3aR,4S,6aS)-2-[4-(trifluoromethyl)benzyl]octahydrocyclopenta[c]pyrrol-4-yl}-L-norvalinamide

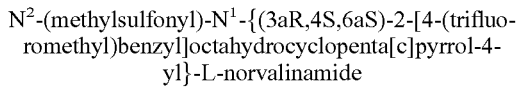

The title compound was prepared by substituting N¹-{(3aR,4S,6aS)-2-[4-(trifluoromethyl)benzyl]octahydrocyclopenta[c]pyrrol-4-yl}-L-norvalinamide from Example 382 for (S)-tert-butyl 2-amino-4-methylpentanoate in the procedure described in Example 242 Step A: ¹H NMR (500 MHz, pyridine-d₅) δ ppm 9.42 (d, J=9.2, 1H), 9.10 (d, J=7.4, 1H), 7.66 (d, J=8.0, 2H), 7.53 (d, J=8.0, 2H), 4.50-4.39 (m, 2H), 3.60 (d, J=13.7, 1H), 3.49 (d, J=13.7, 1H), 3.19 (s, 3H), 2.89 (dd, J=9.1, 2.4, 1H), 2.65-2.58 (m, 1H), 2.58-2.51 (m, 1H), 2.46-2.40 (m, 1H), 2.35 (dd, J=9.0, 2.5, 1H), 2.28-2.23 (m, 1H), 2.13 (dt, J=11.9, 6.0, 1H), 1.98 (tt, J=13.2, 6.5, 1H), 1.94-1.83 (m, 2H), 1.63 (dt, J=19.4, 7.6, 1H), 1.58-1.47 (m, 2H), 1.42 (dt, J=14.6, 6.3, 1H), 0.77 (t, J=7.4, 3H); MS (ESI+) m/z 462 (M+H)⁺.

Example 522

N²-(isopropylsulfonyl)-N¹-{(3aS,4R,6aR)-2-[3-(trifluoromethyl)benzyl]octahydrocyclopenta[c]pyrrol-4-yl}-L-leucinamide

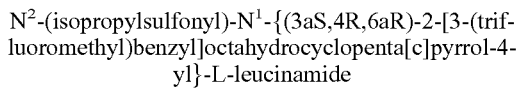

The title compound was prepared by substituting N¹-{(3aS,4R,6aR)-2-[3-(trifluoromethyl)benzyl]octahydrocyclopenta[c]pyrrol-4-yl}-L-leucinamide from Example 170 Step B for (S)-tert-butyl 2-amino-4-methylpentanoate and propane-2-sulfonylchloride for methanesulfonyl chloride in the procedure described in Example 242 Step A: ¹H NMR (500 MHz, pyridine-d₅) δ ppm 9.34 (d, J=9.2, 1H), 9.12 (d, J=7.4, 1H), 7.75 (d, J=12.2, 2H), 7.61 (d, J=7.5, 1H), 7.45 (t, J=7.8, 1H), 4.50-4.41 (m, 2H), 3.58 (d, J=13.5, 1H), 3.51 (d, J=13.4, 1H), 3.38-3.31 (m, 1H), 2.89 (d, J=9.6, 1H), 2.56 (qd, J=5.6, 1.6, 2H), 2.41-2.34 (m, 2H), 2.25 (dd, J=8.7, 6.7, 1H), 2.19-2.12 (m, 1H), 2.06-1.97 (m, 1H), 1.95-1.86 (m, 3H), 1.79-1.66 (m, 2H), 1.46 (d, J=6.8, 6H), 0.82 (d, J=6.5, 1H); MS (ESI+) m/z 504 (M+H)⁺.

Example 523

N²-(phenylsulfonyl)-N¹-{(3aS,4R,6aR)-2-[3-(trifluoromethyl)benzyl]octahydrocyclopenta[c]pyrrol-4-yl}-L-leucinamide

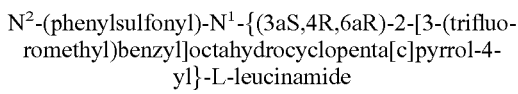

The title compound was prepared by substituting N¹-{(3aS,4R,6aR)-2-[3-(trifluoromethyl)benzyl]octahydrocyclopenta[c]pyrrol-4-yl}-L-leucinamide from Example 170 Step B for (S)-tert-butyl 2-amino-4-methylpentanoate and benzenesulfonyl chloride for methanesulfonyl chloride in the procedure described in Example 242 Step A: ¹H NMR (500 MHz, pyridine-d₅) δ ppm 10.09-9.90 (m, 1H), 8.77 (d, J=7.3, 1H), 8.18 (dd, J=8.0, 1.5, 2H), 7.78 (s, 1H), 7.62 (d, J=7.9, 1H), 7.51-7.34 (m, 5H), 4.36 (dd, J=9.4, 5.5, 1H), 4.16-4.08 (m, 1H), 3.59 (d, J=13.5, 1H), 3.49 (d, J=13.6, 1H), 2.60 (dd, J=9.1, 3.0, 1H), 2.51-2.42 (m, 1H), 2.33 (dd, J=8.9, 7.6, 1H), 2.27 (dd, J=11.1, 6.5, 2H), 2.24-2.17 (m, 1H), 2.05 (td, J=12.1, 5.9, 1H), 1.98 (dt, J=13.8, 6.7, 1H), 1.88-1.79 (m, 2H), 1.72 (ddd, J=13.7, 8.6, 5.4, 1H), 1.58 (dt, J=19.1, 7.0, 1H), 1.36 (dt, J=20.4, 6.2, 1H), 0.81 (d, J=6.7, 3H), 0.77 (d, J=6.5, 3H); MS (ESI+) m/z 538 (M+H)⁺.

Example 524

N²-(cyclopentylsulfonyl)-N¹-{(3aS,4R,6aR)-2-[3-(trifluoromethyl)benzyl]octahydrocyclopenta[c]pyrrol-4-yl}-L-leucinamide

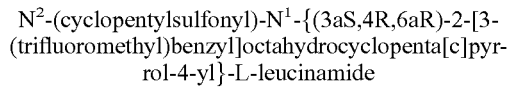

The title compound was prepared by substituting N¹-{(3aS,4R,6aR)-2-[3-(trifluoromethyl)benzyl]octahydrocyclopenta[c]pyrrol-4-yl}-L-leucinamide from Example 170 Step B for (S)-tert-butyl 2-amino-4-methylpentanoate and cyclopentanesulfonyl chloride for methanesulfonyl chloride in the procedure described in Example 242 Step A: ¹H NMR (500 MHz, pyridine-d₅) δ ppm 9.30 (d, J=9.6, 1H), 9.12 (d, J=7.5, 1H), 7.76 (d, J=15.6, 2H), 7.45 (dd, J=17.4, 9.7, 2H), 4.53-4.44 (m, 2H), 3.59 (d, J=13.4, 1H), 3.53 (d, J=13.7, 1H), 2.91 (d, J=8.0, 1H), 2.60-2.54 (m, 2H), 2.39 (t, J=9.0, 2H), 2.34-2.10 (m, 6H), 2.08-1.99 (m, 2H), 1.96-1.85 (m, 3H), 1.79-1.63 (m, 3H), 1.49-1.35 (m, 3H), 0.82 (d, J=6.6, 6H); MS (ESI+) m/z 530 (M+H)⁺.

Example 525 isopropyl(S)-4,4-dimethyl-1-oxo-1-((3aR,4S,6aS)-2-(4-(trifluoromethyl)benzyl)octahydrocyclopenta[c]pyrrol-4-ylamino)pentan-2-ylcarbamate

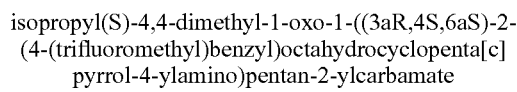

The title compound was prepared by substituting 4-methyl-N¹-{(3aR,4S,6aS)-2-[4-(trifluoromethyl)benzyl]octahydrocyclopenta[c]pyrrol-4-yl}-L-leucinamide from Example 519 Step B for (S)-tert-butyl 2-amino-4-methylpentanoate and isopropyl carbonochloridate for methanesulfonyl chloride in the procedure described in Example 242 Step A: ¹H NMR (400 MHz, pyridine-d₅) δ ppm 8.38 (d, J=9.0, 1H), 7.65 (d, J=8.1, 2H), 7.51 (d, J=8.0, 2H), 5.08 (dt, J=12.8, 6.5, 1H), 4.81 (td, J=8.5, 5.3, 1H), 4.46-4.38 (m, 1H), 3.57 (d, J=13.7, 1H), 3.46 (d, J=13.8, 1H), 2.88 (dd, J=8.8, 1.7, 1H), 2.63-2.54 (m, 1H), 2.49 (tt, J=4.3, 3.3, 1H), 2.43-2.36 (m, 1H), 2.31 (dd, J=8.9, 2.5, 1H), 2.25-2.21 (m, 1H), 2.21-2.17 (m, 1H), 2.16 (d, J=4.8, 1H), 2.10-1.99 (m, 1H), 1.90-1.77 (m, 2H), 1.59 (ddd, J=14.7, 12.6, 7.8, 1H), 1.41-1.32 (m, 1H), 1.23 (d, J=6.2, 3H), 1.14 (d, J=6.2, 3H), 0.98 (s, 9H); MS (ESI+) m/z 498 (M+H)⁺.

Example 526 isopropyl(S)-3,3-dimethyl-1-oxo-1-((3aR,4S,6aS)-2-(4-(trifluoromethyl)benzyl)octahydrocyclopenta[c]pyrrol-4-ylamino)butan-2-ylcarbamate

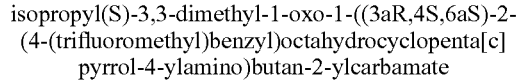

The title compound was prepared by substituting 3-methyl-N¹-{(3aR,4S,6aS)-2-[4-(trifluoromethyl)benzyl]octahydrocyclopenta[c]pyrrol-4-yl}-L-valinamide from Example 520 Step B for (S)-tert-butyl 2-amino-4-methylpentanoate and isopropyl carbonochloridate for methanesulfonyl chloride in the procedure described in Example 242 Step A: ¹H NMR (400 MHz, pyridine-d₅) δ ppm 8.84 (d, J=7.3, 1H), 8.05 (d, J=9.6, 1H), 7.66 (d, J=8.1, 2H), 7.52 (d, J=8.0, 2H), 5.06 (dt, J=12.6, 6.3, 1H), 4.67 (d, J=9.8, 1H), 4.44 (p, J=7.3, 1H), 3.61 (d, J=13.8, 1H), 3.47 (d, J=13.7, 1H), 2.89 (dd, J=9.0, 2.5, 1H), 2.66-2.58 (m, 1H), 2.57-2.50 (m, 1H), 2.49-2.41 (m, 1H), 2.29 (dt, J=15.8, 7.5, 2H), 2.00 (td, J=11.5, 5.3, 1H), 1.85 (dt, J=20.3, 6.6, 1H), 1.54 (dt, J=15.1, 7.3, 1H), 1.41-1.30 (m, 1H), 1.24 (d, J=6.2, 3H), 1.19 (s, 9H), 1.12 (d, J=6.0, 3H); MS (ESI+) m/z 484 (M+H)⁺.

Example 527 cyclopentyl(S)-1-oxo-1-((3aR,4S,6aS)-2-(4-(trifluoromethyl)benzyl)octahydrocyclopenta[c]pyrrol-4-ylamino)pentan-2-ylcarbamate The title compound was prepared by substituting N$^1$-{(3aR,4S,6aS)-2-[4-(trifluoromethyl)benzyl]octahydrocyclopenta[c]pyrrol-4-yl}-L-norvalinamide from Example 382 for (S)-tert-butyl 2-amino-4-methylpentanoate and cyclopentyl carbonochloridate for methanesulfonyl chloride in the procedure described in Example 242 Step A: $^1$H NMR (400 MHz, pyridine-d$_5$) δ ppm 8.76 (d, J=1.7, 1H), 8.22 (d, J=8.4, 1H), 7.65 (d, J=8.1, 2H), 7.51 (d, J=7.9, 2H), 5.32-5.24 (m, 1H), 4.71 (dd, J=14.3, 7.9, 1H), 4.49-4.39 (m, 1H), 3.57 (d, J=13.7, 1H), 3.46 (d, J=14.0, 1H), 2.87 (dd, J=8.8, 1.7, 1H), 2.63-2.50 (m, 2H), 2.41 (dd, J=8.6, 7.5, 1H), 2.31 (dd, J=8.0, 1.8, 1H), 2.27-2.20 (m, 1H), 2.12-1.98 (m, 2H), 1.93-1.82 (m, 2H), 1.81-1.73 (m, 2H), 1.73-1.65 (m, 2H), 1.65-1.55 (m, 3H), 1.54-1.45 (m, 2H), 1.45-1.31 (m, 3H), 0.81 (t, J=7.4, 3H); MS (ESI+) m/z 496 (M+H)$^+$.

Example 528

N$^2$-(2,2-dimethylpropanoyl)-N$^1$-{(3aR,4S,6aS)-2-[4-(trifluoromethyl)benzyl]octahydrocyclopenta[c]pyrrol-4-yl}-L-norvalinamide The title compound was prepared by substituting N$^1$-{(3aR,4S,6aS)-2-[4-(trifluoromethyl)benzyl]octahydrocyclopenta[c]pyrrol-4-yl}-L-norvalinamide from Example 382 for (S)-tert-butyl 2-amino-4-methylpentanoate and pivaloyl chloride for methanesulfonyl chloride in the procedure described in Example 242 Step A: $^1$H NMR (500 MHz, pyridine-d$_5$) δ ppm 8.70 (d, J=7.6, 1H), 7.72 (d, J=7.9, 1H), 7.65 (d, J=8.0, 2H), 7.51 (d, J=8.0, 2H), 4.45-4.36 (m, 1H), 3.57 (d, J=13.9, 1H), 3.47 (d, J=13.8, 1H), 2.85 (dd, J=9.1, 2.0, 1H), 2.60-2.51 (m, 2H), 2.42 (dd, J=8.8, 6.9, 1H), 2.32 (dd, J=8.9, 2.0, 1H), 2.28-2.23 (m, 1H), 2.06 (dq, J=12.1, 6.0, 1H), 1.97 (dq, J=9.4, 6.4, 1H), 1.90-1.75 (m, 2H), 1.59 (dt, J=14.2, 7.3, 1H), 1.51-1.37 (m, 3H), 1.36 (s, 1H), 1.31 (s, 9H), 0.79 (t, J=7.4, 3H); MS (ESI+) m/z 468 (M+H)$^+$.

Example 529 tert-butyl(S)-1-((3aR,4S,6aS)-2-(3-chloro-4-fluorophenylsulfonyl)octahydrocyclopenta[c]pyrrol-4-ylamino)-1-oxopentan-2-yl(methyl)carbamate The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (S)-N-((3aS,4R,6aR)-2-benzyloctahydrocyclopenta[c]pyrrol-4-yl)-4-methyl-2-morpholinopentanamide and 3-chloro-4-fluorobenzene-1-sulfonyl chloride for 3-(trifluoromethyl)benzene-1-sulfonyl chloride in the procedure described in Example 319: $^1$H NMR (300 MHz, CDCl$_3$) ppm 7.88 (dd, J=6.7, 2.2 Hz, 1H), 7.70 (ddd, J=8.6, 4.4, 2.2 Hz, 1H), 7.26-7.33 (m, 1H), 5.73-6.40 (m, 1H), 4.43 (d, J=4.3 Hz, 1H), 3.85-3.95 (m, 1H), 3.40-3.52 (m, 1H), 3.09 (dd, J=9.6, 3.2 Hz, 1H), 3.05 (dd, J=10.1, 8.3 Hz, 1H), 2.97 (dd, J=9.6, 7.4 Hz, 1H), 2.73 (s, 3H), 2.63-2.76 (m, 2H), 2.32-2.42 (m, 1H), 1.76-2.09 (m, 3H), 1.58-1.72 (m, 1H), 1.46 (s, 9H), 1.19-1.34 (m, 3H), 0.94 (t, J=7.3 Hz, 3H); MS (ESI+) m/z 532 (M+H)$^+$.

Example 530 tert-butyl methyl((S)-1-oxo-1-((3aR,4S,6aS)-2-(pyridin-3-ylsulfonyl)octahydrocyclopenta[c]pyrrol-4-ylamino)pentan-2-yl)carbamate The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (S)-N-((3aS,4R,6aR)-2-benzyloctahydrocyclopenta[c]pyrrol-4-yl)-4-methyl-2-morpholinopentanamide and pyridine-3-sulfonyl chloride for 3-(trifluoromethyl)benzene-1-sulfonyl chloride in the procedure described in Example 319: $^1$H NMR (300 MHz, CDCl$_3$) δ ppm 9.01-9.04 (bs, 1H), 8.80-8.85 (bs, 1H), 8.09 (ddd, J=8.0, 2.2, 1.7 Hz, 1H), 7.49 (dd, J=8.0, 4.8 Hz, 1H), 5.78-6.33 (m, 1H), 4.32-4.52 (m, 1H), 3.84-3.95 (m, 1H), 3.40-3.52 (m, 1H), 3.05-3.15 (m, 2H), 3.02 (dd, J=9.7, 7.4 Hz, 1H), 2.73 (s, 3H), 2.61-2.75 (m, 1H), 2.33-2.50 (m, 1H), 1.77-2.07 (m, 3H), 1.53-1.71 (m, 2H), 1.46 (s, 9H), 1.18-1.32 (m, 3H), 0.94 (t, J=7.3 Hz, 3H); MS (ESI+) m/z 481 (M+H)$^+$.

Example 531 tert-butyl methyl((S)-1-oxo-1-((3aR,4S,6aS)-2-(thiophen-2-ylsulfonyl)octahydrocyclopenta[c]pyrrol-4-ylamino)pentan-2-yl)carbamate The title compound was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (S)-N-((3aS,4R,6aR)-2-benzyloctahydrocyclopenta[c]pyrrol-4-yl)-4-methyl-2-morpholinopentanamide and thiophene-2-sulfonyl chloride for 3-(trifluoromethyl)benzene-1-sulfonyl chloride in the procedure described in Example 319: $^1$H NMR (300 MHz, CDCl$_3$) δ ppm 7.62 (dd, J=5.0, 1.3 Hz, 1H), 7.56 (dd, J=3.7, 1.3 Hz, 1H), 7.16 (dd, J=5.0, 3.7 Hz, 1H), 5.75-6.30 (m, 1H), 4.33-4.53 (m, 1H), 3.88-3.97 (m, 1H), 3.37 (dd, J=10.2, 3.6 Hz, 1H), 3.04-3.20 (m, 3H), 2.73 (s, 3H), 2.63-2.75 (m, 1H), 2.36-2.50 (m, 1H), 1.77-2.10 (m, 3H), 1.55-1.71 (m, 1H), 1.46 (s, 9H), 1.35-1.55 (m, 2H), 1.19-1.32 (m, 2H), 0.94 (t, J=7.3 Hz, 3H); MS (ESI+) m/z 486 (M+H)$^+$.

Example 532

N$^2$-methyl-N$^1$-((3aR,4S,6aS)-2-{[4-(trifluoromethoxy)phenyl]sulfonyl}octahydrocyclopenta[c]pyrrol-4-yl)-L-norvalinamide Step A: tert-Butyl methyl((S)-1-oxo-1-((3aR,4S,6aS)-2-{[4-(trifluoromethoxy)phenyl]sulfonyl}octahydrocyclopenta[c]pyrrol-4-ylamino)pentan-2-yl)carbamate was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (S)-N-((3aS,4R,6aR)-2-benzyloctahydrocyclopenta[c]pyrrol-4-yl)-4-methyl-2-morpholinopentanamide and 4-(trifluoromethoxy)benzene-1-sulfonyl chloride for 3-(trifluoromethyl)benzene-1-sulfonyl chloride in the procedure described in Example 319: MS (APCI+) m/z 564 (M+H)$^+$.

Step B: The title compound was prepared by substituting tert-butyl methyl((S)-1-oxo-1-((3aR,4S,6aS)-2-{[4-(trifluoromethoxy)phenyl]sulfonyl}octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)

carbamate in the procedure described in Example 348: $^1$H NMR (500 MHz, pyridine-$d_5$) δ ppm 9.99-10.02 (m, 1H), 8.05-8.07 (m, 2H), 7.50-7.52 (m, 2H), 4.55-4.59 (m, 1H), 4.26-4.36 (m, 1H), 3.73 (dd, J=9.9, 2.8 Hz, 1H), 3.18 (dd, J=9.6, 2.9 Hz, 1H), 3.11 (dd, J=9.9, 7.9 Hz, 1H), 2.92 (s, 3H), 2.88-2.94 (m, 1H), 2.73-2.86 (m, 1H), 2.62-2.68 (m, 1H), 2.19-2.40 (m, 2H), 1.97-2.07 (m, 2H), 1.77-1.87 (m, 1H), 1.51-1.75 (m, 2H), 1.31-1.38 (m, 1H), 0.85 (t, J=7.3 Hz, 3H); MS (ESI+) m/z 464 (M+H)$^+$.

Example 533

N$^2$-methyl-N$^1$-[(3aR,4S,6aS)-2-(thien-2-ylsulfonyl)octahydrocyclopenta[c]pyrrol-4-yl]-L-norvalinamide The title compound was prepared by substituting tert-butyl methyl((S)-1-oxo-1-((3aR,4S,6aS)-2-(thiophen-2-ylsulfonyl)octahydrocyclopenta[c]pyrrol-4-ylamino)pentan-2-yl)carbamate from Example 531 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 10.02-10.04 (m, 1H), 7.86 (d, J=5.4 Hz, 1H), 7.76 (d, J=4.2 Hz, 1H), 7.18-7.22 (m, 1H), 6.93-6.93 (m, 1H), 4.65 (dd, J=9.1, 4.8 Hz, 1H), 4.28-4.36 (m, 1H), 3.72 (dd, J=10.0, 3.0 Hz, 1H), 3.24 (dd, J=10.0, 8.0 Hz, 1H), 3.19 (dd, J=9.7, 3.1 Hz, 1H), 3.04 (dd, J=9.7, 7.7 Hz, 1H), 2.94 (s, 3H), 2.78-2.84 (m, 1H), 2.66-2.72 (m, 1H), 2.35-2.42 (m, 1H), 2.22-2.30 (m, 1H), 1.98-2.11 (m, 2H), 1.81-1.89 (m, 1H), 1.66-1.77 (m, 1H), 1.54-1.66 (m, 1H), 1.31-1.38 (m, 1H), 0.86 (t, J=7.3 Hz, 3H); MS (ESI+) m/z 386 (M+H)$^+$.

Example 534

N$^1$-{(3aR,4S,6aS)-2-[(3-chloro-4-fluorophenyl)sulfonyl]octahydrocyclopenta[c]pyrrol-4-yl}-N$^2$-methyl-L-norvalinamide The title compound was prepared by substituting tert-butyl (S)-1-((3aR,4S,6aS)-2-(3-chloro-4-fluorophenylsulfonyl)octahydrocyclopenta[c]pyrrol-4-ylamino)-1-oxopentan-2-yl(methyl)carbamate from Example 529 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 10.05-10.07 (m, 1H), 8.19 (dd, J=6.8, 2.2 Hz, 1H), 7.89 (ddd, J=8.6, 4.4, 2.2 Hz, 1H), 7.44 (t, J=8.7 Hz, 1H), 4.66 (dd, J=9.1, 4.8 Hz, 1H), 4.27-4.36 (m, 1H), 3.72 (dd, J=9.9, 2.9 Hz, 1H), 3.06-3.18 (m, 2H), 2.94 (s, 3H), 2.90-2.93 (m, 1H), 2.80-2.85 (m, 1H), 2.67-2.73 (m, 1H), 2.35-2.42 (m, 1H), 2.22-2.30 (m, 1H), 1.99-2.10 (m, 2H), 1.82-1.90 (m, 1H), 1.66-1.76 (m, 1H), 1.53-1.65 (m, 1H), 1.33-1.40 (m, 1H), 0.85 (t, J=7.3 Hz, 3H); MS (ESI+) m/z 432 (M+H)$^+$.

Example 535

N$^2$-methyl-N$^1$-[(3aR,4S,6aS)-2-(pyridin-3-ylsulfonyl)octahydrocyclopenta[c]pyrrol-4-yl]-L-norvalinamide The title compound was prepared by substituting tert-butyl methyl((S)-1-oxo-1-((3aR,4S,6aS)-2-(pyridin-3-ylsulfonyl)octahydrocyclopenta[c]pyrrol-4-ylamino)pentan-2-yl)carbamate from Example 530 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 10.18-10.21 (m, 1H), 9.34 (d, J=2.3 Hz, 1H), 8.92 (dd, J=4.8, 1.6 Hz, 1H), 8.25 (ddd, J=8.0, 2.4, 1.6 Hz, 1H), 7.50 (dd, J=8.0, 4.8 Hz, 1H), 4.73 (dd, J=9.3, 4.6 Hz, 1H), 4.30 (p, J=6.3 Hz, 1H), 3.71 (dd, J=10.0, 2.9 Hz, 1H), 3.08-3.21 (m, 2H), 2.87-3.07 (m, 4H), 2.78-2.83 (m, 1H), 2.64-2.70 (m, 1H), 2.40-2.47 (m, 1H), 2.26-2.34 (m, 1H), 1.98-2.17 (m, 2H), 1.78-1.92 (m, 1H), 1.55-1.77 (m, 2H), 1.29-1.36 (m, 1H), 0.84 (t, J=7.3 Hz, 3H); MS (ESI+) m/z 381 (M+H)$^+$.

Example 536

N$^1$-{(3aR,4S,6aS)-2-[(4-cyanophenyl)sulfonyl]octahydrocyclopenta[c]pyrrol-4-yl}-N$^2$-methyl-L-norvalinamide Step A: tert-Butyl methyl((S)-1-oxo-1-((3aR,4S,6aS)-2-[(4-cyanophenyl)sulfonyl]octahydrocyclopenta[c]pyrrol-4-ylamino)pentan-2-yl)carbamate was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (S)-N-((3aS,4R,6aR)-2-benzyloctahydrocyclopenta[c]pyrrol-4-yl)-4-methyl-2-morpholinopentanamide and 4-cyanobenzene-1-sulfonyl chloride for 3-(trifluoromethyl)benzene-1-sulfonyl chloride in the procedure described in Example 319: MS (APCI+) m/z 505 (M+H)$^+$.

Step B: The title compound was prepared by substituting tert-butyl methyl((S)-1-oxo-1-((3aR,4S,6aS)-2-[(4-cyanophenyl)sulfonyl]octahydrocyclopenta[c]pyrrol-4-ylamino)pentan-2-yl)carbamate from Step A for tert-butyl (S)-1-((3aR,4S,6aS)-2-benzyloctahydrocyclopenta[c]pyrrol-4-ylamino)-4-methyl-1-oxopentan-2-yl(methyl)carbamate in the procedure described in Example 348: $^1$H NMR (500 MHz, pyridine-$d_5$) δ ppm 10.09-10.11 (m, 1H), 8.05-8.07 (m, 2H), 7.94-7.96 (m, 2H), 4.68 (dd, J=9.2, 4.6 Hz, 1H), 4.26-4.35 (m, 1H), 3.71 (dd, J=10.0, 3.0 Hz, 1H), 3.14-3.18 (m, 2H), 2.93-2.99 (m, 1H), 2.95 (s, 3H), 2.80-2.86 (m, 1H), 2.67-2.73 (m, 1H), 2.36-2.43 (m, 1H), 2.23-2.31 (m, 1H), 1.99-2.14 (m, 2H), 1.83-1.90 (m, 1H), 1.65-1.75 (m, 1H), 1.55-1.65 (m, 1H), 1.31-1.40 (m, 1H), 0.85 (t, J=7.3 Hz, 3H); MS (ESI+) m/z 405 (M+H)$^+$.

Example 537

N$^1$-{(3aR,4S,6aS)-2-[(4-methoxyphenyl)sulfonyl]octahydrocyclopenta[c]pyrrol-4-yl}-N$^2$-methyl-L-norvalinamide Step A: tert-Butyl methyl((S)-1-((3aR,4S,6aS)-octahydrocyclopenta[c]pyrrol-4-ylamino)-1-oxopentan-2-yl)carbamate was prepared by substituting tert-butyl methyl((S)-1-oxo-1-((3aR,4S,6aS)-2-benzyloctahydrocyclopenta[c]pyrrol-4-ylamino)pentan-2-yl)carbamate from Example 313 Step A for (S)-N-((3aS,4R,6aR)-2-benzyloctahydrocyclopenta[c]pyrrol-4-yl)-4-methyl-2-morpholinopentanamide in the procedure described in Example 319 Step A: $^1$H NMR (500 MHz, pyridine-$d_5$) δ ppm 8.44-8.32 (m, 1H), 4.76-4.57 (m, 1H), 4.41-4.26 (m, 1H), 3.30 (dd, J=11.1, 1.6, 1H), 3.17-2.95 (m, 5H), 2.78 (d, J=9.8, 1H), 2.60 (s, 2H), 2.11-1.93 (m, 2H), 1.91-1.71 (m, 2H), 1.62-1.53 (m, 1H), 1.46 (s, 9H), 1.40-1.24 (m, 4H), 0.84 (t, J=6.0, 3H); MS (ESI+) m/z 340 (M+H)$^+$.

Step B: The title compound was prepared by combining tert-butyl methyl((S)-1-((3aR,4S,6aS)-octahydrocyclopenta[c]pyrrol-4-ylamino)-1-oxopentan-2-yl)carbamate (0.075 g, 0.221 mmol) from Step A with 4-methoxybenzene-1-sulfonyl chloride (0.050 g, 0.243 mmol) and diisopropylethylamine (0.042 mL, 0.243 mmol) in dichloromethane (5 mL). The reaction was stirred at ambient temperature overnight and volatiles were removed in vacuo. To the resulting mixture was added 4 N HCl/dioxane (5 mL), and the resultant reaction mixture was stirred at ambient temperature for 30 minutes. The volatiles were removed in vacuo, and the crude material was purified by preparative reverse-phase HPLC (Phenomenex® Luna® C8(2) 5 µm 100 Å AXIA column, 30×75 mm, 10-95% gradient of acetonitrile in 0.1% aqueous trifluoroacetic acid, flow rate 50 mL/minute) to afford the title compound as the trifluoroacetic acid salt: $^1$H NMR (500 MHz, pyridine-$d_5$) δ ppm 9.83 (d, J=6.7 Hz, 1H), 7.94-7.97 (m, 2H), 7.09-7.13 (m, 2H), 4.39 (t, J=6.8 Hz, 1H), 4.32 (p, J=6.5 Hz, 1H), 3.73 (s, 3H), 3.69-3.76 (m, 1H), 3.04-3.19 (m, 2H), 2.87-2.95 (m, 1H), 2.90 (s, 3H), 2.64-2.71 (m, 1H), 2.56-2.64 (m, 1H), 2.07-2.19 (m, 2H), 1.96-2.04 (m, 1H), 1.86-1.96 (m, 1H), 1.62-1.71 (m, 1H), 1.47-1.61 (m, 2H), 1.29-1.39 (m, 1H), 0.80 (t, J=7.3 Hz, 3H); MS (ESI+) m/z 410 (M+H)$^+$.

Example 538

$N^1$-((3aR,4S,6aS)-2-{[3,5-bis(trifluoromethyl)phenyl]sulfonyl}octahydrocyclopenta[c]pyrrol-4-yl)-$N^2$-methyl-L-norvalinamide The title compound was prepared by substituting 3,5-bis(trifluoromethyl)phenyl-1-sulfonyl chloride for 4-methoxybenzene-1-sulfonyl chloride in the procedure described in Example 537: $^1$H NMR (500 MHz, pyridine-$d_5$) δ ppm 9.73 (d, J=6.7 Hz, 1H), 8.84 (s, 1H), 8.63 (s, 2H), 8.46-8.47 (bs, 1H), 4.47 (t, J=6.7 Hz, 1H), 4.26-4.34 (m, 1H), 3.87 (dd, J=10.0, 2.6 Hz, 1H), 3.20-3.29 (m, 2H), 3.03 (dd, J=9.5, 7.7 Hz, 1H), 2.96 (s, 3H), 2.69-2.77 (m, 1H), 2.60-2.69 (m, 1H), 2.04-2.17 (m, 2H), 1.90-2.05 (m, 2H), 1.66-1.74 (m, 1H), 1.43-1.61 (m, 2H), 1.27-1.37 (m, 1H), 0.78 (t, J=7.3 Hz, 3H).

Example 539

$N^1$-{(3aR,4S,6aS)-2-[(2-chloro-4-fluorophenyl)sulfonyl]octahydrocyclopenta[c]pyrrol-4-yl}-$N^2$-methyl-L-norvalinamide The title compound was prepared by substituting 2-chloro-4-fluorophenyl-1-sulfonyl chloride for 4-methoxybenzene-1-sulfonyl chloride in the procedure described in Example 537: $^1$H NMR (500 MHz, pyridine-$d_5$) δ ppm 9.84-9.86 (m, 1H), 8.22 (dd, J=8.9, 6.0 Hz, 1H), 7.45 (dd, J=8.5, 2.4 Hz, 1H), 7.19-7.23 (m, 1H), 4.46 (t, J=6.8 Hz, 1H), 4.30-4.39 (m, 1H), 3.81 (dd, J=10.1, 3.0 Hz, 1H), 3.48 (dd, J=10.1, 7.7 Hz, 1H), 3.23-3.35 (m, 2H), 2.94 (s, 3H), 2.75-2.82 (m, 1H), 2.67-2.75 (m, 1H), 2.02-2.19 (m, 3H), 1.92-1.99 (m, 1H), 1.73 (dq, J=12.5, 8.1 Hz, 1H), 1.47-1.62 (m, 2H), 1.39 (ddt, J=9.1, 13.0, 6.5 Hz, 1H), 0.80 (t, J=7.3 Hz, 3H); MS (ESI-) m/z 430 (M-H)$^-$.

Example 540

$N^2$-methyl-$N^1$-[(3aR,4S,6aS)-2-(1-naphthylsulfonyl)octahydrocyclopenta[c]pyrrol-4-yl]-L-norvalinamide The title compound was prepared by substituting 1-naphthyl-1-sulfonyl chloride for 4-methoxybenzene-1-sulfonyl chloride in the procedure described in Example 537: $^1$H NMR (500 MHz, pyridine-$d_5$) δ ppm 9.74-9.78 (m, 1H), 9.25 (d, J=8.7 Hz, 1H), 8.43 (d, J=7.3 Hz, 1H), 8.12 (d, J=8.2 Hz, 1H), 7.98 (d, J=8.2 Hz, 1H), 7.69 (t, J=7.8 Hz, 1H), 7.54-7.57 (m, 1H), 4.38 (t, J=6.8 Hz, 1H), 4.26-4.32 (m, 1H), 3.83 (dd, J=9.9, 2.7 Hz, 1H), 3.29 (dd, J=9.9, 7.8 Hz, 1H), 3.22 (dd, J=9.7, 2.7 Hz, 1H), 3.08 (dd, J=9.6, 7.5 Hz, 1H), 2.89 (s, 3H), 2.59-2.66 (m, 1H), 2.50-2.59 (m, 1H), 2.02-2.15 (m, 2H), 1.80-2.00 (m, 2H), 1.57-1.67 (m, 1H), 1.45-1.55 (m, 2H), 1.23-1.30 (m, 1H), 0.78 (t, J=7.3 Hz, 3H); MS (ESI-) m/z 428 (M-H)$^-$.

Example 541

$N^1$-((3aR,4S,6aS)-2-{[4-bromo-3-(trifluoromethyl)phenyl]sulfonyl}octahydrocyclopenta[c]pyrrol-4-yl)-$N^2$-methyl-L-norvalinamide The title compound was prepared by substituting 4-bromo-3-(trifluoromethyl)phenyl-1-sulfonyl chloride for 4-methoxybenzene-1-sulfonyl chloride in the procedure described in Example 537: $^1$H NMR (500 MHz, pyridine-$d_5$) δ ppm 9.81-9.83 (m, 1H), 8.32 (d, J=2.0 Hz, 1H), 8.04 (dd, J=8.3, 2.0 Hz, 1H), 8.01 (d, J=8.3 Hz, 1H), 6.60-8.44 (bs, 1H), 4.33-4.38 (m, 1H), 4.26-4.33 (m, 1H), 3.82 (dd, J=9.9, 2.6 Hz, 1H), 3.21 (dd, J=9.8, 2.7 Hz, 1H), 3.18 (dd, J=9.8, 7.9 Hz, 1H), 2.96 (dd, J=9.6, 7.5 Hz, 1H), 2.89 (s, 3H), 2.69-2.76 (m, 1H), 2.61-2.69 (m, 1H), 2.05-2.17 (m, 2H), 1.97-2.05 (m, 1H), 1.89-1.97 (m, 1H), 1.64-1.72 (m, 1H), 1.45-1.59 (m, 2H), 1.34 (ddt, J=9.3, 13.0, 6.5 Hz, 1H), 0.79 (t, J=7.3 Hz, 3H); MS (ESI-) m/z 524 (M-H)$^-$.

Example 542

$N^1$-{(3aR,4S,6aS)-2-[(3,4-dichlorophenyl)sulfonyl]octahydrocyclopenta[c]pyrrol-4-yl}-$N^2$-methyl-L-norvalinamide The title compound was prepared by substituting 3,4-dichlorophenyl-1-sulfonyl chloride for 4-methoxybenzene-1-sulfonyl chloride in the procedure described in Example 537: $^1$H NMR (500 MHz, pyridine-$d_5$) δ ppm 9.84-9.86 (m, 1H), 7.41-8.78 (bs, 1H), 7.82 (dd, J=8.3, 2.1 Hz, 1H), 7.69 (d, J=8.3 Hz, 1H), 7.58-7.59 (bs, 1H), 4.45 (t, J=6.8 Hz, 1H), 4.30 (p, J=6.7 Hz, 1H), 3.76 (dd, J=9.9, 2.7 Hz, 1H), 3.16 (dd, J=9.9, 2.9 Hz, 1H), 3.14 (dd, J=10.0, 8.0 Hz, 1H), 2.94 (s, 3H), 2.89-2.95 (m, 1H), 2.70-2.75 (m, 1H), 2.62-2.69 (m, 1H), 2.06-2.18 (m, 2H), 1.97-2.04 (m, 1H), 1.90-1.96 (m, 1H), 1.65-1.73 (m, 1H), 1.46-1.62 (m, 2H), 1.30-1.37 (m, 1H), 0.80 (t, J=7.3 Hz, 3H); MS (ESI-) m/z 446 (M-H)$^-$.

Example 543

$N^1$-{(3aR,4S,6aS)-2-[(4-tert-butylphenyl)sulfonyl]octahydrocyclopenta[c]pyrrol-4-yl}-$N^2$-methyl-L-norvalinamide The title compound was prepared by substituting 4-tert-butylphenyl-sulfonyl chloride for 4-methoxybenzene-1-sulfonyl chloride in the procedure described in Example 537: $^1$H NMR (500 MHz, pyridine-$d_5$) δ ppm 9.85 (d, J=6.8 Hz, 1H), 7.96-7.99 (m, 2H), 7.58-7.66 (m, 2H), 4.43 (t, J=6.8 Hz, 1H), 4.27-4.33 (m, 1H), 3.78 (dd, J=9.8, 2.5 Hz, 1H), 3.20 (dd, J=9.6, 2.6 Hz, 1H), 3.11 (dd, J=9.8, 7.7 Hz, 1H), 2.93 (s, 3H), 2.90 (dd, J=9.5, 7.6 Hz, 1H), 2.47-2.62 (m, 2H), 2.08-2.18 (m, 2H), 1.93-2.01 (m, 1H), 1.85-1.92 (m, 1H), 1.60-1.68 (m, 1H), 1.48-1.59 (m, 2H), 1.28-1.39 (m, 1H), 1.26 (s, 9H), 0.81 (t, J=7.3 Hz, 3H); MS (ESI-0 m/z 436 (M+H)$^+$.

Example 544

N$^1$-[(3aR,4S,6aS)-2-(1,1'-biphenyl-4-ylsulfonyl)octahydrocyclopenta[c]pyrrol-4-yl]-N$^2$-methyl-L-norvalinamide The title compound was prepared by substituting 1,1'-biphenyl-4-sulfonyl chloride for 4-methoxybenzene-1-sulfonyl chloride in the procedure described in Example 537: $^1$H NMR (500 MHz, pyridine-d$_5$) δ ppm 9.86-9.88 (m, 1H), 8.07-8.09 (m, 2H), 7.86-7.88 (m, 2H), 7.71-7.75 (m, 2H), 7.48-7.53 (m, 2H), 7.41-7.47 (m, 1H), 4.44 (t, J=6.8 Hz, 1H), 4.29-4.36 (m, 1H), 3.78 (dd, J=9.9, 2.7 Hz, 1H), 3.21 (dd, J=9.7, 2.7 Hz, 1H), 3.15 (dd, J=9.8, 7.9 Hz, 1H), 2.95 (dd, J=9.5, 7.7 Hz, 1H), 2.93 (s, 3H), 2.64-2.71 (m, 1H), 2.56-2.64 (m, 1H), 2.06-2.19 (m, 2H), 1.97-2.04 (m, 1H), 1.88-1.97 (m, 1H), 1.62-1.73 (m, 1H), 1.48-1.62 (m, 2H), 1.30-1.40 (m, 1H), 0.80 (t, J=7.3 Hz, 3H); MS (ESI+) m/z 456 (M+H)$^+$.

Example 545

N$^1$-{(3aR,4S,6aS)-2-[(3,4-dimethoxyphenyl)sulfonyl]octahydrocyclopenta[c]pyrrol-4-yl}-N$^2$-methyl-L-norvalinamide The title compound was prepared by substituting 3,4-dimethoxyphenyl-sulfonyl chloride for 4-methoxybenzene-1-sulfonyl chloride in the procedure described in Example 537: $^1$H NMR (500 MHz, pyridine-d$_5$) δ ppm 9.86 (d, J=6.9 Hz, 1H), 7.66 (dd, J=8.4, 2.0 Hz, 1H), 7.55 (d, J=2.0 Hz, 1H), 7.08 (d, J=8.4 Hz, 1H), 4.38-4.43 (m, 1H), 4.31-4.38 (m, 1H), 3.81 (s, 3H), 3.78 (dd, J=10.2, 2.8 Hz, 1H), 3.76 (s, 3H), 3.17-3.23 (m, 2H), 3.00 (dd, J=9.6, 7.5 Hz, 1H), 2.91 (s, 3H), 2.68-2.75 (m, 1H), 2.60-2.68 (m, 1H), 2.06-2.18 (m, 2H), 1.98-2.06 (m, 1H), 1.88-1.98 (m, 1H), 1.64-1.73 (m, 1H), 1.49-1.59 (m, 2H), 1.33-1.40 (m, 1H), 0.79 (t, J=7.3 Hz, 3H); MS (ESI−) m/z 438 (M−H)$^-$.

Example 546

N$^1$-{(3aR,4S,6aS)-2-[(3-cyanophenyl)sulfonyl]octahydrocyclopenta[c]pyrrol-4-yl}-N$^2$-methyl-L-norvalinamide The title compound was prepared by substituting 3-cyanophenyl-sulfonyl chloride for 4-methoxybenzene-1-sulfonyl chloride in the procedure described in Example 537: $^1$H NMR (500 MHz, pyridine-d$_5$) δ ppm 9.86-9.88 (m, 1H), 8.56 (s, 1H), 8.18 (d, J=8.0 Hz, 1H), 7.96 (d, J=7.8 Hz, 1H), 7.66 (t, J=7.8 Hz, 1H), 4.39-4.44 (m, 1H), 4.23-4.32 (m, 1H), 3.77 (dd, J=10.0, 2.7 Hz, 1H), 3.18 (dd, J=9.8, 2.9 Hz, 1H), 3.14 (dd, J=9.9, 7.8 Hz, 1H), 2.93-2.96 (m, 1H), 2.91 (s, 3H), 2.65-2.72 (m, 1H), 2.58-2.65 (m, 1H), 2.04-2.18 (m, 2H), 1.95-2.03 (m, 1H), 1.87-1.95 (m, 1H), 1.68 (dq, J=12.3, 8.1 Hz, 1H), 1.45-1.59 (m, 2H), 1.27-1.38 (m, 1H), 0.79 (t, J=7.3 Hz, 3H); MS (ESI+) m/z 405 (M+H)$^+$.

Example 547

N$^1$-[(3aR,4S,6aS)-2-(2-furylsulfonyl)octahydrocyclopenta[c]pyrrol-4-yl]-N$^2$-methyl-L-norvalinamide The title compound was prepared by substituting 2-furyl-sulfonyl chloride for 4-methoxybenzene-1-sulfonyl chloride in the procedure described in Example 537: $^1$H NMR (500 MHz, pyridine-d$_5$) δ ppm 9.88-9.90 (m, 1H), 7.86-7.87 (m, 1H), 7.26-7.28 (m, 1H), 6.58 (dd, J=3.4, 1.8 Hz, 1H), 4.42 (t, J=6.8 Hz, 1H), 4.24-4.33 (m, 1H), 3.79 (dd, J=10.3, 3.2 Hz, 1H), 3.46 (dd, J=10.3, 7.8 Hz, 1H), 3.20-3.32 (m, 2H), 2.92 (s, 3H), 2.67-2.75 (m, 1H), 2.60-2.68 (m, 1H), 2.06-2.20 (m, 2H), 1.97-2.05 (m, 1H), 1.88-1.95 (m, 1H), 1.71 (dq, J=12.5, 8.0 Hz, 1H), 1.46-1.62 (m, 2H), 1.30 (ddt, J=8.9, 13.0, 6.5 Hz, 1H), 0.81 (t, J=7.3 Hz, 3H); MS (ESI+) m/z 370 (M+H)$^+$.

Example 548

N$^1$-{(3aR,4S,6aS)-2-[(2,3-dichlorophenyl)sulfonyl]octahydrocyclopenta[c]pyrrol-4-yl}-N$^2$-methyl-L-norvalinamide The title compound was prepared by substituting 2,3-dichlorophenylsulfonyl chloride for 4-methoxybenzene-1-sulfonyl chloride in the procedure described in Example 537: $^1$H NMR (500 MHz, pyridine-d$_5$) δ ppm 9.84-9.86 (m, 1H), 8.14 (dd, J=7.9, 1.5 Hz, 1H), 7.68 (dd, J=8.0, 1.5 Hz, 1H), 7.34 (t, J=8.0 Hz, 1H), 4.49 (t, J=6.8 Hz, 1H), 4.32-4.38 (m, 1H), 3.84-3.90 (m, 1H), 3.51 (dd, J=10.2, 7.7 Hz, 1H), 3.26-3.41 (m, 2H), 2.95 (s, 3H), 2.76-2.82 (m, 1H), 2.68-2.75 (m, 1H), 2.09-2.19 (m, 2H), 2.01-2.09 (m, 1H), 1.90-2.00 (m, 1H), 1.73 (dq, J=12.5, 8.1 Hz, 1H), 1.46-1.64 (m, 2H), 1.35-1.42 (m, 1H), 0.80 (t, J=7.3 Hz, 3H); MS (ESI+) m/z 448 (M+H)$^+$.

Example 549

N$^2$-methyl-N$^1$-((3aR,4S,6aS)-2-{[4-(trifluoromethyl)benzyl]sulfonyl}octahydrocyclopenta[c]pyrrol-4-yl)-L-norvalinamide The title compound was prepared by substituting 4-(trifluoromethyl)benzyl-sulfonyl chloride for 4-methoxybenzene-1-sulfonyl chloride in the procedure described in Example 537: $^1$H NMR (500 MHz, pyridine-d$_5$) δ ppm 9.72-9.74 (m, 1H), 7.79-7.81 (m, 2H), 7.68-7.70 (m, 2H), 4.75-4.75 (bs, 2H), 4.51 (dd, J=8.3, 6.3 Hz, 1H), 4.33 (p, J=6.7 Hz, 1H), 3.78 (dd, J=10.1, 3.1 Hz, 1H), 3.62 (dd, J=10.2, 7.5 Hz, 1H), 3.45 (dd, J=9.9, 7.5 Hz, 1H), 3.23 (dd, J=9.9, 3.7 Hz, 1H), 2.90 (s, 3H), 2.68-2.85 (m, 2H), 2.02-2.15 (m, 3H), 1.91-1.98 (m, 1H), 1.75 (dq, J=12.4, 8.1 Hz, 1H), 1.43-1.64 (m, 2H), 1.30-1.39 (m, 1H), 0.81 (t, J=7.3 Hz, 3H); MS (ESI+) m/z 462 (M+H)$^+$.

Example 550

N$^2$-methyl-N$^1$-((3aR,4S,6aS)-2-{[2-(trifluoromethyl)phenyl]sulfonyl}octahydrocyclopenta[c]pyrrol-4-yl)-L-norvalinamide The title compound was prepared by substituting 2-(trifluoromethyl)phenyl-sulfonyl chloride for 4-methoxybenzene-1-sulfonyl chloride in the procedure described in Example 537: $^1$H NMR (500 MHz, pyridine-d$_5$) δ ppm 9.81-9.83 (m, 1H), 8.26 (d, J=7.9 Hz, 1H), 7.93 (d, J=7.8 Hz, 1H), 7.73 (t, J=7.7 Hz, 1H), 7.67 (t, J=7.7 Hz, 1H), 4.50 (t, J=6.8 Hz, 1H), 4.31 (p, J=6.7 Hz, 1H), 3.83 (dd, J=10.1, 2.9 Hz, 1H), 3.36 (dd, J=10.1, 7.7 Hz, 1H), 3.29 (dd, J=9.9, 3.1 Hz, 1H), 3.18 (dd, J=9.9, 7.5 Hz, 1H), 2.95 (s, 3H), 2.75-2.80 (m, 1H), 2.65-2.73 (m, 1H), 2.14 (q, J=7.5 Hz, 2H), 1.99-2.06 (m, 1H), 1.91-1.98 (m, 1H), 1.68-1.76 (m, 1H), 1.47-1.65 (m, 2H), 1.36 (ddt, J=9.2, 12.9, 6.5 Hz, 1H), 0.80 (t, J=7.3 Hz, 3H); MS (ESI+) m/z 448 (M+H)$^+$.

Example 551

N¹-{(3aR,4S,6aS)-2-[(3-bromophenyl)sulfonyl]octahydrocyclopenta[c]pyrrol-4-yl}-N²-methyl-L-norvalinamide The title compound was prepared by substituting 3-bromobenzene-1-sulfonyl chloride for 4-methoxybenzene-1-sulfonyl chloride in the procedure described in Example 537: $^1$H NMR (500 MHz, pyridine-$d_5$) δ ppm 9.78-9.80 (m, 1H), 8.26 (t, J=1.8 Hz, 1H), 7.90 (dt, J=7.8, 1.2 Hz, 1H), 7.78 (ddd, J=8.0, 1.9, 1.0 Hz, 1H), 7.43 (t, J=7.9 Hz, 1H), 4.42 (dd, J=7.9, 5.8 Hz, 1H), 4.29 (p, J=6.7 Hz, 1H), 3.75 (dd, J=9.9, 2.7 Hz, 1H), 3.15 (dd, J=9.7, 2.8 Hz, 1H), 3.10 (dd, J=9.9, 7.7 Hz, 1H), 2.92 (s, 3H), 2.88 (dd, J=9.6, 7.5 Hz, 1H), 2.62-2.68 (m, 1H), 2.55-2.61 (m, 1H), 2.04-2.20 (m, 2H), 1.86-2.03 (m, 2H), 1.63-1.70 (m, 1H), 1.48-1.60 (m, 2H), 1.31 (ddt, J=9.2, 12.9, 6.5 Hz, 1H), 0.80 (t, J=7.3 Hz, 3H); MS (ESI−) m/z 456 (M−H)$^−$.

Example 552

N¹-((3aR,4S,6aS)-2-{[2-chloro-4-(trifluoromethyl)phenyl]sulfonyl}octahydrocyclopenta[c]pyrrol-4-yl)-N²-methyl-L-norvalinamide The title compound was prepared by substituting 2-chloro-4-(trifluoromethyl)phenylsulfonyl chloride for 4-methoxybenzene-1-sulfonyl chloride in the procedure described in Example 537: $^1$H NMR (500 MHz, pyridine-$d_5$) δ ppm 10.09-10.11 (m, 1H), 8.33 (d, J=8.2 Hz, 1H), 7.99-8.00 (bs, 1H), 7.73-7.75 (m, 1H), 4.66-4.70 (m, 1H), 4.35-4.44 (m, 1H), 3.85 (dd, J=10.3, 3.2 Hz, 1H), 3.55 (d, J=8.7 Hz, 1H), 3.30-3.42 (m, 2H), 2.95 (s, 3H), 2.88-2.95 (m, 1H), 2.75-2.86 (m, 1H), 2.35-2.41 (m, 1H), 2.22-2.30 (m, 1H), 1.99-2.19 (m, 2H), 1.89-1.95 (m, 1H), 1.54-1.77 (m, 2H), 1.39-1.47 (m, 1H), 0.85 (t, J=7.3 Hz, 3H); MS (ESI−) m/z 480 (M−H)$^−$.

Example 553

N¹-((3aR,4S,6aS)-2-{[2-chloro-5-(trifluoromethyl)phenyl]sulfonyl}octahydrocyclopenta[c]pyrrol-4-yl)-N²-methyl-L-norvalinamide The title compound was prepared by substituting 2-chloro-5-(trifluoromethyl)phenylsulfonyl chloride for 4-methoxybenzene-1-sulfonyl chloride in the procedure described in Example 537: $^1$H NMR (400 MHz, pyridine-$d_5$) δ ppm 10.09-10.12 (m, 1H), 8.54 (d, J=2.2 Hz, 1H), 7.82 (dd, J=8.3, 2.2 Hz, 1H), 7.76 (d, J=8.3 Hz, 1H), 4.73 (dd, J=9.1, 4.6 Hz, 1H), 4.35-4.43 (m, 1H), 3.84 (dd, J=10.2, 3.2 Hz, 1H), 3.56 (dd, J=10.2, 7.8 Hz, 1H), 3.29-3.40 (m, 2H), 2.96 (s, 3H), 2.89-3.00 (m, 1H), 2.76-2.88 (m, 1H), 2.35-2.44 (m, 1H), 2.21-2.33 (m, 1H), 2.05-2.19 (m, 2H), 1.88-1.98 (m, 1H), 1.66-1.79 (m, 1H), 1.53-1.66 (m, 1H), 1.38-1.48 (m, 1H), 0.85 (t, J=7.3 Hz, 3H); MS (ESI−) m/z 480 (M−H)$^−$.

Example 554

N²-methyl-N¹-{(3aR,4S,6aS)-2-[3-(trifluoromethyl)benzoyl]octahydrocyclopenta[c]pyrrol-4-yl}-L-norvalinamide The title compound was prepared by substituting 3-(trifluoromethyl)benzoyl chloride for 4-methoxybenzene-1-sulfonyl chloride in the procedure described in Example 537: $^1$H NMR (400 MHz, pyridine-$d_5$) δ ppm 7.98 (s, 1H), 7.80 (d, J=7.7, 1H), 7.65 (d, J=7.9, 1H), 7.52-7.40 (m, 3H), 4.34-4.19 (m, 1H), 3.88-3.74 (m, 3H), 3.66 (d, J=8.2, 1H), 3.44 (s, 1H), 2.85-2.52 (m, 5H), 2.51-2.38 (m, OH), 2.11 (dt, J=12.6, 6.2, 1H), 1.91 (dddd, J=22.0, 15.6, 10.7, 4.6, 3H), 1.72 (dq, J=12.8, 8.0, 1H), 1.57-1.17 (m, 4H), 0.83 (t, J=7.3, 3H); MS (ESI+) m/z 412 (M+H)$^+$.

Example 555

N-[(3aR,4S,6aS)-2-benzyloctahydrocyclopenta[c]pyrrol-4-yl]-N-isopropyl-3-(trifluoromethyl)benzenesulfonamide Step A: (3aR,4S,6aS)-2-Benzyl-N-isopropyloctahydrocyclopenta[c]pyrrol-4-amine was prepared by substituting (3aR,4S,6aS)-2-benzyloctahydrocyclopenta[c]pyrrol-4-amine from Example 33 Step A for (3aS,4R,6aR)-2-(3-(trifluoromethyl)phenylsulfonyl)octahydrocyclopenta[c]pyrrol-4-amine and acetone for pivalaldehyde in the procedure described in Example 281: $^1$H NMR (500 MHz, pyridine-$d_5$) δ ppm 7.48 (d, J=7.5, 2H), 7.39 (t, J=7.5, 2H), 7.29 (t, J=7.3, 1H), 3.61-3.51 (m, 2H), 3.05 (dd, J=12.1, 5.4, 1H), 2.87-2.78 (m, 1H), 2.61-2.51 (m, 2H), 2.43-2.36 (m, 2H), 2.35-2.30 (m, 1H), 2.28-2.21 (m, 1H), 2.00-1.93 (m, 1H), 1.93-1.87 (m, 1H), 1.42-1.28 (m, 3H), 1.05-0.98 (m, 6H); MS (ESI+) m/z 259 (M+H)$^+$.

Step B: The title compound was prepared by substituting (3aR,4S,6aS)-2-benzyl-N-isopropyloctahydrocyclopenta[c]pyrrol-4-amine from Step A for (S)-tert-butyl 2-amino-4-methylpentanoate and 3-(trifluoromethyl)benzene-1-sulfonylchloride for methanesulfonyl chloride in the procedure described in Example 242: $^1$H NMR (500 MHz, pyridine-$d_5$) δ ppm 8.43 (s, 1H), 8.30-8.21 (m, 1H), 7.84 (d, J=7.6, 1H), 7.66-7.59 (m, 1H), 7.40 (ddd, J=12.7, 8.4, 2.6, 4H), 7.32-7.27 (m, 1H), 3.82-3.70 (m, 2H), 3.51 (d, J=2.0, 2H), 2.82-2.74 (m, 1H), 2.67-2.62 (m, 1H), 2.52-2.43 (m, 3H), 2.09-2.04 (m, 1H), 1.99-1.95 (m, 1H), 1.91-1.79 (m, 2H), 1.75-1.65 (m, 1H), 1.26 (dd, J=6.8, 2.6, 6H); MS (ESI+) m/z 467 (M+H)$^+$.

Example 556

N-[(3aR,4S,6aS)-2-benzyloctahydrocyclopenta[c]pyrrol-4-yl]-3-(trifluoromethyl)benzenesulfonamide The title compound was prepared by substituting (3aR,4S,6aS)-2-benzyloctahydrocyclopenta[c]pyrrol-4-amine from Example 33 Step A for (S)-tert-butyl 2-amino-4-methylpentanoate and 3-(trifluoromethyl)benzene-1-sulfonylchloride for methanesulfonyl chloride in the procedure described in Example 242 Step A: $^1$H NMR (500 MHz, pyridine-$d_5$) δ ppm 9.49 (d, J=7.2, 1H), 8.43 (s, 1H), 8.30 (d, J=7.9, 1H), 7.81 (d, J=7.9, 1H), 7.60 (d, J=7.9, 1H), 7.37 (dd, J=9.6, 3.8, 4H), 7.33-7.26 (m, 1H), 3.83-3.75 (m, 1H), 3.50 (d, J=13.1, 1H), 3.44 (d, J=13.1, 1H), 2.61 (dd, J=9.2, 2.0, 1H), 2.56-2.43 (m, 2H), 2.35 (dd, J=9.1, 2.1, 1H), 2.21-2.13 (m, 2H), 1.99 (td, J=11.7, 5.8, 1H), 1.82 (ddd, J=12.5, 10.2, 5.6, 1H), 1.63-1.53 (m, 1H), 1.29 (ddt, J=12.7, 10.0, 6.4, 1H); MS (ESI+) m/z 442 (M+NH$_4$)$^+$.

Example 557

N-isopropyl-N-[(3aR,4S,6aS)-2-(N-methyl-L-leucyl)octahydrocyclopenta[c]pyrrol-4-yl]-3-(trifluoromethyl)benzenesulfonamide The title compound was prepared by substituting N-[(3aR,4S,6aS)-2-benzyloctahydrocyclopenta[c]pyrrol-4-yl]-N-isopropyl-3-(trifluoromethyl)benzenesulfonamide from Example 555 for N-((3aR,4S,6aS)-2-benzyloctahydrocyclopenta[c]pyrrol-4-yl)-2,2-bis(4-fluorophenyl)acetamide in the procedure described in Example 459: $^1$H NMR (400 MHz, pyridine-$d_5$) δ ppm 8.30 (s, 1H), 8.17 (d, J=7.8, 1H), 7.79 (d, J=8.1, 1H), 7.61 (t, J=7.8, 1H), 3.90-3.80 (m, 2H), 3.77-3.67 (m, 4H), 3.39 (dd, J=9.0, 4.2, 1H), 3.10-3.01 (m, 1H), 2.82-2.70 (m, 1H), 2.39 (s, 3H), 2.13-2.01 (m, 1H), 2.02-1.83 (m, 3H), 1.51 (t, J=6.7, 2H), 1.29 (d, J=6.8, 5H), 1.23 (d, J=6.8, 3H), 0.97-0.89 (m, 6H); MS (ESI+) m/z 504 (M+H)$^+$.

Example 558

N-[(3aR,4S,6aS)-2-(N-methyl-L-leucyl)octahydrocyclopenta[c]pyrrol-4-yl]-3-(trifluoromethyl)benzenesulfonamide The title compound was prepared by substituting N-[(3aR,4S,6aS)-2-benzyloctahydrocyclopenta[c]pyrrol-4-yl]-3-(trifluoromethyl)benzenesulfonamide from Example 556 for N-((3aR,4S,6aS)-2-benzyloctahydrocyclopenta[c]pyrrol-4-yl)-2,2-bis(4-fluorophenyl)acetamide in the procedure described in Example 459: $^1$H NMR (400 MHz, pyridine-$d_5$) δ ppm 8.88 (qt, J=7.3, 2.9, 1H), 8.35 (s, 1H), 8.24 (d, J=7.9, 1H), 7.79 (d, J=7.9, 1H), 7.59 (t, J=8.0, 1H), 3.79-3.70 (m, 3H), 3.68-3.53 (m, 2H), 3.37 (ddd, J=8.4, 7.7, 2.4, 1H), 2.77-2.62 (m, 2H), 2.37 (s, 3H), 2.06-1.87 (m, 3H), 1.75-1.63 (m, 1H), 1.53-1.44 (m, 2H), 1.38-1.24 (m, 1H), 0.92 (dd, J=8.8, 6.7, 7H); MS (ESI+) m/z 462 (M+H)$^+$.

Example 559

N-cyclopropyl-N-[(3aS*,4S*,6aR*)-[2-(N-methyl-L-leucyl)octahydrocyclopenta[c]pyrrol-4-yl]-3-(trifluoromethyl)benzenesulfonamide The title compound was prepared by substituting N-[(3aS*,4S*,6aR*)-2-benzyloctahydrocyclopenta[c]pyrrol-4-yl]-N-cyclopropyl-3-(trifluoromethyl)benzenesulfonamide from Example 199 for N-((3aR,4S,6aS)-2-benzyloctahydrocyclopenta[c]pyrrol-4-yl)-2,2-bis(4-fluorophenyl)acetamide in the procedure described in Example 459: $^1$H NMR (500 MHz, pyridine-$d_5$) δ ppm 8.50 (s, 1H), 8.39-8.31 (m, 1H), 7.96 (dd, J=20.3, 7.8, 1H), 7.82-7.71 (m, 1H), 4.20 (dd, J=13.1, 5.0, 0.5H), 4.12 (dt, J=13.2, 6.7, 0.5H), 4.04-3.98 (m, 0.5H), 3.97-3.80 (m, 1.5H), 3.72 (ddd, J=22.3, 16.1, 9.9, 1H), 3.60 (dt, J=8.6, 7.6, 0.5H), 3.53-3.38 (m, 2H), 3.29-3.21 (m, 0.5H), 2.72-2.65 (m, 0.5H), 2.63-2.52 (m, 0.5H), 2.48 (s, 0.5H), 2.42 (d, J=4.6, 2H), 2.39 (s, 0.5H), 2.15-1.97 (m, 3H), 1.92-1.82 (m, 1H), 1.75-1.68 (m, 1H), 1.67-1.34 (m, 5H), 1.04 (d, J=6.6, 1H), 0.99-0.94 (m, 3H), 0.91 (dt, J=14.0, 5.1, 3H), 0.85-0.71 (m, 1.5H), 0.69-0.59 (m, 0.5H); MS (ESI+) m/z 502 (M+H)$^+$.

Example 560

4-fluoro-N-{(3aR,4S,6aS)-2-[6-(trifluoromethyl)pyridin-2-yl]octahydrocyclopenta[c]pyrrol-4-yl}benzamide The title compound was prepared by substituting 4-fluorobenzoic acid for N-(tert-butoxycarbonyl)-L-leucine and (3aR,4S,6aS)-2-(6-(trifluoromethyl)pyridin-2-yl)octahydrocyclopenta[c]pyrrol-4-amine from Example 264 Step A for (3aR,4S,6aS)-2-benzyloctahydrocyclopenta[c]pyrrol-4-amine in the procedure described in Example 221: $^1$H NMR (500 MHz, pyridine-$d_5$) δ ppm 8.90 (d, J=6.9, 1H), 8.27-8.21 (m, 2H), 7.55-7.50 (m, 1H), 7.20-7.14 (m, 2H), 6.99 (d, J=7.2, 1H), 6.53 (d, J=8.6, 1H), 4.61-4.54 (m, 1H), 3.80 (dd, J=11.0, 3.7, 1H), 3.63 (dd, J=10.9, 8.2, 1H), 3.51 (dd, J=10.8, 8.4, 1H), 3.30 (dd, J=10.9, 4.6, 1H), 2.88-2.81 (m, 1H), 2.76-2.67 (m, 1H), 2.23 (ddd, J=19.5, 7.1, 4.7, 1H), 1.93 (dtd, J=12.7, 8.0, 4.6, 1H), 1.81 (ddd, J=16.4, 12.7, 8.1, 1H), 1.40 (dt, J=13.2, 7.6, 1H); MS (ESI+) m/z 394 (M+H)$^+$.

Example 561

4-fluoro-N-{(3aR,4S,6aS)-2-[6-(trifluoromethyl)pyridin-2-yl]octahydrocyclopenta[c]pyrrol-4-yl}benzamide p-Fluorobenzoic acid (56.8 mg, 0.405 mmol), 1-hydroxybenzotriazole hydrate (62.1 mg, 0.405 mmol 1), and (3aR,4S,6aS)-2-(6-(trifluoromethyl)pyridin-2-yl)octahydrocyclopenta[c]pyrrol-4-amine from Example 264 Step A (100 mg, 0.369 mmol) were combined in dichloromethane (1.2 mL) to give a colorless solution. After 20 minutes, $N^1$-((ethylimino)methylene)-$N^3,N^3$-dimethylpropane-1,3-diamine (0.072 mL, 0.405 mmol) was added and the reaction mixture was stirred at room temperature overnight. The reaction mixture was quenched with water and extracted with 2×2 mL of dichloromethane. The combined extracts were applied directly to a 12 g silica gel cartridge and purified with a gradient of 1-10% methanol in (2 N ammonia)/dichloromethane over 20 minutes to give the title compound: $^1$H NMR (500 MHz, pyridine-$d_5$) δ ppm 8.90 (d, J=6.9, 1H), 8.29-8.19 (m, 2H), 7.56-7.47 (m, 1H), 7.17 (ddd, J=9.7, 5.9, 2.5, 2H), 6.99 (d, J=7.2, 1H), 6.53 (d, J=8.6, 1H), 4.64-4.52 (m, 1H), 3.80 (dd, J=11.0, 3.7, 1H), 3.63 (dd, J=10.9, 8.2, 1H), 3.51 (dd, J=10.8, 8.4, 1H), 3.30 (dd, J=10.9, 4.6, 1H), 2.90-2.77 (m, 1H), 2.77-2.64 (m, 1H), 2.23 (ddd, J=19.5, 7.1, 4.7, 1H), 1.93 (dtd, J=12.7, 8.0, 4.6, 1H), 1.81 (ddd, J=16.4, 12.7, 8.1, 1H), 1.40 (dt, J=13.2, 7.6, 1H); MS (ESI+) m/z 394 (M+H)$^+$.

Example 562

2-hydroxy-N-{(3aR,4S,6aS)-2-[6-(trifluoromethyl)pyridin-2-yl]octahydrocyclopenta[c]pyrrol-4-yl}benzamide The title compound was prepared by substituting salicylic acid for p-fluorobenzoic acid in the procedure described in Example 561: $^1$H NMR (500 MHz, pyridine-$d_5$) δ ppm 13.58 (s, 1H), 9.18 (d, J=6.9, 1H), 8.23 (dd, J=8.0, 1.6, 1H), 7.52 (d, J=7.9, 1H), 7.43-7.34 (m, 1H), 7.20 (d, J=1.0, 1H), 6.99 (d, J=7.2, 1H), 6.89-6.81 (m, 1H), 6.55 (d, J=8.6, 1H), 4.54-4.45 (m, 1H), 3.75 (dd, J=11.0, 3.7, 1H), 3.60 (dd, J=10.9, 8.1, 1H), 3.49 (dd, J=10.8, 8.4, 1H), 3.29 (dd, J=10.9, 4.6, 1H), 2.83-2.74 (m, 1H), 2.73-2.61 (m, 1H), 2.23-2.11 (m, 1H), 1.94-1.84 (m, 1H), 1.76 (ddd, J=16.4, 12.7, 8.1, 1H), 1.37 (dt, J=13.2, 7.4, 1H); MS (ESI+) m/z 392 (M+H)$^+$.

Example 563

2-fluoro-N-{(3aR,4S,6aS)-2-[6-(trifluoromethyl)pyridin-2-yl]octahydrocyclopenta[c]pyrrol-4-yl}benzamide The title compound was prepared by substituting o-fluorobenzoic acid for p-fluorobenzoic acid in the procedure described in Example 561: $^1$H NMR (500 MHz, pyridine-$d_5$) δ ppm 8.69 (s, 1H), 8.03 (td, J=7.5, 1.8, 1H), 7.52 (t, J=7.9, 1H), 7.39-7.28 (m, 1H), 7.13 (dddd, J=10.9, 9.2, 8.0, 1.0, 2H), 6.99 (d, J=7.2, 1H), 6.53 (d, J=8.6, 1H), 4.57 (p, J=6.8, 1H), 3.78 (dd, J=11.0, 3.9, 1H), 3.70-3.61 (m, 1H), 3.53 (dd, J=10.9, 8.3, 1H), 3.32 (dd, J=11.0, 4.5, 1H), 2.92-2.82 (m, 1H), 2.81-2.70 (m, 1H), 2.23 (tt, J=12.5, 6.1, 1H), 1.97 (dtd, J=13.0, 8.0, 5.1, 1H), 1.82 (ddd, J=15.6, 12.7, 7.9, 1H), 1.42 (ddd, J=15.4, 10.5, 6.8, 1H); MS (ESI+) m/z 394 (M+H)+.

Example 564

3-fluoro-N-{(3aR,4S,6aS)-2-[6-(trifluoromethyl)pyridin-2-yl]octahydrocyclopenta[c]pyrrol-4-yl}benzamide The title compound was prepared by substituting m-fluorobenzoic acid for p-fluorobenzoic acid in the procedure described in Example 561: $^1$H NMR (500 MHz, pyridine-$d_5$) δ ppm 9.05-8.88 (m, 1H), 8.08-7.94 (m, 2H), 7.52 (dd, J=11.8, 4.0, 1H), 7.40-7.29 (m, 1H), 7.24 (ddd, J=8.4, 2.6, 0.9, 1H), 6.99 (d, J=7.3, 1H), 6.53 (d, J=8.6, 1H), 4.63-4.51 (m, 1H), 3.84-3.76 (m, 1H), 3.64 (ddd, J=14.2, 7.7, 3.2, 1H), 3.55-3.47 (m, 1H), 3.35-3.25 (m, 1H), 2.85 (tdd, J=8.7, 6.0, 3.8, 1H), 2.77-2.64 (m, 1H), 2.24 (dtd, J=12.1, 7.2, 4.7, 1H), 2.00-1.88 (m, 1H), 1.86-1.74 (m, 1H), 1.46-1.33 (m, 1H); MS (ESI+) m/z 394 (M+H)+.

Example 565

3,4-difluoro-N-{(3aR,4S,6aS)-2-[6-(trifluoromethyl)pyridin-2-yl]octahydrocyclopenta[c]pyrrol-4-yl}benzamide The title compound was prepared by substituting 3,4-difluorobenzoic acid for p-fluorobenzoic acid in the procedure described in Example 561: $^1$H NMR (500 MHz, pyridine-$d_5$) δ ppm 8.99 (d, J=6.9, 1H), 8.13 (ddd, J=11.4, 7.8, 2.1, 1H), 8.02-7.92 (m, 1H), 7.52 (t, J=7.9, 1H), 7.33-7.23 (m, 1H), 7.00 (d, J=7.2, 1H), 6.54 (d, J=8.6, 1H), 4.60-4.49 (m, 1H), 3.80 (dd, J=11.0, 3.8, 1H), 3.63 (dd, J=11.0, 8.1, 1H), 3.51 (dd, J=10.9, 8.3, 1H), 3.30 (dd, J=11.0, 4.7, 1H), 2.89-2.79 (m, 1H), 2.72 (dt, J=13.5, 6.8, 1H), 2.30-2.17 (m, 1H), 1.99-1.88 (m, 1H), 1.80 (ddd, J=16.3, 12.6, 8.0, 1H), 1.40 (dt, J=13.1, 7.7, 1H); MS (ESI+) m/z 412 (M+H)+.

Example 566

3-chloro-4-fluoro-N-{(3aR,4S,6aS)-2-[6-(trifluoromethyl)pyridin-2-yl]octahydrocyclopenta[c]pyrrol-4-yl}benzamide The title compound was prepared by substituting 3-chloro-4-fluorobenzoic acid for p-fluorobenzoic acid in the procedure described in Example 561: $^1$H NMR (500 MHz, pyridine-$d_5$) δ ppm 9.06 (d, J=6.9, 1H), 8.32 (dd, J=7.2, 2.2, 1H), 8.12 (ddd, J=8.6, 4.7, 2.2, 1H), 7.53 (t, J=7.9, 1H), 7.25 (t, J=8.8, 1H), 7.00 (d, J=7.2, 1H), 6.55 (d, J=8.6, 1H), 4.61-4.52 (m, 1H), 3.81 (dd, J=11.0, 3.7, 1H), 3.65 (dd, J=10.9, 8.1, 1H), 3.52 (dd, J=10.8, 8.4, 1H), 3.31 (dd, J=10.9, 4.6, 1H), 2.91-2.82 (m, 1H), 2.78-2.67 (m, 1H), 2.25 (qd, J=7.1, 4.7, 1H), 1.95 (dtd, J=12.7, 7.7, 4.7, 1H), 1.83 (ddd, J=16.3, 12.7, 8.1, 1H), 1.41 (dt, J=13.2, 7.8, 1H); MS (ESI+) m/z 428 (M+H)+.

Example 567

(2S)-2-hydroxy-4-methyl-N-{(3aR,4S,6aS)-2-[6-(trifluoromethyl)pyridin-2-yl]octahydrocyclopenta[c]pyrrol-4-yl}pentanamide The title compound was prepared by substituting (S)-2-hydroxy-4-methylpentanoic acid for p-fluorobenzoic acid in the procedure described in Example 561: $^1$H NMR (500 MHz, pyridine-$d_5$) δ ppm 8.22-8.11 (m, 1H), 7.53-7.45 (m, 1H), 7.29 (t, J=4.8, 1H), 7.04-6.85 (m, 1H), 6.49 (d, J=8.6, 1H), 4.65-4.54 (m, 1H), 4.49-4.37 (m, 1H), 3.74-3.65 (m, 1H), 3.58-3.42 (m, 2H), 3.33-3.19 (m, 1H), 2.78-2.58 (m, 2H), 2.25-2.08 (m, 2H), 2.05-1.82 (m, 3H), 1.78-1.64 (m, 1H), 1.47-1.29 (m, 1H), 1.05-0.87 (m, 6H); MS (ESI+) m/z 386 (M+H)+.

Example 568

N-{(3aR,4S,6aS)-2-[5-(trifluoromethyl)pyridin-2-yl]octahydrocyclopenta[c]pyrrol-4-yl}-1H-indole-2-carboxamide The title compound was prepared by substituting 1H-indole-2-carboxylic acid for p-fluorobenzoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 561: $^1$H NMR (500 MHz, pyridine-$d_5$) δ ppm 13.17 (s, 1H), 8.96 (d, J=7.4, 1H), 8.62 (s, 1H), 7.83-7.78 (m, 1H), 7.75 (d, J=8.0, 1H), 7.67 (dd, J=8.9, 2.5, 1H), 7.46 (dd, J=2.1, 0.8, 1H), 7.40 (ddd, J=8.2, 7.0, 1.2, 1H), 7.24 (dd, J=8.0, 0.9, 1H), 6.37 (d, J=9.0, 1H), 4.69-4.58 (m, 1H), 3.84 (d, J=8.5, 1H), 3.67-3.52 (m, 2H), 3.38-3.27 (m, 1H), 2.84 (dt, J=8.3, 6.1, 1H), 2.71 (dt, J=8.4, 6.7, 1H), 2.22 (dt, J=11.9, 7.1, 1H), 1.91 (ddd, J=16.5, 8.2, 3.9, 1H), 1.80 (ddd, J=16.6, 12.5, 8.2, 1H), 1.40 (dt, J=12.9, 7.6, 1H); MS (ESI+) m/z 415 (M+H)+.

Example 569

N-{(3aR,4S,6aS)-2-[6-(trifluoromethyl)pyridin-2-yl]octahydrocyclopenta[c]pyrrol-4-yl}quinoline-2-carboxamide The title compound was prepared by substituting quinoline-2-carboxylic acid for p-fluorobenzoic acid in the procedure described in Example 561: $^1$H NMR (500 MHz, pyridine-$d_5$) δ ppm $^1$H NMR (400 MHz, pyridine-$d_5$) δ 9.18 (d, J=7.9, 1H), 8.57 (d, J=8.5, 1H), 8.35 (d, J=8.3, 1H), 8.12-8.02 (m, 1H), 7.91 (dd, J=8.2, 1.1, 1H), 7.73 (ddd, J=8.4, 6.9, 1.5, 1H), 7.61-7.56 (m, 1H), 7.55-7.47 (m, 1H), 6.99 (d, J=7.2, 1H), 6.53 (d, J=8.6, 1H), 4.66-4.50 (m, 1H), 3.79 (dd, J=11.0, 3.5, 1H), 3.63-3.48 (m, 2H), 3.32 (dd, J=10.9, 4.8, 1H), 2.87 (ddd, J=11.5, 9.2, 3.5, 1H), 2.81-2.70 (m, 1H), 2.25-2.17 (m, 1H), 2.04-1.92 (m, 1H), 1.84 (dq, J=12.7, 8.2, 1H), 1.47-1.35 (m, 1H); MS (ESI+) m/z 427 (M+H)+.

Example 570

N-{(3aR,4S,6aS)-2-[6-(trifluoromethyl)pyridin-2-yl]octahydrocyclopenta[c]pyrrol-4-yl}-1H-indole-2-carboxamide The title compound was prepared by substituting 1H-indole-2-carboxylic acid for p-fluorobenzoic acid in the procedure described in Example 561: $^1$H NMR (500 MHz, pyridine-$d_5$) δ ppm 13.16 (s, 1H), 8.92 (d, J=7.4, 1H), 7.83-7.78 (m, 1H), 7.75 (d, J=8.1, 1H), 7.54-7.48 (m, 1H), 7.46 (d, J=1.4, 1H), 7.42-7.38 (m, 1H), 7.23 (dd, J=8.0, 0.8, 1H), 6.98 (d, J=7.2, 1H), 6.49 (d, J=8.6, 1H), 4.66-4.56 (m, 1H), 3.76 (dd, J=11.0, 3.6, 1H), 3.56 (dd, J=10.8, 8.1, 1H), 3.50 (dd, J=10.8, 8.5, 1H), 3.28 (dd, J=10.9, 4.8, 1H), 2.82 (ddd, J=12.2, 8.9, 3.8, 1H), 2.72-2.61 (m, 1H), 2.24-2.16 (m, 1H), 1.95-1.84 (m, 1H), 1.78 (dq, J=12.7, 8.2, 1H), 1.37 (dt, J=13.2, 7.8, 1H); MS (ESI+) m/z 415 (M+H)+.

Example 571

5-(2-thienyl)-N-{(3aR,4S,6aS)-2-[6-(trifluoromethyl)pyridin-2-yl]octahydrocyclopenta[c]pyrrol-4-yl}-2-furamide The title compound was prepared by substituting 5-(thiophen-2-yl)furan-2-carboxylic acid for p-fluorobenzoic acid in the procedure described in Example 561: $^1$H NMR (400 MHz, pyridine-d$_5$) δ ppm 9.03 (d, J=7.5, 1H), 7.52 (t, J=7.9, 1H), 7.44 (d, J=3.6, 1H), 7.39 (dd, J=5.1, 1.2, 1H), 7.18 (dd, J=3.6, 1.2, 1H), 7.01-6.91 (m, 2H), 6.74 (d, J=3.6, 1H), 6.58-6.47 (m, 1H), 4.63-4.53 (m, 1H), 3.78 (dd, J=11.0, 3.5, 1H), 3.57 (dd, J=10.9, 8.0, 1H), 3.50 (dd, J=10.9, 8.5, 1H), 3.28 (dd, J=11.0, 4.8, 1H), 2.90-2.82 (m, 1H), 2.74-2.61 (m, 1H), 2.25-2.09 (m, 1H), 1.97-1.74 (m, 2H), 1.36 (dt, J=11.4, 7.0, 1H); MS (ESI+) m/z 448 (M+H)+.

Example 572

4-methyl-N-{(3aR,4S,6aS)-2-[6-(trifluoromethyl)pyridin-2-yl]octahydrocyclopenta[c]pyrrol-4-yl}-1H-pyrrole-2-carboxamide The title compound was prepared by substituting 4-methyl-1H-pyrrole-2-carboxylic acid for p-fluorobenzoic acid in the procedure described in Example 561: $^1$H NMR (400 MHz, pyridine-d$_5$) δ ppm 12.56 (s, 1H), 8.32 (d, J=7.4, 1H), 7.50 (t, J=7.9, 1H), 7.04-7.00 (m, 1H), 6.97 (dd, J=4.6, 2.6, 2H), 6.48 (d, J=8.6, 1H), 4.65-4.53 (m, 1H), 3.74 (dd, J=11.0, 3.6, 1H), 3.52 (ddd, J=17.4, 10.9, 8.2, 2H), 3.26 (dd, J=11.0, 4.9, 1H), 2.79 (ddd, J=11.8, 9.3, 3.6, 1H), 2.72-2.58 (m, 1H), 2.23-2.08 (m, 4H), 1.93-1.83 (m, 1H), 1.75 (dq, J=12.7, 8.3, 1H), 1.35 (dt, J=13.0, 7.8, 1H); MS (ESI+) m/z 379 (M+H)+.

Example 573

1-hydroxy-N-{(3aR,4S,6aS)-2-[6-(trifluoromethyl)pyridin-2-yl]octahydrocyclopenta[c]pyrrol-4-yl}cyclopentanecarboxamide The title compound was prepared by substituting 1-hydroxycyclopentanecarboxylic acid for p-fluorobenzoic acid in the procedure described in Example 561: $^1$H NMR (500 MHz, pyridine-d$_5$) δ ppm 8.12 (d, J=7.6, 1H), 7.49 (t, J=7.9, 1H), 7.07 (s, 1H), 6.97 (d, J=7.2, 1H), 6.47 (d, J=8.6, 1H), 4.44-4.33 (m, 1H), 3.67 (dd, J=10.9, 2.6, 1H), 3.57-3.40 (m, 2H), 3.27 (dd, J=10.9, 3.4, 1H), 2.73-2.62 (m, 2H), 2.62-2.45 (m, 2H), 2.16-2.01 (m, 3H), 2.01-1.91 (m, 2H), 1.90-1.75 (m, 3H), 1.64 (dq, J=12.7, 8.2, 1H), 1.34 (dtd, J=12.8, 8.1, 5.0, 1H); MS (ESI+) m/z 384 (M+H)+.

Example 574

N-{(3aR,4S,6aS)-2-[6-(trifluoromethyl)pyridin-2-yl]octahydrocyclopenta[c]pyrrol-4-yl}-4H-furo[3,2-b]pyrrole-5-carboxamide The title compound was prepared by substituting 4H-furo[3,2-b]pyrrole-5-carboxylic acid for p-fluorobenzoic acid in the procedure described in Example 561: $^1$H NMR (400 MHz, pyridine-d$_5$) δ ppm 12.92 (s, 1H), 8.62 (d, J=7.4, 1H), 7.73 (d, J=2.2, 1H), 7.50 (t, J=7.9, 1H), 7.24 (s, 1H), 6.97 (d, J=7.2, 1H), 6.77 (dd, J=2.1, 0.6, 1H), 6.48 (d, J=8.6, 1H), 4.67-4.55 (m, 1H), 3.75 (dd, J=11.0, 3.6, 1H), 3.51 (ddd, J=22.0, 10.9, 8.2, 2H), 3.26 (dd, J=11.0, 4.8, 1H), 2.77 (ddd, J=14.5, 8.6, 3.7, 1H), 2.68-2.56 (m, 1H), 2.23-2.09 (m, 1H), 1.92-1.79 (m, 1H), 1.73 (ddd, J=16.6, 12.6, 8.2, 1H), 1.34 (dt, J=13.1, 7.7, 1H); MS (ESI+) m/z 405 (M+H)+.

Example 575

4-chloro-N-{(3aR,4S,6aS)-2-[6-(trifluoromethyl)pyridin-2-yl]octahydrocyclopenta[c]pyrrol-4-yl}-1H-pyrrole-2-carboxamide The title compound was prepared by substituting 4-chloro-1H-pyrrole-2-carboxylic acid for p-fluorobenzoic acid in the procedure described in Example 561: $^1$H NMR (400 MHz, pyridine-d$_5$) δ ppm 13.48 (s, 1H), 8.57 (d, J=7.4, 1H), 7.54-7.45 (m, 1H), 7.35 (dd, J=3.0, 1.6, 1H), 7.14 (dd, J=2.7, 1.6, 1H), 6.98 (d, J=7.2, 1H), 6.48 (d, J=8.6, 1H), 4.62-4.48 (m, 1H), 3.73 (dd, J=11.0, 3.6, 1H), 3.52 (ddd, J=23.4, 10.9, 8.2, 2H), 3.25 (dd, J=10.9, 4.8, 1H), 2.76 (ddd, J=11.9, 9.2, 3.6, 1H), 2.68-2.57 (m, 1H), 2.22-2.08 (m, 1H), 1.92-1.81 (m, 1H), 1.72 (dq, J=12.7, 8.2, 1H), 1.40-1.29 (m, 1H); MS (ESI+) m/z 399 (M+H)+.

Example 576

5-methyl-N-{(3aR,4S,6aS)-2-[6-(trifluoromethyl)pyridin-2-yl]octahydrocyclopenta[c]pyrrol-4-yl}-2-furamide The title compound was prepared by substituting 5-methylfuran-2-carboxylic acid for p-fluorobenzoic acid in the procedure described in Example 561: $^1$H NMR (500 MHz, pyridine-d$_5$) δ ppm 8.69 (d, J=7.5, 1H), 7.51 (t, J=7.9, 1H), 7.27 (d, J=3.1, 1H), 6.98 (d, J=7.2, 1H), 6.52 (d, J=8.6, 1H), 6.17-6.02 (m, 1H), 4.61-4.53 (m, 1H), 3.78 (dd, J=10.9, 3.4, 1H), 3.59 (dd, J=10.8, 8.1, 1H), 3.52 (dd, J=10.7, 8.6, 1H), 3.29 (dd, J=10.9, 4.8, 1H), 2.86 (ddd, J=11.8, 8.7, 3.6, 1H), 2.78-2.68 (m, 1H), 2.24-2.15 (m, 1H), 1.99 (s, 3H), 1.94 (ddd, J=17.0, 8.2, 4.0, 1H), 1.84 (dq, J=12.6, 8.3, 1H), 1.39 (dt, J=13.1, 7.6, 1H); MS (ESI+) m/z 380 (M+H)+.

Example 577

3-hydroxy-N-{(3aR,4S,6aS)-2-[6-(trifluoromethyl)pyridin-2-yl]octahydrocyclopenta[c]pyrrol-4-yl}benzamide The title compound was prepared by substituting 3-hydroxybenzoic acid for p-fluorobenzoic acid in the procedure described in Example 561: $^1$H NMR (500 MHz, pyridine-d$_5$) δ ppm 11.87 (s, 1H), 8.82 (d, J=7.1, 1H), 8.14-8.05 (m, 1H), 7.81-7.75 (m, 1H), 7.50 (t, J=7.9, 1H), 7.36 (t, J=7.8, 1H), 7.30 (ddd, J=8.1, 2.5, 1.0, 1H), 6.98 (d, J=7.2, 1H), 6.50 (d, J=8.6, 1H), 4.63-4.52 (m, 1H), 3.78 (dd, J=10.9, 3.7, 1H), 3.64-3.56 (m, 1H), 3.51 (dd, J=10.9, 8.4, 1H), 3.30 (dd, J=10.9, 4.6, 1H), 2.89-2.79 (m, 1H), 2.75-2.65 (m, 1H), 2.22 (dtd, J=12.0, 7.1, 4.6, 1H), 1.98-1.88 (m, 1H), 1.82 (ddd, J=16.5, 12.6, 8.1, 1H), 1.38 (dt, J=13.2, 7.5, 1H); MS (ESI+) m/z 392 (M+H)+.

Example 578

(2R)-2-hydroxy-4-methyl-N-{(3aR,4S,6aS)-2-[6-(trifluoromethyl)pyridin-2-yl]octahydrocyclopenta[c]pyrrol-4-yl}pentanamide The title compound was prepared by substituting (R)-2-hydroxy-4-methylpentanoic acid for p-fluorobenzoic acid in the procedure described in Example 561: ¹H NMR (400 MHz, pyridine-$d_5$) δ ppm 8.19 (d, J=7.5, 1H), 7.52-7.47 (m, 1H), 7.28 (d, J=5.7, 1H), 6.98 (d, J=7.2, 1H), 6.50 (d, J=8.6, 1H), 4.56 (ddd, J=9.4, 5.6, 3.6, 1H), 4.46-4.37 (m, 1H), 3.72 (dd, J=11.0, 3.0, 1H), 3.54 (ddd, J=26.0, 10.7, 7.7, 2H), 3.29 (dd, J=11.0, 4.0, 1H), 2.77-2.66 (m, 2H), 2.24-2.08 (m, 2H), 2.01 (ddd, J=12.8, 9.1, 3.5, 1H), 1.96-1.85 (m, 2H), 1.69 (dq, J=12.7, 8.1, 1H), 1.38 (dt, J=12.8, 6.3, 1H), 0.98 (dd, J=11.1, 6.7, 6H); MS (ESI+) m/z 386 (M+H)⁺.

Example 579

5-methyl-N-{(3aR,4S,6aS)-2-[6-(trifluoromethyl)pyridin-2-yl]octahydrocyclopenta[c]pyrrol-4-yl}pyrazine-2-carboxamide The title compound was prepared by substituting 5-methylpyrazine-2-carboxylic acid for p-fluorobenzoic acid in the procedure described in Example 561: ¹H NMR (400 MHz, pyridine-$d_5$) δ ppm 9.56 (d, J=1.4, 1H), 8.83 (d, J=8.5, 1H), 8.40 (d, J=0.9, 1H), 7.54-7.51 (m, 1H), 7.00 (d, J=7.2, 1H), 6.54 (d, J=8.6, 1H), 4.61-4.45 (m, 1H), 3.78 (dd, J=11.1, 3.4, 1H), 3.65-3.47 (m, 2H), 3.32 (dd, J=10.7, 4.7, 1H), 2.92-2.83 (m, 1H), 2.82-2.73 (m, 1H), 2.49 (s, 3H), 2.25-2.14 (m, 1H), 2.02-1.93 (m, 1H), 1.83 (ddd, J=16.6, 12.6, 8.2, 1H), 1.42 (ddd, J=13.3, 10.6, 6.6, 1H); MS (ESI+) m/z 392 (M+H)⁺.

Example 580

(2S)-2-hydroxy-3,3-dimethyl-N-{(3aR,4S,6aS)-2-[6-(trifluoromethyl)pyridin-2-yl]octahydrocyclopenta[c]pyrrol-4-yl}butanamide The title compound was prepared by substituting (S)-2-hydroxy-3,3-dimethylbutanoic acid for p-fluorobenzoic acid in the procedure described in Example 561: ¹H NMR (500 MHz, pyridine-$d_5$) δ ppm 7.97 (d, J=7.7, 1H), 7.53-7.46 (m, 1H), 7.33 (d, J=5.5, 1H), 6.98 (d, J=7.2, 1H), 6.47 (d, J=8.6, 1H), 4.42-4.34 (m, 1H), 4.20 (d, J=5.4, 1H), 3.63 (dd, J=11.0, 3.0, 1H), 3.52-3.45 (m, 2H), 3.25 (dd, J=10.8, 4.2, 1H), 2.74-2.62 (m, 2H), 2.12 (dt, J=12.3, 7.1, 1H), 1.91 (td, J=13.0, 8.1, 1H), 1.67 (dq, J=12.7, 8.2, 1H), 1.42-1.31 (m, 1H), 1.28 (s, 9H); MS (ESI+) m/z 386 (M+H)⁺.

Example 581

5-methyl-N-{(3aR,4S,6aS)-2-[6-(trifluoromethyl)pyridin-2-yl]octahydrocyclopenta[c]pyrrol-4-yl}-1,2-oxazole-4-carboxamide The title compound was prepared by substituting 5-methylisoxazole-4-carboxylic acid for p-fluorobenzoic acid in the procedure described in Example 561: ¹H NMR (400 MHz, pyridine-$d_5$) δ ppm 9.09-9.00 (m, 1H), 8.76 (s, 1H), 7.52 (t, J=7.9, 1H), 6.99 (d, J=7.3, 1H), 6.53 (d, J=8.6, 1H), 4.52-4.43 (m, 1H), 3.77 (dd, J=11.0, 3.7, 1H), 3.65-3.57 (m, 1H), 3.53-3.42 (m, 1H), 3.27 (dd, J=10.9, 4.6, 1H), 2.81-2.71 (m, 4H), 2.70-2.59 (m, 1H), 2.25-2.11 (m, 1H), 1.87 (dtd, J=12.6, 8.0, 4.6, 1H), 1.77-1.64 (m, 1H), 1.41-1.28 (m, 1H); MS (ESI+) m/z 381 (M+H)⁺.

Example 582

4,4,4-trifluoro-N-{(3aR,4S,6aS)-2-[6-(trifluoromethyl)pyridin-2-yl]octahydrocyclopenta[c]pyrrol-4-yl}butanamide The title compound was prepared by substituting 4,4,4-trifluorobutanoic acid for p-fluorobenzoic acid in the procedure described in Example 561: ¹H NMR (500 MHz, pyridine-$d_5$) δ ppm 8.83 (d, J=6.9, 1H), 7.52 (t, J=7.9, 1H), 6.99 (d, J=7.2, 1H), 6.52 (d, J=8.6, 1H), 4.41-4.32 (m, 1H), 3.71 (dd, J=11.0, 3.2, 1H), 3.61 (dd, J=10.9, 7.7, 1H), 3.51 (dd, J=10.8, 7.9, 1H), 3.27 (dd, J=10.9, 3.6, 1H), 2.81-2.67 (m, 4H), 2.64 (ddd, J=13.5, 8.3, 4.1, 2H), 2.14 (td, J=12.6, 7.0, 1H), 1.96-1.86 (m, 1H), 1.68 (dq, J=12.8, 7.9, 1H), 1.37 (dtd, J=12.8, 7.8, 4.9, 1H); MS (ESI+) m/z 396 (M+H)⁺.

Example 583

3-cyclopropyl-N-{(3aR,4S,6aS)-2-[6-(trifluoromethyl)pyridin-2-yl]octahydrocyclopenta[c]pyrrol-4-yl}-1H-pyrazole-5-carboxamide The title compound was prepared by substituting 3-cyclopropyl-1H-pyrazole-5-carboxylic acid for p-fluorobenzoic acid in the procedure described in Example 561: ¹H NMR (500 MHz, pyridine-$d_5$) δ ppm 14.41 (s, 1H), 8.28 (d, J=7.6, 1H), 7.50 (t, J=7.9, 1H), 6.97 (d, J=7.2, 1H), 6.93 (s, 1H), 6.48 (d, J=8.6, 1H), 4.63-4.52 (m, 1H), 3.75 (dd, J=10.9, 3.4, 1H), 3.51 (dd, J=19.0, 8.3, 2H), 3.29 (dd, J=10.8, 4.5, 1H), 2.83-2.76 (m, 1H), 2.71 (dd, J=17.6, 9.4, 1H), 2.16 (dt, J=12.0, 7.0, 1H), 2.03-1.96 (m, 1H), 1.91 (ddd, J=12.6, 8.4, 4.5, 1H), 1.76 (dq, J=12.7, 8.3, 1H), 1.37 (td, J=13.4, 7.9, 1H), 0.90-0.83 (m, 2H), 0.82-0.75 (m, 2H); MS (ESI+) m/z 406 (M+H)⁺.

Example 584 cis-4-hydroxy-N-{(3aR,4S,6aS)-2-[6-(trifluoromethyl)pyridin-2-yl]octahydrocyclopenta[c]pyrrol-4-yl}cyclohexanecarboxamide The title compound was prepared by substituting (cis)-4-hydroxycyclohexanecarboxylic acid for p-fluorobenzoic acid in the procedure described in Example 561: ¹H NMR (500 MHz, pyridine-$d_5$) δ ppm 8.22 (d, J=7.1, 1H), 7.50 (t, J=7.9, 1H), 6.98 (d, J=7.2, 1H), 6.50 (d, J=8.6, 1H), 5.88 (d, J=3.6, 1H), 4.43-4.37 (m, 1H), 4.18 (d, J=3.4, 1H), 3.71 (dd, J=10.9, 3.3, 1H), 3.61 (dd, J=10.8, 7.7, 1H), 3.52 (dd, J=10.8, 7.9, 1H), 3.28 (dd, J=11.0, 3.7, 1H), 2.78-2.68 (m, 2H), 2.61-2.50 (m, 2H), 2.45 (tt, J=10.6, 3.4, 1H), 2.19-2.03 (m, 3H), 1.98-1.89 (m, 1H), 1.84-1.75 (m, 2H), 1.71 (dq, J=12.8, 7.9, 1H), 1.65-1.55 (m, 2H), 1.37 (dtd, J=12.8, 7.8, 5.1, 1H); MS (ESI+) m/z 398 (M+H)⁺.

Example 585

(2S)-3,3,3-trifluoro-2-hydroxy-N-{(3aR,4S,6aS)-2-[6-(trifluoromethyl)pyridin-2-yl]octahydrocyclopenta[c]pyrrol-4-yl}propanamide The title compound was prepared by substituting (S)-3,3,3-trifluoro-2-hydroxypropanoic acid for p-fluorobenzoic acid in the procedure described in Example 561: ¹H NMR (500 MHz, pyridine-$d_5$) δ ppm 9.72 (s, 1H), 8.79 (d, J=7.5, 1H), 7.54-7.44 (m, 1H), 6.98 (dd, J=7.2, 3.7, 1H), 6.48 (d, J=8.5, 1H), 5.18 (d, J=7.3, 1H), 4.47-4.36 (m, 1H), 3.67 (dd, J=10.9, 3.7, 1H), 3.58-3.43 (m, 2H), 3.28 (dd, J=11.0, 4.5, 1H), 2.81-2.74 (m, 1H), 2.70 (ddd, J=11.5, 8.1, 2.8, 1H), 2.12 (qd, J=7.2, 4.9, 1H), 1.91 (dtd, J=12.9, 8.0, 4.8, 1H), 1.76 (dq, J=12.8, 8.1, 1H), 1.41-1.29 (m, 1H); MS (ESI+) m/z 398 (M+H)⁺.

Example 586

4,4,4-trifluoro-3-hydroxy-N-{(3aR,4S,6aS)-2-[6-(trifluoromethyl)pyridin-2-yl]octahydrocyclopenta[c]pyrrol-4-yl}butanamide The title compound was prepared by substituting 4,4,4-trifluoro-3-hydroxybutanoic acid for p-fluorobenzoic acid in the procedure described in Example 561: $^1$H NMR (500 MHz, pyridine-$d_5$) δ ppm 9.03 (t, J=6.0, 1H), 8.88 (dd, J=18.5, 6.8, 1H), 7.54-7.45 (m, 1H), 6.98 (dd, J=7.2, 4.8, 1H), 6.51 (d, J=8.5, 0.5H), 6.44 (d, J=8.5, 0.5H), 5.19 (dd, J=14.3, 7.3, 1H), 4.48-4.37 (m, 1H), 3.72 (dd, J=10.8, 3.8, 0.5H), 3.68-3.60 (m, 1H), 3.51 (ddd, J=25.3, 16.4, 7.9, 1.5H), 3.29-3.20 (m, 1H), 3.05-2.87 (m, 2H), 2.81-2.63 (m, 2H), 2.21-2.04 (m, 1H), 1.91 (td, J=13.5, 7.9, 1H), 1.77-1.61 (m, 1H), 1.36 (dt, J=13.0, 5.4, 1H); MS (ESI+) m/z 412 (M+H)$^+$.

Example 587

$N^2$,4-dimethyl-N-{(3aR,4S,6aS)-2-[6-(trifluoromethyl)pyridin-2-yl]octahydrocyclopenta[c]pyrrol-4-yl}-L-leucinamide (3aR,4S,6aS)-2-(6-(Trifluoromethyl)pyridin-2-yl)octahydrocyclopenta[c]pyrrol-4-amine from Example 264 Step A (95.7 mg, 0.353 mmol) was combined with (S)-2-(tert-butoxycarbonyl(methyl)amino)-4,4-dimethylpentanoic acid (101 mg, 0.388 mmol) and 1-hydroxybenzotriazole hydrate (59.4 mg, 0.388 mmol) in dichloromethane (1 mL). After 20 minutes, $N^1$-((ethylimino)methylene)-$N^3$,$N^3$-dimethylpropane-1,3-diamine (0.068 mL, 0.388 mmol) was added and the reaction mixture was stirred at room temperature overnight. The reaction mixture was quenched with water and extracted with 2×2 mL of dichloromethane. The combined extracts were applied directly to a 12 g silica gel cartridge and purified with a gradient of 1-10% methanol in (2 N ammonia)/dichloromethane. The resulting oil was treated with 4 N hydrogen chloride in 1,4-dioxane (1 mL, 4 mmol) for 3 hours at room temperature. The solvent was removed under a stream of nitrogen and the residue basified with aqueous sodium bicarbonate and extracted with 2×2 mL of dichloromethane. The combined extracts were applied directly to a 12 g silica gel cartridge and purified with a gradient of 1-10% methanol in (2 N ammonia)/dichloromethane to give the title compound: $^1$H NMR (500 MHz, pyridine-$d_5$) δ ppm 8.36 (d, J=7.3, 1H), 7.51 (t, J=7.9, 1H), 6.98 (d, J=7.2, 1H), 6.52 (d, J=8.6, 1H), 4.45-4.35 (m, 1H), 3.74 (dd, J=10.9, 2.8, 1H), 3.62 (dd, J=10.8, 7.5, 1H), 3.52 (dd, J=10.7, 7.8, 1H), 3.29 (dd, J=10.8, 3.4, 1H), 3.24-3.18 (m, 1H), 2.79-2.64 (m, 2H), 2.42 (s, 3H), 2.14 (td, J=12.5, 7.0, 1H), 2.01-1.79 (m, 3H), 1.69 (dq, J=12.8, 8.0, 1H), 1.51 (dd, J=14.1, 6.6, 1H), 1.44-1.33 (m, 1H), 1.00 (s, 9H); MS (ESI+) m/z 413 (M+H)$^+$.

Example 588

$N^2$-methyl-N-{(3aR,4S,6aS)-2-[6-(trifluoromethyl)pyridin-2-yl]octahydrocyclopenta[c]pyrrol-4-yl}-L-norvalinamide The title compound was prepared by substituting N-(tert-butoxycarbonyl)-N-methyl-L-norvaline for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.24 (d, J=7.3, 1H), 7.51 (t, J=7.9, 1H), 6.98 (d, J=7.2, 1H), 6.51 (d, J=8.6, 1H), 4.45-4.35 (m, 1H), 3.72 (dd, J=10.9, 2.9, 1H), 3.61 (dd, J=10.8, 7.6, 1H), 3.52 (dd, J=10.8, 7.9, 1H), 3.29 (dd, J=10.9, 3.6, 1H), 3.22-3.14 (m, 1H), 2.73 (h, J=8.8, 2H), 2.42 (s, 3H), 2.12 (tt, J=11.0, 5.6, 1H), 2.13-2.01 (m, 1H), 1.92 (td, J=13.2, 8.0, 1H), 1.82 (ddt, J=15.8, 9.7, 6.1, 1H), 1.75-1.61 (m, 2H), 1.59-1.44 (m, 2H), 1.38 (dtd, J=12.9, 7.9, 4.9, 1H), 0.87 (t, J=7.4, 3H); MS (ESI+) m/z 385 (M+H)$^+$.

Example 589

$N^2$-methyl-N-{(3aR,4S,6aS)-2-[6-(trifluoromethyl)pyridin-2-yl]octahydrocyclopenta[c]pyrrol-4-yl}-L-norleucinamide The title compound was prepared by substituting N-(tert-butoxycarbonyl)-N-methyl-L-norleucine for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.25 (d, J=7.3, 1H), 7.51 (t, J=7.9, 1H), 6.98 (d, J=7.2, 1H), 6.51 (d, J=8.6, 1H), 4.46-4.35 (m, 1H), 3.73 (dd, J=10.9, 2.8, 1H), 3.66-3.57 (m, 2H), 3.53 (dd, J=10.7, 8.0, 1H), 3.29 (dd, J=10.8, 3.5, 1H), 3.22-3.11 (m, 1H), 2.79-2.65 (m, 2H), 2.44 (s, 3H), 2.13 (td, J=12.5, 7.1, 1H), 1.98-1.80 (m, 2H), 1.77-1.61 (m, 2H), 1.55-1.33 (m, 3H), 1.31-1.22 (m, 2H), 0.83 (t, J=7.3, 3H); MS (ESI+) m/z 399 (M+H)$^+$.

Example 590

$N^2$-methyl-N-{(3aR,4S,6aS)-2-[6-(trifluoromethyl)pyridin-2-yl]octahydrocyclopenta[c]pyrrol-4-yl}-L-leucinamide The title compound was prepared by substituting N-(tert-butoxycarbonyl)-N-methyl-L-leucine for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.32 (d, J=7.3, 1H), 7.51 (dd, J=11.7, 4.2, 1H), 6.98 (d, J=7.2, 1H), 6.52 (d, J=8.6, 1H), 4.44-4.37 (m, 1H), 3.73 (dd, J=10.9, 2.9, 1H), 3.63 (ddd, J=10.8, 7.0, 2.2, 1H), 3.56-3.48 (m, 1H), 3.29 (dd, J=10.9, 3.5, 1H), 3.27-3.21 (m, 1H), 2.78-2.67 (m, 2H), 2.44 (s, 3H), 2.18-2.10 (m, 1H), 2.09-1.98 (m, 1H), 1.97-1.86 (m, 2H), 1.77-1.64 (m, 2H), 1.60 (ddd, J=13.7, 8.3, 6.3, 1H), 1.44-1.34 (m, 1H), 0.93 (d, J=6.6, 3H), 0.88 (d, J=6.6, 3H); MS (ESI+) m/z 399 (M+H)$^+$.

Example 591

3-methyl-N-{(3aR,4S,6aS)-2-[6-(trifluoromethyl)pyridin-2-yl]octahydrocyclopenta[c]pyrrol-4-yl}-L-valinamide The title compound was prepared by substituting N-(tert-butoxycarbonyl)-L-tert-leucine for (S)-2-(tert-butoxycarbonyl(methyl)amino)-4,4-dimethylpentanoic acid in the procedure described in Example 587: $^1$H NMR (500 MHz, pyridine-$d_5$) δ ppm $^1$H NMR (400 MHz, pyridine-D5) δ 8.27 (d, J=6.9, 1H), 7.51 (t, J=7.9, 1H), 6.98 (d, J=7.2, 1H), 6.51 (d, J=8.6, 1H), 4.42-4.32 (m, 1H), 3.70 (dd, J=10.9, 3.1, 1H), 3.61 (dd, J=10.9, 7.6, 1H), 3.52 (dd, J=10.8, 7.9, 1H), 3.33-3.23 (m, 2H), 2.78-2.64 (m, 2H), 2.29-2.01 (m, 2H), 2.14-2.04 (m, 1H), 1.91 (dt, J=13.2, 6.6, 1H), 1.63 (dq, J=12.8, 7.9, 1H), 1.41-1.29 (m, 1H), 1.17 (s, 9H); MS (ESI+) m/z 385 (M+H)$^+$.

Example 592

(4R)-4-fluoro-N-{(3aR,4S,6aS)-2-[6-(trifluoromethyl)pyridin-2-yl]octahydrocyclopenta[c]pyrrol-4-yl}-L-prolinamide The title compound was prepared by substituting N-(tert-butoxycarbonyl)-trans-4-fluoro-L-proline for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.29 (d, J=7.5, 1H), 7.50 (t, J=7.9, 1H), 6.98 (d, J=7.2, 1H), 6.49 (d, J=8.6, 1H), 5.28-5.12 (m, 1H), 4.33-4.22 (m, 2H), 3.66 (dd, J=11.0, 3.6, 1H), 3.63-3.55 (m, 1H), 3.56-3.45 (m, 2H), 3.36-3.23 (m, 2H), 2.90 (dd, J=37.3, 12.4, 1H), 2.74-2.52 (m, 3H), 2.24 (dddd, J=39.4, 14.8, 8.0, 4.4, 1H), 2.08 (td, J=12.4, 7.1, 1H), 1.89 (dtd, J=13.1, 8.0, 5.0, 1H), 1.60 (dq, J=12.7, 8.0, 1H), 1.35 (dtd, J=13.4, 7.9, 5.7, 1H); MS (ESI+) m/z 387 (M+H)$^+$.

Example 593

(2S,3aS,7aS)-N-{(3aR,4S,6aS)-2-[6-(trifluoromethyl)pyridin-2-yl]octahydrocyclopenta[c]pyrrol-4-yl}octahydro-1H-indole-2-carboxamide The title compound was prepared by substituting (2S,3aS,7aS)-1-(tert-butoxycarbonyl)octahydro-1H-indole-2-carboxylic acid for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.31 (d, J=7.9, 1H), 7.51 (t, J=7.9, 1H), 6.98 (d, J=7.2, 1H), 6.49 (d, J=8.6, 1H), 4.37-4.25 (m, 1H), 3.94 (dd, J=10.6, 4.7, 1H), 3.63 (dd, J=11.0, 3.8, 1H), 3.52 (dt, J=10.8, 7.9, 2H), 3.25 (ddd, J=14.2, 10.1, 4.6, 2H), 3.24-2.99 (m, 1H), 2.76-2.67 (m, 1H), 2.63-2.55 (m, 1H), 2.26 (ddd, J=12.8, 10.6, 7.0, 1H), 2.08 (td, J=12.7, 6.8, 1H), 2.00 (dt, J=12.9, 4.5, 1H), 1.95-1.80 (m, 2H), 1.70-1.28 (m, 9H), 1.16 (ddd, J=15.3, 11.0, 7.9, 1H); MS (ESI+) m/z 423 (M+H)$^+$.

Example 594

1-amino-N-{(3aR,4S,6aS)-2-[6-(trifluoromethyl)pyridin-2-yl]octahydrocyclopenta[c]pyrrol-4-yl}cyclopentanecarboxamide The title compound was prepared by substituting 1-(tert-butoxycarbonylamino)cyclopentanecarboxylic acid for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.36 (d, J=7.5, 1H), 7.51-7.46 (m, 1H), 6.97 (d, J=7.2, 1H), 6.47 (d, J=8.6, 1H), 4.33-4.25 (m, 1H), 3.66 (dd, J=11.0, 3.7, 1H), 3.51 (ddd, J=24.2, 10.9, 8.1, 2H), 3.26 (dd, J=10.9, 4.4, 1H), 2.66 (td, J=8.5, 4.2, 1H), 2.60 (dt, J=12.7, 7.2, 1H), 2.53-2.43 (m, 2H), 2.33-2.12 (br m, 2H), 2.08 (dt, J=12.4, 7.1, 1H), 1.87 (dtd, J=13.2, 8.0, 5.1, 1H), 1.83-1.73 (m, 4H), 1.70-1.52 (m, 3H), 1.34 (ddd, J=18.8, 10.6, 6.8, 1H); MS (ESI+) m/z 383 (M+H)$^+$.

Example 595

4,4-difluoro-N-{(3aR,4S,6aS)-2-[6-(trifluoromethyl)pyridin-2-yl]octahydrocyclopenta[c]pyrrol-4-yl}-L-prolinamide The title compound was prepared by substituting N-(tert-butoxycarbonyl)-4,4-difluoro-L-proline for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.40 (d, J=7.6, 1H), 7.53-7.47 (m, 1H), 6.98 (d, J=7.3, 1H), 6.49 (d, J=8.6, 1H), 4.34-4.27 (m, 1H), 4.23 (dd, J=15.0, 8.3, 1H), 3.95 (q, J=8.0, 1H), 3.65 (dd, J=11.0, 3.4, 1H), 3.51 (ddd, J=26.5, 10.9, 8.0, 2H), 3.43-3.28 (m, 2H), 3.25 (dd, J=10.8, 4.3, 1H), 2.80 (ddd, J=14.7, 11.4, 5.5, 1H), 2.75-2.61 (m, 3H), 2.09 (td, J=12.4, 7.1, 1H), 1.89 (dtd, J=13.1, 8.0, 5.1, 1H), 1.63 (dq, J=12.8, 8.0, 1H), 1.35 (dtd, J=13.3, 7.9, 5.4, 1H); MS (ESI+) m/z 405 (M+H)$^+$.

Example 596

(4S)-4-fluoro-N-{(3aR,4S,6aS)-2-[6-(trifluoromethyl)pyridin-2-yl]octahydrocyclopenta[c]pyrrol-4-yl}-L-prolinamide The title compound was prepared by substituting N-(tert-butoxycarbonyl)-cis-4-fluoro-L-proline for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.32 (d, J=7.6, 1H), 7.50 (t, J=7.9, 1H), 6.97 (d, J=7.2, 1H), 6.46 (d, J=8.6, 1H), 5.16 (dt, J=54.2, 4.2, 1H), 4.33-4.24 (m, 1H), 4.02 (d, J=8.0, 1H), 3.61 (dd, J=11.0, 3.6, 1H), 3.55-3.44 (m, 2H), 3.33 (dd, J=22.3, 12.6, 2H), 3.23 (dd, J=10.9, 4.5, 1H), 3.09 (dd, J=35.7, 11.6, 1H), 2.71-2.56 (m, 3H), 2.24 (dddd, J=38.4, 14.7, 10.1, 4.7, 1H), 2.06 (td, J=12.6, 7.1, 1H), 1.86 (dtd, J=13.3, 8.1, 5.3, 1H), 1.61 (dq, J=12.8, 8.0, 1H), 1.32 (dtd, J=13.2, 7.8, 5.4, 1H); MS (ESI+) m/z 387 (M+H)$^+$.

Example 597

(2S)-N-{(3aR,4S,6aS)-2-[6-(trifluoromethyl)pyridin-2-yl]octahydrocyclopenta[c]pyrrol-4-yl}piperidine-2-carboxamide The title compound was prepared by substituting (S)-1-(tert-butoxycarbonyl)piperidine-2-carboxylic acid for (S)-2-(tert-butoxycarbonyl(methyl)amino)-4,4-dimethylpentanoic acid in the procedure described in Example 587: $^1$H NMR (500 MHz, pyridine-$d_5$) δ ppm 7.81 (d, J=7.5, 1H), 7.50 (t, J=7.9, 1H), 6.98 (d, J=7.2, 1H), 6.48 (d, J=8.6, 1H), 4.36-4.28 (m, 1H), 3.66 (dd, J=11.0, 3.5, 1H), 3.51 (ddd, J=24.8, 10.9, 8.0, 2H), 3.36 (dd, J=10.4, 3.2, 1H), 3.25 (dd, J=10.9, 4.5, 1H), 3.02 (dd, J=14.6, 3.5, 1H), 2.74-2.56 (m, 3H), 2.54-2.30 (m, 1H), 2.08 (ddd, J=13.2, 9.4, 5.1, 2H), 1.89 (dtd, J=13.0, 8.0, 5.0, 1H), 1.70 (dd, J=8.0, 4.1, 1H), 1.66-1.53 (m, 2H), 1.36 (ddt, J=16.5, 13.7, 8.2, 4H); MS (ESI+) m/z 383 (M+H)$^+$.

Example 598

N-{(3aR,4S,6aS)-2-[6-(trifluoromethyl)pyridin-2-yl]octahydrocyclopenta[c]pyrrol-4-yl}-L-prolinamide The title compound was prepared by substituting N-(tert-butoxycarbonyl)-L-proline for (S)-2-(tert-butoxycarbonyl(methyl)amino)-4,4-dimethylpentanoic acid in the procedure described in Example 587: $^1$H NMR (500 MHz, pyridine-$d_5$) δ ppm 8.23 (d, J=7.5, 1H), 7.50 (t, J=7.9, 1H), 6.98 (d, J=7.2, 1H), 6.48 (d, J=8.6, 1H), 4.33-4.24 (m, 1H), 3.91 (dd, J=8.5, 6.0, 1H), 3.65 (dd, J=11.0, 3.6, 1H), 3.56-3.45 (m, 2H), 3.25 (dd, J=10.9, 4.6, 1H), 2.99-3.17 (br m, 1H), 2.95-2.82 (m, 2H), 2.72-2.64 (m, 1H), 2.63-2.56 (m, 1H), 2.15-2.01 (m, 3H), 1.92-1.84 (m, 1H), 1.68-1.49 (m, 3H), 1.35 (dtd, J=13.4, 7.9, 5.7, 1H); MS (ESI+) m/z 369 (M+H)+.

Example 599

N$^2$-methyl-N-{(3aR,4S,6aS)-2-[5-(trifluoromethyl)pyridin-2-yl]octahydrocyclopenta[c]pyrrol-4-yl}-L-norvalinamide The title compound was prepared by substituting N-(tert-butoxycarbonyl)-N-methyl-L-norvaline for (S)-2-(tert-butoxycarbonyl(methyl)amino)-4,4-dimethylpentanoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-d$_5$) δ ppm 8.67-8.57 (m, 1H), 8.30 (d, J=7.4, 1H), 7.68 (dd, J=8.9, 2.4, 1H), 6.40 (d, J=8.9, 1H), 4.48-4.37 (m, 1H), 3.87-3.78 (m, 1H), 3.67 (dd, J=11.1, 7.4, 1H), 3.59 (dd, J=10.7, 8.1, 1H), 3.37-3.29 (m, 1H), 3.20 (dd, J=6.9, 6.2, 1H), 2.82-2.67 (m, 2H), 2.43 (s, 3H), 2.16 (dtd, J=12.4, 7.2, 4.9, 1H), 2.00-1.90 (m, 1H), 1.83 (ddt, J=12.8, 9.5, 6.3, 1H), 1.76-1.64 (m, 2H), 1.60-1.35 (m, 4H), 0.86 (t, J=7.3, 3H); MS (ESI+) m/z 385 (M+H)+.

Example 600

N$^2$-methyl-N-{(3aR,4S,6aS)-2-[5-(trifluoromethyl)pyridin-2-yl]octahydrocyclopenta[c]pyrrol-4-yl}-L-leucinamide The title compound was prepared by substituting N-(tert-butoxycarbonyl)-N-methyl-L-leucine for (S)-2-(tert-butoxycarbonyl(methyl)amino)-4,4-dimethylpentanoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-d$_5$) δ ppm 8.63 (s, 1H), 8.37 (d, J=7.5, 1H), 7.68 (dd, J=8.9, 2.5, 1H), 6.40 (d, J=8.9, 1H), 4.49-4.38 (m, 1H), 3.83 (d, J=10.7, 1H), 3.68 (dd, J=11.0, 7.3, 1H), 3.63-3.52 (m, 1H), 3.33 (d, J=8.2, 1H), 3.27 (dd, J=8.3, 5.9, 1H), 2.77 (h, J=8.8, 2H), 2.45 (s, 3H), 2.17 (dt, J=12.4, 7.1, 1H), 2.14-1.98 (m, 1H), 2.02-1.86 (m, 2H), 1.79-1.67 (m, 2H), 1.66-1.55 (m, 1H), 1.48-1.36 (m, 1H), 0.94 (d, J=6.6, 3H), 0.88 (d, J=6.6, 3H); MS (ESI+) m/z 399 (M+H)+.

Example 601

N$^2$-methyl-N-{(3aR,4S,6aS)-2-[5-(trifluoromethyl)pyridin-2-yl]octahydrocyclopenta[c]pyrrol-4-yl}-L-norleucinamide The title compound was prepared by substituting N-(tert-butoxycarbonyl)-N-methyl-L-norleucine for (S)-2-(tert-butoxycarbonyl(methyl)amino)-4,4-dimethylpentanoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.64-8.59 (m, 1H), 8.27 (d, J=7.5, 1H), 7.68 (dd, J=8.9, 2.5, 1H), 6.39 (d, J=8.9, 1H), 4.47-4.39 (m, 1H), 3.83 (d, J=10.5, 1H), 3.71-3.64 (m, 1H), 3.62-3.54 (m, 1H), 3.33 (d, J=8.5, 1H), 3.19 (dd, J=6.9, 6.2, 1H), 2.81-2.70 (m, 2H), 2.44 (s, 3H), 2.21-2.13 (m, 1H), 2.16-2.03 (m, 1H), 2.01-1.90 (m, 1H), 1.86 (ddt, J=13.3, 10.3, 5.9, 1H), 1.77-1.64 (m, 2H), 1.55-1.37 (m, 3H), 1.32-1.20 (m, 2H), 0.83 (t, J=7.3, 3H); MS (ESI+) m/z 399 (M+H)+.

Example 602

N$^2$,4-dimethyl-N-{(3aR,4S,6aS)-2-[5-(trifluoromethyl)pyridin-2-yl]octahydrocyclopenta[c]pyrrol-4-yl}-L-leucinamide The title compound was prepared by substituting (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.63 (dd, J=1.5, 0.8, 1H), 8.39 (d, J=7.4, 1H), 7.68 (dd, J=8.9, 2.5, 1H), 6.40 (d, J=8.9, 1H), 4.47-4.38 (m, 1H), 3.84 (d, J=10.6, 1H), 3.73-3.65 (m, 1H), 3.63-3.53 (m, 1H), 3.33 (d, J=8.9, 1H), 3.23 (dd, J=6.5, 5.1, 1H), 2.83-2.69 (m, 2H), 2.43 (s, 3H), 2.17 (ddd, J=19.4, 7.1, 4.9, 1H), 2.03-1.89 (m, 2H), 1.93-1.79 (m, 1H), 1.71 (dq, J=12.7, 8.2, 1H), 1.52 (dd, J=14.1, 6.6, 1H), 1.41 (dtd, J=13.0, 8.1, 4.8, 1H), 1.00 (s, 9H); MS (ESI+) m/z 413 (M+H)+.

Example 603

(2S,3aS,7aS)-N-{(3aR,4S,6aS)-2-[5-(trifluoromethyl)pyridin-2-yl]octahydrocyclopenta[c]pyrrol-4-yl}octahydro-1H-indole-2-carboxamide The title compound was prepared by substituting (2S,3aS,7aS)-1-(tert-butoxycarbonyl)octahydro-1H-indole-2-carboxylic acid for (S)-2-(tert-butoxycarbonyl(methyl)amino)-4,4-dimethylpentanoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.66-8.59 (m, 1H), 8.32 (d, J=7.9, 1H), 7.67 (dd, J=8.9, 2.5, 1H), 6.36 (d, J=8.9, 1H), 4.38-4.29 (m, 1H), 3.94 (dd, J=10.6, 4.7, 1H), 3.72 (d, J=8.1, 1H), 3.58 (t, J=9.5, 2H), 3.33 (d, J=6.7, 1H), 3.23 (dd, J=9.4, 4.7, 1H), 3.18-2.94 (m, 1H), 2.80-2.68 (m, 1H), 2.66-2.57 (m, 1H), 2.27 (ddd, J=12.8, 10.6, 7.0, 1H), 2.15-2.05 (m, 1H), 1.96 (dddd, J=18.4, 16.6, 8.6, 4.9, 2H), 1.88-1.79 (m, 1H), 1.70-1.35 (m, 8H), 1.35-1.27 (m, 1H), 1.16 (tt, J=15.5, 6.5, 1H); MS (ESI+) m/z 423 (M+H)+.

Example 604

(2S)-N-{(3aR,4S,6aS)-2-[5-(trifluoromethyl)pyridin-2-yl]octahydrocyclopenta[c]pyrrol-4-yl}indoline-2-carboxamide The title compound was prepared by substituting (S)-1-(tert-butoxycarbonyl)indoline-2-carboxylic acid for (S)-2-(tert-butoxycarbonyl(methyl)amino)-4,4-dimethylpentanoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-d$_5$) δ ppm 8.63 (dd, J=1.6, 0.8, 1H), 8.21 (d, J=7.6, 1H), 7.67 (dd, J=9.0, 2.5, 1H), 7.19-7.07 (m, 2H), 6.83 (dd, J=11.7, 4.3, 2H), 6.54-6.46 (m, 1H), 6.35 (d, J=8.9, 1H), 4.69 (td, J=10.8, 3.5, 1H), 4.46-4.30 (m, 1H), 3.82-3.71 (m, 1H), 3.65-3.48 (m, 3H), 3.42-3.24 (m, 2H), 2.80-2.62 (m, 2H), 2.19-2.03 (m, 1H), 1.97-1.80 (m, 1H), 1.62 (dq, J=12.8, 8.2, 1H), 1.45-1.28 (m, 1H); MS (ESI+) m/z 417 (M+H)+.

Example 605

(3aR,4S,6aS)-2-[3-(trifluoromethyl)phenyl]octahydrocyclopenta[c]pyrrol-4-amine

Step A: tert-Butyl(3aR,4S,6aS)-octahydrocyclopenta[c]pyrrol-4-ylcarbamate from Example 252 Step B (50.3 mg, 0.222 mmol), tris(dibenzylidineacetone)dipalladium(0) (4.07 mg, 4.45 μmol), 2,2'-bis(diphenylphosphino)-1,1'-binaphthyl (8.30 mg, 0.013 mmol), potassium phosphate, tribasic (54.2 mg, 0.311 mmol) and 1-bromo-3-(trifluoromethyl) benzene (0.032 mL, 0.233 mmol) were combined in toluene (2 mL) and put under nitrogen. The reaction mixture was heated at 80° C. overnight. The reaction was quenched with water (1 mL), the phases were separated, and the organic phase was applied to a 4 g silica gel cartridge and purified using a gradient of 1-20% ethyl acetate/hexanes over 15 minutes to give tert-butyl(3aR,4S,6aS)-2-(3-(trifluoromethyl) phenyl)octahydrocyclopenta[c]pyrrol-4-ylcarbamate: $^1$H NMR (400 MHz, pyridine-$d_5$) δ ppm 7.73 (d, J=6.3, 1H), 7.33 (t, J=7.8, 1H), 7.06 (d, J=7.4, 1H), 6.91 (s, 1H), 6.76 (d, J=7.9, 1H), 4.13-4.02 (m, 1H), 3.44 (d, J=10.0, 1H), 3.34-3.27 (m, 1H), 3.21-3.12 (m, 1H), 2.99 (d, J=10.1, 1H), 2.81-2.70 (m, 2H), 2.12 (td, J=12.6, 6.4, 1H), 2.06-1.95 (m, 1H), 1.73 (dq, J=15.0, 7.5, 1H), 1.55 (s, 9H), 1.44-1.34 (m, 1H); MS (ESI+) m/z 371 (M+H)+.

Step B: tert-Butyl(3aR,4S,6aS)-2-(3-(trifluoromethyl) phenyl)octahydrocyclopenta[c]pyrrol-4-ylcarbamate (29 mg, 0.078 mmol) from Step A was treated with 4 N hydrogen chloride in 1,4-dioxane (0.5 mL, 2 mmol) for 3 hours at room temperature. The solvent was removed under a stream of nitrogen and the residue basified with aqueous sodium bicarbonate and extracted with 2×2 mL of dichloromethane. The extracts were applied directly to a 12 g silica gel cartridge and purified with a gradient of 1-10% methanol in (2 N ammonia)/dichloromethane to give the title compound: $^1$H NMR (400 MHz, pyridine-$d_5$) δ ppm 7.35 (t, J=7.9, 1H), 7.06 (d, J=7.6, 1H), 6.91 (s, 1H), 6.77 (dd, J=8.3, 2.4, 1H), 3.23-3.14 (m, 3H), 3.11 (dd, J=12.0, 5.7, 1H), 2.95 (dd, J=9.7, 4.4, 1H), 2.80-2.70 (m, 1H), 2.37-2.29 (m, 1H), 2.05 (ddt, J=16.5, 12.9, 6.3, 1H), 1.94-1.84 (m, 1H), 1.82-1.60 (m, 2H), 1.47-1.29 (m, 2H); MS (ESI+) m/z 271 (M+H)+.

Example 606

N$^2$-methyl-N-{(3aR,4S,6aS)-2-[3-(trifluoromethyl) phenyl]octahydrocyclopenta[c]pyrrol-4-yl}-L-leucinamide The title compound was prepared by substituting N-(tert-butoxycarbonyl)-N-methyl-L-leucine for (S)-2-(tert-butoxycarbonyl(methyl)amino)-4,4-dimethylpentanoic acid and (3aR,4S,6aS)-2-[3-(trifluoromethyl)phenyl]octahydrocyclopenta[c]pyrrol-4-amine from Example 605 Step B for (3aR, 4S,6aS)-2-(6-(trifluoromethyl)pyridin-2-yl)octahydrocyclopenta[c]pyrrol-4-amine in the procedure described in Example 587: $^1$H NMR (500 MHz, pyridine-$d_5$) δ ppm 8.34 (d, J=7.4, 1H), 7.34 (t, J=7.9, 1H), 7.06 (d, J=7.6, 1H), 6.94 (s, 1H), 6.78 (dd, J=8.3, 2.2, 1H), 4.46-4.38 (m, 1H), 3.55 (dd, J=9.9, 2.8, 1H), 3.37-3.32 (m, 1H), 3.27 (dd, J=8.3, 5.8, 1H), 3.17 (dd, J=9.5, 7.9, 1H), 3.01 (dd, J=9.7, 3.3, 1H), 2.79-2.70 (m, 2H), 2.46 (s, 3H), 0.2-1.86 (br s, 1H), 2.13 (dt, J=12.5, 6.7, 1H), 2.01-1.87 (m, 2H), 1.79-1.65 (m, 2H), 1.65-1.57 (m, 1H), 1.46-1.38 (m, 1H), 0.94 (d, J=6.6, 3H), 0.88 (d, J=6.6, 3H); MS (ESI+) m/z 398 (M+H)+.

Example 607

(3aR,4S,6aS)-2-[4-(trifluoromethyl)phenyl]octahydrocyclopenta[c]pyrrol-4-amine

The title compound was prepared by substituting 1-bromo-4-(trifluoromethyl)benzene for 1-bromo-3-(trifluoromethyl) benzene in the procedure described in Example 605: $^1$H NMR (500 MHz, pyridine-$d_5$) δ ppm 7.59 (d, J=12.2, 2H), 6.62 (d, J=8.7, 2H), 3.27-3.18 (m, 3H), 3.09 (dd, J=12.0, 5.9, 1H), 2.96 (dd, J=9.9, 4.6, 1H), 2.79-2.69 (m, 1H), 2.37-2.29 (m, 1H), 2.07-1.98 (m, 1H), 1.93-1.85 (m, 1H), 1.83-1.71 (m, 2H), 1.46-1.37 (m, 1H), 1.33 (dtd, J=12.6, 7.5, 4.9, 1H); MS (ESI+) m/z 271 (M+H)+.

Example 608

N$^2$-methyl-N-{(3aR,4S,6aS)-2-[4-(trifluoromethyl) phenyl]octahydrocyclopenta[c]pyrrol-4-yl}-L-leucinamide The title compound was prepared by substituting N-(tert-butoxycarbonyl)-N-methyl-L-leucine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-$d_5$) δ ppm 8.34 (d, J=7.4, 1H), 7.57 (d, J=4.2, 2H), 6.63 (d, J=8.7, 2H), 4.44-4.37 (m, 1H), 3.56 (dd, J=10.2, 2.9, 1H), 3.39 (dd, J=10.0, 7.6, 1H), 3.30-3.21 (m, 2H), 3.03 (dd, J=9.9, 3.5, 1H), 2.79-2.68 (m, 2H), 2.47 (s, 3H), 2.12 (dt, J=12.4, 6.9, 1H), 2.08-2.01 (m, 1H), 2.00-1.88 (m, 2H), 1.79-1.57 (m, 3H), 1.39 (dtd, J=13.1, 8.0, 5.1, 1H), 0.94 (d, J=6.6, 3H), 0.88 (d, J=6.6, 3H); MS (ESI+) m/z 398 (M+H)+.

Example 609

(3aR,4S,6aS)-N-isopropyl-2-[6-(trifluoromethyl) pyridin-2-yl]octahydrocyclopenta[c]pyrrol-4-amine (3aR,4S,6aS)-2-(6-(Trifluoromethyl)pyridin-2-yl)octahydrocyclopenta[c]pyrrol-4-amine from Example 264 Step A (44 mg, 0.162 mmol) and acetone (14.13 mg, 0.243 mmol) were combined in dichloromethane (0.5 mL). Acetic acid (0.5 mL) was added. The reaction mixture was stirred at ambient temperature for 30 minutes, then PS-cyanoborohydride (146 mg, 0.324 mmol) was added. After 18 hours, the reaction mixture was filtered and the solvent removed under a stream of nitrogen. The crude material was applied to a 4 g silica gel cartridge and purified with a gradient of 1-10% methanol in (2 N ammonia)/dichloromethane to give to give the title compound: $^1$H NMR (500 MHz, pyridine-$d_5$) δ ppm 7.57-7.52 (m, 1H), 6.99 (d, J=7.2, 1H), 6.55 (d, J=8.6, 1H), 3.62-3.54 (m, 1H), 3.54-3.45 (m, 2H), 3.25 (dd, J=10.7, 4.3, 1H), 3.03 (dd, J=11.8, 5.9, 1H), 2.83 (dt, J=12.4, 6.2, 1H), 2.76-2.67 (m, 1H), 2.49-2.41 (m, 1H), 2.02-1.92 (m, 2H), 1.45-1.29 (m, 3H), 1.06 (d, J=6.2, 3H), 1.03 (d, J=6.2, 3H); MS (ESI+) m/z 314 (M+H)+.

Example 610

(3aR,4S,6aS)-N-isobutyl-2-[6-(trifluoromethyl)pyridin-2-yl]octahydrocyclopenta[c]pyrrol-4-amine The title compound was prepared by substituting isobutyraldehyde for acetone in the procedure described in Example 609: $^1$H NMR (500 MHz, pyridine-$d_5$) δ ppm 7.56-7.50 (m, 1H), 6.99 (d, J=7.3, 1H), 6.55 (d, J=8.6, 1H), 3.59 (dd, J=10.6, 8.8, 1H), 3.51 (dd, J=10.6, 8.3, 1H), 3.45 (dd, J=10.9, 4.4, 1H), 3.25 (dd, J=10.7, 4.2, 1H), 2.87 (dd, J=11.0, 5.7, 1H), 2.77-2.68 (m, 1H), 2.50-2.43 (m, 1H), 2.39 (t, J=5.6, 2H), 2.02-1.90 (m, 2H), 1.68 (dt, J=13.3, 6.7, 1H), 1.43 (ddd, J=12.8, 7.9, 6.5, 1H), 1.34 (ddd, J=16.7, 13.7, 8.1, 1H), 1.29-1.22 (br s, 1H), 0.98-0.90 (m, 6H); MS (ESI+) m/z 328 (M+H)$^+$.

Example 611

(3aR,4S,6aS)-N-(3,3-dimethylbutyl)-2-[6-(trifluoromethyl)pyridin-2-yl]octahydrocyclopenta[c]pyrrol-4-amine The title compound was prepared by substituting 3,3-dimethylbutanal for acetone in the procedure described in Example 609: $^1$H NMR (500 MHz, pyridine-$d_5$) δ ppm 7.56-7.51 (m, 1H), 6.99 (d, J=7.2, 1H), 6.55 (d, J=8.6, 1H), 3.64-3.57 (m, 1H), 3.55-3.44 (m, 2H), 3.29-3.23 (m, 1H), 2.93 (dd, J=10.8, 5.6, 1H), 2.79-2.71 (m, 1H), 2.69-2.58 (m, 2H), 2.51 (tt, J=8.6, 4.5, 1H), 2.04-1.92 (m, 2H), 1.52-1.31 (m, 4H), 1.34-1.17 (m, 1H), 0.91 (s, 9H); MS (ESI+) m/z 356 (M+H)$^+$.

Example 612

(3aR,4S,6aS)-N-(1H-indol-2-ylmethyl)-2-[6-(trifluoromethyl)pyridin-2-yl]octahydrocyclopenta[c]pyrrol-4-amine The title compound was prepared by substituting 1H-indole-2-carbaldehyde for acetone in the procedure described in Example 609: $^1$H NMR (500 MHz, pyridine-$d_5$) δ ppm 12.01 (s, 1H), 7.81 (d, J=7.6, 1H), 7.62 (d, J=8.0, 1H), 7.54-7.50 (m, 1H), 7.27 (dtd, J=15.8, 7.1, 1.2, 2H), 6.98 (d, J=7.2, 1H), 6.66 (d, J=1.1, 1H), 6.48 (d, J=8.6, 1H), 4.12-4.04 (m, 2H), 3.55-3.49 (m, 1H), 3.45 (dd, J=10.6, 8.4, 1H), 3.41-3.35 (m, 1H), 3.25-3.18 (m, 1H), 3.05-3.00 (m, 1H), 2.75-2.66 (m, 1H), 2.52 (tt, J=8.8, 4.6, 1H), 2.12-2.05 (br m, 1H), 1.98-1.90 (m, 2H), 1.53-1.43 (m, 1H), 1.34-1.25 (m, 1H); MS (ESI+) m/z 401 (M+H)$^+$.

Example 613

(3aR,4S,6aS)-N-[(5-fluoro-1H-indol-2-yl)methyl]-2-[6-(trifluoromethyl)pyridin-2-yl]octahydrocyclopenta[c]pyrrol-4-amine The title compound was prepared by substituting 5-fluoro-1H-indole-2-carbaldehyde for acetone in the procedure described in Example 609: $^1$H NMR (500 MHz, pyridine-$d_5$) δppm 12.14 (s, 1H), 7.52 (ddd, J=13.8, 7.3, 4.1, 3H), 7.10 (td, J=9.1, 2.6, 1H), 6.99 (d, J=7.2, 1H), 6.60 (d, J=1.0, 1H), 6.48 (d, J=8.6, 1H), 4.11-3.99 (m, 2H), 3.57-3.42 (m, 2H), 3.39 (dd, J=11.0, 4.3, 1H), 3.21 (dd, J=10.7, 4.1, 1H), 3.00 (dd, J=11.0, 5.6, 1H), 2.76-2.63 (m, 1H), 2.50 (ddd, J=13.1, 8.7, 4.6, 1H), 2.27-2.02 (bs, 1H), 1.99-1.87 (m, 2H), 1.47 (ddd, J=16.0, 8.4, 2.2, 1H), 1.36-1.23 (m, 1H); MS (ESI+) m/z 419 (M+H)$^+$.

Example 614

(3aR,4S,6aS)-N-[(5-fluoro-1H-indol-2-yl)methyl]-2-[5-(trifluoromethyl)pyridin-2-yl]octahydrocyclopenta[c]pyrrol-4-amine The title compound was prepared by combining 5-fluoro-1H-indole-2-carbaldehyde (30.1 mg, 0.184 mmol) and (3aR,4S,6aS)-2-(5-(trifluoromethyl)pyridin-2-yl)octahydrocyclopenta[c]pyrrol-4-amine (50 mg, 0.184 mmol) from Example 262 Step B in dichloromethane (0.2 mL) to give a colorless solution. 0.2 mL of acetic acid was added. The reaction was stirred at ambient temperature for 30 minutes, then PS-cyanoborohydride (166 mg, 0.369 mmol) was added. After 18 hours, the reaction was filtered and the solvent was removed in vacuo. The crude material was purified using a 12 g silica gel cartridge eluted with 1-10% methanol (2 N ammonia)/dichloromethane to give the title compound: $^1$H NMR (500 MHz, pyridine-$d_5$) δ ppm 12.14 (s, 1H), 8.64 (dd, J=1.5, 0.7, 1H), 7.69 (dd, J=8.9, 2.5, 1H), 7.54-7.46 (m, 2H), 7.14-7.07 (m, 1H), 6.61 (d, J=1.2, 1H), 6.36 (d, J=8.9, 1H), 4.12-4.00 (m, 2H), 3.56 (ddd, J=21.0, 9.4, 3.4, 2H), 3.48-3.40 (m, 1H), 3.28 (ddd, J=3.7, 2.1, 0.9, 1H), 3.04 (dd, J=11.0, 5.8, 1H), 2.78-2.68 (m, 1H), 2.57-2.50 (m, 1H), 2.31-2.04 (m, 1H), 2.02-1.91 (m, 2H), 1.55-1.44 (m, 1H), 1.38-1.28 (m, 1H); MS (ESI+) m/z 419 (M+H)$^+$.

Example 615

(3aR,4S,6aS)-N-[(5-fluoro-1H-indol-2-yl)methyl]-2-[4-(trifluoromethyl)phenyl]octahydrocyclopenta[c]pyrrol-4-amine The title compound was prepared by substituting (3aR,4S,6aS)-2-[4-(trifluoromethyl)phenyl]octahydrocyclopenta[c]pyrrol-4-amine from Example 607 for (3aR,4S,6aS)-2-(5-(trifluoromethyl)pyridin-2-yl)octahydrocyclopenta[c]pyrrol-4-amine in the procedure described in Example 614: $^1$H NMR (500 MHz, pyridine-$d_5$) δ ppm 12.16 (s, 1H), 7.60-7.58 (m, 2H), 7.55-7.49 (m, 2H), 7.11 (td, J=9.1, 2.5, 1H), 6.61 (dd, J=12.7, 4.9, 3H), 4.14-4.03 (m, 2H), 3.29-3.19 (m, 2H), 3.14 (dd, J=10.0, 4.3, 1H), 3.00 (ddd, J=13.9, 10.5, 5.0, 2H), 2.76-2.66 (m, 1H), 2.52 (tt, J=8.8, 4.5, 1H), 2.14 (s, 1H), 2.03-1.89 (m, 2H), 1.55-1.45 (m, 1H), 1.36-1.25 (m, 1H); MS (ESI+) m/z 418 (M+H)$^+$.

Example 616

(3aR,4S,6aS)-N-[(5-fluoro-1H-indol-2-yl)methyl]-2-[3-(trifluoromethyl)phenyl]octahydrocyclopenta[c]pyrrol-4-amine The title compound was prepared by substituting (3aR,4S,6aS)-2-[3-(trifluoromethyl)phenyl]octahydrocyclopenta[c]pyrrol-4-amine from Example 605 for (3aR,4S,6aS)-2-(5-(trifluoromethyl)pyridin-2-yl)octahydrocyclopenta[c]pyrrol-4-amine in the procedure described in Example 614: $^1$H NMR (400 MHz, pyridine-$d_5$) δ ppm 12.15 (s, 1H), 7.52 (dt, J=8.8, 3.6, 2H), 7.36 (t, J=7.9, 1H), 7.09 (ddd, J=12.9, 9.9, 5.1, 2H), 6.88 (s, 1H), 6.74 (dd, J=8.3, 2.2, 1H), 6.62 (d, J=1.2, 1H), 4.15-4.05 (m, 2H), 3.16 (ddt, J=14.0, 10.3, 7.0, 3H), 3.02 (dd, J=10.9, 5.7, 1H), 2.96 (dd, J=9.7, 4.0, 1H), 2.78-2.65 (m, 1H), 2.52 (tt, J=8.9, 4.5, 1H), 2.43-2.05 (m, 1H), 2.05-1.88 (m, 2H), 1.55-1.43 (m, 1H), 1.38-1.25 (m, 1H); MS (ESI+) m/z 418 (M+H)$^+$.

Example 617

(4R)-4-fluoro-N-{(3aR,4S,6aS)-2-[3-(trifluoromethyl)phenyl]octahydrocyclopenta[c]pyrrol-4-yl}-L-prolinamide Step 1: To a solution of (2S,4R)-1-(tert-butoxycarbonyl)-4-fluoropyrrolidine-2-carboxylic acid (2.87 g, 12.31 mmol) and (3aR,4S,6aS)-2-benzyloctahydrocyclopenta[c]pyrrol-4-amine from Example 33 Step A (2.93 g, 13.54 mmol) in dichloromethane (16.97 mL) was added 1-hydroxybenzotriazole hydrate (2.073 g, 13.54 mmol). After 2 minutes, $N^1$-((ethylimino)methylene)-$N^3$,$N^3$-dimethylpropane-1,3-diamine (2.388 mL, 13.54 mmol) was added and the reaction was stirred at ambient temperature overnight. The reaction was quenched with saturated aqueous sodium bicarbonate solution and extracted with dichloromethane. The solvent was removed in vacuo. The crude material was purified using an 80 g silica gel cartridge eluted with a gradient of 0-5% methanol (2 N ammonia)/dichloromethane over 20 minutes to give (2S,4R)-tert-butyl 2-((3aR,4S,6aS)-2-benzyloctahydrocyclopenta[c]pyrrol-4-ylcarbamoyl)-4-fluoropyrrolidine-1-carboxylate: $^1$H NMR (400 MHz, pyridine-$d_5$) δ ppm 7.70 (s, 1H), 7.38-7.36 (m, 2H), 7.33-7.26 (m, 2H), 7.24-7.17 (m, 1H), 5.19 (dd, J=53.5, 3.3, 1H), 4.59 (t, J=7.8, 1H), 4.31-4.22 (m, 1H), 4.04-3.92 (m, 1H), 3.68 (dd, J=12.9, 3.7, 1H), 3.62-3.57 (m, 1H), 3.60-3.45 (m, 2H), 2.83-2.76 (m, 1H), 2.56-2.58 (m, 1H), 2.52-2.43 (m, 3H), 2.35 (m, 3H), 2.10 (dq, J=12.5, 6.3, 1H), 1.92-1.82 (m, 1H), 1.67-1.57 (m, 1H), 1.49 (s, 9H), 1.46-1.36 (m, 1H); MS (ESI+) m/z 432 (M+H)$^+$.

Step 2: To a solution of (2S,4R)-tert-butyl 2-((3aR,4S,6aS)-2-benzyloctahydrocyclopenta[c]pyrrol-4-ylcarbamoyl)-4-fluoropyrrolidine-1-carboxylate (4.59 g, 10.64 mmol) from Step 1 in ethanol (45 mL) was added to 20% Pd(OH)$_2$—C, wet (0.918 g, 6.54 mmol) in a 250 mL stainless steel pressure bottle. The mixture was shaken under 30 psi of hydrogen at 50° C. for 45 minutes. The mixture was filtered through a nylon membrane and the solvent removed in vacuo to give (2S,4R)-tert-butyl 4-fluoro-2-((3aR,4S,6aS)-octahydrocyclopenta[c]pyrrol-4-ylcarbamoyl)pyrrolidine-1-carboxylate: $^1$H NMR (400 MHz, pyridine-$d_5$, 90° C.) δ ppm 7.87 (s, 1H), 5.21 (dd, J=53.6, 3.0, 1H), 4.61 (t, J=7.8, 1H), 4.24-4.14 (m, 1H), 3.91 (dd, J=11.6, 3.1, 2H), 3.66 (ddd, J=34.5, 12.8, 3.6, 1H), 3.15-3.05 (m, 2H), 2.96 (dd, J=10.7, 7.3, 1H), 2.68 (dd, J=10.7, 3.7, 1H), 2.64-2.57 (m, 1H), 2.57-2.31 (m, 3H), 2.10-2.00 (m, 1H), 1.95-1.85 (m, 1H), 1.70-1.58 (m, 1H), 1.49 (s, 9H), 1.41-1.30 (m, 1H); MS (ESI+) m/z 342 (M+H)$^+$.

Step 3: In a 4 mL vial under nitrogen was added (2S,4R)-tert-butyl 4-fluoro-2-((3aR,4S,6aS)-octahydrocyclopenta[c]pyrrol-4-ylcarbamoyl)pyrrolidine-1-carboxylate (70 mg, 0.205 mmol) from Step 2,1-bromo-3-(trifluoromethyl)benzene (0.030 mL, 0.215 mmol), potassium phosphate, tribasic (71.4 mg, 0.410 mmol), tris(dibenzylideneacetone)dipalladium(0) (3.75 mg, 4.10 μmol) and 2-dicyclohexylphosphino-2',4',6'-triisopropylbiphenyl (X-PHOS, 7.82 mg, 0.016 mmol) in t-amyl alcohol (0.5 mL). The reaction was put under nitrogen, then heated at 80° C. for 18 hours. The crude material was applied to a 12 g silica gel cartridge with dichloromethane and purified using a gradient of 0-20% acetone/hexane over 20 minutes to give (2S,4R)-tert-butyl 4-fluoro-2-((3aR,4S,6aS)-2-(3-(trifluoromethyl)phenyl)octahydrocyclopenta[c]pyrrol-4-ylcarbamoyl)pyrrolidine-1-carboxylate: $^1$H NMR (400 MHz, pyridine-$d_5$, 90° C.) δ ppm 8.00-7.87 (m, 1H), 7.28 (t, J=7.9, 1H), 7.00 (d, J=7.7, 1H), 6.75 (dd, J=8.4, 2.0, 1H), 5.23 (dd, J=53.6, 3.1, 1H), 4.64 (t, J=7.8, 1H), 4.26 (dt, J=12.2, 6.1, 1H), 4.08-3.98 (m, 1H), 3.67 (ddd, J=34.5, 12.9, 3.7, 1H), 3.47 (dd, J=9.9, 3.5, 1H), 3.36 (dd, J=9.9, 7.8, 1H), 3.22 (dd, J=9.6, 7.9, 1H), 3.02 (dd, J=9.7, 3.8, 1H), 2.75 (dtd, J=17.2, 8.4, 4.5, 2H), 2.57-2.36 (m, 2H), 2.12 (dt, J=12.6, 6.4, 1H), 2.05-1.94 (m, 1H), 1.72 (ddd, J=15.0, 12.7, 7.6, 1H), 1.51 (s, 9H), 1.50-1.38 (m, 2H); MS (ESI+) m/z 486 (M+H)$^+$.

Step 4: In a 4 mL vial was added (2S,4R)-tert-butyl 4-fluoro-2-((3aR,4S,6aS)-2-(3-(trifluoromethyl)phenyl)octahydrocyclopenta[c]pyrrol-4-ylcarbamoyl)pyrrolidine-1-carboxylate from Step 3 (63 mg, 0.130 mmol) and 4 N HCl in 1,4-dioxane (0.487 mL, 1.948 mmol) to give a colorless solution. The reaction was stirred at room temperature overnight, and the solvent was then removed in vacuo. The residue was purified using a 12 g silica gel cartridge eluted with a gradient of 0-2.5% methanol (2 N ammonia)/dichloromethane over 20 minutes to give (4S)-4-fluoro-N-{(3aR,4S,6aS)-2-[3-(trifluoromethyl)phenyl]octahydrocyclopenta[c]pyrrol-4-yl}-L-prolinamide: $^1$H NMR (500 MHz, pyridine-$d_5$) δ ppm 8.31 (d, J=7.5, 1H), 7.33 (dd, J=10.1, 5.7, 1H), 7.06 (d, J=7.6, 1H), 6.90 (s, 1H), 6.75 (dd, J=8.3, 2.1, 1H), 5.30-5.12 (m, 1H), 4.30 (dt, J=14.4, 7.3, 2H), 3.72-3.55 (bs, 1H), 3.50-3.43 (m, 1H), 3.32 (ddd, J=21.0, 13.1, 0.8, 1H), 3.23 (dd, J=9.9, 8.0, 1H), 3.13 (dd, J=9.5, 8.2, 1H), 2.99 (dd, J=9.7, 4.1, 1H), 2.96-2.84 (m, 1H), 2.76-2.67 (m, 1H), 2.66-2.52 (m, 2H), 2.26 (dddd, J=39.3, 14.8, 7.9, 4.3, 1H), 2.07 (td, J=12.3, 6.8, 1H), 1.93 (dtd, J=13.1, 7.9, 5.2, 1H), 1.60 (ddd, J=16.0, 12.6, 7.8, 1H), 1.38 (dddd, J=13.2, 7.7, 6.7, 1H); MS (ESI+) m/z 386 (M+H)$^+$.

Example 618

$N^2$-methyl-N-{(3aR,4S,6aS)-2-[2-(trifluoromethyl)phenyl]octahydrocyclopenta[c]pyrrol-4-yl}-L-leucinamide Step 1: To a microwave vial under nitrogen was added tert-butyl(3aR,4S,6aS)-octahydrocyclopenta[c]pyrrol-4-ylcarbamate from Example 216 step B (290 mg, 1.281 mmol), 1-bromo-2-(trifluoromethyl)benzene (0.183 mL, 1.345 mmol), potassium phosphate, tribasic (446 mg, 2.56 mmol), tris(dibenzylideneacetone)dipalladium(0) (23.47 mg, 0.026 mmol) and 2-dicyclohexylphosphino-2',4',6'-triisopropylbiphenyl (X-PHOS, 48.9 mg, 0.103 mmol) in t-amyl alcohol (2.0 mL). The reaction was heated at 80° C. for 18 hours. The reaction was diluted with ethyl acetate (35 mL) and quenched with water (75 mL). The organic phase was removed, and the aqueous layer extracted with 50 mL of ethyl acetate. The solvent was removed in vacuo. The crude material was applied to a 24 g silica gel cartridge with ether and purified using 1-50% ethyl acetate/hexanes to give tert-butyl (3aR,4S,6aS)-2-(2-(trifluoromethyl)phenyl)octahydrocyclopenta[c]pyrrol-4-ylcarbamate: $^1$H NMR (400 MHz, pyridine-$d_5$) δ ppm 7.66 (d, J=7.8, 1H), 7.45 (t, J=7.6, 1H), 7.25 (d, J=8.1, 1H), 7.11 (t, J=7.5, 1H), 4.21 (s, 1H), 3.40 (d, J=9.1, 1H), 3.11 (dd, J=9.1, 6.9, 1H), 3.03-2.88 (m, 2H), 2.69 (d, J=11.5, 2H), 2.17 (dt, J=11.4, 5.7, 1H), 2.04-1.91 (m, 1H), 1.67 (dd, J=18.5, 7.9, 1H), 1.60-1.46 (m, 11H); MS (ESI+) m/z 371 (M+H)$^+$.

Step 2: In a 4 mL vial tert-butyl(3aR,4S,6aS)-2-(2-(trifluoromethyl)phenyl)octahydrocyclopenta[c]pyrrol-4-ylcarbamate from Step 1 (79 mg, 0.213 mmol) was dissolved in 4 N HCl in 1,4-dioxane (1 mL, 4.00 mmol) to give a solution. An oil slowly gummed out of the reaction. The reaction was stirred at ambient temperature for 4 hours and volatiles were removed to give the HCl salt. The crude material was chromatographed using a 4 g silica gel cartridge with 1-10% methanol (2 N ammonia)/dichloromethane to give (3aR,4S, 6aS)-2-(2-(trifluoromethyl)phenyl)octahydrocyclopenta[c]pyrrol-4-amine: $^1$H NMR (400 MHz, pyridine-d$_5$) δ ppm 7.67 (dd, J=7.9, 1.4, 1H), 7.48 (t, J=7.8, 1H), 7.25 (d, J=8.2, 1H), 7.11 (t, J=7.6, 1H), 4.79 (s, 2H), 3.26 (dd, J=12.4, 5.3, 1H), 3.13 (dd, J=9.2, 2.5, 1H), 3.07-3.00 (m, 1H), 3.00-2.90 (m, 2H), 2.67 (td, J=9.0, 4.6, 1H), 2.34-2.24 (m, 1H), 2.07-1.92 (m, 2H), 1.54-1.44 (m, 1H), 1.42-1.33 (m, 1H); MS (ESI+) m/z 271 (M+H)$^+$.

Step 3: To a 4 mL vial was added (3aR,4S,6aS)-2-(2-(trifluoromethyl)phenyl)octahydrocyclopenta[c]pyrrol-4-amine from Step 2 (21.6 mg, 0.080 mmol), N-(tert-butoxycarbonyl)-N-methyl-L-leucine (21.56 mg, 0.088 mmol), and 1-hydroxybenzotriazole hydrate (13.46 mg, 0.088 mmol) in dichloromethane (1 mL) to give a colorless solution. After 20 minutes, N$^1$-((ethylimino)methylene)-N$^3$,N$^3$-dimethylpropane-1,3-diamine (0.016 mL, 0.088 mmol) was added. The reaction mixture was stirred at ambient temperature for 18 hours. The reaction was diluted with 1 mL of dichloromethane and quenched with 2 mL of water. The aqueous layer was extracted with more dichloromethane (2×2 mL), the solvent was removed in vacuo, and the crude material was applied to a 24 g silica gel cartridge and purified with 1-50% ethyl acetate/hexanes to give tert-butyl methyl((S)-4-methyl-1-oxo-1-((3aR,4S,6aS)-2-(2-(trifluoromethyl)phenyl)octahydrocyclopenta[c]pyrrol-4-ylamino)pentan-2-yl)carbamate: $^1$H NMR (500 MHz, pyridine-d$_5$) δ ppm 8.34 (d, J=6.8, 1H), 7.69-7.62 (m, 1H), 7.45 (t, J=7.4, 1H), 7.26 (d, J=8.2, 1H), 7.11 (t, J=7.6, 1H), 5.17 (s, 1H), 4.46 (s, 1H), 3.45 (d, J=8.8, 1H), 3.08 (d, J=24.1, 4H), 2.98-2.87 (m, 2H), 2.63 (s, 2H), 2.09 (s, 1H), 1.86 (ddd, J=23.7, 16.2, 10.4, 3H), 1.70-1.51 (m, 3H), 1.48 (s, 9H), 0.90 (d, J=6.5, 3H), 0.86 (d, J=6.5, 3H); MS (ESI+) m/z 498 (M+H)$^+$.

Step 4: In a 4 mL vial tert-butyl methyl((S)-4-methyl-1-oxo-1-((3aR,4S,6aS)-2-(2-(trifluoromethyl)phenyl)octahydrocyclopenta[c]pyrrol-4-ylamino)pentan-2-yl)carbamate from Step 3 (40 mg, 0.080 mmol) was dissolved in 4 N HCl in 1,4-dioxane (1 mL, 4.00 mmol). An oil slowly gummed out of the solution. The reaction was stirred at ambient temperature for 18 hours, and then the solvent was removed under a stream of nitrogen. The crude material was purified using a 4 g silica gel cartridge with 1-10% methanol (2 N ammonia)/dichloromethane to give N$^2$-methyl-N-{(3aR,4S,6aS)-2-[2-(trifluoromethyl)phenyl]octahydrocyclopenta[c]pyrrol-4-yl}-L-leucinamide: $^1$H NMR (400 MHz, pyridine-d$_5$) δ ppm 8.28 (d, J=5.2, 1H), 7.66 (d, J=7.8, 1H), 7.46 (t, J=7.4, 1H), 7.27 (d, J=8.3, 1H), 7.11 (t, J=7.7, 1H), 4.56-4.46 (m, 1H), 3.47 (d, J=9.3, 1H), 3.30-3.23 (m, 1H), 3.16-3.09 (m, 1H), 3.02-2.91 (m, 2H), 2.68 (dd, J=14.4, 10.2, 2H), 2.45 (s, 3H), 2.20 (dd, J=11.1, 5.9, 1H), 2.00-1.86 (m, 2H), 1.79-1.70 (m, 1H), 1.69-1.54 (m, 3H), 0.93 (d, J=6.5, 3H), 0.86 (d, J=6.5, 3H); MS (ESI+) m/z 398 (M+H)$^+$.

Example 619

N-[(3aR,4S,6aS)-2-(2-fluorophenyl)octahydrocyclopenta[c]pyrrol-4-yl]-N$^2$-methyl-L-leucinamide Step 1: tert-Butyl(S)-1-((3aR,4S,6aS)-2-benzyloctahydrocyclopenta[c]pyrrol-4-ylamino)-4-methyl-1-oxopentan-2-yl(methyl)carbamate (0.833 g, 1.878 mmol) from Example 222 and ethanol (10 mL) were added to 20% Pd(OH)$_2$—C, wet (0.167 g, 1.186 mmol) in a 50 mL pressure bottle and stirred for 4 hours at 30 psi and ambient temperature. The mixture was filtered through a nylon membrane and the solvent was removed in vacuo to give tert-butyl methyl((S)-4-methyl-1-((3aR,4S,6aS)-octahydrocyclopenta[c]pyrrol-4-ylamino)-1-oxopentan-2-yl)carbamate: $^1$H NMR (500 MHz, pyridine-d$_5$) δ ppm 8.36-8.23 (m, 1H), 5.20-5.12 (m, 1H), 4.33-4.25 (m, 1H), 3.14-3.03 (m, 4H), 2.96-2.88 (m, 1H), 2.79 (ddd, J=12.7, 8.0, 2.0 Hz, 1H), 2.63-2.55 (m, 1H), 2.52-2.42 (m, 2H), 2.06-1.89 (m, 2H), 1.89-1.79 (m, 3H), 1.64-1.53 (m, 2H), 1.47 (s, 9H), 1.29-1.20 (m, 1H), 0.92-0.83 (m, 6H); MS (ESI+) m/z 354 (M+H)$^+$.

Step 2: To a microwave vial under nitrogen was added tert-butyl methyl((S)-4-methyl-1-((3aR,4S,6aS)-octahydrocyclopenta[c]pyrrol-4-ylamino)-1-oxopentan-2-yl)carbamate from Step 1 (118 mg, 0.334 mmol), 1-bromo-2-fluorobenzene (0.038 mL, 0.350 mmol), potassium phosphate, tribasic (116 mg, 0.668 mmol), tris(dibenzylideneacetone)dipalladium(0) (6.11 mg, 6.68 μmol) and 2-dicyclohexylphosphino-2',4',6'-triisopropylbiphenyl (X-PHOS, 12.73 mg, 0.027 mmol) in t-amyl alcohol (1.0 mL). The reaction was heated at 80° C. for 18 hours. The solvent was removed and the solids were washed with 2×2 mL of ethyl acetate. The solvent was removed under a stream of nitrogen. The crude material was applied to a 12 g silica gel cartridge with ether and purified using 1-50% ethyl acetate/hexanes to give tert-butyl(S)-1-((3aR,4S,6aS)-2-(2-fluorophenyl)octahydrocyclopenta[c]pyrrol-4-ylamino)-4-methyl-1-oxopentan-2-yl(methyl)carbamate: $^1$H NMR (500 MHz, pyridine-d$_5$) δ ppm 8.47-8.39 (m, 1H), 7.12 (ddd, J=13.9, 8.0, 1.4, 1H), 7.06 (td, J=7.8, 1.4, 1H), 6.86-6.77 (m, 2H), 5.17 (ddd, J=10.0, 7.5, 1.0, 1H), 4.46-4.35 (m, 1H), 3.65 (d, J=9.4, 1H), 3.30-3.21 (m, 1H), 3.17 (d, J=9.1, 1H), 3.13-3.03 (m, 4H), 2.69-2.57 (m, 2H), 2.11-1.98 (m, 1H), 1.94-1.82 (m, 3H), 1.66-1.55 (m, 2H), 1.48 (s, 9H), 1.39 (dddd, J=21.2, 19.9, 9.7, 4.0, 1H), 0.91 (d, J=6.5, 3H), 0.87 (d, J=6.6, 3H); MS (ESI+) m/z 448 (M+H)$^+$.

Step 3: In a 4 mL vial tert-butyl(S)-1-((3aR,4S,6aS)-2-(2-fluorophenyl)octahydrocyclopenta[c]pyrrol-4-ylamino)-4-methyl-1-oxopentan-2-yl(methyl)carbamate from Step 2 (72 mg, 0.161 mmol) was dissolved in 4 N HCl in 1,4-dioxane (1 mL, 4.00 mmol). An oil slowly gummed out of solution. The reaction was stirred at room temperature for 18 hours, and the solvent was removed under a stream of nitrogen. The crude material was purified using a 12 g silica gel cartridge with 1-10% methanol (2 N ammonia)/dichloromethane to give N-[(3aR,4S,6aS)-2-(2-fluorophenyl)octahydrocyclopenta[c]pyrrol-4-yl]-N$^2$-methyl-L-leucinamide: $^1$H NMR (500 MHz, pyridine-d$_5$) δ ppm 8.29 (d, J=7.4, 1H), 7.16-7.09 (m, 1H), 7.06 (tt, J=4.8, 2.4, 1H), 6.86-6.78 (m, 2H), 4.49-4.41 (m, 1H), 3.67 (d, J=9.6, 1H), 3.31-3.23 (m, 2H), 3.21 (d, J=9.5, 1H), 3.11 (dd, J=9.3, 7.0, 1H), 2.71-2.63 (m, 2H), 2.45 (s, 3H), 2.14-1.95 (br m, 1H), 2.10 (td, J=12.1, 6.1, 1H), 1.99-1.87 (m, 2H), 1.74 (ddd, J=13.7, 7.8, 5.9, 1H), 1.69-1.57 (m, 2H), 1.49-1.40 (m, 1H), 0.94 (t, J=4.5, 3H), 0.87 (d, J=6.6, 3H); MS (ESI+) m/z 348 (M+H)$^+$.

Example 620

N-[(3aR,4S,6aS)-2-(4-fluorophenyl)octahydrocyclopenta[c]pyrrol-4-yl]-N$^2$-methyl-L-leucinamide The title compound was prepared by substituting 1-bromo-4-fluorobenzene for 1-bromo-2-fluorobenzene in the procedure described in Example 619: $^1$H NMR (500 MHz, pyridine-d$_5$) δ ppm 8.30 (d, J=7.4, 1H), 7.13-7.07 (m, 2H), 6.67-6.61 (m, 2H), 4.46-4.38 (m, 1H), 3.55 (dd, J=9.7, 2.6, 1H), 3.25 (ddd, J=9.6, 8.1, 5.4, 2H), 3.11-3.07 (m, 1H), 3.02 (dd, J=9.4, 3.0, 1H), 2.76-2.66 (m, 2H), 2.46 (s, 3H), 2.12-2.05 (m, 1H), 2.09-1.19 (br m, 1H), 2.00-1.88 (m, 2H), 1.75 (ddd, J=13.6, 7.9, 5.8, 1H), 1.70-1.58 (m, 2H), 1.40 (dddd, J=12.7, 8.4, 6.0, 3.9, 1H), 0.94 (d, J=6.6, 3H), 0.88 (d, J=6.6, 3H); MS (ESI+) m/z 348 (M+H)$^+$.

Example 621

N-{(3aR,4S,6aS)-2-[4-fluoro-3-(trifluoromethyl)phenyl]octahydrocyclopenta[c]pyrrol-4-yl}-$N^2$-methyl-L-leucinamide The title compound was prepared by substituting 4-bromo-1-fluoro-2-(trifluoromethyl)benzene for 1-bromo-2-fluorobenzene in the procedure described in Example 619: $^1$H NMR (500 MHz, pyridine-$d_5$) δ ppm 8.35-8.31 (m, 1H), 7.19-7.14 (m, 1H), 6.82 (dd, J=5.8, 2.9, 1H), 6.73 (ddd, J=8.6, 5.0, 2.5, 1H), 4.47-4.40 (m, 1H), 3.54 (dd, J=9.8, 2.8, 1H), 3.32-3.24 (m, 2H), 3.14-3.09 (m, 1H), 2.99 (dd, J=9.5, 3.3, 1H), 2.79-2.70 (m, 2H), 2.46 (s, 3H), 2.17-2.10 (m, 1H), 2.07-1.86 (br m, 1H), 2.03-1.88 (m, 2H), 1.78-1.66 (m, 2H), 1.64-1.58 (m, 1H), 1.49-1.40 (m, 1H), 0.94 (d, J=6.6, 3H), 0.88 (d, J=6.6, 3H); MS (ESI+) m/z 416 (M+H)$^+$.

Example 622

(4R)-4-fluoro-N-{(3aR,4S,6aS)-2-[2-(trifluoromethyl)phenyl]octahydrocyclopenta[c]pyrrol-4-yl}-L-prolinamide The title compound was prepared by substituting (2S,4R)-1-(tert-butoxycarbonyl)-4-fluoropyrrolidine-2-carboxylic acid for N-(tert-butoxycarbonyl)-N-methyl-L-leucine in the procedure described in Example 618: $^1$H NMR (500 MHz, pyridine-$d_5$) δ ppm 8.23 (d, J=7.5, 1H), 7.66 (dd, J=7.9, 1.4, 1H), 7.48-7.42 (m, 1H), 7.24 (d, J=8.2, 1H), 7.11 (t, J=7.6, 1H), 5.18 (dt, J=54.3, 3.6, 1H), 4.44-4.34 (m, 1H), 4.23 (t, J=8.0, 1H), 3.62-3.51 (bs, 1H), 3.41 (dd, J=9.2, 1.9, 1H), 3.36-3.24 (m, 1H), 3.06 (dd, J=9.2, 7.3, 1H), 3.00-2.84 (m, 3H), 2.67-2.60 (m, 1H), 2.59-2.47 (m, 2H), 2.24 (dddd, J=39.3, 14.8, 7.9, 4.4, 1H), 2.12 (dt, J=11.4, 5.8, 1H), 1.92 (ddd, J=11.4, 7.9, 6.0, 1H), 1.64-1.48 (m, 2H); MS (ESI+) m/z 386 (M+H)$^+$.

Example 623

(4R)-4-fluoro-N-{(3aR,4S,6aS)-2-[2-fluoro-3-(trifluoromethyl)phenyl]octahydrocyclopenta[c]pyrrol-4-yl}-L-prolinamide The title compound was prepared by substituting 1-bromo-2-fluoro-3-(trifluoromethyl)benzene for 1-bromo-3-(trifluoromethyl)benzene in the procedure described in Example 617: $^1$H NMR (400 MHz, pyridine-$d_5$) δ ppm 8.30 (d, J=7.7, 1H), 7.13-7.02 (m, 2H), 6.94-6.82 (m, 1H), 5.32-5.08 (m, 1H), 4.31 (ddt, J=16.0, 14.3, 7.1, 2H), 3.67-3.55 (m, 2H), 3.31 (ddd, J=21.7, 13.4, 1.4, 1H), 3.24-3.14 (m, 2H), 3.13-3.05 (m, 1H), 3.00-2.81 (m, 1H), 2.70-2.50 (m, 3H), 2.25 (dddd, J=39.3, 14.8, 7.9, 4.4, 1H), 2.06 (dt, J=11.7, 6.5, 1H), 1.98-1.86 (m, 1H), 1.63-1.51 (m, 1H), 1.41 (ddt, J=13.0, 9.1, 6.6, 1H); MS (ESI+) m/z 404 (M+H)$^+$.

Example 624

$N^2$-methyl-N-{(3aR,4S,6aS)-2-[4-(trifluoromethoxy)phenyl]octahydrocyclopenta[c]pyrrol-4-yl}-L-leucinamide The title compound was prepared by substituting 1-bromo-4-(trifluoromethoxy)benzene for 1-bromo-2-fluorobenzene in the procedure described in Example 619: $^1$H NMR (500 MHz, pyridine-$d_5$) δ ppm 8.32 (d, J=7.5, 1H), 7.26-7.22 (m, 2H), 6.64-6.57 (m, 2H), 4.45-4.38 (m, 1H), 3.55 (dd, J=9.8, 2.7, 1H), 3.28 (ddd, J=14.1, 9.0, 6.7, 2H), 3.15 (dd, J=9.4, 7.8, 1H), 3.01 (dd, J=9.6, 3.2, 1H), 2.79-2.67 (m, 2H), 2.46 (s, 3H), 2.11 (dt, J=12.4, 6.7, 1H), 2.08-2.00 (m, 1H), 2.00-1.88 (m, 2H), 1.78-1.58 (m, 3H), 1.40 (dtd, J=13.3, 8.1, 5.3, 1H), 0.94 (d, J=6.6, 3H), 0.88 (d, J=6.6, 3H); MS (ESI+) m/z 414 (M+H)$^+$.

Example 625

$N^2$-methyl-N-{(3aR,4S,6aS)-2-[3-(trifluoromethoxy)phenyl]octahydrocyclopenta[c]pyrrol-4-yl}-L-leucinamide The title compound was prepared by substituting 1-bromo-3-(trifluoromethoxy)benzene for 1-bromo-2-fluorobenzene in the procedure described in Example 619: $^1$H NMR (500 MHz, pyridine-$d_5$) δ ppm 8.33 (d, J=7.4, 1H), 7.25 (t, J=8.2, 1H), 6.70 (d, J=8.0, 1H), 6.60 (s, 1H), 6.56 (dd, J=8.3, 2.1, 1H), 4.44-4.37 (m, 1H), 3.54 (dd, J=9.9, 2.8, 1H), 3.34 (dd, J=9.8, 7.7, 1H), 3.26 (dd, J=8.3, 5.8, 1H), 3.17 (dd, J=9.5, 7.9, 1H), 3.00 (dd, J=9.7, 3.3, 1H), 2.76-2.69 (m, 2H), 2.46 (s, 3H), 2.11 (dt, J=12.4, 6.7, 1H), 2.06-1.94 (br m, 1H), 1.93 (qd, J=13.1, 6.0, 2H), 1.78-1.66 (m, 2H), 1.61 (ddd, J=13.7, 9.5, 5.3, 1H), 1.39 (dtd, J=13.0, 7.9, 5.2, 1H), 0.94 (d, J=6.6, 3H), 0.88 (d, J=6.6, 3H); MS (ESI+) m/z 414 (M+H)$^+$.

Example 626

(4R)-4-fluoro-N-{(3aR,4S,6aS)-2-[4-fluoro-3-(trifluoromethyl)phenyl]octahydrocyclopenta[c]pyrrol-4-yl}-L-prolinamide The title compound was prepared by substituting 1-bromo-4-fluoro-3-(trifluoromethyl)benzene for 1-bromo-3-(trifluoromethyl)benzene in the procedure described in Example 617: $^1$H NMR (500 MHz, pyridine-$d_5$) δ ppm 8.33 (d, J=7.6, 1H), 7.17 (t, J=9.7, 1H), 6.78 (dd, J=5.7, 3.0, 1H), 6.69 (dt, J=8.6, 3.5, 1H), 5.21 (dt, J=54.4, 3.6, 1H), 4.31 (dt, J=12.6, 7.7, 2H), 3.64 (bs, 1H), 3.45 (dd, J=9.7, 3.2, 1H), 3.37-3.27 (m, 1H), 3.18 (dd, J=9.6, 8.0, 1H), 3.11-3.03 (m, 1H), 3.00-2.85 (m, 2H), 2.77-2.68 (m, 1H), 2.67-2.53 (m, 2H), 2.27 (dddd, J=39.4, 14.8, 8.0, 4.4, 1H), 2.09 (td, J=12.2, 6.7, 1H), 1.95 (dtd, J=13.0, 7.8, 5.1, 1H), 1.61 (ddd, J=16.0, 12.5, 7.9, 1H), 1.41 (dt, J=13.2, 6.8, 1H); MS (ESI+) m/z 404 (M+H)$^+$.

Example 627

(4R)-4-fluoro-N-{(3aR,4S,6aS)-2-[3-(trifluoromethoxy)phenyl]octahydrocyclopenta[c]pyrrol-4-yl}-L-prolinamide The title compound was prepared by substituting 1-bromo-3-(trifluoromethoxy)benzene for 1-bromo-3-(trifluoromethyl)benzene in the procedure described in Example 617: $^1$H NMR (500 MHz, pyridine-$d_5$) δ ppm 8.30 (d, J=7.7, 1H), 7.25 (t, J=8.2, 1H), 6.70 (d, J=8.1, 1H), 6.59-6.48 (m, 2H), 5.31-5.10 (m, 1H), 4.28 (m, 2H), 3.71-3.55 (m, 1H), 3.46 (dd, J=10.0, 3.4, 1H), 3.37-3.27 (m, 1H), 3.23 (dd, J=9.9, 8.0, 1H), 3.13 (dd, J=9.6, 8.2, 1H), 3.02-2.97 (m, 1H), 2.89 (dd, J=19.6, 18.7, 1H), 2.75-2.66 (m, 1H), 2.65-2.53 (m, 2H), 2.26 (dddd, J=39.3, 14.8, 7.9, 4.4, 1H), 2.05 (td, J=12.3, 6.8, 1H), 1.91 (dtd, J=13.0, 7.9, 5.1, 1H), 1.59 (ddd, J=16.0, 12.6, 7.8, 1H), 1.42-1.29 (m, 1H); MS (ESI+) m/z 402 (M+H)$^+$.

Example 628

N-[(3aR,4S,6aS)-2-(3-chlorophenyl)octahydrocyclopenta[c]pyrrol-4-yl]-N²-methyl-L-leucinamide The title compound was prepared by substituting 1-bromo-3-chlorobenzene for 1-bromo-2-fluorobenzene in the procedure described in Example 619: ¹H NMR (400 MHz, pyridine-$d_5$) δ ppm 8.33 (d, J=7.4, 1H), 7.18 (t, J=8.1, 1H), 6.83 (dd, J=7.6, 1.6, 1H), 6.76 (t, J=2.1, 1H), 6.54 (dd, J=8.2, 2.1, 1H), 4.44-4.36 (m, 1H), 3.51 (dd, J=10.0, 2.8, 1H), 3.34-3.24 (m, 2H), 3.14 (dd, J=9.6, 7.9, 1H), 2.97 (dd, J=9.7, 3.2, 1H), 2.75-2.65 (m, 2H), 2.46 (s, 3H), 2.10 (dt, J=12.4, 6.7, 1H), 2.00-1.87 (m, 2H), 1.80-1.56 (br m, 1H), 1.79-1.57 (m, 3H), 1.38 (dtd, J=12.7, 7.9, 5.0, 1H), 0.94 (d, J=6.6, 3H), 0.88 (d, J=6.6, 3H); MS (ESI+) m/z 364 (M+H)⁺.

Example 629

N-[(3aR,4S,6aS)-2-(3-fluorophenyl)octahydrocyclopenta[c]pyrrol-4-yl]-N²-methyl-L-leucinamide The title compound was prepared by substituting 1-bromo-3-fluorobenzene for 1-bromo-2-fluorobenzene in the procedure described in Example 619: ¹H NMR (400 MHz, pyridine-$d_5$) δ ppm 8.33 (d, J=7.2, 1H), 7.22 (dd, J=12.2, 11.2, 1H), 6.58 (td, J=8.3, 2.2, 1H), 6.51 (dt, J=12.5, 2.3, 1H), 6.45 (dd, J=8.2, 1.9, 1H), 4.44-4.36 (m, 1H), 3.54 (dd, J=9.9, 2.8, 1H), 3.33 (dd, J=9.9, 7.7, 1H), 3.27 (dd, J=8.3, 5.9, 1H), 3.17 (dd, J=9.6, 7.9, 1H), 3.01 (dd, J=9.7, 3.3, 1H), 2.72 (h, J=9.1, 2H), 2.46 (s, 3H), 2.10 (dt, J=12.4, 7.0, 1H), 2.00-1.87 (m, 2H), 1.95-1.70 (br m, 1H), 1.78-1.57 (m, 3H), 1.43-1.33 (m, 1H), 0.94 (d, J=6.6, 3H), 0.88 (d, J=6.6, 3H); MS (ESI+) m/z 348 (M+H)⁺.

Example 630

N²-methyl-N-[(3aR,4S,6aS)-2-(2-methylphenyl)octahydrocyclopenta[c]pyrrol-4-yl]-L-leucinamide The title compound was prepared by substituting 1-bromo-2-methylbenzene for 1-bromo-2-fluorobenzene in the procedure described in Example 619: ¹H NMR (400 MHz, pyridine-$d_5$) δ ppm 8.28 (d, J=7.7, 1H), 7.24-7.17 (m, 2H), 7.01 (ddd, J=7.5, 5.9, 2.1, 2H), 4.54 (tt, J=8.1, 5.8, 1H), 3.47 (dd, J=9.3, 1.6, 1H), 3.26 (dd, J=8.2, 6.0, 1H), 2.90 (ddd, J=11.2, 9.4, 4.4, 2H), 2.80 (dd, J=9.2, 6.6, 1H), 2.70-2.54 (m, 2H), 2.45 (s, 3H), 2.40 (s, 3H), 2.15 (td, J=11.5, 5.9, 1H), 2.05-1.91 (br m, 1H), 2.02-1.86 (m, 2H), 1.75 (ddd, J=13.6, 7.8, 5.9, 1H), 1.68-1.57 (m, 2H), 1.51 (ddt, J=12.7, 9.7, 6.2, 1H), 0.93 (d, J=6.6, 3H), 0.87 (d, J=6.6, 3H); MS (ESI+) m/z 344 (M+H)⁺.

Example 631

(4R)-4-fluoro-N-{(3aR,4S,6aS)-2-[4-(trifluoromethoxy)phenyl]octahydrocyclopenta[c]pyrrol-4-yl}-L-prolinamide The title compound was prepared by substituting 1-bromo-4-(trifluoromethoxy)benzene for 1-bromo-3-(trifluoromethyl)benzene in the procedure described in Example 617: ¹H NMR (400 MHz, pyridine-$d_5$) δ ppm 8.31 (d, J=7.6, 1H), 7.20 (m, 2H), 6.62-6.54 (m, 2H), 5.31-5.10 (m, 1H), 4.30 (dt, J=13.6, 7.8, 2H), 3.63 (bs, 1H), 3.47 (dd, J=9.9, 3.2, 1H), 3.32 (ddd, J=21.6, 13.5, 2.0, 1H), 3.20 (dd, J=9.8, 7.9, 1H), 3.11 (dd, J=9.5, 8.1, 1H), 2.99 (dd, J=9.6, 3.8, 1H), 2.97-2.82 (m, 1H), 2.76-2.52 (m, 3H), 2.26 (dddd, J=39.4, 14.8, 8.0, 4.4, 1H), 2.06 (tt, J=12.1, 6.1, 1H), 1.92 (dtd, J=13.0, 7.8, 5.1, 1H), 1.59 (ddd, J=16.0, 12.5, 7.8, 1H), 1.43-1.30 (m, 1H); MS (ESI+) m/z 402 (M+H)⁺.

Example 632

(4R)-N-[(3aR,4S,6aS)-2-(3-cyanophenyl)octahydrocyclopenta[c]pyrrol-4-yl]-4-fluoro-L-prolinamide The title compound was prepared by substituting 3-bromobenzonitrile for 1-bromo-3-(trifluoromethyl)benzene in the procedure described in Example 617: ¹H NMR (500 MHz, pyridine-$d_5$) δ ppm 8.32 (d, J=7.6, 1H), 7.24 (d, J=7.9, 1H), 7.04 (dd, J=8.8, 4.1, 1H), 6.90-6.86 (m, 1H), 6.77-6.70 (m, 1H), 5.29-5.12 (m, 1H), 4.28 (dt, J=10.1, 8.0, 2H), 3.74-3.55 (bs, 1H), 3.43 (dd, J=10.0, 3.4, 1H), 3.37-3.27 (m, 1H), 3.23-3.17 (m, 1H), 3.13-3.08 (m, 1H), 2.98-2.85 (m, 2H), 2.74-2.66 (m, 1H), 2.65-2.54 (m, 2H), 2.27 (dddd, J=39.3, 14.8, 7.9, 4.4, 1H), 2.08 (tt, J=12.2, 6.0, 1H), 1.93 (dtd, J=13.0, 7.9, 5.0, 1H), 1.60 (ddd, J=16.2, 12.6, 7.9, 1H), 1.45-1.31 (m, 1H); MS (ESI+) m/z 343 (M+H)⁺.

Example 633

(4R)-N-[(3aR,4S,6aS)-2-(4-cyanophenyl)octahydrocyclopenta[c]pyrrol-4-yl]-4-fluoro-L-prolinamide The title compound was prepared by substituting 4-bromobenzonitrile for 1-bromo-3-(trifluoromethyl)benzene in the procedure described in Example 617: ¹H NMR (500 MHz, pyridine-$d_5$) δ ppm 8.32 (d, J=7.5, 1H), 7.56-7.46 (m, 2H), 6.50-6.45 (m, 2H), 5.20 (dt, J=54.4, 3.6, 1H), 4.33-4.19 (m, 2H), 3.71-3.55 (bs, 1H), 3.44 (dd, J=10.5, 3.6, 1H), 3.36-3.25 (m, 2H), 3.20 (dd, J=10.1, 8.4, 1H), 3.01-2.83 (m, 2H), 2.68 (qd, J=8.3, 4.2, 1H), 2.65-2.53 (m, 2H), 2.26 (dddd, J=39.4, 14.8, 7.9, 4.4, 1H), 2.07 (tt, J=12.3, 6.1, 1H), 1.90 (dtd, J=13.0, 8.0, 4.9, 1H), 1.61 (dq, J=12.7, 8.1, 1H), 1.34 (dt, J=13.4, 7.8, 1H); MS (ESI+) m/z 343 (M+H)⁺.

Example 634

N-[(3aR,4S,6aS)-2-(2-chlorophenyl)octahydrocyclopenta[c]pyrrol-4-yl]-N²-methyl-L-leucinamide The title compound was prepared by substituting 1-bromo-2-chlorobenzene for 1-bromo-2-fluorobenzene in the procedure described in Example 619: ¹H NMR (400 MHz, pyridine-$d_5$) δ ppm 8.31 (d, J=7.3, 1H), 7.43 (dd, J=7.9, 1.3, 1H), 7.20-7.16 (m, 1H), 6.98 (dd, J=8.1, 1.3, 1H), 6.93 (td, J=7.6, 1.4, 1H), 4.59-4.50 (m, 1H), 3.68 (d, J=8.9, 1H), 3.27 (dd, J=8.2, 6.0, 1H), 3.23-3.18 (m, 1H), 3.08 (dd, J=9.3, 6.8, 1H), 2.89 (dd, J=9.1, 6.5, 1H), 2.66 (qd, J=8.5, 1.8, 2H), 2.46 (s, 3H), 2.22-2.13 (m, 1H), 2.02-1.86 (m, 2H), 1.74 (ddd, J=15.4, 10.7, 6.8, 1H), 1.72-1.65 (m, 1H), 1.68-1.53 (m, 3H), 0.94 (d, J=6.6, 3H), 0.88 (d, J=6.6, 3H); MS (ESI+) m/z 364 (M+H)⁺.

Example 635

N-{(3aR,4S,6aS)-2-[2-fluoro-3-(trifluoromethyl)phenyl]octahydrocyclopenta[c]pyrrol-4-yl}-N²-methyl-L-leucinamide The title compound was prepared by substituting 1-bromo-2-fluoro-3-(trifluoromethyl)benzene for 1-bromo-2-fluorobenzene in the procedure described in Example 619: ¹H NMR (400 MHz, pyridine-$d_5$) δ ppm 8.34 (d, J=7.1, 1H), 7.11-7.03 (m, 2H), 6.96-6.89 (m, 1H), 4.48-4.40 (m, 1H), 3.69 (d, J=9.8, 1H), 3.28 (ddd, J=10.4, 9.0, 6.7, 2H), 3.16 (dt, J=12.7, 9.6, 2H), 2.75-2.60 (m, 2H), 2.46 (s, 3H), 2.12 (tt, J=9.6, 4.9, 1H), 2.10-1.99 (m, 1H), 2.02-1.86 (m, 2H), 1.79-1.57 (m, 3H), 1.50-1.39 (m, 1H), 0.94 (d, J=6.5, 3H), 0.88 (d, J=6.5, 3H); MS (ESI+) m/z 416 (M+H)+.

Example 636

N²-methyl-N-[(3aR,4S,6aS)-2-(3-methylphenyl)octahydrocyclopenta[c]pyrrol-4-yl]-L-leucinamide The title compound was prepared by substituting 1-bromo-3-methylbenzene for 1-bromo-2-fluorobenzene in the procedure described in Example 619: ¹H NMR (400 MHz, pyridine-d₅) δ ppm 8.35-8.29 (m, 1H), 7.24 (d, J=7.6, 1H), 6.67 (d, J=7.6, 1H), 6.59 (d, J=7.5, 2H), 4.48-4.39 (m, 1H), 3.61 (dd, J=9.8, 2.5, 1H), 3.34 (dd, J=9.7, 7.6, 1H), 3.27 (dd, J=8.2, 5.9, 1H), 3.18 (dd, J=9.4, 7.6, 1H), 3.07 (dd, J=9.6, 2.9, 1H), 2.78-2.66 (m, 2H), 2.46 (s, 3H), 2.29 (s, 3H), 2.15-2.05 (m, 1H), 2.08-1.97 (m, 1H), 2.02-1.87 (m, 2H), 1.79-1.57 (m, 3H), 1.41 (dtd, J=18.1, 8.0, 5.2, 1H), 0.94 (d, J=6.6, 3H), 0.88 (d, J=6.5, 3H); MS (ESI+) m/z 344 (M+H)+.

Example 637

(4R)-4-fluoro-N-{(3aR,4S,6aS)-2-[4-(trifluoromethyl)pyridin-2-yl]octahydrocyclopenta[c]pyrrol-4-yl}-L-prolinamide Step 1: In a 4 mL vial were combined (2S,4R)-tert-butyl 4-fluoro-2-((3aR,4S,6aS)-octahydrocyclopenta[c]pyrrol-4-ylcarbamoyl)pyrrolidine-1-carboxylate from Example 617 Step 2 (80 mg, 0.234 mmol), 2-bromo-4-(trifluoromethyl)pyridine (74.1 mg, 0.328 mmol), and triethylamine (0.131 mL, 0.937 mmol) in ethanol (0.1 mL). The reaction was heated at 82° C. for 1 day. To the reaction mixture was added 90% water/ethanol (1 mL), and then the liquid layer was decanted. This crude material was purified using a 12 g silica gel cartridge eluted with a gradient of 0-60% acetone/hexane over 20 minutes to give (2S,4R)-tert-butyl 4-fluoro-2-((3aR,4S,6aS)-2-(4-(trifluoromethyl)pyridin-2-yl)octahydrocyclopenta[c]pyrrol-4-ylcarbamoyl)pyrrolidine-1-carboxylate: ¹H NMR (400 MHz, pyridine-d₅, 90° C.) δ ppm 8.34 (d, J=5.2, 1H), 7.93 (bs, 1H), 6.73 (d, J=5.1, 1H), 6.60 (s, 1H), 5.33-5.10 (m, 1H), 4.62 (t, J=7.9, 1H), 4.34-4.22 (m, 1H), 3.96 (dd, J=21.9, 13.0, 1H), 3.66 (tdd, J=16.6, 12.2, 5.7, 3H), 3.57-3.50 (m, 1H), 3.30 (dd, J=10.9, 4.3, 1H), 2.76 (tdd, J=13.1, 8.5, 4.5, 2H), 2.54-2.35 (m, 2H), 2.16 (dd, J=12.5, 5.8, 1H), 2.04-1.91 (m, 1H), 1.72 (ddd, J=15.3, 12.9, 7.8, 1H), 1.51 (s, 9H), 1.44 (dd, J=9.2, 4.0, 1H); MS (ESI+) m/z 487 (M+H)+.

Step 2: The title compound was prepared by substituting (2S,4R)-tert-butyl 4-fluoro-2-((3aR,4S,6aS)-2-(4-(trifluoromethyl)pyridin-2-yl)octahydrocyclopenta[c]pyrrol-4-ylcarbamoyl)pyrrolidine-1-carboxylate from Step 1 for (2S,4R)-tert-butyl 4-fluoro-2-((3aR,4S,6aS)-2-(3-(trifluoromethyl)phenyl)octahydrocyclopenta[c]pyrrol-4-ylcarbamoyl)pyrrolidine-1-carboxylate in the procedure described in Step 4 of Example 617: ¹H NMR (400 MHz, pyridine-d₅) δ ppm 8.41 (d, J=5.1, 1H), 8.36-8.29 (m, 1H), 6.84-6.75 (m, 1H), 6.60 (s, 1H), 5.31-5.10 (m, 1H), 4.31 (ddd, J=21.7, 15.1, 7.8, 2H), 3.74 (dd, J=11.1, 3.5, 1H), 3.61 (bs, 1H), 3.54 (ddd, J=16.3, 11.0, 8.1, 2H), 3.31 (ddd, J=20.1, 12.3, 3.3, 2H), 2.91 (ddd, J=15.1, 13.1, 1.6, 1H), 2.79-2.63 (m, 2H), 2.64-2.51 (m, 1H), 2.34-2.17 (m, 1H), 2.17-2.08 (m, 1H), 1.93 (dtd, J=13.0, 8.0, 5.0, 1H), 1.63 (dq, J=12.7, 8.0, 1H), 1.41 (dtd, J=13.3, 7.8, 5.5, 1H); MS (ESI+) m/z 387 (M+H)+.

Example 638

(4R)-4-fluoro-N-{(3aR,4S,6aS)-2-[2-(trifluoromethyl)pyridin-4-yl]octahydrocyclopenta[c]pyrrol-4-yl}-L-prolinamide The title compound was prepared by substituting 4-bromo-2-(trifluoromethyl)pyridine for 2-bromo-4-(trifluoromethyl)pyridine in the procedure described in Example 637: ¹H NMR (400 MHz, pyridine-d₅) δ ppm 8.41 (d, J=5.8, 1H), 8.37 (d, J=7.4, 1H), 6.82 (d, J=2.3, 1H), 6.45 (dd, J=5.8, 2.2, 1H), 5.21 (dt, J=54.4, 3.5, 1H), 4.35-4.24 (m, 2H), 3.74-3.56 (bs, 1H), 3.46 (dd, J=10.6, 3.8, 1H), 3.39-3.19 (m, 3H), 3.01-2.84 (m, 2H), 2.79-2.52 (m, 3H), 2.26 (dddd, J=39.3, 14.8, 7.9, 4.3, 1H), 2.14 (ddd, J=19.6, 10.2, 5.0, 1H), 1.94 (dtd, J=12.9, 8.0, 4.9, 1H), 1.65 (dq, J=12.8, 8.1, 1H), 1.40 (dtd, J=13.4, 7.9, 5.8, 1H); MS (ESI+) m/z 387 (M+H)+.

Example 639

N-[(3aR,4S,6aS)-2-(4-chlorophenyl)octahydrocyclopenta[c]pyrrol-4-yl]-N²-methyl-L-leucinamide The title compound was prepared by substituting 1-bromo-4-chlorobenzene for 1-bromo-2-fluorobenzene in the procedure described in Example 619: ¹H NMR (500 MHz, pyridine-d₅) δ ppm 8.41-8.35 (m, 1H), 7.33 (d, 1H), 6.60 (d, J=8.4, 2H), 4.44-4.35 (m, 1H), 3.54-3.48 (m, 1H), 3.32-3.24 (m, 2H), 3.12 (t, J=7.9, 1H), 2.99 (d, J=7.8, 1H), 2.75-2.69 (m, 2H), 2.47 (s, 3H), 2.20-1.86 (m, 3H), 1.75 (dt, J=13.6, 6.8, 2H), 1.73-1.57 (m, 2H), 1.50-1.22 (m, 2H), 0.94 (d, J=6.6, 3H), 0.89 (d, J=6.6, 3H); MS (ESI+) m/z 364 (M+H)+.

Example 640

(4R)-4-fluoro-N-[(3aR,4S,6aS)-2-(3-fluorophenyl)octahydrocyclopenta[c]pyrrol-4-yl]-L-prolinamide The title compound was prepared by substituting 1-bromo-3-fluorobenzene for 1-bromo-3-(trifluoromethyl)benzene in the procedure described in Example 617: ¹H NMR (400 MHz, pyridine-d₅) δ ppm 8.29 (d, J=7.5, 1H), 7.21 (m, 1H), 6.58 (td, J=8.3, 2.2, 1H), 6.48 (dt, J=12.5, 2.3, 1H), 6.42 (dd, J=8.2, 2.0, 1H), 5.30-5.10 (m, 1H), 4.33-4.21 (m, 2H), 3.64 (bs, 1H), 3.47 (dd, J=10.0, 3.3, 1H), 3.32 (ddd, J=21.7, 13.5, 2.1, 1H), 3.23 (dd, J=9.9, 7.9, 1H), 3.13 (dd, J=9.6, 8.1, 1H), 3.01-2.83 (m, 2H), 2.71-2.51 (m, 3H), 2.26 (dddd, J=39.3, 14.8, 7.9, 4.4, 1H), 2.05 (tt, J=12.2, 6.0, 1H), 1.91 (dtd, J=13.0, 7.8, 5.1, 1H), 1.58 (ddd, J=16.0, 12.5, 7.7, 1H), 1.42-1.28 (m, 1H); MS (ESI+) m/z 336 (M+H)+.

Example 641

(4R)-4-fluoro-N-[(3aR,4S,6aS)-2-(4-fluorophenyl)octahydrocyclopenta[c]pyrrol-4-yl]-L-prolinamide The title compound was prepared by substituting 1-bromo-4-fluorobenzene for 1-bromo-3-(trifluoromethyl)benzene in the procedure described in Example 617: ¹H NMR (400 MHz, pyridine-d₅) δ ppm 8.29 (d, J=7.7, 1H), 7.14-7.05 (m, 2H), 6.65-6.56 (m, 2H), 5.31-5.09 (m, 1H), 4.30 (dt, J=15.5, 7.1, 2H), 3.63 (dddd, J=12.1, 6.4, 4.2, 2.7, 1H), 3.48 (dd, J=9.7, 3.1, 1H), 3.32 (ddd, J=21.7, 13.5, 2.1, 1H), 3.14 (dd, J=9.6, 7.8, 1H), 3.05 (dd, J=9.3, 7.8, 1H), 3.01-2.83 (m, 2H), 2.73-2.51 (m, 3H), 2.26 (dddd, J=39.3, 14.8, 8.0, 4.4, 1H), 2.03 (dt, J=12.0, 6.5, 1H), 1.96-1.86 (m, 1H), 1.62-1.51 (m, 1H), 1.36 (ddt, J=13.0, 8.8, 6.6, 1H); MS (ESI+) m/z 336 (M+H)+.

Example 642

(4R)-4-fluoro-N-[(3aR,4S,6aS)-2-(3-methylphenyl) octahydrocyclopenta[c]pyrrol-4-yl]-L-prolinamide The title compound was prepared by substituting 1-bromo-3-methylbenzene for 1-bromo-3-(trifluoromethyl)benzene in the procedure described in Example 617: $^1$H NMR (400 MHz, pyridine-$d_5$) δ ppm 8.28 (d, J=7.6, 1H), 7.23 (dd, J=6.8, 2.1, 1H), 6.67 (d, J=7.4, 1H), 6.56 (d, J=6.3, 2H), 5.30-5.09 (m, 1H), 4.30 (dt, J=16.3, 7.9, 2H), 3.73-3.56 (bs, 1H), 3.53 (dd, J=9.9, 3.2, 1H), 3.37-3.27 (m, 1H), 3.23 (dd, J=9.8, 7.8, 1H), 3.14 (dd, J=9.5, 7.9, 1H), 3.05 (dd, J=9.6, 3.7, 1H), 2.91 (ddd, J=38.3, 13.5, 2.7, 1H), 2.74-2.64 (m, 1H), 2.63-2.50 (m, 2H), 2.29 (s, 3H), 2.35-2.17 (m, 1H), 2.05 (td, J=12.2, 6.6, 1H), 1.92 (dtd, J=12.9, 7.7, 5.2, 1H), 1.57 (ddd, J=15.9, 12.4, 7.5, 1H), 1.43-1.32 (m, 1H); MS (ESI+) m/z 332 (M+H)+.

Example 643

(4R)-N-[(3aR,4S,6aS)-2-(3-chlorophenyl)octahydrocyclopenta[c]pyrrol-4-yl]-4-fluoro-L-prolinamide The title compound was prepared by substituting 1-bromo-3-chlorobenzene for 1-bromo-3-(trifluoromethyl)benzene in the procedure described in Example 617: $^1$H NMR (400 MHz, pyridine-$d_5$) δ ppm 8.30 (d, J=7.6, 1H), 7.16 (d, J=8.1, 1H), 6.86-6.79 (m, 1H), 6.72 (t, J=2.1, 1H), 6.56-6.47 (m, 1H), 5.30-5.11 (m, 1H), 4.93-4.87 (bs, 1H), 4.27 (dt, J=10.0, 7.9, 2H), 3.43 (dd, J=10.0, 3.3, 1H), 3.32 (ddd, J=21.7, 13.4, 2.1, 1H), 3.20 (dd, J=10.0, 7.9, 1H), 3.10 (dd, J=9.6, 8.1, 1H), 2.99-2.83 (m, 2H), 2.71-2.50 (m, 3H), 2.26 (dddd, J=39.3, 14.8, 7.9, 4.4, 1H), 2.05 (dt, J=12.2, 4.2, 1H), 1.96-1.87 (m, 1H), 1.58 (ddd, J=16.0, 12.5, 7.7, 1H), 1.40-1.29 (m, 1H); MS (ESI+) m/z 352 (M+H)+.

Example 644

(4R)-N-[(3aR,4S,6aS)-2-(4-chlorophenyl)octahydrocyclopenta[c]pyrrol-4-yl]-4-fluoro-L-prolinamide The title compound was prepared by substituting 1-bromo-4-chlorobenzene for 1-bromo-3-(trifluoromethyl)benzene in the procedure described in Example 617: $^1$H NMR (400 MHz, pyridine-$d_5$) δ ppm 8.29 (d, J=7.5, 1H), 7.34-7.27 (m, 2H), 6.61-6.53 (m, 2H), 5.30-5.11 (m, 1H), 4.32-4.22 (m, 2H), 3.69-3.53 (bs, 1H), 3.44 (dd, J=9.9, 3.3, 1H), 3.31 (ddd, J=21.7, 13.5, 2.0, 1H), 3.17 (dd, J=9.8, 7.9, 1H), 3.08 (dd, J=9.5, 8.1, 1H), 2.91 (ddd, J=16.2, 11.6, 3.3, 2H), 2.72-2.51 (m, 3H), 2.25 (dddd, J=39.3, 14.8, 7.9, 4.4, 1H), 2.03 (td, J=12.2, 6.7, 1H), 1.90 (dtd, J=12.9, 7.7, 5.1, 1H), 1.57 (ddd, J=16.0, 12.4, 7.7, 1H), 1.39-1.27 (m, 1H); MS (ESI+) m/z 352 (M+H)+.

Example 645

(4R)-4-fluoro-N-[(3aR,4S,6aS)-2-(3-methoxyphenyl)octahydrocyclopenta[c]pyrrol-4-yl]-L-prolinamide The title compound was prepared by substituting 1-bromo-3-methoxylbenzene for 1-bromo-3-(trifluoromethyl)benzene in the procedure described in Example 617: $^1$H NMR (400 MHz, pyridine-$d_5$) δ ppm 8.29 (d, J=7.7, 1H), 7.25 (t, J=8.1, 1H), 6.50 (dd, J=8.0, 2.2, 1H), 6.44-6.35 (m, 2H), 5.29-5.10 (m, 1H), 4.35-4.23 (m, 2H), 3.73 (s, 3H), 3.62 (dd, J=3.8, 2.2, 1H), 3.52 (dd, J=9.9, 3.2, 1H), 3.38-3.22 (m, 2H), 3.16 (dd, J=9.5, 8.0, 1H), 3.05 (dd, J=9.6, 3.8, 1H), 2.99-2.81 (m, 1H), 2.72-2.51 (m, 3H), 2.25 (dddd, J=39.3, 14.8, 7.9, 4.4, 1H), 2.04 (td, J=12.2, 6.6, 1H), 1.91 (dtd, J=13.0, 7.7, 5.3, 1H), 1.57 (ddd, J=15.8, 12.5, 7.6, 1H), 1.43-1.29 (m, 1H); MS (ESI+) m/z 348 (M+H)+.

Example 646

N-[(3aR,4S,6aS)-2-(3-cyanophenyl)octahydrocyclopenta[c]pyrrol-4-yl]-$N^2$-methyl-L-leucinamide The title compound was prepared by substituting 3-bromobenzonitrile for 1-bromo-2-fluorobenzene in the procedure described in Example 619: $^1$H NMR (500 MHz, pyridine-$d_5$) δ ppm 8.36 (d, J=7.4, 1H), 7.27-7.22 (m, 1H), 7.03 (d, J=7.5, 1H), 6.95-6.90 (m, 1H), 6.77 (dd, J=8.5, 2.5, 1H), 4.44-4.37 (m, 1H), 3.51 (dd, J=10.0, 2.7, 1H), 3.34-3.25 (m, 2H), 3.15 (dd, J=9.5, 7.9, 1H), 2.98 (dd, J=9.7, 3.4, 1H), 2.79-2.69 (m, 2H), 2.47 (s, 3H), 2.18-2.09 (m, 1H), 2.11-1.98 (m, 1H), 2.02-1.87 (m, 2H), 1.78-1.67 (m, 2H), 1.62 (ddd, J=14.2, 10.4, 6.3, 1H), 1.41 (dtd, J=13.2, 8.0, 5.2, 1H), 0.94 (d, J=6.6, 3H), 0.88 (d, J=6.6, 3H); MS (ESI+) m/z 355 (M+H)+.

Example 647

N-[(3aR,4S,6aS)-2-(4-cyanophenyl)octahydrocyclopenta[c]pyrrol-4-yl]-$N^2$-methyl-L-leucinamide The title compound was prepared by substituting 4-bromobenzonitrile for 1-bromo-2-fluorobenzene in the procedure described in Example 619: $^1$H NMR (500 MHz, pyridine-$d_5$) δ ppm 8.36 (d, J=7.4, 1H), 7.56-7.51 (m, 2H), 6.55-6.48 (m, 2H), 4.41-4.34 (m, 1H), 3.52 (dd, J=10.5, 3.1, 1H), 3.39 (dd, J=10.3, 7.7, 1H), 3.29-3.21 (m, 2H), 2.98 (dd, J=10.2, 3.8, 1H), 2.79-2.67 (m, 2H), 2.46 (s, 3H), 2.12 (ddd, J=19.5, 7.1, 5.3, 1H), 2.11-1.99 (m, 1H), 1.99-1.88 (m, 2H), 1.78-1.66 (m, 2H), 1.65-1.57 (m, 1H), 1.37 (dtd, J=13.1, 7.9, 5.1, 1H), 0.94 (d, J=6.6, 3H), 0.88 (d, J=6.6, 3H); MS (ESI+) m/z 355 (M+H)+.

Example 648

$N^2$-methyl-N-[(3aR,4S,6aS)-2-(4-methylphenyl)octahydrocyclopenta[c]pyrrol-4-yl]-L-leucinamide The title compound was prepared by substituting 1-bromo-4-methylbenzene for 1-bromo-2-fluorobenzene in the procedure described in Example 619: $^1$H NMR (500 MHz, pyridine-$d_5$) δ ppm 8.31 (d, J=7.4, 1H), 7.12 (d, J=8.3, 2H), 6.70 (d, J=8.5, 2H), 4.46-4.39 (m, 1H), 3.59 (dd, J=9.7, 2.6, 1H), 3.31-3.24 (m, 2H), 3.14 (dd, J=9.3, 7.5, 1H), 3.06 (dd, J=9.4, 2.9, 1H), 2.76-2.66 (m, 2H), 2.46 (s, 3H), 2.23 (s, 3H), 2.08 (td, J=12.4, 6.4, 1H), 2.06-1.97 (m, 1H), 2.00-1.88 (m, 2H), 1.75 (ddd, J=13.7, 7.9, 5.9, 1H), 1.70-1.57 (m, 2H), 1.45-1.34 (m, 1H), 0.94 (d, J=6.6, 3H), 0.88 (d, J=6.6, 3H); MS (ESI+) m/z 344 (M+H)+.

Example 649

(3aR,4S,6aS)-N-(4-methylbenzyl)-2-[6-(trifluoromethyl)pyridin-2-yl]octahydrocyclopenta[c]pyrrol-4-amine The title compound was prepared by substituting p-tolualdehyde for acetone in the procedure described in Example 609: ¹H NMR (500 MHz, pyridine-$d_5$) δ 7.53 (dd, J=13.1, 8.0, 3H), 7.15 (d, J=7.8, 2H), 7.00 (d, J=7.2, 1H), 6.52 (d, J=8.6, 1H), 4.17-4.08 (m, 2H), 3.63 (dd, J=11.0, 8.5, 1H), 3.51 (dd, J=11.1, 4.4, 1H), 3.46-3.39 (m, 1H), 3.32 (d, J=5.0, 1H), 3.27-3.21 (m, 1H), 2.94 (ddd, J=11.9, 7.6, 4.3, 1H), 2.85 (tt, J=12.9, 6.6, 1H), 2.20 (s, 3H), 2.12 (dd, J=13.0, 6.5, 1H), 2.03 (td, J=12.8, 7.7, 1H), 1.85 (dt, J=13.5, 5.2, 1H), 1.35 (tt, J=15.0, 7.5, 1H), 1.35-1.22 (m, 1H); MS (ESI+) m/z 376 (M+H)⁺.

Example 650

(3aR,4S,6aS)-N-[(5-fluoro-1H-indol-2-yl)methyl]-2-{[3-(trifluoromethyl)phenyl]sulfonyl}octahydrocyclopenta[c]pyrrol-4-amine The title compound was prepared by substituting (3aR,4S,6aS)-2-(3-(trifluoromethyl)phenylsulfonyl)octahydrocyclopenta[c]pyrrol-4-amine from Example 252 Step D for (3aR,4S,6aS)-2-(5-(trifluoromethyl)pyridin-2-yl)octahydrocyclopenta[c]pyrrol-4-amine in the procedure described in Example 614: ¹H NMR (400 MHz, pyridine-$d_5$) δ ppm 12.09-12.11 (bs, 1H), 8.35-8.36 (bs, 1H), 8.18 (d, J=7.9 Hz, 1H), 7.92 (dd, J=7.9, 1.7 Hz, 1H), 7.72 (t, J=7.8 Hz, 1H), 7.47-7.51 (m, 2H), 7.11 (td, J=9.2, 2.4 Hz, 1H), 6.56 (d, J=1.9 Hz, 1H), 3.94-4.04 (m, 2H), 3.34 (dd, J=9.8, 3.2 Hz, 1H), 3.13 (dd, J=9.6, 3.0 Hz, 1H), 2.98 (dd, J=9.8, 8.2 Hz, 1H), 2.87-2.94 (m, 2H), 2.45-2.52 (m, 1H), 2.26-2.33 (m, 1H), 1.77-1.90 (m, 2H), 1.25-1.36 (m, 1H), 1.14-1.25 (m, 1H); MS (ESI−) m/z 480 (M−H)⁻; MS (ESI+) m/z 482 (M+H)⁺.

Example 651

(4R)-N-[(3aR,4S,6aS)-2-(2-cyanophenyl)octahydrocyclopenta[c]pyrrol-4-yl]-4-fluoro-L-prolinamide The title compound was prepared by substituting 2-bromobenzonitrile for 1-bromo-3-(trifluoromethyl)benzene in the procedure described in Example 617: ¹H NMR (400 MHz, pyridine-$d_5$) δ ppm 8.30 (d, J=7.6, 1H), 7.54 (dd, J=7.8, 1.7, 1H), 7.33 (ddd, J=8.8, 7.2, 1.7, 1H), 6.76-6.71 (m, 1H), 6.67 (d, J=8.6, 1H), 5.30-5.08 (m, 1H), 4.29 (ddd, J=19.1, 15.0, 7.7, 2H), 3.72 (dd, J=10.1, 3.3, 1H), 3.65-3.56 (m, 1H), 3.56-3.41 (m, 3H), 3.30 (ddd, J=20.9, 13.4, 1.4, 1H), 2.90 (ddd, J=38.4, 14.0, 1.1, 1H), 2.71-2.49 (m, 3H), 2.24 (dddd, J=39.3, 14.8, 8.0, 4.4, 1H), 2.09 (qd, J=7.0, 5.1, 1H), 1.88 (dtd, J=13.0, 7.8, 5.0, 1H), 1.58 (ddd, J=15.8, 12.5, 7.9, 1H), 1.50-1.38 (m, 1H); MS (ESI+) m/z 343 (M+H)⁺.

Example 652

(4R)-4-fluoro-N-[(3aR,4S,6aS)-2-(4-methylphenyl)octahydrocyclopenta[c]pyrrol-4-yl]-L-prolinamide The title compound was prepared by substituting 1-bromo-4-methylbenzene for 1-bromo-3-(trifluoromethyl)benzene in the procedure described in Example 617: ¹H NMR (400 MHz, pyridine-$d_5$) δ ppm 8.28 (d, J=7.7, 1H), 7.12 (d, J=8.2, 2H), 6.71-6.62 (m, 2H), 5.20 (dt, J=54.3, 3.5, 1H), 4.36-4.24 (m, 2H), 3.69-3.56 (m, 1H), 3.52 (dd, J=9.8, 3.1, 1H), 3.38-3.24 (m, 1H), 3.19 (dd, J=9.7, 7.8, 1H), 3.07 (qd, J=9.5, 5.7, 2H), 2.92 (dd, J=38.3, 13.4, 2.7, 1H), 2.74-2.51 (m, 3H), 2.35-2.17 (m, 1H), 2.23 (s, 3H), 2.02 (td, J=12.1, 6.5, 1H), 1.97-1.85 (m, 1H), 1.62-1.50 (m, 1H), 1.36 (ddt, J=13.0, 8.7, 6.6, 1H); MS (ESI+) m/z 332 (M+H)⁺.

Example 653

(4R)-4-fluoro-N-[(3aR,4S,6aS)-2-(4-methoxyphenyl)octahydrocyclopenta[c]pyrrol-4-yl]-L-prolinamide The title compound was prepared by substituting 1-bromo-4-methoxybenzene for 1-bromo-3-(trifluoromethyl)benzene in the procedure described in Example 617: ¹H NMR (500 MHz, pyridine-$d_5$) δ ppm 8.29 (d, J=7.5, 1H), 7.04-6.97 (m, 2H), 6.77-6.71 (m, 2H), 5.29-5.11 (m, 1H), 4.36-4.24 (m, 2H), 3.68 (s, 3H), 3.65-3.58 (m, 1H), 3.52 (dd, J=9.6, 3.0, 1H), 3.38-3.27 (m, 1H), 3.14 (dd, J=9.5, 7.8, 1H), 3.04 (d, J=5.6, 2H), 2.99-2.84 (m, 1H), 2.73-2.65 (m, 1H), 2.64-2.53 (m, 2H), 2.26 (dddd, J=39.4, 14.8, 7.9, 4.4, 1H), 2.03 (td, J=12.1, 6.3, 1H), 1.92 (dtd, J=13.0, 7.6, 5.3, 1H), 1.56 (ddd, J=15.9, 12.3, 7.6, 1H), 1.38 (ddt, J=12.9, 8.7, 6.5, 1H); MS (ESI+) m/z 348 (M+H)⁺.

Example 654

(3aR,4S,6aS)-N-[(5-fluoro-1H-indol-2-yl)methyl]-2-{[4-(trifluoromethyl)phenyl]sulfonyl}octahydrocyclopenta[c]pyrrol-4-amine The title compound was prepared by substituting (3aR,4S,6aS)-2-(4-(trifluoromethyl)phenylsulfonyl)octahydrocyclopenta[c]pyrrol-4-amine from Example 256 Step A for (3aR,4S,6aS)-2-(5-(trifluoromethyl)pyridin-2-yl)octahydrocyclopenta[c]pyrrol-4-amine in the procedure described in Example 614: ¹H NMR (400 MHz, pyridine-$d_5$) δ ppm 12.10 (s, 1H), 8.12 (d, J=8.2 Hz, 2H), 7.90 (d, J=8.2 Hz, 2H), 7.50 (dt, J=8.9, 3.5 Hz, 2H), 7.15-7.06 (m, 1H), 6.58 (d, J=1.3 Hz, 1H), 4.03 (q, J=14.0 Hz, 2H), 3.35 (dd, J=9.9, 3.3 Hz, 1H), 3.12 (dd, J=9.7, 3.2 Hz, 1H), 3.06-2.91 (m, 3H), 2.53 (d, J=6.5 Hz, 1H), 2.38 (dd, J=10.9, 6.3 Hz, 1H), 1.91-1.75 (m, 2H), 1.42-1.32 (m, 1H), 1.28-1.13 (m, 1H); MS (ESI+) m/z 482 (M+H)⁺.

Example 655

(4R)-N-{(3aR,4S,6aS)-2-[5-(difluoromethyl)-3-thienyl]octahydrocyclopenta[c]pyrrol-4-yl}-4-fluoro-L-prolinamide The title compound was prepared by substituting 4-bromo-2-(difluoromethyl)thiophene for 1-bromo-3-(trifluoromethyl)benzene in the procedure described in Example 617: ¹H NMR (500 MHz, pyridine-$d_5$) δ ppm 8.29 (d, J=7.6, 1H), 7.26 (t, J=56.0, 1H), 7.16 (m, 1H), 6.19 (s, 1H), 5.30-5.12 (m, 1H), 4.34-4.24 (m, 2H), 3.66-3.57 (m, 1H), 3.47 (dd, J=9.5, 2.8, 1H), 3.32 (ddd, J=21.5, 13.5, 1.6, 1H), 3.07 (dd, J=9.4, 7.7, 1H), 2.97 (d, J=5.5, 2H), 2.91 (dd, J=30.7, 7.7, 1H), 2.71-2.51 (m, 3H), 2.26 (dddd, J=39.4, 14.7, 7.9, 4.4, 1H), 2.02 (td, J=11.9, 6.2, 1H), 1.96-1.86 (m, 1H), 1.55 (ddd, J=15.3, 12.2, 8.4, 1H), 1.37 (ddt, J=13.0, 9.1, 6.6, 1H); MS (ESI+) m/z 374 (M+H)⁺.

Example 656

(4R)-4-fluoro-N-{(3aR,4S,6aS)-2-[2-(trifluoromethoxy)phenyl]octahydrocyclopenta[c]pyrrol-4-yl}-L-prolinamide The title compound was prepared by substituting 1-bromo-2-(trifluoromethoxy)benzene for 1-bromo-3-(trifluoromethyl)benzene in the procedure described in Example 617: ¹H NMR (500 MHz, pyridine-d$_5$) δ ppm 8.28 (d, J=7.5, 1H), 7.31-7.26 (m, 1H), 7.19 (d, J=1.5, 1H), 6.93-6.84 (m, 2H), 5.19 (dt, J=54.4, 3.5, 1H), 4.36-4.29 (m, 1H), 4.26 (t, J=8.1, 1H), 3.60 (dd, J=9.7, 2.5, 2H), 3.37-3.22 (m, 2H), 3.14 (dd, J=9.7, 7.6, 1H), 3.00 (dd, J=9.5, 7.4, 1H), 2.92 (ddd, J=38.5, 13.6, 2.5, 1H), 2.70-2.62 (m, 1H), 2.61-2.51 (m, 2H), 2.25 (dddd, J=39.4, 14.8, 7.9, 4.4, 1H), 2.08 (td, J=11.9, 6.1, 1H), 2.00-1.88 (m, 1H), 1.65-1.53 (m, 1H), 1.52-1.43 (m, 1H); MS (ESI+) m/z 402 (M+H)$^+$.

Example 657

N-{(3aR,4S,6aS)-2-[3-fluoro-4-(trifluoromethoxy)phenyl]octahydrocyclopenta[c]pyrrol-4-yl}-N$^2$-methyl-L-leucinamide The title compound was prepared by substituting 4-bromo-2-fluoro-1-(trifluoromethoxy)benzene for 1-bromo-2-fluorobenzene in the procedure described in Example 619: $^1$H NMR (500 MHz, pyridine-d$_5$) δ ppm 8.35 (d, J=7.5, 1H), 7.28-7.23 (m, 1H), 6.50 (dd, J=13.5, 2.8, 1H), 6.32 (dd, J=9.1, 2.7, 0.9, 1H), 4.42 (dd, J=6.5, 5.4, 1H), 3.52 (dd, J=10.0, 2.9, 1H), 3.33 (dd, J=9.9, 7.6, 1H), 3.27 (dd, J=8.3, 5.8, 1H), 3.17 (dd, J=9.6, 7.9, 1H), 2.98 (dd, J=9.7, 3.6, 1H), 2.75 (ddd, J=16.1, 6.8, 4.0, 2H), 2.46 (s, 3H), 2.19-2.10 (m, 1H), 2.10-2.00 (bs, 1H), 2.00-1.86 (m, 2H), 1.79-1.67 (m, 2H), 1.62 (ddd, J=13.6, 8.3, 6.3, 1H), 1.48-1.38 (m, 1H), 0.94 (d, J=6.6, 3H), 0.88 (d, J=6.6, 3H); MS (ESI+) m/z 432 (M+H)$^+$.

Example 658

(4R)-4-fluoro-N-[(3aR,4S,6aS)-2-(2-methylphenyl)octahydrocyclopenta[c]pyrrol-4-yl]-L-prolinamide The title compound was prepared by substituting 1-bromo-2-methylbenzene for 1-bromo-3-(trifluoromethyl)benzene in the procedure described in Example 617: $^1$H NMR (500 MHz, pyridine-d$_5$) δ ppm 8.26 (d, J=7.8, 1H), 7.24-7.16 (m, 2H), 7.01 (ddd, J=13.1, 9.7, 4.5, 2H), 5.28-5.09 (m, 1H), 4.42 (dq, J=8.2, 6.0, 1H), 4.25 (t, J=8.1, 1H), 3.67-3.54 (bs, 1H), 3.41 (dd, J=9.3, 1.7, 1H), 3.31 (ddd, J=21.7, 13.4, 1.8, 1H), 3.00-2.81 (m, 3H), 2.77 (dd, J=9.2, 7.0, 1H), 2.67-2.52 (m, 2H), 2.52-2.44 (m, 1H), 2.38 (s, 3H), 2.25 (dddd, J=39.3, 14.8, 7.9, 4.4, 1H), 2.13-2.04 (m, 1H), 1.98-1.88 (m, 1H), 1.60-1.41 (m, 2H); MS (ESI+) m/z 332 (M+H)$^+$.

Example 659

(4R)-N-[(3aR,4S,6aS)-2-(2-chlorophenyl)octahydrocyclopenta[c]pyrrol-4-yl]-4-fluoro-L-prolinamide The title compound was prepared by substituting 1-bromo-2-chlorobenzene for 1-bromo-3-(trifluoromethyl)benzene in the procedure described in Example 617: $^1$H NMR (500 MHz, pyridine-d$_5$) δ ppm 8.26 (d, J=7.7, 1H), 7.42 (dd, J=7.9, 1.5, 1H), 7.20-7.15 (m, 1H), 6.98-6.89 (m, 2H), 5.27-5.11 (m, 1H), 4.47-4.38 (m, 1H), 4.25 (t, J=8.1, 1H), 3.66 (dd, J=4.0, 2.1, 1H), 3.69-3.53 (bs, 1H), 3.31 (ddd, J=21.7, 13.5, 2.2, 1H), 3.22 (dd, J=9.2, 2.2, 1H), 3.00 (dd, J=9.4, 7.2, 1H), 2.91 (ddd, J=13.5, 12.0, 4.2, 1H), 2.84 (dd, J=9.2, 7.1, 1H), 2.68-2.47 (m, 3H), 2.25 (dddd, J=39.4, 14.8, 7.9, 4.4, 1H), 2.15-2.07 (m, 1H), 1.97-1.86 (m, 1H), 1.62-1.49 (m, 2H); MS (ESI+) m/z 352 (M+H)$^+$.

Example 660

(4R)-4-fluoro-N-{(3aR,4S,6aS)-2-[3-(trifluoromethyl)pyridin-2-yl]octahydrocyclopenta[c]pyrrol-4-yl}-L-prolinamide The title compound was prepared by substituting 2-bromo-3-(trifluoromethyl)pyridine for 2-bromo-4-(trifluoromethyl)pyridine in the procedure described in Example 637: $^1$H NMR (400 MHz, pyridine-d$_5$) δ ppm 8.41 (dd, J=4.4, 1.4, 1H), 8.28 (d, J=7.6, 1H), 7.83 (dd, J=7.8, 1.7, 1H), 6.72 (dd, J=7.7, 4.7, 1H), 5.18 (dt, J=54.5, 3.6, 1H), 4.41-4.29 (m, 1H), 4.23 (t, J=8.1, 1H), 3.92 (dd, J=11.3, 3.2, 1H), 3.73 (dd, J=11.3, 7.7, 1H), 3.62-3.45 (m, 3H), 3.29 (ddd, J=21.8, 13.4, 1.7, 1H), 2.91 (ddd, J=38.4, 13.3, 2.5, 1H), 2.68 (qd, J=7.7, 4.0, 1H), 2.63-2.46 (m, 2H), 2.34-2.15 (m, 1H), 2.15-2.03 (m, 1H), 1.91 (dtd, J=13.1, 7.8, 5.2, 1H), 1.60 (ddd, J=15.6, 12.5, 7.8, 1H), 1.50-1.39 (m, 1H); MS (ESI+) m/z 387 (M+H)$^+$.

Example 661

(4R)-4-fluoro-N-[(3aR,4S,6aS)-2-(2-fluorophenyl)octahydrocyclopenta[c]pyrrol-4-yl]-L-prolinamide The title compound was prepared by substituting 1-bromo-2-fluorobenzene for 1-bromo-3-(trifluoromethyl)benzene in the procedure described in Example 617: $^1$H NMR (400 MHz, pyridine-d$_5$) δ ppm 8.28 (d, J=7.6, 1H), 7.16-7.02 (m, 2H), 6.82 (dddd, J=15.0, 9.4, 6.4, 1.6, 2H), 5.29-5.09 (m, 1H), 4.94 (m, 1H), 4.39-4.30 (m, 1H), 4.26 (t, J=8.1, 1H), 3.61 (dd, J=9.7, 1.5, 1H), 3.31 (ddd, J=21.7, 13.5, 2.2, 1H), 3.23-3.15 (m, 2H), 3.07 (dd, J=9.4, 7.6, 1H), 2.91 (ddd, J=38.4, 13.5, 3.0, 1H), 2.68-2.50 (m, 3H), 2.25 (dddd, J=39.3, 14.8, 8.0, 4.4, 1H), 2.04 (dt, J=11.9, 5.9, 1H), 1.96-1.85 (m, 1H), 1.61-1.49 (m, 1H), 1.42 (ddt, J=12.9, 9.0, 6.5, 1H); MS (ESI+) m/z 336 (M+H)$^+$.

Example 662

(4R)-4-fluoro-N-[(3aR,4S,6aS)-2-(2-methoxyphenyl)octahydrocyclopenta[c]pyrrol-4-yl]-L-prolinamide The title compound was prepared by substituting 1-bromo-2-methoxybenzene for 1-bromo-3-(trifluoromethyl)benzene in the procedure described in Example 617: $^1$H NMR (500 MHz, pyridine-d$_5$) δ ppm 8.27 (d, J=7.8, 1H), 7.02-6.96 (m, 2H), 6.96-6.91 (m, 1H), 6.89-6.78 (m, 1H), 5.27-5.11 (m, 1H), 4.43 (dq, J=7.8, 5.8, 1H), 4.26 (t, J=8.1, 1H), 3.74 (s, 3H), 3.66 (dd, J=9.6, 2.7, 1H), 3.50-3.65 (bs, 1H), 3.31 (ddd, J=21.8, 13.5, 2.1, 1H), 3.24 (dd, J=9.4, 2.8, 1H), 3.10 (dd, J=9.6, 7.4, 1H), 2.99 (dd, J=9.3, 7.3, 1H), 2.97-2.82 (m, 1H), 2.72-2.49 (m, 3H), 2.25 (dddd, J=39.4, 14.8, 8.0, 4.4, 1H), 2.12-2.03 (m, 1H), 1.99-1.87 (m, 1H), 1.61-1.44 (m, 2H); MS (ESI+) m/z 348 (M+H)$^+$.

Example 663

(3aR,4S,6aS)-N-(1H-pyrazol-5-ylmethyl)-2-[6-(trifluoromethyl)pyridin-2-yl]octahydrocyclopenta[c]pyrrol-4-amine The title compound was prepared by substituting 1H-pyrazole-5-carbaldehyde for acetone in the procedure described in Example 609: $^1$H NMR (500 MHz, pyridine-d$_5$) δ ppm 8.27 (d, J=5.9 Hz, 1H), 7.45-7.40 (m, 2H), 7.38-7.32 (m, 2H), 7.27 (dd, J=10.3, 4.3 Hz, 1H), 4.45-4.33 (m, 1H), 3.59 (d, J=13.1 Hz, 1H), 3.44 (d, J=13.2 Hz, 1H), 3.07 (d, J=23.2 Hz, 3H), 2.86-2.80 (m, 1H), 2.54-2.37 (m, 3H), 2.32 (d, J=8.6 Hz, 1H), 2.27-2.18 (m, 1H), 2.13-1.98 (m, 1H), 1.94-1.86 (m, 1H), 1.88-1.71 (m, 3H), 1.57 (td, J=13.4, 6.6 Hz, 2H), 1.48 (d, J=8.9 Hz, 9H), 1.40-1.31 (m, 1H), 0.86 (dd, J=19.8, 6.5 Hz, 6H); MS (ESI+) m/z 352 (M+H)$^+$.

Example 664

(3aR,4S,6aS)-N-[(3-methyl-1H-indol-2-yl)methyl]-2-[6-(trifluoromethyl)pyridin-2-yl]octahydrocyclopenta[c]pyrrol-4-amine The title compound was prepared by substituting 3-methyl-1H-indole-2-carbaldehyde for acetone in the procedure described in Example 609: $^1$H NMR (500 MHz, pyridine-d$_5$) δppm 12.20 (s, 1H), 7.63 (dd, J=8.2, 0.7 Hz, 2H), 7.56-7.50 (m, 1H), 7.29 (ddd, J=8.3, 7.0, 1.1 Hz, 1H), 7.24-7.18 (m, 2H), 7.01 (d, J=7.2 Hz, 1H), 6.50 (d, J=8.6 Hz, 1H), 4.60 (d, J=14.5 Hz, 2H), 3.68-3.54 (m, 3H), 3.39 (dd, J=10.7, 7.9 Hz, 1H), 3.26 (dd, J=10.8, 3.7 Hz, 1H), 3.11 (dd, J=8.5, 4.5 Hz, 1H), 2.91 (d, J=4.1 Hz, 1H), 2.50 (s, 1H), 2.30-2.23 (m, 3H), 2.09-1.98 (m, 2H), 1.44-1.35 (m, 1H); MS (ESI+) m/z 415 (M+H)$^+$.

Example 665

(3aR,4S,6aS)-N-[(5-chloro-1H-indol-2-yl)methyl]-2-[6-(trifluoromethyl)pyridin-2-yl]octahydrocyclopenta[c]pyrrol-4-amine The title compound was prepared by substituting 5-chloro-1H-indole-2-carbaldehyde for acetone in the procedure described in Example 609: $^1$H NMR (500 MHz, pyridine-d$_5$) δppm 12.71 (s, 1H), 7.70 (d, J=2.0 Hz, 1H), 7.56-7.50 (m, 2H), 7.28 (dd, J=8.6, 2.0 Hz, 1H), 7.01 (d, J=7.2 Hz, 1H), 6.68 (d, J=1.4 Hz, 1H), 6.50 (d, J=8.6 Hz, 1H), 4.56-4.49 (m, 2H), 3.63 (dd, J=11.1, 8.4 Hz, 1H), 3.56 (dd, J=11.2, 4.5 Hz, 1H), 3.50 (dd, J=11.6, 6.8 Hz, 1H), 3.41 (dd, J=10.7, 8.0 Hz, 1H), 3.25 (dd, J=10.7, 3.8 Hz, 1H), 3.01 (tt, J=8.6, 4.5 Hz, 1H), 2.91-2.82 (m, 1H), 2.50 (s, 1H), 2.20 (td, J=12.3, 7.0 Hz, 1H), 2.02 (dtd, J=12.6, 7.7, 4.8 Hz, 1H), 1.92 (dt, J=15.1, 7.9 Hz, 1H), 1.37 (dt, J=15.4, 7.3 Hz, 1H); MS (ESI+) m/z 435 (M+H)$^+$.

Example 666

(3aR,4S,6aS)-N-{[3-(4-chlorophenyl)-1H-pyrazol-4-yl]methyl}-2-[6-(trifluoromethyl)pyridin-2-yl]octahydrocyclopenta[c]pyrrol-4-amine The title compound was prepared by substituting 3-(4-chlorophenyl)-1H-pyrazole-4-carbaldehyde for acetone in the procedure described in Example 609: $^1$H NMR (400 MHz, methanol-d$_4$) d 7.72 (d, J=12.2, 2H), 7.61 (t, J=7.9, 3H), 7.46 (d, J=8.4, 2H), 6.89 (d, J=7.3, 1H), 6.61 (d, J=8.6, 1H), 3.81 (q, J=13.5, 2H), 3.56-3.44 (m, 2H), 3.35 (dd, J=12.9, 4.1, 2H), 2.95 (dd, J=12.0, 6.2, 1H), 2.91-2.83 (m, 1H), 2.53 (ddd, J=13.3, 8.9, 4.7, 1H), 2.13-1.98 (m, 2H), 1.56-1.39 (m, 2H); MS (ESI+) m/z 461 (M+H)$^+$.

Example 667

(3aR,4S,6aS)-N-[(5-fluoro-3-methyl-1H-indol-2-yl)methyl]-2-[6-(trifluoromethyl)pyridin-2-yl]octahydrocyclopenta[c]pyrrol-4-amine The title compound was prepared by substituting 5-fluoro-3-methyl-1H-indole-2-carbaldehyde for acetone in the procedure described in Example 609: $^1$H NMR (500 MHz, pyridine-d$_5$) δ ppm 12.32 (s, 1H), 7.54-7.49 (m, 2H), 7.36 (dd, J=9.7, 2.5 Hz, 1H), 7.13-7.08 (m, 1H), 7.01 (d, J=7.2 Hz, 1H), 6.50 (d, J=8.6 Hz, 1H), 4.58-4.50 (m, 2H), 3.65 (dd, J=11.2, 8.4 Hz, 1H), 3.61-3.54 (m, 2H), 3.40 (dd, J=10.7, 8.0 Hz, 1H), 3.26 (dd, J=10.7, 3.8 Hz, 1H), 3.11-3.04 (m, 1H), 2.94-2.85 (m, 1H), 2.50 (s, 1H), 2.29-2.21 (m, 4H), 2.10-1.94 (m, 2H), 1.45-1.35 (m, 1H); MS (ESI+) m/z 433 (M+H)$^+$.

Example 668

(3aR,4S,6aS)-N-[(5-methoxy-3-methyl-1H-indol-2-yl)methyl]-2-[6-(trifluoromethyl)pyridin-2-yl]octahydrocyclopenta[c]pyrrol-4-amine The title compound was prepared by substituting 5-methoxy-3-methyl-1H-indole-2-carbaldehyde for acetone in the procedure described in Example 609: $^1$H NMR (500 MHz, pyridine-d$_5$) δ ppm 12.10 (s, 1H), 7.56-7.51 (m, 2H), 7.12-7.07 (m, 1H), 7.01 (d, J=7.2 Hz, 1H), 6.50 (d, J=8.6 Hz, 1H), 4.63-4.56 (m, 2H), 3.80 (s, 3H), 3.65 (td, J=11.2, 7.5 Hz, 2H), 3.58 (dd, J=11.2, 4.6 Hz, 1H), 3.40 (dd, J=10.7, 7.9 Hz, 1H), 3.26 (dd, J=10.8, 3.7 Hz, 1H), 3.15 (ddd, J=13.2, 8.9, 4.6 Hz, 1H), 2.96-2.88 (m, 1H), 2.51-2.48 (m, 1H), 2.32-2.24 (m, 4H), 2.11-2.01 (m, 2H), 1.44-1.35 (m, 1H); MS (ESI+) m/z 445 (M+H)$^+$.

Example 669

(3aR,4S,6aS)-N-{[3-(2-thienyl)-1H-pyrazol-4-yl]methyl}-2-[6-(trifluoromethyl)pyridin-2-yl]octahydrocyclopenta[c]pyrrol-4-amine The title compound was prepared by substituting 3-(2-thienyl)-1H-pyrazole-4-carbaldehyde for acetone in the procedure described in Example 609: $^1$H NMR (500 MHz, pyridine-d$_5$) δ ppm 8.39 (s, 1H), 7.71 (dd, J=3.6, 1.0 Hz, 1H), 7.56-7.51 (m, 1H), 7.49 (dd, J=5.1, 1.1 Hz, 1H), 7.19 (dd, J=5.1, 3.6 Hz, 1H), 7.00 (d, J=7.2 Hz, 1H), 6.52 (d, J=8.6 Hz, 1H), 4.49 (s, 2H), 3.64-3.59 (m, 1H), 3.58-3.49 (m, 2H), 3.46-3.39 (m, 1H), 3.29-3.24 (m, 1H), 3.11-3.03 (m, 1H), 2.93-2.84 (m, 1H), 2.52-2.48 (m, 2H), 2.23-2.15 (m, 1H), 2.10-2.02 (m, 1H), 2.02-1.92 (m, 1H), 1.43-1.35 (m, 1H); MS (ESI+) m/z 434 (M+H)$^+$.

Example 670

(3aR,4S,6aS)-N-[(4-methyl-1H-imidazol-2-yl)methyl]-2-[6-(trifluoromethyl)pyridin-2-yl]octahydrocyclopenta[c]pyrrol-4-amine The title compound was prepared by substituting 4-methyl-1H-imidazole-2-carbaldehyde for acetone in the procedure described in Example 609: $^1$H NMR (500 MHz, pyridine-d$_5$) δ ppm 7.56-7.51 (m, 1H), 7.03 (d, J=1.1 Hz, 1H), 7.02-6.98 (m, 1H), 6.53 (d, J=8.6 Hz, 1H), 4.56-4.47 (m, 2H), 3.59-3.51 (m, 2H), 3.40 (ddd, J=11.6, 7.6, 4.3 Hz, 2H), 3.23 (ddd, J=10.6, 4.6, 2.3 Hz, 1H), 2.91-2.84 (m, 1H), 2.83-2.74 (m, 1H), 2.50 (s, 2H), 2.23 (dd, J=7.3, 0.5 Hz, 3H), 2.15-2.06 (m, 1H), 1.97 (dtd, J=12.9, 7.7, 5.0 Hz, 1H), 1.79 (ddd, J=14.8, 12.9, 7.9 Hz, 1H), 1.36-1.27 (m, 1H); MS (ESI+) m/z 466 (M+H)$^+$.

Example 671

(3aR,4S,6aS)-N-[(7-methyl-1H-indol-3-yl)methyl]-2-[6-(trifluoromethyl)pyridin-2-yl]octahydrocyclopenta[c]pyrrol-4-amine The title compound was prepared by substituting 7-methyl-1H-indole-3-carbaldehyde for acetone in the procedure described in Example 609: ¹H NMR (500 MHz, pyridine-d₅) δ ppm 11.82 (s, 1H), 7.92 (d, J=7.9, 1H), 7.52 (d, J=7.9, 1H), 7.32-7.24 (m, 2H), 7.15 (d, J=7.0, 1H), 6.98 (d, J=7.2, 1H), 6.50 (d, J=8.6, 1H), 4.18 (q, J=12.8, 2H), 3.62-3.56 (m, 1H), 3.51 (dd, J=10.5, 8.3, 1H), 3.43 (dd, J=10.8, 4.3, 1H), 3.26 (dd, J=10.7, 3.7, 1H), 3.14 (dd, J=10.5, 5.7, 1H), 2.82-2.73 (m, 1H), 2.63 (td, J=8.7, 4.4, 1H), 2.58 (s, 3H), 2.02 (dt, J=11.4, 4.9, 2H), 1.65-1.54 (m, 1H), 1.35 (tt, J=7.9, 4.6, 1H), 1.35-1.24 (m, 1H); MS (ESI+) m/z 415 (M+H)⁺.

Example 672

(3aR,4S,6aS)-N-{[3-(4-fluorophenyl)-1H-pyrazol-4-yl]methyl}-2-[6-(trifluoromethyl)pyridin-2-yl]octahydrocyclopenta[c]pyrrol-4-amine The title compound was prepared by substituting 3-(4-fluorophenyl)-1H-pyrazole-4-carbaldehyde for acetone in the procedure described in Example 609: ¹H NMR (500 MHz, pyridine-d₅) δ ppm 7.54-7.47 (m, 1H), 7.12-6.97 (m, 2H), 4.98-4.75 (m, 15H), 3.85-3.41 (m, 3H), 3.42-3.20 (m, 2H), 3.01-2.89 (m, 1H), 2.52 (s, 2H), 2.50 (s, 1H), 2.38-2.04 (m, 3H), 1.55-1.24 (m, 1H); MS (ESI+) m/z 446 (M+H)⁺.

Example 673

(3aR,4S,6aS)-N-{[3-(4-methylphenyl)-1H-pyrazol-4-yl]methyl}-2-[6-(trifluoromethyl)pyridin-2-yl]octahydrocyclopenta[c]pyrrol-4-amine The title compound was prepared by substituting 3-(4-methylphenyl)-1H-pyrazole-4-carbaldehyde for acetone in the procedure described in Example 609: ¹H NMR (500 MHz, pyridine-d₅) δ ppm 8.53 (s, 1H), 7.74 (d, J=8.1 Hz, 2H), 7.55-7.50 (m, 1H), 7.27 (d, J=7.8 Hz, 2H), 7.00 (d, J=7.2 Hz, 1H), 6.47 (d, J=8.6 Hz, 1H), 4.96-4.92 (m, 1H), 4.68 (s, 2H), 3.64 (dt, J=11.3, 5.5 Hz, 1H), 3.51 (ddd, J=16.1, 11.3, 6.7 Hz, 2H), 3.37 (dd, J=10.7, 7.9 Hz, 1H), 3.28-3.19 (m, 2H), 2.97-2.86 (m, 1H), 2.50 (s, 1H), 2.30-2.25 (m, 3H), 2.25-1.99 (m, 3H), 1.39-1.29 (m, 1H); MS (ESI+) m/z 442 (M+H)⁺.

Example 674

(3aR,4S,6aS)-N-[(2-butyl-1H-imidazol-4-yl)methyl]-2-[6-(trifluoromethyl)pyridin-2-yl]octahydrocyclopenta[c]pyrrol-4-amine The title compound was prepared by substituting 2-butyl-1H-imidazole-4-carbaldehyde for acetone in the procedure described in Example 609: ¹H NMR (500 MHz, pyridine-d₅) δ ppm 7.55-7.50 (m, 2H), 7.00 (d, J=7.2 Hz, 1H), 6.52 (d, J=8.6 Hz, 1H), 5.29-5.23 (m, 1H), 4.63-4.54 (m, 2H), 3.77 (dd, J=12.2, 7.2 Hz, 1H), 3.70-3.63 (m, 2H), 3.39 (dd, J=10.7, 8.0 Hz, 1H), 3.36-3.29 (m, 1H), 3.25 (dd, J=10.8, 3.8 Hz, 1H), 3.00-2.90 (m, 1H), 2.84-2.78 (m, 2H), 2.51 (s, 1H), 2.29 (dt, J=11.9, 7.2 Hz, 1H), 2.18 (ddd, J=18.2, 14.6, 6.3 Hz, 1H), 2.07 (dtd, J=12.4, 7.6, 4.7 Hz, 1H), 1.71 (dt, J=21.0, 7.5 Hz, 2H), 1.37 (dt, J=16.2, 7.3 Hz, 1H), 1.29-1.20 (m, 2H), 0.78 (dd, J=9.1, 5.6 Hz, 3H); MS (ESI+) m/z 408 (M+H)⁺.

Example 675

(3aR,4S,6aS)-N-(1H-imidazol-2-ylmethyl)-2-[6-(trifluoromethyl)pyridin-2-yl]octahydrocyclopenta[c]pyrrol-4-amine The title compound was prepared by substituting 1H-imidazole-2-carbaldehyde for acetone in the procedure described in Example 609: ¹H NMR (500 MHz, pyridine-d₅) δ ppm 7.55-7.51 (m, 1H), 7.33 (s, 2H), 7.00 (d, J=7.2 Hz, 1H), 6.52 (d, J=8.6 Hz, 1H), 4.63-4.55 (m, 2H), 3.63-3.48 (m, 3H), 3.43-3.37 (m, 1H), 3.26-3.21 (m, 1H), 2.99-2.92 (m, 1H), 2.87-2.78 (m, 1H), 2.50 (s, 2H), 2.18-2.09 (m, 1H), 1.99 (dtd, J=17.9, 7.8, 5.2 Hz, 1H), 1.89-1.80 (m, 1H), 1.38-1.29 (m, 1H); MS (ESI+) m/z 352 (M+H)⁺.

Example 676

(3aR,4S,6aS)-N-[(2-methyl-1H-imidazol-4-yl)methyl]-2-[6-(trifluoromethyl)pyridin-2-yl]octahydrocyclopenta[c]pyrrol-4-amine The title compound was prepared by substituting 2-methyl-1H-imidazole-4-carbaldehyde for acetone in the procedure described in Example 609: ¹H NMR (400 MHz, pyridine-d₅) δ ppm 12.78-12.33 (m, 1H), 7.53 (t, J=7.9, 1H), 7.15 (s, 1H), 6.98 (d, J=7.2, 1H), 6.50 (d, J=8.6, 1H), 4.07-3.82 (m, 2H), 3.59-3.37 (m, 3H), 3.26-3.18 (m, 1H), 3.16-2.95 (m, 1H), 2.78-2.66 (m, 1H), 2.62-2.51 (m, 1H), 2.48 (s, 3H), 2.03-1.90 (m, 2H), 1.59-1.41 (m, 1H), 1.38-1.24 (m, 1H). (NH not found); MS (ESI+) m/z 366 (M+H)⁺.

Example 677

(3aR,4S,6aS)-N-(1H-imidazol-4-ylmethyl)-2-[6-(trifluoromethyl)pyridin-2-yl]octahydrocyclopenta[c]pyrrol-4-amine The title compound was prepared by substituting 1H-imidazole-4-carbaldehyde for acetone in the procedure described in Example 609: ¹H NMR (500 MHz, pyridine-d₅) δ ppm 7.54-7.47 (m, 1H), 7.12-6.97 (m, 2H), 4.98-4.75 (m, 15H), 3.85-3.41 (m, 3H), 3.42-3.20 (m, 2H), 3.01-2.89 (m, 1H), 2.52 (s, 2H), 2.50 (s, 1H), 2.38-2.04 (m, 3H), 1.55-1.24 (m, 1H); MS (ESI+) m/z 352 (M+H)⁺.

Example 678

(3aR,4S,6aS)-N-[(5-fluoro-1H-indol-3-yl)methyl]-2-[6-(trifluoromethyl)pyridin-2-yl]octahydrocyclopenta[c]pyrrol-4-amine The title compound was prepared by substituting 5-fluoro-1H-indole-3-carbaldehyde for acetone in the procedure described in Example 609: ¹H NMR (500 MHz, pyridine-d₅) δppm 7.54-7.47 (m, 1H), 7.12-6.97 (m, 2H), 4.98-4.75 (m, 15H), 3.85-3.41 (m, 3H), 3.42-3.20 (m, 2H), 3.01-2.89 (m, 1H), 2.52 (s, 2H), 2.50 (s, 1H), 2.38-2.04 (m, 3H), 1.55-1.24 (m, 1H); MS (ESI+) m/z 419 (M+H)⁺.

Example 679

(3aR,4S,6aS)-N-[(3-chloro-1H-indol-2-yl)methyl]-2-[6-(trifluoromethyl)pyridin-2-yl]octahydrocyclopenta[c]pyrrol-4-amine The title compound was prepared by substituting 3-chloro-1H-indole-2-carbaldehyde for acetone in the procedure described in Example 609: ¹H NMR (500 MHz, pyridine-d₅) δppm 7.54-7.47 (m, 1H), 7.12-6.97 (m, 2H), 4.98-4.75 (m, 15H), 3.85-3.41 (m, 3H), 3.42-3.20 (m, 2H), 3.01-2.89 (m, 1H), 2.52 (s, 2H), 2.50 (s, 1H), 2.38-2.04 (m, 3H), 1.55-1.24 (m, 1H); MS (ESI+) m/z 435 (M+H)⁺.

Example 680

(3aR,4S,6aS)-N-[(5-chloro-1H-indol-3-yl)methyl]-2-[6-(trifluoromethyl)pyridin-2-yl]octahydrocyclopenta[c]pyrrol-4-amine The title compound was prepared by substituting 5-chloro-1H-indole-3-carbaldehyde for acetone in the procedure described in Example 609: $^1$H NMR (400 MHz, pyridine-d$_5$) δppm 12.14 (d, J=0.6, 1H), 8.13 (d, J=2.1, 1H), 7.56 (d, J=2.4, 1H), 7.51 (d, J=8.6, 2H), 7.33 (dd, J=8.6, 2.1, 1H), 6.98 (d, J=7.2, 1H), 6.51 (d, J=8.6, 1H), 4.16-4.01 (m, 2H), 3.59 (dd, J=10.9, 8.6, 1H), 3.51 (dd, J=10.8, 8.2, 1H), 3.44 (dd, J=11.0, 4.5, 1H), 3.26 (dd, J=10.8, 4.3, 1H), 3.10 (dd, J=10.6, 5.6, 1H), 2.84-2.70 (m, 1H), 2.60 (dq, J=6.6, 4.6, 1H), 2.08-1.95 (m, 2H), 1.93-1.74 (m, 1H), 1.63-1.49 (m, 1H), 1.35 (tdd, J=6.9, 5.6, 2.8, 1H); MS (ESI+) m/z 435 (M+H)$^+$.

Example 681

(3aR,4S,6aS)-N-{[3-(4-methoxyphenyl)-1H-pyrazol-4-yl]methyl}-2-[6-(trifluoromethyl)pyridin-2-yl]octahydrocyclopenta[c]pyrrol-4-amine The title compound was prepared by substituting 3-(4-methoxyphenyl)-1H-pyrazole-4-carbaldehyde for acetone in the procedure described in Example 609: $^1$H NMR (500 MHz, pyridine-d$_5$) δ ppm 8.53 (s, 1H), 7.81-7.75 (m, 2H), 7.52 (t, J=7.9 Hz, 1H), 7.13-7.06 (m, 2H), 7.00 (d, J=7.2 Hz, 1H), 6.47 (d, J=8.6 Hz, 1H), 5.41-5.29 (m, 2H), 4.70 (s, 2H), 3.73-3.70 (m, 3H), 3.68 (dd, J=7.4, 4.2 Hz, 1H), 3.56 (dd, J=11.2, 8.6 Hz, 1H), 3.50 (dd, J=11.2, 4.8 Hz, 1H), 3.36 (dd, J=10.8, 7.9 Hz, 1H), 3.31-3.21 (m, 2H), 2.97-2.88 (m, 1H), 2.25-2.09 (m, 2H), 2.04 (dtd, J=12.6, 7.5, 4.9 Hz, 1H), 1.35 (ddd, J=16.1, 13.2, 7.5 Hz, 1H); MS (ESI+) m/z 458 (M+H)$^+$.

Example 682

(3aR,4S,6aS)-N-[(3-phenyl-1H-pyrazol-4-yl)methyl]-2-[6-(trifluoromethyl)pyridin-2-yl]octahydrocyclopenta[c]pyrrol-4-amine The title compound was prepared by substituting 3-phenyl-1H-pyrazole-4-carbaldehyde for acetone in the procedure described in Example 609: $^1$H NMR (500 MHz, pyridine-d$_5$) δ ppm 8.53 (s, 1H), 7.81-7.75 (m, 2H), 7.52 (t, J=7.9 Hz, 1H), 7.13-7.06 (m, 2H), 7.00 (d, J=7.2 Hz, 1H), 6.47 (d, J=8.6 Hz, 1H), 5.41-5.29 (m, 2H), 4.70 (s, 2H), 3.73-3.70 (m, 3H), 3.68 (dd, J=7.4, 4.2 Hz, 1H), 3.56 (dd, J=11.2, 8.6 Hz, 1H), 3.50 (dd, J=11.2, 4.8 Hz, 1H), 3.36 (dd, J=10.8, 7.9 Hz, 1H), 3.31-3.21 (m, 2H), 2.97-2.88 (m, 1H), 2.25-2.09 (m, 2H), 2.04 (dtd, J=12.6, 7.5, 4.9 Hz, 1H), 1.35 (ddd, J=16.1, 13.2, 7.5 Hz, 1H); MS (ESI+) m/z 428 (M+H)$^+$.

Example 683

(3aR,4S,6aS)-N-(1H-benzimidazol-2-ylmethyl)-2-[6-(trifluoromethyl)pyridin-2-yl]octahydrocyclopenta[c]pyrrol-4-amine The title compound was prepared by substituting 1H-benzimidazole-2-carbaldehyde for acetone in the procedure described in Example 609: $^1$H NMR (500 MHz, pyridine-d$_5$) δppm 7.82 (dd, J=6.0, 3.1 Hz, 2H), 7.55-7.49 (m, 1H), 7.35-7.29 (m, 2H), 6.99 (d, J=7.2 Hz, 1H), 6.50 (d, J=8.6 Hz, 1H), 5.96-5.80 (m, 2H), 4.96-4.88 (m, 2H), 3.77 (dd, J=11.7, 6.6 Hz, 1H), 3.67-3.58 (m, 2H), 3.39 (dd, J=10.8, 8.0 Hz, 1H), 3.25 (dd, J=10.8, 3.8 Hz, 1H), 3.18-3.11 (m, 1H), 2.94-2.84 (m, 1H), 2.26-2.18 (m, 1H), 2.09-1.98 (m, 2H), 1.35 (qd, J=8.9, 4.6 Hz, 1H); MS (ESI+) m/z 402 (M+H)$^+$.

Example 684

(3aR,4S,6aS)-N-(1H-indol-3-ylmethyl)-2-[6-(trifluoromethyl)pyridin-2-yl]octahydrocyclopenta[c]pyrrol-4-amine The title compound was prepared by substituting 1H-indole-3-carbaldehyde for acetone in the procedure described in Example 609: $^1$H NMR (500 MHz, pyridine-d$_5$) δ ppm 12.47-12.38 (m, 1H), 7.97 (d, J=7.6 Hz, 1H), 7.94 (d, J=2.2 Hz, 1H), 7.54-7.49 (m, 1H), 7.43-7.35 (m, 1H), 7.29 (ddd, J=8.1, 7.0, 1.1 Hz, 1H), 7.00 (t, J=7.7 Hz, 1H), 6.47 (d, J=8.5 Hz, 1H), 4.72 (d, J=4.2 Hz, 2H), 4.55-4.45 (m, 1H), 3.75-3.59 (m, 2H), 3.56-3.49 (m, 1H), 3.43-3.36 (m, 1H), 3.30-3.21 (m, 2H), 2.99-2.90 (m, 1H), 2.50 (s, 1H), 2.34-2.24 (m, 1H), 2.20-2.04 (m, 2H), 1.46-1.33 (m, 1H); MS (ESI+) m/z 401 (M+H)$^+$.

Example 685

(3aR,4S,6aS)-N-[(5-methoxy-1H-indol-3-yl)methyl]-2-[6-(trifluoromethyl)pyridin-2-yl]octahydrocyclopenta[c]pyrrol-4-amine The title compound was prepared by substituting 5-methoxy-1H-indole-3-carbaldehyde for acetone in the procedure described in Example 609: $^1$H NMR (500 MHz, pyridine-d$_5$) δ ppm 11.77 (s, 1H), 7.65 (d, J=2.4 Hz, 1H), 7.56-7.50 (m, 3H), 7.14 (dd, J=8.7, 2.4, 1H), 6.98 (d, J=7.2 Hz, 1H), 6.50 (d, J=8.6 Hz, 1H), 4.17 (q, J=13.1, 2H), 3.88 (s, 3H), 3.64-3.56 (m, 1H), 3.51 (dd, J=10.6, 8.3, 1H), 3.44 (dd, J=10.6, 4.4, 1H), 3.26 (dd, J=10.8, 4.1, 1H), 3.14 (dd, J=10.6, 5.7, 1H), 2.83-2.74 (m, 1H), 2.63 (ddd, J=13.0, 8.7, 4.6, 1H), 2.08-1.99 (m, 2H), 1.94-1.69 (m, 1H), 1.64-1.54 (m, 1H), 1.41-1.31 (m, 1H); MS (ESI+) m/z 431 (M+H)$^+$.

Example 686

(3aR,4S,6aS)-N-[(6-fluoro-1H-indol-3-yl)methyl]-2-[6-(trifluoromethyl)pyridin-2-yl]octahydrocyclopenta[c]pyrrol-4-amine The title compound was prepared by substituting 6-fluoro-1H-indole-3-carbaldehyde for acetone in the procedure described in Example 609: $^1$H NMR (400 MHz, pyridine-d$_5$) δppm 12.03 (s, 1H), 7.95 (dd, J=8.6, 5.5, 1H), 7.53 (t, J=7.9, 2H), 7.38 (dd, J=9.9, 2.2, 1H), 7.13 (ddd, J=9.7, 8.7, 2.4, 1H), 6.98 (d, J=7.2, 1H), 6.51 (d, J=8.6, 1H), 4.17-4.07 (m, 2H), 3.59 (dd, J=10.8, 8.7, 1H), 3.51 (dd, J=10.7, 8.2, 1H), 3.45 (dd, J=11.0, 4.5, 1H), 3.26 (dd, J=10.8, 4.3, 1H), 3.12 (dd, J=10.6, 5.7, 1H), 2.85-2.73 (m, 1H), 2.63 (dq, J=13.3, 4.4, 1H), 2.08-1.97 (m, 2H), 2.01-1.62 (m, 1H), 1.65-1.53 (m, 1H), 1.42-1.30 (m, 1H); MS (ESI+) m/z 419 (M+H)$^+$.

Example 687

(3aR,4S,6aS)-N-{[3-(3,5-difluorophenyl)-1H-pyrazol-4-yl]methyl}-2-[6-(trifluoromethyl)pyridin-2-yl]octahydrocyclopenta[c]pyrrol-4-amine The title compound was prepared by substituting 3-(3,5-difluorophenyl)-1H-pyrazole-4-carbaldehyde for acetone in the procedure described in Example 609: $^1$H NMR (400

MHz, methanol-$d_4$) δ ppm 7.80-7.81 (bs, 1H), 7.59-7.64 (m, 1H), 7.31-7.40 (m, 2H), 6.95-7.01 (m, 1H), 6.91 (d, J=7.2 Hz, 1H), 6.65 (d, J=8.5 Hz, 1H), 3.90-3.99 (m, 2H), 3.56 (dd, J=11.3, 8.2 Hz, 1H), 3.54 (dd, J=11.4, 8.1 Hz, 1H), 3.45 (dd, J=11.0, 4.3 Hz, 1H), 3.37 (dd, J=10.8, 3.8 Hz, 1H), 3.15 (t, J=5.8 Hz, 1H), 2.90-2.98 (m, 1H), 2.61-2.69 (m, 1H), 2.06-2.21 (m, 2H), 1.46-1.68 (m, 2H); MS (ESI+) m/z 464 (M+H)$^+$.

Example 688

(3aR,4S,6aS)-N-[(2-phenyl-1H-imidazol-4-yl)methyl]-2-[6-(trifluoromethyl)pyridin-2-yl]octahydrocyclopenta[c]pyrrol-4-amine The title compound was prepared by substituting 2-phenyl-1H-imidazole-4-carbaldehyde for acetone in the procedure described in Example 609: $^1$H NMR (500 MHz, pyridine-$d_5$) δ 8.53 (s, 1H), 7.81-7.75 (m, 2H), 7.52 (t, J=7.9 Hz, 1H), 7.13-7.06 (m, 2H), 7.00 (d, J=7.2 Hz, 1H), 6.47 (d, J=8.6 Hz, 1H), 5.41-5.29 (m, 2H), 4.70 (s, 2H), 3.73-3.70 (m, 3H), 3.68 (dd, J=7.4, 4.2 Hz, 1H), 3.56 (dd, J=11.2, 8.6 Hz, 1H), 3.50 (dd, J=11.2, 4.8 Hz, 1H), 3.36 (dd, J=10.8, 7.9 Hz, 1H), 3.31-3.21 (m, 2H), 2.97-2.88 (m, 1H), 2.25-2.09 (m, 2H), 2.04 (dtd, J=12.6, 7.5, 4.9 Hz, 1H), 1.35 (ddd, J=16.1, 13.2, 7.5 Hz, 1H); MS (ESI+) m/z 428 (M+H)$^+$.

Example 689

(3aR,4S,6aS)-N-[(4-methoxy-1H-indol-3-yl)methyl]-2-[6-(trifluoromethyl)pyridin-2-yl]octahydrocyclopenta[c]pyrrol-4-amine The title compound was prepared by substituting 4-methoxy-1H-indole-3-carbaldehyde for acetone in the procedure described in Example 609: $^1$H NMR (500 MHz, pyridine-$d_5$) δ ppm 11.94 (s, 1H), 7.55-7.49 (m, 1H), 7.44 (d, J=2.0, 1H), 7.30-7.23 (m, 2H), 6.98 (d, J=7.2, 1H), 6.65 (dd, J=7.5, 0.8, 1H), 6.49 (d, J=8.6, 1H), 4.36-4.28 (m, 2H), 3.91 (s, 3H), 3.61-3.54 (m, 1H), 3.51 (dd, J=10.5, 8.3, 1H), 3.45 (dd, J=10.6, 4.2, 1H), 3.25 (dd, J=10.7, 4.1, 1H), 3.18 (dd, J=10.6, 5.7, 1H), 2.86-2.76 (m, 1H), 2.67 (ddd, J=12.2, 8.1, 4.2, 1H), 2.65-2.11 (m, 1H), 2.10-1.95 (m, 2H), 1.68-1.57 (m, 1H), 1.42-1.32 (m, 1H); MS (ESI+) m/z 431 (M+H)$^+$.

Example 690

(3aR,4S,6aS)-N-[(5-fluoro-1H-pyrrolo[2,3-b]pyridin-3-yl)methyl]-2-[6-(trifluoromethyl)pyridin-2-yl]octahydrocyclopenta[c]pyrrol-4-amine The title compound was prepared by substituting 5-fluoro-1H-pyrrolo[2,3-b]pyridine-3-carbaldehyde for acetone in the procedure described in Example 609: $^1$H NMR (400 MHz, pyridine-$d_5$) δ ppm 12.89 (s, 1H), 8.51 (dd, J=2.7, 1.7, 1H), 8.09 (dd, J=9.3, 2.7, 1H), 7.70 (d, J=2.4, 1H), 7.56-7.48 (m, 1H), 6.99 (d, J=7.2, 1H), 6.52 (d, J=8.6, 1H), 4.09-3.98 (m, 2H), 3.61 (dd, J=10.9, 8.6, 1H), 3.52 (dd, J=10.7, 8.2, 1H), 3.46 (dd, J=11.0, 4.5, 1H), 3.27 (dd, J=10.8, 4.2, 1H), 3.08 (dd, J=10.8, 5.7, 1H), 2.85-2.74 (m, 1H), 2.66-2.56 (m, 1H), 2.04 (tdd, J=10.6, 5.8, 2.5, 2H), 1.98-1.81 (bs, 1H), 1.65-1.52 (m, 1H), 1.44-1.32 (m, 1H); MS (ESI+) m/z 420 (M+H)$^+$.

Example 691

(3aR,4S,6aS)-N-[(6-fluoro-1H-benzimidazol-2-yl)methyl]-2-[6-(trifluoromethyl)pyridin-2-yl]octahydrocyclopenta[c]pyrrol-4-amine The title compound was prepared by substituting 6-fluoro-1H-benzimidazole-2-carbaldehyde for acetone in the procedure described in Example 609: $^1$H NMR (400 MHz, methanol-$d_4$) δ ppm 7.58 (t, J=7.9, 1H), 7.49 (dd, J=8.8, 4.7, 1H), 7.23 (dd, J=9.1, 2.4, 1H), 7.00 (ddd, J=9.7, 8.9, 2.5, 1H), 6.87 (d, J=7.3, 1H), 6.62 (d, J=8.6, 1H), 4.09-3.98 (m, 2H), 3.61-3.50 (m, 2H), 3.45 (dd, J=11.1, 4.2, 1H), 3.34 (dd, J=10.9, 4.0, 1H), 3.01 (ddd, J=11.4, 7.3, 4.1, 1H), 2.97-2.88 (m, 1H), 2.65-2.56 (m, 1H), 2.17-2.05 (m, 2H), 1.62-1.44 (m, 2H); MS (ESI+) m/z 420 (M+H)$^+$.

Example 692

(3aR,4S,6aS)-N-[(4-chloro-1H-indol-3-yl)methyl]-2-[6-(trifluoromethyl)pyridin-2-yl]octahydrocyclopenta[c]pyrrol-4-amine The title compound was prepared by substituting 4-chloro-1H-indole-3-carbaldehyde for acetone in the procedure described in Example 609: $^1$H NMR (500 MHz, pyridine-$d_5$) δppm 12.91 (s, 1H), 8.19 (d, J=2.5 Hz, 1H), 7.56-7.51 (m, 1H), 7.41 (dd, J=7.8, 1.1 Hz, 1H), 7.10-6.99 (m, 3H), 6.55 (d, J=8.6 Hz, 1H), 4.97 (dd, J=22.4, 13.3 Hz, 2H), 4.85-4.82 (m, 1H), 3.83 (dd, J=12.0, 6.9 Hz, 1H), 3.76-3.67 (m, 2H), 3.41 (dd, J=10.7, 8.0 Hz, 1H), 3.39-3.33 (m, 1H), 3.30 (dd, J=10.8, 3.7 Hz, 1H), 2.96 (pd, J=7.7, 3.8 Hz, 1H), 2.41-2.32 (m, 1H), 2.31-2.22 (m, 1H), 2.15-2.08 (m, 1H), 1.49-1.39 (m, 1H); MS (ESI+) m/z 428 (M+H)$^+$.

Example 693

(3aR,4S,6aS)-N-(1H-pyrrolo[2,3-b]pyridin-2-ylmethyl)-2-[6-(trifluoromethyl)pyridin-2-yl]octahydrocyclopenta[c]pyrrol-4-amine The title compound was prepared by substituting 1H-pyrrolo[2,3-b]pyridine-2-carbaldehyde for acetone in the procedure described in Example 609: $^1$H NMR (500 MHz, pyridine-$d_5$) δ ppm 12.91 (s, 1H), 8.19 (d, J=2.5 Hz, 1H), 7.56-7.51 (m, 1H), 7.41 (dd, J=7.8, 1.1 Hz, 1H), 7.10-6.99 (m, 3H), 6.55 (d, J=8.6 Hz, 1H), 4.97 (dd, J=22.4, 13.3 Hz, 8H), 4.85-4.82 (m, 1H), 3.83 (dd, J=12.0, 6.9 Hz, 1H), 3.76-3.67 (m, 2H), 3.41 (dd, J=10.7, 8.0 Hz, 1H), 3.39-3.33 (m, 1H), 3.30 (dd, J=10.8, 3.7 Hz, 1H), 2.96 (pd, J=7.7, 3.8 Hz, 1H), 2.41-2.32 (m, 1H), 2.31-2.22 (m, 1H), 2.15-2.08 (m, 1H), 1.49-1.39 (m, 1H); MS (ESI+) m/z 428 (M+H)$^+$.

Example 694

(3aR,4S,6aS)-N-(1H-1,2,3-triazol-4-ylmethyl)-2-[6-(trifluoromethyl)pyridin-2-yl]octahydrocyclopenta[c]pyrrol-4-amine The title compound was prepared by substituting 1H-1,2,3-triazole-4-carbaldehyde for acetone in the procedure described in Example 609: $^1$H NMR (400 MHz, pyridine-$d_5$) δ ppm 16.46 (bs, 1H), 8.04 (s, 1H), 7.55-7.46 (m, 1H), 6.98 (d, J=7.2, 1H), 6.52 (d, J=8.6, 1H), 4.20-4.07 (m, 2H), 3.62-3.54

(m, 1H), 3.52-3.47 (m, 1H), 3.44 (dd, J=11.0, 4.5, 1H), 3.24 (dd, J=10.8, 4.2, 1H), 3.07 (dd, J=10.7, 5.7, 1H), 2.81-2.70 (m, 1H), 2.63-2.53 (m, 1H), 2.35-2.08 (bs, 1H), 2.04-1.94 (m, 2H), 1.60-1.47 (m, 1H), 1.40-1.28 (m, 1H); MS (ESI+) m/z 353 (M+H)+.

Example 695

(3aR,4S,6aS)-N-[(3-methyl-1H-pyrazol-4-yl)methyl]-2-[6-(trifluoromethyl)pyridin-2-yl]octahydrocyclopenta[c]pyrrol-4-amine The title compound was prepared by substituting 3-methyl-1H-pyrazole-4-carbaldehyde for acetone in the procedure described in Example 609: $^1$H NMR (500 MHz, pyridine-$d_5$) δ ppm 12.91 (s, 1H), 8.19 (d, J=2.5 Hz, 1H), 7.56-7.51 (m, 1H), 7.41 (dd, J=7.8, 1.1 Hz, 1H), 7.10-6.99 (m, 3H), 6.55 (d, J=8.6 Hz, 1H), 4.97 (dd, J=22.4, 13.3 Hz, 8H), 4.85-4.82 (m, 1H), 3.83 (dd, J=12.0, 6.9 Hz, 1H), 3.76-3.67 (m, 2H), 3.41 (dd, J=10.7, 8.0 Hz, 1H), 3.39-3.33 (m, 1H), 3.30 (dd, J=10.8, 3.7 Hz, 1H), 2.96 (pd, J=7.7, 3.8 Hz, 1H), 2.41-2.32 (m, 1H), 2.31-2.22 (m, 1H), 2.15-2.08 (m, 1H), 1.49-1.39 (m, 1H); MS (ESI+) m/z 366 (M+H)+.

Example 696

(3aR,4S,6aS)-N-(1H-pyrazol-4-ylmethyl)-2-[6-(trifluoromethyl)pyridin-2-yl]octahydrocyclopenta[c]pyrrol-4-amine The title compound was prepared by substituting 1H-pyrazole-4-carbaldehyde for acetone in the procedure described in Example 609: $^1$H NMR (500 MHz, pyridine-$d_5$) δ ppm 12.91 (s, 1H), 8.19 (d, J=2.5 Hz, 1H), 7.56-7.51 (m, 1H), 7.41 (dd, J=7.8, 1.1 Hz, 1H), 7.10-6.99 (m, 3H), 6.55 (d, J=8.6 Hz, 1H), 4.97 (dd, J=22.4, 13.3 Hz, 8H), 4.85-4.82 (m, 1H), 3.83 (dd, J=12.0, 6.9 Hz, 1H), 3.76-3.67 (m, 2H), 3.41 (dd, J=10.7, 8.0 Hz, 1H), 3.39-3.33 (m, 1H), 3.30 (dd, J=10.8, 3.7 Hz, 1H), 2.96 (pd, J=7.7, 3.8 Hz, 1H), 2.41-2.32 (m, 1H), 2.31-2.22 (m, 1H), 2.15-2.08 (m, 1H), 1.49-1.39 (m, 1H); MS (ESI+) m/z 352 (M+H)+.

Example 697

5-fluoro-N-{(3aR,4S,6aS)-2-[6-(trifluoromethyl)pyridin-2-yl]octahydrocyclopenta[c]pyrrol-4-yl}-1H-indole-2-carboxamide The title compound was prepared by substituting 5-fluoro-1H-indole-2-carboxylic acid for (S)-2-(tert-butoxycarbonyl (methyl)amino)-4,4-dimethylpentanoic acid in the procedure described in Example 587: $^1$H NMR (500 MHz, pyridine-$d_5$) δ ppm 13.29 (s, 1H), 9.00 (d, J=7.3, 1H), 7.71 (dd, J=8.9, 4.5, 1H), 7.51 (t, J=7.9, 1H), 7.45 (dd, J=9.7, 2.5, 1H), 7.42 (d, J=1.4, 1H), 7.24 (dd, J=9.1, 2.5, 1H), 6.99 (d, J=7.2, 1H), 6.50 (d, J=8.6, 1H), 4.66-4.56 (m, 1H), 3.76 (dd, J=10.9, 3.6, 1H), 3.57 (dd, J=10.9, 8.1, 1H), 3.50 (dd, J=10.8, 8.5, 1H), 3.28 (dd, J=10.9, 4.8, 1H), 2.83 (ddd, J=14.5, 8.7, 3.7, 1H), 2.74-2.61 (m, 1H), 2.21 (ddd, J=19.5, 7.1, 4.5, 1H), 1.95-1.85 (m, 1H), 1.80 (dq, J=12.7, 8.2, 1H), 1.38 (dt, J=13.2, 7.9, 1H); MS (ESI+) m/z 433 (M+H)+.

Example 698

(4R)-4-fluoro-N-{(3aR,4S,6aS)-2-[4-fluoro-2-(trifluoromethyl)phenyl]octahydrocyclopenta[c]pyrrol-4-yl}-L-prolinamide The title compound was prepared by substituting 1-bromo-2-trifluoromethoxy-4-fluorobenzene for 1-bromo-3-(trifluoromethyl)benzene in the procedure described in Example 617: $^1$H NMR (400 MHz, pyridine-$d_5$) δ ppm 8.23 (d, J=7.5, 1H), 7.45 (dd, J=9.1, 2.8, 1H), 7.34-7.23 (m, 2H), 5.19 (dt, J=54.4, 3.6, 1H), 4.43-4.33 (m, 1H), 4.23 (t, J=8.1, 1H), 3.66-3.46 (bs, 1H), 3.39-3.24 (m, 2H), 2.99 (dd, J=9.0, 7.2, 1H), 2.97-2.79 (m, 3H), 2.70-2.48 (m, 3H), 2.24 (dddd, J=39.3, 14.8, 7.9, 4.4, 1H), 2.11 (dt, J=7.9, 5.5, 1H), 1.98-1.85 (m, 1H), 1.64-1.48 (m, 2H); MS (ESI+) m/z 404 (M+H)+.

Example 699

$N^2$-methyl-N-{(3aR,4S,6aS)-2-[2-(trifluoromethoxy)phenyl]octahydrocyclopenta[c]pyrrol-4-yl}-L-leucinamide The title compound was prepared by substituting 1-bromo-2-(trifluoromethoxy)benzene for 1-bromo-2-fluorobenzene in the procedure described in Example 619: $^1$H NMR (500 MHz, pyridine-$d_5$) δ ppm 8.31 (d, J=5.8, 1H), 7.29 (d, J=7.9, 1H), 7.19 (d, J=1.4, 1H), 6.93-6.85 (m, 2H), 4.48-4.40 (m, 1H), 3.67 (d, J=9.1, 1H), 3.29-3.19 (m, 3H), 3.04 (dd, J=9.2, 6.9, 1H), 2.68 (s, 2H), 2.50-2.42 (m, 3H), 2.20-2.10 (m, 1H), 2.14-2.00 (m, 1H), 1.97 (ddt, J=20.7, 14.1, 5.1, 2H), 1.74 (ddd, J=13.6, 7.8, 5.9, 1H), 1.69-1.57 (m, 2H), 1.55-1.45 (m, 1H), 0.94 (d, J=6.6, 3H), 0.87 (d, J=8.6, 3H); MS (ESI+) m/z 414 (M+H)+.

Example 700

4-chloro-N-{(3aR,4S,6aS)-2-[6-(trifluoromethyl)pyridin-2-yl]octahydrocyclopenta[c]pyrrol-4-yl}benzenesulfonamide To a solution of (3aR,4S,6aS)-2-(6-(trifluoromethyl)pyridin-2-yl)octahydrocyclopenta[c]pyrrol-4-amine from Example 264 Step A (0.050 g, 0.184 mmol) in dichloromethane (0.3 mL) was added triethylamine (0.051 mL, 0.369 mmol) followed by 4-chlorobenzene-1-sulfonyl chloride (0.047 g, 0.221 mmol). The reaction was stirred at ambient temperature overnight. The crude material was purified using a 12 g silica gel cartridge eluting with 5-50% ethyl acetate/hexanes over 25 minutes to give the title compound: $^1$H NMR (400 MHz, pyridine-$d_5$) δ ppm 8.58 (s, 1H), 8.01-7.95 (m, 2H), 7.47-7.41 (m, 3H), 6.93 (d, J=7.3, 1H), 6.45 (d, J=8.5, 1H), 3.79-3.68 (m, 1H), 3.52-3.43 (m, 3H), 3.25 (dd, J=11.0, 4.1, 1H), 2.83-2.66 (m, 2H), 2.07-1.90 (m, 2H), 1.69 (dq, J=12.7, 7.9, 1H), 1.39-1.27 (m, 1H); MS (ESI+) m/z 446 (M+H)+.

Example 701

2-chloro-N-{(3aR,4S,6aS)-2-[6-(trifluoromethyl)pyridin-2-yl]octahydrocyclopenta[c]pyrrol-4-yl}benzenesulfonamide The title compound was prepared by substituting 2-chlorobenzene-1-sulfonyl chloride for 4-chlorobenzene-1-sulfonyl chloride in the procedure described in Example 700: $^1$H NMR (400 MHz, pyridine-$d_5$) δ ppm 8.49 (s, 1H), 8.27 (dd, J=7.8, 1.8, 1H), 7.50-7.42 (m, 2H), 7.38 (td, J=7.7, 1.8, 1H), 7.33-7.27 (m, 1H), 6.92 (d, J=7.2, 1H), 6.43 (d, J=8.5, 1H), 3.77-3.67 (m, 1H), 3.50-3.43 (m, 1H), 3.45-3.38 (m, 2H), 3.22 (dd, J=10.9, 4.4, 1H), 2.88-2.66 (m, 2H), 2.03-1.90 (m, 2H), 1.85-1.66 (m, 1H), 1.37-1.23 (m, 1H); MS (DCI+) m/z 446 (M+H)+.

Example 702

3-fluoro-N-{(3aR,4S,6aS)-2-[6-(trifluoromethyl)pyridin-2-yl]octahydrocyclopenta[c]pyrrol-4-yl}benzenesulfonamide The title compound was prepared by substituting 3-fluorobenzene-1-sulfonyl chloride for 4-chlorobenzene-1-sulfonyl chloride in the procedure described in Example 700: $^1$H NMR (400 MHz, pyridine-$d_5$) δ ppm 7.88-7.78 (m, 2H), 7.48-7.37 (m, 2H), 7.26-7.19 (m, 1H), 6.93 (d, J=7.3, 1H), 6.46 (d, J=8.5, 1H), 3.80-3.71 (m, 1H), 3.52-3.43 (m, 3H), 3.24 (dd, J=11.0, 4.1, 1H), 2.83-2.66 (m, 2H), 2.10-1.98 (m, 1H), 2.00-1.88 (m, 1H), 1.76-1.63 (m, 1H), 1.39-1.27 (m, 1H); MS (ESI+) m/z 430 (M+H)$^+$.

Example 703

2-fluoro-N-{(3aR,4S,6aS)-2-[6-(trifluoromethyl)pyridin-2-yl]octahydrocyclopenta[c]pyrrol-4-yl}benzenesulfonamide The title compound was prepared by substituting 2-fluorobenzene-1-sulfonyl chloride for 4-chlorobenzene-1-sulfonyl chloride in the procedure described in Example 700: $^1$H NMR (400 MHz, pyridine-$d_5$) δ ppm 8.80 (s, 1H), 8.11-8.03 (m, 1H), 7.50-7.38 (m, 2H), 7.27-7.16 (m, 2H), 6.92 (d, J=7.2, 1H), 6.45 (d, J=8.5, 1H), 3.81 (s, 1H), 3.51-3.39 (m, 3H), 3.23 (dd, J=11.0, 4.4, 1H), 2.88-2.67 (m, 2H), 2.08-1.90 (m, 2H), 1.81-1.68 (m, 1H), 1.43-1.25 (m, 1H); MS (ESI+) m/z 430 (M+H)$^+$.

Example 704

3-chloro-N-{(3aR,4S,6aS)-2-[6-(trifluoromethyl)pyridin-2-yl]octahydrocyclopenta[c]pyrrol-4-yl}benzenesulfonamide The title compound was prepared by substituting 3-chlorobenzene-1-sulfonyl chloride for 4-chlorobenzene-1-sulfonyl chloride in the procedure described in Example 700: $^1$H NMR (400 MHz, pyridine-$d_5$) δ ppm 8.10 (t, J=1.8, 1H), 7.94 (ddt, J=7.7, 1.8, 0.9, 1H), 7.51-7.45 (m, 2H), 7.41-7.33 (m, 1H), 6.93 (d, J=7.3, 1H), 6.47 (d, J=8.5, 1H), 3.80-3.58 (m, 1H), 3.49-3.44 (m, J=5.3, 3H), 3.24 (dd, J=11.0, 4.1, 1H), 2.81-2.67 (m, 2H), 2.12-1.97 (m, 1H), 1.98-1.89 (m, 1H), 1.69 (dq, J=12.7, 8.0, 1H), 1.41-1.25 (m, 1H); MS (ESI+) m/z 446 (M+H)$^+$.

Example 705

4-fluoro-N-{(3aR,4S,6aS)-2-[6-(trifluoromethyl)pyridin-2-yl]octahydrocyclopenta[c]pyrrol-4-yl}benzenesulfonamide The title compound was prepared by substituting 4-fluorobenzene-1-sulfonyl chloride for 4-chlorobenzene-1-sulfonyl chloride in the procedure described in Example 700: $^1$H NMR (400 MHz, pyridine-$d_5$) δ ppm 8.45 (d, J=23.3, 1H), 8.10-8.03 (m, 2H), 7.48 (t, J=7.9, 1H), 7.20-7.16 (m, 2H), 6.93 (d, J=7.2, 1H), 6.46 (d, J=8.5, 1H), 3.52-3.41 (m, 3H), 3.24 (dd, J=10.9, 4.1, 1H), 2.83-2.67 (m, 2H), 2.09-1.97 (m, 1H), 1.99-1.88 (m, 1H), 1.69 (dq, J=12.6, 7.9, 1H), 1.39-1.27 (m, 1H); MS (ESI+) m/z 430 (M+H)$^+$.

Example 706

$N^2$-{(3aR,4S,6aS)-2-[6-(trifluoromethyl)pyridin-2-yl]octahydrocyclopenta[c]pyrrol-4-yl}-L-leucinamide Step 1: (3aR,6aS)-2-Benzylhexahydrocyclopenta[c]pyrrol-4(5H)-one (1.462 g, 6.79 mmol) [prepared as described by Santora, V. J. et. al. Bioorganic & Medicinal Chemistry Letters (2008), 18, 1490-1494] was dissolved in methanol (20 mL) and cooled in a dry ice/acetone bath to −40° C. Sodium borohydride (0.514 g, 13.58 mmol) was added in portions over 5 minutes. The reaction mixture was allowed to warm to room temperature overnight, then it was quenched with saturated aqueous ammonium chloride, diluted with water, and extracted with 3×150 mL of ethyl acetate. The combined extracts were dried (Na$_2$SO$_4$) and the solvent was removed in vacuo to give (3aR,4R,6aS)-2-benzyloctahydrocyclopenta[c]pyrrol-4-ol: $^1$H NMR (300 MHz, CDCl$_3$) δ ppm 7.45-7.38 (m, 2H), 7.34 (dd, J=10.2, 4.7, 2H), 7.30-7.24 (m, 1H), 5.63 (s, 1H), 4.30 (dd, J=11.4, 6.2, 1H), 3.54 (q, J=13.0, 2H), 3.17 (dd, J=9.3, 3.3, 1H), 2.57 (dtd, J=10.0, 7.1, 3.2, 1H), 2.48 (dtt, J=17.5, 8.7, 4.3, 1H), 2.44-2.38 (m, 2H), 2.31 (dd, J=9.2, 7.4, 1H), 2.04-1.96 (m, 1H), 1.76-1.61 (m, 2H), 1.47-1.40 (m, 1H); MS (ESI+) m/z 217 (M+H)$^+$.

Step 2: (3aR,4R,6aS)-2-Benzyloctahydrocyclopenta[c]pyrrol-4-ol (2.88 g, 13.25 mmol) from Step 1 and ethanol (40 mL) were added to 20% Pd(OH)$_2$—C, wet (0.576 g, 4.10 mmol) in a 250 mL stainless steel pressure bottle and stirred for 2 hours under 30 psi hydrogen gas at 50° C. The mixture was filtered through a nylon membrane and the solvent was removed in vacuo to give (3aR,4R,6aS)-octahydrocyclopenta[c]pyrrol-4-ol: $^1$H NMR (500 MHz, pyridine-$d_5$) δ ppm 4.82 (s, 4H), 4.37 (dd, J=10.5, 4.8, 1H), 3.52 (dd, J=10.8, 1.7, 1H), 2.96-2.86 (m, 1H), 2.76 (dd, J=10.8, 6.9, 1H), 2.71 (dd, J=10.8, 1.8, 1H), 2.56-2.45 (m, 2H), 1.89 (td, J=11.7, 5.3, 1H), 1.80 (ddd, J=12.5, 10.3, 6.8, 1H), 1.66-1.58 (m, 1H), 1.50-1.42 (m, 1H); MS (ESI+) m/z 128 (M+H)

Step 3: (3aR,4R,6aS)-Octahydrocyclopenta[c]pyrrol-4-ol (1.65 g, 12.97 mmol) from Step 2,2-bromo-6-(trifluoromethyl)pyridine (3.66 g, 16.22 mmol), and triethylamine (7.23 mL, 51.9 mmol) were combined in ethanol (7.23 mL). The reaction mixture was heated at 80° C. for 24 hours, and the solvent was evaporated in vacuo. The crude material was purified by silica gel chromatography using 0-40% ethyl acetate/hexane as eluent to give (3aR,4R,6aS)-2-(6-(trifluoromethyl)pyridin-2-yl)octahydrocyclopenta[c]pyrrol-4-ol: $^1$H NMR (500 MHz, pyridine-$d_5$) δ ppm 7.47 (t, J=7.9, 1H), 6.94 (d, J=7.2, 1H), 6.53 (d, J=8.6, 1H), 6.38 (d, J=4.1, 1H), 4.47-4.38 (m, 1H), 4.12 (dd, J=11.0, 4.3, 1H), 3.70-3.63 (m, 1H), 3.53 (t, J=10.0, 1H), 3.38 (dd, J=10.4, 4.6, 1H), 2.80-2.73 (m, 1H), 2.72-2.64 (m, 1H), 1.97-1.74 (m, 3H), 1.64-1.56 (m, 1H); MS (ESI+) m/z 273 (M+H)$^+$.

Step 4: To a solution of (3aR,4R,6aS)-2-(6-(trifluoromethyl)pyridin-2-yl)octahydrocyclopenta[c]pyrrol-4-ol (3.2 g, 11.75 mmol) from Step 3 in dichloromethane (15 mL) was added triethylamine (4.10 mL, 29.4 mmol) followed by 1-methylimidazole (0.281 mL, 3.53 mmol). The solution was cooled to 0° C. and 4-bromobenzene-1-sulfonyl chloride (4.50 g, 17.63 mmol) was added. The solution was warmed to room temperature and stirred for 16 hours. The reaction mixture was diluted with dichloromethane (12 mL) and washed with aqueous hydrogen chloride (0.1 N, 10 mL×2) and water (10 mL). The organic phase was dried over sodium sulfate and concentrated. The crude material was purified by silica gel chromatography using 0-60% dichloromethane/hexane as eluent to give (3aR,4R,6aS)-2-(6-(trifluoromethyl)pyridin-2-yl)octahydrocyclopenta[c]pyrrol-4-yl 4-bromobenzenesulfonate: $^1$H NMR (500 MHz, pyridine-d$_5$) δ ppm 7.99-7.90 (m, 2H), 7.77-7.67 (m, 2H), 7.51 (t, J=7.9, 1H), 6.99 (d, J=7.3, 1H), 6.45 (d, J=8.6, 1H), 5.17 (q, J=6.1, 1H), 3.69 (dd, J=11.4, 4.6, 1H), 3.57-3.47 (m, 1H), 3.37 (dd, J=11.4, 8.9, 1H), 3.23 (dd, J=10.7, 4.5, 1H), 2.90-2.78 (m, 1H), 2.67-2.54 (m, 1H), 2.02-1.88 (m, 1H), 1.80 (dq, J=8.2, 6.0, 1H), 1.70 (dtd, J=13.5, 8.6, 7.0, 1H), 1.51-1.37 (m, 1H); MS (ESI+) m/z 491 (M+H)$^+$.

Step 5: The title compound was prepared by combining (3aR,4R,6aS)-2-(6-(trifluoromethyl)pyridin-2-yl)octahydrocyclopenta[c]pyrrol-4-yl-4-bromobenzenesulfonate from Step 4 (150 mg, 0.305 mmol) and (S)-2-amino-4-methylpentanamide (119 mg, 0.916 mmol) in acetonitrile (0.2 mL). The reaction mixture was heated at 85° C. for 3 days, and the acetonitrile was evaporated. This material was purified using a 12 g silica gel cartridge eluted with a gradient of 0-3% methanol (2 N ammonia)/dichloromethane over 20 minutes to give crude product. It was further purified on 2×0.25 mm thin-layer chromatography plate eluted with 45% methanol (2 N ammonia)/dichloromethane to give N$^2$-{(3aR,4S,6aS)-2-[6-(trifluoromethyl)pyridin-2-yl]octahydrocyclopenta[c]pyrrol-4-yl}-L-leucinamide: $^1$H NMR (500 MHz, pyridine-d$_5$) δ ppm 8.25 (s, 1H), 7.99 (s, 1H), 7.52 (t, J=7.9, 1H), 6.98 (d, J=7.2, 1H), 6.49 (d, J=8.6, 1H), 3.60 (dd, J=10.6, 9.0, 1H), 3.55-3.40 (m, 3H), 3.24 (dd, J=10.8, 3.7, 1H), 3.17 (dd, J=10.2, 5.7, 1H), 2.83-2.71 (m, 1H), 2.64-2.55 (m, 1H), 2.30-2.10 (bs, 1H) 2.08-1.93 (m, 3H), 1.76 (ddd, J=13.5, 8.1, 5.5, 1H), 1.71-1.64 (m, 1H), 1.58 (dd, J=12.7, 5.8, 1H), 1.31 (dd, J=12.7, 5.9, 1H), 0.96 (d, J=6.6, 3H), 0.93 (d, J=6.6, 3H); MS (ESI+) m/z 385 (M+H)$^+$.

Example 707

N$^2$-methyl-N-[(3aR,4S,6aS)-2-{4-[(trifluoromethyl)thio]phenyl}octahydrocyclopenta[c]pyrrol-4-yl]-L-leucinamide The title compound was prepared by substituting (4-bromophenyl)(trifluoromethyl)sulfane for 1-bromo-2-fluorobenzene in the procedure described in Example 619: $^1$H NMR (400 MHz, pyridine-d$_5$) δ ppm 7.74-7.68 (m, 1H), 7.51-7.48 (m, 2H), 6.61-6.55 (m, 2H), 4.32-4.22 (m, 1H), 3.50 (dd, J=10.2, 3.8, 1H), 3.39 (dd, J=10.2, 7.8, 1H), 3.27 (dd, J=9.9, 8.0, 1H), 3.16 (dd, J=7.8, 5.7, 1H), 3.03 (dd, J=9.9, 4.2, 1H), 2.83-2.62 (m, 1H), 2.41 (s, 3H), 2.17-2.04 (m, 1H), 2.03-1.80 (m, 2H), 1.76-1.58 (m, 2H), 1.53 (ddd, J=13.7, 7.7, 6.1, 1H), 1.48-1.36 (m, 1H), 0.94 (d, J=6.5, 3H), 0.90 (d, J=6.5, 3H); MS (ESI+) m/z 430 (M+H)$^+$.

Example 708

N-{(3aR,4S,6aS)-2-[6-(trifluoromethyl)pyridin-2-yl]octahydrocyclopenta[c]pyrrol-4-yl}benzenesulfonamide The title compound was prepared by substituting benzenesulfonyl chloride for 4-chlorobenzene-1-sulfonyl chloride in the procedure described in Example 700: $^1$H NMR (400 MHz, pyridine-d$_5$) δ ppm 8.40 (d, J=6.2, 1H), 8.09-8.03 (m, 2H), 7.47-7.37 (m, 3H), 6.92 (d, J=7.2, 1H), 6.44 (d, J=8.5, 1H), 3.80-3.69 (m, 1H), 3.51-3.39 (m, 3H), 3.24 (dd, J=10.9, 4.2, 1H), 2.82-2.65 (m, 2H), 2.06-1.88 (m, 3H), 1.69 (dq, J=12.6, 7.9, 1H), 1.37-1.25 (m, 1H); MS (ESI+) m/z 412 (M+H)$^+$.

Example 709

1-(4-fluorophenyl)-3-{(3aR,4S,6aS)-2-[6-(trifluoromethyl)pyridin-2-yl]octahydrocyclopenta[c]pyrrol-4-yl}urea To a solution of (3aR,4S,6aS)-2-(6-(trifluoromethyl)pyridin-2-yl)octahydrocyclopenta[c]pyrrol-4-amine from Example 264 Step A (0.050 g, 0.184 mmol) in dichloromethane (0.1 mL) was added 1-fluoro-4-isocyanatobenzene (0.025 mL, 0.221 mmol). The reaction was stirred at ambient temperature for 30 minutes. The reaction was diluted with ether and sonicated, then filtered and washed with ether to give the title compound: $^1$H NMR (400 MHz, pyridine-d$_5$) δ ppm 8.45 (s, 1H), 7.63 (dd, J=9.1, 4.9, 2H), 7.46 (t, J=7.9, 1H), 7.00 (t, J=8.8, 2H), 6.93 (d, J=8.8, 1H), 6.51 (d, J=7.7, 1H), 6.21 (d, J=6.7, 1H), 4.27-4.12 (m, 1H), 3.73-3.44 (m, 3H), 3.28 (dd, J=11.0, 4.0, 1H), 2.77-2.57 (m, 2H), 2.12 (td, J=12.7, 6.8, 1H), 1.87 (td, J=13.3, 7.9, 1H), 1.57 (dq, J=12.8, 7.8, 1H), 1.37 (dtd, J=13.2, 7.8, 5.3, 1H); MS (ESI+) m/z 409 (M+H)$^+$.

Example 710

3-chloro-4-fluoro-N-{(3aR,4S,6aS)-2-[6-(trifluoromethyl)pyridin-2-yl]octahydrocyclopenta[c]pyrrol-4-yl}benzenesulfonamide The title compound was prepared by substituting 3-chloro-4-fluorobenzene-1-sulfonyl chloride for 4-chlorobenzene-1-sulfonyl chloride in the procedure described in Example 700: $^1$H NMR (400 MHz, pyridine-d$_5$) δ ppm 8.75-8.66 (m, 1H), 8.21-8.10 (m, 1H), 7.95 (ddd, J=8.6, 4.4, 2.2, 1H), 7.50-7.44 (m, 1H), 7.26 (t, J=8.7, 1H), 6.93 (d, J=7.2, 1H), 6.46 (d, J=8.5, 1H), 3.80-3.71 (m, 1H), 3.52-3.43 (m, 3H), 3.24 (dd, J=10.9, 4.1, 1H), 2.83-2.66 (m, 2H), 2.12-2.00 (m, 1H), 2.01-1.90 (m, 1H), 1.70 (dq, J=12.7, 8.0, 1H), 1.40-1.28 (m, 1H); MS (ESI+) m/z 464 (M+H)$^+$.

Example 711

1-tert-butyl-3-{(3aR,4S,6aS)-2-[6-(trifluoromethyl)pyridin-2-yl]octahydrocyclopenta[c]pyrrol-4-yl}urea The title compound was prepared by substituting 2-isocyanato-2-methylpropane for 1-fluoro-4-isocyanatobenzene in the procedure described in Example 709: $^1$H NMR (400 MHz, pyridine-d$_5$) δ ppm 7.47-7.41 (m, 1H), 6.90 (d, J=7.3, 1H), 6.46 (d, J=8.6, 1H), 5.80-5.70 (m, 1H), 5.42 (d, J=0.4, 1H), 4.12 (tt, J=12.0, 6.0, 1H), 3.60 (qd, J=11.1, 6.0, 2H), 3.51 (dd, J=11.1, 8.0, 1H), 3.27 (dd, J=11.0, 4.3, 1H), 2.70-2.56 (m, 2H), 2.12-2.03 (m, 1H), 1.91-1.80 (m, 1H), 1.58-1.45 (m, 1H), 1.41 (s, 9H), 1.37-1.29 (m, 1H); MS (ESI+) m/z 371 (M+H)$^+$.

Example 712

N$^2$-methyl-N-[(3aR,4S,6aS)-2-{3-[(trifluoromethyl)thio]phenyl}octahydrocyclopenta[c]pyrrol-4-yl]-L-leucinamide The title compound was prepared by substituting (3-bromophenyl)(trifluoromethyl)sulfane for 1-bromo-2-fluororobenzene in the procedure described in Example 619: ¹H NMR (400 MHz, pyridine-d₅) δ ppm 7.74-7.67 (m, 1H), 7.23 (d, J=6.56, 1H), 7.02 (d, J=7.6, 1H), 6.94 (bs, 1H), 6.70 (dd, J=8.4, 2.6, 1H), 4.33-4.22 (m, 1H), 3.48 (dd, J=10.0, 3.7, 1H), 3.35 (dd, J=9.9, 7.9, 1H), 3.22 (dd, J=9.7, 7.9, 1H), 3.16 (dd, J=7.9, 5.7, 1H), 3.02 (dd, J=9.7, 4.0, 1H), 2.83-2.62 (m, 2H), 2.41 (s, 3H), 2.10 (dq, J=12.6, 6.3, 1H), 2.03-1.79 (m, 2H), 1.76-1.58 (m, 2H), 1.53 (ddd, J=13.7, 7.7, 6.1, 1H), 1.42 (dtd, J=13.1, 7.6, 5.6, 1H), 0.94 (d, J=6.6, 3H), 0.90 (d, J=6.6, 3H); MS (ESI+) m/z 430 (M+H)⁺.

Example 713

1-(4-chlorophenyl)-3-{(3aR,4S,6aS)-2-[6-(trifluoromethyl)pyridin-2-yl]octahydrocyclopenta[c]pyrrol-4-yl}urea The title compound was prepared by substituting 1-chloro-4-isocyanatobenzene for 1-fluoro-4-isocyanatobenzene in the procedure described in Example 709: ¹H NMR (400 MHz, pyridine d-5) δ ppm 8.67 (s, 1H), 7.77-7.71 (m, 2H), 7.55 (d, J=8.0, 1H), 7.38-7.32 (m, 2H), 7.02 (d, J=8.5 1H), 6.60 (d, J=8.5, 1H), 6.34 (d, J=6.6, 1H), 4.32-4.25 (m, 1H), 3.79-3.66 (m, J=11.1, 5.8, 2H), 3.62 (dd, J=11.0, 7.9, 1H), 3.38 (dd, J=11.0, 4.1, 1H), 2.86-2.68 (m, 2H), 2.29-2.14 (m, 1H), 2.03-1.86 (m, 1H), 1.73-1.58 (m, 1H), 1.47 (td, J=13.0, 7.7, 1H); MS (ESI+) m/z 425 (M+H)⁺.

Example 714

1-(3-chloro-4-fluorophenyl)-3-{(3aR,4S,6aS)-2-[6-(trifluoromethyl)pyridin-2-yl]octahydrocyclopenta[c]pyrrol-4-yl}urea The title compound was prepared by substituting 2-chloro-1-fluoro-4-isocyanatobenzene for 1-fluoro-4-isocyanatobenzene in the procedure described in Example 709: ¹H NMR (400 MHz, pyridine-d₅) δ ppm 7.98 (dd, J=6.7, 2.6, 1H), 7.49-7.43 (m, 1H), 7.38 (ddd, J=8.9, 4.1, 2.7, 1H), 7.02 (s, 1H), 6.92 (d, J=7.3, 1H), 6.51 (d, J=8.6, 1H), 6.29 (s, 1H), 4.17 (dd, J=12.6, 5.9, 1H), 3.64 (ddd, J=18.6, 11.1, 5.8, 2H), 3.52 (dd, J=11.0, 7.8, 1H), 3.28 (dd, J=11.0, 4.0, 1H), 2.67 (t, J=13.6, 2H), 2.12 (td, J=12.8, 7.1, 1H), 1.86 (dt, J=13.5, 6.7, 1H), 1.57 (dt, J=15.1, 7.8, 1H), 1.46-1.26 (m, 1H); MS (ESI+) m/z 443 (M+H)⁺.

Example 715

(3aR,4S,6aS)-N-[(5-fluoro-1H-indol-2-yl)methyl]-2-[3-(trifluoromethoxy)phenyl]octahydrocyclopenta[c]pyrrol-4-amine Step 1: (3aR,4S,6aS)-2-(3-(Trifluoromethoxy)phenyl)octahydrocyclopenta[c]pyrrol-4-amine was prepared by substituting 1-bromo-3-(trifluoromethoxy)benzene for 1-bromo-2-(trifluoromethyl)benzene in the procedure described in Example 618 Step 1 and Step 2: ¹H NMR (400 MHz, pyridine-d₅) δ ppm 7.26 (dd, J=12.1, 4.5 Hz, 1H), 6.69 (d, J=7.4 Hz, 1H), 6.59-6.50 (m, 2H), 3.23-3.14 (m, 3H), 3.09 (dd, J=12.0, 5.8 Hz, 1H), 2.94 (dd, J=9.7, 4.4 Hz, 1H), 2.79-2.68 (m, 1H), 2.37-2.29 (m, 1H), 2.08-1.97 (m, 1H), 1.93-1.83 (m, 1H), 1.68 (d, J=40.6 Hz, 1H), 1.46-1.26 (m, 3H); MS (ESI+) m/z 287 (M+H)⁺.

Step 2: The title compound was prepared by substituting (3aR,4S,6aS)-2-(3-(trifluoromethoxy)phenyl)octahydrocyclopenta[c]pyrrol-4-amine from Step 1 for (3aR,4S,6aS)-2-(5-(trifluoromethyl)pyridin-2-yl)octahydrocyclopenta[c] pyrrol-4-amine in the procedure described in Example 614: ¹H NMR (400 MHz, methanol-d₄) δ 10.72 (bs, 1H), 7.39 (dd, J=8.9, 4.4, 1H), 7.27-7.19 (m, 2H), 7.02-6.92 (m, 1H), 6.68 (s, 1H), 6.64 (dd, J=8.3, 2.4, 1H), 6.61-6.55 (m, 1H), 6.50 (bs, 1H), 4.44 (d, J=3.7, 2H), 3.64-3.48 (m, 1H), 3.45-3.37 (m, 2H), 3.11-2.98 (m, 1H), 2.97-2.83 (m, 1H), 2.50-2.31 (m, 1H), 2.28-2.15 (m, 1H), 2.01 (s, 1H), 1.94-1.57 (m, 2H), 1.31-1.16 (m, 2H); MS (ESI+) m/z 434 (M+H)⁺.

Example 716

(3aR,4S,6aS)-N-[(5-fluoro-1H-indol-2-yl)methyl]-2-[4-(trifluoromethoxy)phenyl]octahydrocyclopenta[c]pyrrol-4-amine Step 1: (3aR,4S,6aS)-2-(4-(Trifluoromethoxy)phenyl)octahydrocyclopenta[c]pyrrol-4-amine was prepared by substituting 1-bromo-4-(trifluoromethoxy)benzene for 1-bromo-2-(trifluoromethyl)benzene in the procedure described in Example 618 Step 1 and Step 2: ¹H NMR (400 MHz, pyridine-d₅) δ ppm 7.26 (dd, J=12.1, 4.5 Hz, 1H), 6.69 (d, J=7.4 Hz, 1H), 6.59-6.50 (m, 2H), 3.23-3.14 (m, 3H), 3.09 (dd, J=12.0, 5.8 Hz, 1H), 2.94 (dd, J=9.7, 4.4 Hz, 1H), 2.79-2.68 (m, 1H), 2.37-2.29 (m, 1H), 2.08-1.97 (m, 1H), 1.93-1.83 (m, 1H), 1.68 (d, J=40.6 Hz, 1H), 1.46-1.26 (m, 3H); MS (ESI+) m/z 287 (M+H)⁺.

Step 2: The title compound was prepared by substituting (3aR,4S,6aS)-2-(4-(trifluoromethoxy)phenyl)octahydrocyclopenta[c]pyrrol-4-amine from Step 1 for (3aR,4S,6aS)-2-(5-(trifluoromethyl)pyridin-2-yl)octahydrocyclopenta[c]pyrrol-4-amine in the procedure described in Example 614: ¹H NMR (400 MHz, methanol-d₄) δ ppm 7.39 (dd, J=8.9, 4.4, 1H), 7.24 (dd, J=9.6, 2.5, 1H), 7.09 (d, J=8.4, 2H), 6.97 (td, J=9.2, 2.5, 1H), 6.79-6.61 (m, 3H), 4.55-4.34 (m, 2H), 3.58 (dd, J=12.9, 7.1, 1H), 3.44-3.33 (m, 2H), 3.25 (dd, J=14.2, 6.8, 3H), 3.03 (d, J=7.4, 1H), 2.88 (dd, J=10.5, 6.4, 1H), 2.43-2.31 (m, 1H), 2.29-2.15 (m, 1H), 2.01 (s, 1H), 1.92-1.79 (m, 1H), 1.70-1.58 (m, 1H); MS (ESI+) m/z 434 (M+H)⁺.

Example 717

1-(4-chlorophenyl)-N-{(3aR,4S,6aS)-2-[6-(trifluoromethyl)pyridin-2-yl]octahydrocyclopenta[c]pyrrol-4-yl}methanesulfonamide The title compound was prepared by substituting 3-chloro-4-fluorobenzene-1-sulfonyl chloride for 4-chlorobenzene-1-sulfonyl chloride in the procedure described in Example 700: ¹H NMR (400 MHz, pyridine-d₅) δ ppm 8.08-7.98 (m, 1H), 7.50-7.44 (m, 2H), 7.33-7.23 (m, 2H), 6.94 (d, J=7.3, 1H), 6.52 (d, J=8.5, 1H), 4.46 (d, J=2.7, 2H), 3.84-3.72 (m, 1H), 3.58 (dtd, J=19.0, 11.0, 5.9, 3H), 3.27 (dd, J=11.0, 4.2, 1H), 2.87-2.64 (m, 2H), 2.27-2.10 (m, 1H), 2.06-1.92 (m, 1H), 1.79 (dd, J=12.8, 7.7, 1H), 1.37 (dd, J=13.2, 5.4, 1H); MS (ESI+) m/z 460 (M+H)⁺.

Example 718

N²-methyl-N-{(3aR,4S,6aS)-2-[3-(trifluoromethoxy)phenyl]octahydrocyclopenta[c]pyrrol-4-yl}-L-norvalinamide The title compound was prepared by substituting N-(tert-butoxycarbonyl)-N-methyl-L-norvaline for (S)-2-(tert-butoxycarbonyl(methyl)amino)-4,4-dimethylpentanoic acid and (3aR,4S,6aS)-2-(3-(trifluoromethoxy)phenyl)octahydrocyclopenta[c]pyrrol-4-amine from Example 715 Step 1 for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-d$_5$, temperature 90° C.) δ ppm 7.63-7.68 (bs, 1H), 7.18 (t, J=8.4 Hz, 1H), 6.60-6.64 (m, 1H), 6.51-6.54 (m, 2H), 4.27 (dt, J=13.2, 6.6 Hz, 1H), 3.47 (dd, J=9.9, 3.8 Hz, 1H), 3.35 (dd, J=9.9, 7.9 Hz, 1H), 3.22 (dd, J=9.6, 8.0 Hz, 1H), 3.10 (dd, J=6.9, 5.8 Hz, 1H), 3.01 (dd, J=9.6, 4.1 Hz, 1H), 2.63-2.80 (m, 2H), 2.39 (s, 3H), 2.05-2.13 (m, 1H), 1.92-2.01 (m, 1H), 1.74-1.83 (m, 1H), 1.58-1.69 (m, 2H), 1.37-1.54 (m, 3H), 0.88 (t, J=7.3 Hz, 3H); MS (ESI+) m/z 400 (M+H)$^+$.

Example 719

N$^2$-methyl-N-{(3aR,4S,6aS)-2-[4-(trifluoromethoxy) phenyl]octahydrocyclopenta[c]pyrrol-4-yl}-L-norvalinamide The title compound was prepared by substituting N-(tert-butoxycarbonyl)-N-methyl-L-norvaline for (S)-2-(tert-butoxycarbonyl(methyl)amino)-4,4-dimethylpentanoic acid and (3aR,4S,6aS)-2-(4-(trifluoromethoxy)phenyl)octahydrocyclopenta[c]pyrrol-4-amine from Example 716 Step 1 for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-d$_5$, temperature 90° C.) δ ppm 7.60-7.71 (m, 1H), 7.10-7.15 (m, 2H), 6.56-6.59 (m, 2H), 4.24-4.32 (m, 1H), 3.47 (dd, J=9.9, 3.6 Hz, 1H), 3.31 (dd, J=9.8, 7.9 Hz, 1H), 3.19 (dd, J=9.5, 7.9 Hz, 1H), 3.10 (dd, J=6.9, 5.8 Hz, 1H), 3.01 (dd, J=9.6, 4.0 Hz, 1H), 2.71-2.83 (m, 1H), 2.56-2.70 (m, 1H), 2.40 (s, 3H), 2.09 (dq, J=12.6, 6.3 Hz, 1H), 1.92-2.01 (m, 1H), 1.74-1.83 (m, 1H), 1.58-1.70 (m, 2H), 1.38-1.53 (m, 3H), 0.88 (t, J=7.3 Hz, 3H); MS (ESI+) m/z 400 (M+H)$^+$.

Example 720

(3aR,4S,6aS)-N-[(1-methyl-1H-indol-2-yl)methyl]-2-[6-(trifluoromethyl)pyridin-2-yl]octahydrocyclopenta[c]pyrrol-4-amine The title compound was prepared by substituting 1-methylindole-2-carboxaldehyde for acetone in the procedure described in Example 609: $^1$H NMR (400 MHz, methanol-d$_4$) δppm 7.58 (t, J=7.9 Hz, 1H), 7.46 (d, J=7.8 Hz, 1H), 7.32 (dd, J=8.2, 1.0 Hz, 1H), 7.11 (ddd, J=8.2, 7.0, 1.2 Hz, 1H), 6.99 (ddd, J=7.9, 7.0, 0.9 Hz, 1H), 6.88 (d, J=7.2 Hz, 1H), 6.62 (d, J=8.5 Hz, 1H), 6.42 (s, 1H), 3.93-4.02 (m, 2H), 3.77 (s, 3H), 3.60 (dd, J=11.0, 8.3 Hz, 1H), 3.54 (dd, J=10.8, 8.0 Hz, 1H), 3.46 (dd, J=11.0, 4.4 Hz, 1H), 3.37 (dd, J=9.3, 5.5 Hz, 1H), 3.07-3.12 (m, 1H), 2.86-2.98 (m, 1H), 2.59-2.67 (m, 1H), 2.06-2.17 (m, 1H), 1.46-1.65 (m, 2H); MS (ESI+) m/z 415 (M+H)$^+$.

Example 721

(3aR,4S,6aS)-N-(thieno[2,3-c]pyridin-2-ylmethyl)-2-[6-(trifluoromethyl)pyridin-2-yl]octahydrocyclopenta[c]pyrrol-4-amine The title compound was prepared by substituting thieno[2,3-c]pyridin-2-carboxaldehyde for acetone in the procedure described in Example 609: $^1$H NMR (400 MHz, methanol-d$_4$) δ ppm 9.01 (s, 1H), 8.35 (d, J=5.2 Hz, 1H), 7.73 (d, J=5.0 Hz, 1H), 7.57 (d, J=7.9 Hz, 1H), 7.39 (s, 1H), 6.87 (d, J=7.2 Hz, 1H), 6.63 (d, J=8.5 Hz, 1H), 4.13-4.23 (m, 2H), 3.46-3.63 (m, 3H), 3.30-3.37 (m, 1H), 3.02-3.07 (m, 1H), 2.89-2.97 (m, 1H), 2.59-2.66 (m, 1H), 2.09-2.18 (m, 2H), 1.46-1.61 (m, 2H); MS (ESI+) m/z 419 (M+H)$^+$.

Example 722

N$^2$-methyl-N-{(3aR,4S,6aS)-2-[4-(trifluoromethyl) pyrimidin-2-yl]octahydrocyclopenta[c]pyrrol-4-yl}-L-leucinamide The title compound was prepared by substituting tert-butyl methyl((S)-4-methyl-1-((3aR,4S,6aS)-octahydrocyclopenta [c]pyrrol-4-ylamino)-1-oxopentan-2-yl)carbamate from Example 619 Step 1 for (2S,4S)-tert-butyl 4-fluoro-2-((3aR, 4S,6aS)-octahydrocyclopenta[c]pyrrol-4-ylcarbamoyl)pyrrolidine-1-carboxylate and 2-bromo-4-(trifluoromethyl)pyrimidine for 2-bromo-4-(trifluoromethyl)pyridine in the procedure described in Example 637: $^1$H NMR (400 MHz, pyridine-d$_5$) δ ppm 8.49 (d, J=4.8, 1H), 7.75-7.64 (m, 1H), 6.74 (d, J=4.8, 1H), 4.29 (dt, J=14.2, 7.2, 1H), 3.83 (d, J=4.5, 1H), 3.75 (dd, J=11.9, 8.2, 1H), 3.46 (dd, J=11.9, 4.8, 1H), 3.17-3.09 (m, 1H), 2.83-2.65 (m, 2H), 2.38 (s, 3H), 2.19-2.09 (m, 1H), 2.01-1.89 (m, 1H), 1.84 (dq, J=13.1, 6.6, 1H), 1.73-1.60 (m, 2H), 1.56-1.37 (m, 2H), 0.93 (d, J=6.6, 3H), 0.89 (d, J=6.6, 3H); MS (ESI+) m/z 400 (M+H)$^+$.

Example 723

N$^2$-methyl-N-{(3aR,4S,6aS)-2-[2-(trifluoromethyl) pyrimidin-4-yl]octahydrocyclopenta[c]pyrrol-4-yl}-L-leucinamide The title compound was prepared by substituting tert-butyl methyl((S)-4-methyl-1-((3aR,4S,6aS)-octahydrocyclopenta [c]pyrrol-4-ylamino)-1-oxopentan-2-yl)carbamate from Example 619 Step 1 for (2S,4S)-tert-butyl 4-fluoro-2-((3aR, 4S,6aS)-octahydrocyclopenta[c]pyrrol-4-ylcarbamoyl)pyrrolidine-1-carboxylate and 4-chloro-2-(trifluoromethyl)pyrimidine for 2-bromo-4-(trifluoromethyl)pyridine in the procedure described in Example 637: $^1$H NMR (400 MHz, pyridine-d$_5$) δ ppm 8.23 (d, J=6.1, 1H), 7.73 (dd, J=6.7, 4.2, 1H), 6.34 (d, J=6.1, 1H), 4.25 (dt, J=14.3, 7.2, 1H), 3.73-3.52 (m, 3H), 3.28 (dd, J=11.2, 4.0, 1H), 3.15 (dd, J=7.9, 5.8, 1H), 2.83-2.65 (m, 2H), 2.39 (d, J=0.5, 3H), 2.13 (td, J=12.5, 7.3, 1H), 2.01-1.90 (m, 1H), 1.93-1.67 (br m, 1H), 1.85 (td, J=13.4, 6.6, 1H), 1.74-1.60 (m, 2H), 1.52 (ddd, J=14.0, 7.9, 6.3, 1H), 1.41 (td, J=13.3, 7.9, 1H), 0.93 (d, J=6.6, 3H), 0.89 (d, J=6.6, 3H); MS (ESI+) m/z 400 (M+H)$^+$.

Example 724

N$^2$-methyl-N-{(3aR,4S,6aS)-2-[6-(trifluoromethyl) pyridazin-3-yl]octahydrocyclopenta[c]pyrrol-4-yl}-L-leucinamide The title compound was prepared by substituting tert-butyl methyl((S)-4-methyl-1-((3aR,4S,6aS)-octahydrocyclopenta [c]pyrrol-4-ylamino)-1-oxopentan-2-yl)carbamate from Example 619 Step 1 for (2S,4S)-tert-butyl 4-fluoro-2-((3aR, 4S,6aS)-octahydrocyclopenta[c]pyrrol-4-ylcarbamoyl)pyrrolidine-1-carboxylate and 3-chloro-6-(trifluoromethyl)pyridazine for 2-bromo-4-(trifluoromethyl)pyridine in the procedure described in Example 637: $^1$H NMR (400 MHz, pyridine-d$_5$) δ ppm 7.76 (s, 1H), 7.46 (d, J=9.4, 1H), 6.66 (d, J=9.4, 1H), 4.34-4.25 (m, 1H), 3.82 (d, J=3.9, 2H), 3.75-3.64 (m, 2H), 3.44 (dd, J=11.3, 4.7, 1H), 3.16 (dd, J=7.9, 5.8, 1H), 2.88-2.68 (m, 2H), 2.40 (s, 3H), 2.20-2.09 (m, 1H), 1.98 (dtd, J=13.1, 8.0, 5.0, 1H), 1.91-1.80 (m, 1H), 1.74-1.62 (m, 2H), 1.48 (dddd, J=15.8, 13.4, 7.9, 6.0, 2H), 0.94 (d, J=6.6, 3H), 0.90 (d, J=6.6, 3H); MS (ESI+) m/z 400 (M+H)$^+$.

Example 725

(3aR,4S,6aS)-N-[(1-methyl-1H-pyrazol-5-yl)methyl]-2-[6-(trifluoromethyl)pyridin-2-yl]octahydrocyclopenta[c]pyrrol-4-amine The title compound was prepared by substituting 2-methyl-2H-pyrazole-3-carboxaldehyde for acetone in the procedure described in Example 609: $^1$H NMR (500 MHz, methanol-d$_4$) δ ppm 7.61 (t, J=7.9 Hz, 1H), 7.37 (d, J=1.9 Hz, 1H), 6.89 (d, J=7.2 Hz, 1H), 6.66 (d, J=8.6 Hz, 1H), 6.28 (d, J=1.9 Hz, 1H), 3.86 (s, 3H), 3.82-3.90 (m, 2H), 3.61 (dd, J=11.0, 8.3 Hz, 1H), 3.54 (dd, J=10.7, 8.0 Hz, 1H), 3.48 (dd, J=11.0, 4.2 Hz, 1H), 3.36 (dd, J=11.1, 4.1 Hz, 1H), 3.01-3.05 (m, 1H), 2.91-2.97 (m, 1H), 2.58-2.64 (m, 1H), 2.09-2.17 (m, 2H), 1.47-1.61 (m, 2H); MS (ESI+) m/z 366 (M+H)$^+$.

Example 726

(3aR,4S,6aS)-N-[(5-chloro-2-phenyl-1H-imidazol-4-yl)methyl]-2-[6-(trifluoromethyl)pyridin-2-yl]octahydrocyclopenta[c]pyrrol-4-amine The title compound was prepared by substituting 5-chloro-2-phenyl-1H-imidazole-4-carbaldehyde for acetone in the procedure described in Example 609: $^1$H NMR (400 MHz, methanol-d$_4$) δ ppm 7.79-7.85 (m, 2H), 7.58 (t, J=7.9 Hz, 1H), 7.43-7.49 (m, 2H), 7.38-7.42 (m, 1H), 6.88 (d, J=7.2 Hz, 1H), 6.64 (d, J=8.5 Hz, 1H), 3.88-3.93 (m, 1H), 3.84-3.88 (m, 1H), 3.62 (dd, J=11.0, 8.2 Hz, 1H), 3.55 (dd, J=10.7, 7.9 Hz, 1H), 3.48 (dd, J=11.0, 4.3 Hz, 1H), 3.37 (dd, J=10.9, 4.0 Hz, 1H), 3.05 (q, J=5.9 Hz, 1H), 2.90-2.99 (m, 1H), 2.60-2.67 (m, 1H), 2.05-2.25 (m, 2H), 1.45-1.67 (m, 2H); MS (APCI+) m/z 462 (M+H)$^+$.

Example 727

(3aR,4S,6aS)-N-(thieno[2,3-b]pyridin-2-ylmethyl)-2-[6-(trifluoromethyl)pyridin-2-yl]octahydrocyclopenta[c]pyrrol-4-amine The title compound was prepared by substituting thieno[2,3-b]pyridine-2-carbaldehyde for acetone in the procedure described in Example 609: $^1$H NMR (400 MHz, methanol-d$_4$) δ ppm 8.43 (dd, J=4.7, 1.6 Hz, 1H), 8.12 (dd, J=8.0, 1.6 Hz, 1H), 7.58 (t, J=7.9 Hz, 1H), 7.38 (dd, J=8.0, 4.7 Hz, 1H), 7.28 (s, 1H), 6.87 (d, J=7.2 Hz, 1H), 6.63 (d, J=8.5 Hz, 1H), 4.14 (d, J=4.0 Hz, 2H), 3.59 (dd, J=11.0, 8.4 Hz, 1H), 3.53 (dd, J=10.8, 8.1 Hz, 1H), 3.47 (dd, J=11.0, 4.3 Hz, 1H), 3.35 (dd, J=10.8, 4.0 Hz, 1H), 3.07 (q, J=6.1 Hz, 1H), 2.89-2.99 (m, 1H), 2.60-2.67 (m, 1H), 2.09-2.19 (m, 2H), 1.45-1.64 (m, 2H); MS (ESI+) m/z 419 (M+H)$^+$.

Example 728

(3aR,4S,6aS)-N-(2,1,3-benzothiadiazol-4-ylmethyl)-2-[6-(trifluoromethyl)pyridin-2-yl]octahydrocyclopenta[c]pyrrol-4-amine The title compound was prepared by substituting 2,1,3-benzothiadiazole-4-carbaldehyde for acetone in the procedure described in Example 609: $^1$H NMR (400 MHz, methanol-d$_4$) δ ppm 7.93-7.98 (m, 1H), 7.63-7.69 (m, 2H), 7.57-7.62 (m, 1H), 6.89 (d, J=7.2 Hz, 1H), 6.62 (d, J=8.5 Hz, 1H), 4.36-4.41 (m, 1H), 4.30-4.35 (m, 1H), 3.60 (dd, J=11.0, 8.2 Hz, 1H), 3.53 (dd, J=10.7, 7.9 Hz, 1H), 3.44 (dd, J=11.0, 4.3 Hz, 1H), 3.34 (dd, J=10.7, 4.0 Hz, 1H), 3.06-3.11 (m, 1H), 2.89-3.02 (m, 1H), 2.66-2.73 (m, 1H), 2.08-2.22 (m, 2H), 1.60-1.70 (m, 1H), 1.46-1.56 (m, 1H); MS (ESI+) m/z 420 (M+H)$^+$.

Example 729

N-{(3aR,4S,6aS)-2-[3-(difluoromethyl)phenyl]octahydrocyclopenta[c]pyrrol-4-yl}-N$^2$-methyl-L-leucinamide The title compound was prepared by substituting 1-bromo-3-(difluoromethyl)benzene for 1-bromo-2-fluorobenzene in the procedure described in Example 619: $^1$H NMR (400 MHz, pyridine-d$_5$) δ ppm 8.32 (d, J=7.5, 1H), 7.34 (t, J=7.9, 1H), 7.05 (d, J=7.5, 1H), 6.99 (t, J=56.5, 1H), 6.76 (d, J=8.3, 1H), 5.06 (d, J=24.0, 1H), 4.45-4.37 (m, 1H), 3.56 (dd, J=9.9, 2.8, 1H), 3.34 (dd, J=9.8, 7.7, 1H), 3.27 (dd, J=8.2, 5.9, 1H), 3.17 (dd, J=9.5, 7.9, 1H), 3.02 (dd, J=9.7, 3.2, 1H), 2.79-2.67 (m, 2H), 2.46 (s, 3H), 2.11 (td, J=12.4, 6.5, 1H), 2.07-1.95 (m, 1H), 2.01-1.87 (m, 2H), 1.79-1.57 (m, 3H), 1.40 (td, J=12.9, 8.1, 1H), 0.94 (d, J=6.6, 3H), 0.88 (d, J=6.6, 3H); MS (ESI+) m/z 380 (M+H)$^+$.

Example 730

N-[(3aR,4S,6aS)-2-(2,3-difluorophenyl)octahydrocyclopenta[c]pyrrol-4-yl]-N$^2$-methyl-L-leucinamide The title compound was prepared by substituting 1-bromo-2,3-difluorobenzene for 1-bromo-2-fluorobenzene in the procedure described in Example 619: $^1$H NMR (400 MHz, pyridine-d$_5$) δ ppm 8.31 (d, J=7.2, 1H), 6.96-6.89 (m, 1H), 6.72 (dddd, J=9.8, 8.3, 7.0, 1.4, 1H), 6.54-6.48 (m, 1H), 4.47-4.39 (m, 1H), 3.67 (d, J=9.8, 1H), 3.33 (dd, J=9.7, 6.9, 1H), 3.26 (dd, J=8.2, 5.9, 1H), 3.22-3.13 (m, 2H), 2.74-2.62 (m, 2H), 2.45 (s, 3H), 2.16-2.06 (m, 1H), 2.00 (dd, J=24.7, 17.5, 1H), 2.01-1.86 (m, 2H), 1.79-1.56 (m, 3H), 1.43 (td, J=12.6, 8.7, 1H), 0.94 (d, J=6.6, 3H), 0.88 (d, J=6.6, 3H); MS (ESI+) m/z 366 (M+H)$^+$.

Example 731

(3aR,4S,6aS)-N-[(1-methyl-1H-benzimidazol-2-yl)methyl]-2-[6-(trifluoromethyl)pyridin-2-yl]octahydrocyclopenta[c]pyrrol-4-amine The title compound was prepared by substituting 1-methyl-1H-benzimidazole-2-carbaldehyde for acetone in the procedure described in Example 609: $^1$H NMR (400 MHz, methanol-d$_4$) δ ppm 7.55-7.62 (m, 2H), 7.47-7.50 (m, 1H), 7.22-7.32 (m, 2H), 6.87 (d, J=7.2 Hz, 1H), 6.62 (d, J=8.5 Hz, 1H), 4.12 (d, J=3.5 Hz, 2H), 3.90 (s, 3H), 3.58 (dd, J=11.1, 8.4 Hz, 1H), 3.54 (dd, J=10.7, 7.9 Hz, 1H), 3.46 (dd, J=11.0, 4.3 Hz, 1H), 3.35 (dd, J=10.8, 4.1 Hz, 1H), 3.04-3.09 (m, 1H), 2.88-2.95 (m, 1H), 2.58-2.65 (m, 1H), 2.08-2.15 (m, 2H), 1.45-1.62 (m, 2H); MS (ESI+) m/z 416 (M+H)$^+$.

Example 732

(3aR,4S,6aS)-N-(2,1,3-benzothiadiazol-5-ylmethyl)-2-[6-(trifluoromethyl)pyridin-2-yl]octahydrocyclopenta[c]pyrrol-4-amine The title compound was prepared by substituting benzo[c][1,2,5]thiadiazole-5-carbaldehyde for acetone in the procedure described in Example 609: ¹H NMR (400 MHz, methanol-d₄) δ ppm 7.96-8.01 (m, 2H), 7.73 (dd, J=9.0, 1.7 Hz, 1H), 7.56-7.61 (m, 1H), 6.88 (d, J=7.2 Hz, 1H), 6.63 (d, J=8.5 Hz, 1H), 4.03 (d, J=4.9 Hz, 2H), 3.62 (dd, J=11.0, 8.3 Hz, 1H), 3.54 (dd, J=10.8, 7.9 Hz, 1H), 3.48 (dd, J=11.1, 4.2 Hz, 1H), 3.36 (dd, J=10.9, 4.0 Hz, 1H), 3.05-3.11 (m, 1H), 2.91-3.01 (m, 1H), 2.64-2.71 (m, 1H), 2.09-2.22 (m, 2H), 1.59-1.68 (m, 1H), 1.46-1.56 (m, 1H); MS (ESI+) m/z 420 (M+H)⁺.

Example 733 tert-butyl methyl{(2S)-3-methyl-1-[(3aR,4S,6aS)-octahydrocyclopenta[c]pyrrol-4-ylamino]-1-oxobutan-2-yl}carbamate Step 1: The tert-butyl(S)-1-((3aR,4S,6aS)-2-benzyloctahydrocyclopenta[c]pyrrol-4-ylamino)-3-methyl-1-oxobutan-2-yl(methyl)carbamate was prepared by substituting N-(tert-butoxycarbonyl)-N-methyl-L-norvaline for N-(tert-butoxycarbonyl)-L-leucine in the procedure described in Example 221: ¹H NMR (500 MHz, pyridine-d₅) δ ppm 8.45 (d, J=7.8 Hz, 1H), 7.44 (d, J=7.1 Hz, 2H), 7.36 (t, J=7.6 Hz, 2H), 7.27 (t, J=7.3 Hz, 1H), 4.62 (d, J=11.1 Hz, 1H), 4.45-4.37 (m, 1H), 3.61 (d, J=13.1 Hz, 1H), 3.44 (d, J=13.1 Hz, 1H), 3.13 (s, 2H), 2.86 (d, J=7.6 Hz, 1H), 2.59-2.37 (m, 4H), 2.33 (d, J=9.3 Hz, 1H), 2.28-2.19 (m, 1H), 2.04 (dt, J=14.1, 7.0 Hz, 1H), 1.86-1.76 (m, 1H), 1.48 (s, 9H), 1.43-1.30 (m, 3H), 1.03 (t, J=13.8 Hz, 3H), 0.87 (t, J=10.7 Hz, 3H); MS (ESI+) m/z 430 (M+H)⁺.

Step 2: The title compound was prepared by substituting tert-butyl(S)-1-((3aR,4S,6aS)-2-benzyloctahydrocyclopenta[c]pyrrol-4-ylamino)-3-methyl-1-oxobutan-2-yl(methyl)carbamate from Step 1 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 619 Step 1: ¹H NMR (400 MHz, pyridine-d₅) δ ppm 7.33-7.25 (m, 1H), 4.34 (d, J=10.6, 1H), 4.18-4.09 (m, 1H), 3.01 (s, 3H), 2.96 (dd, J=10.8, 3.4, 1H), 2.89 (dd, J=10.8, 7.2, 1H), 2.80 (dd, J=10.4, 7.2, 1H), 2.55 (dd, J=10.3, 3.2, 1H), 2.52-2.34 (m, 3H), 1.95 (td, J=11.9, 5.9, 1H), 1.89-1.78 (m, 1H), 1.54-1.49 (m, 1H), 1.47 (s, 9H), 1.32-1.19 (m, 1H), 1.02 (d, J=6.5, 3H), 0.88 (d, J=6.7, 3H); MS (ESI+) m/z 340 (M+H)⁺.

Example 734

N²-methyl-N-{(3aR,4S,6aS)-2-[5-(trifluoromethyl)-1,3,4-thiadiazol-2-yl]octahydrocyclopenta[c]pyrrol-4-yl}-L-leucinamide The title compound was prepared by substituting 2-bromo-5-(trifluoromethyl)-1,3,4-thiadiazole for 1-bromo-2-fluorobenzene in the procedure described in Example 619: ¹H NMR (500 MHz, pyridine-d₅) δ ppm 8.42 (d, J=7.3, 1H), 4.47-4.39 (m, 1H), 3.86 (dd, J=10.8, 3.2, 1H), 3.73 (dd, J=10.8, 7.6, 1H), 3.61 (dd, J=10.6, 8.1, 1H), 3.34 (dd, J=10.7, 4.3, 1H), 3.26 (dd, J=8.3, 5.8, 1H), 2.89-2.77 (m, 2H), 2.44 (s, 3H), 2.20-2.13 (m, 1H), 2.15-1.99 (m, 1H), 2.00-1.87 (m, 2H), 1.78-1.67 (m, 2H), 1.64-1.56 (m, 1H), 1.48-1.37 (m, 1H), 0.93 (d, J=6.6, 3H), 0.87 (d, J=6.6, 3H); MS (ESI+) m/z 406 (M+H)⁺.

Example 735

N²-methyl-N-{(3aR,4S,6aS)-2-[6-(trifluoromethyl)pyridin-3-yl]octahydrocyclopenta[c]pyrrol-4-yl}-L-leucinamide The title compound was prepared by substituting 5-bromo-2-(trifluoromethyl)pyridine for 1-bromo-2-fluorobenzene in the procedure described in Example 619: ¹H NMR (500 MHz, pyridine-d₅) δ ppm 8.42 (d, J=7.5 Hz, 1H), 8.18 (d, J=2.8 Hz, 1H), 6.84 (dd, J=8.7, 2.8 Hz, 1H), 4.47-4.35 (m, 1H), 3.56 (dd, J=10.2, 2.8 Hz, 1H), 3.40 (dd, J=10.1, 7.7 Hz, 1H), 3.26 (ddd, J=17.7, 8.9, 6.9 Hz, 2H), 3.03 (dd, J=10.0, 3.6 Hz, 1H), 2.77 (h, J=8.9 Hz, 2H), 2.60 (s, 1H), 2.47 (s, 3H), 2.34 (s, 1H), 2.15 (ddd, J=14.3, 7.9, 3.5 Hz, 1H), 2.05-1.86 (m, 2H), 1.81-1.56 (m, 3H), 1.41 (dtd, J=13.1, 8.0, 5.0 Hz, 1H), 0.94 (d, J=6.6 Hz, 3H), 0.89 (d, J=6.6 Hz, 3H); MS (ESI+) m/z 399 (M+H)⁺.

Example 736

N²-methyl-N-{(3aR,4S,6aS)-2-[5-(trifluoromethyl)pyridin-3-yl]octahydrocyclopenta[c]pyrrol-4-yl}-L-leucinamide The title compound was prepared by substituting 3-bromo-5-(trifluoromethyl)pyridine for 1-bromo-2-fluorobenzene in the procedure described in Example 619: ¹H NMR (500 MHz, pyridine-d₅) δ ppm 8.48 (s, 1H), 8.37 (t, J=5.1, 2H), 7.08 (t, J=2.1, 1H), 4.49-4.39 (m, 1H), 3.58 (dd, J=10.0, 2.9, 1H), 3.38 (dd, J=9.9, 7.7, 1H), 3.27 (dd, J=8.3, 5.8, 1H), 3.21 (dd, J=9.6, 8.0, 1H), 3.04 (dd, J=9.8, 3.6, 1H), 2.78 (h, J=9.0, 2H), 2.46 (s, 3H), 2.16 (td, J=12.4, 6.9, 1H), 2.12-2.03 (m, 1H), 2.03-1.88 (m, 2H), 1.79-1.67 (m, 2H), 1.61 (ddd, J=13.6, 8.4, 6.3, 1H), 1.45 (dtd, J=13.0, 8.0, 5.0, 1H), 0.94 (d, J=6.6, 3H), 0.88 (d, J=6.6, 3H); MS (ESI+) m/z 399 (M+H)⁺.

Example 737

N-{(3aR,4S,6aS)-2-[4-fluoro-2-(trifluoromethyl)phenyl]octahydrocyclopenta[c]pyrrol-4-yl}-N²-methyl-L-leucinamide The title compound was prepared by substituting 1-bromo-4-fluoro-2-(trifluoromethyl)benzene for 1-bromo-2-fluorobenzene in the procedure described in Example 619: ¹H NMR (500 MHz, pyridine-d₅) δ ppm 8.25 (d, J=7.4 Hz, 1H), 7.46 (dd, J=9.1, 2.9, 1H), 7.33 (dd, J=8.9, 5.1, 1H), 7.31-7.25 (m, 1H), 4.54-4.47 (m, 1H), 3.41 (dd, J=9.0, 1.5, 1H), 3.25 (dd, J=8.2, 6.0, 1H), 3.05 (dd, J=9.0, 6.8, 1H), 2.92-2.85 (m, 2H), 2.72-2.60 (m, 2H), 2.45 (s, 3H), 2.24-2.16 (m, 1H), 2.15-2.01 (m, 1H), 1.93 (ddt, J=19.8, 13.2, 6.3, 2H), 1.73 (ddd, J=13.6, 7.8, 5.9, 1H), 1.68-1.55 (m, 3H), 0.93 (d, J=6.6, 3H), 0.87 (d, J=6.6, 3H); MS (ESI+) m/z 416 (M+H)⁺.

Example 738

N²-methyl-N-{(3aS,4R,6aR)-2-[5-(trifluoromethyl)pyridin-2-yl]octahydrocyclopenta[c]pyrrol-4-yl}-L-leucinamide The title compound was prepared by substituting tert-butyl methyl((S)-4-methyl-1-((3aS,4R,6aR)-octahydrocyclopenta[c]pyrrol-4-ylamino)-1-oxopentan-2-yl)carbamate from Example 349 for (2S,4S)-tert-butyl 4-fluoro-2-((3aR,4S,6aS)-octahydrocyclopenta[c]pyrrol-4-ylcarbamoyl)pyrrolidine-1-carboxylate and 2-bromo-5-(trifluoromethyl)pyridine for 2-bromo-4-(trifluoromethyl)pyridine in the procedure described in Example 637: ¹H NMR (500 MHz, pyridine-d₅) δ ppm 8.62 (dd, J=1.6, 0.7, 1H), 8.37 (d, J=7.5, 1H), 7.67 (dd, J=8.9, 2.5, 1H), 6.39 (d, J=8.9, 1H), 4.51-4.38 (m, 1H), 3.83 (d, J=9.7, 1H), 3.74-3.64 (m, 1H), 3.63-3.53 (m, 1H), 3.37-3.29 (m, 1H), 3.24 (dd, J=8.3, 5.8, 1H), 2.82-2.68 (m, 2H), 2.45 (s, 3H), 2.23-2.13 (m, 1H), 2.12-1.99 (bs, 1H), 2.00-1.87

(m, 2H), 1.79-1.67 (m, 2H), 1.67-1.57 (m, 1H), 1.42 (dtd, J=13.2, 8.0, 5.1, 1H), 0.93 (d, J=6.6, 3H), 0.87 (d, J=6.6, 3H); MS (ESI+) m/z 399 (M+H)+.

Example 739

N²-methyl-N-{(3aS,4R,6aR)-2-[4-(trifluoromethoxy)phenyl]octahydrocyclopenta[c]pyrrol-4-yl}-L-leucinamide The title compound was prepared by substituting 1-bromo-4-(trifluoromethoxy)benzene for 1-bromo-2-fluorobenzene and tert-butyl methyl((S)-4-methyl-1-((3aS,4R,6aR)-octahydrocyclopenta[c]pyrrol-4-ylamino)-1-oxopentan-2-yl)carbamate from Example 349 for (2S,4S)-tert-butyl 4-fluoro-2-((3aR,4S,6aS)-octahydrocyclopenta[c]pyrrol-4-ylcarbamoyl)pyrrolidine-1-carboxylate in the procedure described in Example 619: ¹H NMR (500 MHz, pyridine-d₅) δ ppm 8.34 (d, J=7.6, 1H), 7.22-7.19 (m, 2H), 6.63-6.57 (m, 2H), 4.47-4.37 (m, 1H), 3.55 (dd, J=9.8, 2.9, 1H), 3.27 (ddd, J=14.2, 9.1, 6.7, 2H), 3.15 (dd, J=9.5, 7.8, 1H), 3.01 (dd, J=9.6, 3.5, 1H), 2.78-2.66 (m, 2H), 2.46 (s, 3H), 2.12 (dt, J=12.4, 6.7, 1H), 2.09-2.00 (m, 1H), 2.00-1.87 (m, 2H), 1.75 (ddd, J=10.4, 8.1, 4.2, 1H), 1.71-1.58 (m, 2H), 1.44-1.36 (m, 1H), 0.93 (d, J=6.6, 3H), 0.88 (d, J=6.6, 3H); MS (ESI+) m/z 414 (M+H)+.

Example 740

N²-methyl-N-{(3aS,4R,6aR)-2-[4-(trifluoromethyl)phenyl]octahydrocyclopenta[c]pyrrol-4-yl}-L-leucinamide The title compound was prepared by substituting 1-bromo-4-(trifluoromethyl)benzene for 1-bromo-2-fluorobenzene and tert-butyl methyl((S)-4-methyl-1-((3aS,4R,6aR)-octahydrocyclopenta[c]pyrrol-4-ylamino)-1-oxopentan-2-yl)carbamate from Example 349 for (2S,4S)-tert-butyl 4-fluoro-2-((3aR,4S,6aS)-octahydrocyclopenta[c]pyrrol-4-ylcarbamoyl)pyrrolidine-1-carboxylate in the procedure described in Example 619: ¹H NMR (500 MHz, pyridine-d₅) δ ppm 8.36 (d, J=7.5, 1H), 7.58 (d, J=8.6, 2H), 6.63 (d, J=8.7, 2H), 4.47-4.34 (m, 1H), 3.56 (dd, J=10.2, 3.0, 1H), 3.38 (dd, J=10.0, 7.6, 1H), 3.28-3.20 (m, 2H), 3.02 (dd, J=9.9, 3.7, 1H), 2.78-2.66 (m, 2H), 2.46 (s, 3H), 2.18-2.09 (m, 1H), 2.06 (s, 1H), 2.00-1.87 (m, 2H), 1.79-1.57 (m, 3H), 1.39 (dtd, J=13.2, 8.0, 5.2, 1H), 0.94 (d, J=6.6, 3H), 0.88 (d, J=6.6, 3H); MS (ESI+) m/z 398 (M+H)+.

Example 741

(3aR,4S,6aS)-N-{[2-(4-chlorophenyl)-1,3-oxazol-4-yl]methyl}-2-[6-(trifluoromethyl)pyridin-2-yl]octahydrocyclopenta[c]pyrrol-4-amine The title compound was prepared by substituting 2-(4-chlorophenyl)-1,3-oxazole-4-carbaldehyde for acetone in the procedure described in Example 609: ¹H NMR (400 MHz, methanol-d₄) δ ppm 8.03-7.97 (m, 2H), 7.97 (s, 1H), 7.60 (td, J=7.9, 0.9, 1H), 7.55-7.49 (m, 2H), 6.90 (d, J=7.2, 1H), 6.67 (d, J=8.6, 1H), 3.97 (dd, J=2.9, 0.9, 2H), 3.66 (dd, J=11.2, 8.1, 1H), 3.62-3.50 (m, 2H), 3.39 (dd, J=10.8, 3.9,1H), 3.26 (dd, J=12.4, 6.9, 1H), 3.05-2.92 (m, 1H), 2.77-2.68 (m, 1H), 2.30-2.07 (m, 2H), 1.93 (s, 2H [CH₃COO]), 1.79-1.50 (m, 2H); MS (ESI+) m/z 463 (M+H)+.

Example 742

(3aR,4S,6aS)-N-({2-[4-(trifluoromethyl)phenyl]-1H-imidazol-4-yl}methyl)-2-[6-(trifluoromethyl)pyridin-2-yl]octahydrocyclopenta[c]pyrrol-4-amine The title compound was prepared by substituting 2-[4-(trifluoromethyl)phenyl]-1H-imidazole-4-carbaldehyde for acetone in the procedure described in Example 609: ¹H NMR (400 MHz, methanol-d₄) δ ppm 8.08-8.00 (m, 2H), 7.79-7.72 (m, 2H), 7.65-7.57 (m, 1H), 7.34-7.30 (m, 1H), 6.94-6.89 (m, 1H), 6.70-6.65 (m, 1H), 4.16-4.04 (m, 2H), 3.73-3.50 (m, 3H), 3.45-3.37 (m, 2H), 3.07-2.96 (m, 1H), 2.84-2.75 (m, 1H), 2.36-2.25 (m, 1H), 2.23-2.11 (m, 1H), 1.93 (s, 3H [CH₃COO]), 1.82-1.69 (m, 1H), 1.65-1.54 (m, 1H); MS (ESI+) m/z 496 (M+H)+.

Example 743

(3aR,4S,6aS)-N-{[2-(4-fluorophenyl)-1,3-oxazol-4-yl]methyl}-2-[6-(trifluoromethyl)pyridin-2-yl]octahydrocyclopenta[c]pyrrol-4-amine The title compound was prepared by substituting 2-(4-fluorophenyl)-1,3-oxazole-4-carbaldehyde for acetone in the procedure described in Example 609: ¹H NMR (400 MHz, methanol-d₄) δ ppm 8.06 (dd, J=9.0, 5.3, 2H), 7.97 (s, 1H), 7.67-7.52 (m, 1H), 7.25 (t, J=8.8, 2H), 6.91 (d, J=7.3, 1H), 6.68 (d, J=8.6, 1H), 3.99 (dd, J=2.7, 0.7, 2H), 3.74-3.48 (m, 3H), 3.46-3.37 (m, 1H), 3.08-2.91 (m, 1H), 2.82-2.61 (m, 1H), 2.33-2.05 (m, 2H), 1.94 (s, 2H), 1.76-1.63 (m, 1H), 1.62-1.51 (m, 1H); MS (ESI+) m/z 447 (M+H)+.

Example 744

(3aR,4S,6aS)-N-{[4-(4-fluorophenyl)-1H-imidazol-2-yl]methyl}-2-[6-(trifluoromethyl)pyridin-2-yl]octahydrocyclopenta[c]pyrrol-4-amine The title compound was prepared by substituting 4-(4-fluorophenyl)-1H-imidazole-2-carbaldehyde for acetone in the procedure described in Example 609: ¹H NMR (500 MHz, methanol-d₄) δ ppm 7.74-7.66 (m, 2H), 7.58 (dd, J=11.9, 4.0 Hz, 1H), 7.36 (s, 1H), 7.13-7.05 (m, 2H), 6.89 (d, J=7.3 Hz, 1H), 6.65 (d, J=8.6 Hz, 1H), 4.09-3.99 (m, 2H), 3.62 (dd, J=11.2, 8.3 Hz, 1H), 3.56-3.48 (m, 2H), 3.40-3.33 (m, 3H), 3.16 (dd, J=12.1, 6.6 Hz, 1H), 2.96 (pd, J=7.9, 4.0 Hz, 1H), 2.68 (td, J=9.0, 4.7 Hz, 1H), 2.22-2.09 (m, 2H), 1.71-1.59 (m, 1H), 1.58-1.48 (m, 1H); MS (ESI+) m/z 446 (M+H)+.

Example 745

(3aR,4S,6aS)-N-{[4-(4-chlorophenyl)-1H-imidazol-2-yl]methyl}-2-[6-(trifluoromethyl)pyridin-2-yl]octahydrocyclopenta[c]pyrrol-4-amine The title compound was prepared by substituting 4-(4-chlorophenyl)-1H-imidazole-2-carbaldehyde for acetone in the procedure described in Example 609: ¹H NMR (500 MHz, methanol-d₄) δ ppm 7.74-7.66 (m, 2H), 7.58 (dd, J=11.9, 4.0 Hz, 1H), 7.36 (s, 1H), 7.13-7.05 (m, 2H), 6.89 (d, J=7.3 Hz, 1H), 6.65 (d, J=8.6 Hz, 1H), 4.09-3.99 (m, 2H), 3.62 (dd, J=11.2, 8.3 Hz, 1H), 3.56-3.48 (m, 2H), 3.40-3.33 (m, 3H), 3.16 (dd, J=12.1, 6.6 Hz, 1H), 2.96 (pd, J=7.9, 4.0

Hz, 1H), 2.68 (td, J=9.0, 4.7 Hz, 1H), 2.22-2.09 (m, 2H), 1.71-1.59 (m, 1H), 1.58-1.48 (m, 1H); MS (ESI+) m/z 462 (M+H)$^+$.

Example 746

(3aR,4S,6aS)-N-[(4-phenyl-1H-imidazol-2-yl)methyl]-2-[6-(trifluoromethyl)pyridin-2-yl]octahydrocyclopenta[c]pyrrol-4-amine The title compound was prepared by substituting 4-phenyl-1H-imidazole-2-carbaldehyde for acetone in the procedure described in Example 609: $^1$H NMR (500 MHz, methanol-d$_4$) δ ppm 7.70-7.65 (m, 2H), 7.58 (t, J=7.9 Hz, 1H), 7.40-7.33 (m, 3H), 7.23 (ddd, J=8.6, 2.3, 1.1 Hz, 1H), 6.89 (d, J=7.3 Hz, 1H), 6.65 (d, J=8.6 Hz, 1H), 4.05-3.97 (m, 2H), 3.62 (dd, J=11.1, 8.3 Hz, 1H), 3.52 (ddd, J=13.0, 11.0, 6.1 Hz, 2H), 3.39-3.34 (m, 1H), 3.17-3.09 (m, 1H), 3.01-2.92 (m, 1H), 2.70-2.63 (m, 1H), 2.22-2.08 (m, 2H), 1.95 (d, J=3.3 Hz, 2H), 1.68-1.59 (m, 1H), 1.57-1.48 (m, 1H); MS (ESI+) m/z 428 (M+H)$^+$.

Example 747

N$^2$-methyl-N-{(3aR,4S,6aS)-2-[4-(trifluoromethyl)phenyl]octahydrocyclopenta[c]pyrrol-4-yl}-L-valinamide The title compound was prepared by substituting 1-bromo-4-(trifluoromethyl)benzene for 1-bromo-2-fluorobenzene and tert-butyl methyl{(2S)-3-methyl-1-[(3aR,4S,6aS)-octahydrocyclopenta[c]pyrrol-4-ylamino]-1-oxobutan-2-yl}carbamate from Example 733 for tert-butyl methyl((S)-4-methyl-1-((3aR,4S,6aS)-octahydrocyclopenta[c]pyrrol-4-ylamino)-1-oxopentan-2-yl)carbamate in the procedure described in Example 619: $^1$H NMR (400 MHz, methanol-d$_4$) δ ppm 7.41 (d, J=8.6, 2H), 6.69 (d, J=8.7, 2H), 4.08 (dd, J=13.1, 6.2, 1H), 3.49-3.37 (m, 3H), 3.23 (dd, J=9.9, 4.2, 1H), 3.04-2.85 (m, 1H), 2.74 (d, J=6.6, 1H), 2.65 (dd, J=13.5, 6.5, 1H), 2.29 (s, 3H), 2.24-2.02 (m, 2H), 1.88 (tt, J=13.5, 6.9, 1H), 1.74-1.50 (m, 2H), 0.97 (dd, J=11.5, 6.8, 6H); MS (ESI+) m/z 384 (M+H)$^+$.

Example 748

(3aR,4S,6aS)-N-[(5-fluoro-1-methyl-1H-indol-2-yl)methyl]-2-[6-(trifluoromethyl)pyridin-2-yl]octahydrocyclopenta[c]pyrrol-4-amine The title compound was prepared by substituting 5-fluoro-1-methyl-1H-indole-2-carbaldehyde for acetone in the procedure described in Example 609: $^1$H NMR (500 MHz, methanol-d$_4$) δ ppm 7.74-7.66 (m, 2H), 7.58 (dd, J=11.9, 4.0 Hz, 1H), 7.36 (s, 1H), 7.13-7.05 (m, 2H), 6.89 (d, J=7.3 Hz, 1H), 6.65 (d, J=8.6 Hz, 1H), 4.09-3.99 (m, 2H), 3.62 (dd, J=11.2, 8.3 Hz, 1H), 3.56-3.48 (m, 2H), 3.40-3.33 (m, 3H), 3.16 (dd, J=12.1, 6.6 Hz, 1H), 2.96 (pd, J=7.9, 4.0 Hz, 1H), 2.68 (td, J=9.0, 4.7 Hz, 1H), 2.22-2.09 (m, 2H), 1.71-1.59 (m, 1H), 1.58-1.48 (m, 1H); MS (ESI+) m/z 432 (M+H)$^+$.

Example 749

N$^2$-methyl-N-{(3aR,4S,6aS)-2-[4-(trifluoromethyl)phenyl]octahydrocyclopenta[c]pyrrol-4-yl}-L-serinamide The title compound was prepared by substituting N-(tert-butoxycarbonyl)-N-methyl-L-serine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.30 (d, J=7.7, 1H), 7.56 (s, 2H), 6.71 (d, J=5.6, 1H), 6.60 (d, J=8.7, 2H), 4.41-4.34 (m, 1H), 4.29 (dd, J=10.4, 5.2, 1H), 4.21-4.14 (m, 1H), 3.56-3.48 (m, 2H), 3.32 (dd, J=9.9, 7.8, 1H), 3.20 (dd, J=9.8, 7.8, 1H), 3.00 (dd, J=10.0, 3.4, 1H), 2.74-2.64 (m, 2H), 2.50 (s, 3H), 2.7-2.4 (br m, 1H), 2.10-2.01 (m, 1H), 1.97-1.88 (m, 1H), 1.68-1.59 (m, 1H), 1.41-1.28 (m, 1H); MS (ESI+) m/z 372 (M+H)$^+$.

Example 750

N$^2$-methyl-N-{(3aR,4S,6aS)-2-[4-(trifluoromethyl)phenyl]octahydrocyclopenta[c]pyrrol-4-yl}-L-allothreoninamide The title compound was prepared by substituting N-(tert-butoxycarbonyl)-N-methyl-L-allothreonine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.38 (d, J=7.4, 1H), 7.57 (d, J=4.6, 2H), 6.62 (d, J=8.7, 2H), 6.35 (d, J=4.6, 1H), 4.42-4.30 (m, 2H), 3.54 (dd, J=10.1, 2.7, 1H), 3.37 (dd, J=9.9, 7.7, 1H), 3.22 (t, J=8.6, 2H), 3.01 (dd, J=9.9, 3.3, 1H), 2.71 (s, 2H), 2.7-2.6 (br m, 1H), 2.50 (s, 3H), 2.07 (td, J=12.4, 6.9, 1H), 1.93 (td, J=13.2, 8.0, 1H), 1.65 (dq, J=12.7, 7.9, 1H), 1.56 (d, J=6.3, 3H), 1.36 (dtd, J=13.2, 8.0, 5.1, 1H); MS (ESI+) m/z 386 (M+H)$^+$.

Example 751

N-{(3aR,4S,6aS)-2-[4-(trifluoromethyl)phenyl]octahydrocyclopenta[c]pyrrol-4-yl}glycinamide The title compound was prepared by substituting N-(tert-butoxycarbonyl)-L-glycine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.27 (d, J=6.9, 1H), 7.58 (d, J=8.7, 2H), 6.61 (d, J=8.7, 2H), 4.39-4.29 (m, 1H), 3.57 (s, 2H), 3.51 (dd, J=10.2, 3.4, 1H), 3.30 (dd, J=10.0, 7.9, 1H), 3.20 (dd, J=9.6, 8.4, 1H), 3.00 (dd, J=9.9, 4.2, 1H), 2.69 (ddd, J=16.0, 8.3, 4.3, 1H), 2.66-2.59 (m, 1H), 2.51-2.17 (bs, 2H), 2.11-2.01 (m, 1H), 1.91 (dtd, J=13.0, 7.9, 5.0, 1H), 1.61 (dq, J=12.6, 8.0, 1H), 1.41-1.29 (m, 1H); MS (ESI+) m/z 328 (M+H)$^+$.

Example 752

N$^2$-methyl-N-{(3aR,4S,6aS)-2-[4-(trifluoromethyl)phenyl]octahydrocyclopenta[c]pyrrol-4-yl}glycinamide The title compound was prepared by substituting N-(tert-butoxycarbonyl)-N-methyl-L-glycine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-$d_5$) δ ppm 8.11 (d, J=7.3, 1H), 7.57 (d, J=8.6, 2H), 6.61 (d, J=8.7, 2H), 4.42-4.27 (m, 1H), 3.51 (dd, J=10.2, 3.3, 1H), 3.42 (d, J=1.0, 2H), 3.32 (dd, J=10.1, 7.8, 1H), 3.21 (dd, J=9.8, 8.1, 1H), 3.00 (dd, J=9.9, 4.1, 1H), 2.74-2.60 (m, 2H), 2.45-2.35 (bs, 1H), 2.40 (s, 3H), 2.08 (ddd, J=19.2, 7.0, 5.1, 1H), 1.92 (dtd, J=12.9, 7.9, 5.0, 1H), 1.62 (ddd, J=16.0, 12.6, 7.9, 1H), 1.42-1.27 (m, 1H); MS (ESI+) m/z 342 (M+H)$^+$.

Example 753

N$^2$-methyl-N-{(3aR,4S,6aS)-2-[4-(trifluoromethyl)phenyl]octahydrocyclopenta[c]pyrrol-4-yl}-L-alaninamide The title compound was prepared by substituting N-(tert-butoxycarbonyl)-N-methyl-L-alanine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-$d_5$) δ ppm 8.16 (d, J=7.4, 1H), 7.57 (d, J=8.6, 2H), 6.62 (d, J=8.7, 2H), 4.36 (dd, J=13.0, 6.9, 1H), 3.53 (dd, J=10.2, 3.4, 1H), 3.39-3.33 (m, 1H), 3.29 (q, J=6.9, 1H), 3.22 (dd, J=9.7, 8.1, 1H), 3.01 (dd, J=9.9, 4.0, 1H), 2.77-2.63 (m, 2H), 2.42 (s, 3H), 2.20-2.13 (bs, 1H), 2.12-2.03 (m, 1H), 1.99-1.86 (m, 1H), 1.64 (dq, J=12.7, 7.9, 1H), 1.41 (d, J=6.8, 3H), 1.39-1.32 (m, 1H); MS (ESI+) m/z 356 (M+H)$^+$.

Example 754

N$^2$,2-dimethyl-N-{(3aR,4S,6aS)-2-[4-(trifluoromethyl)phenyl]octahydrocyclopenta[c]pyrrol-4-yl}alaninamide The title compound was prepared by substituting N-(tert-butoxycarbonyl)-N,2-dimethyl-L-alanine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-$d_5$) δ ppm 7.95 (d, J=7.5, 1H), 7.57 (d, J=8.7, 2H), 6.61 (d, J=8.7, 2H), 4.33-4.21 (m, 1H), 3.50 (dd, J=10.2, 3.6, 1H), 3.33 (dd, J=10.1, 8.0, 1H), 3.21 (dd, J=9.7, 8.3, 1H), 3.00 (dd, J=9.9, 4.2, 1H), 2.75-2.65 (m, 1H), 2.65-2.55 (m, 1H), 2.32 (s, 3H), 2.06 (ddd, J=19.3, 7.0, 5.1, 1H), 2.04-1.96 (bs, 1H), 1.98-1.85 (m, 1H), 1.65-1.53 (m, 1H), 1.44 (s, 3H), 1.42 (s, 3H), 1.40-1.30 (m, 1H); MS (ESI+) m/z 370 (M+H)$^+$.

Example 755

(2S)-2-amino-N-{(3aR,4S,6aS)-2-[4-(trifluoromethyl)phenyl]octahydrocyclopenta[c]pyrrol-4-yl}butanamide The title compound was prepared by substituting (S)-N-(tert-butoxycarbonyl)-2-aminobutyric acid for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-$d_5$) δ ppm 8.33 (d, J=7.1, 1H), 7.57 (d, J=8.7, 2H), 6.61 (d, J=8.7, 2H), 4.38-4.30 (m, 1H), 3.52 (ddd, J=12.9, 8.7, 4.2, 2H), 3.32 (dd, J=10.1, 7.9, 1H), 3.21 (dd, J=9.7, 8.1, 1H), 3.00 (dd, J=9.9, 4.1, 1H), 2.75-2.61 (m, 2H), 2.34-2.10 (m, 2H), 2.11-1.96 (m, 2H), 1.92 (dtd, J=13.1, 7.9, 5.1, 1H), 1.81-1.71 (m, 1H), 1.62 (dq, J=12.7, 7.9, 1H), 1.40-1.30 (m, 1H), 1.03 (t, J=7.4, 3H); MS (ESI+) m/z 356 (M+H)$^+$.

Example 756

N$^2$-methyl-N-{(3aR,4S,6aS)-2-[4-(trifluoromethoxy)phenyl]octahydrocyclopenta[c]pyrrol-4-yl}-L-valinamide The title compound was prepared by substituting 1-bromo-4-(trifluoromethoxy)benzene for 1-bromo-2-fluorobenzene and tert-butyl methyl{(2S)-3-methyl-1-[(3aR,4S,6aS)-octahydrocyclopenta[c]pyrrol-4-ylamino]-1-oxobutan-2-yl}carbamate from Example 733 for tert-butyl methyl((S)-4-methyl-1-((3aR,4S,6aS)-octahydrocyclopenta[c]pyrrol-4-ylamino)-1-oxopentan-2-yl)carbamate in the procedure described in Example 619: $^1$H NMR (500 MHz, pyridine-$d_5$) δ ppm 8.29 (d, J=7.4, 1H), 7.22 (d, J=8.9, 2H), 6.61 (d, J=9.1, 2H), 4.47-4.37 (m, 1H), 3.54 (dd, J=9.8, 2.8, 1H), 3.30 (dd, J=9.7, 7.6, 1H), 3.19-3.11 (m, 1H), 3.01 (dd, J=9.6, 3.4, 1H), 2.95 (d, J=5.8, 1H), 2.78-2.67 (m, 2H), 2.45 (s, 3H), 2.20-1.91 (m, 4H), 1.67 (ddd, J=15.9, 12.5, 7.7, 1H), 1.44-1.34 (m, 1H), 1.09 (dd, J=6.8, 1.0, 6H); MS (ESI+) m/z 400 (M+H)$^+$.

Example 757

N$^2$-methyl-N-{(3aR,4S,6aS)-2-[3-(trifluoromethyl)phenyl]octahydrocyclopenta[c]pyrrol-4-yl}-L-valinamide The title compound was prepared by substituting 1-bromo-3-(trifluoromethyl)benzene for 1-bromo-2-fluorobenzene and tert-butyl methyl{(2S)-3-methyl-1-[(3aR,4S,6aS)-octahydrocyclopenta[c]pyrrol-4-ylamino]-1-oxobutan-2-yl}carbamate from Example 733 for tert-butyl methyl((S)-4-methyl-1-((3aR,4S,6aS)-octahydrocyclopenta[c]pyrrol-4-ylamino)-1-oxopentan-2-yl)carbamate in the procedure described in Example 619 Steps 2 and 3: $^1$H NMR (500 MHz, pyridine-$d_5$) δ ppm 8.33-8.27 (m, 1H), 7.34 (t, J=7.9, 1H), 7.07 (d, J=7.6, 1H), 6.95 (bs, 1H), 6.79 (dd, J=8.3, 2.4, 1H), 4.47-4.39 (m, 1H), 3.54 (dd, J=9.8, 2.8, 1H), 3.35 (dd, J=9.8, 7.4, 1H), 3.17 (dd, J=9.6, 7.4, 1H), 3.01 (dd, J=9.7, 3.2, 1H), 2.95 (d, J=5.8, 1H), 2.77-2.71 (m, 2H), 2.45 (s, 2H), 2.20-1.93 (m, 3H), 1.69 (dq, J=12.6, 7.8, 1H), 1.47-1.36 (m, 1H), 1.12-1.01 (m, 6H); MS (ESI+) m/z 384 (M+H)$^+$.

Example 758

N$^2$-methyl-N-{(3aR,4S,6aS)-2-[3-(trifluoromethoxy)phenyl]octahydrocyclopenta[c]pyrrol-4-yl}-L-valinamide The title compound was prepared by substituting 1-bromo-3-(trifluoromethoxy)benzene for 1-bromo-2-fluorobenzene and tert-butyl methyl{(2S)-3-methyl-1-[(3aR,4S,6aS)-octahydrocyclopenta[c]pyrrol-4-ylamino]-1-oxobutan-2-yl}carbamate from Example 733 for tert-butyl methyl((S)-4-methyl-1-((3aR,4S,6aS)-octahydrocyclopenta[c]pyrrol-4-ylamino)-1-oxopentan-2-yl)carbamate in the procedure described in Example 619 Steps 2 and 3: $^1$H NMR (500 MHz, pyridine-d$_5$) δ ppm 8.29 (d, J=7.4, 1H), 7.25 (t, J=8.2, 1H), 6.70 (dd, J=8.0, 0.9, 1H), 6.63-6.54 (m, 2H), 4.41 (dd, J=6.6, 5.1, 1H), 3.53 (dd, J=9.9, 2.9, 1H), 3.34 (dd, J=9.8, 7.7, 1H), 3.17 (dd, J=9.6, 7.9, 1H), 3.00 (dd, J=9.7, 3.4, 1H), 2.94 (d, J=5.8, 1H), 2.72 (dd, J=9.3, 7.3, 2H), 2.44 (s, 3H), 2.22-1.89 (m, 4H), 1.73-1.62 (m, 1H), 1.44-1.34 (m, 1H), 1.08 (dd, J=6.8, 1.4, 6H); MS (ESI+) m/z 400 (M+H)$^+$.

Example 759

N$^2$-methyl-N-{(3aR,4S,6aS)-2-[4-(trifluoromethyl)phenyl]octahydrocyclopenta[c]pyrrol-4-yl}-L-norvalinamide The title compound was prepared by substituting (S)-N-(tert-butoxycarbonyl)-N-methyl-L-norvaline for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.27 (d, J=7.4, 1H), 7.58 (d, J=8.3, 2H), 6.63 (d, J=8.7, 2H), 4.40 (dd, J=6.7, 5.4, 1H), 3.55 (dd, J=10.2, 3.1, 1H), 3.38 (dd, J=10.0, 7.6, 1H), 3.22 (ddd, J=10.5, 8.4, 7.0, 2H), 3.02 (dd, J=9.9, 3.7, 1H), 2.78-2.66 (m, 2H), 2.45 (s, 3H), 2.21-2.01 (m, 2H), 1.95 (ddd, J=12.9, 7.9, 2.7, 1H), 1.88-1.79 (m, 1H), 1.77-1.63 (m, 2H), 1.58-1.46 (m, 2H), 1.42-1.32 (m, 1H), 0.87 (t, J=7.4, 3H); MS (ESI+) m/z 384 (M+H)$^+$.

Example 760

N$^2$-methyl-N-{(3aR,4S,6aS)-2-[4-(trifluoromethyl)phenyl]octahydrocyclopenta[c]pyrrol-4-yl}-D-leucinamide The title compound was prepared by substituting (S)-N-(tert-butoxycarbonyl)-N-methyl-D-leucine for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-d$_5$) δ ppm 8.36 (d, J=7.4, 1H), 7.57 (d, J=8.6, 2H), 6.63 (d, J=8.7, 2H), 4.46-4.37 (m, 1H), 3.56 (dd, J=10.1, 3.0, 1H), 3.38 (dd, J=10.0, 7.6, 1H), 3.30-3.19 (m, 2H), 3.02 (dd, J=9.9, 3.7, 1H), 2.73 (ddd, J=13.1, 8.2, 6.7, 2H), 2.46 (s, 3H), 2.18-2.09 (m, 1H), 2.11-2.01 (m, 1H), 2.00-1.87 (m, 2H), 1.80-1.58 (m, 3H), 1.39 (dtd, J=13.2, 8.0, 5.2, 1H), 0.94 (d, J=6.6, 3H), 0.88 (d, J=6.6, 3H); MS (ESI+) m/z 398 (M+H)$^+$.

Example 761

N$^2$-isopropyl-N-{(3aR,4S,6aS)-2-[4-(trifluoromethyl)phenyl]octahydrocyclopenta[c]pyrrol-4-yl}glycinamide The title compound was prepared by substituting N-{(3aR,4S,6aS)-2-[4-(trifluoromethyl)phenyl]octahydrocyclopenta[c]pyrrol-4-yl}glycinamide from Example 751 for (3aR,4S,6aS)-2-(6-(trifluoromethyl)pyridin-2-yl)octahydrocyclopenta[c]pyrrol-4-amine in the procedure described in Example 609: $^1$H NMR (500 MHz, pyridine-d$_5$) δ ppm 8.15 (d, J=7.5, 1H), 7.57 (d, J=8.6, 2H), 6.61 (d, J=8.7, 2H), 4.40-4.31 (m, 1H), 3.51 (dt, J=5.4, 2.7, 1H), 3.46 (d, J=0.7, 2H), 3.31 (dd, J=10.1, 7.9, 1H), 3.21 (dd, J=9.7, 8.2, 1H), 3.01 (dd, J=9.9, 4.2, 1H), 2.76 (dt, J=12.5, 6.3, 1H), 2.73-2.59 (m, 2H), 2.44-2.28 (bs, 1H), 2.07 (ddd, J=19.3, 7.0, 5.2, 1H), 1.92 (dtd, J=13.1, 7.9, 5.0, 1H), 1.62 (dq, J=12.6, 8.0, 1H), 1.41-1.30 (m, 1H), 1.03 (d, J=3.8, 3H), 1.02 (d, J=3.8, 3H); MS (ESI+) m/z 370 (M+H)$^+$.

Example 762

(2S)-2-(isopropylamino)-N-{(3aR,4S,6aS)-2-[4-(trifluoromethyl)phenyl]octahydrocyclopenta[c]pyrrol-4-yl}butanamide The title compound was prepared by substituting (2S)-2-amino-N-{(3aR,4S,6aS)-2-[4-(trifluoromethyl)phenyl]octahydrocyclopenta[c]pyrrol-4-yl}butanamide from Example 755 for (3aR,4S,6aS)-2-(6-(trifluoromethyl)pyridin-2-yl)octahydrocyclopenta[c]pyrrol-4-amine in the procedure described in Example 609: $^1$H NMR (500 MHz, pyridine-d$_5$) δ ppm 8.34 (d, J=7.3, 1H), 7.58 (d, J=8.7, 2H), 6.64 (d, J=8.7, 2H), 4.42-4.34 (m, 1H), 3.53 (dd, J=10.1, 3.2, 1H), 3.39 (dd, J=10.0, 7.7, 1H), 3.30 (t, J=6.4, 1H), 3.24 (dd, J=9.7, 7.9, 1H), 3.03 (dd, J=9.9, 3.7, 1H), 2.87 (hept, J=6.2, 1H), 2.78-2.67 (m, 2H), 2.10 (td, J=12.6, 6.9, 1H), 2.05-1.84 (m, 3H), 1.80-1.72 (m, 1H), 1.71-1.61 (m, 1H), 1.39 (dtd, J=13.2, 7.8, 5.2, 1H), 1.09 (d, J=6.3, 3H), 1.06-1.02 (m, 6H); MS (ESI+) m/z 398 (M+H)$^+$.

Example 763

N$^2$-methyl-N-{(3aR,4S,6aS)-2-[5-(trifluoromethyl)pyridin-2-yl]octahydrocyclopenta[c]pyrrol-4-yl}-L-valinamide The title compound was prepared by substituting tert-butyl methyl{(2S)-3-methyl-1-[(3aR,4S,6aS)-octahydrocyclopenta[c]pyrrol-4-ylamino]-1-oxobutan-2-yl}carbamate from Example 733 for (2S,4S)-tert-butyl 4-fluoro-2-((3aR,4S,6aS)-octahydrocyclopenta[c]pyrrol-4-ylcarbamoyl)pyrrolidine-1-carboxylate and 2-bromo-5-(trifluoromethyl)pyridine for 2-bromo-4-(trifluoromethyl)pyridine in the procedure described in Example 637: $^1$H NMR (500 MHz, pyridine-d$_5$) δ ppm 8.63 (dd, J=1.6, 0.8, 1H), 8.31 (d, J=7.5, 1H), 7.67 (dt, J=19.9, 10.0, 1H), 6.40 (d, J=8.9, 1H), 4.50-4.37 (m, 1H), 3.83 (d, J=10.4, 1H), 3.72-3.63 (m, 1H), 3.61-3.51 (m, 1H), 3.33 (dt, J=8.4, 1H), 2.94 (d, J=5.8, 1H), 2.81-2.67 (m, 2H), 2.43 (s, 3H), 2.23-1.87 (m, 4H), 1.69 (dq, J=12.7, 8.2, 1H), 1.41 (dtd, J=13.2, 8.0, 5.0, 1H), 1.08 (dd, J=6.9, 2.1, 6H); MS (ESI+) m/z 385 (M+H)$^+$.

Example 764

N$^2$-methyl-N-{(3aR,4S,6aS)-2-[6-(trifluoromethyl)pyridin-2-yl]octahydrocyclopenta[c]pyrrol-4-yl}-L-valinamide The title compound was prepared by substituting tert-butyl methyl{(2S)-3-methyl-1-[(3aR,4S,6aS)-octahydrocyclopenta[c]pyrrol-4-ylamino]-1-oxobutan-2-yl}carbamate from Example 733 for (2S,4S)-tert-butyl 4-fluoro-2-((3aR,4S,6aS)-octahydrocyclopenta[c]pyrrol-4-ylcarbamoyl)pyrrolidine-1-carboxylate and 2-bromo-6-(trifluoromethyl)pyridine for 2-bromo-4-(trifluoromethyl)pyridine in the procedure described in Example 637: $^1$H NMR (500 MHz, pyridine-d$_5$) δ ppm 8.28 (d, J=7.4, 1H), 7.53-7.46 (m, 1H), 6.98 (t, J=6.4, 1H), 6.52 (d, J=8.6, 1H), 4.47-4.36 (m, 1H), 3.72 (dd, J=10.9, 2.9, 1H), 3.65-3.58 (m, 1H), 3.53 (dd, J=10.8, 8.0, 1H), 3.29

(dd, J=11.0, 3.6, 1H), 2.93 (d, J=5.8, 1H), 2.73 (t, J=5.7, 2H), 2.42 (s, 3H), 2.18-2.09 (m, 2H), 1.97-1.88 (m, 1H), 1.67 (dq, J=12.8, 8.0, 1H), 1.38 (dtd, J=12.9, 7.9, 4.9, 1H), 1.07 (dd, J=6.8, 2.2, 6H); MS (ESI+) m/z 385 (M+H)$^+$.

Example 765

N$^2$-methyl-N-{(3aR,4S,6aS)-2-[4-(trifluoromethyl)pyridin-3-yl]octahydrocyclopenta[c]pyrrol-4-yl}-L-leucinamide The title compound was prepared by substituting 3-bromo-4-(trifluoromethyl)pyridine for 1-bromo-2-fluorobenzene in the procedure described in Example 619: $^1$H NMR (500 MHz, pyridine-d$_5$) δ ppm 8.66 (s, 1H), 8.44 (d, J=4.9, 1H), 8.31 (d, J=7.3, 1H), 7.44 (d, J=5.0, 1H), 4.50-4.42 (m, 1H), 3.65-3.59 (m, 1H), 3.27 (ddd, J=14.1, 8.8, 6.3, 2H), 3.10 (d, J=4.0, 2H), 2.74-2.62 (m, 2H), 2.45 (s, 3H), 2.16 (dt, J=11.9, 6.4, 1H), 2.11-1.97 (m, 1H), 2.00-1.87 (m, 2H), 1.74 (ddd, J=13.6, 7.8, 5.9, 1H), 1.69-1.56 (m, 2H), 1.55-1.47 (m, 1H), 0.93 (d, J=6.6, 3H), 0.87 (d, J=6.6, 3H); MS (ESI+) m/z 399 (M+H)$^+$.

Example 766

N-{(3aR,4S,6aS)-2-[3-bromo-5-(trifluoromethyl)pyridin-2-yl]octahydrocyclopenta[c]pyrrol-4-yl}-N$^2$-methyl-L-leucinamide The title compound was prepared by substituting 3-bromo-2-fluoro-5-(trifluoromethyl)pyridine for 1-bromo-2-fluorobenzene in the procedure described in Example 619: $^1$H NMR (500 MHz, pyridine-d$_5$) δ ppm 8.48 (dd, J=2.0, 0.9, 1H), 8.36 (d, J=7.5, 1H), 8.08 (d, J=2.1, 1H), 4.54-4.47 (m, 1H), 4.19 (dd, J=11.5, 2.6, 1H), 3.87 (dd, J=11.4, 7.2, 1H), 3.77-3.68 (m, 2H), 3.26 (dd, J=8.2, 5.9, 1H), 2.72 (pt, J=8.9, 4.4, 2H), 2.45 (s, 3H), 2.21 (tt, J=12.4, 6.1, 1H), 2.16-2.00 (m, 1H), 2.01-1.87 (m, 2H), 1.77-1.66 (m, 2H), 1.60 (ddd, J=13.7, 8.2, 6.4, 1H), 1.49 (dtd, J=13.2, 8.0, 5.0, 1H), 0.93 (d, J=6.6, 3H), 0.87 (d, J=6.6, 3H); MS (ESI+) m/z 479 (M+H)$^+$.

Example 767

N$^2$-methyl-N-{(3aR,4S,6aS)-2-[2-(trifluoromethyl)pyridin-3-yl]octahydrocyclopenta[c]pyrrol-4-yl}-L-leucinamide The title compound was prepared by substituting 3-bromo-2-(trifluoromethyl)pyridine for 1-bromo-2-fluorobenzene in the procedure described in Example 619: $^1$H NMR (500 MHz, pyridine-d$_5$) δ ppm 8.34 (d, J=3.2, 1H), 8.30 (d, J=7.3, 1H), 7.45 (d, J=7.9, 1H), 7.32 (dd, J=8.4, 4.3, 1H), 4.53-4.44 (m, 1H), 3.55 (dd, J=9.6, 1.6, 1H), 3.25 (dd, J=8.2, 5.9, 1H), 3.18 (dd, J=9.5, 6.8, 1H), 3.07 (dd, J=9.4, 2.0, 1H), 2.99 (dd, J=9.3, 6.7, 1H), 2.75-2.65 (m, 2H), 2.45 (s, 3H), 2.17 (td, J=11.9, 6.2, 1H), 2.09-1.97 (m, 1H), 2.02-1.87 (m, 2H), 1.74 (ddd, J=13.7, 7.8, 6.0, 1H), 1.70-1.51 (m, 3H), 0.94 (d, J=6.6, 3H), 0.87 (d, J=6.6, 3H); MS (ESI+) m/z 399 (M+H)$^+$.

Example 768

N$^2$-methyl-N-{(3aS,4R,6aR)-2-[4-(trifluoromethyl)phenyl]octahydrocyclopenta[c]pyrrol-4-yl}-D-leucinamide Step 1: tert-Butyl(R)-1-((3aS,4R,6aR)-2-Benzyloctahydrocyclopenta[c]pyrrol-4-ylamino)-4-methyl-1-oxopentan-2-yl(methyl)carbamate was prepared by substituting N-(tert-butoxycarbonyl)-N-methyl-D-leucine for N-(tert-butoxycarbonyl)-L-leucine and (3aS,4R,6aR)-2-benzyloctahydrocyclopenta[c]pyrrol-4-amine from Example 16 Steps A-E for (3aR,4S,6aR)-2-benzyloctahydrocyclopenta[c]pyrrol-4-amine in the procedure described in Example 221: $^1$H NMR (500 MHz, pyridine-d$_5$) δ ppm 8.27 (d, J=5.9 Hz, 1H), 7.45-7.40 (m, 2H), 7.38-7.32 (m, 2H), 7.27 (dd, J=10.3, 4.3 Hz, 1H), 4.45-4.33 (m, 1H), 3.59 (d, J=13.1 Hz, 1H), 3.44 (d, J=13.2 Hz, 1H), 3.07 (d, J=23.2 Hz, 3H), 2.86-2.80 (m, 1H), 2.54-2.37 (m, 3H), 2.32 (d, J=8.6 Hz, 1H), 2.27-2.18 (m, 1H), 2.13-1.98 (m, 1H), 1.94-1.86 (m, 1H), 1.88-1.71 (m, 3H), 1.57 (td, J=13.4, 6.6 Hz, 2H), 1.48 (d, J=8.9 Hz, 9H), 1.40-1.31 (m, 1H), 0.86 (dd, J=19.8, 6.5 Hz, 6H); MS (ESI+) m/z 444 (M+H)$^+$.

Step 2: The title compound was prepared by substituting 1-bromo-4-(trifluoromethyl)benzene for 1-bromo-2-fluorobenzene and tert-butyl(R)-1-((3aS,4R,6aR)-2-benzyloctahydrocyclopenta[c]pyrrol-4-ylamino)-4-methyl-1-oxopentan-2-yl(methyl)carbamate from Step 1 for tert-butyl(S)-1-((3aR,4S,6aS)-2-benzyloctahydrocyclopenta[c]pyrrol-4-ylamino)-4-methyl-1-oxopentan-2-yl(methyl)carbamate in the procedure described in Example 619: $^1$H NMR (500 MHz, pyridine-d$_5$) δ ppm 8.34 (d, J=7.4, 1H), 7.57 (s, 2H), 6.63 (d, J=8.7, 2H), 4.44-4.37 (m, 1H), 3.56 (dd, J=10.2, 2.9, 1H), 3.39 (dd, J=10.0, 7.6, 1H), 3.29-3.21 (m, 2H), 3.03 (dd, J=9.9, 3.5, 1H), 2.79-2.69 (m, 2H), 2.46 (s, 3H), 2.12 (dt, J=12.5, 7.0, 1H), 2.09-2.00 (m, 1H), 2.00-1.88 (m, 2H), 1.78-1.66 (m, 2H), 1.66-1.58 (m, 1H), 1.39 (dtd, J=13.1, 8.0, 5.1, 1H), 0.94 (d, J=6.6, 3H), 0.88 (d, J=6.6, 3H); MS (ESI+) m/z 398 (M+H)$^+$.

Example 769

N-{(3aR,4S,6aS)-2-[3-(difluoromethyl)-4-fluorophenyl]octahydrocyclopenta[c]pyrrol-4-yl}-N$^2$-methyl-L-leucinamide The title compound was prepared by substituting 4-bromo-2-(difluoromethyl)-1-fluorobenzene for 1-bromo-2-fluorobenzene in the procedure described in Example 619: $^1$H NMR (500 MHz, pyridine-d$_5$) δ ppm 8.32 (d, J=7.4, 1H), 7.26 (t, J=55.0, 1H), 7.12 (t, J=9.5, 1H), 6.91 (dd, J=5.5, 3.0, 1H), 6.71-6.65 (m, 1H), 4.46-4.37 (m, 1H), 3.53 (dd, J=9.7, 2.7, 1H), 3.31-3.23 (m, 2H), 3.14-3.06 (m, 1H), 2.98 (dd, J=9.5, 3.1, 1H), 2.79-2.67 (m, 2H), 2.46 (s, 3H), 2.14-2.08 (m, 1H), 2.08-1.98 (m, 1H), 2.01-1.87 (m, 2H), 1.78-1.57 (m, 3H), 1.47-1.36 (m, 1H), 0.94 (d, J=6.6, 3H), 0.88 (d, J=6.6, 3H); MS (ESI+) m/z 398 (M+H)$^+$.

Example 770

N-{(3aR,4S,6aS)-2-[2-(difluoromethyl)-5-fluorophenyl]octahydrocyclopenta[c]pyrrol-4-yl}-N$^2$-methyl-L-leucinamide The title compound was prepared by substituting 2-bromo-1-(difluoromethyl)-4-fluorobenzene for 1-bromo-2-fluorobenzene in the procedure described in Example 619: 1H NMR (500 MHz, pyridine-d$_5$) δ ppm 8.31 (d, J=7.7, 1H), 7.54 (dd, J=9.0, 3.0, 1H), 7.49 (td, J=55.0, 1.2, 1H), 7.19 (d, J=3.0, 1H), 7.14 (dd, J=8.9, 4.9, 1H), 4.51 (ddd, J=14.4, 8.5, 6.1, 1H), 3.42 (dd, J=9.3, 1.8, 1H), 3.25 (dd, J=8.2, 5.9, 1H), 2.99 (dd, J=9.3, 6.8, 1H), 2.88 (dd, J=9.1, 7.1, 1H), 2.81 (dd, J=9.2, 2.1, 1H), 2.69-2.61 (m, 1H), 2.61-2.55 (m, 1H), 2.45 (s, 3H), 2.12-2.06 (m, 1H), 2.08-1.98 (m, 1H), 2.01-1.87 (m, 2H), 1.74 (ddd, J=13.7, 7.8, 5.9, 1H), 1.66-1.57 (m, 2H), 1.47 (ddt, J=13.0, 10.3, 6.5, 1H), 0.93 (d, J=6.6, 3H), 0.87 (d, J=6.6, 3H); MS (ESI+) m/z 398 (M+H)⁺.

Example 771

N-{(3aR,4S,6aS)-2-[2-(difluoromethyl)phenyl]octahydrocyclopenta[c]pyrrol-4-yl}-$N^2$-methyl-L-leucinamide The title compound was prepared by substituting 1-bromo-2-(difluoromethyl)benzene for 1-bromo-2-fluorobenzene in the procedure described in Example 619: $^1$H NMR (500 MHz, pyridine-$d_5$) δ ppm 8.30 (d, J=7.7, 1H), 7.79 (d, J=7.6, 1H), 7.53 (t, J=55.3, 1H), 7.43-7.38 (m, 1H), 7.18-7.10 (m, 2H), 4.52 (ddd, J=14.4, 8.3, 6.1, 1H), 3.49 (dd, J=9.4, 1.7, 1H), 3.25 (dd, J=8.2, 5.9, 1H), 3.04 (dd, J=9.4, 6.8, 1H), 2.94 (dd, J=9.2, 7.1, 1H), 2.87 (dd, J=9.3, 2.2, 1H), 2.69-2.55 (m, 2H), 2.44 (s, 3H), 2.09 (ddd, J=11.9, 10.5, 6.1, 1H), 2.06-1.98 (m, 1H), 2.00-1.86 (m, 2H), 1.74 (ddd, J=13.6, 7.8, 5.9, 1H), 1.67-1.57 (m, 2H), 1.52-1.42 (m, 1H), 0.93 (d, J=6.6, 3H), 0.87 (d, J=6.6, 3H); MS (ESI+) m/z 380 (M+H)⁺.

Example 772

N-{(3aR,4S,6aS)-2-[4-fluoro-3-(trifluoromethoxy)phenyl]octahydrocyclopenta[c]pyrrol-4-yl}-$N^2$-methyl-L-leucinamide The title compound was prepared by substituting 4-bromo-1-fluoro-2-(trifluoromethoxy)benzene for 1-bromo-2-fluorobenzene in the procedure described in Example 619: $^1$H NMR (500 MHz, pyridine-$d_5$) δ ppm 8.34 (d, J=7.3, 1H), 7.18 (dd, J=10.0, 9.2, 1H), 6.69-6.64 (m, 1H), 6.50 (dt, J=9.1, 3.3, 1H), 4.46-4.37 (m, 1H), 3.52 (dd, J=9.8, 2.7, 1H), 3.30-3.23 (m, 2H), 3.14-3.08 (m, 1H), 2.98 (dd, J=9.5, 3.2, 1H), 2.80-2.68 (m, 2H), 2.46 (s, 3H), 2.11 (dt, J=11.7, 6.4, 1H), 2.09-1.98 (m, 1H), 2.01-1.88 (m, 2H), 1.78-1.57 (m, 3H), 1.46-1.36 (m, 1H), 0.94 (d, J=6.6, 3H), 0.88 (d, J=6.6, 3H); MS (ESI+) m/z 432 (M+H)⁺.

Example 773

N-[(3aR,4S,6aS)-2-(3-chloro-4-fluorophenyl)octahydrocyclopenta[c]pyrrol-4-yl]-$N^2$-methyl-L-leucinamide The title compound was prepared by substituting 4-bromo-2-chloro-1-fluorobenzene for 1-bromo-2-fluorobenzene in the procedure described in Example 619: $^1$H NMR (400 MHz, pyridine-$d_5$) δ ppm 8.38 (d, J=7.8, 1H), 7.13 (t, J=9.0, 1H), 6.74 (dd, J=6.2, 2.9, 1H), 6.52-6.46 (m, 1H), 4.41 (tt, J=12.2, 6.0, 1H), 3.49 (dd, J=9.8, 2.7, 1H), 3.31-3.22 (m, 2H), 3.09 (dd, J=9.3, 7.8, 1H), 2.96 (dd, J=9.5, 3.1, 1H), 2.77-2.69 (m, 2H), 2.47 (s, 3H), 2.17-2.07 (m, 1H), 1.94 (dt, J=20.8, 6.8, 3H), 1.80-1.58 (m, 4H), 1.46-1.36 (m, 1H), 0.94 (d, J=6.6, 3H), 0.89 (d, J=6.6, 3H); MS (ESI+) m/z 382 (M+H)⁺.

Example 774

N-{(3aR,4S,6aS)-2-[2-fluoro-4-(trifluoromethoxy)phenyl]octahydrocyclopenta[c]pyrrol-4-yl}-$N^2$-methyl-L-leucinamide The title compound was prepared by substituting 1-bromo-2-fluoro-4-(trifluoromethoxy)benzene for 1-bromo-2-fluorobenzene in the procedure described in Example 619: $^1$H NMR (500 MHz, pyridine-$d_5$) δ ppm 8.40 (d, J=7.4, 1H), 7.17 (dd, J=13.2, 2.3, 1H), 7.03 (d, J=8.8, 1H), 6.74 (t, J=9.4, 1H), 4.48-4.42 (m, 1H), 3.64 (d, J=9.8, 1H), 3.29 (dt, J=9.5, 6.3, 2H), 3.18 (d, J=9.5, 1H), 3.14-3.09 (m, 1H), 2.75-2.65 (m, 2H), 2.47 (s, 3H), 2.18-2.08 (m, 1H), 2.10-1.92 (br m, 1H), 2.02-1.87 (m, 2H), 1.80-1.58 (m, 3H), 1.51-1.40 (m, 1H), 0.94 (d, J=6.6, 3H), 0.89 (d, J=6.6, 3H); MS (ESI+) m/z 432 (M+H)⁺.

Example 775

3-cyclopropyl-$N^2$-methyl-N-{(3aR,4S,6aS)-2-[4-(trifluoromethoxy)phenyl]octahydrocyclopenta[c]pyrrol-4-yl}-L-alaninamide The title compound was prepared by substituting 3-cyclopropyl-N-(tert-butoxycarbonyl)-N-methyl-L-alanine for (S)-2-(tert-butoxycarbonyl(methyl)amino)-4,4-dimethylpentanoic acid and (3aR,4S,6aS)-2-(4-(trifluoromethoxy)phenyl)octahydrocyclopenta[c]pyrrol-4-amine from Example 716 Step 1 for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-$d_5$) δ ppm 8.28 (d, J=7.6, 1H), 7.22 (s, 2H), 6.65-6.54 (m, 2H), 4.46-4.36 (m, 1H), 3.55 (dd, J=9.9, 2.7, 1H), 3.35-3.24 (m, 2H), 3.15 (dd, J=9.5, 7.8, 1H), 3.02 (dd, J=9.6, 3.3, 1H), 2.79-2.67 (m, 2H), 2.46 (d, J=9.2, 3H), 2.17-2.05 (m, 1H), 2.02-1.91 (m, 1H), 1.84 (dd, J=30.5, 23.8, 1H), 1.83-1.62 (m, 3H), 1.45-1.35 (m, 1H), 0.99-0.86 (m, 1H), 0.53-0.38 (m, 2H), 0.19-0.07 (m, 2H); MS (ESI+) m/z 412 (M+H)⁺.

Example 776

3-cyclopropyl-N-{(3aR,4S,6aS)-2-[4-(trifluoromethoxy)phenyl]octahydrocyclopenta[c]pyrrol-4-yl}-L-alaninamide The title compound was prepared by substituting 3-cyclopropyl-N-(tert-butoxycarbonyl)-L-alanine for (S)-2-(tert-butoxycarbonyl(methyl)amino)-4,4-dimethylpentanoic acid and (3aR,4S,6aS)-2-(4-(trifluoromethoxy)phenyl)octahydrocyclopenta[c]pyrrol-4-amine from Example 716 Step 1 for (3aR,4S,6aS)-2-(6-(trifluoromethyl)pyridin-2-yl)octahydrocyclopenta[c]pyrrol-4-amine in the procedure described in Example 587: $^1$H NMR (400 MHz, pyridine-$d_5$) δ ppm 8.33 (d, J=7.6, 1H), 7.20-7.18 (m, 2H), 6.62-6.54 (m, 2H), 4.40-4.32 (m, 1H), 3.71 (dd, J=7.4, 5.3, 1H), 3.52 (dd, J=9.9, 3.0, 1H), 3.24 (dd, J=9.8, 7.6, 1H), 3.13 (dd, J=9.6, 7.8, 1H), 3.00 (dd, J=9.6, 3.6, 1H), 2.77-2.60 (m, 2H), 2.33 (s, 2H), 2.08 (dt, J=12.2, 6.7, 1H), 1.99-1.83 (m, 2H), 1.73 (dt, J=13.9, 7.1, 1H), 1.63 (ddd, J=16.0, 12.4, 7.7, 1H), 1.37 (td, J=12.8, 7.1, 1H), 0.94 (dt, J=12.1, 4.9, 1H), 0.52-0.37 (m, 2H), 0.21-0.07 (m, 2H); MS (ESI+) m/z 398 (M+H)⁺.

Example 777

3-cyclopropyl-$N^2$,$N^2$-dimethyl-N-{(3aR,4S,6aS)-2-[4-(trifluoromethoxy)phenyl]octahydrocyclopenta[c]pyrrol-4-yl}-L-alaninamide The title compound was prepared by treating a solution of 3-cyclopropyl-N-{(3aR,4S,6aS)-2-[4-(trifluoromethoxy)phenyl]octahydrocyclopenta[c]pyrrol-4-yl}-L-alaninamide from Example 776 (31 mg, 0.078 mmol) in dichloromethane (1 mL) with formaldehyde (0.017 mL, 0.234 mmol), followed by addition of acetic acid (0.2 mL) and sodium cyanoborohydride (19.61 mg, 0.312 mmol). After 60 minutes, the reaction was quenched with 1 mL of saturated aqueous sodium bicarbonate, and the crude material was purified using a 12 g silica gel cartridge eluted with 1-10% methanol (2 N ammonia)/dichloromethane to give the title compound: $^1$H NMR (400 MHz, pyridine-$d_5$) δppm 8.22 (d, J=7.4, 1H), 7.20 (d, J=0.9, 2H), 6.64-6.57 (m, 2H), 4.45-4.35 (m, 1H), 3.55 (dd, J=9.9, 2.7, 1H), 3.29 (dd, J=9.7, 7.7, 1H), 3.17 (ddd, J=17.3, 9.0, 6.3, 2H), 3.01 (dd, J=9.6, 3.3, 1H), 2.79-2.66 (m, 2H), 2.35 (s, 6H), 2.16-2.06 (m, 1H), 1.98 (tdd, J=13.3, 7.2, 4.0, 2H), 1.70 (ddd, J=16.2, 12.4, 7.7, 1H), 1.51 (ddd, J=13.6, 7.5, 4.7, 1H), 1.40 (dddd, J=10.1, 8.5, 7.1, 5.3, 1H), 1.03-0.89 (m, 1H), 0.53-0.42 (m, 2H), 0.23-0.18 (m, 1H), 0.11-0.05 (m, 1H); MS (ESI+) m/z 426 (M+H)$^+$.

Example 778

1-tert-butyl-3-{(3aR,4S,6aS)-2-[4-(trifluoromethoxy)phenyl]octahydrocyclopenta[c]pyrrol-4-yl}urea The title compound was prepared by substituting 2-isocyanato-2-methylpropane for 1-fluoro-4-isocyanatobenzene and (3aR,4S,6aS)-2-(4-(trifluoromethoxy)phenyl)octahydrocyclopenta[c]pyrrol-4-amine from Example 716 Step 1 for (3aR,4S,6aS)-2-(6-(trifluoromethyl)pyridin-2-yl)octahydrocyclopenta[c]pyrrol-4-amine in the procedure described in Example 709: $^1$H NMR (500 MHz, pyridine-$d_5$) δ ppm 7.19 (d, J=9.0 Hz, 2H), 6.61-6.51 (m, 2H), 6.26 (d, J=7.1 Hz, 1H), 5.89 (s, 1H), 4.30-4.18 (m, 1H), 3.51 (dd, J=9.8, 3.2 Hz, 1H), 3.24 (dd, J=9.7, 7.8 Hz, 1H), 3.10 (dd, J=9.4, 7.8 Hz, 1H), 2.95 (dd, J=9.6, 3.5 Hz, 1H), 2.71-2.54 (m, 2H), 2.11-2.00 (m, 1H), 1.93-1.79 (m, 1H), 1.56-1.49 (m, 1H), 1.47 (s, 9H), 1.40-1.23 (m, 1H); MS (ESI+) m/z 386 (M+H)$^+$.

Example 779

1-tert-butyl-3-{(3aR,4S,6aS)-2-[3-(trifluoromethoxy)phenyl]octahydrocyclopenta[c]pyrrol-4-yl}urea The title compound was prepared by substituting 2-isocyanato-2-methylpropane for 1-fluoro-4-isocyanatobenzene and (3aR,4S,6aS)-2-(3-(trifluoromethoxy)phenyl)octahydrocyclopenta[c]pyrrol-4-amine from Example 715 Step 1 for (3aR,4S,6aS)-2-(6-(trifluoromethyl)pyridin-2-yl)octahydrocyclopenta[c]pyrrol-4-amine in the procedure described in Example 709: $^1$H NMR (500 MHz, pyridine-$d_5$) δ ppm 7.24 (d, J=8.2 Hz, 1H), 6.68 (dd, J=8.1, 0.9 Hz, 1H), 6.57-6.47 (m, 2H), 6.25 (d, J=7.1 Hz, 1H), 5.89 (s, 1H), 4.26-4.18 (m, 1H), 3.49 (dd, J=9.9, 3.2 Hz, 1H), 3.27 (dd, J=9.8, 7.8 Hz, 1H), 3.12 (dd, J=9.6, 7.8 Hz, 1H), 2.94 (dd, J=9.7, 3.4 Hz, 1H), 2.68-2.56 (m, 2H), 2.06 (td, J=12.6, 6.4 Hz, 1H), 1.85 (td, J=13.2, 7.7 Hz, 1H), 1.56-1.49 (m, 1H), 1.47 (s, 9H), 1.35-1.26 (m, 1H); MS (ESI+) m/z 386 (M+H)$^+$.

Example 780

(4R)-4-fluoro-N-{(3aR,4S,6aS)-2-[5-(trifluoromethyl)pyridin-2-yl]octahydrocyclopenta[c]pyrrol-4-yl}-L-prolinamide The title compound was prepared by substituting N-(tert-butoxycarbonyl)-trans-4-fluoro-L-proline for (S)-2-(tert-butoxycarbonyl(methyl)amino)-4,4-dimethylpentanoic acid and (3aR,4S,6aS)-2-(5-(trifluoromethyl)pyridin-2-yl)octahydrocyclopenta[c]pyrrol-4-amine from Example 262 Step B for (3aR,4S,6aS)-2-(6-(trifluoromethyl)pyridin-2-yl)octahydrocyclopenta[c]pyrrol-4-amine in the procedure described in Example 587: 1H NMR (500 MHz, pyridine-$d_5$) δ ppm 8.65-8.59 (m, 1H), 8.33 (d, J=7.5 Hz, 1H), 7.67 (dd, J=8.9, 2.5 Hz, 1H), 6.36 (d, J=8.9 Hz, 1H), 5.20 (dt, J=54.4, 3.5 Hz, 1H), 4.36-4.23 (m, 2H), 3.75 (d, J=8.4 Hz, 1H), 3.66-3.52 (m, 3H), 3.30 (dt, J=15.2, 7.6 Hz, 2H), 2.91 (dd, J=38.5, 11.2 Hz, 1H), 2.77-2.68 (m, 1H), 2.68-2.52 (m, 2H), 2.25 (dddd, J=39.3, 14.8, 7.9, 4.4 Hz, 1H), 2.11 (ddd, J=19.5, 7.2, 4.9 Hz, 1H), 1.92 (dtd, J=13.0, 8.1, 4.8 Hz, 1H), 1.62 (dq, J=12.7, 8.2 Hz, 1H), 1.39 (dtd, J=13.4, 7.9, 5.7 Hz, 1H); MS (ESI+) m/z 387 (M+H)$^+$.

Example 781

(4R)-4-fluoro-N-{(3aR,4S,6aS)-2-[4-(trifluoromethyl)phenyl]octahydrocyclopenta[c]pyrrol-4-yl}-L-prolinamide The title compound was prepared by substituting N-(tert-butoxycarbonyl)-trans-4-fluoro-L-proline for (S)-2-(tert-butoxycarbonyl(methyl)amino)-4,4-dimethylpentanoic acid and (3aR,4S,6aS)-2-[4-(trifluoromethyl)phenyl]octahydrocyclopenta[c]pyrrol-4-amine from Example 607 for (3aR,4S,6aS)-2-(6-(trifluoromethyl)pyridin-2-yl)octahydrocyclopenta[c]pyrrol-4-amine in the procedure described in Example 587: $^1$H NMR (500 MHz, pyridine-$d_5$) δ ppm 8.32 (d, J=7.5, 1H), 7.57 (d, J=7.7, 2H), 6.60 (d, J=8.7, 2H), 5.30-5.12 (m, 1H), 4.34-4.24 (m, 2H), 3.62 (s, 1H), 3.48 (dd, J=10.2, 3.5, 1H), 3.37-3.26 (m, 2H), 3.19 (dd, J=12.2, 5.8, 1H), 3.05-2.98 (m, 1H), 2.97-2.84 (m, 1H), 2.76-2.65 (m, 1H), 2.59 (dddd, J=14.7, 10.3, 8.4, 3.9, 2H), 2.26 (dddd, J=39.3, 14.8, 7.9, 4.4, 1H), 2.10-2.02 (m, 1H), 1.92 (dtd, J=13.0, 8.0, 5.0, 1H), 1.60 (dq, J=12.6, 8.0, 1H), 1.41-1.30 (m, 1H); MS (ESI+) m/z 386 (M+H)$^+$.

The following compounds are prepared using the synthetic methodologies described in the above examples:

(4S)-4-fluoro-N-{(3aR,4S,6aS)-2-[4-(trifluoromethyl)phenyl]octahydrocyclopenta[c]pyrrol-4-yl}-L-prolinamide;

(4S)-4-fluoro-N-{(3aR,4S,6aS)-2-[5-(trifluoromethyl)-2-thienyl]octahydrocyclopenta[c]pyrrol-4-yl}-L-prolinamide;

(4S)-4-fluoro-N-{(3aR,4S,6aS)-2-[2-(trifluoromethyl)-3-thienyl]octahydrocyclopenta[c]pyrrol-4-yl}-L-prolinamide;

N-[(3aR,4S,6aS)-2-(2-methoxyphenyl)octahydrocyclopenta[c]pyrrol-4-yl]-N$^2$-methyl-L-leucinamide;

N-[(3aR,4S,6aS)-2-(3-methoxyphenyl)octahydrocyclopenta[c]pyrrol-4-yl]-N$^2$-methyl-L-leucinamide;

N-[(3aR,4S,6aS)-2-(4-methoxyphenyl)octahydrocyclopenta[c]pyrrol-4-yl]-N$^2$-methyl-L-leucinamide;

N-[(3aR,4S,6aS)-2-(2-cyanophenyl)octahydrocyclopenta[c]pyrrol-4-yl]-N$^2$-methyl-L-leucinamide;

N$^2$-methyl-N-{(3aR,4S,6aS)-2-[5-(trifluoromethyl)-2-thienyl]octahydrocyclopenta[c]pyrrol-4-yl}-L-leucinamide;

N$^2$-methyl-N-{(3aR,4S,6aS)-2-[2-(trifluoromethyl)-3-thienyl]octahydrocyclopenta[c]pyrrol-4-yl}-L-leucinamide; and N-{(3aR,4S,6aS)-2-[5-(difluoromethyl)-3-thienyl]octahydrocyclopenta[c]pyrrol-4-yl}-N$^2$-methyl-L-leucinamide.

Many variations in the invention can suggest themselves to those skilled in the art in light of the foregoing detailed description. All such obvious variations are within the full intended scope of the appended claims.

We claim:
1. A compound of formula (I),

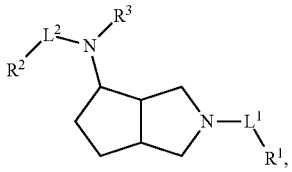

or a pharmaceutically acceptable salt thereof, wherein
$L^1$-$R^1$ taken together are $G^1$;
$L^2$ is —$(CR^cR^d)_p$—, C(O), C(O)N($R^4$), S(O)$_2$, SO$_2$N($R^5$), or C(O)O;
$R^2$ is alkyl, haloalkyl, hydroxyalkyl, $G^2$, -$G^2$-$G^3$, —C($R^c$)($G^2$)($G^3$), —CH(OH)CF$_3$, —$(CR^cR^d)_p$—CH(OH)CF$_3$, —$(CR^cR^d)_p$-$G^2$, —$(CR^cR^d)_p$—CH($G^2$)($G^3$), —$(CR^gR^h)_q$—N($R^5$)—C(O)O(alkyl), —$(CR^gR^h)_q$—N($R^5$)—C(O)O-$G^2$, —$(CR^gR^h)_q$—N($R^5$)—C(O)(alkyl), —$(CR^gR^h)_q$—N($R^5$)—SO$_2R^6$, —$(CR^gR^h)_q$—N($R^4$)($R^5$), —$(CR^gR^h)_q$—N($R^5$)—C(O)N($R^5$)-(alkyl), —$(CR^gR^h)_q$—N($R^5$)—C(O)N($R^5$)-$G^2$, or —C(O)N($R^4$)($R^5$); or
p, at each occurrence, is 1, 2, 3, 4, 5, or 6;
q, at each occurrence, is 1, 2, 3, 4, or 5;
$R^c$ and $R^d$, at each occurrence, are each independently hydrogen, alkyl, arylalkyl, halogen, haloalkyl or O$R^7$; or
$R^c$ and $R^d$, together with the carbon atom to which they are attached, optionally form a $C_{3-6}$ cycloalkyl ring;
$R^g$ and $R^h$, at each occurrence, are each independently hydrogen, alkyl, halogen, haloalkyl, hydroxyalkyl, O$R^7$, cycloalkylalkyl, heteroaryl, arylalkyl, or heteroarylalkyl; wherein the aryl, cycloalkyl and heteroaryl groups of aryl, cycloalkyl and heteroaryl are each independently unsubstituted or substituted with 1, 2, 3, 4, or 5 substituents independently selected from the group consisting of alkyl and haloalkyl;
$G^1$ is monocyclic aryl or monocyclic heteroaryl; wherein $G^1$ is unsubstituted or substituted with 1, 2, 3, 4, or 5 substituents selected from the group consisting of alkyl, alkenyl, alkynyl, cyano, haloalkyl, halogen, nitro, oxo, phenyl, N($R^7$)$_2$, N($R^7$)C(O)$R^7$, O$R^7$, C(O)$R^7$, C(O)O$R^7$, C(O)N($R^7$)$_2$, S$R^7$, SO$_2R^8$, and SO$_2$N($R^7$)$_2$;
$G^2$ and $G^3$ at each occurrence, are each independently aryl, cycloalkyl, cycloalkenyl, heteroaryl, or heterocycle; wherein $G^2$ and $G^3$ at each occurrence are each independently unsubstituted or substituted with 1, 2, 3, 4, or 5 substituents selected from the group consisting of alkyl, alkenyl, alkynyl, cyano, haloalkyl, halogen, nitro, oxo, phenyl, N($R^7$)$_2$, N($R^7$)C(O)$R^7$, O$R^7$, C(O)$R^7$, C(O)O$R^7$, C(O)N($R^7$)$_2$, S$R^7$, SO$_2R^8$, and SO$_2$N($R^7$)$_2$;
$R^3$ is hydrogen, alkyl, haloalkyl, cycloalkyl, or cycloalkylalkyl;
$R^4$, $R^5$, and $R^7$, at each occurrence, are each independently hydrogen, alkyl, aryl, arylalkyl, cycloalkyl, cycloalkylalkyl, or haloalkyl; wherein said aryl, the aryl of arylalkyl and cycloalkyl are independently unsubstituted or substituted with 1, 2 3, 4, or 5 substituents independently selected from the group consisting of alkyl, haloalkyl, and halogen; and
$R^6$ is alkyl, aryl, cycloalkyl, cycloalkenyl, heteroaryl, or heterocycle; wherein said aryl, heteroaryl, and heterocycle are independently unsubstituted or substituted with 1, 2 3, 4, or 5 substituents independently selected from the group consisting of alkyl, haloalkyl, and halogen;
$R^8$ is alkyl or haloalkyl.

2. The compound or salt according to claim 1, wherein
$G^1$ is monocyclic aryl;
$L^2$ is C(O);
$R^2$ is —$(CR^cR^d)_p$-$G^2$; wherein $G^2$ is aryl;
p is 1;
$R^c$ and $R^d$, together with the carbon atom to which they are attached form a $C_{3-6}$ cycloalkyl ring; and
$R^3$ is hydrogen.

3. The compound or salt according to claim 1, wherein
$L^2$ is C(O);
$R^2$ is —$(CR^cR^d)_p$-$G^2$; wherein $G^2$ is aryl and p is 1 or 2;
$R^c$ and $R^d$, at each occurrence are independently hydrogen, alkyl, or arylalkyl; and
$R^3$ is hydrogen or alkyl.

4. The compound or salt according to claim 1, wherein
$G^1$ is monocyclic aryl;
$L^2$ is C(O)N($R^4$), wherein $R^4$ is alkyl;
$R^2$ is $G^2$, wherein $G^2$ is aryl; and
$R^3$ is hydrogen.

5. The compound or salt according to claim 1, wherein
$L^2$ is C(O);
$R^2$ is —$(CR^cR^d)_p$-$G^2$; wherein
$R^c$ and $R^d$ at each occurrence are independently hydrogen, alkyl or O$R^7$;
p is 1;
$G^2$ is cycloalkyl or heterocycle; wherein said cycloalkyl or heterocycle is unsubstituted or substituted with 1, 2, 3, 4, or 5 substituents independently selected from the group consisting of alkyl, haloalkyl, halogen, oxo and C(O)O$R^7$;
$R^7$ is hydrogen; and
$R^3$ is hydrogen.

6. The compound or salt according to claim 1, wherein
$G^1$ is monocyclic aryl; and
$R^3$ is hydrogen or cycloalkyl.

7. The compound or salt according to claim 1, wherein
$G^1$ is monocyclic aryl;
$L^2$ is C(O);
$R^2$ is —C($R^c$)($G^2$)($G^3$), or —$(CR^cR^d)_p$—CH($G^2$)($G^3$); wherein $G^2$ is aryl and $G^3$ is aryl or cycloalkyl;
$R^c$ and $R^d$ are each hydrogen; and
$R^3$ is hydrogen.

8. The compound or salt according to claim 1, wherein
$L^2$ is C(O);
$R^2$ is —C($R^c$)($G^2$)($G^3$); wherein $G^2$ and $G^3$ are each cycloalkyl;
$R^c$ hydrogen or O$R^7$, wherein $R^7$ is hydrogen; and
$R^3$ is hydrogen.

9. The compound or salt according to claim 1, wherein
$G^1$ is aryl;
$L^2$ is C(O);
$R^2$ is alkyl or $G^2$, wherein $G^2$ is cycloalkyl or heterocycle; and
$R^3$ is hydrogen.

10. The compound or salt according to claim 1, wherein
$L^2$ is C(O);
$R^2$ is —$(CR^gR^h)_q$—N($R^5$)—C(O)O(alkyl), —$(CR^gR^h)_q$—N($R^5$)—C(O)O-$G^2$, —$(CR^gR^h)_q$—N($R^5$)—C(O)(alkyl), —$(CR^gR^h)_q$—N($R^5$)—SO$_2$—$R^6$, —$(CR^gR^h)_q$—N($R^4$)($R^5$), —$(CR^gR^h)_q$—N($R^5$)—C(O)N($R^5$)-(alkyl), or —$(CR^gR^h)_q$—N($R^5$)—C(O)N($R^5$)-$G^2$;
q is 1 or 2;

$R^g$ and $R^h$, at each occurrence, are each independently hydrogen, alkyl, arylalkyl, or cycloalkylalkyl;

$R^4$ and $R^5$ at each occurrence, are each independently hydrogen, alkyl, arylalkyl, cycloalkyl or cycloalkylalkyl;

$R^6$ is alkyl, aryl, or cycloalkyl;

$G^2$ is aryl or cycloalkyl; and $R^3$ is hydrogen, alkyl, cycloalkyl or cycloalkylalkyl.

11. The compound or salt according to claim 1, wherein
$L^2$ is $S(O)_2$;
$R^2$ is $G^2$, wherein $G^2$ is aryl or heteroaryl; and
$R^3$ is hydrogen, alkyl or cycloalkyl.

12. The compound or salt according to claim 1, wherein
$L^2$ is $C(O)$;
$R^2$ is $—(CR^cR^d)_p-G^2$; wherein $G^2$ is aryl;
p is 1;
$R^c$ and $R^d$, at each occurrence, are each independently hydrogen or alkyl; and
$R^3$ is hydrogen.

13. The compound or salt according to claim 1, wherein
$L^2$ is $—(CR^cR^d)_p—$;
$R^c$ and $R^d$ are each independently hydrogen or alkyl;
p is 1;
$R^2$ is $—C(O)N(R^4)(R^5)$ or $G^2$;
$R^4$ and $R^5$ are each independently hydrogen or alkyl;
$G^2$ is aryl, cycloalkyl or heteroaryl; or
$L^2$-$R^2$ taken together are hydrogen, alkyl, $G^2$, or $—C(R^c)(G^2)(G^3)$, wherein $G^2$ and $G^3$ are each aryl or heteroaryl and $R^c$ is hydrogen; and
$R^3$ is hydrogen or alkyl.

14. The compound or salt according to claim 1, wherein
$L^2$ is $C(O)$ or $S(O)_2$;
$R^2$ is $G^2$ or $—C(R^c)(G^2)(G^3)$, wherein $G^2$ and $G^3$ are each aryl or heteroaryl and $R^c$ is hydrogen; and
$R^3$ is hydrogen, alkyl, or cycloalkyl.

15. The compound or salt according to claim 1, wherein
$R^5$ at each occurrence is independently hydrogen, alkyl or cycloalkyl;
$L^2$ is $C(O)$;
$R^2$ is $—(CR^gR^h)_qN(R^4)(R^5)$ or $—(CR^gR^h)_q—N(R^5)C(O)O(alkyl)$;
q is 1 or 2;
$R^4$ is hydrogen or alkyl;
$R^g$ and $R^h$ at each occurrence are each independently hydrogen or alkyl; and
$R^3$ is hydrogen.

16. The compound or salt of claim 1, wherein
$L^2$ is $C(O)$;
$R^2$ is haloalkyl, hydroxyalkyl, $—CH(OH)CF_3$, $—(CR^cR^d)_p—CH(OH)CF_3$, $—(CR^gR^h)_qN(R^4)(R^5)$ or $—(CR^gR^h)_q—N(R^5)C(O)O(alkyl)$;
p is 1 or 2;
q is 1 or 2;
$R^4$ is hydrogen, alkyl, or cycloalkylalkyl;
$R^5$ is hydrogen or alkyl;
$R^c$ and $R^d$ at each occurrence are each independently hydrogen or alkyl;
$R^g$ and $R^h$ at each occurrence are each independently hydrogen, alkyl, cycloalkylalkyl, or hydroxyalkyl; and
$R^3$ is hydrogen.

17. The compound or salt of claim 1, wherein
$L^2$ is $C(O)$ or $S(O)_2$;
$R^2$ is $G^2$ or $G^2$-$G^3$, wherein $G^2$ is aryl or heteroaryl and $G^3$ is aryl or heteroaryl; and
$R^3$ is hydrogen or alkyl.

18. The compound or salt of claim 1, wherein
$L^2$ is $—(CR^cR^d)_p—$;
$R^c$ and $R^d$, at each occurrence, are each independently hydrogen or alkyl;
p is 1, 2, or 3;
$R^2$ is $G^2$ or $G^2$-$G^3$, wherein $G^2$ is aryl or heteroaryl and $G^3$ is aryl or heteroaryl; and
$R^3$ is hydrogen or alkyl.

19. The compound or salt of claim 1, wherein
$L^2$ is $C(O)N(R^4)$, wherein $R^4$ is hydrogen;
$R^2$ is alkyl or $G^2$ or $G^2$-$G^3$, wherein $G^2$ is aryl or heteroaryl and $G^3$ is aryl or heteroaryl; and
$R^3$ is hydrogen or alkyl.

20. The compound or salt of claim 1, wherein
$L^2$ is $C(O)$ or $S(O)_2$;
$R^2$ is , $—C(R^c)(G^2)(G^3)$, $—(CR^cR^d)_p-G^2$, or $—(CR^cR^d)_p—CH(G^2)(G^3)$;
Rc and Rd, at each occurrence, are each independently hydrogen or alkyl;
p is 1, 2, or 3;
$G^2$ and $G^3$ are independently aryl or heteroaryl; and
$R^3$ is hydrogen or alkyl.

21. The compound according to claim 1, or a pharmaceutically acceptable salt thereof, wherein the compound is selected from the group consisting of:

tert-butyl(S)-4,4-dimethyl-1-oxo-1-((3aR,4S,6aS)-2-(5-(trifluoromethyl)pyridin-2-yl)octahydrocyclopenta[c]pyrrol-4-ylamino)pentan-2-ylcarbamate;

isopropyl(S)-1-oxo-1-((3aR,4S,6aS)-2-(5-(trifluoromethyl)pyridin-2-yl)octahydrocyclopenta[c]pyrrol-4-ylamino)pentan-2-ylcarbamate;

tert-butyl(S)-4,4-dimethyl-1-oxo-1-((3aR,4S,6aS)-2-(6-(trifluoromethyl)pyridin-2-yl)octahydrocyclopenta[c]pyrrol-4-ylamino)pentan-2-ylcarbamate;

tert-butyl(S)-4,4-dimethyl-1-((3aR,4S,6aS)-2-(2-(methylsulfonyl)pyrimidin-5-yl)octahydrocyclopenta[c]pyrrol-4-ylamino)-1-oxopentan-2-ylcarbamate;

4-methyl-$N^1$-{(3aR,4S,6aS)-2-[5-(trifluoromethyl)pyridine-2-yl]octahydrocyclopenta[c]pyrrol-4-yl}-L-leucinamide;

4-methyl-$N^1$-{(3aR,4S,6aS)-2-[6-(trifluoromethyl)pyridine-2-yl]octahydrocyclopenta[c]pyrrol-4-yl}-L-leucinamide;

4-methyl-$N^1$-{(3aR,4S,6aS)-2-[2-(methylsulfonyl)pyridine-5-yl]octahydrocyclopenta[c]pyrrol-4-yl}-L-leucinamide;

$N^2$-(cyclopropylmethyl)-4-methyl-$N^1$-{(3aR,4S,6aS)-2-[5-trifluoromethyl)pyridine-2-yl]octahydrocyclopenta[c]pyrrol-4-yl}-L-leucinamide;

$N^2$-(cyclopropylmethyl)-4-methyl-$N^1$-{(3aR,4S,6aS)-2-[6-trifluoromethyl)pyridine-2-yl]octahydrocyclopenta[c]pyrrol-4-yl}-L-leucinamide;

$N^2$-isopropyl-4-methyl-$N^1$-{(3aR,4S,6aS)-2-[5-trifluoromethyl)pyridine-2-yl]octahydrocyclopenta[c]pyrrol-4-yl}-L-leucinamide;

$N^2$-isopropyl-4-methyl-$N^1$-{(3aR,4S,6aS)-2-[6-trifluoromethyl)pyridine-2-yl]octahydrocyclopenta[c]pyrrol-4-yl}-L-leucinamide;

$N^2$-isopropyl-4-methyl-$N^1$-{(3aR,4S,6aS)-2-[2-methylsulfonyl)pyrimidin-5-yl]octahydrocyclopenta[c]pyrrol-4-yl}-L-leucinamide;

4-fluoro-N-{(3aR,4S,6aS)-2-[6-(trifluoromethyl)pyridin-2-yl]octahydrocyclopenta[c]pyrrol-4-yl}benzamide;

4-fluoro-N-{(3aR,4S,6aS)-2-[6-(trifluoromethyl)pyridin-2-yl]octahydrocyclopenta[c]pyrrol-4-yl}benzamide;

2-hydroxy-N-{(3aR,4S, 6aS)-2-[6-(trifluoromethyl)pyridin-2-yl]octahydrocyclopenta[c]pyrrol-4-yl}benzamide;

2-fluoro-N-{(3aR,4S,6aS)-2-[6-(trifluoromethyl)pyridin-2-yl]octahydrocyclopenta[c]pyrrol-4-yl}benzamide;
3-fluoro-N-{(3aR,4S,6aS)-2-[6-(trifluoromethyl)pyridin-2-yl]octahydrocyclopenta[c]pyrrol-4-yl}benzamide;
3,4-difluoro-N-{(3aR,4S,6aS)-2-[6-(trifluoromethyl)pyridin-2-yl]octahydrocyclopenta[c]pyrrol-4-yl}benzamide;
3-chloro-4-fluoro-N-{(3aR,4S, 6aS)-2-[6-(trifluoromethyl)pyridin-2-yl]octahydrocyclopenta[c]pyrrol-4-yl}benzamide;
(2S)-2-hydroxy-4-methyl-N-{(3aR,4S, 6aS)-2-[6-(trifluoromethyl)pyridin-2-yl]octahydrocyclopenta[c]pyrrol-4-yl}pentanamide;
N-{(3aR,4S,6aS)-2-[5-(trifluoromethyl)pyridin-2-yl]octahydrocyclopenta[c]pyrrol-4-yl}-1H-indole-2-carboxamide;
N-{(3aR,4S, 6aS)-2-[6-(trifluoromethyl)pyridin-2-yl]octahydrocyclopenta[c]pyrrol-4-yl}quinoline-2-carboxamide;
N-{(3aR,4S,6aS)-2-[6-(trifluoromethyl)pyridin-2-yl]octahydrocyclopenta[c]pyrrol-4-yl}-1H-indole-2-carboxamide;
5-(2-thienyl)-N-{(3aR,4S,6aS)-2-[6-(trifluoromethyl)pyridin-2-yl]octahydrocyclopenta[c]pyrrol-4-yl}-2-furamide;
4-methyl-N-{(3aR,4S,6aS)-2-[6-(trifluoromethyl)pyridin-2-yl]octahydrocyclopenta[c]pyrrol-4-yl}-1H-pyrrole-2-carboxamide;
1-hydroxy-N-{(3aR,4S,6aS)-2-[6-(trifluoromethyl)pyridin-2-yl]octahydrocyclopenta[c]pyrrol-4-yl}cyclopentanecarboxamide;
N-{(3aR,4S,6aS)-2-[6-(trifluoromethyl)pyridin-2-yl]octahydrocyclopenta[c]pyrrol-4-yl}-4H-furo[3,2-b]pyrrole-5-carboxamide;
4-chloro-N-{(3aR,4S,6aS)-2-[6-(trifluoromethyl)pyridin-2-yl]octahydrocyclopenta[c]pyrrol-4-yl}-1H-pyrrole-2-carboxamide;
5-methyl-N-{(3aR,4S,6aS)-2-[6-(trifluoromethyl)pyridin-2-yl]octahydrocyclopenta[c]pyrrol-4-yl}-2-furamide;
3-hydroxy-N-{(3aR,4S,6aS)-2-[6-(trifluoromethyl)pyridin-2-yl]octahydrocyclopenta[c]pyrrol-4-yl}benzamide;
(2R)-2-hydroxy-4-methyl-N-{(3aR,4S,6aS)-2-[6-(trifluoromethyl)pyridin-2-yl]octahydrocyclopenta[c]pyrrol-4-yl}pentanamide;
5-methyl-N-{(3aR,4S,6aS)-2-[6-(trifluoromethyl)pyridin-2-yl]octahydrocyclopenta[c]pyrrol-4-yl}pyrazine-2-carboxamide;
(2S)-2-hydroxy-3,3-dimethyl-N-{(3aR,4S,6aS)-2-[6-(trifluoromethyl)pyridin-2-yl]octahydrocyclopenta[c]pyrrol-4-yl}butanamide;
5-methyl-N-{(3aR,4S,6aS)-2-[6-(trifluoromethyl)pyridin-2-yl]octahydrocyclopenta[c]pyrrol-4-yl}-1,2-oxazole-4-carboxamide;
4,4,4-trifluoro-N-{(3aR,4S,6aS)-2-[6-(trifluoromethyl)pyridin-2-yl]octahydrocyclopenta[c]pyrrol-4-yl}butanamide;
3-cyclopropyl-N-{(3aR,4S,6aS)-2-[6-(trifluoromethyl)pyridin-2-yl]octahydrocyclopenta[c]pyrrol-4-yl}-1H-pyrazole-5-carboxamide;
cis-4-hydroxy-N-{(3aR,4S,6aS)-2-[6-(trifluoromethyl)pyridin-2-yl]octahydrocyclopenta[c]pyrrol-4-yl}cyclohexanecarboxamide;
(2S)-3,3,3-trifluoro-2-hydroxy-N-{(3aR,4S,6aS)-2-[6-(trifluoromethyl)pyridin-2-yl]octahydrocyclopenta[c]pyrrol-4-yl}propanamide;
4,4,4-trifluoro-3-hydroxy-N-{(3aR,4S,6aS)-2-[6-(trifluoromethyl)pyridin-2-yl]octahydrocyclopenta[c]pyrrol-4-yl}butanamide;
$N^2$,4-dimethyl-N-{(3aR,4S,6aS)-2-[6-(trifluoromethyl)pyridin-2-yl]octahydrocyclopenta[c]pyrrol-4-yl}-L-leucinamide;
$N^2$-methyl-N-{(3aR,4S,6aS)-2-[6-(trifluoromethyl)pyridin-2-yl]octahydrocyclopenta[c]pyrrol-4-yl}-L-norvalinamide;
$N^2$-methyl-N-{(3aR,4S,6aS)-2-[6-(trifluoromethyl)pyridin-2-yl]octahydrocyclopenta[c]pyrrol-4-yl}-L-norleucinamide;
$N^2$-methyl-N-{(3aR,4S,6aS)-2-[6-(trifluoromethyl)pyridin-2-yl]octahydrocyclopenta[c]pyrrol-4-yl}-L-leucinamide;
3-methyl-N-{(3aR,4S,6aS)-2-[6-(trifluoromethyl)pyridin-2-yl]octahydrocyclopenta[c]pyrrol-4-yl}-L-valinamide;
(4R)-4-fluoro-N-{(3aR,4S,6aS)-2-[6-(trifluoromethyl)pyridin-2-yl]octahydrocyclopenta[c]pyrrol-4-yl}-L-prolinamide;
(2S,3aS,7aS)-N-{(3aR,4S,6aS)-2-[6-(trifluoromethyl)pyridin-2-yl]octahydrocyclopenta[c]pyrrol-4-yl}octahydro-1H-indole-2-carboxamide;
1-amino-N-{(3aR,4S,6aS)-2-[6-(trifluoromethyl)pyridin-2-yl]octahydrocyclopenta[c]pyrrol-4-yl}cyclopentanecarboxamide;
4,4-difluoro-N-{(3aR,4S,6aS)-2-[6-(trifluoromethyl)pyridin-2-yl]octahydrocyclopenta[c]pyrrol-4-yl}-L-prolinamide;
(4S)-4-fluoro-N-{(3aR,4S,6aS)-2-[6-(trifluoromethyl)pyridin-2-yl]octahydrocyclopenta[c]pyrrol-4-yl}-L-prolinamide;
(2S)-N-{(3aR,4S,6aS)-2-[6-(trifluoromethyl)pyridin-2-yl]octahydrocyclopenta[c]pyrrol-4-yl}piperidine-2-carboxamide;
N-{(3aR,4S,6aS)-2-[6-(trifluoromethyl)pyridin-2-yl]octahydrocyclopenta[c]pyrrol-4-yl}-L-prolinamide;
$N^2$-methyl-N-{(3aR,4S,6aS)-2-[5-(trifluoromethyl)pyridin-2-yl]octahydrocyclopenta[c]pyrrol-4-yl}-L-norvalinamide;
$N^2$-methyl-N-{(3aR,4S,6aS)-2-[5-(trifluoromethyl)pyridin-2-yl]octahydrocyclopenta[c]pyrrol-4-yl}-L-leucinamide;
$N^2$-methyl-N-{(3aR,4S,6aS)-2-[5-(trifluoromethyl)pyridin-2-yl]octahydrocyclopenta[c]pyrrol-4-yl}-L-norleucinamide;
$N^2$,4-dimethyl-N-{(3aR,4S,6aS)-2-[5-(trifluoromethyl)pyridin-2-yl]octahydrocyclopenta[c]pyrrol-4-yl}-L-leucinamide;
(2S,3aS,7aS)-N-{(3aR,4S,6aS)-2-[5-(trifluoromethyl)pyridin-2-yl]octahydrocyclopenta[c]pyrrol-4-yl}octahydro-1H-indole-2-carboxamide;
(2S)-N-{(3aR,4S,6aS)-2-[5-(trifluoromethyl)pyridin-2-yl]octahydrocyclopenta[c]pyrrol-4-yl}-indoline-2-carboxamide;
$N^2$-methyl-N-{(3aR,4S,6aS)-2-[3-(trifluoromethyl)phenyl]octahydrocyclopenta[c]pyrrol-4-yl}-L-leucinamide;
$N^2$-methyl-N-{(3aR,4S,6aS)-2-[4-(trifluoromethyl)phenyl]octahydrocyclopenta[c]pyrrol-4-yl}-L-leucinamide;
(3aR,4S,6aS)-N-(1H-indol-2-ylmethyl)-2-[6-(trifluoromethyl)pyridin-2-yl]octahydrocyclopenta[c]pyrrol-4-amine;

(3aR,4S,6aS)-N-[(5-fluoro-1H-indol-2-yl)methyl]-2-[6-(trifluoromethyl)pyridin-2-yl]octahydrocyclopenta[c]pyrrol-4-amine;

(3aR,4S,6aS)-N-[(5-fluoro-1H-indol-2-yl)methyl]-2-[5-(trifluoromethyl)pyridin-2-yl]octahydrocyclopenta[c]pyrrol-4-amine;

(3aR,4S,6aS)-N-[(5-fluoro-1H-indol-2-yl)methyl]-2-[4-(trifluoromethyl)phenyl]octahydrocyclopenta[c]pyrrol-4-amine;

(3aR,4S,6aS)-N-[(5-fluoro-1H-indol-2-yl)methyl]-2-[3-(trifluoromethyl)phenyl]octahydrocyclopenta[c]pyrrol-4-amine;

(4R)-4-fluoro-N-{(3aR,4S,6aS)-2-[3-(trifluoromethyl)phenyl]octahydrocyclopenta[c]pyrrol-4-yl}-L-prolinamide;

$N^2$-methyl-N-{(3aR,4S,6aS)-2-[2-(trifluoromethyl)phenyl]octahydrocyclopenta[c]pyrrol-4-yl}-L-leucinamide;

N-[(3aR,4S,6aS)-2-(2-fluorophenyl)octahydrocyclopenta[c]pyrrol-4-yl]-$N^2$-methyl-L-leucinamide;

N-[(3aR,4S,6aS)-2-(4-fluorophenyl)octahydrocyclopenta[c]pyrrol-4-yl]-$N^2$-methyl-L-leucinamide;

N-{(3aR,4S,6aS)-2-[4-fluoro-3-(trifluoromethyl)phenyl]octahydrocyclopenta[c]pyrrol-4-yl}-$N^2$-methyl-L-leucinamide;

(4R)-4-fluoro-N-{(3aR,4S,6aS)-2-[2-(trifluoromethyl)phenyl]octahydrocyclopenta[c]pyrrol-4-yl}-L-prolinamide;

(4R)-4-fluoro-N-{(3aR,4S,6aS)-2-[2-fluoro-3-(trifluoromethyl)phenyl]octahydrocyclopenta[c]pyrrol-4-yl}-L-prolinamide;

$N^2$-methyl-N-{(3aR,4S,6aS)-2-[4-(trifluoromethoxy)phenyl]octahydrocyclopenta[c]pyrrol-4-yl}-L-leucinamide;

$N^2$-methyl-N-{(3aR,4S,6aS)-2-[3-(trifluoromethoxy)phenyl]octahydrocyclopenta[c]pyrrol-4-yl}-L-leucinamide;

(4R)-4-fluoro-N-{(3aR,4S,6aS)-2-[4-fluoro-3-(trifluoromethyl)phenyl]octahydrocyclopenta[c]pyrrol-4-yl}-L-prolinamide;

(4R)-4-fluoro-N-{(3aR,4S,6aS)-2-[3-(trifluoromethoxy)phenyl]octahydrocyclopenta[c]pyrrol-4-yl}-L-prolinamide;

N-[(3aR,4S,6aS)-2-(3-chlorophenyl)octahydrocyclopenta[c]pyrrol-4-yl]-$N^2$-methyl-L-leucinamide;

N-[(3aR,4S,6aS)-2-(3-fluorophenyl)octahydrocyclopenta[c]pyrrol-4-yl]-$N^2$-methyl-L-leucinamide;

$N^2$-methyl-N-[(3aR,4S,6aS)-2-(2-methylphenyl)octahydrocyclopenta[c]pyrrol-4-yl]-L-leucinamide;

(4R)-4-fluoro-N-{(3aR,4S,6aS)-2-[4-(trifluoromethoxy)phenyl]octahydrocyclopenta[c]pyrrol-4-yl}-L-prolinamide;

(4R)-N-[(3aR,4S,6aS)-2-(3-cyanophenyl)octahydrocyclopenta[c]pyrrol-4-yl]-4-fluoro-L-prolinamide;

(4R)-N-[(3aR,4S,6aS)-2-(4-cyanophenyl)octahydrocyclopenta[c]pyrrol-4-yl]-4-fluoro-L-prolinamide;

N-[(3aR,4S,6aS)-2-(2-chlorophenyl)octahydrocyclopenta[c]pyrrol-4-yl]-$N^2$-methyl-L-leucinamide;

N-{(3aR,4S,6aS)-2-[2-fluoro-3-(trifluoromethyl)phenyl]octahydrocyclopenta[c]pyrrol-4-yl}-$N^2$-methyl-L-leucinamide;

$N^2$-methyl-N-[(3aR,4S,6aS)-2-(3-methylphenyl)octahydrocyclopenta[c]pyrrol-4-yl]-L-leucinamide;

(4R)-4-fluoro-N-{(3aR,4S,6aS)-2-[4-(trifluoromethyl)pyridin-2-yl]octahydrocyclopenta[c]pyrrol-4-yl}-L-prolinamide;

(4R)-4-fluoro-N-{(3aR,4S,6aS)-2-[2-(trifluoromethyl)pyridin-4-yl]octahydrocyclopenta[c]pyrrol-4-yl}-L-prolinamide;

N-[(3aR,4S,6aS)-2-(4-chlorophenyl)octahydrocyclopenta[c]pyrrol-4-yl]-$N^2$-methyl-L-leucinamide;

(4R)-4-fluoro-N-[(3aR,4S,6aS)-2-(3-fluorophenyl)octahydrocyclopenta[c]pyrrol-4-yl]-L-prolinamide;

(4R)-4-fluoro-N-[(3aR,4S,6aS)-2-(4-fluorophenyl)octahydrocyclopenta[c]pyrrol-4-yl]-L-prolinamide;

(4R)-4-fluoro-N-[(3aR,4S,6aS)-2-(3-methylphenyl)octahydrocyclopenta[c]pyrrol-4-yl]-L-prolinamide;

(4R)-N-[(3aR,4S,6aS)-2-(3-chlorophenyl)octahydrocyclopenta[c]pyrrol-4-yl]-4-fluoro-L-prolinamide;

(4R)-N-[(3aR,4S,6aS)-2-(4-chlorophenyl)octahydrocyclopenta[c]pyrrol-4-yl]-4-fluoro-L-prolinamide;

(4R)-4-fluoro-N-[(3aR,4S,6aS)-2-(3-methoxyphenyl)octahydrocyclopenta[c]pyrrol-4-yl]-L-prolinamide;

N-[(3aR,4S,6aS)-2-(3-cyanophenyl)octahydrocyclopenta[c]pyrrol-4-yl]-$N^2$-methyl-L-leucinamide;

N-[(3aR,4S,6aS)-2-(4-cyanophenyl)octahydrocyclopenta[c]pyrrol-4-yl]-$N^2$-methyl-L-leucinamide;

$N^2$-methyl-N-[(3aR,4S,6aS)-2-(4-methylphenyl)octahydrocyclopenta[c]pyrrol-4-yl]-L-leucinamide;

(3aR,4S,6aS)-N-(4-methylbenzyl)-2-[6-(trifluoromethyl)pyridin-2-yl]octahydrocyclopenta[c]pyrrol-4-amine;

(3aR,4S,6aS)-N-[(5-fluoro-1H-indol-2-yl)methyl]-2-{[3-(trifluoromethyl)phenyl]sulfonyl}octahydrocyclopenta[c]pyrrol-4-amine;

(4R)-N-[(3aR,4S,6aS)-2-(2-cyanophenyl)octahydrocyclopenta[c]pyrrol-4-yl]-4-fluoro-L-prolinamide;

(4R)-4-fluoro-N-[(3aR,4S,6aS)-2-(4-methylphenyl)octahydrocyclopenta[c]pyrrol-4-yl]-L-prolinamide;

(4R)-4-fluoro-N-[(3aR,4S,6aS)-2-(4-methoxyphenyl)octahydrocyclopenta[c]pyrrol-4-yl]-L-prolinamide;

(3aR,4S,6aS)-N-[(5-fluoro-1H-indol-2-yl)methyl]-2-{[4-(trifluoromethyl)phenyl]sulfonyl}octahydrocyclopenta[c]pyrrol-4-amine;

(4R)-N-{(3aR,4S,6aS)-2-[5-(difluoromethyl)-3-thienyl]octahydrocyclopenta[c]pyrrol-4-yl}-4-fluoro-L-prolinamide;

(4R)-4-fluoro-N-{(3aR,4S,6aS)-2-[2-(trifluoromethoxy)phenyl]octahydrocyclopenta[c]pyrrol-4-yl}-L-prolinamide;

N-{(3aR,4S,6aS)-2-[3-fluoro-4-(trifluoromethoxy)phenyl]octahydrocyclopenta[c]pyrrol-4-yl}-$N^2$-methyl-L-leucinamide;

(4R)-4-fluoro-N-[(3aR,4S,6aS)-2-(2-methylphenyl)octahydrocyclopenta[c]pyrrol-4-yl]-L-prolinamide;

(4R)-N-[(3aR,4S,6aS)-2-(2-chlorophenyl)octahydrocyclopenta[c]pyrrol-4-yl]-4-fluoro-L-prolinamide;

(4R)-4-fluoro-N-{(3aR,4S,6aS)-2-[3-(trifluoromethyl)pyridin-2-yl]octahydrocyclopenta[c]pyrrol-4-yl}-L-prolinamide;

(4R)-4-fluoro-N-[(3aR,4S,6aS)-2-(2-fluorophenyl)octahydrocyclopenta[c]pyrrol-4-yl]-L-prolinamide;

(4R)-4-fluoro-N-[(3aR,4S,6aS)-2-(2-methoxyphenyl)octahydrocyclopenta[c]pyrrol-4-yl]-L-prolinamide;

(3aR,4S,6aS)-N-(1H-pyrazol-5-ylmethyl)-2-[6-(trifluoromethyl)pyridin-2-yl]octahydrocyclopenta[c]pyrrol-4-amine;

(3aR,4S,6aS)-N-[(3-methyl-1H-indol-2-yl)methyl]-2-[6-(trifluoromethyl)pyridin-2-yl]octahydrocyclopenta[c]pyrrol-4-amine;

(3aR,4S,6aS)-N-[(5-chloro-1H-indol-2-yl)methyl]-2-[6-(trifluoromethyl)pyridin-2-yl]octahydrocyclopenta[c]pyrrol-4-amine;

(3aR,4S,6aS)-N-{[3-(4-chlorophenyl)-1H-pyrazol-4-yl]
methyl}-2-[6-(trifluoromethyl)pyridin-2-yl]octahydro-
cyclopenta[c]pyrrol-4-amine;
(3aR,4S,6aS)-N-[(5-fluoro-3-methyl-1H-indol-2-yl)me-
thyl]-2-[6-(trifluoromethyl)pyridin-2-yl]octahydrocy-
clopenta[c]pyrrol-4-amine;
(3aR,4S,6aS)-N-[(5-methoxy-3-methyl-1H-indol-2-yl)
methyl]-2-[6-(trifluoromethyl)pyridin-2-yl]octahydro-
cyclopenta[c]pyrrol-4-amine;
(3aR,4S,6aS)-N-{[3-(2-thienyl)-1H-pyrazol-4-yl]me-
thyl}-2-[6-(trifluoromethyl)pyridin-2-yl]octahydrocy-
clopenta[c]pyrrol-4-amine;
(3aR,4S,6aS)-N-[(4-methyl-1H-imidazol-2-yl)methyl]-2-
[6-(trifluoromethyl)pyridin-2-yl]octahydrocyclopenta
[c]pyrrol-4-amine;
(3aR,4S,6aS)-N-[(7-methyl-1H-indol-3-yl)methyl]-2-[6-
(trifluoromethyl)pyridin-2-yl]octahydrocyclopenta[c]
pyrrol-4-amine;
(3aR,4S,6aS)-N-{[3-(4-fluorophenyl)-1H-pyrazol-4-yl]
methyl}-2-[6-(trifluoromethyl)pyridin-2-yl]octahydro-
cyclopenta[c]pyrrol-4-amine;
(3aR,4S,6aS)-N-{[3-(4-methylphenyl)-1H-pyrazol-4-yl]
methyl}-2-[6-(trifluoromethyl)pyridin-2-yl]octahydro-
cyclopenta[c]pyrrol-4-amine;
(3aR,4S,6aS)-N-[(2-butyl-1H-imidazol-4-yl)methyl]-2-
[6-(trifluoromethyl)pyridin-2-yl]octahydrocyclopenta
[c]pyrrol-4-amine;
(3aR,4S,6aS)-N-(1H-imidazol-2-ylmethyl)-2-[6-(trifluo-
romethyl)pyridin-2-yl]octahydrocyclopenta[c]pyrrol-
4-amine;
(3aR,4S,6aS)-N-[(2-methyl-1H-imidazol-4-yl)methyl]-2-
[6-(trifluoromethyl)pyridin-2-yl]octahydrocyclopenta
[c]pyrrol-4-amine;
(3aR,4S,6aS)-N-(1H-imidazol-4-ylmethyl)-2-[6-(trifluo-
romethyl)pyridin-2-yl]octahydrocyclopenta[c]pyrrol-
4-amine;
(3aR,4S,6aS)-N-[(5-fluoro-1H-indol-3-yl)methyl]-2-[6-
(trifluoromethyl)pyridin-2-yl]octahydrocyclopenta[c]
pyrrol-4-amine;
(3aR,4S,6aS)-N-[(3-chloro-1H-indol-3-yl)methyl]-2-[6-
(trifluoromethyl)pyridin-2-yl]octahydrocyclopenta[c]
pyrrol-4-amine;
(3aR,4S,6aS)-N-[(5-chloro-1H-indol-3-yl)methyl]-2-[6-
(trifluoromethyl)pyridin-2-yl]octahydrocyclopenta[c]
pyrrol-4-amine;
(3aR,4S,6aS)-N-{[3-(4-methoxyphenyl)-1H-pyrazol-4-
yl]methyl}-2-[6-(trifluoromethyl)pyridin-2-yl]octahy-
drocyclopenta[c]pyrrol-4-amine;
(3aR,4S,6aS)-N-[(3-phenyl-1H-pyrazol-4-yl)methyl]-2-
[6-(trifluoromethyl)pyridin-2-yl]octahydrocyclopenta
[c]pyrrol-4-amine;
(3aR,4S,6aS)-N-(1H-benzimidazol-2-ylmethyl)-2-[6-(tri-
fluoromethyl)pyridin-2-yl]octahydrocyclopenta[c]pyr-
rol-4-amine;
(3aR,4S,6aS)-N-(1H-indol-3-ylmethyl)-2-[6-(trifluorom-
ethyl)pyridin-2-yl]octahydrocyclopenta[c]pyrrol-4-
amine;
(3aR,4S,6aS)-N-[(5-methoxy-1H-indol-3-yl)methyl]-2-
[6-(trifluoromethyl)pyridin-2-yl]octahydrocyclopenta
[c]pyrrol-4-amine;
(3aR,4S,6aS)-N-[(6-fluoro-1H-indol-3-yl)methyl]-2-[6-
(trifluoromethyl)pyridin-2-yl]octahydrocyclopenta[c]
pyrrol-4-amine;
(3aR,4S,6aS)-N-{[3-(3,5-difluorophenyl)-1H-pyrazol-4-
yl]methyl}-2-[6-(trifluoromethyl)pyridin-2-yl]octahy-
drocyclopenta[c]pyrrol-4-amine;
(3aR,4S,6aS)-N-[(2-phenyl-1H-imidazol-4-yl)methyl]-2-
[6-(trifluoromethyl)pyridin-2-yl]octahydrocyclopenta
[c]pyrrol-4-amine;
(3aR,4S,6aS)-N-[(4-methoxy-1H-indol-3-yl)methyl]-2-
[6-(trifluoromethyl)pyridin-2-yl]octahydrocyclopenta
[c]pyrrol-4-amine;
(3aR,4S,6aS)-N-[(5-fluoro-1H-pyrrolo[2,3-b]pyridin-3-
yl)methyl]-2-[6-(trifluoromethyl)pyridin-2-yl]octahy-
drocyclopenta[c]pyrrol-4-amine;
(3aR,4S,6aS)-N-[(6-fluoro-1H-benzimidazol-2-yl)me-
thyl]-2-[6-(trifluoromethyl)pyridin-2-yl]octahydrocy-
clopenta[c]pyrrol-4-amine;
(3aR,4S,6aS)-N-[(4-chloro-1H-indol-3-yl)methyl]-2-[6-
(trifluoromethyl)pyridin-2-yl]octahydrocyclopenta[c]
pyrrol-4-amine;
(3aR,4S,6aS)-N-(1H-pyrrolo[2,3-b]pyridin-2-ylmethyl)-
2-[6-(trifluoromethyl)pyridin-2-yl]octahydrocyclo-
penta[c]pyrrol-4-amine;
(3aR,4S,6aS)-N-(1H-1,2,3-triazol-4-ylmethyl)-2-[6-(trif-
luoromethyl)pyridin-2-yl]octahydrocyclopenta[c]pyr-
rol-4-amine;
(3aR,4S,6aS)-N-[(3-methyl-1H-pyrazol-4-yl)methyl]-2-
[6-(trifluoromethyl)pyridin-2-yl]octahydrocyclopenta
[c]pyrrol-4-amine;
(3aR,4S,6aS)-N-(1H-pyrazol-4-ylmethyl)-2-[6-(trifluo-
romethyl)pyridin-2-yl]octahydrocyclopenta[c]pyrrol-
4-amine;
5-fluoro-N-{(3aR,4S,6aS)-2-[6-(trifluoromethyl)pyridin-
2-yl]octahydrocyclopenta[c]pyrrol-4-yl}-1H-indole-2-
carboxamide;
(4R)-4-fluoro-N-{(3aR,4S,6aS)-2-[4-fluoro-2-(trifluo-
romethyl)phenyl]octahydrocyclopenta[c]pyrrol-4-yl}-
L-prolinamide;
$N^2$-methyl-N-{(3aR,4S,6aS)-2-[2-(trifluoromethoxy)
phenyl]octahydrocyclopenta[c]pyrrol-4-yl}-L-leucina-
mide;
4-chloro-N-{(3aR,4S,6aS)-2-[6-(trifluoromethyl)pyridin-
2-yl]octahydrocyclopenta[c]pyrrol-4-
yl}benzenesulfonamide;
2-chloro-N-{(3aR,4S,6aS)-2-[6-(trifluoromethyl)pyridin-
2-yl]octahydrocyclopenta[c]pyrrol-4-
yl}benzenesulfonamide;
3-fluoro-N-{(3aR,4S,6aS)-2-[6-(trifluoromethyl)pyridin-
2-yl]octahydrocyclopenta[c]pyrrol-4-
yl}benzenesulfonamide;
2-fluoro-N-{(3aR,4S,6aS)-2-[6-(trifluoromethyl)pyridin-
2-yl]octahydrocyclopenta[c]pyrrol-4-
yl}benzenesulfonamide;
3-chloro-N-{(3aR,4S,6aS)-2-[6-(trifluoromethyl)pyridin-
2-yl]octahydrocyclopenta[c]pyrrol-4-
yl}benzenesulfonamide;
4-fluoro-N-{(3aR,4S,6aS)-2-[6-(trifluoromethyl)pyridin-
2-yl]octahydrocyclopenta[c]pyrrol-4-
yl}benzenesulfonamide;
$N^2$-{(3aR,4S,6aS)-2-[6-(trifluoromethyl)pyridin-2-yl]oc-
tahydrocyclopenta[c]pyrrol-4-yl}-L-leucinamide;
$N^2$-methyl-N-[(3aR,4S,6aS)-2-{4-[(trifluoromethyl)thio]
phenyl}octahydrocyclopenta[c]pyrrol-4-yl-]-L-leuci-
namide;
N-{(3aR,4S,6aS)-2-[6-(trifluoromethyl)pyridin-2-yl]oc-
tahydrocyclopenta[c]pyrrol-4-yl}benzenesulfonamide;
1-(4-fluorophenyl)-3-{(3aR,4S,6aS)-2-[6-(trifluorom-
ethyl)pyridin-2-yl]octahydrocyclopenta[c]pyrrol-4-
yl}-urea;
3-chloro-4-fluoro-N-{(3aR,4S,6aS)-2-[6-(trifluorom-
ethyl)pyridin-2-yl]octahydrocyclopenta[c]pyrrol-4-
yl}benzenesulfonamide;

1-tert-butyl-3-{(3aR,4S,6aS)-2-[6-(trifluoromethyl)pyridin-2-yl]octahydrocyclopenta[c]pyrrol-4-yl}-urea;
$N^2$-methyl-N-[(3aR,4S,6aS)-2-{3-[(trifluoromethyl)thio]phenyl}octahydrocyclopenta[c]pyrrol-4yl]-L-leucinamide;
1-(4-chlorophenyl)-3-{(3aR,4S,6aS)-2-[6-(trifluoromethyl)pyridin-2-yl]octahydrocyclopenta[c]pyrrol-4-yl}-urea;
1-(3-chloro-4-fluorophenyl)-3-{(3aR,4S,6aS)-2-[6-(trifluoromethyl)pyridin-2-yl]octahydrocyclopenta[c]pyrrol-4-yl}-urea;
(3aR,4S,6aS)-N-[(5-fluoro-1H-indol-2-yl)methyl]-2-[3-(trifluoromethoxy)phenyl]octahydrocyclopenta[c]pyrrol-4-amine;
(3aR,4S,6aS)-N-[(5-fluoro-1H-indol-2-yl)methyl]-2-[4-(trifluoromethoxy)phenyl]octahydrocyclopenta[c]pyrrol-4-amine;
1-(4-chlorophenyl)-N-{(3aR,4S,6aS)-2-[6-(trifluoromethyl)pyridin-2-yl]octahydrocyclopenta[c]pyrrol-4-yl}-methanesulfonamide;
$N^2$-methyl-N-{(3aR,4S,6aS)-2-[3-(trifluoromethoxy)phenyl]octahydrocyclopenta[c]pyrrol-4-yl}-L-norvalinamide;
$N^2$-methyl-N-{(3aR,4S,6aS)-2-[4-(trifluoromethoxy)phenyl]octahydrocyclopenta[c]pyrrol-4-yl}-L-norvalinamide;
(3aR,4S,6aS)-N-[(1-methyl-1H-indol-2-yl)methyl]-2-[6-(trifluoromethyl)pyridin-2-yl]octahydrocyclopenta[c]pyrrol-4-amine;
(3aR,4S,6aS)-N-(thieno[2,3-c]pyridin-2-ylmethyl)-2-[6-(trifluoromethyl)pyridin-2-yl]octahydrocyclopenta[c]pyrrol-4-amine;
$N^2$-methyl-N-{(3aR,4S,6aS)-2-[4-(trifluoromethyl)pyrimidin-2-yl]octahydrocyclopenta[c]pyrrol-4-yl}-L-leucinamide;
$N^2$-methyl-N-{(3aR,4S,6aS)-2-[2-(trifluoromethyl)pyrimidin-4-yl]octahydrocyclopenta[c]pyrrol-4-yl}-L-leucinamide;
$N^2$-methyl-N-{(3aR,4S,6aS)-2-[6-(trifluoromethyl)pyridazin-3-yl]octahydrocyclopenta[c]pyrrol-4-yl}-L-leucinamide;
(3aR,4S,6aS)-N-[(1-methyl-1H-pyrazol-5-yl)methyl]-2-[6-(trifluoromethyl)pyridin-2-yl]octahydrocyclopenta[c]pyrrol-4-amine;
(3aR,4S,6aS)-N-[(5-chloro-2-phenyl-1H-imidazol-4-yl)methyl]-2-[6-(trifluoromethyl)pyridin-2-yl]octahydrocyclopenta[c]pyrrol-4-amine;
(3aR,4S,6aS)-N-(thieno[2,3-b]pyridin-2-ylmethyl)-2-[6-(trifluoromethyl)pyridin-2-yl]octahydrocyclopenta[c]pyrrol-4-amine;
(3aR,4S,6aS)-N-(2,1,3-benzothiadiazol-4-ylmethyl)-2-[6-(trifluoromethyl)pyridin-2-yl]octahydrocyclopenta[c]pyrrol-4-amine;
N-{(3aR,4S,6aS)-2-[3-(difluoromethyl)phenyl]octahydrocyclopenta[c]pyrrol-4-yl}-$N^2$-methyl-L-leucinamide;
N-[(3aR,4S,6aS)-2-(2,3-difluorrophenyl)octahydrocyclopenta[c]pyrrol-4-yl]-$N^2$-methyl-L-leucinamide;
(3aR,4S,6aS)-N-[(1-methyl-1H-benzimidazol-2-yl)methyl]-2-[6-(trifluoromethyl)pyridin-2-yl]octahydrocyclopenta[c]pyrrol-4-amine;
tert-butyl methyl{(2S)-3-methyl-1-[(3aR,4S,6aS)-octahydrocyclopenta[c]pyrrol-4-ylamino]-1-oxobutan-2-yl}-carbamate;
$N^2$-methyl-N-{(3aR,4S,6aS)-2-[5-(trifluoromethyl)-1,3,4-thiadiazol-2-yl]octahydrocyclopenta[c]pyrrol-4-yl}-L-leucinamide;
$N^2$-methyl-N-{(3aR,4S,6aS)-2-[6-(trifluoromethyl)pyridin-3-yl]octahydrocyclopenta[c]pyrrol-4-yl}-L-leucinamide;
$N^2$-methyl-N-{(3aR,4S,6aS)-2-[5-(trifluoromethyl)pyridin-3-yl]octahydrocyclopenta[c]pyrrol-4-yl}-L-leucinamide;
N-{(3aR,4S,6aS)-2-[4-fluoro-2-(trifluoromethyl)phenyl]octahydrocyclopenta[c]pyrrol-4-yl}-$N^2$-methyl-L-leucinamide;
$N^2$-methyl-N-{(3aS,4R,6aR)-2-[5-(trifluoromethyl)pyridin-2-yl]octahydrocyclopenta[c]pyrrol-4-yl}-L-leucinamide;
$N^2$-methyl-N-{(3aS,4R,6aR)-2-[4-(trifluoromethoxy)phenyl]octahydrocyclopenta[c]pyrrol-4-yl}-L-leucinamide;
$N^2$-methyl-N-{(3aS,4R,6aR)-2-[4-(trifluoromethyl)phenyl]octahydrocyclopenta[c]pyrrol-4-yl}-L-leucinamide;
(3aR,4S,6aS)-N-{[2-(4-chlorophenyl)-1,3-oxazol-4-yl]methyl}-2-[6-(trifluoromethyl)pyridin-2-yl]octahydrocyclopenta[c]pyrrol-4-amine;
(3aR,4S,6aS)-N-({2-[4-(trifluoromethyl)phenyl]-1H-imidazol-4-yl}methyl)-2-[6-(trifluoromethyl)pyridin-2-yl]octahydrocyclopenta[c]pyrrol-4-amine;
(3aR,4S,6aS)-N-{[2-(4-fluorophenyl)-1,3-oxazol-4-yl]methyl}-2-[6-(trifluoromethyl)pyridin-2-yl]octahydrocyclopenta[c]pyrrol-4-amine;
(3aR,4S,6aS)-N-{[4-(4-fluorophenyl)-1H-imidazol-2-yl]methyl}-2-[6-(trifluoromethyl)pyridin-2-yl]octahydrocyclopenta[c]pyrrol-4-amine;
(3aR,4S,6aS)-N-{[4-(4-chlorophenyl)-1H-imidazol-2-yl]methyl}-2-[6-(trifluoromethyl)pyridin-2-yl]octahydrocyclopenta[c]pyrrol-4-amine;
(3aR,4S,6aS)-N-[(4-phenyl-1H-imidazol-2-yl)methyl]-2-[6-(trifluoromethyl)pyridin-2-yl]octahydrocyclopenta[c]pyrrol-4-amine;
$N^2$-methyl-N-{(3aR,4S,6aS)-2-[4-(trifluoromethyl)phenyl]octahydrocyclopenta[c]pyrrol-4-yl}-L-valinamide;
(3aR,4S,6aS)-N-[(5-fluoro-1-methyl-1H-indol-2-yl)methyl]-2-[6-(trifluoromethyl)pyridin-2-yl]octahydrocyclopenta[c]pyrrol-4-amine;
$N^2$-methyl-N-{(3aR,4S,6aS)-2-[4-(trifluoromethyl)phenyl]octahydrocyclopenta[c]pyrrol-4-yl}-L-serinamide;
$N^2$-methyl-N-{(3aR,4S,6aS)-2-[4-(trifluoromethyl)phenyl]octahydrocyclopenta[c]pyrrol-4-yl}-L-allothreoninamide;
N-{(3aR,4S,6aS)-2-[4-(trifluoromethyl)phenyl]octahydrocyclopenta[c]pyrrol-4-yl}-glycinamide;
$N^2$-methyl-N-{(3aR,4S,6aS)-2-[4-(trifluoromethyl)phenyl]octahydrocyclopenta[c]pyrrol-4-yl}-glycinamide;
$N^2$-methyl-N-{(3aR,4S,6aS)-2-[4-(trifluoromethyl)phenyl]octahydrocyclopenta[c]pyrrol-4-yl}-L-alaninamide;
$N^2$,2-dimethyl-N-{(3aR,4S,6aS)-2-[4-(trifluoromethyl)phenyl]octahydrocyclopenta[c]pyrrol-4-yl}-alaninamide;
(2S)-2-amino-N-{(3aR,4S,6aS)-2-[4-(trifluoromethyl)phenyl]octahydrocyclopenta[c]pyrrol-4-yl}butanamide;
$N^2$-methyl-N-{(3aR,4S,6aS)-2-[4-(trifluoromethoxy)phenyl]octahydrocyclopenta[c]pyrrol-4-yl}-L-valinamide;
$N^2$-methyl-N-{(3aR,4S,6aS)-2-[3-(trifluoromethyl)phenyl]octahydrocyclopenta[c]pyrrol-4-yl}-L-valinamide;
$N^2$-methyl-N-{(3aR,4S,6aS)-2-[3-(trifluoromethoxy)phenyl]octahydrocyclopenta[c]pyrrol-4-yl}-L-valinamide;

$N^2$-methyl-N-{(3aR,4S,6aS)-2-[4-(trifluoromethyl)phenyl]octahydrocyclopenta[c]pyrrol-4-yl}-L-norvalinamide;

$N^2$-methyl-N-{(3aR,4S,6aS)-2-[4-(trifluoromethyl)phenyl]octahydrocyclopenta[c]pyrrol-4-yl}-D-leucinamide;

$N^2$-isopropyl-N-{(3aR,4S,6aS)-2-[4-(trifluoromethyl)phenyl]octahydrocyclopenta[c]pyrrol-4-yl}-glycinamide;

(2S)-2-(isopropylamino)-N-{(3aR,4S,6aS)-2-[4-(trifluoromethyl)phenyl]octahydrocyclopenta[c]pyrrol-4-yl}butanamide;

$N^2$-methyl-N-{(3aR,4S,6aS)-2-[5-(trifluoromethyl)pyridin-2-yl]octahydrocyclopenta[c]pyrrol-4-yl}-L-valinamide;

$N^2$-methyl-N-{(3aR,4S,6aS)-2-[6-(trifluoromethyl)pyridin-2-yl]octahydrocyclopenta[c]pyrrol-4-yl}-L-valinamide;

$N^2$-methyl-N-{(3aR,4S,6aS)-2-[4-(trifluoromethyl)pyridin-3-yl]octahydrocyclopenta[c]pyrrol-4-yl}-L-leucinamide;

N-{(3aR,4S,6aS)-2-[3-bromo-5-(trifluoromethyl)pyridin-2-yl]octahydrocyclopenta[c]pyrrol-4-yl}-$N^2$-methyl-L-leucinamide;

$N^2$-methyl-N-{(3aR,4S,6aS)-2-[2-(trifluoromethyl)pyridin-3-yl]octahydrocyclopenta[c]pyrrol-4-yl}-L-leucinamide;

$N^2$-methyl-N-{(3aS,4R,6aR)-2-[4-(trifluoromethyl)phenyl]octahydrocyclopenta[c]pyrrol-4-yl}-D-leucinamide;

N-{(3aR,4S,6aS)-2-[3-(difluoromethyl)-4-fluorophenyl]octahydrocyclopenta[c]pyrrol-4-yl}-$N^2$-methyl-L-leucinamide;

N-{(3aR,4S,6aS)-2-[2-(difluorormethyl)-5-fluorophenyl]octahydrocyclopenta[c]pyrrol-4-yl}-$N^2$-methyl-L-leucinamide;

N-{(3aR,4S,6aS)-2-[2-(difluorormethyl)phenyl]octahydrocyclopenta[c]pyrrol-4-yl}-$N^2$-methyl-L-leucinamide;

N-{(3aR,4S,6aS)-2-[4-fluoro-3-(trifluoromethoxy)phenyl]octahydrocyclopenta[c]pyrrol-4-yl}-$N^2$-methyl-L-leucinamide;

N-[(3aR,4S,6aS)-2-(3-chloro-4-fluorophenyl)octahydrocyclopenta[c]pyrrol-4-yl]-$N^2$-methyl-L-leucinamide;

N-{(3aR,4S,6aS)-2-[2-fluoro-4-(trifluoromethoxy)phenyl]octahydrocyclopenta[c]pyrrol-4-yl}-$N^2$-methyl-L-leucinamide;

3-cyclopropyl-$N^2$-methyl-N-{(3aR,4S,6aS)-2-[4-(trifluoromethoxy)phenyl]octahydrocyclopenta[c]pyrrol-4-yl}-L-alaninamide;

3-cyclopropyl-N-{(3aR,4S,6aS)-2-[4-(trifluoromethoxy)phenyl]octahydrocyclopenta[c]pyrrol-4-yl}-L-alaninamide;

3-cyclopropyl-$N^2$,$N^2$-dimethyl-N-{(3aR,4S,6aS)-2-[4-(trifluorornethoxy)phenyl]octahydrocyclopenta[c]pyrrol-4-yl}-L-alaninamide;

1-tert-butyl-3-{(3aR,4S,6aS)-2-[4-(trifluoromethoxy)phenyl]octahydrocyclopenta[c]pyrrol-4-yl}-urea;

1-tert-butyl-3-{(3aR,4S,6aS)-2-[3-(trifluoromethoxy)phenyl]octahydrocyclopenta[c]pyrrol-4-yl}-urea;

(4R)-4-fluoro-N-{(3aR,4S,6aS)-2-[5-(trifluoromethyl)pyridin-2-yl]octahydrocyclopenta[c]pyrrol-4-yl}-L-prolinamide;

(4R)-4-fluoro-N-{(3aR,4S,6aS)-2-[4-(trifluoromethyl)phenyl]octahydrocyclopenta[c]pyrrol-4-yl}-L-prolinamide;

(4S)-4-fluoro-N-{(3aR,4S,6aS)-2-[4-(trifluoromethyl)phenyl]octahydrocyclopenta[c]pyrrol-4-yl}-L-prolinamide;

(4S)-4-fluoro-N-{(3aR,4S,6aS)-2-[5-(trifluoromethyl)-2-thienyl]octahydrocyclopenta[c]pyrrol-4-yl}-L-prolinamide;

(4S)-4-fluoro-N-{(3aR,4S,6aS)-2-[2-(trifluoromethyl)-3-thienyl]octahydrocyclopenta[c]pyrrol-4-yl}-L-prolinamide;

N-[(3aR,4S,6aS)-2-(2-methoxyphenyl)octahydrocyclopenta[c]pyrrol-4-yl]-$N^2$-methyl-L-leucinamide;

N-[(3aR,4S,6aS)-2-(3-methoxyphenyl)octahydrocyclopenta[c]pyrrol-4-yl]-$N^2$-methyl-L-leucinamide;

N-[(3aR,4S,6aS)-2-(4-methoxyphenyl)octahydrocyclopenta[c]pyrrol-4-yl]-$N^2$-methyl-L-leucinamide;

N-[(3aR,4S,6aS)-2-(2-cyanophenyl)octahydrocyclopenta[c]pyrrol-4-yl]-$N^2$-methyl-L-leucinamide;

$N^2$-methyl-N-{(3aR,4S,6aS)-2-[5-(trifluoromethyl)-2-thienyl]octahydrocyclopenta[c]pyrrol-4-yl}-L-leucinamide;

$N^2$-methyl-N-{(3aR,4S,6aS)-2-[2-(trifluoromethyl)-3-thienyl]octahydrocyclopenta[c]pyrrol-4-yl}-L-leucinamide; and N-{(3aR,4S,6aS)-2-[5-(difluoromethyl)-3-thienyl]octahydrocyclopenta[c]pyrrol-4-yl}-$N^2$-methyl-L-leucinamide.

22. A pharmaceutical composition comprising a therapeutically effective amount of a compound of formula (I) according to claim 1 or a pharmaceutically acceptable salt thereof, in combination with a pharmaceutically acceptable carrier.

23. A method of treating pain in a subject in need thereof, comprising:
administering to the subject a therapeutically suitable amount of a compound of formula (I) according to claim 1, or a pharmaceutically acceptable salt thereof, wherein the pain is acute pain, chronic pain, neuropathic pain, inflammatory pain, visceral pain, cancer pain, allodynia, fibromyalgia, sciatica, back pain, and headache pain including migraine, or combinations thereof.

* * * * *